US012528785B2

(12) United States Patent
Ji et al.

(10) Patent No.: US 12,528,785 B2
(45) **Date of Patent: *Jan. 20, 2026**

(54) MDM2 DEGRADERS AND USES THEREOF

(71) Applicant: Kymera Therapeutics, Inc., Watertown, MA (US)

(72) Inventors: Nan Ji, Arlington, MA (US); Matthew M. Weiss, Boston, MA (US); Xiaozhang Zheng, Lexington, MA (US); Xiao Zhu, Winchester, MA (US)

(73) Assignee: Kymera Therapeutics, Inc., Watertown, MA (US)

( * ) Notice: Subject to any disclaimer, the term of this patent is extended or adjusted under 35 U.S.C. 154(b) by 325 days.

This patent is subject to a terminal disclaimer.

(21) Appl. No.: 17/912,416

(22) PCT Filed: Mar. 19, 2021

(86) PCT No.: PCT/US2021/023233

§ 371 (c)(1),
(2) Date: Sep. 16, 2022

(87) PCT Pub. No.: WO2021/188948

PCT Pub. Date: Sep. 23, 2021

(65) Prior Publication Data

US 2024/0424110 A1 Dec. 26, 2024

Related U.S. Application Data

(60) Provisional application No. 63/123,315, filed on Dec. 9, 2020, provisional application No. 62/991,763, filed on Mar. 19, 2020.

(51) Int. Cl.

| | |
|---|---|
| ***C07D 401/14*** | (2006.01) |
| ***A61K 47/54*** | (2017.01) |
| ***A61K 47/55*** | (2017.01) |
| ***C07D 487/10*** | (2006.01) |
| ***C07D 519/00*** | (2006.01) |

(52) U.S. Cl.

CPC .......... *C07D 401/14* (2013.01); *A61K 47/545* (2017.08); *A61K 47/55* (2017.08); *C07D 487/10* (2013.01); *C07D 519/00* (2013.01)

(58) Field of Classification Search

CPC ... C07D 401/14; C07D 487/10; C07D 519/00
USPC .......................................................... 514/326
See application file for complete search history.

(56) References Cited

U.S. PATENT DOCUMENTS

| | | | |
|---|---|---|---|
| 4,650,750 | A | 3/1987 | Giese |
| 4,709,016 | A | 11/1987 | Giese |
| 5,217,866 | A | 6/1993 | Summerton et al. |
| 5,360,811 | A | 11/1994 | Tegeler et al. |
| 5,360,819 | A | 11/1994 | Giese |
| 5,516,931 | A | 5/1996 | Giese et al. |
| 5,602,273 | A | 2/1997 | Giese et al. |
| 5,604,104 | A | 2/1997 | Giese et al. |
| 5,610,020 | A | 3/1997 | Giese et al. |
| 5,650,270 | A | 7/1997 | Giese et al. |
| 5,721,246 | A | 2/1998 | Yoshino et al. |
| 6,306,663 | B1 | 10/2001 | Kenten et al. |
| 6,552,065 | B2 | 4/2003 | Remiszewski et al. |
| 6,559,280 | B2 | 5/2003 | Kenten et al. |
| 6,617,346 | B1 | 9/2003 | Kong et al. |
| 6,627,754 | B2 | 9/2003 | Blumenkopf et al. |
| 6,734,302 | B2 | 5/2004 | Kong et al. |
| 6,916,833 | B2 | 7/2005 | Kim et al. |
| 6,949,537 | B2 | 9/2005 | Garlich et al. |
| 7,041,298 | B2 | 5/2006 | Deshaies et al. |
| 7,060,713 | B2 | 6/2006 | Kim et al. |
| 7,071,189 | B2 | 7/2006 | Kawashima et al. |
| 7,074,620 | B2 | 7/2006 | Kenten et al. |
| 7,083,983 | B2 | 8/2006 | Lane et al. |
| 7,132,421 | B2 | 11/2006 | Fotuhi et al. |
| 7,173,015 | B2 | 2/2007 | Schreiber et al. |
| 7,208,157 | B2 | 4/2007 | Dashaies et al. |
| 7,273,920 | B2 | 9/2007 | Kenten et al. |
| 7,307,077 | B2 | 12/2007 | Kawashima et al. |
| 7,390,799 | B2 | 6/2008 | Bruncko et al. |
| 7,402,325 | B2 | 7/2008 | Addington |
| 7,425,638 | B2 | 9/2008 | Haley et al. |
| 7,449,458 | B2 | 11/2008 | Bhamidipati et al. |
| 7,495,007 | B2 | 2/2009 | Chen et al. |
| 7,501,496 | B1 | 3/2009 | Endl et al. |
| 7,514,444 | B2 | 4/2009 | Honigberg et al. |
| 7,528,143 | B2 | 5/2009 | Noronha et al. |
| 7,553,833 | B2 | 6/2009 | Yatake |

(Continued)

FOREIGN PATENT DOCUMENTS

| | | | |
|---|---|---|---|
| CN | 105085620 | B | 5/2018 |
| WO | WO-1996007655 | A1 | 3/1996 |

(Continued)

OTHER PUBLICATIONS

Eldridge, "The TP53 Gene and Its Role in Cancer", verywell health, 2023, 6 pages.
Golub et al., "Molecular classification of cancer: class discovery and class prediction by gene expression monitoring", Science, Oct. 15, 1999, 286(5439):531-537.
"Acute Leukemia", Merck Manual (Online Edition), 2013, 6 pages.
Damasio, "Alzheimer's Disease and related dementias", Cecil Textbook of Medicine, 20th Edition, 1996, vol. 2, pp. 1992-1996.
Gura T., "Systems for identifying new drugs are often faulty," Science, 1997, 278(5340):1041-1042.
Johnson et al., "Relationships between drug activity in NCl preclinical in vitro and in vivo models and early clinical trials," British Journal of Cancer, 2001, 84(10):1424-1431.
Layzer, Robert B., "Degenerative diseases of the nervous system", Cecil Textbook of Medicine, 20th Edition, 1996, vol. 2, pp. 2050-2057.

(Continued)

*Primary Examiner* — Kahsay Habte
(74) *Attorney, Agent, or Firm* — Dechert LLP; Andrea L.C. Reid; Todd K. Macklin

(57) ABSTRACT

The present invention relates to compounds and methods useful for the modulation of mouse double minute 2 homolog ("MDM2") protein via ubiquitination and/or degradation by compounds according to the present invention.

20 Claims, No Drawings

(56) References Cited

U.S. PATENT DOCUMENTS

| | | | |
|---|---|---|---|
| 7,557,210 | B2 | 7/2009 | Singh et al. |
| 7,576,082 | B2 | 8/2009 | Luk et al. |
| 7,579,368 | B2 | 8/2009 | Fotouhi et al. |
| 7,598,257 | B2 | 10/2009 | Rodgers et al. |
| 7,622,496 | B2 | 11/2009 | Larsen et al. |
| 7,625,895 | B2 | 12/2009 | Dominique et al. |
| 7,638,548 | B2 | 12/2009 | Liu et al. |
| 7,667,039 | B2 | 2/2010 | Garcia-Echeverria et al. |
| 7,713,943 | B2 | 5/2010 | Klippel-Giese et al. |
| 7,737,174 | B2 | 6/2010 | Wang et al. |
| 7,759,383 | B2 | 7/2010 | Wang et al. |
| 7,781,433 | B2 | 8/2010 | Chuckowree et al. |
| 7,932,260 | B2 | 4/2011 | Fowler et al. |
| 7,989,622 | B2 | 8/2011 | Bajalieh et al. |
| 8,138,347 | B2 | 3/2012 | Knight et al. |
| 8,217,035 | B2 | 7/2012 | Burger et al. |
| 8,338,439 | B2 | 12/2012 | Singh et al. |
| 8,486,941 | B2 | 7/2013 | Burns et al. |
| 8,518,984 | B2 | 8/2013 | Wang et al. |
| 8,629,141 | B2 | 1/2014 | Wang et al. |
| 8,658,170 | B2 | 2/2014 | Errico et al. |
| 8,680,132 | B2 | 3/2014 | Wang et al. |
| 8,906,682 | B2 | 12/2014 | June et al. |
| 9,500,653 | B2 | 11/2016 | Crews et al. |
| 9,632,089 | B2 | 4/2017 | Crews et al. |
| 9,694,084 | B2 | 7/2017 | Bradner et al. |
| 9,750,816 | B2 | 9/2017 | Bradner et al. |
| 9,770,512 | B2 | 9/2017 | Bradner et al. |
| 9,821,068 | B2 | 11/2017 | Bradner et al. |
| 9,993,472 | B2 | 6/2018 | Laberge et al. |
| 10,125,114 | B2 | 11/2018 | Bradner et al. |
| 10,336,744 | B2 | 7/2019 | Harling et al. |
| 10,874,743 | B2 | 12/2020 | Mainolfi et al. |
| 11,292,792 | B2 | 4/2022 | Ji et al. |
| 11,358,948 | B2 | 6/2022 | Mainolfi et al. |
| 11,512,080 | B2 | 11/2022 | Mainolfi et al. |
| 11,932,624 | B2 * | 3/2024 | Ji ......................... C07D 519/00 |
| 2001/0053782 | A1 | 12/2001 | Blumenkopf et al. |
| 2002/0042427 | A1 | 4/2002 | Tang et al. |
| 2002/0068063 | A1 | 6/2002 | Deshaies et al. |
| 2002/0132977 | A1 | 9/2002 | Yuan et al. |
| 2002/0183360 | A1 | 12/2002 | Muller et al. |
| 2004/0029902 | A1 | 2/2004 | Singh et al. |
| 2004/0048859 | A1 | 3/2004 | Germann et al. |
| 2004/0106569 | A1 | 6/2004 | Klippel-Giese et al. |
| 2004/0116421 | A1 | 6/2004 | Kawashima et al. |
| 2004/0242631 | A1 | 12/2004 | Garlich et al. |
| 2005/0014802 | A1 | 1/2005 | Attardo et al. |
| 2005/0075306 | A1 | 4/2005 | Schreiber et al. |
| 2005/0137137 | A1 | 6/2005 | Lane et al. |
| 2005/0227932 | A1 | 10/2005 | Lu et al. |
| 2005/0288287 | A1 | 12/2005 | Fotouhi et al. |
| 2006/0211657 | A1 | 9/2006 | Singh et al. |
| 2006/0211718 | A1 | 9/2006 | Weissman et al. |
| 2006/0211757 | A1 | 9/2006 | Wang et al. |
| 2007/0098719 | A1 | 5/2007 | Smith et al. |
| 2007/0135461 | A1 | 6/2007 | Rodgers et al. |
| 2007/0191405 | A1 | 8/2007 | Noronha et al. |
| 2008/0076768 | A1 | 3/2008 | Chuckowree et al. |
| 2008/0108636 | A1 | 5/2008 | Honigberg et al. |
| 2008/0171723 | A1 | 7/2008 | Khan |
| 2008/0194579 | A1 | 8/2008 | Garcia-Echeverria et al. |
| 2008/0261917 | A1 | 10/2008 | Willems et al. |
| 2008/0275067 | A1 | 11/2008 | Fowler et al. |
| 2009/0030181 | A1 | 1/2009 | Han et al. |
| 2009/0055944 | A1 | 2/2009 | Korman et al. |
| 2009/0136494 | A1 | 5/2009 | Ponath et al. |
| 2009/0143364 | A1 | 6/2009 | Fotouhi et al. |
| 2009/0227542 | A1 | 9/2009 | Khan |
| 2009/0233903 | A1 | 9/2009 | Rodgers et al. |
| 2009/0312310 | A1 | 12/2009 | Kawato et al. |
| 2010/0048593 | A1 | 2/2010 | Weissman et al. |
| 2010/0087440 | A1 | 4/2010 | Bajjalieh et al. |
| 2010/0150892 | A1 | 6/2010 | Han |
| 2010/0197671 | A1 | 8/2010 | Burns et al. |
| 2010/0197686 | A1 | 8/2010 | Xing et al. |
| 2010/0203056 | A1 | 8/2010 | Irving et al. |
| 2010/0233183 | A1 | 9/2010 | Triebel et al. |
| 2010/0247554 | A1 | 9/2010 | Lemke et al. |
| 2010/0249092 | A1 | 9/2010 | Singh et al. |
| 2010/0249126 | A1 | 9/2010 | Burger et al. |
| 2011/0008331 | A1 | 1/2011 | Triebel |
| 2011/0053941 | A1 | 3/2011 | Mautino et al. |
| 2011/0136796 | A1 | 6/2011 | Mautino et al. |
| 2011/0165156 | A1 | 7/2011 | Dimoudis et al. |
| 2011/0223611 | A1 | 9/2011 | Salamone et al. |
| 2011/0274683 | A1 | 11/2011 | Wong et al. |
| 2012/0189639 | A1 | 7/2012 | Schebye et al. |
| 2012/0277217 | A1 | 11/2012 | Mautino et al. |
| 2012/0329997 | A1 | 12/2012 | Fertig et al. |
| 2013/0005949 | A1 | 1/2013 | Fertig et al. |
| 2013/0149236 | A1 | 6/2013 | Johnson et al. |
| 2013/0190340 | A1 | 7/2013 | Hedstrom et al. |
| 2014/0066625 | A1 | 3/2014 | Mautino et al. |
| 2014/0079699 | A1 | 3/2014 | Wong et al. |
| 2014/0079706 | A1 | 3/2014 | Cannarile et al. |
| 2014/0093511 | A1 | 4/2014 | Lonberg et al. |
| 2014/0302523 | A1 | 10/2014 | Crews et al. |
| 2014/0336363 | A1 | 11/2014 | Fertig et al. |
| 2014/0341917 | A1 | 11/2014 | Nastri et al. |
| 2014/0356322 | A1 | 12/2014 | Crews et al. |
| 2015/0225449 | A1 | 8/2015 | Donnell et al. |
| 2015/0274738 | A1 | 10/2015 | Gray et al. |
| 2015/0291562 | A1 | 10/2015 | Crew et al. |
| 2015/0374678 | A1 | 12/2015 | Chamberlain et al. |
| 2016/0000764 | A1 | 1/2016 | Weinstabl et al. |
| 2016/0022642 | A1 | 1/2016 | Crews et al. |
| 2016/0045607 | A1 | 2/2016 | Crew et al. |
| 2016/0058872 | A1 | 3/2016 | Crew et al. |
| 2016/0176916 | A1 | 6/2016 | Bradner et al. |
| 2016/0214972 | A1 | 7/2016 | Jin et al. |
| 2016/0235730 | A1 | 8/2016 | Bradner et al. |
| 2016/0235731 | A1 | 8/2016 | Bradner et al. |
| 2016/0243247 | A1 | 8/2016 | Bradner et al. |
| 2016/0256468 | A1 | 9/2016 | Schafer et al. |
| 2016/0272596 | A1 | 9/2016 | Chen et al. |
| 2016/0272639 | A1 | 9/2016 | Crew et al. |
| 2017/0001990 | A1 | 1/2017 | Chen et al. |
| 2017/0008904 | A1 | 1/2017 | Crew et al. |
| 2017/0022189 | A1 | 1/2017 | Zhang |
| 2017/0037004 | A1 | 2/2017 | Crew et al. |
| 2017/0065719 | A1 | 3/2017 | Qian et al. |
| 2017/0121321 | A1 | 5/2017 | Crews et al. |
| 2017/0281784 | A1 | 10/2017 | Wang et al. |
| 2017/0327469 | A1 | 11/2017 | Crew et al. |
| 2018/0009779 | A1 | 1/2018 | Bradner et al. |
| 2018/0015087 | A1 | 1/2018 | Liu et al. |
| 2018/0085465 | A1 | 3/2018 | Bradner et al. |
| 2018/0118733 | A1 | 5/2018 | Harling et al. |
| 2018/0134684 | A1 | 5/2018 | Bradner et al. |
| 2018/0147202 | A1 | 5/2018 | Crew et al. |
| 2018/0194724 | A1 | 7/2018 | Kemp et al. |
| 2018/0228907 | A1 | 8/2018 | Crew et al. |
| 2019/0071415 | A1 | 3/2019 | Bradner et al. |
| 2019/0076539 | A1 | 3/2019 | Phillips et al. |
| 2019/0076540 | A1 | 3/2019 | Phillips et al. |
| 2019/0076541 | A1 | 3/2019 | Phillips et al. |
| 2019/0076542 | A1 | 3/2019 | Phillips et al. |
| 2019/0127387 | A1 | 5/2019 | Wang et al. |
| 2019/0151457 | A1 | 5/2019 | Bradner et al. |
| 2019/0192668 | A1 | 6/2019 | Mainolfi et al. |
| 2019/0276474 | A1 | 9/2019 | Chan et al. |
| 2020/0010468 | A1 | 1/2020 | Ji et al. |
| 2020/0109149 | A1 | 4/2020 | Wang et al. |
| 2020/0347045 | A1 | 11/2020 | Mainolfi et al. |
| 2020/0377469 | A1 | 12/2020 | Mainolfi et al. |
| 2021/0002296 | A1 | 1/2021 | Mainolfi et al. |
| 2021/0179560 | A1 | 6/2021 | Bartberger et al. |
| 2021/0309666 | A1 | 10/2021 | Wang et al. |
| 2022/0281831 | A1 | 9/2022 | Ji et al. |
| 2022/0306631 | A1 | 9/2022 | Ji et al. |
| 2022/0356185 | A1 | 11/2022 | Ji et al. |
| 2022/0411432 | A1 | 12/2022 | Wang et al. |
| 2023/0038512 | A1 | 2/2023 | Mainolfi et al. |

(56) References Cited

U.S. PATENT DOCUMENTS

2023/0072658 A1 3/2023 Ji et al.
2023/0233546 A1 7/2023 Schalm et al.
2023/0234950 A1 7/2023 Mainolfi et al.
2025/0034147 A1 1/2025 Weiss

FOREIGN PATENT DOCUMENTS

WO WO-2001042246 A2 6/2001
WO WO-2002020740 A2 3/2002
WO WO-2002088112 A1 11/2002
WO WO-2003063794 A2 8/2003
WO WO-2004019973 A1 3/2004
WO WO-2004089925 A1 10/2004
WO WO-2004106328 A1 12/2004
WO WO-2005007623 A2 1/2005
WO WO-2005113554 A2 12/2005
WO WO-2006029879 A2 3/2006
WO WO-2006078846 A1 7/2006
WO WO-2006105021 A2 10/2006
WO WO-2006122806 A2 11/2006
WO WO-2007005874 A2 1/2007
WO WO-2007016176 A2 2/2007
WO WO-2007044729 A2 4/2007
WO WO-2007053452 A1 5/2007
WO WO-2007070514 A1 6/2007
WO WO-2007084786 A1 7/2007
WO WO-2007129161 A2 11/2007
WO WO-2008039218 A2 4/2008
WO WO-2008109943 A1 9/2008
WO WO-2008118802 A1 10/2008
WO WO-2008132601 A1 11/2008
WO WO-2009009116 A2 1/2009
WO WO-2009044273 A2 4/2009
WO WO-2009073620 A2 6/2009
WO WO-2009114512 A1 9/2009
WO WO-2009132238 A3 10/2009
WO WO-2010019570 A2 2/2010
WO WO-2010077634 A1 7/2010
WO WO-2011028683 A1 3/2011
WO WO-2011056652 A1 5/2011
WO WO-2011070024 A1 6/2011
WO WO-2011090760 A1 7/2011
WO WO-2011107553 A1 9/2011
WO WO-2011109400 A2 9/2011
WO WO-2011131407 A1 10/2011
WO WO-2011140249 A2 11/2011
WO WO-2012003281 A3 1/2012
WO WO-2012032433 A1 3/2012
WO WO-2012078559 A2 6/2012
WO WO-2012142237 A1 10/2012
WO WO-2012145493 A1 10/2012
WO WO-2013079174 A1 6/2013
WO WO-2013087699 A1 6/2013
WO WO-2013106643 A2 7/2013
WO WO-2013106646 A2 7/2013
WO WO-2013119716 A1 8/2013
WO WO-2013132044 A1 9/2013
WO WO-2013169264 A1 11/2013
WO WO-2014008218 A1 1/2014
WO WO-2014036357 A1 3/2014
WO WO-2014044622 A1 3/2014
WO WO-2014063061 A1 4/2014
WO WO-2014108452 A1 7/2014
WO WO-2015071393 A1 5/2015
WO WO-2015160845 A3 10/2015
WO WO-2016105518 A1 6/2016
WO WO-2016118666 A1 7/2016
WO WO-2016149668 A1 9/2016
WO WO-2016169989 A1 10/2016
WO WO-2016197032 A1 12/2016
WO WO-2016197114 A1 12/2016
WO WO-2017007612 A1 1/2017
WO WO-2017011371 A1 1/2017
WO WO-2017011590 A1 1/2017
WO WO-2017030814 A1 2/2017
WO WO-2017059280 A1 4/2017
WO WO-2017079267 A1 5/2017
WO WO-2017117473 A1 7/2017
WO WO-2017117474 A1 7/2017
WO WO-2017161119 A1 9/2017
WO WO-2017176708 A1 10/2017
WO WO-2017176957 A1 10/2017
WO WO-2017176958 A1 10/2017
WO WO-2017197036 A1 11/2017
WO WO-2017197046 A1 11/2017
WO WO-2017197051 A1 11/2017
WO WO-2017197055 A1 11/2017
WO WO-2017197056 A1 11/2017
WO WO-2017201449 A1 11/2017
WO WO-2017211924 A1 12/2017
WO WO-2018089736 A1 5/2018
WO WO-2018098367 A1 5/2018
WO WO-2018144649 A1 8/2018
WO WO-2018237026 A1 12/2018
WO WO-2019043214 A1 3/2019
WO WO-2019060693 A1 3/2019
WO WO-2019060742 A1 3/2019
WO WO-2019084026 A1 5/2019
WO WO-2019084030 A1 5/2019
WO WO-2019099868 A1 5/2019
WO WO-2019099926 A1 5/2019
WO WO-2019133531 A1 7/2019
WO WO-2019140380 A1 7/2019
WO WO-2019140387 A1 7/2019
WO WO-2019165229 A1 8/2019
WO 2019236483 A1 12/2019
WO WO-2020010177 A1 1/2020
WO WO-2020010210 A1 1/2020
WO WO-2020010227 A1 1/2020
WO 2020038415 A1 2/2020
WO WO-2020076660 A1 4/2020
WO 2020232115 A1 11/2020
WO WO-2021011631 A1 1/2021
WO 2021083949 A1 5/2021
WO WO-2021188948 A1 9/2021
WO 2022120118 A1 6/2022
WO 2022159644 A1 7/2022
WO 2023049790 A2 3/2023
WO 2023114933 A1 6/2023
WO 2023239697 A1 12/2023
WO 2024197216 A2 9/2024
WO 2024197218 A2 9/2024
WO 2024197219 A1 9/2024
WO 2024197221 A2 9/2024
WO 2025096262 A1 5/2025

OTHER PUBLICATIONS

Pearce et al., "Failure modes in anticancer drug discovery and development," Cancer Drug Design and Discovery, Edited by Stephen Neidle, Chapter 18, 2008, pp. 424-435.
Riedinger et al., "Inhibitors of MDM2 and MDMX: a structural perspective", Future Med Chem., Sep. 2009, 1 (6):1075-1094.
Simone, "Oncology: Introduction", Cecil Textbook of Medicine, 20th Edition, 1996, vol. 1, pp. 1004-1010.
Wang et al., "Development of MDM2 Degraders based on Ligands Derived from Ugi Reactions: Lessons and Discoveries", Eur J Med Chem, 2015, 219(113425):47 pages.
PCT International Preliminary Report on Patentability received from PCT/US2018/052181, dated Apr. 2, 2020, 8 pages.
PCT International Preliminary Report on Patentability received from PCT/US2019/013491, dated Jul. 23, 2020, 7 pages.
PCT International Preliminary Report on Patentability received from PCT/US2019/040462 dated Jan. 21, 2021, 6 pages.
PCT International Preliminary Report on Patentability received from PCT/US2020/042105, dated Jan. 27, 2022, 7 pages.
PCT International Preliminary Report on Patentability received from PCT/US2021/023233, dated Sep. 29, 2022, 9 pages.
PCT International Search Report and Written Opinion received from PCT/US2022/076841, dated Mar. 2, 2023, 12 pages.
PCT International Search Report and Written Opinion received from PCT/US2021/023233, dated Jul. 28, 2021, 13 pages.

(56) References Cited

OTHER PUBLICATIONS

PCT International Search Report and Written Opinion received from PCT/US2023/024543, dated Sep. 19, 2023, 11 pages.
National Center for Biotechnology Information, "3-(3-Methyl-2-oxo-5-piperidin-4-ylbenzimidazol-1-yl)piperidine-2,6-dlone: Pubchem CID 155170296" Pubchem entry (online), pp. 1-12, Dec. 19, 2020; Retrieved on Jul. 31, 2023 from the Internet: (https://pubchem.ncbi.nlm.nih.gov/compound/155170296#section=WIPO-PATENTSCOPE).
Li et al. "Discovery of MD-224 as a First-in-Class, Highly Potent, and Efficacious Proteolysis Targeting Chimera Murine Double Minute 2 Degrader Capable of Achieving Complete and Durable Tumor Regression," J Med Chem. 2019;62(2):448-466.
PCT International Search Report and Written Opinion from PCT/US2022/081699, dated Mar. 28, 2023.
Aguilar et al., "Discovery of 4-((3'R,4'S,5'R)-6"-Chloro-4'-(3-chloro-2-fluorophenyl)-1'-ethyl-2'-oxodispiro[cyclohexane-1,2'-pyrrolidine-3',3"-indoline]-5'-carboxamido)bicyclo[2.2.2]octane-1-carboxylic Acid (AA-115/APG-115): A Potent and Orally Active Murine Double Minute 2 (MDM2) Inhibitor in Clinical Development", Journal of Medicinal Chemistry, Apr. 13, 2017, 60(7):2819-2839.
Takahashi et al., "Safety and pharmacokinetics of milademetan, a MDM2 inhibitor, in Japanese patients with solid tumors: A phase I study", Cancer Science, Jun. 2021, 112(6):2361-2370.
Wurz et al., "Targeted Degradation of MDM2 as a New Approach to Improve the Efficacy of MDM2-p53 Inhibitors", Journal of Medicinal Chemistry, Jan. 24, 2019, 62(2):445-447.
International Preliminary Report on Patentability received for PCT Application No. PCT/US2022/076841, dated Apr. 4, 2024, 9 pages.
International Search Report and Written Opinion received for PCT Application No. PCT/US2024/021045, dated Aug. 27, 2024, 11 pages.
International Search Report and Written Opinion received for PCT Application No. PCT/US2024/021047, dated Aug. 21, 2024, 9 pages.
International Search Report and Written Opinion received for PCT Application No. PCT/US2024/021049, dated Jul. 1, 2024, 9 pages.
International Search Report and Written Opinion received for PCT Application No. PCT/US2024/021054, dated Aug. 27, 2024, 12 pages.
International Search Report and Written Opinion received for PCT Application No. PCT/US2024/052620, dated Dec. 23, 2024, 13 pages.
U.S. Appl. No. 18/872,432 of Davis et al., filed Dec. 6, 2024.
Adams et al., "Big opportunities for small molecules in immuno-oncology," Nat Rev Drug Discov. 2015;14(9):603-22.
Aruri et al., "Metal-free Cross-Dehydrogenative Coupling of HN-azoles with a-C(sp3)-H Amides via C—H Activation and Its Mechanistic and Application Studies," J Org Chem. 2017;82(2):1000-1012.
Assmann et al., "Single-nucleotide polymorphisms p53 G72C and Mdm2 T309G in patients with psoriasis, psoriatic arthritis, and SAPHO syndrome," Rheumatol. Int. 2010;30(10):1273-6.
Berge et al., "Pharmaceutical salts," J Pharm Sci. Jan. 1977;66(1):1-19.
Berndsen et al., "New insights into ubiquitin E3 ligase mechanism," Nat Struct Mol Biol. 2014;21(4):301-7.
Boichenko et al., "A FRET-Based Assay for the Identification and Characterization of Cereblon Ligands," J Med Chem. 2016;59(2):770-4.
CAS STN Abstract, RN 1787975-60-3 (Pub. Jun. 24, 2015).
CAS STN Abstract, RN 1795294-81-3 (Pub. Jul. 6, 2015).
CAS STN Abstract, RN 1795451-20-5 (Pub. Jul. 6, 2015).
CAS STN Abstract, RN 1795527-49-9 (Pub. Jul. 6, 2015).
CAS STN Abstract, RN 1871221-08-7 (Pub. Feb. 21, 2016).
CAS STN Abstract, RN 1878956-45-6 (Pub. Mar. 3, 2016).
CAS STN Abstract, RN 1878983-55-1 (Pub. Mar. 3, 2016).
CAS STN Abstract, RN 742039-47-0 (Pub. Sep. 10, 2004).
CAS STN Abstract, RN 779303-42-3 (Pub. Nov. 12, 2004).
Chang et al., "What is the functional role of the thalidomide binding protein cereblon?" Int J Biochem Mol Biol. 2011;2(3):287-94.
Charrier et al., "Desulfonylative radical ring closure onto aromatics. A modular route to benzazepin-2-ones and 5-arylpiperidin-2-ones," Org Lett. 2012;14(8):2018-21.
Chene, "Inhibiting the p53-MDM2 interaction: an important target for cancer therapy," Nat Rev Cancer. 2003;3(2):102-9.
Connolly et al., "Complexities of TGF-beta Targeted Cancer Therapy," Int J Biol Sci. 2012;8(7):964-978.
Contino-Pepin et al., "Preliminary biological evaluations of new thalidomide analogues for multiple sclerosis application," Bioorg Med Chem Lett. 2009;19(3):878-81.
Crews, "Targeting the Undruggable Proteome: The Small Molecules of My Dreams," Chem Biol. 2010;17(6):551-5.
Deshaies and Joazeiro, "RING domain E3 ubiquitin ligases," Annu Rev Biochem. 2009;78:399-434.
Ebrahim et al., "MDM2 beyond cancer: podoptosis, development, inflammation, and tissue regeneration," Histol Histopathol. 2015;30(11):1271-82.
Engel et al., "CHOP regulates the p53-MDM2 axis and is required for neuronal survival after seizures," Brain. 2013;136(2):577.
Fischer et al., "Structure of the DDB1-CRBN E3 ubiquitin ligase in complex with thalidomide," Nature. 2014;512(7512):49-53.
Hagner et al., "CC-122, a pleiotropic pathway modifier, mimics an interferon response and has antitumor activity in DLBCL," Blood. 2015;126(6):779-89.
Han et al., "TSLP induces mast cell development and aggravates allergic reactions through the activation of MDM2 and STAT6," J Invest Dermatol. 2014;134(10):2521-2530.
Herman et al., "Discovery of Mdm2-MdmX E3 Ligase Inhibitors Using a Cell-Based Ubiquitination Assay," Cancer Discov. 2011;1(4):312-325.
Hines et al., "MDM2-Recruiting PROTAC Offers Superior, Synergistic Antiproliferative Activity via Simultaneous Degradation of BRD4 and Stabilization of p53," Cancer Res. 2019;79(1):251-262.
Iconomou and Saunders, "Systematic approaches to identify E3 ligase substrates," Biochem J. 2016;473(22):4083-4101.
Ihling et al., "Co-expression of p53 and MDM2 in human atherosclerosis: implications for the regulation of cellularity of atherosclerotic lesions," J Pathol. 1998;185(3):303-12.
Ito et al., "Identification of a primary target of thalidomide teratogenicity," Science. 2010;327(5971):1345-50.
Izumi et al., "MDM2 is a novel E3 ligase for HIV-1 Vif," Retrovirology. 2009;6:1.
Jatiani et al., "Jak/STAT pathways in cytokine signaling and myeloproliferative disorders: approaches for targeted therapies," Genes Cancer. 2010;1(10):979-93.
Kester et al., "Optimization of Benzodiazepinones as Selective Inhibitors of the X-Linked Inhibitor of Apoptosis Protein (XIAP) Second Baculovirus IAP Repeat (BIR2) Domain," J Med Chem. 2013;56(20):7788-803.
Kleiman et al., "A single nucleotide polymorphism in the Mdm2 promoter and risk of sepsis," Am J Surg. 2009;197(1):43-8.
Krönke et al., "Lenalidomide causes selective degradation of IKZF1 and IKZF3 in multiple myeloma cells" Science. 2014;343(6168):301-305.
Lebakken et al., "A Fluorescence Lifetime Based Binding Assay to Characterize Kinase Inhibitors," J Biomol Screen. 2007;12(6):828-41.
Li et al., "Genome-wide and functional annotation of human E3 ubiquitin ligases identifies MULAN, a mitochondrial E3 that regulates the organelle's dynamics and signaling," PLoS One. 2008;3(1):e1487.
Lu et al., "Hijacking the E3 Ubiquitin Ligase Cereblon to Efficiently Target BRD4," Chem Biol. 2015;2(6):755-63.
Lu et al., "The myeloma drug lenalidomide promotes the cereblon-dependent destruction of Ikaros proteins," Science. 2014;343(6168):305-309.
Lust et al., "Induction of a Chronic Disease State in patients With Smoldering of Indolent Multiple Myeloma by Targeting Interleukin 1β-Induced Interleukin 6 Production and the Myeloma Proliferative Component," Mayo Clin Proc. 2009;84(2):114-22.

(56) References Cited

OTHER PUBLICATIONS

Matyskiela et al., "A Cereblon Modulator (CC-220) with Improved Degradation of Ikaros and Aiolos," J Med Chem. 2018;61(2):535-542.
Moll and Petrenko, "The MDM2-p53 interaction," Mol Cancer Res. 2003;1(14):1001-8.
Muller et al., "Amino-Substituted Thalidomide Analogs: Potent Inhibitors of TNF-? Production," Bioorg Med Chem Lett. 1999;9(11):1625-30.
Ohoka et al., "In Vivo Knockdown of Pathogenic Proteins via Specific and Nongenetic Inhibitor of Apoptosis Protein (IAP)-dependent Protein Erasers (SNIPERs)," J Bio Chem. 2017;292(11):4556-4570.
Okazaki et al., "A rheostat for immune responses: the unique properties of PD-1 and their advantages for clinical application," Nat. Immunol. 2013; 14(12): 1212-1218.
PCT International Search Report and Written Opinion from PCT/US2018/052181, dated Feb. 26, 2019.
PCT International Search Report and Written Opinion from PCT/US2018/052242, dated Jan. 30, 2019.
PCT International Search Report and Written Opinion from PCT/US2018/067304, dated Apr. 30, 2019.
PCT International Search Report and Written Opinion from PCT/US2019/013481, dated Mar. 15, 2019.
PCT International Search Report and Written Opinion from PCT/US2019/013491, dated Mar. 18, 2019.
PCT International Search Report and Written Opinion from PCT/US2019/040462, dated Sep. 20, 2019.
PCT International Search Report and Written Opinion from PCT/US2019/040520, dated Nov. 13, 2019.
PCT International Search Report and Written Opinion from PCT/US2019/040545, dated Oct. 21, 2019.
PCT International Search Report and Written Opinion from PCT/US2019/064070, dated Apr. 6, 2020.
PCT International Search Report and Written Opinion from PCT/US2020/042105, dated Nov. 20, 2020.
Pei et al., "STAT3 inhibition enhances CDN-induced STING signaling and antitumor immunity," Cancer Lett. 2019;450:110-122.
Piya et al., "BRD4 Proteolysis Targeting Chimera (PROTAC) Leads to Sustained Degradation of BRD4 with Broad Activity Against Acute Leukemias and Overcomes Stroma Mediated Resistance by Modulating Surface Expression of CXCR4," Blood. 2016;126(23): 675-676.
Priyadarshini et al., "Copper catalyzed oxidative cross-coupling of aromatic amines with 2-pyrrolidinone: a facile synthesis of N-aryl-r-amino-r-lactams," Tetrahedron. 2014;70(36):6068-6074.
Pubmed Compound Summary for CID 101524675, "(2R)-3-Fluoro-2-(2-methylpropyl)-3-phenyl-1,3-azasilinan-6-one," *U.S. National Library of Medicine*, created Dec. 18, 2015, https://pubchem.ncbi.nlm.nih.gov/compound/101524675. Date Accessed: Sep. 5, 2019 (5 pages).
Pubmed Compound Summary for CID 102164987, "3-[(4S)-2,5-Dioxo-4-phenylimidazolidine-1-yl]-2,6-piperidinedione," U.S. National Library of Medicine, created Dec. 24, 2015, https://pubchem.ncbi.nlm.nih.gov/compound/102164987. Date Accessed: Feb. 25, 2020 (7 pages).
Pubmed Compound Summary for CID 110491408, 3-(5-Amino-2-oxo-3H-benzimidazol-1-yl)piperidine-2,6-dione, *U.S. Library of Medicine*, created Jan. 18, 2016, https://pubchem.ncbi.nlm.nih.gov/compound/110491408. Date Accessed: Feb. 25, 2020 (7 pages).
Pubmed Compound Summary for CID 110491555, 3-(6-Amino-2-oxo-3H-benzimidazol-1-yl)piperidine-2,6-dione, U.S. Library of Medicine, created Jan. 18, 2016, https://pubchem.ncbi.nlm.nih.gov/compound/110491555. Date Accessed: Feb. 25, 2020 (7 pages).
Pubmed Compound Summary for CID 115370667, "5-(2-Oxoimidazolidin-1-yl)piperidin-2-one." U.S. National Library of Medicine, created Oct. 22, 2012, https://pubchem.ncbi.nlm.nih.gov/compound/115370667. Date Accessed: Feb. 25, 2020 (10 pages).
Pubmed Compound Summary for CID 138728787, "3-(6-Ethylpyrido[2,3-b]indol-9-yl)piperidine-2,6-dione," U.S. National Library of Medicine, created Jul. 20, 2019, https://pubchem.ncbi.nlm.nih.gov/compound/138728787. Date Accessed: Sep. 5, 2019 (6 pages).
Pubmed Compound Summary for CID 17607528, "4-(Carbazol-9-ylmethyl)-1,3-oxazolidin-2-one," U.S. National Library of Medicine, Nov. 13, 2007, https://pubchem.ncbi.nlm.nih.gov/compound/17607528. Date Accessed: Feb. 25, 2020 (6 pages).
Pubmed Compound Summary for CID 63661260,"5-[2-(1-Chloroethyl)benzimidazol-1-yl]piperidin-2-one," U.S. National Library of Medicine, created Oct. 22, 2012, https://pubchem.ncbi.nlm.nih.gov/compound/63661260. Date Accessed: Sep. 4, 2019 (6 pages).
Pubmed Compound Summary for CID 63661460, "6-Oxo-1-(6-oxopiperidin-3-yl)piperidine-3-carboxylic acid," U.S. National Library of Medicine, created Oct. 22, 2012, https://pubchem.ncbi.nlm.nih.gov/compound/63661460. Date Accessed: Feb. 25, 2020 (7 pages).
Pubmed Compound Summary for CID 65967733, "3-(2,5-Dioxo-3-phenylpyrrolidin-1-yl)piperidine-2,6-dione," *U.S. National Library of Medicine*, created Dec. 24, 2015, https://pubchem.ncbi.nlm.nih.gov/compound/65967733. Date Accessed: Feb. 25, 2020 (7 pages).
Pubmed Compound Summary for CID 65968760, "1-(2,6-Dioxopiperidin-3-yl)benzimidazole-5-carboxylic acid," U.S. National Library of Medicine, created Oct. 24, 2012, https://pubchem.ncbi.nlm.nih.gov/compound/65968760. Date Accessed: Sep. 4, 2019 (6 pages).
Pubmed Compound Summary for CID 67258040, "[1-(9H-Fluoren-9-yl)-1-(6-oxopiperidin-3-yl)ethyl] hydrogen carbonate," *U.S. National Library of Medicine*, Nov. 30, 2012 https://pubchem.ncbi.nlm.nih.gov/compound/67258040. Date Accessed: Feb. 25, 2020 (9 pages).
Pubmed Compound Summary for CID 83543479, "5(Aminomethyl)-5-(1H-indol-3-yl)piperidin-2-one," *U.S. National Library of Medicine*, created Oct. 20, 2014, https://pubchem.ncbi.nlm.nih.gov/compound/83543479. Date Accessed: Feb. 25, 2020 (6 pages).
Pubmed Compound Summary for CID 84036945, 1-Piperidin-3-yl-3H-indol-2-one, *U.S. Library of Medicine*, created Oct. 20, 2014, https://pubchem.ncbi.nlm.nih.gov/compound/84036945. Date Accessed: Feb. 25, 2020 (7 pages).
Pubmed Compound Summary for CID 86793742, 3-[(6-chloro-1H-1,3-benzodiazol-2-yl)sulfanyl]piperidine-2,6-dione, created Feb. 7, 2015, https://pubchem.ncbi.nlm.nih.gov/compound/86793742. Date Accessed: Jan. 10, 2022.
Pubmed Compound Summary for CID 91648396, 3-[(4-Fluorophenyl)sulfanyl]piperidine-2,6-dione, created Mar. 20, 2015, https://pubchem.ncbi.nlm.nih.gov/compound/91648396#section=Structures. Date Accessed: Jan. 10, 2022.
Pubmed Compound Summary for CID 99784232, (3S)-3-(4-fluorophenyl)sulfanylpiperidine-2,6-dione, created Dec. 11, 2015, https://pubchem.ncbi.nlm.nih.gov/compound/99784232. Date Accessed: Jan. 10, 2022.
Raina et al., "Chemical Inducers of Targeted Protein Degradation," J Biol Chem. 2010;285(15):11057-60.
Ramirez et al., "Defining causative factors contributing in the activation of hedgehog signaling in diffuse large B-cell lymphoma," Leuk. Res. 2012;36(10):1267-73.
Ronnebaum et al., "Synthesis of 1, 2, 3-triazole 'click' analogues of thalidomide," Tetrahedron. 2016;72(40): 6136-6141.
Ross et al., "Bispecific T cell engager (BITE®) antibody constructs can mediate bystander tumor cell killing," PLoS One. 2017; 12(8): e0183390.
Rostovtsev et al., "A Stepwise Huisgen Cycloaddition Process: Copper(I)-Catalyzed Regioselective "Ligation" of Azides and Terminal Alkynes," Angew Chem Int Ed Engl. 2002;41(14):2596-9.
Schnnekloth et al., "Chemical approaches to controlling intracellular protein degradation," Chembiochem. 2005;6(1):40-46.
Secchiero et al., "The MDM2 inhibitor Nutlin-3 attenuates streptozotocin-induced diabetes mellitus and increases serum level of IL-12p40," Acta Diabetol. 2013;50(6):899-906.
Seitz et al., "Sulfenylation and Halogenation of Di- and Trianions Derived from Substituted Glutarimides," Synthetic Communications. 1977;7(6):367-374.
Sen et al., "Transcriptional signaling by double-stranded RNA: role of TLR3," Cytokine Growth Factor Rev. 2005;16(1):1-14.

(56) References Cited

OTHER PUBLICATIONS

Shanmugasundaram et al., "A modular PROTAC design for target destruction using a degradation signal based on a single amino acid," J Biol Chem. 2019;294(41):15172-15175.
Spradin et al., "Harnessing the Anti-Cancer Natural Product Nimbolide for Targeted Protein Degradation," bioRxiv.org, https://www.biorxiv.org/content/biorxiv/early/2019/04/09/436998.full.pdf. Date Accessed, Oct. 3, 2019.
Spratt et al., "RBR E3 ubiquitin ligases: new structures, new insights, new question," Biochem J. 2014;458(3);421-37.
Stewart et al., "Efforts toward elucidating Thalidomide's molecular target: an expedient synthesis of the first Thalidomide biotin analogue," Organic & Biomolecular Chemistry. 2010;8(18): 4059-4062.
Sun et al., "Carbohydrate and protein immobilization onto solid surfaces by sequential Diels-Alder and azide-alkyne cycloadditions," Bioconjug Chem. 2006;17(1):52-7.
Thomasova et al., "p53-Independent Roles of MDM2 in NF-?B Signaling: Implications for Cancer Therapy, Wound Healing, and Autoimmune Diseases," Neoplasia. 2012;14(12):1097-1101.
Toogood, "Small molecule immuno-oncology therapeutic agents," Bioorg. Med. Chem. Lett. 2018;28(3):319-329.
Toure and Crews, "Small-Molecule PROTACS: New Approaches to Protein Degradation," Angew Chem Int Ed Engl. 2016;55(6):1966-73.
Uehara et al., "Selective degradation of splicing factor CAPER? by anticancer sulfonamides," Nat Chem Biol. 2017;13(6):675-680.
Varfolomeev et al., "IAP antagonists induce autoubiquitination of c-IAPs, NF-kappaB activation, and TNFalpha-dependent apoptosis," Cell. 2007;131(4):669-81.
Vassilev, "MDM2 inhibitors for cancer therapy," Trends Mol Med. 2007;13(1):23-31.
Wang et al., "Roles of F-box proteins in cancer," Nat Rev Cancer. 2014;14(4):233-47.
Ward et al., "Covalent Ligand Screening Uncovers a RNF4 E3 Ligase Recruiter for Targeted Protein Degradation Applications," *bioRxiv.org*, https://www.biorxiv.org/content/biorxiv/early/2018/11/16/439125.full.pdf. Date Accessed, Oct. 3, 2019 (24 pages).
Weaver, "Epidemiology of gout," Cleve Clin J Med. 2008;75 Suppl 5:S9-12.
Winter et al., "Selective Target Protein Degradation via Phthalimide Conjugation," Science. 2015;348(6241):1376-1381.
Wu et al., "The p53-mdm-2 autoregulatory feedback loop," Genes Dev. 1993;7(7A):1126-32.
Xia and Chen, "Iron-catalyzed N-alkylation of azoles via cleavage of an sp3 C—H bond adjacent to a nitrogen atom," J Org Chem. 2012;77(20):9366-73.
Yang et al., "Combined effects of p53 and MDM2 polymorphisms on susceptibility and surgical prognosis in hepatitis B virus-related hepatocellular carcinoma," Protein Cell. 2013;4(1):71-81.
Yang et al., "Exploiting synthetic lethality for the therapy of ABC diffuse large B cell lymphoma," Cancer Cell. 2012;21(6):723-37.
Zhang et al., "Electrophilic PROTACs that degrade nuclear proteins by engaging DCAF16," *bioRxiv.org*, https://www.biorxiv.org/content/biorxiv/early/2018/10/15/443804.full.pdf. Date Accessed, Oct. 3, 2019.
Zhang et al., "Fluorescence polarization assay and inhibitor design for MDM2/p53 interaction," Analytical Biochem. 2004;331(1):138-46.
Zhang et al., "MDM2 promotes rheumatoid arthritis via activation of MAPK and NF-?B," Int Immunopharmacol. 2016;30:69-73.
Zhou et al., "Targets of curcumin," Curr Drug Targets. 2011;12(3):332-347.
Zimmer et al., "Genotypic interaction and gender specificity of common genetic variants in the p53/mdm2 network in Crohn's disease," Digestion. 2010;81(4):246-51.
Zinc 170596280, Date Added Aug. 8, 2015, https://zinc.docking.org/substances/ZINC000170596280/. Date Accessed: Jan. 10, 2022.
Zou et al., "PD-L1 (B7-H1) and PD-1 pathway blockade for cancer therapy: Mechanisms, response biomarkers, and combinations," Sci. Transl. Med. 2016;8(328):328rv4.

* cited by examiner

MDM2 DEGRADERS AND USES THEREOF

CROSS-REFERENCE TO RELATED APPLICATIONS

This application is a national stage filing under U.S.C. § 371 of PCT International Application PCT/US2021/023233, filed Mar. 19, 2021, which claims the benefit of U.S. Provisional Application No. 62/991,763, filed Mar. 19, 2020 and U.S. Provisional Application No. 63/123,315, filed Dec. 9, 2020, the entirety of each of which is hereby incorporated by reference.

TECHNICAL FIELD OF THE INVENTION

The present invention relates to compounds and methods useful for the modulation of mouse double minute 2 homolog ("MDM2") protein via ubiquitination and/or degradation by compounds according to the present invention. The invention also provides pharmaceutically acceptable compositions comprising compounds of the present invention and methods of using said compositions in the treatment of various disorders.

BACKGROUND OF THE INVENTION

Ubiquitin-Proteasome Pathway (UPP) is a critical pathway that regulates key regulator proteins and degrades misfolded or abnormal proteins. UPP is central to multiple cellular processes, and if defective or imbalanced, it leads to pathogenesis of a variety of diseases. The covalent attachment of ubiquitin to specific protein substrates is achieved through the action of E3 ubiquitin ligases.

There are over 600 E3 ubiquitin ligases which facilitate the ubiquitination of different proteins in vivo, which can be divided into four families: HECT-domain E3s, U-box E3s, monomeric RING E3s and multi-subunit E3s. See generally Li et al. (PLOS One, 2008, 3, 1487) titled "Genome-wide and functional annotation of human E3 ubiquitin ligases identifies MULAN, a mitochondrial E3 that regulates the organelle's dynamics and signaling."; Berndsen et al. (Nat. Struct. Mol. Biol., 2014, 21, 301-307) titled "New insights into ubiquitin E3 ligase mechanism"; Deshaies et al. (Ann. Rev. Biochem., 2009, 78, 399-434) titled "RING domain E3 ubiquitin ligases."; Spratt et al. (Biochem. 2014, 458, 421-437) titled "RBR E3 ubiquitin ligases: new structures, new insights, new questions."; and Wang et al. (Nat. Rev. Cancer., 2014, 14, 233-347) titled "Roles of F-box proteins in cancer."

UPP plays a key role in the degradation of short-lived and regulatory proteins important in a variety of basic cellular processes, including regulation of the cell cycle, modulation of cell surface receptors and ion channels, and antigen presentation. The pathway has been implicated in several forms of malignancy, in the pathogenesis of several genetic diseases (including cystic fibrosis, Angelman's syndrome, and Liddle syndrome), in immune surveillance/viral pathogenesis, and in the pathology of muscle wasting. Many diseases are associated with an abnormal UPP and negatively affect cell cycle and division, the cellular response to stress and to extracellular modulators, morphogenesis of neuronal networks, modulation of cell surface receptors, ion channels, the secretory pathway, DNA repair and biogenesis of organelles.

Aberrations in the process have recently been implicated in the pathogenesis of several diseases, both inherited and acquired. These diseases fall into two major groups: (a) those that result from loss of function with the resultant stabilization of certain proteins, and (b) those that result from gain of function, i.e. abnormal or accelerated degradation of the protein target.

The UPP is used to induce selective protein degradation, including use of fusion proteins to artificially ubiquitinate target proteins and synthetic small-molecule probes to induce proteasome-dependent degradation. Bifunctional compounds composed of a target protein-binding ligand and an E3 ubiquitin ligase ligand, induced proteasome-mediated degradation of selected proteins via their recruitment to E3 ubiquitin ligase and subsequent ubiquitination. These drug-like molecules offer the possibility of temporal control over protein expression. Such compounds are capable of inducing the inactivation of a protein of interest upon addition to cells or administration to an animal or human, and could be useful as biochemical reagents and lead to a new paradigm for the treatment of diseases by removing pathogenic or oncogenic proteins (Crews C, Chemistry & Biology, 2010, 17(6):551-555; Schnnekloth J S Jr., Chembiochem, 2005, 6(1):40-46).

An ongoing need exists in the art for effective treatments for disease, especially hyperplasia and cancer, such as breast cancer. However, non-specific effects, and the inability to target and modulate certain classes of proteins altogether, such as transcription factors, remain as obstacles to the development of effective anti-cancer agents. As such, small molecule therapeutic agents that leverage E3 ligase mediated protein degradation to target cancer-associated proteins such as mouse double minute 2 homolog ("MDM2") hold promise as therapeutic agents. Accordingly, there remains a need to find compounds that are MDM2 degraders useful as therapeutic agents.

SUMMARY OF THE INVENTION

The present application relates novel bifunctional compounds, which function to recruit MDM2 protein to E3 ubiquitin ligase for degradation, and methods of preparation and uses thereof. In particular, the present disclosure provides bifunctional compounds, which find utility as modulators of targeted ubiquitination of MDM2, which is then degraded and/or otherwise inhibited by the bifunctional compounds as described herein. Also provided are monovalent compounds, which find utility as inducers of targeted ubiquitination of MDM2, which are then degraded and/or otherwise inhibited by the monovalent compounds as described herein. An advantage of the compounds provided herein is that a broad range of pharmacological activities is possible, consistent with the degradation/inhibition of MDM2. In addition, the description provides methods of using an effective amount of the compounds as described herein for the treatment or amelioration of a disease condition, such as cancer, e.g., breast cancer.

The present application further relates to targeted degradation of MDM2 protein through the use of bifunctional molecules, including bifunctional molecules that link a cereblon-binding moiety to a ligand that binds MDM2 protein.

It has now been found that compounds of this invention, and pharmaceutically acceptable compositions thereof, are effective as degraders of MDM2 protein. Such compounds have the general formula I:

I

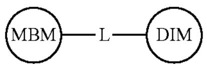

or a pharmaceutically acceptable salt thereof, wherein each variable is as defined and described herein.

Compounds of the present invention, and pharmaceutically acceptable compositions thereof, are useful for treating a variety of diseases, disorders or conditions, associated with regulation of signaling pathways implicating MDM2 protein. Such diseases, disorders, or conditions include those described herein.

Compounds provided by this invention are also useful for the study of MDM2 protein in biological and pathological phenomena; the study of intracellular signal transduction pathways occurring in bodily tissues; and the comparative evaluation of new MDM2 inhibitors or MDM2 degraders or other regulators of cell cycling, metastasis, angiogenesis, and immune cell evasion, in vitro or in vivo.

DETAILED DESCRIPTION OF CERTAIN EMBODIMENTS

1. General Description of Certain Embodiments of the Invention

Compounds of the present invention, and compositions thereof, are useful as degraders and/or inhibitors of MDM2 protein. In some embodiments, a provided compound degrades and/or inhibits MDM2 protein.

In certain embodiments, the present invention provides a compound of formula I:

I

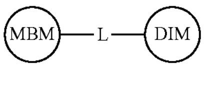

or a pharmaceutically acceptable salt thereof, wherein:

MBM is a MDM2 binding moiety capable of binding MDM2 protein;

L is a bivalent moiety that connects MBM to DIM; and

DIM is a degradation inducing moiety, such as a ligase binding moiety (LBM), lysine mimetic, or hydrogen atom.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic, bicyclic, bridged bicyclic, or spirocyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

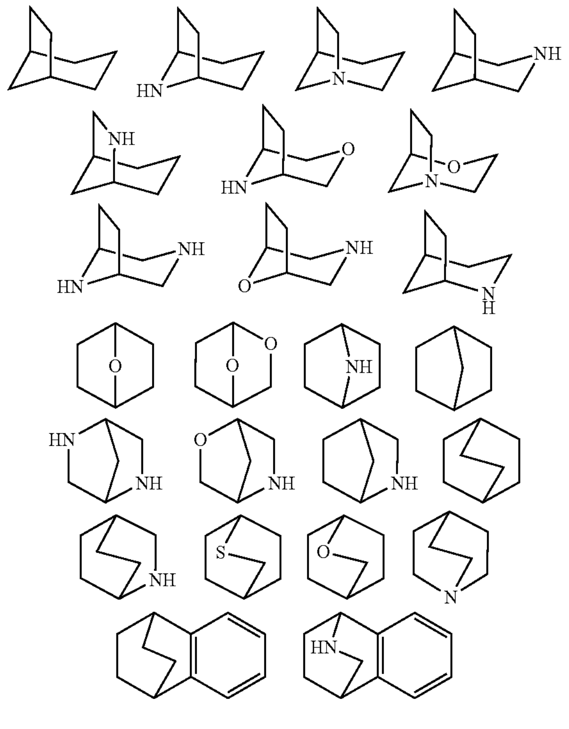

-continued

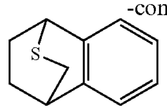 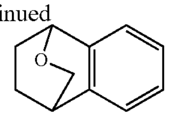

The term “lower alkyl” refers to a $C_{1-4}$ straight or branched alkyl group. Exemplary lower alkyl groups are methyl, ethyl, propyl, isopropyl, butyl, isobutyl, and tert-butyl.

The term “lower haloalkyl” refers to a $C_{1-4}$ straight or branched alkyl group that is substituted with one or more halogen atoms.

The term “heteroatom” means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term “unsaturated,” as used herein, means that a moiety has one or more units of unsaturation.

As used herein, the term “bivalent $C_{1-8}$ (or $C_{1-6}$) saturated or unsaturated, straight or branched, hydrocarbon chain”, refers to bivalent alkylene, alkenylene, and alkynylene chains that are straight or branched as defined herein.

The term “alkylene” refers to a bivalent alkyl group. An “alkylene chain” is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term “alkenylene” refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term “cyclopropylenyl” refers to a bivalent cyclopropyl group of the following structure:

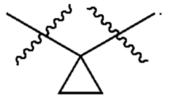 [SMILES: *C1(*)CC1]

The term “halogen” means F, Cl, Br, or I.

The term “aryl” used alone or as part of a larger moiety as in “aralkyl,” “aralkoxy,” or “aryloxyalkyl,” refers to monocyclic or bicyclic ring systems having a total of five to fourteen ring members, wherein at least one ring in the system is aromatic and wherein each ring in the system contains 3 to 7 ring members. The term “aryl” may be used interchangeably with the term “aryl ring.” In certain embodiments of the present invention, “aryl” refers to an aromatic ring system which includes, but not limited to, phenyl, biphenyl, naphthyl, anthracyl and the like, which may bear one or more substituents. Also included within the scope of the term “aryl,” as it is used herein, is a group in which an aromatic ring is fused to one or more non-aromatic rings, such as indanyl, phthalimidyl, naphthimidyl, phenanthridinyl, or tetrahydronaphthyl, and the like.

The terms “heteroaryl” and “heteroar-,” used alone or as part of a larger moiety, e.g., “heteroaralkyl,” or “heteroaralkoxy,” refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term “heteroatom” refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms “heteroaryl” and “heteroar-”, as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. A heteroaryl ring may include one or more oxo (=O) or thioxo (=S) substituent. The term “heteroaryl” may be used interchangeably with the terms “heteroaryl ring,” “heteroaryl group,” or “heteroaromatic,” any of which terms include rings that are optionally substituted. The term “heteroaralkyl” refers to an alkyl group substituted by a heteroaryl, wherein the alkyl and heteroaryl portions independently are optionally substituted.

As used herein, the terms “heterocycle,” “heterocyclyl,” “heterocyclic radical,” and “heterocyclic ring” are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term “nitrogen” includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+NR$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms “heterocycle,” “heterocyclyl,” “heterocyclyl ring,” “heterocyclic group,” “heterocyclic moiety,” and “heterocyclic radical,” are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be monocyclic, bicyclic, bridged bicyclic, or spirocyclic. A heterocyclic ring may include one or more oxo (=O) or thioxo (=S) substituent. The term “heterocyclylalkyl” refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted" means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R^\circ$; —$(CH_2)_{0-4}OR^\circ$; —$O(CH_2)_{0-4}R^\circ$, —O—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —CH═CHPh, which may be substituted with $R^\circ$; —$(CH_2)_{0-4}O(CH_2)_{0-1}$-pyridyl which may be substituted with $R^\circ$; —$NO_2$; —CN; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —$OC(O)(CH_2)_{0-4}SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —$SC(S)SR^\circ$; —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; —$OP(O)(OR^\circ)_2$; $SiR^\circ_3$; —($C_{1-4}$ straight or branched alkylene)O—$N(R^\circ)_2$; or —($C_{1-4}$ straight or branched alkylene)C(O)O—$N(R^\circ)_2$, wherein each $R^\circ$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, —$(CH_2)_{0-2}R^\bullet$, -(halo$R^\bullet$), —$(CH_2)_{0-2}OH$, —$(CH_2)_{0-2}OR^\bullet$, —$(CH_2)_{0-2}CH(OR^\bullet)_2$; —O(halo$R^\bullet$), —CN, —$N_3$, —$(CH_2)_{0-2}C(O)R^\bullet$, —$(CH_2)_{0-2}C(O)OH$, —$(CH_2)_{0-2}C(O)OR^\bullet$, —$(CH_2)_{0-2}SR^\bullet$, —$(CH_2)_{0-2}SH$, —$(CH_2)_{0-2}NH_2$, —$(CH_2)_{0-2}NHR^\bullet$, —$(CH_2)_{0-2}NR^\bullet_2$, —$NO_2$, —$SiR^\bullet_3$, —$OSiR^\bullet_3$, —$C(O)SR^\bullet$, —($C_{1-4}$ straight or branched alkylene)$C(O)OR^\bullet$, or —$SSR^\bullet$ wherein each $R^\bullet$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include ═O and ═S.

Suitable divalent substituents on a saturated carbon atom of an "optionally substituted" group include the following: ═O, ═S, ═$NNR^*_2$, ═$NNHC(O)R^*$, ═$NNHC(O)OR^*$, ═$NNHS(O)_2R^*$, ═$NR^*$, ═$NOR^*$, —$O(C(R^*_2))_{2-3}O$—, or —$S(C(R^*_2))_{2-3}S$—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR^*_2)_{2-3}O$—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, —$R^\bullet$, -(halo$R^\bullet$), —OH, —$OR^\bullet$, —O(halo$R^\bullet$), —CN, —C(O)OH, —$C(O)OR^\bullet$, —$NH_2$, —$NHR^\bullet$, —$NR^\bullet_2$, or —$NO_2$, wherein each $R^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^\dagger$, —$NR^\dagger_2$, —$C(O)R^\dagger$, —$C(O)OR^\dagger$, —$C(O)C(O)R^\dagger$, —$C(O)CH_2C(O)R^\dagger$, —$S(O)_2R^\dagger$, —$S(O)_2NR^\dagger_2$, —$C(S)NR^\dagger_2$, —$C(NH)NR^\dagger_2$, or —$N(R^\dagger)S(O)_2R^\dagger$; wherein each $R^\dagger$ is independently hydrogen, $C_{1-}$_aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, —$R^\bullet$, -(halo$R^\bullet$), —OH, —$OR^\bullet$, —O(halo$R^\bullet$), —CN, —C(O)OH, —$C(O)OR^\bullet$, —$NH_2$, —$NHR^\bullet$, —$NR^\bullet_2$, or —$NO_2$, wherein each $R^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate. In some embodiments, the provided compounds are purified in salt form for convenience and/or ease of purification, e.g., using an acidic or basic mobile phase during chromatography. Salts forms of the provided compounds formed during chromotagraphic purification are contemplated herein and are readily apparent to those having skill in the art.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention As used herein, the term "provided compound" refers to any genus, subgenus, and/or species set forth herein.

As used herein, the term "inhibitor" is defined as a compound that binds to and/or inhibits MDM2 protein with measurable affinity. In certain embodiments, an inhibitor has an $IC_{50}$ and/or binding constant of less than about 50 μM, less than about 1 μM, less than about 500 nM, less than about 100 nM, less than about 10 nM, or less than about 1 nM.

As used herein, the term "degrader" is defined as a heterobifunctional compound that binds to and/or inhibits both MDM2 protein and an E3 ligase with measurable affinity resulting in the ubiquitination and subsequent degradation of the MDM2 protein. In certain embodiments, a degrader has an $DC_{50}$ of less than about 50 μM, less than about 1 μM, less than about 500 nM, less than about 100 nM, less than about 10 nM, or less than about 1 nM. As used herein, the term "monovalent" refers to a degrader compound without an appended E3 ligase binding moiety.

A compound of the present invention may be tethered to a detectable moiety. It will be appreciated that such compounds are useful as imaging agents. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41:2596-9 and Sun et al., Bioconjugate Chem., 2006, 17:52-7.

As used herein, the term "detectable moiety" is used interchangeably with the term "label" and relates to any moiety capable of being detected, e.g., primary labels and secondary labels. Primary labels, such as radioisotopes (e.g., tritium, $^{32}P$, $^{33}P$, $^{35}S$, or $^{14}C$), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360,8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "measurable affinity" and "measurably inhibit," as used herein, means a measurable change in MDM2 protein activity between a sample comprising a compound of the present invention, or composition thereof, and MDM2 protein, and an equivalent sample comprising MDM2 protein, in the absence of said compound, or composition thereof.

3. Description of Exemplary Embodiments

As described above, in certain embodiments, the present invention provides a compound of formula I:

I

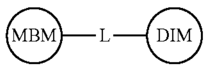

or a pharmaceutically acceptable salt thereof, wherein:

MBM is a MDM2 binding moiety capable of binding MDM2 protein;

L is a bivalent moiety that connects MBM to DIM; and

DIM is a degradation inducing moiety, such as a ligase binding moiety (LBM), lysine mimetic, or hydrogen atom.

MDM2 Binding Moiety (MBM)

In certain embodiments, the present invention provides a compound of Formula I, wherein MBM is a compound of formula I-aaa-1, I-aaa-2, I-aaa-3, I-aaa-4, I-aaa-5, I-aaa-6, I-aaa-7, I-aaa-8, I-aaa-9, I-aaa-10, I-aaa-11, I-aaa-12, I-aaa-13, I-aaa-14, I-aaa-15, I-aaa-16, I-aaa-17, I-aaa-18, I-aaa-19, or I-aaa-20 respectively:

I-aaa-1

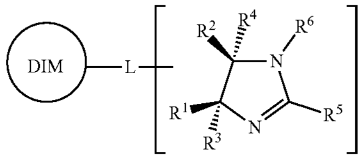

I-aaa-2

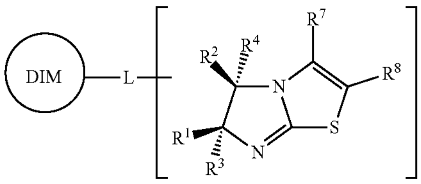

I-aaa-3

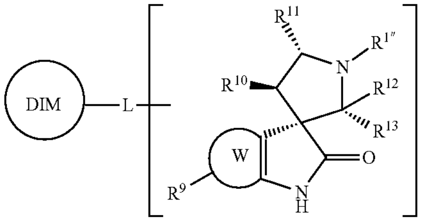

I-aaa-4

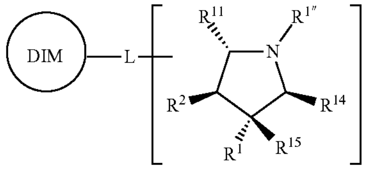

I-aaa-5

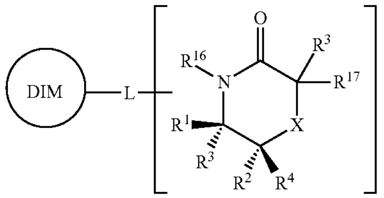

I-aaa-6

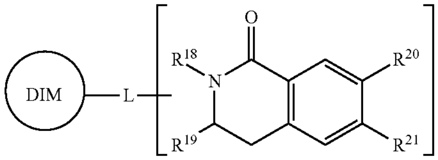

I-aaa-7

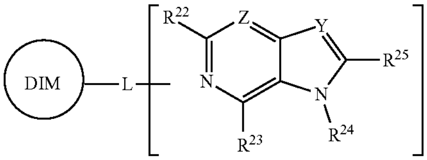

I-aaa-8

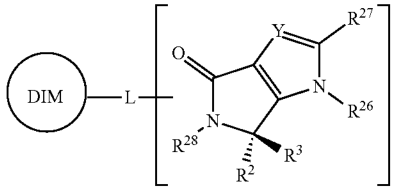

-continued
I-aaa-9
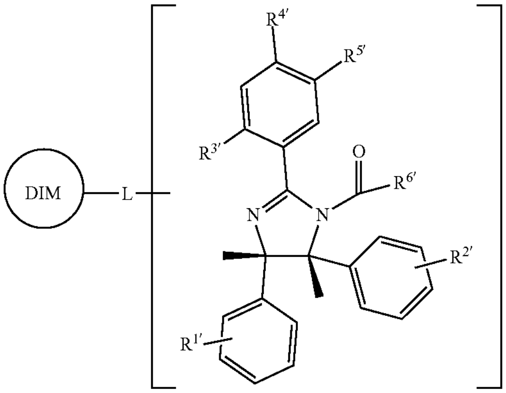
I-aaa-10
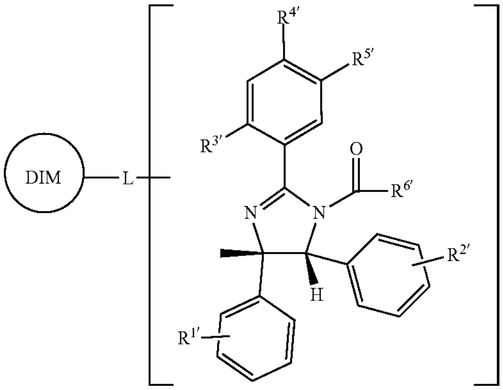
I-aaa-11
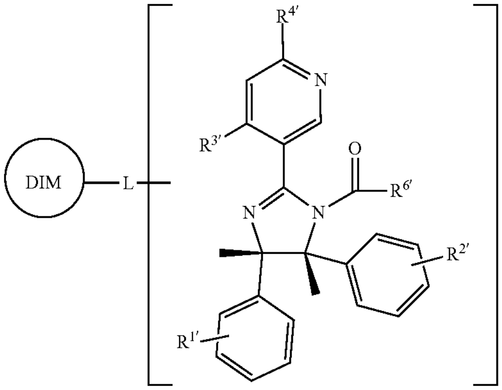
I-aaa-12
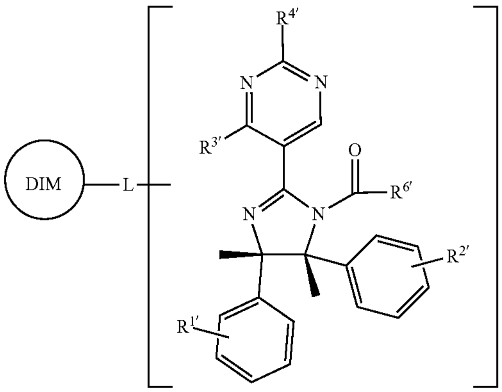
-continued
I-aaa-13
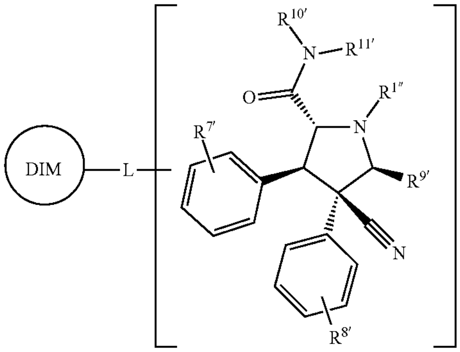
I-aaa-14
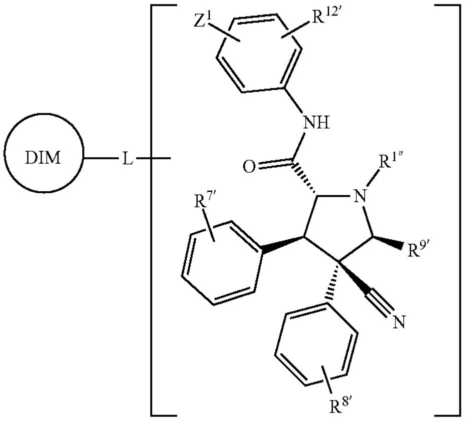
I-aaa-15
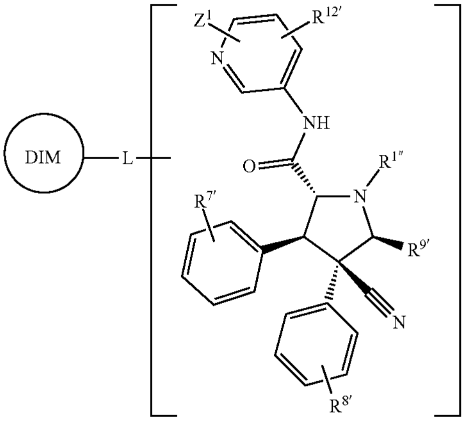
I-aaa-16
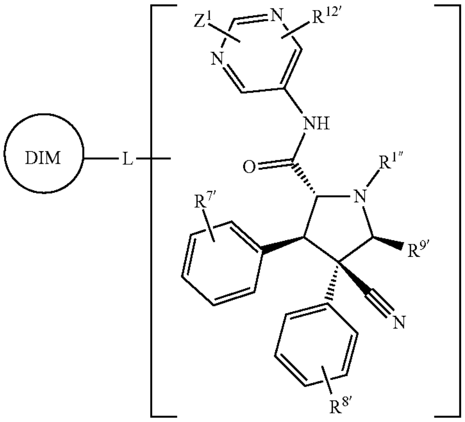

-continued

I-aaa-17

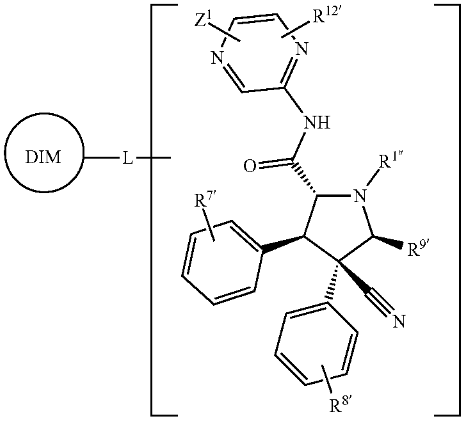

I-aaa-18

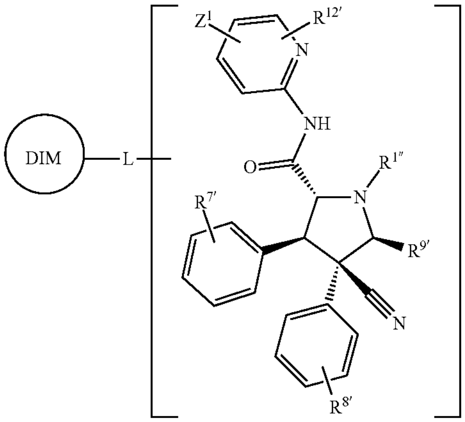

I-aaa-19

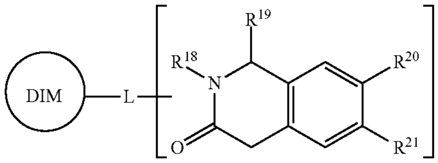

I-aaa-20

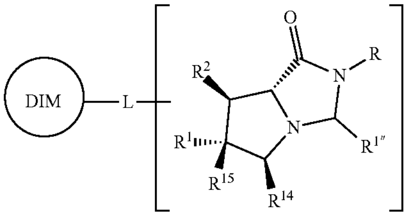

or a pharmaceutically acceptable salt thereof, wherein L and DIM are as defined above and described in embodiments herein, and wherein:

X is selected from —$CR_2$—, —O—, —S—, —S(O)—, —$S(O)_2$—, and —NR—;

each R is independently hydrogen or an optionally substituted group selected from $C_{1-6}$ aliphatic, phenyl, a 4-7 membered saturated or partially unsaturated carbocyclic or heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same atom are optionally taken together with their intervening atoms to form a 4-7 membered saturated, partially unsaturated, or heteroaryl ring having 0-3 heteroatoms, in addition to the atom from which they are attached, independently selected from nitrogen, oxygen, and sulfur.

Y and Z are independently selected from —CR═ and —N═;

Ring W is fused ring selected from benzo and a 5-6 membered heteroaryl with 1-4 heteroatoms independently selected from nitrogen, oxygen or sulfur;

$R^1$ and $R^2$ are independently an optionally substituted monocyclic or bicyclic ring selected from phenyl, a 5-10 membered aryl, and a 5-10 membered heteroaryl containing 1-4 heteroatoms independently selected from nitrogen, oxygen, and sulfur;

$R^3$ and $R^4$ are independently selected from hydrogen and $C_{1-6}$ alkyl;

$R^5$ is selected from an optionally substituted monocyclic or bicyclic ring selected from phenyl, a 5-10 membered aryl, and a 5-10 membered heteroaryl containing 1-4 heteroatoms independently selected from nitrogen, oxygen, and sulfur;

$R^6$ is selected from hydrogen, —C(O)R, —C(O)OR, and —C(O)$NR_2$;

$R^7$ is selected from hydrogen and $R^A$;

each $R^A$ is independently an optionally substituted group selected from $C_{1-6}$ aliphatic, phenyl, a 3-7 membered saturated or partially unsaturated carbocyclic or heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$R^8$ is selected from —C(O)R and $R^A$;

$R^9$ is a mono-, bis-, or tri-substituent on Ring W, wherein each of the substituents are independently selected from halogen and an optionally substituted $C_{1-6}$ aliphatic;

$R^{10}$ is selected from an optionally substituted monocyclic or bicyclic ring selected from phenyl, a 5-10 membered aryl, and a 5-10 membered heteroaryl containing 1-4 heteroatoms independently selected from nitrogen, oxygen, and sulfur;

$R^{11}$ is —C(O)OR or —C(O)$NR_2$;

$R^{12}$ and $R^{13}$ are independently selected from hydrogen and $R^A$, or:

$R^{12}$ and $R^{13}$ are optionally taken together with their intervening atoms to form an optionally substituted 3-8 membered saturated, partially unsaturated, carbocyclic or heterocyclic ring having 1-3 heteroatoms independently selected from nitrogen, oxygen, and sulfur;

$R^{14}$ is $R^A$;

$R^{15}$ is —CN;

$R^{16}$ is selected from $R^A$, —OR, —$(CR_2)_{0-6}$—C(O)R, —$(CR_2)_{0-6}$—C(O)OR, —$(CR_2)_{0-6}$—C(O)$NR_2$, —$(CR_2)_{0-6}$—$S(O)_2R$, —$(CR_2)_{0-6}$—N(R)$S(O)_2R$, —$(CR_2)_{0-6}$—$S(O)_2NR_2$;

$R^{17}$ is selected from —$(CR_2)_{0-6}$—C(O)$NR_2$;

$R^{18}$ and $R^{19}$ are independently selected from hydrogen and $R^A$;

$R^{20}$ and $R^{21}$ are independently selected from hydrogen, $R^A$, halogen, and —OR, or:

$R^{20}$ and $R^{21}$ are optionally taken together with their intervening atoms to form a fused 5-7 membered partially unsaturated carbocyclic or heterocyclic ring having 1-3 heteroatoms independently selected from nitrogen, oxygen, and sulfur, or a fused 5-6 membered heteroaryl ring having 1-3 heteroatoms independently selected from nitrogen, oxygen, and sulfur;

$R^{22}$, $R^{23}$, $R^{25}$, and $R^{27}$ are independently selected from hydrogen, $R^A$, halogen, —C(O)R, —C(O)OR, —C(O)$NR_2$, —$NR_2$, —OR, —S(O)R, —$S(O)_2R$, —$S(O)_2NR_2$;

$R^{24}$, $R^{26}$, and $R^{28}$ are independently selected from hydrogen, $R^A$, —C(O)R, —C(O)OR, —C(O)$NR_2$, —S(O)R, —$S(O)_2R$, and —$S(O)_2NR_2$;

$R^{1'}$ and $R^{2'}$ are independently selected from halogen, —C≡CR, —CN, —$CF_3$, and —$NO_2$;

$R^{3'}$ is —OR;

$R^{4'}$, $R^{5'}$, $R^{6'}$ are independently selected from hydrogen, halogen, $R^A$, —CN, —$CF_3$, —$NR_2$, —OR, —SR, and —$S(O)_2R$;

$R^{7'}$ is a mono-, bis-, or tri-substituent, wherein each of the substituents are independently selected from halogen;

$R^{8'}$ is a mono-, bis-, or tri-substituent, wherein each of the substituents are independently selected from hydrogen, halogen, $R^A$, —CN, —C≡CR, —$NO_2$, and —OR;

$R^{9'}$ is $R^A$;

$Z^1$ is selected from hydrogen, halogen, and —OR;

$R^{10'}$ and $R^{11'}$ are independently selected from hydrogen and $R^A$;

$R^{12'}$ is selected from —C(O)R, —C(O)OR, —C(O)$NR_2$, —OR, —$S(O)_2R$, —$S(O)_2NR_2$, and —S(O)R; and $R^{1''}$ is selected from hydrogen and $R^A$.

As defined herein and described above, wherein a formula is depicted using square brackets, e.g.,

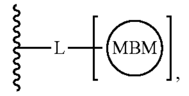

L is attached to a modifiable carbon, oxygen, nitrogen or sulfur atom within MBM including substitution or replacement of a defined group in MBM.

In certain embodiments, the present invention provides a compound of Formula I, wherein MBM is a compound of formula I-bbb-1, I-bbb-2, and I-bbb-3, respectively:

I-bbb-1

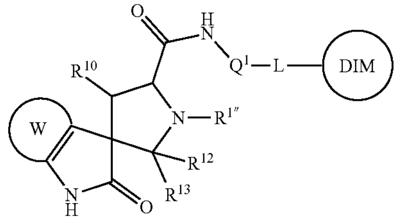

I-bbb-2

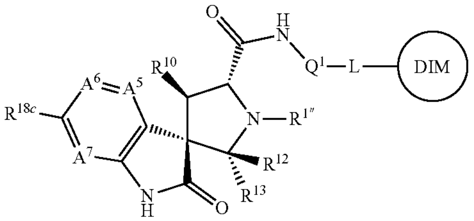

-continued

I-bbb-3

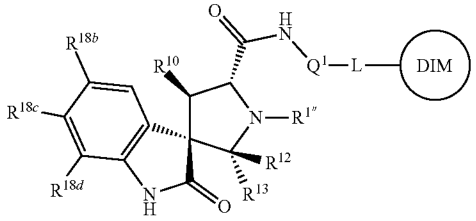

or a pharmaceutically acceptable salt thereof, wherein L and DIM are as defined above and described in embodiments herein, and wherein:

$R^{1''}$ is selected from hydrogen and $R^A$;

each $R^A$ is independently an optionally substituted group selected from $C_{1-6}$ aliphatic, phenyl, a 3-7 membered saturated or partially unsaturated carbocyclic or heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$R^{10}$ is selected from an optionally substituted monocyclic or bicyclic ring selected from phenyl, a 5-10 membered aryl, and a 5-10 membered heteroaryl containing 1-4 heteroatoms independently selected from nitrogen, oxygen, and sulfur;

$R_{12}$ and $R_{13}$ are each independently selected from hydrogen and $R^A$, or:

$R^{12}$ and $R^{13}$ are optionally taken together with their intervening atoms to form an optionally substituted 4-8 membered saturated, partially unsaturated, carbocyclic or heterocyclic ring having 1-3 heteroatoms independently selected from nitrogen, oxygen, and sulfur;

$A^5$ is selected from —C($R^{18a}$)= and —N=;

$A^6$ is selected from —C($R^{18b}$)= and —N=;

$A^7$ is selected from —C($R^{18d}$)= and —N=;

$R^{18a}$, $R^{18b}$, $R^{18}$, and $R^{18d}$ are each independently selected from hydrogen, halogen, $R^A$, and —OR;

each R is independently hydrogen or an optionally substituted group selected from $C_{1-6}$ aliphatic, phenyl, a 4-7 membered saturated or partially unsaturated carbocyclic or heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring W is an optionally substituted fused ring selected from benzo and a 5-6 membered heteroaryl with 1-4 heteroatoms independently selected from nitrogen, oxygen and sulfur; and $Q^1$ is and optionally substituted bivalent group selected from alkylenyl, phenylenyl, heteroarylenyl, cycloalkylenyl, and heterocyclenyl.

As defined above and described herein, X is selected from —$CR_2$—, —O—, —S—, —S(O)—, —$S(O)_2$—, and —NR—.

In some embodiments, X is —$CR_2$—. In some embodiments, X is —O—. In some embodiments, X is —S—. In some embodiments, X is —S(O)—. In some embodiments, X is —$S(O)_2$—. In some embodiments, X is —NR—. In some embodiments, X is —$CH_2$—.

In some embodiments, X is a selected from those depicted in Table 1.

As defined above and described herein, each R is independently hydrogen or an optionally substituted group selected from $C_{1-6}$ aliphatic, phenyl, a 4-7 membered saturated or partially unsaturated carbocyclic or heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur, or two R groups on the same atom are optionally taken together with their intervening atoms to form a 4-7 membered saturated, partially unsaturated, or heteroaryl ring having 0-3 heteroatoms, in addition to the atom from which they are attached, independently selected from nitrogen, oxygen, and sulfur.

In some embodiments, R is hydrogen. In some embodiments, R is an optionally substituted $C_{1-6}$ aliphatic. In some embodiments, R is an optionally substituted phenyl. In some embodiments, R is an optionally substituted 4-7 membered saturated or partially unsaturated carbocyclic or heterocyclic ring having 1-2 heteroatoms independently selected from nitrogen, oxygen, and sulfur. In some embodiments, R is an optionally substituted 5-6 membered heteroaryl ring having 1-4 heteroatoms independently selected from nitrogen, oxygen, and sulfur. In some embodiments, two R groups on the same atom are optionally taken together with their intervening atoms to form a 4-7 membered saturated, partially unsaturated, or heteroaryl ring having 0-3 heteroatoms, in addition to the atom from which they are attached, independently selected from nitrogen, oxygen, and sulfur.

In some embodiments, R is

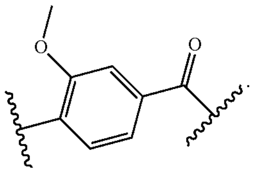 [SMILES: *C(=O)c1ccc(*)c(OC)c1]

In some embodiments, R is

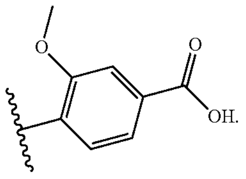 [SMILES: *c1ccc(C(=O)O)cc1OC]

In some embodiments, R is selected from those depicted in Table 1.

As defined above and described herein, Y and Z are independently selected from —CR═ and —N═.

In some embodiments, Y is —CR═. In some embodiments, Y is —N═. In some embodiments, Z is —CR═. In some embodiments, Z is —N═.

In some embodiments, Y and Z are selected from those depicted in Table 1.

As defined above and described herein, Ring W is fused ring selected from benzo and a 5-6 membered heteroaryl with 1-4 heteroatoms independently selected from nitrogen, oxygen or sulfur.

In some embodiments, Ring W is benzo. In some embodiments, Ring W is a 5-6 membered fused heteroaryl ring with 1-4 heteroatoms independently selected from nitrogen, oxygen or sulfur.

In some embodiments, Ring W is selected from those depicted in Table 1.

As defined above and described herein, $R^1$ and $R^2$ are independently an optionally substituted monocyclic or bicyclic ring selected from phenyl, a 5-10 membered aryl, and a 5-10 membered heteroaryl containing 1-4 heteroatoms independently selected from nitrogen, oxygen, and sulfur.

In some embodiments, $R^1$ is an optionally substituted phenyl. In some embodiments, $R^1$ is an optionally substituted 5-10 membered aryl. In some embodiments, $R^1$ is an optionally substituted 5-10 membered heteroaryl containing 1-4 heteroatoms independently selected from nitrogen, oxygen, and sulfur. In some embodiments, $R^1$ is

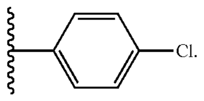 [SMILES: *c1ccc(Cl)cc1]

In some embodiments, $R^1$ is

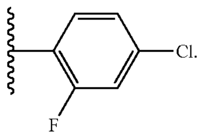 [SMILES: *c1ccc(Cl)cc1F]

In some embodiments, $R^2$ is an optionally substituted phenyl. In some embodiments, $R^1$ is an optionally substituted 5-10 membered aryl. In some embodiments, $R^1$ is an optionally substituted 5-10 membered heteroaryl containing 1-4 heteroatoms independently selected from nitrogen, oxygen, and sulfur. In some embodiments, $R^2$ is

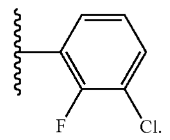 [SMILES: *c1cccc(Cl)c1F]

In some embodiments, $R^2$ is

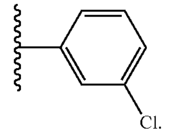 [SMILES: *c1cccc(Cl)c1]

In some embodiments, $R^2$ is

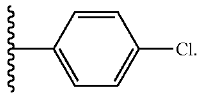 [SMILES: *c1ccc(Cl)cc1]

In some embodiments, $R^1$ and $R^2$ are selected from those depicted in Table 1.

As defined above and described herein, $R^3$ and $R^4$ are independently selected from hydrogen and $C_{1-6}$ alkyl.

In some embodiments, $R^3$ is hydrogen. In some embodiments, $R^3$ is $C_{1-6}$ alkyl. In some embodiments, $R^3$ is methyl.

In some embodiments, $R^4$ is hydrogen. In some embodiments, $R^4$ is $C_{1-6}$ alkyl. In some embodiments, $R^4$ is methyl.

In some embodiments, $R^3$ and $R^4$ are selected from those depicted in Table 1.

As defined above and described herein, $R^5$ is selected from an optionally substituted monocyclic or bicyclic ring selected from phenyl, a 5-10 membered aryl, and a 5-10 membered heteroaryl containing 1-4 heteroatoms independently selected from nitrogen, oxygen, and sulfur.

In some embodiments, $R^5$ is an optionally substituted phenyl. In some embodiments, $R^5$ is an optionally substituted 5-10 membered aryl. In some embodiments, $R^5$ is an optionally substituted 5-10 membered heteroaryl containing 1-4 heteroatoms independently selected from nitrogen, oxygen, and sulfur. In some embodiments, $R^5$ is

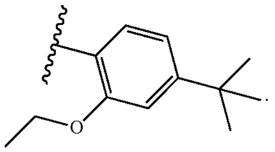 [SMILES: *c1ccc(C(C)(C)C)cc1OCC]

In some embodiments, $R^5$ is selected from those depicted in Table 1.

As defined above and described herein, $R^6$ is selected from hydrogen, —C(O)R, —C(O)OR, and —C(O)$NR_2$.

In some embodiments, $R^6$ is hydrogen. In some embodiments, $R^6$ is —C(O)R. In some embodiments, $R^6$ is —C(O)OR. In some embodiments, $R^6$ is —C(O)$NR_2$. In some embodiments, $R^6$ is

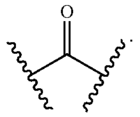 [SMILES: *C(*)=O]

In some embodiments, $R^6$ is selected from those depicted in Table 1.

As defined above and described herein, $R^7$ is selected from hydrogen and $R^A$.

In some embodiments, $R^7$ is hydrogen. In some embodiments, $R^7$ is $R^A$.

In some embodiments, $R^7$ is selected from those depicted in Table 1.

As defined above and described herein, each $R^A$ is independently an optionally substituted group selected from $C_{1-6}$ aliphatic, phenyl, a 3-7 membered saturated or partially unsaturated carbocyclic or heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur.

In some embodiments, $R^A$ is an optionally substituted $C_{1-6}$ aliphatic. In some embodiments, $R^A$ is an optionally substituted phenyl. In some embodiments, $R^A$ is an optionally substituted 3-7 membered saturated or partially unsaturated carbocyclic or heterocyclic ring having 1-2 heteroatoms independently selected from nitrogen, oxygen, and sulfur. In some embodiments, $R^A$ is an optionally substituted 5-6 membered heteroaryl ring having 1-4 heteroatoms independently selected from nitrogen, oxygen, and sulfur.

In some embodiments, $R^A$ is selected from those depicted in Table 1.

As defined above and described herein, $R^8$ is selected from —C(O)R and $R^A$.

In some embodiments, $R^8$ is —C(O)R. In some embodiments, $R^8$ is $R^A$.

In some embodiments, $R^8$ is selected from those depicted in Table 1.

As defined above and described herein, $R^9$ is a mono-, bis-, or tri-substituent on Ring W, wherein each of the substituents are independently selected from halogen and an optionally substituted $C_{1-6}$ aliphatic.

In some embodiments, $R^9$ is a mono-substituent on Ring W. In some embodiments, $R^9$ is a bis-substituent on Ring W. In some embodiments, $R^9$ is a tri-substituent on Ring W. In some embodiments, each $R^9$ is selected from halogen and an optionally substituted $C_{1-6}$ aliphatic. In some embodiments, $R^9$ is chloro.

In some embodiments, $R^9$ is selected from those depicted in Table 1.

As defined above and described herein, $R^{10}$ is selected from an optionally substituted monocyclic or bicyclic ring selected from phenyl, a 5-10 membered aryl, and a 5-10 membered heteroaryl containing 1-4 heteroatoms independently selected from nitrogen, oxygen, and sulfur.

In some embodiments, $R^{10}$ is an optionally substituted phenyl. In some embodiments, $R^{10}$ is an optionally substituted 5-10 membered aryl. In some embodiments, $R^{10}$ is an optionally substituted 5-10 membered heteroaryl containing 1-4 heteroatoms independently selected from nitrogen, oxygen, and sulfur. In some embodiments, $R^{10}$ is

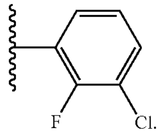 [SMILES: *c1cccc(Cl)c1F]

In some embodiments, $R^{10}$ is

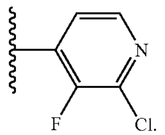 [SMILES: *c1ccnc(Cl)c1F]

In some embodiments, $R^{10}$ is selected from those depicted in Table 1.

As defined above and described herein, $R^{11}$ is —C(O)OR or —C(O)$NR_2$.

In some embodiments, $R^{11}$ is —C(O)$NR_2$. In some embodiments, $R^{11}$ is —C(O)OR. In some embodiments, $R^{11}$ is —C(O)OH. In some embodiments, $R^{11}$ is

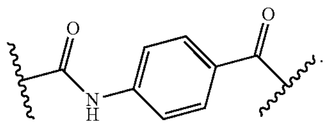 [SMILES: *C(=O)Nc1ccc(C(*)=O)cc1]

In some embodiments, $R^{11}$ is

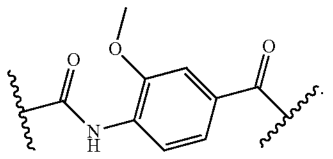 [SMILES: *C(=O)Nc1ccc(C(*)=O)cc1OC]

In some embodiments, $R^{11}$ is

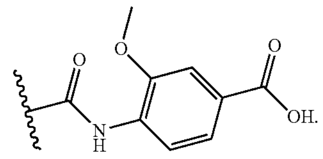 [SMILES: *C(=O)Nc1ccc(C(=O)O)cc1OC]

In some embodiments, $R^{11}$ is

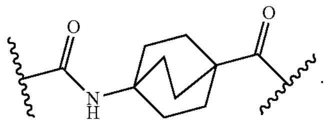 [SMILES: *C(=O)NC12CCC(C(*)=O)(CC1)CC2]

In some embodiments, $R^{11}$ is

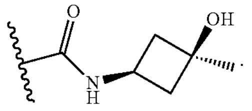 [SMILES: *C(=O)N[C@H]1C[C@@](C)(O)C1]

In some embodiments, $R^{11}$ is selected from those depicted in Table 1.

As defined above and described herein, $R^{12}$ and $R^{13}$ are independently selected from hydrogen and $R^A$, or $R^{12}$ and $R^{13}$ are optionally taken together with their intervening atoms to form an optionally substituted 3-8 membered saturated, partially unsaturated, carbocyclic or heterocyclic ring having 1-3 heteroatoms independently selected from nitrogen, oxygen, and sulfur.

In some embodiments, $R^{12}$ is hydrogen. In some embodiments, $R^{12}$ is $R^A$. In some embodiments, $R^{13}$ is hydrogen. In some embodiments, $R^3$ is $R^A$. In some embodiments, $R^{12}$ and $R^{13}$ are taken together with their intervening atoms to form an optionally substituted 3-8 membered saturated, partially unsaturated, carbocyclic or heterocyclic ring having 1-3 heteroatoms independently selected from nitrogen, oxygen, and sulfur. In some embodiments, $R^{12}$ and $R^{13}$ are taken together to form

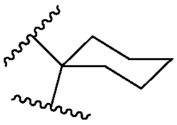 [SMILES: *C1(*)CCCCC1]

In some embodiments, $R^{12}$ and $R^{13}$ are taken together to form

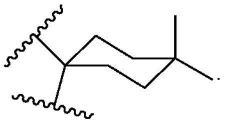 [SMILES: *C1(*)CCC(C)(C)CC1]

In some embodiments, $R^{12}$ and $R^{13}$ are selected from those depicted in Table 1.

As defined above and described herein, $R^{14}$ is $R^A$.

In some embodiments, $R^{14}$ is $R^A$. In some embodiments, $R^{14}$ is

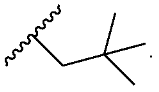 [SMILES: *CC(C)(C)C]

In some embodiments, $R^{14}$ is selected from those depicted in Table 1.

As defined above and described herein, $R^{15}$ is —CN.

In some embodiments, $R^{15}$ is —CN.

In some embodiments, $R^{15}$ is selected from those depicted in Table 1.

As defined above and described herein, $R^{16}$ is selected from $R^A$, —OR, $—(CR_2)_{0-6}—C(O)R$, $—(CR_2)_{0-6}—C(O)OR$, $—(CR_2)_{0-6}—C(O)NR_2$, $—(CR_2)_{0-6}—S(O)_2R$, $—(CR_2)_{0-6}—N(R)S(O)_2R$, $—(CR_2)_{0-6}—S(O)_2NR_2$.

In some embodiments, $R^6$ is $R^A$. In some embodiments, $R^{16}$ is —OR. In some embodiments, $R^{16}$ is $—(CR_2)_{0-6}—C(O)R$. In some embodiments, $R^{16}$ is $—(CR_2)_{0-6}—C(O)OR$. In some embodiments, $R^{16}$ is $—(CR_2)_{0-6}—C(O)NR_2$. In some embodiments, $R^{16}$ is $—(CR_2)_{0-6}—S(O)_2R$. In some embodiments, $R^{16}$ is $—(CR_2)_{0-6}—N(R)S(O)_2R$. In some embodiments, $R^{16}$ is $—(CR_2)_{0-6}—S(O)_2NR_2$. In some embodiments

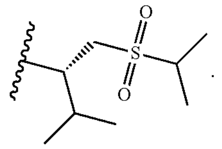 [SMILES: *[C@H](CS(=O)(=O)C(C)C)C(C)C]

In some embodiments, $R^{16}$ is selected from those depicted in Table 1.

As defined above and described herein, $R^{17}$ is selected from $—(CR_2)_{0-6}—C(O)NR_2$.

In some embodiments, $R^{17}$ is $—(CR_2)_{0-6}—C(O)NR_2$. In some embodiments, $R^{17}$ is

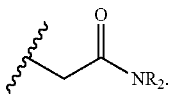

In some embodiments, $R^{17}$ is

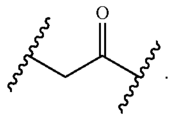 [SMILES: *CC(*)=O]

In some embodiments, $R^{17}$ is selected from those depicted in Table 1.

As defined above and described herein, $R^{18}$ and $R^{19}$ are independently selected from hydrogen and $R^A$.

In some embodiments, $R^{18}$ is hydrogen. In some embodiments, $R^{18}$ is $R^A$. In some embodiments, $R^{18}$ is

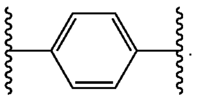

In some embodiments, $R^{19}$ is hydrogen. In some embodiments, $R^{19}$ is $R^A$. In some embodiments, $R^{18}$ is

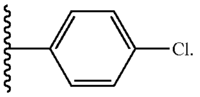 [SMILES: *c1ccc(Cl)cc1]

In some embodiments, $R^{18}$ and $R^{19}$ are selected from those depicted in Table 1.

As defined above and described herein, $R^{20}$ and $R^{21}$ are independently selected from hydrogen, $R^A$, halogen, and —OR, or $R^{20}$ and $R^{21}$ are optionally taken together with their intervening atoms to form a fused 5-7 membered partially unsaturated carbocyclic or heterocyclic ring having 1-3 heteroatoms independently selected from nitrogen, oxygen, and sulfur, or a fused 5-6 membered heteroaryl ring having 1-3 heteroatoms independently selected from nitrogen, oxygen, and sulfur.

In some embodiments, $R^{20}$ is hydrogen. In some embodiments, $R^{20}$ is $R^A$. In some embodiments, $R^{20}$ is halogen. In some embodiments, $R^{20}$ is —OR. In some embodiments, $R^{20}$ is —OMe. In some embodiments, $R^{20}$ is —OiPr. In some embodiments, $R^{21}$ is hydrogen. In some embodiments, $R^{21}$ is $R^A$. In some embodiments, $R^{21}$ is halogen. In some embodiments, $R^{21}$ is —OR. In some embodiments, $R^{21}$ is —OMe. In some embodiments, $R^{21}$ is —OiPr. In some embodiments, $R^{20}$ and $R^{21}$ are taken together with their intervening atoms to form a fused 5-7 membered partially unsaturated carbocyclic or heterocyclic ring having 1-3 heteroatoms independently selected from nitrogen, oxygen, and sulfur, or a fused 5-6 membered heteroaryl ring having 1-3 heteroatoms independently selected from nitrogen, oxygen, and sulfur.

In some embodiments, $R^{20}$ and $R^{21}$ are selected from those depicted in Table 1.

As defined above and described herein, $R^{22}$, $R^{23}$, $R^{25}$, and $R^{27}$ are independently selected from hydrogen, $R^A$, halogen, —C(O)R, —C(O)OR, —C(O)$NR_2$, —$NR_2$, —OR, —S(O)R, —$S(O)_2R$, —$S(O)_2NR_2$.

In some embodiments, one or more of $R^{22}$, $R^{23}$, $R^{25}$, and $R^{27}$ is hydrogen. In some embodiments, one or more of $R^{22}$, $R^{23}$, $R^{25}$, and $R^{27}$ is $R^A$. In some embodiments, one or more of $R^{22}$, $R^{23}$, $R^{25}$, and $R^{27}$ is halogen. In some embodiments, one or more of $R^{22}$, $R^{23}$, $R^{25}$, and $R^{27}$ is —C(O)R. In some embodiments, one or more of $R^{22}$, $R^{23}$, $R^{25}$, and $R^{27}$ is —C(O)OR. In some embodiments, one or more of $R^{22}$, $R^{23}$, $R^{25}$, and $R^{27}$ is —C(O)$NR_2$. In some embodiments, one or more of $R^{22}$, $R^{23}$, $R^{25}$, and $R^{27}$ is —$NR_2$. In some embodiments, one or more of $R^{22}$, $R^{23}$, $R^{25}$, and $R^{27}$ is —OR. In some embodiments, one or more of $R^{22}$, $R^{23}$, $R^{25}$, and $R^{27}$ is —S(O)R. In some embodiments, one or more of $R^{22}$, $R^{23}$, $R^{25}$, and $R^{27}$ is —$S(O)_2R$. In some embodiments, one or more of $R^{22}$, $R^{23}$, $R^{25}$, and $R^{27}$ is —$S(O)_2NR_2$.

In some embodiments, $R^{22}$, $R^{23}$, $R^{25}$, and $R^{27}$ are selected from those depicted in Table 1.

As defined above and described herein, $R^{24}$, $R^{26}$, and $R^{28}$ are independently selected from hydrogen, $R^A$, —C(O)R, —C(O)OR, —C(O)$NR_2$, —S(O)R, —$S(O)_2R$, and —$S(O)_2NR_2$.

In some embodiments, one or more of $R^{24}$, $R^{26}$, and $R^{28}$ is hydrogen. In some embodiments, one or more of $R^{24}$, $R^{26}$ and $R^{28}$ is $R^A$. In some embodiments, one or more of $R^{24}$, $R^{26}$, and $R^{28}$ is $R^A$—C(O)R. In some embodiments, one or more of $R^{24}$, $R^{26}$, and $R^{28}$ is $R^A$. In some embodiments, one or more of $R^{24}$, $R^{26}$ and $R^{28}$ is —C(O)OR. In some embodiments, one or more of $R^{24}$, $R^{26}$ and $R^{28}$ is —C(O)$NR_2$. In some embodiments, one or more of $R^{24}$, $R^{26}$ and $R^{28}$ is —S(O)R. In some embodiments, one or more of $R^{24}$, $R^{26}$ and $R^{28}$ is —$S(O)_2R$. In some embodiments, one or more of $R^{24}$, $R^{26}$, and $R^{28}$ is —$S(O)_2NR_2$.

In some embodiments, $R^{24}$, $R^{26}$, and $R^{28}$ are selected from those depicted in Table 1.

As defined above and described herein, $R^{1'}$ and $R^{2'}$ are independently selected from halogen, —C≡CR, —CN, —$CF_3$, and —$NO_2$.

In some embodiments, $R^{1'}$ is halogen. In some embodiments, $R^{1'}$ is —C≡CR. In some embodiments, $R^{1'}$ is —CN. In some embodiments, $R^{1'}$ is —$CF_3$. In some embodiments, $R^{1'}$ is —$NO_2$. In some embodiments, $R^{1'}$ is chloro. In some embodiments, $R^{2'}$ is halogen. In some embodiments, $R^{2'}$ is —C≡CR. In some embodiments, $R^{2'}$ is —CN. In some embodiments, $R^{2'}$ is —$CF_3$. In some embodiments, $R^{2'}$ is —$NO_2$. In some embodiments, $R^{2'}$ is chloro.

In some embodiments, $R^{1'}$ and $R^{2'}$ are selected from those depicted in Table 1.

As defined above and described herein, $R^{3'}$ is —OR.

In some embodiments, $R^{3'}$ is —OR. In some embodiments, $R^{3'}$ is —OEt.

In some embodiments, $R^{3'}$ selected from those depicted in Table 1.

As defined above and described herein, $R^{4'}$, $R^{5'}$, and $R^{6'}$ are independently selected from hydrogen, halogen, $R^A$, —CN, —$CF_3$, —$NR_2$, —OR, —SR, and —$S(O)_2R$.

In some embodiments, one of more of $R^{4'}$, $R^{5'}$, and $R^{6'}$ is hydrogen. In some embodiments, one of more of $R^{4'}$, $R^{5'}$, and $R^{6'}$ is halogen. In some embodiments, one of more of $R^{4'}$, $R^{5'}$, and $R^{6'}$ is $R^A$. In some embodiments, one of more of $R^{4'}$, $R^{5'}$, and $R^{6'}$ is —CN. In some embodiments, one of more of $R^{4'}$, $R^{5'}$, and $R^{6'}$ is —$CF_3$. In some embodiments, one of more of $R^{4'}$, $R^{5'}$, and $R^{6'}$ is —$NR_2$. In some embodiments, one of more of $R^{4'}$, $R^{5'}$, and $R^{6'}$ is —OR. In some embodiments, one of more of $R^{4'}$, $R^{5'}$, and $R^{6'}$ is —SR. In some embodiments, one of more of $R^{4'}$, $R^{5'}$, and $R^{6'}$ is —$S(O)_2R$. In some embodiments, $R^{4'}$ is tert-butyl.

In some embodiments, $R^{4'}$, $R^{5'}$, and $R^{6'}$ are selected from those depicted in Table 1.

As defined above and described herein, $R^{7'}$ is a mono-, bis-, or tri-substituent, wherein each of the substituents are independently selected from halogen.

In some embodiments, $R^{7'}$ is a mono-substituent. In some embodiments, $R^{7'}$ is a bis-substituent. In some embodiments, $R^{7'}$ is a tri-substituent. In some embodiments, $R^{7'}$ is halogen. In some embodiments, $R^{7'}$ is chloro. In some embodiments, $R^{7'}$ is fluoro.

In some embodiments, $R^{7'}$ is selected from those depicted in Table 1.

As defined above and described herein, $R^{8'}$ is a mono-, bis-, or tri-substituent, wherein each of the substituents are independently selected from hydrogen, halogen, $R^A$, —CN, —C≡CR, —$NO_2$, and —OR.

In some embodiments, $R^{8'}$ is a mono-substituent. In some embodiments, $R^{8'}$ is a bis-substituent. In some embodiments, $R^{8'}$ is a tri-substituent. In some embodiments, $R^{8'}$ is hydrogen. In some embodiments, $R^{8'}$ is halogen. In some embodiments, $R^{8'}$ is $R^A$. In some embodiments, $R^{8'}$ is —CN. In some embodiments, $R^{8'}$ is —C≡CR. In some embodiments, $R^{8'}$ is —$NO_2$. In some embodiments, $R^{8'}$ is —OR. In some embodiments, $R^{8'}$ is chloro. In some embodiments, $R^{8'}$ is fluoro.

In some embodiments, $R^{8'}$ is selected from those depicted in Table 1.

As defined above and described herein, $R^{9'}$ is $R^A$.

In some embodiments, $R^{9'}$ is $R^A$.

In some embodiments, $R^{9'}$ is selected from those depicted in Table 1.

As defined above and described herein, $Z^1$ is selected from hydrogen, halogen, and —OR.

In some embodiments, $Z^1$ is hydrogen. In some embodiments, $Z^1$ is halogen. In some embodiments, $Z^1$ is —OR.

As defined above and described herein, $R^{10'}$ and $R^{11'}$ are independently selected from hydrogen and $R^A$.

In some embodiments, $R^{10'}$ is hydrogen. In some embodiments, $R^{10'}$ is $R^A$. In some embodiments, $R^{11'}$ is hydrogen. In some embodiments, $R^{11'}$ is $R^A$.

In some embodiments, $R^{10'}$ and $R^{11'}$ are selected from those depicted in Table 1.

As defined above and described herein, $R^{12'}$ is selected from —C(O)R, —C(O)OR, —C(O)$NR_2$, —OR, —$S(O)_2R$, —$S(O)_2NR_2$, and —S(O)R.

In some embodiments, $R^{12'}$ is —C(O)R. In some embodiments, $R^{12'}$ is —C(O)OR. In some embodiments, $R^{12'}$ is —C(O)$NR_2$. In some embodiments, $R^{12'}$ is —OR. In some embodiments, $R^{12'}$ is —$S(O)_2R$. In some embodiments, $R^{12'}$ is —$S(O)_2NR_2$. In some embodiments, $R^{12'}$ is —S(O)R.

In some embodiments, $R^{12'}$ is selected from those depicted in Table 1.

As defined above and described herein, $R^{1''}$ is selected from hydrogen and $R^A$.

In some embodiments, $R^{1''}$ is hydrogen. In some embodiments, $R^{1''}$ is $R^A$. In some embodiments, $R^{1''}$ is n-pentyl. In some embodiments, $R^{1''}$ is n-hexyl.

In some embodiments, $R^{1''}$ is selected from those depicted in Table 1.

As defined above and described herein, $A^5$ is selected from —C($R^{18a}$)= and —N=.

In some embodiments, $A^5$ is —C($R^{18a}$)=. In some embodiments, $A^5$ is —N=.

In some embodiments, $A^5$ is selected from those depicted in Table 1.

As defined above and described herein, $A^6$ is selected from —C($R^{18b}$)= and —N=.

In some embodiments, $A^6$ is —C($R^{18b}$)=. In some embodiments, $A^6$ is —N=.

In some embodiments, $A^6$ is selected from those depicted in Table 1.

As defined above and described herein, $A^7$ is selected from —C($R^{18d}$)= and —N=.

In some embodiments, $A^7$ is —C($R^{18d}$)=. In some embodiments, $A^7$ is —N=.

In some embodiments, $A^7$ is selected from those depicted in Table 1.

As defined above and described herein, $R^{18a}$, $R^{18b}$, $R^{18c}$, and $R^{18d}$ are each independently selected from hydrogen, halogen, $R^A$, and —OR.

In some embodiments, one or more of $R^{18a}$, $R^{18b}$, $R^{18c}$, and $R^{18d}$ are hydrogen. In some embodiments, one or more of $R^{18a}$, $R^{18b}$, $R^{18c}$, and $R^{18d}$ are halogen. In some embodiments, one or more of $R^{18a}$, $R^{18b}$, $R^{18c}$, and $R^{18d}$ are $R^A$. In some embodiments, one or more of $R^{18a}$, $R^{18b}$, $R^{18c}$, and $R^{18d}$ are —OR. In some embodiments, $R^{18c}$ is chloro.

In some embodiments, $R^{18a}$, $R^{18b}$, $R^{18c}$, and $R^{18d}$ are selected from those depicted in Table 1.

As defined above and described herein, $Q^1$ is and optionally substituted bivalent group selected from alkylenyl, phenylenyl, heteroarylenyl, cycloalkylenyl, and heterocyclenyl.

In some embodiments, $Q^1$ is an optionally substituted alkylenyl. In some embodiments, $Q^1$ is an optionally substituted phenylenyl. In some embodiments, $Q^1$ is an optionally substituted heteroarylenyl. In some embodiments, $Q^1$ is an optionally substituted cycloalkylenyl. In some embodiments, $Q^1$ is an optionally substituted heterocyclenyl. In some embodiments, $Q^1$ is

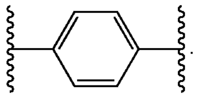

In some embodiments, $Q^1$ is

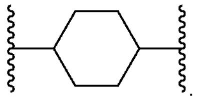 [SMILES: *C1CCC(*)CC1]

In some embodiments, $Q^1$ is

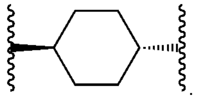 [SMILES: *[C@H]1CC[C@H](*)CC1]

In some embodiments, $Q^1$ is

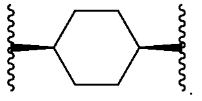 [SMILES: *[C@H]1CC[C@@H](*)CC1]

In some embodiments, $Q^1$ is

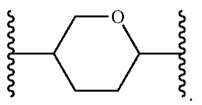

In some embodiments, $Q^1$ is

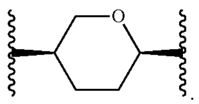 [SMILES: *[C@@H]1CC[C@H](*)OC1]

In some embodiments, $Q^1$ is

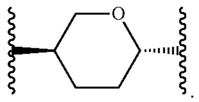

In some embodiments, $Q^1$ is

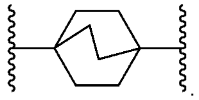

In some embodiments, $Q^1$ is

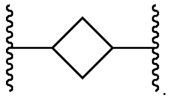 [SMILES: *C1CC(*)C1]

In some embodiments, $Q^1$ is

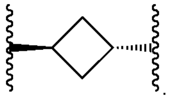 [SMILES: *[C@H]1C[C@H](*)C1]

In some embodiments, $Q^1$ is

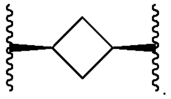 [SMILES: *[C@H]1C[C@@H](*)C1]

In some embodiments, $Q^1$ is selected from those depicted in Table 1.

In some embodiments, MBM is

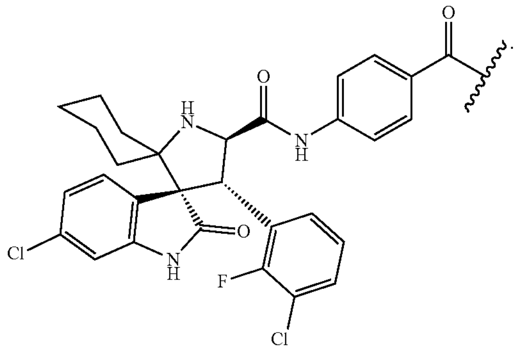 [SMILES: *C(=O)c1ccc(NC(=O)[C@@H]2NC3(CCCCC3)[C@@]3(C(=O)Nc4cc(Cl)ccc43)[C@H]2c2cccc(Cl)c2F)cc1]

In some embodiments, MBM is

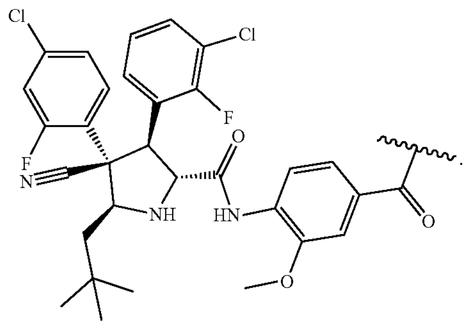 [SMILES: *C(=O)c1ccc(NC(=O)[C@@H]2N[C@@H](CC(C)(C)C)[C@](C#N)(c3ccc(Cl)cc3F)[C@H]2c2cccc(Cl)c2F)c(OC)c1]

In some embodiments, MBM is

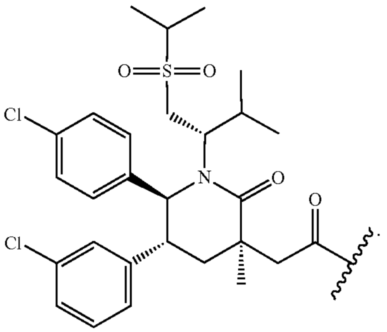 [SMILES: *C(=O)C[C@@]1(C)C[C@H](c2cccc(Cl)c2)[C@@H](c2ccc(Cl)cc2)N([C@H](CS(=O)(=O)C(C)C)C(C)C)C1=O]

In some embodiments, MBM is

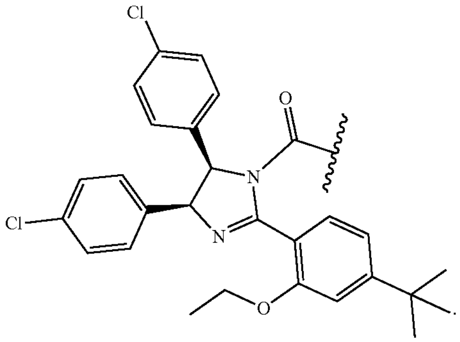 [SMILES: *C(=O)N1C(c2ccc(C(C)(C)C)cc2OCC)=N[C@@H](c2ccc(Cl)cc2)[C@H]1c1ccc(Cl)cc1]

In some embodiments, MBM is

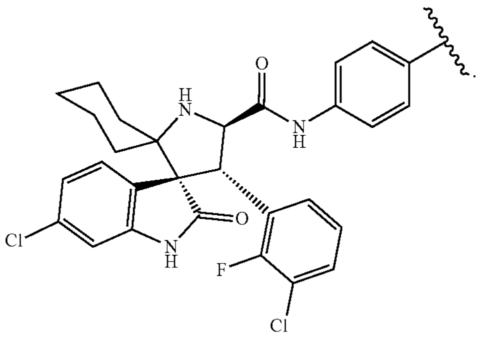 [SMILES: *c1ccc(NC(=O)[C@@H]2NC3(CCCCC3)[C@@]3(C(=O)Nc4cc(Cl)ccc43)[C@H]2c2cccc(Cl)c2F)cc1]

In some embodiments, MBM is
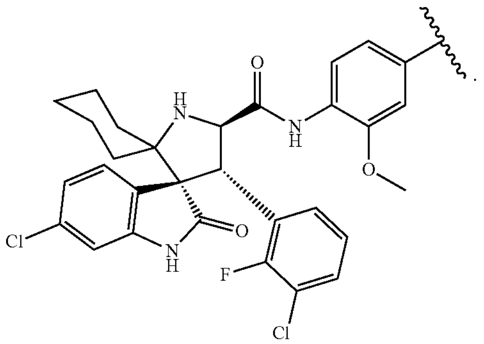 [SMILES: *c1ccc(NC(=O)[C@@H]2NC3(CCCCC3)[C@@]3(C(=O)Nc4cc(Cl)ccc43)[C@H]2c2cccc(Cl)c2F)c(OC)c1]
In some embodiments, MBM is
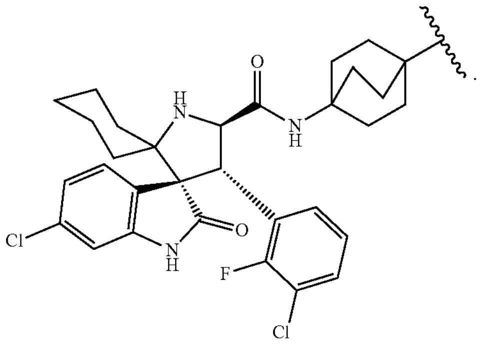 [SMILES: *C12CCC(NC(=O)[C@@H]3NC4(CCCCC4)[C@@]4(C(=O)Nc5cc(Cl)ccc54)[C@H]3c3cccc(Cl)c3F)(CC1)CC2]
In some embodiments, MBM is
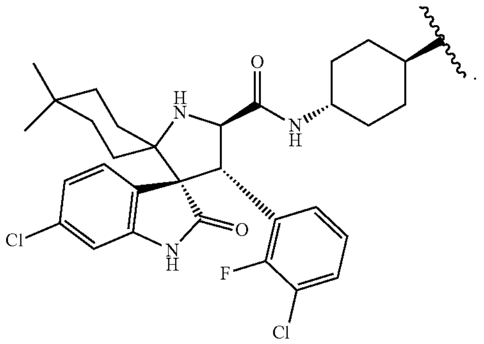 [SMILES: *[C@H]1CC[C@H](NC(=O)[C@@H]2NC3(CCC(C)(C)CC3)[C@@]3(C(=O)Nc4cc(Cl)ccc43)[C@H]2c2cccc(Cl)c2F)CC1]
In some embodiments, MBM is
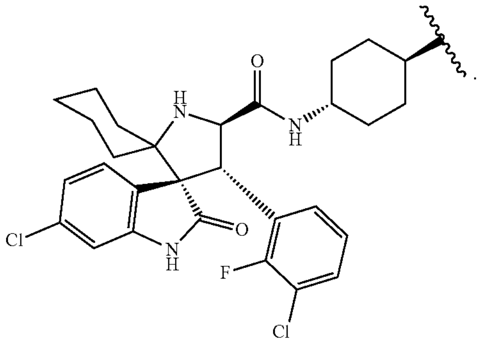 [SMILES: *[C@H]1CC[C@H](NC(=O)[C@@H]2NC3(CCCCC3)[C@@]3(C(=O)Nc4cc(Cl)ccc43)[C@H]2c2cccc(Cl)c2F)CC1]
In some embodiments, MBM is
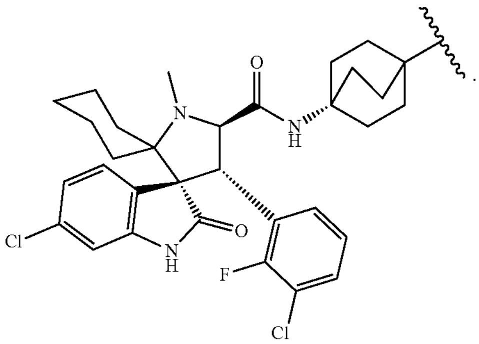
In some embodiments, MBM is
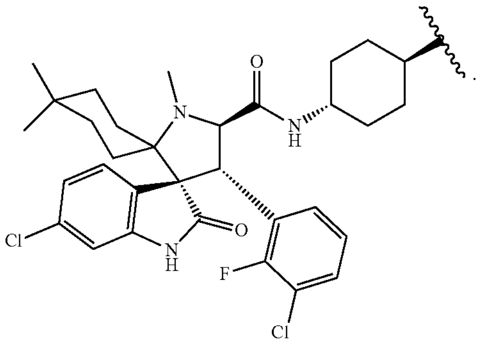 [SMILES: *[C@H]1CC[C@H](NC(=O)[C@H]2[C@H](c3cccc(Cl)c3F)[C@]3(C(=O)Nc4cc(Cl)ccc43)C3(CCC(C)(C)CC3)N2C)CC1]
In some embodiments, MBM is
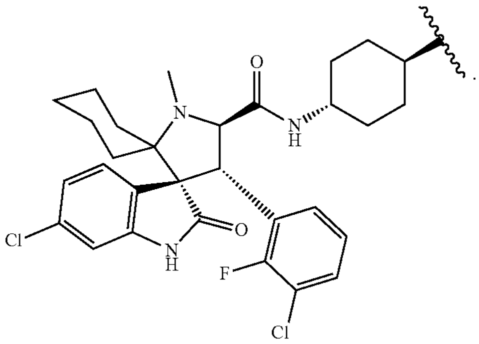 [SMILES: *[C@H]1CC[C@H](NC(=O)[C@H]2[C@H](c3cccc(Cl)c3F)[C@]3(C(=O)Nc4cc(Cl)ccc43)C3(CCCCC3)N2C)CC1]
In some embodiments, MBM is
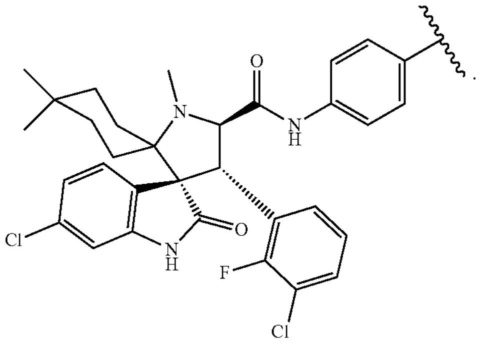 [SMILES: *c1ccc(NC(=O)[C@H]2[C@H](c3cccc(Cl)c3F)[C@]3(C(=O)Nc4cc(Cl)ccc43)C3(CCC(C)(C)CC3)N2C)cc1]

In some embodiments, MBM is
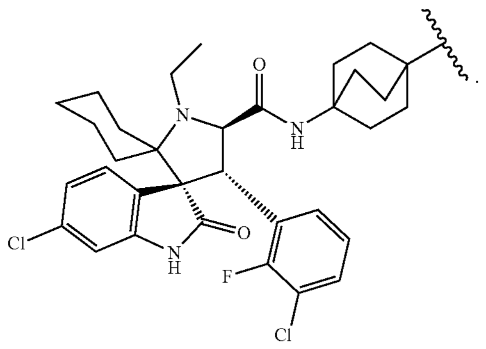 [SMILES: *C12CCC(NC(=O)[C@H]3[C@H](c4cccc(Cl)c4F)[C@]4(C(=O)Nc5cc(Cl)ccc54)C4(CCCCC4)N3CC)(CC1)CC2]
In some embodiments, MBM is
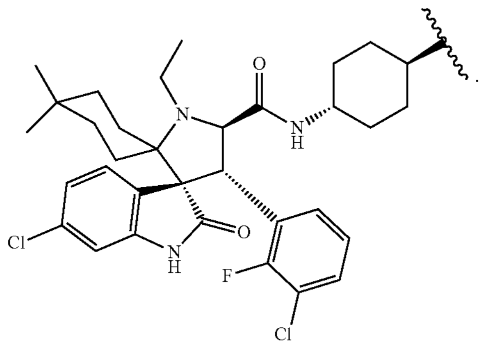 [SMILES: *[C@H]1CC[C@H](NC(=O)[C@H]2[C@H](c3cccc(Cl)c3F)[C@]3(C(=O)Nc4cc(Cl)ccc43)C3(CCC(C)(C)CC3)N2CC)CC1]
In some embodiments, MBM is
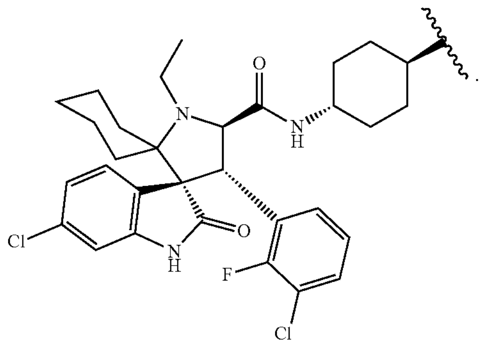 [SMILES: *[C@H]1CC[C@H](NC(=O)[C@H]2[C@H](c3cccc(Cl)c3F)[C@]3(C(=O)Nc4cc(Cl)ccc43)C3(CCCCC3)N2CC)CC1]
In some embodiments, MBM is
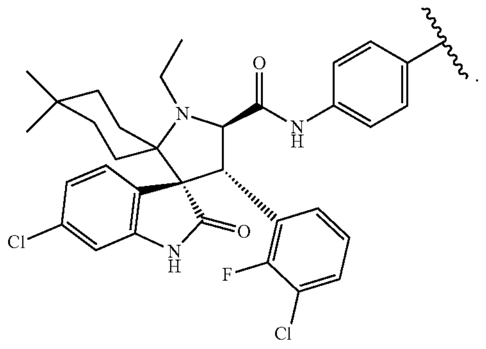 [SMILES: *c1ccc(NC(=O)[C@H]2[C@H](c3cccc(Cl)c3F)[C@]3(C(=O)Nc4cc(Cl)ccc43)C3(CCC(C)(C)CC3)N2CC)cc1]
In some embodiments, MBM is
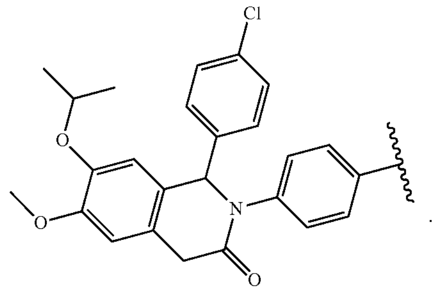 [SMILES: *c1ccc(N2C(=O)Cc3cc(OC)c(OC(C)C)cc3C2c2ccc(Cl)cc2)cc1]
In some embodiments, MBM is
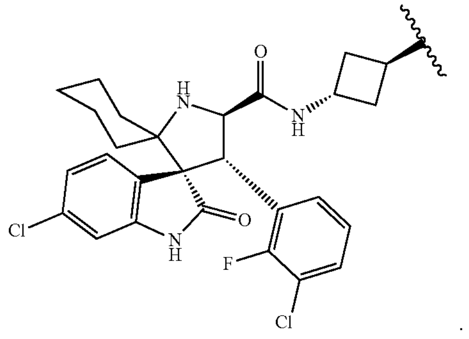 [SMILES: *[C@H]1C[C@H](NC(=O)[C@@H]2NC3(CCCCC3)[C@@]3(C(=O)Nc4cc(Cl)ccc43)[C@H]2c2cccc(Cl)c2F)C1]
In some embodiments, MBM is
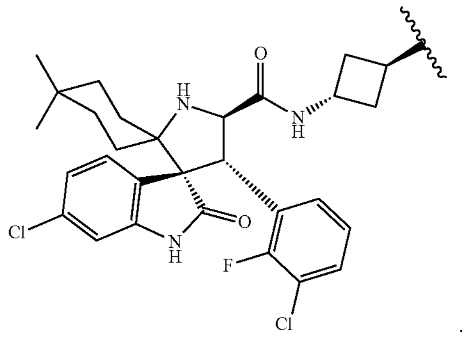 [SMILES: *[C@H]1C[C@H](NC(=O)[C@@H]2NC3(CCC(C)(C)CC3)[C@@]3(C(=O)Nc4cc(Cl)ccc43)[C@H]2c2cccc(Cl)c2F)C1]
In some embodiments, MBM is
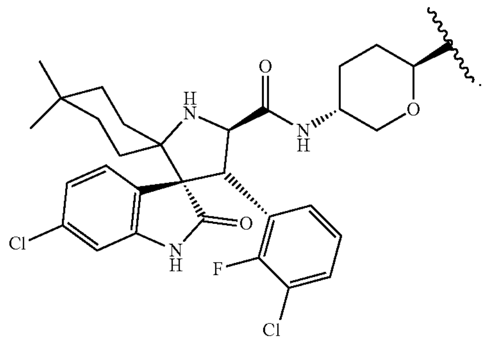

In some embodiments MBM is
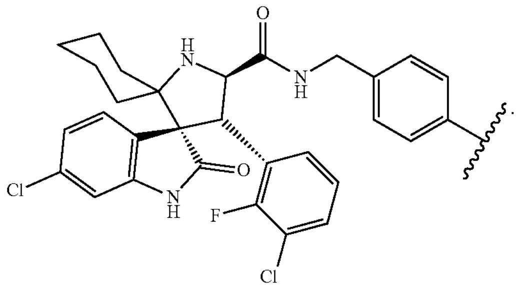
In some embodiments, MBM is
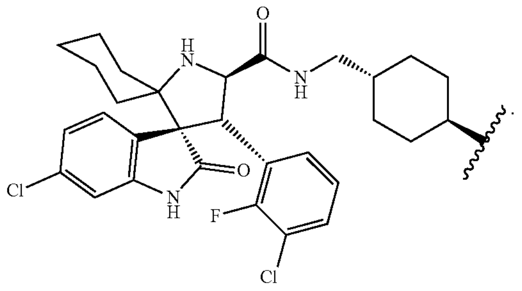
In some embodiments, MBM is
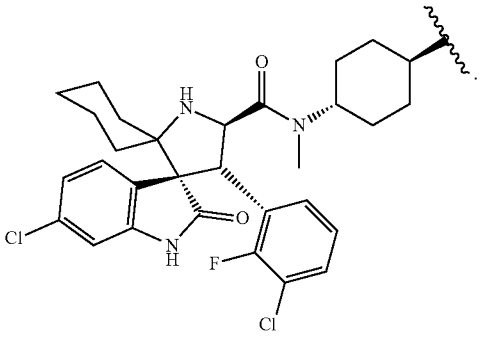
In some embodiments, MBM is
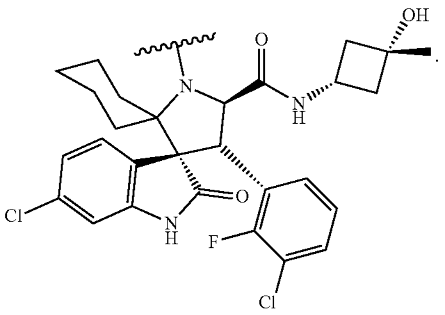
In some embodiments, MBM is
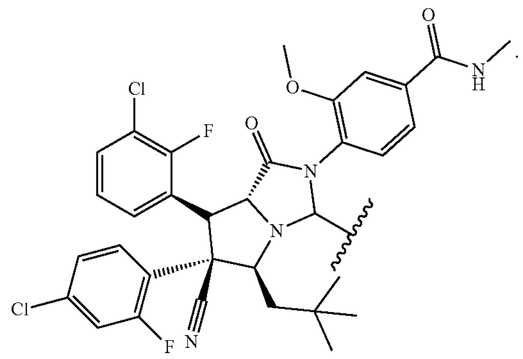
In some embodiments, MBM is
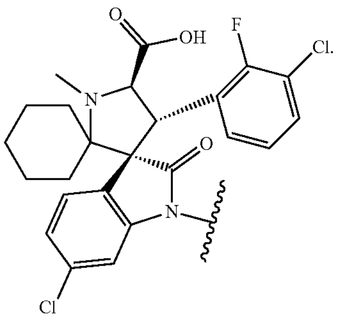 [SMILES: *N1C(=O)[C@@]2(c3ccc(Cl)cc31)[C@@H](c1cccc(Cl)c1F)[C@H](C(=O)O)N(C)C21CCCCC1]
In some embodiments, MBM is
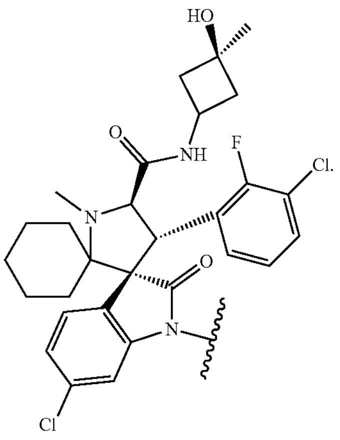

In some embodiments, MBM is

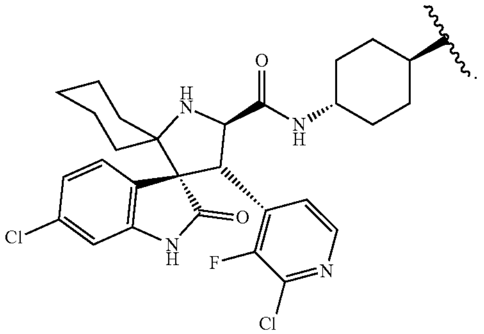

In some embodiments, MBM is

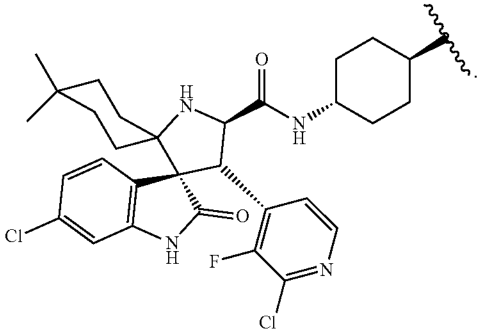

In some embodiments, MBM is

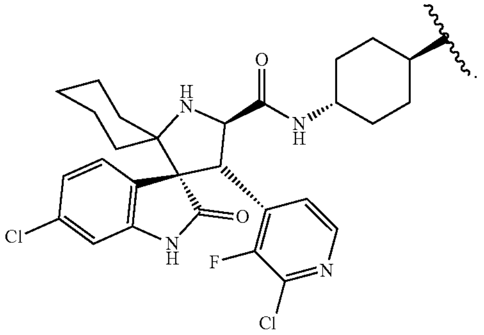

In some embodiments, MBM is

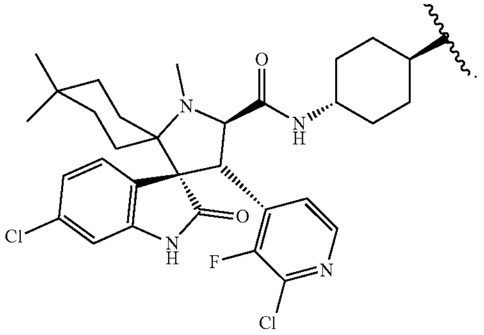

In some embodiments, MBM is

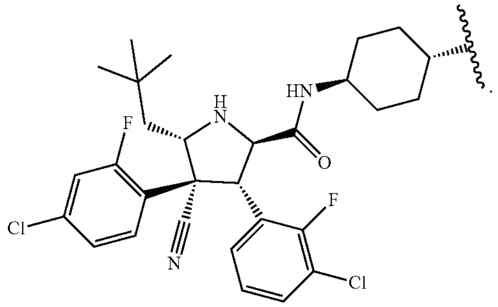 [SMILES: *[C@H]1CC[C@H](NC(=O)[C@@H]2N[C@@H](CC(C)(C)C)[C@](C#N)(c3ccc(Cl)cc3F)[C@H]2c2cccc(Cl)c2F)CC1]

In some embodiments, MBM is

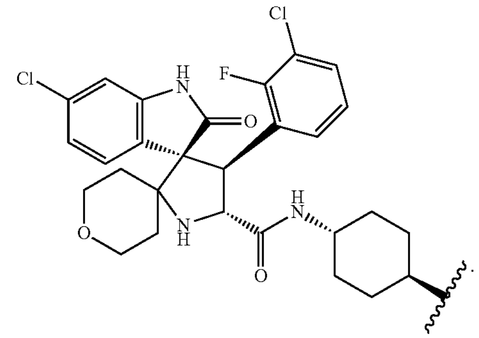 [SMILES: *[C@H]1CC[C@H](NC(=O)[C@@H]2NC3(CCOCC3)[C@@]3(C(=O)Nc4cc(Cl)ccc43)[C@H]2c2cccc(Cl)c2F)CC1]

In some embodiments, MBM is

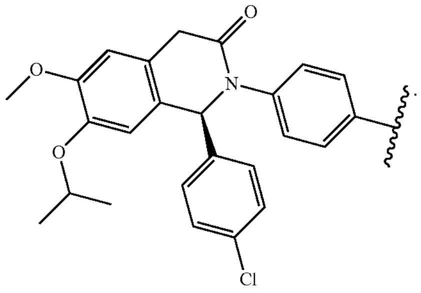 [SMILES: *c1ccc(N2C(=O)Cc3cc(OC)c(OC(C)C)cc3[C@@H]2c2ccc(Cl)cc2)cc1]

Ligase Binding Moiety (LBM)

In some embodiments, LBM is an E3 ligase ligand.

As defined herein and described below, wherein a formula is depicted using square brackets, e.g.,

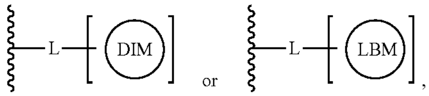

L is attached to a modifiable carbon, oxygen, nitrogen or sulfur atom within DIM or LBM including substitution or replacement of a defined group in DIM or LBM.

In certain embodiments, the present invention provides a compound of formula I, wherein LBM is an E3 ubiquitin ligase (cereblon) binding moiety thereby forming a compound of formula I-a:

I-a

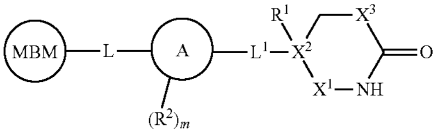

or a pharmaceutically acceptable salt thereof, wherein L and MBM are as defined above and described herein, and wherein:

$X^1$ is a bivalent moiety selected from a covalent bond, —$CH_2$—, —$CHCF_3$—, —$SO_2$—, —S(O)—, —P(O)R—, —P(O)OR—, —P(O)$NR_2$—, —C(O)—, —C(S)—, or

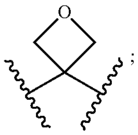 [SMILES: *C1(*)COC1]

;

$X^2$ is a carbon atom or silicon atom;

$X^3$ is a bivalent moiety selected from —$CR_2$—, —NR—, —O—, —S—, or —Si($R^2$)—;

$R^1$ is hydrogen, deuterium, halogen, —CN, —OR, —SR, —S(O)R, —$S(O)_2R$, —$N(R)_2$, —$P(O)(OR)_2$, —P(O)($NR_2$)OR, —$P(O)(NR_2)_2$, —$Si(OH)_2R$, —$Si(OH)(R)_2$, —$Si(R)_3$, or an optionally substituted $C_{1-4}$ aliphatic;

each $R^2$ is independently hydrogen, deuterium, —$R^6$, halogen, —CN, —$NO_2$, —OR, —SR, —$N(R)_2$, —$Si(R)_3$, —$S(O)_2R$, —$S(O)_2N(R)_2$, —S(O)R, —C(O)R, —C(O)OR, —C(O)$N(R)_2$, —C(O)N(R)OR, —$C(R)_2$N(R)C(O)R, —$C(R)_2$N(R)C(O)$N(R)_2$, —OC(O)R, —OC(O)$N(R)_2$, —OP(O)$R_2$, —OP(O)$(OR)_2$, —OP(O)(OR)($NR_2$), —OP(O)$(NR_2)_2$—, —N(R)C(O)OR, —N(R)C(O)R, —N(R)C(O)$N(R)_2$, —N(R)$S(O)_2R$, —NP(O)$R_2$, —N(R)P(O)$(OR)_2$, —N(R)P(O)(OR)($NR_2$), —N(R)P(O)$(NR_2)_2$, or —N(R)$S(O)_2R$;

Ring A is a bi- or tricyclic ring selected from

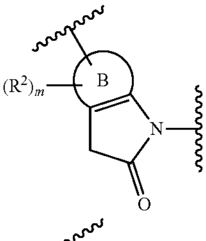

,

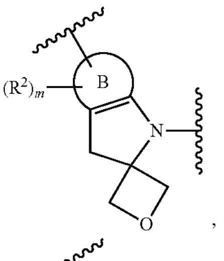

,

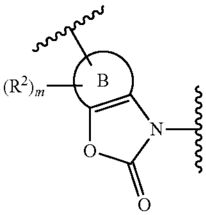

,

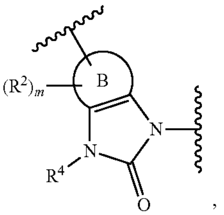

,

-continued

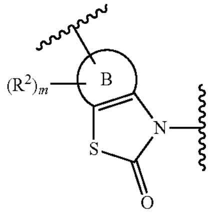

,

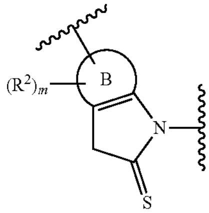

,

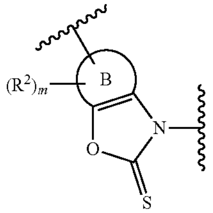

,

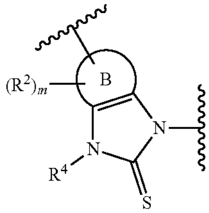

,

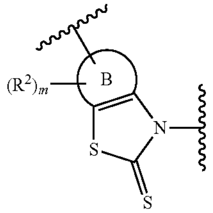

,

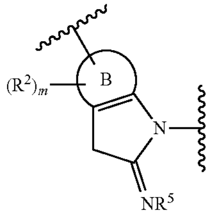

,

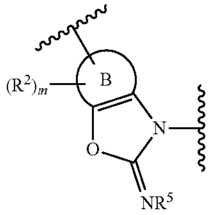

,

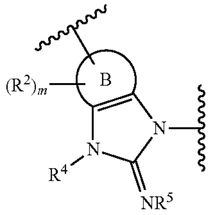

,

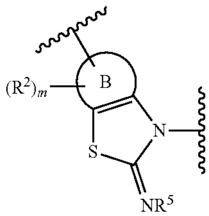

,

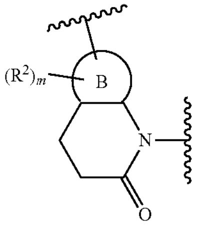

,

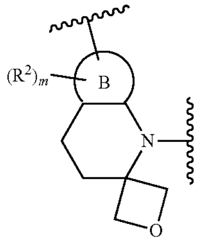

,

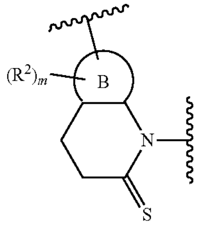

,

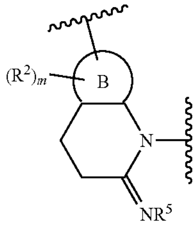

,

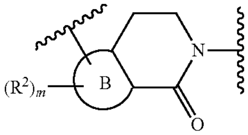

,

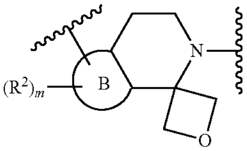

,

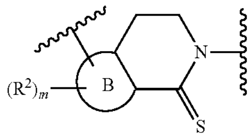

,

-continued
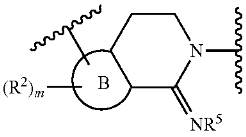
,
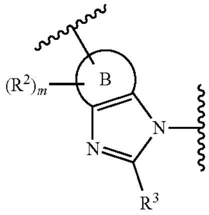
,
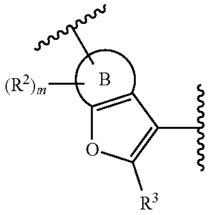
,
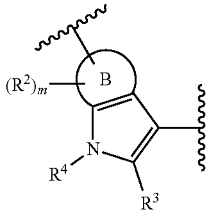
,
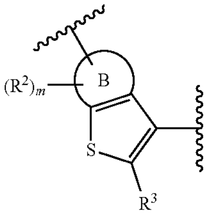
,
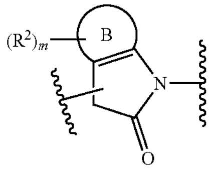
,
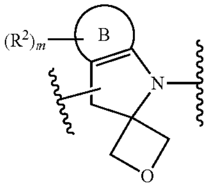
,
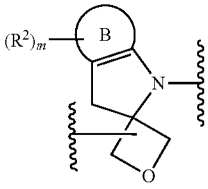
,
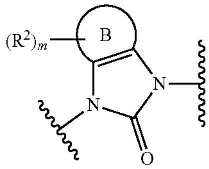
,
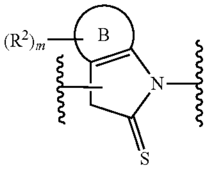
,
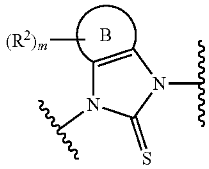
,
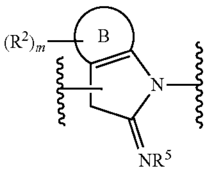
,
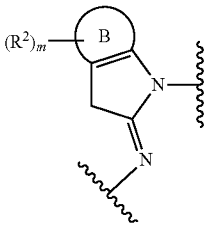
,
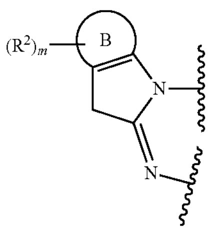
,
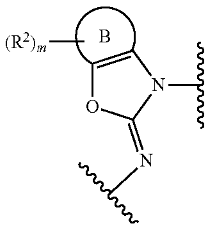
,
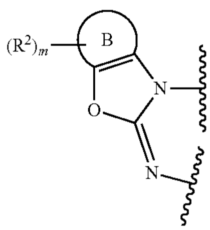
,
-continued
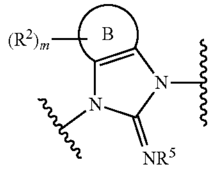
,
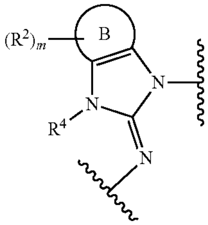
,
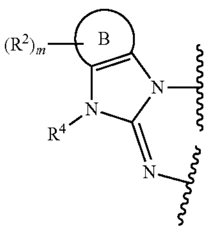
,
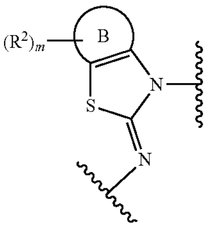
,
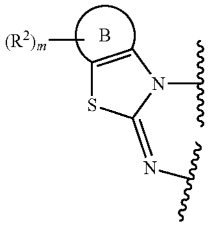
,
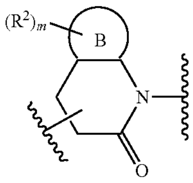
,
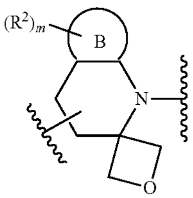
,
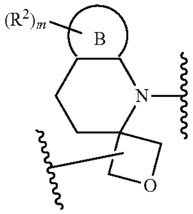
,
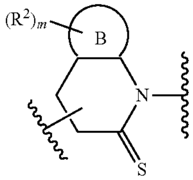
,
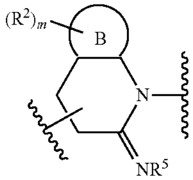
,
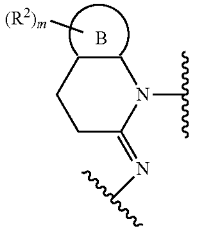
,
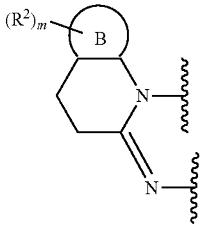
,
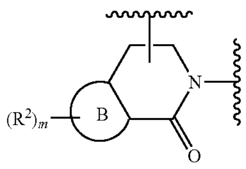
,
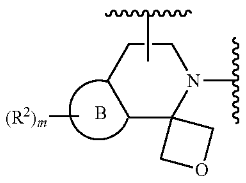
,
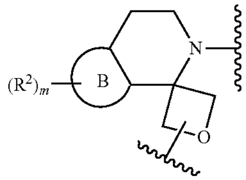
,
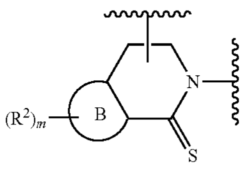
, -continued

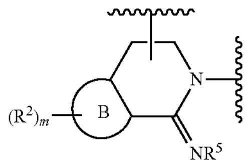
,
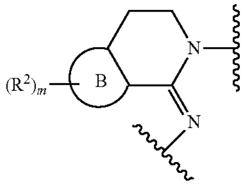
,
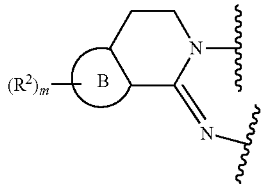
,
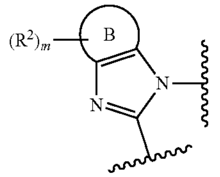
,
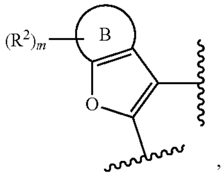
,
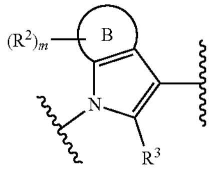
,
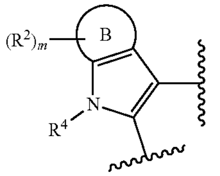
, or
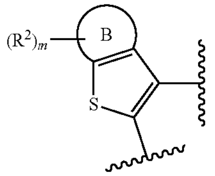
, wherein Ring B is a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

$R^3$ is selected from hydrogen, halogen, —OR, —$N(R)_2$, or —SR;

each $R^4$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —N(R)C(O)OR, —N(R)C(O)R, —$N(R)C(O)NR_2$, or —$N(R)S(O)_2R$;

$R^5$ is hydrogen, $C_{1-4}$ aliphatic, or —CN;

each $R^6$ is independently an optionally substituted group selected from $C_{1-6}$ aliphatic, phenyl, a 3-7 membered saturated or partially unsaturated carbocyclic or heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —$C(R)_2$—, —CH(R)—, —$C(F)_2$—, —N(R)—, —$S(O)_2$— or —(C)═CH—;

m is 0, 1, 2, 3 or 4;

each $R^6$ is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

Where a point of attachment of —$(R^2)_m$ is depicted on Ring B, it is intended, and one of ordinary skill in the art would appreciate, that the point of attachment of —$(R^2)_m$ may be on Ring A and may also be at any available carbon or nitrogen atom on Ring A including the ring to which Ring B is fused. Where —$R^2$ is attached to a nitrogen atom bound to $R^4$ or R, $R^4$ or $R^5$ is absent and —$R^2$ takes the place of the $R^4$ or $R^5$ group. Where —$R^2$ is attached to a carbon atom bound to $R^3$, $R^3$ is absent and —$R^2$ takes the place of the $R^3$ group.

In some embodiments, a compound of formula I-a above is provided as a compound of formula I-a' or formula I-a":

I-a'

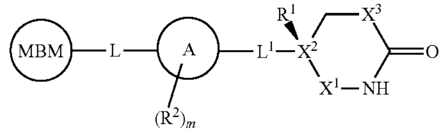

I-a"

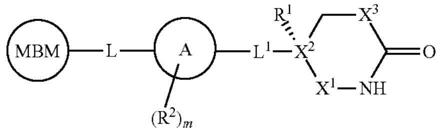

or a pharmaceutically acceptable salt thereof, wherein:

each of MBM, Ring A, L, $L^1$, $R^1$, $R^2$, $X^1$, $X^2$, $X^3$, and m is as defined above.

In certain embodiments, the present invention provides a compound of Formula I, wherein LBM is an E3 ubiquitin ligase (cereblon) binding moiety thereby forming a compound of formula I-b:

I-b

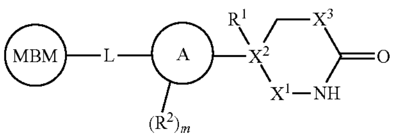

or a pharmaceutically acceptable salt thereof, wherein L and MBM are as defined above and described in embodiments herein, and wherein:

$X^1$ is a bivalent moiety selected from a covalent bond, —$CH_2$—, —$CHCF_3$—, —$SO_2$—, —S(O)—, —P(O)R—, —P(O)OR—, —$P(O)NR_2$—, —C(O)—, —C(S)—, or

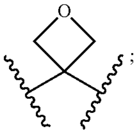 [SMILES: *C1(*)COC1];

$X^2$ is a carbon atom or silicon atom;

$X^3$ is a bivalent moiety selected from —$CR_2$—, —NR—, —O—, —S—, or —$Si(R_2)$—;

$R^1$ is hydrogen, deuterium, halogen, —CN, —OR, —SR, —S(O)R, —$S(O)_2R$, —$N(R)_2$, —$P(O)(OR)_2$, —$P(O)(NR_2)OR$, —$P(O)(NR_2)_2$, —$Si(OH)_2R$, —$Si(OH)(R)_2$, —$Si(R)_3$, or an optionally substituted $C_{1-4}$ aliphatic;

each $R^2$ is independently hydrogen, deuterium, —R, halogen, —CN, —$NO_2$, —OR, —SR, —$N(R)_2$, —$Si(R)_3$, —$S(O)_2R$, —$S(O)_2N(R)_2$, —S(O)R, —C(O)R, —C(O)OR, —$C(O)N(R)_2$, —C(O)N(R)OR, —$C(R)_2N(R)C(O)R$, —$C(R)_2N(R)C(O)N(R)_2$, —OC(O)R, —$OC(O)N(R)_2$, —$OP(O)R_2$, —$OP(O)(OR)_2$, —$OP(O)(OR)(NR_2)$, —$OP(O)(NR_2)_2$—, —N(R)C(O)OR, —N(R)C(O)R, —$N(R)C(O)N(R)_2$, —$N(R)S(O)_2R$, —$NP(O)R_2$, —$N(R)P(O)(OR)_2$, —$N(R)P(O)(OR)(NR_2)$, —$N(R)P(O)(NR_2)_2$, or —$N(R)S(O)_2R$; $(R^2)_m$ B Ring A is a bi- or tricyclic ring selected from

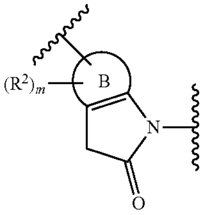

wherein Ring B is other than imidazo or benzo,

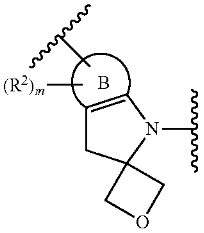,

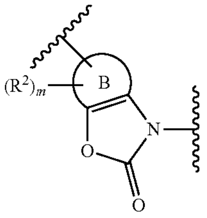

wherein Ring B is other than benzo,

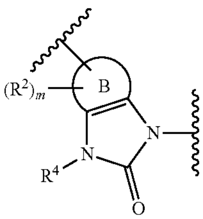

wherein Ring B is other than benzo,

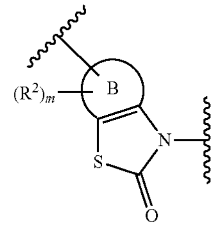,

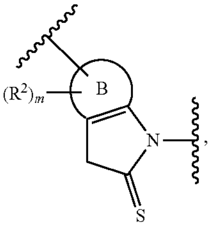,

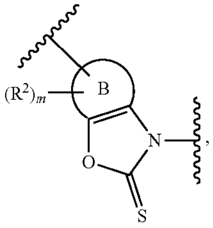,

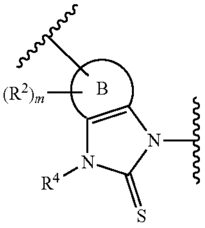,

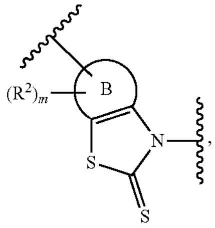,

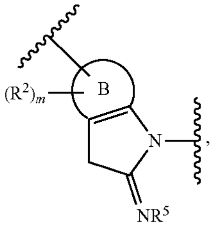,

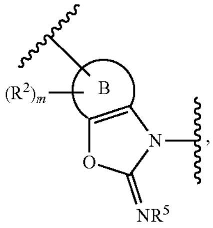,

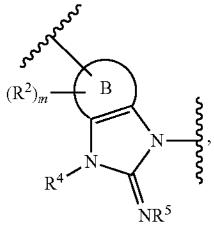,

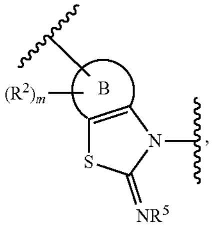,

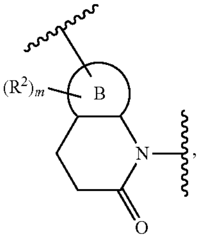,

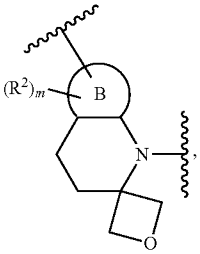,

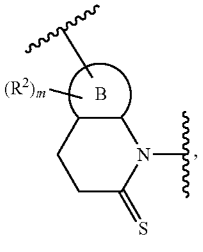,

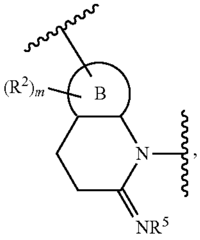,

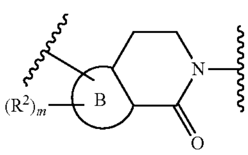

wherein Ring B is other than benzo,

-continued
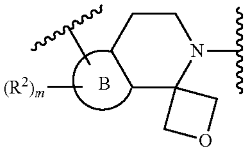
,
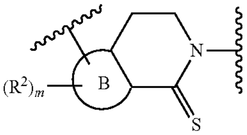
,
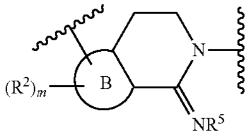
,
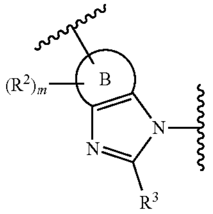
,
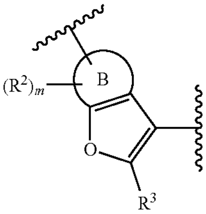
,
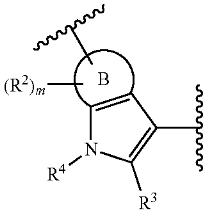
,
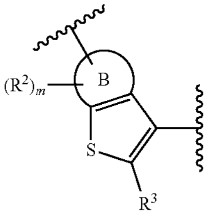
,
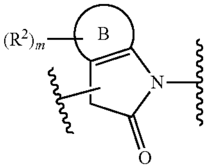
,
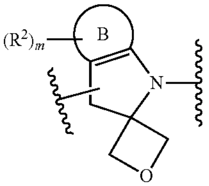
,
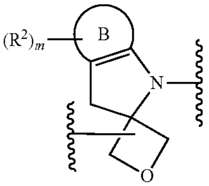
,
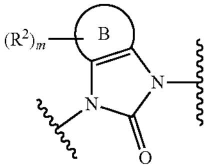
,
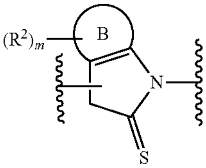
,
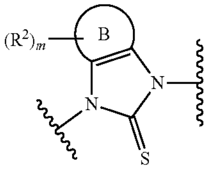
,
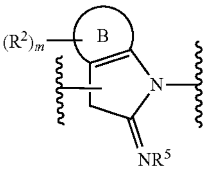
,
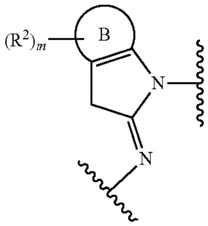
,
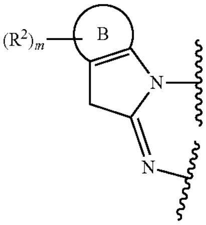
,
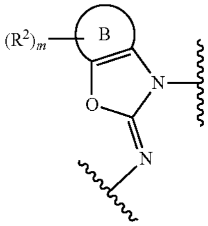
,
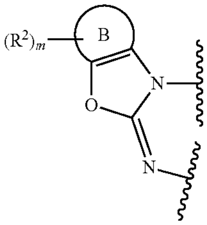
,
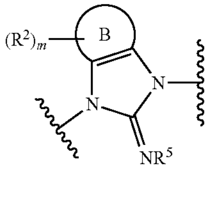
,
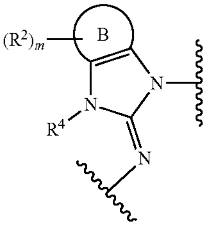
,
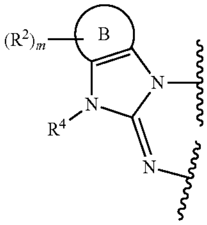
,
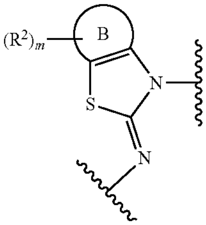
,
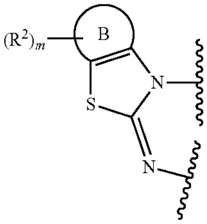
,
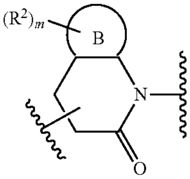
,
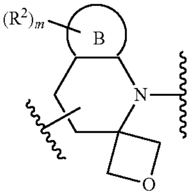
,
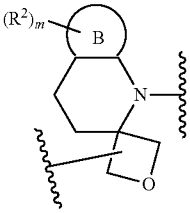
,
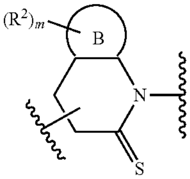
,
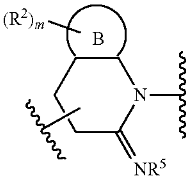
,
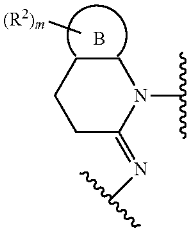
,
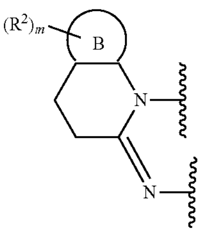
,
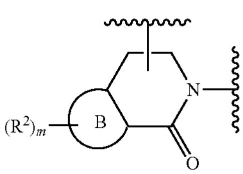
,
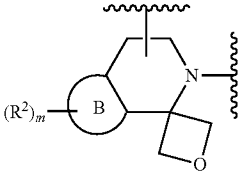
, -continued

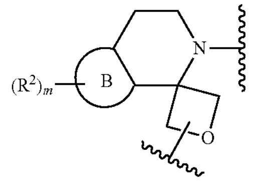

,

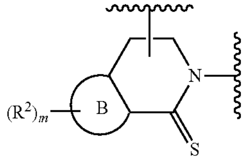

,

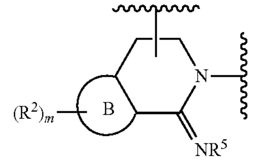

,

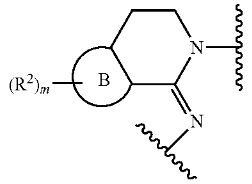

,

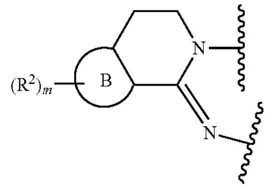

,

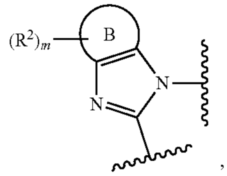

,

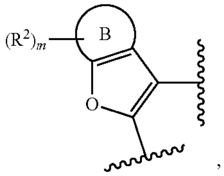

,

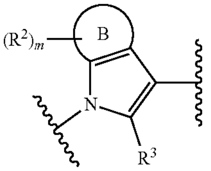

,

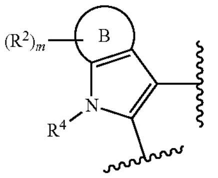

, or

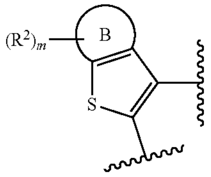

wherein

- Ring B is a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;
- $R^3$ is selected from hydrogen, halogen, —OR, —$N(R)_2$, or —SR;
- each $R^4$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)$S(O)_2R$;
- $R^5$ is hydrogen, $C_{1-4}$ aliphatic, or —CN;
- each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;
- m is 0, 1, 2, 3 or 4; and
- each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
- two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

Where a point of attachment of —$(R^2)_m$ is depicted on Ring B, it is intended, and one of ordinary skill in the art would appreciate, that the point of attachment of —$(R^2)_m$ may be on Ring A and may also be at any available carbon or nitrogen atom on Ring A including the ring to which Ring B is fused. Where —$R^2$ is attached to a nitrogen atom bound to $R^4$ or $R^5$, $R^4$ or $R^5$ is absent and —$R^2$ takes the place of the $R^4$ or $R^5$ group. Where —$R^2$ is attached to a carbon atom bound to $R^3$, $R^3$ is absent and —$R^2$ takes the place of the $R^3$ group.

In some embodiments, the compound of formula I-b above is provided as a compound of formula I-b' or formula I-b":

I-b'

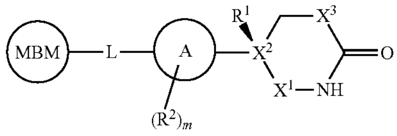

I-b"

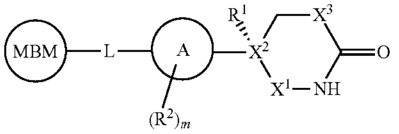

or a pharmaceutically acceptable salt thereof, wherein:

each of MBM, Ring A, L, $R^1$, $R^2$, $X^1$, $X^2$, $X^3$, and m is as defined above.

In certain embodiments, the present invention provides a compound of Formula I, wherein LBM is an E3 ubiquitin ligase (cereblon) binding moiety thereby forming a compound of formula I-c:

I-c

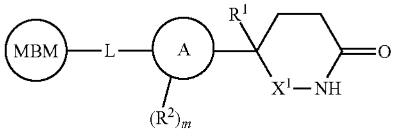

or a pharmaceutically acceptable salt thereof, wherein L and MBM are as defined above and described in embodiments herein, and wherein:

$X^1$ is a bivalent moiety selected from a covalent bond, —$CH_2$—, —C(O)—, —C(S)—, or

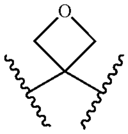;
$R^1$ is hydrogen, deuterium, halogen, —CN, —OR, —SR, —S(O)R, —$S(O)_2R$, —$NR_2$, or an optionally substituted $C_{1-4}$ aliphatic;
each $R^2$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)$S(O)_2R$;
Ring A is a bi- or tricyclic ring selected from
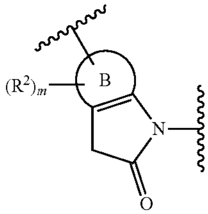,
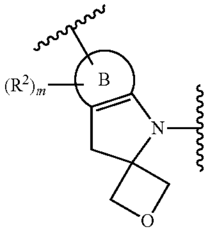,
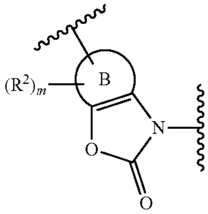,
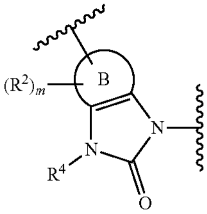,
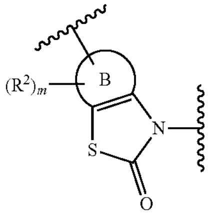,
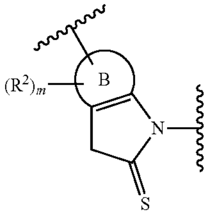,
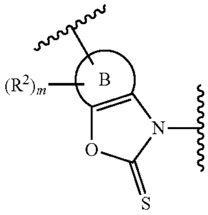,
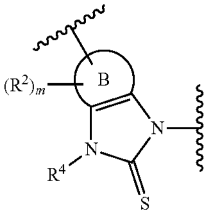,
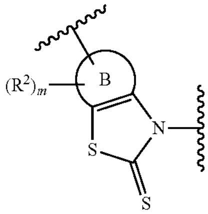,
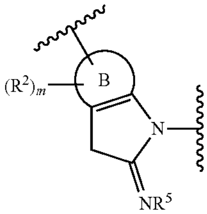,
-continued
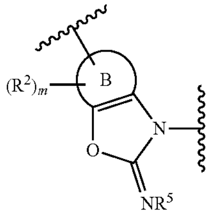,
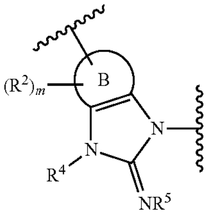,
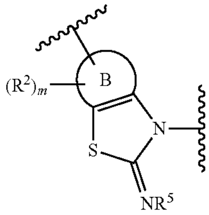,
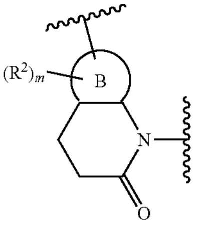,
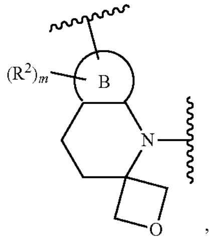,
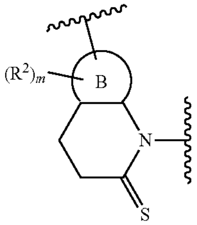,
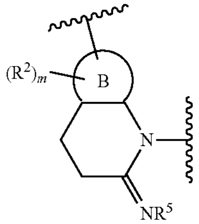,
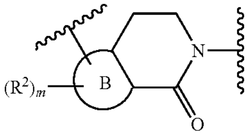,
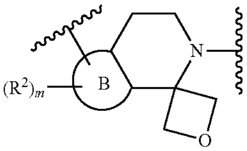,
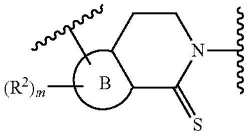,
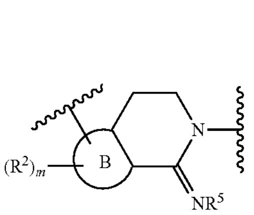,
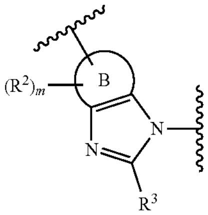,
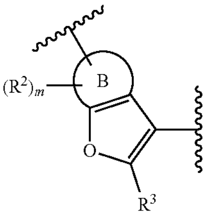,
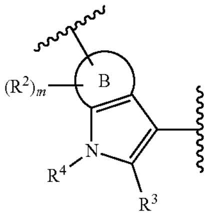,
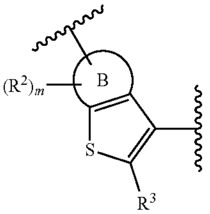,
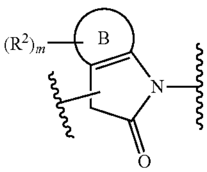, -continued
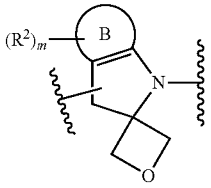 , 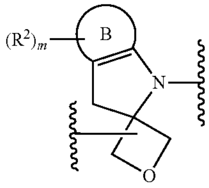 ,
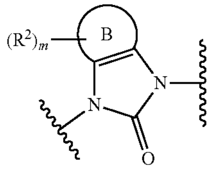 , 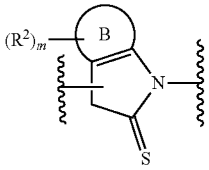 ,
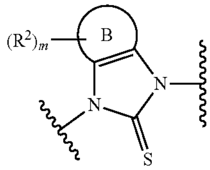 , 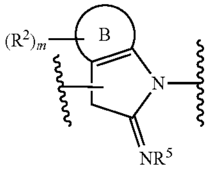 ,
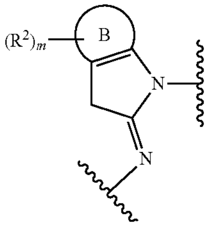 , 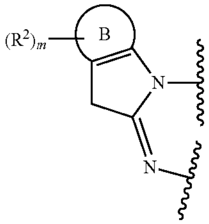 ,
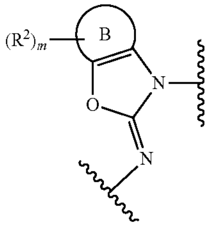 , 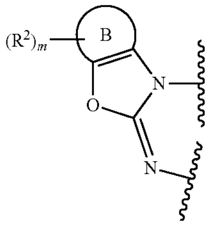 ,
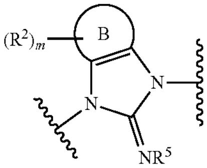 , 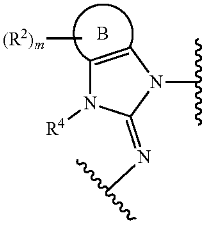 ,
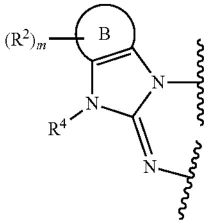 , 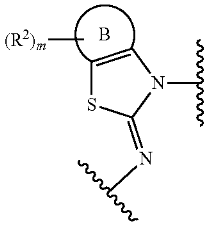 ,
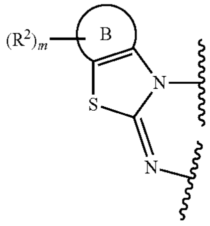 , 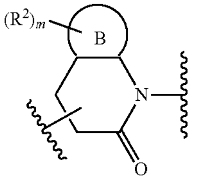 ,
-continued
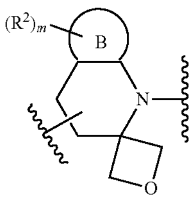 , 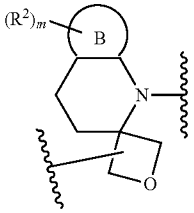 ,
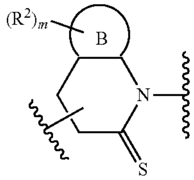 , 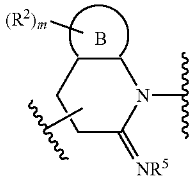 ,
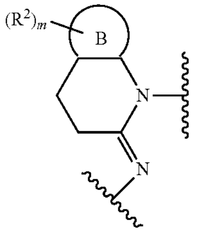 , 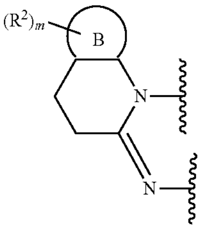 ,
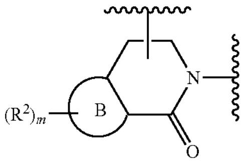 , 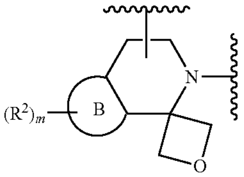 ,
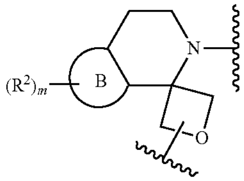 , 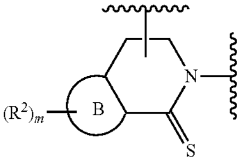 ,
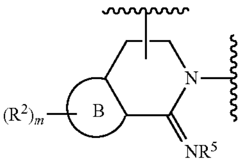 , 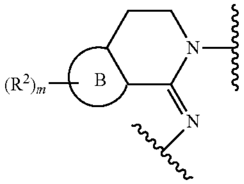 ,
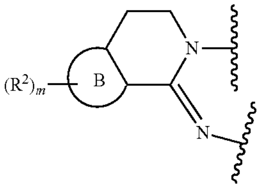 , 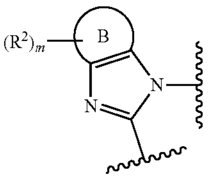 ,
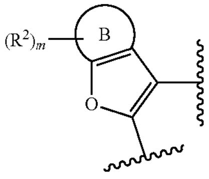 , 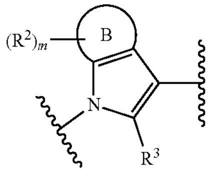 ,
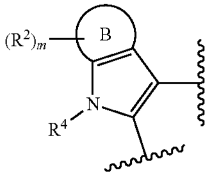 , or 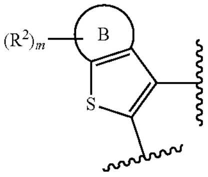

wherein

Ring B is a fused ring selected from 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

$R^3$ is selected from hydrogen, halogen, —OR, —$N(R)_2$, or —SR;

each $R^4$ is independently hydrogen, —R, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —N(R)C(O)OR, —N(R)C(O)R, —$N(R)C(O)NR_2$, or —$N(R)S(O)_2R$;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, 2, 3 or 4; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

Where a point of attachment of —$(R^2)_m$ is depicted on Ring B, it is intended, and one of ordinary skill in the art would appreciate, that the point of attachment of —$(R^2)_m$ may be on Ring A and may also be at any available carbon or nitrogen atom on Ring A including the ring to which Ring B is fused. Where —$R^2$ is attached to a nitrogen atom bound to $R^4$ or R, $R^4$ or $R^5$ is absent and —$R^2$ takes the place of the $R^4$ or $R^5$ group. Where —$R^2$ is attached to a carbon atom bound to $R^3$, $R^3$ is absent and —$R^2$ takes the place of the $R^3$ group.

In some embodiments, the compound of formula I-c above is provided as a compound of formula I-c' or formula I-c":

I-c'

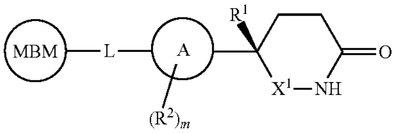

I-c"

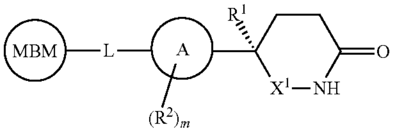

or a pharmaceutically acceptable salt thereof, wherein: each of MBM, Ring A, L, $R^1$, $R^2$, $X^1$, and m is as defined above.

In certain embodiments, the present invention provides a compound of formula I, wherein LBM is an E3 ubiquitin ligase (cereblon) binding moiety thereby forming a compound of formula I-d:

I-d

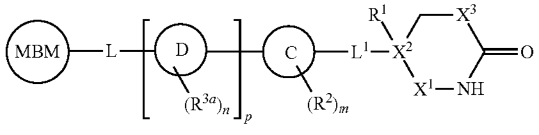

or a pharmaceutically acceptable salt thereof, wherein, L and MBM are as defined above and described in embodiments herein, and wherein:

$X^1$ is a bivalent moiety selected from a covalent bond, —$CH_2$—, —$CHCF_3$—, —$SO_2$—, —S(O)—, —P(O)R—, —P(O)OR—, —$P(O)NR_2$—, —C(O)—, —C(S)—, or

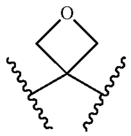

;

$X^2$ is a carbon atom or silicon atom;

$X^3$ is a bivalent moiety selected from —$CR_2$—, —NR—, —O—, —S—, or —$Si(R^2)$—;

$R^1$ is hydrogen, deuterium, halogen, —CN, —OR, —SR, —S(O)R, —$S(O)_2R$, —$NR_2$, —$P(O)(OR)_2$, —$P(O)(NR_2)OR$, —$P(O)(NR_2)_2$, —$Si(OH)_2R$, —$Si(OH)(R)_2$, —$Si(R)_3$, or an optionally substituted $C_{1-4}$ aliphatic;

Ring C is a monocyclic or bicyclic ring selected from

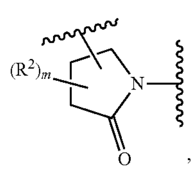

,

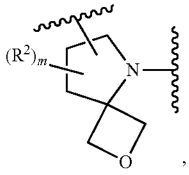

,

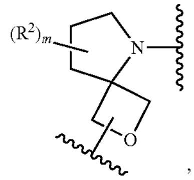

,

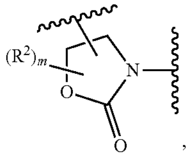

,

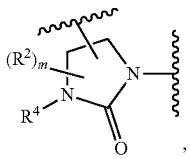

,

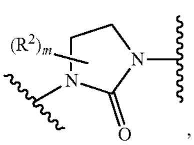

,

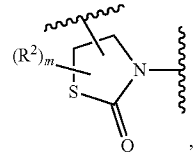

,

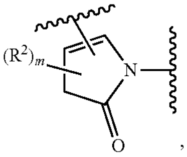

,

-continued

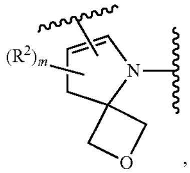 , 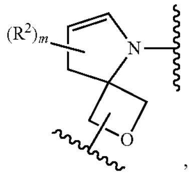 ,

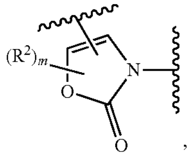 , 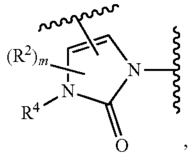 ,

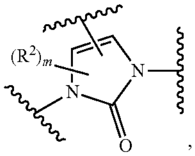 , 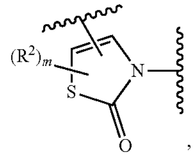 ,

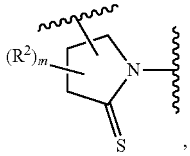 , 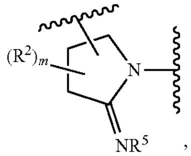 ,

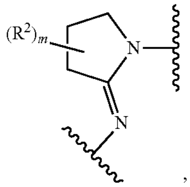 , 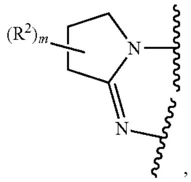 ,

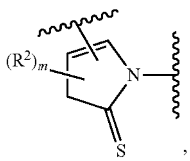 , 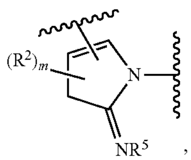 ,

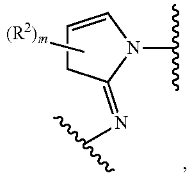 , 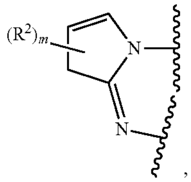 ,

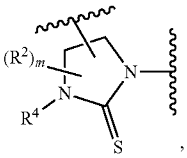 , 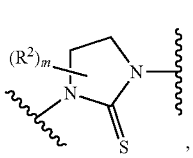 ,

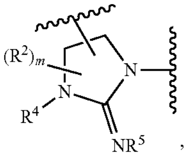 , 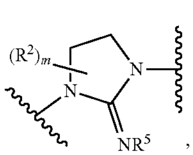 ,

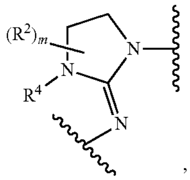 , 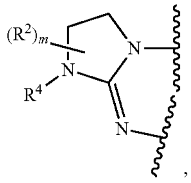 ,

-continued

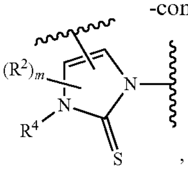 , 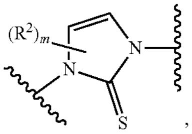 ,

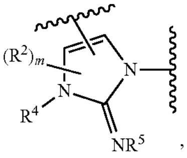 , 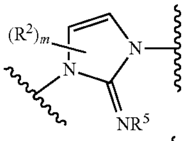 ,

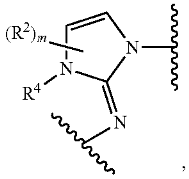 , 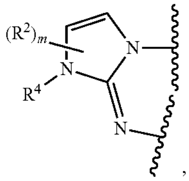 ,

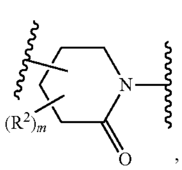 , 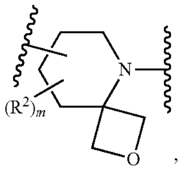 , 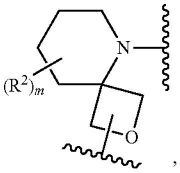 ,

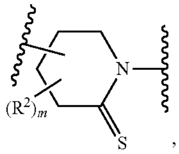 , 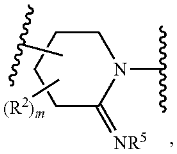 ,

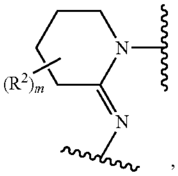 , or 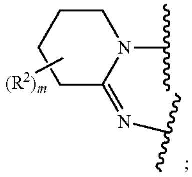 ;

each of $R^2$ and $R^{3a}$ is independently hydrogen, deuterium, —$R^6$, halogen, —CN, —$NO_2$, —OR, —SR, —$N(R)_2$, —$Si(R)_3$, —$S(O)_2R$, —$S(O)_2N(R)_2$, —S(O)R, —C(O)R, —C(O)OR, —$C(O)N(R)_2$, —C(O)N(R)OR, —$C(R)_2$ N(R)C(O)R, —$C(R)_2N(R)C(O)N(R)_2$, —OC(O)R, —$OC(O)N(R)_2$, —$OP(O)R_2$, —$OP(O)(OR)_2$, —$OP(O)(OR)(NR_2)$, —$OP(O)(NR_2)_2$—, —N(R)C(O)OR, —N(R)C(O)R, —$N(R)C(O)N(R)_2$, —$N(R)S(O)_2R$, —$NP(O)R_2$, —$N(R)P(O)(R)_2$, —$N(R)P(O)(OR)(NR_2)$, —$N(R)P(O)(NR_2)_2$, or —$N(R)S(O)_2R$;

Ring D is selected from a 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

each $R^4$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —$N(R)S(O)_2R$;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —$C(R)_2$—, —CH(R)—, —$C(F)_2$—, —N(R)—, —$S(O)_2$— or —(C)=CH—;

m is 0, 1, 2, 3 or 4;

n is 0, 1, 2, 3 or 4;

p is 0 or 1, wherein when p is 0, the bond connecting Ring C and Ring D is connected to

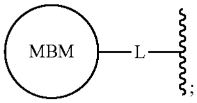;

and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, a compound of formula I-d above is provided as a compound of formula I-d' or formula I-d":

I-d'

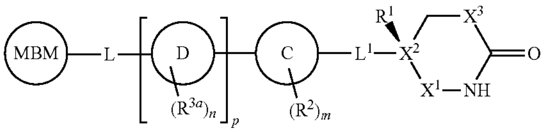

I-d"

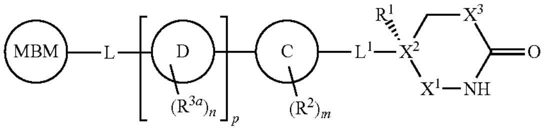

or a pharmaceutically acceptable salt thereof, wherein:

each of MBM, Ring C, Ring D, L, $L^1$, $R^1$, $R^2$, $R^{3a}$, $X^1$, $X^2$, $X^3$, n, m, and p is as defined above.

In certain embodiments, the present invention provides a compound of Formula I, wherein LBM is an E3 ubiquitin ligase (cereblon) binding moiety thereby forming a compound of formula I-e:

I-e

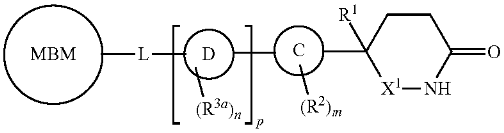

or a pharmaceutically acceptable salt thereof, wherein L and MBM are as defined above and described in embodiments herein, and wherein:

$X^1$ is a bivalent moiety selected from a covalent bond, —$CH_2$—, —C(O)—, —C(S)—,

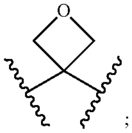 [SMILES: *C1(*)COC1];

$R^1$ is hydrogen, deuterium, halogen, —CN, —OR, —SR, —S(O)R, —$S(O)_2$R, —$NR_2$, or an optionally substituted $C_{1-4}$ aliphatic;

Ring C is a monocyclic or bicyclic ring selected from

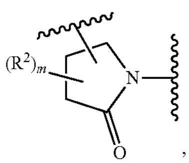, 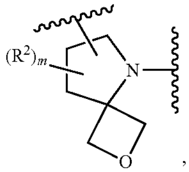,

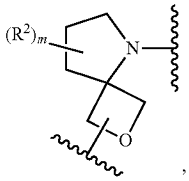, 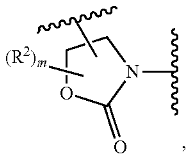,

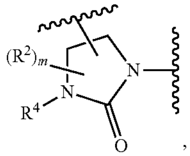, 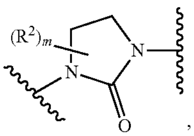,

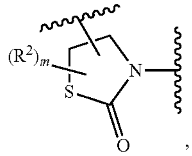, 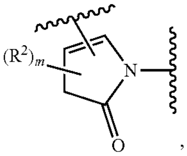,

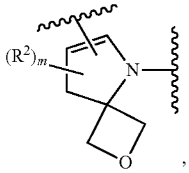, 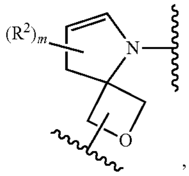,

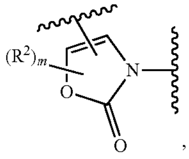, 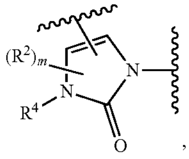,

-continued

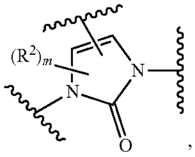,
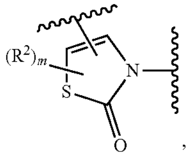,
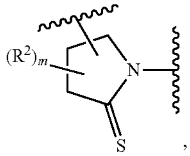,
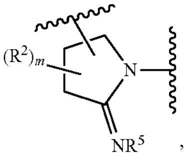,
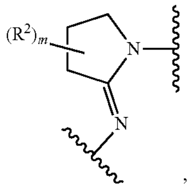,
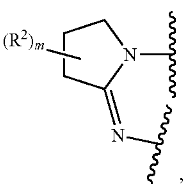,
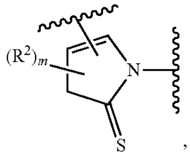,
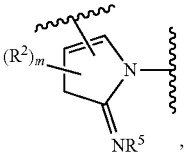,
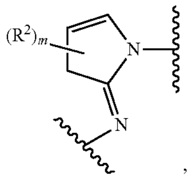,
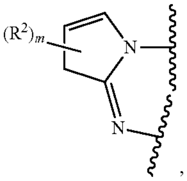,
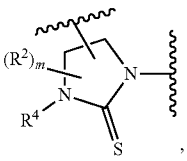,
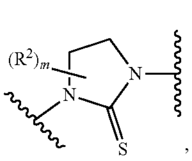,
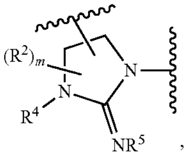,
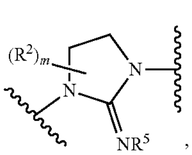,
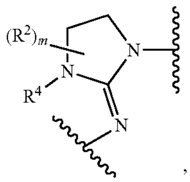,
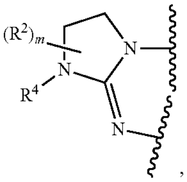,
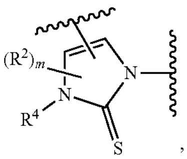,
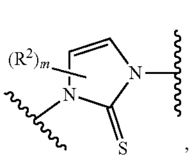,
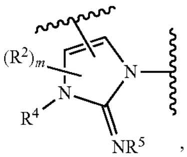,
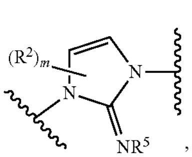, -continued

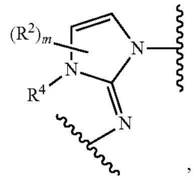,
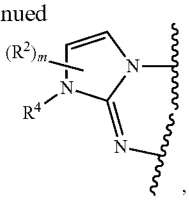,
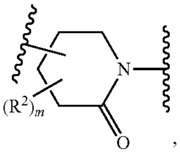,
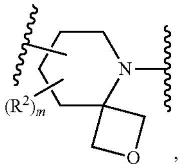,
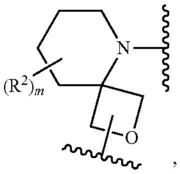,
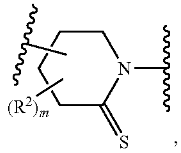,
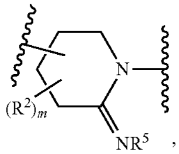,
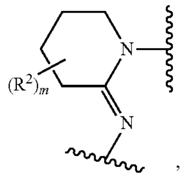, or
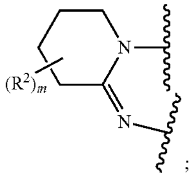;

each of $R^2$ and $R^{3a}$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —N(R)C(O)OR, —N(R)C(O)R, —$N(R)C(O)NR_2$, or —$N(R)S(O)_2R$;

Ring D is selected from 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

each $R^4$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —N(R)C(O)OR, —N(R)C(O)R, —$N(R)C(O)NR_2$, or —$N(R)S(O)_2R$;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, or 2;

n is 0, 1, 2, 3 or 4;

p is 0 or 1, wherein when p is 0, the bond connecting Ring C and Ring D is connected to

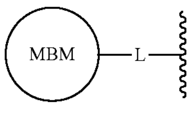

and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, a compound of formula I-e above is provided as a compound of formula I-e' or formula I-e":

I-e'

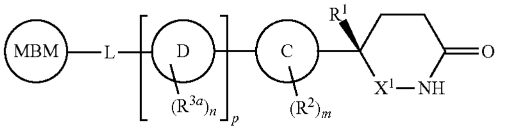

I-e"

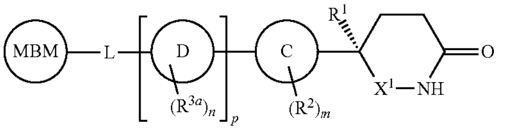

or a pharmaceutically acceptable salt thereof, wherein:

each of MBM, Ring C, Ring D, L, $R^1$, $R^2$, $R^{3a}$, $X^1$, n, m, and p is as defined above.

In certain embodiments, the present invention provides a compound of formula I, wherein LBM is an E3 ubiquitin ligase (cereblon) binding moiety thereby forming a compound of formula I-f:

I-f

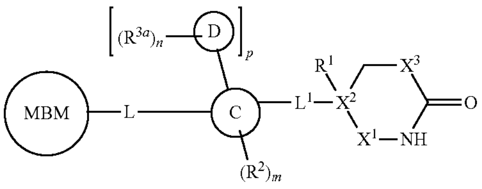

or a pharmaceutically acceptable salt thereof, wherein L and MBM are as defined above and described in embodiments herein, and wherein:

$X^1$ is a bivalent moiety selected from a covalent bond, —$CH_2$—, —$CHCF_3$—, —$SO_2$—, —S(O)—, —P(O)R—, —P(O)OR—, —P(O)$NR_2$—, —C(O)—, —C(S)—, or

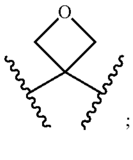

;

$X^2$ is a carbon atom or silicon atom;

$X^3$ is a bivalent moiety selected from —$CR_2$—, —NR—, —O—, —S—, or —Si($R^2$)—;

$R^1$ is hydrogen, deuterium, halogen, —CN, —OR, —SR, —S(O)R, —S(O)$_2$R, —$NR_2$, —P(O)(OR)$_2$, —P(O)($NR_2$)OR, —P(O)($NR_2$)$_2$, —Si(OH)$_2$R, —Si(OH)(R)$_2$, —Si(R)$_3$, or an optionally substituted $C_{1-4}$ aliphatic;

Ring C is a monocyclic or bicyclic ring selected from

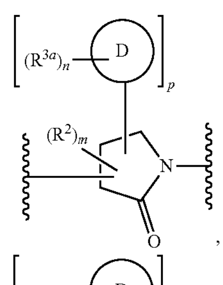

,

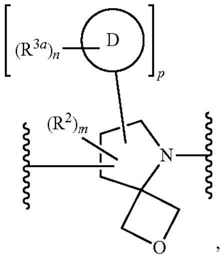

,

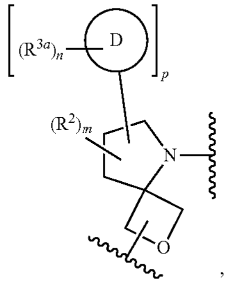

,

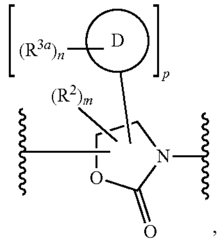

,

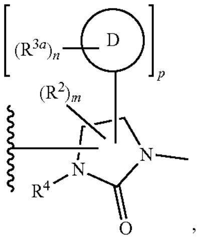

,

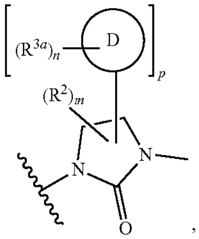

,

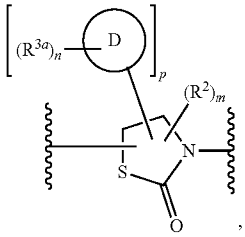

,

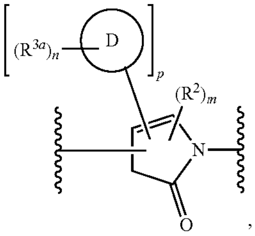

,

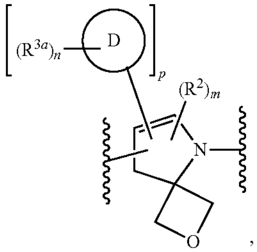

,

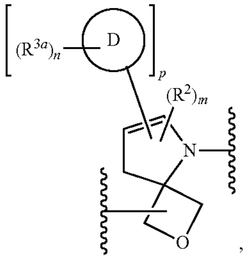

,

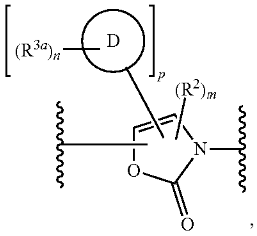

,

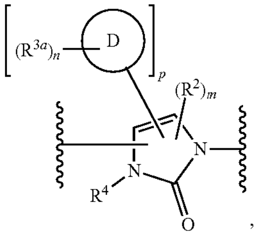

,

-continued
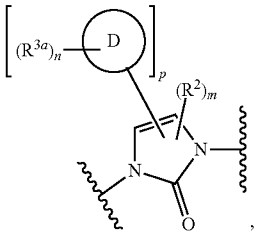
,
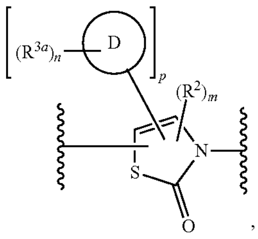
,
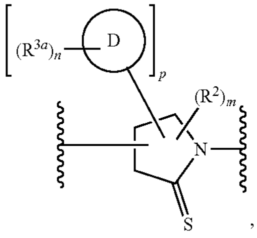
,
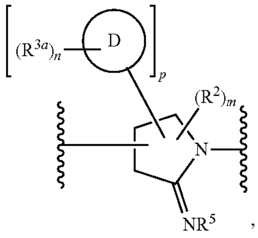
,
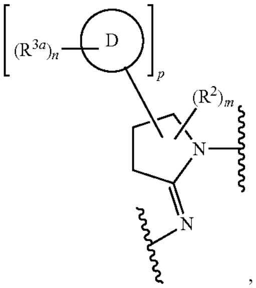
,
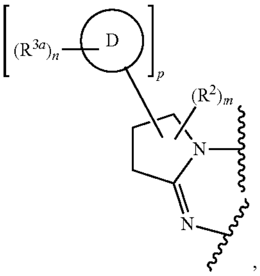
,
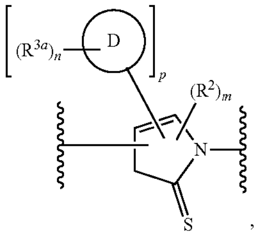
,
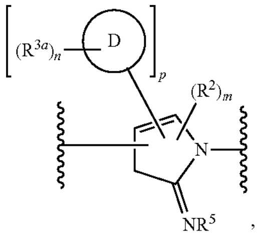
,
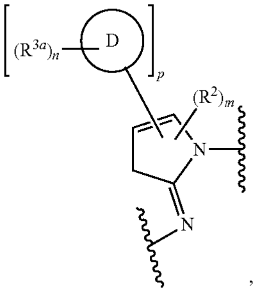
,
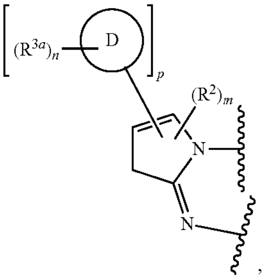
,
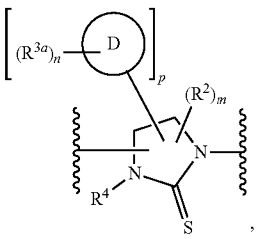
,
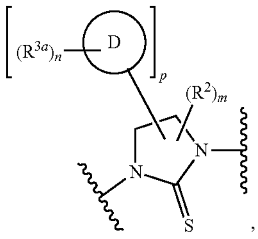
,
-continued
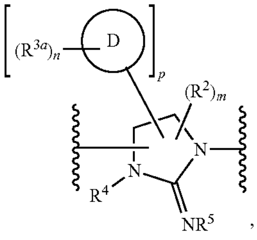
,
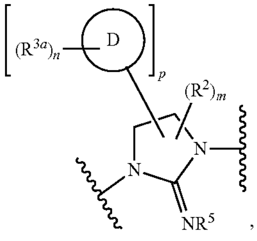
,
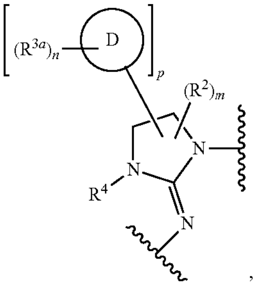
,
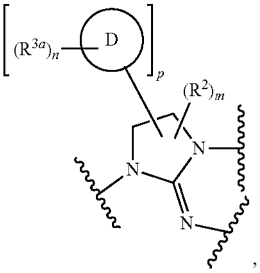
,
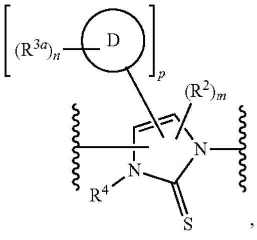
,
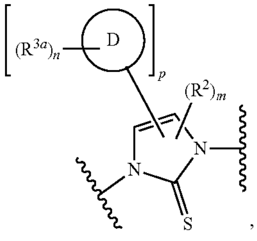
,
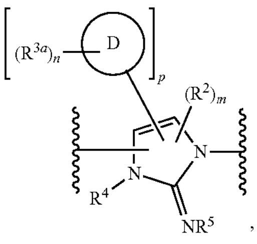
,
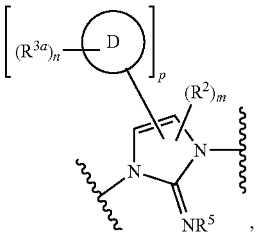
,
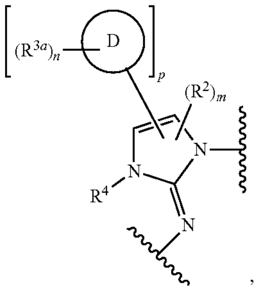
,
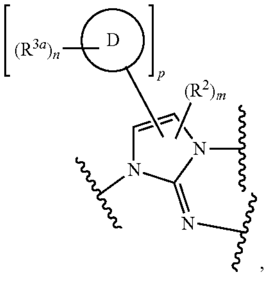
,
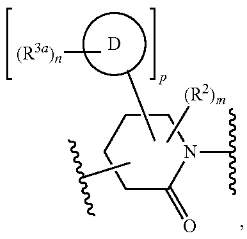
,
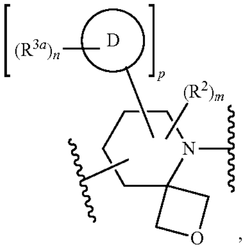
, -continued

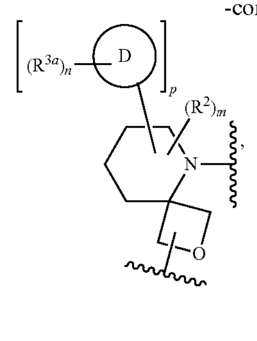

,

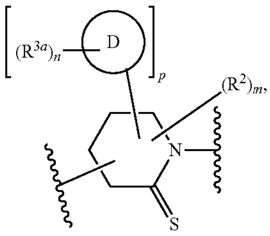

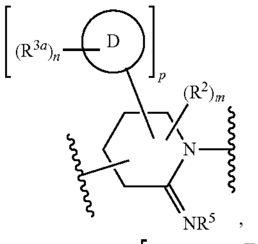

,

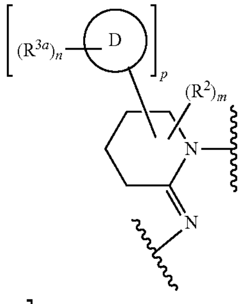

, or

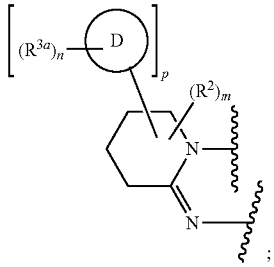

;

each or $R^2$ and $R^{3a}$ is independently hydrogen, deuterium, —R, halogen, —CN, —$NO_2$, —OR, —SR, —$N(R)_2$, —$Si(R)_3$, —$S(O)_2R$, —$S(O)_2N(R)_2$, —S(O)R, —C(O)R, —C(O)OR, —$C(O)N(R)_2$, —C(O)N(R)OR, —$C(R)_2$ N(R)C(O)R, —$C(R)_2N(R)C(O)N(R)_2$, —OC(O)R, —$OC(O)N(R)_2$, —$OP(O)R_2$, —$OP(O)(OR)_2$, —$OP(O)(OR)(NR_2)$, —$OP(O)(NR_2)_2$—, —N(R)C(O)OR, —N(R)C(O)R, —$N(R)C(O)N(R)_2$, —$N(R)S(O)_2R$, —$NP(O)R_2$, —$N(R)P(O)(OR)_2$, —$N(R)P(O)(OR)(NR_2)$, —$N(R)P(O)(NR_2)_2$, or —$N(R)S(O)_2R$;

Ring D is selected from 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

each $R^4$ is independently hydrogen, —R, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —N(R)C(O)OR, —N(R)C(O)R, —$N(R)C(O)NR_2$, or —$N(R)S(O)_2R$;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —$C(R)_2$—, —CH(R)—, —$C(F)_2$—, —N(R)—, —$S(O)_2$— or —(C)═CH—;

m is 0, 1, 2, 3 or 4;

n is 0, 1, 2, 3 or 4;

p is 0 or 1; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, a compound of formula I-f above is provided as a compound of formula I-f' or formula I-f'':

I-f'

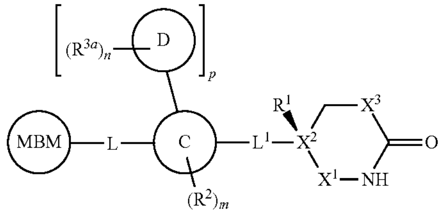

I-f''

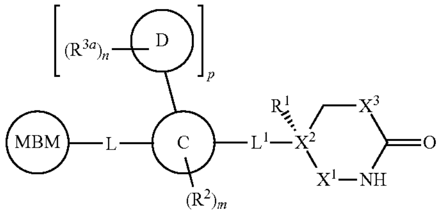

or a pharmaceutically acceptable salt thereof, wherein:

each of MBM, Ring C, Ring D, L, $L^1$, $R^1$, $R^2$, $R^{3a}$, $X^1$, $X^2$, $X^3$, m, n, and p is as defined above.

In certain embodiments, the present invention provides a compound of Formula I, wherein LBM is an E3 ubiquitin ligase (cereblon) binding moiety thereby forming a compound of formula I-g:

I-g

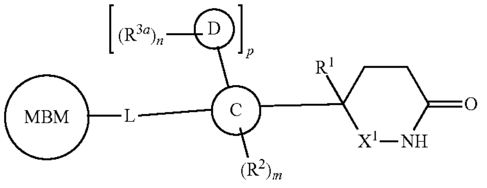

or a pharmaceutically acceptable salt thereof, wherein L and MBM are as defined above and described in embodiments herein, and wherein:

$X^1$ is a bivalent moiety selected from a covalent bond, $—CH_2—$, —C(O)—, —C(S)—,
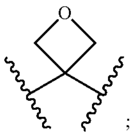;
$R^1$ is hydrogen, deuterium, halogen, —CN, —OR, —SR, —S(O)R, $—S(O)_2R$, $—NR_2$, or an optionally substituted $C_{1-4}$ aliphatic;
Ring C is a monocyclic or bicyclic ring selected from
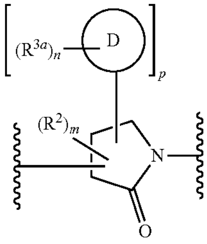, 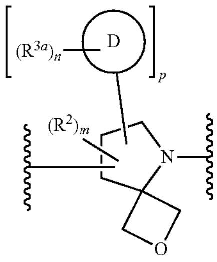, 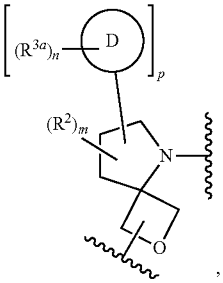, 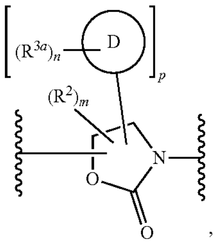, 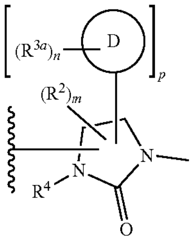, 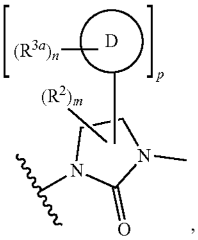, 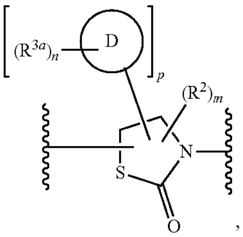, 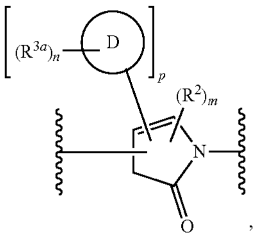, 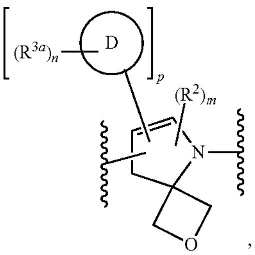, 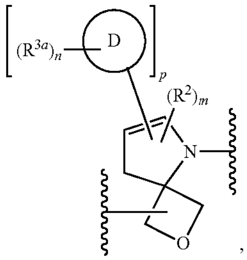,
-continued
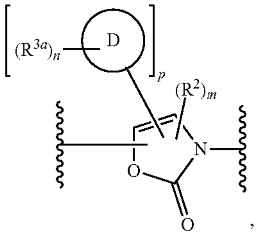, 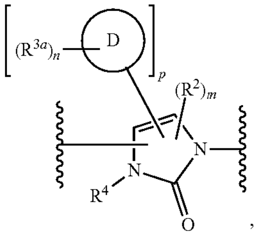, 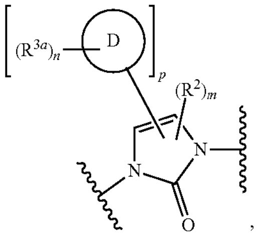, 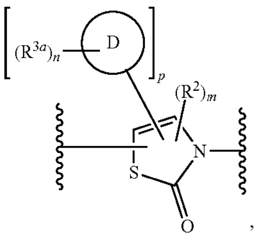, 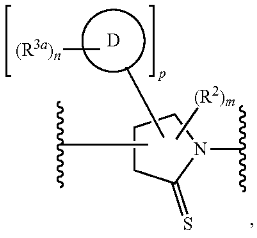, 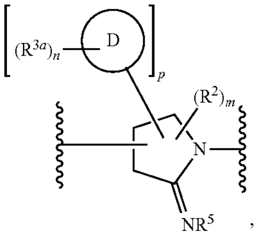, 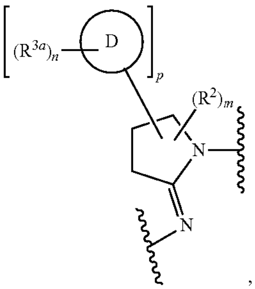, 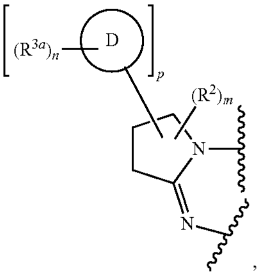, 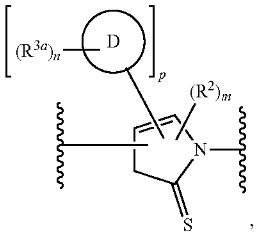, 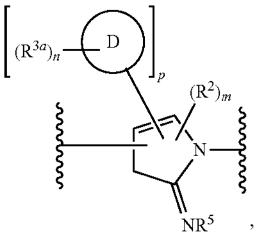, 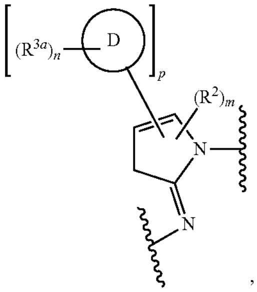, 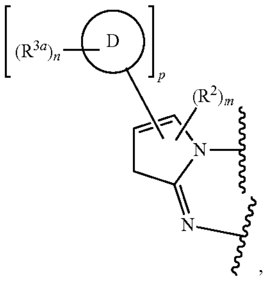, -continued

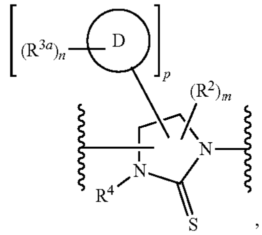
,
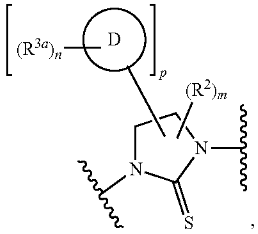
,
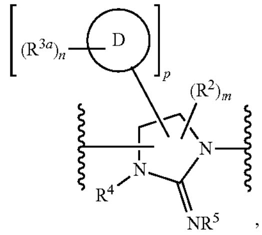
,
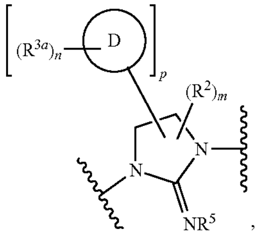
,
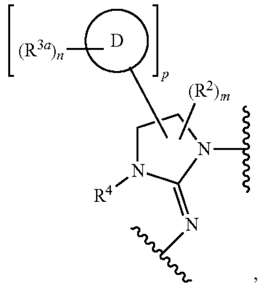
,
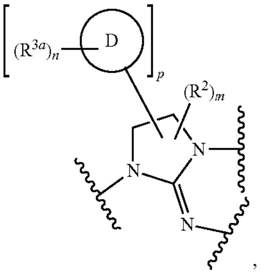
,
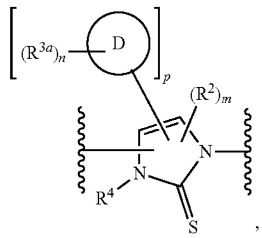
,
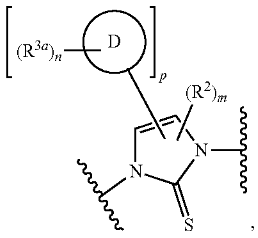
,
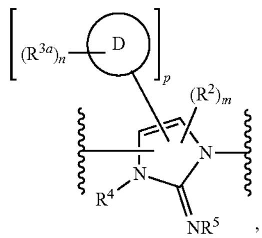
,
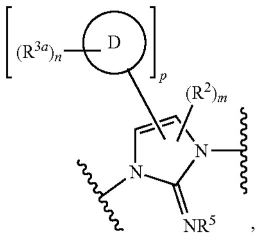
,
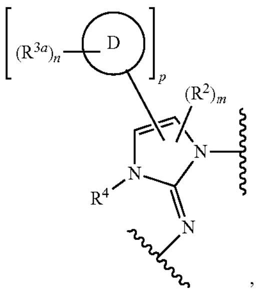
,
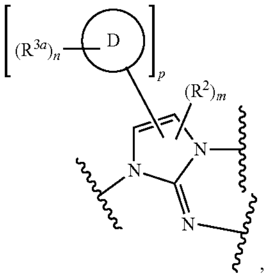
, -continued

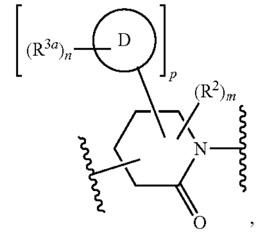
,
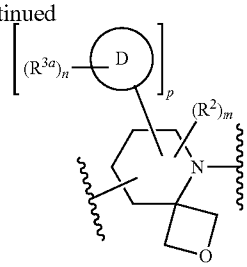
,
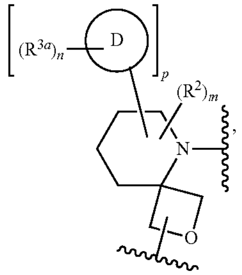
,
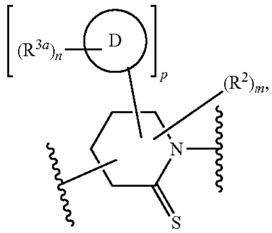
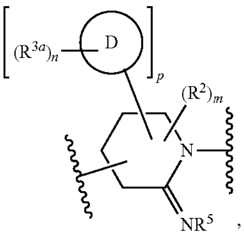
,
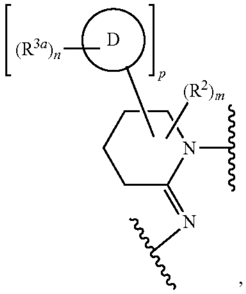
, or
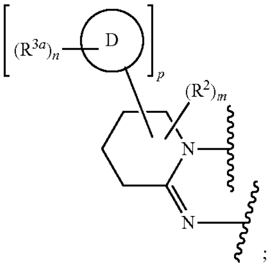
;

each of $R^2$, $R^{3a}$, and $R^4$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —N(R)C(O)OR, —N(R)C(O)R, —$N(R)C(O)NR_2$, or —$N(R)S(O)_2R$;

Ring D is selected from 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, or 2;

n is 0, 1, 2, 3, or 4;

p is 0 or 1; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, a compound of formula I-g above is provided as a compound of formula I-g' or formula I-g":

I-g'

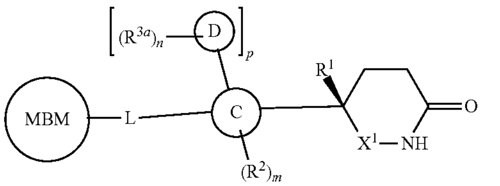

I-g"

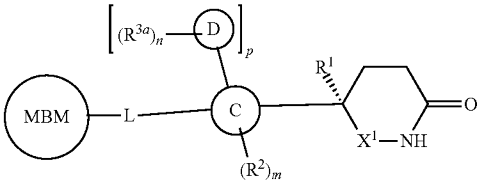

or a pharmaceutically acceptable salt thereof, wherein:

each of MBM, Ring C, Ring D, L, $R^1$, $R^2$, $R^{3a}$, $X^1$, m, n, and p is as defined above.

In certain embodiments, the present invention provides a compound of Formula I, wherein LBM is an E3 ubiquitin ligase (cereblon) binding moiety thereby forming a compound of formula I-h:

I-h

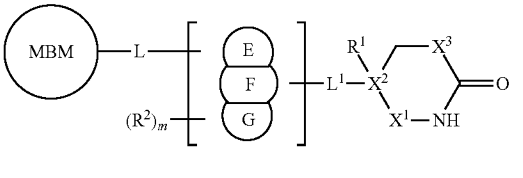

or a pharmaceutically acceptable salt thereof, wherein L and MBM are as defined above and described in embodiments herein, and wherein:

$X^1$ is a bivalent moiety selected from a covalent bond, —$CH_2$—, —$CHCF_3$—, —$SO_2$—, —S(O)—, —P(O)R—, —P(O)OR—, —P(O)$NR_2$—, —C(O)—, —C(S)—, or

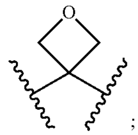 [SMILES: *C1(*)COC1]

;

$X^2$ is a carbon atom or silicon atom;

$X^3$ is a bivalent moiety selected from —$CR_2$—, —NR—, —O—, —S—, or —Si($R^2$)—;

$R^1$ is hydrogen, deuterium, halogen, —CN, —OR, —SR, —S(O)R, —S(O)$_2$R, —N(R)$_2$, —P(O)(OR)$_2$, —P(O)($NR_2$)OR, —P(O)($NR_2$)$_2$, —Si(OH)$_2$R, —Si(OH)(R)$_2$, —Si(R)$_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, —$R^6$, halogen, —CN, —$NO_2$, —OR, —SR, —N(R)$_2$, —Si(R)$_3$, —S(O)$_2$R, —S(O)$_2$N(R)$_2$, —S(O)R, —C(O)R, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, —OP(O)$R_2$, —OP(O)(OR)$_2$, —OP(O)(OR)($NR_2$), —OP(O)($NR_2$)$_2$—, —N(R)C(O)OR, —N(R)C(O)R, —N(R)C(O)N(R)$_2$, —N(R)S(O)$_2$R, —NP(O)$R_2$, —N(R)P(O)(OR)$_2$, —N(R)P(O)(OR)($NR_2$), —N(R)P(O)($NR_2$)$_2$, or —N(R)S(O)$_2$R;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each of Ring E, Ring F, and Ring G is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur, wherein each of Ring E, Ring F, and Ring G is independently and optionally further substituted with 1-2 oxo groups;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —C(R)$_2$—, —CH(R)—, —C(F)$_2$—, —N(R)—, —S(O)$_2$— or —(C)═CH—; and m is 0, 1, 2, 3, 4, 5, 6, 7, 8, 9, 10, 11, 12, 13, 14, 15, or 16.

Where a point of attachment of

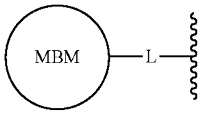

is depicted on Ring E, Ring F, or Ring G, it is intended and one of ordinary skill in the art would appreciate, that the point of attachment of

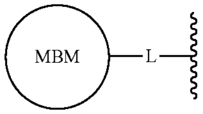

may be on any available carbon or nitrogen atom on Ring E, Ring F, or Ring G, including the ring to which Ring E or Ring G are fused to Ring F.

Where a point of attachment of $—(R^2)_m$ is depicted on Ring E, Ring F, or Ring G, it is intended, and one of ordinary skill in the art would appreciate, that the point of attachment of $—(R^2)_m$ may be at any available carbon or nitrogen atom on Ring E, Ring F, or Ring G including the carbon atom to which Ring E or Ring G are fused to Ring F.

Where a point of attachment of

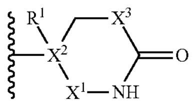

is depicted on Ring E, Ring F, or Ring G, it is intended, and one of ordinary skill in the art would appreciate, that the point of attachment of

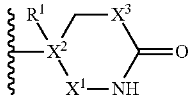

may be on any available carbon or nitrogen atom on Ring E, Ring F, or Ring G, including the carbon atom to which Ring E or Ring G are fused to Ring F.

In some embodiments, a compound of formula I-h above is provided as a compound of formula I-h' or formula I-h".

I-h'

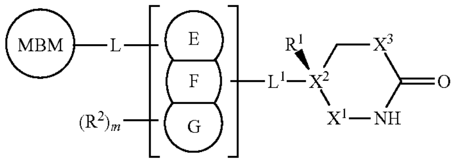

-continued

I-h"

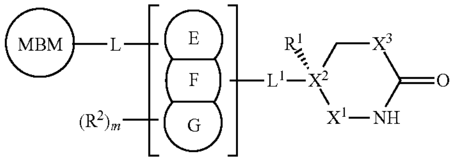

or a pharmaceutically acceptable salt thereof, wherein:

each of MBM, Ring E, Ring F, Ring G, L, $L^1$, $R^1$, $R^2$, $X^1$, $X^2$, $X^3$, and m is as defined above.

In certain embodiments, the present invention provides a compound of Formula I, wherein LBM is an E3 ubiquitin ligase (cereblon) binding moiety thereby forming a compound of formula I-i:

I-i

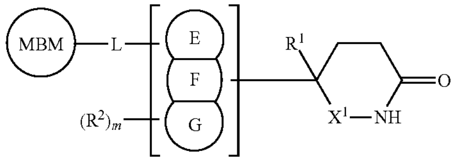

or a pharmaceutically acceptable salt thereof, wherein L and MBM are as defined above and described in embodiments herein, and wherein:

$X^1$ is a bivalent moiety selected from a covalent bond, $—CH_2—$, $—C(O)—$, $—C(S)—$, or

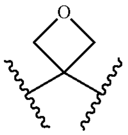

;

$R^1$ is hydrogen, deuterium, halogen, —CN, —OR, —SR, —S(O)R, $—S(O)_2R$, $—N(R)_2$, $—Si(R)_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, $—R^6$, halogen, —CN, $—NO_2$, —OR, —SR, $—N(R)_2$, $—Si(R)_3$, $—S(O)_2R$, $—S(O)_2N(R)_2$, —S(O)R, —C(O)R, —C(O)OR, $—C(O)N(R)_2$, —C(O)N(R)OR, $—C(R)_2N(R)C(O)R$, $—C(R)_2N(R)C(O)N(R)_2$, —OC(O)R, $—OC(O)N(R)_2$, —N(R)C(O)OR, —N(R)C(O)R, $—N(R)C(O)N(R)_2$, or $—N(R)S(O)_2R$;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each of Ring E, Ring F, and Ring G is independently a fused ring selected from 6-membered aryl containing 0-3 nitrogens, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-3 heteroatoms independently selected from nitrogen, oxygen or sulfur, wherein each of Ring E, Ring F, and Ring G is independently and optionally further substituted with 1-2 oxo groups; and m is 0, 1, 2, 3, or 4.

Where a point of attachment of

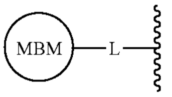

is depicted on Ring E, Ring F, or Ring G, it is intended, and one of ordinary skill in the art would appreciate, that the point of attachment of

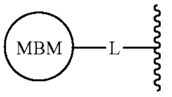

may be on any available carbon or nitrogen atom on Ring E, Ring F, or Ring G, including the ring to which Ring E or Ring G are fused to Ring F.

Where a point of attachment of —$(R^2)_m$ is depicted on Ring E, Ring F, or Ring G, it is intended, and one of ordinary skill in the art would appreciate, that the point of attachment of —$(R^2)_m$ may be at any available carbon or nitrogen atom on Ring E, Ring F, or Ring G including the carbon atom to which Ring E or Ring G are fused to Ring F.

In some embodiments, a compound of formula I-i above is provided as a compound of formula I-i' or formula I-i".

I-i'

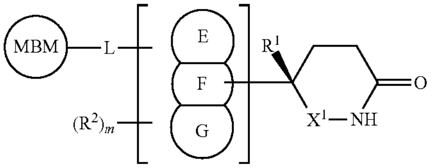

I-i''

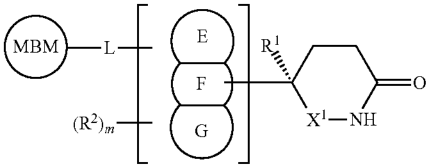

or a pharmaceutically acceptable salt thereof, wherein: each of MBM, L, Ring E, Ring F, Ring G, L, $R^1$, $R^2$, $X^1$, and m is as defined above.

In certain embodiments, the present invention provides a compound of Formula I, wherein LBM is an E3 ubiquitin ligase (cereblon) binding moiety thereby forming a compound of formula I-k:

I-k

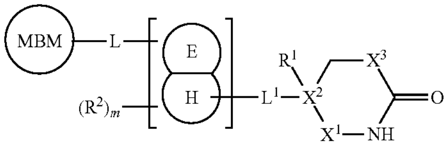

or a pharmaceutically acceptable salt thereof, wherein L and MBM are as defined above and described in embodiments herein, and wherein:

$X^1$ is a bivalent moiety selected from a covalent bond, —$CH_2$—, —$CHCF_3$—, —$SO_2$—, —S(O)—, —P(O)R—, —P(O)OR—, —P(O)$NR_2$—, —C(O)—, —C(S)—, or

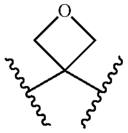

;

$X^2$ is a carbon atom or silicon atom;

$X^3$ is a bivalent moiety selected from —$CR_2$—, —NR—, —O—, —S—, or —Si($R^2$)—;

$R^1$ is hydrogen, deuterium, halogen, —CN, —OR, —SR, —S(O)R, —$S(O)_2R$, —$N(R)_2$, —$P(O)(OR)_2$, —P(O)($NR_2$)OR, —$P(O)(NR_2)_2$, —$Si(OH)_2R$, —$Si(OH)(R)_2$, —$Si(R)_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, —$R^6$, halogen, —CN, —$NO_2$, —OR, —SR, —$N(R)_2$, —$Si(R)_3$, —$S(O)_2R$, —$S(O)_2N(R)_2$, —S(O)R, —C(O)R, —C(O)OR, —C(O)$N(R)_2$, —C(O)N(R)OR, —$C(R)_2$N(R)C(O)R, —$C(R)_2$N(R)C(O)$N(R)_2$, —OC(O)R, —OC(O)$N(R)_2$, —OP(O)$R_2$, —OP(O)$(OR)_2$, —OP(O)(OR)($NR_2$), —OP(O)$(NR_2)_2$—, —N(R)C(O)OR, —N(R)C(O)R, —N(R)C(O)$N(R)_2$, —N(R)$S(O)_2R$, —NP(O)$R_2$, —N(R)P(O)$(OR)_2$, —N(R)P(O)(OR)($NR_2$), —N(R)P(O)$(NR_2)_2$, or —N(R)$S(O)_2R$;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring E is a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

Ring H is a fused ring selected from a 7-9 membered saturated or partially unsaturated carbocyclyl or heterocyclyl ring with 1-3 heteroatoms independently selected from boron, nitrogen, oxygen, silicon, or sulfur, wherein Ring E is optionally further substituted with 1-2 oxo groups;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —C(R)$_2$—, —CH(R)—, —C(F)$_2$—, —N(R)—, —S(O)$_2$— or —(C)═CH—;

m is 0, 1, 2, 3, or 4.

Where a point of attachment of

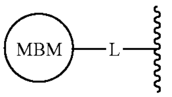

is depicted on Ring E or Ring H, it is intended, and one of ordinary skill in the art would appreciate, that the point of attachment of

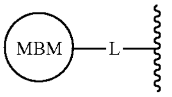

may be on any available carbon or nitrogen atom on Ring E or Ring H including the carbon atom to which Ring E and Ring H are fused.

Where a point of attachment of —$(R^2)_m$ is depicted on Ring E and Ring H, it is intended, and one of ordinary skill in the art would appreciate, that the point of attachment of —$(R^2)_m$ may be on any available carbon or nitrogen atom on Ring E or Ring H including the carbon atom to which Ring E and Ring H are fused.

Where a point of attachment of

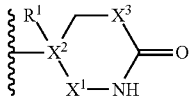

is depicted on Ring E and Ring H, it is intended, and one of ordinary skill in the art would appreciate, that the point of attachment of

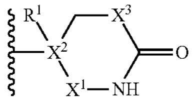

may be on any available carbon or nitrogen atom on Ring E or Ring H including the carbon atom to which Ring E and Ring H are fused.

In some embodiments, a compound of formula I-k above is provided as a compound of formula I-k' or formula I-k":

I-k'

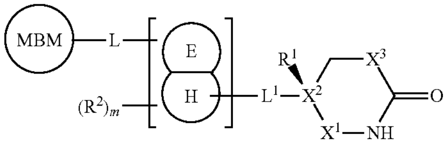

I-k"

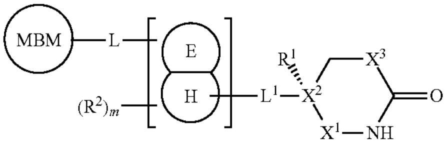

or a pharmaceutically acceptable salt thereof, wherein:

each of MBM, Ring E, Ring H, L, $L^1$, $R^1$, $R^2$, $X^1$, $X^2$, $X^3$, and m is as defined above.

In certain embodiments, the present invention provides a compound of Formula I, wherein LBM is an E3 ubiquitin ligase (cereblon) binding moiety thereby forming a compound of formula I-1:

I-l

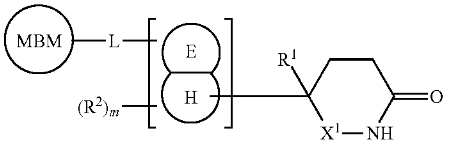

or a pharmaceutically acceptable salt thereof, wherein L and MBM are as defined above and described in embodiments herein, and wherein:

$X^1$ is a bivalent moiety selected from a covalent bond, —CH$_2$—, —C(O)—, —C(S)—, or

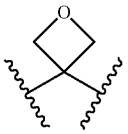 ;

$R^1$ is hydrogen, deuterium, halogen, —CN, —OR, —SR, —S(O)R, —S(O)$_2$R, —N(R)$_2$, —Si(R)$_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, —R, halogen, —CN, —$NO_2$, —OR, —SR, —$N(R)_2$, —$Si(R)_3$, —$S(O)_2R$, —$S(O)_2N(R)_2$, —S(O)R, —C(O)R, —C(O)OR, —$C(O)N(R)_2$, —C(O)N(R)OR, —$C(R)_2N(R)C(O)R$, —$C(R)_2N(R)C(O)N(R)_2$, —OC(O)R, —$OC(O)N(R)_2$, —N(R)C(O)OR, —N(R)C(O)R, —$N(R)C(O)N(R)_2$, or —$N(R)S(O)_2R$;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring E is a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

Ring H is a ring selected from a 7-9 membered saturated or partially unsaturated carbocyclyl or heterocyclyl ring with 1-3 heteroatoms independently selected from boron, nitrogen, oxygen, silicon, or sulfur, wherein Ring E is optionally further substituted with 1-2 oxo groups; and m is 0, 1, 2, 3, or 4.

Where a point of attachment of

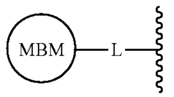

is depicted on Ring E or Ring H, it is intended, and one of ordinary skill in the art would appreciate, that the point of attachment of

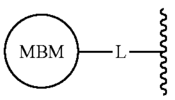

may be on any available carbon or nitrogen atom on Ring E or Ring H including the carbon atom to which Ring E and Ring H are fused.

Where a point of attachment of —$(R^2)_m$ is depicted on Ring E and Ring H, it is intended, and one of ordinary skill in the art would appreciate, that the point of attachment of —$(R^2)_m$ may be on any available carbon or nitrogen atom on Ring E or Ring H including the carbon atom to which Ring E and Ring H are fused.

Where a point of attachment of

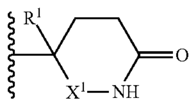

is depicted on Ring E and Ring H, it is intended, and one of ordinary skill in the art would appreciate, that the point of attachment of

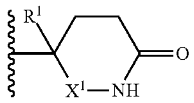

may be on any available carbon or nitrogen atom on Ring E or Ring H including the carbon atom to which Ring E and Ring H are fused.

In some embodiments, a compound of formula I-1 above is provided as a compound of formula I-I' or formula I-1":

I-1'

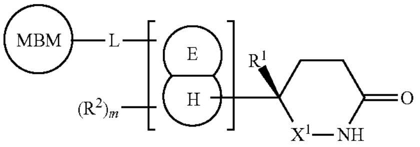

I-1"

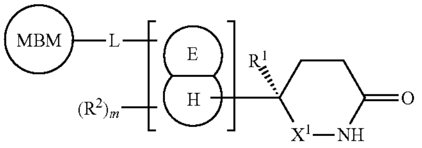

or a pharmaceutically acceptable salt thereof, wherein:

each of MBM, Ring E, Ring H, L, $R^1$, $R^2$, $X^1$, and m is as defined above.

In some embodiments, a compound of formula I-m above is provided as a compound of formula I-m-1:

I-m-1

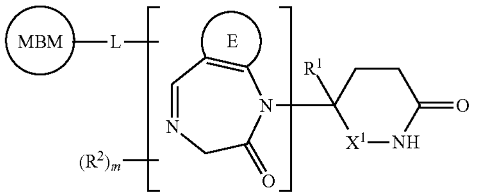

or a pharmaceutically acceptable salt thereof, wherein:

each of MBM, L, Ring E, $X^1$, $R^1$, $R^2$, and m is as defined above.

In certain embodiments, the present invention provides a compound of Formula I, wherein LBM is an E3 ubiquitin ligase (cereblon) binding moiety thereby forming a compound of formula I-n:

I-n

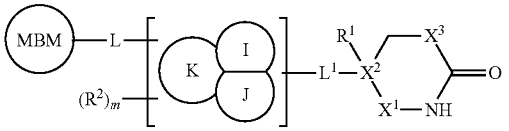

or a pharmaceutically acceptable salt thereof, wherein:

$X^1$ is a bivalent moiety selected from a covalent bond, —$CH_2$—, —$CHCF_3$—, —$SO_2$—, —S(O)—, —P(O)R—, —P(O)OR—, —P(O)$NR_2$—, —C(O)—, —C(S)—, or,

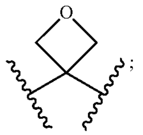

$X^2$ is a carbon atom or silicon atom;

$X^3$ is a bivalent moiety selected from —$CR_2$—, —NR—, —O—, —S—, or —Si($R_2$)—;

$R^1$ is hydrogen, deuterium, halogen, —CN, —OR, —SR, —S(O)R, —S(O)$_2$R, —$NR_2$, —P(O)(OR)$_2$, —P(O)($NR_2$)OR, —P(O)($NR_2$)$_2$, —Si(OH)$_2$R, —Si(OH)(R)$_2$, —Si(R)$_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, —$R^6$, halogen, —CN, —$NO_2$, —OR, —SR, —N(R)$_2$, —Si(R)$_3$, —S(O)$_2$R, —S(O)$_2$N(R)$_2$, —S(O)R, —C(O)R, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, —OP(O)$R_2$, —OP(O)(OR)$_2$, —OP(O)(OR)($NR_2$), —OP(O)($NR_2$)$_2$—, —N(R)C(O)OR, —N(R)C(O)R, —N(R)C(O)N(R)$_2$, —N(R)S(O)$_2$P, —NP(O)$R_2$, —N(R)P(O)(OR)$_2$, —N(R)P(O)(OR)($NR_2$), —N(R)P(O)($NR_2$)$_2$, or —N(R)S(O)$_2$R;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each of Ring I and J is independently a fused ring selected from 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

Ring K is a fused ring selected from a 6-12 membered saturated or partially unsaturated carbocyclyl or heterocyclyl ring with 1-3 heteroatoms independently selected from boron, nitrogen, oxygen, silicon, or sulfur, wherein Ring H is optionally further substituted with 1-2 oxo groups;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —C(R)$_2$—, —CH(R)—, —C(F)$_2$—, —N(R)—, —S(O)$_2$— or —(C)=CH—; and m is 0, 1, 2, 3, or 4.

Where a point of attachment of

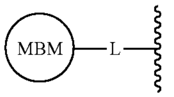

is depicted on Ring I, Ring J, and Ring K, it is intended, and one of ordinary skill in the art would appreciate, that the point of attachment of

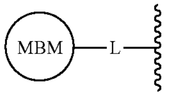

may be on any available carbon or nitrogen atom on Ring I, Ring J, or Ring K, including the carbon atom to which Ring I, Ring J, and Ring K are fused.

Where a point of attachment of —$(R^2)_m$ is depicted on Ring I, Ring J, and Ring K, it is intended, and one of ordinary skill in the art would appreciate, that the point of attachment of —$(R^2)_m$ may be on any available carbon or nitrogen atom on Ring I, Ring J, or Ring K, including the carbon atom to which Ring I, Ring J, and Ring K are fused.

Where a point of attachment of

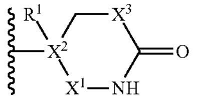

is depicted on Ring I, Ring J, and Ring K, it is intended, and one of ordinary skill in the art would appreciate, that the point of attachment of

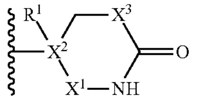

may be on any available carbon or nitrogen atom on Ring I, Ring J, or Ring K, including the carbon atom to which Ring I, Ring J, and Ring K are fused.

In some embodiments, a compound of formula I-n above is provided as a compound of formula I-n' or formula I-n":

I-n'

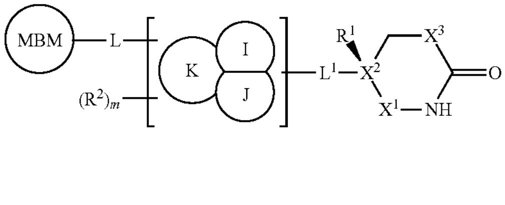

-continued

I-n''

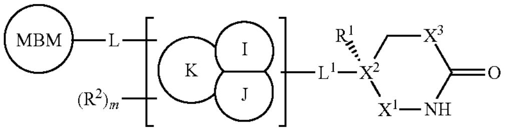

or a pharmaceutically acceptable salt thereof, wherein:

each of MBM, Ring I, Ring J, Ring K, L, $L^1$, $R^1$, $R^2$, $X^1$, $X^2$, $X^3$, and m is as defined above.

In certain embodiments, the present invention provides a compound of formula I-o:

I-o

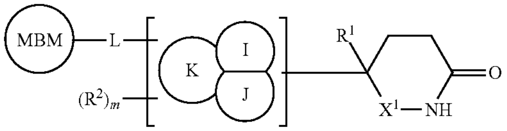

or a pharmaceutically acceptable salt thereof, wherein:

$X^1$ is a bivalent moiety selected from a covalent bond, $—CH_2—$, —C(O)—, —C(S)—, or

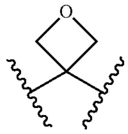

;

$R^1$ is hydrogen, deuterium, halogen, —CN, —OR, —SR, —S(O)R, $—S(O)_2R$, $—N(R)_2$, $—Si(R)_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, $—R^6$, halogen, —CN, $—NO_2$, —OR, —SR, $—N(R)_2$, $—Si(R)_3$, $—S(O)_2R$, $—S(O)_2N(R)_2$, —S(O)R, —C(O)R, —C(O)OR, $—C(O)N(R)_2$, —C(O)N(R)OR, $—C(R)_2N(R)C(O)R$, $—C(R)_2N(R)C(O)N(R)_2$, —OC(O)R, $—OC(O)N(R)_2$, —N(R)C(O)OR, —N(R)C(O)R, $—N(R)C(O)N(R)_2$, or $—N(R)S(O)_2R$;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each of Ring I and J is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

Ring K is a fused ring selected from a 6-12 membered saturated or partially unsaturated carbocyclyl or heterocyclyl ring with 1-3 heteroatoms independently selected from boron, nitrogen, oxygen, silicon, or sulfur, wherein Ring H is optionally further substituted with 1-2 oxo groups; and m is 0, 1, 2, 3, or 4.

Where a point of attachment of

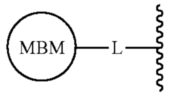

is depicted on Ring I, Ring J, and Ring K, it is intended, and one of ordinary skill in the art would appreciate, that the point of attachment of

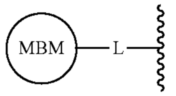

may be on any available carbon or nitrogen atom on Ring I, Ring J, or Ring K, including the carbon atom to which Ring I, Ring J, and Ring K are fused.

Where a point of attachment of $—(R^2)_m$ is depicted on Ring I, Ring J, and Ring K, it is intended, and one of ordinary skill in the art would appreciate, that the point of attachment of $—(R^2)_m$ may be on any available carbon or nitrogen atom on Ring I, Ring J, or Ring K, including the carbon atom to which Ring I, Ring J, and Ring K are fused.

Where a point of attachment of

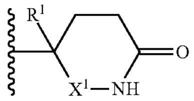

is depicted on Ring I, Ring J, and Ring K, it is intended, and one of ordinary skill in the art would appreciate, that the point of attachment of

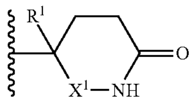

may be on any available carbon or nitrogen atom on Ring I, Ring J, or Ring K, including the carbon atom to which Ring I, Ring J, and Ring K are fused.

In some embodiments, a compound of formula I-o above is provided as a compound of formula I-o' or formula I-o'':

I-o′

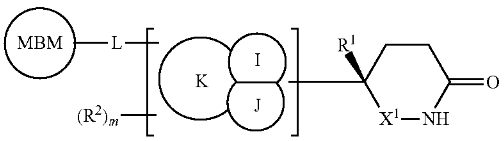

I-o″

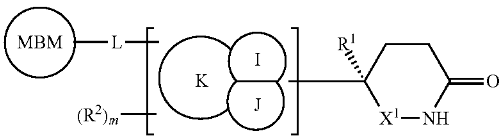

or a pharmaceutically acceptable salt thereof, wherein:

each of MBM, Ring I, Ring J, Ring K, L, $R^1$, $R^2$, $X^1$, and m is as defined above.

In some embodiments, a compound of formula I-o above is provided as a compound of formula I-o-1:

I-o-1

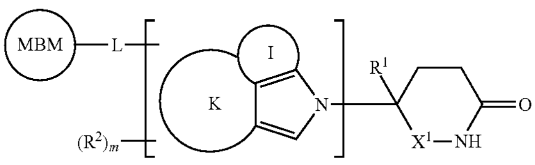

or a pharmaceutically acceptable salt thereof, wherein:

each of MBM, L, Ring I, Ring K, $X^1$, $R^1$, $R^2$, and m is as defined above.

In certain embodiments, the present invention provides a compound of Formula I, wherein LBM is an E3 ubiquitin ligase (cereblon) binding moiety thereby forming a compound of formula I-o-2 or I-o-3:

I-o-2

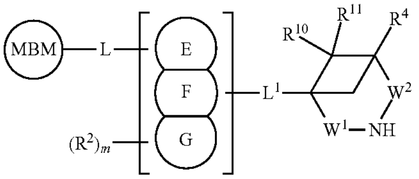

I-o-3

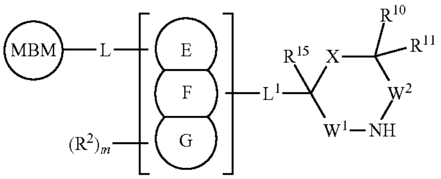

or a pharmaceutically acceptable salt thereof, wherein L and MBM are as defined above and described in embodiments herein, and wherein:

each $R^2$ is independently hydrogen, deuterium, —$R^6$, halogen, —CN, —$NO_2$, —OR, —SR, —$NR_2$, —$SiR_3$, —$S(O)_2R$, —$S(O)_2NR_2$, —S(O)R, —C(O)R, —C(O)OR, —C(O)$NR_2$, —C(O)N(R)OR, —$C(R)_2N(R)C(O)R$, —$C(R)_2N(R)C(O)N(R)_2$, —OC(O)R, —OC(O)N$(R)_2$, —$OP(O)R_2$, —$OP(O)(OR)_2$, —$OP(O)(OR)NR_2$, —$OP(O)(NR_2)_2$—, —N(R)C(O)OR, —N(R)C(O)R, —N(R)C(O)$NR_2$, —N(R)$S(O)_2R$, —$NP(O)R_2$, —N(R)P(O)$(OR)_2$, —N(R)P(O)(OR)$NR_2$, —N(R)P(O)$(NR_2)_2$, or —N(R)$S(O)_2R$;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each of Ring E, Ring F, and Ring G is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur, wherein each of Ring E, Ring F, and Ring G is independently and optionally further substituted with 1-2 oxo groups;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —$C(R)_2$—, —CH(R)—, —$C(F)_2$—, —N(R)—, —S—, —$S(O)_2$— or —(C)═CH—;

m is 0, 1, 2, 3, 4, 5, 6, 7, 8, 9, 10, 11, 12, 13, 14, 15, or 16; and $R^4$, $R^{10}$, $R^{11}$, $R^{15}$, $W^1$, $W^2$, and X is as defined in WO 2019/099868, the entirety of each of which is herein incorporated by reference.

Where a point of attachment of

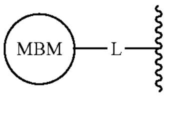

is depicted on Ring E, Ring F, or Ring G, it is intended, and one of ordinary skill in the art would appreciate, that the point of attachment of

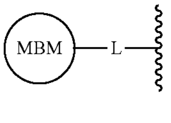

may be on any available carbon or nitrogen atom on Ring E, Ring F, or Ring G, including the ring to which Ring E or Ring G are fused to Ring F.

Where a point of attachment of —$(R^2)_m$ is depicted on Ring E, Ring F, or Ring G, it is intended, and one of ordinary skill in the art would appreciate, that the point of attachment of —$(R^2)_m$ may be at any available carbon or nitrogen atom on Ring E, Ring F, or Ring G including the carbon atom to which Ring E or Ring G are fused to Ring F.

Where a point of attachment of

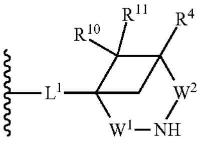

or

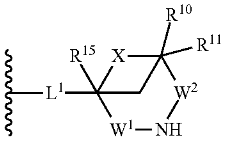

is depicted on Ring E, Ring F, or Ring G, it is intended, and one of ordinary skill in the art would appreciate, that the point of attachment of

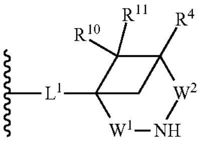

or

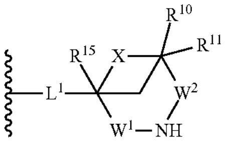

may be on any available carbon or nitrogen atom on Ring E, Ring F, or Ring G, including the carbon atom to which Ring E or Ring G are fused to Ring F.

As described above, in another aspect, the present invention provides a compound of Formula I-ii:

I-ii

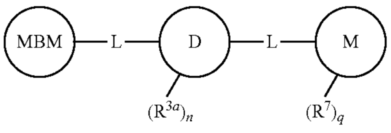

or a pharmaceutically acceptable salt thereof, wherein L and MBM are as defined above and described in embodiments herein, and wherein:

Ring M is selected from

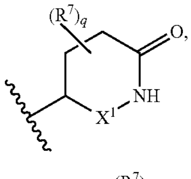

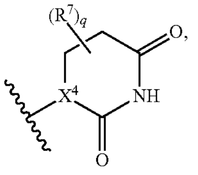

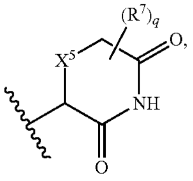

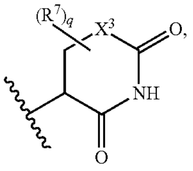

-continued

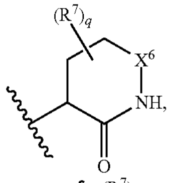

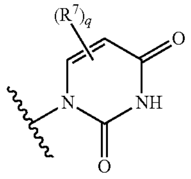

,

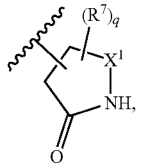

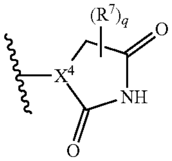

,

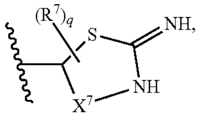

or

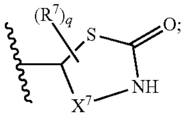

each of $X^1$, $X^6$, and $X^7$ is independently a bivalent moiety selected from a covalent bond, —$CH_2$—, —$CHCF_3$—, —$SO_2$—, —S(O)—, —P(O)R—, —P(O)OR—, —P(O)$NR_2$—, —C(O)—, —C(S)—, or

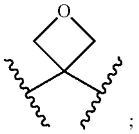 [SMILES: *C1(*)COC1]

;

each of $X^3$ and $X^5$ is independently a bivalent moiety selected from a covalent bond, —$CR_2$—, —NR—, —O—, —S—, or —$SiR_2$—;

$X^4$ is a trivalent moiety selected from

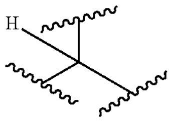

,

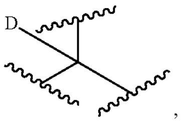

,

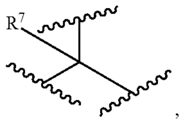

,

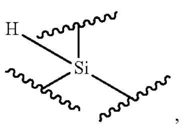

,

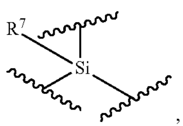

,

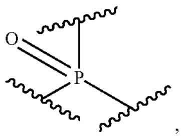

, or

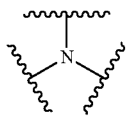

;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^{3a}$ is independently hydrogen, deuterium, —$R^6$, halogen, —CN, —$NO_2$, —OR, —SR, —$NR_2$, —$SiR_3$, —$S(O)_2R$, —$S(O)_2NR_2$, —S(O)R, —C(O)R, —C(O)OR, —C(O)$NR_2$, —C(O)N(R)OR, —$C(R)_2N(R)C(O)R$, —$C(R)_2N(R)C(O)N(R)_2$, —OC(O)R, —OC(O)N$(R)_2$, —OP(O)$R_2$, —OP(O)$(OR)_2$, —OP(O)(OR)$NR_2$, —OP(O)$(NR_2)_2$—, —N(R)C(O)OR, —N(R)C(O)R, —N(R)C(O)$NR_2$, —N(R)S$(O)_2$R, —NP(O)$R_2$, —N(R)P(O)$(OR)_2$, —N(R)P(O)(OR)$NR_2$, —N(R)P(O)$(NR_2)_2$, or —N(R)S$(O)_2$R;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each $R^7$ is independently hydrogen, deuterium, halogen, —CN, —OR, —SR, —S(O)R, —S$(O)_2$R, —$NR_2$, —P(O)$(OR)_2$, —P(O)$(NR_2)$OR, —P(O)$(NR_2)_2$, —Si(OH)$R_2$, —Si$(OH)_2$R, —$SiR_3$, or an optionally substituted $C_{1-4}$ aliphatic; or $R^7$ and $X^1$ or $X^3$ are taken together with their intervening atoms to form a 5-7 membered saturated, partially unsaturated, carbocyclic ring or heterocyclic ring having 1-3 heteroatoms, independently selected from boron, nitrogen, oxygen, silicon, or sulfur;

two $R^7$ groups on the same carbon are optionally taken together with their intervening atoms to form a 3-6 membered spiro fused ring or a 4-7 membered heterocyclic ring having 1-2 heteroatoms independently selected from boron, nitrogen, oxygen, silicon, or sulfur; two $R^7$ groups on adjacent carbon atoms are optionally taken together with their intervening atoms to form a 3-7 membered saturated, partially unsaturated, carbocyclic ring or heterocyclic ring having 1-3 heteroatoms independently selected from boron, nitrogen, oxygen, silicon, or sulfur, or a 7-13 membered saturated, partially unsaturated, bridged heterocyclic ring, or a spiro heterocyclic ring having 1-3 heteroatoms, independently selected from boron, nitrogen, oxygen, silicon, or sulfur;

Ring D is selected from 6 to 10-membered aryl or heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —C$(R)_2$—, —CH(R)—, —C$(F)_2$—, —N(R)—, —S—, —S$(O)_2$— or —(C)═CH—;

n is 0, 1, 2, 3, or 4; and q is 0, 1, 2, 3, or 4.

As defined above and described herein, $X^1$ is a bivalent moiety selected from a covalent bond, —$CH_2$—, —C$(R)_2$—, —C(O)—, —C(S)—, —CH(R)—, —CH$(CF_3)$—, —P(O)(OR)—, —P(O)(R)—, —P(O)$(NR_2)$—, —S(O)—,

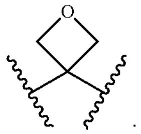 [SMILES: *C1(*)COC1]

In some embodiments, $X^1$ is a covalent bond. In some embodiments, $X^1$ is —$CH_2$—. In some embodiments, $X^1$ is —C$(R)_2$—. In some embodiments, $X^1$ is —C(O)—. In some embodiments, $X^1$ is —C(S)—. In some embodiments, $X^1$ is —CH(R)—. In some embodiments, $X^1$ is —CH$(CF_3)$—. In some embodiments, $X^1$ is —P(O)(OR)—. In some embodiments, $X^1$ is —P(O)(R)—. In some embodiments, $X^1$ is —P(O)$(NR_2)$—. In some embodiments, $X^1$ is —S(O)—. In some embodiments, $X^1$ is —S$(O)_2$—. In some embodiments, $X^1$ is

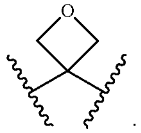 [SMILES: *C1(*)COC1]

In some embodiments, $X^1$ is selected from those depicted in Table 1, below.

As defined above and described herein, $X^2$ is a carbon atom or silicon atom.

In some embodiments, $X^2$ is a carbon atom. In some embodiments, $X^2$ is a silicon atom.

In some embodiments, $X^2$ is selected from those depicted in Table 1, below.

As defined above and described herein, $X^3$ is a bivalent moiety selected from —$CH_2$—, —C$(R)_2$—, —N(R)—, —$CF_2$—, —CHF—, —S—, —CH(R)—, —Si$(R_2)$—, or —O—.

In some embodiments, $X^3$ is —$CH_2$—. In some embodiments, $X^1$ is —C$(R)_2$—. In some embodiments, $X^3$ is —N(R)—. In some embodiments, $X^3$ is —$CF_2$—. In some embodiments, $X^3$ is —CHF—. In some embodiments, $X^3$ is —S—. In some embodiments, $X^3$ is —CH(R)—. In some embodiments, $X^3$ is —Si$(R_2)$—. In some embodiments, $X^3$ is —O—.

In some embodiments, $X^3$ is selected from those depicted in Table 1, below.

As defined above and described herein, $R^1$ is hydrogen, deuterium, halogen, —CN, —OR, —SR, —S(O)R, —S$(O)_2$R, —$NR_2$, —P(O)$(OR)_2$, —P(O)$(NR_2)$OR, —P(O)$(NR_2)_2$, —Si$(OH)_2$R, —Si(OH)$(R)_2$, —Si$(R)_3$, an optionally substituted $C_{1-4}$ aliphatic, or $R^1$ and $X^1$ or $X^4$ are taken together with their intervening atoms to form a 5-7 membered saturated, partially unsaturated, carbocyclic ring or heterocyclic ring having 1-3 heteroatoms, independently selected from nitrogen, oxygen, or sulfur.

In some embodiments, $R^1$ is hydrogen. In some embodiments, $R^1$ is deuterium. In some embodiments, $R^1$ is halogen. In some embodiments, $R^1$ is —CN. In some embodiments, $R^1$ is —OR. In some embodiments, $R^1$ is —SR. In some embodiments, $R^1$ is —S(O)R. In some embodiments, $R^1$ is —S$(O)_2$R. In some embodiments, $R^1$ is —$NR_2$. In some embodiments, $R^1$ is —P(O)$(OR)_2$. In some embodiments, $R^1$ is —P(O)$(NR_2)$OR. In some embodiments, $R^1$ is —P(O)$(NR_2)_2$. In some embodiments, $R^1$ is —Si$(OH)_2$R. In some embodiments, $R^1$ is —Si(OH)$(R)_2$. In some embodiments, $R^1$ is —Si$(R)_3$. In some embodiments, $R^1$ is an optionally substituted $C_{1-4}$ aliphatic. In some embodiments, $R^1$ and $X^1$ or $X^4$ are taken together with their intervening atoms to form a 5-7 membered saturated, partially unsaturated, carbocyclic ring or heterocyclic ring having 1-3 heteroatoms, independently selected from nitrogen, oxygen, or sulfur.

In some embodiments, $R^1$ is selected from those depicted in Table 1, below.

As defined above and described herein, each R is independently hydrogen, deuterium, or an optionally substituted group selected from $C_{1-6}$ aliphatic, phenyl, a 4-7 membered saturated or partially unsaturated heterocyclic having 1-3 heteroatoms independently selected from boron, nitrogen, oxygen, silicon, and sulfur, and a 5-6 membered heteroaryl ring having 1-4 heteroatoms independently selected from boron, nitrogen, oxygen, silicon, and sulfur, or two R groups on the same nitrogen are taken together with their intervening atoms to form a 4-7 membered saturated, partially unsaturated, or heteroaryl ring having 0-3 heteroatoms, in addition to the nitrogen, independently selected from boron, nitrogen, oxygen, silicon, and sulfur.

In some embodiments, R is hydrogen. In some embodiments, R is deuterium. In some embodiments, R is optionally substituted $C_{1-6}$ aliphatic. In some embodiments, R is optionally substituted phenyl. In some embodiments, R is optionally substituted 4-7 membered saturated or partially unsaturated heterocyclic having 1-3 heteroatoms independently selected from boron, nitrogen, oxygen, silicon, and sulfur. In some embodiments, R is optionally substituted 5-6 membered heteroaryl ring having 1-4 heteroatoms independently selected from boron, nitrogen, oxygen, silicon, and sulfur. In some embodiments, two R groups on the same nitrogen are taken together with their intervening atoms to form a 4-7 membered saturated, partially unsaturated, or heteroaryl ring having 0-3 heteroatoms, in addition to the nitrogen, independently selected from boron, nitrogen, oxygen, silicon, and sulfur.

In some embodiments, R is selected from those depicted in Table 1, below.

As defined above and described herein, each of $R^2$ and $R^{3a}$ is independently hydrogen, deuterium, —$R^6$, halogen, —CN, —$NO_2$, —OR, —$Si(OH)_2R$, —$Si(OH)R_2$, —SR, —$NR_2$, —$SiR_3$, —$S(O)_2R$, —$S(O)_2NR_2$, —S(O)R, —C(O)R, —C(O)OR, —$C(O)NR_2$, —C(O)N(R)OR, —$C(R)_2N(R)C(O)R$, —$C(R)_2N(R)C(O)NR_2$, —OC(O)R, —$OC(O)NR_2$, —$OP(O)R_2$, —$OP(O)(OR)_2$, —$OP(O)(OR)NR_2$, —$OP(O)(NR_2)_2$—, —N(R)C(O)OR, —N(R)C(O)R, —$N(R)C(O)NR_2$, —$N(R)S(O)_2R$, —$NP(O)R_2$, —$N(R)P(O)(OR)_2$, —$N(R)P(O)(OR)NR_2$, —$N(R)P(O)(NR_2)_2$, or —$N(R)S(O)_2R$.

In some embodiments, $R^2$ and $R^{3a}$ is independently hydrogen. In some embodiments, $R^2$ and $R^{3a}$ is independently deuterium. In some embodiments, $R^2$ and $R^{3a}$ is independently —R. In some embodiments, $R^2$ and $R^{3a}$ is independently halogen. In some embodiments, $R^2$ and $R^{3a}$ is independently —CN. In some embodiments, $R^2$ and $R^{3a}$ is independently —$NO_2$. In some embodiments, $R^2$ and $R^{3a}$ is independently —OR. In some embodiments, $R^2$ and $R^{3a}$ is independently —$Si(OH)_2R$. In some embodiments, $R^2$ and $R^{3a}$ is independently —$Si(OH)R_2$. In some embodiments, $R^2$ and $R^{3a}$ is independently —SR. In some embodiments, $R^2$ and $R^{3a}$ is independently —$NR_2$. In some embodiments, $R^2$ and $R^{3a}$ is independently —$SiR_3$. In some embodiments, $R^2$ and $R^{3a}$ is independently —$S(O)_2R$. In some embodiments, $R^2$ and $R^{3a}$ is independently —$S(O)_2NR_2$. In some embodiments, $R^2$ and $R^{3a}$ is independently —S(O)R. In some embodiments, $R^2$ and $R^{3a}$ is independently —C(O)R. In some embodiments, $R^2$ and $R^{3a}$ is independently —C(O)OR. In some embodiments, $R^2$ and $R^{3a}$ is independently —$C(O)NR_2$. In some embodiments, $R^2$ and $R^{3a}$ is independently —C(O)N(R)OR. In some embodiments, $R^2$ and $R^{3a}$ is independently —$C(R)_2N(R)C(O)R$. In some embodiments, $R^2$ and $R^{3a}$ is independently —$C(R)_2N(R)C(O)NR_2$. In some embodiments, $R^2$ and $R^{3a}$ is independently —OC(O)R. In some embodiments, $R^2$ and $R^{3a}$ is independently —$OC(O)NR_2$. In some embodiments, $R^2$ and $R^{3a}$ is independently —$OP(O)R_2$. In some embodiments, $R^2$ and $R^{3a}$ is independently —$OP(O)(OR)_2$. In some embodiments, $R^2$ and $R^{3a}$ is independently —$OP(O)(OR)NR_2$. In some embodiments, $R^2$ and $R^{3a}$ is independently —$OP(O)(NR_2)_2$—. In some embodiments, $R^2$ and $R^{3a}$ is independently —N(R)C(O)OR. In some embodiments, $R^2$ and $R^{3a}$ is independently —N(R)C(O)R. In some embodiments, $R^2$ and $R^{3a}$ is independently —$N(R)C(O)NR_2$. In some embodiments, $R^2$ and $R^{3a}$ is independently —$NP(O)R_2$. In some embodiments, $R^2$ and $R^{3a}$ is independently —$N(R)P(O)(OR)_2$. In some embodiments, $R^2$ and $R^{3a}$ is independently —$N(R)P(O)(OR)NR_2$. In some embodiments, $R^2$ and $R^{3a}$ is independently —$N(R)P(O)(NR_2)_2$. In some embodiments, $R^2$ and $R^{3a}$ is independently —$N(R)S(O)_2R$.

In some embodiments, $R^2$ and $R^{3a}$ is independently —OH. In some embodiments, $R^2$ and $R^{3a}$ is independently —$NH_2$. In some embodiments, $R^2$ and $R^{3a}$ is independently —$CH_2NH_2$. In some embodiments, $R^2$ and $R^{3a}$ is independently —$CH_2NHCOMe$. In some embodiments, $R^2$ and $R^{3a}$ is independently —$CH_2NHCONHMe$. In some embodiments, $R^2$ and $R^{3a}$ is independently —NHCOMe. In some embodiments, $R^2$ and $R^{3a}$ is independently —NHCONHEt. In some embodiments, $R^2$ and $R^{3a}$ is independently —$SiMe_3$. In some embodiments, $R^2$ and $R^{3a}$ is independently —$SiMe_2OH$. In some embodiments, $R^2$ and $R^{3a}$ is independently —$SiMe(OH)_2$. In some embodiments $R^2$ and $R^{3a}$ is independently

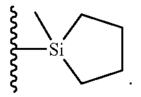 [SMILES: *[Si]1(C)CCCC1]

In some embodiments, $R^2$ and $R^{3a}$ is independently Br. In some embodiments, $R^2$ and $R^{3a}$ is independently Cl. In some embodiments, $R^2$ and $R^{3a}$ is independently F. In some embodiments, $R^2$ and $R^{3a}$ is independently Me. In some embodiments, $R^2$ and $R^{3a}$ is independently —NHMe. In some embodiments, $R^2$ and $R^{3a}$ is independently —$NMe_2$. In some embodiments, $R^2$ and $R^{3a}$ is independently —$NHCO_2Et$. In some embodiments, $R^2$ and $R^{3a}$ is independently —CN. In some embodiments, $R^2$ and $R^{3a}$ is independently —$CH_2Ph$. In some embodiments, $R^2$ and $R^{3a}$ is independently —$NHCO_2tBu$. In some embodiments, $R^2$ and $R^{3a}$ is independently —$CO_2tBu$. In some embodiments, $R^2$ and $R^{3a}$ is independently —OMe. In some embodiments, $R^2$ and $R^{3a}$ is independently —$CF_3$.

In some embodiments, $R^2$ or $R^{3a}$ is selected from those depicted in Table 1, below.

As defined above and described herein, $R^3$ is hydrogen, deuterium, halogen, —CN, —$NO_2$, —OR, —$NR_2$, —SR, —$S(O)_2R$, —$S(O)_2NR_2$, —S(O)R, —C(O)R, —C(O)OR, —$C(O)NR_2$, —C(O)NR(OR), —OC(O)R, —$OC(O)NR_2$, —$OP(O)(OR)_2$, —$OP(O)(NR_2)_2$, —$OP(O)(OR)NR_2$, —N(R)C(O)R, —N(R)C(O)OR, —$N(R)C(O)NR_2$, —$N(R)S(O)_2R$, —$N(R)S(O)_2NR_2$, —$N(R)P(O)(OR)_2$, —N(R)P(O)

(OR)$NR_2$, —P(O)$(OR)_2$, —P(O)($NR_2$)OR, —P(O)$(NR_2)_2$, —Si$(OH)_2$R, —Si(OH)$(R)_2$, or —Si$(R)_3$.

In some embodiments, $R^3$ is hydrogen. In some embodiments, $R^3$ is deuterium. In some embodiments, $R^3$ is halogen. In some embodiments, $R^3$ is —CN. In some embodiments, $R^3$ is —$NO_2$. In some embodiments, $R^3$ is —OR. In some embodiments, $R^3$ is —$NR_2$. In some embodiments, $R^3$ is —SR. In some embodiments, $R^3$ is —S$(O)_2$R. In some embodiments, $R^3$ is —S$(O)_2NR_2$. In some embodiments, $R^3$ is —S(O)R. In some embodiments, $R^3$ is —C(O)R. In some embodiments, $R^3$ is —C(O)OR. In some embodiments, $R^3$ is —C(O)$NR_2$. In some embodiments, $R^3$ is —C(O)NR(OR). In some embodiments, $R^3$ is —OC(O)R. In some embodiments, $R^3$ is —OC(O)$NR_2$. In some embodiments, $R^3$ is —OP(O)$(OR)_2$. In some embodiments, $R^3$ is —OP(O)$(NR_2)_2$. In some embodiments, $R^3$ is —OP(O)(OR)$NR_2$. In some embodiments, $R^3$ is —N(R)C(O)R. In some embodiments, $R^3$ is —N(R)C(O)OR. In some embodiments, $R^3$ is —N(R)C(O)$NR_2$. In some embodiments, $R^3$ is —N(R)S$(O)_2$R. In some embodiments, $R^3$ is —N(R)S$(O)_2NR_2$. In some embodiments, $R^3$ is —N(R)P(O)$(OR)_2$. In some embodiments, $R^3$ is —N(R)P(O)(OR)$NR_2$. In some embodiments, $R^3$ is —P(O)$(OR)_2$. In some embodiments, $R^3$ is —P(O)($NR_2$)OR. In some embodiments, $R^3$ is —P(O)$(NR_2)_2$. In some embodiments, $R^3$ is —Si$(OH)_2$R. In some embodiments, $R^3$ is —Si(OH)$(R)_2$. In some embodiments, $R^3$ is —Si$(R)_3$.

In some embodiments, $R^3$ is methyl. In some embodiments, $R^3$ is —$OCH_3$. In some embodiments, $R^3$ is chloro.

In some embodiments, $R^3$ is selected from those depicted in Table 1, below.

As defined above and described herein, each $R^4$ is independently hydrogen, deuterium, —$R^6$, halogen, —CN, —$NO_2$, —OR, —SR, —$NR_2$, —S$(O)_2$R, —S$(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, —N(R)S$(O)_2$R, —P(O)$(OR)_2$, —P(O)($NR_2$)OR, or —P(O)$(NR_2)_2$.

In some embodiments, $R^4$ is hydrogen. In some embodiments, $R^4$ is —$R^6$. In some embodiments, $R^4$ is halogen. In some embodiments, $R^4$ is —CN. In some embodiments, $R^4$ is —$NO_2$. In some embodiments, $R^4$ is —OR. In some embodiments, $R^4$ is —SR. In some embodiments, $R^4$ is —$NR_2$. In some embodiments, $R^4$ is —S$(O)_2$R. In some embodiments, $R^4$ is —S$(O)_2NR_2$. In some embodiments, $R^4$ is —S(O)R. In some embodiments, $R^4$ is —C(O)R. In some embodiments, $R^4$ is —C(O)OR. In some embodiments, $R^4$ is —C(O)$NR_2$. In some embodiments, $R^4$ is —C(O)N(R)OR. In some embodiments, $R^4$ is —OC(O)R. In some embodiments, $R^4$ is —OC(O)$NR_2$. In some embodiments, $R^4$ is —N(R)C(O)OR. In some embodiments, $R^4$ is —N(R)C(O)R. In some embodiments, $R^4$ is —N(R)C(O)$NR_2$. In some embodiments, $R^4$ is —N(R)S$(O)_2$R. In some embodiments, $R^4$ is —P(O)$(OR)_2$. In some embodiments, $R^4$ is —P(O)($NR_2$)OR. In some embodiments, $R^4$ is —P(O)$(NR_2)_2$.

In some embodiments, $R^4$ is methyl. In some embodiments, $R^4$ is ethyl. In some embodiments, $R^4$ is cyclopropyl.

In some embodiments, $R^4$ is selected from those depicted in Table 1, below.

As defined above and described herein, $R^5$ is hydrogen, deuterium, an optionally substitute $C_{1-4}$ aliphatic, or —CN.

In some embodiments, $R^5$ is hydrogen. In some embodiments, $R^5$ is deuterium. In some embodiments, $R^5$ is an optionally substituted $C_{1-4}$ aliphatic. In some embodiments, $R^5$ is —CN.

In some embodiments, $R^5$ is selected from those depicted in Table 1, below.

As defined above and described herein, each $R^6$ is independently an optionally substituted group selected from $C_{1-6}$ aliphatic, phenyl, a 4-7 membered saturated or partially unsaturated heterocyclic ring having 1-3 heteroatoms independently selected from boron, nitrogen, oxygen, silicon, and sulfur, and a 5-6 membered heteroaryl ring having 1-4 heteroatoms independently selected from boron, nitrogen, oxygen, silicon, and sulfur.

In some embodiments, $R^6$ is an optionally substituted $C_{1-6}$ aliphatic. In some embodiments, $R^6$ is an optionally substituted phenyl. In some embodiments, $R^6$ is an optionally substituted 4-7 membered saturated or partially unsaturated heterocyclic ring having 1-3 heteroatoms independently selected from boron, nitrogen, oxygen, silicon, and sulfur. In some embodiments, $R^6$ is an optionally substituted 5-6 membered heteroaryl ring having 1-4 heteroatoms independently selected from boron, nitrogen, oxygen, silicon, and sulfur.

In some embodiments, $R^6$ is selected from those depicted in Table 1, below.

As defined generally above, each $R^7$ is independently hydrogen, deuterium, halogen, —CN, —OR, —SR, —S(O)R, —S$(O)_2$R, —N$(R)_2$, —P(O)$(R)_2$, —P(O)$(OR)_2$, —P(O)($NR_2$)OR, —P(O)$(NR_2)_2$, —Si(OH)$R_2$, —Si$(OH)_2$R, —Si$R_3$, or an optionally substituted $C_{1-4}$ aliphatic, or $R^7$ and $X^1$ or $X^3$ are taken together with their intervening atoms to form a 5-7 membered saturated, partially unsaturated, carbocyclic ring or heterocyclic ring having 1-3 heteroatoms, independently selected from boron, nitrogen, oxygen, silicon, or sulfur, or two $R^7$ groups on the same carbon are optionally taken together with their intervening atoms to form a 3-6 membered spiro fused ring or a 4-7 membered heterocyclic ring having 1-2 heteroatoms independently selected from boron, nitrogen, oxygen, silicon, or sulfur, or two $R^7$ groups on adjacent carbon atoms are optionally taken together with their intervening atoms to form a 3-7 membered saturated, partially unsaturated, carbocyclic ring or heterocyclic ring having 1-3 heteroatoms independently selected from boron, nitrogen, oxygen, silicon, or sulfur, or a 7-13 membered saturated, partially unsaturated, bridged heterocyclic ring, or a spiro heterocyclic ring having 1-3 heteroatoms, independently selected from boron, nitrogen, oxygen, silicon, or sulfur.

In some embodiments, $R^7$ is hydrogen. In some embodiments, $R^7$ is deuterium. In some embodiments, $R^7$ is halogen. In some embodiments, $R^7$ is —CN. In some embodiments, $R^7$ is —OR. In some embodiments, $R^7$ is —SR. In some embodiments, $R^7$ is —S(O)R. In some embodiments, $R^7$ is —S$(O)_2$R. In some embodiments, $R^7$ is —$NR_2$. In some embodiments, $R^7$ is —Si$(R)_3$. In some embodiments, $R^7$ is —P(O)$(R)_2$. In some embodiments, $R^7$ is —P(O)$(OR)_2$. In some embodiments, $R^7$ is —P(O)($NR_2$)OR. In some embodiments, $R^7$ is —P(O)$(NR_2)_2$. In some embodiments, $R^7$ is —Si(OH)$R_2$. In some embodiments, $R^7$ is —Si$(OH)_2$R. In some embodiments, $R^7$ is an optionally substituted $C_{1-4}$ aliphatic. In some embodiments, $R^7$ and $X^1$ or $X^3$ are taken together with their intervening atoms to form a 5-7 membered saturated, partially unsaturated, carbocyclic ring or heterocyclic ring having 1-3 heteroatoms, independently selected from boron, nitrogen, oxygen, silicon, or sulfur. In some embodiments, two $R^7$ groups on the same carbon are optionally taken together with their intervening atoms to form a 3-6 membered spiro fused ring or a 4-7 membered heterocyclic ring having 1-2 heteroatoms independently selected from boron, nitrogen, oxygen, silicon, or sulfur. In some embodiments, two $R^7$ groups on adjacent carbon atoms are optionally taken together with their intervening atoms to form a 3-7 membered saturated, partially unsaturated, carbocyclic ring or heterocyclic ring having 1-3 heteroatoms independently selected from boron, nitrogen, oxygen, silicon, or sulfur. In some embodiments, two $R^7$ groups on adjacent carbon atoms are optionally taken together with their intervening atoms to form a 7-13 membered saturated, partially unsaturated, bridged heterocyclic ring, or a spiro heterocyclic ring having 1-3 heteroatoms, independently selected from boron, nitrogen, oxygen, silicon, or sulfur.

In some embodiments, $R^7$ is selected from hydrogen, halogen, —CN, —OR, —$NR_2$, or $C_{1-4}$ alkyl. In some embodiments, $R^7$ is selected from hydrogen, halogen, —CN, or $C_{1-4}$ alkyl. In some embodiments, $R^7$ is fluoro. In some embodiments, two $R^7$ groups on the same carbon are optionally taken together with their intervening atoms to form a 3- or 4-membered spiro fused ring.

In some embodiments, $R^7$ is selected from those depicted in Table 1 below.

As defined above and described herein, Ring A is a bi- or tricyclic ring selected from

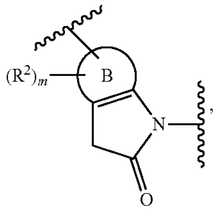
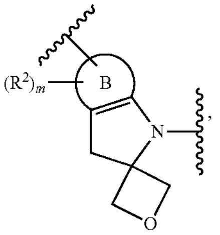
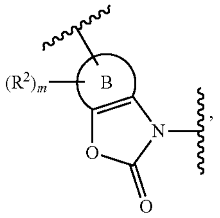
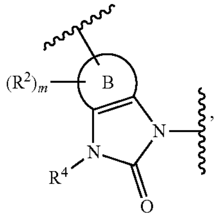
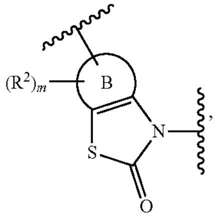
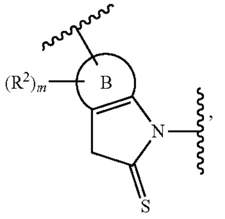
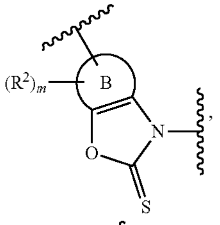
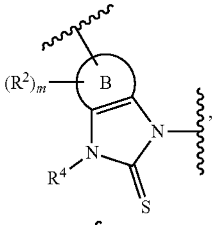
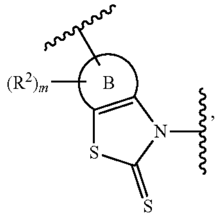
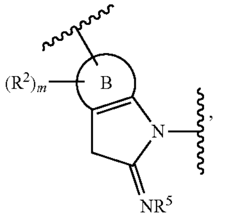

-continued

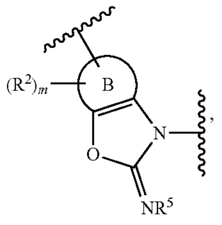
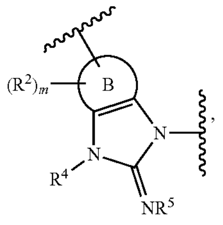
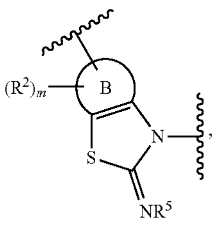
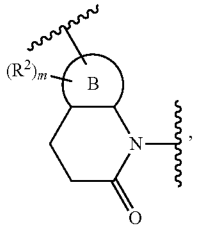
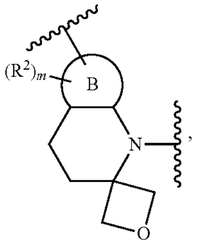
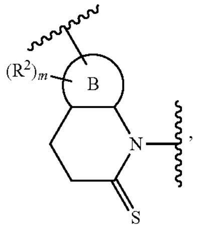
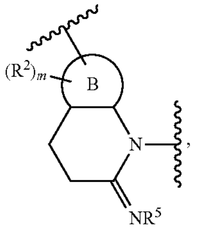
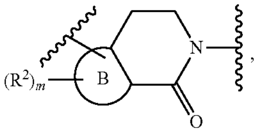
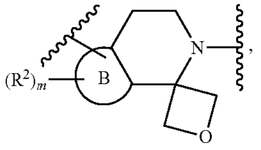
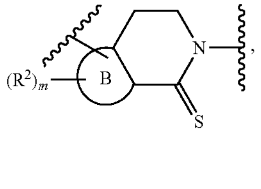
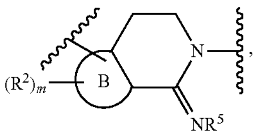
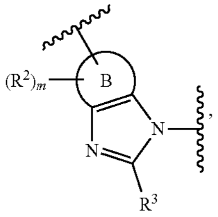
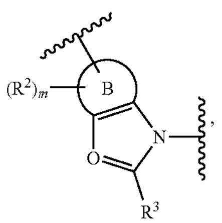
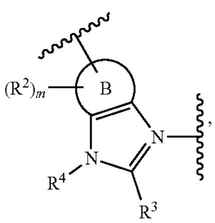
or -continued
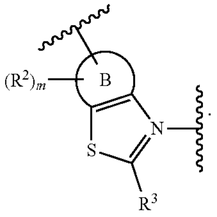
In some embodiments, Ring A is
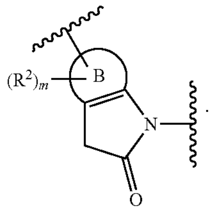
In some embodiments, Ring A is
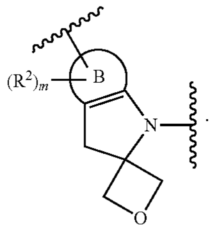
In some embodiments, Ring A is
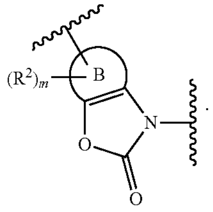
In some embodiments, Ring A is
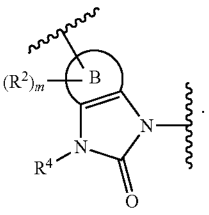
In some embodiments, Ring A is
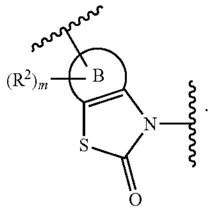
In some embodiments, Ring A is
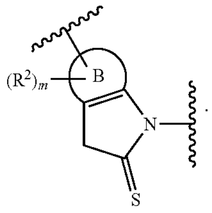
In some embodiments, Ring A is
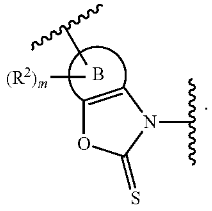
In some embodiments, Ring A is
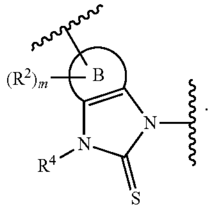
In some embodiments, Ring A is
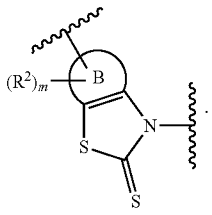

In some embodiments, Ring A is
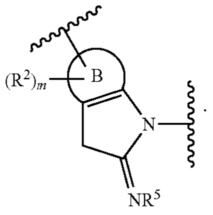
In some embodiments, Ring A is
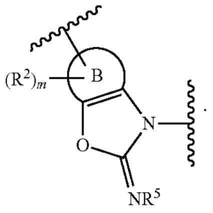
In some embodiments, Ring A is
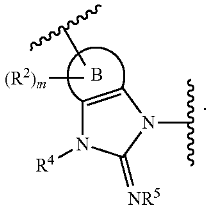
In some embodiments, Ring A is
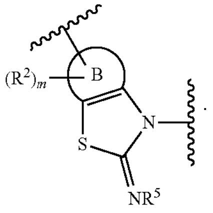
In some embodiments,
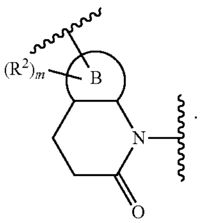
In some embodiments, Ring A is
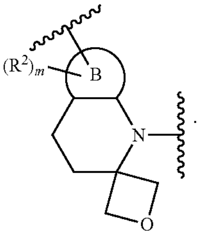
In some embodiments, Ring A is
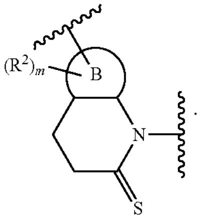
In some embodiments, Ring A is
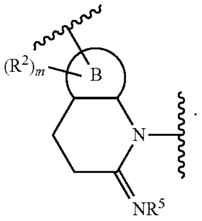
In some embodiments, Ring A is
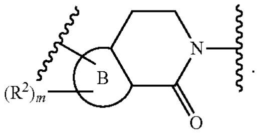
In some embodiments, Ring A is
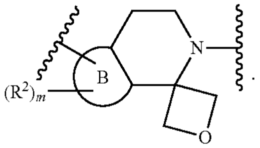
In some embodiments, Ring A is
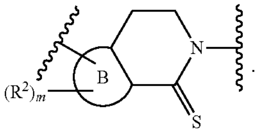

In some embodiments, Ring A is
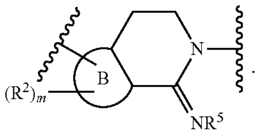
In some embodiments, Ring A is
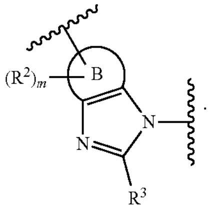
In some embodiments, Ring A is
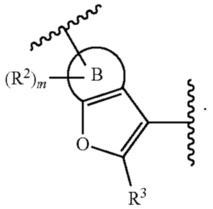
In some embodiments, Ring A is
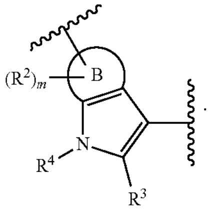
In some embodiments, Ring A is
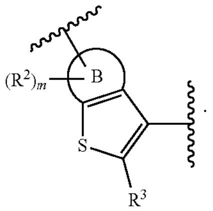
In some embodiments, Ring A is
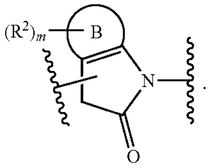
In some embodiments, Ring A is
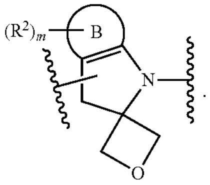
In some embodiments, Ring A is
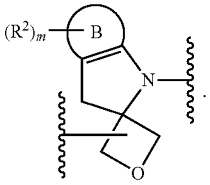
In some embodiments, Ring A is
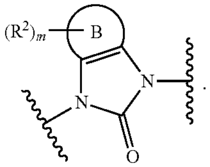
In some embodiments, Ring A is
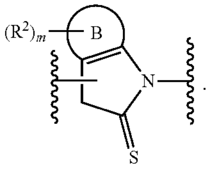
In some embodiments, Ring A is
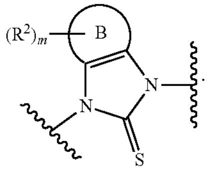

In some embodiments, Ring A is
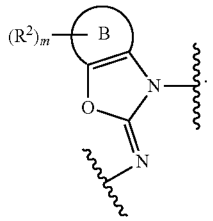
In some embodiments, Ring A is
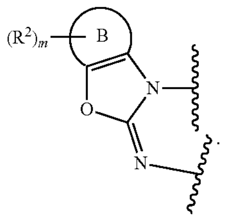
In some embodiments, Ring A is
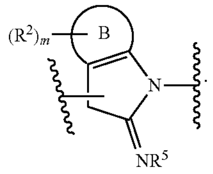
In some embodiments, Ring A is
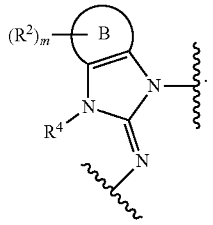
In some embodiments, Ring A is
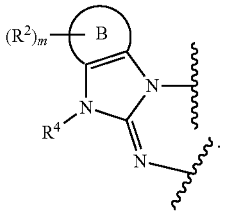
In some embodiments, Ring A is
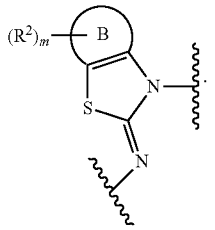
In some embodiments, Ring A is
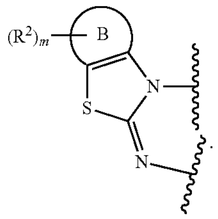
In some embodiments, Ring A is
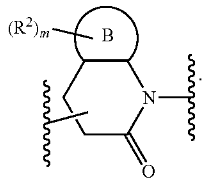
In some embodiments, Ring A is
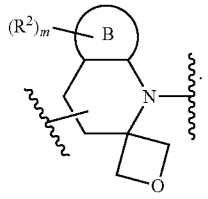
In some embodiments, Ring A is
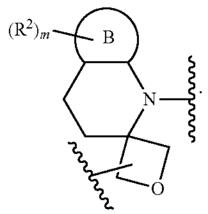

In some embodiments, Ring A is
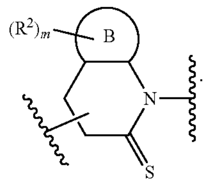
In some embodiments, Ring A is
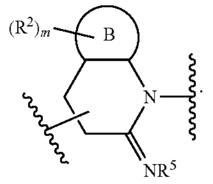
In some embodiments, Ring A is
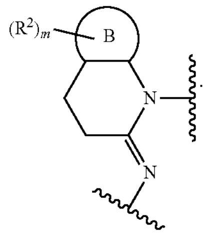
In some embodiments, Ring A is
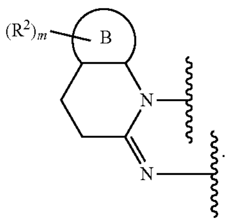
In some embodiments, Ring A is
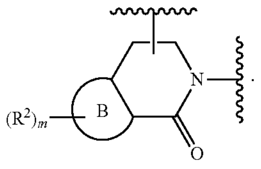
In some embodiments, Ring A is
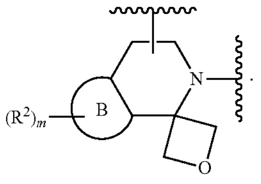
In some embodiments, Ring A is
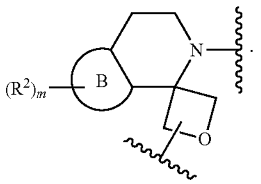
In some embodiments, Ring A is
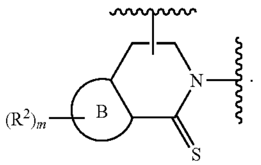
In some embodiments, Ring A is
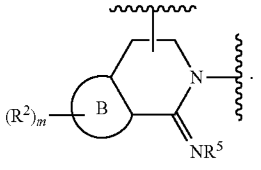
In some embodiments, Ring A is
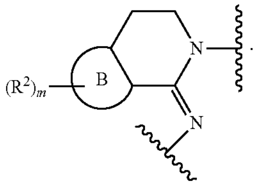
In some embodiments, Ring A is
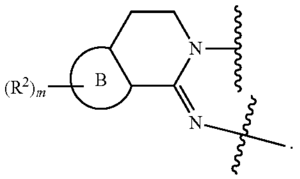

In some embodiments, Ring A is

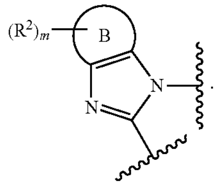

In some embodiments, Ring A is

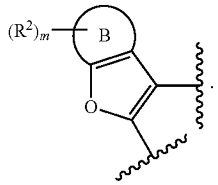

In some embodiments, Ring A is

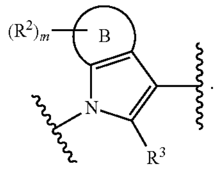

In some embodiments, Ring A is

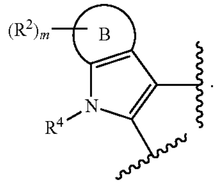

In some embodiments, Ring A is

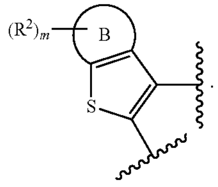

In some embodiments, Ring A is selected from those depicted in Table 1, below.

As defined above and described herein, Ring B is a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

In some embodiments, Ring B is a fused 6-membered aryl. In some embodiments, Ring B is a fused 6-membered heteroaryl containing 1-4 heteroatoms independently selected from nitrogen, oxygen, or sulfur. In some embodiments, Ring B is a fused 5 to 7-membered saturated or partially unsaturated carbocyclyl. In some embodiments, Ring B is fused 5 to 7-membered saturated or partially saturated heterocyclyl with 1-3 heteroatoms independently selected from boron, nitrogen, oxygen, silicon, or sulfur. In some embodiments, Ring B is fused 5-membered heteroaryl with 1-4 heteroatoms independently selected from boron, nitrogen, oxygen, silicon, or sulfur.

In some embodiments, Ring B is

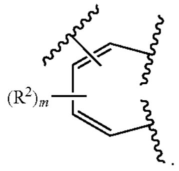

In some embodiments, Ring B is

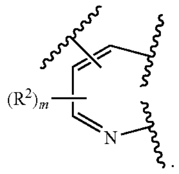

In some embodiments, Ring B is

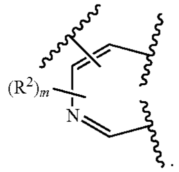

In some embodiments, Ring B is

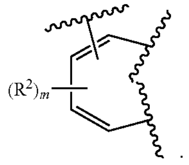

In some embodiments, Ring B is

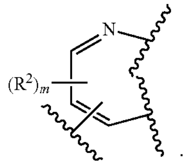

In some embodiments, each Ring B is

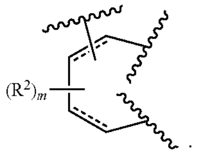

In some embodiments, each Ring B is

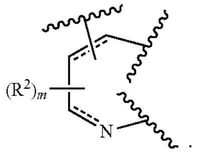

In some embodiments, each Ring B is

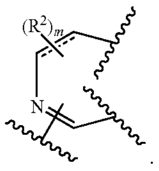

In some embodiments, each Ring B is

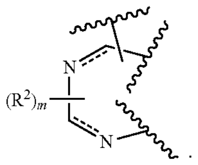

In some embodiments, Ring B is

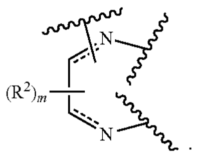

In some embodiments, Ring B is

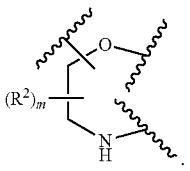

In some embodiments, Ring B is

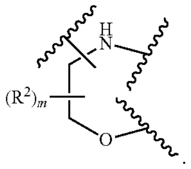

In some embodiments, Ring B is

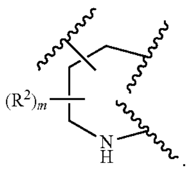

In some embodiments, Ring B is

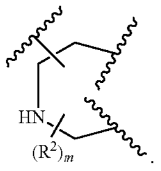

In some embodiments, Ring B is

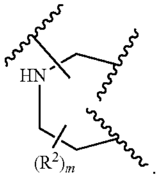

In some embodiments, Ring B is

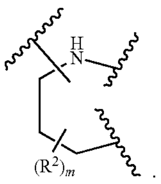

In some embodiments, Ring B is

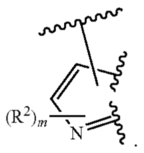

In some embodiments, Ring B is

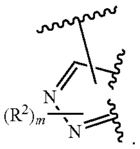

In some embodiments, Ring B is

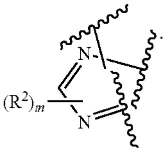

In some embodiments, Ring B is

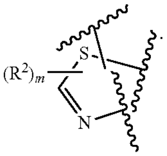

In some embodiments, Ring B is

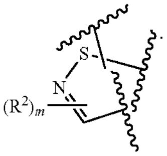

In some embodiments, Ring B is

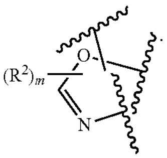

In some embodiments, Ring B is

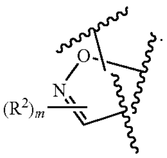

In some embodiments, Ring B is

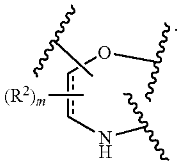

In some embodiments, Ring B is

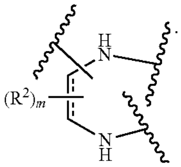

In some embodiments, Ring B is

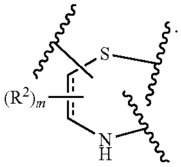

In some embodiments, Ring B is

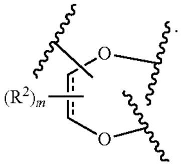

In some embodiments, Ring B is

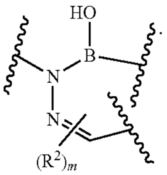

In some embodiments, Ring B is selected from

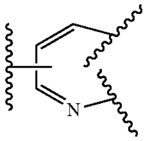

,

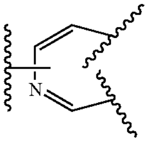

,

-continued
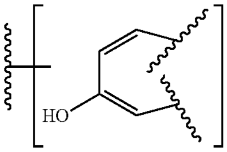,
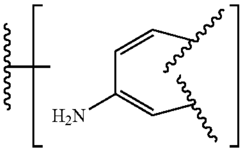,
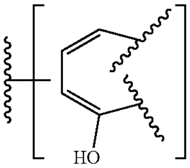,
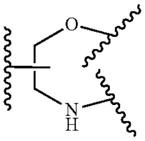,
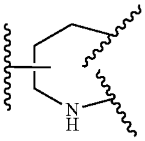,
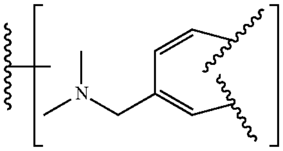,
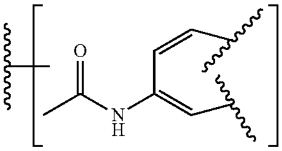,
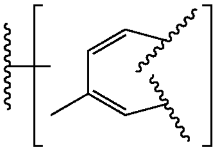,
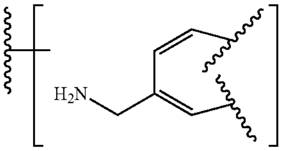,
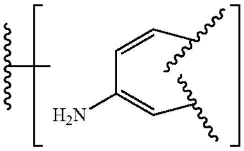,
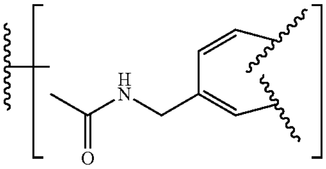,
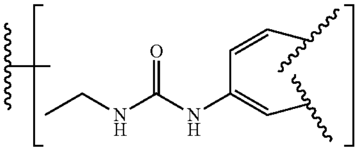,
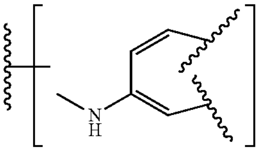,
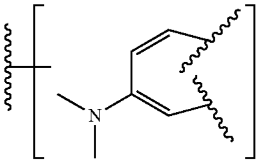,
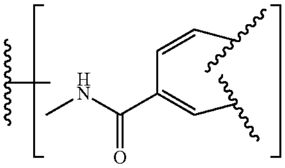,
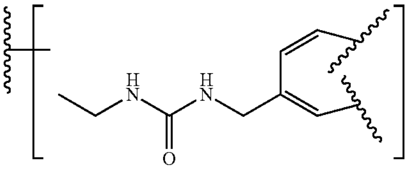,
-continued
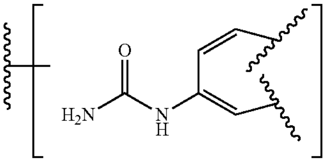,
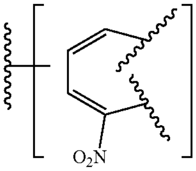,
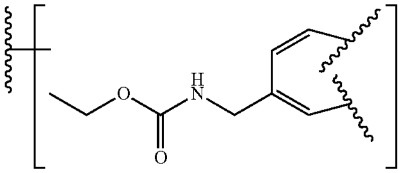,
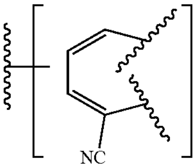,
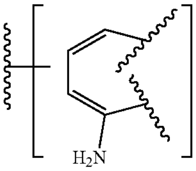,
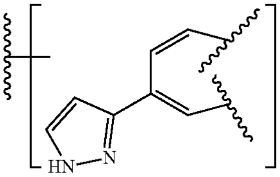,
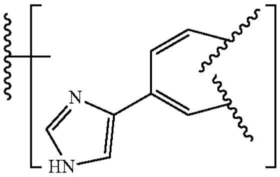, or
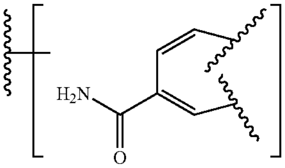.
In some embodiments, Ring B is selected from those depicted in Table 1, below.
As defined above and described herein, Ring C is a monocyclic or bicyclic ring selected from
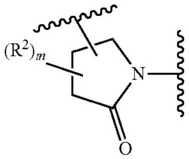,
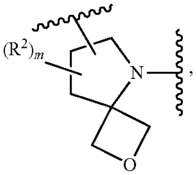,
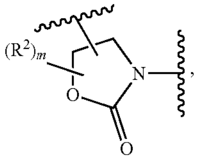,
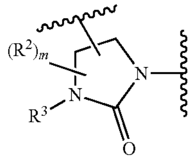,
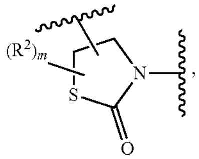,
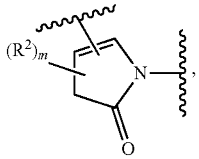, -continued
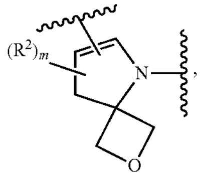, 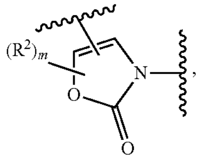,
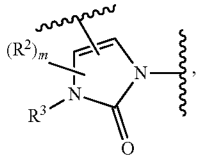, 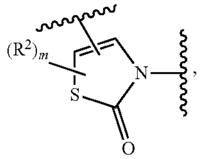,
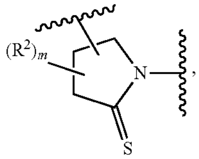, 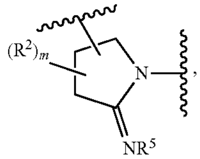,
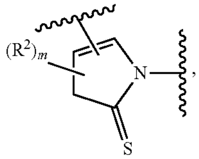, 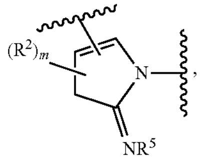,
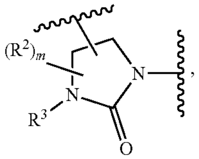, 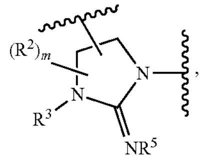,
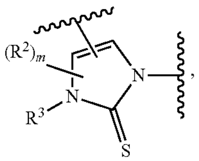, 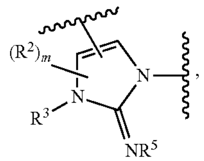,
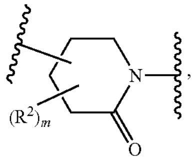, 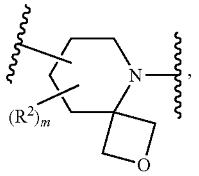,
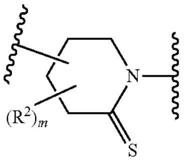 or 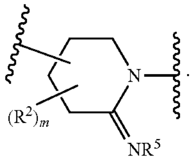.
In some embodiments, Ring C is
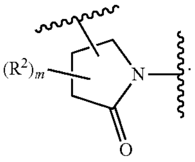.
In some embodiments, Ring C is
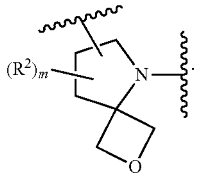.
In some embodiments, Ring C is
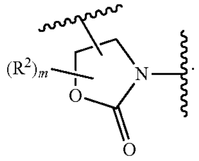.
In some embodiments, Ring C is
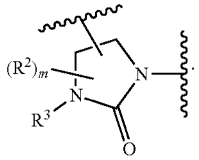.
In some embodiments, Ring C is
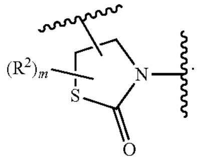.
In some embodiments, Ring C is
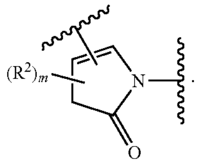.
In some embodiments, Ring C is
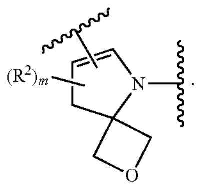.

In some embodiments, Ring C is
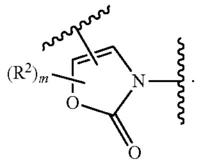
In some embodiments, Ring C is
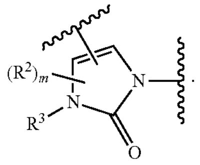
In some embodiments, Ring C is
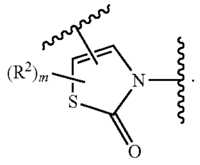
In some embodiments, Ring C is
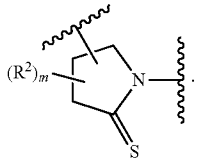
In some embodiments, Ring C is
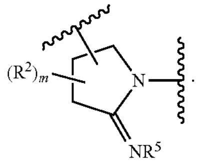
In some embodiments, Ring C is
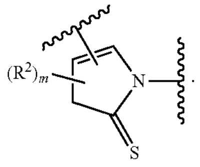
In some embodiments, Ring C is
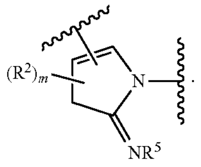
In some embodiments, Ring C is
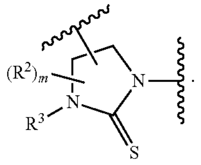
In some embodiments, Ring C is
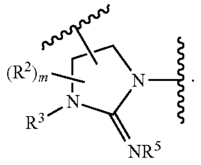
In some embodiments, Ring C is
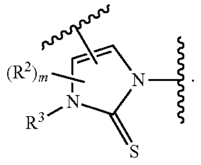
In some embodiments, Ring C is
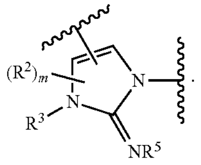
In some embodiments, Ring C is
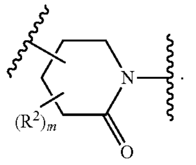

In some embodiments, Ring C is
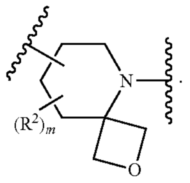
In some embodiments, Ring C is
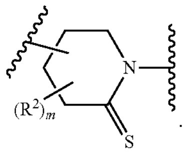
In some embodiments, Ring C is
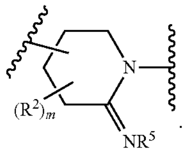
In some embodiments, Ring C is
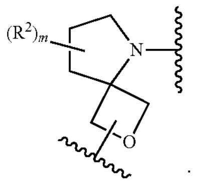
In some embodiments, Ring C is
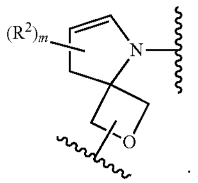
In some embodiments, Ring C is
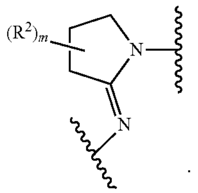
In some embodiments, Ring C is
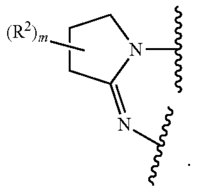
In some embodiments, Ring C is
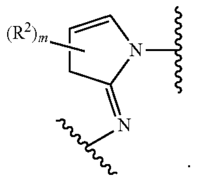
In some embodiments, Ring C is
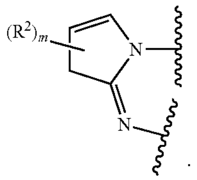
In some embodiments, Ring C is
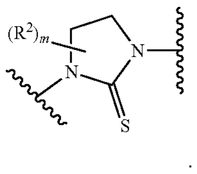
In some embodiments, Ring C is
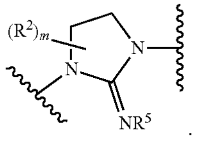
In some embodiments, Ring C is
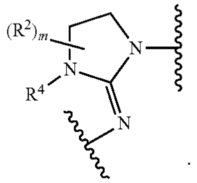

In some embodiments, Ring C is
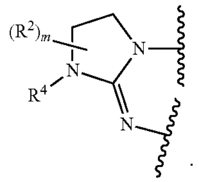
.
In some embodiments, Ring C is
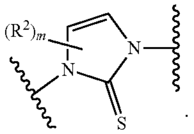
.
In some embodiments, Ring C is
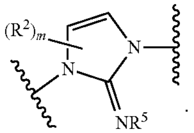
.
In some embodiments, Ring C is
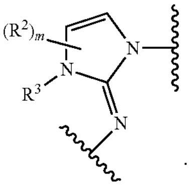
.
In some embodiments, Ring C is
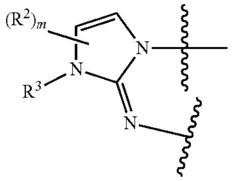
.
In some embodiments, Ring C is
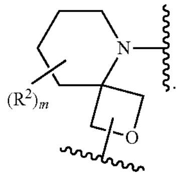
.
In some embodiments, Ring C is
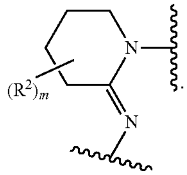
.
In some embodiments, Ring C is
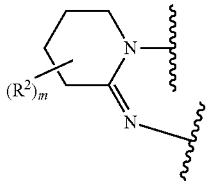
.
In some embodiments, Ring C is a monocyclic or bicyclic ring selected from
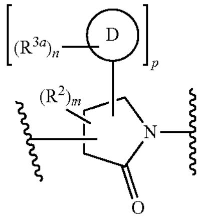
,
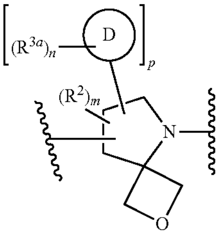
,
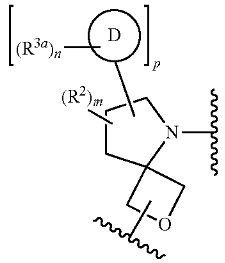
,
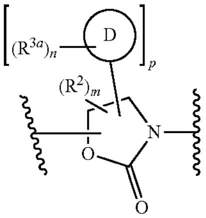
,
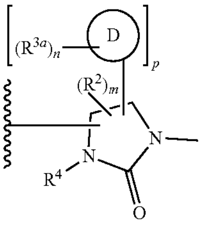
,
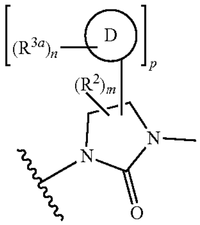
,
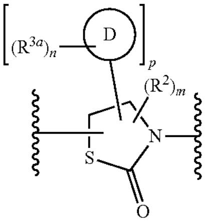
,
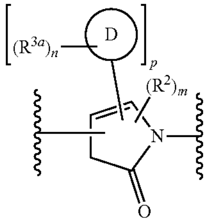
, -continued
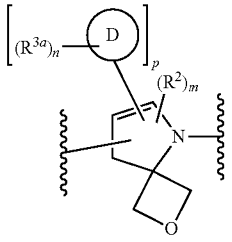,
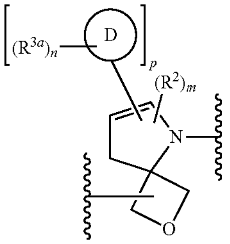,
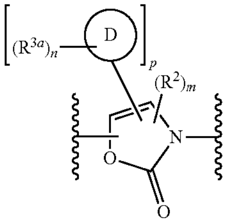,
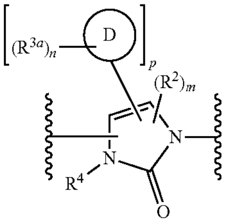,
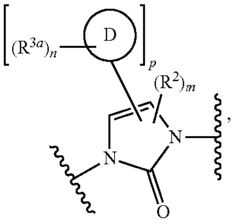,
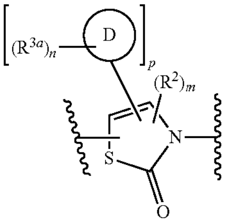,
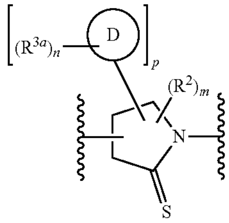,
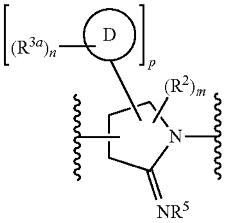,
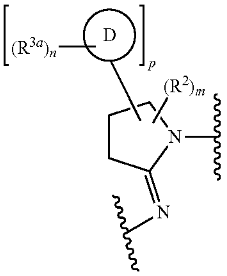,
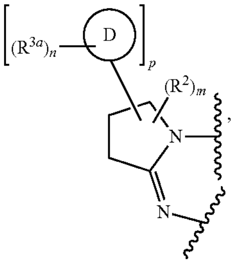,
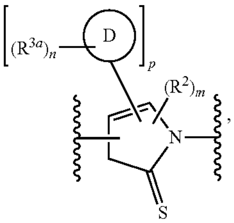,
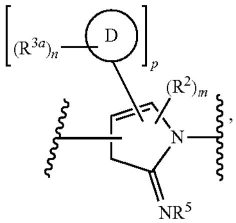,
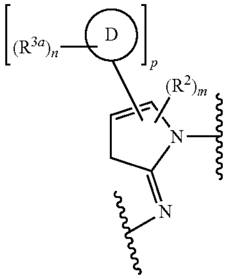,
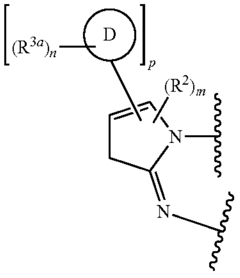,
-continued
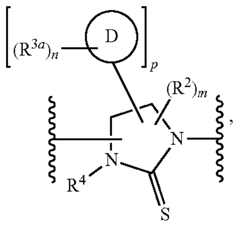,
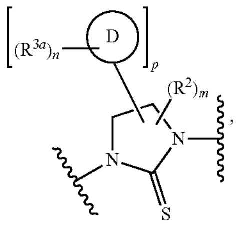,
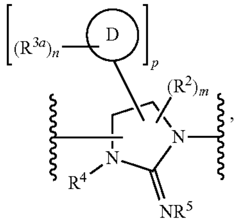,
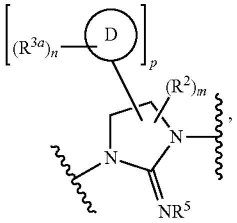,
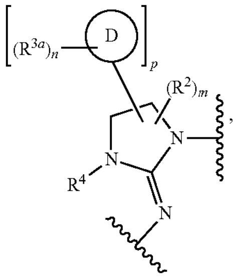,
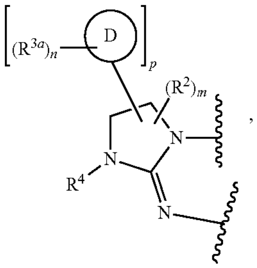,
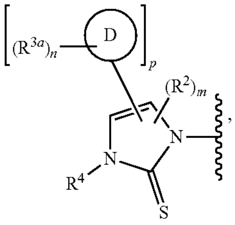,
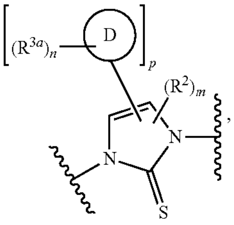,
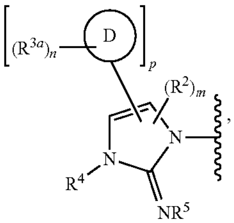,
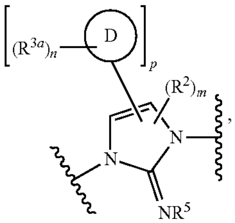,
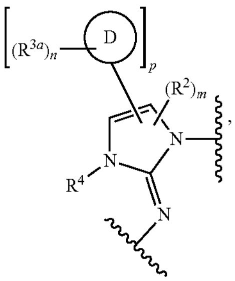,
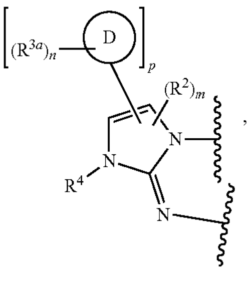,
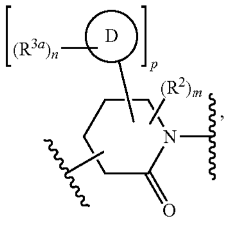,
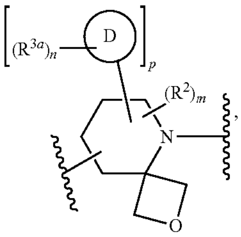, -continued

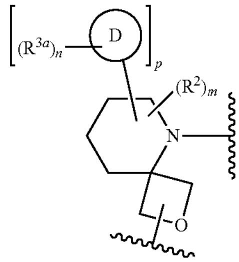

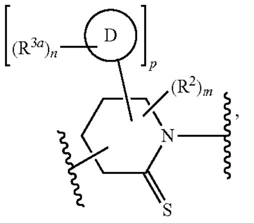

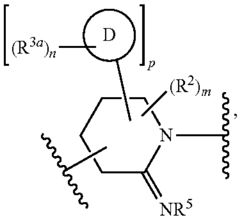

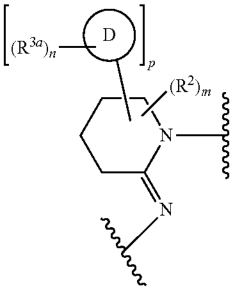

or

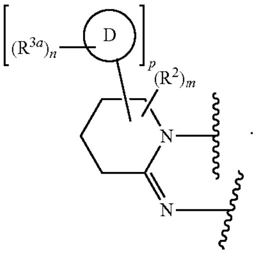

In some embodiments, Ring C is selected from

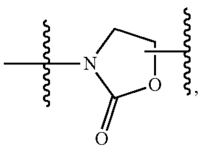

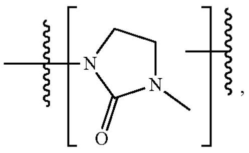

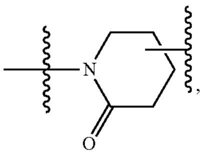

or

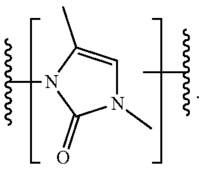

In some embodiments, Ring C is selected from

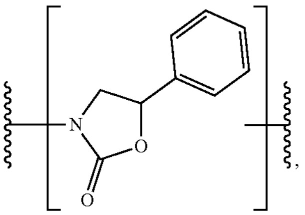

-continued

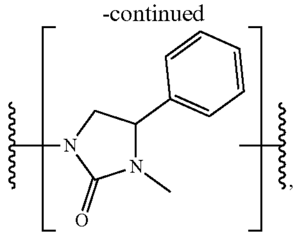

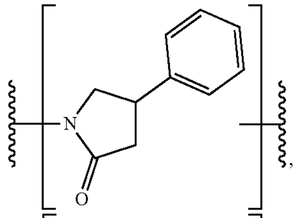

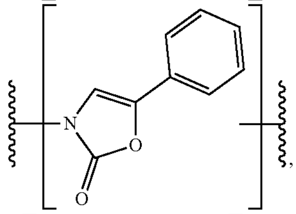

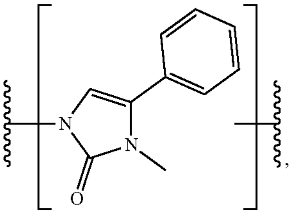

or

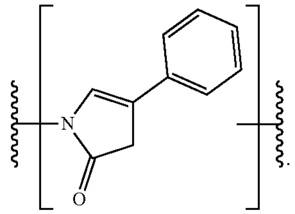

In some embodiments, Ring C is selected from those depicted in Table 1, below.

As defined above and described herein, Ring D is a ring selected from 6 to 10-membered aryl or heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

In some embodiments, Ring D is a 6 to 10-membered aryl. In some embodiments, Ring D is a 6 to 10-membered heteroaryl containing 1-4 heteroatoms independently selected from nitrogen, oxygen, or sulfur. In some embodiments, Ring D is a 5 to 7-membered saturated or partially unsaturated carbocyclyl. In some embodiments, Ring D is 5 to 7-membered saturated or partially saturated heterocyclyl with 1-3 heteroatoms independently selected from boron, nitrogen, oxygen, silicon, or sulfur. In some embodiments, Ring D is 5-membered heteroaryl with 1-4 heteroatoms independently selected from boron, nitrogen, oxygen, silicon, or sulfur.

In some embodiments, Ring D is isoquinoline. In some embodiments, Ring D is imidazo[1,2-a]pyridine.

In some embodiments, Ring D is selected from those depicted in Table 1, below.

As defined above and described herein, each of Ring E, Ring F, and Ring G is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur, wherein each of Ring E, Ring F, and Ring G is independently and optionally further substituted with 1-2 oxo groups.

In some embodiments, each Ring E, Ring F, and Ring G is independently a 6-membered aryl. In some embodiments, each Ring E, Ring F, and Ring G is independently a 6-membered heteroaryl containing 1-4 heteroatoms independently selected from nitrogen, oxygen, or sulfur. In some embodiments, each Ring E, Ring F, and Ring G is independently a 5 to 7-membered saturated or partially unsaturated carbocyclyl. In some embodiments, each Ring E, Ring F, and Ring G is independently a 5 to 7-membered saturated or partially unsaturated heterocyclyl with 1-3 heteroatoms independently selected from boron, nitrogen, oxygen, silicon, or sulfur. In some embodiments, each Ring E, Ring F, and Ring G is independently a 5-membered heteroaryl with 1-4 heteroatoms independently selected from nitrogen, oxygen or sulfur. In some embodiments, each of Ring E, Ring F, and Ring G is independently and optionally further substituted with 1-2 oxo groups.

In some embodiments, Ring F is

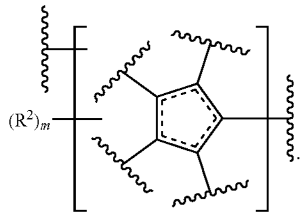

In some embodiments, Ring F is

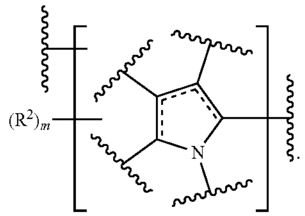

In some embodiments, Ring F is

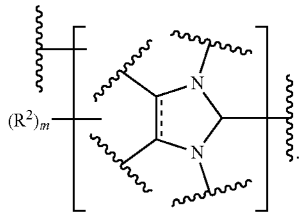

In some embodiments, Ring F is

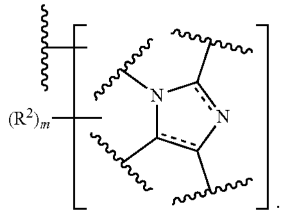

In some embodiments, Ring F is

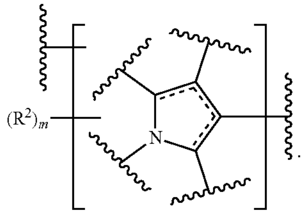

In some embodiments, Ring F is

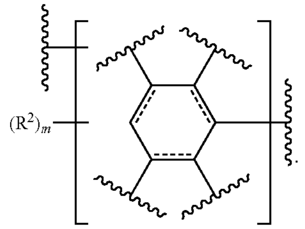

In some embodiments, Ring F is

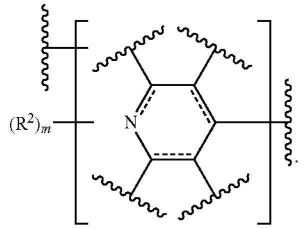

In some embodiments, Ring F is
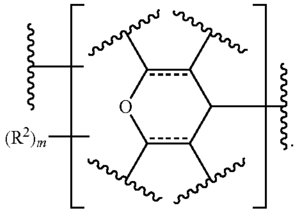
In some embodiments, Ring F is
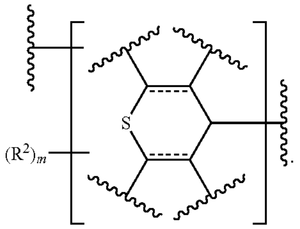
In some embodiments, Ring F is
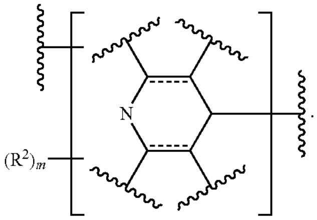
In some embodiments, Ring F is
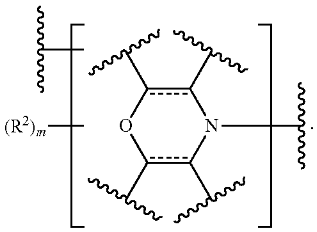
In embodiments, Ring F is
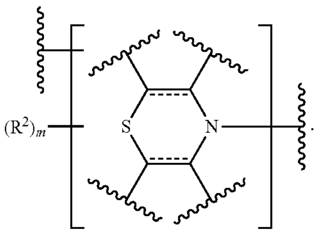
In some embodiments, Ring F is
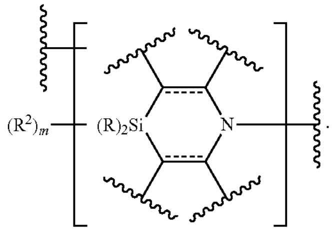
In some embodiments, Ring F is
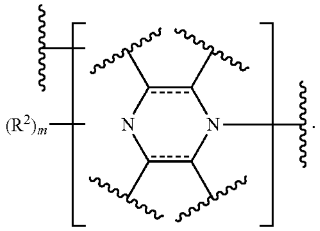
In some embodiments, Ring F is
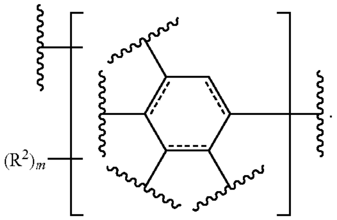
In some embodiments, Ring F is
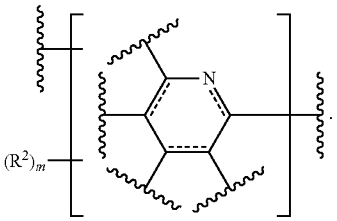
In some embodiments, Ring F is
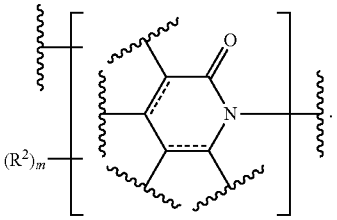

In some embodiments, Ring F is
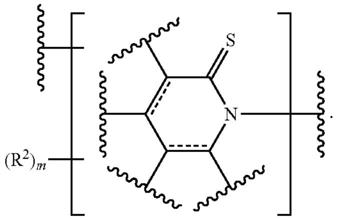
In some embodiments, Ring F is
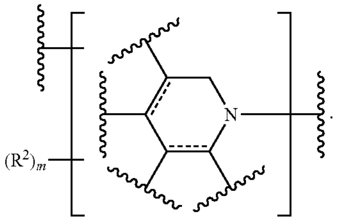
In some embodiments, Ring F is
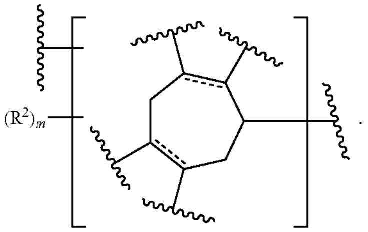
In some embodiments, Ring F is
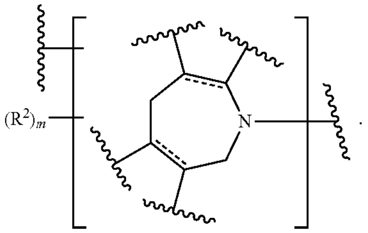
In some embodiments, Ring F is
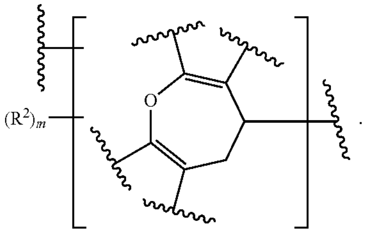
In some embodiments, Ring F is
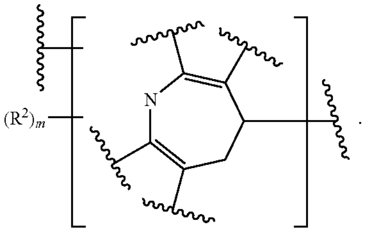
In some embodiments, Ring F is
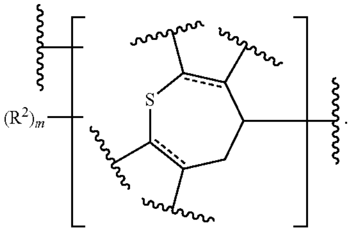
In some embodiments, Ring F is
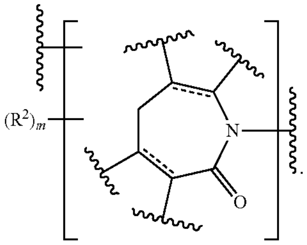
In some embodiments, Ring F is
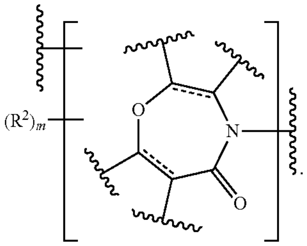
In some embodiments, Ring F is
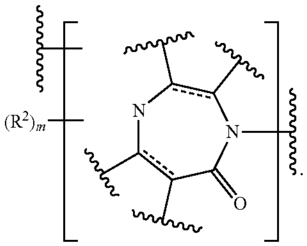

In some embodiments, Ring F is
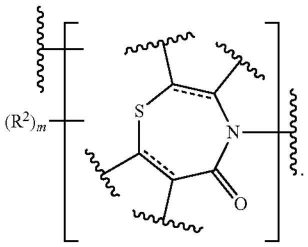
In some embodiments, Ring F is
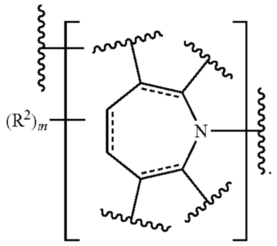
In some embodiments, Ring F is
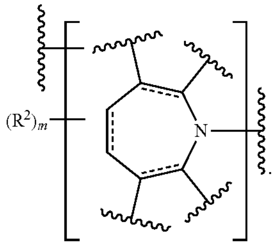
In some embodiments, Ring F is
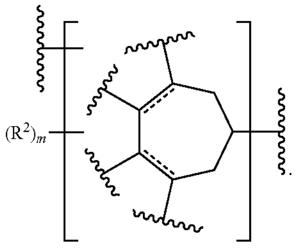
In some embodiments, Ring F is
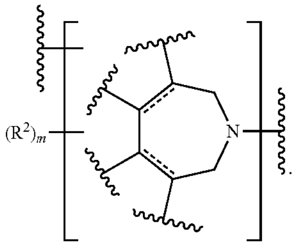
In some embodiments, Ring F is
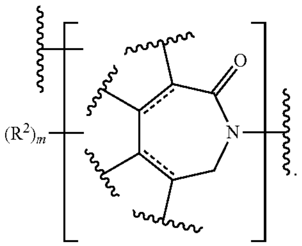
In some embodiments, Ring F is
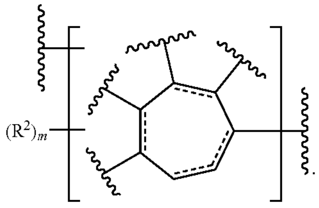
In some embodiments, Ring F is
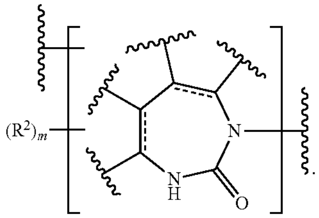
In some embodiments, Ring F is
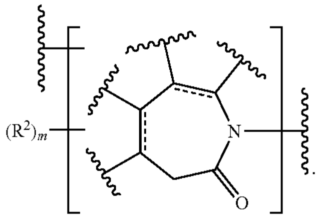
In some embodiments, each Ring E and Ring G is independently
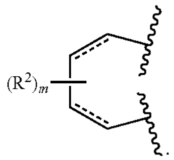

In some embodiments, each Ring E and Ring G is independently

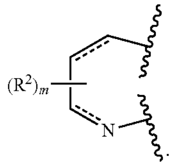

In some embodiments, each Ring E and Ring G is independently

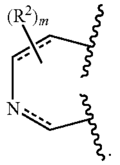

In some embodiments, each Ring E and Ring G is independently

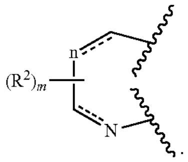

In some embodiments, Ring E and Ring G is independently

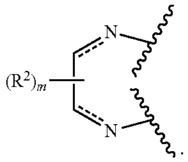

In some embodiments, Ring E and Ring G is independently is

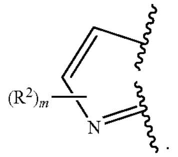

In some embodiments, Ring E and Ring G is independently

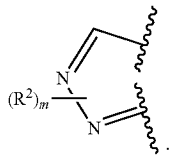

In some embodiments, Ring E and Ring G is independently

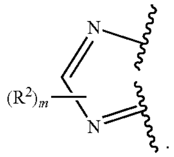

In some embodiments, Ring E and Ring G is independently

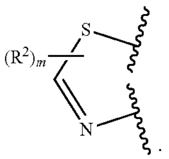

In some embodiments, Ring E and Ring G is independently
In some embodiments, Ring E and Ring G is independently

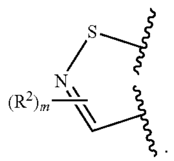

In some embodiments, Ring E and Ring G is independently

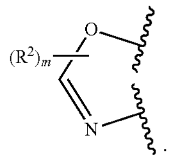

In some embodiments, Ring E and Ring G is independently

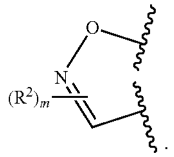

In some embodiments, Ring E and Ring G is independently

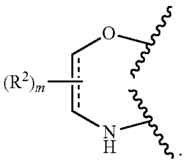

In some embodiments, Ring E and Ring G is independently

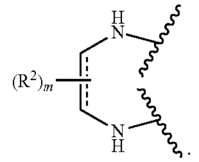

In some embodiments, Ring E and Ring G is independently

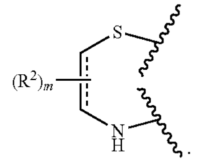

In some embodiments, Ring E and Ring G is independently

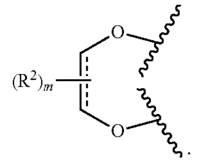

In some embodiments, Ring E and Ring G is independently

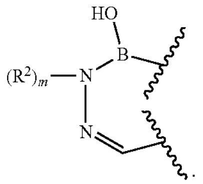

In some embodiments, Ring E, Ring F, and Ring G is

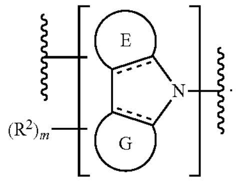

In some embodiments, Ring E, Ring F, and Ring G is

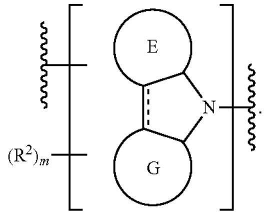

In some embodiment, Ring E, Ring F, and Ring G is

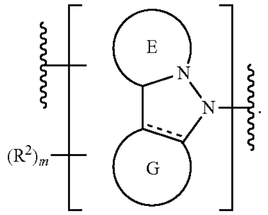

In some embodiments, Ring E, Ring F, and Ring G is

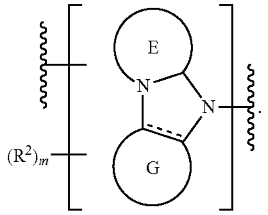

In some embodiments, Ring E, Ring F, and Ring G is

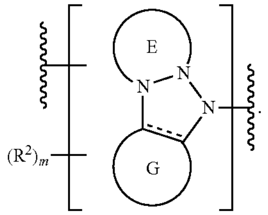

In some embodiments, Ring E, Ring F, and Ring G is

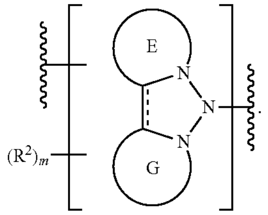

In some embodiments, Ring E, Ring F, and Ring G is

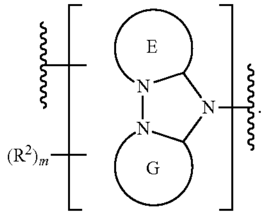

In some embodiments, Ring E, Ring F, and Ring G is

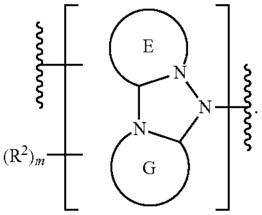

In some embodiments, Ring E, Ring F, and Ring G is

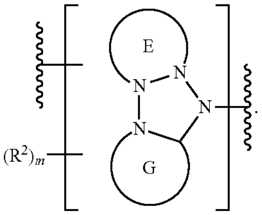

In some embodiments, Ring E, Ring F, and Ring G is

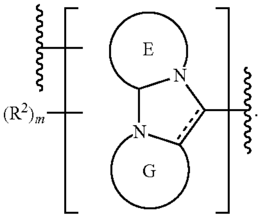

In some embodiments, Ring E, Ring F, and Ring G is

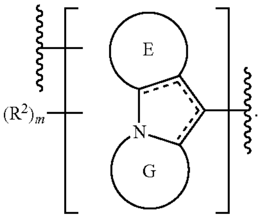

In some embodiments, Ring E, Ring F, and Ring G is

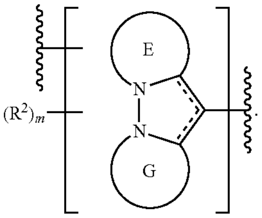

In some embodiments, Ring E, Ring F, and Ring G is

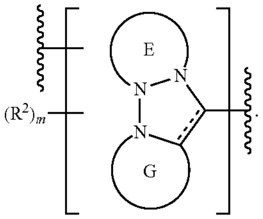

In some embodiments, Ring E, Ring F, and Ring G is

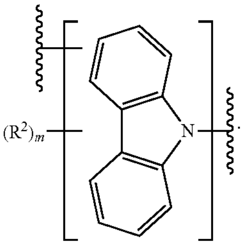

In some embodiments, Ring E, Ring F, and Ring G is

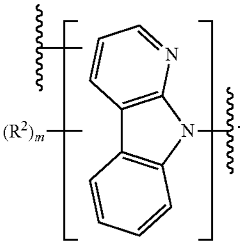

In some embodiments, Ring E, Ring F, and Ring G is

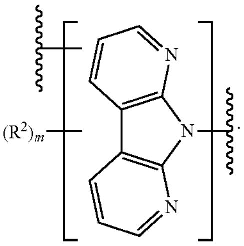

In some embodiments, Ring E, Ring F, and Ring G is

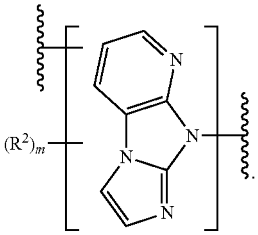

In some embodiments, Ring E, Ring F, and Ring G is

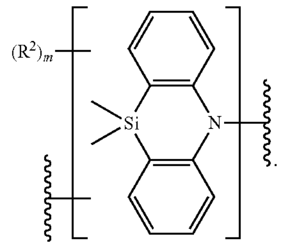

In some embodiments, Ring E, Ring F, and Ring G is

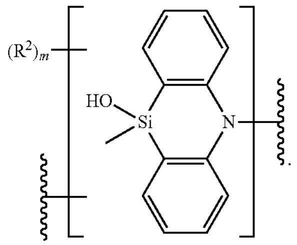

In some embodiments, Ring E, Ring F, and Ring G is

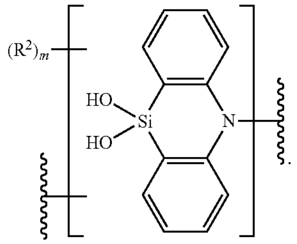

In some embodiments, Ring E, Ring F, and Ring G is

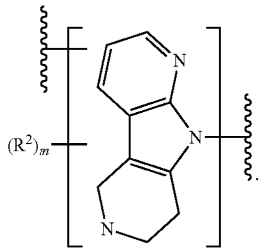

In some embodiments, Ring E, Ring F, and Ring G is

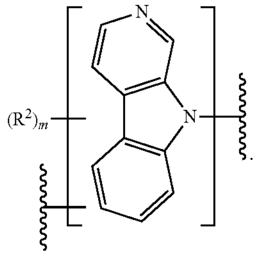

In some embodiments, Ring E, Ring F, and Ring G is

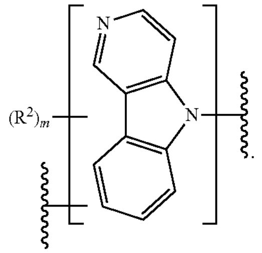

In some embodiments, Ring E, Ring F, and Ring G is

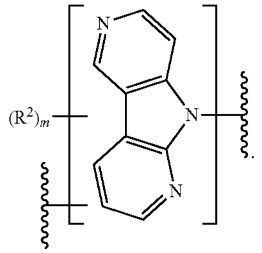

In some embodiments, Ring E, Ring F, and Ring G is

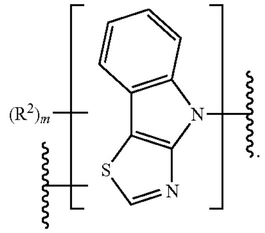

In some embodiments, Ring E, Ring F, and Ring G is

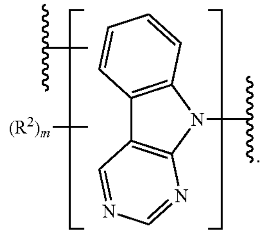

In some embodiments, Ring E, Ring F, and Ring G is

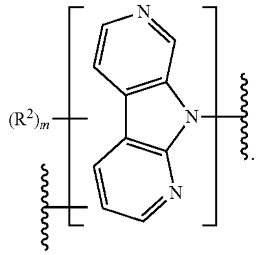

In some embodiments, Ring E, Ring F, and Ring G is

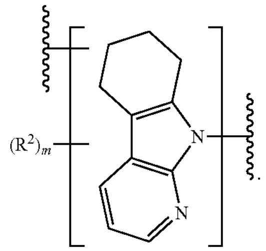

In some embodiments, Ring E, Ring F, and Ring G is

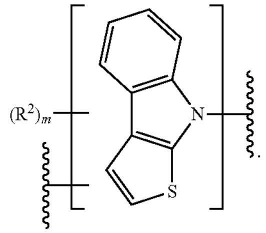

In some embodiments, Ring E, Ring F, and Ring G is

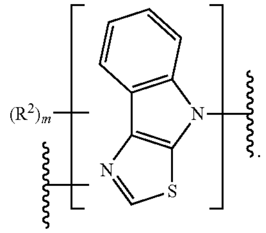

In some embodiments, Ring E, Ring F, and Ring G is

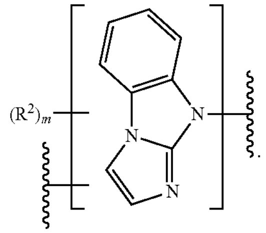

In some embodiments, Ring E, Ring F, and Ring G is

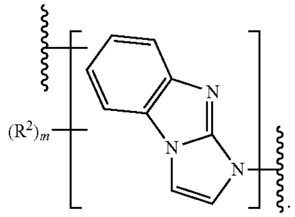

In some embodiments, Ring E, Ring F, and Ring G is

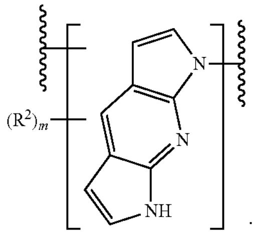

In some embodiments, Ring E, Ring F, and Ring G is

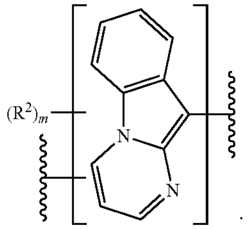

In some embodiments, Ring E, Ring F, and Ring G is

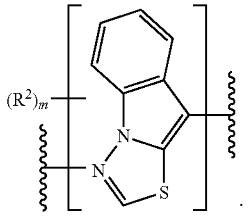

In some embodiments, Ring E, Ring F, and Ring G is selected from those depicted in Table 1, below.

As defined above and described herein, Ring H is a ring selected from a 7-9 membered saturated or partially unsaturated carbocyclyl or heterocyclyl ring with 1-3 heteroatoms independently selected from boron, nitrogen, oxygen, silicon, or sulfur, wherein Ring E is optionally further substituted with 1-2 oxo groups.

In some embodiments, Ring H is a ring selected from a 7-9 membered saturated or partially unsaturated carbocyclyl or heterocyclyl ring with 1-3 heteroatoms independently selected from boron, nitrogen, oxygen, silicon, or sulfur, wherein Ring H is optionally further substituted with 1-2 oxo groups.

In some embodiments, Ring H is

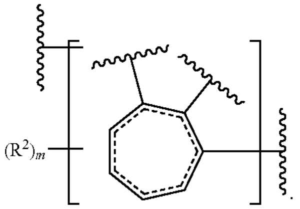

In some embodiments, Ring H is
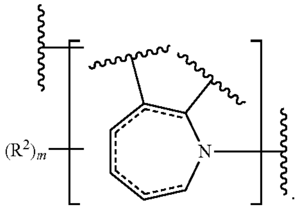
In some embodiments, Ring H is
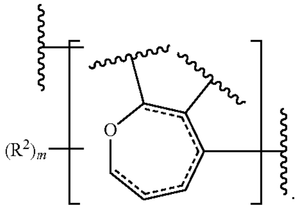
In some embodiments, Ring H is
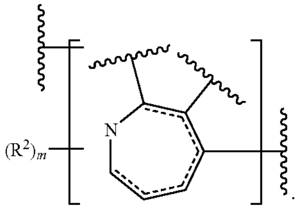
In some embodiments, Ring H is
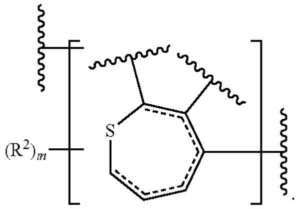
In some embodiments, Ring H is
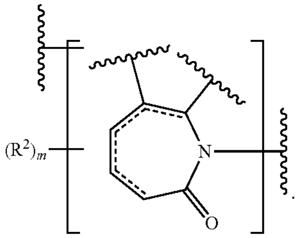
In some embodiments, Ring H is
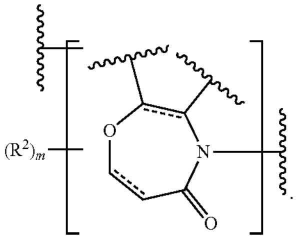
In some embodiments, Ring H is
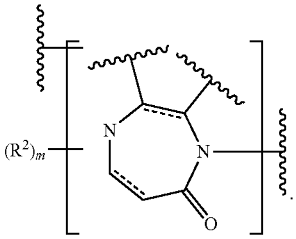
In some embodiments, Ring H is
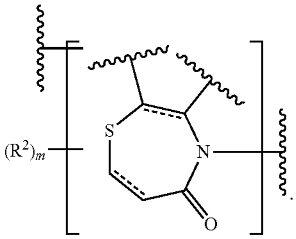
some embodiments, Ring H is
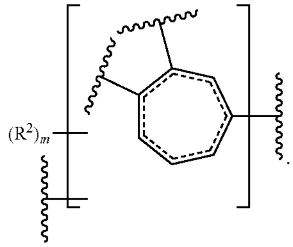
In some embodiments, Ring H is
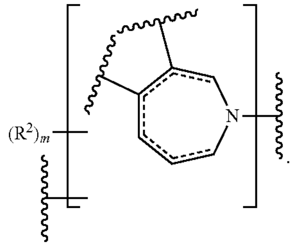

In some embodiments, Ring H is
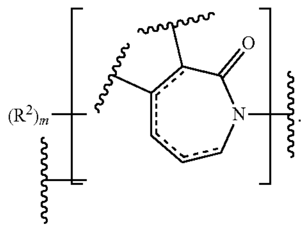
In some embodiments, Ring H is
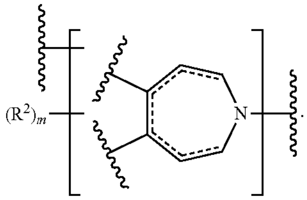
In some embodiments, Ring H is
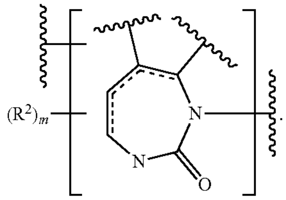
In some embodiments, Ring H is
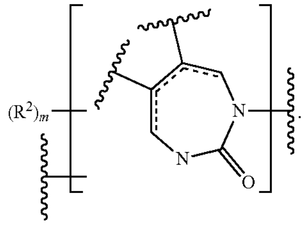
In some embodiments, Ring H is
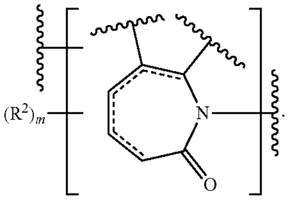
In some embodiments, Ring H is
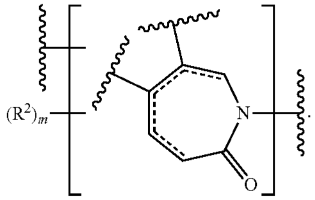
In some embodiments, Ring H is
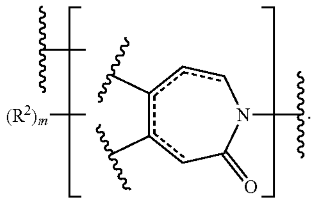
In some embodiments, Ring H is
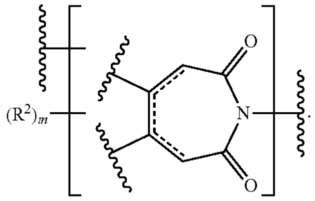
In some embodiments, Ring H is
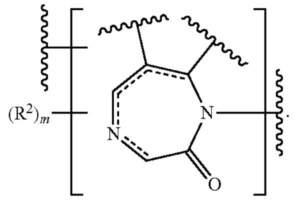
In some embodiments, Ring
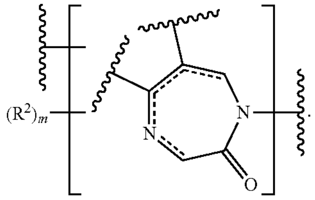

In some embodiments, Ring E and Ring H is

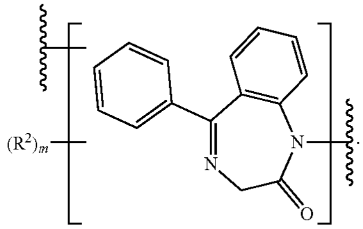

In some embodiments, Ring E and Ring H is selected from those depicted in Table 1, below.

As defined above and described herein, each of Ring I and Ring J is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur In some embodiments, each of Ring I and Ring J is independently a 6-membered aryl. In some embodiments, each of Ring I and Ring J is independently a 6-membered heteroaryl containing 1-4 heteroatoms independently selected from nitrogen, oxygen, or sulfur. In some embodiments, each of Ring I and Ring J is independently a 5 to 7-membered saturated or partially unsaturated carbocyclyl. In some embodiments, each of Ring I and Ring J is independently a 5 to 7-membered saturated or partially unsaturated heterocyclyl ring with 1-3 heteroatoms independently selected from boron, nitrogen, oxygen, silicon, or sulfur. In some embodiments, each of Ring I and Ring J is independently a 5-membered heteroaryl with 1-3 heteroatoms independently selected from nitrogen, oxygen or sulfur.

In some embodiments, each Ring I and Ring J is independently

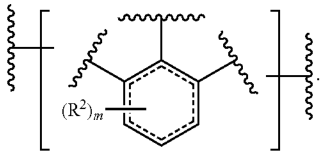

In some embodiments, each Ring I and Ring J is independently

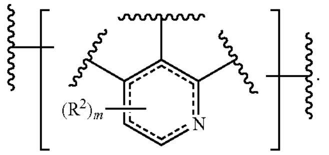

In some embodiments, each Ring I and Ring J is independently

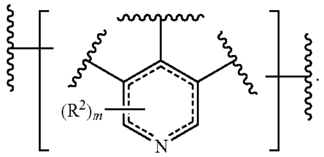

In some embodiments, each Ring I and Ring J is independently

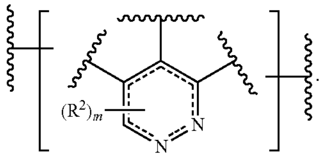

In some embodiments, Ring I and Ring J is independently

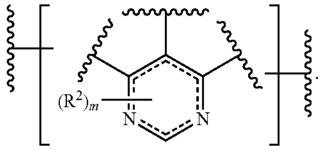

In some embodiments, Ring I and Ring J is independently is

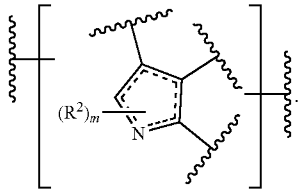

In some embodiments, Ring I and Ring J is independently

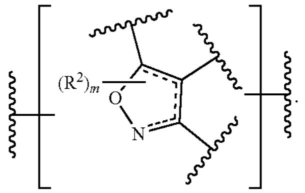

In some embodiments, Ring I and Ring J is independently

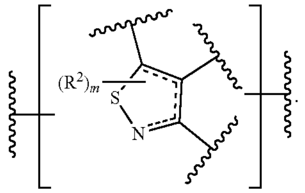

As defined above and described herein, Ring K is a fused ring selected from a 6-12 membered saturated or partially unsaturated carbocyclyl or heterocyclyl ring with 1-3 heteroatoms independently selected from boron, nitrogen, oxygen, silicon, or sulfur, wherein Ring H is optionally further substituted with 1-2 oxo groups.

In some embodiments, Ring K is a fused ring selected from a 6-12 membered saturated or partially unsaturated carbocyclyl. In some embodiments, Ring K is a 6-12 membered saturated or partially unsaturated heterocyclyl ring with 1-3 heteroatoms independently selected from boron, nitrogen, oxygen, silicon, or sulfur. In some embodiments, Ring K is optionally further substituted with 1-2 oxo groups.

In some embodiments, Ring K is

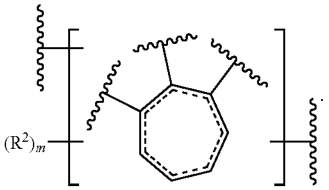

In some embodiments, Ring K is

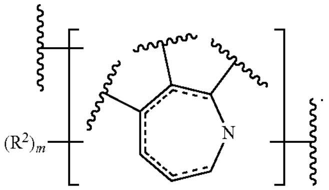

In some embodiments, Ring K is

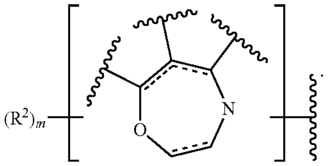

In some embodiments, Ring K is

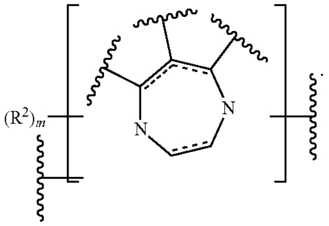

In some embodiments, Ring K is

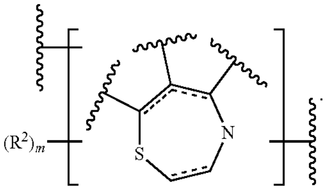

In some embodiments, Ring K is

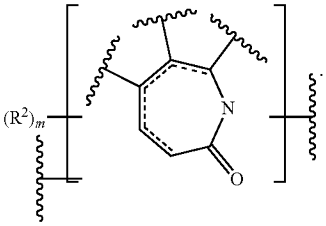

In some embodiments, Ring K is

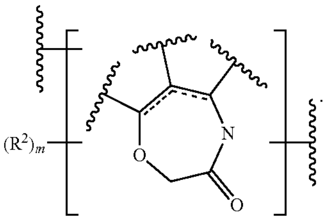

In some embodiments, Ring K is

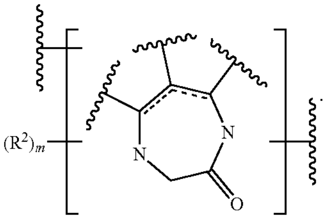

In some embodiments, Ring K is

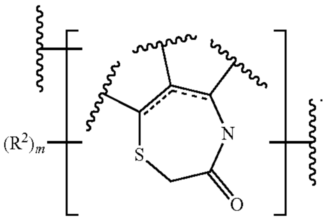

some embodiments, Ring K is

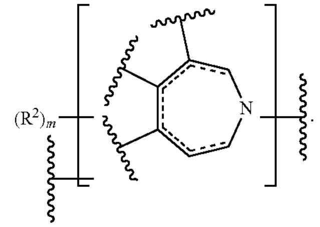

In some embodiments, Ring K is

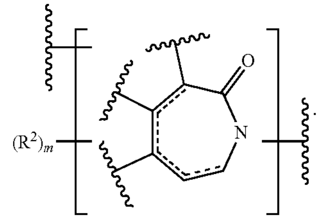

In some embodiments, Ring K is

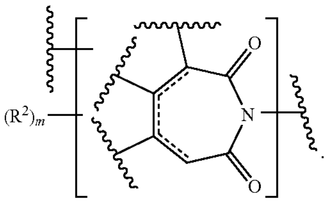

In some embodiments, Ring K is

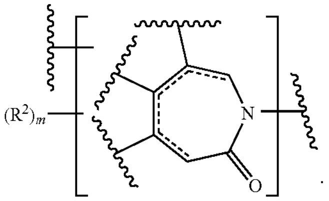

In some embodiments, Ring K is

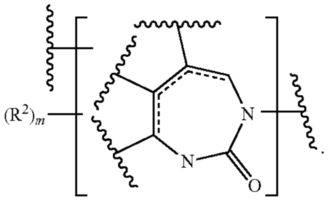

In some embodiments, Ring K is

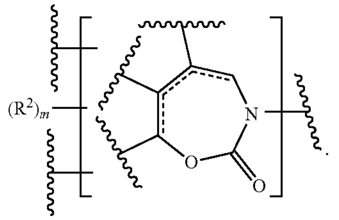

In some embodiments, Ring I, Ring J, and Ring K is

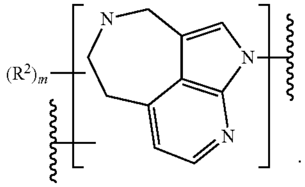

In some embodiments, Ring I, Ring J, and Ring K is selected from those depicted in Table 1, below.

As defined above and described herein, Ring M is selected from

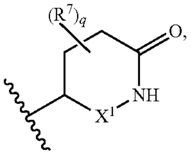 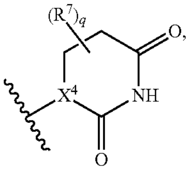

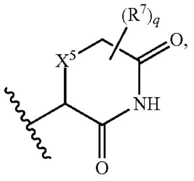 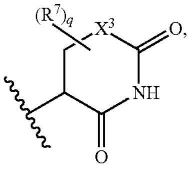

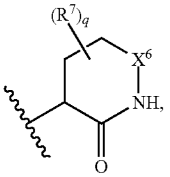 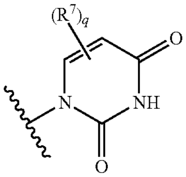 ,

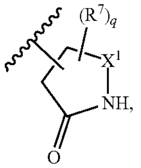 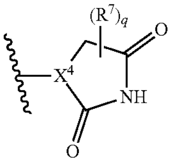 ,

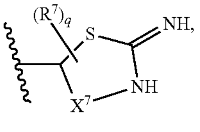 or 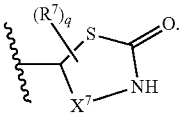

In some embodiments, Ring M is

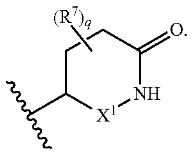

In some embodiments, Ring M is

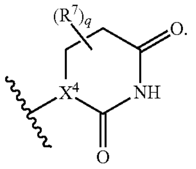

In some embodiments, Ring M is

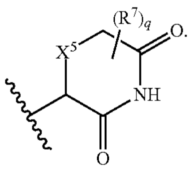

In some embodiments, Ring M is

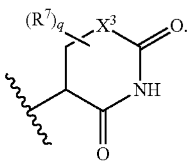

In some embodiments, Ring M is

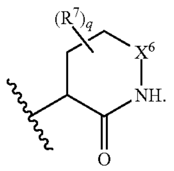

In some embodiments, Ring M is

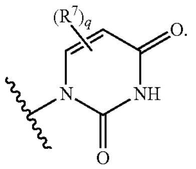

In some embodiments, Ring M is

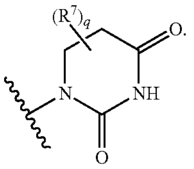

In some embodiments, Ring M is

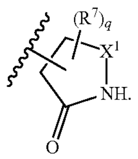

In some embodiments, Ring M is

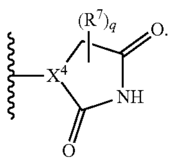

In some embodiments, Ring M is

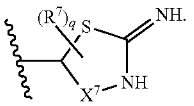

In some embodiments, Ring M is

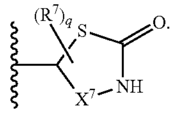

In some embodiments, Ring M is selected from those depicted in Table 1 below.

As defined above and described here, L is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —$C(R)_2$—, —CH(R)—, —$C(F)_2$—, —N(R)—, —S—, —$S(O)_2$— or —(C)═CH—;

In some embodiments, $L^1$ is a covalent bond. In some embodiments, $L^1$ is a $C_{1-3}$ aliphatic. In some embodiments, $L^1$ is —$CH_2$—. In some embodiments, $L^1$ is —C(D)(H)—. In some embodiments, $L^1$ is —$C(D)_2$-. In some embodiments, $L^1$ is —$CH_2CH_2$—. In some embodiments, $L^1$ is —NR—. In some embodiments, $L^1$ is —$CH_2NR$—. In some embodiments, $L^1$ is or —O—. In some embodiments, $L^1$ is —$CH_2O$—. In some embodiments, L is —S—. In some embodiments, $L^1$ is —OC(O)—. In some embodiments, $L^1$ is —C(O)O—. In some embodiments, $L^1$ is —C(O)—. In some embodiments, $L^1$ is —S(O)—. In some embodiments, $L^1$ is —$S(O)_2$—. In some embodiments, $L^1$ is —$NRS(O)_2$—. In some embodiments, $L^1$ is —$S(O)_2NR$—. In some embodiments, $L^1$ is —NRC(O)—. In some embodiments, $L^1$ is —C(O)NR—.

In some embodiments, Ring $L^1$ is selected from those depicted in Table 1 below.

As defined above and described herein, ⎓ is a single or double bond.

In some embodiments, ⎓ is a single bond. In some embodiments, ⎓ is a double bond.

In some embodiments, ⎓ is selected from those depicted in Table 1, below.

As defined above and described herein, m is 0, 1, 2, 3, 4, 5, 6, 7, 8, 9, 10, 11, 12, 13, 14, 15, or 16.

In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10. In some embodiments, m is 11. In some embodiments, m is 12. In some embodiments, m is 13. In some embodiments, m is 14. In some embodiments, m is 15. In some embodiments, m is 16.

In some embodiments, m is selected from those depicted in Table 1, below.

As defined above and described herein, n is 0, 1, 2, 3 or 4.

In some embodiments, n is 0. In some embodiments, n is 1. In some embodiments, n is 2. In some embodiments, n is 3. In some embodiments, n is 4.

In some embodiments, n is selected from those depicted in Table 1, below.

As defined above and described herein, p is 0 or 1.

In some embodiments, p is 0. In some embodiments, p is 1.

In some embodiments, p is selected from those depicted in Table 1, below.

In some embodiments, LBM is

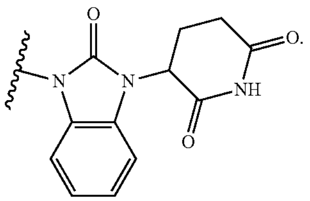 [SMILES: *n1c(=O)n(C2CCC(=O)NC2=O)c2ccccc21]

In some embodiments, LBM is

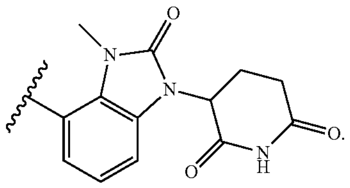 [SMILES: *c1cccc2c1n(C)c(=O)n2C1CCC(=O)NC1=O]

In some embodiments, LBM is

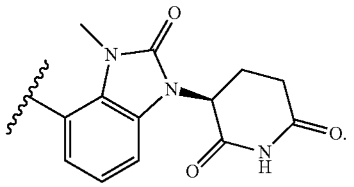 [SMILES: *c1cccc2c1n(C)c(=O)n2[C@H]1CCC(=O)NC1=O]

In some embodiments, LBM is

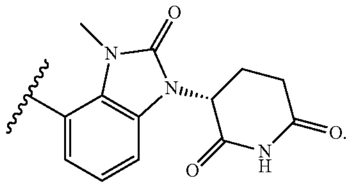 [SMILES: *c1cccc2c1n(C)c(=O)n2[C@@H]1CCC(=O)NC1=O]

In some embodiments, LBM is

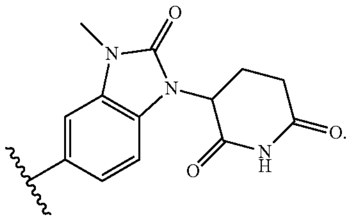 [SMILES: *c1ccc2c(c1)n(C)c(=O)n2C1CCC(=O)NC1=O]

In some embodiments, LBM is

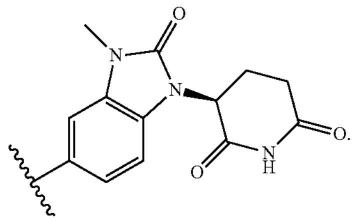 [SMILES: *c1ccc2c(c1)n(C)c(=O)n2[C@H]1CCC(=O)NC1=O]

In some embodiments, LBM is

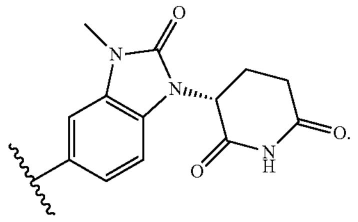 [SMILES: *c1ccc2c(c1)n(C)c(=O)n2[C@@H]1CCC(=O)NC1=O]

In some embodiments, LBM is
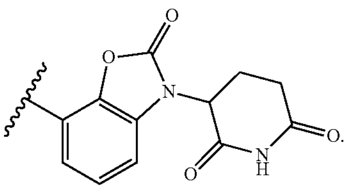 [SMILES: *c1cccc2c1oc(=O)n2C1CCC(=O)NC1=O]
In some embodiments, LBM is
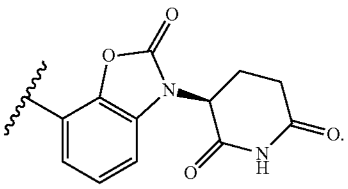 [SMILES: *c1cccc2c1oc(=O)n2[C@H]1CCC(=O)NC1=O]
In some embodiments, LBM is
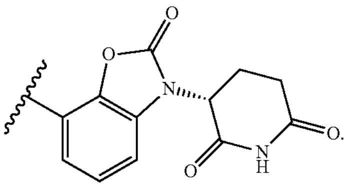 [SMILES: *c1cccc2c1oc(=O)n2[C@@H]1CCC(=O)NC1=O]
In some embodiments, LBM is
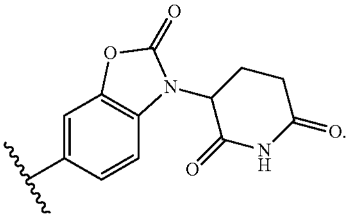 [SMILES: *c1ccc2c(c1)oc(=O)n2C1CCC(=O)NC1=O]
In some embodiments, LBM is
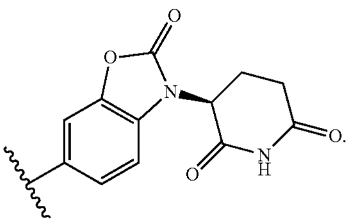 [SMILES: *c1ccc2c(c1)oc(=O)n2[C@H]1CCC(=O)NC1=O]
In some embodiments, LBM is
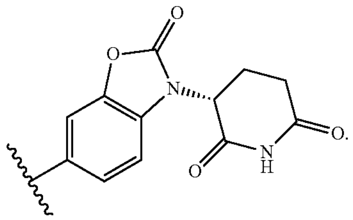 [SMILES: *c1ccc2c(c1)oc(=O)n2[C@@H]1CCC(=O)NC1=O]
In some embodiments, LBM is
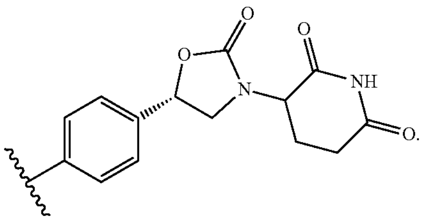 [SMILES: *c1ccc([C@H]2CN(C3CCC(=O)NC3=O)C(=O)O2)cc1]
In some embodiments, LBM is
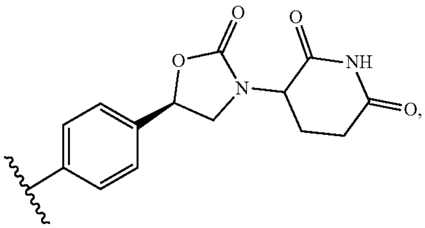 [SMILES: *c1ccc([C@@H]2CN(C3CCC(=O)NC3=O)C(=O)O2)cc1]
In some embodiments, LBM is
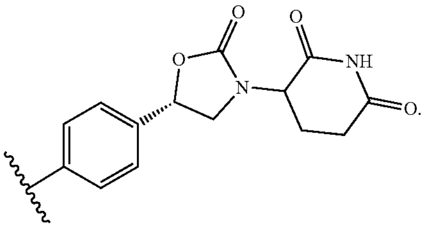 [SMILES: *c1ccc([C@H]2CN(C3CCC(=O)NC3=O)C(=O)O2)cc1]
In some embodiments, LBM is
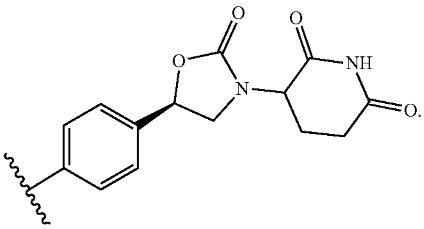 [SMILES: *c1ccc([C@@H]2CN(C3CCC(=O)NC3=O)C(=O)O2)cc1]

In some embodiments, LBM is

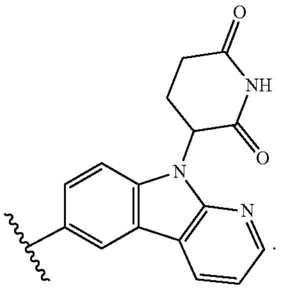 [SMILES: *c1ccc2c(c1)c1cccnc1n2C1CCC(=O)NC1=O]

In some embodiments, LBM is

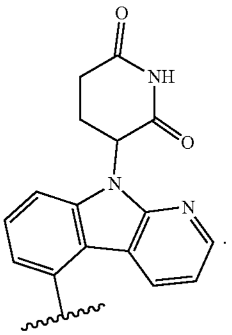 [SMILES: *c1cccc2c1c1cccnc1n2C1CCC(=O)NC1=O]

In some embodiments, LBM is

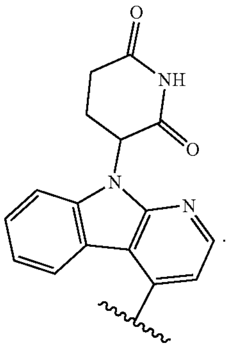 [SMILES: *c1ccnc2c1c1ccccc1n2C1CCC(=O)NC1=O]

In some embodiments, LBM is

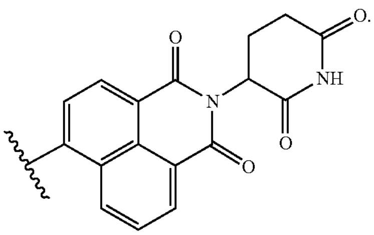 [SMILES: *c1ccc2c3c(cccc13)C(=O)N(C1CCC(=O)NC1=O)C2=O]

In some embodiments, LBM is

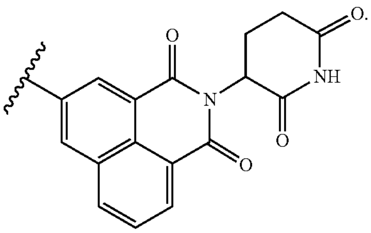 [SMILES: *c1cc2c3c(cccc3c1)C(=O)N(C1CCC(=O)NC1=O)C2=O]

In some embodiments, LBM is

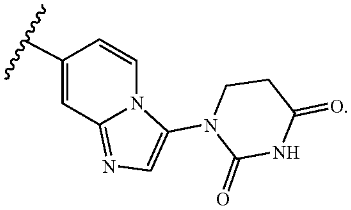 [SMILES: *c1ccn2c(N3CCC(=O)NC3=O)cnc2c1]

In some embodiments, LBM is

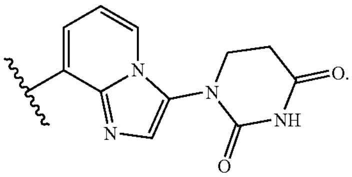 [SMILES: *c1cccn2c(N3CCC(=O)NC3=O)cnc12]

In some embodiments, LBM is

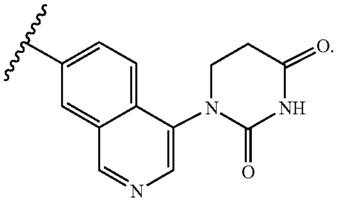 [SMILES: *c1ccc2c(N3CCC(=O)NC3=O)cncc2c1]

In some embodiments, LBM is

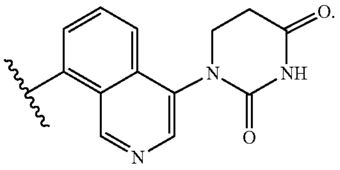 [SMILES: *c1cccc2c(N3CCC(=O)NC3=O)cncc12]

In certain embodiments, the present invention provides a compound of Formula I, wherein LBM is an E3 ubiquitin ligase (cereblon) binding moiety thereby forming a compound of formula I-p-1, I-p-2, or I-p-3 respectively:

I-p-1

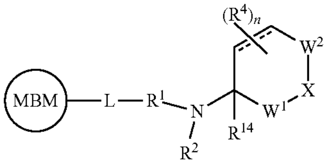

I-p-2

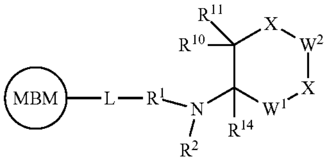

I-p-3

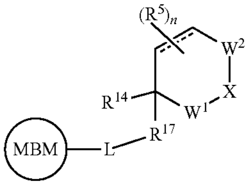

or a pharmaceutically acceptable salt thereof, wherein L and MBM are as defined above and described herein, and wherein each of the variables RR, $R^2$, $R^4$, $R^5$, $R^{10}$, $R^{11}$, $R^{14}$, $R^{17}$, $W^1$, $W^2$, X, ⎓ and n is as defined in WO 2017/197051 which is herein incorporated by reference in its entirety and wherein

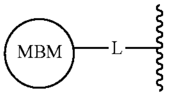

is attached to $R^1$, the ring formed by combining $R^1$ and $R^2$, or $R^{17}$ at the site of attachment of $R^{12}$ as defined in WO 2017/197051 such that

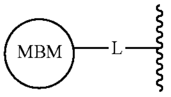

takes the place of the $R^{12}$ substituent.

In some embodiments, the present invention provides a compound of formula I, wherein LBM is an E3 ubiquitin ligase (cereblon) binding moiety thereby forming a compound of formula I-p-4, I-p-5, I-p-6, or I-p-7, respectively:

I-p-4

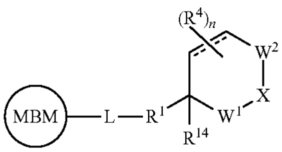

I-p-5

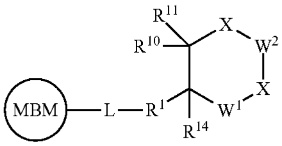

-continued

I-p-6

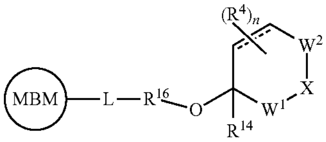

I-p-7

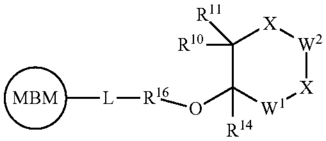

or a pharmaceutically acceptable salt thereof, wherein L and MBM are as defined above and described herein, and wherein each of the variables $R^1$, $R^4$, $R^{10}$, $R^{11}$, $R^{14}$, $R^{16}$, $W^1$, $W^2$, X, ⎓ an n is as defined in WO 2018/237026, the entirety of each of which is herein incorporated by reference, and wherein

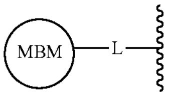

is attached to $R^1$ or $R^{16}$ at the site of attachment of $R^{12}$ as defined in WO 2018/237026, such that

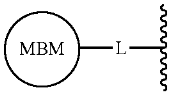

takes the place of the $R^{12}$ substituent.

In certain embodiments, the present invention provides a compound of Formula I, wherein LBM is a MDM2 (i.e. human double minute 2 or HDM2) E3 ligase binding moiety thereby forming a compound of formula I-q-1, I-q-2, I-q-3, I-q-4, I-q-5, I-q-6, I-q-7, I-q-8, I-q-9, I-q-10, I-q-11, I-q-12, I-q-13, I-q-14, I-q-15, I-q-16, I-q-17, or I-q-18 respectively:

I-q-1

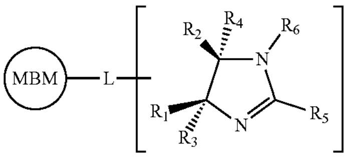

I-q-2

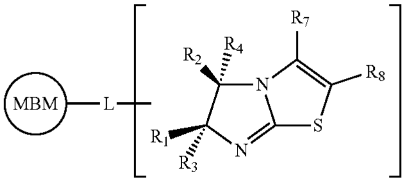

-continued
I-q-3
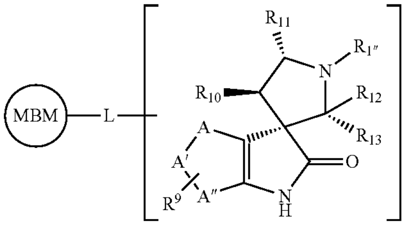
I-q-4
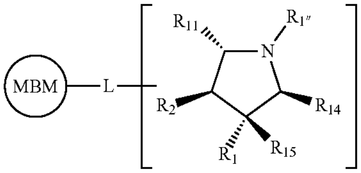
I-q-5
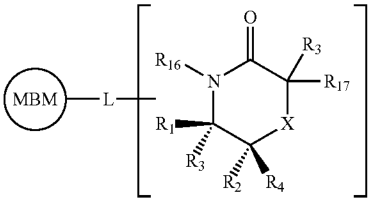
I-q-6
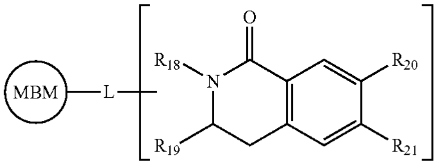
I-q-7
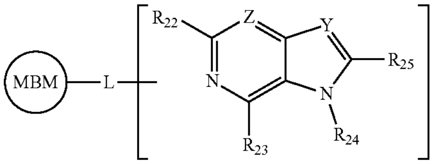
I-q-8
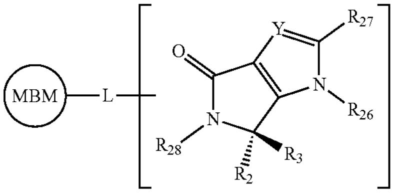
I-q-9
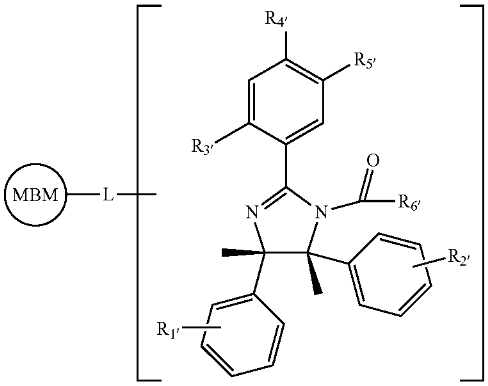
-continued
I-q-10
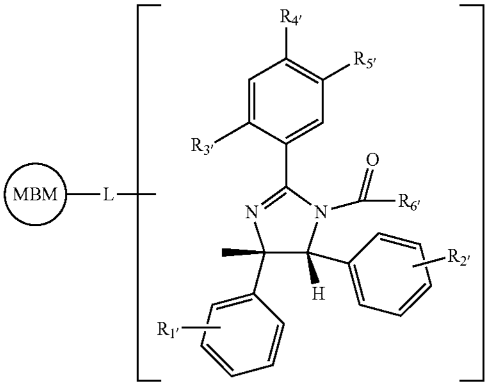
I-q-11
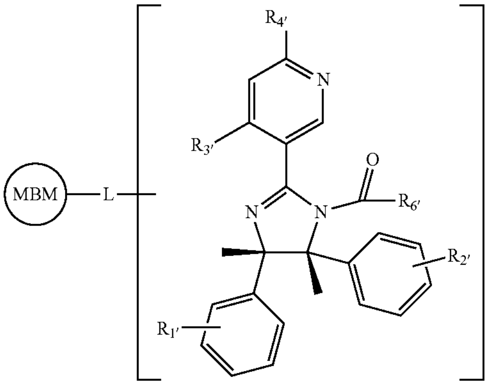
I-q-12
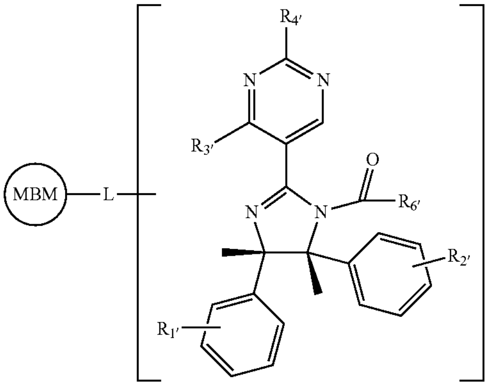
I-q-13
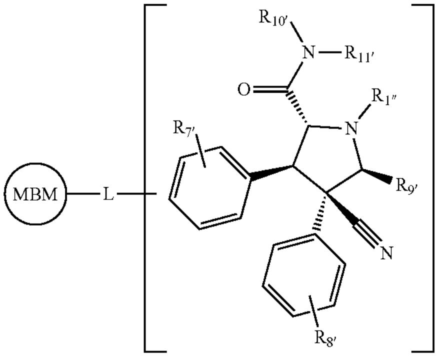

-continued

I-q-14

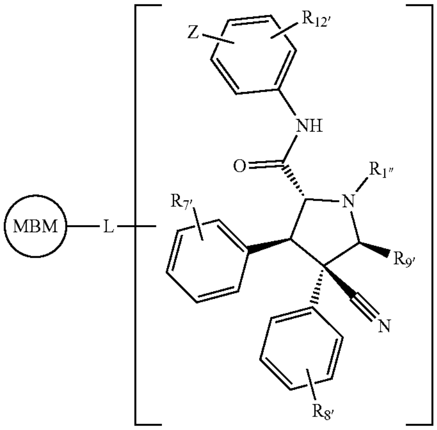

I-q-15

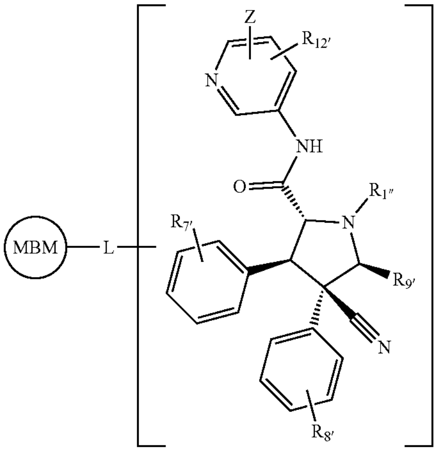

I-q-16

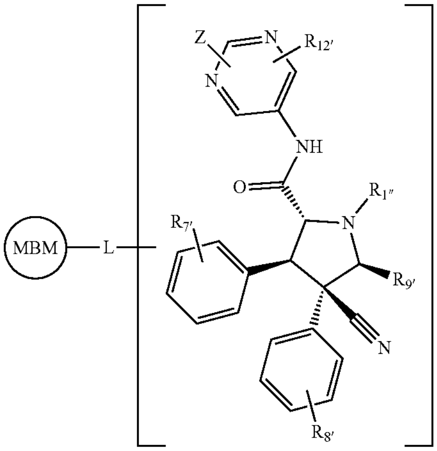

-continued

I-q-17

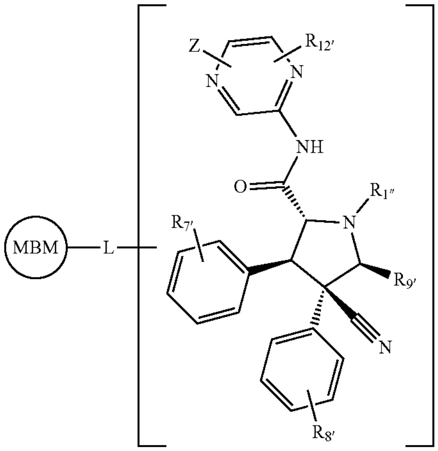

I-q-18

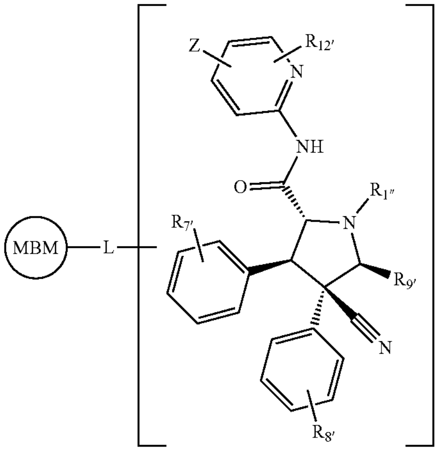

or a pharmaceutically acceptable salt thereof, wherein L and MDM2 are as defined above and described in embodiments herein, and wherein each of the variables $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{1'}$, $R_{2'}$, $R_{3'}$, $R_{4'}$, $R_{5'}$, $R_{6'}$, $R_{7'}$, $R_{8'}$, $R_{9'}$, $R_{10'}$, $R_{11'}$, $R_{12'}$, $R_{1''}$, A, A', A", X, Y, and Z is as defined and described in WO 2017/011371 and US 2017/008904, the entirety of each of which is herein incorporated by reference.

In some embodiments, a compound of formulae I-q-1, I-q-2, I-q-3, I-q-4, I-q-5, I-q-6, I-q-7, I-q-8, I-q-9, I-q-10, I-q-11, I-q-12, I-q-13, I-q-14, I-q-15, I-q-16, I-q-17, or I-q-18 is defined by the definitions of formula I-aaa-1, I-aaa-2, I-aaa-3, I-aaa-4, I-aaa-5, I-aaa-6, I-aaa-7, I-aaa-8, I-aaa-9, I-aaa-10, I-aaa-11, I-aaa-12, I-aaa-13, I-aaa-14, I-aaa-15, I-aaa-16, I-aaa-17, I-aaa-18, I-aaa-19, or I-aaa-20 above.

In certain embodiments, the present invention provides a compound of Formula I, wherein LBM is a MDM2 (i.e. human double minute 2 or HDM2) E3 ligase binding moiety thereby forming a compound of formula I-q-19, I-q-20, or I-q-21 respectively:

I-q-19

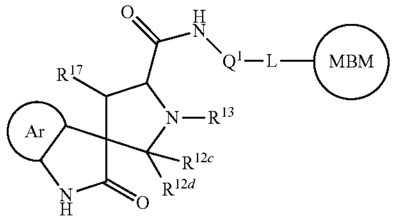

I-q-20

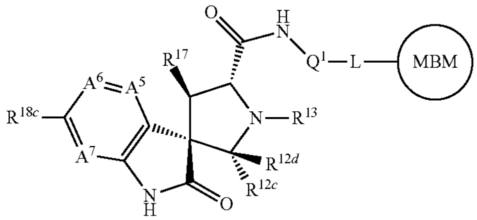

I-q-21

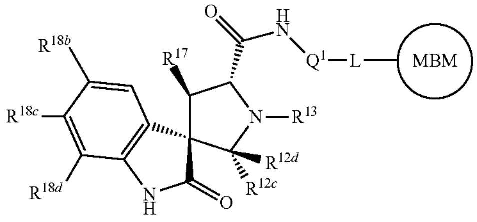

or a pharmaceutically acceptable salt thereof, wherein L and MDM2 are as defined above and described in embodiments herein, and wherein each of the variables $R^{12c}$, $R^{12d}$, $R^{13}$, $R^{17}$, $R^{18b}$, $R^{18c}$, $R^{18d}$, $A^5$, $A^6$, $A^7$, $Q^1$, and Ar is as defined and described in WO 2017/176957 and US2019/127387, the entirety of each of which is herein incorporated by reference.

In some embodiments, a compound of formulae I-q-19, I-q-20, or I-q-21 is defined by the definitions of formula I-bbb-1, I-bbb-2, and I-bbb-3 above.

In some embodiments, the present invention provides a compound of formula I, wherein LBM is an E3 ubiquitin ligase (cereblon) binding moiety thereby forming a compound of formula I-r-1 or I-r-3, respectively:

I-r-1

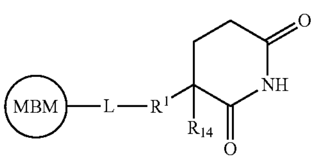

I-r-3

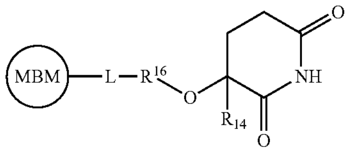

or a pharmaceutically acceptable salt thereof, wherein L and MBM are as defined above and described herein, and wherein each of the variables $R^1$, $R^{14}$, and $R^{16}$ is as defined in WO 2018/237026, the entirety of each of which is herein incorporated by reference, and wherein

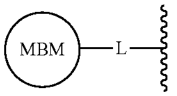

is attached to $R^1$ or $R^{16}$ at the site of attachment of $R^{12}$ as defined in WO 2018/237026, such that

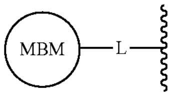

takes the place of the $R^{12}$ substituent.

In certain embodiments, the present invention provides a compound of formula I, wherein LBM is an E3 ubiquitin ligase (cereblon) binding moiety thereby forming a compound of formula I-s:

I-s

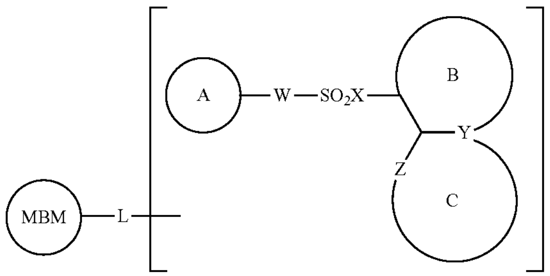

or a pharmaceutically acceptable salt thereof, wherein L and MBM are as defined above and described in embodiments herein, and wherein each of the variables A, B, C, W, X, Y, and Z is as described and defined in U.S. Pat. No. 5,721,246, the entirety of each of which is herein incorporated by reference.

In certain embodiments, the present invention provides a compound of formula I, wherein LBM is an E3 ubiquitin ligase (cereblon) binding moiety thereby forming a compound of formula I-t:

I-t

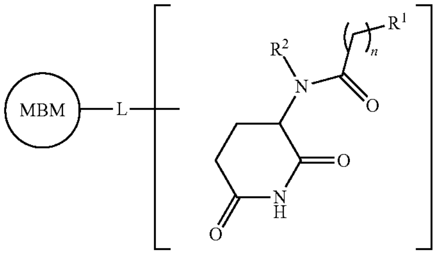

or a pharmaceutically acceptable salt thereof, wherein L and MBM are as defined above and described in embodiments herein, and wherein each of the variables $R_1$, $R_2$, and n is as described and defined in WO 2019/043214, the entirety of each of which is herein incorporated by reference.

In some embodiments, LBM is a IAP E3 Ubiquitin ligase binding moiety recited in Varfolomeev, E. et al., *IAP Antagonists Induce Autoubiquitination of c-IAPs, NF-κB activation, and TNFα-Dependent Apoptosis*, Cell, 2007, 131(4): 669-81, such as, for example:

MV1

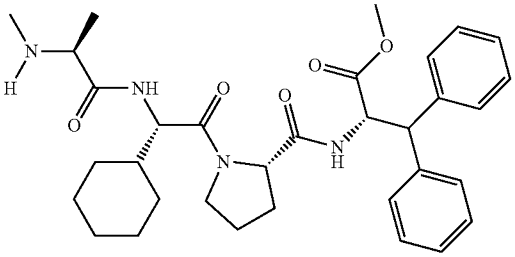

, and

BV6

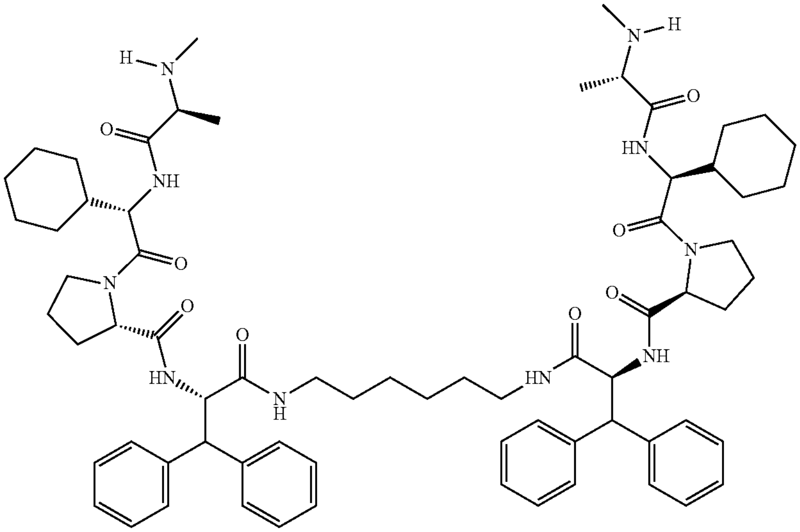

wherein

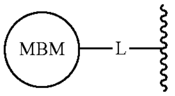

is attached to a modifiable carbon, oxygen, nitrogen or sulfur atom.

In certain embodiments, the present invention provides a compound of Formula I, wherein LBM is an IAP E3 ubiquitin ligase binding moiety thereby forming a compound of formula I-u-1, I-u-2, I-u-3, or I-u-4 respectively:

I-u-1

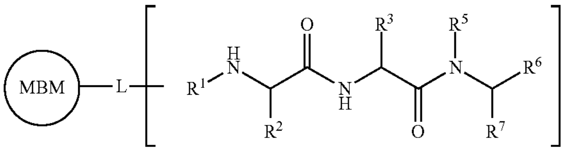

I-u-2

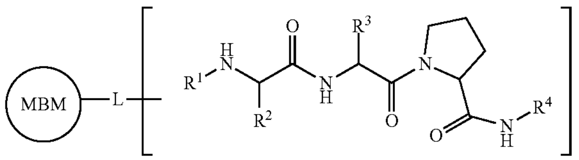

-continued

I-u-3

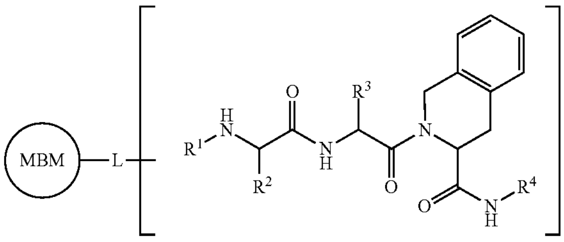

I-u-4

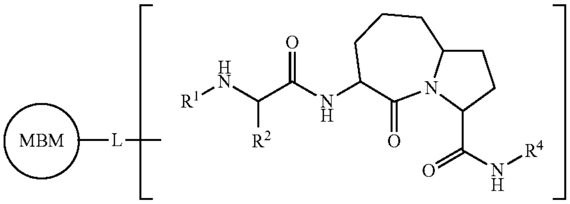

or a pharmaceutically acceptable salt thereof, wherein L and MBM are as defined above and described in embodiments herein, and wherein each of the variables $R^1$, $R^2$, $R^3$, $R^4$, $R^5$, $R^6$, and $R^7$, is as defined and described in WO 2017/011590 and US 2007/037004, the entirety of each of which is herein incorporated by reference.

In certain embodiments, the present invention provides a compound of formula I, wherein LBM is an IAP binding moiety thereby forming a compound of formula I-v:

I-v

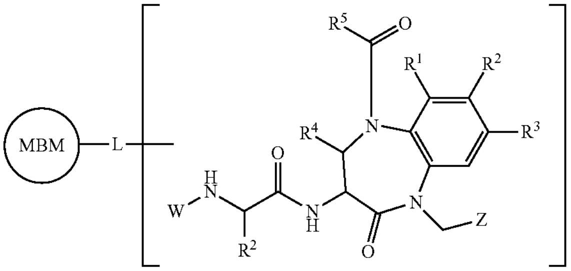

or a pharmaceutically acceptable salt thereof, wherein L and MBM are as defined above and described in embodiments herein, and wherein each of the variables W, Y, Z, $R^1$, $R^2$, $R^3$, $R^4$, and $R^5$ is as described and defined in WO 2014/044622, US 2015/0225449. WO 2015/071393, and US 2016/0272596, the entirety of each of which is herein incorporated by reference.

In certain embodiments, the present invention provides a compound of formula I, wherein LBM is a MDM2 binding moiety thereby forming a compound of formula I-w:

I-w

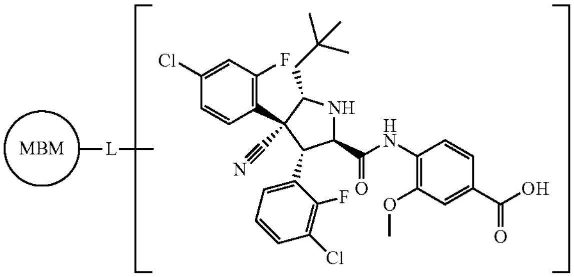

or a pharmaceutically acceptable salt thereof, as described and defined in Hines, J. et al., Cancer Res. (DOI: 10.1158/0008-5472.CAN-18-2918), the entirety of each of which is herein incorporated by reference.

In certain embodiments, the present invention provides a compound of formula I, wherein LBM is a DCAF16 binding moiety thereby forming a compound of formula I-x:

I-x

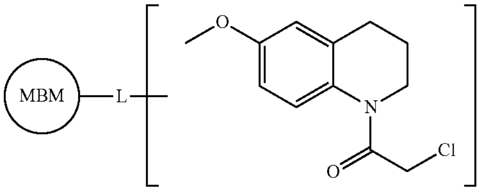

or a pharmaceutically acceptable salt thereof, as described and defined in Zhang, X. et al., *bioRxiv* (doi: https://doi.org/10.1101/443804), the entirety of each of which is herein incorporated by reference.

In certain embodiments, the present invention provides a compound of formula I, wherein LBM is a RNF114 binding moiety thereby forming a compound of formula I-y:

I-y

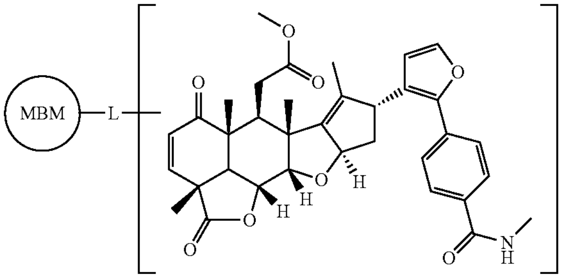

or a pharmaceutically acceptable salt thereof, as described and defined in Spradin, J. N. et al., *bioRxiv* (doi: https://doi.org/10.1101/436998), the entirety of each of which is herein incorporated by reference.

In certain embodiments, the present invention provides a compound of formula I, wherein LBM is a RNF4 binding moiety thereby forming a compound of formula I-z:

I-z

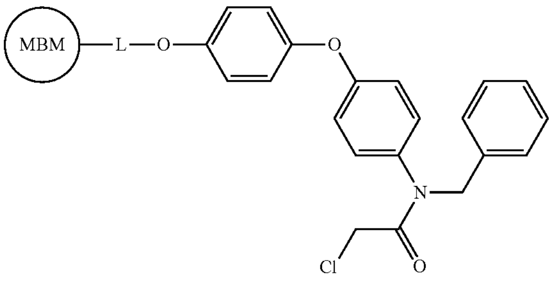

or a pharmaceutically acceptable salt thereof, as described and defined in Ward, C. C., et al., *bioRxiv* (doi: https://doi.org/10.1101/439125), the entirety of each of which is herein incorporated by reference.

In certain embodiments, the present invention provides a compound of formula I, wherein LBM is a VHL binding moiety thereby forming a compound of formula I-aa-1 or I-aa-2:

I-aa-1

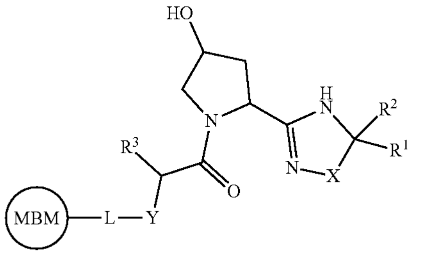

-continued

I-aa-2

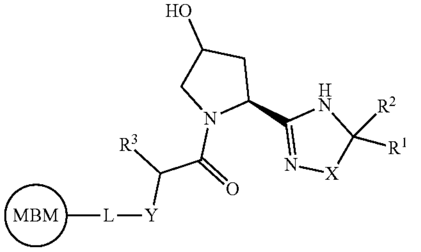

or a pharmaceutically acceptable salt thereof, wherein L and MBM are as defined above and described in embodiments herein, and wherein each of the variables $R^1$, $R^2$, $R^3$, X, and Y is as defined and described in WO 2019/084026, the entirety of each of which is herein incorporated by reference.

In certain embodiments, the present invention provides a compound of formula I, wherein LBM is a VHL binding moiety thereby forming a compound of formula I-aa-3 or I-aa-3:

I-aa-3

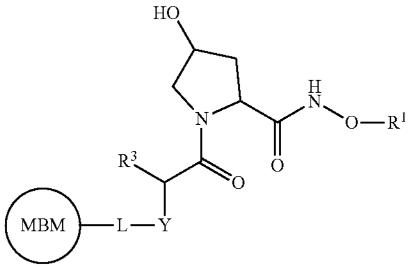

I-aa-4

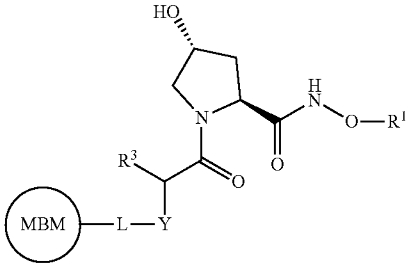

or a pharmaceutically acceptable salt thereof, wherein L and MBM are as defined above and described in embodiments herein, and wherein each of the variables $R^1$, $R^3$, and Y is as defined and described in WO 2019/084030, the entirety of each of which is herein incorporated by reference.

In certain embodiments, the present invention provides a compound of formula I, wherein LBM is a E3 ubiquitin ligase (cereblon) binding moiety thereby forming a compound of formula I-bb-1, I-bb-2, I-bb-3, or I-bb-4:

I-bb-1

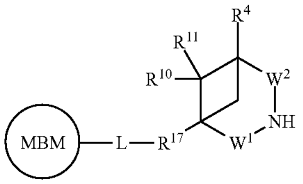

-continued

I-bb-2

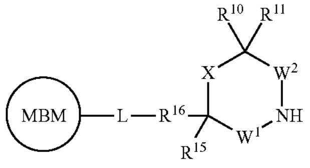

I-bb-3

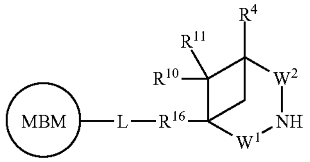

I-bb-4

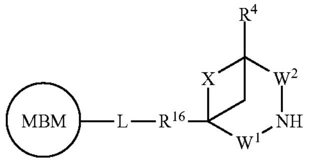

or a pharmaceutically acceptable salt thereof, wherein L and MBM are as defined above and described herein, and wherein each of the variables $R^4$, $R^{10}$, $R^{11}$, $R^{15}$, $R^{16}$, $R^{17}$, $W^1$, $W^2$, and X is as defined in WO 2019/099868 which is herein incorporated by reference in its entirety, and wherein

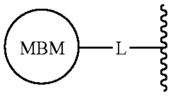

is attached to $R^{17}$ or $R^{16}$ at the site of attachment of $R^{12}$ as defined in WO 2018/237026, such that

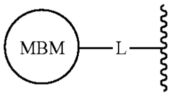

takes the place of the $R^{12}$ substituent.

In some embodiments, LBM is

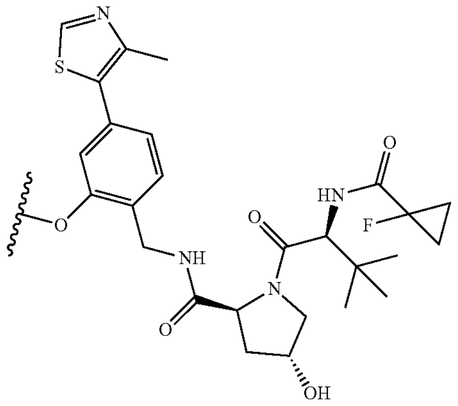
.

In some embodiments, LBM is
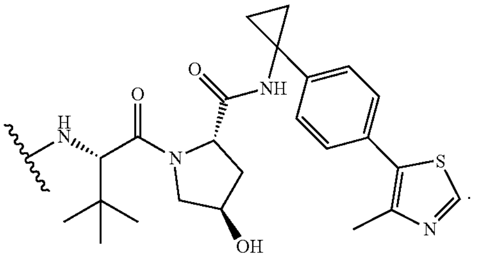 [SMILES: *N[C@H](C(=O)N1C[C@H](O)C[C@H]1C(=O)NC1(c2ccc(-c3scnc3C)cc2)CC1)C(C)(C)C]
In some embodiments, LBM is
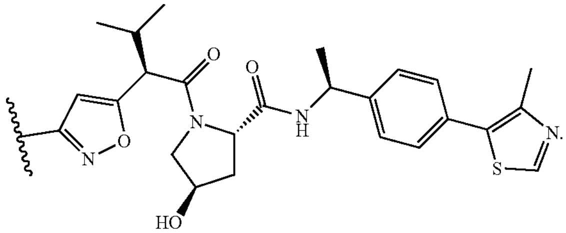 [SMILES: *c1cc([C@H](C(=O)N2C[C@H](O)C[C@H]2C(=O)N[C@@H](C)c2ccc(-c3scnc3C)cc2)C(C)C)on1]
In some embodiments, LBM is
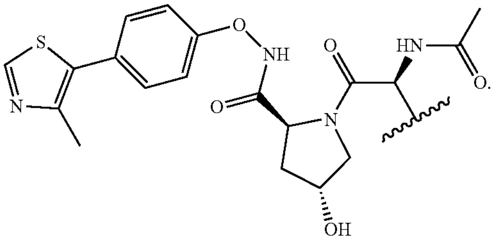 [SMILES: *[C@H](NC(C)=O)C(=O)N1C[C@H](O)C[C@H]1C(=O)NOc1ccc(-c2scnc2C)cc1]
In some embodiments, LBM is
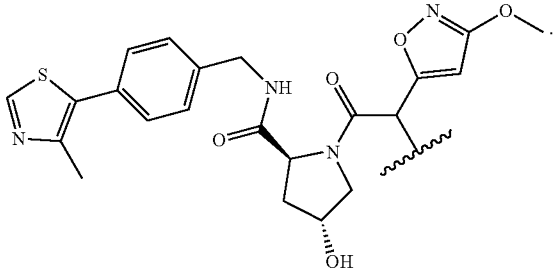 [SMILES: *C(C(=O)N1C[C@H](O)C[C@H]1C(=O)NCc1ccc(-c2scnc2C)cc1)c1cc(OC)no1]
In some embodiments, LBM is
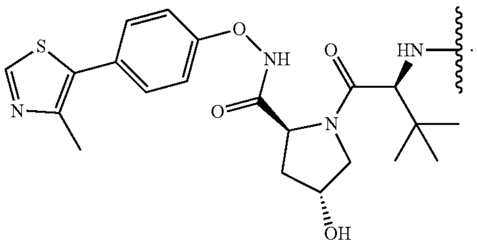 [SMILES: *N[C@H](C(=O)N1C[C@H](O)C[C@H]1C(=O)NOc1ccc(-c2scnc2C)cc1)C(C)(C)C]
In some embodiments, LBM is
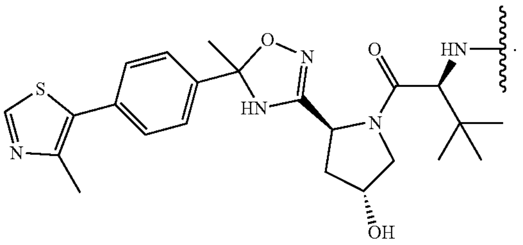 [SMILES: *N[C@H](C(=O)N1C[C@H](O)C[C@H]1C1=NOC(C)(c2ccc(-c3scnc3C)cc2)N1)C(C)(C)C]
In some embodiments, LBM is
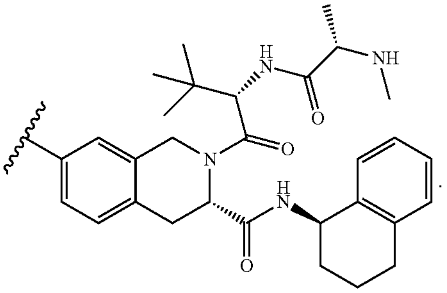 [SMILES: *c1ccc2c(c1)CN(C(=O)[C@@H](NC(=O)[C@H](C)NC)C(C)(C)C)[C@H](C(=O)N[C@@H]1CCCc3ccccc31)C2]
In some embodiments, LBM is
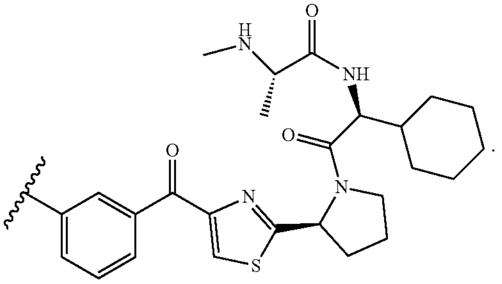 [SMILES: *c1cccc(C(=O)c2csc([C@@H]3CCCN3C(=O)[C@@H](NC(=O)[C@H](C)NC)C3CCCCC3)n2)c1]
In some embodiments, LBM is
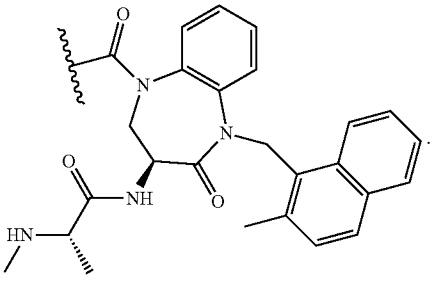 [SMILES: *C(=O)N1C[C@H](NC(=O)[C@H](C)NC)C(=O)N(Cc2c(C)ccc3ccccc23)c2ccccc21]

In some embodiments, LBM is
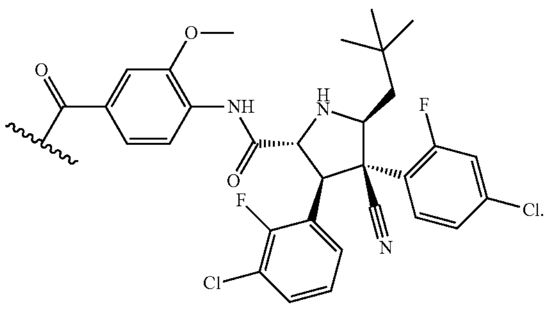 [SMILES: *C(=O)c1ccc(NC(=O)[C@@H]2N[C@@H](CC(C)(C)C)[C@](C#N)(c3ccc(Cl)cc3F)[C@H]2c2cccc(Cl)c2F)c(OC)c1]
In some embodiments, LBM is
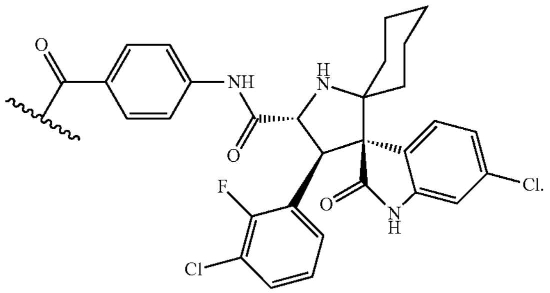 [SMILES: *C(=O)c1ccc(NC(=O)[C@@H]2NC3(CCCCC3)[C@@]3(C(=O)Nc4cc(Cl)ccc43)[C@H]2c2cccc(Cl)c2F)cc1]
In some embodiments, LBM is
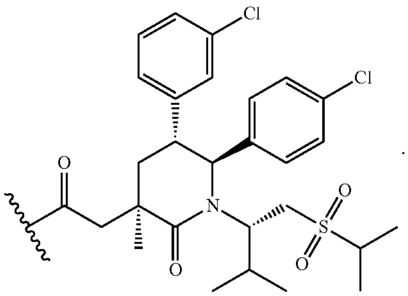 [SMILES: *C(=O)C[C@@]1(C)C[C@H](c2cccc(Cl)c2)[C@@H](c2ccc(Cl)cc2)N([C@H](CS(=O)(=O)C(C)C)C(C)C)C1=O]
In some embodiments, LBM is
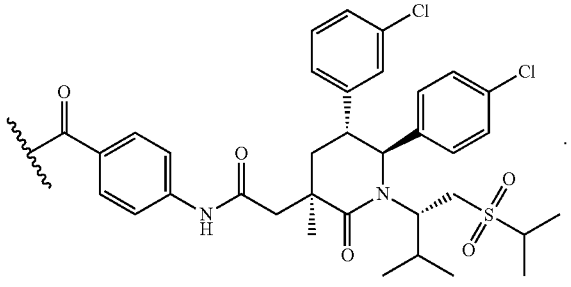 [SMILES: *C(=O)c1ccc(NC(=O)C[C@@]2(C)C[C@H](c3cccc(Cl)c3)[C@@H](c3ccc(Cl)cc3)N([C@H](CS(=O)(=O)C(C)C)C(C)C)C2=O)cc1]
In some embodiments, LBM is
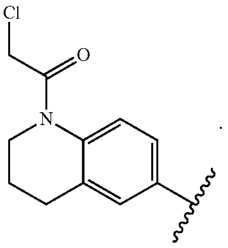 [SMILES: *c1ccc2c(c1)CCCN2C(=O)CCl]
In some embodiments, LBM is
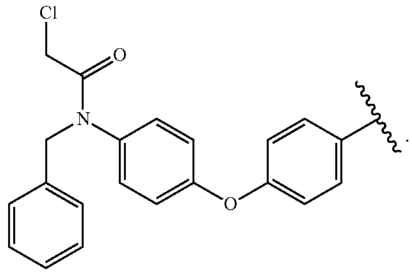 [SMILES: *c1ccc(Oc2ccc(N(Cc3ccccc3)C(=O)CCl)cc2)cc1]
In some embodiments, LBM is
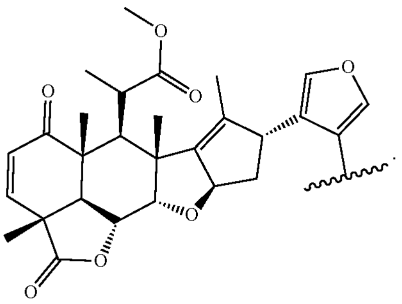 [SMILES: *c1cocc1[C@@H]1C[C@H]2O[C@@H]3[C@@H]4OC(=O)[C@]5(C)C=CC(=O)[C@](C)([C@@H](C(C)C(=O)OC)[C@]3(C)C2=C1C)[C@@H]45]
In some embodiments, LBM is
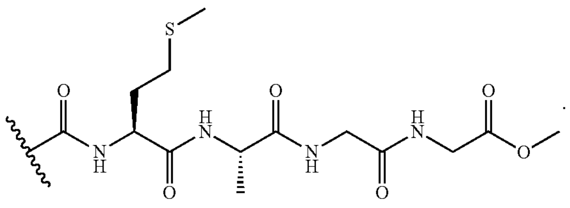 [SMILES: *C(=O)N[C@@H](CCSC)C(=O)N[C@@H](C)C(=O)NCC(=O)NCC(=O)OC]
In some embodiments, LBM is
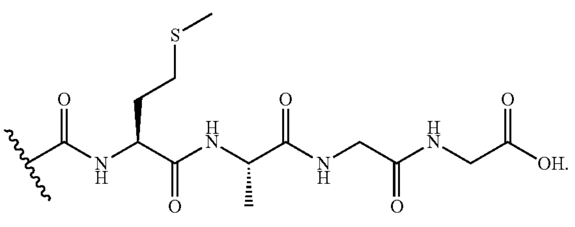 [SMILES: *C(=O)N[C@@H](CCSC)C(=O)N[C@@H](C)C(=O)NCC(=O)NCC(=O)O]

In some embodiments, LBM is

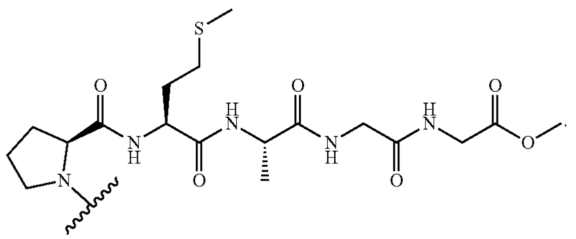 [SMILES: *N1CCC[C@H]1C(=O)N[C@@H](CCSC)C(=O)N[C@@H](C)C(=O)NCC(=O)NCC(=O)OC]

In some embodiments, LBM is

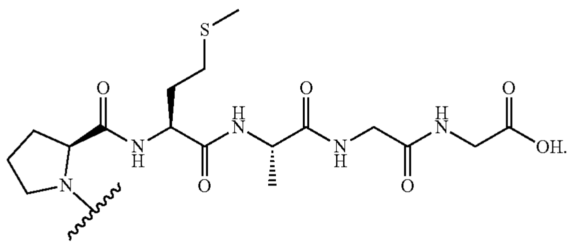 [SMILES: *N1CCC[C@H]1C(=O)N[C@@H](CCSC)C(=O)N[C@@H](C)C(=O)NCC(=O)NCC(=O)O]

In some embodiments, LBM is

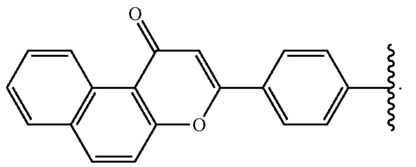 [SMILES: *c1ccc(-c2cc(=O)c3c(ccc4ccccc43)o2)cc1]

In some embodiments, LBM is

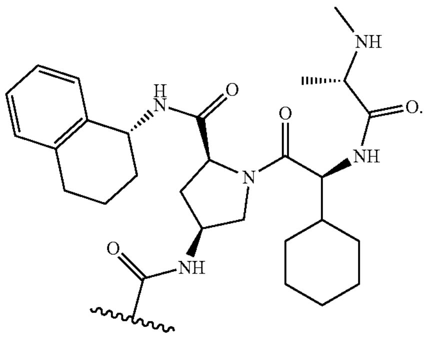 [SMILES: *C(=O)N[C@H]1C[C@@H](C(=O)N[C@@H]2CCCc3ccccc32)N(C(=O)[C@@H](NC(=O)[C@H](C)NC)C2CCCCC2)C1]

In some embodiments, LBM is

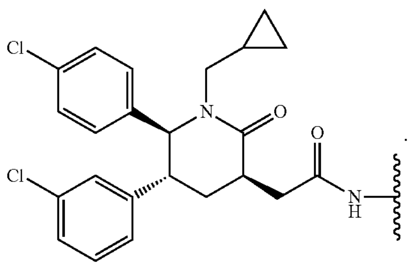 [SMILES: *NC(=O)C[C@H]1C[C@H](c2cccc(Cl)c2)[C@@H](c2ccc(Cl)cc2)N(CC2CC2)C1=O]

In some embodiments, LBM is

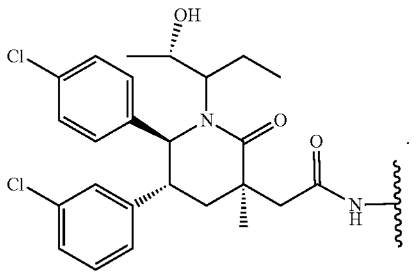 [SMILES: *NC(=O)C[C@@]1(C)C[C@H](c2cccc(Cl)c2)[C@@H](c2ccc(Cl)cc2)N(C(CC)[C@H](C)O)C1=O]

In some embodiments, LBM is

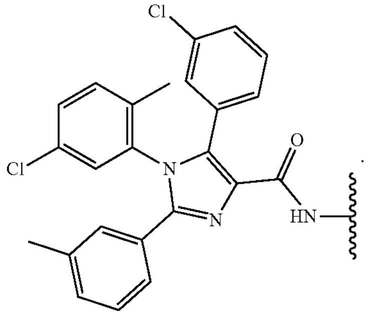 [SMILES: *NC(=O)c1nc(-c2cccc(C)c2)n(-c2cc(Cl)ccc2C)c1-c1cccc(Cl)c1]

In some embodiments, LBM is

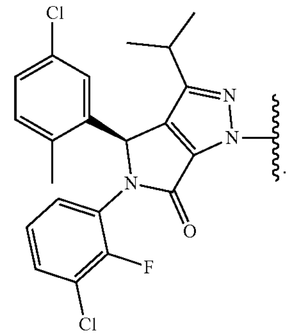 [SMILES: *n1nc(C(C)C)c2c1C(=O)N(c1cccc(Cl)c1F)[C@H]2c1cc(Cl)ccc1C]

In certain embodiments, the present invention provides a compound of formula I, wherein LBM is a E3 ubiquitin ligase (cereblon) binding moiety thereby forming a compound of formula formula I-cc:

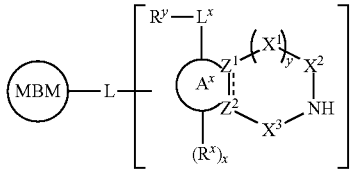

or a pharmaceutically acceptable salt thereof, wherein L and MBM are as defined above and described in embodiments herein, wherein:

each $X^1$ is independently —$CH_2$—, —O—, —NR—, —$CF_2$—,

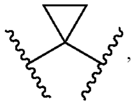 [SMILES: *C1(*)CC1],

—C(O)—, —C(S)—, or

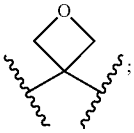 [SMILES: *C1(*)COC1];

$X^2$ and $X^3$ are independently —$CH_2$—, —C(O)—, —C(S)—, or

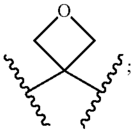;

$Z^1$ and $Z^2$ are independently a carbon atom or a nitrogen atom;

Ring $A^x$ is a fused ring selected from benzo or a 5-6 membered heteroaryl ring having 1-4 heteroatoms independently selected from nitrogen, oxygen, and sulfur;

$L^x$ is a covalent bond or a $C_{1-3}$ bivalent straight or branched saturated or unsaturated hydrocarbon chain wherein 1-2 methylene units of the chain are independently and optionally replaced with —O—, —S—, —C(O)—, —C(S)—, —$CR_2$—, —CRF—, —$CF_2$—, —NR—, or —$S(O)_2$—;

each $R^x$ is independently selected from hydrogen, deuterium, $R^z$, halogen, —CN, —$NO_2$, —OR, —SR, —$NR_2$, —$S(O)_2R$, —$S(O)_2NR_2$, —S(O)R, —$CF_2R$, —$CF_3$, —$CR_2(OR)$, —$CR_2(NR_2)$, —C(O)R, —C(O)OR, —C(O)$NR_2$, —C(O)N(R)OR, —OC(O)R, —OC(O)$NR_2$, —C(S)$NR_2$, —N(R)C(O)OR, —N(R)C(O)R, —N(R)C(O)$NR_2$, —N(R)$S(O)_2R$, —OP(O)$R_2$, —OP(O)$(OR)_2$, —OP(O)(OR)$NR_2$, —OP(O)$(NR_2)_2$, —Si(OR)$R_2$, and —$SiR_3$; or two $R^x$ groups are optionally taken together to form an optionally substituted 5-8 membered partially unsaturated or aryl fused ring having 0-2 heteroatoms independently selected from nitrogen, oxygen, or sulfur;

each R is independently selected from hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same carbon or nitrogen are optionally taken together with their intervening atoms to form an optionally substituted 4-7 membered saturated, partially unsaturated, or heteroaryl ring having 0-3 heteroatoms, in addition to the carbon or nitrogen, independently selected from nitrogen, oxygen, and sulfur;

$R^y$ is selected from

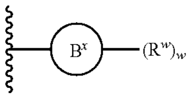

or hydrogen;

Ring $B^x$ is phenyl, a 4-10 membered saturated or partially unsaturated monocyclic, bicyclic carbocyclic or heterocyclic ring having 1-3 heteroatoms independently selected from nitrogen, oxygen, and sulfur, or a 5-6 membered heteroaryl ring having 1-4 heteroatoms independently selected from nitrogen, oxygen, and sulfur, wherein Ring $B^x$ is further optionally substituted with 1-2 oxo groups;

each $R^w$ is independently selected from hydrogen, deuterium, $R^z$, halogen, —CN, —$NO_2$, —OR, —SR, —$NR_2$, —$S(O)_2R$, —$S(O)_2NR_2$, —S(O)R, —$CF_2R$, —$CF_3$, —$CR_2(OR)$, —$CR_2(NR_2)$, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, —N(R)$S(O)_2R$, —OP(O)$R_2$, —OP(O)$(OR)_2$, —OP(O)(OR)$NR_2$, —OP(O)$(NR_2)_2$, and —$SiR_3$;

each $R^z$ is independently selected from an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

---- is a single or double bond;

x is 0, 1, 2, 3 or 4;

y is 0, 1 or 2; and w is 0, 1, 2, 3 or 4.

As defined above and described herein, each $X^1$ is independently —$CH_2$—, —O—, —NR—, —$CF_2$—,

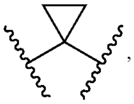 [SMILES: *C1(*)CC1],

—C(O)—, —C(S)—, or

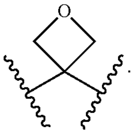 [SMILES: *C1(*)COC1].

In some embodiments, $X^1$ is a covalent bond. In some embodiments, $X^1$ is —$CH_2$—. In some embodiments, $X^1$ is —O—. In some embodiments, $X^1$ is —NR—. In some embodiments, $X^1$ is —$CF_2$—. In some embodiments, $X^1$ is

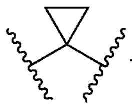 [SMILES: *C1(*)CC1]

In some embodiments, $X^1$ is —C(O)—. In some embodiments, $X^1$ is —C(S)—. In some embodiments, $X^1$ is

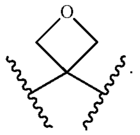 [SMILES: *C1(*)COC1]

In certain embodiments, $X^1$ is selected from those shown in the compounds of Table 1.

As defined above and described herein, $X^2$ and $X^3$ are independently —$CH_2$—, —C(O)—, —C(S)—, or

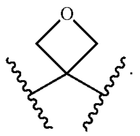 [SMILES: *C1(*)COC1]

In some embodiments, $X^2$ and $X^3$ are independently —$CH_2$—. In some embodiments, $X^2$ and $X^3$ are independently —C(O)—. In some embodiments, $X^2$ and $X^3$ are independently —C(S)—. In some embodiments, $X^2$ and $X^3$ are independently

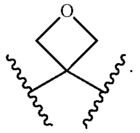 [SMILES: *C1(*)COC1]

In certain embodiments, $X^2$ and $X^3$ are independently selected from those shown in the compounds of Table 1.

As define above and described herein, $Z^1$ and $Z^2$ are independently a carbon atom or a nitrogen atom.

In some embodiments, $Z^1$ and $Z^2$ are independently a carbon atom. In some embodiments, $Z^1$ and $Z^2$ are independently a carbon atom.

In certain embodiments, $Z^1$ and $Z^2$ are independently selected from those shown in the compounds of Table 1.

As defined above and described herein, Ring $A^x$ is fused ring selected from benzo or a 5-6 membered heteroaryl ring having 1-4 heteroatoms independently selected from nitrogen, oxygen, and sulfur.

In some embodiments, Ring $A^x$ is benzo. In some embodiments, Ring $A^x$ is a 5-6 membered heteroaryl ring having 1-4 heteroatoms independently selected from nitrogen, oxygen, and sulfur.

In some embodiments, Ring $A^x$ is

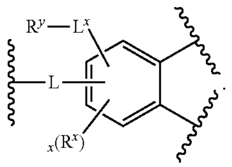

In some embodiments, Ring $A^x$ is

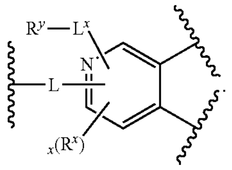

In some embodiments, Ring $A^x$ is

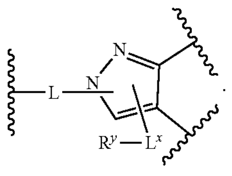

In some embodiments, Ring $A^x$ is

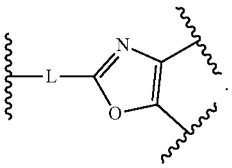

In certain embodiments, Ring $A^x$ is selected from those shown in the compounds of Table 1.

As defined above and described herein, LU is a covalent bond or a $C_{1-3}$ bivalent straight or branched saturated or unsaturated hydrocarbon chain wherein 1-2 methylene units of the chain are independently and optionally replaced with —O—, —S—, —C(O)—, —C(S)—, —$CR_2$—, —CRF—, —$CF_2$—, —NR—, or —$S(O)_2$—.

In some embodiments, LU is a covalent bond. In some embodiments, LU is a $C_{1-3}$ bivalent straight or branched saturated or unsaturated hydrocarbon chain wherein 1-2 methylene units of the chain are independently and optionally replaced with —O—, —S—, —C(O)—, —C(S)—, —$CR_2$—, —CRF—, —$CF_2$—, —NR—, or —$S(O)_2$—.

In some embodiments, $L^x$ is —C(O)—.

In certain embodiments, $L^x$ is selected from those shown in the compounds of Table 1.

As defined above and described herein, each $R^x$ is independently selected from hydrogen, deuterium, $R^z$, halogen, —CN, —$NO_2$, —OR, —SR, —$NR_2$, —$S(O)_2R$, —$S(O)_2NR_2$, —S(O)R, —$CF_2R$, —$CF_3$, —$CR_2$(OR), —$CR_2$($NR_2$), —C(O)R, —C(O)OR, —C(O)$NR_2$, —C(O)N(R)OR, —OC(O)R, —OC(O)$NR_2$, —C(S)$NR_2$, —N(R)C(O)OR, —N(R)C(O)R, —N(R)C(O)$NR_2$, —N(R)S(O)$_2$R, —OP(O)$R_2$, —OP(O)(OR)$_2$, —OP(O)(OR)$NR_2$, —OP(O)($NR_2$)$_2$, —Si(OR)$R_2$, and —$SiR_3$, or two $R^x$ groups are optionally taken together to form an optionally substituted 5-8 membered partially unsaturated or aryl fused ring having 0-2 heteroatoms independently selected from nitrogen, oxygen, or sulfur.

In some embodiments, $R^x$ is hydrogen. In some embodiments, $R^x$ is deuterium. In some embodiments, $R^x$ is $R^z$. In some embodiments, $R^x$ is halogen. In some embodiments, $R^x$ is —CN. In some embodiments, $R^x$ is —$NO_2$. In some embodiments, $R^x$ is —OR. In some embodiments, $R^x$ is —SR. In some embodiments, $R^x$ is —$NR_2$. In some embodiments, $R^x$ is —S(O)$_2$R. In some embodiments, $R^x$ is —S(O)$_2$ $NR_2$. In some embodiments, $R^x$ is —S(O)R. In some embodiments, $R^x$ is —$CF_2$R. In some embodiments, $R^x$ is —$CF_3$. In some embodiments, $R^x$ is —$CR_2$(OR). In some embodiments, $R^x$ is —$CR_2$($NR_2$). In some embodiments, $R^x$ is —C(O)R. In some embodiments, $R^x$ is —C(O)OR. In some embodiments, $R^x$ is —C(O)$NR_2$. In some embodiments, $R^x$ is —C(O)N(R)OR. In some embodiments, $R^x$ is —OC(O)R. In some embodiments, $R^x$ is —OC(O)$NR_2$. In some embodiments, $R^x$ is —C(S)$NR_2$. In some embodiments, $R^x$ is —N(R)C(O)OR. In some embodiments, $R^x$ is —N(R)C(O)R. In some embodiments, $R^x$ is —N(R)C(O)$NR_2$. In some embodiments, $R^x$ is —N(R)S(O)$_2$R. In some embodiments, $R^x$ is —OP(O)$R_2$. In some embodiments, $R^x$ is —OP(O)(OR)$_2$. In some embodiments, $R^x$ is —OP(O)(OR)$NR_2$. In some embodiments, $R^x$ is —OP(O)($NR_2$)$_2$. In some embodiments, $R^x$ is —Si(OR)$R_2$. In some embodiments, $R^x$ is —$SiR_3$. In some embodiments, two $R^x$ groups are optionally taken together to form an optionally substituted 5-8 membered partially unsaturated or aryl fused ring having 0-2 heteroatoms independently selected from nitrogen, oxygen, or sulfur.

In some embodiments, $R^x$ is fluoro. In some embodiments, $R^x$ is bromo. In some embodiments, $R^x$ is methyl. In some embodiments, $R^x$ is —OH. In some embodiments, $R^x$ is —$NH_2$. In some embodiments, $R^x$ is —$NHCH_3$. In some embodiments, $R^x$ is —N($CH_3$)$_2$. In some embodiments, $R^x$ is —NHCH($CH_3$)$_2$. In some embodiments, $R^x$ is —$NHSO_2CH_3$. In some embodiments, $R^x$ is —$CH_2OH$. In some embodiments, $R^x$ is —$CH_2NH_2$. In some embodiments, $R^x$ is —C(O)$NH_2$. In some embodiments, $R^x$ is —C(O)$NHCH_3$. In some embodiments, $R^x$ is

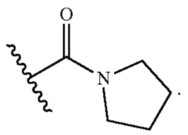 [SMILES: *C(=O)N1CCCC1]

In some embodiments, $R^x$ is

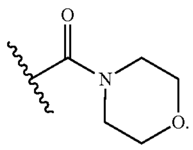 [SMILES: *C(=O)N1CCOCC1]

In some embodiments, $R^x$ is

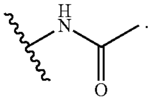

In some embodiments, $R^x$ is

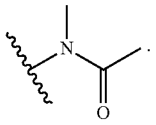

In some embodiments, $R^x$ is

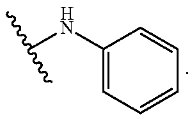

In some embodiments, $R^x$ is

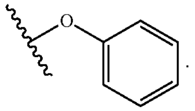

In some embodiments, $R^x$ is

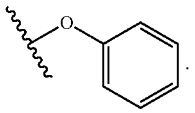

In some embodiments, $R^x$ is

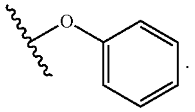

In some embodiments, $R^x$ is

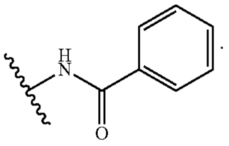 [SMILES: *NC(=O)c1ccccc1]

In some embodiments, $R^x$ is

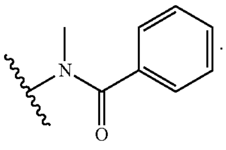 [SMILES: *N(C)C(=O)c1ccccc1]

In certain embodiments, each $R^x$ is independently selected from those shown in the compounds of Table 1.

As defined above and described here, each R is independently selected from hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or two R groups on the same carbon or nitrogen are optionally taken together with their intervening atoms to form an optionally substituted 4-7 membered saturated, partially unsaturated, or heteroaryl ring having 0-3 heteroatoms, in addition to the carbon or nitrogen, independently selected from nitrogen, oxygen, and sulfur.

In some embodiments, R is hydrogen. In some embodiments, R is an optionally substituted $C_{1-6}$ aliphatic. In some embodiments, R is an optionally substituted phenyl. In some embodiments, R is an optionally substituted 4-7 membered saturated or partially unsaturated heterocyclic having 1-2 heteroatoms independently selected from nitrogen, oxygen, and sulfur. In some embodiments, R is an optionally substituted a 5-6 membered heteroaryl ring having 1-4 heteroatoms independently selected from nitrogen, oxygen, and sulfur. In some embodiments, two R groups on the same carbon or nitrogen are optionally taken together with their intervening atoms to form an optionally substituted 4-7 membered saturated, partially unsaturated, or heteroaryl ring having 0-3 heteroatoms, in addition to the carbon or nitrogen, independently selected from nitrogen, oxygen, and sulfur.

As defined above and described herein, $R^y$ is selected from

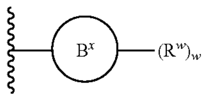

or hydrogen.

In some embodiment $R^y$ is

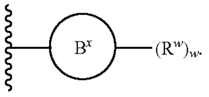

In some embodiments, $R^y$ is hydrogen.

In certain embodiments, $R^y$ is selected from those shown in the compounds of Table 1.

As defined above and described herein, Ring $B^x$ is phenyl, a 4-10 membered saturated or partially unsaturated monocyclic, bicyclic carbocyclic or heterocyclic ring having 1-3 heteroatoms independently selected from nitrogen, oxygen, and sulfur, or a 5-6 membered heteroaryl ring having 1-4 heteroatoms independently selected from nitrogen, oxygen, and sulfur, wherein Ring $B^x$ is further optionally substituted with 1-2 oxo groups.

In some embodiments, Ring $B^x$ is phenyl. In some embodiments, Ring $B^x$ is a 4-10 membered saturated or partially unsaturated monocyclic, bicyclic carbocyclic or heterocyclic ring having 1-3 heteroatoms independently selected from nitrogen, oxygen, and sulfur In some embodiments, Ring $B^x$ is a 5-6 membered heteroaryl ring having 1-4 heteroatoms independently selected from nitrogen, oxygen, and sulfur. In some embodiments, Ring $B^x$ is further optionally substituted with 1-2 oxo groups.

In some embodiments, Ring $B^x$ is

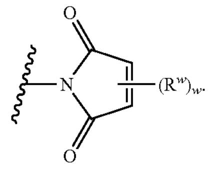

In some embodiments, Ring $B^x$ is

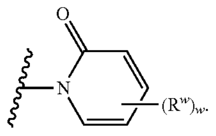

In some embodiments, Ring $B^x$ is

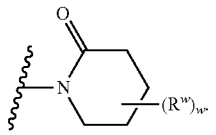

In some embodiments Ring $B^x$ is

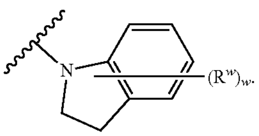

In some embodiments Ring $B^x$ is

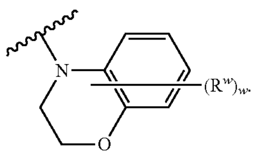

In certain embodiments, Ring $B^x$ is selected from those shown in the compounds of Table 1.

As defined above and described herein, each $R^w$ is independently selected from hydrogen, deuterium, $R^z$, halogen, —CN, —$NO_2$, —OR, —SR, —$NR_2$, —$S(O)_2R$, —$S(O)_2NR_2$, —S(O)R, —$CF_2R$, —$CF_3$, —$CR_2(OR)$, —$CR_2(NR_2)$, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, —N(R)S$(O)_2$R, —OP(O)$R_2$, —OP(O)$(OR)_2$, —OP(O)(OR)$NR_2$, —OP(O)$(NR_2)_2$, and —$SiR_3$.

In some embodiments, $R^w$ is hydrogen. In some embodiments, $R^w$ is deuterium. In some embodiments, $R^w$ is $R^z$. In some embodiments, $R^w$ is halogen. In some embodiments, $R^w$ is —CN. In some embodiments, $R^w$ is —$NO_2$. In some embodiments, $R^w$ is —OR. In some embodiments, $R^w$ is —SR. In some embodiments, $R^w$ is —$NR_2$. In some embodiments, $R^w$ is —S$(O)_2$R. In some embodiments, $R^w$ is —S$(O)_2$ $NR_2$. In some embodiments, $R^w$ is —S(O)R. In some embodiments, $R^w$ is —$CF_2$R. In some embodiments, $R^w$ is —$CF_3$. In some embodiments, $R^w$ is —$CR_2$(OR). In some embodiments, $R^w$ is —$CR_2$($NR_2$). In some embodiments, $R^w$ is —C(O)R. In some embodiments, $R^w$ is —C(O)OR. In some embodiments, $R^w$ is —C(O)$NR_2$. In some embodiments, $R^w$ is —C(O)N(R)OR. In some embodiments, $R^w$ is —OC(O)R. In some embodiments, $R^w$ is —OC(O)$NR_2$. In some embodiments, $R^w$ is —N(R)C(O)OR. In some embodiments, $R^w$ is —N(R)C(O)R. In some embodiments, $R^w$ is —N(R)C(O)$NR_2$. In some embodiments, $R^w$ is —N(R)S$(O)_2$ R. In some embodiments, $R^w$ is —OP(O)$R_2$. In some embodiments, $R^w$ is —OP(O)$(OR)_2$. In some embodiments, $R^w$ is —OP(O)(OR)$NR_2$. In some embodiments, $R^w$ is —OP(O)$(NR_2)_2$. In some embodiments, $R^w$ is —$SiR_3$.

In certain embodiments, $R^w$ is selected from those shown in the compounds of Table 1.

As defined above and described herein, each $R^z$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur.

In some embodiments, $R^z$ is an optionally substituted $C_{1-6}$ aliphatic. In some embodiments, $R^z$ is an optionally substituted phenyl. In some embodiments, $R^z$ is an optionally substituted 4-7 membered saturated or partially unsaturated heterocyclic ring having 1-2 heteroatoms independently selected from nitrogen, oxygen, and sulfur. In some embodiments, $R^z$ is an optionally substituted 5-6 membered heteroaryl ring having 1-4 heteroatoms independently selected from nitrogen, oxygen, and sulfur.

In some embodiments, $R^z$ is

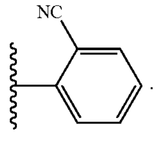 [SMILES: *c1ccccc1C#N]

In some embodiments, $R^z$ is

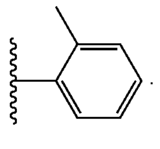 [SMILES: *c1ccccc1C]

In some embodiments, $R^z$ is

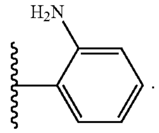 [SMILES: *c1ccccc1N]

In some embodiments, $R^z$ is

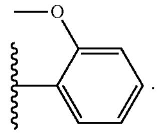 [SMILES: *c1ccccc1OC]

In some embodiments, $R^z$ is

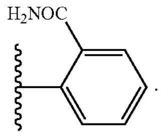 [SMILES: *c1ccccc1C(N)=O]

In some embodiments, $R^z$ is

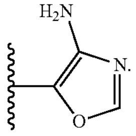

In some embodiments, $R^z$ is

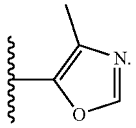 [SMILES: *c1ocnc1C]

In certain embodiments, $R^z$ is selected from those shown in the compounds of Table 1.

As defined above and described herein, ---- is a single or double bond.

In some embodiments, ---- is a single bond. In some embodiments, ---- is a double bond.

In certain embodiments, ---- is selected from those shown in the compounds of Table 1.

As defined above and described herein, w is 0, 1, 2, 3 or 4.

In some embodiments, w is 0. In some embodiments, w is 1. In some embodiments, w is 2. In some embodiments, w is 3. In some embodiments, w is 4.

In certain embodiments, w is selected from those shown in the compounds of Table 1.

As defined above and described herein, x is 0, 1, 2, 3 or 4.

In some embodiments, x is 0. In some embodiments, x is 1. In some embodiments, m is 2. In some embodiments, x is 3. In some embodiments, x is 4.

In certain embodiments, x is selected from those shown in the compounds of Table 1.

As defined above and described herein, y is 0, 1 or 2.

In some embodiments, y is 0. In some embodiments, y is 1. In some embodiments, y is 2.

In certain embodiments, y is selected from those shown in the compounds of Table 1.

In some embodiments, the present invention provides a compound of formula I-cc, wherein Ring $A^x$ is benzo, y is 1, $X^1$ is —$CH_2$—, $X^2$ and $X^3$ are —C(O)—, and $Z^1$ and $Z^2$ are carbon atoms as shown, to provide a compound of formula I-cc-1:

I-cc-1

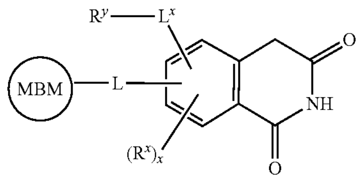

or a pharmaceutically acceptable salt thereof, wherein each of MBM, L, Lx, $R^x$, $R^y$, and x is as defined above and described in embodiments herein, both singly and in combination.

In some embodiments, the present invention provides a compound of formula I-cc, wherein Ring $A^x$ is imidazolyl, y is 1, $X^1$ is —$CH_2$—, $X^2$ and $X^3$ are —C(O)—, and $Z^1$ and $Z^2$ are carbon atoms as shown, to provide a compound of formula I-cc2:

I-cc-2

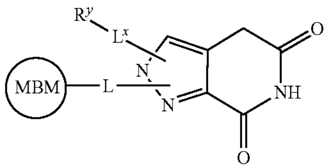

or a pharmaceutically acceptable salt thereof, wherein each of MBM, L, Lx, and $R^y$ is as defined above and described in embodiments herein, both singly and in combination.

In some embodiments, the present invention provides a compound of formula I-cc, wherein Ring $A^x$ is imidazolyl, y is 1, $X^1$ is —$CH_2$—, $X^2$ and $X^3$ are —C(O)—, and $Z^1$ and $Z^2$ are carbon atoms as shown, to provide a compound of formula I-cc-3:

I-cc-3

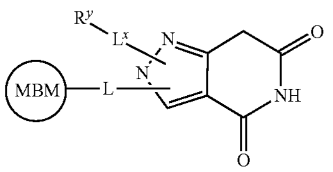

or a pharmaceutically acceptable salt thereof, wherein each of MBM, L, $L^x$, and $R^y$ is as defined above and described in embodiments herein, both singly and in combination.

In some embodiments, the present invention provides a compound of formula I-cc, wherein Ring $A^x$ is oxazolyl, y is 1, $X^1$ is —$CH_2$—, $X^2$ and $X^3$ are —C(O)—, and $Z^1$ and $Z^2$ are carbon atoms as shown, to provide a compound of formula I-cc-4:

I-cc-4

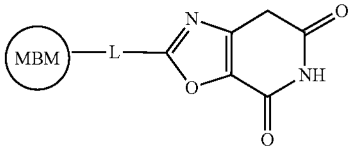

or a pharmaceutically acceptable salt thereof, wherein each of MBM and L is as defined above and described in embodiments herein, both singly and in combination.

In some embodiments, the present invention provides a compound of formula I-cc, wherein Ring $A^x$ is benzo, y is 0, $X^2$ and $X^3$ are —C(O)—, and $Z^1$ and $Z^2$ are carbon atoms as shown, to provide a compound of formula I-cc-5:

I-cc-5

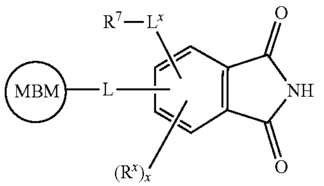

or a pharmaceutically acceptable salt thereof, wherein each of MBM, L, $L^x$, $R^x$, $R^y$, and x is as defined above and described in embodiments herein, both singly and in combination.

In some embodiments, the present invention provides a compound of formula I-cc, wherein Ring $A^x$ is benzo, y is 1, $X^1$ is —O—, $X^2$ and $X^3$ are —C(O)—, and Z and $Z^2$ are carbon atoms as shown, to provide a compound of formula I-cc-6:

I-cc-6

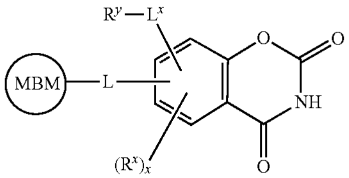

or a pharmaceutically acceptable salt thereof, wherein each of MBM, L, $L^x$, $R^x$, $R^y$, and x is as defined above and described in embodiments herein, both singly and in combination.

In some embodiments, the present invention provides a compound of formula I-cc, wherein Ring $A^x$ is benzo, y is 1, $X^1$ is —NR—, $X^2$ and $X^3$ are —C(O)—, and Z and $Z^2$ are carbon atoms as shown, to provide a compound of formula I-cc-7:

I-cc-7

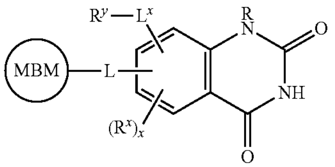

or a pharmaceutically acceptable salt thereof, wherein each of MBM, L, $L^x$, R, $R^x$, $R^y$, and x is as defined above and described in embodiments herein, both singly and in combination.

In some embodiments, the present invention provides a compound of formula I-cc, wherein Ring $A^x$ is benzo, y is 1, $X^1$ is —$CF_2$—, $X^2$ and $X^3$ are —C(O)—, and $Z^1$ and $Z^2$ are carbon atoms as shown, to provide a compound of formula I-cc-8:

I-cc-8

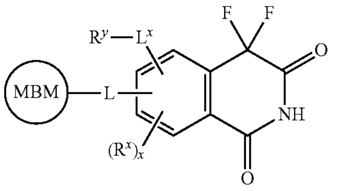

or a pharmaceutically acceptable salt thereof, wherein each of MBM, L, $L^x$, $R^x$, $R^y$, and x is as defined above and described in embodiments herein, both singly and in combination.

In some embodiments, the present invention provides a compound of formula I-cc, wherein Ring $A^x$ is benzo, y is 1, $X^1$ is

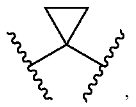

, $X^2$ and $X^3$ are —C(O)—, and $Z^1$ and $Z^2$ are carbon atoms as shown, to provide a compound of formula I-cc-9:

I-cc-9

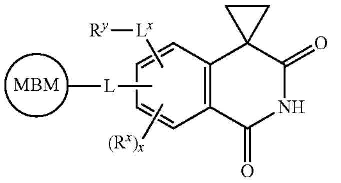

or a pharmaceutically acceptable salt thereof, wherein each of MBM, L, $L^x$, $R^x$, $R^y$, and x is as defined above and described in embodiments herein, both singly and in combination.

In some embodiments, the present invention provides a compound of formula I-cc, wherein Ring Ax is pyridyl, y is 1, $X^1$ is —$CH_2$—, $X^2$ and $X^3$ are —C(O)—, and $Z^1$ and $Z^2$ are carbon atoms as shown, to provide a compound of formula I-cc-10:

I-cc-10

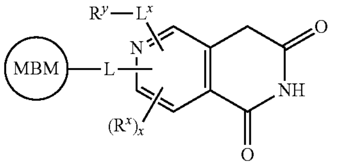

or a pharmaceutically acceptable salt thereof, wherein each of MBM, L, $L^x$, $R^x$, $R^y$, and x is as defined above and described in embodiments herein, both singly and in combination.

In some embodiments, the present invention provides a compound of formula I-cc, wherein Ring $A^x$ is pyridyl, y is 1, $X^1$ is —$CH_2$—, $X^2$ and $X^3$ are —C(O)—, and $Z^1$ and $Z^2$ are carbon atoms as shown, to provide a compound of formula I-cc-11:

I-cc-11

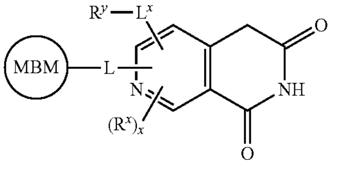

or a pharmaceutically acceptable salt thereof, wherein each of MBM, L, $L^x$, $R^x$, $R^y$, and x is as defined above and described in embodiments herein, both singly and in combination.

In some embodiments, the present invention provides a compound of formula I-cc, wherein Ring A is benzo, y is 1, $X^1$, $X^2$ and $X^3$ are —C(O)—, and $Z^1$ and $Z^2$ are carbon atoms as shown, to provide a compound of formula I-cc-12:

I-cc-12

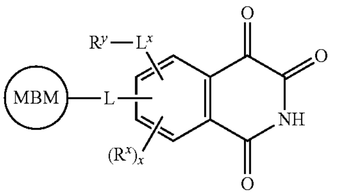

or a pharmaceutically acceptable salt thereof, wherein each of MBM, L, $L^x$, $R^x$, $R^y$, and x is as defined above and described in embodiments herein, both singly and in combination.

In some embodiments, LBM is

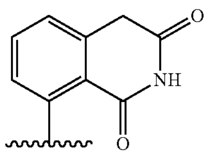

.

In some embodiments, LBM is

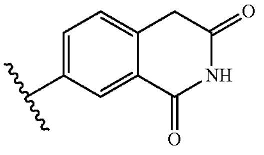

.

In some embodiments, LBM is

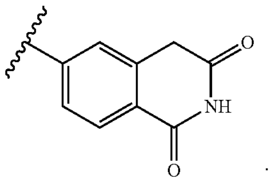 [SMILES: *c1ccc2c(c1)CC(=O)NC2=O]

In some embodiments, LBM is

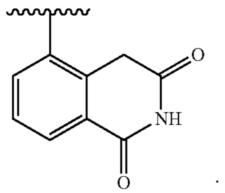 [SMILES: *c1cccc2c1CC(=O)NC2=O]

In some embodiments, LBM is

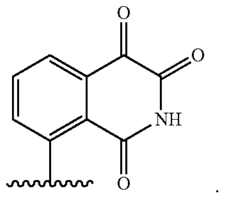 [SMILES: *c1cccc2c1C(=O)NC(=O)C2=O]

In some embodiments, LBM is

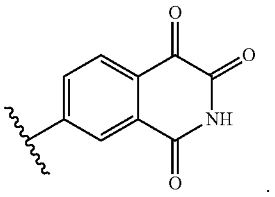 [SMILES: *c1ccc2c(c1)C(=O)NC(=O)C2=O]

In some embodiments, LBM is

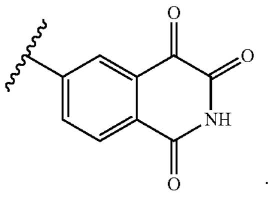 [SMILES: *c1ccc2c(c1)C(=O)C(=O)NC2=O]

In some embodiments, LBM is

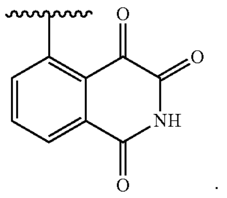 [SMILES: *c1cccc2c1C(=O)C(=O)NC2=O]

In some embodiments, LBM is selected from those in Table 1.

In certain embodiments, the present invention provides a compound of formula I, wherein LBM is a RPN13 binding moiety thereby forming a compound of formula I-dd:

I-dd

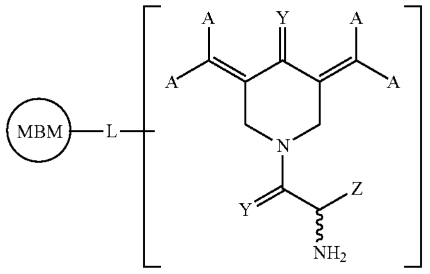

or a pharmaceutically acceptable salt thereof, wherein L and MBM are as defined above and described in embodiments herein, and wherein each of the variables A, Y, and Z is as described and defined in WO 2019/165229, the entirety of each of which is herein incorporated by reference.

In certain embodiments, the present invention provides a compound of formula I, wherein LBM is a Ubr1 binding moiety as described in Shanmugasundaram, K. et al, J. Bio. Chem. 2019, doi: 10.1074/jbc.AC119.010790, the entirety of each of which is herein incorporated by reference, thereby forming a compound of formula I-ee-1 or I-ee-2:

I-ee-1

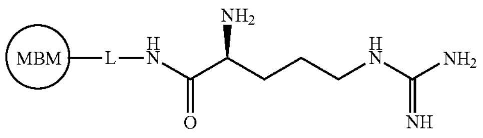

I-ee-2

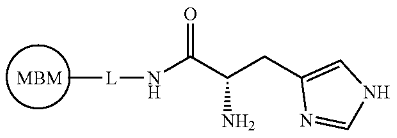

or a pharmaceutically acceptable salt thereof, wherein L and MBM are as defined above and described in embodiments herein.

In certain embodiments, the present invention provides a compound of formula I, wherein LBM is a CRBN binding moiety thereby forming a compound of formula I-ff:

I-ff

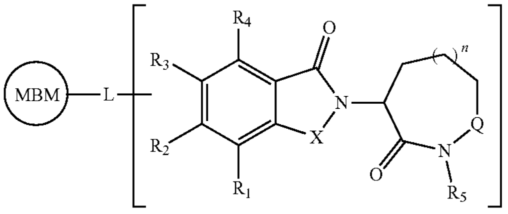

or a pharmaceutically acceptable salt thereof, wherein L and MBM are as defined above and described in embodiments herein, and wherein each of the variables $R_1$, $R_2$, $R_3$, $R_4$, $R_5$, Q, X, and n is as described and defined in US 2019/276474, the entirety of each of which is herein incorporated by reference.

In certain embodiments, the present invention provides a compound of formula I, wherein LBM is a CRBN E3 ubiquitin ligase binding moiety thereby forming a compound of formula I-gg-1, I-gg-2, I-gg-3 or I-gg-4:

I-gg-1

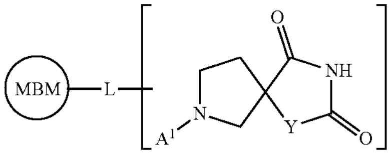

I-gg-2

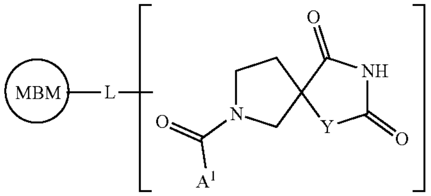

I-gg-3

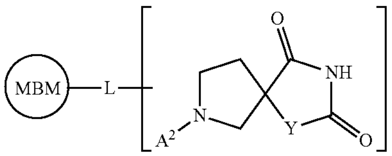

I-gg-4

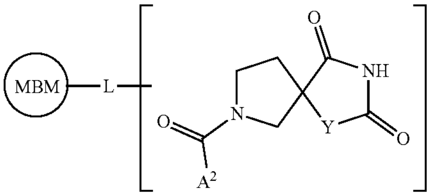

or a pharmaceutically acceptable salt thereof, wherein L and MBM are as defined above and described in embodiments herein, and wherein each of the variables Y, $A^1$, and $A^3$ is as described and defined in WO 2019/236483, the entirety of each of which is herein incorporated by reference.

In some embodiments, the present invention provides the compound of formula I-c, wherein MBM is

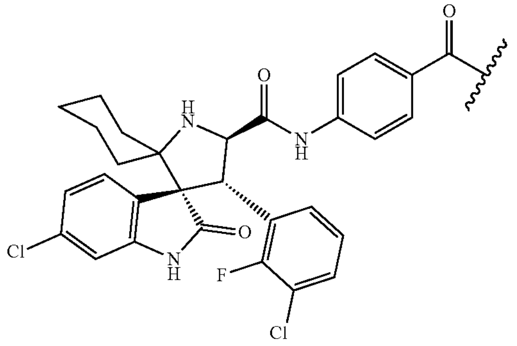 [SMILES: *C(=O)c1ccc(NC(=O)[C@@H]2NC3(CCCCC3)[C@@]3(C(=O)Nc4cc(Cl)ccc43)[C@H]2c2cccc(Cl)c2F)cc1]

as shown, thereby providing a compound of formula I-hh-1:

I-hh-1

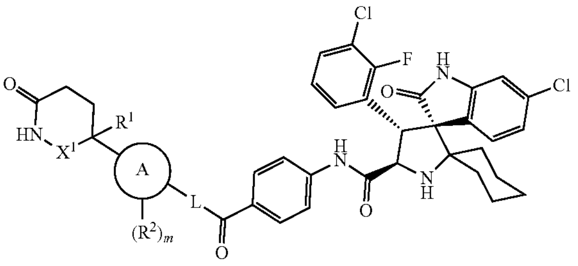

or a pharmaceutically acceptable salt thereof, wherein each of $X^1$, $R^1$, $R^2$, Ring A, m, and L is as defined above and described in embodiments herein, both singly and in combination.

In some embodiments, the present invention provides the compound of formula I-c, wherein Ring A is

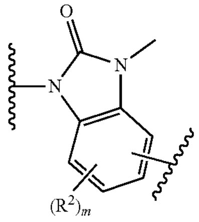

,

MBM is

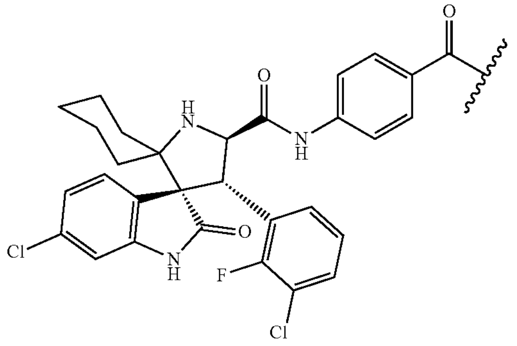 [SMILES: *C(=O)c1ccc(NC(=O)[C@@H]2NC3(CCCCC3)[C@@]3(C(=O)Nc4cc(Cl)ccc43)[C@H]2c2cccc(Cl)c2F)cc1]

as shown, thereby providing a compound of formula I-hh-2:

I-hh-2

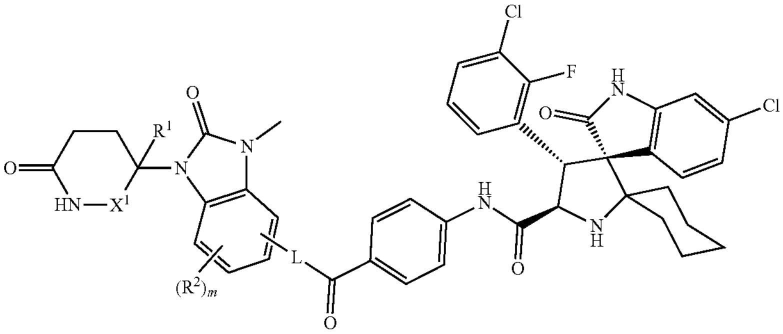

or a pharmaceutically acceptable salt thereof, wherein each of X, $R^1$, $R^2$, m, and L is as defined above and described in embodiments herein, both singly and in combination.

In some embodiments, the present invention provides the compound of formula I-c, wherein MBM is

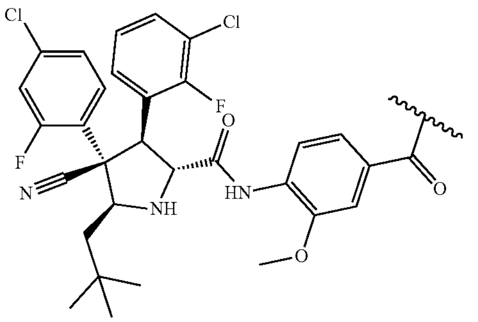 [SMILES: *C(=O)c1ccc(NC(=O)[C@@H]2N[C@@H](CC(C)(C)C)[C@](C#N)(c3ccc(Cl)cc3F)[C@H]2c2cccc(Cl)c2F)c(OC)c1]

as shown, thereby providing a compound of formula I-hh-3:

I-hh-3

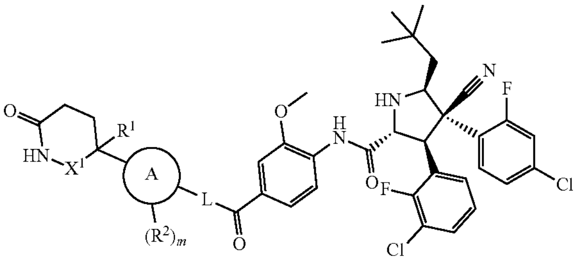

or a pharmaceutically acceptable salt thereof, wherein each of $X^1$, $R^1$, $R^2$, Ring A, m, and L is as defined above and described in embodiments herein, both singly and in combination.

In some embodiments, the present invention provides the compound of formula I-c, wherein Ring A is

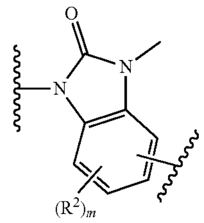

,

MBM is

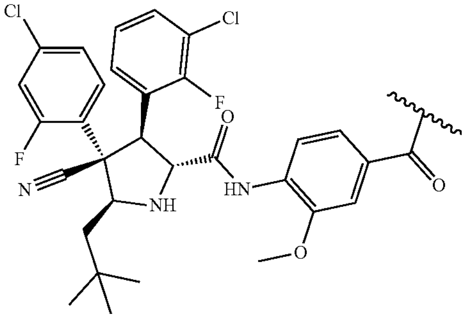 [SMILES: *C(=O)c1ccc(NC(=O)[C@@H]2N[C@@H](CC(C)(C)C)[C@](C#N)(c3ccc(Cl)cc3F)[C@H]2c2cccc(Cl)c2F)c(OC)c1]

as shown, thereby providing a compound of formula I-hh-4:

I-hh-4

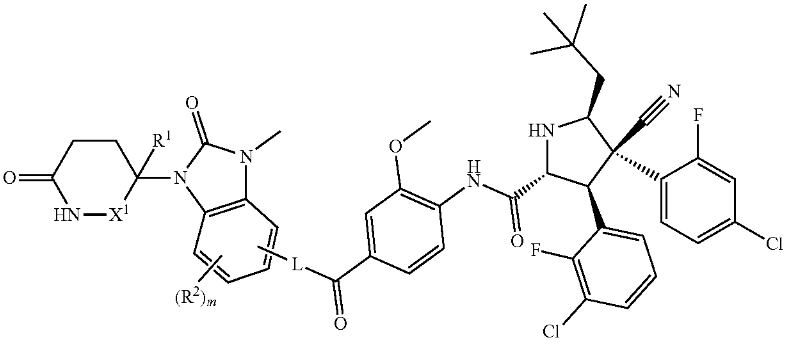

or a pharmaceutically acceptable salt thereof, wherein each of $X^1$, $R^1$, $R^2$, m, and L is as defined above and described in embodiments herein, both singly and in combination.

In some embodiments, the present invention provides the compound of formula I-c, wherein MBM is

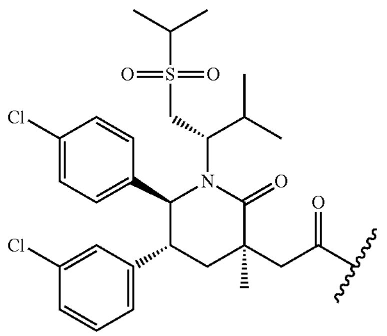 [SMILES: *C(=O)C[C@@]1(C)C[C@H](c2cccc(Cl)c2)[C@@H](c2ccc(Cl)cc2)N([C@H](CS(=O)(=O)C(C)C)C(C)C)C1=O]

as shown, thereby providing a compound of formula I-hh-5:

I-hh-5

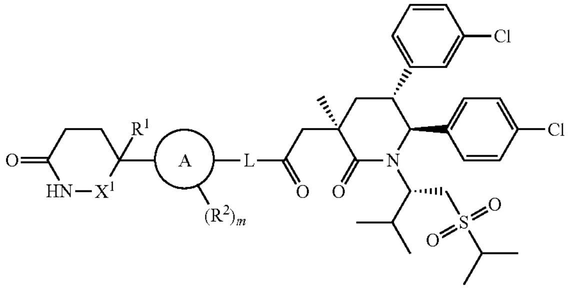

or a pharmaceutically acceptable salt thereof, wherein each of X, $R^1$, $R^2$, Ring A, m, and L is as defined above and described in embodiments herein, both singly and in combination.

In some embodiments, the present invention provides the compound of formula I-c, wherein Ring A is

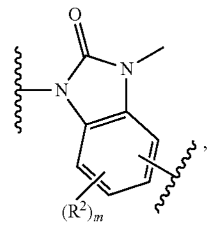

MBM is

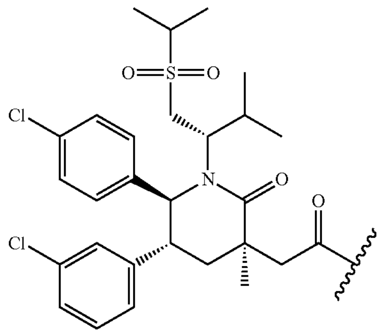 [SMILES: *C(=O)C[C@@]1(C)C[C@H](c2cccc(Cl)c2)[C@@H](c2ccc(Cl)cc2)N([C@H](CS(=O)(=O)C(C)C)C(C)C)C1=O]

as shown, thereby providing a compound of formula I-hh-6:

I-hh-6

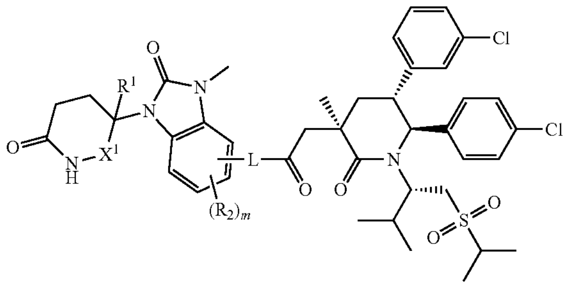

or a pharmaceutically acceptable salt thereof, wherein each of $X^1$, $R^1$, $R^2$, m, and L is as defined above and described in embodiments herein, both singly and in combination.

In some embodiments, the present invention provides the compound of formula I-c, wherein MBM is

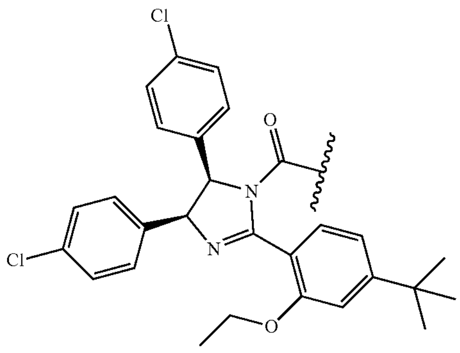 [SMILES: *C(=O)N1C(c2ccc(C(C)(C)C)cc2OCC)=N[C@@H](c2ccc(Cl)cc2)[C@H]1c1ccc(Cl)cc1]

as shown, thereby providing a compound of formula I-hh-7:

I-hh-7

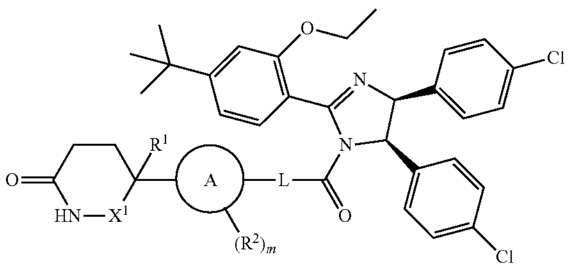

or a pharmaceutically acceptable salt thereof, wherein each of $X^1$, $R^1$, $R^2$, Ring A, m, and L is as defined above and described in embodiments herein, both singly and in combination.

In some embodiments, the present invention provides the compound of formula I-c, wherein Ring A is

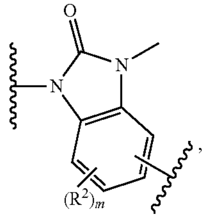

MBM is

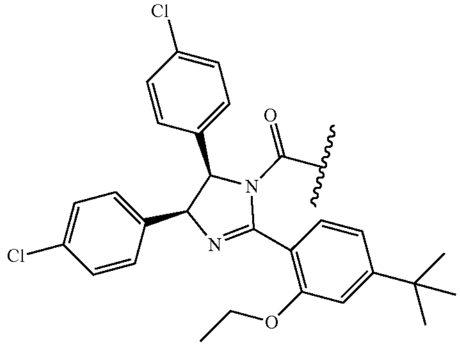 [SMILES: *C(=O)N1C(c2ccc(C(C)(C)C)cc2OCC)=N[C@@H](c2ccc(Cl)cc2)[C@H]1c1ccc(Cl)cc1]

as shown, thereby providing a compound of formula I-hh-8:

I-hh-8

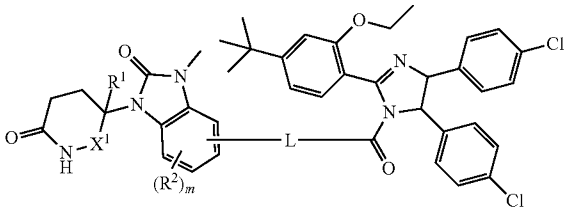

or a pharmaceutically acceptable salt thereof, wherein each of $X^1$, $R^1$, $R^2$, m, and L is as defined above and described in embodiments herein, both singly and in combination.

In some embodiments, the present invention provides a compound of formula I-ii, wherein MBM is

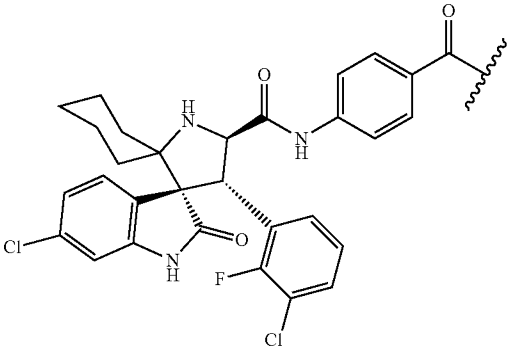 [SMILES: *C(=O)c1ccc(NC(=O)[C@@H]2NC3(CCCCC3)[C@@]3(C(=O)Nc4cc(Cl)ccc43)[C@H]2c2cccc(Cl)c2F)cc1]

as shown, to provide a compound of formula I-ii-1:

I-ii-1

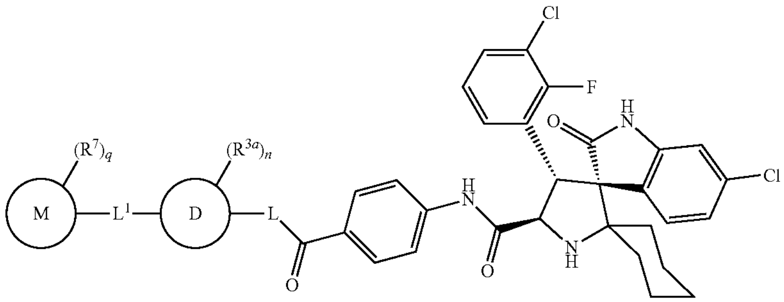

or a pharmaceutically acceptable salt thereof, wherein each of Ring M, Ring D, L, $L^1$, $R^{3a}$, $R^7$, n, and q is as defined above and described in embodiments herein, both singly and in combination.

In some embodiments, the present invention provides a compound of formula I-ii, wherein MBM is

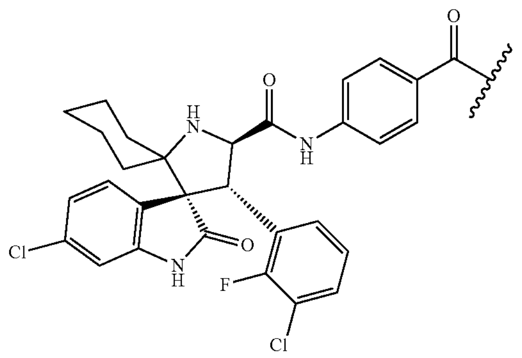 [SMILES: *C(=O)c1ccc(NC(=O)[C@@H]2NC3(CCCCC3)[C@@]3(C(=O)Nc4cc(Cl)ccc43)[C@H]2c2cccc(Cl)c2F)cc1]

and LBM is

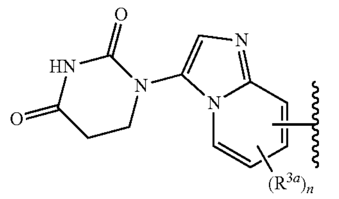

as shown, to provide a compound of formula I-ii-2:

I-ii-2

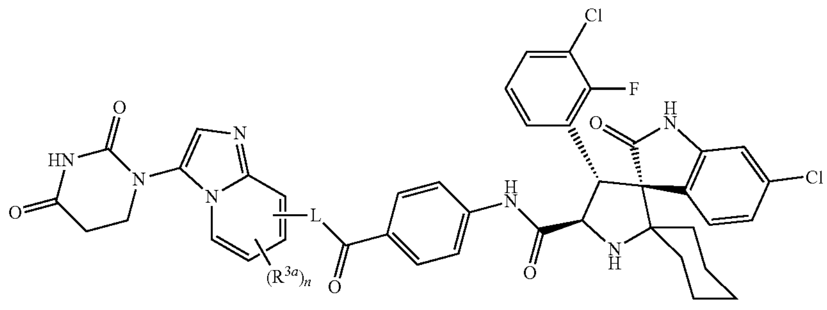

or a pharmaceutically acceptable salt thereof, wherein each of L, $R^{3a}$, and n is as defined above and described in embodiments herein, both singly and in combination.

In some embodiments, the present invention provides a compound of formula I-ii, wherein MBM is

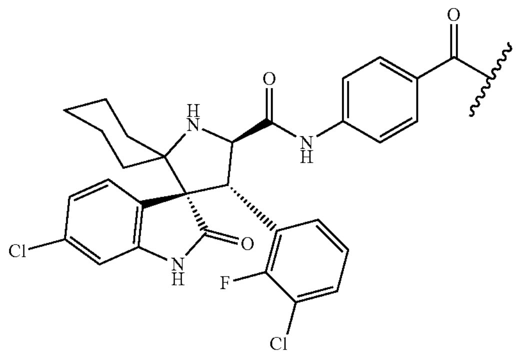 [SMILES: *C(=O)c1ccc(NC(=O)[C@@H]2NC3(CCCCC3)[C@@]3(C(=O)Nc4cc(Cl)ccc43)[C@H]2c2cccc(Cl)c2F)cc1]

and LBM is

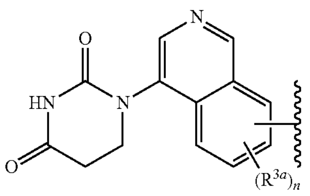

as shown, to provide a compound of formula I-ii-3:

I-ii-3

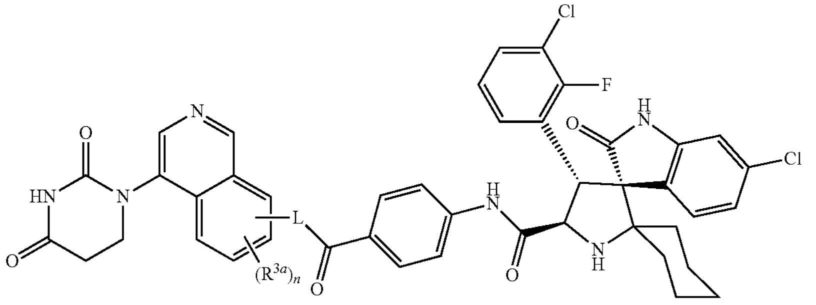

or a pharmaceutically acceptable salt thereof, wherein each of L, $R^{3a}$, and n is as defined above and described in embodiments herein, both singly and in combination.

In some embodiments, the present invention provides a compound of formula I-ii, wherein MBM is

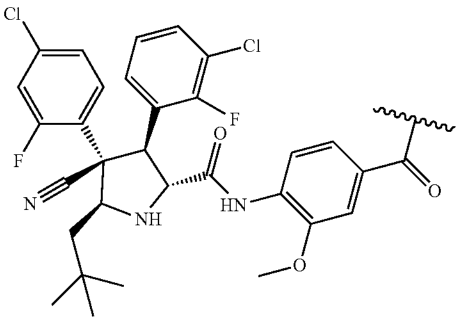 [SMILES: *C(=O)c1ccc(NC(=O)[C@@H]2N[C@@H](CC(C)(C)C)[C@](C#N)(c3ccc(Cl)cc3F)[C@H]2c2cccc(Cl)c2F)c(OC)c1]

as shown, to provide a compound of formula I-ii-4:

I-ii-4

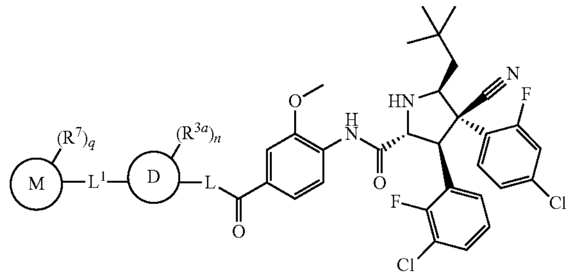

or a pharmaceutically acceptable salt thereof, wherein each of Ring M, Ring D, L, $L^1$, $R^{3a}$, $R^7$, n, and q is as defined above and described in embodiments herein, both singly and in combination.

In some embodiments, the present invention provides a compound of formula I-ii, wherein MBM is

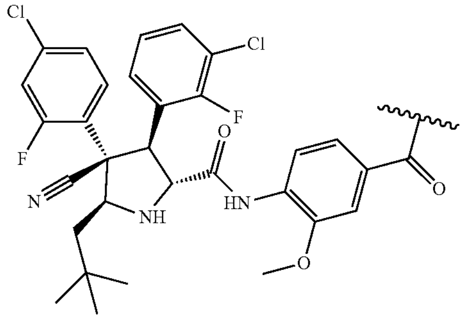 [SMILES: *C(=O)c1ccc(NC(=O)[C@@H]2N[C@@H](CC(C)(C)C)[C@](C#N)(c3ccc(Cl)cc3F)[C@H]2c2cccc(Cl)c2F)c(OC)c1]

and LBM is

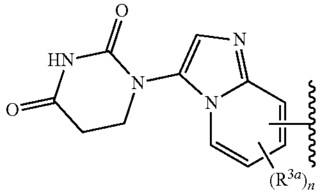

as shown, to provide a compound of formula I-ii-5:

I-ii-5

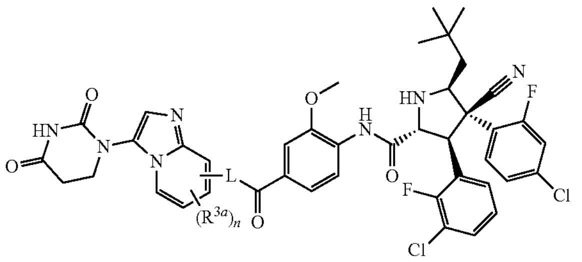

or a pharmaceutically acceptable salt thereof, wherein each of L, $R^{3a}$, and n is as defined above and described in embodiments herein, both singly and in combination.

In some embodiments, the present invention provides a compound of formula I-ii, wherein MBM is

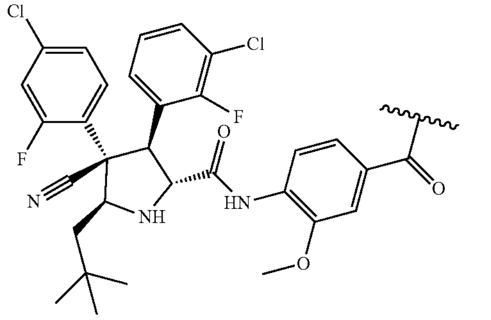 [SMILES: *C(=O)c1ccc(NC(=O)[C@@H]2N[C@@H](CC(C)(C)C)[C@](C#N)(c3ccc(Cl)cc3F)[C@H]2c2cccc(Cl)c2F)c(OC)c1]

and LBM is

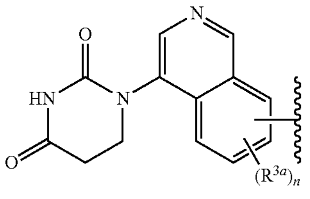

as shown, to provide a compound of formula I-ii-6:

I-ii-6

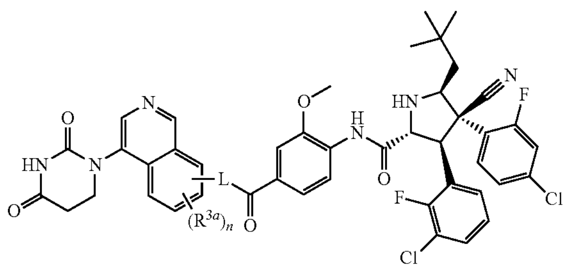

or a pharmaceutically acceptable salt thereof, wherein each of L, $R^{3a}$, and n is as defined above and described in embodiments herein, both singly and in combination.

In some embodiments, the present invention provides a compound of formula I-bbb-4:

I-bbb-4

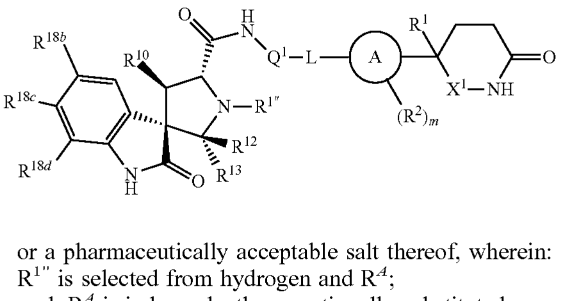

or a pharmaceutically acceptable salt thereof, wherein:

$R^{1''}$ is selected from hydrogen and $R^A$;

each $R^A$ is independently an optionally substituted group selected from $C_{1-6}$ aliphatic, phenyl, a 3-7 membered saturated or partially unsaturated carbocyclic or heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$R^{10}$ is selected from an optionally substituted monocyclic or bicyclic ring selected from phenyl, a 5-10 membered aryl, and a 5-10 membered heteroaryl containing 1-4 heteroatoms independently selected from nitrogen, oxygen, and sulfur;

$R_{12}$ and $R_{13}$ are each independently selected from hydrogen and $R^A$, or:

$R^{12}$ and $R^{13}$ are optionally taken together with their intervening atoms to form an optionally substituted 4-8 membered saturated, partially unsaturated, carbocyclic or heterocyclic ring having 1-3 heteroatoms independently selected from nitrogen, oxygen, and sulfur;

$R^{18b}$, $R^{18c}$, and $R^{18d}$ are each independently selected from hydrogen, halogen, $R^A$, and —OR; $Q^1$ is and optionally substituted bivalent group selected from alkylenyl, phenylenyl, heteroarylenyl, cycloalkylenyl, and heterocyclenyl;

$L^1$ is a covalent bond or a bivalent, saturated or partially unsaturated, straight or branched $C_{1-20}$ hydrocarbon chain, wherein 0-6 methylene units of L are independently replaced by -Cy-, —O—, —NR—, —S—, —C(O)O—, —C(O)—, —S(O)—, —$SO_2$—, —$NRSO_2$—, —$SO_2NR$—, —NRC(O)—, —C(O)NR—, —OC(O)NR—, or —NRC(O)O—;

each -Cy- is independently an optionally substituted bivalent ring selected from phenylenyl, an 8-10 membered bicyclic arylenyl, a 4-7 membered saturated or partially unsaturated carbocyclylenyl, a 4-11 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-11 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, and sulfur;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur;

r is 0, 1, 2, 3, 4, 5, 6, 7, 8, 9, or 10;

$X^1$ is a bivalent moiety selected from a covalent bond, $—CH_2—$, $—C(O)—$, $—C(S)—$, or

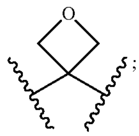 [SMILES: *C1(*)COC1]

;

$R^1$ is hydrogen, deuterium, halogen, —CN, —OR, —SR, $—S(O)R$, $—S(O)_2R$, $—NR_2$, or an optionally substituted $C_{1-4}$ aliphatic;

each $R^2$ is independently hydrogen, $R^6$, halogen, —CN, $—NO_2$, —OR, —SR, $—NR_2$, $—S(O)_2R$, $—S(O)_2NR_2$, $—S(O)R$, $—C(O)R$, $—C(O)OR$, $—C(O)NR_2$, $—C(O)N(R)OR$, $—OC(O)R$, $—OC(O)NR_2$, $—N(R)C(O)OR$, $—N(R)C(O)R$, $—N(R)C(O)NR_2$, or $—N(R)S(O)_2R$;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a bi- or tricyclic ring selected from

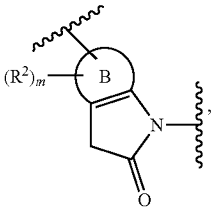,

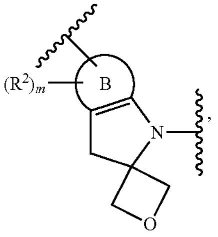,

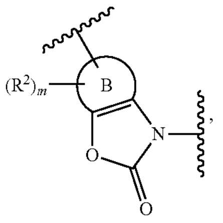,

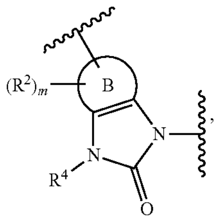,

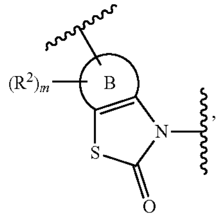,

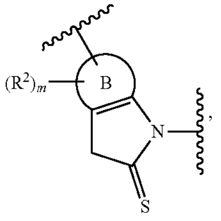,

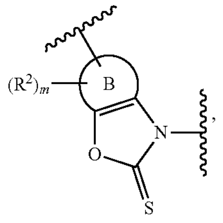,

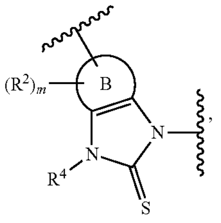,

-continued

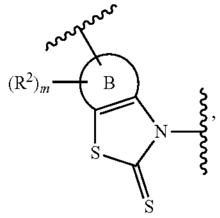,

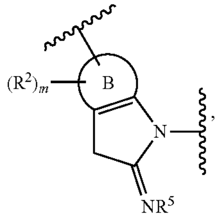,

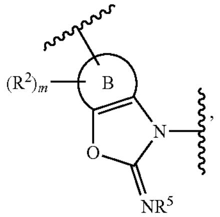,

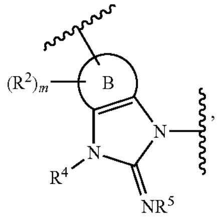,

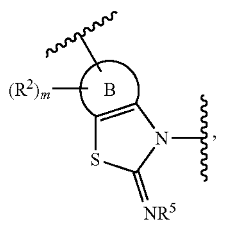,

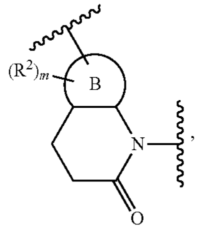,

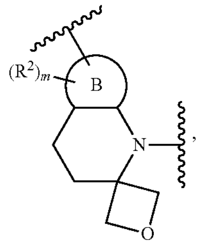,

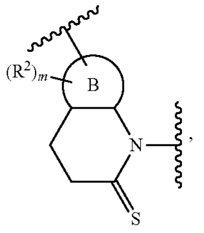,

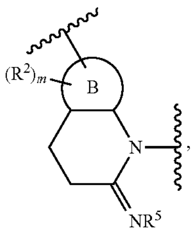,

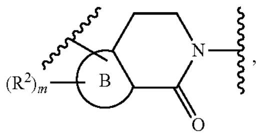,

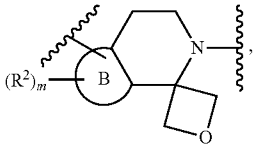,

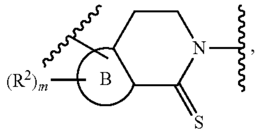,

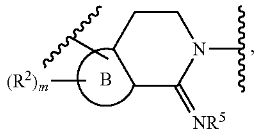,

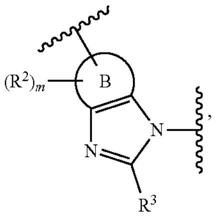,

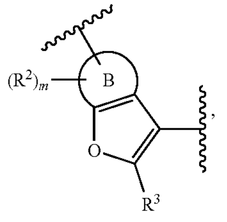,

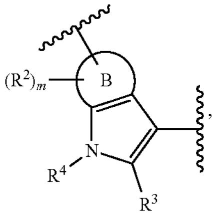,

-continued
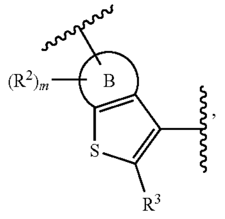
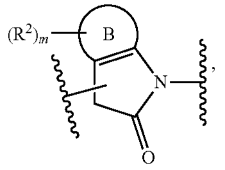
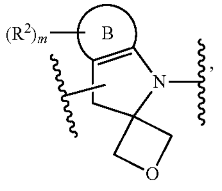
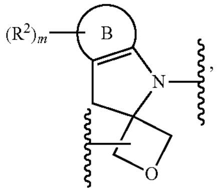
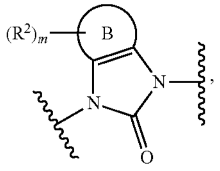
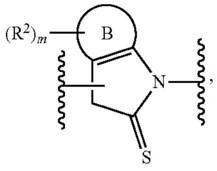
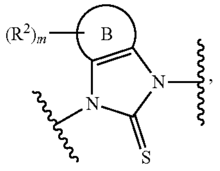
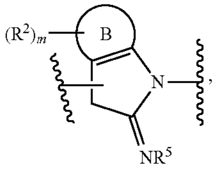
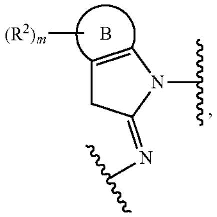
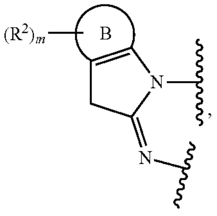
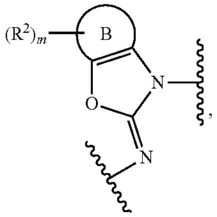
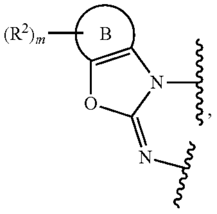
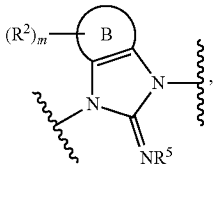
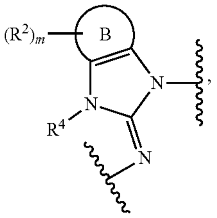
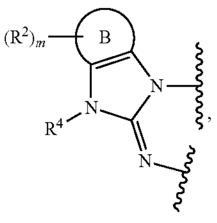
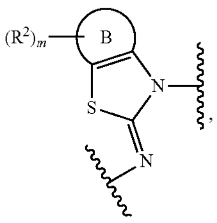
-continued
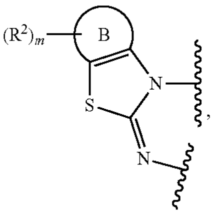
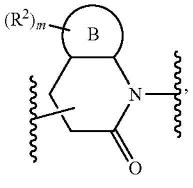
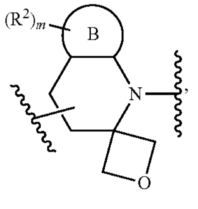
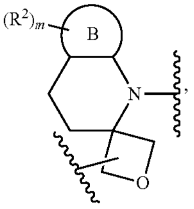
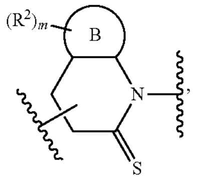
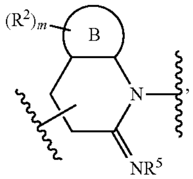
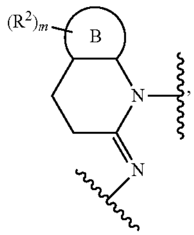
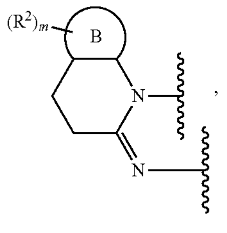
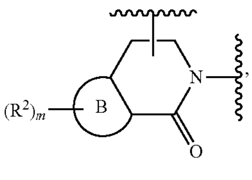
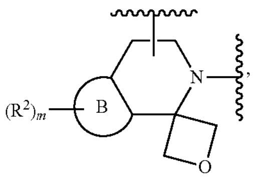
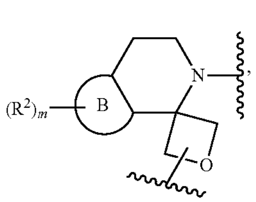
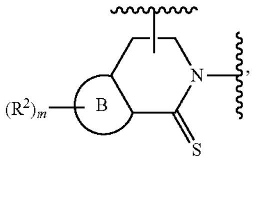
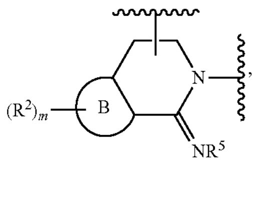
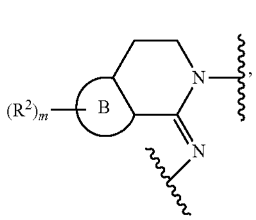
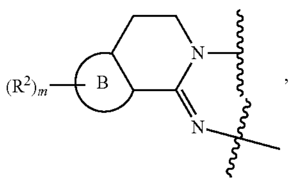
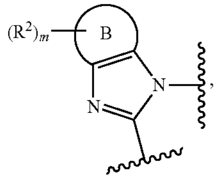

-continued

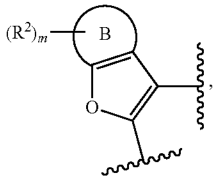,

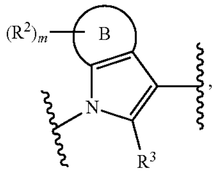,

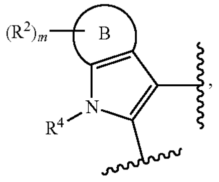, or

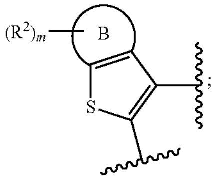;

Ring B is a fused ring selected from 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-4 heteroatoms independently selected from nitrogen, oxygen or sulfur;

$R^3$ is selected from hydrogen, halogen, —OR, —$N(R)_2$, or —SR;

each $R^4$ is independently hydrogen, $R^6$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —N(R)C(O)OR, —N(R)C(O)R, —$N(R)C(O)NR_2$, or —$N(R)S(O)_2R$;

$R^5$ is hydrogen, $C_{1-4}$ aliphatic, or —CN; and m is 0, 1, 2, 3 or 4.

In some embodiments, the present invention provides a compound of formula I-bbb-4 as any one of the following formulae:

I-bbb-5

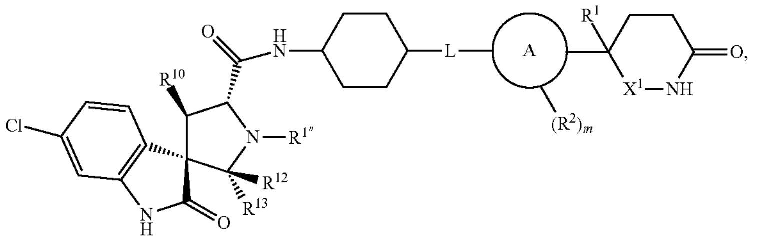

I-bbb-6

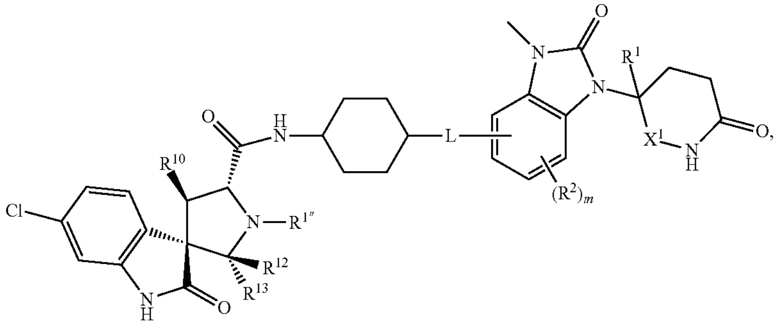

I-bbb-7

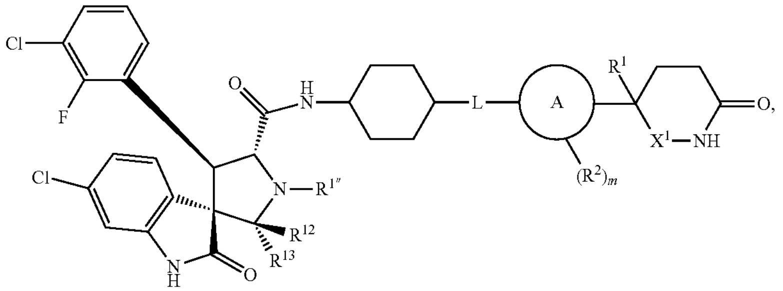

-continued
I-bbb-8
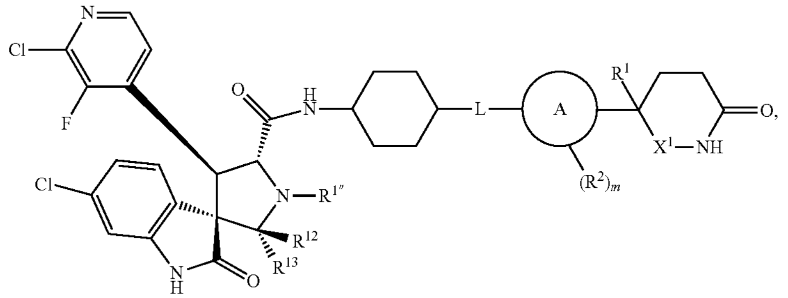
I-bbb-9
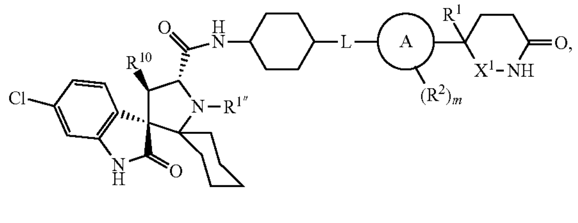
I-bbb-10
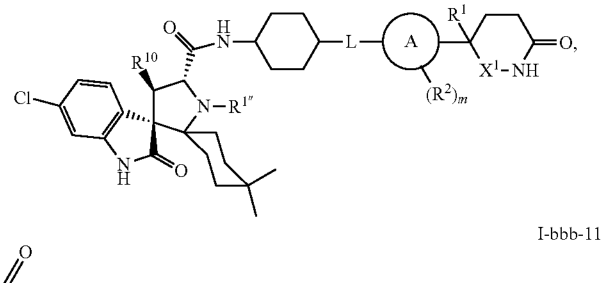
I-bbb-11
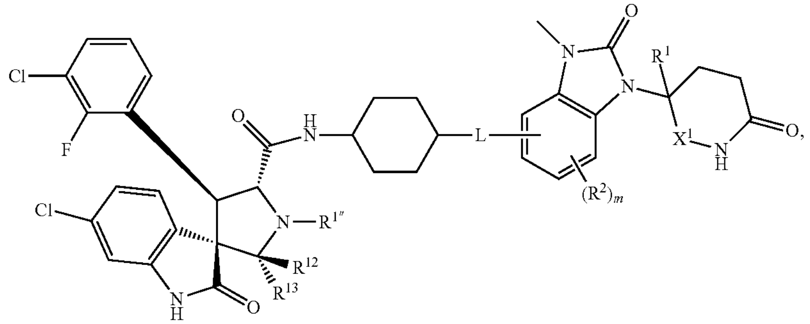
I-bbb-12
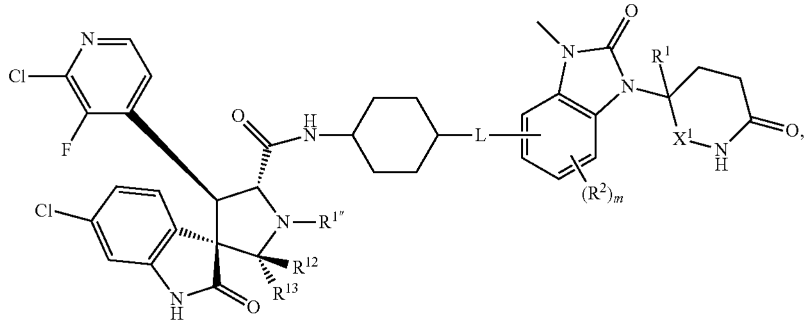
I-bbb-13
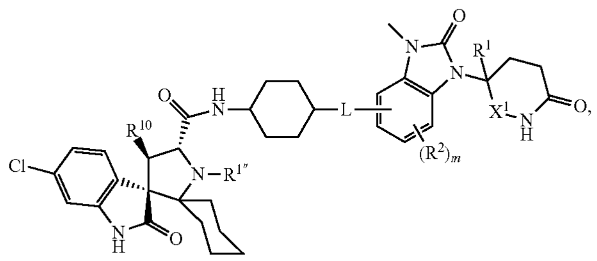
I-bbb-14
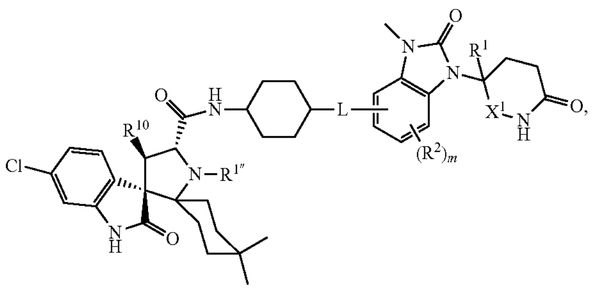
or a pharmaceutically acceptable salt thereof, wherein each of $X^1$, $R^1$, $R^2$, Ring A, m, L, $R^{1''}$, $R^{10}$, $R^{12}$, and $R^3$ is as defined above and described in embodiments herein, both singly and in combination.

In some embodiments, the present invention provides a compound of formula I-bbb-4:

I-bbb-15

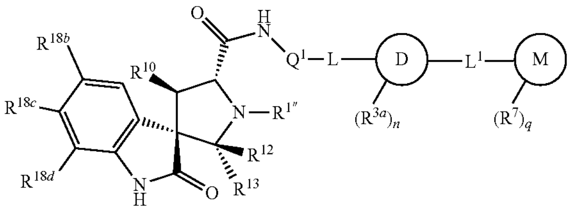

or a pharmaceutically acceptable salt thereof, wherein:

$R^{1''}$ is selected from hydrogen and $R^A$;

each $R^A$ is independently an optionally substituted group selected from $C_{1-6}$ aliphatic, phenyl, a 3-7 membered saturated or partially unsaturated carbocyclic or heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$R^{10}$ is selected from an optionally substituted monocyclic or bicyclic ring selected from phenyl, a 5-10 membered aryl, and a 5-10 membered heteroaryl containing 1-4 heteroatoms independently selected from nitrogen, oxygen, and sulfur;

$R_{12}$ and $R_{13}$ are each independently selected from hydrogen and $R^A$, or:

$R^{12}$ and $R^{13}$ are optionally taken together with their intervening atoms to form an optionally substituted 4-8 membered saturated, partially unsaturated, carbocyclic or heterocyclic ring having 1-3 heteroatoms independently selected from nitrogen, oxygen, and sulfur;

$R^{18b}$, $R^{18c}$, and $R^{18d}$ are each independently selected from hydrogen, halogen, $R^A$, and —OR; $Q^1$ is and optionally substituted bivalent group selected from alkylenyl, phenylenyl, heteroarylenyl, cycloalkylenyl, and heterocyclenyl;

$L^1$ is a covalent bond or a bivalent, saturated or partially unsaturated, straight or branched $C_{1-20}$ hydrocarbon chain, wherein 0-6 methylene units of L are independently replaced by -Cy-, —O—, —NR—, —S—, —C(O)O—, —C(O)—, —S(O)—, $—SO_2—$, $—NRSO_2—$, $—SO_2NR—$, —NRC(O)—, —C(O)NR—, —OC(O)NR—, or —NRC(O)O—;

each -Cy- is independently an optionally substituted bivalent ring selected from phenylenyl, an 8-10 membered bicyclic arylenyl, a 4-7 membered saturated or partially unsaturated carbocyclylenyl, a 4-11 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-11 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur, each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur;

r is 0, 1, 2, 3, 4, 5, 6, 7, 8, 9, or 10;

Ring M is selected from

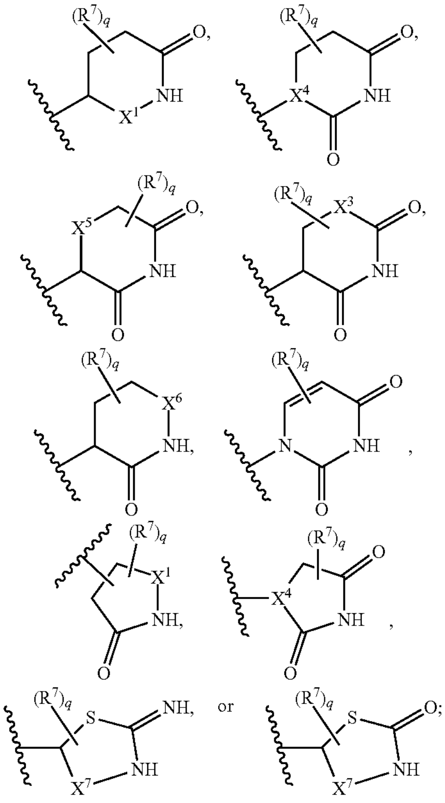

each of $X^1$, $X^6$, and $X^7$ is independently a bivalent moiety selected from a covalent bond, $—CH_2—$, $—CHCF_3—$, $—SO_2—$, —S(O)—, —P(O)R—, —P(O)OR—, $—P(O)NR_2—$, —C(O)—, —C(S)—, or

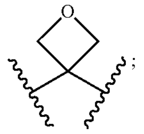 [SMILES: *C1(*)COC1]

each of $X^3$ and $X^5$ is independently a bivalent moiety selected from a covalent bond, $—CR_2—$, —NR—, —O—, —S—, or $—SiR_2—$;

$X^4$ is a trivalent moiety selected from

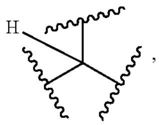, 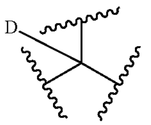, 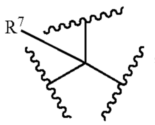, 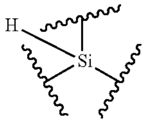, 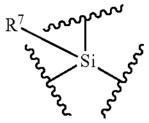, 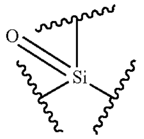, or 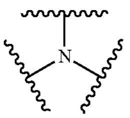;

each $R^{3a}$ is independently hydrogen, deuterium, $R^6$, halogen, —CN, —$NO_2$, —OR, —SR, —$NR_2$, —$SiR_3$, —$S(O)_2R$, —$S(O)_2NR_2$, —S(O)R, —C(O)R, —C(O)OR, —C(O)$NR_2$, —C(O)N(R)OR, —$C(R)_2N(R)C(O)R$, —$C(R)_2N(R)C(O)N(R)_2$, —OC(O)R, —OC(O)N$(R)_2$, —OP(O)$R_2$, —OP(O)$(OR)_2$, —OP(O)(OR)$NR_2$, —OP(O)$(NR_2)_2$—, —N(R)C(O)OR, —N(R)C(O)R, —N(R)C(O)$NR_2$, —N(R)$S(O)_2R$, —NP(O)$R_2$, —N(R)P(O)$(OR)_2$, —N(R)P(O)(OR)$NR_2$, —N(R)P(O)$(NR_2)_2$, or —N(R)$S(O)_2R$;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each $R^7$ is independently hydrogen, deuterium, halogen, —CN, —OR, —SR, —S(O)R, —$S(O)_2R$, —$NR_2$, —P(O)$(OR)_2$, —P(O)$(NR_2)$OR, —P(O)$(NR_2)_2$, —Si$(OH)R_2$, —$Si(OH)_2R$, —$SiR_3$, or an optionally substituted $C_{1-4}$ aliphatic; or $R^7$ and $X^1$ or $X^3$ are taken together with their intervening atoms to form a 5-7 membered saturated, partially unsaturated, carbocyclic ring or heterocyclic ring having 1-3 heteroatoms, independently selected from boron, nitrogen, oxygen, silicon, or sulfur;

two $R^7$ groups on the same carbon are optionally taken together with their intervening atoms to form a 3-6 membered spiro fused ring or a 4-7 membered heterocyclic ring having 1-2 heteroatoms independently selected from boron, nitrogen, oxygen, silicon, or sulfur;

two $R^7$ groups on adjacent carbon atoms are optionally taken together with their intervening atoms to form a 3-7 membered saturated, partially unsaturated, carbocyclic ring or heterocyclic ring having 1-3 heteroatoms independently selected from boron, nitrogen, oxygen, silicon, or sulfur, or a 7-13 membered saturated, partially unsaturated, bridged heterocyclic ring, or a spiro heterocyclic ring having 1-3 heteroatoms, independently selected from boron, nitrogen, oxygen, silicon, or sulfur;

Ring D is selected from 6 to 10-membered aryl or heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, and sulfur, or 5-membered heteroaryl with 1-4 heteroatoms independently selected from nitrogen, oxygen and sulfur;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —$C(R)_2$—, —CH(R)—, —$C(F)_2$—, —N(R)—, —S—, —$S(O)_2$— or —(C)═CH—;

n is 0, 1, 2, 3, or 4; and q is 0, 1, 2, 3, or 4.

In some embodiments, the present invention provides a compound of formula I-bbb-15 as any one of the following formulae:

I-bbb-16

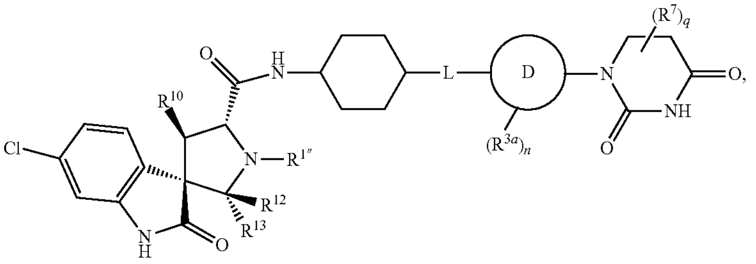

I-bbb-17

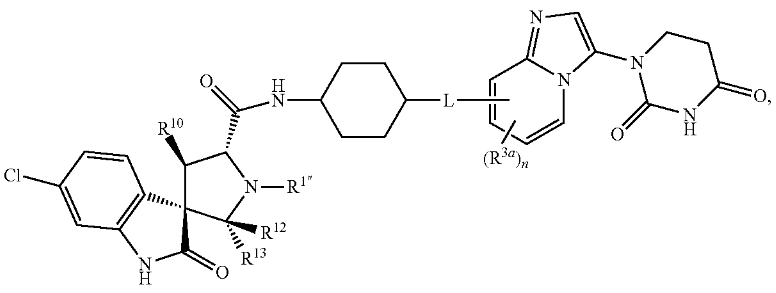

-continued
I-bbb-18
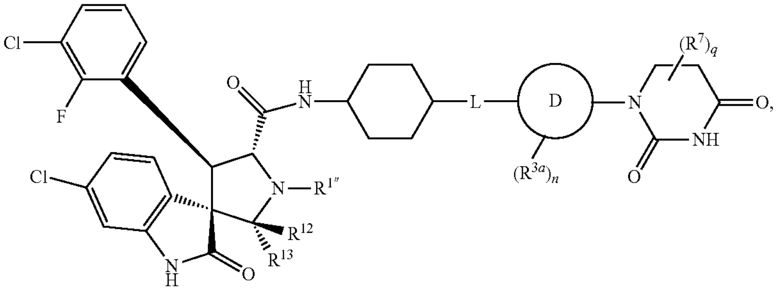
I-bbb-19
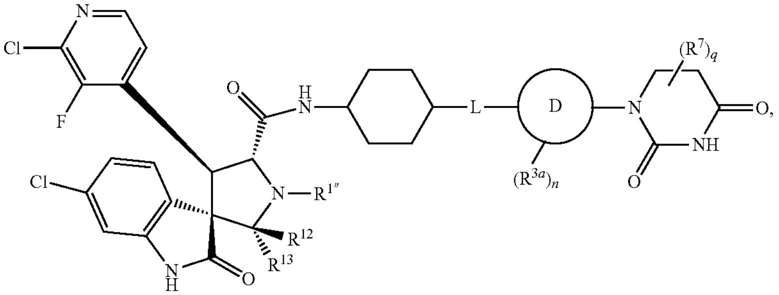
I-bbb-20
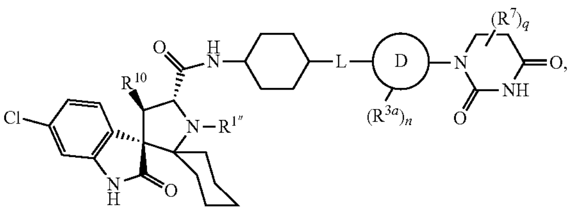
I-bbb-21
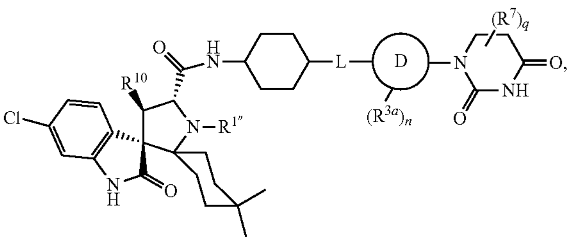
I-bbb-22
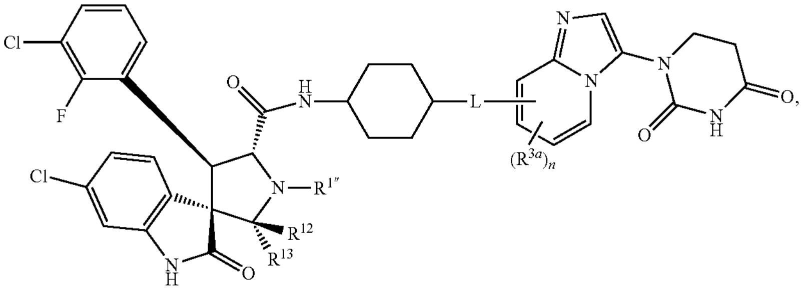
I-bbb-23
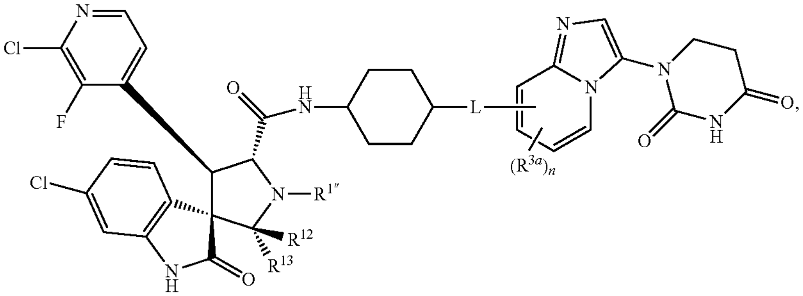

-continued

I-bbb-24

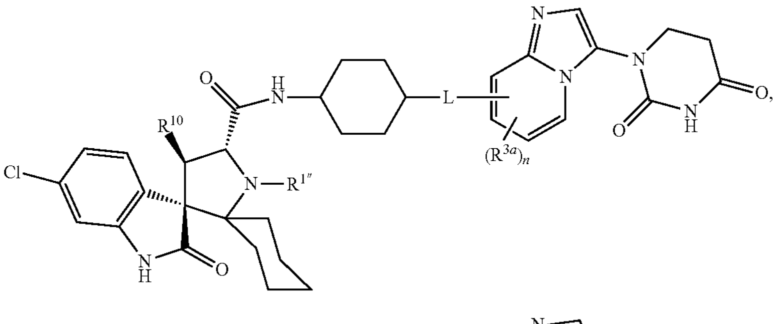

I-bbb-25

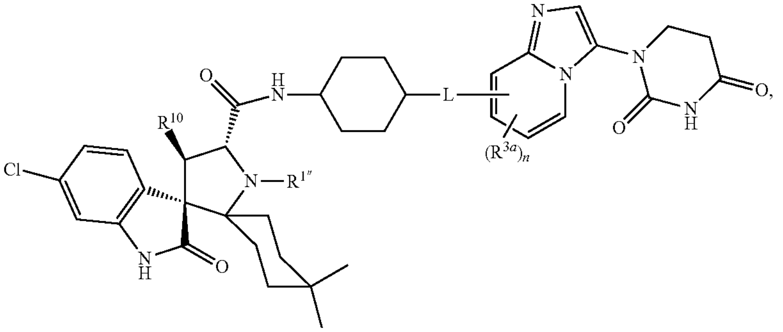

or a pharmaceutically acceptable salt thereof, wherein each of $R^3$, $R^7$, Ring D, n, q, L, $R^{1''}$, $R^{10}$, $R^{12}$, and $R^3$ is as defined above and described in embodiments herein, both singly and in combination.

Degradation Inducing Moiety (DIM)

In certain embodiments, the present invention provides a compound of formula I:

I

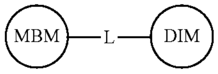

or a pharmaceutically acceptable salt thereof, wherein L and MBM are as described above and herein, and DIM is a degradation inducing moiety selected from LBM, a lysine mimetic, or a hydrogen atom.

In some embodiments, DIM is LBM as described above and herein. In some embodiments, DIM is a lysine mimetic. In some embodiments, the covalent attachment of ubiquitin to MDM2 protein is achieved through the action of a lysine mimetic. In some embodiments, upon the binding of a compound of formula I to MDM2, the moiety that mimics a lysine undergoes ubiquitination thereby marking MDM2 for degradation via the Ubiquitin-Proteasome Pathway (UPP).

In some embodiments, DIM is

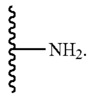

In some embodiments, DIM is

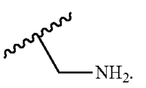

In some embodiments, DIM is

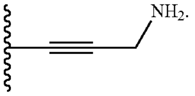 [SMILES: *C#CCN]

In some embodiments, DIM is selected from those depicted in Table 1, below.

In some embodiments, the present invention provides the compound of formula I as a compound of formula I-aaaa:

I-aaaa

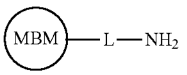

or a pharmaceutically acceptable salt thereof, wherein each of STAT and L is as defined above and described in embodiments herein, both singly and in combination.

In some embodiments, the present invention provides the compound of formula I as a compound of formula I-bbbb:

I-bbbb

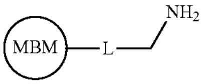

or a pharmaceutically acceptable salt thereof, wherein each of STAT and L is as defined above and described in embodiments herein, both singly and in combination.

In some embodiments, the present invention provides the compound of formula I as a compound of formula I-cccc:

I-cccc

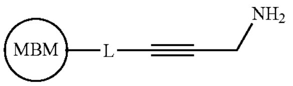

or a pharmaceutically acceptable salt thereof, wherein each of STAT and L is as defined above and described in embodiments herein, both singly and in combination.

In certain embodiments, the present invention provides a compound of Formula I, wherein DIM is a lysine mimetic

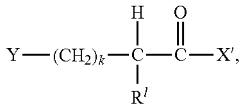

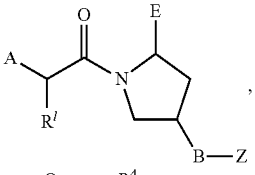

, or

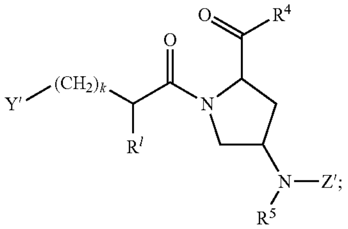

thereby forming a compound of Formulae I-dddd-1, I-dddd-2, or I-dddd-3, respectively:

I-dddd-1

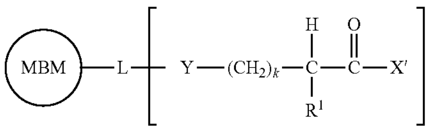

I-dddd-2

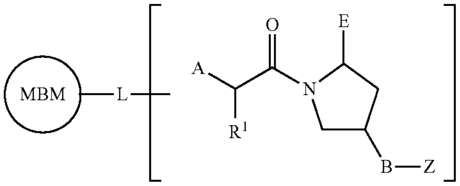

I-dddd-3

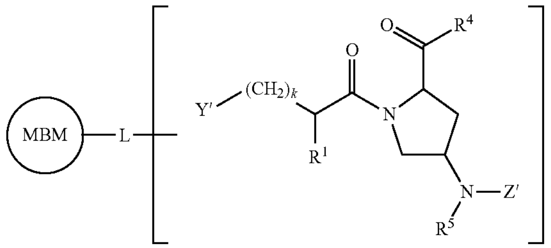

or a pharmaceutically acceptable salt thereof, wherein L and MBM are as defined above and described in embodiments herein, and wherein each of the variables $R^1$, $R^4$, R, A, B, E, Y, Y', Z, Z', and k are as defined and described in U.S. Pat. No. 7,622,496, the entirety of each of which is herein incorporated by reference.

Hydrogen Atom

In some embodiments, DIM is a hydrogen atom. In some embodiments, the covalent attachment of ubiquitin MDM2 protein is achieved through a provided compound wherein DIM is a hydrogen atom. In some embodiments, upon the binding of a compound of formula I to MDM2, the moiety being hydrogen effectuates ubiquitination thereby marking STAT1 for degradation via the Ubiquitin-Proteasome Pathway (UPP).

In some embodiments, DIM is selected from those depicted in Table 1, below.

In some embodiments, the present invention provides the compound of formula I wherein DIM is a hydrogen atom, thereby forming a compound of formula I-dddd-4:

I-dddd-4

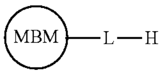

or a pharmaceutically acceptable salt thereof, wherein each of STAT and L is as defined above and described in embodiments herein, both singly and in combination.

Linker (L)

As defined above and described herein, L is a bivalent moiety that connects MBM to LBM or MBM to DIM.

In some embodiments, L is a bivalent moiety that connects MBM to LBM. In some embodiments, L is a bivalent moiety that connects MBM to DIM. In some embodiments, L is a bivalent moiety that connects MBM to a lysine mimetic.

In some embodiments, L is a covalent bond or a bivalent, saturated or partially unsaturated, straight or branched $C_{1-50}$ hydrocarbon chain, wherein 0-6 methylene units of L are independently replaced by —C(D)(H)—, —$C(D)_2$-, -Cy-, —O—, —N(R)—, —$Si(R)_2$—, —Si(OH)(R)—, —$Si(OH)_2$—, —P(O)(OR)—, —P(O)(R)—, —$P(O)(NR_2)$—, —S—, —OC(O)—, —C(O)O—, —C(O)—, —S(O)—, —$S(O)_2$—, —$N(R)S(O)_2$—, —$S(O)_2N(R)$—, —N(R)C(O)—, —C(O)N(R)—, —OC(O)N(R)—, —N(R)C(O)O—,

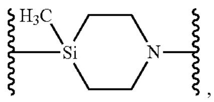

,

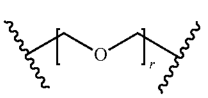

,

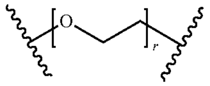

,

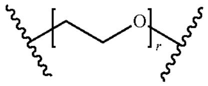

,

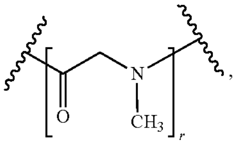

, or

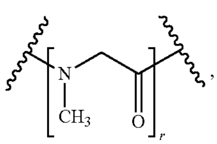

, wherein:

each -Cy- is independently an optionally substituted bivalent ring selected from phenylenyl, an 8-10 membered bicyclic arylenyl, a 4-7 membered saturated or partially unsaturated carbocyclylenyl, a 4-11 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-11 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur, each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur, and;

r is 0, 1, 2, 3, 4, 5, 6, 7, 8, 9, or 10.

In some embodiments, L is selected from those depicted in Table 1, below.

In some embodiments, each -Cy- is independently an optionally substituted bivalent phenylenyl. In some embodiments, each -Cy- is independently an optionally substituted 8-10 membered bicyclic arylenyl. In some embodiments, each -Cy- is independently an optionally substituted 4-7 membered saturated or partially unsaturated carbocyclylenyl. In some embodiments, each -Cy- is independently an optionally substituted 4-11 membered saturated or partially unsaturated spiro carbocyclylenyl. In some embodiments, each -Cy- is independently an optionally substituted 8-10 membered bicyclic saturated or partially unsaturated carbocyclylenyl. In some embodiments, each -Cy-is independently an optionally substituted 4-7 membered saturated or partially unsaturated heterocyclylenyl having 1-2 heteroatoms independently selected from nitrogen, oxygen, and sulfur. In some embodiments, each -Cy- is independently an optionally substituted 4-11 membered saturated or partially unsaturated spiro heterocyclylenyl having 1-2 heteroatoms independently selected from nitrogen, oxygen, and sulfur. In some embodiments, each -Cy- is independently an optionally substituted 8-10 membered bicyclic saturated or partially unsaturated heterocyclylenyl having 1-2 heteroatoms independently selected from nitrogen, oxygen, and sulfur. In some embodiments, each -Cy- is independently an optionally substituted 5-6 membered heteroarylenyl having 1-4 heteroatoms independently selected from nitrogen, oxygen, and sulfur. In some embodiments, each -Cy- is independently an optionally substituted 8-10 membered bicyclic heteroarylenyl having 1-5 heteroatoms independently selected from nitrogen, oxygen, or sulfur.

In some embodiments, -Cy- is

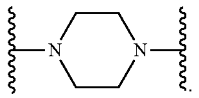

In some embodiments, -Cy- is selected from those depicted in Table 1 or Table 1A, below.

In some embodiments, r is 0. In some embodiments, r is 1. In some embodiments, r is 2. In some embodiments, r is 3. In some embodiments, r is 4. In some embodiments, r is 5. In some embodiments, r is 6. In some embodiments, r is 7. In some embodiments, r is 8. In some embodiments, r is 9. In some embodiments, r is 10.

In some embodiments, r is selected from those depicted in Table 1 or Table 1A, below.

In some embodiments, L is

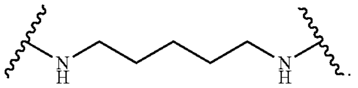 [SMILES: *NCCCCCN*]

In some embodiments, L is

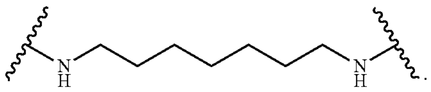 [SMILES: *NCCCCCCCN*]

In some embodiments, L is

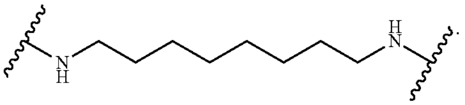 [SMILES: *NCCCCCCCCN*]

In some embodiments, L is

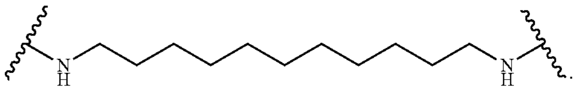 [SMILES: *NCCCCCCCCCCCN*]

In some embodiments, L is

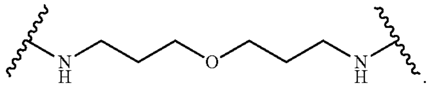 [SMILES: *NCCCOCCCN*]

In some embodiments, L is

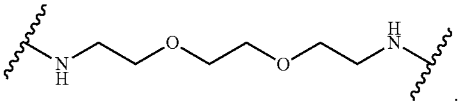 [SMILES: *NCCOCCOCCN*]

In some embodiments, L is
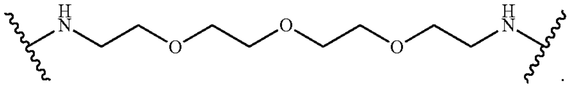 [SMILES: *NCCOCCOCCOCCN*]
In some embodiments, L is
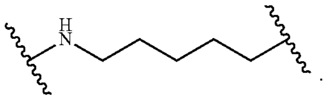 [SMILES: *CCCCCN*]
In some embodiments, L is
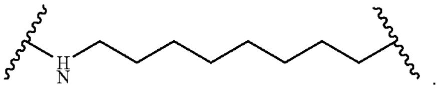 [SMILES: *CCCCCCCCN*]
In some embodiments, L is
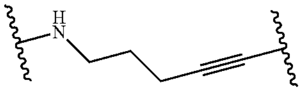
In some embodiments, L is
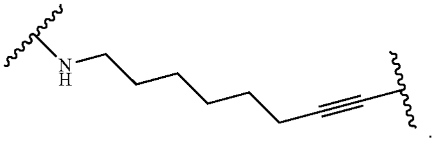 [SMILES: *C#CCCCCCCN*]
In some embodiments, L is
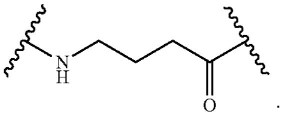 [SMILES: *NCCCC(*)=O]
In some embodiments, L is
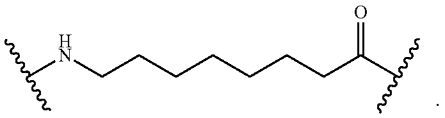 [SMILES: *NCCCCCCCC(*)=O]
In some embodiments, L is
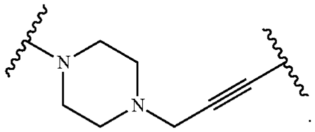 [SMILES: *C#CCN1CCN(*)CC1]
In some embodiments, L is
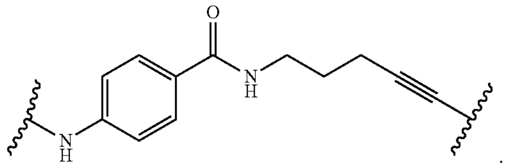 [SMILES: *C#CCCCNC(=O)c1ccc(N*)cc1]
In some embodiments, L is
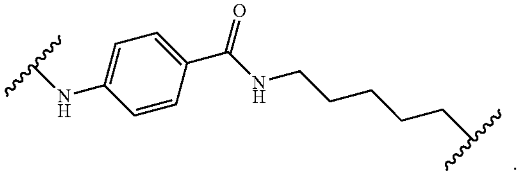 [SMILES: *CCCCCNC(=O)c1ccc(N*)cc1]
In some embodiments, L is
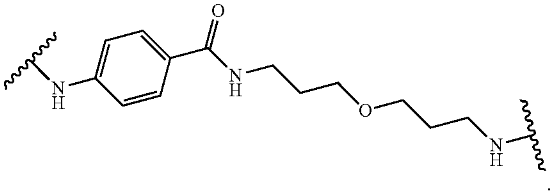 [SMILES: *NCCCOCCCNC(=O)c1ccc(N*)cc1]
In some embodiments, L is
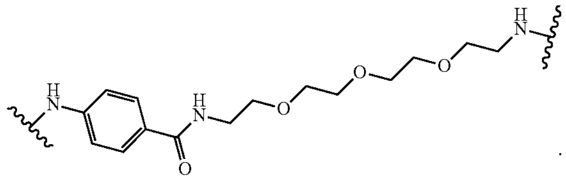 [SMILES: *NCCOCCOCCOCCNC(=O)c1ccc(N*)cc1]

In some embodiments, L is
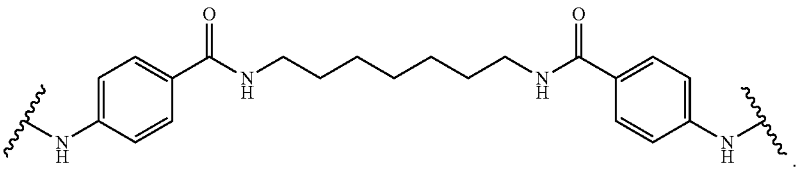 [SMILES: *Nc1ccc(C(=O)NCCCCCCCNC(=O)c2ccc(N*)cc2)cc1]
In some embodiments, L is
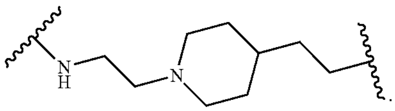 [SMILES: *CCC1CCN(CCN*)CC1]
In some embodiments, L is
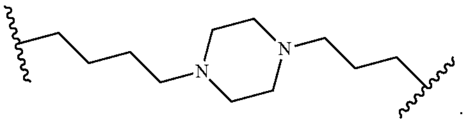 [SMILES: *CCCCN1CCN(CCC*)CC1]
In some embodiments, L is
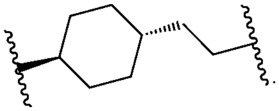 [SMILES: *CC[C@H]1CC[C@H](*)CC1]
In some embodiments, L is
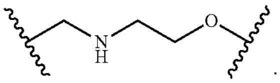 [SMILES: *CNCCO*]
In some embodiments, L is
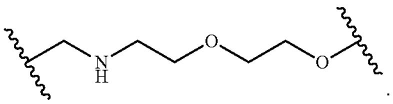 [SMILES: *CNCCOCCO*]
In some embodiments, L is
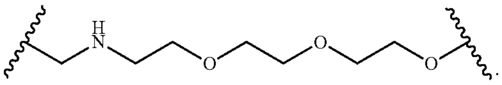 [SMILES: *CNCCOCCOCCO*]
In some embodiments, L is
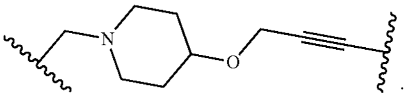 [SMILES: *C#CCOC1CCN(C*)CC1]
In some embodiments, L is
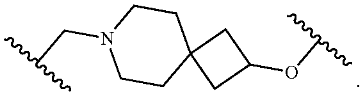 [SMILES: *CN1CCC2(CC1)CC(O*)C2]
In some embodiments, L is
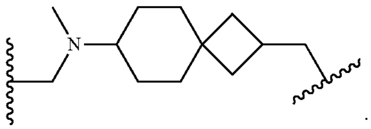 [SMILES: *CC1CC2(CCC(N(C)C*)CC2)C1]
In some embodiments, L is
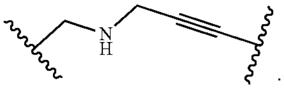 [SMILES: *C#CCNC*]
In some embodiments, L is
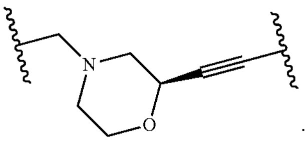 [SMILES: *C#C[C@@H]1CN(C*)CCO1]
In some embodiments, L is
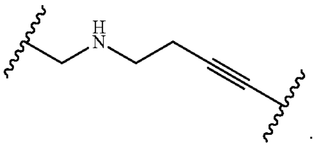 [SMILES: *C#CCCNC*]

In some embodiments, L is
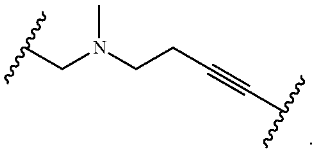 [SMILES: *C#CCCN(C)C*]
In some embodiments, L is
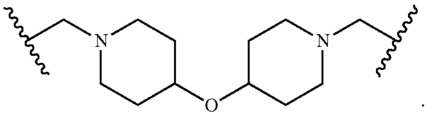 [SMILES: *CN1CCC(OC2CCN(C*)CC2)CC1]
In some embodiments, L is
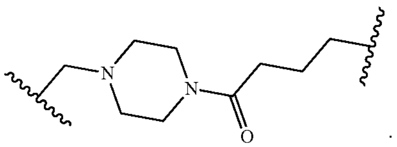 [SMILES: *CCCC(=O)N1CCN(C*)CC1]
In some embodiments, L is
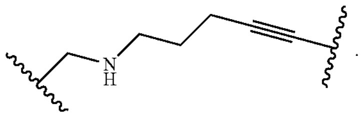 [SMILES: *C#CCCCNC*]
In some embodiments, L is
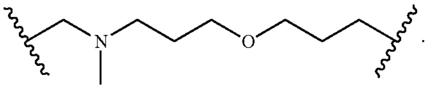 [SMILES: *CCCOCCCN(C)C*]
In some embodiments, L is
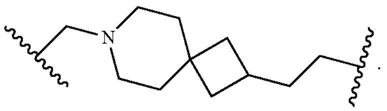 [SMILES: *CCC1CC2(CCN(C*)CC2)C1]
In some embodiments, L is
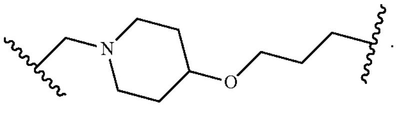 [SMILES: *CCCOC1CCN(C*)CC1]
In some embodiments, L is
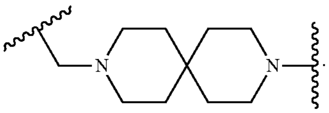 [SMILES: *CN1CCC2(CCN(*)CC2)CC1]
In some embodiments, L is
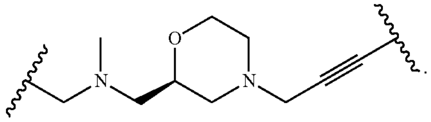 [SMILES: *C#CCN1CCO[C@H](CN(C)C*)C1]
In some embodiments, L is
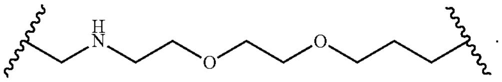 [SMILES: *CCCOCCOCCNC*]
In some embodiments, L is
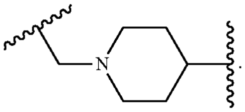
In some embodiments L is
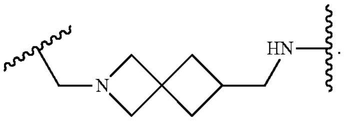 [SMILES: *CN1CC2(CC(CN*)C2)C1]
In some
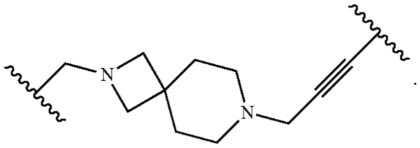 [SMILES: *C#CCN1CCC2(CC1)CN(C*)C2]
In some embodiments, L is
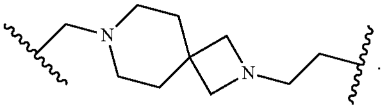 [SMILES: *CCN1CC2(CCN(C*)CC2)C1]

In some embodiments, L is
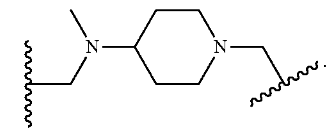
In some embodiments, L is
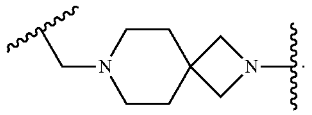 [SMILES: *CN1CCC2(CC1)CN(*)C2]
In some embodiments, L is
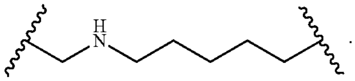 [SMILES: *CCCCCNC*]
In some embodiments, L is
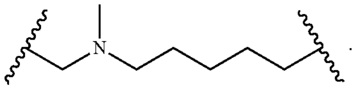 [SMILES: *CCCCCN(C)C*]
In some embodiments, L is
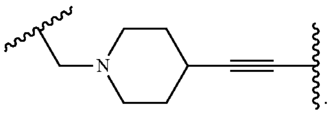 [SMILES: *C#CC1CCN(C*)CC1]
In some embodiments, L is
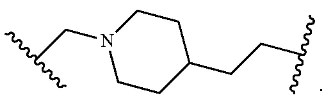 [SMILES: *CCC1CCN(C*)CC1]
In some embodiments, L is
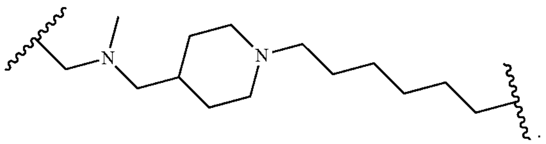 [SMILES: *CCCCCCN1CCC(CN(C)C*)CC1]
In some embodiments, L is
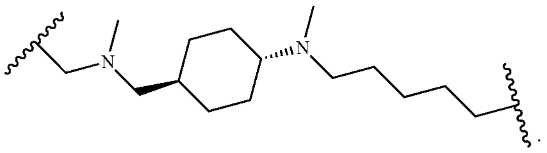 [SMILES: *CCCCCN(C)[C@H]1CC[C@H](CN(C)C*)CC1]
In some embodiments, L is
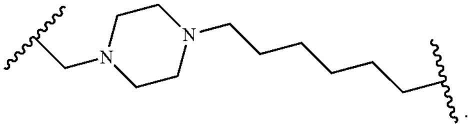 [SMILES: *CCCCCCN1CCN(C*)CC1]
In some embodiments, L is
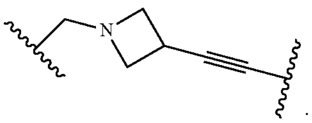 [SMILES: *C#CC1CN(C*)C1]
In some embodiments, L is
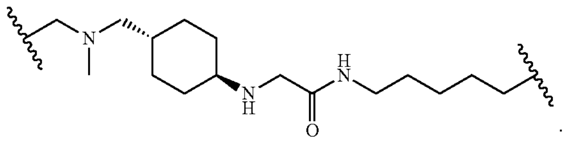 [SMILES: *CCCCCNC(=O)CN[C@H]1CC[C@H](CN(C)C*)CC1]
In some embodiments, L is
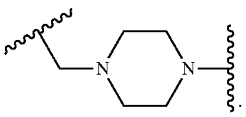
In some embodiments, L is
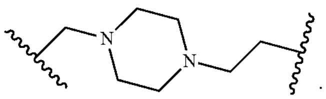 [SMILES: *CCN1CCN(C*)CC1]
In some embodiments, L is
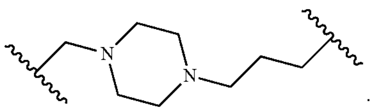 [SMILES: *CCCN1CCN(C*)CC1]

In some embodiments, L is
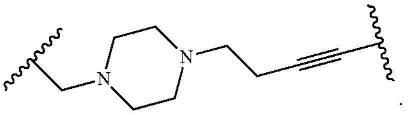 [SMILES: *C#CCCN1CCN(C*)CC1]
In some embodiments, L is
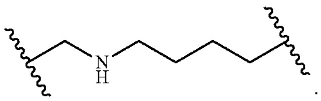 [SMILES: *CCCCNC*]
In some embodiments, L is
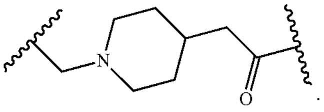 [SMILES: *CN1CCC(CC(*)=O)CC1]
In some embodiments, L is
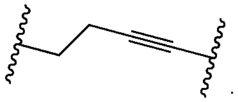
In some embodiments, L is
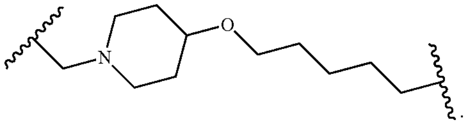 [SMILES: *CCCCCOC1CCN(C*)CC1]
In some embodiments, L is
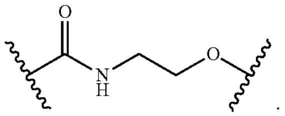 [SMILES: *OCCNC(*)=O]
In some embodiments, L is
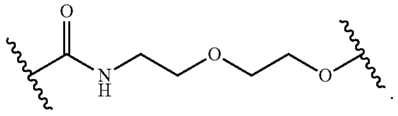 [SMILES: *OCCOCCNC(*)=O]
In some embodiments, L is
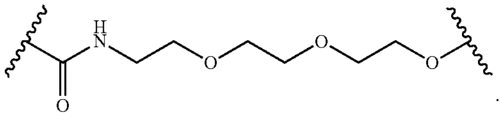 [SMILES: *OCCOCCOCCNC(*)=O]
In some embodiments, L is
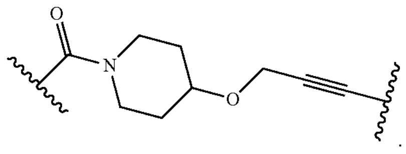 [SMILES: *C#CCOC1CCN(C(*)=O)CC1]
In some embodiments, L is
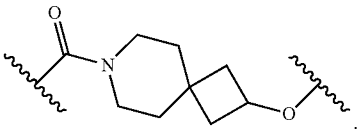 [SMILES: *OC1CC2(CCN(C(*)=O)CC2)C1]
In some embodiments, L is
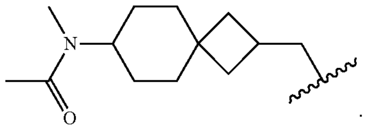 [SMILES: *CC1CC2(CCC(N(C)C(C)=O)CC2)C1]
In some embodiments, L is
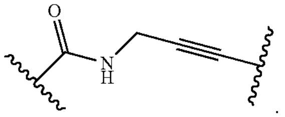 [SMILES: *C#CCNC(*)=O]
In some embodiments, L is
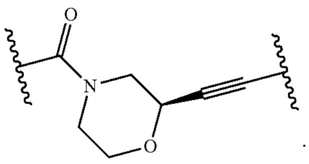 [SMILES: *C#C[C@@H]1CN(C(*)=O)CCO1]
In some embodiments, L is
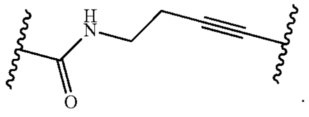 [SMILES: *C#CCCNC(*)=O]

In
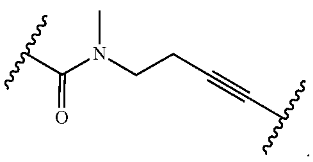 [SMILES: *C#CCCN(C)C(*)=O]
some embodiments, L is
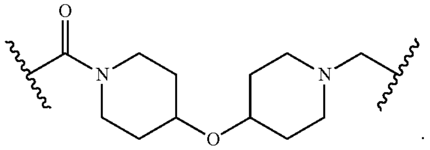 [SMILES: *CN1CCC(OC2CCN(C(*)=O)CC2)CC1]
In some embodiments, L is
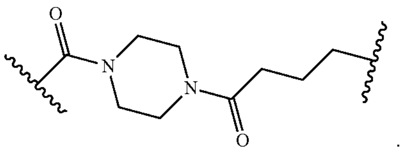 [SMILES: *CCCC(=O)N1CCN(C(*)=O)CC1]
In some embodiments, L is
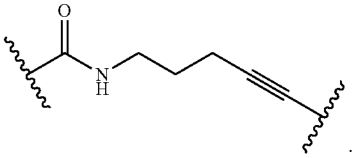 [SMILES: *C#CCCCNC(*)=O]
In some embodiments, L is
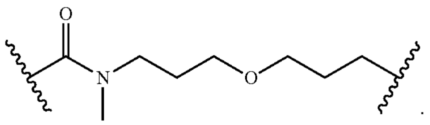 [SMILES: *CCCOCCCN(C)C(*)=O]
In some embodiments L is
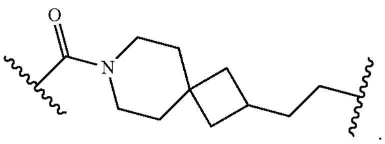 [SMILES: *CCC1CC2(CCN(C(*)=O)CC2)C1]
In some embodiments, L is
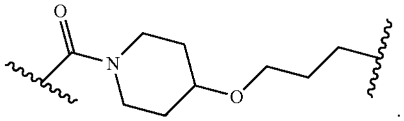 [SMILES: *CCCOC1CCN(C(*)=O)CC1]
In some embodiments, L is
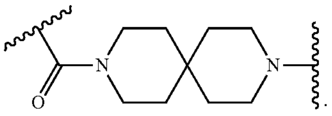 [SMILES: *C(=O)N1CCC2(CCN(*)CC2)CC1]
In some embodiments, L is
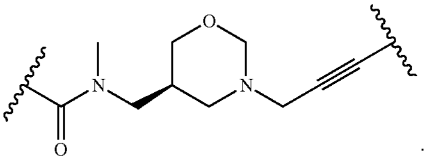
In some embodiments, L is
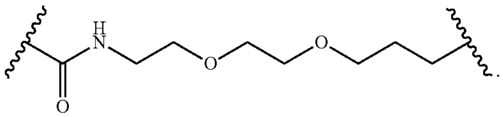 [SMILES: *CCCOCCOCCNC(*)=O]
In some embodiments, L is
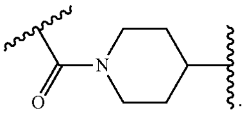 [SMILES: *C(=O)N1CCC(*)CC1]
In some embodiments, L is
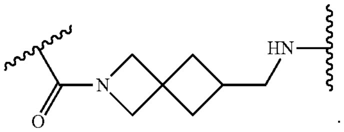 [SMILES: *NCC1CC2(C1)CN(C(*)=O)C2]
In some embodiments, L is
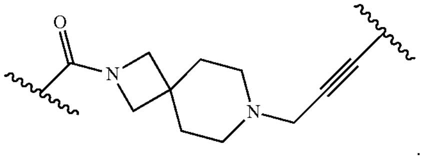 [SMILES: *C#CCN1CCC2(CC1)CN(C(*)=O)C2]

In some embodiments, L is
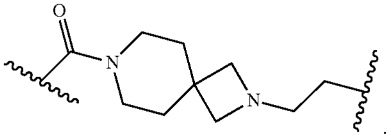 [SMILES: *CCN1CC2(CCN(C(*)=O)CC2)C1]
In some embodiments, L is
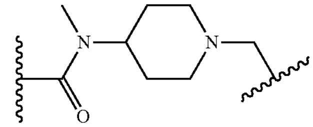 [SMILES: *CN1CCC(N(C)C(*)=O)CC1]
In some embodiments, L is
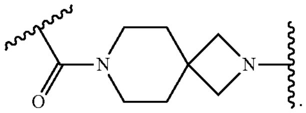 [SMILES: *C(=O)N1CCC2(CC1)CN(*)C2]
In some embodiments, L is
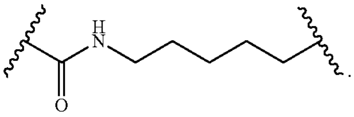 [SMILES: *CCCCCNC(*)=O]
In some embodiments, L is
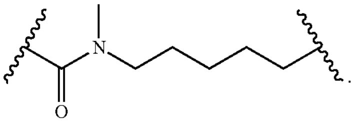 [SMILES: *CCCCCN(C)C(*)=O]
In some embodiments, L is
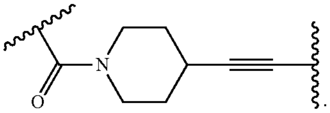 [SMILES: *C#CC1CCN(C(*)=O)CC1]
In some embodiments, L is
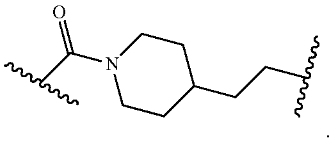 [SMILES: *CCC1CCN(C(*)=O)CC1]
In some embodiments, L is
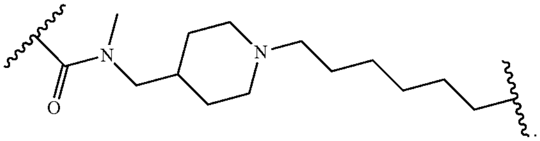 [SMILES: *CCCCCCN1CCC(CN(C)C(*)=O)CC1]
In some embodiments, L is
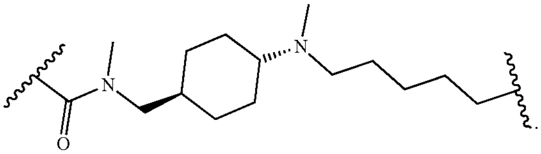
In some embodiments, L is
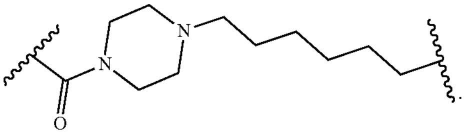 [SMILES: *CCCCCCN1CCN(C(*)=O)CC1]
In some embodiments, L is
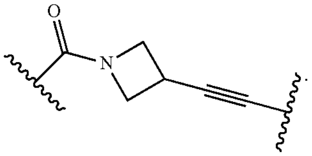 [SMILES: *C#CC1CN(C(*)=O)C1]
In some embodiments, L is
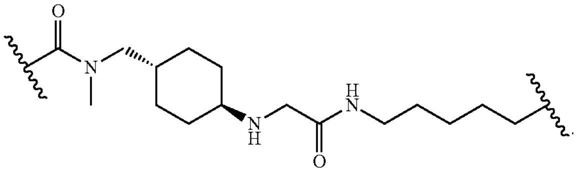 [SMILES: *CCCCCNC(=O)CN[C@H]1CC[C@H](CN(C)C(*)=O)CC1]
In some embodiments, L is
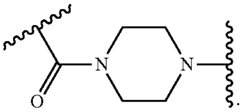
In some embodiments, L is
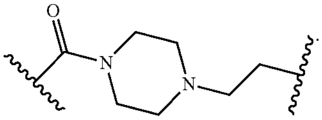 [SMILES: *CCN1CCN(C(*)=O)CC1]

In some embodiments, L is

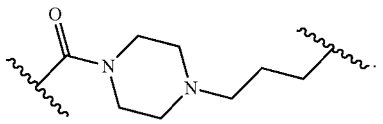 [SMILES: *CCCN1CCN(C(*)=O)CC1]

In some embodiments, L is

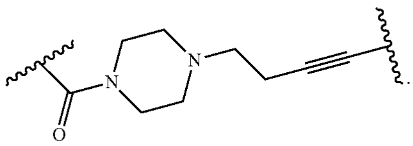 [SMILES: *C#CCCN1CCN(C(*)=O)CC1]

In some embodiments, L is

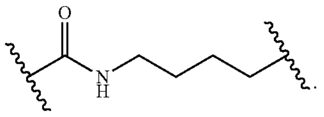 [SMILES: *CCCCNC(*)=O]

In some embodiments, L is

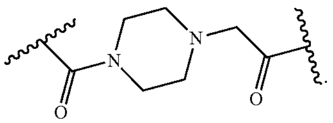 [SMILES: *C(=O)CN1CCN(C(*)=O)CC1]

In some embodiments, L is

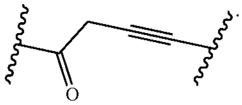 [SMILES: *C#CCC(*)=O]

In some embodiments, L is

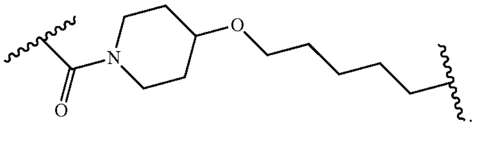 [SMILES: *CCCCCOC1CCN(C(*)=O)CC1]

In some embodiments, L is selected from those depicted in Table 1 or Table 1A, below.

Without limitation, the point of attachment of L to MBM and DIM can be, for example when L is

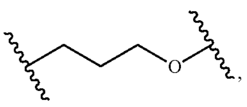 [SMILES: *CCCO*]

either

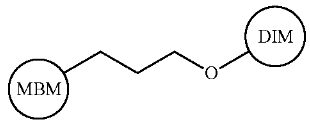

or

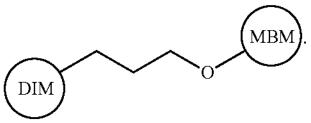

In some embodiments, a provided compound or pharmaceutically acceptable salt thereof, is selected from those wherein MBM is

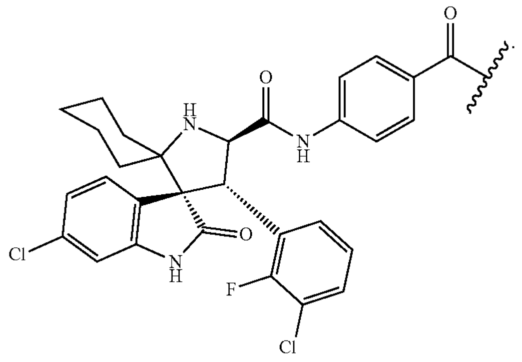 [SMILES: *C(=O)c1ccc(NC(=O)[C@@H]2NC3(CCCCC3)[C@@]3(C(=O)Nc4cc(Cl)ccc43)[C@H]2c2cccc(Cl)c2F)cc1]

LBM is selected from any of those in Table A below, and L is selected from any of those in Table B below.

In some embodiments, a provided compound or pharmaceutically acceptable salt thereof, is selected from those wherein MBM is

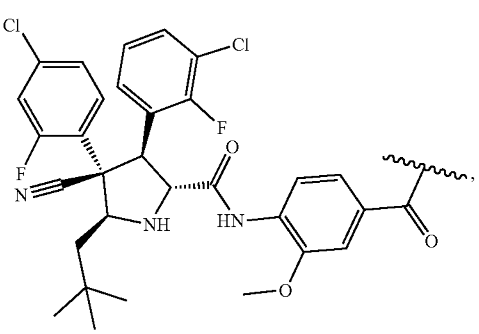 [SMILES: *C(=O)c1ccc(NC(=O)[C@@H]2N[C@@H](CC(C)(C)C)[C@](C#N)(c3ccc(Cl)cc3F)[C@H]2c2cccc(Cl)c2F)c(OC)c1]

LBM is selected from any of those in Table A below, and L is selected from any of those in Table B below.

In some embodiments, a provided compound or pharmaceutically acceptable salt thereof, is selected from those wherein MBM is

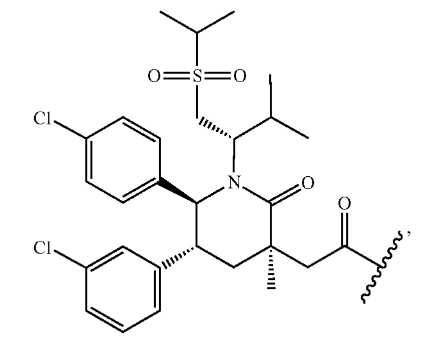 [SMILES: *C(=O)C[C@@]1(C)C[C@H](c2cccc(Cl)c2)[C@@H](c2ccc(Cl)cc2)N([C@H](CS(=O)(=O)C(C)C)C(C)C)C1=O]

LBM is selected from any of those in Table A below, and L is selected from any of those in Table B below.

In some embodiments, a provided compound or pharmaceutically acceptable salt thereof, is selected from those wherein MBM is

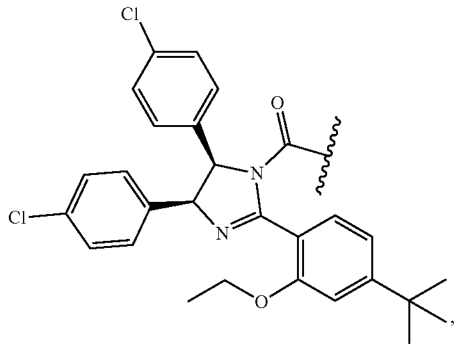 [SMILES: *C(=O)N1C(c2ccc(C(C)(C)C)cc2OCC)=N[C@@H](c2ccc(Cl)cc2)[C@H]1c1ccc(Cl)cc1]

LBM is selected from any of those in Table A below, and L is selected from any of those in Table B below.

In some embodiments, a provided compound or pharmaceutically acceptable salt thereof, is selected from those wherein MBM is

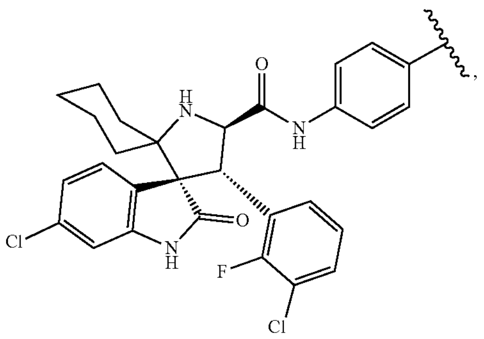 [SMILES: *c1ccc(NC(=O)[C@@H]2NC3(CCCCC3)[C@@]3(C(=O)Nc4cc(Cl)ccc43)[C@H]2c2cccc(Cl)c2F)cc1]

LBM is selected from any of those in Table A below, and L is selected from any of those in Table B below.

In some embodiments, a provided compound or pharmaceutically acceptable salt thereof, is selected from those wherein MBM is

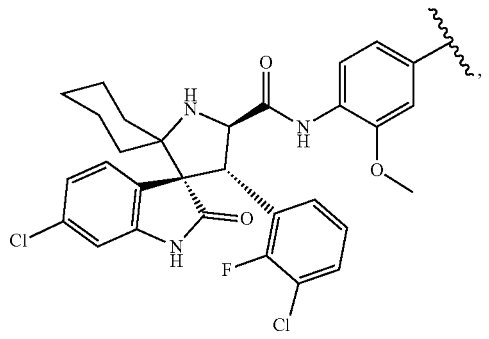 [SMILES: *c1ccc(NC(=O)[C@@H]2NC3(CCCCC3)[C@@]3(C(=O)Nc4cc(Cl)ccc43)[C@H]2c2cccc(Cl)c2F)c(OC)c1]

LBM is selected from any of those in Table A below, and L is selected from any of those in Table B below.

In some embodiments, a provided compound or pharmaceutically acceptable salt thereof, is selected from those wherein MBM is

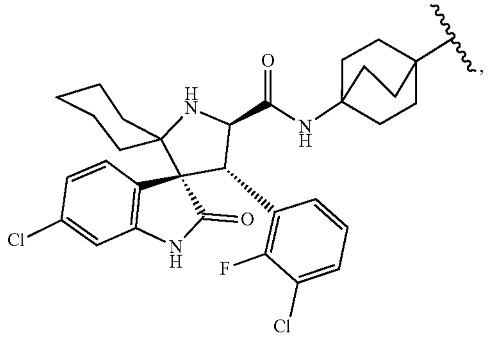 [SMILES: *C12CCC(NC(=O)[C@@H]3NC4(CCCCC4)[C@@]4(C(=O)Nc5cc(Cl)ccc54)[C@H]3c3cccc(Cl)c3F)(CC1)CC2]

LBM is selected from any of those in Table A below, and L is selected from any of those in Table B below.

In some embodiments, a provided compound or pharmaceutically acceptable salt thereof, is selected from those wherein MBM is

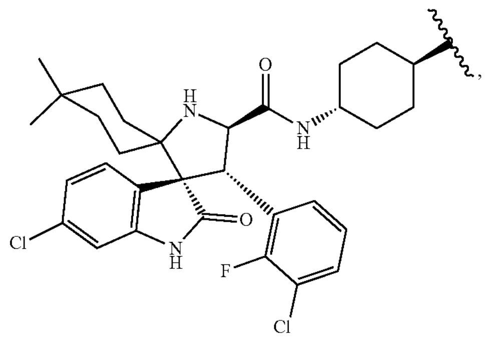 [SMILES: *[C@H]1CC[C@H](NC(=O)[C@@H]2NC3(CCC(C)(C)CC3)[C@@]3(C(=O)Nc4cc(Cl)ccc43)[C@H]2c2cccc(Cl)c2F)CC1]

LBM is selected from any of those in Table A below, and L is selected from any of those in Table B below.

In some embodiments, a provided compound or pharmaceutically acceptable salt thereof, is selected from those wherein MBM is

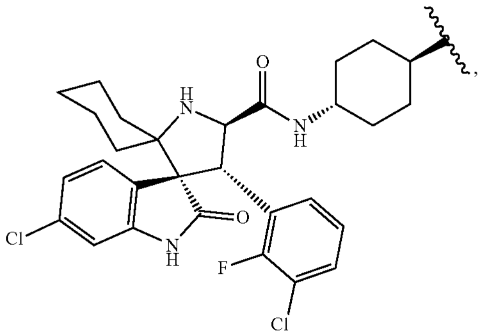 [SMILES: *[C@H]1CC[C@H](NC(=O)[C@@H]2NC3(CCCCC3)[C@@]3(C(=O)Nc4cc(Cl)ccc43)[C@H]2c2cccc(Cl)c2F)CC1]

LBM is selected from any of those in Table A below, and L is selected from any of those in Table B below.

In some embodiments, a provided compound or pharmaceutically acceptable salt thereof, is selected from those wherein MBM is

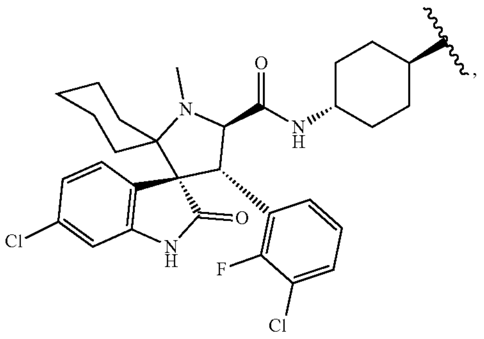

LBM is selected from any of those in Table A below, and L is selected from any of those in Table B below.

In some embodiments, a provided compound or pharmaceutically acceptable salt thereof, is selected from those wherein MBM is

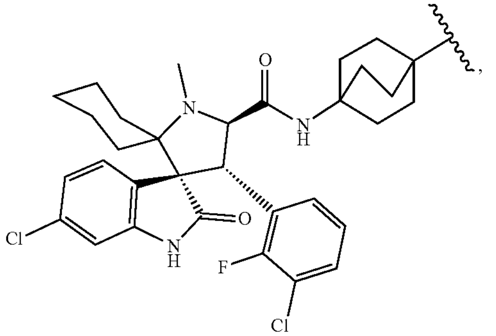 [SMILES: *C12CCC(NC(=O)[C@H]3[C@H](c4cccc(Cl)c4F)[C@]4(C(=O)Nc5cc(Cl)ccc54)C4(CCCCC4)N3C)(CC1)CC2]

LBM is selected from any of those in Table A below, and L is selected from any of those in Table B below.

In some embodiments, a provided compound or pharmaceutically acceptable salt thereof, is selected from those wherein MBM is

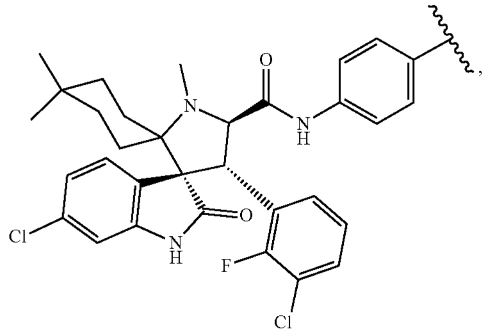

LBM is selected from any of those in Table A below, and L is selected from any of those in Table B below.

In some embodiments, a provided compound or pharmaceutically acceptable salt thereof, is selected from those wherein MBM is

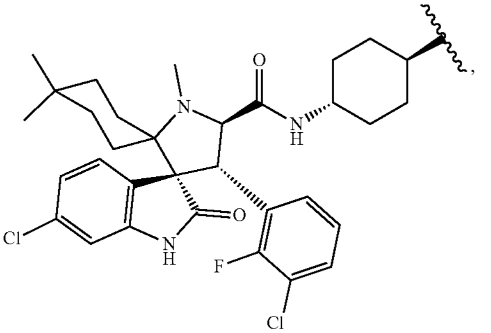 [SMILES: *[C@H]1CC[C@H](NC(=O)[C@H]2[C@H](c3cccc(Cl)c3F)[C@]3(C(=O)Nc4cc(Cl)ccc43)C3(CCC(C)(C)CC3)N2C)CC1]

LBM is selected from any of those in Table A below, and L is selected from any of those in Table B below.

In some embodiments, a provided compound or pharmaceutically acceptable salt thereof, is selected from those wherein MBM is

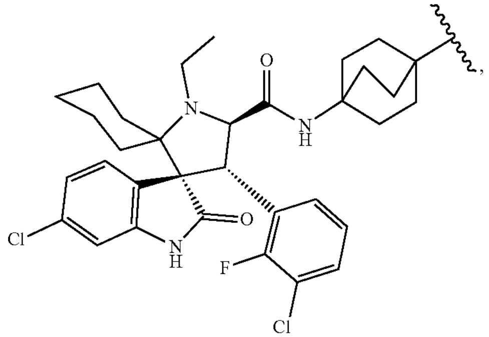 [SMILES: *C12CCC(NC(=O)[C@H]3[C@H](c4cccc(Cl)c4F)[C@]4(C(=O)Nc5cc(Cl)ccc54)C4(CCCCC4)N3CC)(CC1)CC2]

LBM is selected from any of those in Table A below, and L is selected from any of those in Table B below.

In some embodiments, a provided compound or pharmaceutically acceptable salt thereof, is selected from those wherein MBM is

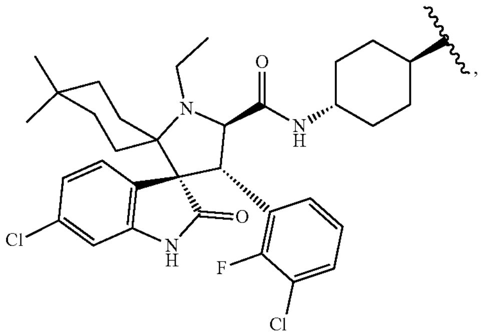 [SMILES: *[C@H]1CC[C@H](NC(=O)[C@H]2[C@H](c3cccc(Cl)c3F)[C@]3(C(=O)Nc4cc(Cl)ccc43)C3(CCC(C)(C)CC3)N2CC)CC1]

LBM is selected from any of those in Table A below, and L is selected from any of those in Table B below.

In some embodiments, a provided compound or pharmaceutically acceptable salt thereof, is selected from those wherein MBM is

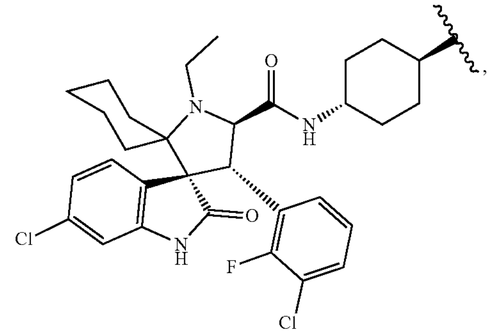 [SMILES: *[C@H]1CC[C@H](NC(=O)[C@H]2[C@H](c3cccc(Cl)c3F)[C@]3(C(=O)Nc4cc(Cl)ccc43)C3(CCCCC3)N2CC)CC1]

LBM is selected from any of those in Table A below, and L is selected from any of those in Table B below.

In some embodiments, a provided compound or pharmaceutically acceptable salt thereof, is selected from those wherein MBM is

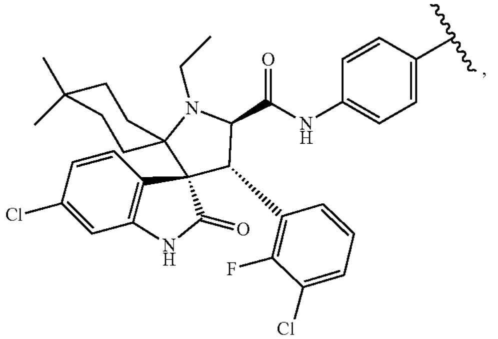 [SMILES: *c1ccc(NC(=O)[C@H]2[C@H](c3cccc(Cl)c3F)[C@]3(C(=O)Nc4cc(Cl)ccc43)C3(CCC(C)(C)CC3)N2CC)cc1]

LBM is selected from any of those in Table A below, and L is selected from any of those in Table B below.

In some embodiments, a provided compound or pharmaceutically acceptable salt thereof, is selected from those wherein MBM is

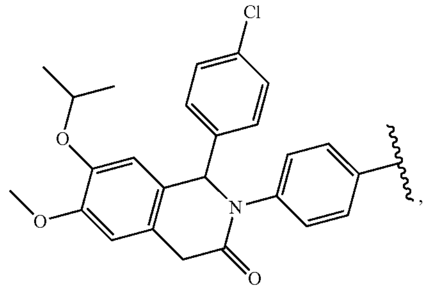 [SMILES: *c1ccc(N2C(=O)Cc3cc(OC)c(OC(C)C)cc3C2c2ccc(Cl)cc2)cc1]

LBM is selected from any of those in Table A below, and L is selected from any of those in Table B below.

In some embodiments, a provided compound or pharmaceutically acceptable salt thereof, is selected from those wherein MBM is

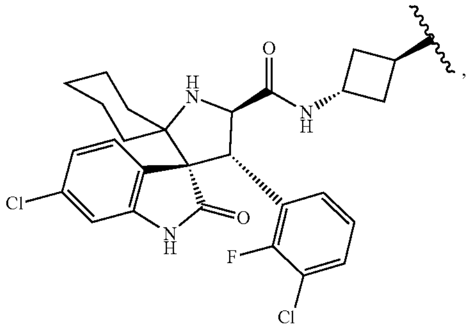 [SMILES: *[C@H]1C[C@H](NC(=O)[C@@H]2NC3(CCCCC3)[C@@]3(C(=O)Nc4cc(Cl)ccc43)[C@H]2c2cccc(Cl)c2F)C1]

LBM is selected from any of those in Table A below, and L is selected from any of those in Table B below.

In some embodiments, a provided compound or pharmaceutically acceptable salt thereof, is selected from those wherein MBM is

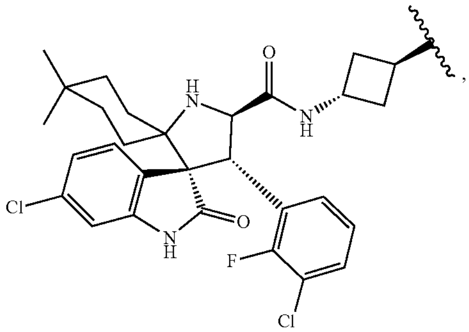 [SMILES: *[C@H]1C[C@H](NC(=O)[C@@H]2NC3(CCC(C)(C)CC3)[C@@]3(C(=O)Nc4cc(Cl)ccc43)[C@H]2c2cccc(Cl)c2F)C1]

LBM is selected from any of those in Table A below, and L is selected from any of those in Table B below.

In some embodiments, a provided compound or pharmaceutically acceptable salt thereof, is selected from those wherein MBM is

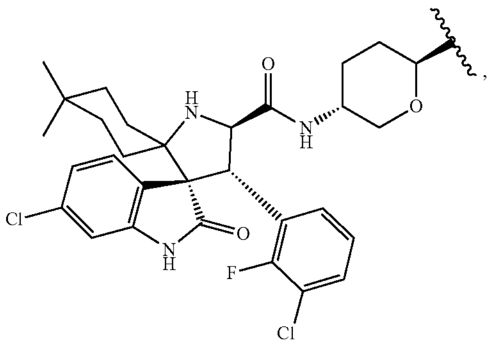 [SMILES: *[C@@H]1CC[C@@H](NC(=O)[C@@H]2NC3(CCC(C)(C)CC3)[C@@]3(C(=O)Nc4cc(Cl)ccc43)[C@H]2c2cccc(Cl)c2F)CO1]

LBM is selected from any of those in Table A below, and L is selected from any of those in Table B below.

In some embodiments, a provided compound or pharmaceutically acceptable salt thereof, is selected from those wherein MBM is

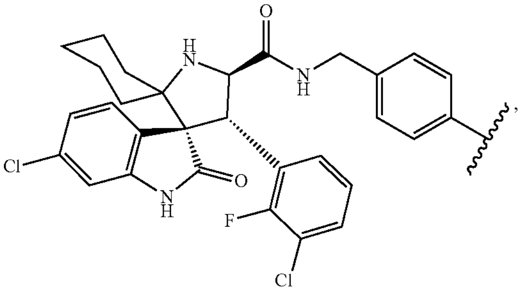 [SMILES: *c1ccc(CNC(=O)[C@@H]2NC3(CCCCC3)[C@@]3(C(=O)Nc4cc(Cl)ccc43)[C@H]2c2cccc(Cl)c2F)cc1]

LBM is selected from any of those in Table A below, and L is selected from any of those in Table B below.

In some embodiments, a provided compound or pharmaceutically acceptable salt thereof, is selected from those wherein MBM is

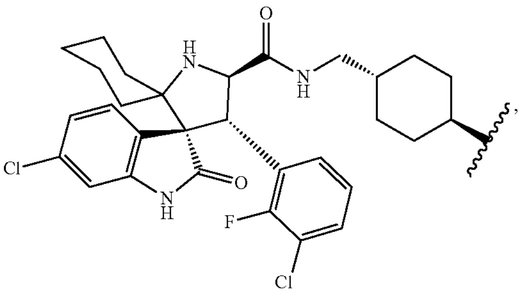 [SMILES: *[C@H]1CC[C@H](CNC(=O)[C@@H]2NC3(CCCCC3)[C@@]3(C(=O)Nc4cc(Cl)ccc43)[C@H]2c2cccc(Cl)c2F)CC1]

LBM is selected from any of those in Table A below, and L is selected from any of those in Table B below.

In some embodiments, MBM is

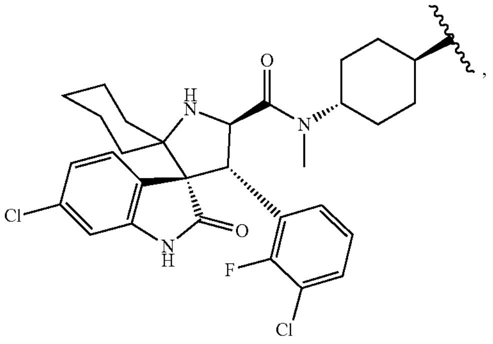 [SMILES: *[C@H]1CC[C@H](N(C)C(=O)[C@@H]2NC3(CCCCC3)[C@@]3(C(=O)Nc4cc(Cl)ccc43)[C@H]2c2cccc(Cl)c2F)CC1]

LBM is selected from any of those in Table A below, and L is selected from any of those in Table B below.

In some embodiments, a provided compound or pharmaceutically acceptable salt thereof, is selected from those wherein MBM is

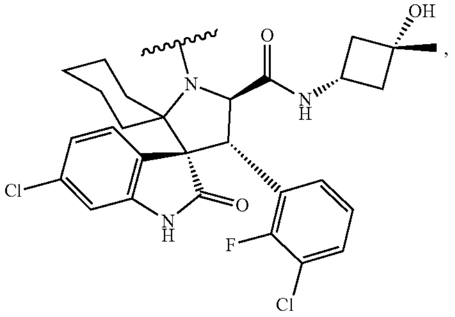 [SMILES: *N1[C@@H](C(=O)N[C@H]2C[C@@](C)(O)C2)[C@H](c2cccc(Cl)c2F)[C@]2(C(=O)Nc3cc(Cl)ccc32)C12CCCCC2]

LBM is selected from any of those in Table A below, and L is selected from any of those in Table B below.

In some embodiments, a provided compound or pharmaceutically acceptable salt thereof, is selected from those wherein MBM is

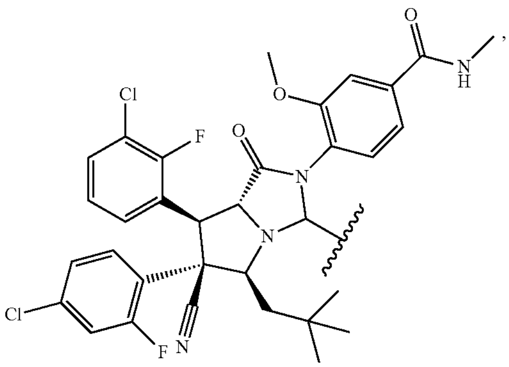

LBM is selected from any of those in Table A below, and L is selected from any of those in Table B below.

In some embodiments, a provided compound or pharmaceutically acceptable salt thereof, is selected from those wherein MBM is

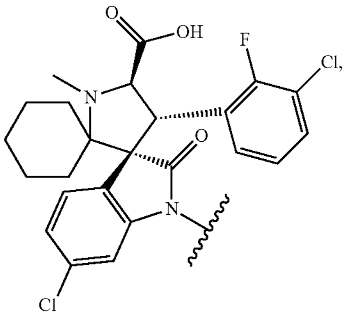 [SMILES: *N1C(=O)[C@@]2(c3ccc(Cl)cc31)[C@@H](c1cccc(Cl)c1F)[C@H](C(=O)O)N(C)C21CCCCC1]

LBM is selected from any of those in Table A below, and L is selected from any of those in Table B below.

In some embodiments, a provided compound or pharmaceutically acceptable salt thereof, is selected from those wherein MBM is

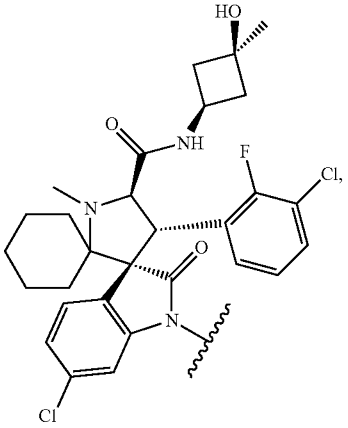 [SMILES: *N1C(=O)[C@@]2(c3ccc(Cl)cc31)[C@@H](c1cccc(Cl)c1F)[C@H](C(=O)N[C@H]1C[C@@](C)(O)C1)N(C)C21CCCCC1]

LBM is selected from any of those in Table A below, and L is selected from any of those in Table B below.

In some embodiments, a provided compound or pharmaceutically acceptable salt thereof, is selected from those wherein MBM is

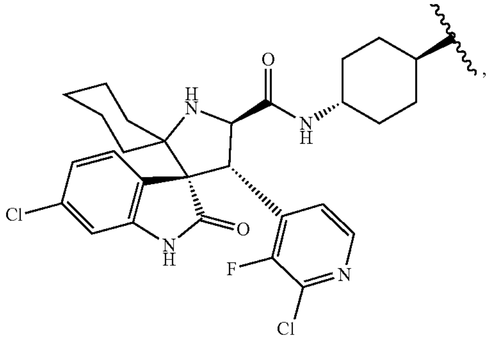 [SMILES: *[C@H]1CC[C@H](NC(=O)[C@@H]2NC3(CCCCC3)[C@@]3(C(=O)Nc4cc(Cl)ccc43)[C@H]2c2ccnc(Cl)c2F)CC1]

LBM is selected from any of those in Table A below, and L is selected from any of those in Table B below.

In some embodiments, a provided compound or pharmaceutically acceptable salt thereof, is selected from those wherein MBM is

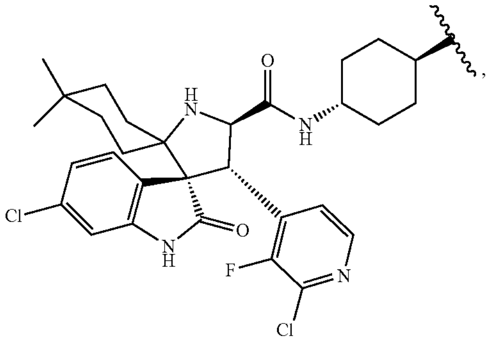 [SMILES: *[C@H]1CC[C@H](NC(=O)[C@@H]2NC3(CCC(C)(C)CC3)[C@@]3(C(=O)Nc4cc(Cl)ccc43)[C@H]2c2ccnc(Cl)c2F)CC1]

LBM is selected from any of those in Table A below, and L is selected from any of those in Table B below.

In some embodiments, a provided compound or pharmaceutically acceptable salt thereof, is selected from those wherein MBM is

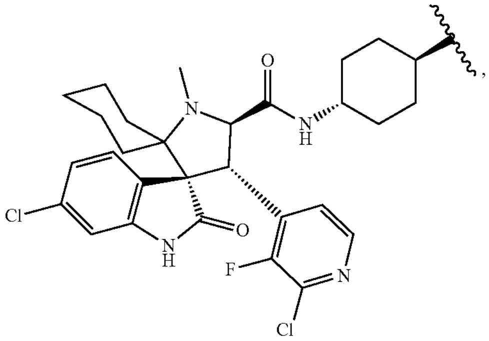 [SMILES: *[C@H]1CC[C@H](NC(=O)[C@H]2[C@H](c3ccnc(Cl)c3F)[C@]3(C(=O)Nc4cc(Cl)ccc43)C3(CCCCC3)N2C)CC1]

LBM is selected from any of those in Table A below, and L is selected from any of those in Table B below.

In some embodiments, a provided compound or pharmaceutically acceptable salt thereof, is selected from those wherein MBM is

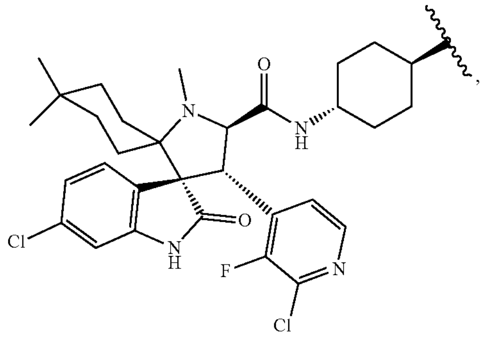 [SMILES: *[C@H]1CC[C@H](NC(=O)[C@H]2[C@H](c3ccnc(Cl)c3F)[C@]3(C(=O)Nc4cc(Cl)ccc43)C3(CCC(C)(C)CC3)N2C)CC1]

LBM is selected from any of those in Table A below, and L is selected from any of those in Table B below.

In some embodiments, a provided compound or pharmaceutically acceptable salt thereof, is selected from those wherein MBM is

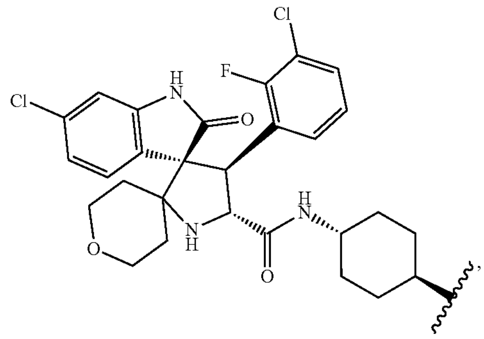

LBM is selected from any of those in Table A below, and L is selected from any of those in Table B below.

In some embodiments, a provided compound or pharmaceutically acceptable salt thereof, is selected from those wherein MBM is

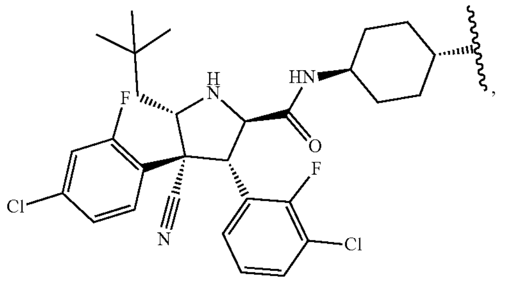 [SMILES: *[C@H]1CC[C@H](NC(=O)[C@@H]2N[C@@H](CC(C)(C)C)[C@](C#N)(c3ccc(Cl)cc3F)[C@H]2c2cccc(Cl)c2F)CC1]

LBM is selected from any of those in Table A below, and L is selected from any of those in Table B below.

In some embodiments, a provided compound or pharmaceutically acceptable salt thereof, is selected from those wherein MBM is

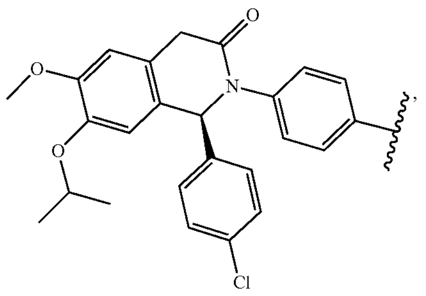 [SMILES: *c1ccc(N2C(=O)Cc3cc(OC)c(OC(C)C)cc3[C@@H]2c2ccc(Cl)cc2)cc1]

LBM is selected from any of those in Table A below, and L is selected from any of those in Table B below.

TABLE A

| Exemplified E3 Ligase Binding Moiety (LBM) | |
| --- | --- |
| 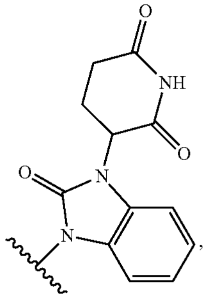 [SMILES: *n1c(=O)n(C2CCC(=O)NC2=O)c2ccccc21] | (e) |
| 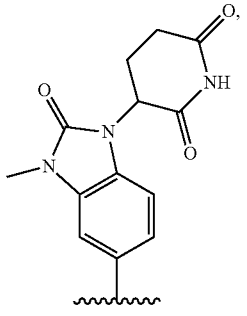 [SMILES: *c1ccc2c(c1)n(C)c(=O)n2C1CCC(=O)NC1=O] | (f) |

TABLE A-continued
| Exemplified E3 Ligase Binding Moiety (LBM) |
| --- |
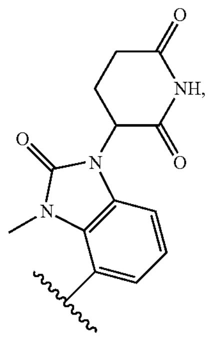 [SMILES: *c1cccc2c1n(C)c(=O)n2C1CCC(=O)NC1=O]
(g)
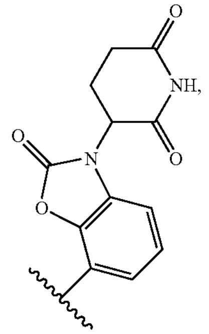 [SMILES: *c1cccc2c1oc(=O)n2C1CCC(=O)NC1=O]
(h)
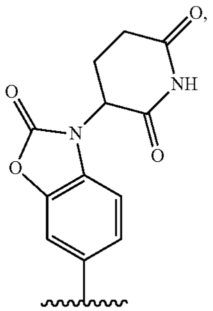 [SMILES: *c1ccc2c(c1)oc(=O)n2C1CCC(=O)NC1=O]
(i)
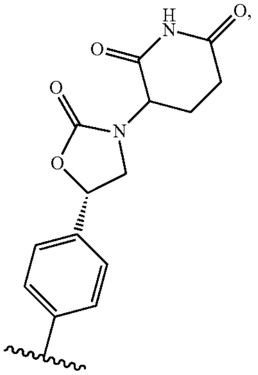 [SMILES: *c1ccc([C@H]2CN(C3CCC(=O)NC3=O)C(=O)O2)cc1]
(j)

TABLE A-continued
| Exemplified E3 Ligase Binding Moiety (LBM) | |
|---|---|
| 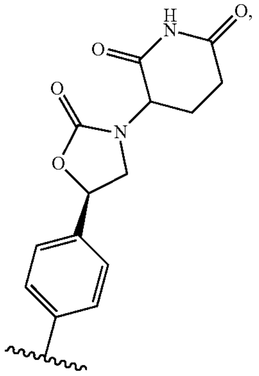 [SMILES: *c1ccc([C@@H]2CN(C3CCC(=O)NC3=O)C(=O)O2)cc1] | (k) |
| 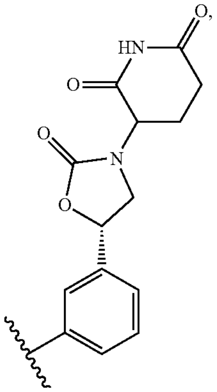 [SMILES: *c1cccc([C@H]2CN(C3CCC(=O)NC3=O)C(=O)O2)c1] | (l) |
| 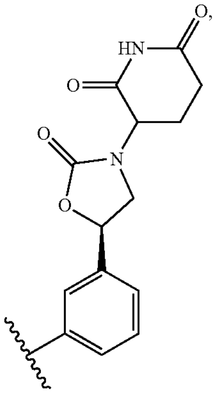 [SMILES: *c1cccc([C@@H]2CN(C3CCC(=O)NC3=O)C(=O)O2)c1] | (m) |
| 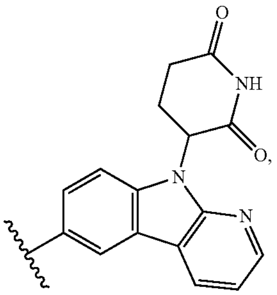 [SMILES: *c1ccc2c(c1)c1cccnc1n2C1CCC(=O)NC1=O] | (n) |

TABLE A-continued
| Exemplified E3 Ligase Binding Moiety (LBM) |
| --- |
| 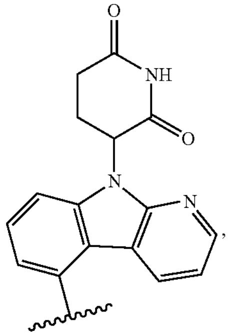 [SMILES: *c1cccc2c1c1cccnc1n2C1CCC(=O)NC1=O], (o) |
| 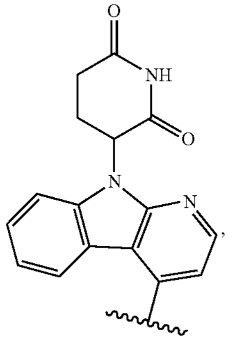 [SMILES: *c1ccnc2c1c1ccccc1n2C1CCC(=O)NC1=O], (p) |
| 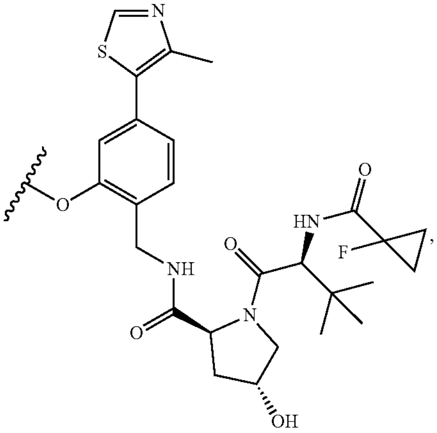 [SMILES: *Oc1cc(-c2scnc2C)ccc1CNC(=O)[C@@H]1C[C@@H](O)CN1C(=O)[C@@H](NC(=O)C1(F)CC1)C(C)(C)C], (n) |
| 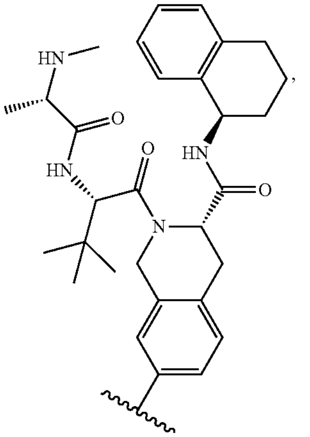 [SMILES: *c1ccc2c(c1)CN(C(=O)[C@@H](NC(=O)[C@H](C)NC)C(C)(C)C)[C@H](C(=O)N[C@@H]1CCCc3ccccc31)C2], (o) |

TABLE A-continued
| Exemplified E3 Ligase Binding Moiety (LBM) |
|---|
| (p) 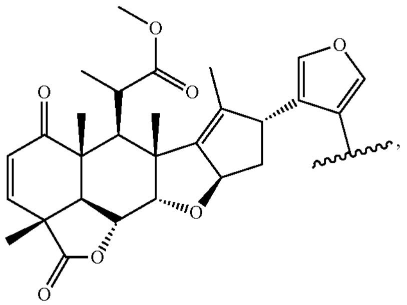 [SMILES: *c1cocc1[C@@H]1C[C@H]2O[C@@H]3[C@@H]4OC(=O)[C@]5(C)C=CC(=O)[C@](C)([C@@H](C(C)C(=O)OC)[C@]3(C)C2=C1C)[C@@H]45] |
| (q) 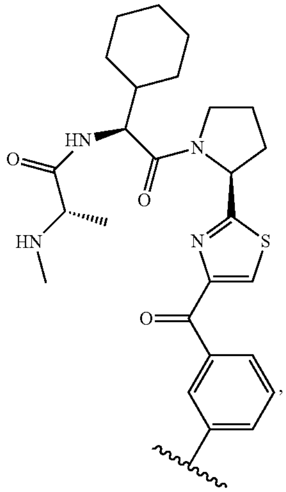 [SMILES: *c1cccc(C(=O)c2csc([C@@H]3CCCN3C(=O)[C@@H](NC(=O)[C@H](C)NC)C3CCCCC3)n2)c1] |
| (r) 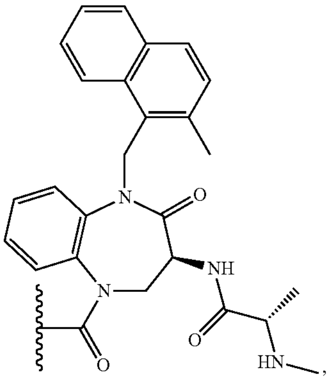 [SMILES: *C(=O)N1C[C@H](NC(=O)[C@H](C)NC)C(=O)N(Cc2c(C)ccc3ccccc23)c2ccccc21] |

TABLE A-continued
Exemplified E3 Ligase Binding Moiety (LBM)
(s)
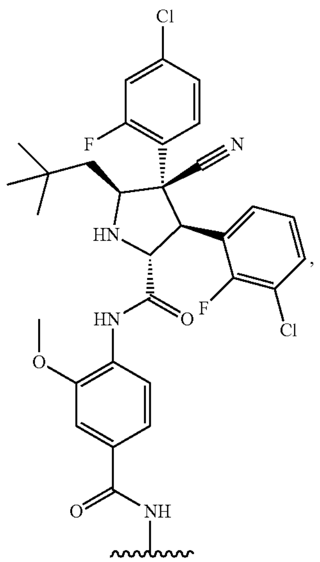 [SMILES: *NC(=O)c1ccc(NC(=O)[C@@H]2N[C@@H](CC(C)(C)C)[C@](C#N)(c3ccc(Cl)cc3F)[C@H]2c2cccc(Cl)c2F)c(OC)c1]
(t)
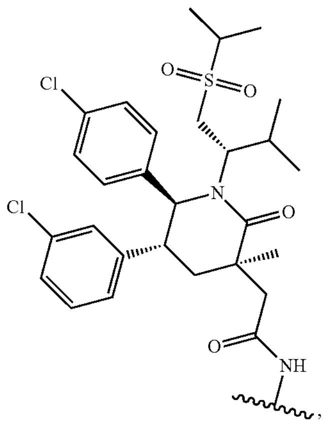 [SMILES: *NC(=O)C[C@@]1(C)C[C@H](c2cccc(Cl)c2)[C@@H](c2ccc(Cl)cc2)N([C@H](CS(=O)(=O)C(C)C)C(C)C)C1=O]
(u)
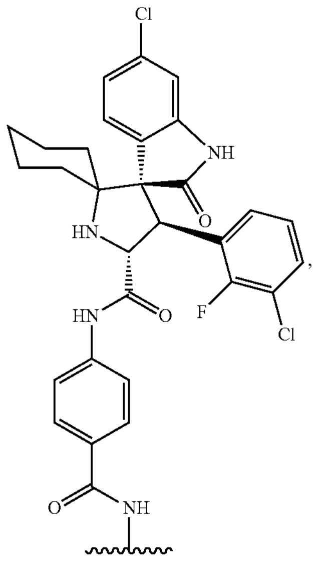 [SMILES: *NC(=O)c1ccc(NC(=O)[C@@H]2NC3(CCCCC3)[C@@]3(C(=O)Nc4cc(Cl)ccc43)[C@H]2c2cccc(Cl)c2F)cc1]

TABLE A-continued
| Exemplified E3 Ligase Binding Moiety (LBM) | |
|---|---|
| 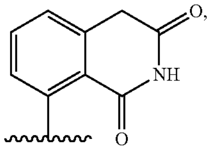 [SMILES: *c1cccc2c1C(=O)NC(=O)C2] | (v) |
| 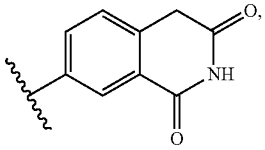 [SMILES: *c1ccc2c(c1)C(=O)NC(=O)C2] | (w) |
| 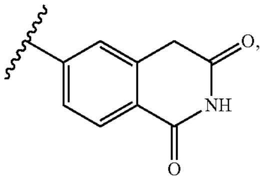 [SMILES: *c1ccc2c(c1)CC(=O)NC2=O] | (x) |
| 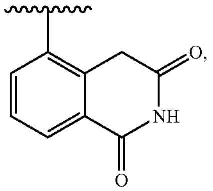 [SMILES: *c1cccc2c1CC(=O)NC2=O] | (y) |
| 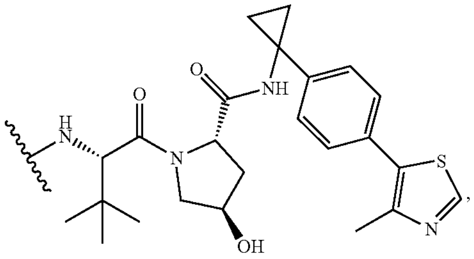 [SMILES: *N[C@H](C(=O)N1C[C@H](O)C[C@H]1C(=O)NC1(c2ccc(-c3scnc3C)cc2)CC1)C(C)(C)C] | (z) |
| 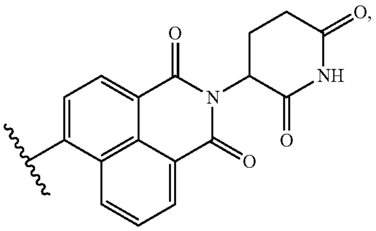 [SMILES: *c1ccc2c3c(cccc13)C(=O)N(C1CCC(=O)NC1=O)C2=O] | (bb) |
| 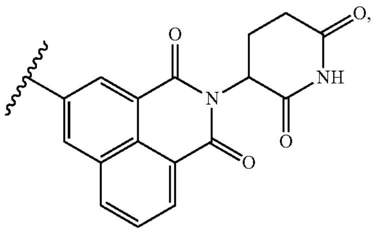 [SMILES: *c1cc2c3c(cccc3c1)C(=O)N(C1CCC(=O)NC1=O)C2=O] | (cc) |

TABLE A-continued
| Exemplified E3 Ligase Binding Moiety (LBM) |
| --- |
| 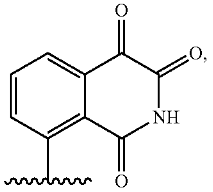 [SMILES: *c1cccc2c1C(=O)NC(=O)C2=O] (dd) |
| 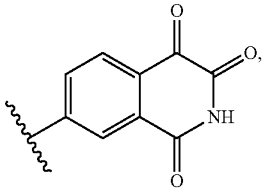 [SMILES: *c1ccc2c(c1)C(=O)NC(=O)C2=O] (ee) |
| 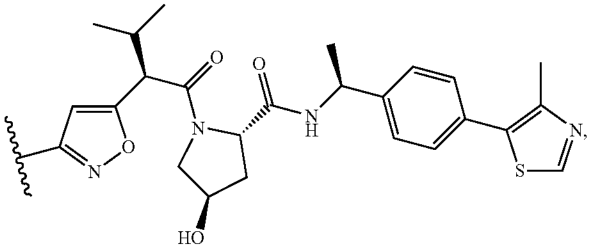 [SMILES: *c1cc([C@H](C(=O)N2C[C@H](O)C[C@H]2C(=O)N[C@@H](C)c2ccc(-c3scnc3C)cc2)C(C)C)on1] (ff) |
| 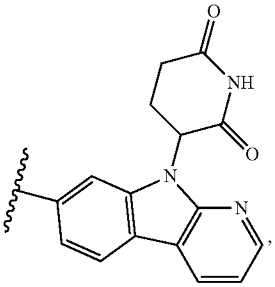 [SMILES: *c1ccc2c3cccnc3n(C3CCC(=O)NC3=O)c2c1] (gg) |
| 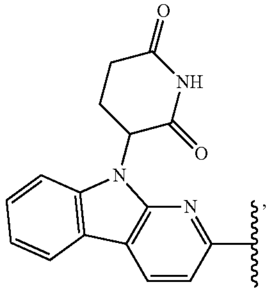 [SMILES: *c1ccc2c3ccccc3n(C3CCC(=O)NC3=O)c2n1] (hh) |
| 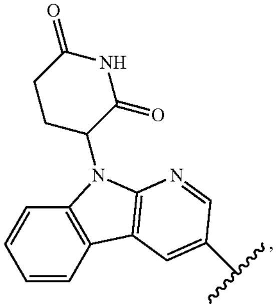 [SMILES: *c1cnc2c(c1)c1ccccc1n2C1CCC(=O)NC1=O] (ii) |

TABLE A-continued
| Exemplified E3 Ligase Binding Moiety (LBM) |
| --- |
| 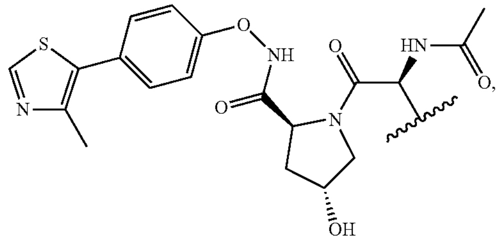 [SMILES: *[C@H](NC(C)=O)C(=O)N1C[C@H](O)C[C@H]1C(=O)NOc1ccc(-c2scnc2C)cc1] (jj) |
| 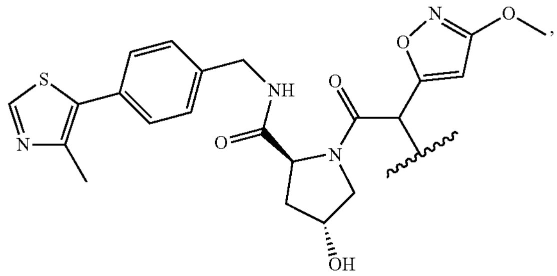 [SMILES: *C(C(=O)N1C[C@H](O)C[C@H]1C(=O)NCc1ccc(-c2scnc2C)cc1)c1cc(OC)no1] (kk) |
| 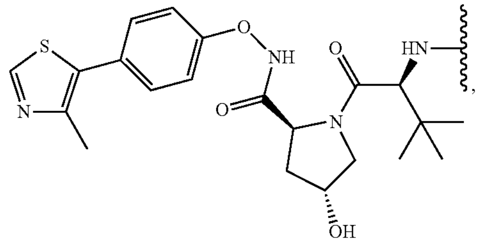 [SMILES: *N[C@H](C(=O)N1C[C@H](O)C[C@H]1C(=O)NOc1ccc(-c2scnc2C)cc1)C(C)(C)C] (ll) |
| 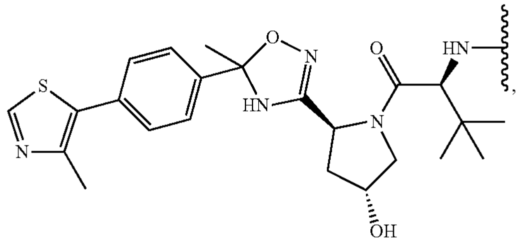 [SMILES: *N[C@H](C(=O)N1C[C@H](O)C[C@H]1C1=NOC(C)(c2ccc(-c3scnc3C)cc2)N1)C(C)(C)C] (mm) |
| 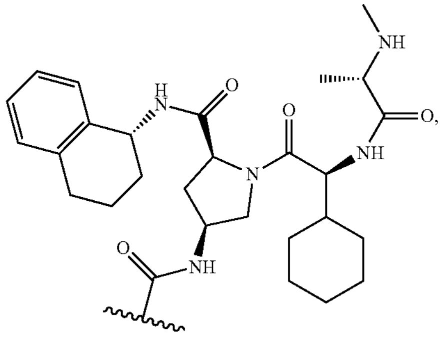 [SMILES: *C(=O)N[C@H]1C[C@@H](C(=O)N[C@@H]2CCCc3ccccc32)N(C(=O)[C@@H](NC(=O)[C@H](C)NC)C2CCCCC2)C1] (nn) |

TABLE A-continued
| Exemplified E3 Ligase Binding Moiety (LBM) |
| --- |
| 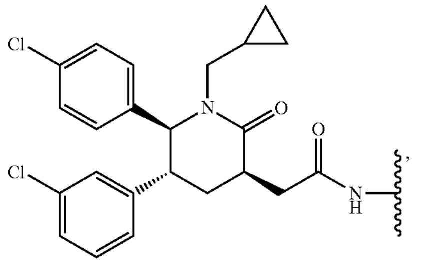 (oo) |
| 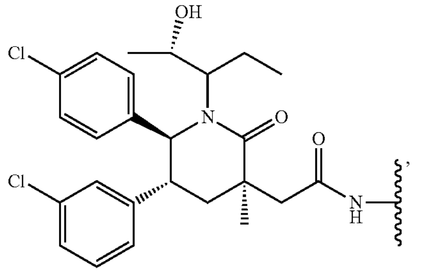 [SMILES: *NC(=O)C[C@@]1(C)C[C@H](c2cccc(Cl)c2)[C@@H](c2ccc(Cl)cc2)N(C(CC)[C@H](C)O)C1=O] (pp) |
| 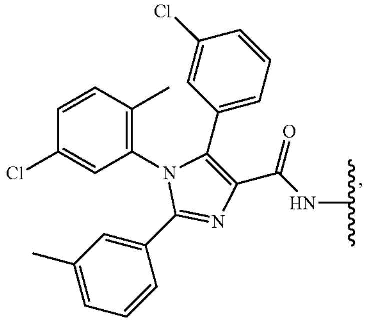 [SMILES: *NC(=O)c1nc(-c2cccc(C)c2)n(-c2cc(Cl)ccc2C)c1-c1cccc(Cl)c1] (qq) |
| 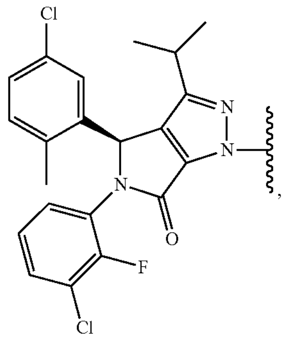 [SMILES: *n1nc(C(C)C)c2c1C(=O)N(c1cccc(Cl)c1F)[C@H]2c1cc(Cl)ccc1C] (rr) |
| 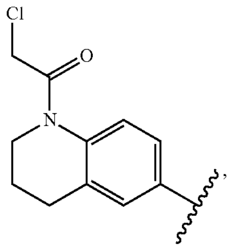 [SMILES: *c1ccc2c(c1)CCCN2C(=O)CCl] (ss) |

TABLE A-continued
| Exemplified E3 Ligase Binding Moiety (LBM) |
| --- |
| 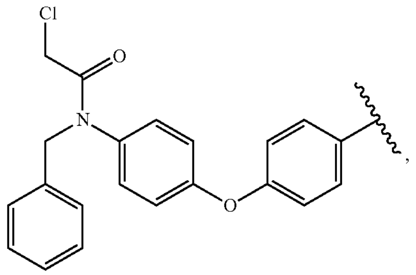 (tt) |
| 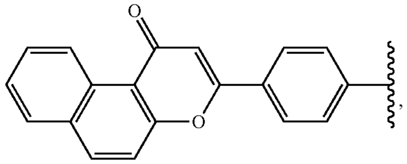 [SMILES: *c1ccc(-c2cc(=O)c3c(ccc4ccccc43)o2)cc1] (uu) |
| 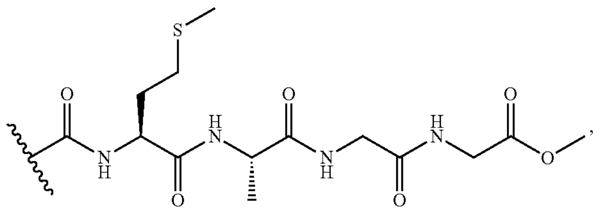 [SMILES: *C(=O)N[C@@H](CCSC)C(=O)N[C@@H](C)C(=O)NCC(=O)NCC(=O)OC] (vv) |
| 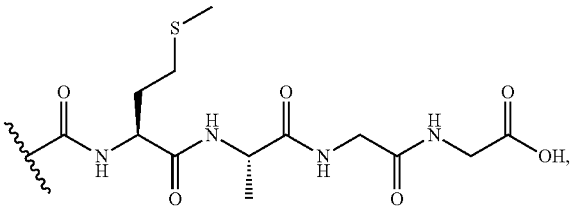 [SMILES: *C(=O)N[C@@H](CCSC)C(=O)N[C@@H](C)C(=O)NCC(=O)NCC(=O)O] (ww) |
| 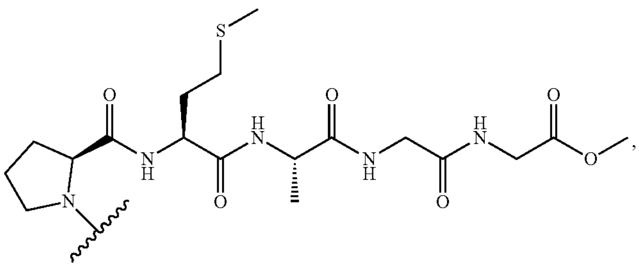 [SMILES: *N1CCC[C@H]1C(=O)N[C@@H](CCSC)C(=O)N[C@@H](C)C(=O)NCC(=O)NCC(=O)OC] (xx) |
| 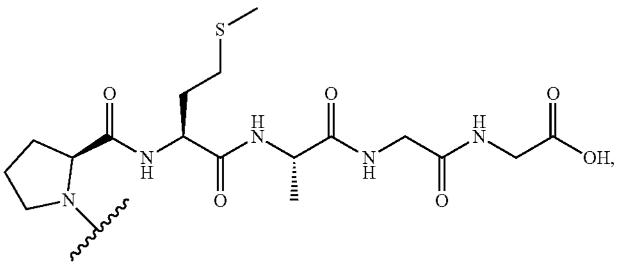 [SMILES: *N1CCC[C@H]1C(=O)N[C@@H](CCSC)C(=O)N[C@@H](C)C(=O)NCC(=O)NCC(=O)O] (yy) |

TABLE A-continued
| Exemplified E3 Ligase Binding Moiety (LBM) | |
|---|---|
| 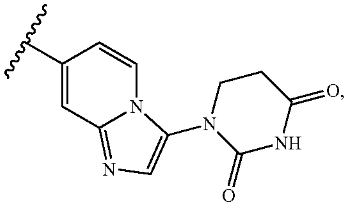 [SMILES: *c1ccn2c(N3CCC(=O)NC3=O)cnc2c1] | (zz) |
| 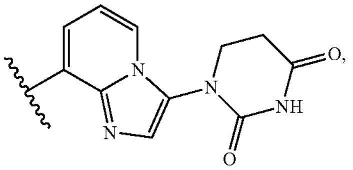 [SMILES: *c1cccn2c(N3CCC(=O)NC3=O)cnc12] | (aaa) |
| 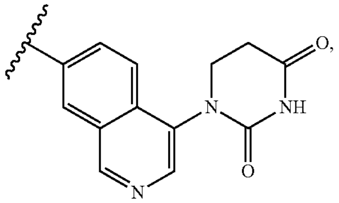 [SMILES: *c1ccc2c(N3CCC(=O)NC3=O)cncc2c1] | (bbb) |
| 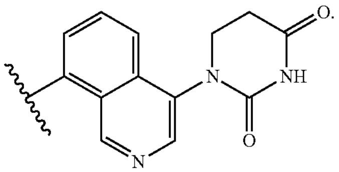 [SMILES: *c1cccc2c(N3CCC(=O)NC3=O)cncc12] | (ccc) |
TABLE B
| Exemplified Linkers (L) | |
|---|---|
| 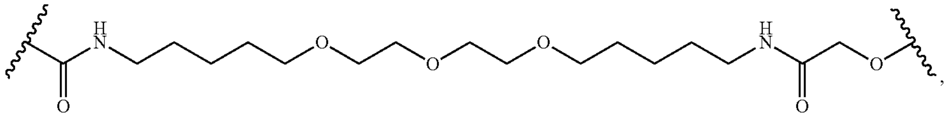 [SMILES: *OCC(=O)NCCCCCOCCOCCOCCCCCNC(*)=O] | (1) |
| 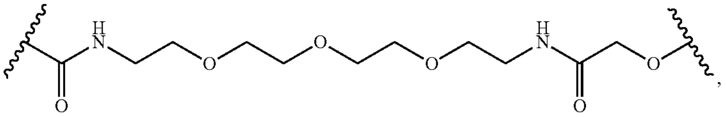 [SMILES: *OCC(=O)NCCOCCOCCOCCNC(*)=O] | (2) |
| 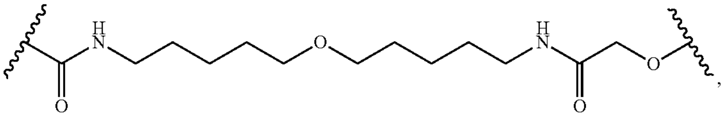 [SMILES: *OCC(=O)NCCCCCOCCCCCNC(*)=O] | (3) |
| 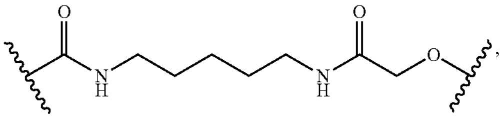 [SMILES: *OCC(=O)NCCCCCNC(*)=O] | (4) |
| 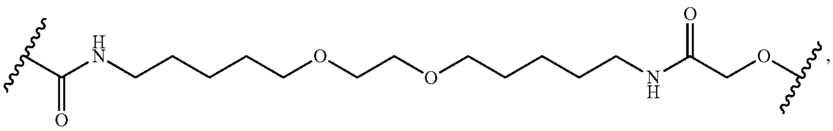 [SMILES: *OCC(=O)NCCCCCOCCOCCCCCNC(*)=O] | (5) |

TABLE B-continued
Exemplified Linkers (L)
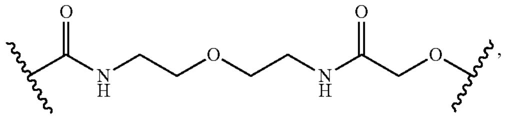 [SMILES: *OCC(=O)NCCOCCNC(*)=O]
(6)
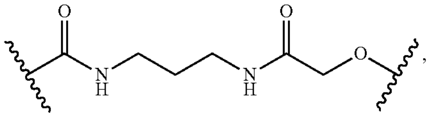 [SMILES: *OCC(=O)NCCCNC(*)=O]
(7)
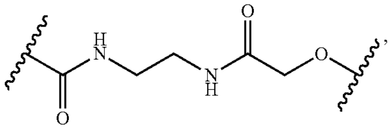 [SMILES: *OCC(=O)NCCNC(*)=O]
(8)
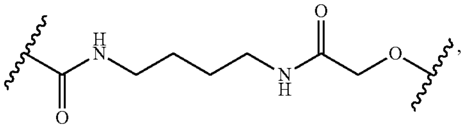 [SMILES: *OCC(=O)NCCCCNC(*)=O]
(9)
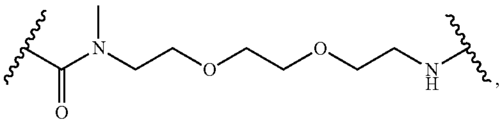 [SMILES: *NCCOCCOCCN(C)C(*)=O]
(10)
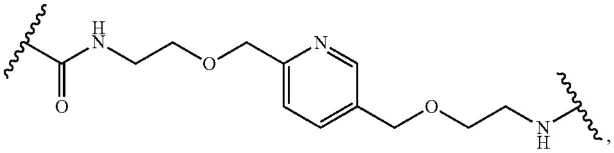 [SMILES: *NCCOCc1ccc(COCCNC(*)=O)nc1]
(11)
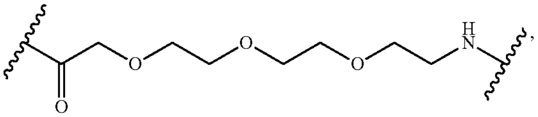 [SMILES: *NCCOCCOCCOCC(*)=O]
(12)
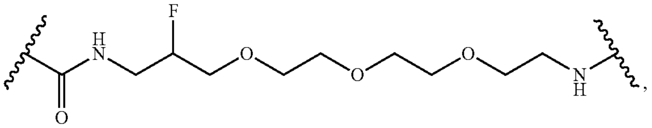 [SMILES: *NCCOCCOCCOCC(F)CNC(*)=O]
(13)
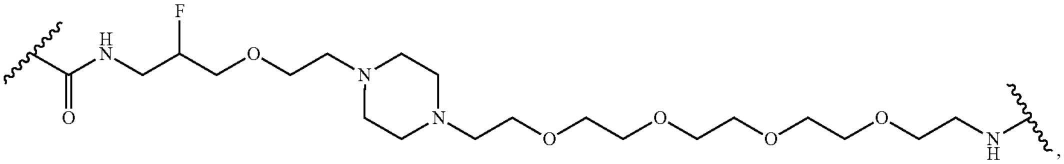 [SMILES: *NCCOCCOCCOCCOCCN1CCN(CCOCC(F)CNC(*)=O)CC1]
(14)
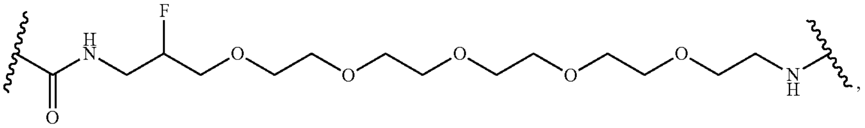 [SMILES: *NCCOCCOCCOCCOCCOCC(F)CNC(*)=O]
(15)
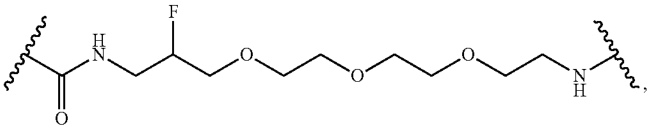 [SMILES: *NCCOCCOCCOCC(F)CNC(*)=O]
(16)

TABLE B-continued
Exemplified Linkers (L)
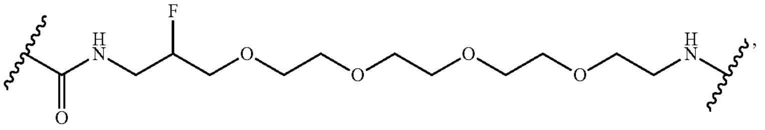 [SMILES: *NCCOCCOCCOCCOCC(F)CNC(*)=O]
(17)
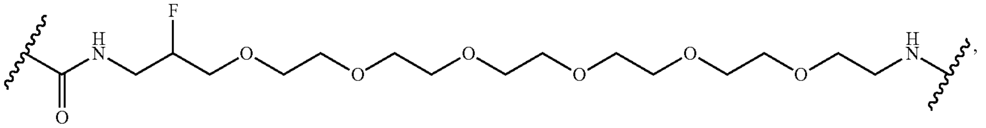 [SMILES: *NCCOCCOCCOCCOCCOCCOCC(F)CNC(*)=O]
(18)
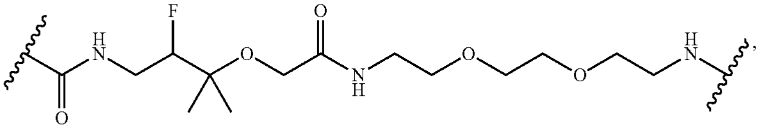 [SMILES: *NCCOCCOCCNC(=O)COC(C)(C)C(F)CNC(*)=O]
(19)
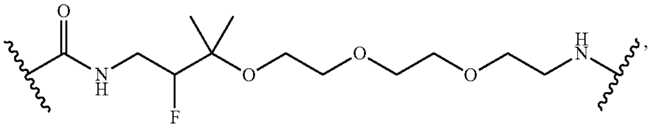 [SMILES: *NCCOCCOCCOC(C)(C)C(F)CNC(*)=O]
(20)
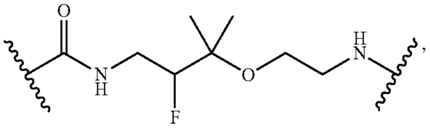 [SMILES: *NCCOC(C)(C)C(F)CNC(*)=O]
(21)
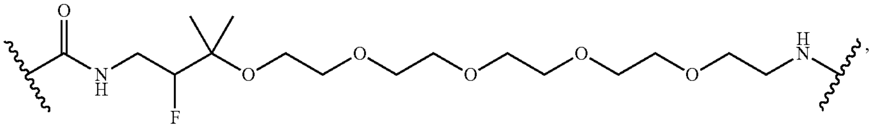 [SMILES: *NCCOCCOCCOCCOCCOC(C)(C)C(F)CNC(*)=O]
(22)
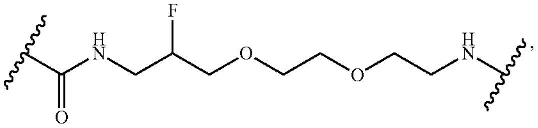 [SMILES: *NCCOCCOCC(F)CNC(*)=O]
(23)
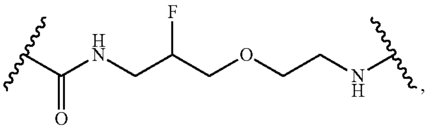 [SMILES: *NCCOCC(F)CNC(*)=O]
(24)
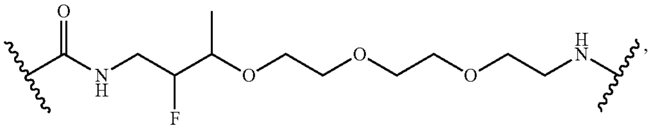 [SMILES: *NCCOCCOCCOC(C)C(F)CNC(*)=O]
(25)
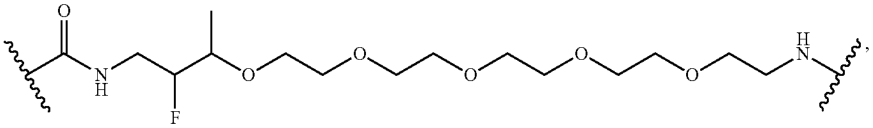 [SMILES: *NCCOCCOCCOCCOCCOC(C)C(F)CNC(*)=O]
(26)
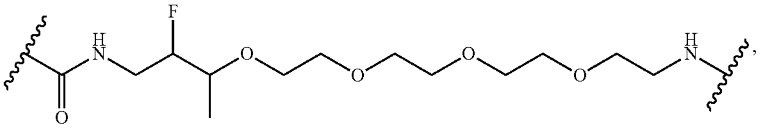 [SMILES: *NCCOCCOCCOCCOC(C)C(F)CNC(*)=O]
(27)

TABLE B-continued
Exemplified Linkers (L)
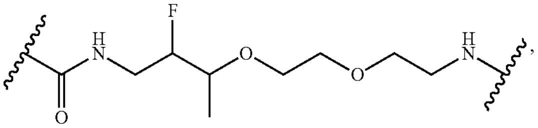 [SMILES: *NCCOCCOC(C)C(F)CNC(*)=O]
(28)
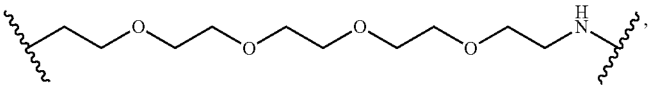 [SMILES: *CCOCCOCCOCCOCCN*]
(29)
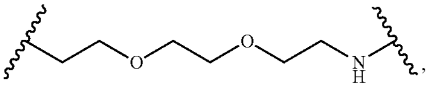 [SMILES: *CCOCCOCCN*]
(30)
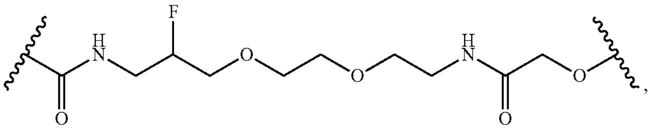 [SMILES: *OCC(=O)NCCOCCOCC(F)CNC(*)=O]
(31)
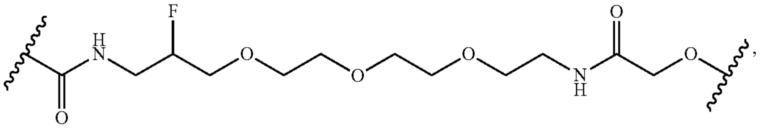 [SMILES: *OCC(=O)NCCOCCOCCOCC(F)CNC(*)=O]
(32)
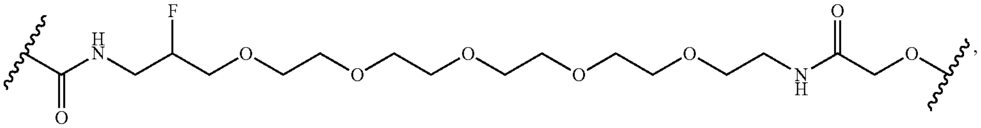 [SMILES: *OCC(=O)NCCOCCOCCOCCOCCOCC(F)CNC(*)=O]
(33)
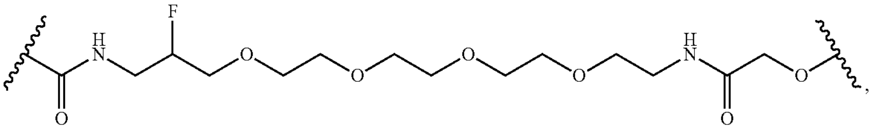 [SMILES: *OCC(=O)NCCOCCOCCOCCOCC(F)CNC(*)=O]
(34)
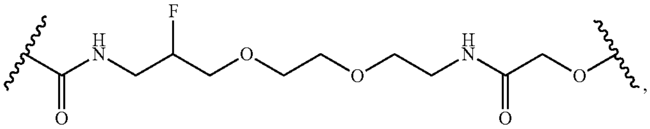 [SMILES: *OCC(=O)NCCOCCOCC(F)CNC(*)=O]
(35)
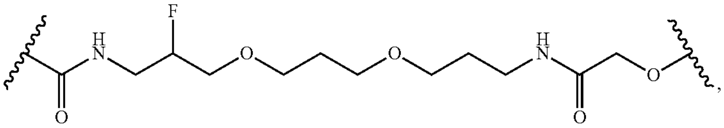 [SMILES: *OCC(=O)NCCCOCCCOCC(F)CNC(*)=O]
(36)
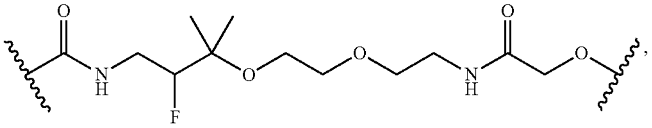 [SMILES: *OCC(=O)NCCOCCOC(C)(C)C(F)CNC(*)=O]
(37)
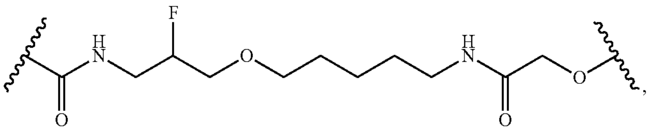 [SMILES: *OCC(=O)NCCCCCOCC(F)CNC(*)=O]
(38)

TABLE B-continued
Exemplified Linkers (L)
(39)
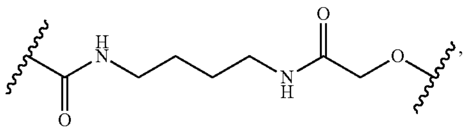 [SMILES: *OCC(=O)NCCCCNC(*)=O]
(40)
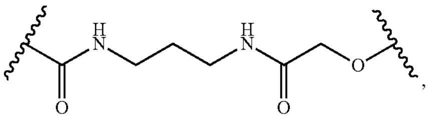 [SMILES: *OCC(=O)NCCCNC(*)=O]
(41)
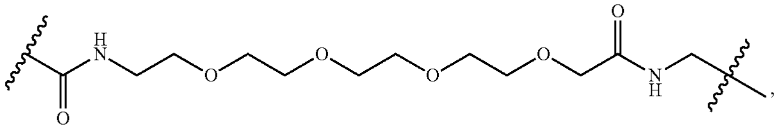 [SMILES: *CNC(=O)COCCOCCOCCOCCNC(*)=O]
(42)
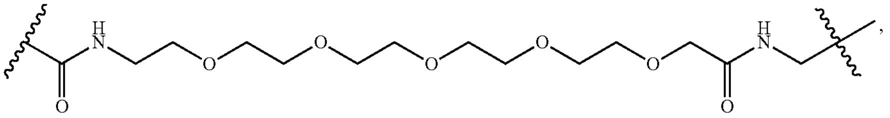 [SMILES: *CNC(=O)COCCOCCOCCOCCOCCNC(*)=O]
(43)
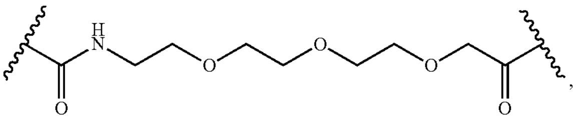 [SMILES: *C(=O)COCCOCCOCCNC(*)=O]
(44)
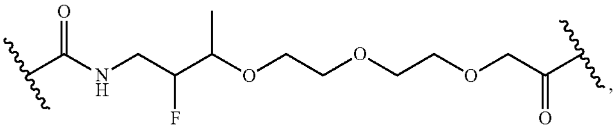 [SMILES: *C(=O)COCCOCCOC(C)C(F)CNC(*)=O]
(45)
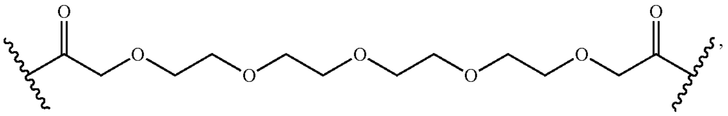 [SMILES: *C(=O)COCCOCCOCCOCCOCC(*)=O]
(46)
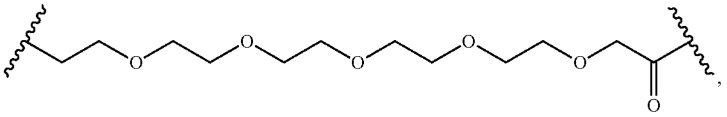 [SMILES: *CCOCCOCCOCCOCCOCC(*)=O]
(47)
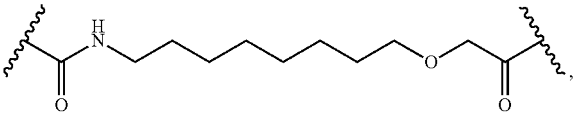 [SMILES: *C(=O)COCCCCCCCCNC(*)=O]
(49)
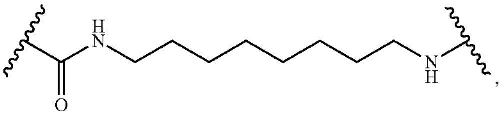 [SMILES: *NCCCCCCCCNC(*)=O]
(50)
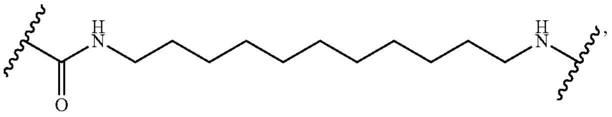 [SMILES: *NCCCCCCCCCCCNC(*)=O]
(51)
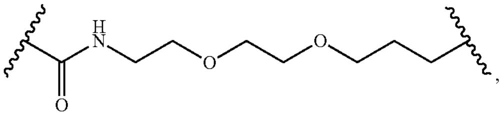 [SMILES: *CCCOCCOCCNC(*)=O]

TABLE B-continued
Exemplified Linkers (L)
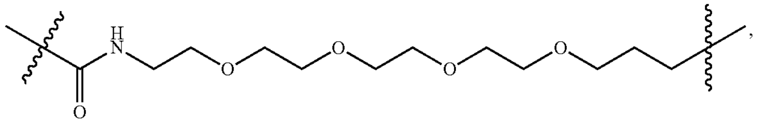 [SMILES: *CCCOCCOCCOCCOCCNC(*)=O]
(52)
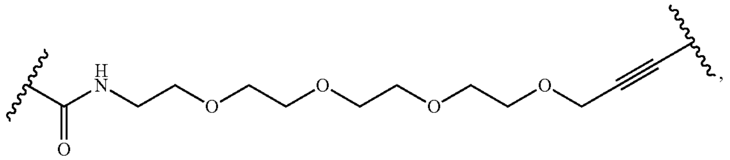 [SMILES: *C#CCOCCOCCOCCOCCNC(*)=O]
(53)
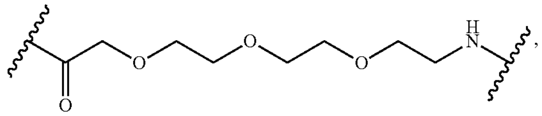
(54)
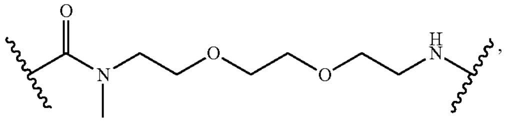 [SMILES: *NCCOCCOCCN(C)C(*)=O]
(55)
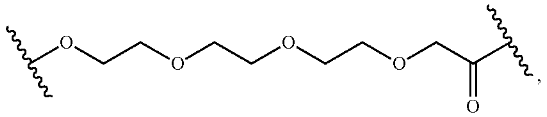 [SMILES: *OCCOCCOCCOCC(*)=O]
(56)
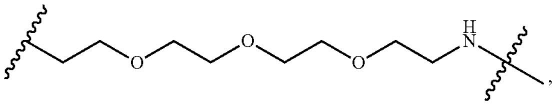 [SMILES: *CCOCCOCCOCCN*]
(57)
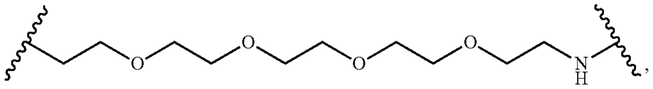 [SMILES: *CCOCCOCCOCCOCCN*]
(58)
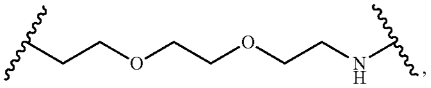 [SMILES: *CCOCCOCCN*]
(59)
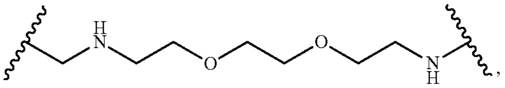 [SMILES: *CNCCOCCOCCN*]
(60)
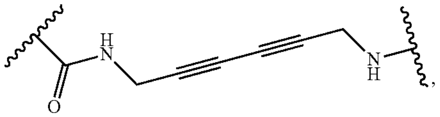 [SMILES: *NCC#CC#CCNC(*)=O]
(61)
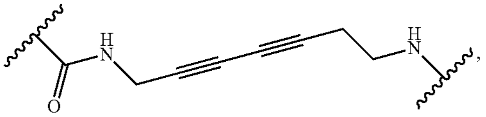 [SMILES: *NCCC#CC#CCNC(*)=O]
(62)
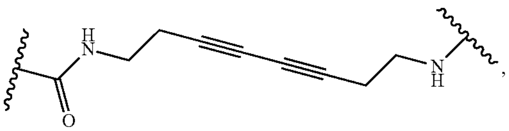 [SMILES: *NCCC#CC#CCCNC(*)=O]
(63)

TABLE B-continued
Exemplified Linkers (L)
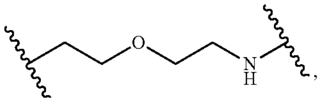 [SMILES: *CCOCCN*]
(64)
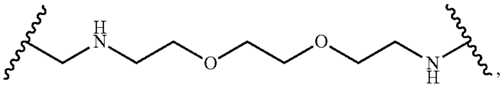 [SMILES: *CNCCOCCOCCN*]
(65)
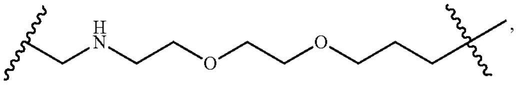 [SMILES: *CCCOCCOCCNC*]
(66)
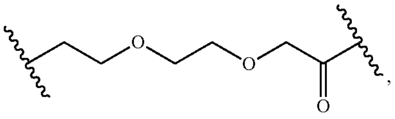 [SMILES: *CCOCCOCC(*)=O]
(67)
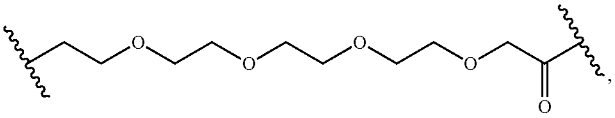 [SMILES: *CCOCCOCCOCCOCC(*)=O]
(68)
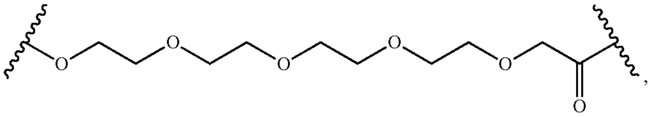 [SMILES: *OCCOCCOCCOCCOCC(*)=O]
(69)
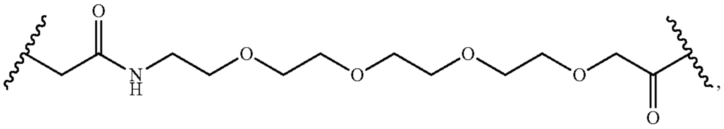 [SMILES: *CC(=O)NCCOCCOCCOCCOCC(*)=O]
(70)
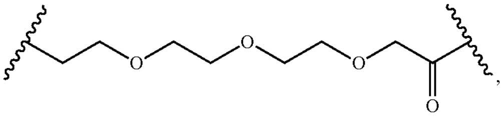 [SMILES: *CCOCCOCCOCC(*)=O]
(71)
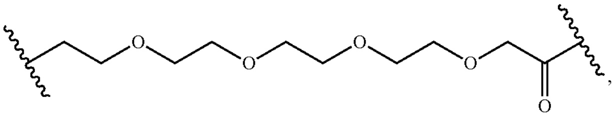 [SMILES: *CCOCCOCCOCCOCC(*)=O]
(72)
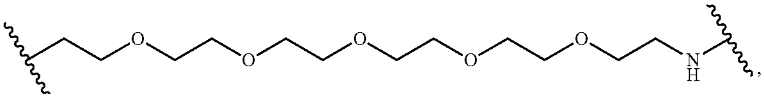 [SMILES: *CCOCCOCCOCCOCCOCCN*]
(73)
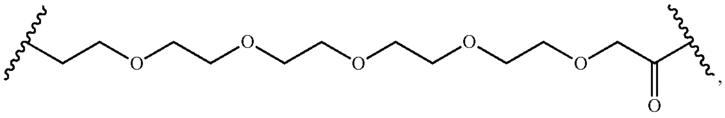 [SMILES: *CCOCCOCCOCCOCCOCC(*)=O]
(74)
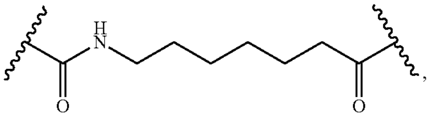 [SMILES: *C(=O)CCCCCCNC(*)=O]
(75)

TABLE B-continued
Exemplified Linkers (L)
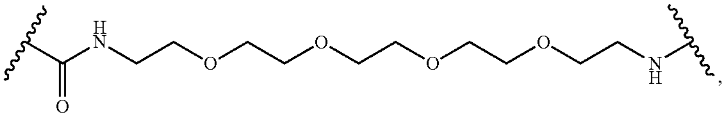 [SMILES: *NCCOCCOCCOCCOCCNC(*)=O]
(76)
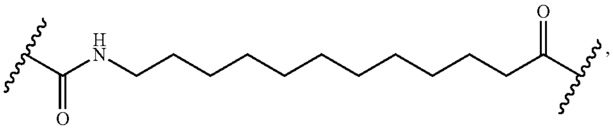 [SMILES: *C(=O)CCCCCCCCCCCNC(*)=O]
(77)
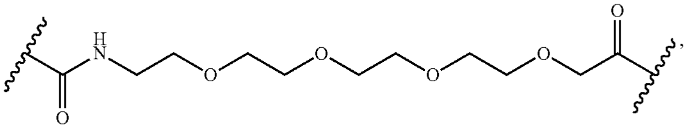 [SMILES: *C(=O)COCCOCCOCCOCCNC(*)=O]
(78)
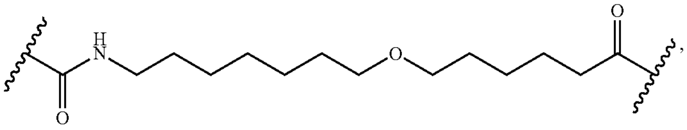 [SMILES: *C(=O)CCCCCOCCCCCCCNC(*)=O]
(79)
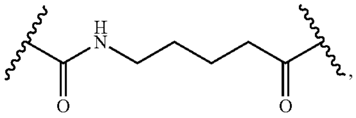 [SMILES: *C(=O)CCCCNC(*)=O]
(80)
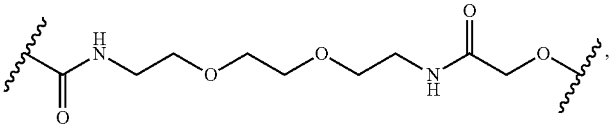 [SMILES: *OCC(=O)NCCOCCOCCNC(*)=O]
(81)
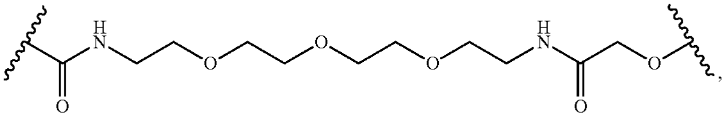 [SMILES: *OCC(=O)NCCOCCOCCOCCNC(*)=O]
(82)
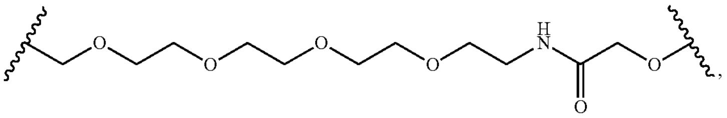 [SMILES: *COCCOCCOCCOCCNC(=O)CO*]
(83)
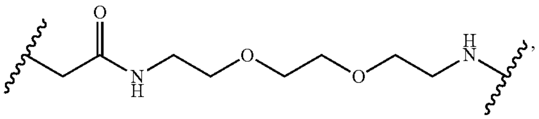 [SMILES: *CC(=O)NCCOCCOCCN*]
(84)
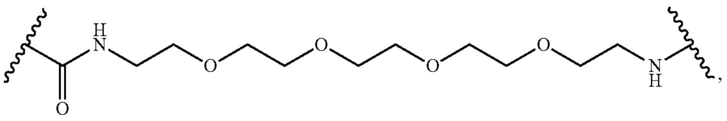 [SMILES: *NCCOCCOCCOCCOCCNC(*)=O]
(85)
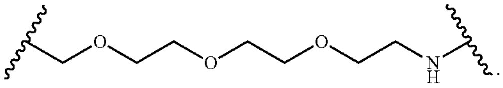 [SMILES: *COCCOCCOCCN*]
(86)
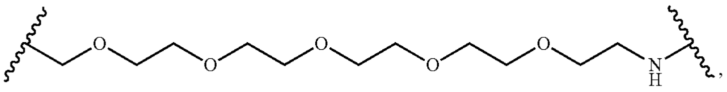 [SMILES: *COCCOCCOCCOCCOCCN*]
(87)

TABLE B-continued
Exemplified Linkers (L)
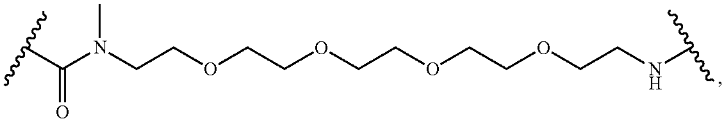 [SMILES: *NCCOCCOCCOCCOCCN(C)C(*)=O]
(88)
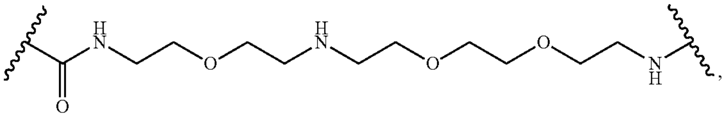 [SMILES: *NCCOCCOCCNCCOCCNC(*)=O]
(89)
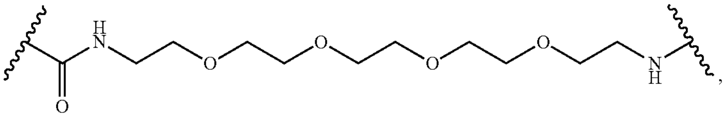 [SMILES: *NCCOCCOCCOCCOCCNC(*)=O]
(90)
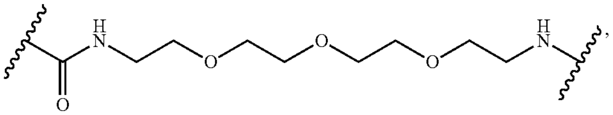 [SMILES: *NCCOCCOCCOCCNC(*)=O]
(91)
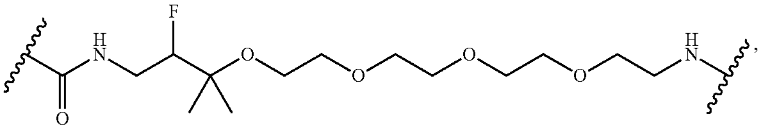 [SMILES: *NCCOCCOCCOCCOC(C)(C)C(F)CNC(*)=O]
(92)
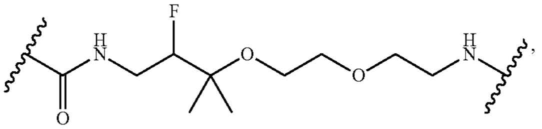 [SMILES: *NCCOCCOC(C)(C)C(F)CNC(*)=O]
(93)
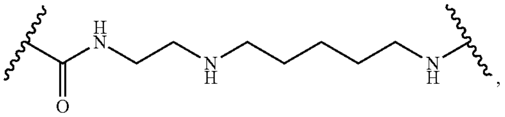 [SMILES: *NCCCCCNCCNC(*)=O]
(94)
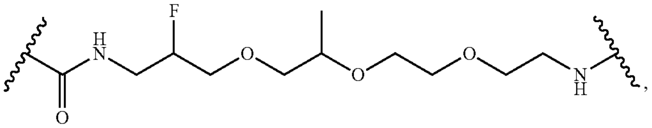 [SMILES: *NCCOCCOC(C)COCC(F)CNC(*)=O]
(95)
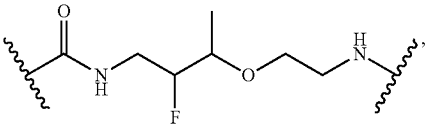 [SMILES: *NCCOC(C)C(F)CNC(*)=O]
(96)
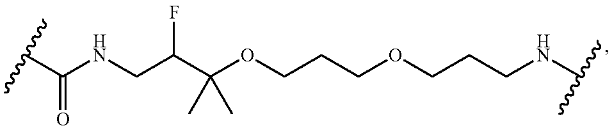 [SMILES: *NCCCOCCCOC(C)(C)C(F)CNC(*)=O]
(97)
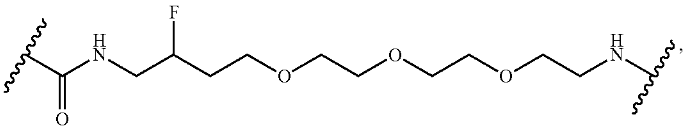 [SMILES: *NCCOCCOCCOCCC(F)CNC(*)=O]
(98)

TABLE B-continued
Exemplified Linkers (L)
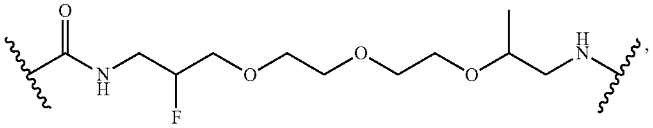 [SMILES: *NCC(C)OCCOCCOCC(F)CNC(*)=O]
(99)
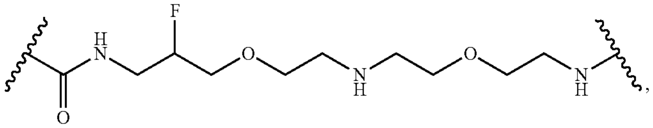 [SMILES: *NCCOCCNCCOCC(F)CNC(*)=O]
(100)
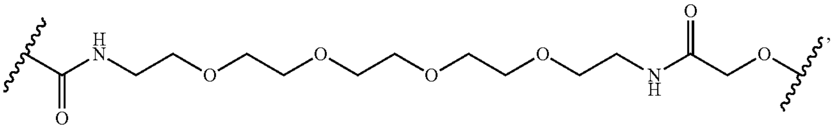 [SMILES: *OCC(=O)NCCOCCOCCOCCOCCNC(*)=O]
(101)
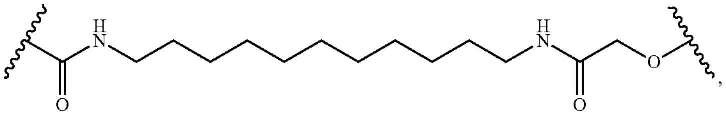 [SMILES: *OCC(=O)NCCCCCCCCCCCNC(*)=O]
(102)
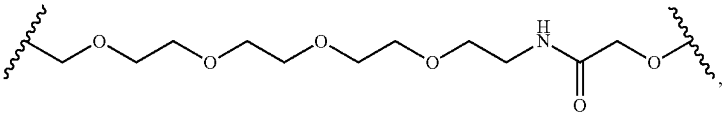 [SMILES: *COCCOCCOCCOCCNC(=O)CO*]
(103)
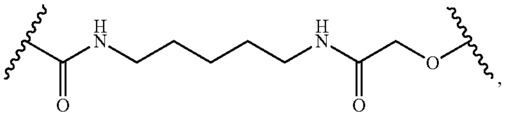 [SMILES: *OCC(=O)NCCCCCNC(*)=O]
(104)
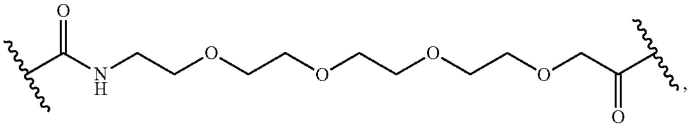 [SMILES: *C(=O)COCCOCCOCCOCCNC(*)=O]
(105)
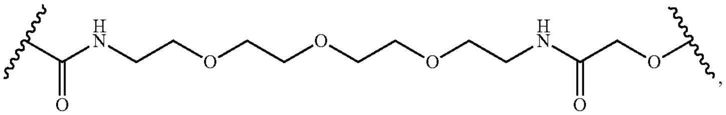 [SMILES: *OCC(=O)NCCOCCOCCOCCNC(*)=O]
(106)
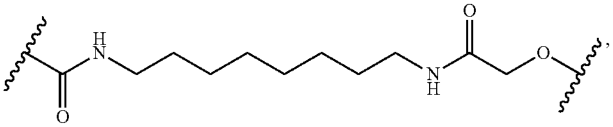 [SMILES: *OCC(=O)NCCCCCCCCNC(*)=O]
(107)
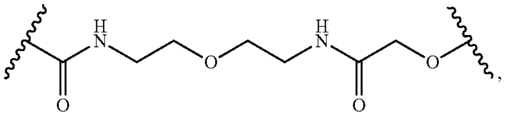 [SMILES: *OCC(=O)NCCOCCNC(*)=O]
(108)
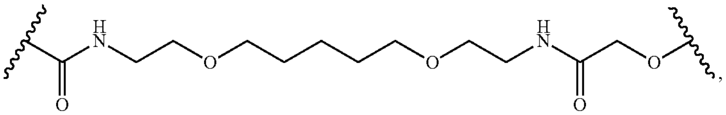
(109)

TABLE B-continued
Exemplified Linkers (L)
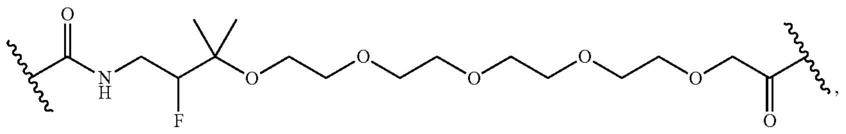 [SMILES: *C(=O)COCCOCCOCCOCCOC(C)(C)C(F)CNC(*)=O]
(110)
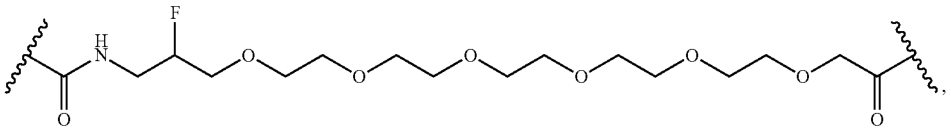 [SMILES: *C(=O)COCCOCCOCCOCCOCCOCC(F)CNC(*)=O]
(111)
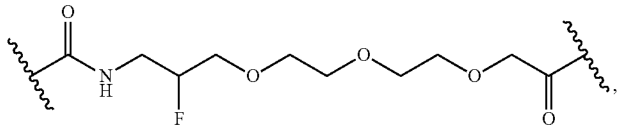 [SMILES: *C(=O)COCCOCCOCC(F)CNC(*)=O]
(112)
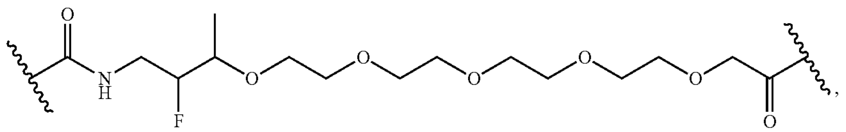 [SMILES: *C(=O)COCCOCCOCCOCCOC(C)C(F)CNC(*)=O]
(113)
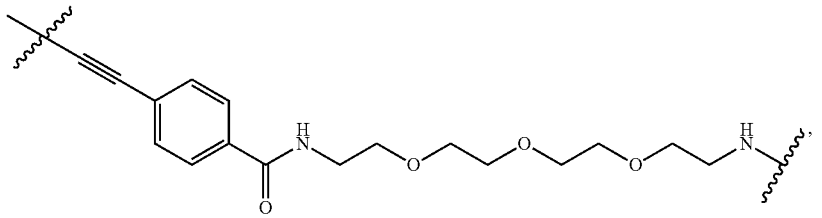 [SMILES: *C#Cc1ccc(C(=O)NCCOCCOCCOCCN*)cc1]
(114)
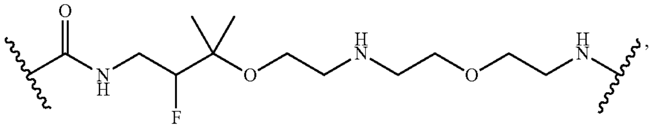 [SMILES: *NCCOCCNCCOC(C)(C)C(F)CNC(*)=O]
(115)
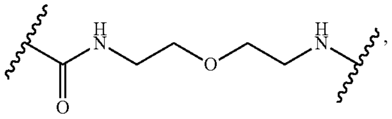 [SMILES: *NCCOCCNC(*)=O]
(116)
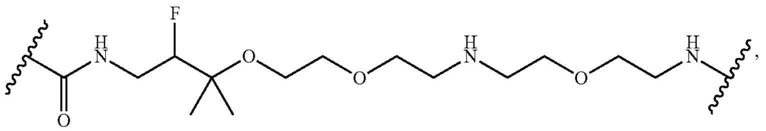 [SMILES: *NCCOCCNCCOCCOC(C)(C)C(F)CNC(*)=O]
(117)
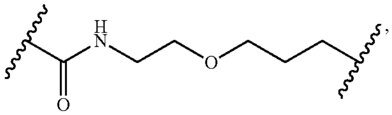 [SMILES: *CCCOCCNC(*)=O]
(118)
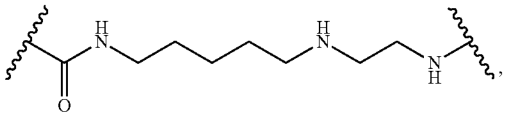 [SMILES: *NCCNCCCCCNC(*)=O]

TABLE B-continued
Exemplified Linkers (L)
(119)
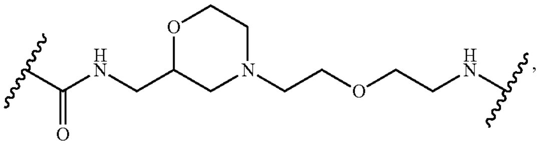 [SMILES: *NCCOCCN1CCOC(CNC(*)=O)C1]
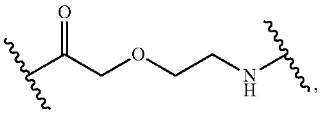 [SMILES: *NCCOCC(*)=O]
(120)
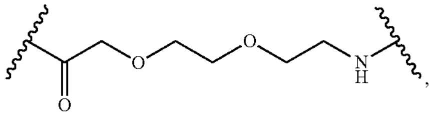 [SMILES: *NCCOCCOCC(*)=O]
(121)
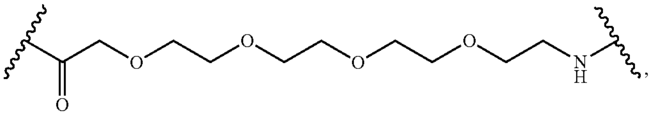 [SMILES: *NCCOCCOCCOCCOCC(*)=O]
(122)
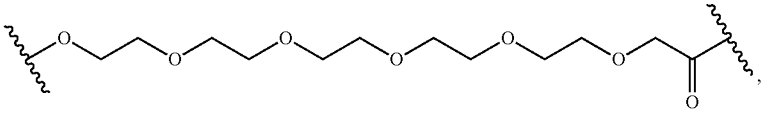 [SMILES: *OCCOCCOCCOCCOCCOCC(*)=O]
(123)
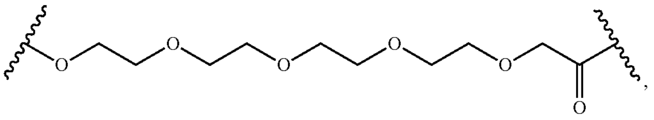 [SMILES: *OCCOCCOCCOCCOCC(*)=O]
(124)
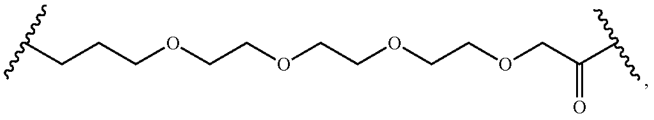 [SMILES: *CCCOCCOCCOCCOCC(*)=O]
(125)
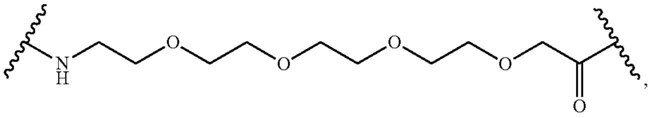 [SMILES: *NCCOCCOCCOCCOCC(*)=O]
(126)
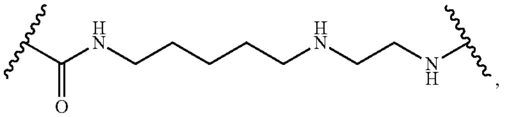 [SMILES: *NCCNCCCCCNC(*)=O]
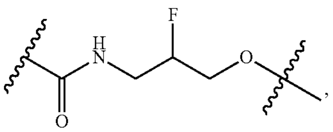 [SMILES: *OCC(F)CNC(*)=O]
(127)
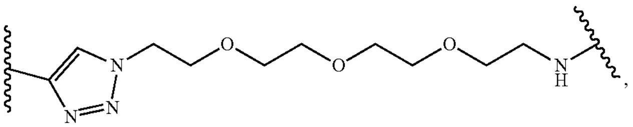 [SMILES: *NCCOCCOCCOCCn1cc(*)nn1]

TABLE B-continued
Exemplified Linkers (L)
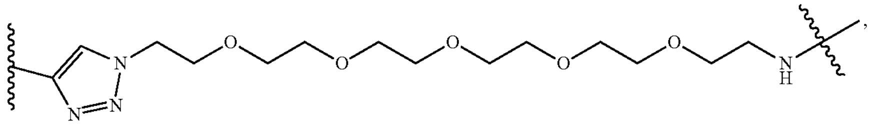 [SMILES: *NCCOCCOCCOCCOCCOCCn1cc(*)nn1]
(128)
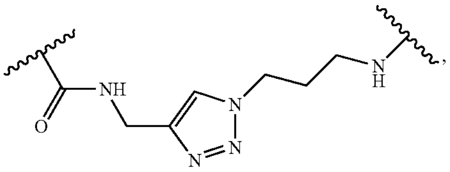 [SMILES: *NCCCn1cc(CNC(*)=O)nn1]
(129)
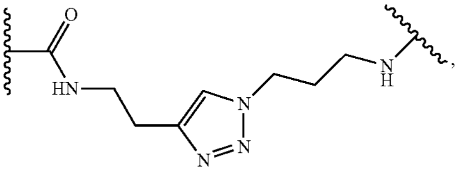 [SMILES: *NCCCn1cc(CCNC(*)=O)nn1]
(130)
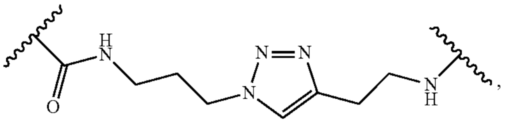 [SMILES: *NCCc1cn(CCCNC(*)=O)nn1]
(131)
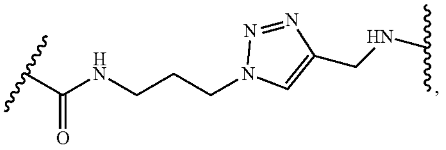 [SMILES: *NCc1cn(CCCNC(*)=O)nn1]
(132)
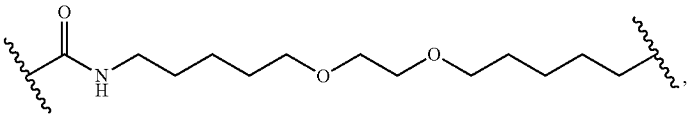 [SMILES: *CCCCCOCCOCCCCCNC(*)=O]
(133)
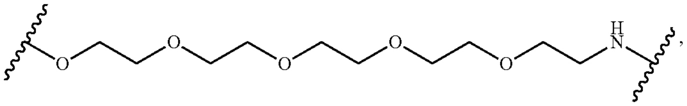 [SMILES: *NCCOCCOCCOCCOCCO*]
(134)
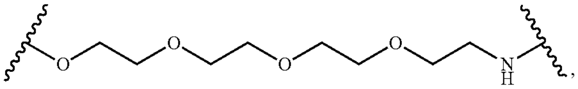 [SMILES: *NCCOCCOCCOCCO*]
(135)
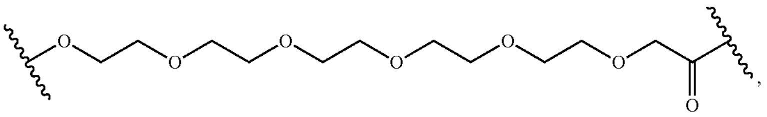 [SMILES: *OCCOCCOCCOCCOCCOCC(*)=O]
(136)
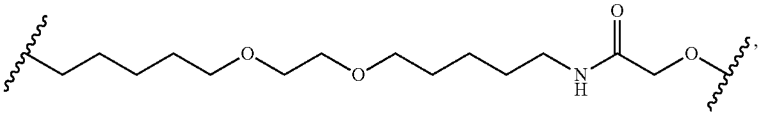 [SMILES: *CCCCCOCCOCCCCCNC(=O)CO*]
(137)
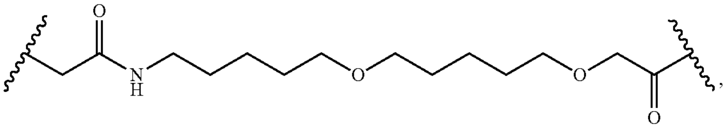 [SMILES: *CC(=O)NCCCCCOCCCCCOCC(*)=O]
(138)

TABLE B-continued
Exemplified Linkers (L)
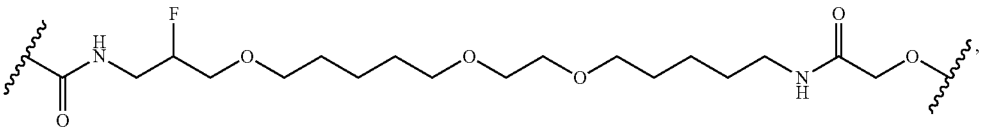 [SMILES: *OCC(=O)NCCCCCOCCOCCCCCOCC(F)CNC(*)=O]
(139)
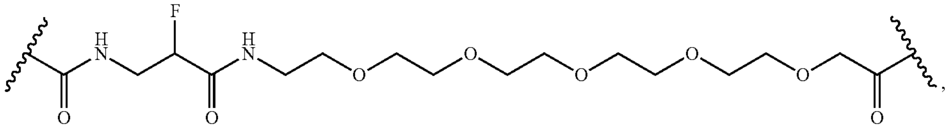 [SMILES: *C(=O)COCCOCCOCCOCCOCCNC(=O)C(F)CNC(*)=O]
(140)
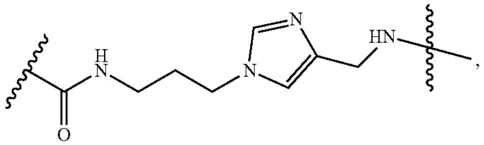 [SMILES: *NCc1cn(CCCNC(*)=O)cn1]
(141)
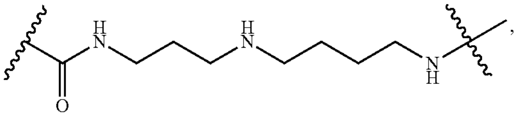 [SMILES: *NCCCCNCCCNC(*)=O]
(142)
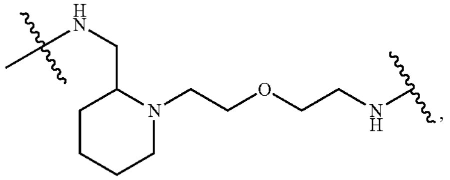 [SMILES: *NCCOCCN1CCCCC1CN*]
(143)
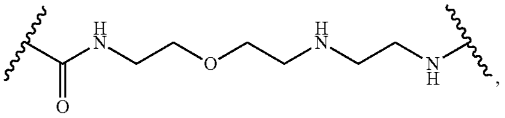 [SMILES: *NCCNCCOCCNC(*)=O]
(144)
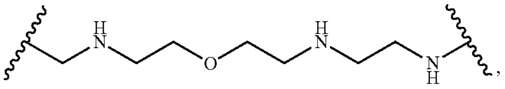 [SMILES: *CNCCOCCNCCN*]
(145)
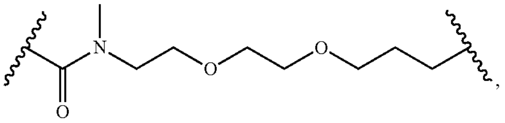 [SMILES: *CCCOCCOCCN(C)C(*)=O]
(146)
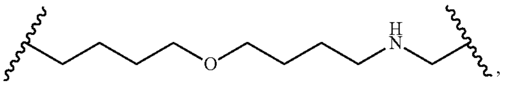 [SMILES: *CCCCOCCCCNC*]
(147)
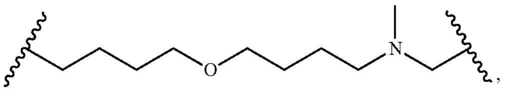 [SMILES: *CCCCOCCCCN(C)C*]
(148)
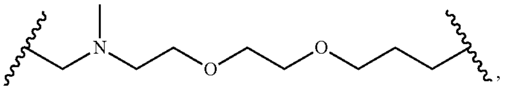 [SMILES: *CCCOCCOCCN(C)C*]
(149)
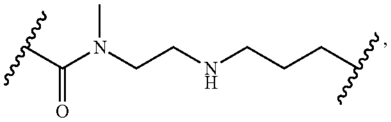 [SMILES: *CCCNCCN(C)C(*)=O]
(150)

TABLE B-continued
Exemplified Linkers (L)
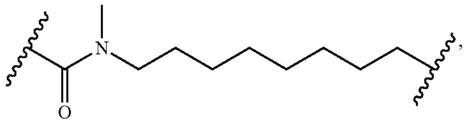 [SMILES: *CCCCCCCCN(C)C(*)=O]
(151)
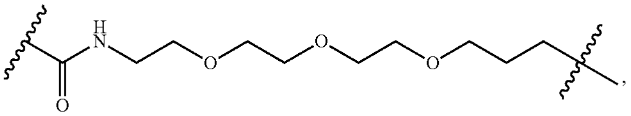 [SMILES: *CCCOCCOCCOCCNC(*)=O]
(152)
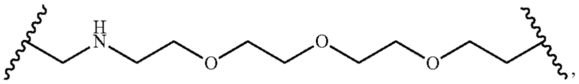 [SMILES: *CCOCCOCCOCCNC*]
(153)
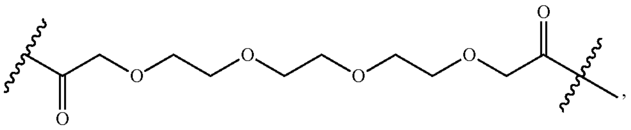 [SMILES: *C(=O)COCCOCCOCCOCC(*)=O]
(154)
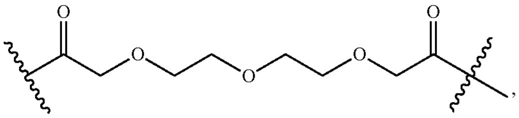 [SMILES: *C(=O)COCCOCCOCC(*)=O]
(155)
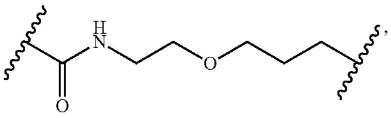 [SMILES: *CCCOCCNC(*)=O]
(156)
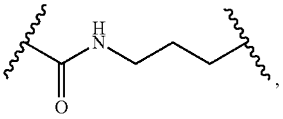 [SMILES: *CCCNC(*)=O]
(157)
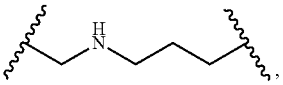 [SMILES: *CCCNC*]
(158)
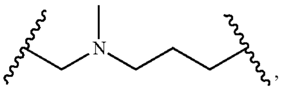 [SMILES: *CCCN(C)C*]
(159)
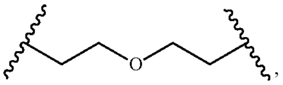 [SMILES: *CCOCC*]
(160)
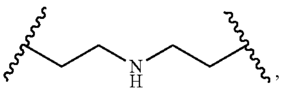 [SMILES: *CCNCC*]
(161)
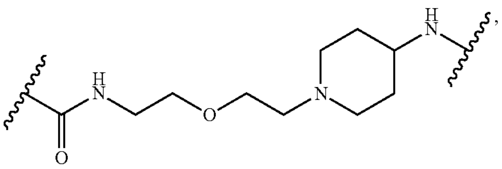 [SMILES: *NC1CCN(CCOCCNC(*)=O)CC1]
(162)

TABLE B-continued
Exemplified Linkers (L)
(163)
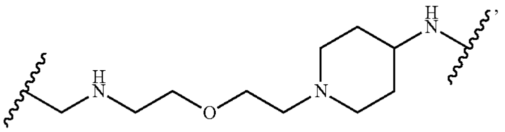 [SMILES: *CNCCOCCN1CCC(N*)CC1]
(164)
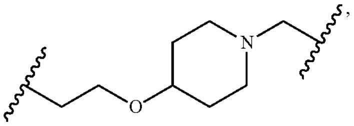 [SMILES: *CCOC1CCN(C*)CC1]
(165)
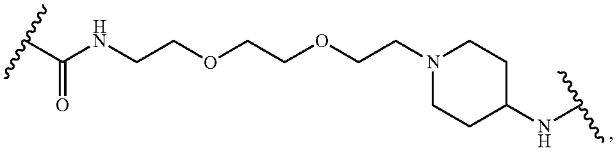 [SMILES: *NC1CCN(CCOCCOCCNC(*)=O)CC1]
(166)
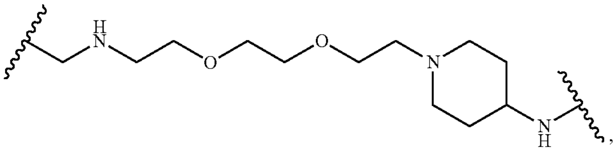 [SMILES: *CNCCOCCOCCN1CCC(N*)CC1]
(167)
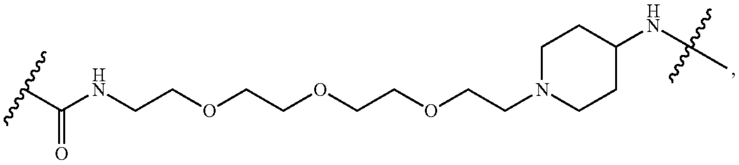 [SMILES: *NC1CCN(CCOCCOCCOCCNC(*)=O)CC1]
(168)
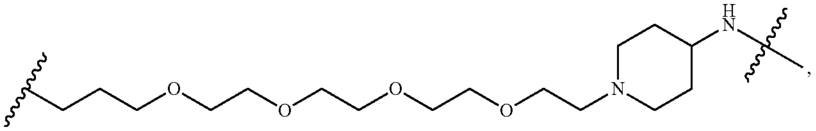 [SMILES: *CCCOCCOCCOCCOCCN1CCC(N*)CC1]
(169)
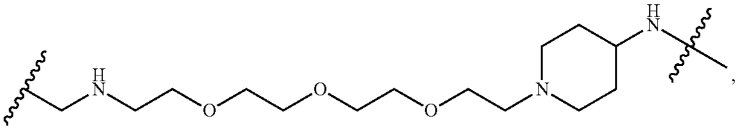 [SMILES: *CNCCOCCOCCOCCN1CCC(N*)CC1]
(170)
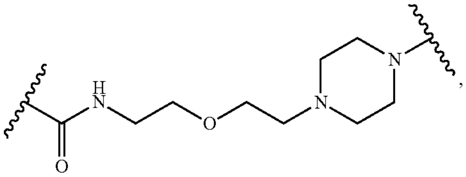 [SMILES: *C(=O)NCCOCCN1CCN(*)CC1]
(171)
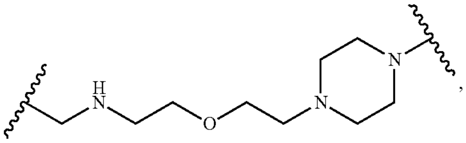 [SMILES: *CNCCOCCN1CCN(*)CC1]

TABLE B-continued
Exemplified Linkers (L)
(172)
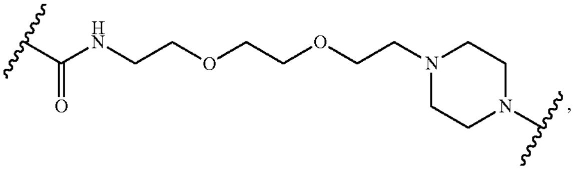 [SMILES: *C(=O)NCCOCCOCCN1CCN(*)CC1]
(173)
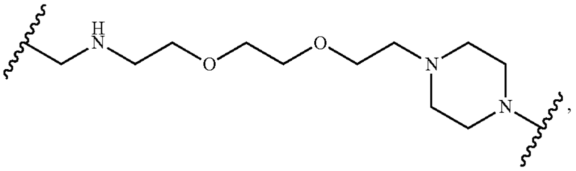 [SMILES: *CNCCOCCOCCN1CCN(*)CC1]
(174)
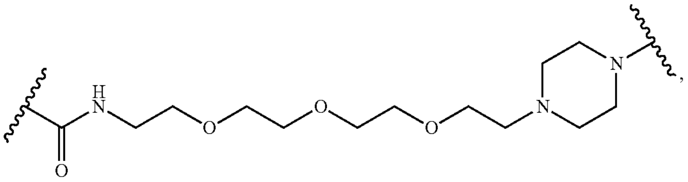 [SMILES: *C(=O)NCCOCCOCCOCCN1CCN(*)CC1]
(175)
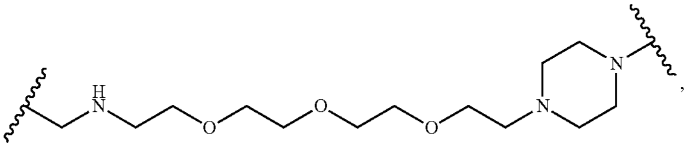 [SMILES: *CNCCOCCOCCOCCN1CCN(*)CC1]
(176)
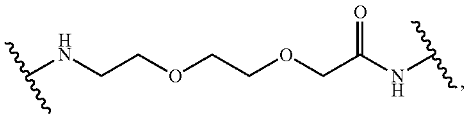 [SMILES: *NCCOCCOCC(=O)N*]
(177)
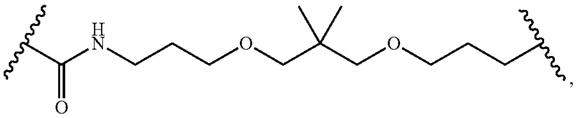 [SMILES: *CCCOCC(C)(C)COCCCNC(*)=O]
(178)
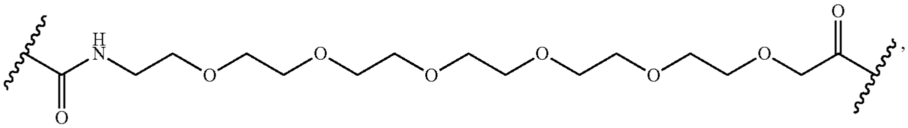 [SMILES: *C(=O)COCCOCCOCCOCCOCCOCCNC(*)=O]
(179)
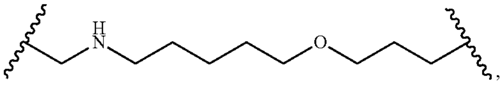 [SMILES: *CCCOCCCCCNC*]
(180)
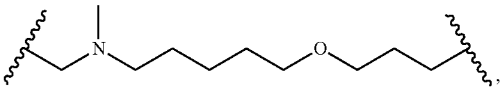 [SMILES: *CCCOCCCCCN(C)C*]
(181)
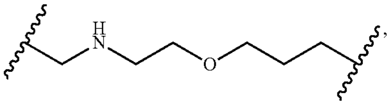 [SMILES: *CCCOCCNC*]
(182)
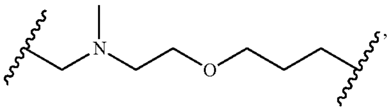 [SMILES: *CCCOCCN(C)C*]

TABLE B-continued
| Exemplified Linkers (L) | |
|---|---|
| 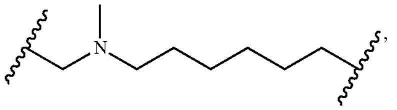 [SMILES: *CCCCCCN(C)C*] | (183) |
| 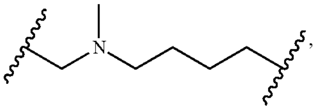 [SMILES: *CCCCN(C)C*] | (184) |
| 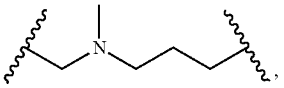 [SMILES: *CCCN(C)C*] | (185) |
| 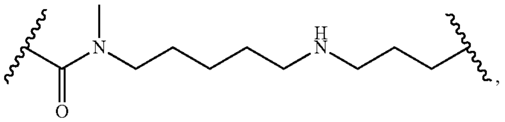 [SMILES: *CCCNCCCCCN(C)C(*)=O] | (186) |
| 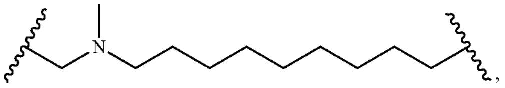 [SMILES: *CCCCCCCCCN(C)C*] | (187) |
| 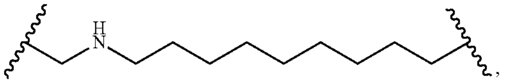 [SMILES: *CCCCCCCCCNC*] | (188) |
| 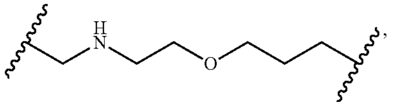 [SMILES: *CCCOCCNC*] | (189) |
| 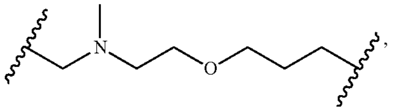 [SMILES: *CCCOCCN(C)C*] | (190) |
| 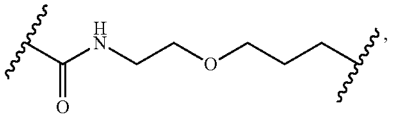 [SMILES: *CCCOCCNC(*)=O] | (191) |
| 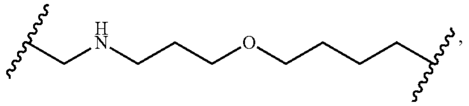 [SMILES: *CCCCOCCCNC*] | (192) |
| 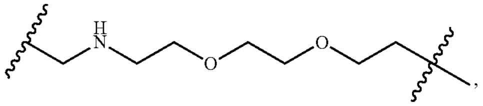 [SMILES: *CCOCCOCCNC*] | (193) |
| 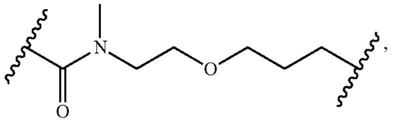 [SMILES: *CCCOCCN(C)C(*)=O] | (194) |
| 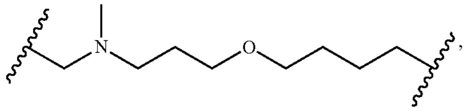 [SMILES: *CCCCOCCCN(C)C*] | (195) |

TABLE B-continued
Exemplified Linkers (L)
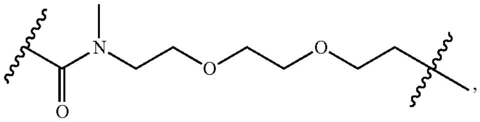 [SMILES: *CCOCCOCCN(C)C(*)=O]
(196)
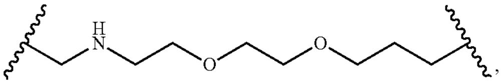 [SMILES: *CCCOCCOCCNC*]
(197)
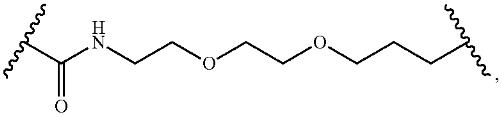 [SMILES: *CCCOCCOCCNC(*)=O]
(198)
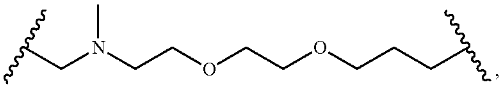 [SMILES: *CCCOCCOCCN(C)C*]
(199)
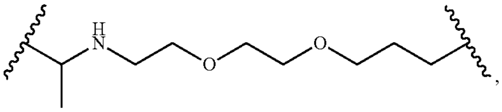 [SMILES: *CCCOCCOCCNC(*)C]
(200)
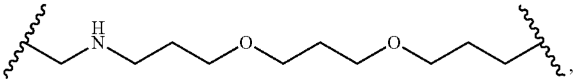 [SMILES: *CCCOCCCOCCCNC*]
(201)
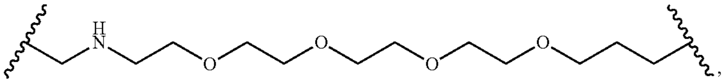 [SMILES: *CCCOCCOCCOCCOCCNC*]
(202)
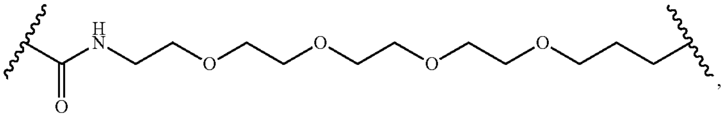 [SMILES: *CCCOCCOCCOCCOCCNC(*)=O]
(203)
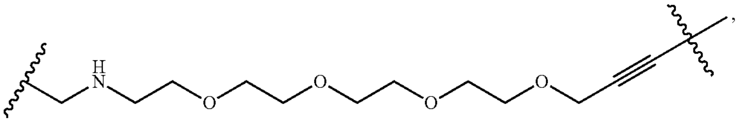 [SMILES: *C#CCOCCOCCOCCOCCNC*]
(204)
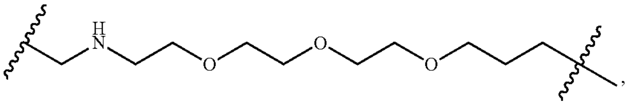 [SMILES: *CCCOCCOCCOCCNC*]
(205)
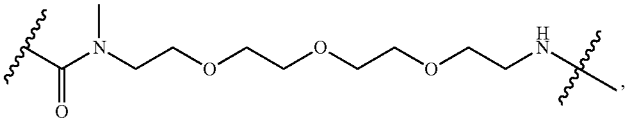 [SMILES: *NCCOCCOCCOCCN(C)C(*)=O]
(206)
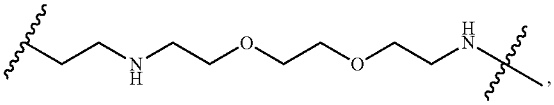 [SMILES: *CCNCCOCCOCCN*]
(207)
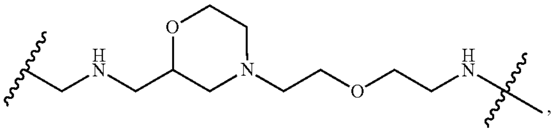 [SMILES: *CNCC1CN(CCOCCN*)CCO1]
(208)

TABLE B-continued
| Exemplified Linkers (L) | |
|---|---|
| 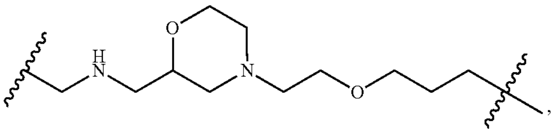 [SMILES: *CCCOCCN1CCOC(CNC*)C1] | (209) |
| 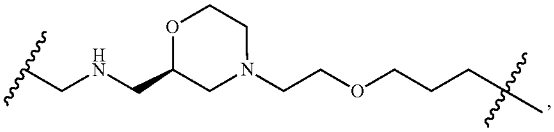 [SMILES: *CCCOCCN1CCO[C@H](CNC*)C1] | (210) |
| 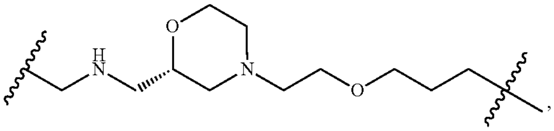 [SMILES: *CCCOCCN1CCO[C@@H](CNC*)C1] | (211) |
| 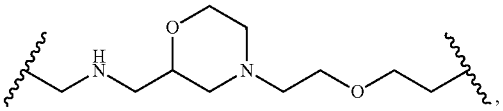 [SMILES: *CCOCCN1CCOC(CNC*)C1] | (212) |
| 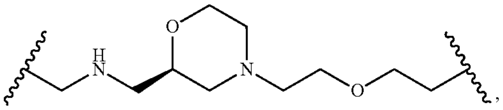 [SMILES: *CCOCCN1CCO[C@H](CNC*)C1] | (213) |
| 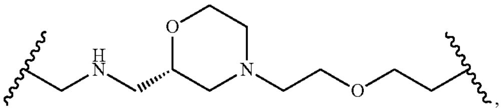 [SMILES: *CCOCCN1CCO[C@@H](CNC*)C1] | (214) |
| 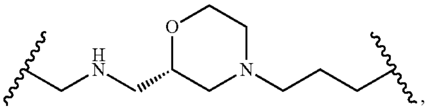 | (215) |
| 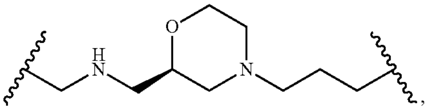 [SMILES: *CCCN1CCO[C@H](CNC*)C1] | (216) |
| 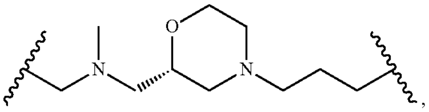 [SMILES: *CCCN1CCO[C@@H](CN(C)C*)C1] | (217) |
| 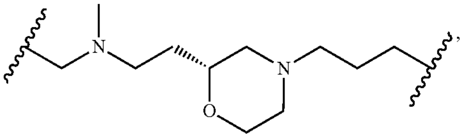 [SMILES: *CCCN1CCO[C@H](CCN(C)C*)C1] | (218) |
| 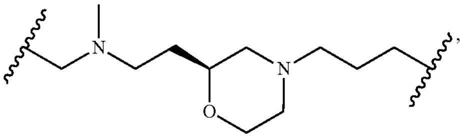 [SMILES: *CCCN1CCO[C@@H](CCN(C)C*)C1] | (219) |

TABLE B-continued
| Exemplified Linkers (L) |
| --- |
(220)
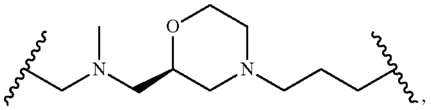
(221)
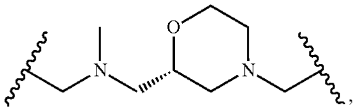 [SMILES: *CN(C)C[C@H]1CN(C*)CCO1]
(222)
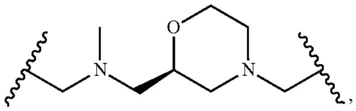 [SMILES: *CN(C)C[C@@H]1CN(C*)CCO1]
(223)
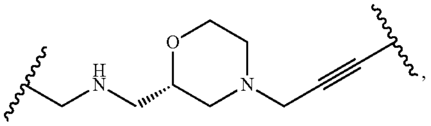 [SMILES: *C#CCN1CCO[C@@H](CNC*)C1]
(224)
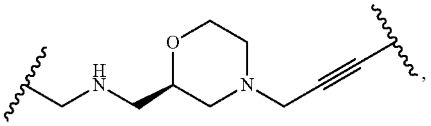 [SMILES: *C#CCN1CCO[C@H](CNC*)C1]
(225)
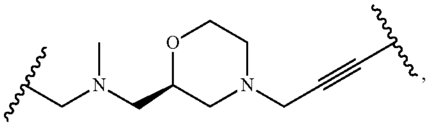 [SMILES: *C#CCN1CCO[C@H](CN(C)C*)C1]
(226)
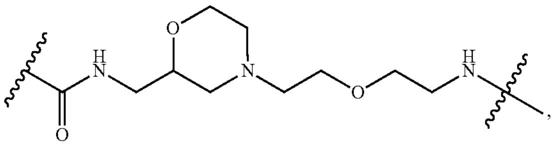 [SMILES: *NCCOCCN1CCOC(CNC(*)=O)C1]
(227)
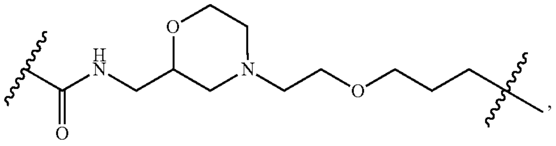 [SMILES: *CCCOCCN1CCOC(CNC(*)=O)C1]
(228)
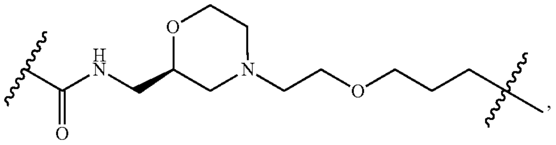 [SMILES: *CCCOCCN1CCO[C@H](CNC(*)=O)C1]
(229)
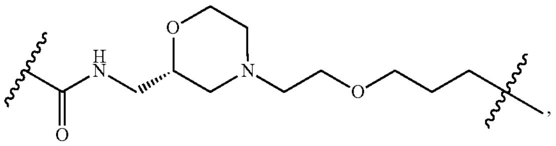 [SMILES: *CCCOCCN1CCO[C@@H](CNC(*)=O)C1]
(230)
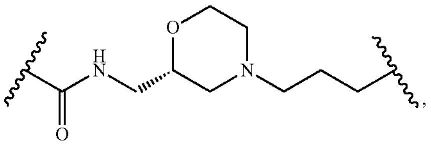 [SMILES: *CCCN1CCO[C@@H](CNC(*)=O)C1]

TABLE B-continued
Exemplified Linkers (L)
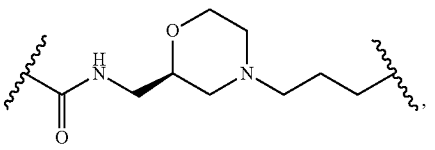 [SMILES: *CCCN1CCO[C@H](CNC(*)=O)C1]
(231)
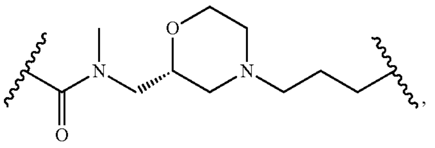 [SMILES: *CCCN1CCO[C@@H](CN(C)C(*)=O)C1]
(232)
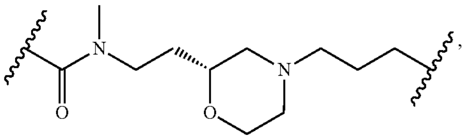 [SMILES: *CCCN1CCO[C@H](CCN(C)C(*)=O)C1]
(233)
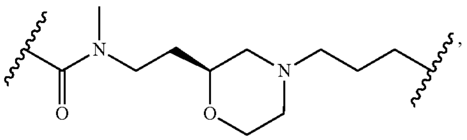 [SMILES: *CCCN1CCO[C@@H](CCN(C)C(*)=O)C1]
(234)
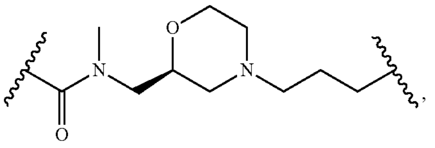 [SMILES: *CCCN1CCO[C@H](CN(C)C(*)=O)C1]
(235)
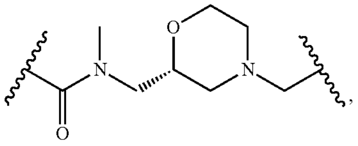 [SMILES: *CN1CCO[C@@H](CN(C)C(*)=O)C1]
(236)
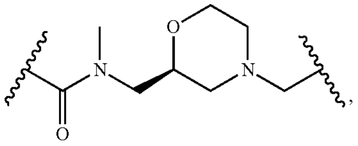 [SMILES: *CN1CCO[C@H](CN(C)C(*)=O)C1]
(237)
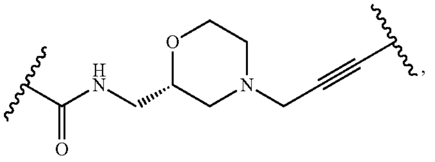 [SMILES: *C#CCN1CCO[C@@H](CNC(*)=O)C1]
(238)
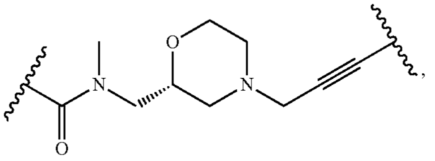 [SMILES: *C#CCN1CCO[C@@H](CN(C)C(*)=O)C1]
(239)

TABLE B-continued
Exemplified Linkers (L)
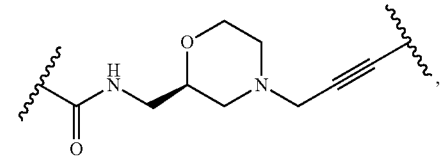 [SMILES: *C#CCN1CCO[C@H](CNC(*)=O)C1]
(240)
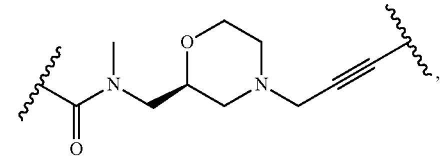 [SMILES: *C#CCN1CCO[C@H](CN(C)C(*)=O)C1]
(241)
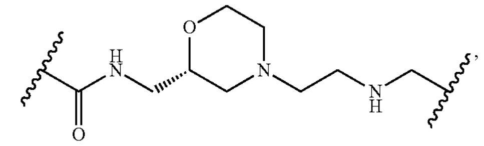 [SMILES: *CNCCN1CCO[C@@H](CNC(*)=O)C1]
(242)
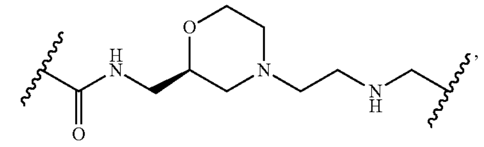 [SMILES: *CNCCN1CCO[C@H](CNC(*)=O)C1]
(243)
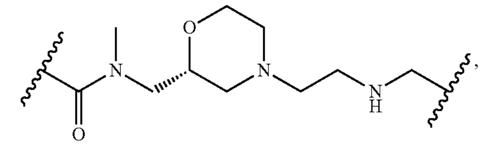 [SMILES: *CNCCN1CCO[C@@H](CN(C)C(*)=O)C1]
(244)
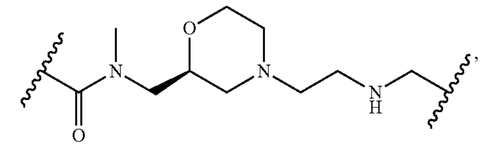 [SMILES: *CNCCN1CCO[C@H](CN(C)C(*)=O)C1]
(245)
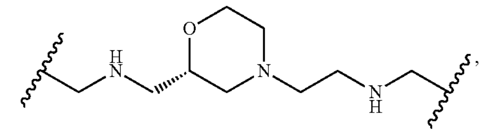 [SMILES: *CNCCN1CCO[C@@H](CNC*)C1]
(246)
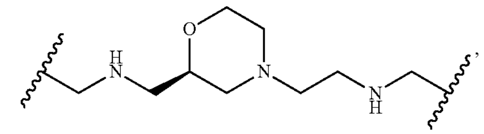 [SMILES: *CNCCN1CCO[C@H](CNC*)C1]
(247)
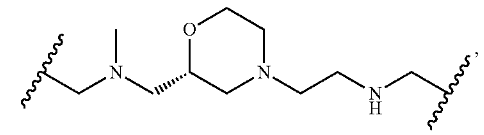 [SMILES: *CNCCN1CCO[C@@H](CN(C)C*)C1]
(248)
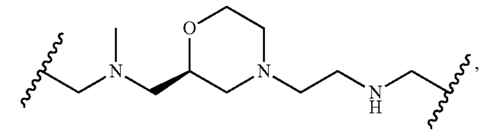 [SMILES: *CNCCN1CCO[C@H](CN(C)C*)C1]
(249)

TABLE B-continued
Exemplified Linkers (L)
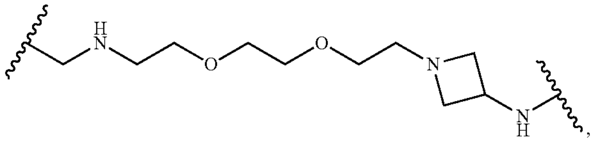 [SMILES: *CNCCOCCOCCN1CC(N*)C1]
(250)
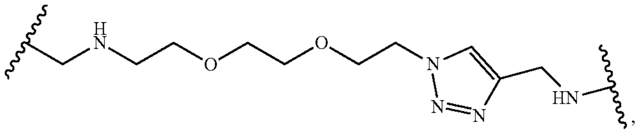 [SMILES: *CNCCOCCOCCn1cc(CN*)nn1]
(251)
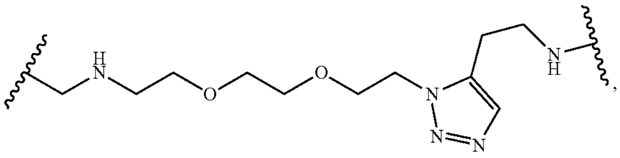 [SMILES: *CNCCOCCOCCn1nncc1CCN*]
(253)
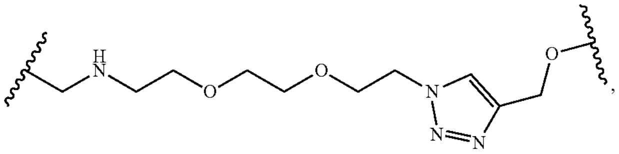 [SMILES: *CNCCOCCOCCn1cc(CO*)nn1]
(254)
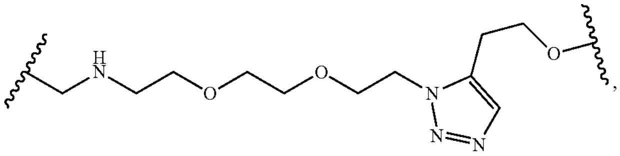 [SMILES: *CNCCOCCOCCn1nncc1CCO*]
(255)
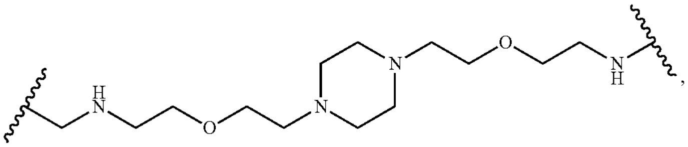 [SMILES: *CNCCOCCN1CCN(CCOCCN*)CC1]
(256)
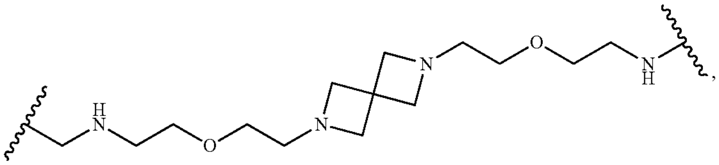 [SMILES: *CNCCOCCN1CC2(CN(CCOCCN*)C2)C1]
(257)
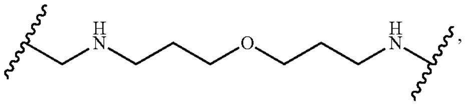 [SMILES: *CNCCCOCCCN*]
(258)
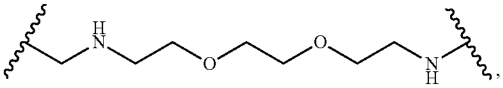 [SMILES: *CNCCOCCOCCN*]
(259)
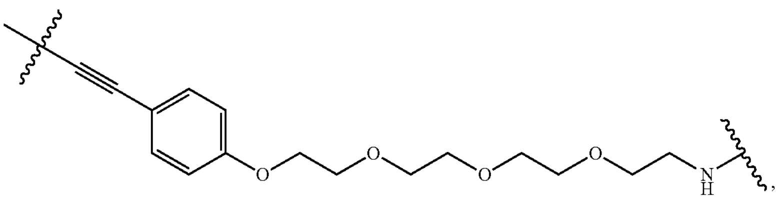 [SMILES: *C#Cc1ccc(OCCOCCOCCOCCN*)cc1]
(260)

TABLE B-continued
Exemplified Linkers (L)
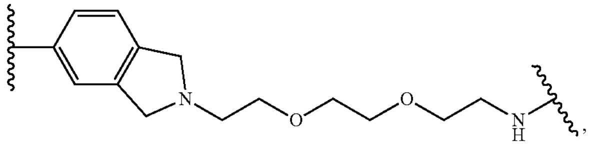 [SMILES: *NCCOCCOCCN1Cc2ccc(*)cc2C1]
(261)
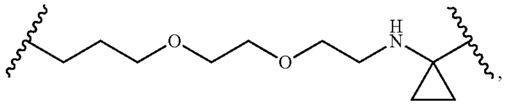 [SMILES: *CCCOCCOCCNC1(*)CC1]
(262)
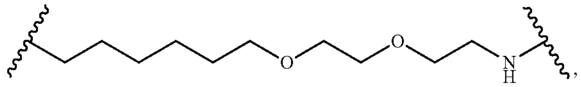 [SMILES: *CCCCCCOCCOCCN*]
(263)
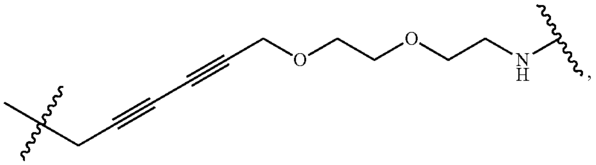 [SMILES: *CC#CC#CCOCCOCCN*]
(264)
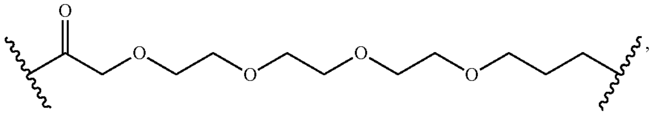 [SMILES: *CCCOCCOCCOCCOCC(*)=O]
(265)
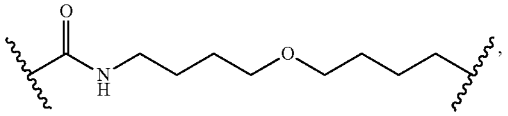 [SMILES: *CCCCOCCCCNC(*)=O]
(266)
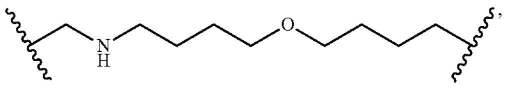 [SMILES: *CCCCOCCCCNC*]
(267)
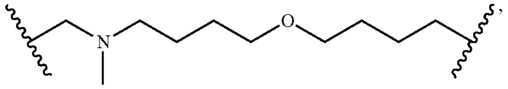 [SMILES: *CCCCOCCCCN(C)C*]
(268)
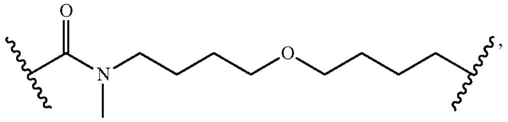 [SMILES: *CCCCOCCCCN(C)C(*)=O]
(269)
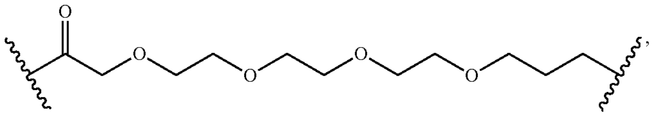 [SMILES: *CCCOCCOCCOCCOCC(*)=O]
(270)
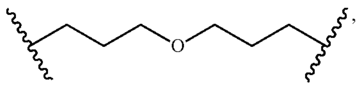
(271)
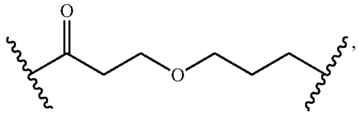 [SMILES: *CCCOCCC(*)=O]
(272)

TABLE B-continued
| Exemplified Linkers (L) |
|---|
| 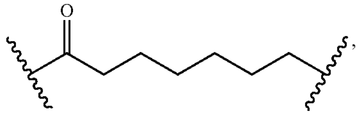 [SMILES: *CCCCCCC(*)=O] (273) |
| 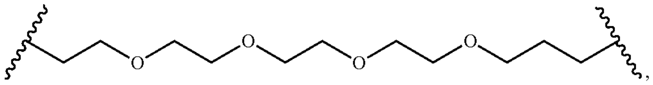 [SMILES: *CCCOCCOCCOCCOCC*] (274) |
| 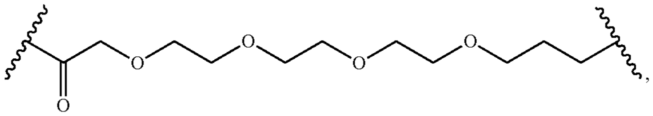 [SMILES: *CCCOCCOCCOCCOCC(*)=O] (275) |
| 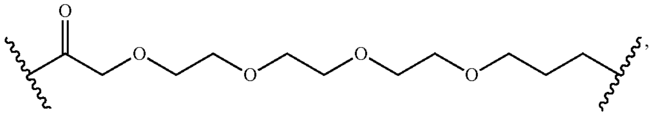 [SMILES: *CCCOCCOCCOCCOCC(*)=O] (276) |
| 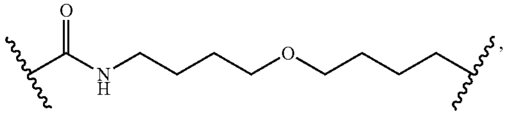 [SMILES: *CCCCOCCCCNC(*)=O] (277) |
| 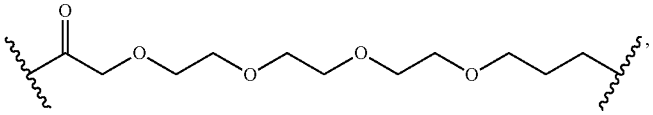 [SMILES: *CCCOCCOCCOCCOCC(*)=O] (278) |
| 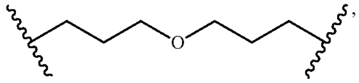 [SMILES: *CCCOCCC*] (279) |
| 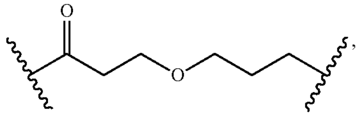 [SMILES: *CCCOCCC(*)=O] (280) |
| 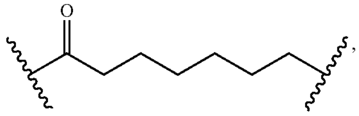 [SMILES: *CCCCCCC(*)=O] (281) |
| 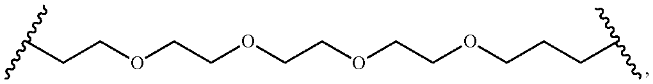 [SMILES: *CCCOCCOCCOCCOCC*] (282) |
| 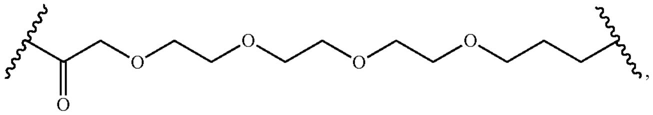 [SMILES: *CCCOCCOCCOCCOCC(*)=O] (283) |
| 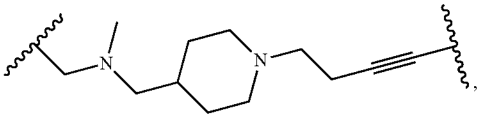 [SMILES: *C#CCCN1CCC(CN(C)C*)CC1] (284) |

TABLE B-continued
| Exemplified Linkers (L) |
|---|
| 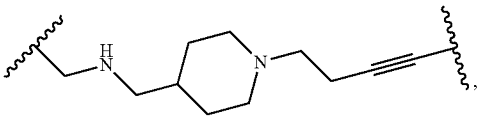 [SMILES: *C#CCCN1CCC(CNC*)CC1] (285) |
| 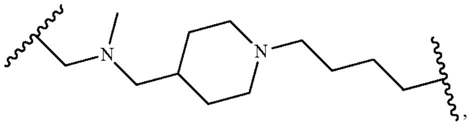 [SMILES: *CCCCN1CCC(CN(C)C*)CC1] (286) |
| 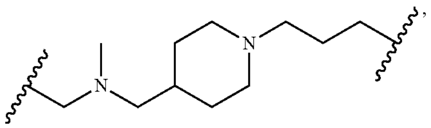 [SMILES: *CCCN1CCC(CN(C)C*)CC1] (287) |
| 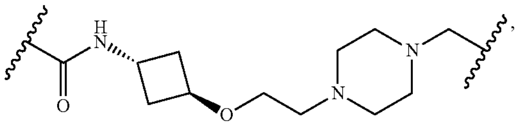 [SMILES: *CN1CCN(CCO[C@H]2C[C@H](NC(*)=O)C2)CC1] (288) |
| 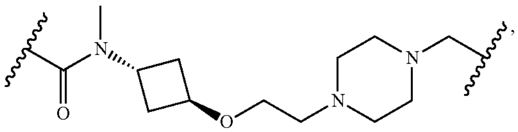 [SMILES: *CN1CCN(CCO[C@H]2C[C@H](N(C)C(*)=O)C2)CC1] (289) |
| 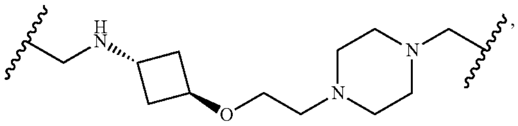 [SMILES: *CN[C@H]1C[C@H](OCCN2CCN(C*)CC2)C1] (290) |
| 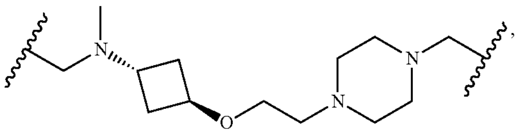 [SMILES: *CN1CCN(CCO[C@H]2C[C@H](N(C)C*)C2)CC1] (291) |
| 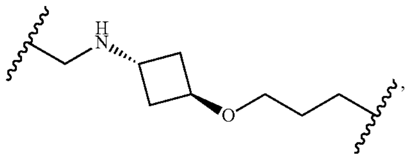 [SMILES: *CCCO[C@H]1C[C@H](NC*)C1] (292) |
| 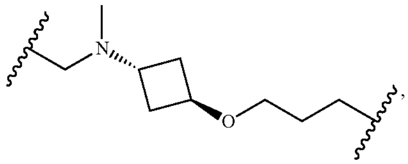 [SMILES: *CCCO[C@H]1C[C@H](N(C)C*)C1] (293) |
| 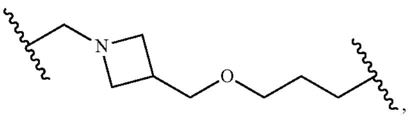 [SMILES: *CCCOCC1CN(C*)C1] (294) |

TABLE B-continued
| Exemplified Linkers (L) |
| --- |
| 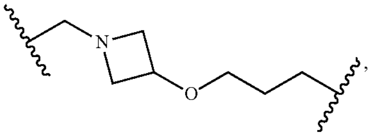 [SMILES: *CCCOC1CN(C*)C1] (295) |
| 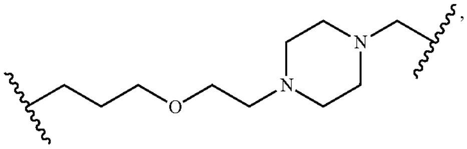 [SMILES: *CCCOCCN1CCN(C*)CC1] (296) |
| 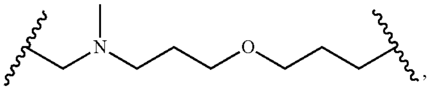 [SMILES: *CCCOCCCN(C)C*] (297) |
| 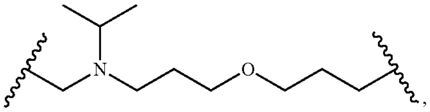 [SMILES: *CCCOCCCN(C*)C(C)C] (298) |
| 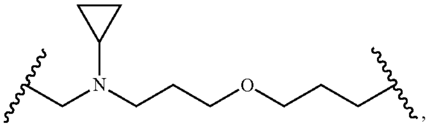 [SMILES: *CCCOCCCN(C*)C1CC1] (299) |
| 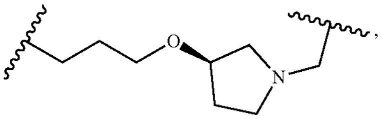 [SMILES: *CCCO[C@@H]1CCN(C*)C1] (300) |
| 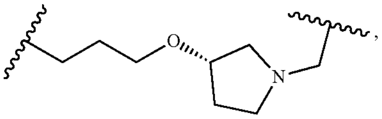 [SMILES: *CCCO[C@H]1CCN(C*)C1] (301) |
| 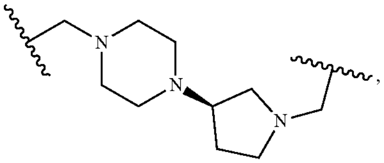 [SMILES: *CN1CCN([C@@H]2CCN(C*)C2)CC1] (302) |
| 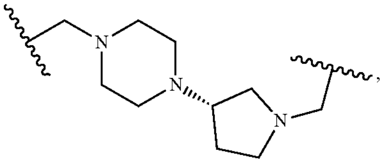 [SMILES: *CN1CCN([C@H]2CCN(C*)C2)CC1] (303) |
| 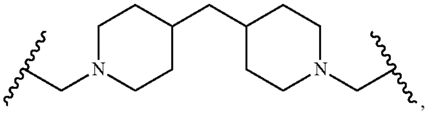 [SMILES: *CN1CCC(CC2CCN(C*)CC2)CC1] (304) |
| 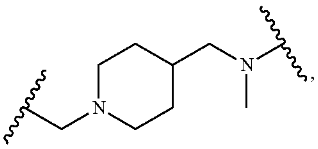 [SMILES: *CN1CCC(CN(*)C)CC1] (305) |

TABLE B-continued
Exemplified Linkers (L)
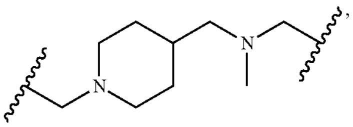 [SMILES: *CN(C)CC1CCN(C*)CC1]
(306)
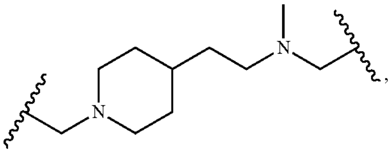 [SMILES: *CN(C)CCC1CCN(C*)CC1]
(307)
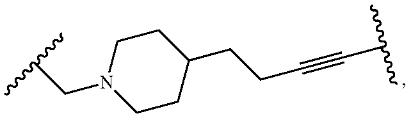 [SMILES: *C#CCCC1CCN(C*)CC1]
(308)
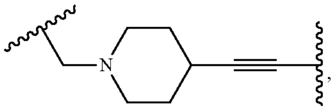 [SMILES: *C#CC1CCN(C*)CC1]
(309)
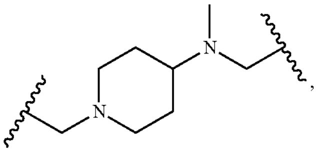 [SMILES: *CN1CCC(N(C)C*)CC1]
(310)
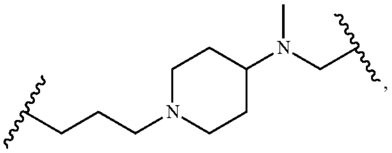 [SMILES: *CCCN1CCC(N(C)C*)CC1]
(311)
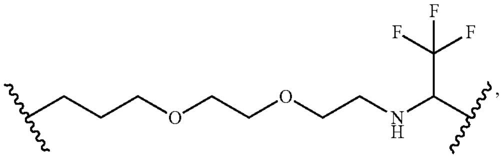 [SMILES: *CCCOCCOCCNC(*)C(F)(F)F]
(312)
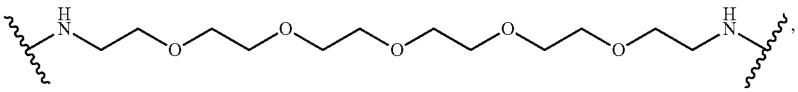 [SMILES: *NCCOCCOCCOCCOCCOCCN*]
(313)
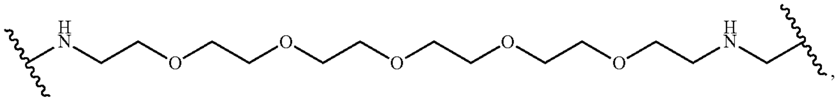 [SMILES: *CNCCOCCOCCOCCOCCOCCN*]
(314)
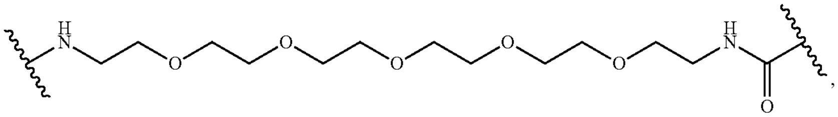 [SMILES: *NCCOCCOCCOCCOCCOCCNC(*)=O]
(315)
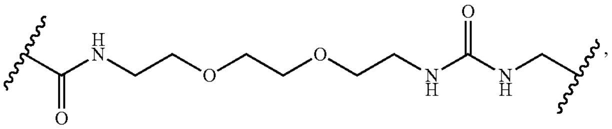 [SMILES: *CNC(=O)NCCOCCOCCNC(*)=O]
(316)

TABLE B-continued
| Exemplified Linkers (L) | |
|---|---|
| 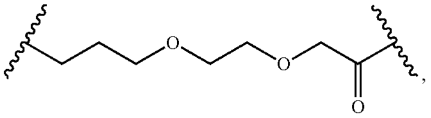 [SMILES: *CCCOCCOCC(*)=O] | (317) |
| 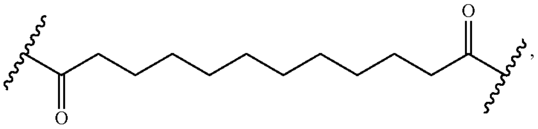 [SMILES: *C(=O)CCCCCCCCCCC(*)=O] | (318) |
| 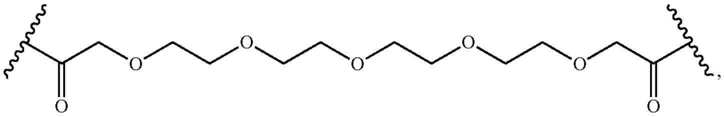 [SMILES: *C(=O)COCCOCCOCCOCCOCC(*)=O] | (319) |
| 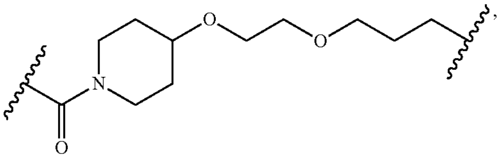 [SMILES: *CCCOCCOC1CCN(C(*)=O)CC1] | (320) |
| 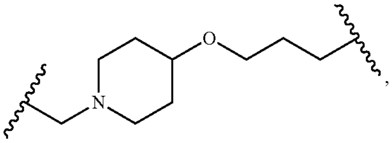 [SMILES: *CCCOC1CCN(C*)CC1] | (321) |
| 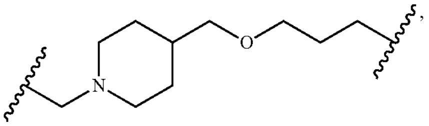 [SMILES: *CCCOCC1CCN(C*)CC1] | (322) |
| 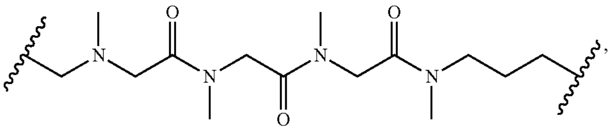 [SMILES: *CCCN(C)C(=O)CN(C)C(=O)CN(C)C(=O)CN(C)C*] | (323) |
| 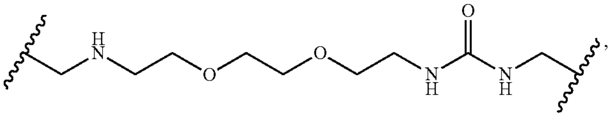 [SMILES: *CNCCOCCOCCNC(=O)NC*] | (324) |
| 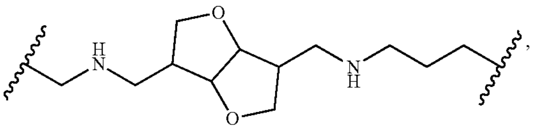 [SMILES: *CCCNCC1COC2C(CNC*)COC12] | (325) |
| 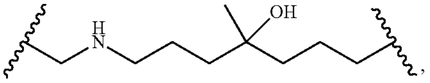 [SMILES: *CCCC(C)(O)CCCNC*] | (326) |
| 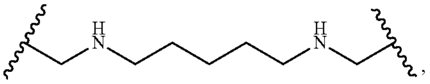 [SMILES: *CNCCCCCNC*] | (327) |
| 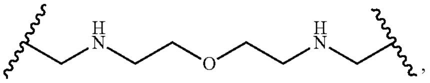 [SMILES: *CNCCOCCNC*] | (328) |

TABLE B-continued
Exemplified Linkers (L)
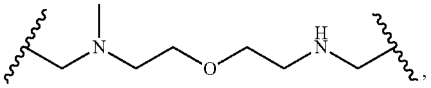 [SMILES: *CNCCOCCN(C)C*]
(329)
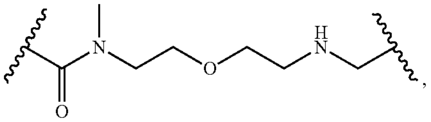 [SMILES: *CNCCOCCN(C)C(*)=O]
(330)
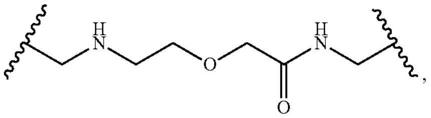 [SMILES: *CNCCOCC(=O)NC*]
(331)
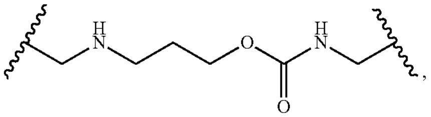 [SMILES: *CNCCCOC(=O)NC*]
(332)
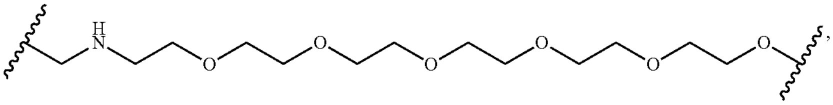 [SMILES: *CNCCOCCOCCOCCOCCOCCO*]
(333)
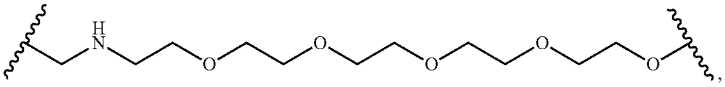 [SMILES: *CNCCOCCOCCOCCOCCO*]
(334)
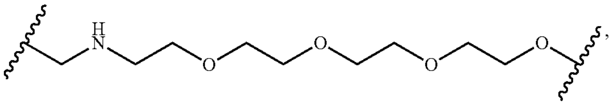 [SMILES: *CNCCOCCOCCOCCO*]
(335)
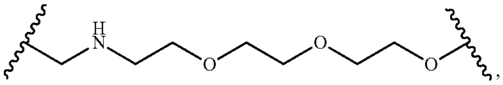 [SMILES: *CNCCOCCOCCO*]
(336)
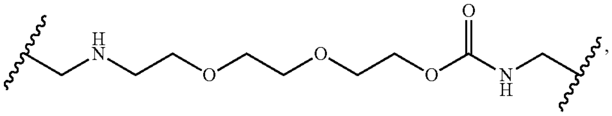 [SMILES: *CNCCOCCOCCOC(=O)NC*]
(337)
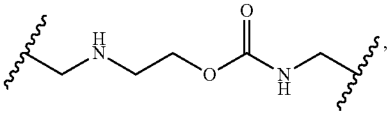 [SMILES: *CNCCOC(=O)NC*]
(338)
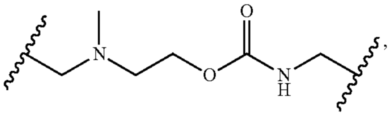 [SMILES: *CNC(=O)OCCN(C)C*]
(339)
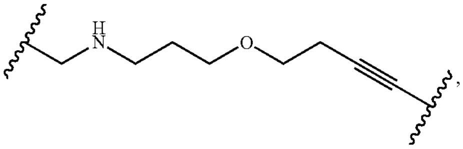 [SMILES: *C#CCCOCCCNC*]
(340)

TABLE B-continued
| Exemplified Linkers (L) |
|---|
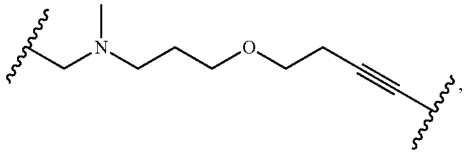 [SMILES: *C#CCCOCCCN(C)C*]
(341)
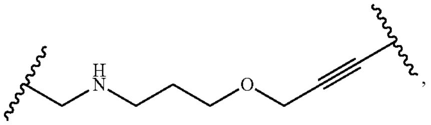 [SMILES: *C#CCOCCCNC*]
(342)
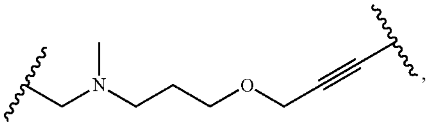 [SMILES: *C#CCOCCCN(C)C*]
(343)
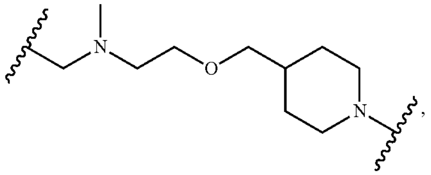 [SMILES: *CN(C)CCOCC1CCN(*)CC1]
(344)
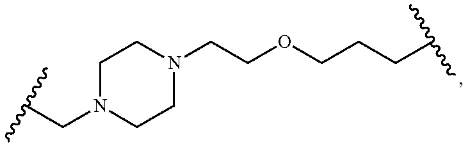 [SMILES: *CCCOCCN1CCN(C*)CC1]
(345)
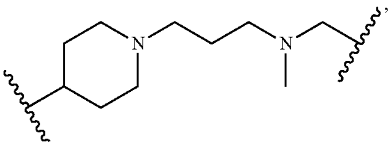 [SMILES: *CN(C)CCCN1CCC(*)CC1]
(346)
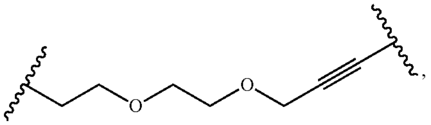 [SMILES: *C#CCOCCOCC*]
(347)
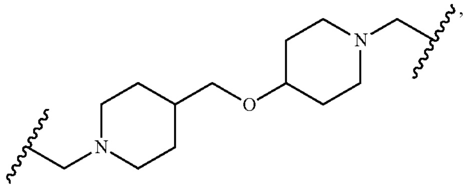 [SMILES: *CN1CCC(COC2CCN(C*)CC2)CC1]
(348)
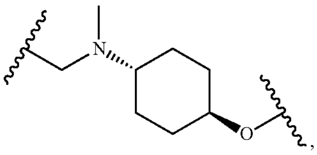 [SMILES: *CN(C)[C@H]1CC[C@H](O*)CC1]
(349)

TABLE B-continued
| Exemplified Linkers (L) |
|---|
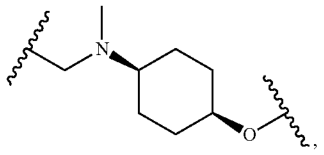 [SMILES: *CN(C)[C@H]1CC[C@@H](O*)CC1]
(350)
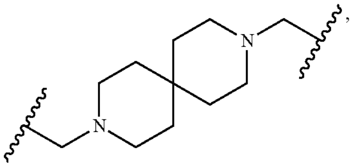 [SMILES: *CN1CCC2(CC1)CCN(C*)CC2]
(351)
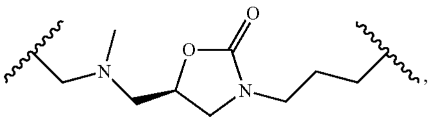 [SMILES: *CCCN1C[C@@H](CN(C)C*)OC1=O]
(352)
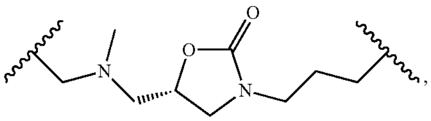 [SMILES: *CCCN1C[C@H](CN(C)C*)OC1=O]
(353)
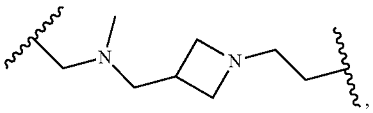 [SMILES: *CCN1CC(CN(C)C*)C1]
(354)
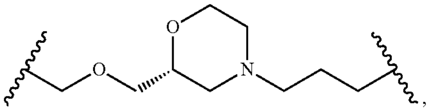
(355)
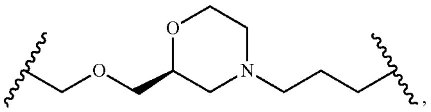 [SMILES: *CCCN1CCO[C@H](COC*)C1]
(356)
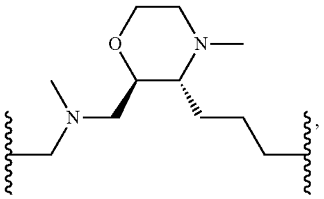 [SMILES: *CCC[C@@H]1[C@@H](CN(C)C*)OCCN1C]
(357)
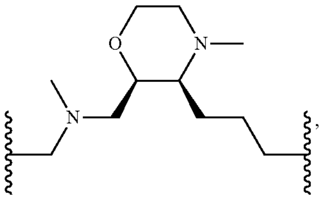 [SMILES: *CCC[C@H]1[C@@H](CN(C)C*)OCCN1C]
(358)

TABLE B-continued
Exemplified Linkers (L)
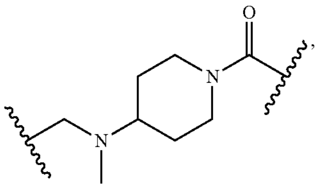 [SMILES: *CN(C)C1CCN(C(*)=O)CC1]
(359)
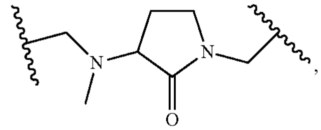 [SMILES: *CN1CCC(N(C)C*)C1=O]
(360)
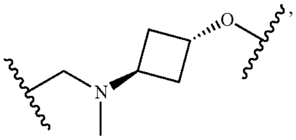 [SMILES: *CN(C)[C@H]1C[C@H](O*)C1]
(361)
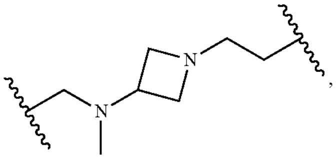 [SMILES: *CCN1CC(N(C)C*)C1]
(362)
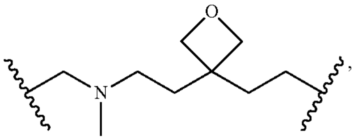 [SMILES: *CCC1(CCN(C)C*)COC1]
(363)
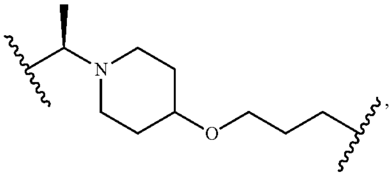 [SMILES: *CCCOC1CCN([C@@H](*)C)CC1]
(364)
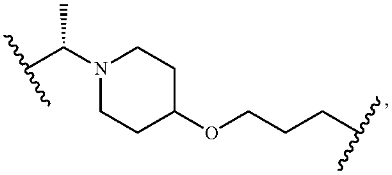 [SMILES: *CCCOC1CCN([C@H](*)C)CC1]
(365)
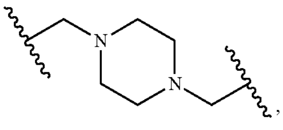 [SMILES: *CN1CCN(C*)CC1]
(366)
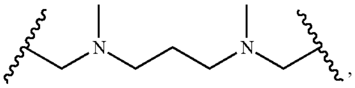 [SMILES: *CN(C)CCCN(C)C*]
(367)
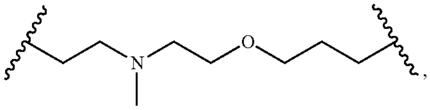 [SMILES: *CCCOCCN(C)CC*]
(368)

TABLE B-continued
| Exemplified Linkers (L) |
|---|
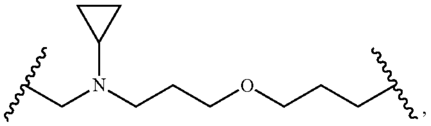 [SMILES: *CCCOCCCN(C*)C1CC1]
(369)
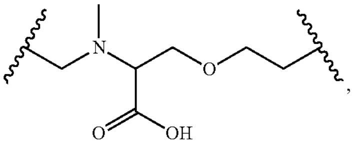 [SMILES: *CCOCC(C(=O)O)N(C)C*]
(370)
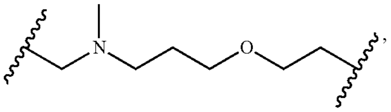 [SMILES: *CCOCCCN(C)C*]
(371)
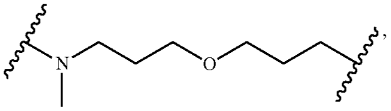 [SMILES: *CCCOCCCN(*)C]
(372)
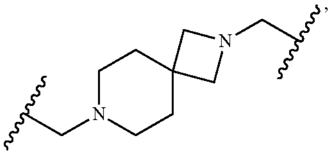 [SMILES: *CN1CCC2(CC1)CN(C*)C2]
(373)
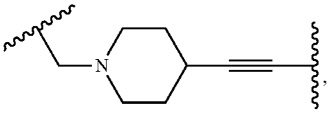 [SMILES: *C#CC1CCN(C*)CC1]
(374)
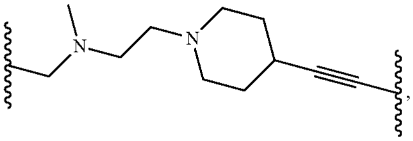 [SMILES: *C#CC1CCN(CCN(C)C*)CC1]
(375)
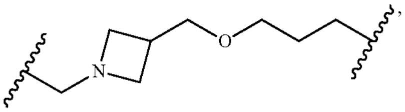 [SMILES: *CCCOCC1CN(C*)C1]
(376)
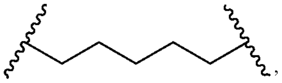 [SMILES: *CCCCC*]
(377)
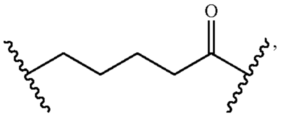 [SMILES: *CCCCC(*)=O]
(378)
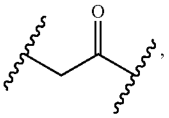 [SMILES: *CC(*)=O]
(379)

TABLE B-continued
Exemplified Linkers (L)
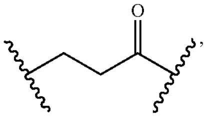 [SMILES: *CCC(*)=O]
(380)
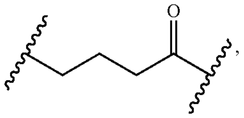 [SMILES: *CCCC(*)=O]
(381)
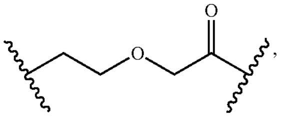 [SMILES: *CCOCC(*)=O]
(382)
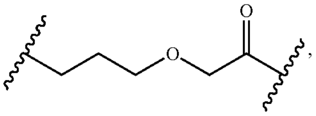 [SMILES: *CCCOCC(*)=O]
(383)
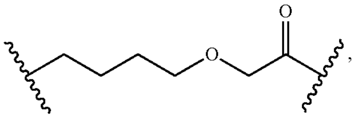 [SMILES: *CCCCOCC(*)=O]
(384)
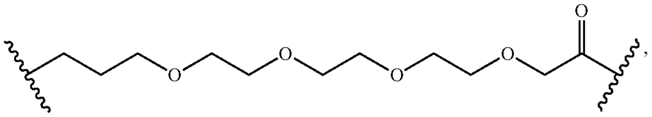 [SMILES: *CCCOCCOCCOCCOCC(*)=O]
(385)
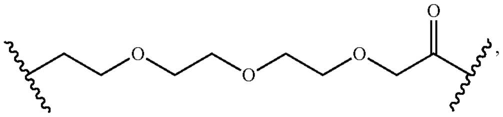 [SMILES: *CCOCCOCCOCC(*)=O]
(386)
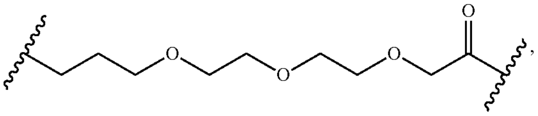 [SMILES: *CCCOCCOCCOCC(*)=O]
(387)
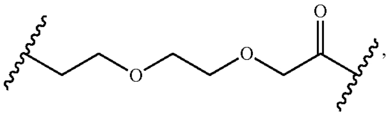 [SMILES: *CCOCCOCC(*)=O]
(388)
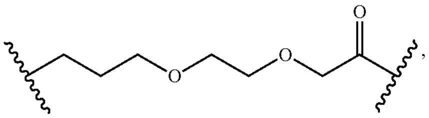 [SMILES: *CCCOCCOCC(*)=O]
(389)
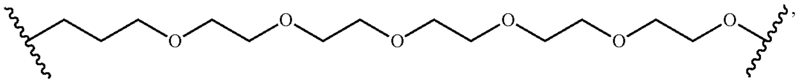 [SMILES: *CCCOCCOCCOCCOCCOCCO*]
(390)
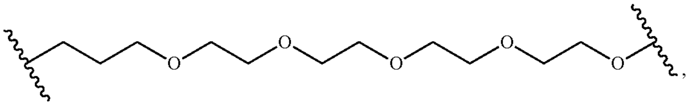 [SMILES: *CCCOCCOCCOCCOCCO*]
(391)

TABLE B-continued
Exemplified Linkers (L)
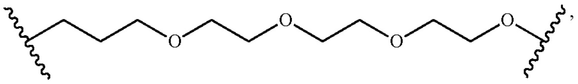 [SMILES: *CCCOCCOCCOCCO*]
(392)
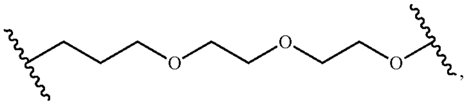 [SMILES: *CCCOCCOCCO*]
(393)
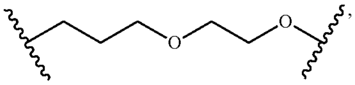 [SMILES: *CCCOCCO*]
(394)
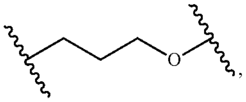 [SMILES: *CCCO*]
(395)
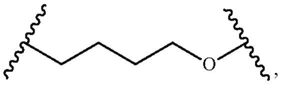 [SMILES: *CCCCO*]
(396)
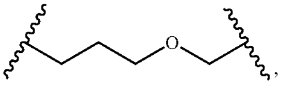 [SMILES: *CCCOC*]
(397)
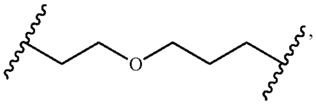 [SMILES: *CCCOCC*]
(398)
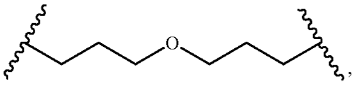 [SMILES: *CCCOCCC*]
(399)
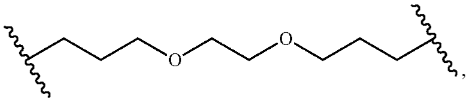 [SMILES: *CCCOCCOCCC*]
(400)
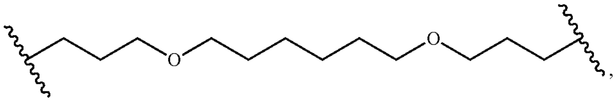 [SMILES: *CCCOCCCCCCOCCC*]
(401)
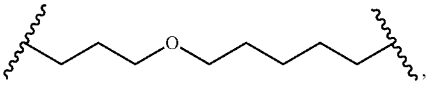 [SMILES: *CCCCCOCCC*]
(402)
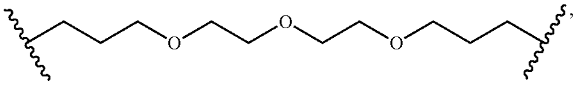 [SMILES: *CCCOCCOCCOCCC*]
(403)
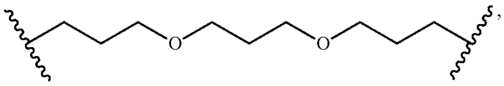 [SMILES: *CCCOCCCOCCC*]
(404)
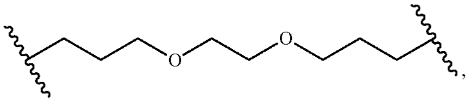 [SMILES: *CCCOCCOCCC*]
(405)

TABLE B-continued
Exemplified Linkers (L)
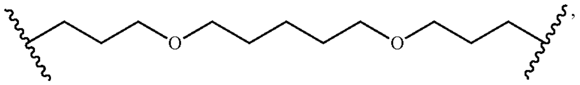 [SMILES: *CCCOCCCCCOCCC*]
(406)
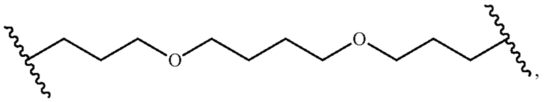 [SMILES: *CCCOCCCCOCCC*]
(407)
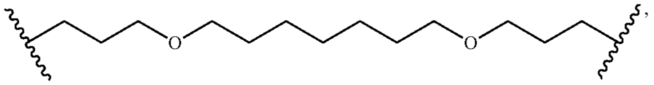 [SMILES: *CCCOCCCCCCCOCCC*]
(408)
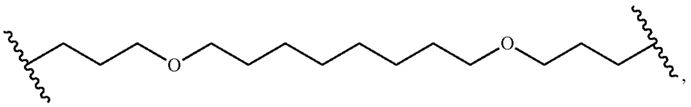 [SMILES: *CCCOCCCCCCCCOCCC*]
(409)
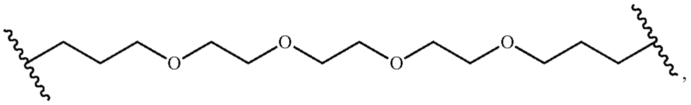 [SMILES: *CCCOCCOCCOCCOCCC*]
(410)
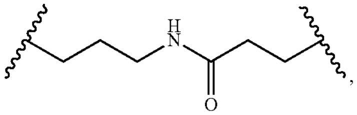 [SMILES: *CCCNC(=O)CC*]
(411)
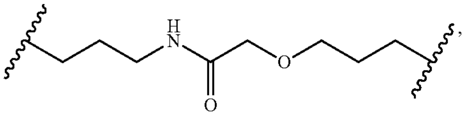 [SMILES: *CCCNC(=O)COCCC*]
(412)
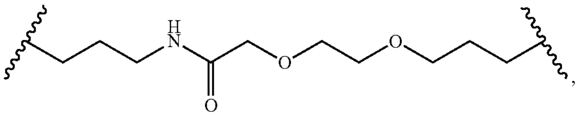 [SMILES: *CCCNC(=O)COCCOCCC*]
(413)
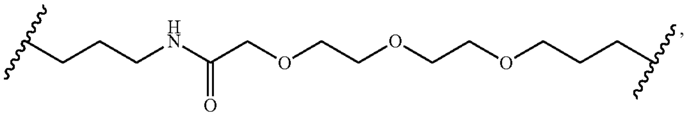 [SMILES: *CCCNC(=O)COCCOCCOCCC*]
(414)
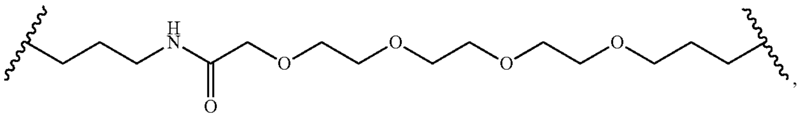 [SMILES: *CCCNC(=O)COCCOCCOCCOCCC*]
(415)
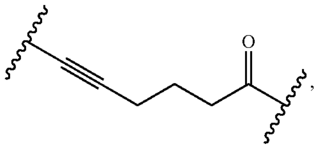 [SMILES: *C#CCCCC(*)=O]
(416)
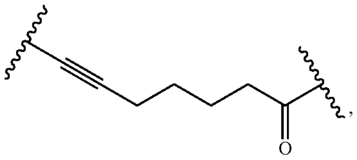 [SMILES: *C#CCCCCC(*)=O]
(417)

TABLE B-continued
| Exemplified Linkers (L) |
| --- |
| 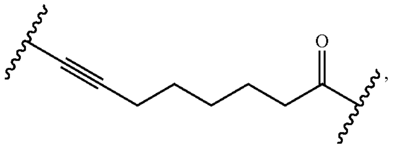 [SMILES: *C#CCCCCCC(*)=O] (418) |
| 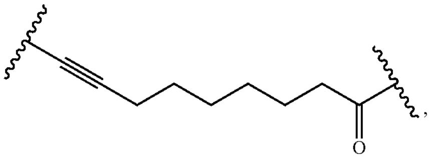 [SMILES: *C#CCCCCCCC(*)=O] (419) |
| 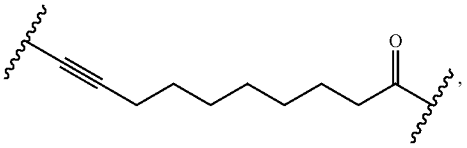 [SMILES: *C#CCCCCCCCC(*)=O] (420) |
| 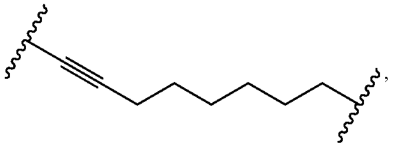 [SMILES: *C#CCCCCCC*] (421) |
| 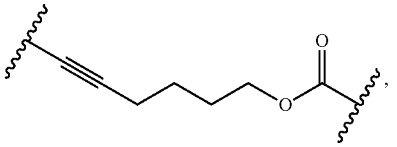 [SMILES: *C#CCCCCOC(*)=O] (422) |
| 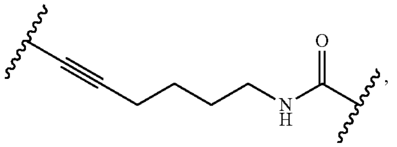 [SMILES: *C#CCCCCNC(*)=O] (423) |
| 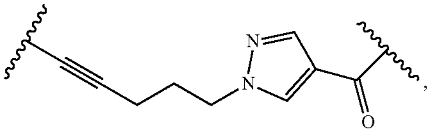 [SMILES: *C#CCCCn1cc(C(*)=O)cn1] (424) |
| 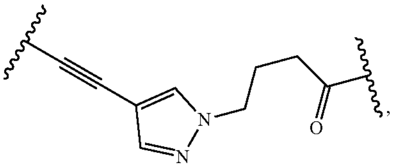 [SMILES: *C#Cc1cnn(CCCC(*)=O)c1] (425) |
| 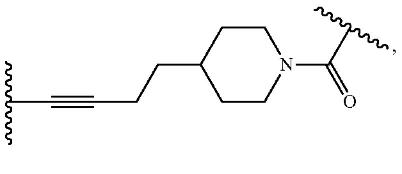 [SMILES: *C#CCCC1CCN(C(*)=O)CC1] (426) |

TABLE B-continued
Exemplified Linkers (L)
(427)
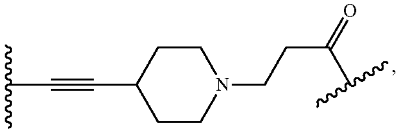 [SMILES: *C#CC1CCN(CCC(*)=O)CC1]
(428)
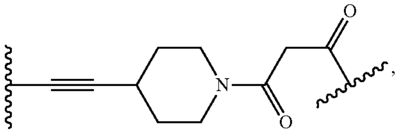 [SMILES: *C#CC1CCN(C(=O)CC(*)=O)CC1]
(429)
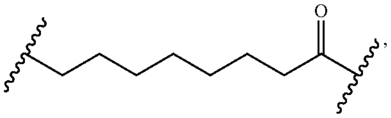 [SMILES: *CCCCCCCC(*)=O]
(430)
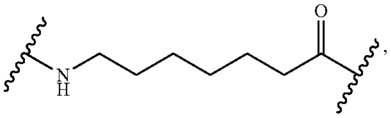 [SMILES: *NCCCCCCC(*)=O]
(431)
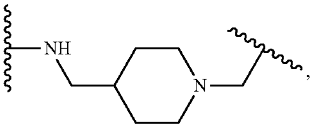 [SMILES: *CN1CCC(CN*)CC1]
(432)
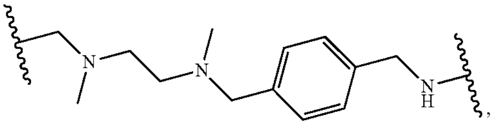 [SMILES: *CN(C)CCN(C)Cc1ccc(CN*)cc1]
(433)
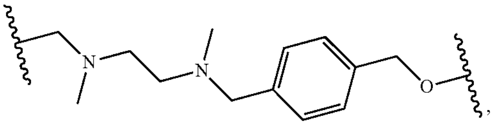 [SMILES: *CN(C)CCN(C)Cc1ccc(CO*)cc1]
(434)
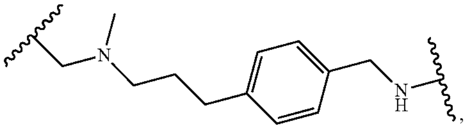 [SMILES: *CN(C)CCCc1ccc(CN*)cc1]
(435)
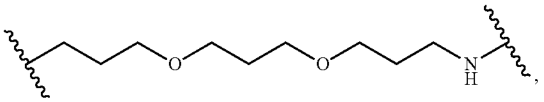 [SMILES: *CCCOCCCOCCCN*]
(436)
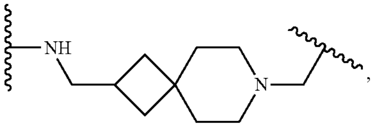 [SMILES: *CN1CCC2(CC1)CC(CN*)C2]
(437)
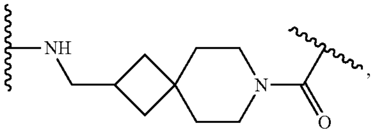 [SMILES: *NCC1CC2(CCN(C(*)=O)CC2)C1]

TABLE B-continued
Exemplified Linkers (L)
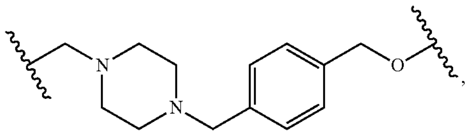 [SMILES: *CN1CCN(Cc2ccc(CO*)cc2)CC1]
(438)
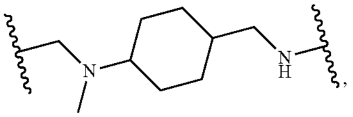 [SMILES: *CN(C)C1CCC(CN*)CC1]
(438)
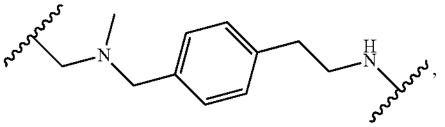 [SMILES: *CN(C)Cc1ccc(CCN*)cc1]
(439)
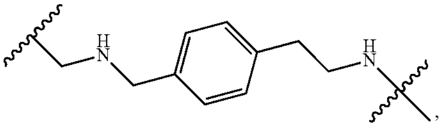 [SMILES: *CNCc1ccc(CCN*)cc1]
(440)
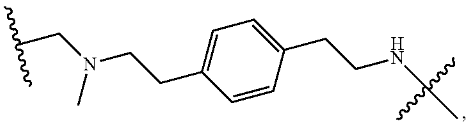 [SMILES: *CN(C)CCc1ccc(CCN*)cc1]
(441)
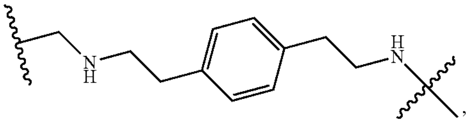 [SMILES: *CNCCc1ccc(CCN*)cc1]
(442)
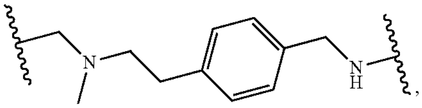 [SMILES: *CN(C)CCc1ccc(CN*)cc1]
(443)
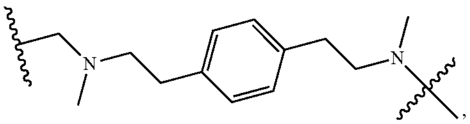 [SMILES: *CN(C)CCc1ccc(CCN(*)C)cc1]
(444)
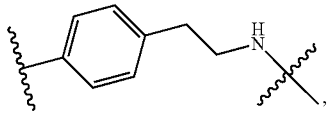 [SMILES: *NCCc1ccc(*)cc1]
(445)
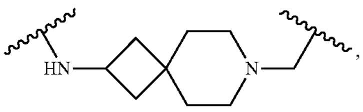 [SMILES: *CN1CCC2(CC1)CC(N*)C2]
(446)
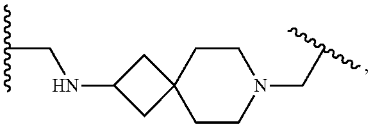 [SMILES: *CNC1CC2(CCN(C*)CC2)C1]
(447)

TABLE B-continued
Exemplified Linkers (L)
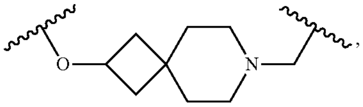 [SMILES: *CN1CCC2(CC1)CC(O*)C2]
(448)
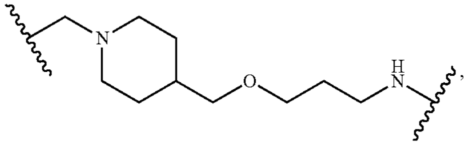 [SMILES: *CN1CCC(COCCCN*)CC1]
(449)
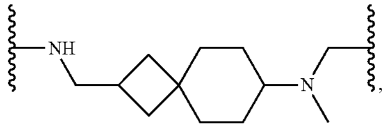 [SMILES: *CN(C)C1CCC2(CC1)CC(CN*)C2]
(450)
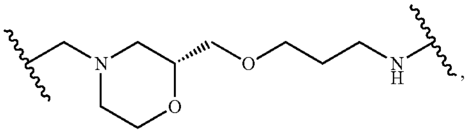
(451)
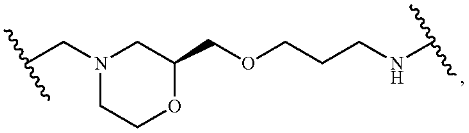
(452)
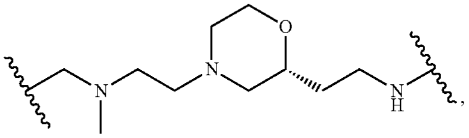 [SMILES: *CN(C)CCN1CCO[C@H](CCN*)C1]
(453)
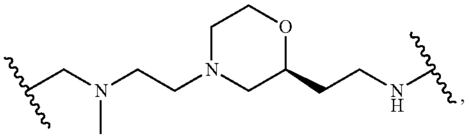 [SMILES: *CN(C)CCN1CCO[C@@H](CCN*)C1]
(454)
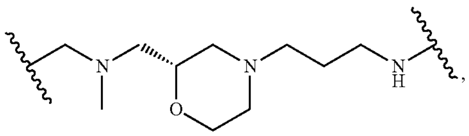 [SMILES: *CN(C)C[C@@H]1CN(CCCN*)CCO1]
(455)
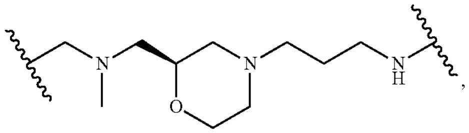 [SMILES: *CN(C)C[C@H]1CN(CCCN*)CCO1]
(456)
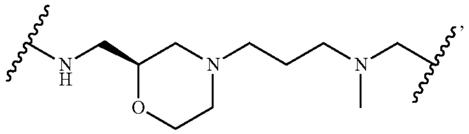 [SMILES: *CN(C)CCCN1CCO[C@@H](CN*)C1]
(457)
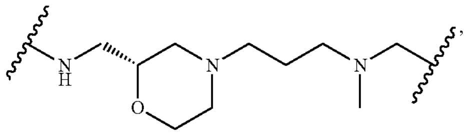 [SMILES: *CN(C)CCCN1CCO[C@H](CN*)C1]
(458)

TABLE B-continued
Exemplified Linkers (L)
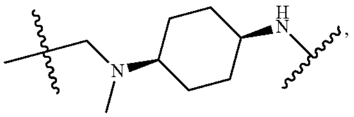 [SMILES: *CN(C)[C@H]1CC[C@@H](N*)CC1]
(459)
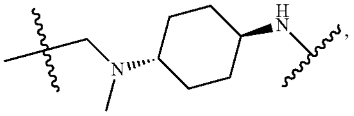 [SMILES: *CN(C)[C@H]1CC[C@H](N*)CC1]
(460)
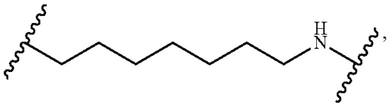 [SMILES: *CCCCCCCN*]
(461)
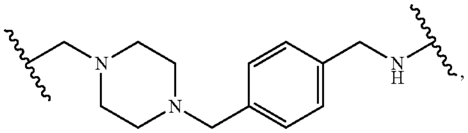 [SMILES: *CN1CCN(Cc2ccc(CN*)cc2)CC1]
(462)
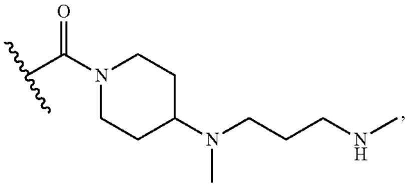 [SMILES: *C(=O)N1CCC(N(C)CCCNC)CC1]
(463)
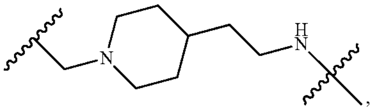 [SMILES: *CN1CCC(CCN*)CC1]
(464)
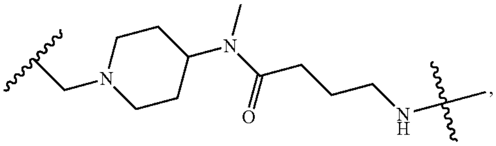 [SMILES: *CN1CCC(N(C)C(=O)CCCN*)CC1]
(465)
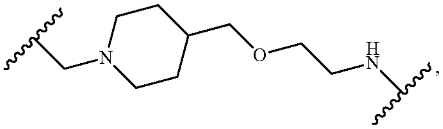 [SMILES: *CN1CCC(COCCN*)CC1]
(466)
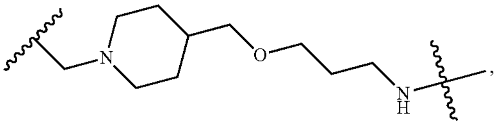 [SMILES: *CN1CCC(COCCCN*)CC1]
(467)
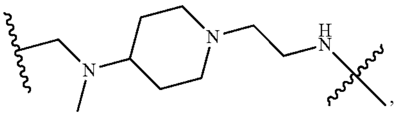 [SMILES: *CN(C)C1CCN(CCN*)CC1]
(468)
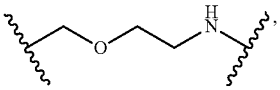 [SMILES: *COCCN*]
(469)

TABLE B-continued
Exemplified Linkers (L)
(470)
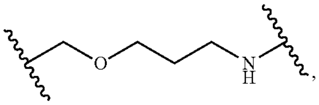 [SMILES: *COCCCN*]
,
(471)
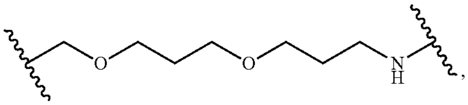 [SMILES: *COCCCOCCCN*]
,
(472)
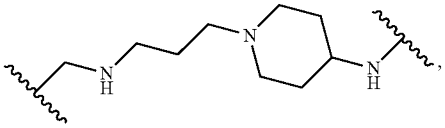 [SMILES: *CNCCCN1CCC(N*)CC1]
,
(473)
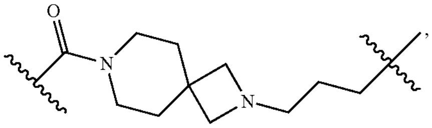 [SMILES: *CCCN1CC2(CCN(C(*)=O)CC2)C1]
,
(474)
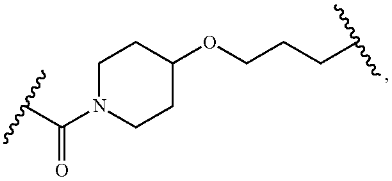 [SMILES: *CCCOC1CCN(C(*)=O)CC1]
,
(475)
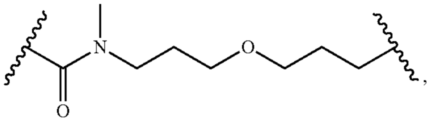 [SMILES: *CCCOCCCN(C)C(*)=O]
,
(475)
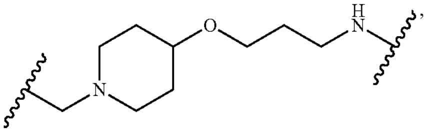 [SMILES: *CN1CCC(OCCCN*)CC1]
,
(476)
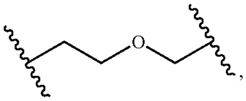 [SMILES: *CCOC*]
,
(477)
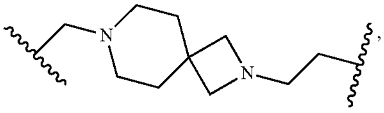 [SMILES: *CCN1CC2(CCN(C*)CC2)C1]
,
(478)
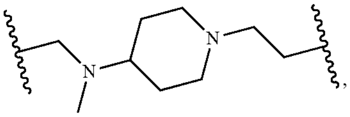 [SMILES: *CCN1CCC(N(C)C*)CC1]
,
(479)
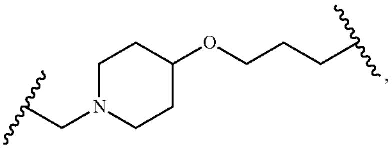 [SMILES: *CCCOC1CCN(C*)CC1]
, TABLE B-continued
| Exemplified Linkers (L) |
| --- |
| 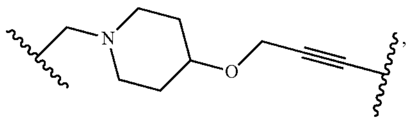 [SMILES: *C#CCOC1CCN(C*)CC1] (480) |
| 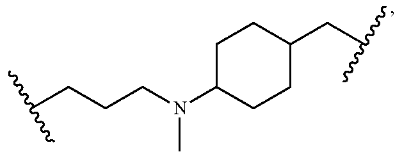 [SMILES: *CCCN(C)C1CCC(C*)CC1] (481) |
| 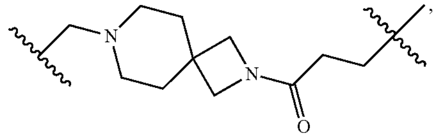 [SMILES: *CCC(=O)N1CC2(CCN(C*)CC2)C1] (482) |
| 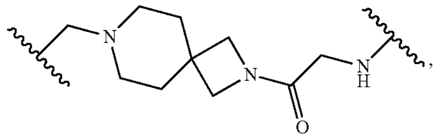 [SMILES: *CN1CCC2(CC1)CN(C(=O)CN*)C2] (483) |
| 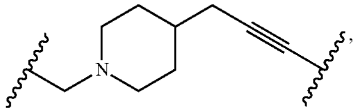 [SMILES: *C#CCC1CCN(C*)CC1] (484) |
| 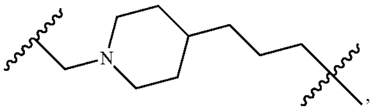 [SMILES: *CCCC1CCN(C*)CC1] (485) |
| 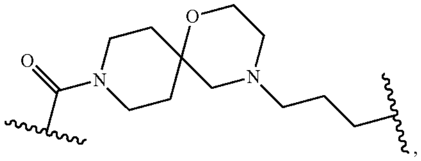 [SMILES: *CCCN1CCOC2(CCN(C(*)=O)CC2)C1] (486) |
| 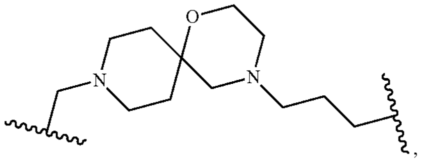 [SMILES: *CCCN1CCOC2(CCN(C*)CC2)C1] (487) |
| 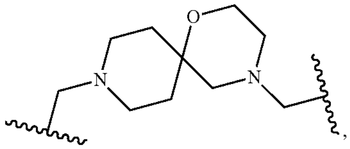 [SMILES: *CN1CCC2(CC1)CN(C*)CCO2] (488) |
| 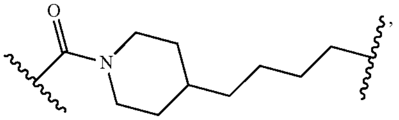 [SMILES: *CCCCC1CCN(C(*)=O)CC1] (489) |

TABLE B-continued
Exemplified Linkers (L)
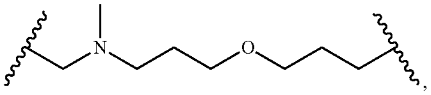 [SMILES: *CCCOCCCN(C)C*]
(490)
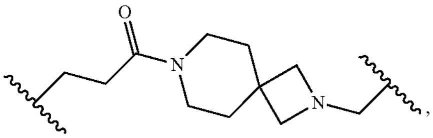 [SMILES: *CCC(=O)N1CCC2(CC1)CN(C*)C2]
(491)
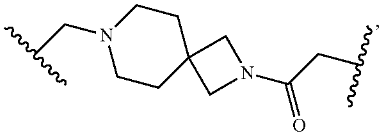 [SMILES: *CC(=O)N1CC2(CCN(C*)CC2)C1]
(492)
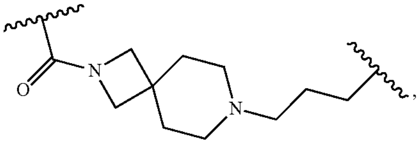 [SMILES: *CCCN1CCC2(CC1)CN(C(*)=O)C2]
(493)
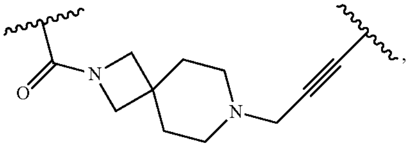 [SMILES: *C#CCN1CCC2(CC1)CN(C(*)=O)C2]
(494)
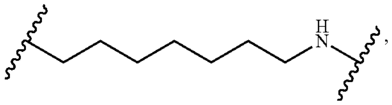 [SMILES: *CCCCCCCN*]
(495)
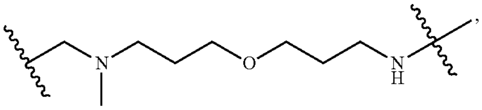 [SMILES: *CN(C)CCCOCCCN*]
(496)
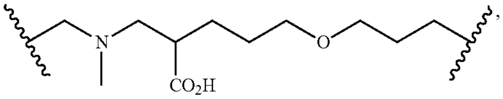 [SMILES: *CCCOCCCC(CN(C)C*)C(=O)O]
(497)
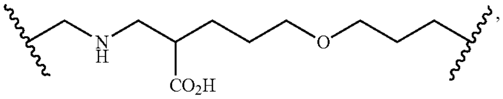 [SMILES: *CCCOCCCC(CNC*)C(=O)O]
(498)
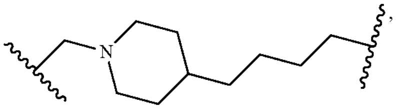 [SMILES: *CCCCC1CCN(C*)CC1]
(499)
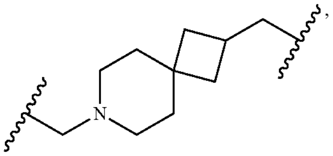 [SMILES: *CC1CC2(CCN(C*)CC2)C1]
(500)

TABLE B-continued
| Exemplified Linkers (L) |
|---|
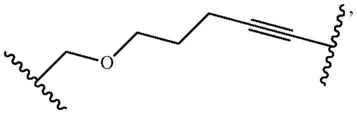 [SMILES: *C#CCCCOC*]
(501)
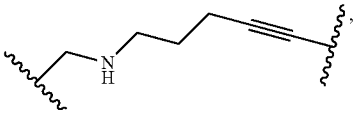 [SMILES: *C#CCCCNC*]
(502)
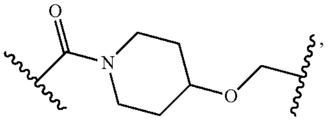 [SMILES: *COC1CCN(C(*)=O)CC1]
(503)
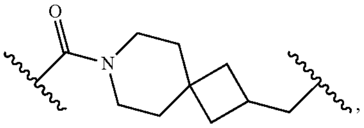 [SMILES: *CC1CC2(CCN(C(*)=O)CC2)C1]
(504)
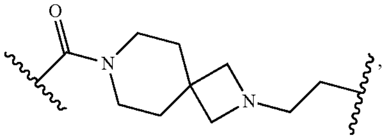
(505)
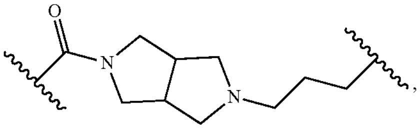 [SMILES: *CCCN1CC2CN(C(*)=O)CC2C1]
(506)
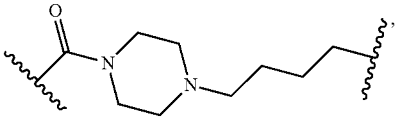 [SMILES: *CCCCN1CCN(C(*)=O)CC1]
(507)
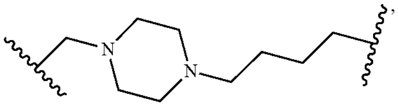 [SMILES: *CCCCN1CCN(C*)CC1]
(508)
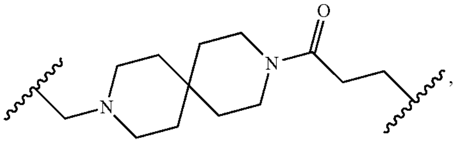 [SMILES: *CCC(=O)N1CCC2(CCN(C*)CC2)CC1]
(509)
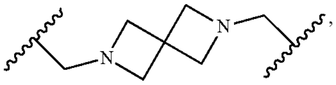 [SMILES: *CN1CC2(C1)CN(C*)C2]
(510)
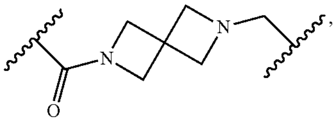 [SMILES: *CN1CC2(C1)CN(C(*)=O)C2]
(511)
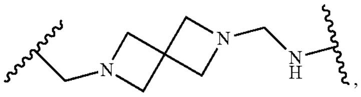 [SMILES: *CN1CC2(C1)CN(CN*)C2]
(512)

TABLE B-continued
Exemplified Linkers (L)
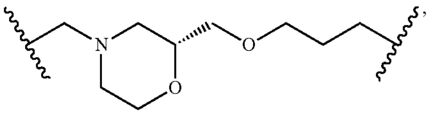 [SMILES: *CCCOC[C@H]1CN(C*)CCO1]
(513)
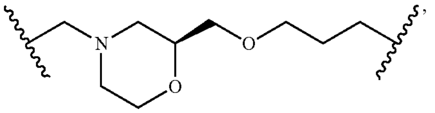 [SMILES: *CCCOC[C@@H]1CN(C*)CCO1]
(514)
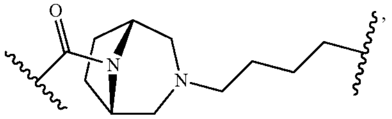 [SMILES: *CCCCN1C[C@H]2CC[C@@H](C1)N2C(*)=O]
(515)
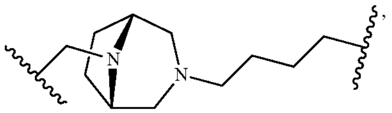 [SMILES: *CCCCN1C[C@H]2CC[C@@H](C1)N2C*]
(516)
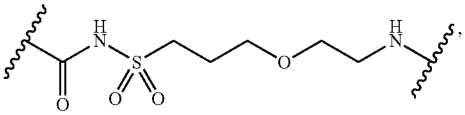 [SMILES: *NCCOCCCS(=O)(=O)NC(*)=O]
(517)
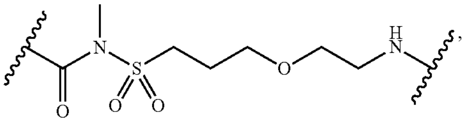 [SMILES: *NCCOCCCS(=O)(=O)N(C)C(*)=O]
(518)
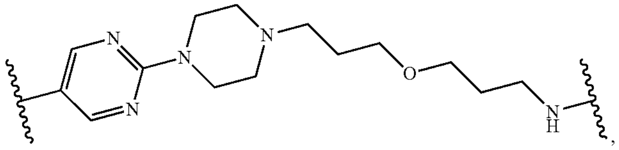 [SMILES: *NCCCOCCCN1CCN(c2ncc(*)cn2)CC1]
(519)
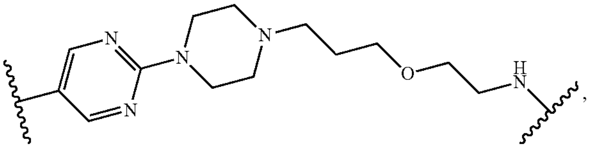 [SMILES: *NCCOCCCN1CCN(c2ncc(*)cn2)CC1]
(520)
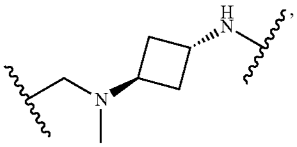 [SMILES: *CN(C)[C@H]1C[C@H](N*)C1]
(521)
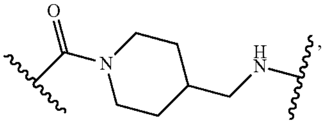 [SMILES: *NCC1CCN(C(*)=O)CC1]
(522)
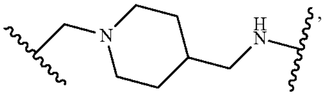 [SMILES: *CN1CCC(CN*)CC1]
(523)

TABLE B-continued
| Exemplified Linkers (L) |
| --- |
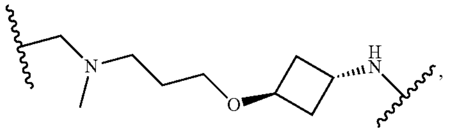 [SMILES: *CN(C)CCCO[C@H]1C[C@H](N*)C1]
(524)
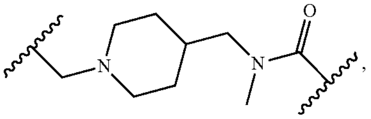 [SMILES: *CN1CCC(CN(C)C(*)=O)CC1]
(525)
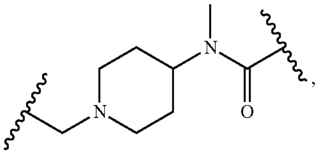 [SMILES: *CN1CCC(N(C)C(*)=O)CC1]
(526)
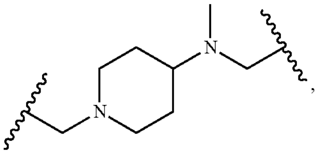 [SMILES: *CN1CCC(N(C)C*)CC1]
(527)
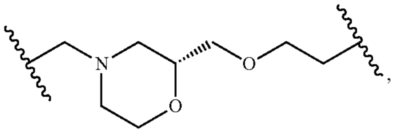 [SMILES: *CCOC[C@H]1CN(C*)CCO1]
(528)
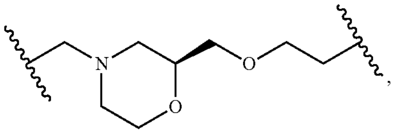 [SMILES: *CCOC[C@@H]1CN(C*)CCO1]
(529)
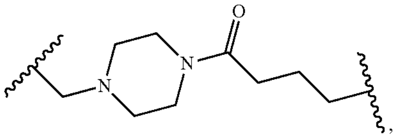 [SMILES: *CCCC(=O)N1CCN(C*)CC1]
(530)
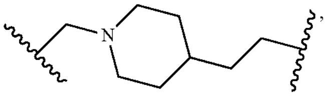 [SMILES: *CCC1CCN(C*)CC1]
(531)
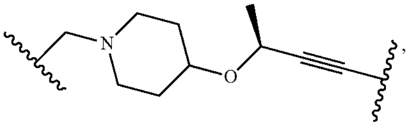 [SMILES: *C#C[C@H](C)OC1CCN(C*)CC1]
(532)
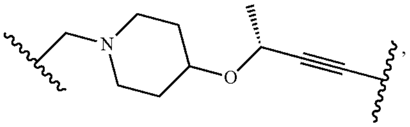 [SMILES: *C#C[C@@H](C)OC1CCN(C*)CC1]
(533)
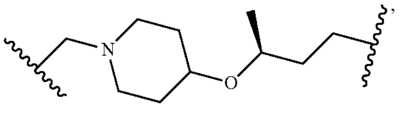 [SMILES: *CC[C@H](C)OC1CCN(C*)CC1]
(534)

TABLE B-continued
Exemplified Linkers (L)
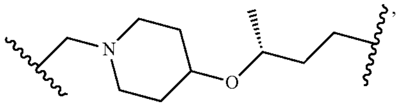 [SMILES: *CC[C@@H](C)OC1CCN(C*)CC1]
(535)
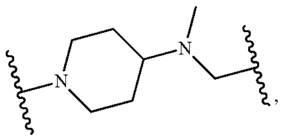 [SMILES: *CN(C)C1CCN(*)CC1]
(536)
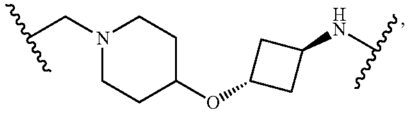 [SMILES: *CN1CCC(O[C@H]2C[C@H](N*)C2)CC1]
(537)
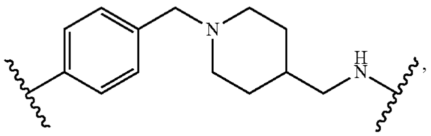 [SMILES: *NCC1CCN(Cc2ccc(*)cc2)CC1]
(538)
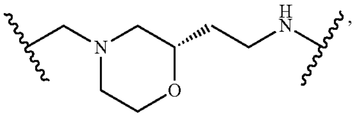 [SMILES: *CN1CCO[C@@H](CCN*)C1]
(539)
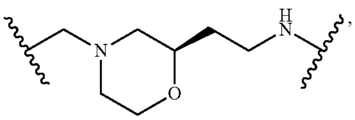 [SMILES: *CN1CCO[C@H](CCN*)C1]
(540)
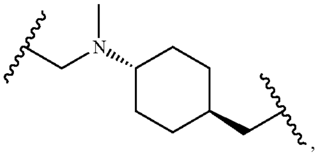 [SMILES: *CN(C)[C@H]1CC[C@H](C*)CC1]
(541)
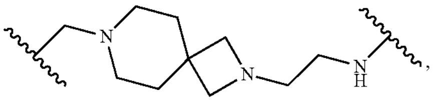 [SMILES: *CN1CCC2(CC1)CN(CCN*)C2]
(542)
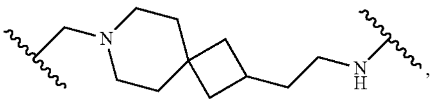 [SMILES: *CN1CCC2(CC1)CC(CCN*)C2]
(543)
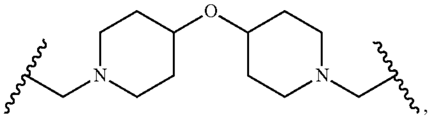 [SMILES: *CN1CCC(OC2CCN(C*)CC2)CC1]
(544)
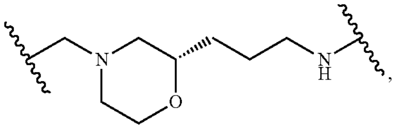 [SMILES: *CN1CCO[C@@H](CCCN*)C1]
(545)

TABLE B-continued
| Exemplified Linkers (L) | |
|---|---|
| 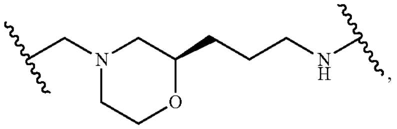 [SMILES: *CN1CCO[C@H](CCCN*)C1] | (546) |
| 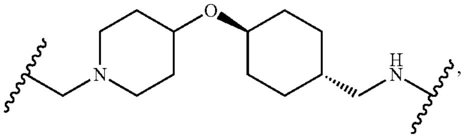 [SMILES: *CN1CCC(O[C@H]2CC[C@H](CN*)CC2)CC1] | (547) |
| 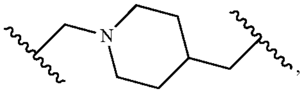 [SMILES: *CC1CCN(C*)CC1] | (548) |
| 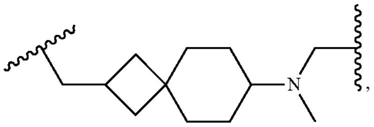 [SMILES: *CC1CC2(CCC(N(C)C*)CC2)C1] | (549) |
| 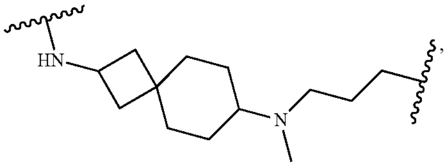 [SMILES: *CCCN(C)C1CCC2(CC1)CC(N*)C2] | (550) |
| 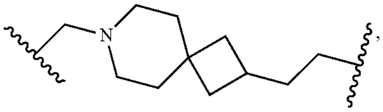 | (551) |
| 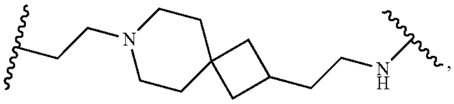 [SMILES: *CCN1CCC2(CC1)CC(CCN*)C2] | (552) |
| 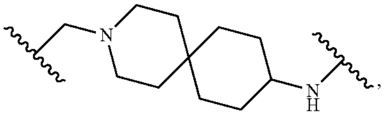 [SMILES: *CN1CCC2(CCC(N*)CC2)CC1] | (553) |
| 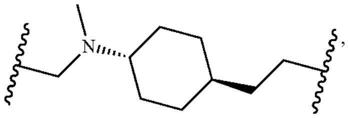 [SMILES: *CC[C@H]1CC[C@H](N(C)C*)CC1] | (554) |
| 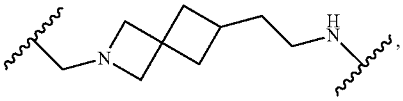 [SMILES: *CN1CC2(CC(CCN*)C2)C1] | (555) |
| 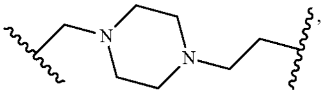 [SMILES: *CCN1CCN(C*)CC1] | (556) |
| 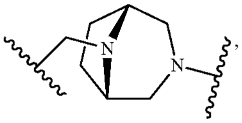 [SMILES: *CN1[C@@H]2CC[C@H]1CN(*)C2] | (557) |

TABLE B-continued
Exemplified Linkers (L)
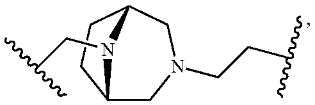 [SMILES: *CCN1C[C@H]2CC[C@@H](C1)N2C*]
(558)
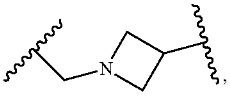 [SMILES: *CN1CC(*)C1]
(559)
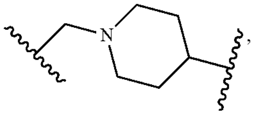 [SMILES: *CN1CCC(*)CC1]
(560)
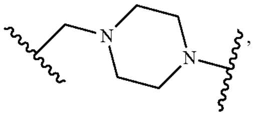 [SMILES: *CN1CCN(*)CC1]
(561)
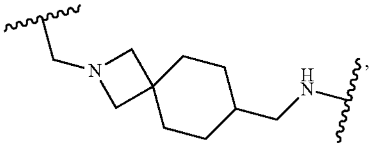 [SMILES: *CN1CC2(CCC(CN*)CC2)C1]
(562)
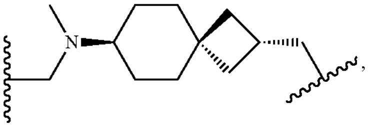
(563)
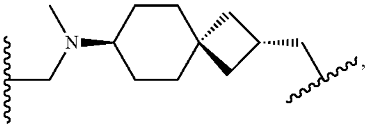
(564)
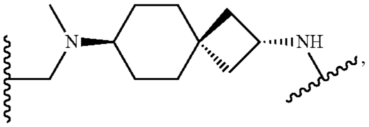
(565)
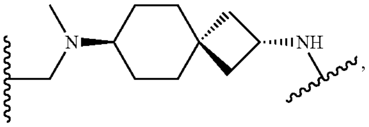
(566)
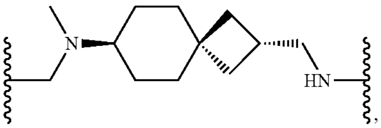
(567)
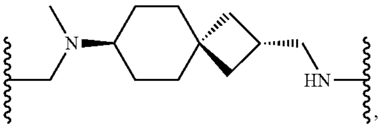
(568)

TABLE B-continued
| Exemplified Linkers (L) | |
|---|---|
| 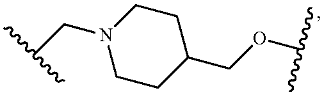 [SMILES: *CN1CCC(CO*)CC1] | (569) |
| 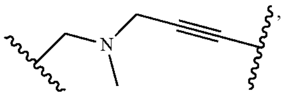 [SMILES: *C#CCN(C)C*] | (570) |
| 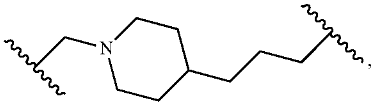 [SMILES: *CCCC1CCN(C*)CC1] | (571) |
| 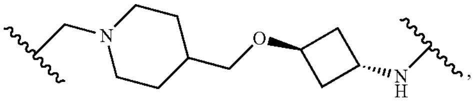 [SMILES: *CN1CCC(CO[C@H]2C[C@H](N*)C2)CC1] | (572) |
| 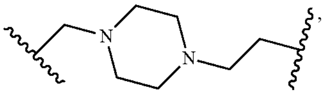 [SMILES: *CCN1CCN(C*)CC1] | (573) |
| 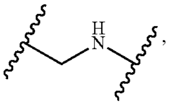 [SMILES: *CN*] | (574) |
| 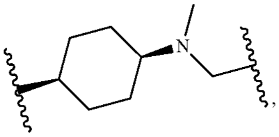 [SMILES: *CN(C)[C@H]1CC[C@@H](*)CC1] | (575) |
| 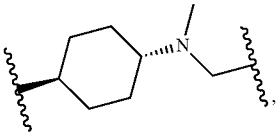 [SMILES: *CN(C)[C@H]1CC[C@H](*)CC1] | (576) |
| 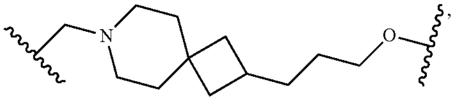 [SMILES: *CN1CCC2(CC1)CC(CCCO*)C2] | (577) |
| 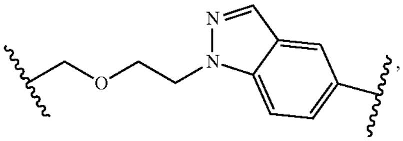 [SMILES: *COCCn1ncc2cc(*)ccc21] | (578) |
| 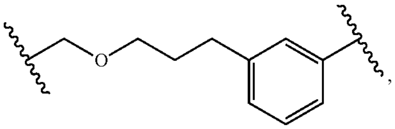 [SMILES: *COCCCc1cccc(*)c1] | (579) |
| 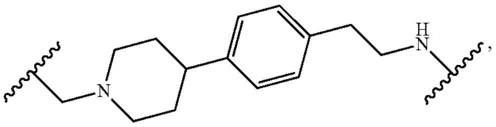 [SMILES: *CN1CCC(c2ccc(CCN*)cc2)CC1] | (580) |

TABLE B-continued
Exemplified Linkers (L)
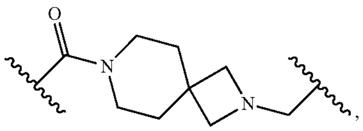 [SMILES: *CN1CC2(CCN(C(*)=O)CC2)C1]
(581)
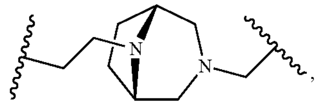 [SMILES: *CCN1[C@@H]2CC[C@H]1CN(C*)C2]
(582)
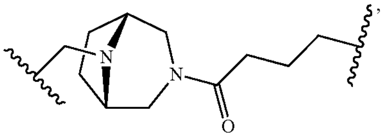 [SMILES: *CCCC(=O)N1C[C@H]2CC[C@@H](C1)N2C*]
(583)
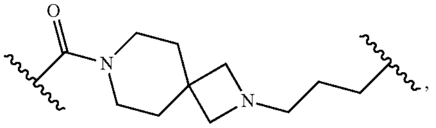 [SMILES: *CCCN1CC2(CCN(C(*)=O)CC2)C1]
(584)
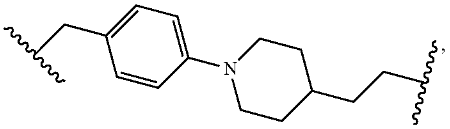 [SMILES: *CCC1CCN(c2ccc(C*)cc2)CC1]
(585)
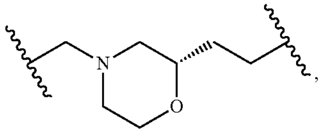 [SMILES: *CC[C@H]1CN(C*)CCO1]
(586)
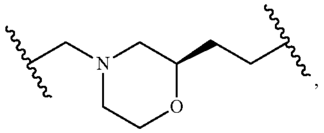 [SMILES: *CC[C@@H]1CN(C*)CCO1]
(587)
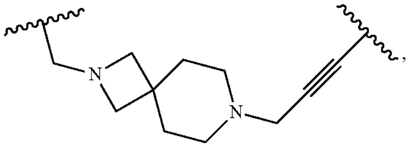 [SMILES: *C#CCN1CCC2(CC1)CN(C*)C2]
(588)
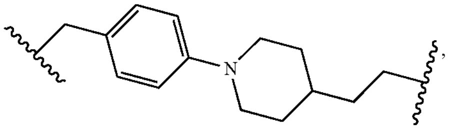 [SMILES: *CCC1CCN(c2ccc(C*)cc2)CC1]
(589)
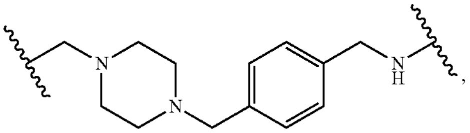 [SMILES: *CN1CCN(Cc2ccc(CN*)cc2)CC1]
(590)
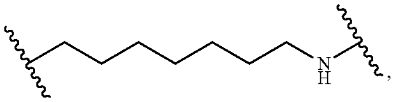 [SMILES: *CCCCCCCN*]
(591)

TABLE B-continued
| Exemplified Linkers (L) |
|---|
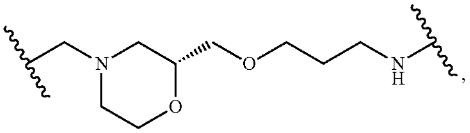 [SMILES: *CN1CCO[C@@H](COCCCN*)C1]
(592)
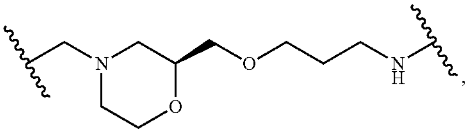 [SMILES: *CN1CCO[C@H](COCCCN*)C1]
(593)
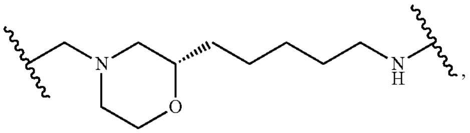 [SMILES: *CN1CCO[C@@H](CCCCCN*)C1]
(594)
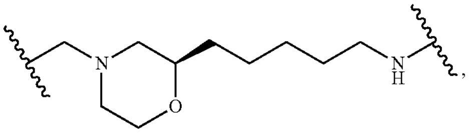 [SMILES: *CN1CCO[C@H](CCCCCN*)C1]
(595)
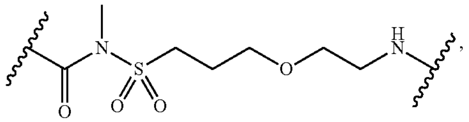 [SMILES: *NCCOCCCS(=O)(=O)N(C)C(*)=O]
(596)
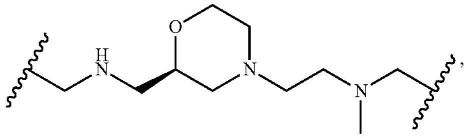 [SMILES: *CNC[C@@H]1CN(CCN(C)C*)CCO1]
(597)
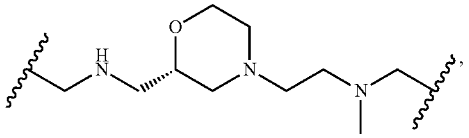 [SMILES: *CNC[C@H]1CN(CCN(C)C*)CCO1]
(598)
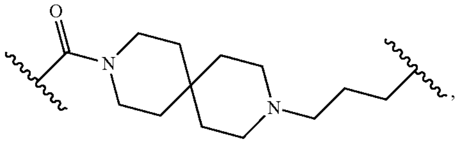 [SMILES: *CCCN1CCC2(CC1)CCN(C(*)=O)CC2]
(599)
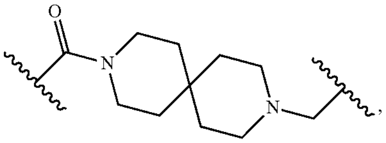 [SMILES: *CN1CCC2(CC1)CCN(C(*)=O)CC2]
(600)
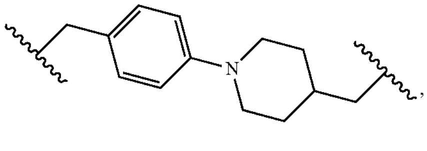 [SMILES: *Cc1ccc(N2CCC(C*)CC2)cc1]
(601)

TABLE B-continued
Exemplified Linkers (L)
(602)
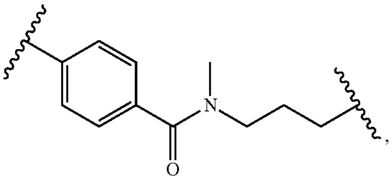 [SMILES: *CCCN(C)C(=O)c1ccc(*)cc1]
(603)
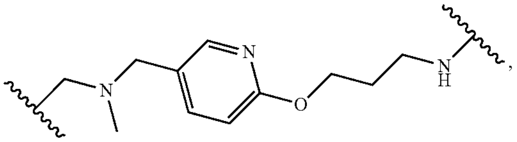 [SMILES: *CN(C)Cc1ccc(OCCCN*)nc1]
(604)
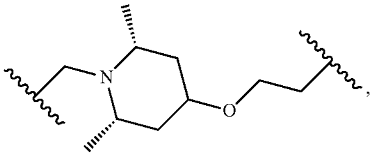 [SMILES: *CCOC1C[C@@H](C)N(C*)[C@@H](C)C1]
(605)
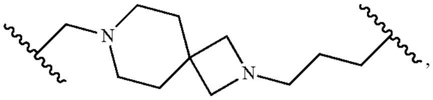 [SMILES: *CCCN1CC2(CCN(C*)CC2)C1]
(606)
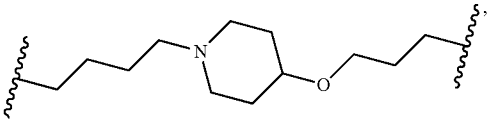 [SMILES: *CCCCN1CCC(OCCC*)CC1]
(607)
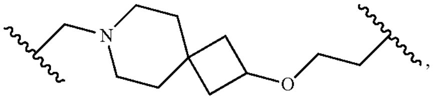 [SMILES: *CCOC1CC2(CCN(C*)CC2)C1]
(608)
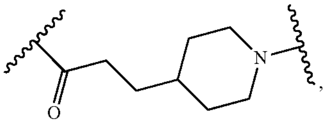 [SMILES: *C(=O)CCC1CCN(*)CC1]
(609)
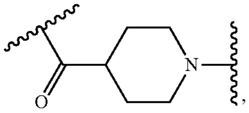 [SMILES: *C(=O)C1CCN(*)CC1]
(610)
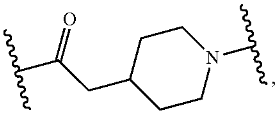 [SMILES: *C(=O)CC1CCN(*)CC1]
(611)
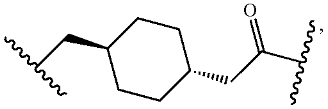 [SMILES: *C[C@H]1CC[C@H](CC(*)=O)CC1]
(612)
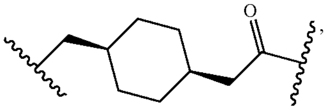 [SMILES: *C[C@H]1CC[C@@H](CC(*)=O)CC1]

TABLE B-continued
| Exemplified Linkers (L) | |
|---|---|
| 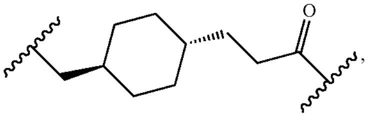 [SMILES: *C[C@H]1CC[C@H](CCC(*)=O)CC1] | (613) |
| 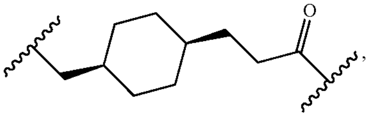 [SMILES: *C[C@H]1CC[C@@H](CCC(*)=O)CC1] | (614) |
| 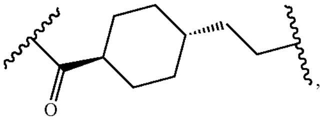 [SMILES: *CC[C@H]1CC[C@H](C(*)=O)CC1] | (615) |
| 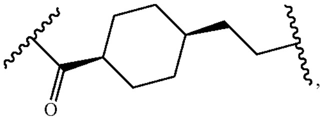 [SMILES: *CC[C@H]1CC[C@@H](C(*)=O)CC1] | (616) |
| 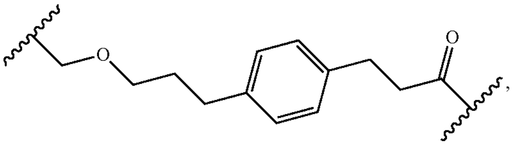 [SMILES: *COCCCc1ccc(CCC(*)=O)cc1] | (617) |
| 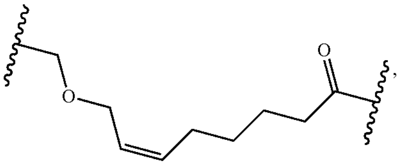 [SMILES: *COC/C=C\CCCCC(*)=O] | (618) |
| 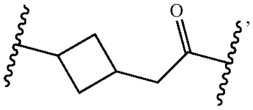 [SMILES: *C(=O)CC1CC(*)C1] | (619) |
| 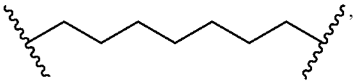 | (620) |
| 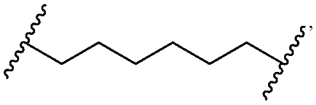 | (621) |
| 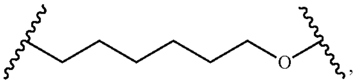 [SMILES: *CCCCCCO*] | (622) |
| 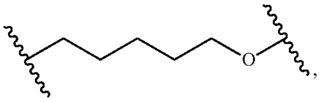 [SMILES: *CCCCCO*] | (623) |
| 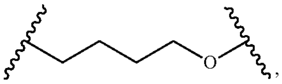 [SMILES: *CCCCO*] | (624) |

TABLE B-continued
Exemplified Linkers (L)
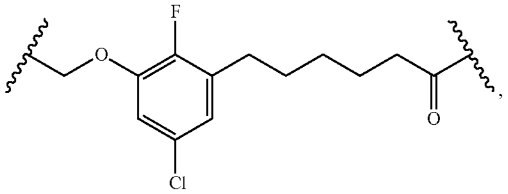 [SMILES: *COc1cc(Cl)cc(CCCCCC(*)=O)c1F]
(625)
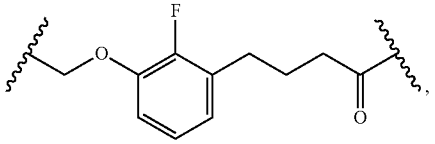
(626)
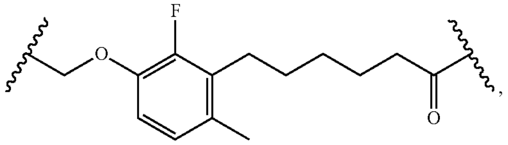 [SMILES: *COc1ccc(C)c(CCCCCC(*)=O)c1F]
(627)
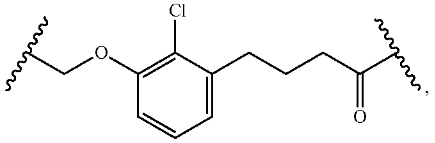
(628)
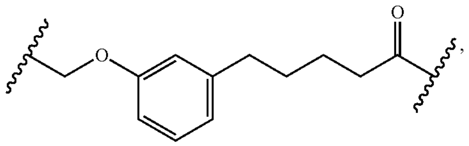 [SMILES: *COc1cccc(CCCCC(*)=O)c1]
(629)
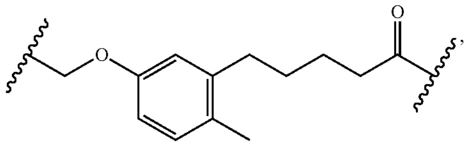 [SMILES: *COc1ccc(C)c(CCCCC(*)=O)c1]
(630)
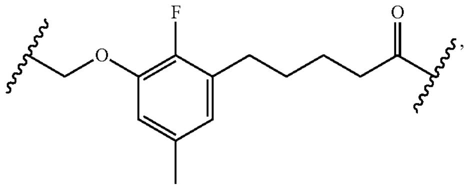 [SMILES: *COc1cc(C)cc(CCCCC(*)=O)c1F]
(631)
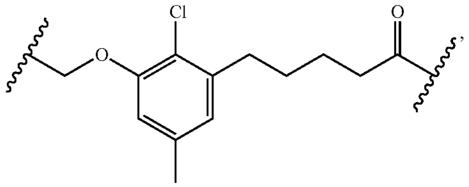 [SMILES: *COc1cc(C)cc(CCCCC(*)=O)c1Cl]
(632)
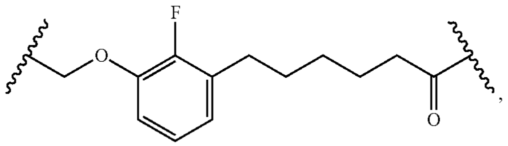 [SMILES: *COc1cccc(CCCCCC(*)=O)c1F]
(633)

TABLE B-continued
| Exemplified Linkers (L) |
|---|
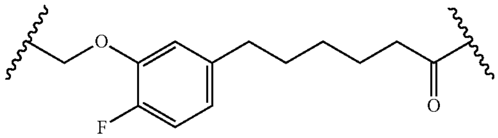
,
(634)
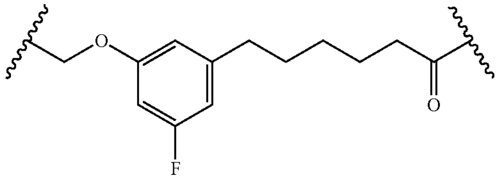
,
(635)
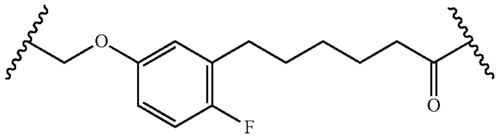
,
(636)
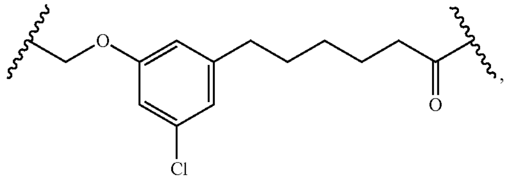 [SMILES: *COc1cc(Cl)cc(CCCCCC(*)=O)c1]
,
(637)
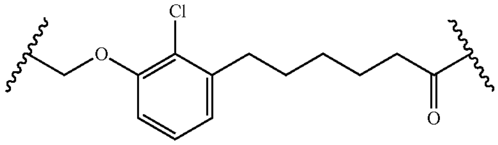
,
(638)
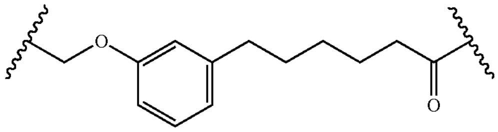
,
(639)
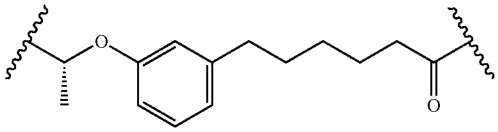
,
(640)
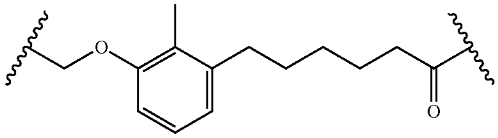
,
(641)
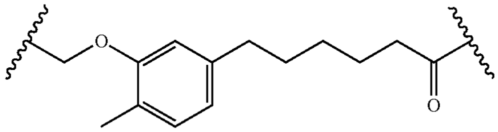
,
(642)
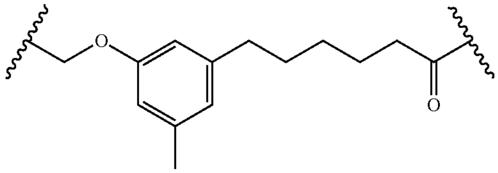
,
(643)

TABLE B-continued
| Exemplified Linkers (L) |
| --- |
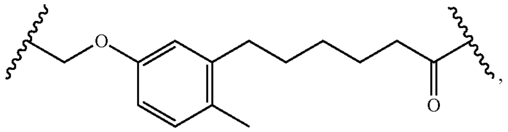 [SMILES: *COc1ccc(C)c(CCCCCC(*)=O)c1]
(644)
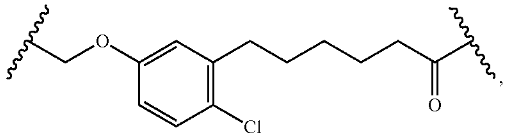 [SMILES: *COc1ccc(Cl)c(CCCCCC(*)=O)c1]
(645)
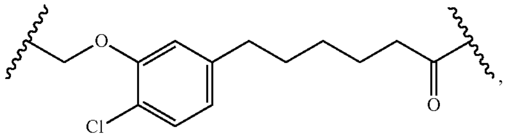 [SMILES: *COc1cc(CCCCCC(*)=O)ccc1Cl]
(646)
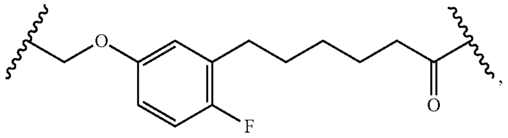 [SMILES: *COc1ccc(F)c(CCCCCC(*)=O)c1]
(647)
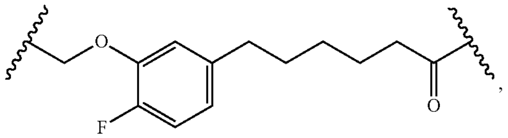 [SMILES: *COc1cc(CCCCCC(*)=O)ccc1F]
(648)
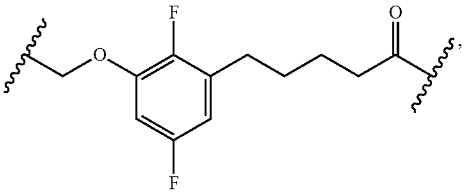 [SMILES: *COc1cc(F)cc(CCCCC(*)=O)c1F]
(649)
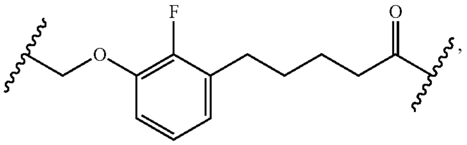 [SMILES: *COc1cccc(CCCCC(*)=O)c1F]
(650)
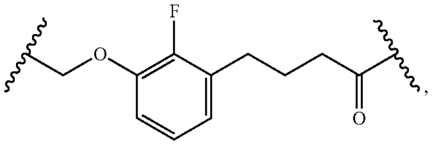 [SMILES: *COc1cccc(CCCC(*)=O)c1F]
(651)
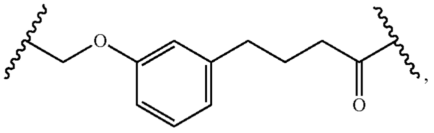 [SMILES: *COc1cccc(CCCC(*)=O)c1]
(652)
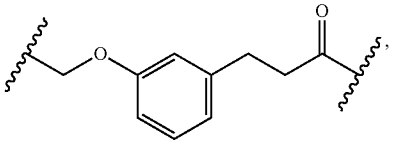 [SMILES: *COc1cccc(CCC(*)=O)c1]
(653)

TABLE B-continued
| Exemplified Linkers (L) |
| --- |
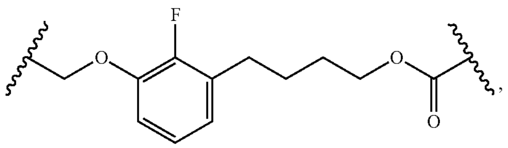 [SMILES: *COc1cccc(CCCCOC(*)=O)c1F]
(654)
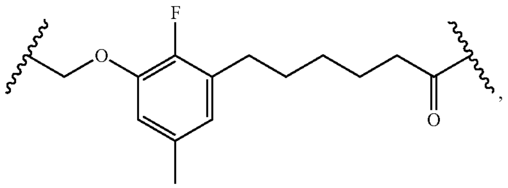 [SMILES: *COc1cc(C)cc(CCCCCC(*)=O)c1F]
(655)
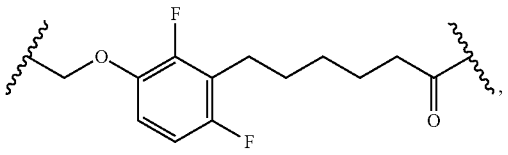 [SMILES: *COc1ccc(F)c(CCCCCC(*)=O)c1F]
(656)
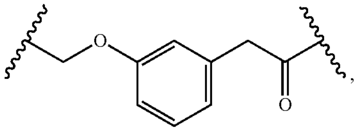 [SMILES: *COc1cccc(CC(*)=O)c1]
(657)
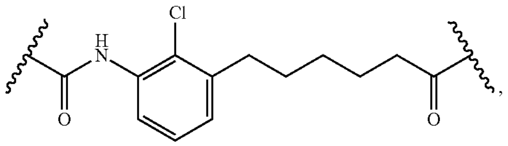 [SMILES: *C(=O)CCCCCc1cccc(NC(*)=O)c1Cl]
(658)
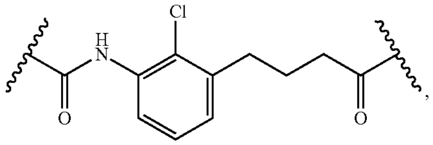 [SMILES: *C(=O)CCCc1cccc(NC(*)=O)c1Cl]
(659)
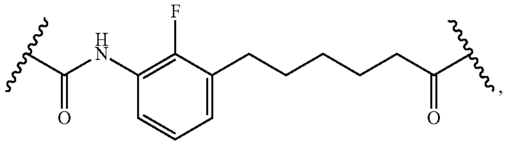 [SMILES: *C(=O)CCCCCc1cccc(NC(*)=O)c1F]
(660)
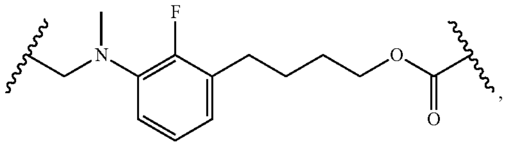 [SMILES: *CN(C)c1cccc(CCCCOC(*)=O)c1F]
(661)
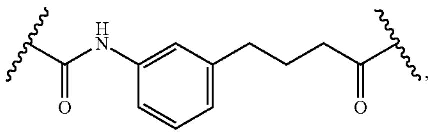 [SMILES: *C(=O)CCCc1cccc(NC(*)=O)c1]
(662)
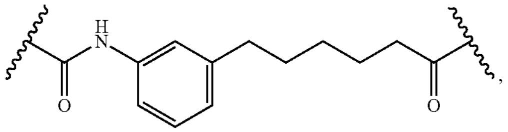 [SMILES: *C(=O)CCCCCc1cccc(NC(*)=O)c1]
(663)

TABLE B-continued
| Exemplified Linkers (L) |
|---|
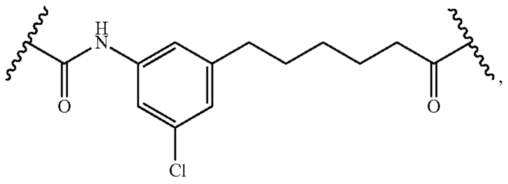
(664)
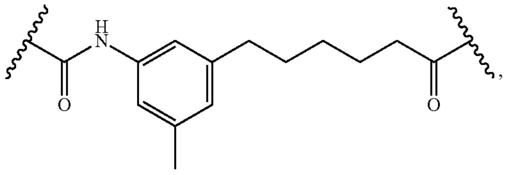 [SMILES: *C(=O)CCCCCc1cc(C)cc(NC(*)=O)c1]
(665)
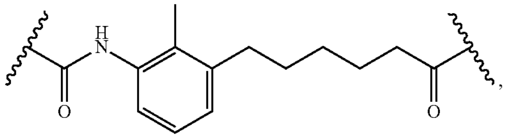 [SMILES: *C(=O)CCCCCc1cccc(NC(*)=O)c1C]
(666)
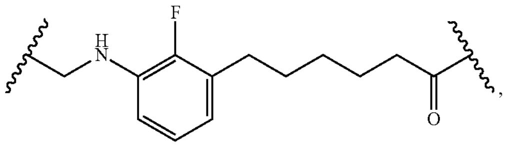 [SMILES: *CNc1cccc(CCCCCC(*)=O)c1F]
(667)
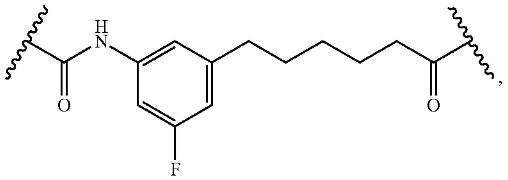 [SMILES: *C(=O)CCCCCc1cc(F)cc(NC(*)=O)c1]
(668)
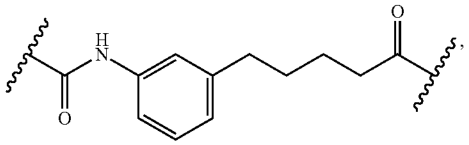 [SMILES: *C(=O)CCCCc1cccc(NC(*)=O)c1]
(669)
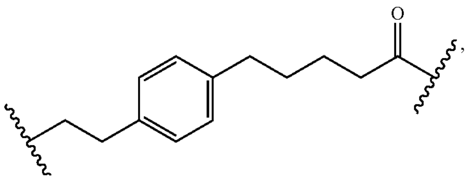 [SMILES: *CCc1ccc(CCCCC(*)=O)cc1]
(670)
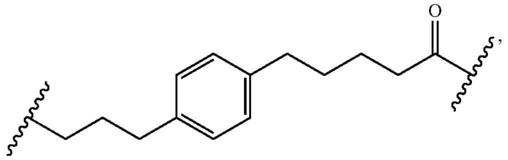 [SMILES: *CCCc1ccc(CCCCC(*)=O)cc1]
(671)
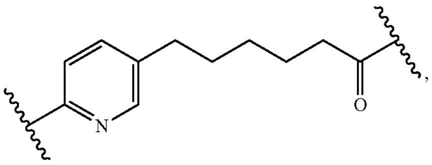 [SMILES: *C(=O)CCCCCc1ccc(*)nc1]
(672)

TABLE B-continued
Exemplified Linkers (L)
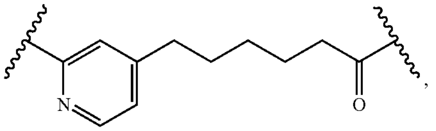 [SMILES: *C(=O)CCCCCc1ccnc(*)c1]
(673)
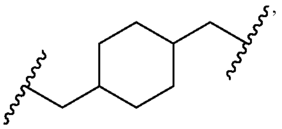 [SMILES: *CC1CCC(C*)CC1]
(674)
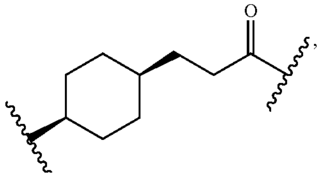 [SMILES: *C(=O)CC[C@H]1CC[C@@H](*)CC1]
(675)
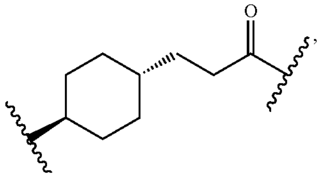 [SMILES: *C(=O)CC[C@H]1CC[C@H](*)CC1]
(676)
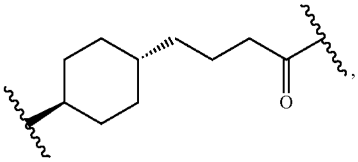 [SMILES: *C(=O)CCC[C@H]1CC[C@H](*)CC1]
(677)
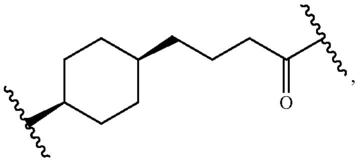 [SMILES: *C(=O)CCC[C@H]1CC[C@@H](*)CC1]
(678)
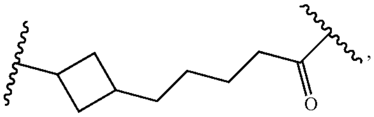 [SMILES: *C(=O)CCCCC1CC(*)C1]
(679)
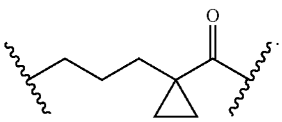 [SMILES: *CCCC1(C(*)=O)CC1]
(680)
In some embodiments, the present invention provides a compound having a MDM2 binding moiety described and disclosed herein, a LBM set forth in Table A above, and a linker set forth in Table B above, or a pharmaceutically acceptable salt thereof.

Exemplary compounds of the invention are set forth in Table 1, below.
TABLE 1
| Exemplary Compounds | |
|---|---|
| I-# | Structure |
| I-1 | 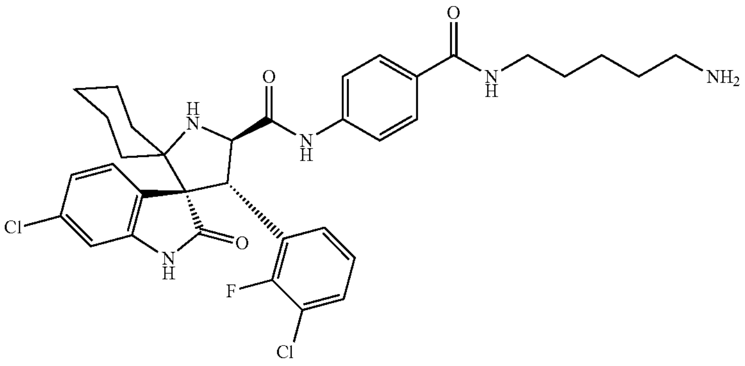 [SMILES: NCCCCCNC(=O)c1ccc(NC(=O)[C@@H]2NC3(CCCCC3)[C@@]3(C(=O)Nc4cc(Cl)ccc43)[C@H]2c2cccc(Cl)c2F)cc1] |
| I-2 | 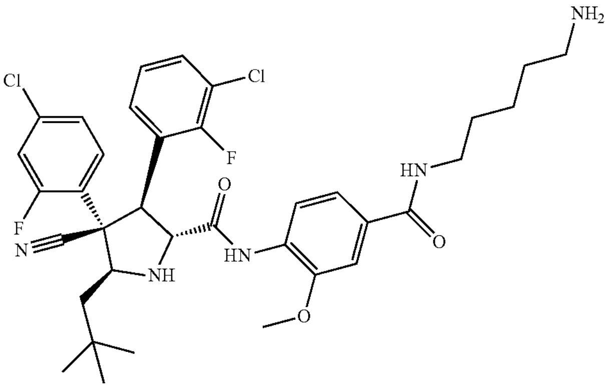 [SMILES: COc1cc(C(=O)NCCCCCN)ccc1NC(=O)[C@@H]1N[C@@H](CC(C)(C)C)[C@](C#N)(c2ccc(Cl)cc2F)[C@H]1c1cccc(Cl)c1F] |
| I-3 | 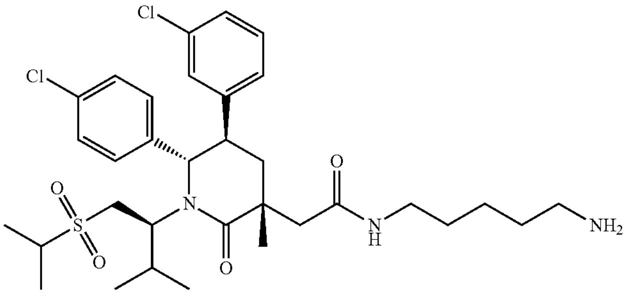 [SMILES: CC(C)[C@@H](CS(=O)(=O)C(C)C)N1C(=O)[C@@](C)(CC(=O)NCCCCCN)C[C@H](c2cccc(Cl)c2)[C@H]1c1ccc(Cl)cc1] |
| I-4 | 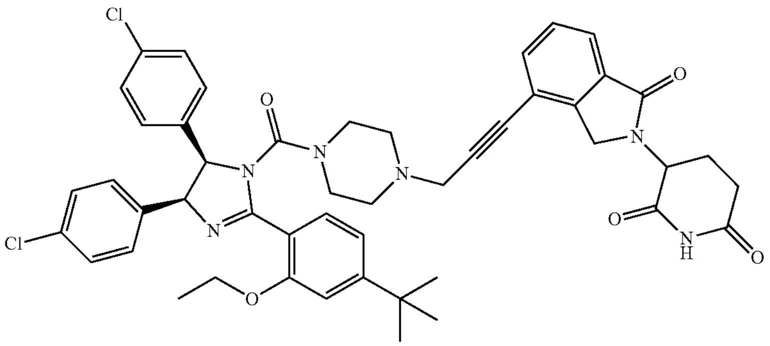 [SMILES: CCOc1cc(C(C)(C)C)ccc1C1=N[C@@H](c2ccc(Cl)cc2)[C@@H](c2ccc(Cl)cc2)N1C(=O)N1CCN(CC#Cc2cccc3c2CN(C2CCC(=O)NC2=O)C3=O)CC1] |

TABLE 1-continued
| Exemplary Compounds | |
|---|---|
| I-# | Structure |
| I-5 | 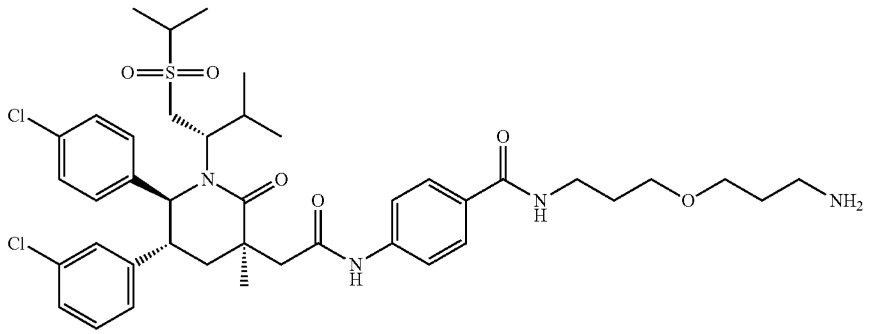 [SMILES: CC(C)[C@@H](CS(=O)(=O)C(C)C)N1C(=O)[C@@](C)(CC(=O)Nc2ccc(C(=O)NCCCOCCCN)cc2)C[C@H](c2cccc(Cl)c2)[C@H]1c1ccc(Cl)cc1] |
| I-6 | 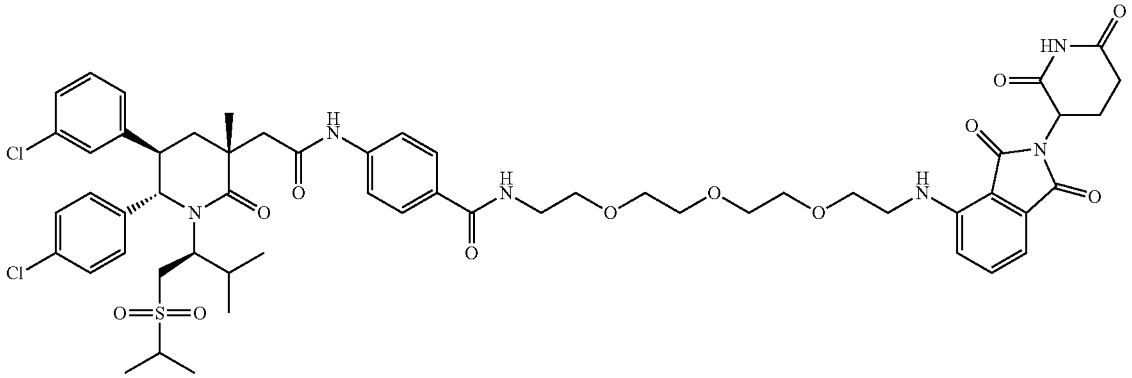 [SMILES: CC(C)[C@@H](CS(=O)(=O)C(C)C)N1C(=O)[C@@](C)(CC(=O)Nc2ccc(C(=O)NCCOCCOCCOCCNc3cccc4c3C(=O)N(C3CCC(=O)NC3=O)C4=O)cc2)C[C@H](c2cccc(Cl)c2)[C@H]1c1ccc(Cl)cc1] |
| I-7 | 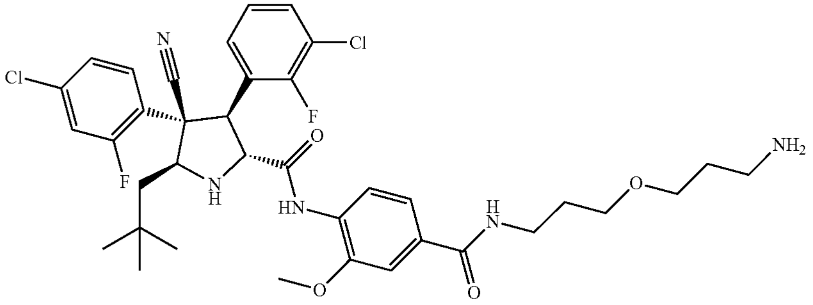 [SMILES: COc1cc(C(=O)NCCCOCCCN)ccc1NC(=O)[C@@H]1N[C@@H](CC(C)(C)C)[C@](C#N)(c2ccc(Cl)cc2F)[C@H]1c1cccc(Cl)c1F] |
| I-8 | 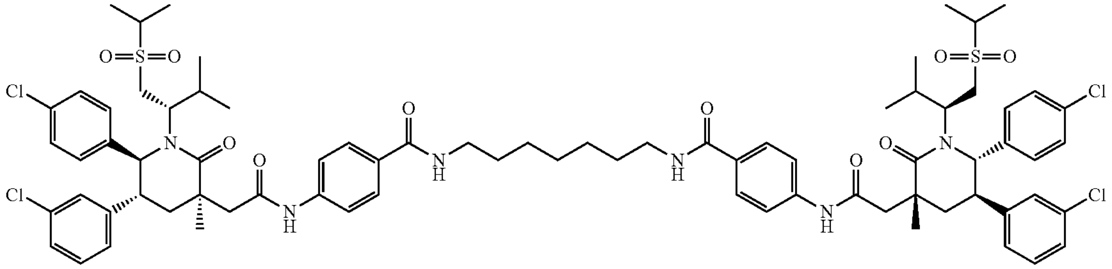 [SMILES: CC(C)[C@@H](CS(=O)(=O)C(C)C)N1C(=O)[C@@](C)(CC(=O)Nc2ccc(C(=O)NCCCCCCCNC(=O)c3ccc(NC(=O)C[C@@]4(C)C[C@H](c5cccc(Cl)c5)[C@@H](c5ccc(Cl)cc5)N([C@H](CS(=O)(=O)C(C)C)C(C)C)C4=O)cc3)cc2)C[C@H](c2cccc(Cl)c2)[C@H]1c1ccc(Cl)cc1] |

TABLE 1-continued
| Exemplary Compounds | |
|---|---|
| I-# | Structure |
| I-9 | 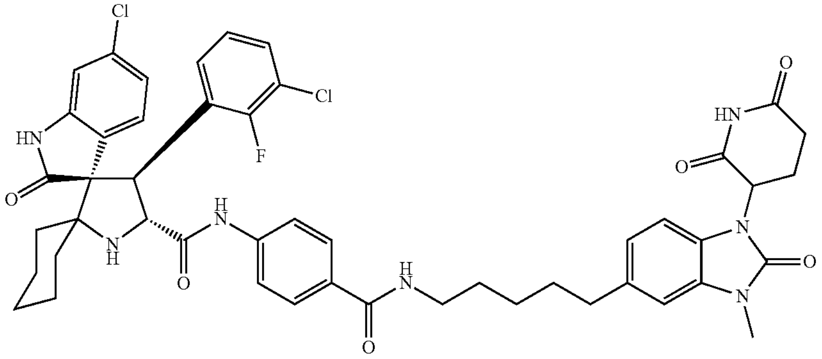 [SMILES: Cn1c(=O)n(C2CCC(=O)NC2=O)c2ccc(CCCCCNC(=O)c3ccc(NC(=O)[C@@H]4NC5(CCCCC5)[C@@]5(C(=O)Nc6cc(Cl)ccc65)[C@H]4c4cccc(Cl)c4F)cc3)cc21] |
| I-10 | 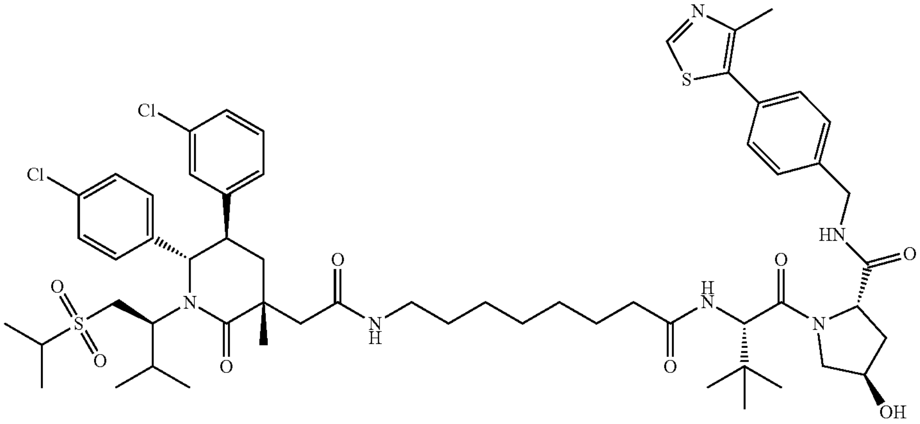 [SMILES: Cc1ncsc1-c1ccc(CNC(=O)[C@@H]2C[C@@H](O)CN2C(=O)[C@@H](NC(=O)CCCCCCCNC(=O)C[C@@]2(C)C[C@H](c3cccc(Cl)c3)[C@@H](c3ccc(Cl)cc3)N([C@H](CS(=O)(=O)C(C)C)C(C)C)C2=O)C(C)(C)C)cc1] |
| I-11 | 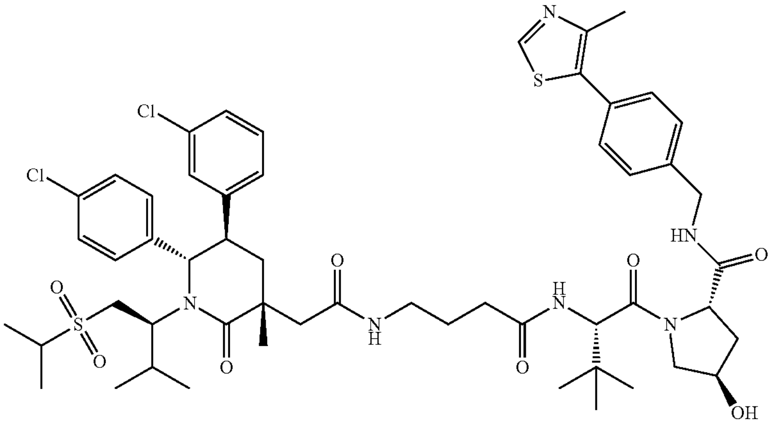 [SMILES: Cc1ncsc1-c1ccc(CNC(=O)[C@@H]2C[C@@H](O)CN2C(=O)[C@@H](NC(=O)CCCNC(=O)C[C@@]2(C)C[C@H](c3cccc(Cl)c3)[C@@H](c3ccc(Cl)cc3)N([C@H](CS(=O)(=O)C(C)C)C(C)C)C2=O)C(C)(C)C)cc1] |

TABLE 1-continued
| Exemplary Compounds | |
|---|---|
| I-# | Structure |
| I-12 | 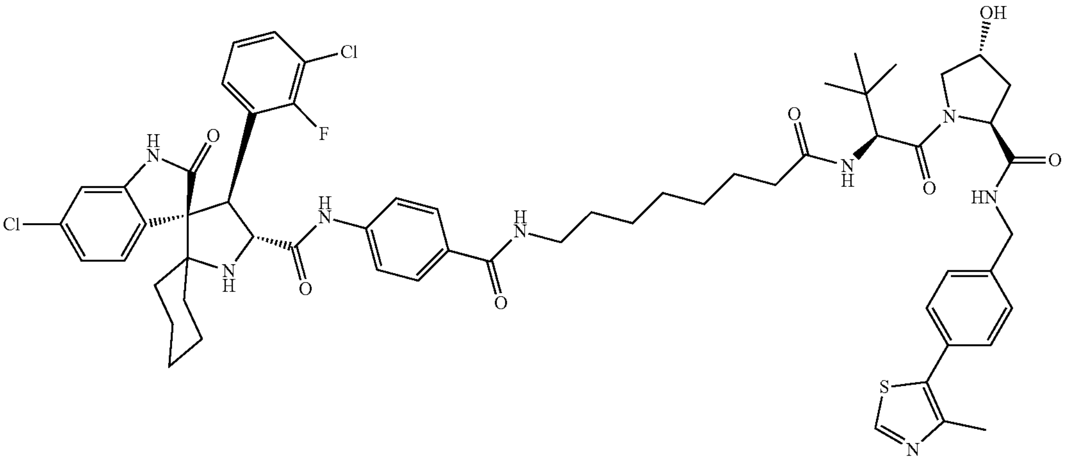 [SMILES: Cc1ncsc1-c1ccc(CNC(=O)[C@@H]2C[C@@H](O)CN2C(=O)[C@@H](NC(=O)CCCCCCCNC(=O)c2ccc(NC(=O)[C@@H]3NC4(CCCCC4)[C@@]4(C(=O)Nc5cc(Cl)ccc54)[C@H]3c3cccc(Cl)c3F)cc2)C(C)(C)C)cc1] |
| I-13 | 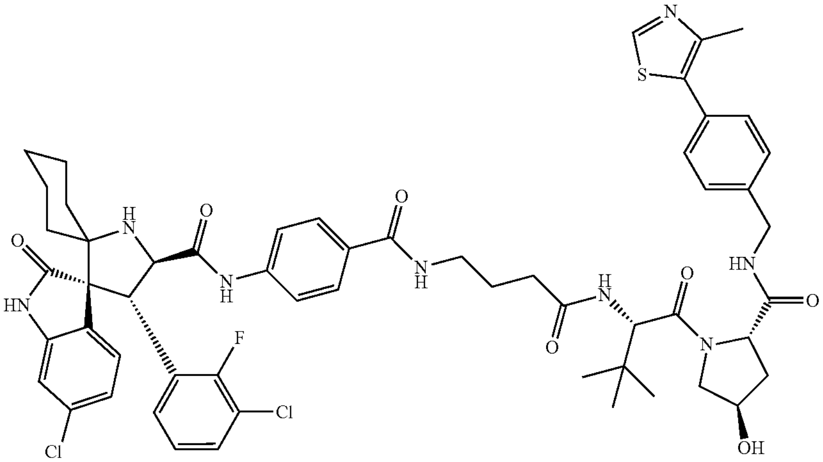 [SMILES: Cc1ncsc1-c1ccc(CNC(=O)[C@@H]2C[C@@H](O)CN2C(=O)[C@@H](NC(=O)CCCNC(=O)c2ccc(NC(=O)[C@@H]3NC4(CCCCC4)[C@@]4(C(=O)Nc5cc(Cl)ccc54)[C@H]3c3cccc(Cl)c3F)cc2)C(C)(C)C)cc1] |
| I-14 | 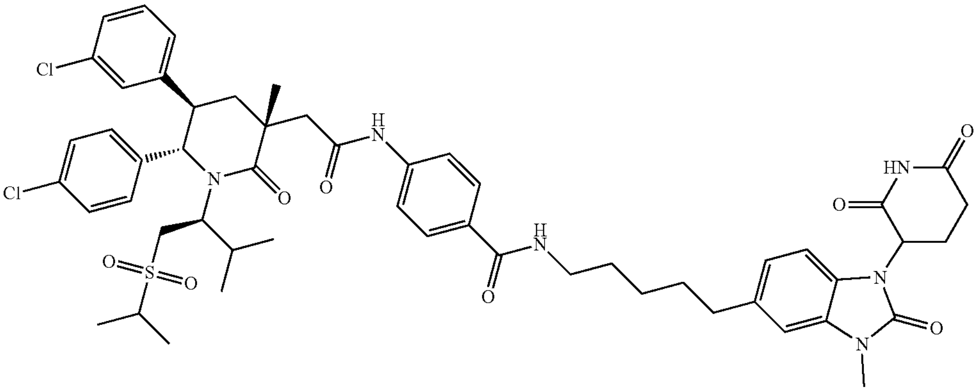 [SMILES: CC(C)[C@@H](CS(=O)(=O)C(C)C)N1C(=O)[C@@](C)(CC(=O)Nc2ccc(C(=O)NCCCCCc3ccc4c(c3)n(C)c(=O)n4C3CCC(=O)NC3=O)cc2)C[C@H](c2cccc(Cl)c2)[C@H]1c1ccc(Cl)cc1] |

TABLE 1-continued
| Exemplary Compounds | |
|---|---|
| I-# | Structure |
| I-15 | 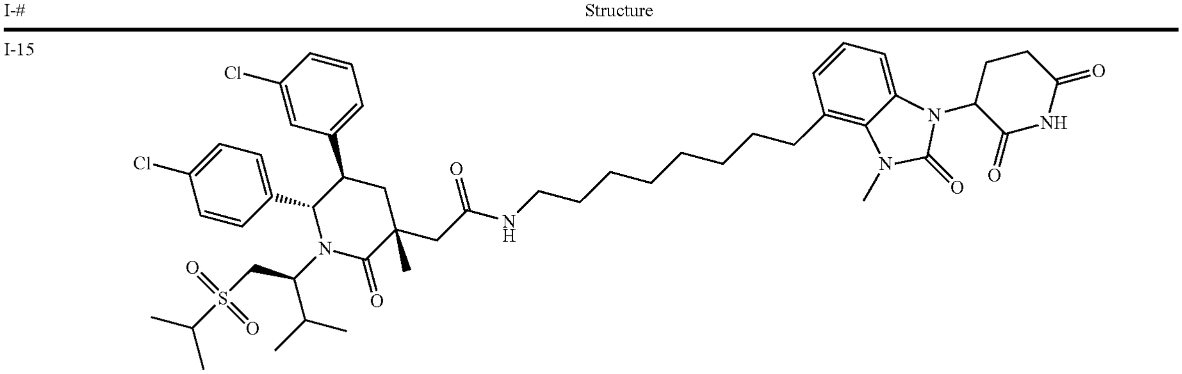 |
| I-16 | 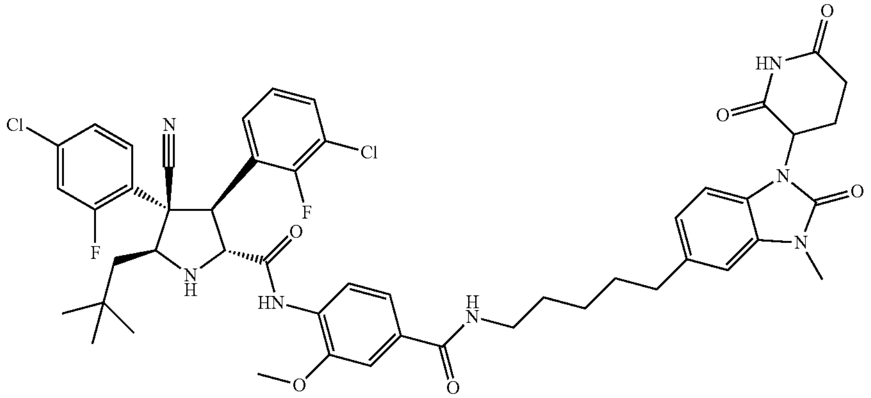 [SMILES: COc1cc(C(=O)NCCCCCc2ccc3c(c2)n(C)c(=O)n3C2CCC(=O)NC2=O)ccc1NC(=O)[C@@H]1N[C@@H](CC(C)(C)C)[C@](C#N)(c2ccc(Cl)cc2F)[C@H]1c1cccc(Cl)c1F] |
| I-17 | 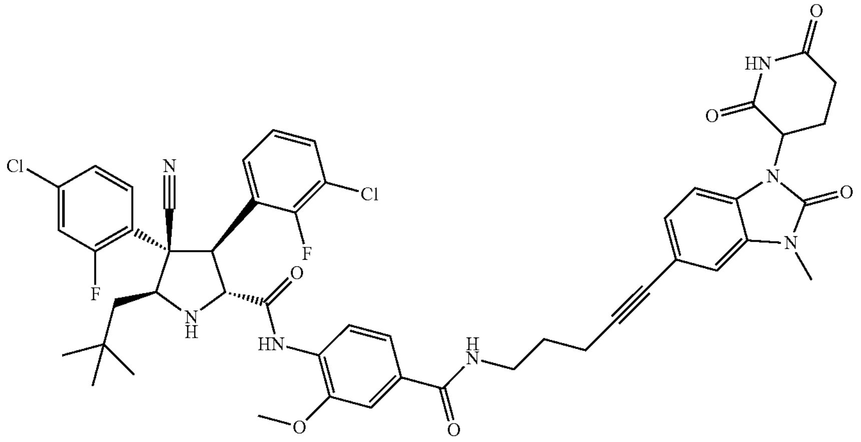 [SMILES: COc1cc(C(=O)NCCCC#Cc2ccc3c(c2)n(C)c(=O)n3C2CCC(=O)NC2=O)ccc1NC(=O)[C@@H]1N[C@@H](CC(C)(C)C)[C@](C#N)(c2ccc(Cl)cc2F)[C@H]1c1cccc(Cl)c1F] |
| I-18 | 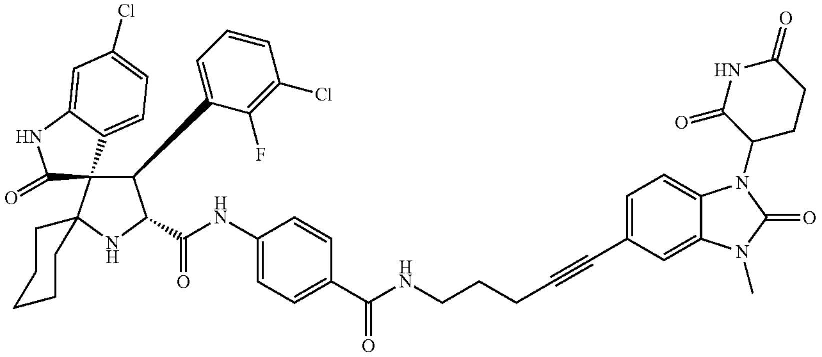 [SMILES: Cn1c(=O)n(C2CCC(=O)NC2=O)c2ccc(C#CCCCNC(=O)c3ccc(NC(=O)[C@@H]4NC5(CCCCC5)[C@@]5(C(=O)Nc6cc(Cl)ccc65)[C@H]4c4cccc(Cl)c4F)cc3)cc21] |

TABLE 1-continued
| Exemplary Compounds | |
|---|---|
| I-# | Structure |
| I-19 | 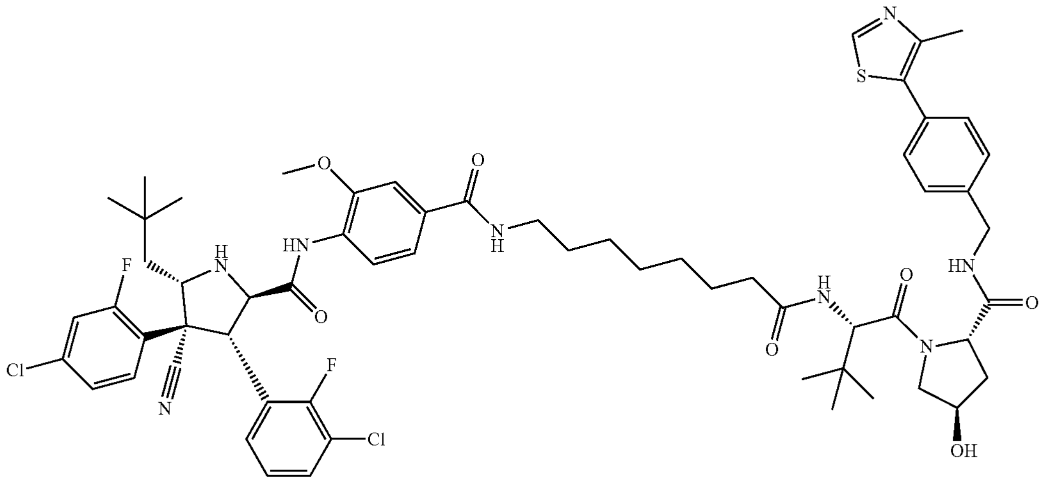 [SMILES: COc1cc(C(=O)NCCCCCCCC(=O)N[C@H](C(=O)N2C[C@H](O)C[C@H]2C(=O)NCc2ccc(-c3scnc3C)cc2)C(C)(C)C)ccc1NC(=O)[C@@H]1N[C@@H](CC(C)(C)C)[C@](C#N)(c2ccc(Cl)cc2F)[C@H]1c1cccc(Cl)c1F] |
| I-20 | 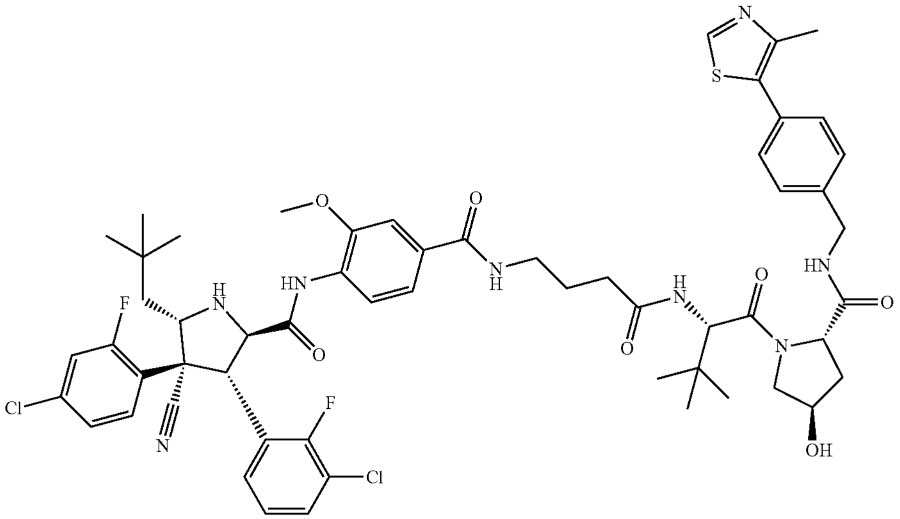 [SMILES: COc1cc(C(=O)NCCCC(=O)N[C@H](C(=O)N2C[C@H](O)C[C@H]2C(=O)NCc2ccc(-c3scnc3C)cc2)C(C)(C)C)ccc1NC(=O)[C@@H]1N[C@@H](CC(C)(C)C)[C@](C#N)(c2ccc(Cl)cc2F)[C@H]1c1cccc(Cl)c1F] |
| I-21 | 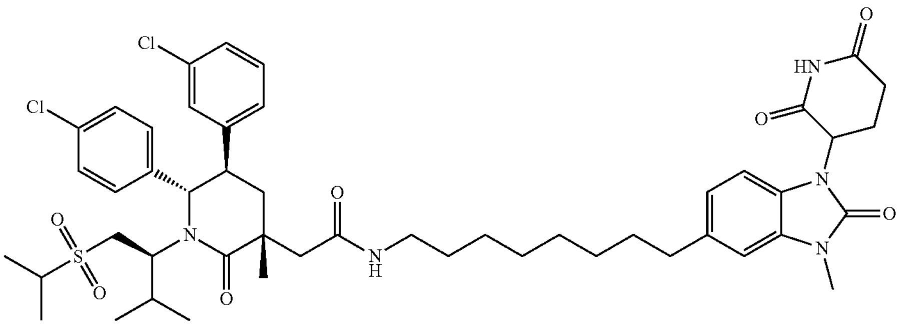 [SMILES: CC(C)[C@@H](CS(=O)(=O)C(C)C)N1C(=O)[C@@](C)(CC(=O)NCCCCCCCCc2ccc3c(c2)n(C)c(=O)n3C2CCC(=O)NC2=O)C[C@H](c2cccc(Cl)c2)[C@H]1c1ccc(Cl)cc1] |

TABLE 1-continued
| Exemplary Compounds | |
|---|---|
| I-# | Structure |
| I-22 | 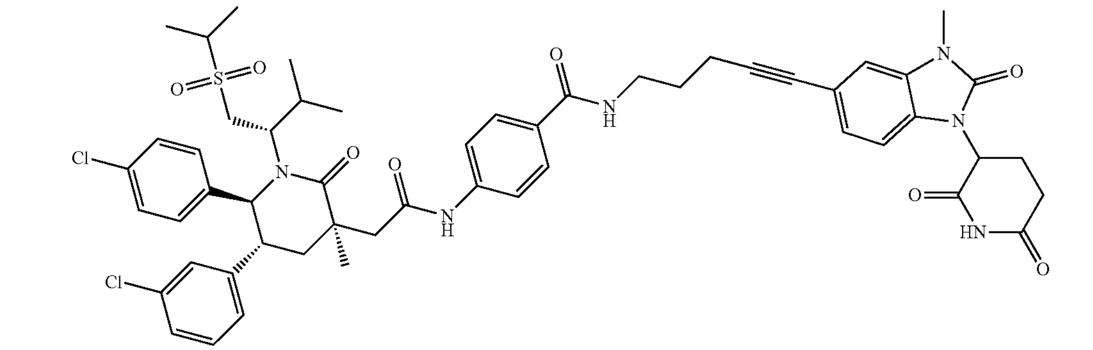 [SMILES: CC(C)[C@@H](CS(=O)(=O)C(C)C)N1C(=O)[C@@](C)(CC(=O)Nc2ccc(C(=O)NCCCC#Cc3ccc4c(c3)n(C)c(=O)n4C3CCC(=O)NC3=O)cc2)C[C@H](c2cccc(Cl)c2)[C@H]1c1ccc(Cl)cc1] |
| I-23 | 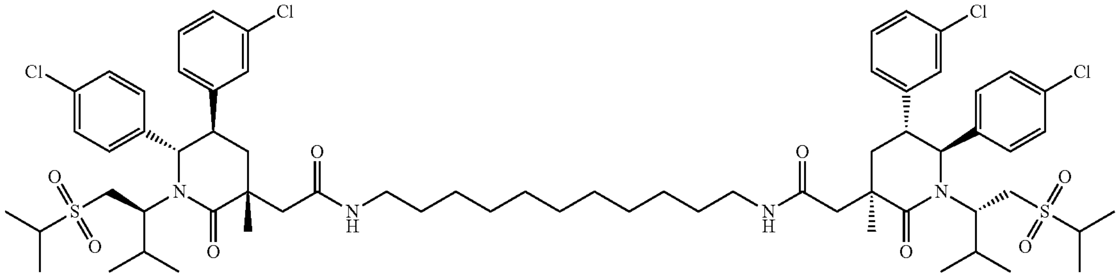 [SMILES: CC(C)[C@@H](CS(=O)(=O)C(C)C)N1C(=O)[C@@](C)(CC(=O)NCCCCCCCCCCCNC(=O)C[C@@]2(C)C[C@H](c3cccc(Cl)c3)[C@@H](c3ccc(Cl)cc3)N([C@H](CS(=O)(=O)C(C)C)C(C)C)C2=O)C[C@H](c2cccc(Cl)c2)[C@H]1c1ccc(Cl)cc1] |
| I-24 | 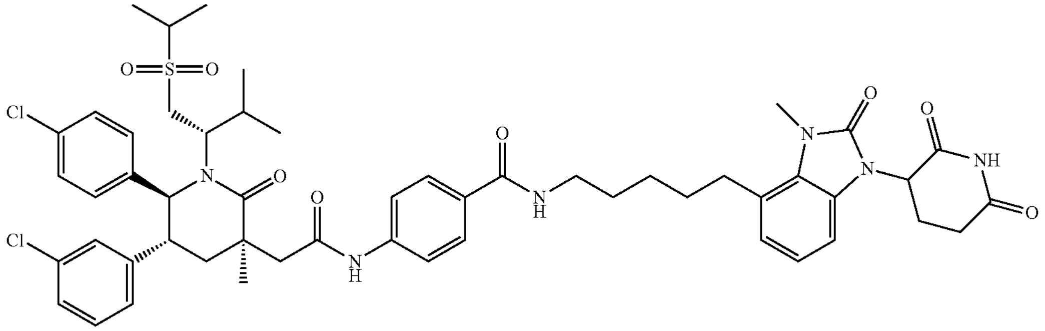 [SMILES: CC(C)[C@@H](CS(=O)(=O)C(C)C)N1C(=O)[C@@](C)(CC(=O)Nc2ccc(C(=O)NCCCCCc3cccc4c3n(C)c(=O)n4C3CCC(=O)NC3=O)cc2)C[C@H](c2cccc(Cl)c2)[C@H]1c1ccc(Cl)cc1] |
| I-25 | 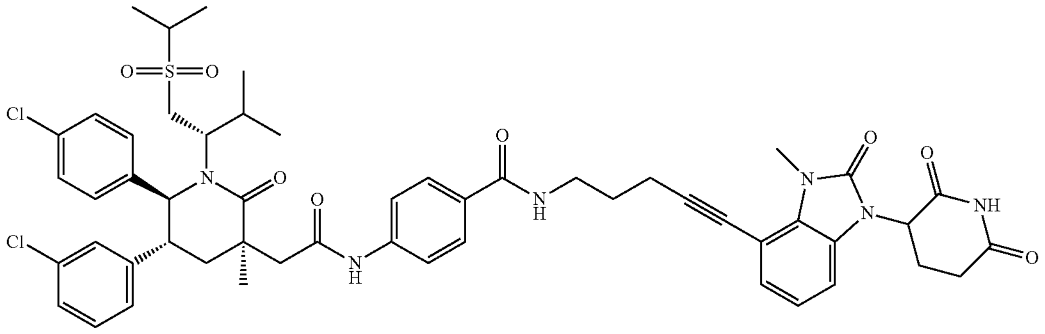 [SMILES: CC(C)[C@@H](CS(=O)(=O)C(C)C)N1C(=O)[C@@](C)(CC(=O)Nc2ccc(C(=O)NCCCC#Cc3cccc4c3n(C)c(=O)n4C3CCC(=O)NC3=O)cc2)C[C@H](c2cccc(Cl)c2)[C@H]1c1ccc(Cl)cc1] |

TABLE 1-continued
| Exemplary Compounds | |
|---|---|
| I-# | Structure |
| I-26 | 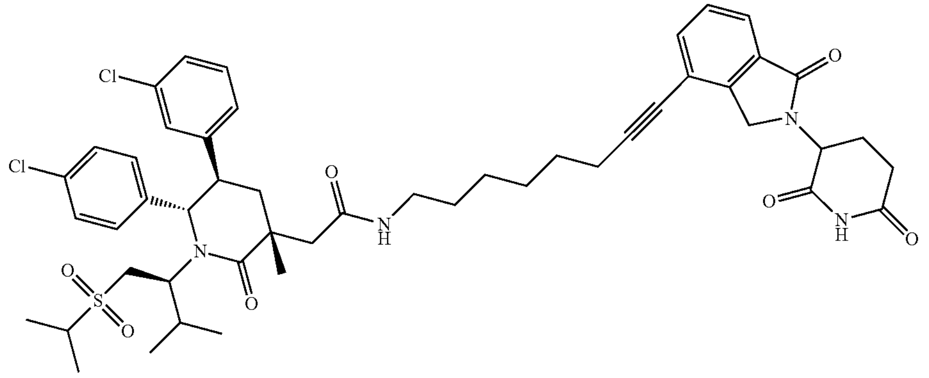 [SMILES: CC(C)[C@@H](CS(=O)(=O)C(C)C)N1C(=O)[C@@](C)(CC(=O)NCCCCCCC#Cc2cccc3c2CN(C2CCC(=O)NC2=O)C3=O)C[C@H](c2cccc(Cl)c2)[C@H]1c1ccc(Cl)cc1] |
| I-27 | 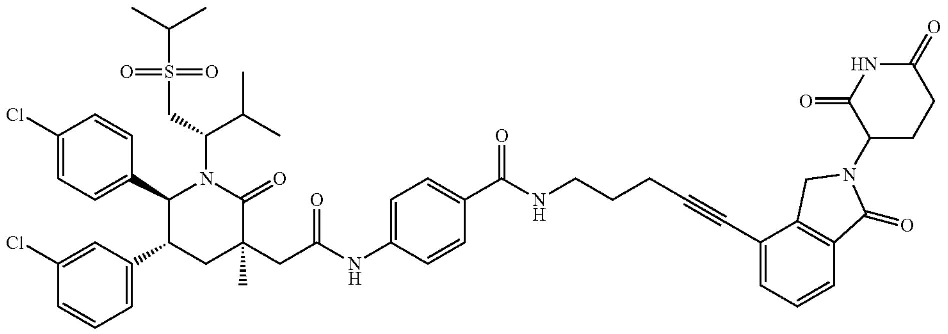 [SMILES: CC(C)[C@@H](CS(=O)(=O)C(C)C)N1C(=O)[C@@](C)(CC(=O)Nc2ccc(C(=O)NCCCC#Cc3cccc4c3CN(C3CCC(=O)NC3=O)C4=O)cc2)C[C@H](c2cccc(Cl)c2)[C@H]1c1ccc(Cl)cc1] |
| I-28 | 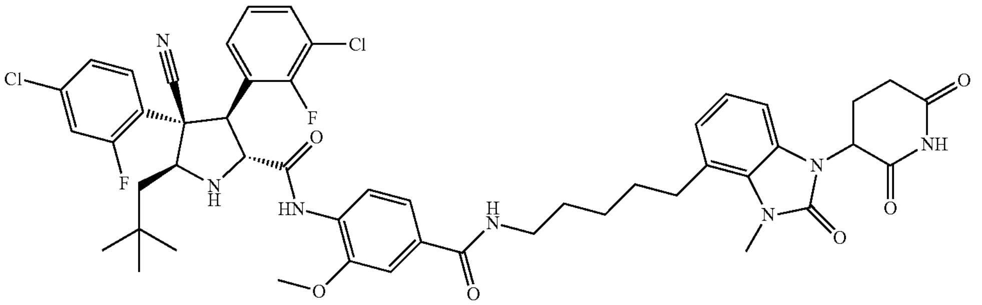 [SMILES: COc1cc(C(=O)NCCCCCc2cccc3c2n(C)c(=O)n3C2CCC(=O)NC2=O)ccc1NC(=O)[C@@H]1N[C@@H](CC(C)(C)C)[C@](C#N)(c2ccc(Cl)cc2F)[C@H]1c1cccc(Cl)c1F] |
| I-29 | 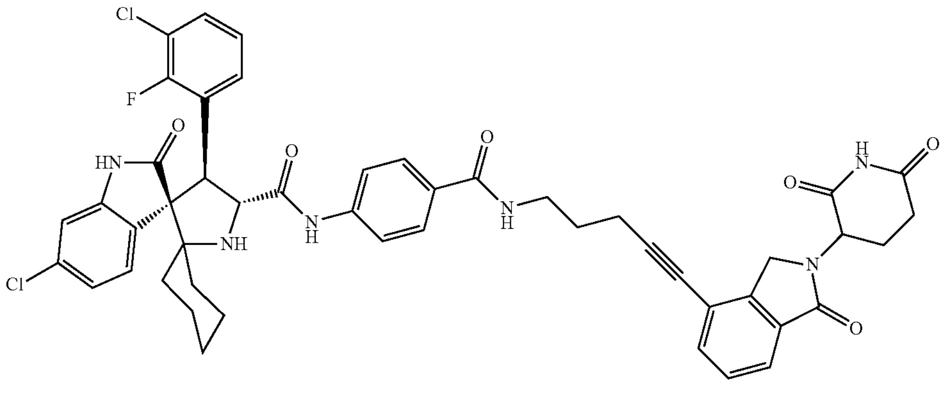 [SMILES: O=C1CCC(N2Cc3c(C#CCCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)cccc3C2=O)C(=O)N1] |

TABLE 1-continued
| Exemplary Compounds | |
|---|---|
| I-# | Structure |
| I-30 | 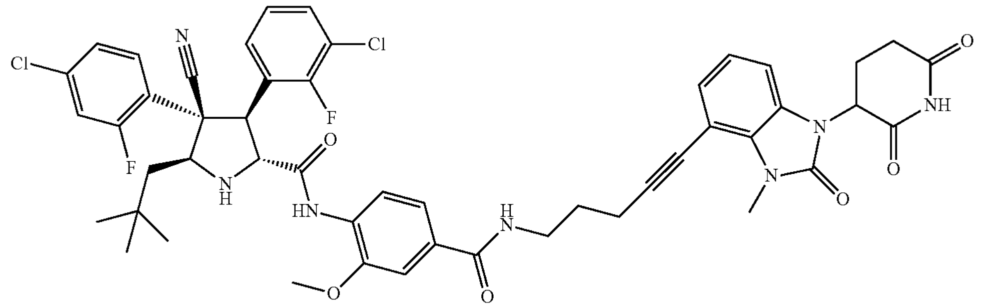 [SMILES: COc1cc(C(=O)NCCCC#Cc2cccc3c2n(C)c(=O)n3C2CCC(=O)NC2=O)ccc1NC(=O)[C@@H]1N[C@@H](CC(C)(C)C)[C@](C#N)(c2ccc(Cl)cc2F)[C@H]1c1cccc(Cl)c1F] |
| I-31 | 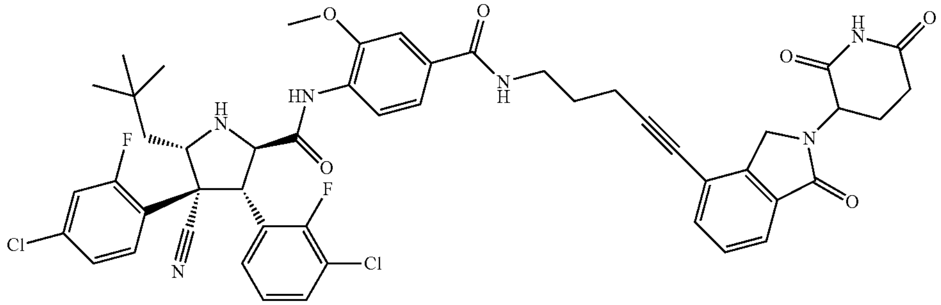 [SMILES: COc1cc(C(=O)NCCCC#Cc2cccc3c2CN(C2CCC(=O)NC2=O)C3=O)ccc1NC(=O)[C@@H]1N[C@@H](CC(C)(C)C)[C@](C#N)(c2ccc(Cl)cc2F)[C@H]1c1cccc(Cl)c1F] |
| I-32 | 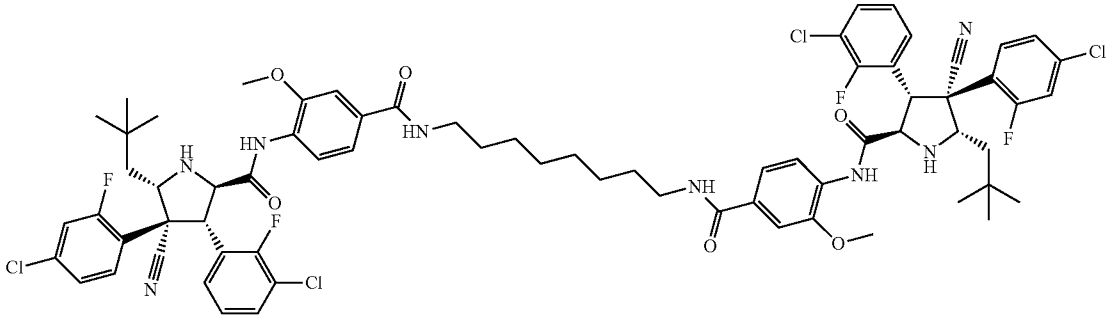 [SMILES: COc1cc(C(=O)NCCCCCCCCNC(=O)c2ccc(NC(=O)[C@@H]3N[C@@H](CC(C)(C)C)[C@](C#N)(c4ccc(Cl)cc4F)[C@H]3c3cccc(Cl)c3F)c(OC)c2)ccc1NC(=O)[C@@H]1N[C@@H](CC(C)(C)C)[C@](C#N)(c2ccc(Cl)cc2F)[C@H]1c1cccc(Cl)c1F] |
| I-33 | 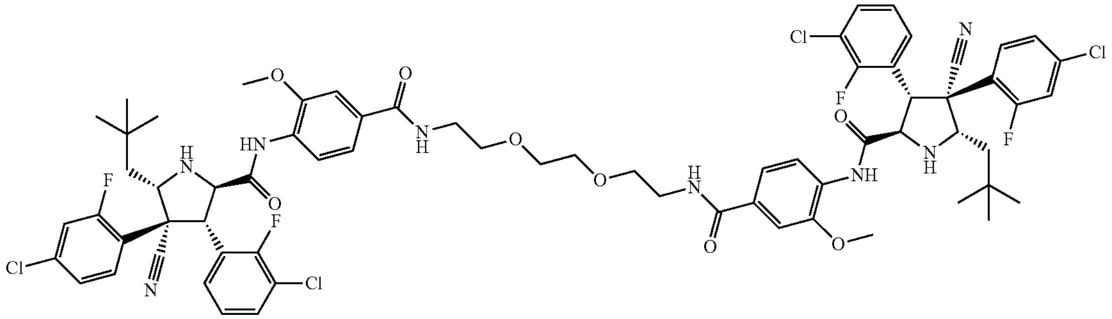 [SMILES: COc1cc(C(=O)NCCOCCOCCNC(=O)c2ccc(NC(=O)[C@@H]3N[C@@H](CC(C)(C)C)[C@](C#N)(c4ccc(Cl)cc4F)[C@H]3c3cccc(Cl)c3F)c(OC)c2)ccc1NC(=O)[C@@H]1N[C@@H](CC(C)(C)C)[C@](C#N)(c2ccc(Cl)cc2F)[C@H]1c1cccc(Cl)c1F] |

TABLE 1-continued
| Exemplary Compounds | |
|---|---|
| I-# | Structure |
| I-34 | 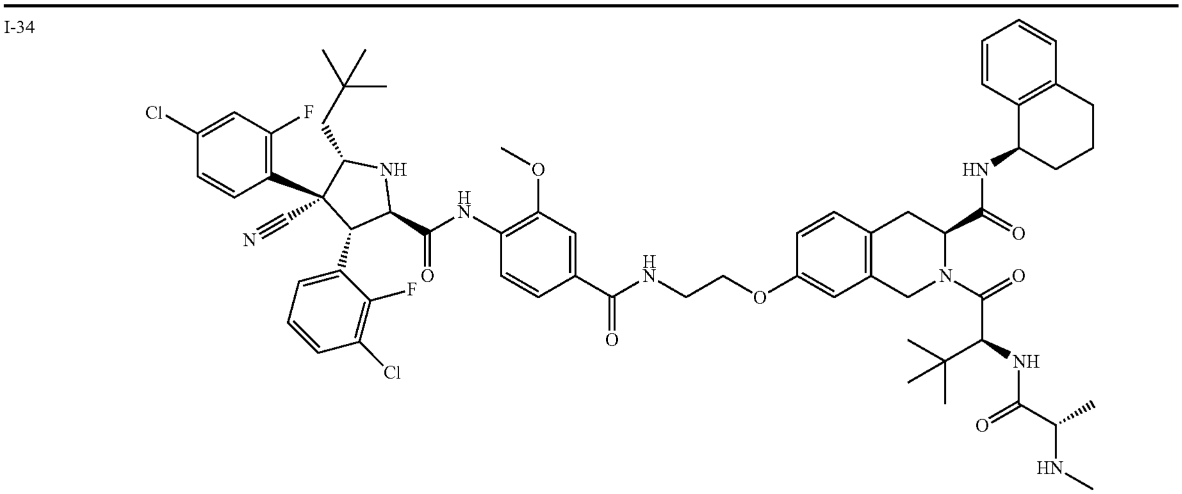 |
| I-35 | 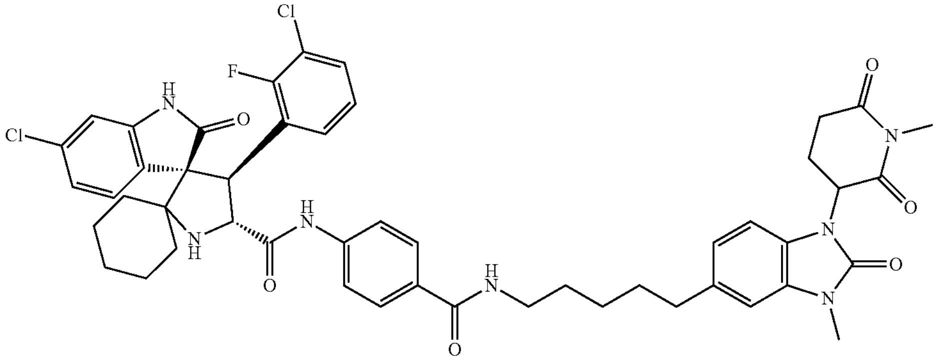 [SMILES: CN1C(=O)CCC(n2c(=O)n(C)c3cc(CCCCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)ccc32)C1=O] |
| I-36 | 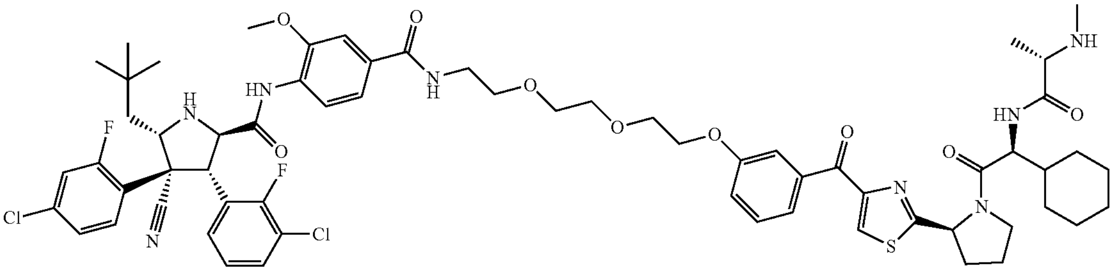 [SMILES: CN[C@@H](C)C(=O)N[C@H](C(=O)N1CCC[C@H]1c1nc(C(=O)c2cccc(OCCOCCOCCNC(=O)c3ccc(NC(=O)[C@@H]4N[C@@H](CC(C)(C)C)[C@](C#N)(c5ccc(Cl)cc5F)[C@H]4c4cccc(Cl)c4F)c(OC)c3)c2)cs1)C1CCCCC1] |
| I-37 | 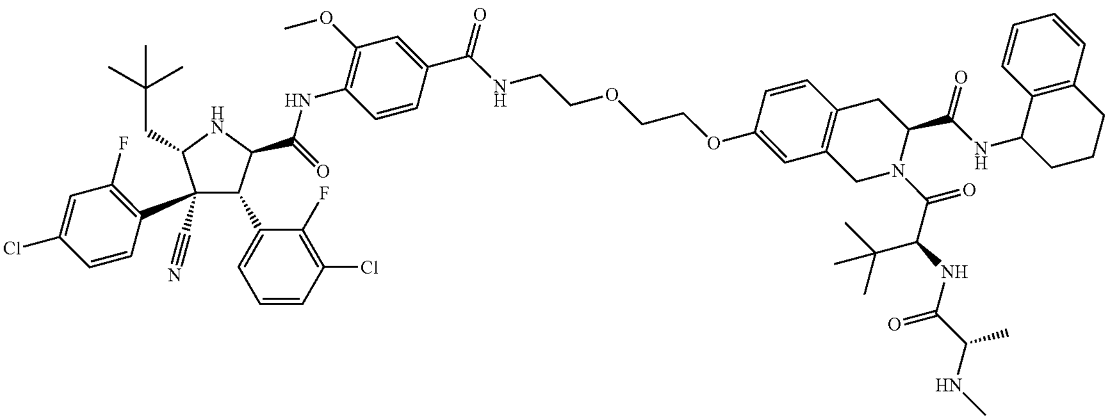 [SMILES: CN[C@@H](C)C(=O)N[C@H](C(=O)N1Cc2cc(OCCOCCNC(=O)c3ccc(NC(=O)[C@@H]4N[C@@H](CC(C)(C)C)[C@](C#N)(c5ccc(Cl)cc5F)[C@H]4c4cccc(Cl)c4F)c(OC)c3)ccc2C[C@H]1C(=O)NC1CCCc2ccccc21)C(C)(C)C] |

TABLE 1-continued
| Exemplary Compounds | |
|---|---|
| I-# | Structure |
| I-38 | 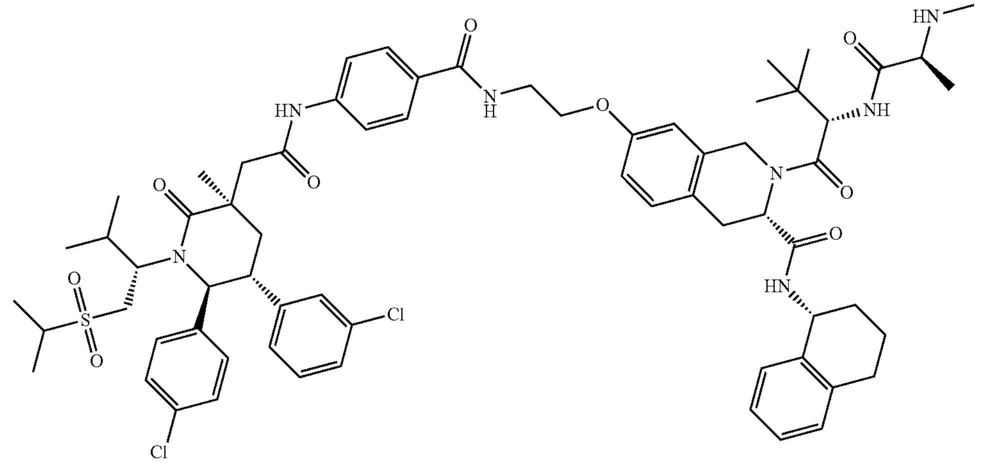 [SMILES: CN[C@@H](C)C(=O)N[C@H](C(=O)N1Cc2cc(OCCNC(=O)c3ccc(NC(=O)C[C@@]4(C)C[C@H](c5cccc(Cl)c5)[C@@H](c5ccc(Cl)cc5)N([C@H](CS(=O)(=O)C(C)C)C(C)C)C4=O)cc3)ccc2C[C@H]1C(=O)N[C@@H]1CCCc2ccccc21)C(C)(C)C] |
| I-39 | 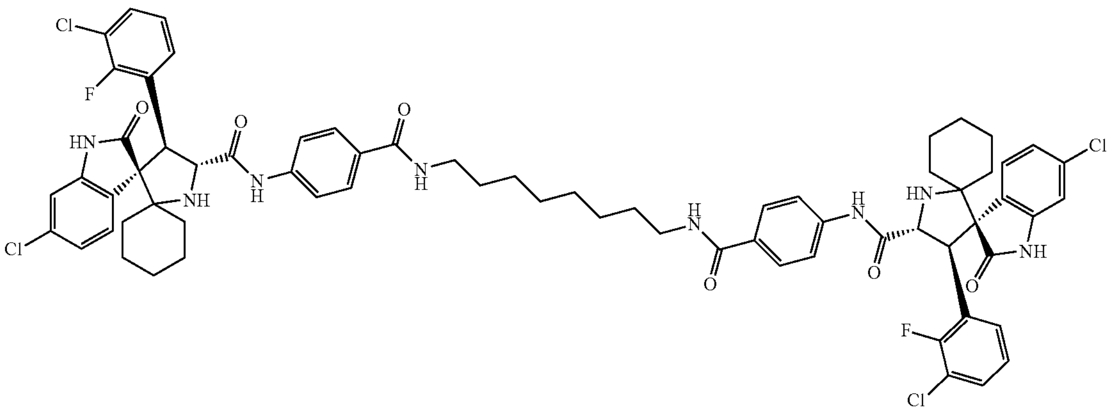 [SMILES: O=C(NCCCCCCCCNC(=O)c1ccc(NC(=O)[C@@H]2NC3(CCCCC3)[C@@]3(C(=O)Nc4cc(Cl)ccc43)[C@H]2c2cccc(Cl)c2F)cc1)c1ccc(NC(=O)[C@@H]2NC3(CCCCC3)[C@@]3(C(=O)Nc4cc(Cl)ccc43)[C@H]2c2cccc(Cl)c2F)cc1] |
| I-40 | 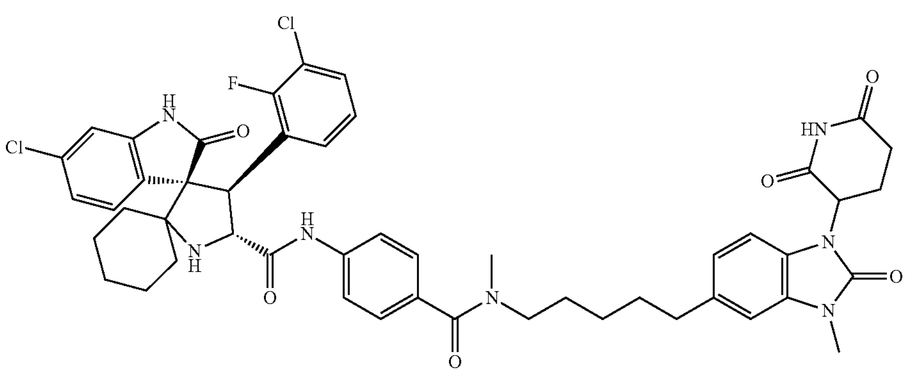 [SMILES: CN(CCCCCc1ccc2c(c1)n(C)c(=O)n2C1CCC(=O)NC1=O)C(=O)c1ccc(NC(=O)[C@@H]2NC3(CCCCC3)[C@@]3(C(=O)Nc4cc(Cl)ccc43)[C@H]2c2cccc(Cl)c2F)cc1] |

TABLE 1-continued
| Exemplary Compounds | |
|---|---|
| I-# | Structure |
| I-41 | 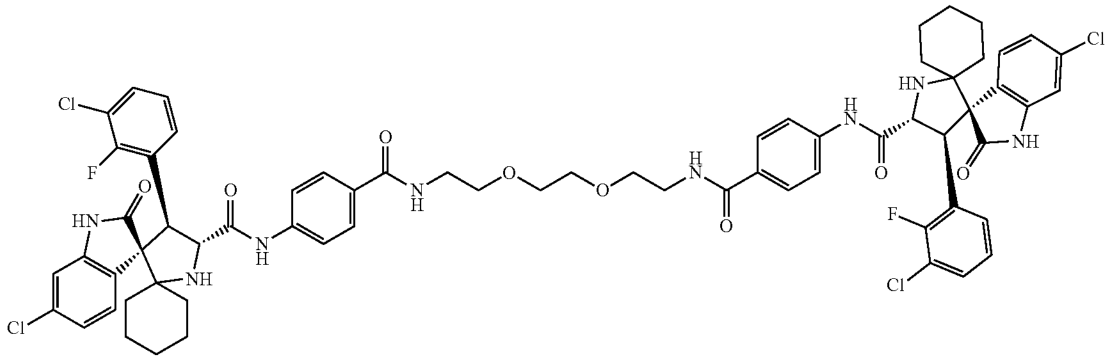 [SMILES: O=C(NCCOCCOCCNC(=O)c1ccc(NC(=O)[C@@H]2NC3(CCCCC3)[C@@]3(C(=O)Nc4cc(Cl)ccc43)[C@H]2c2cccc(Cl)c2F)cc1)c1ccc(NC(=O)[C@@H]2NC3(CCCCC3)[C@@]3(C(=O)Nc4cc(Cl)ccc43)[C@H]2c2cccc(Cl)c2F)cc1] |
| I-42 | 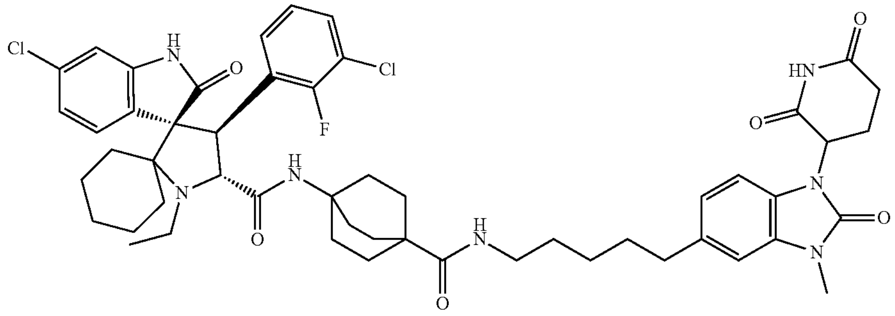 [SMILES: CCN1[C@@H](C(=O)NC23CCC(C(=O)NCCCCCc4ccc5c(c4)n(C)c(=O)n5C4CCC(=O)NC4=O)(CC2)CC3)[C@H](c2cccc(Cl)c2F)[C@]2(C(=O)Nc3cc(Cl)ccc32)C12CCCCC2] |
| I-43 | 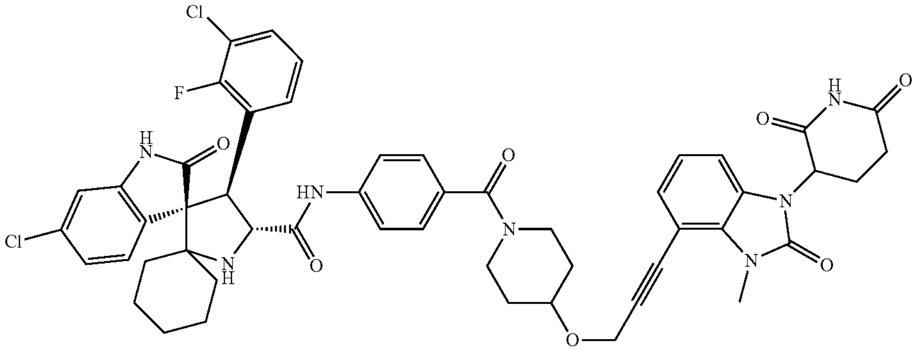 [SMILES: Cn1c(=O)n(C2CCC(=O)NC2=O)c2cccc(C#CCOC3CCN(C(=O)c4ccc(NC(=O)[C@@H]5NC6(CCCCC6)[C@@]6(C(=O)Nc7cc(Cl)ccc76)[C@H]5c5cccc(Cl)c5F)cc4)CC3)c21] |
| I-44 | 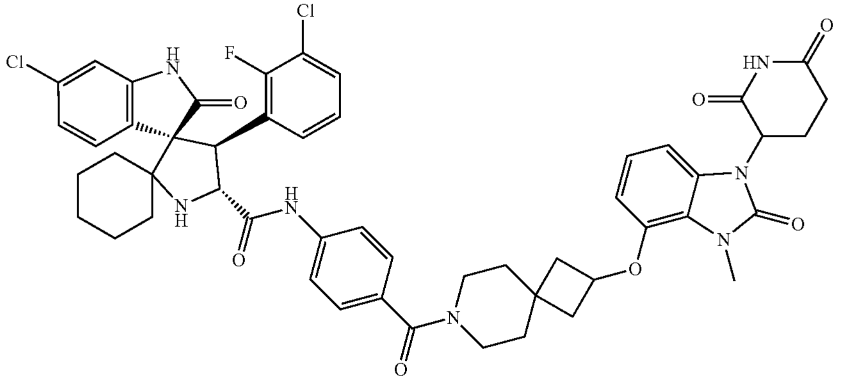 [SMILES: Cn1c(=O)n(C2CCC(=O)NC2=O)c2cccc(OC3CC4(CCN(C(=O)c5ccc(NC(=O)[C@@H]6NC7(CCCCC7)[C@@]7(C(=O)Nc8cc(Cl)ccc87)[C@H]6c6cccc(Cl)c6F)cc5)CC4)C3)c21] |

TABLE 1-continued
| Exemplary Compounds | |
|---|---|
| I-# | Structure |
| I-45 | 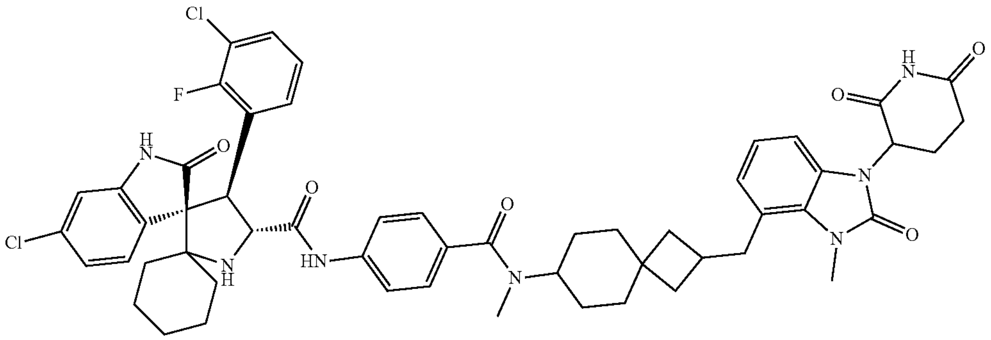 [SMILES: CN(C(=O)c1ccc(NC(=O)[C@@H]2NC3(CCCCC3)[C@@]3(C(=O)Nc4cc(Cl)ccc43)[C@H]2c2cccc(Cl)c2F)cc1)C1CCC2(CC1)CC(Cc1cccc3c1n(C)c(=O)n3C1CCC(=O)NC1=O)C2] |
| I-46 | 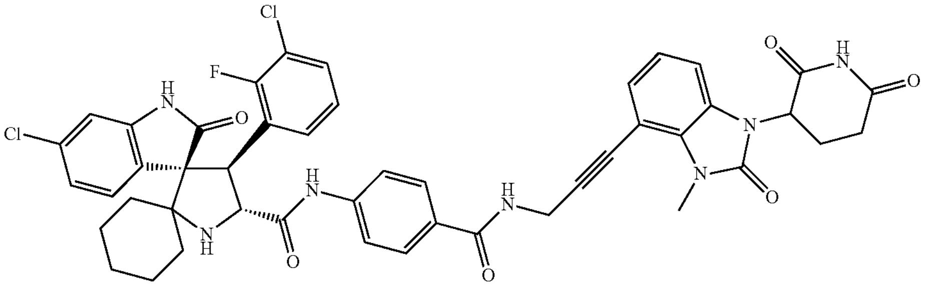 [SMILES: Cn1c(=O)n(C2CCC(=O)NC2=O)c2cccc(C#CCNC(=O)c3ccc(NC(=O)[C@@H]4NC5(CCCCC5)[C@@]5(C(=O)Nc6cc(Cl)ccc65)[C@H]4c4cccc(Cl)c4F)cc3)c21] |
| I-47 | 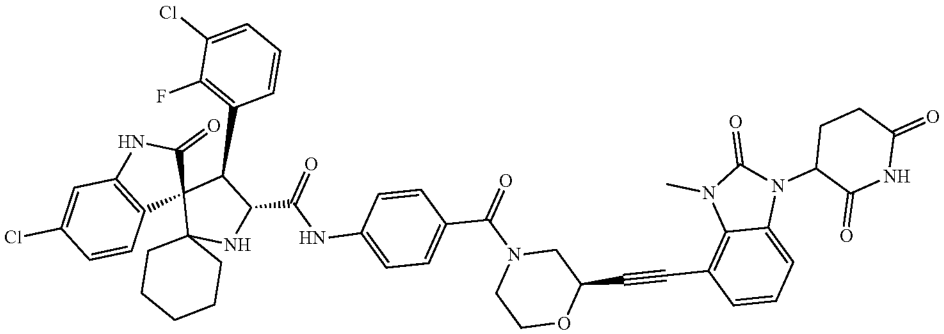 [SMILES: Cn1c(=O)n(C2CCC(=O)NC2=O)c2cccc(C#C[C@@H]3CN(C(=O)c4ccc(NC(=O)[C@@H]5NC6(CCCCC6)[C@@]6(C(=O)Nc7cc(Cl)ccc76)[C@H]5c5cccc(Cl)c5F)cc4)CCO3)c21] |
| I-48 | 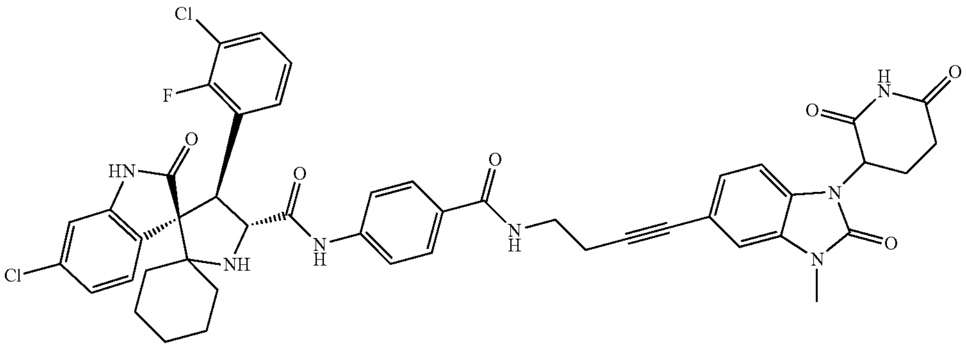 [SMILES: Cn1c(=O)n(C2CCC(=O)NC2=O)c2ccc(C#CCCNC(=O)c3ccc(NC(=O)[C@@H]4NC5(CCCCC5)[C@@]5(C(=O)Nc6cc(Cl)ccc65)[C@H]4c4cccc(Cl)c4F)cc3)cc21] |

TABLE 1-continued
| Exemplary Compounds | |
|---|---|
| I-# | Structure |
| I-49 | 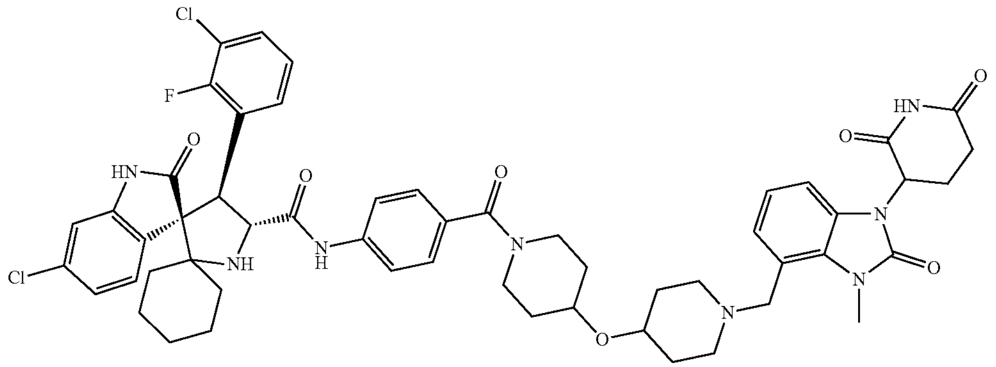 [SMILES: Cn1c(=O)n(C2CCC(=O)NC2=O)c2cccc(CN3CCC(OC4CCN(C(=O)c5ccc(NC(=O)[C@@H]6NC7(CCCCC7)[C@@]7(C(=O)Nc8cc(Cl)ccc87)[C@H]6c6cccc(Cl)c6F)cc5)CC4)CC3)c21] |
| I-50 | 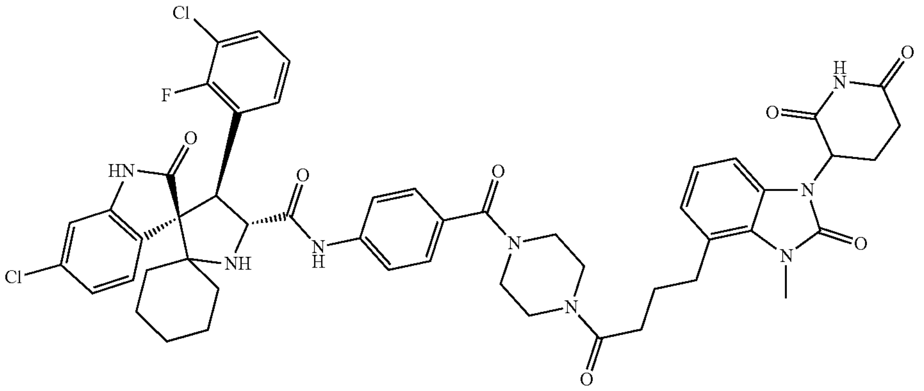 [SMILES: Cn1c(=O)n(C2CCC(=O)NC2=O)c2cccc(CCCC(=O)N3CCN(C(=O)c4ccc(NC(=O)[C@@H]5NC6(CCCCC6)[C@@]6(C(=O)Nc7cc(Cl)ccc76)[C@H]5c5cccc(Cl)c5F)cc4)CC3)c21] |
| I-51 | 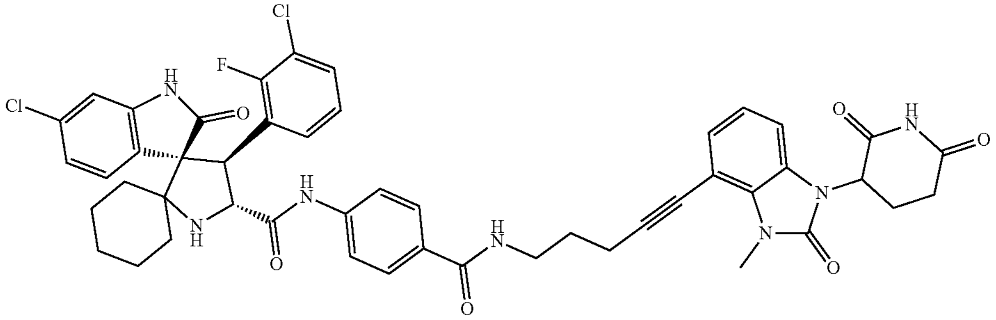 [SMILES: Cn1c(=O)n(C2CCC(=O)NC2=O)c2cccc(C#CCCCNC(=O)c3ccc(NC(=O)[C@@H]4NC5(CCCCC5)[C@@]5(C(=O)Nc6cc(Cl)ccc65)[C@H]4c4cccc(Cl)c4F)cc3)c21] |
| I-52 | 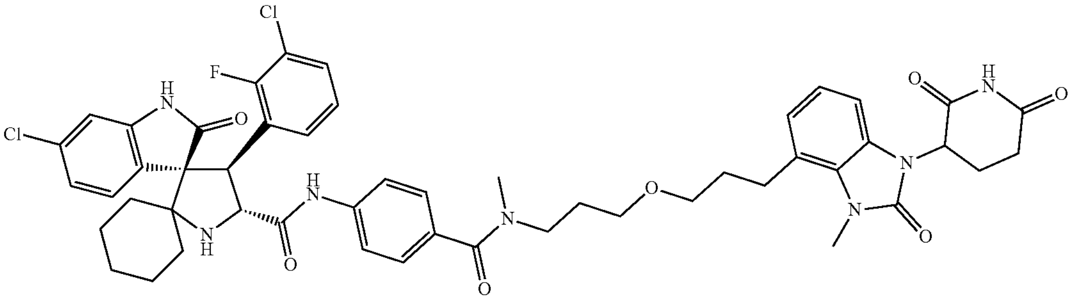 [SMILES: CN(CCCOCCCc1cccc2c1n(C)c(=O)n2C1CCC(=O)NC1=O)C(=O)c1ccc(NC(=O)[C@@H]2NC3(CCCCC3)[C@@]3(C(=O)Nc4cc(Cl)ccc43)[C@H]2c2cccc(Cl)c2F)cc1] |

TABLE 1-continued
| Exemplary Compounds | |
|---|---|
| I-# | Structure |
| I-53 | 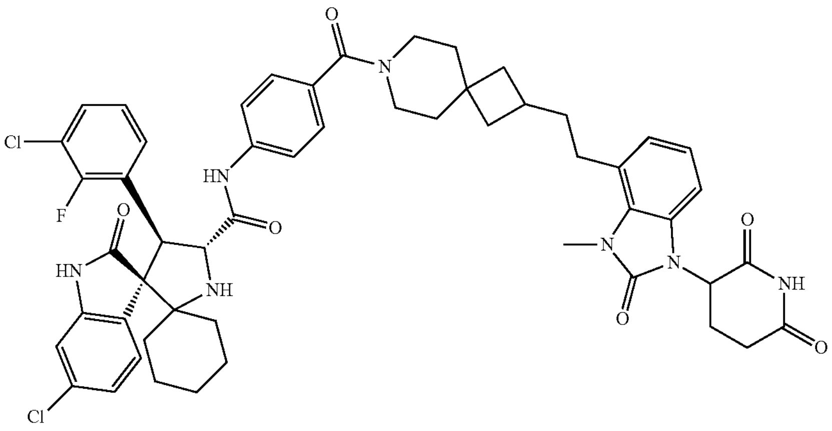 [SMILES: Cn1c(=O)n(C2CCC(=O)NC2=O)c2cccc(CCC3CC4(CCN(C(=O)c5ccc(NC(=O)[C@@H]6NC7(CCCCC7)[C@@]7(C(=O)Nc8cc(Cl)ccc87)[C@H]6c6cccc(Cl)c6F)cc5)CC4)C3)c21] |
| I-54 | 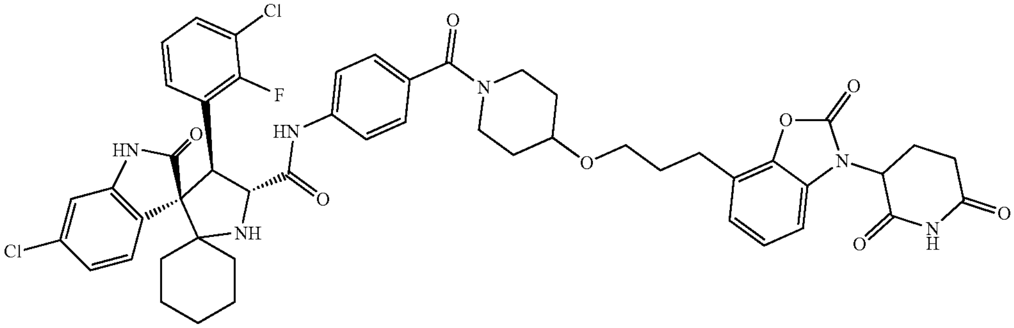 [SMILES: O=C1CCC(n2c(=O)oc3c(CCCOC4CCN(C(=O)c5ccc(NC(=O)[C@@H]6NC7(CCCCC7)[C@@]7(C(=O)Nc8cc(Cl)ccc87)[C@H]6c6cccc(Cl)c6F)cc5)CC4)cccc32)C(=O)N1] |
| I-55 | 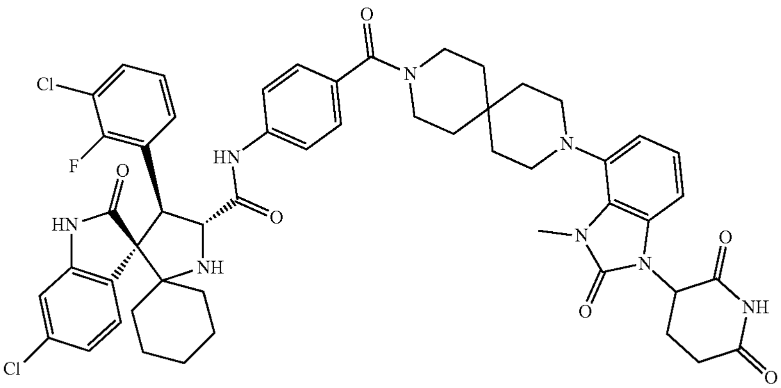 [SMILES: Cn1c(=O)n(C2CCC(=O)NC2=O)c2cccc(N3CCC4(CCN(C(=O)c5ccc(NC(=O)[C@@H]6NC7(CCCCC7)[C@@]7(C(=O)Nc8cc(Cl)ccc87)[C@H]6c6cccc(Cl)c6F)cc5)CC4)CC3)c21] |
| I-56 | 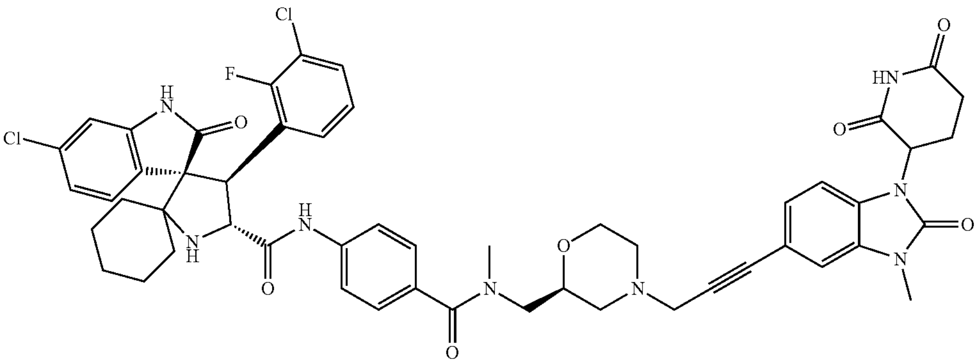 [SMILES: CN(C[C@@H]1CN(CC#Cc2ccc3c(c2)n(C)c(=O)n3C2CCC(=O)NC2=O)CCO1)C(=O)c1ccc(NC(=O)[C@@H]2NC3(CCCCC3)[C@@]3(C(=O)Nc4cc(Cl)ccc43)[C@H]2c2cccc(Cl)c2F)cc1] |

TABLE 1-continued
| Exemplary Compounds | |
|---|---|
| I-# | Structure |
| I-57 | 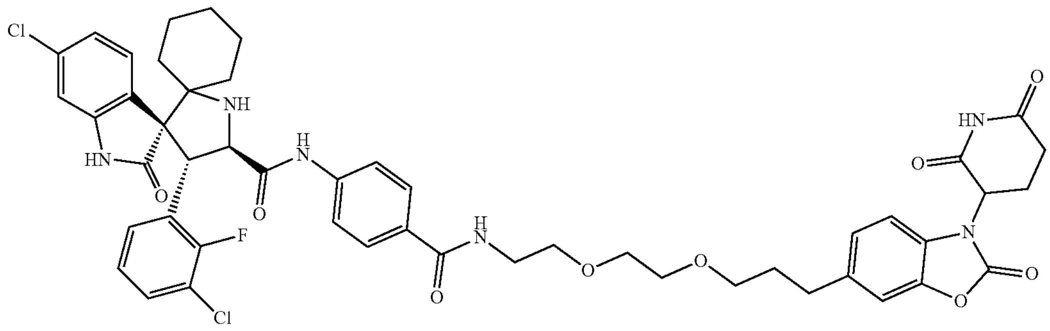 [SMILES: O=C1CCC(n2c(=O)oc3cc(CCCOCCOCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)ccc32)C(=O)N1] |
| I-58 | 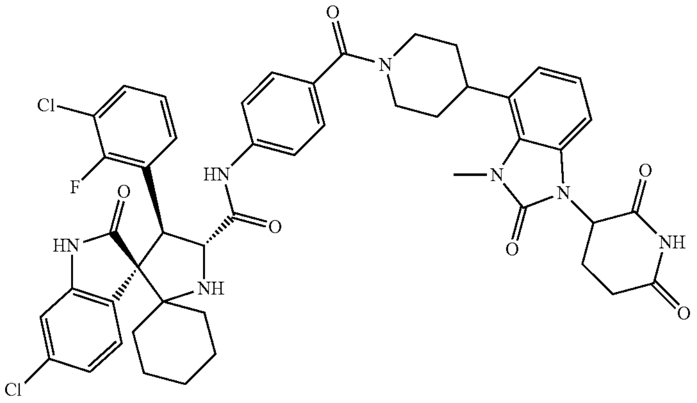 [SMILES: Cn1c(=O)n(C2CCC(=O)NC2=O)c2cccc(C3CCN(C(=O)c4ccc(NC(=O)[C@@H]5NC6(CCCCC6)[C@@]6(C(=O)Nc7cc(Cl)ccc76)[C@H]5c5cccc(Cl)c5F)cc4)CC3)c21] |
| I-59 | 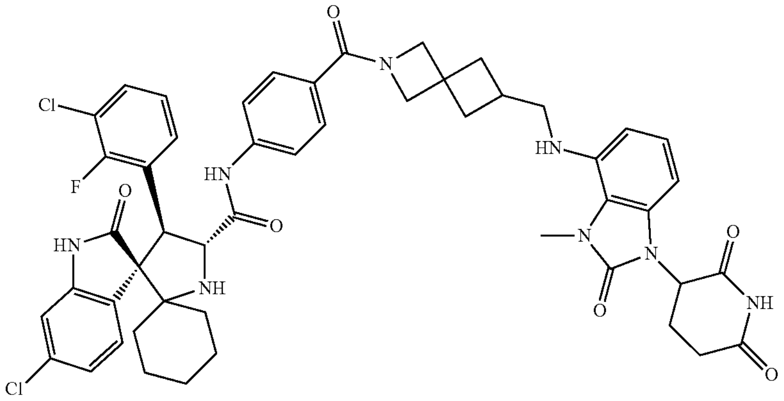 [SMILES: Cn1c(=O)n(C2CCC(=O)NC2=O)c2cccc(NCC3CC4(C3)CN(C(=O)c3ccc(NC(=O)[C@@H]5NC6(CCCCC6)[C@@]6(C(=O)Nc7cc(Cl)ccc76)[C@H]5c5cccc(Cl)c5F)cc3)C4)c21] |
| I-60 | 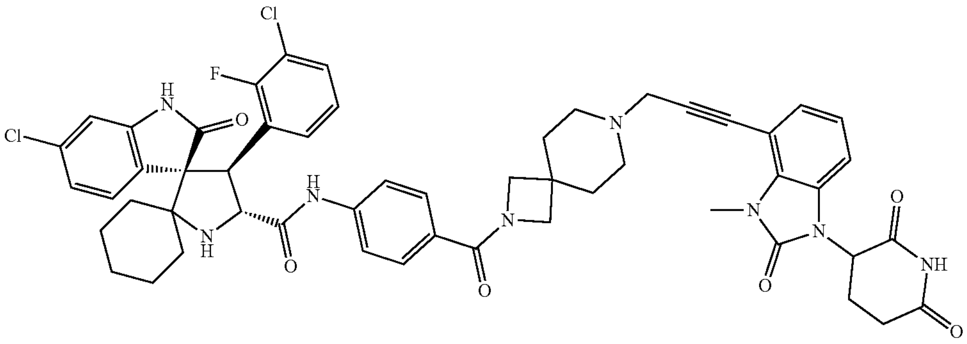 [SMILES: Cn1c(=O)n(C2CCC(=O)NC2=O)c2cccc(C#CCN3CCC4(CC3)CN(C(=O)c3ccc(NC(=O)[C@@H]5NC6(CCCCC6)[C@@]6(C(=O)Nc7cc(Cl)ccc76)[C@H]5c5cccc(Cl)c5F)cc3)C4)c21] |

TABLE 1-continued
| Exemplary Compounds | |
|---|---|
| I-# | Structure |
| I-61 | 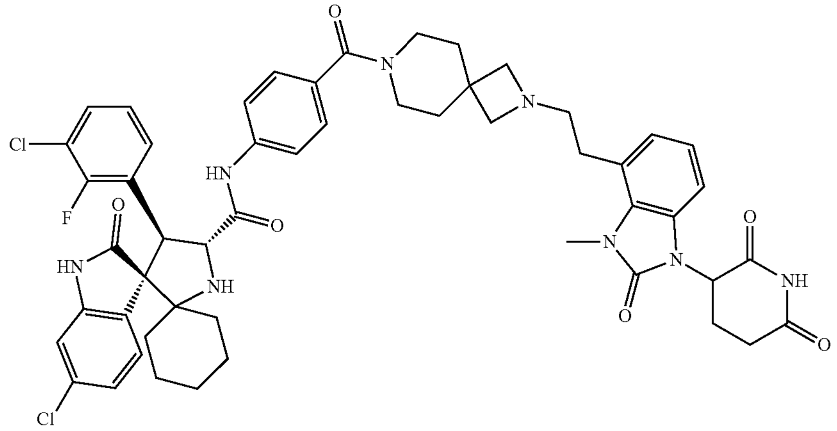 [SMILES: Cn1c(=O)n(C2CCC(=O)NC2=O)c2cccc(CCN3CC4(CCN(C(=O)c5ccc(NC(=O)[C@@H]6NC7(CCCCC7)[C@@]7(C(=O)Nc8cc(Cl)ccc87)[C@H]6c6cccc(Cl)c6F)cc5)CC4)C3)c21] |
| I-62 | 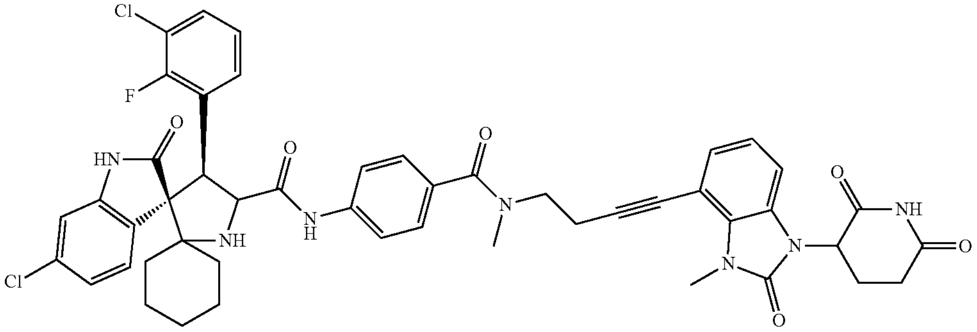 [SMILES: CN(CCC#Cc1cccc2c1n(C)c(=O)n2C1CCC(=O)NC1=O)C(=O)c1ccc(NC(=O)C2NC3(CCCCC3)[C@@]3(C(=O)Nc4cc(Cl)ccc43)[C@H]2c2cccc(Cl)c2F)cc1] |
| I-63 | 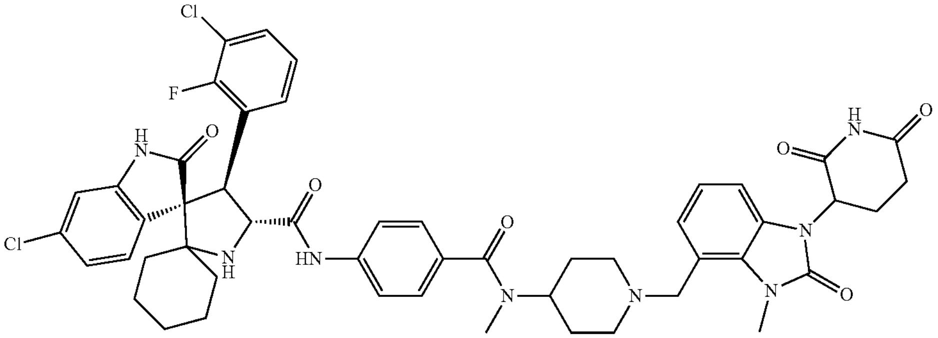 [SMILES: CN(C(=O)c1ccc(NC(=O)[C@@H]2NC3(CCCCC3)[C@@]3(C(=O)Nc4cc(Cl)ccc43)[C@H]2c2cccc(Cl)c2F)cc1)C1CCN(Cc2cccc3c2n(C)c(=O)n3C2CCC(=O)NC2=O)CC1] |
| I-64 | 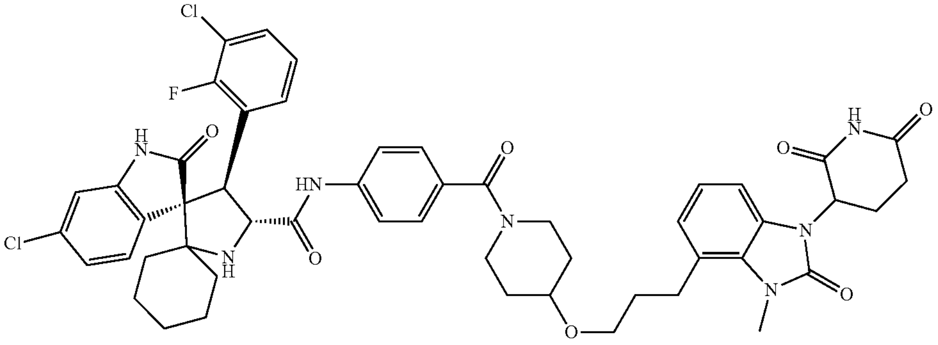 [SMILES: Cn1c(=O)n(C2CCC(=O)NC2=O)c2cccc(CCCOC3CCN(C(=O)c4ccc(NC(=O)[C@@H]5NC6(CCCCC6)[C@@]6(C(=O)Nc7cc(Cl)ccc76)[C@H]5c5cccc(Cl)c5F)cc4)CC3)c21] |

TABLE 1-continued
| Exemplary Compounds | |
|---|---|
| I-# | Structure |
| I-65 | 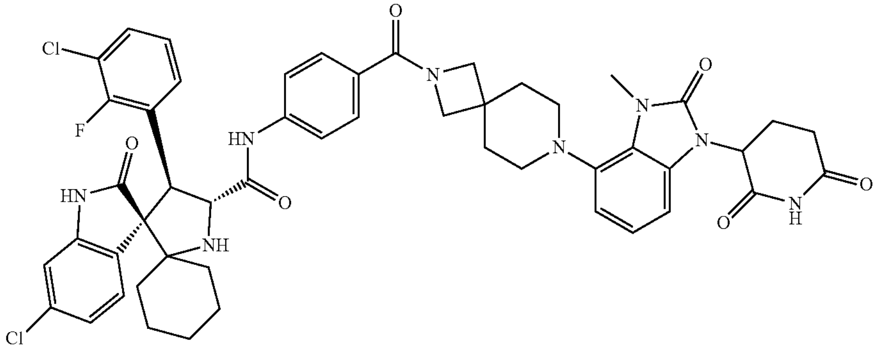 [SMILES: Cn1c(=O)n(C2CCC(=O)NC2=O)c2cccc(N3CCC4(CC3)CN(C(=O)c3ccc(NC(=O)[C@@H]5NC6(CCCCC6)[C@@]6(C(=O)Nc7cc(Cl)ccc76)[C@H]5c5cccc(Cl)c5F)cc3)C4)c21] |
| I-66 | 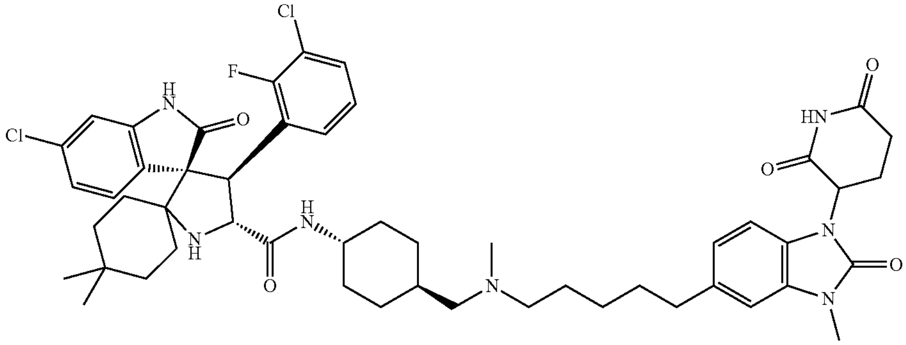 [SMILES: CN(CCCCCc1ccc2c(c1)n(C)c(=O)n2C1CCC(=O)NC1=O)C[C@H]1CC[C@H](NC(=O)[C@@H]2NC3(CCC(C)(C)CC3)[C@@]3(C(=O)Nc4cc(Cl)ccc43)[C@H]2c2cccc(Cl)c2F)CC1] |
| I-67 | 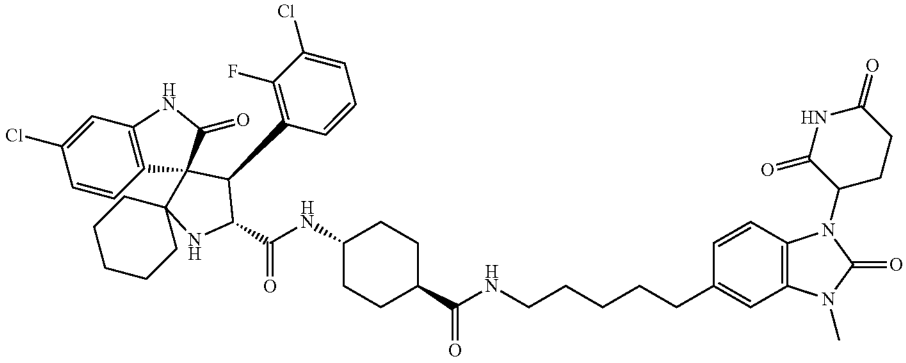 [SMILES: Cn1c(=O)n(C2CCC(=O)NC2=O)c2ccc(CCCCCNC(=O)[C@H]3CC[C@H](NC(=O)[C@@H]4NC5(CCCCC5)[C@@]5(C(=O)Nc6cc(Cl)ccc65)[C@H]4c4cccc(Cl)c4F)CC3)cc21] |
| I-68 | 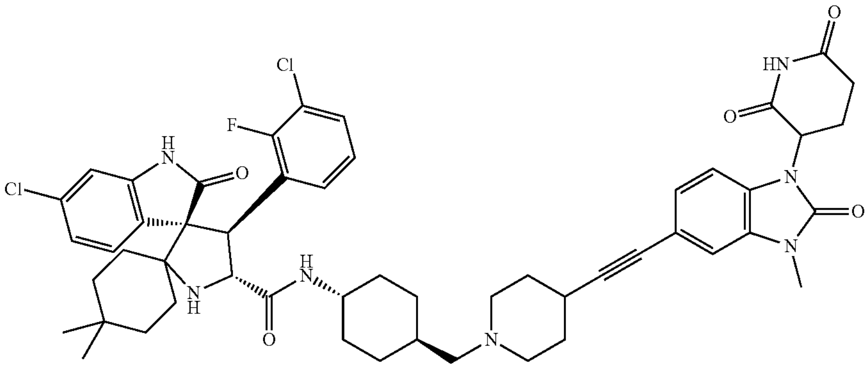 [SMILES: Cn1c(=O)n(C2CCC(=O)NC2=O)c2ccc(C#CC3CCN(C[C@H]4CC[C@H](NC(=O)[C@@H]5NC6(CCC(C)(C)CC6)[C@@]6(C(=O)Nc7cc(Cl)ccc76)[C@H]5c5cccc(Cl)c5F)CC4)CC3)cc21] |

TABLE 1-continued
| Exemplary Compounds | |
|---|---|
| I-# | Structure |
| I-69 | 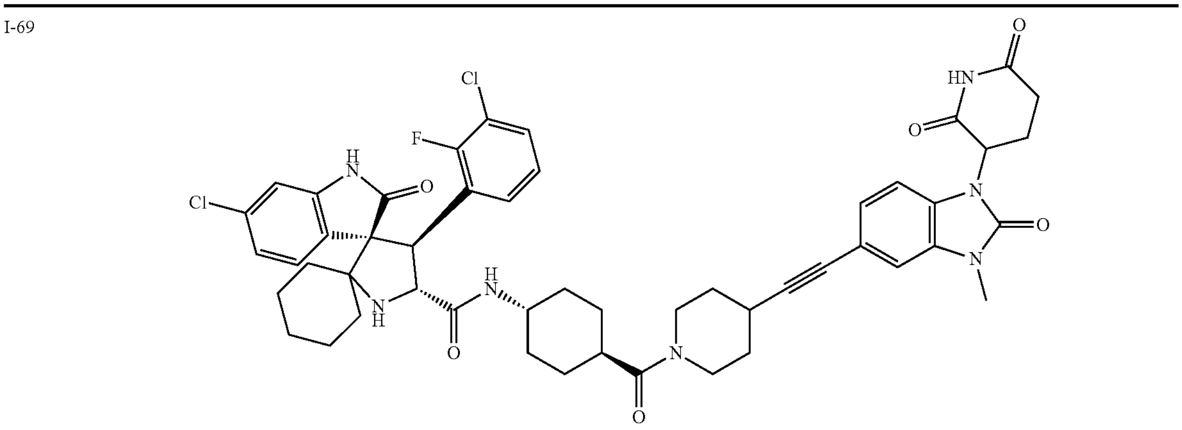 |
| I-70 | 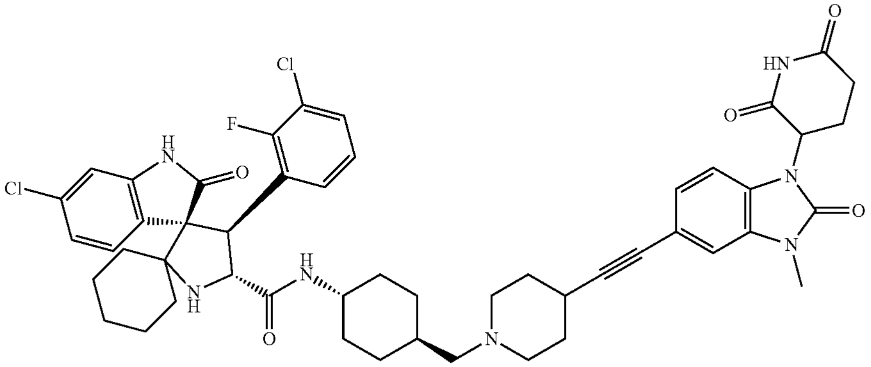 [SMILES: Cn1c(=O)n(C2CCC(=O)NC2=O)c2ccc(C#CC3CCN(C[C@H]4CC[C@H](NC(=O)[C@@H]5NC6(CCCCC6)[C@@]6(C(=O)Nc7cc(Cl)ccc76)[C@H]5c5cccc(Cl)c5F)CC4)CC3)cc21] |
| I-71 | 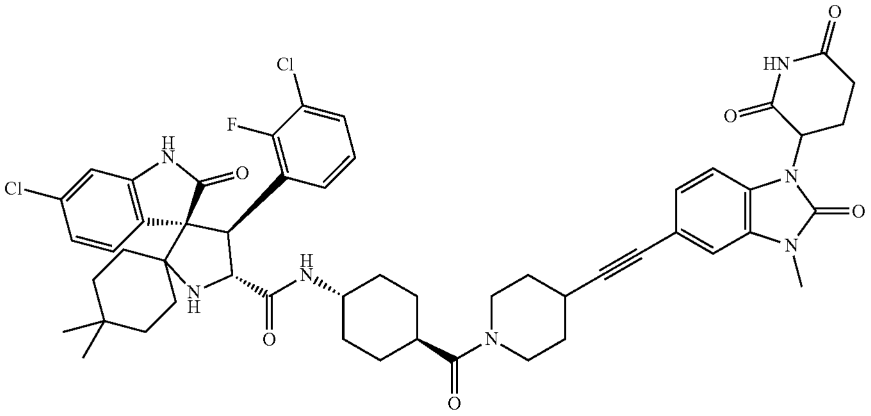 [SMILES: Cn1c(=O)n(C2CCC(=O)NC2=O)c2ccc(C#CC3CCN(C(=O)[C@H]4CC[C@H](NC(=O)[C@@H]5NC6(CCC(C)(C)CC6)[C@@]6(C(=O)Nc7cc(Cl)ccc76)[C@H]5c5cccc(Cl)c5F)CC4)CC3)cc21] |
| I-72 | 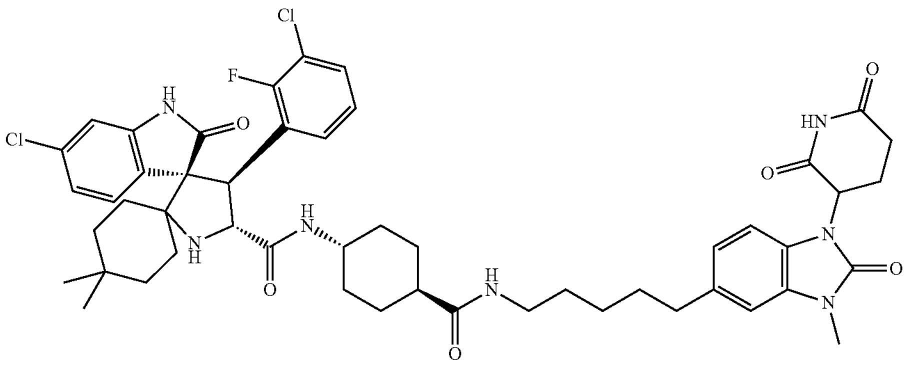 [SMILES: Cn1c(=O)n(C2CCC(=O)NC2=O)c2ccc(CCCCCNC(=O)[C@H]3CC[C@H](NC(=O)[C@@H]4NC5(CCC(C)(C)CC5)[C@@]5(C(=O)Nc6cc(Cl)ccc65)[C@H]4c4cccc(Cl)c4F)CC3)cc21] |

TABLE 1-continued
| Exemplary Compounds | |
|---|---|
| I-# | Structure |
| I-73 | 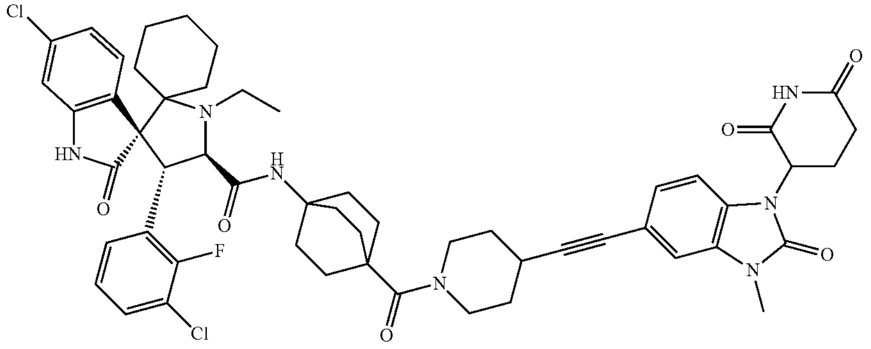 [SMILES: CCN1[C@@H](C(=O)NC23CCC(C(=O)N4CCC(C#Cc5ccc6c(c5)n(C)c(=O)n6C5CCC(=O)NC5=O)CC4)(CC2)CC3)[C@H](c2cccc(Cl)c2F)[C@]2(C(=O)Nc3cc(Cl)ccc32)C12CCCCC2] |
| I-75 | 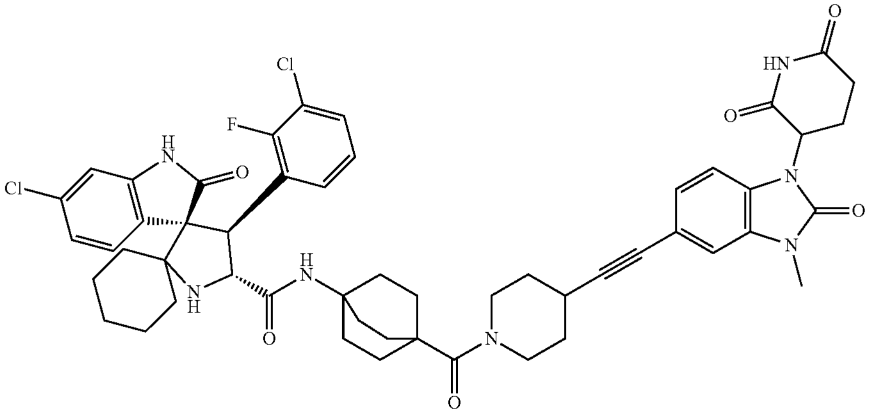 [SMILES: Cn1c(=O)n(C2CCC(=O)NC2=O)c2ccc(C#CC3CCN(C(=O)C45CCC(NC(=O)[C@@H]6NC7(CCCCC7)[C@@]7(C(=O)Nc8cc(Cl)ccc87)[C@H]6c6cccc(Cl)c6F)(CC4)CC5)CC3)cc21] |
| I-76 | 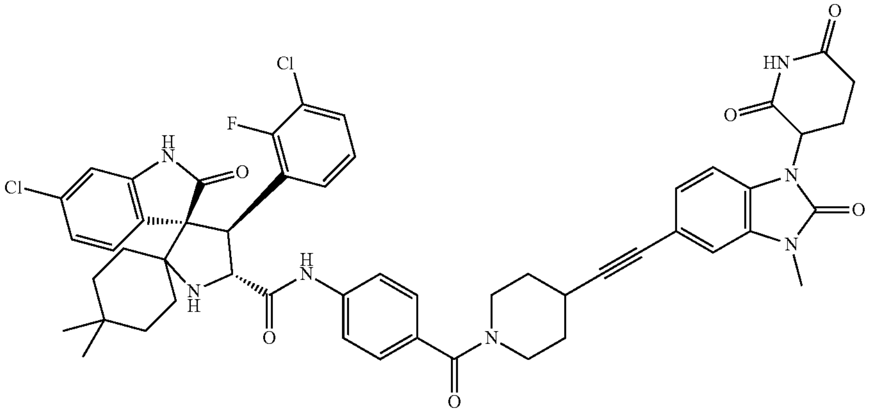 [SMILES: Cn1c(=O)n(C2CCC(=O)NC2=O)c2ccc(C#CC3CCN(C(=O)c4ccc(NC(=O)[C@@H]5NC6(CCC(C)(C)CC6)[C@@]6(C(=O)Nc7cc(Cl)ccc76)[C@H]5c5cccc(Cl)c5F)cc4)CC3)cc21] |
| I-77 | 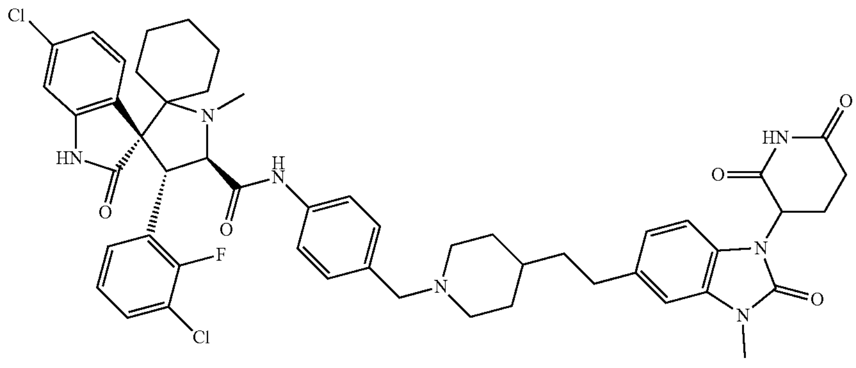 [SMILES: CN1[C@@H](C(=O)Nc2ccc(CN3CCC(CCc4ccc5c(c4)n(C)c(=O)n5C4CCC(=O)NC4=O)CC3)cc2)[C@H](c2cccc(Cl)c2F)[C@]2(C(=O)Nc3cc(Cl)ccc32)C12CCCCC2] |

TABLE 1-continued
| Exemplary Compounds | |
|---|---|
| I-# | Structure |
| I-78 | 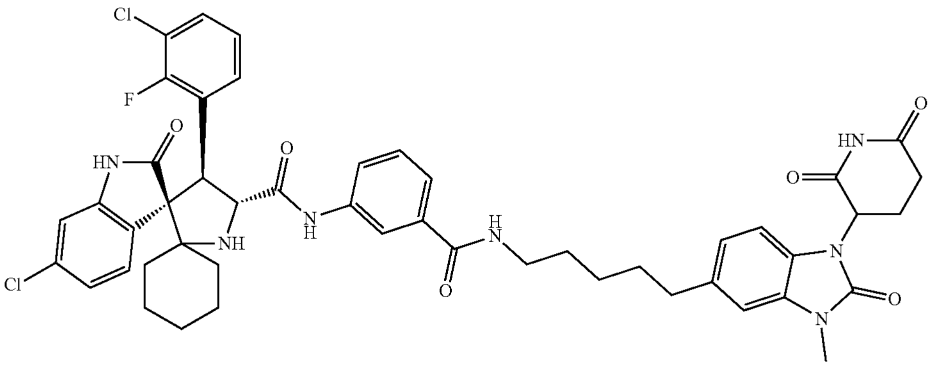 [SMILES: Cn1c(=O)n(C2CCC(=O)NC2=O)c2ccc(CCCCCNC(=O)c3cccc(NC(=O)[C@@H]4NC5(CCCCC5)[C@@]5(C(=O)Nc6cc(Cl)ccc65)[C@H]4c4cccc(Cl)c4F)c3)cc21] |
| I-74 | 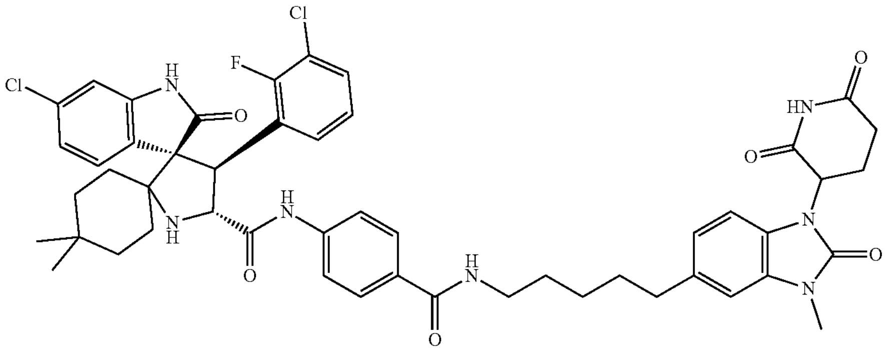 [SMILES: Cn1c(=O)n(C2CCC(=O)NC2=O)c2ccc(CCCCCNC(=O)c3ccc(NC(=O)[C@@H]4NC5(CCC(C)(C)CC5)[C@@]5(C(=O)Nc6cc(Cl)ccc65)[C@H]4c4cccc(Cl)c4F)cc3)cc21] |
| I-79 | 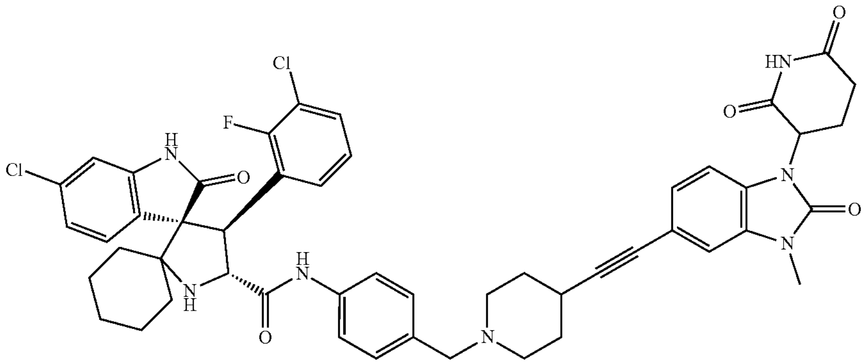 [SMILES: Cn1c(=O)n(C2CCC(=O)NC2=O)c2ccc(C#CC3CCN(Cc4ccc(NC(=O)[C@@H]5NC6(CCCCC6)[C@@]6(C(=O)Nc7cc(Cl)ccc76)[C@H]5c5cccc(Cl)c5F)cc4)CC3)cc21] |
| I-80 | 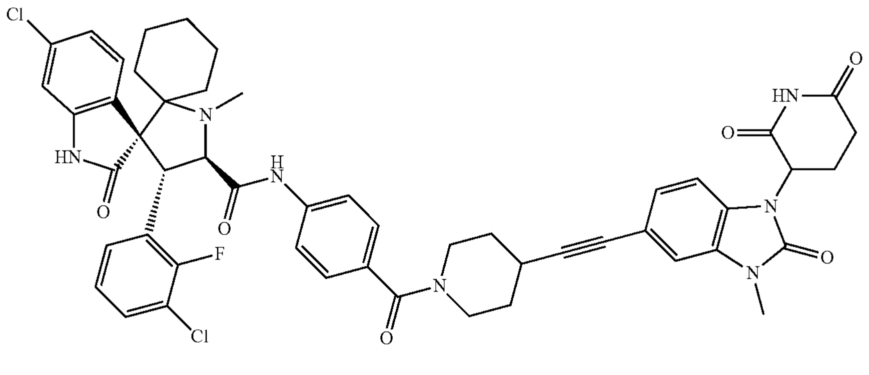 [SMILES: CN1[C@@H](C(=O)Nc2ccc(C(=O)N3CCC(C#Cc4ccc5c(c4)n(C)c(=O)n5C4CCC(=O)NC4=O)CC3)cc2)[C@H](c2cccc(Cl)c2F)[C@]2(C(=O)Nc3cc(Cl)ccc32)C12CCCCC2] |

TABLE 1-continued
| Exemplary Compounds | |
|---|---|
| I-# | Structure |
| I-81 | 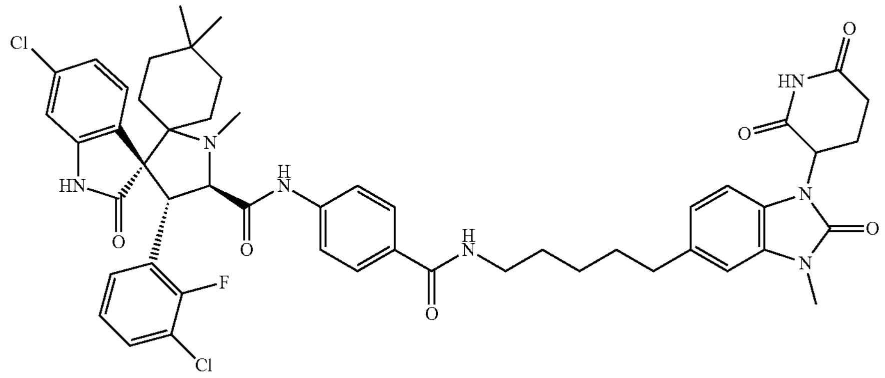 [SMILES: CN1[C@@H](C(=O)Nc2ccc(C(=O)NCCCCCc3ccc4c(c3)n(C)c(=O)n4C3CCC(=O)NC3=O)cc2)[C@H](c2cccc(Cl)c2F)[C@]2(C(=O)Nc3cc(Cl)ccc32)C12CCC(C)(C)CC2] |
| I-82 | 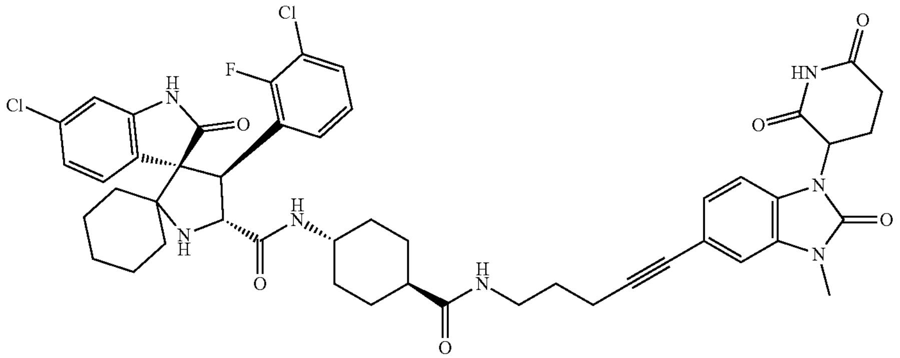 [SMILES: Cn1c(=O)n(C2CCC(=O)NC2=O)c2ccc(C#CCCCNC(=O)[C@H]3CC[C@H](NC(=O)[C@@H]4NC5(CCCCC5)[C@@]5(C(=O)Nc6cc(Cl)ccc65)[C@H]4c4cccc(Cl)c4F)CC3)cc21] |
| I-83 | 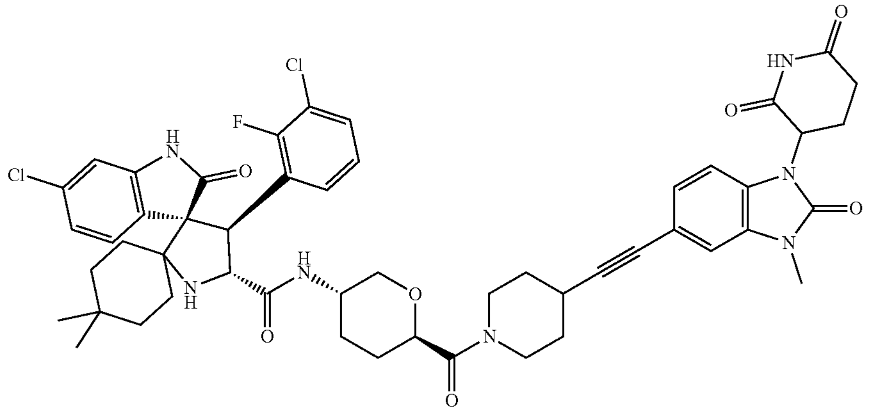 [SMILES: Cn1c(=O)n(C2CCC(=O)NC2=O)c2ccc(C#CC3CCN(C(=O)[C@H]4CC[C@H](NC(=O)[C@@H]5NC6(CCC(C)(C)CC6)[C@@]6(C(=O)Nc7cc(Cl)ccc76)[C@H]5c5cccc(Cl)c5F)CO4)CC3)cc21] |
| I-85 | 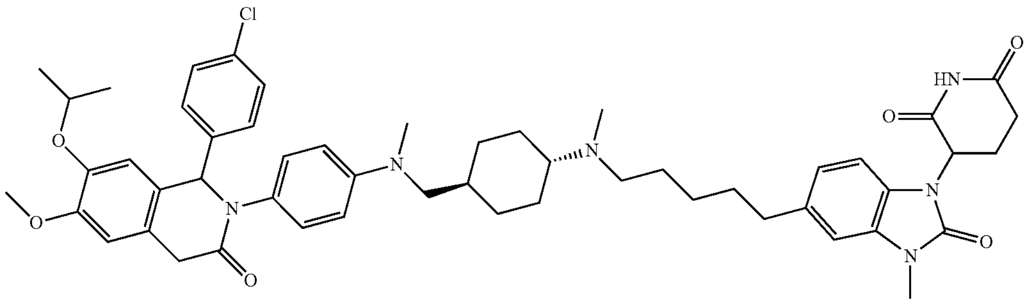 [SMILES: COc1cc2c(cc1OC(C)C)C(c1ccc(Cl)cc1)N(c1ccc(N(C)C[C@H]3CC[C@H](N(C)CCCCCc4ccc5c(c4)n(C)c(=O)n5C4CCC(=O)NC4=O)CC3)cc1)C(=O)C2] |

TABLE 1-continued
| Exemplary Compounds | |
|---|---|
| I-# | Structure |
| I-86 | 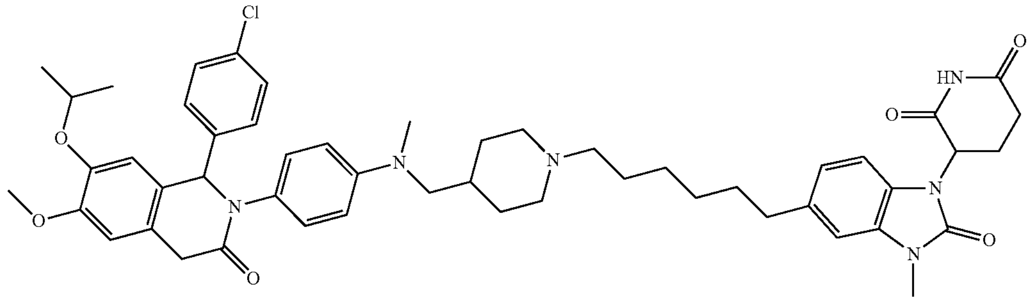 [SMILES: COc1cc2c(cc1OC(C)C)C(c1ccc(Cl)cc1)N(c1ccc(N(C)CC3CCN(CCCCCCc4ccc5c(c4)n(C)c(=O)n5C4CCC(=O)NC4=O)CC3)cc1)C(=O)C2] |
| I-84 | 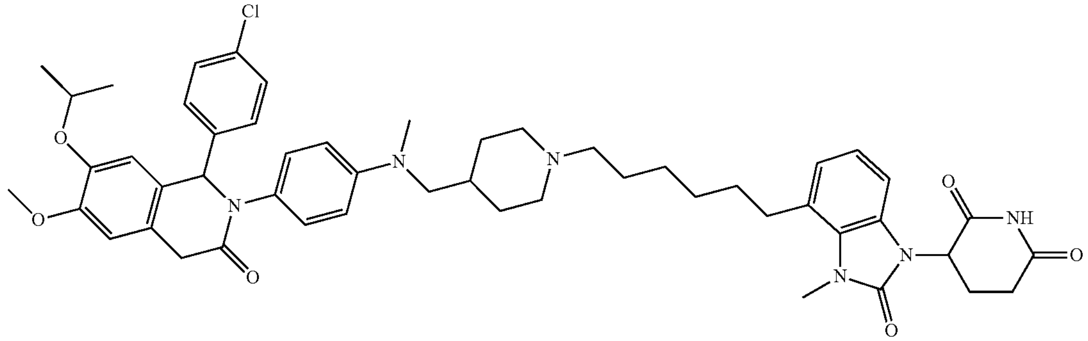 [SMILES: COc1cc2c(cc1OC(C)C)C(c1ccc(Cl)cc1)N(c1ccc(N(C)CC3CCN(CCCCCCc4cccc5c4n(C)c(=O)n5C4CCC(=O)NC4=O)CC3)cc1)C(=O)C2] |
| I-87 | 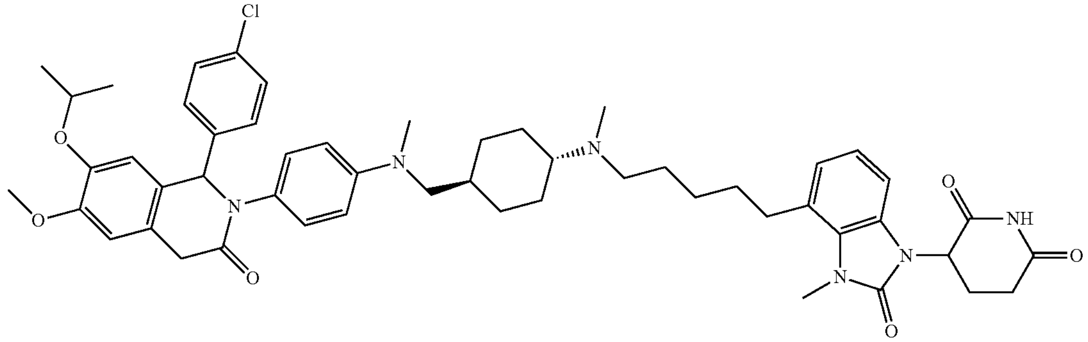 [SMILES: COc1cc2c(cc1OC(C)C)C(c1ccc(Cl)cc1)N(c1ccc(N(C)C[C@H]3CC[C@H](N(C)CCCCCc4cccc5c4n(C)c(=O)n5C4CCC(=O)NC4=O)CC3)cc1)C(=O)C2] |
| I-88 | 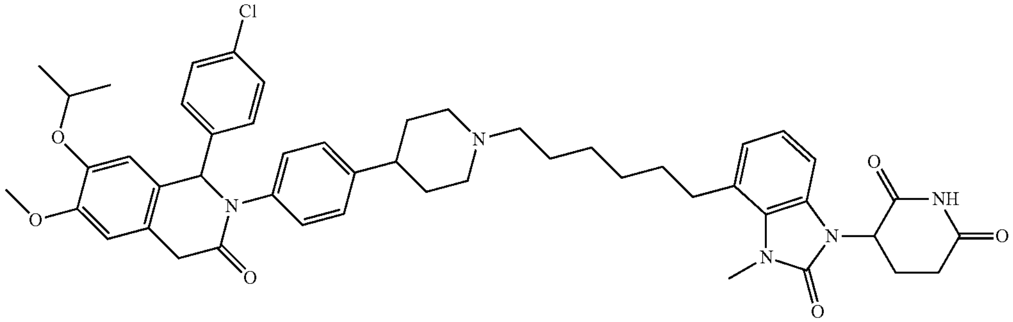 [SMILES: COc1cc2c(cc1OC(C)C)C(c1ccc(Cl)cc1)N(c1ccc(C3CCN(CCCCCCc4cccc5c4n(C)c(=O)n5C4CCC(=O)NC4=O)CC3)cc1)C(=O)C2] |

TABLE 1-continued
| Exemplary Compounds | |
|---|---|
| I-# | Structure |
| I-89 | 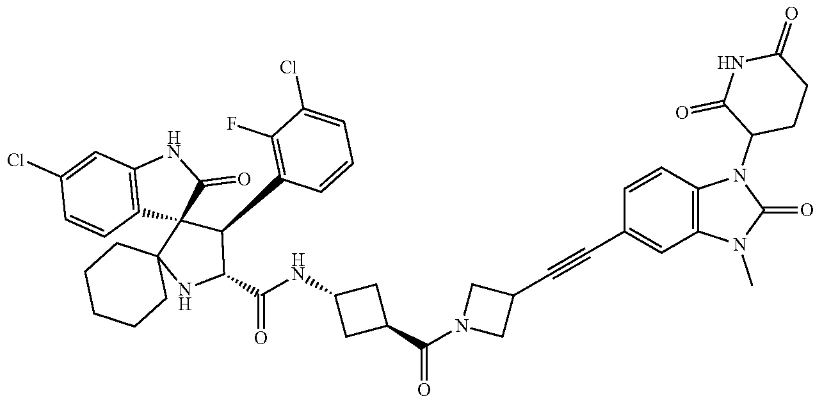 [SMILES: Cn1c(=O)n(C2CCC(=O)NC2=O)c2ccc(C#CC3CN(C(=O)[C@H]4C[C@H](NC(=O)[C@@H]5NC6(CCCCC6)[C@@]6(C(=O)Nc7cc(Cl)ccc76)[C@H]5c5cccc(Cl)c5F)C4)C3)cc21] |
| I-90 | 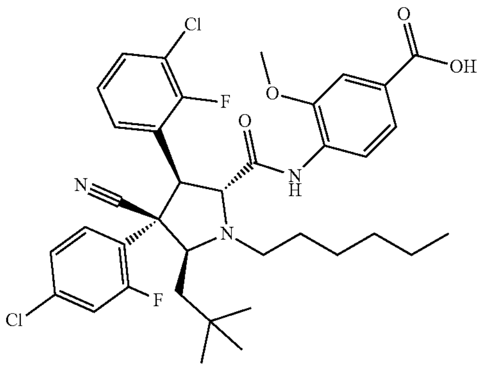 [SMILES: CCCCCCN1[C@@H](CC(C)(C)C)[C@](C#N)(c2ccc(Cl)cc2F)[C@@H](c2cccc(Cl)c2F)[C@@H]1C(=O)Nc1ccc(C(=O)O)cc1OC] |
| I-91 | 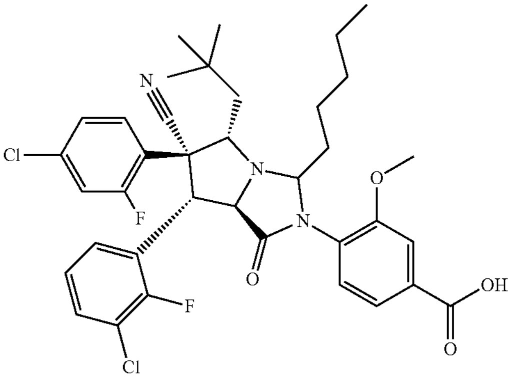 |
| I-92 | 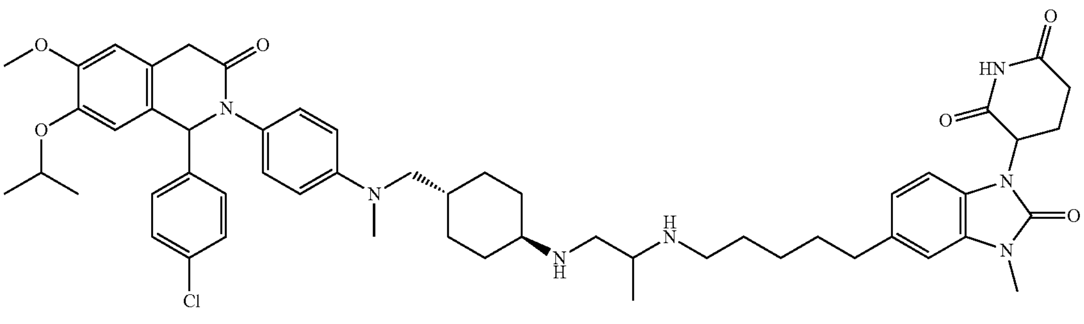 [SMILES: COc1cc2c(cc1OC(C)C)C(c1ccc(Cl)cc1)N(c1ccc(N(C)C[C@H]3CC[C@H](NCC(C)NCCCCCc4ccc5c(c4)n(C)c(=O)n5C4CCC(=O)NC4=O)CC3)cc1)C(=O)C2] |

TABLE 1-continued
| Exemplary Compounds | |
|---|---|
| I-# | Structure |
| I-93 | 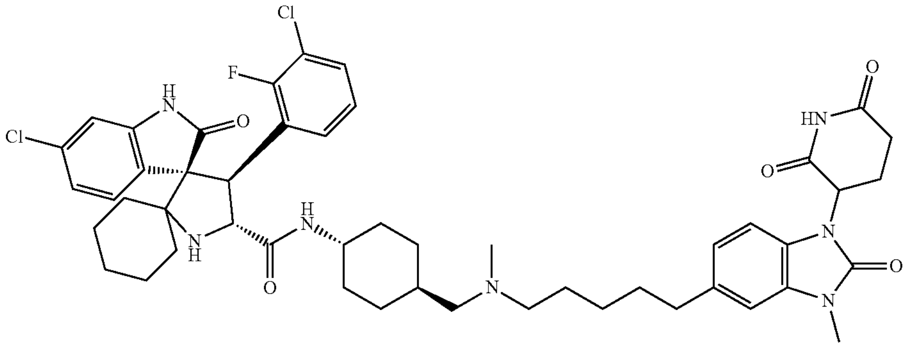 [SMILES: CN(CCCCCc1ccc2c(c1)n(C)c(=O)n2C1CCC(=O)NC1=O)C[C@H]1CC[C@H](NC(=O)[C@@H]2NC3(CCCCC3)[C@@]3(C(=O)Nc4cc(Cl)ccc43)[C@H]2c2cccc(Cl)c2F)CC1] |
| I-94 | 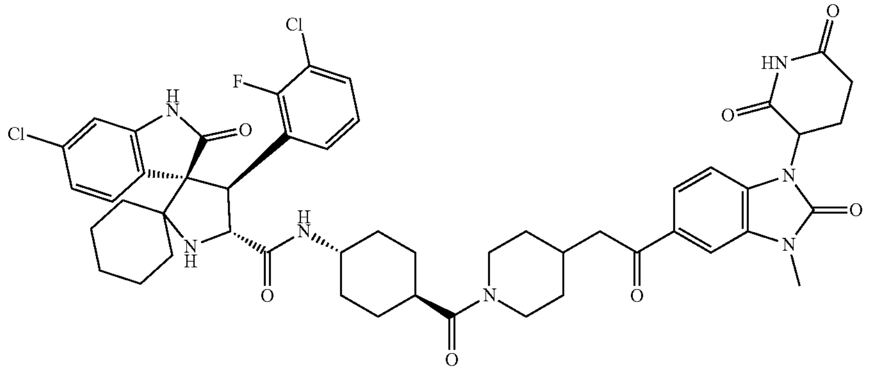 [SMILES: Cn1c(=O)n(C2CCC(=O)NC2=O)c2ccc(C(=O)CC3CCN(C(=O)[C@H]4CC[C@H](NC(=O)[C@@H]5NC6(CCCCC6)[C@@]6(C(=O)Nc7cc(Cl)ccc76)[C@H]5c5cccc(Cl)c5F)CC4)CC3)cc21] |
| I-95 | 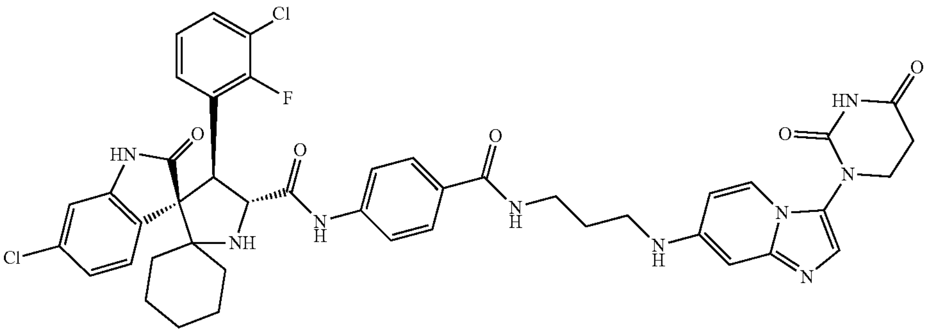 [SMILES: O=C1CCN(c2cnc3cc(NCCCNC(=O)c4ccc(NC(=O)[C@@H]5NC6(CCCCC6)[C@@]6(C(=O)Nc7cc(Cl)ccc76)[C@H]5c5cccc(Cl)c5F)cc4)ccn23)C(=O)N1] |
| I-96 | 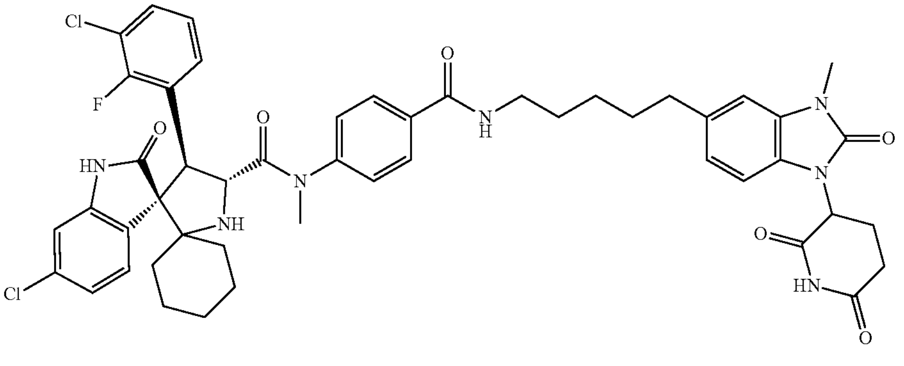 [SMILES: CN(C(=O)[C@@H]1NC2(CCCCC2)[C@@]2(C(=O)Nc3cc(Cl)ccc32)[C@H]1c1cccc(Cl)c1F)c1ccc(C(=O)NCCCCCc2ccc3c(c2)n(C)c(=O)n3C2CCC(=O)NC2=O)cc1] |

TABLE 1-continued
| Exemplary Compounds | |
|---|---|
| I-# | Structure |
| I-97 | 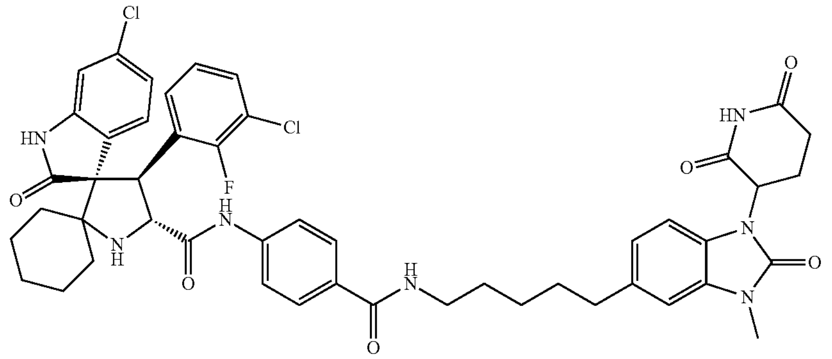 [SMILES: Cn1c(=O)n(C2CCC(=O)NC2=O)c2ccc(CCCCCNC(=O)c3ccc(NC(=O)[C@@H]4NC5(CCCCC5)[C@@]5(C(=O)Nc6cc(Cl)ccc65)[C@H]4c4cccc(Cl)c4F)cc3)cc21] |
| I-98 | 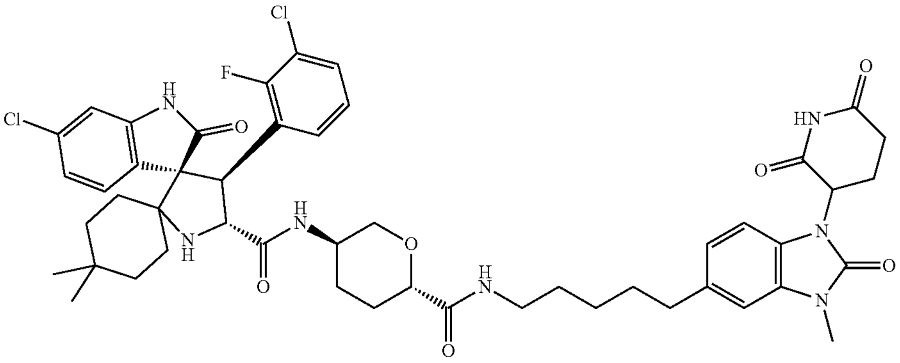 [SMILES: Cn1c(=O)n(C2CCC(=O)NC2=O)c2ccc(CCCCCNC(=O)[C@@H]3CC[C@@H](NC(=O)[C@@H]4NC5(CCC(C)(C)CC5)[C@@]5(C(=O)Nc6cc(Cl)ccc65)[C@H]4c4cccc(Cl)c4F)CO3)cc21] |
| I-99 | 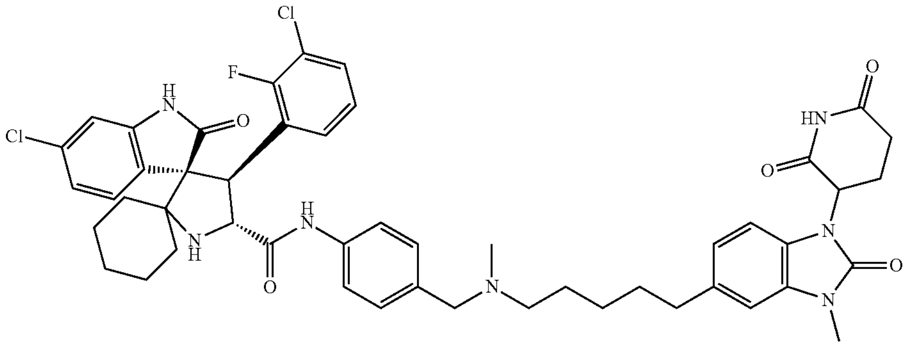 [SMILES: CN(CCCCCc1ccc2c(c1)n(C)c(=O)n2C1CCC(=O)NC1=O)Cc1ccc(NC(=O)[C@@H]2NC3(CCCCC3)[C@@]3(C(=O)Nc4cc(Cl)ccc43)[C@H]2c2cccc(Cl)c2F)cc1] |
| I-100 | 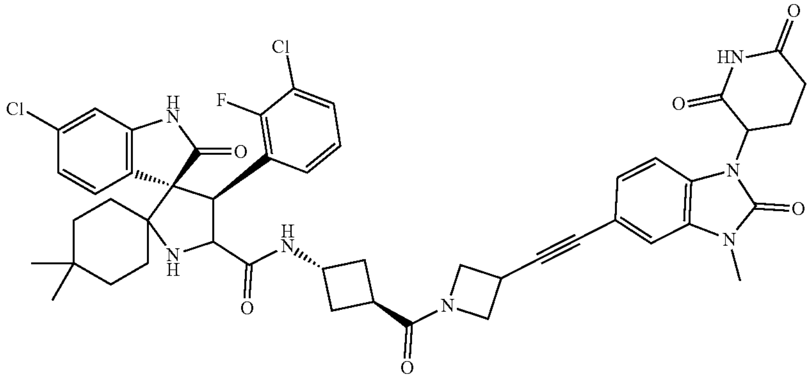 [SMILES: Cn1c(=O)n(C2CCC(=O)NC2=O)c2ccc(C#CC3CN(C(=O)[C@H]4C[C@H](NC(=O)C5NC6(CCC(C)(C)CC6)[C@@]6(C(=O)Nc7cc(Cl)ccc76)[C@H]5c5cccc(Cl)c5F)C4)C3)cc21] |

TABLE 1-continued
| Exemplary Compounds | |
|---|---|
| I-# | Structure |
| I-101 | 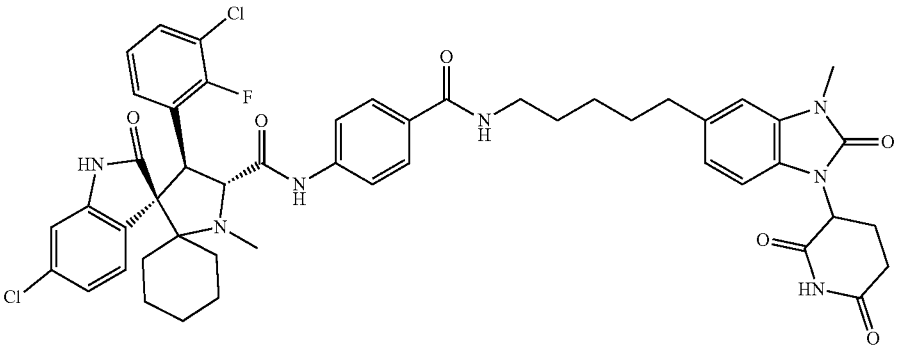 [SMILES: CN1[C@@H](C(=O)Nc2ccc(C(=O)NCCCCCc3ccc4c(c3)n(C)c(=O)n4C3CCC(=O)NC3=O)cc2)[C@H](c2cccc(Cl)c2F)[C@]2(C(=O)Nc3cc(Cl)ccc32)C12CCCCC2] |
| I-102 | 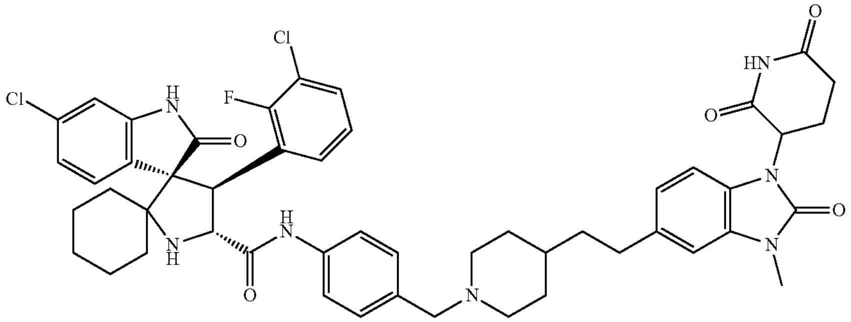 [SMILES: Cn1c(=O)n(C2CCC(=O)NC2=O)c2ccc(CCC3CCN(Cc4ccc(NC(=O)[C@@H]5NC6(CCCCC6)[C@@]6(C(=O)Nc7cc(Cl)ccc76)[C@H]5c5cccc(Cl)c5F)cc4)CC3)cc21] |
| I-103 | 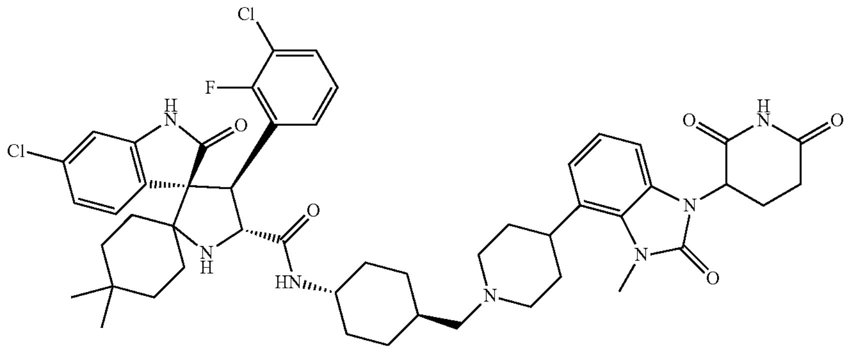 [SMILES: Cn1c(=O)n(C2CCC(=O)NC2=O)c2cccc(C3CCN(C[C@H]4CC[C@H](NC(=O)[C@@H]5NC6(CCC(C)(C)CC6)[C@@]6(C(=O)Nc7cc(Cl)ccc76)[C@H]5c5cccc(Cl)c5F)CC4)CC3)c21] |
| I-104 | 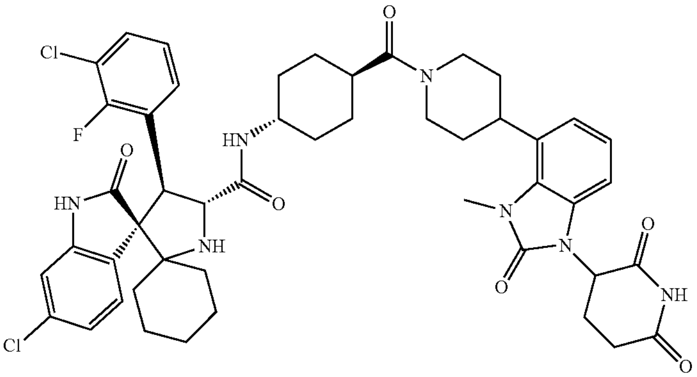 [SMILES: Cn1c(=O)n(C2CCC(=O)NC2=O)c2cccc(C3CCN(C(=O)[C@H]4CC[C@H](NC(=O)[C@@H]5NC6(CCCCC6)[C@@]6(C(=O)Nc7cc(Cl)ccc76)[C@H]5c5cccc(Cl)c5F)CC4)CC3)c21] |

TABLE 1-continued
| Exemplary Compounds | |
|---|---|
| I-# | Structure |
| I-105 | 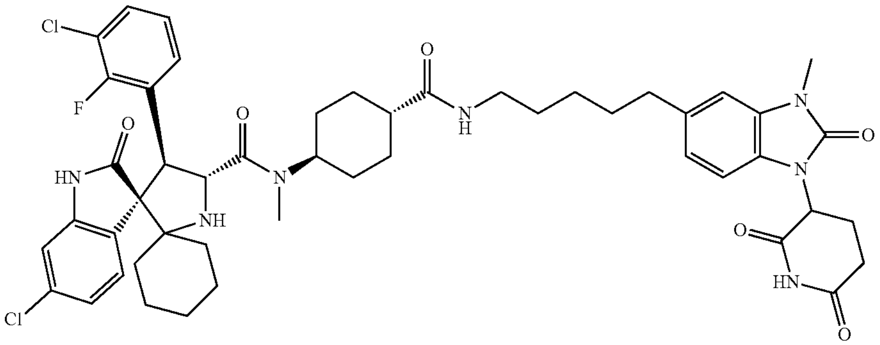 [SMILES: Cn1c(=O)n(C2CCC(=O)NC2=O)c2ccc(CCCCCNC(=O)[C@H]3CC[C@H](N(C)C(=O)[C@@H]4NC5(CCCCC5)[C@@]5(C(=O)Nc6cc(Cl)ccc65)[C@H]4c4cccc(Cl)c4F)CC3)cc21] |
| I-106 | 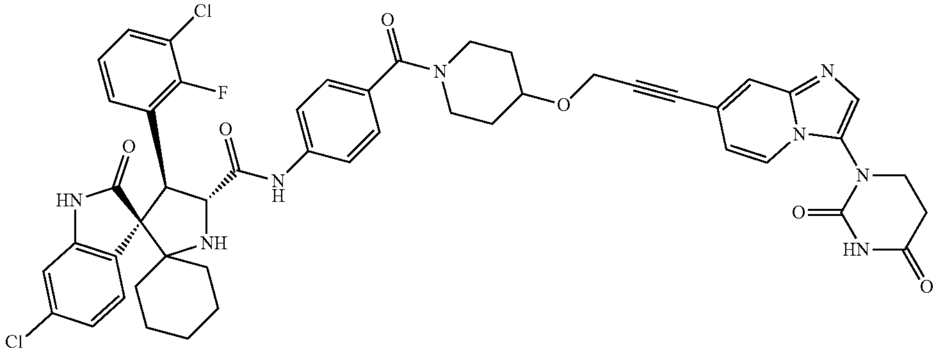 [SMILES: O=C1CCN(c2cnc3cc(C#CCOC4CCN(C(=O)c5ccc(NC(=O)[C@@H]6NC7(CCCCC7)[C@@]7(C(=O)Nc8cc(Cl)ccc87)[C@H]6c6cccc(Cl)c6F)cc5)CC4)ccn23)C(=O)N1] |
| I-107 | 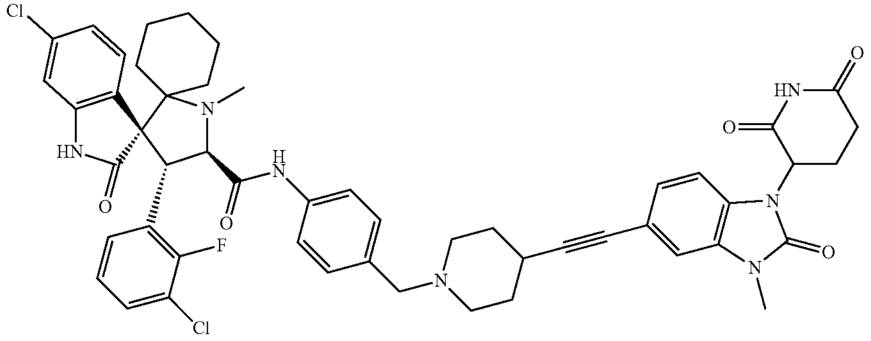 [SMILES: CN1[C@@H](C(=O)Nc2ccc(CN3CCC(C#Cc4ccc5c(c4)n(C)c(=O)n5C4CCC(=O)NC4=O)CC3)cc2)[C@H](c2cccc(Cl)c2F)[C@]2(C(=O)Nc3cc(Cl)ccc32)C12CCCCC2] |
| I-108 | 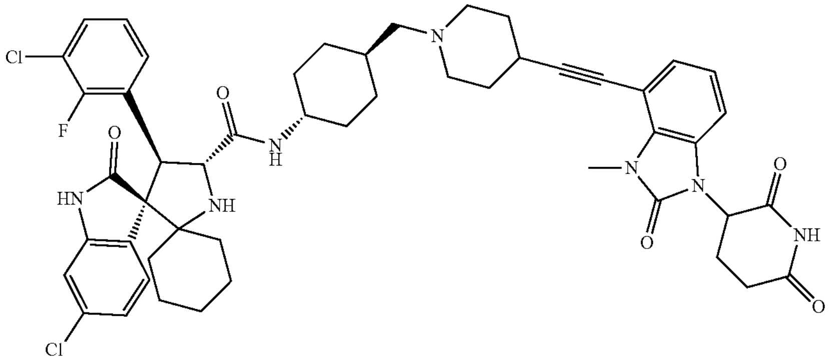 [SMILES: Cn1c(=O)n(C2CCC(=O)NC2=O)c2cccc(C#CC3CCN(C[C@H]4CC[C@H](NC(=O)[C@@H]5NC6(CCCCC6)[C@@]6(C(=O)Nc7cc(Cl)ccc76)[C@H]5c5cccc(Cl)c5F)CC4)CC3)c21] |

TABLE 1-continued
| Exemplary Compounds | |
|---|---|
| I-# | Structure |
| I-109 | 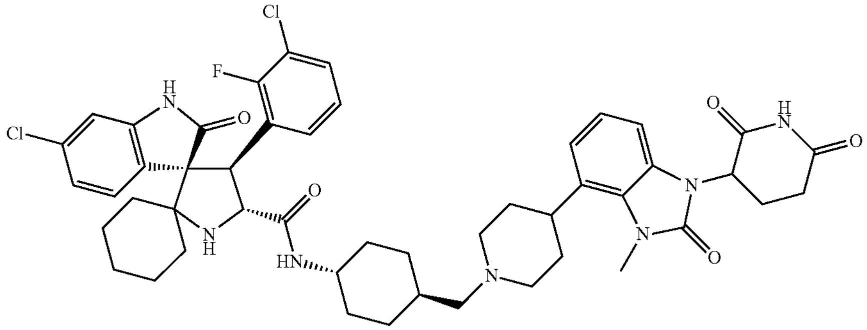 [SMILES: Cn1c(=O)n(C2CCC(=O)NC2=O)c2cccc(C3CCN(C[C@H]4CC[C@H](NC(=O)[C@@H]5NC6(CCCCC6)[C@@]6(C(=O)Nc7cc(Cl)ccc76)[C@H]5c5cccc(Cl)c5F)CC4)CC3)c21] |
| I-110 | 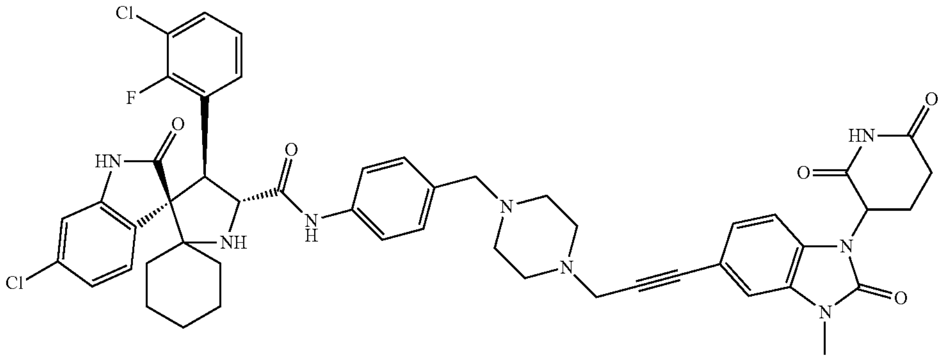 [SMILES: Cn1c(=O)n(C2CCC(=O)NC2=O)c2ccc(C#CCN3CCN(Cc4ccc(NC(=O)[C@@H]5NC6(CCCCC6)[C@@]6(C(=O)Nc7cc(Cl)ccc76)[C@H]5c5cccc(Cl)c5F)cc4)CC3)cc21] |
| I-111 | 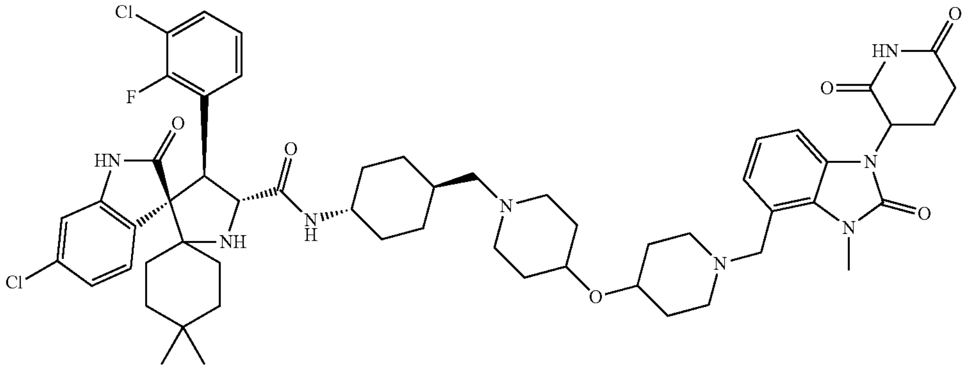 [SMILES: Cn1c(=O)n(C2CCC(=O)NC2=O)c2cccc(CN3CCC(OC4CCN(C[C@H]5CC[C@H](NC(=O)[C@@H]6NC7(CCC(C)(C)CC7)[C@@]7(C(=O)Nc8cc(Cl)ccc87)[C@H]6c6cccc(Cl)c6F)CC5)CC4)CC3)c21] |
| I-112 | 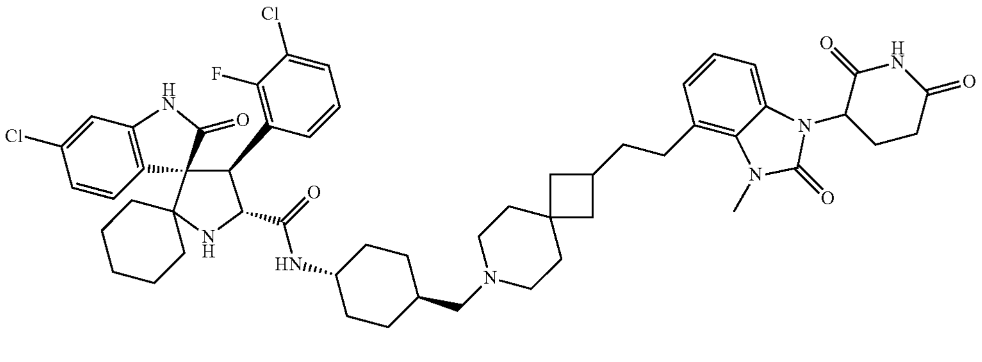 [SMILES: Cn1c(=O)n(C2CCC(=O)NC2=O)c2cccc(CCC3CC4(CCN(C[C@H]5CC[C@H](NC(=O)[C@@H]6NC7(CCCCC7)[C@@]7(C(=O)Nc8cc(Cl)ccc87)[C@H]6c6cccc(Cl)c6F)CC5)CC4)C3)c21] |

TABLE 1-continued
| Exemplary Compounds | |
|---|---|
| I-# | Structure |
| I-113 | 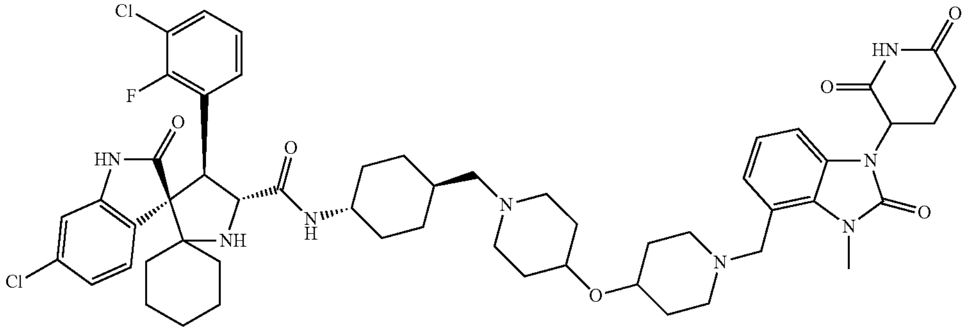 [SMILES: Cn1c(=O)n(C2CCC(=O)NC2=O)c2cccc(CN3CCC(OC4CCN(C[C@H]5CC[C@H](NC(=O)[C@@H]6NC7(CCCCC7)[C@@]7(C(=O)Nc8cc(Cl)ccc87)[C@H]6c6cccc(Cl)c6F)CC5)CC4)CC3)c21] |
| I-114 | 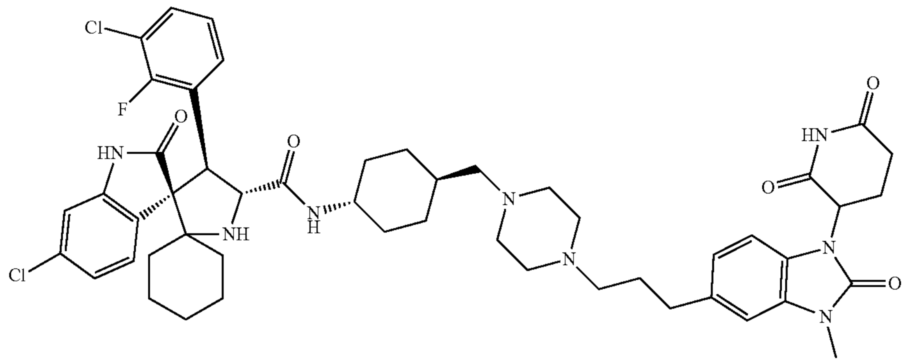 [SMILES: Cn1c(=O)n(C2CCC(=O)NC2=O)c2ccc(CCCN3CCN(C[C@H]4CC[C@H](NC(=O)[C@@H]5NC6(CCCCC6)[C@@]6(C(=O)Nc7cc(Cl)ccc76)[C@H]5c5cccc(Cl)c5F)CC4)CC3)cc21] |
| I-115 | 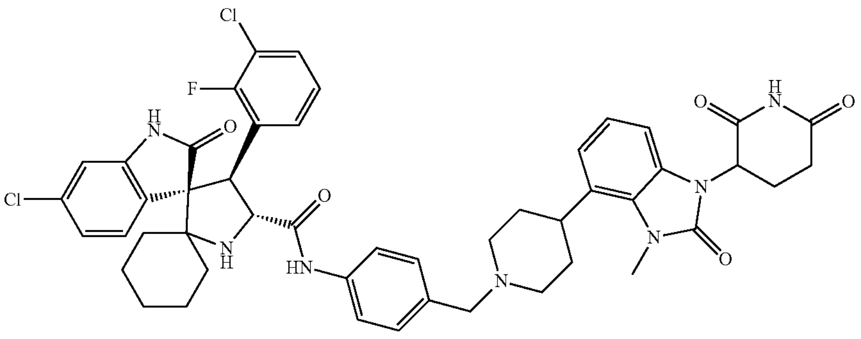 [SMILES: Cn1c(=O)n(C2CCC(=O)NC2=O)c2cccc(C3CCN(Cc4ccc(NC(=O)[C@@H]5NC6(CCCCC6)[C@@]6(C(=O)Nc7cc(Cl)ccc76)[C@H]5c5cccc(Cl)c5F)cc4)CC3)c21] |
| I-116 | 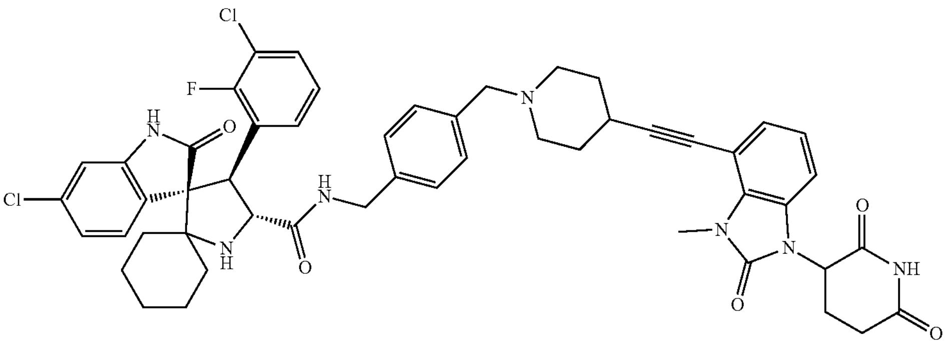 [SMILES: Cn1c(=O)n(C2CCC(=O)NC2=O)c2cccc(C#CC3CCN(Cc4ccc(CNC(=O)[C@@H]5NC6(CCCCC6)[C@@]6(C(=O)Nc7cc(Cl)ccc76)[C@H]5c5cccc(Cl)c5F)cc4)CC3)c21] |

TABLE 1-continued
| Exemplary Compounds | |
|---|---|
| I-# | Structure |
| I-117 | 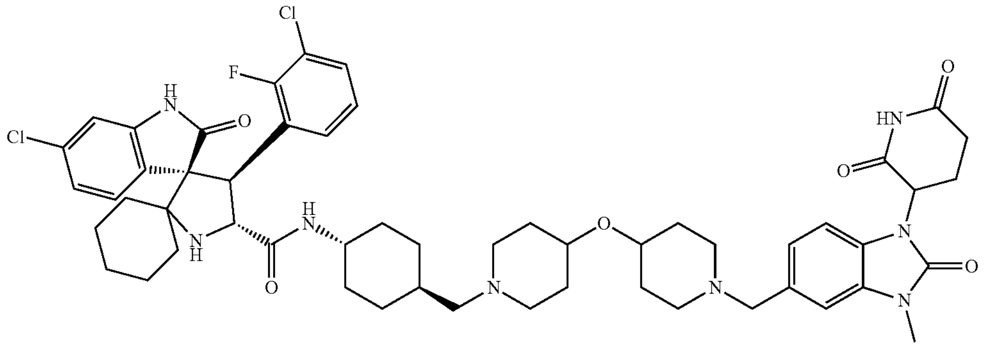 [SMILES: Cn1c(=O)n(C2CCC(=O)NC2=O)c2ccc(CN3CCC(OC4CCN(C[C@H]5CC[C@H](NC(=O)[C@@H]6NC7(CCCCC7)[C@@]7(C(=O)Nc8cc(Cl)ccc87)[C@H]6c6cccc(Cl)c6F)CC5)CC4)CC3)cc21] |
| I-118 | 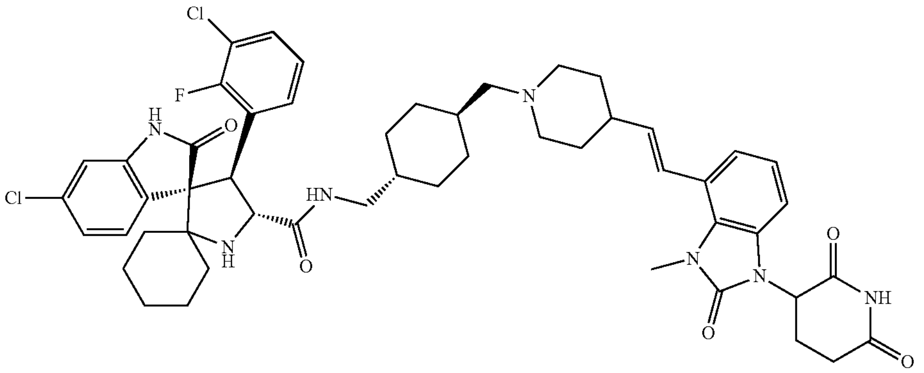 [SMILES: Cn1c(=O)n(C2CCC(=O)NC2=O)c2cccc(/C=C/C3CCN(C[C@H]4CC[C@H](CNC(=O)[C@@H]5NC6(CCCCC6)[C@@]6(C(=O)Nc7cc(Cl)ccc76)[C@H]5c5cccc(Cl)c5F)CC4)CC3)c21] |
| I-119 | 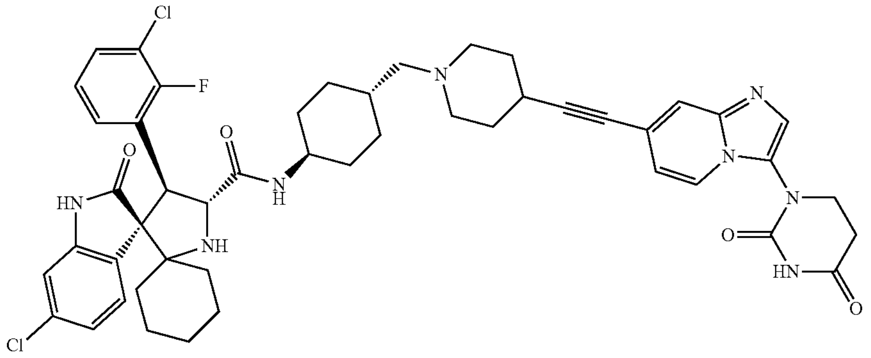 [SMILES: O=C1CCN(c2cnc3cc(C#CC4CCN(C[C@H]5CC[C@H](NC(=O)[C@@H]6NC7(CCCCC7)[C@@]7(C(=O)Nc8cc(Cl)ccc87)[C@H]6c6cccc(Cl)c6F)CC5)CC4)ccn23)C(=O)N1] |
| I-120 | 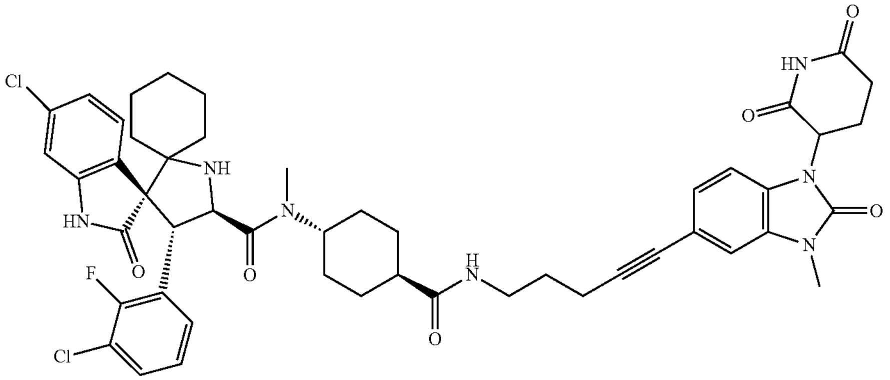 [SMILES: Cn1c(=O)n(C2CCC(=O)NC2=O)c2ccc(C#CCCCNC(=O)[C@H]3CC[C@H](N(C)C(=O)[C@@H]4NC5(CCCCC5)[C@@]5(C(=O)Nc6cc(Cl)ccc65)[C@H]4c4cccc(Cl)c4F)CC3)cc21] |

TABLE 1-continued
| Exemplary Compounds | |
|---|---|
| I-# | Structure |
| I-121 | 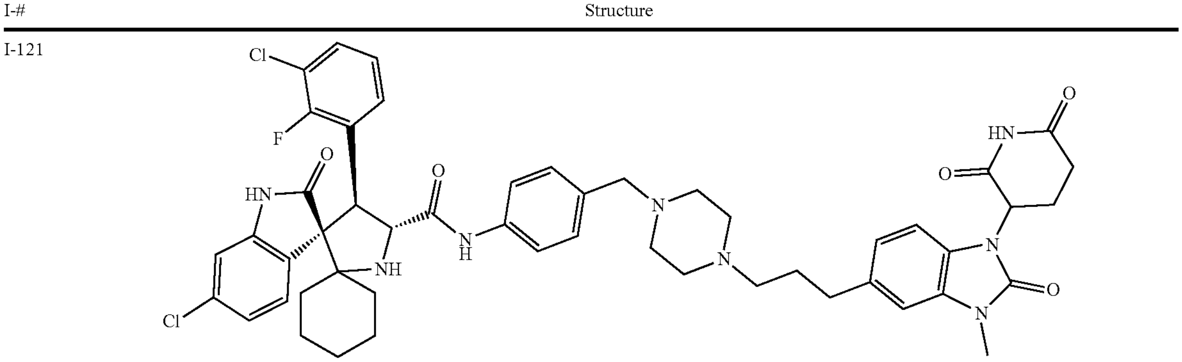 |
| I-122 | 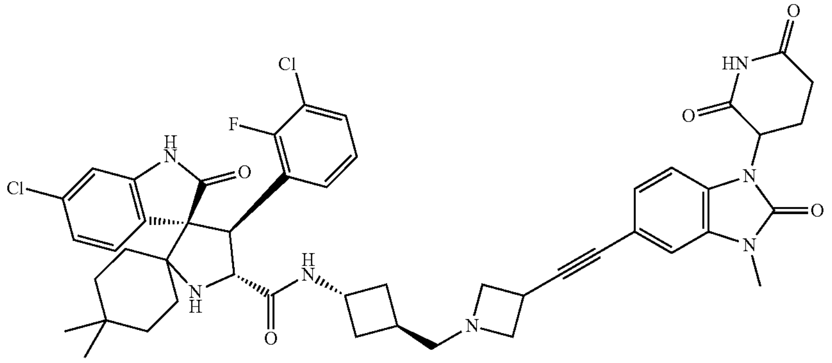 [SMILES: Cn1c(=O)n(C2CCC(=O)NC2=O)c2ccc(C#CC3CN(C[C@H]4C[C@H](NC(=O)[C@@H]5NC6(CCC(C)(C)CC6)[C@@]6(C(=O)Nc7cc(Cl)ccc76)[C@H]5c5cccc(Cl)c5F)C4)C3)cc21] |
| I-123 | 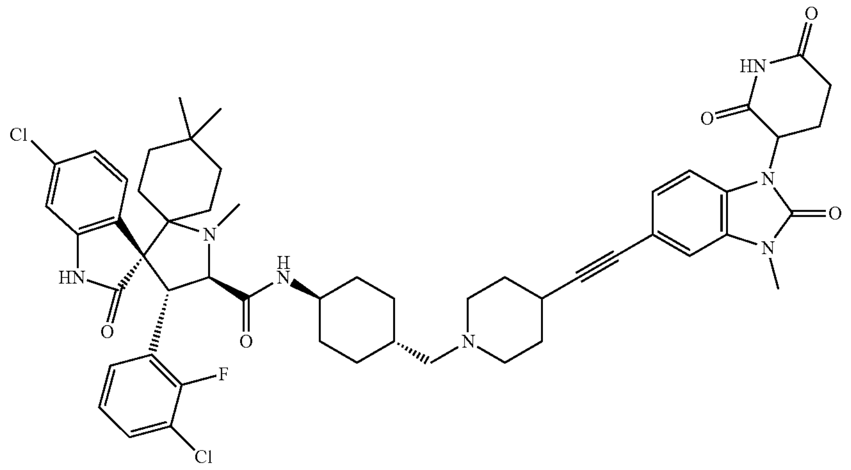 [SMILES: CN1[C@@H](C(=O)N[C@H]2CC[C@H](CN3CCC(C#Cc4ccc5c(c4)n(C)c(=O)n5C4CCC(=O)NC4=O)CC3)CC2)[C@H](c2cccc(Cl)c2F)[C@]2(C(=O)Nc3cc(Cl)ccc32)C12CCC(C)(C)CC2] |
| I-124 | 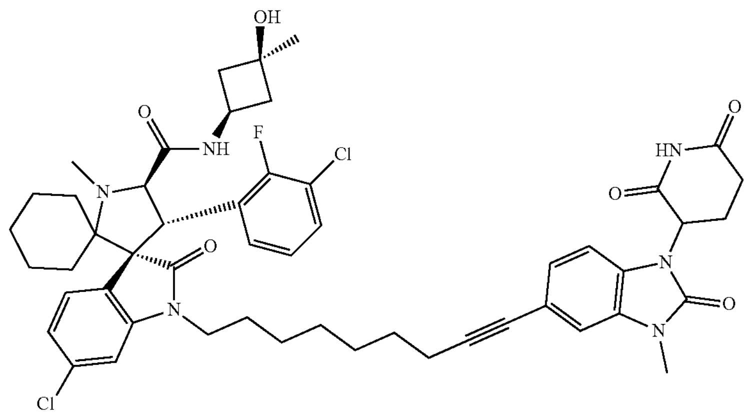 [SMILES: CN1[C@@H](C(=O)N[C@H]2C[C@@](C)(O)C2)[C@H](c2cccc(Cl)c2F)[C@]2(C(=O)N(CCCCCCCC#Cc3ccc4c(c3)n(C)c(=O)n4C3CCC(=O)NC3=O)c3cc(Cl)ccc32)C12CCCCC2] |

TABLE 1-continued
| Exemplary Compounds | |
|---|---|
| I-# | Structure |
| I-125 | 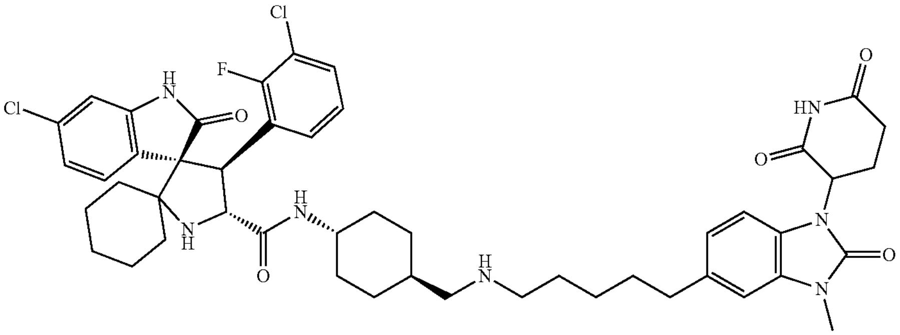 [SMILES: Cn1c(=O)n(C2CCC(=O)NC2=O)c2ccc(CCCCCNC[C@H]3CC[C@H](NC(=O)[C@@H]4NC5(CCCCC5)[C@@]5(C(=O)Nc6cc(Cl)ccc65)[C@H]4c4cccc(Cl)c4F)CC3)cc21] |
| I-126 | 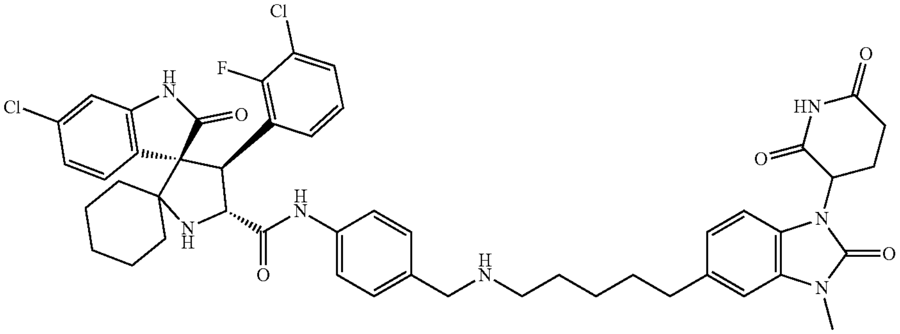 [SMILES: Cn1c(=O)n(C2CCC(=O)NC2=O)c2ccc(CCCCCNCc3ccc(NC(=O)[C@@H]4NC5(CCCCC5)[C@@]5(C(=O)Nc6cc(Cl)ccc65)[C@H]4c4cccc(Cl)c4F)cc3)cc21] |
| I-127 | 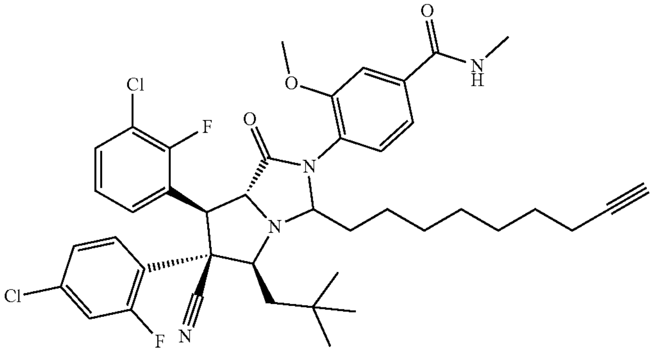 |
| I-128 | 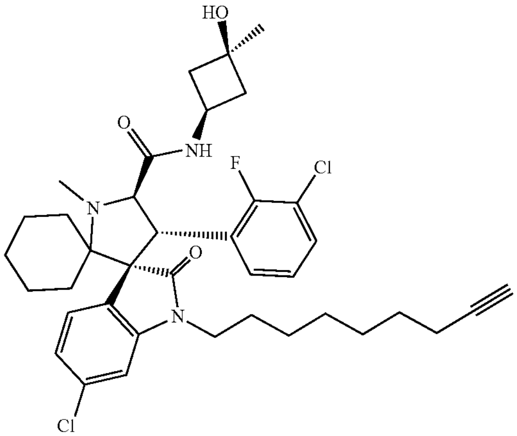 [SMILES: C#CCCCCCCCN1C(=O)[C@@]2(c3ccc(Cl)cc31)[C@@H](c1cccc(Cl)c1F)[C@H](C(=O)N[C@H]1C[C@@](C)(O)C1)N(C)C21CCCCC1] |

TABLE 1-continued
| Exemplary Compounds | |
|---|---|
| I-# | Structure |
| I-129 | 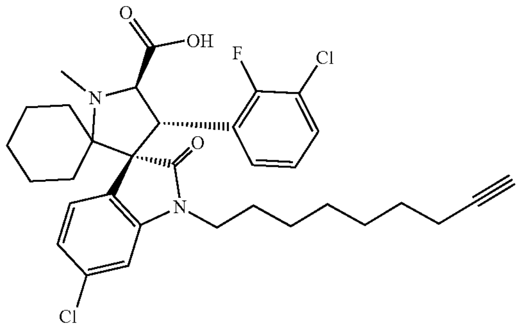 [SMILES: C#CCCCCCCCN1C(=O)[C@@]2(c3ccc(Cl)cc31)[C@@H](c1cccc(Cl)c1F)[C@H](C(=O)O)N(C)C21CCCCC1] |
| I-130 | 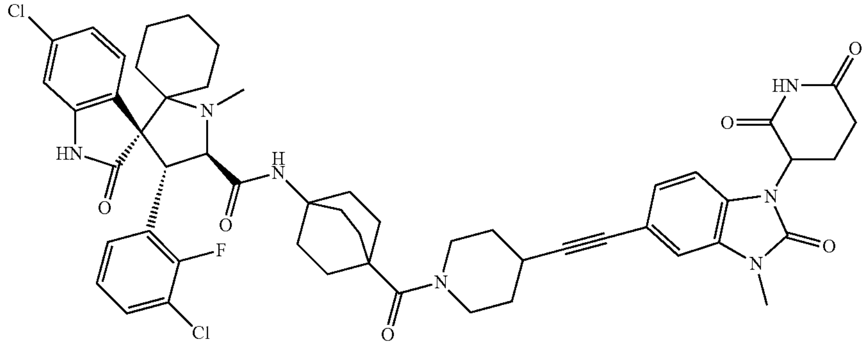 [SMILES: CN1[C@@H](C(=O)NC23CCC(C(=O)N4CCC(C#Cc5ccc6c(c5)n(C)c(=O)n6C5CCC(=O)NC5=O)CC4)(CC2)CC3)[C@H](c2cccc(Cl)c2F)[C@]2(C(=O)Nc3cc(Cl)ccc32)C12CCCCC2] |
| I-131 | 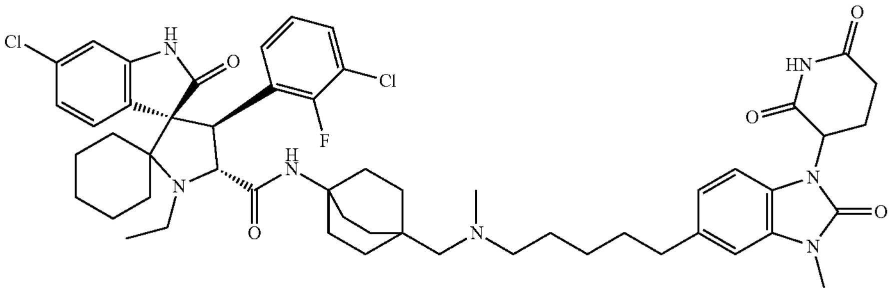 [SMILES: CCN1[C@@H](C(=O)NC23CCC(CN(C)CCCCCc4ccc5c(c4)n(C)c(=O)n5C4CCC(=O)NC4=O)(CC2)CC3)[C@H](c2cccc(Cl)c2F)[C@]2(C(=O)Nc3cc(Cl)ccc32)C12CCCCC2] |
| I-132 | 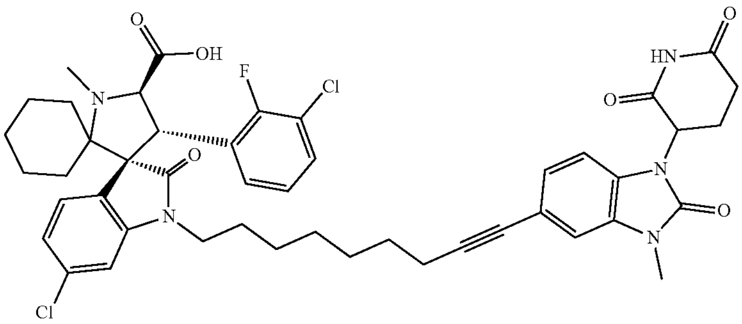 [SMILES: CN1[C@@H](C(=O)O)[C@H](c2cccc(Cl)c2F)[C@]2(C(=O)N(CCCCCCCC#Cc3ccc4c(c3)n(C)c(=O)n4C3CCC(=O)NC3=O)c3cc(Cl)ccc32)C12CCCCC2] |

TABLE 1-continued
| Exemplary Compounds | |
|---|---|
| I-# | Structure |
| I-133 | 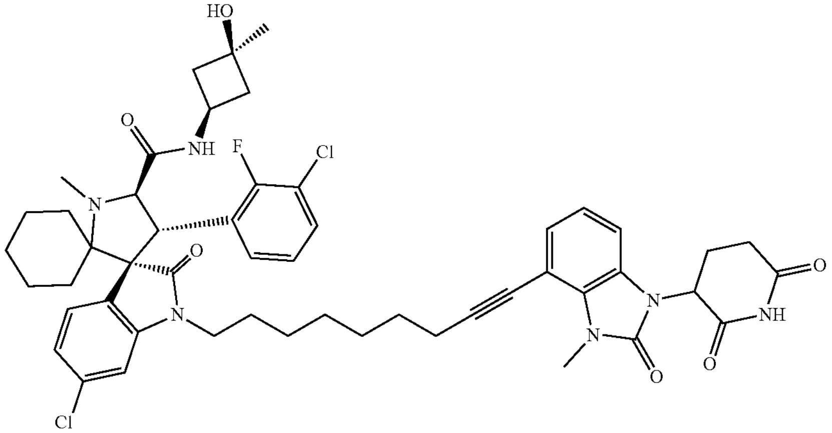 [SMILES: CN1[C@@H](C(=O)N[C@H]2C[C@@](C)(O)C2)[C@H](c2cccc(Cl)c2F)[C@]2(C(=O)N(CCCCCCCC#Cc3cccc4c3n(C)c(=O)n4C3CCC(=O)NC3=O)c3cc(Cl)ccc32)C12CCCCC2] |
| I-134 | 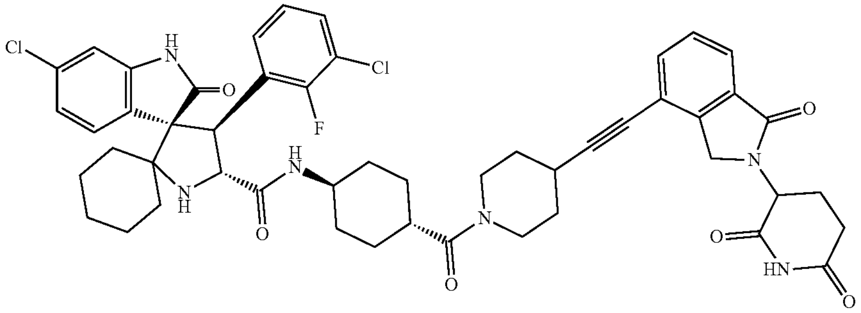 [SMILES: O=C1CCC(N2Cc3c(C#CC4CCN(C(=O)[C@H]5CC[C@H](NC(=O)[C@@H]6NC7(CCCCC7)[C@@]7(C(=O)Nc8cc(Cl)ccc87)[C@H]6c6cccc(Cl)c6F)CC5)CC4)cccc3C2=O)C(=O)N1] |
| I-135 | 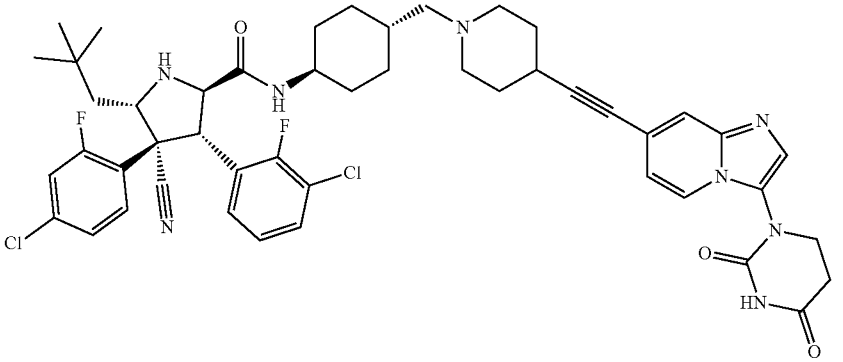 [SMILES: CC(C)(C)C[C@@H]1N[C@@H](C(=O)N[C@H]2CC[C@H](CN3CCC(C#Cc4ccn5c(N6CCC(=O)NC6=O)cnc5c4)CC3)CC2)[C@H](c2cccc(Cl)c2F)[C@@]1(C#N)c1ccc(Cl)cc1F] |
| I-136 | 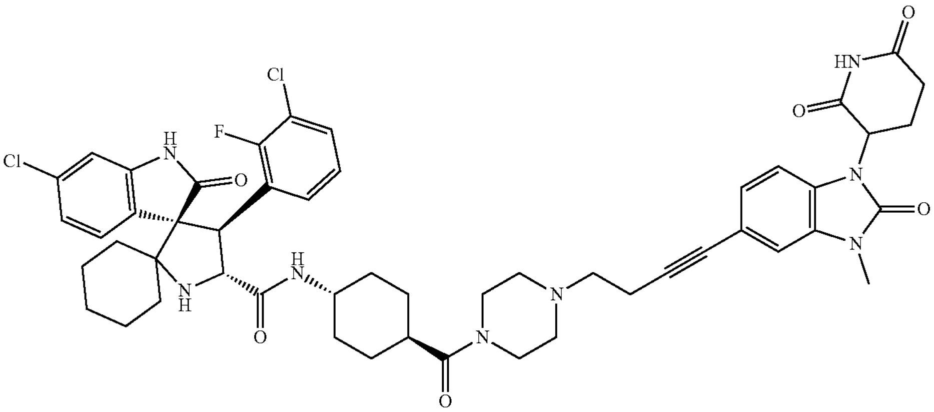 [SMILES: Cn1c(=O)n(C2CCC(=O)NC2=O)c2ccc(C#CCCN3CCN(C(=O)[C@H]4CC[C@H](NC(=O)[C@@H]5NC6(CCCCC6)[C@@]6(C(=O)Nc7cc(Cl)ccc76)[C@H]5c5cccc(Cl)c5F)CC4)CC3)cc21] |

TABLE 1-continued
| Exemplary Compounds | |
|---|---|
| I-# | Structure |
| I-137 | 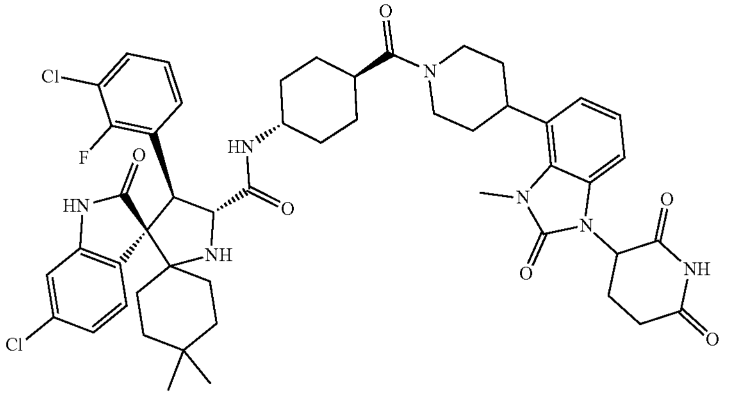 [SMILES: Cn1c(=O)n(C2CCC(=O)NC2=O)c2cccc(C3CCN(C(=O)[C@H]4CC[C@H](NC(=O)[C@@H]5NC6(CCC(C)(C)CC6)[C@@]6(C(=O)Nc7cc(Cl)ccc76)[C@H]5c5cccc(Cl)c5F)CC4)CC3)c21] |
| I-138 | 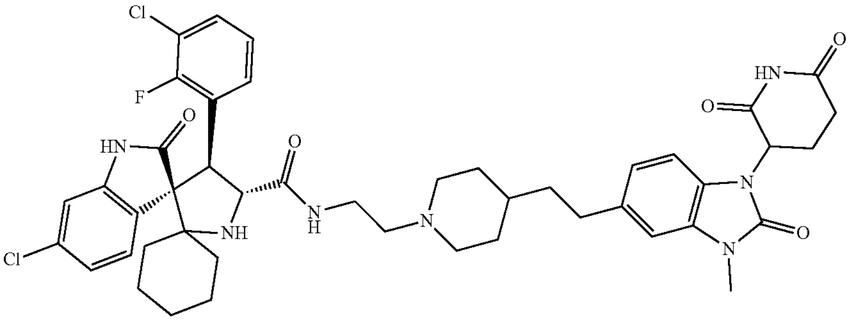 [SMILES: Cn1c(=O)n(C2CCC(=O)NC2=O)c2ccc(CCC3CCN(CCNC(=O)[C@@H]4NC5(CCCCC5)[C@@]5(C(=O)Nc6cc(Cl)ccc65)[C@H]4c4cccc(Cl)c4F)CC3)cc21] |
| I-139 | 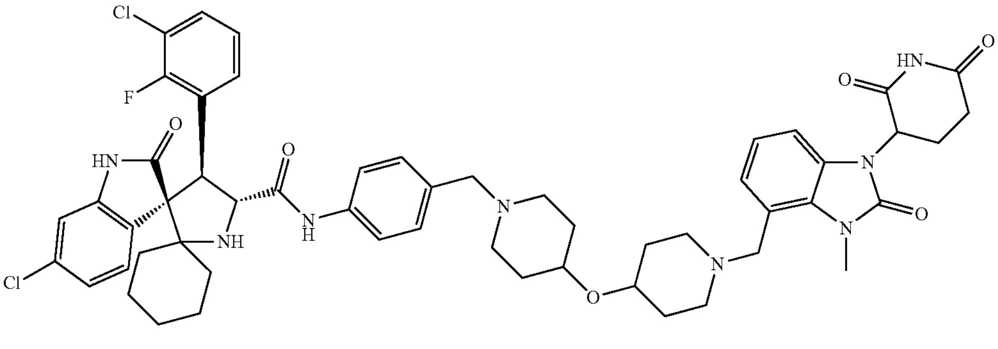 [SMILES: Cn1c(=O)n(C2CCC(=O)NC2=O)c2cccc(CN3CCC(OC4CCN(Cc5ccc(NC(=O)[C@@H]6NC7(CCCCC7)[C@@]7(C(=O)Nc8cc(Cl)ccc87)[C@H]6c6cccc(Cl)c6F)cc5)CC4)CC3)c21] |
| I-140 | 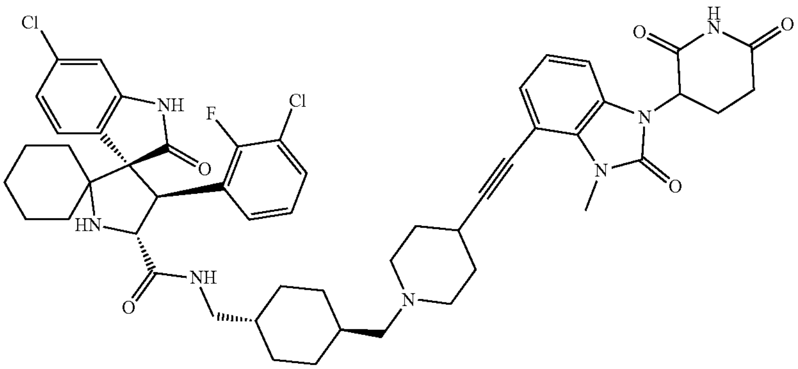 [SMILES: Cn1c(=O)n(C2CCC(=O)NC2=O)c2cccc(C#CC3CCN(C[C@H]4CC[C@H](CNC(=O)[C@@H]5NC6(CCCCC6)[C@@]6(C(=O)Nc7cc(Cl)ccc76)[C@H]5c5cccc(Cl)c5F)CC4)CC3)c21] |

TABLE 1-continued
| Exemplary Compounds | |
|---|---|
| I-# | Structure |
| I-141 | 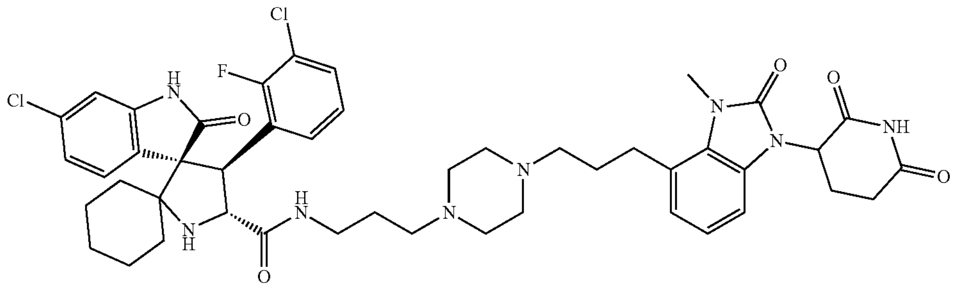 [SMILES: Cn1c(=O)n(C2CCC(=O)NC2=O)c2cccc(CCCN3CCN(CCCNC(=O)[C@@H]4NC5(CCCCC5)[C@@]5(C(=O)Nc6cc(Cl)ccc65)[C@H]4c4cccc(Cl)c4F)CC3)c21] |
| I-142 | 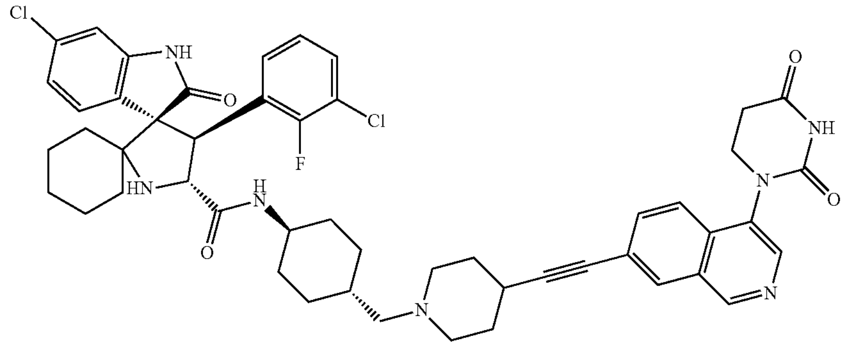 [SMILES: O=C1CCN(c2cncc3cc(C#CC4CCN(C[C@H]5CC[C@H](NC(=O)[C@@H]6NC7(CCCCC7)[C@@]7(C(=O)Nc8cc(Cl)ccc87)[C@H]6c6cccc(Cl)c6F)CC5)CC4)ccc23)C(=O)N1] |
| I-143 | 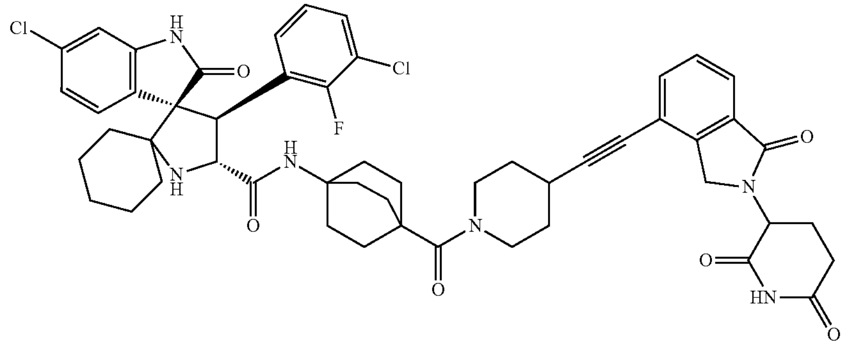 [SMILES: O=C1CCC(N2Cc3c(C#CC4CCN(C(=O)C56CCC(NC(=O)[C@@H]7NC8(CCCCC8)[C@@]8(C(=O)Nc9cc(Cl)ccc98)[C@H]7c7cccc(Cl)c7F)(CC5)CC6)CC4)cccc3C2=O)C(=O)N1] |
| I-144 | 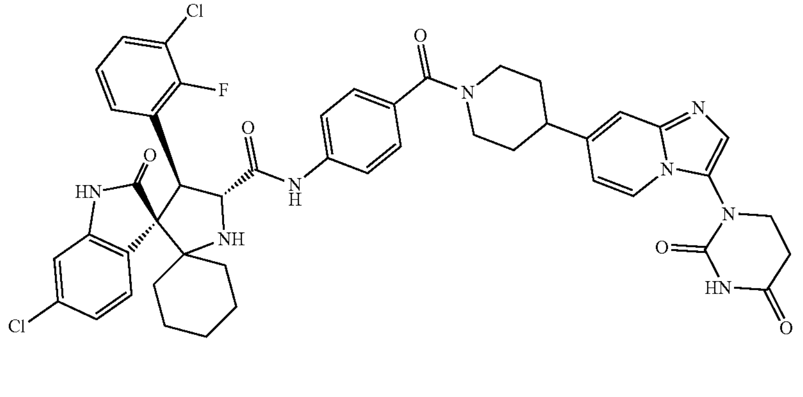 [SMILES: O=C1CCN(c2cnc3cc(C4CCN(C(=O)c5ccc(NC(=O)[C@@H]6NC7(CCCCC7)[C@@]7(C(=O)Nc8cc(Cl)ccc87)[C@H]6c6cccc(Cl)c6F)cc5)CC4)ccn23)C(=O)N1] |

TABLE 1-continued
| Exemplary Compounds | |
|---|---|
| I-# | Structure |
| I-145 | 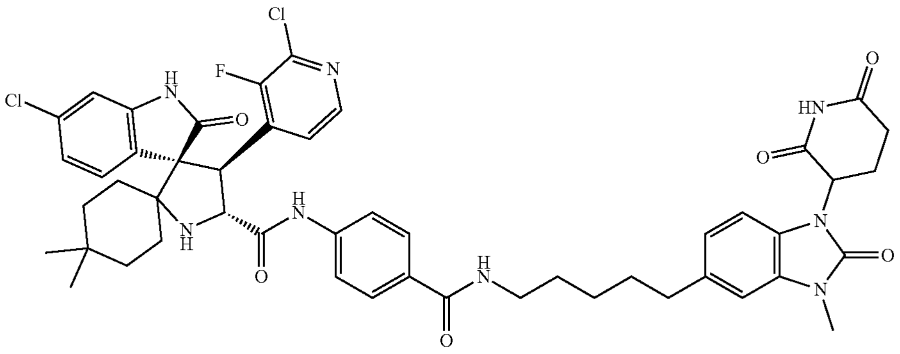 [SMILES: Cn1c(=O)n(C2CCC(=O)NC2=O)c2ccc(CCCCCNC(=O)c3ccc(NC(=O)[C@@H]4NC5(CCC(C)(C)CC5)[C@@]5(C(=O)Nc6cc(Cl)ccc65)[C@H]4c4ccnc(Cl)c4F)cc3)cc21] |
| I-146 | 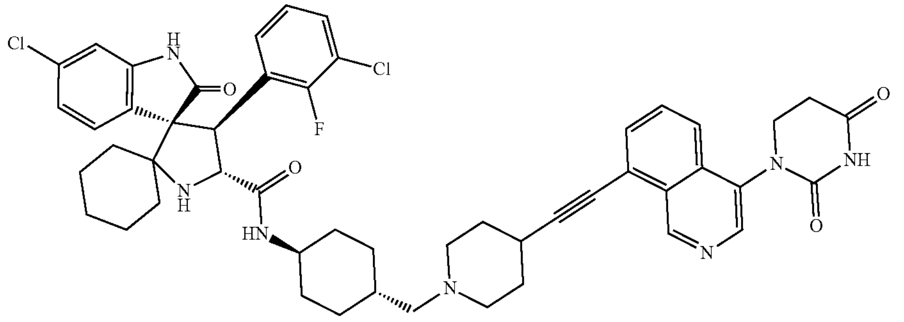 [SMILES: O=C1CCN(c2cncc3c(C#CC4CCN(C[C@H]5CC[C@H](NC(=O)[C@@H]6NC7(CCCCC7)[C@@]7(C(=O)Nc8cc(Cl)ccc87)[C@H]6c6cccc(Cl)c6F)CC5)CC4)cccc23)C(=O)N1] |
| I-147 | 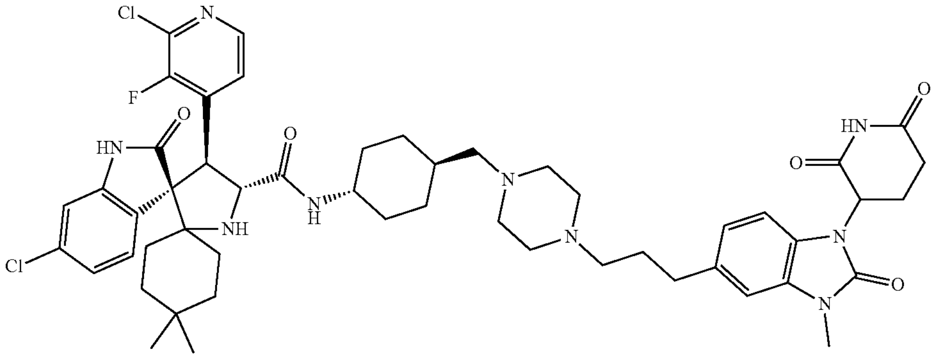 [SMILES: Cn1c(=O)n(C2CCC(=O)NC2=O)c2ccc(CCCN3CCN(C[C@H]4CC[C@H](NC(=O)[C@@H]5NC6(CCC(C)(C)CC6)[C@@]6(C(=O)Nc7cc(Cl)ccc76)[C@H]5c5ccnc(Cl)c5F)CC4)CC3)cc21] |
| I-148 | 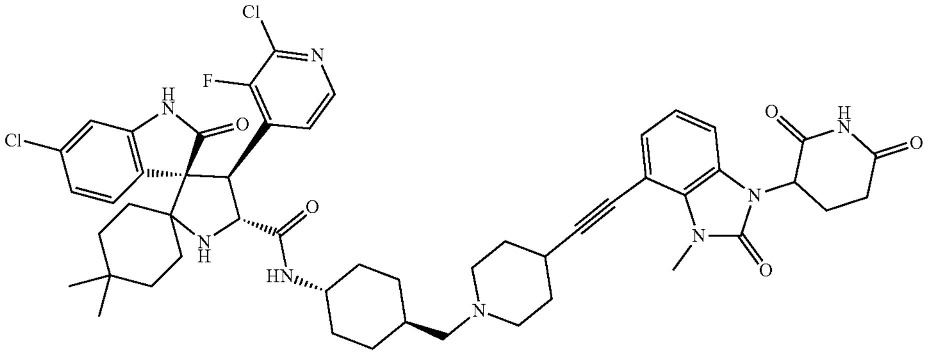 [SMILES: Cn1c(=O)n(C2CCC(=O)NC2=O)c2cccc(C#CC3CCN(C[C@H]4CC[C@H](NC(=O)[C@@H]5NC6(CCC(C)(C)CC6)[C@@]6(C(=O)Nc7cc(Cl)ccc76)[C@H]5c5ccnc(Cl)c5F)CC4)CC3)c21] |

TABLE 1-continued
| Exemplary Compounds | |
|---|---|
| I-# | Structure |
| I-149 | 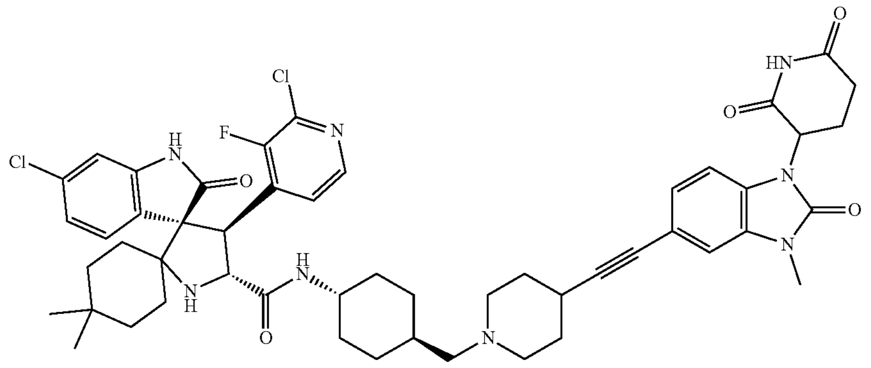 [SMILES: Cn1c(=O)n(C2CCC(=O)NC2=O)c2ccc(C#CC3CCN(C[C@H]4CC[C@H](NC(=O)[C@@H]5NC6(CCC(C)(C)CC6)[C@@]6(C(=O)Nc7cc(Cl)ccc76)[C@H]5c5ccnc(Cl)c5F)CC4)CC3)cc21] |
| I-150 | 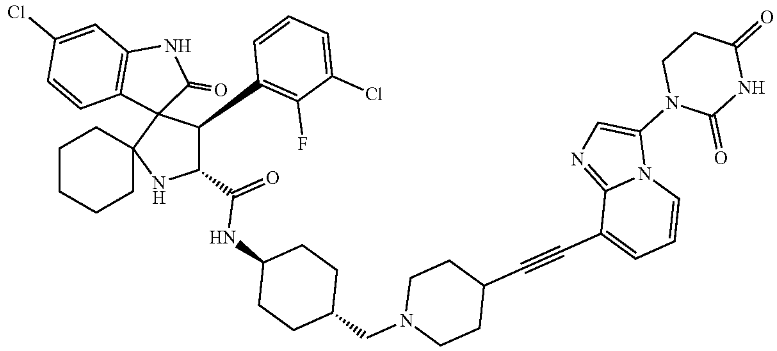 [SMILES: O=C1CCN(c2cnc3c(C#CC4CCN(C[C@H]5CC[C@H](NC(=O)[C@@H]6NC7(CCCCC7)C7(C(=O)Nc8cc(Cl)ccc87)[C@H]6c6cccc(Cl)c6F)CC5)CC4)cccn23)C(=O)N1] |
| I-151 | 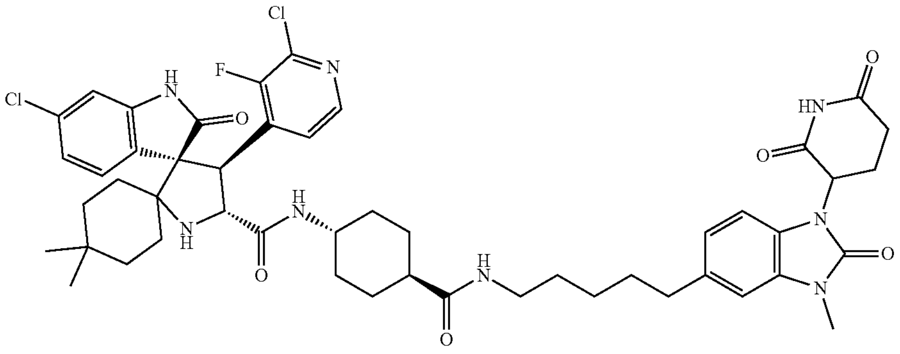 [SMILES: Cn1c(=O)n(C2CCC(=O)NC2=O)c2ccc(CCCCCNC(=O)[C@H]3CC[C@H](NC(=O)[C@@H]4NC5(CCC(C)(C)CC5)[C@@]5(C(=O)Nc6cc(Cl)ccc65)[C@H]4c4ccnc(Cl)c4F)CC3)cc21] |
| I-152 | 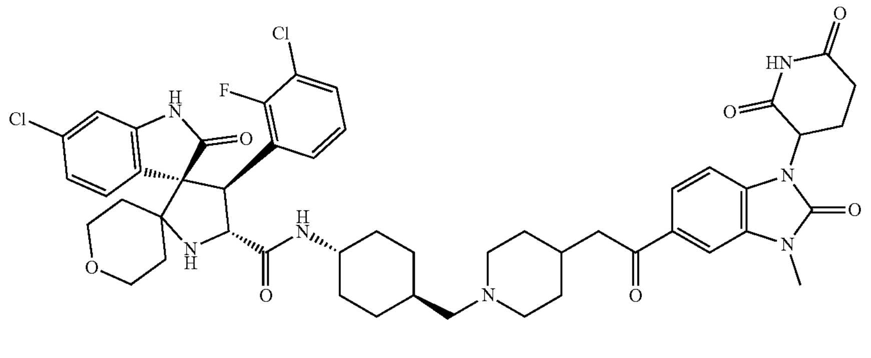 [SMILES: Cn1c(=O)n(C2CCC(=O)NC2=O)c2ccc(C(=O)CC3CCN(C[C@H]4CC[C@H](NC(=O)[C@@H]5NC6(CCOCC6)[C@@]6(C(=O)Nc7cc(Cl)ccc76)[C@H]5c5cccc(Cl)c5F)CC4)CC3)cc21] |

TABLE 1-continued
| Exemplary Compounds | |
|---|---|
| I-# | Structure |
| I-153 | 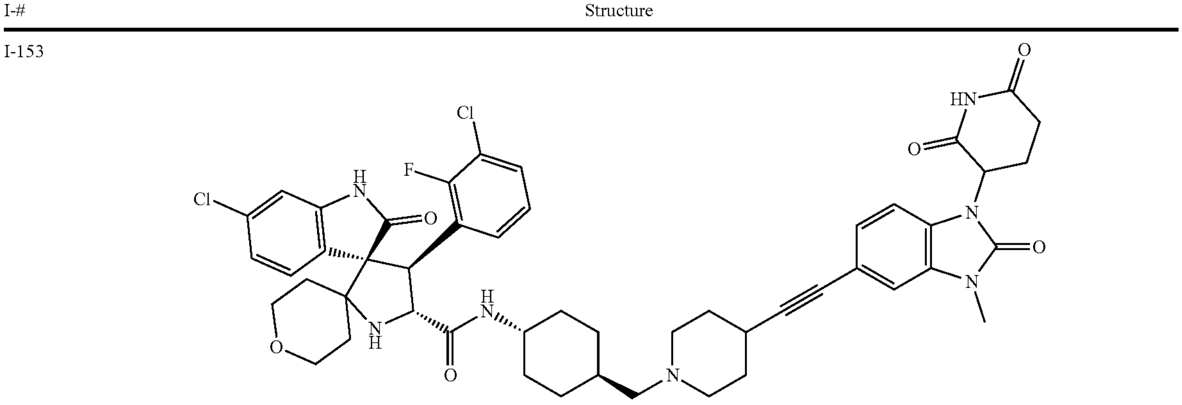 |
| I-154 | 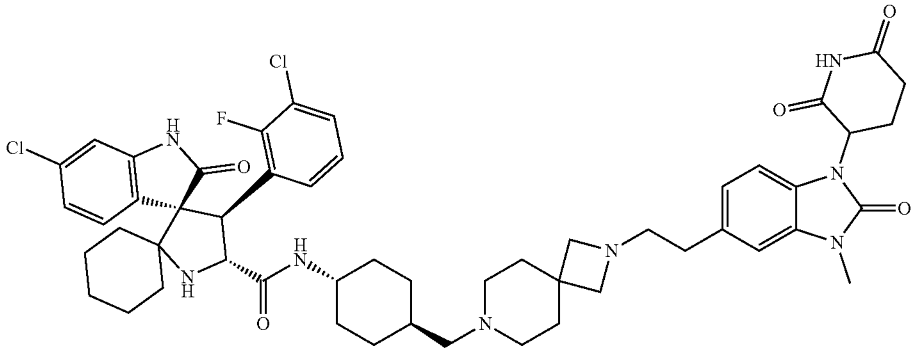 [SMILES: Cn1c(=O)n(C2CCC(=O)NC2=O)c2ccc(CCN3CC4(CCN(C[C@H]5CC[C@H](NC(=O)[C@@H]6NC7(CCCCC7)[C@@]7(C(=O)Nc8cc(Cl)ccc87)[C@H]6c6cccc(Cl)c6F)CC5)CC4)C3)cc21] |
| I-155 | 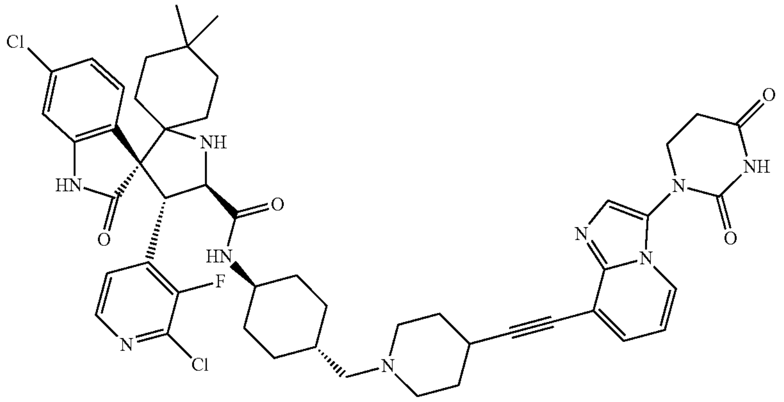 [SMILES: CC1(C)CCC2(CC1)N[C@@H](C(=O)N[C@H]1CC[C@H](CN3CCC(C#Cc4cccn5c(N6CCC(=O)NC6=O)cnc45)CC3)CC1)[C@H](c1ccnc(Cl)c1F)[C@]21C(=O)Nc2cc(Cl)ccc21] |
| I-156 | 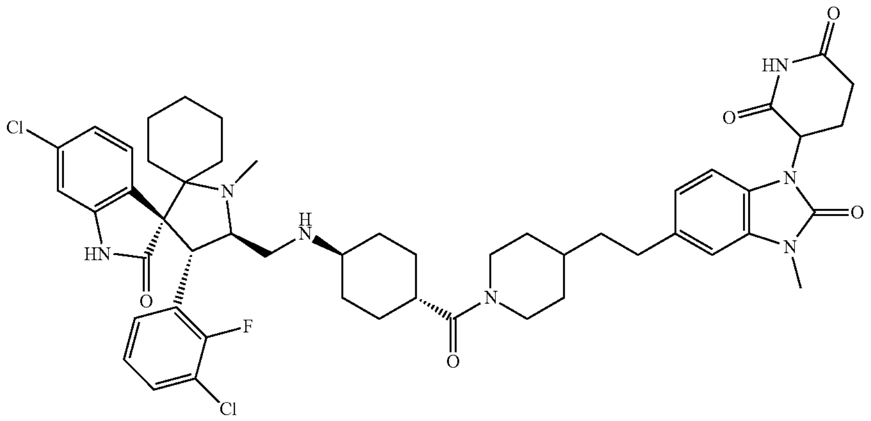 [SMILES: CN1[C@@H](CN[C@H]2CC[C@H](C(=O)N3CCC(CCc4ccc5c(c4)n(C)c(=O)n5C4CCC(=O)NC4=O)CC3)CC2)[C@H](c2cccc(Cl)c2F)[C@]2(C(=O)Nc3cc(Cl)ccc32)C12CCCCC2] |

TABLE 1-continued
| Exemplary Compounds | |
|---|---|
| I-# | Structure |
| I-157 | 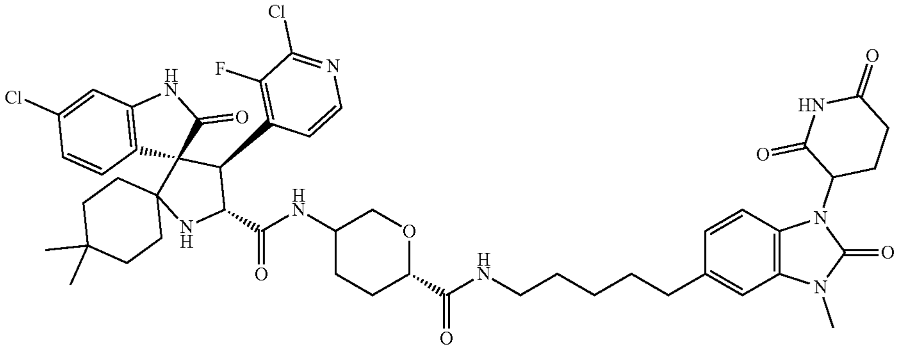 [SMILES: Cn1c(=O)n(C2CCC(=O)NC2=O)c2ccc(CCCCCNC(=O)[C@@H]3CCC(NC(=O)[C@@H]4NC5(CCC(C)(C)CC5)[C@@]5(C(=O)Nc6cc(Cl)ccc65)[C@H]4c4ccnc(Cl)c4F)CO3)cc21] |
| I-158 | 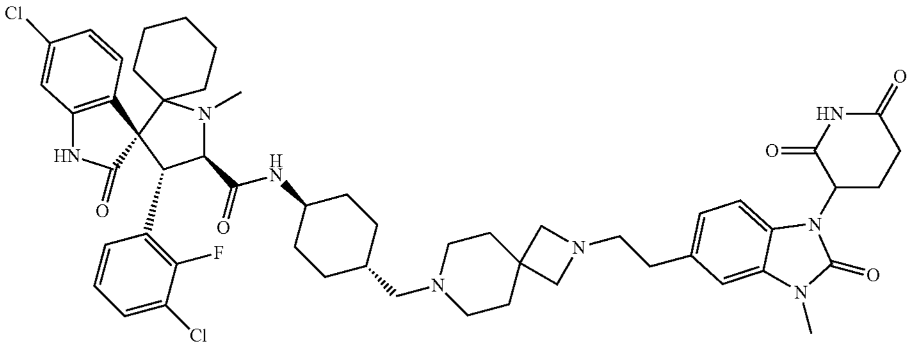 [SMILES: CN1[C@@H](C(=O)N[C@H]2CC[C@H](CN3CCC4(CC3)CN(CCc3ccc5c(c3)n(C)c(=O)n5C3CCC(=O)NC3=O)C4)CC2)[C@H](c2cccc(Cl)c2F)[C@]2(C(=O)Nc3cc(Cl)ccc32)C12CCCCC2] |
| I-159 | 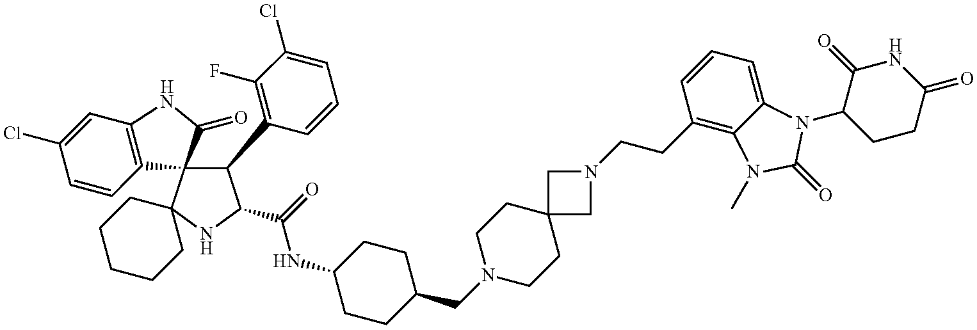 |
| I-160 | 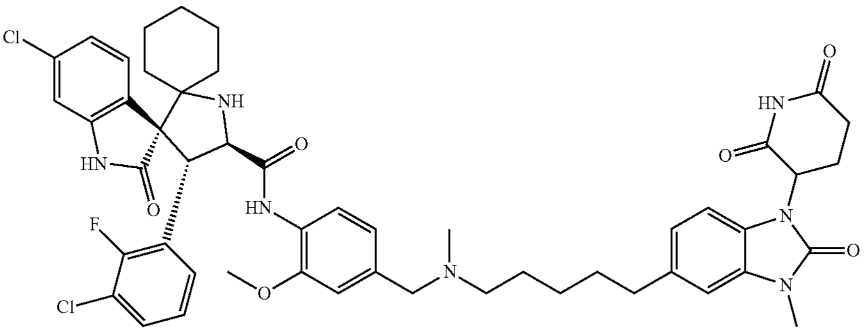 [SMILES: COc1cc(CN(C)CCCCCc2ccc3c(c2)n(C)c(=O)n3C2CCC(=O)NC2=O)ccc1NC(=O)[C@@H]1NC2(CCCCC2)[C@@]2(C(=O)Nc3cc(Cl)ccc32)[C@H]1c1cccc(Cl)c1F] |

TABLE 1-continued
| Exemplary Compounds | |
|---|---|
| I-# | Structure |
| I-161 | 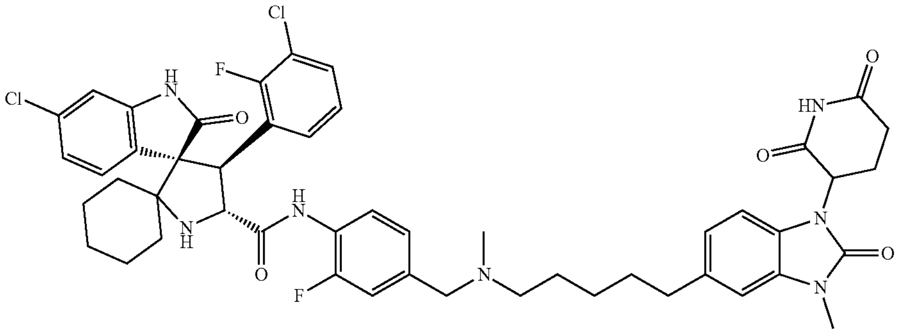 [SMILES: CN(CCCCCc1ccc2c(c1)n(C)c(=O)n2C1CCC(=O)NC1=O)Cc1ccc(NC(=O)[C@@H]2NC3(CCCCC3)[C@@]3(C(=O)Nc4cc(Cl)ccc43)[C@H]2c2cccc(Cl)c2F)c(F)c1] |
| I-162 | 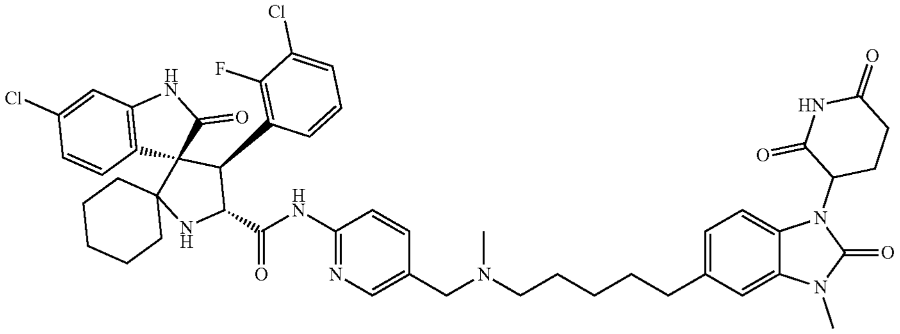 [SMILES: CN(CCCCCc1ccc2c(c1)n(C)c(=O)n2C1CCC(=O)NC1=O)Cc1ccc(NC(=O)[C@@H]2NC3(CCCCC3)[C@@]3(C(=O)Nc4cc(Cl)ccc43)[C@H]2c2cccc(Cl)c2F)nc1] |
| I-163 | 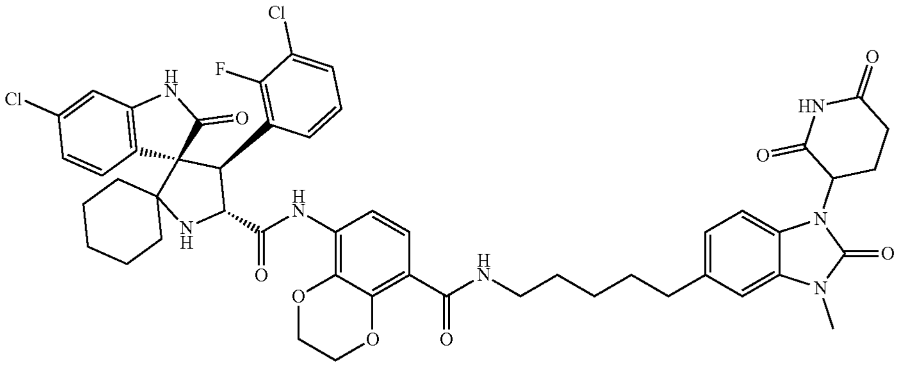 [SMILES: Cn1c(=O)n(C2CCC(=O)NC2=O)c2ccc(CCCCCNC(=O)c3ccc(NC(=O)[C@@H]4NC5(CCCCC5)[C@@]5(C(=O)Nc6cc(Cl)ccc65)[C@H]4c4cccc(Cl)c4F)c4c3OCCO4)cc21] |
| I-164 | 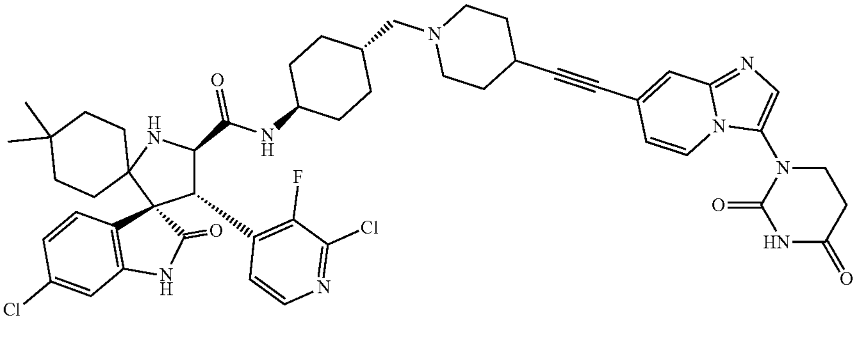 [SMILES: CC1(C)CCC2(CC1)N[C@@H](C(=O)N[C@H]1CC[C@H](CN3CCC(C#Cc4ccn5c(N6CCC(=O)NC6=O)cnc5c4)CC3)CC1)[C@H](c1ccnc(Cl)c1F)[C@]21C(=O)Nc2cc(Cl)ccc21] |

TABLE 1-continued
| Exemplary Compounds | |
|---|---|
| I-# | Structure |
| I-165 | 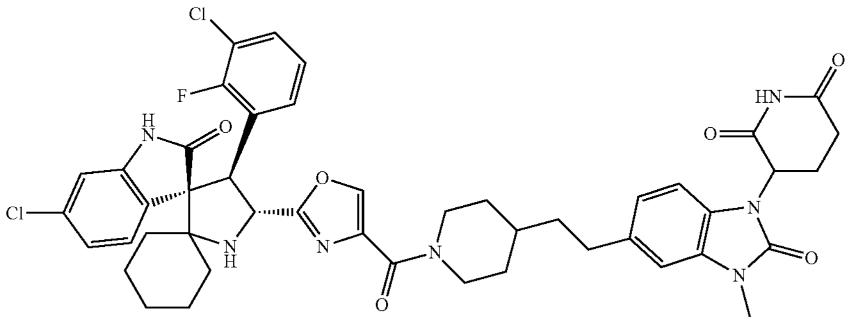 [SMILES: Cn1c(=O)n(C2CCC(=O)NC2=O)c2ccc(CCC3CCN(C(=O)c4coc([C@@H]5NC6(CCCCC6)[C@@]6(C(=O)Nc7cc(Cl)ccc76)[C@H]5c5cccc(Cl)c5F)n4)CC3)cc21] |
| I-166 | 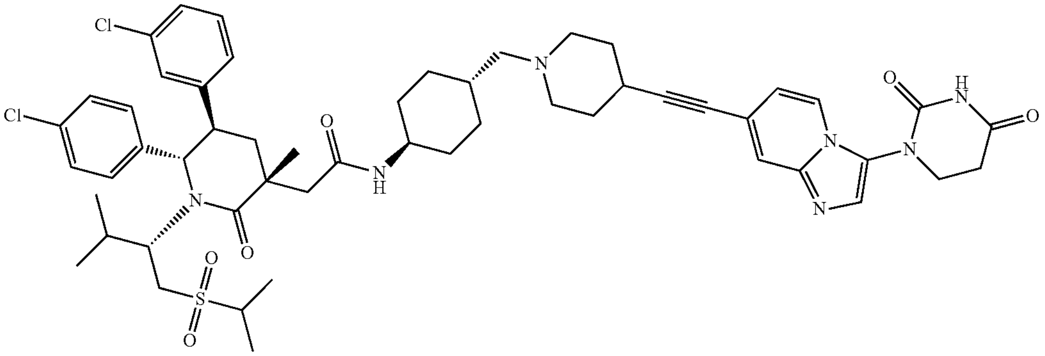 [SMILES: CC(C)[C@@H](CS(=O)(=O)C(C)C)N1C(=O)[C@@](C)(CC(=O)N[C@H]2CC[C@H](CN3CCC(C#Cc4ccn5c(N6CCC(=O)NC6=O)cnc5c4)CC3)CC2)C[C@H](c2cccc(Cl)c2)[C@H]1c1ccc(Cl)cc1] |
| I-167 | 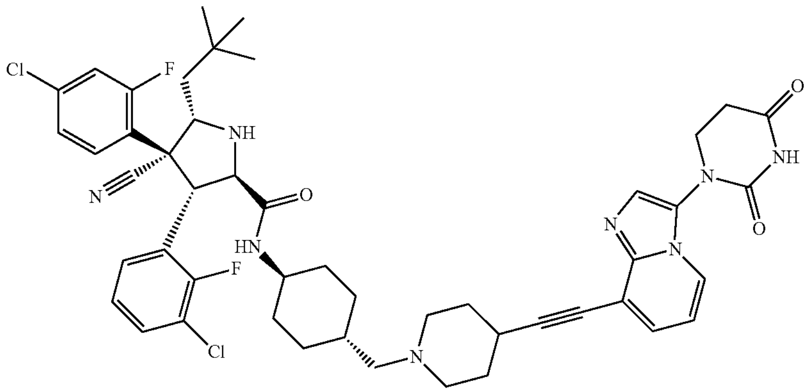 [SMILES: CC(C)(C)C[C@@H]1N[C@@H](C(=O)N[C@H]2CC[C@H](CN3CCC(C#Cc4cccn5c(N6CCC(=O)NC6=O)cnc45)CC3)CC2)[C@H](c2cccc(Cl)c2F)[C@@]1(C#N)c1ccc(Cl)cc1F] |
| I-168 | 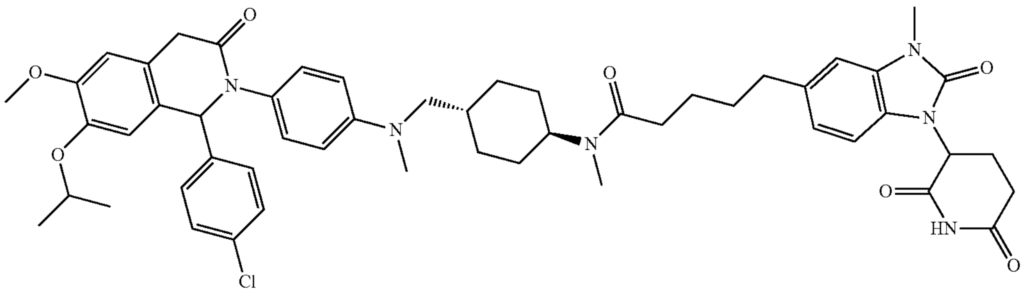 [SMILES: COc1cc2c(cc1OC(C)C)C(c1ccc(Cl)cc1)N(c1ccc(N(C)C[C@H]3CC[C@H](N(C)C(=O)CCCCc4ccc5c(c4)n(C)c(=O)n5C4CCC(=O)NC4=O)CC3)cc1)C(=O)C2] |

TABLE 1-continued
| Exemplary Compounds | |
|---|---|
| I-# | Structure |
| I-169 | 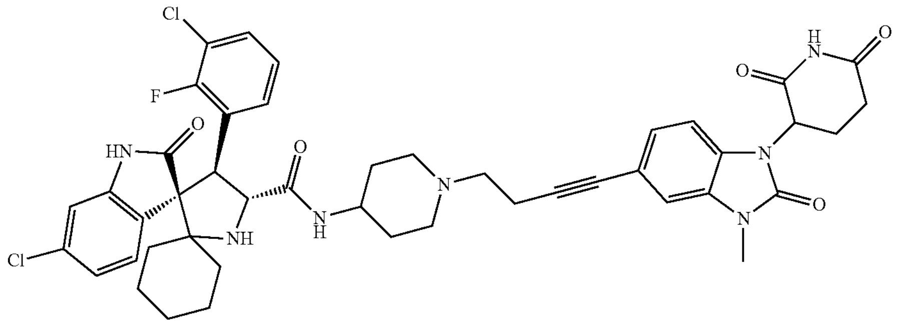 [SMILES: Cn1c(=O)n(C2CCC(=O)NC2=O)c2ccc(C#CCCN3CCC(NC(=O)[C@@H]4NC5(CCCCC5)[C@@]5(C(=O)Nc6cc(Cl)ccc65)[C@H]4c4cccc(Cl)c4F)CC3)cc21] |
| I-170 | 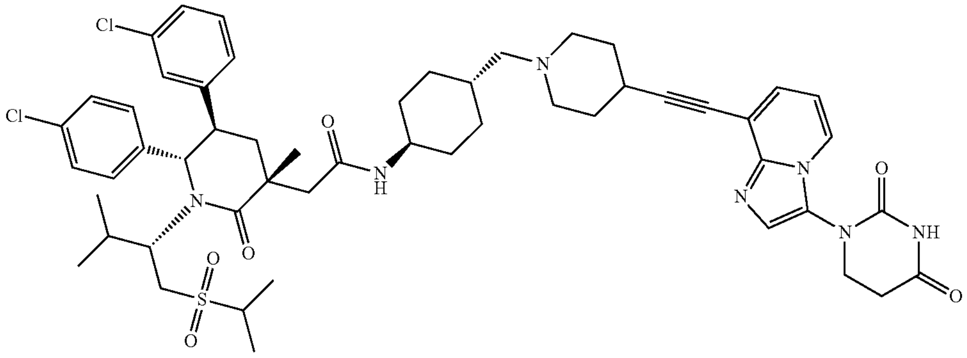 [SMILES: CC(C)[C@@H](CS(=O)(=O)C(C)C)N1C(=O)[C@@](C)(CC(=O)N[C@H]2CC[C@H](CN3CCC(C#Cc4cccn5c(N6CCC(=O)NC6=O)cnc45)CC3)CC2)C[C@H](c2cccc(Cl)c2)[C@H]1c1ccc(Cl)cc1] |
| I-171 | 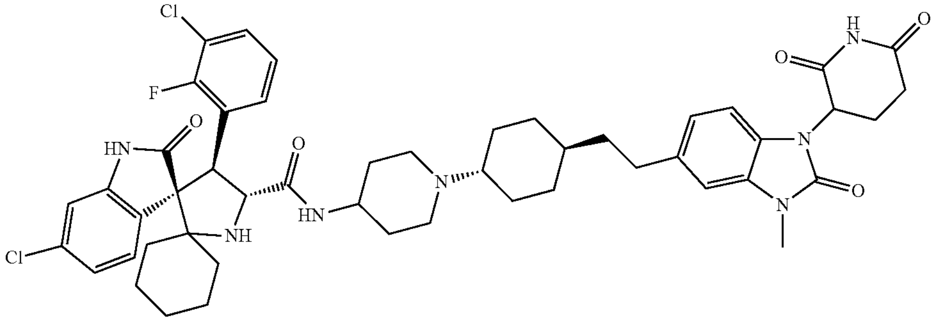 [SMILES: Cn1c(=O)n(C2CCC(=O)NC2=O)c2ccc(CC[C@H]3CC[C@H](N4CCC(NC(=O)[C@@H]5NC6(CCCCC6)[C@@]6(C(=O)Nc7cc(Cl)ccc76)[C@H]5c5cccc(Cl)c5F)CC4)CC3)cc21] |
| I-172 | 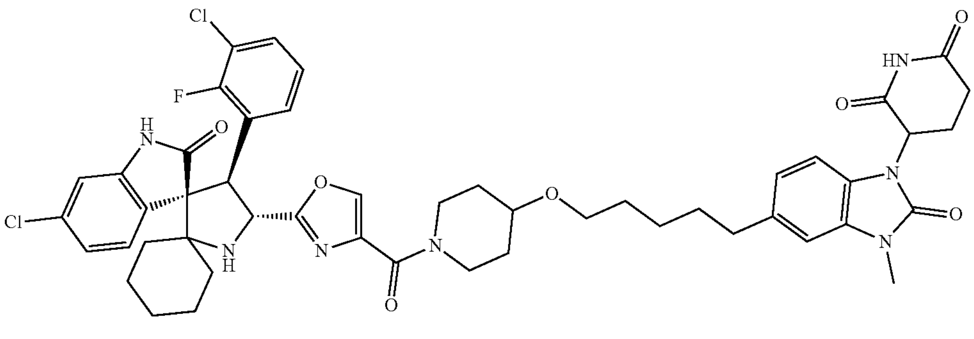 [SMILES: Cn1c(=O)n(C2CCC(=O)NC2=O)c2ccc(CCCCCOC3CCN(C(=O)c4coc([C@@H]5NC6(CCCCC6)[C@@]6(C(=O)Nc7cc(Cl)ccc76)[C@H]5c5cccc(Cl)c5F)n4)CC3)cc21] |

TABLE 1-continued
| Exemplary Compounds | |
|---|---|
| I-# | Structure |
| I-173 | 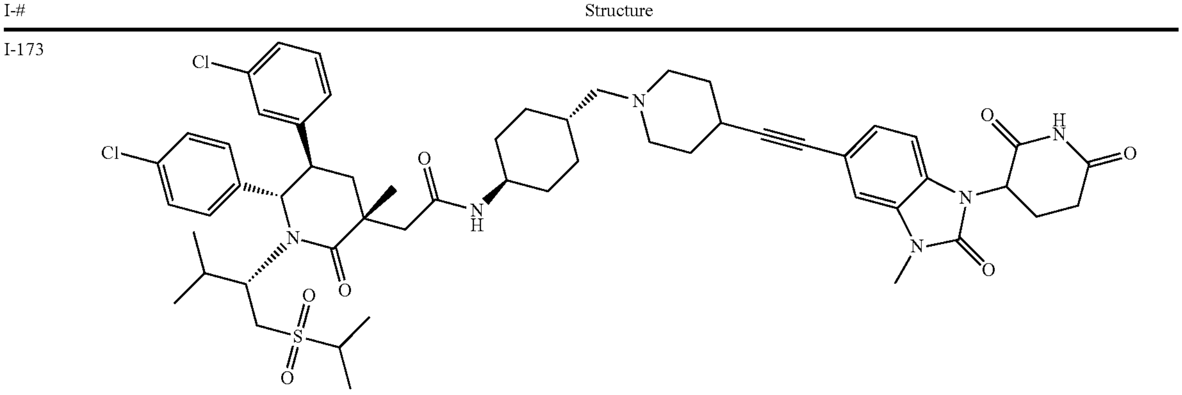 |
| I-174 | 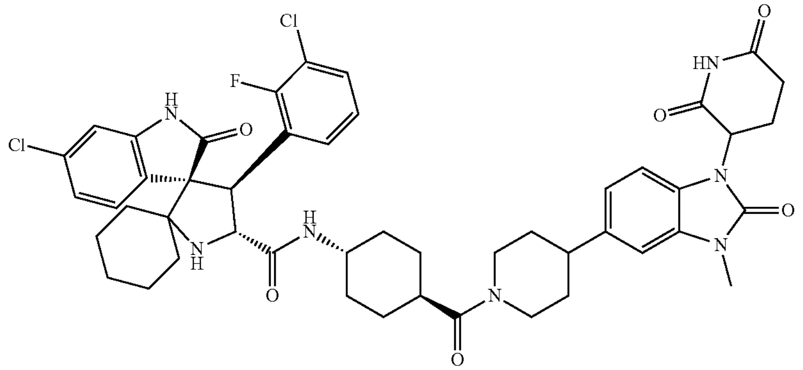 [SMILES: Cn1c(=O)n(C2CCC(=O)NC2=O)c2ccc(C3CCN(C(=O)[C@H]4CC[C@H](NC(=O)[C@@H]5NC6(CCCCC6)[C@@]6(C(=O)Nc7cc(Cl)ccc76)[C@H]5c5cccc(Cl)c5F)CC4)CC3)cc21] |
| I-175 | 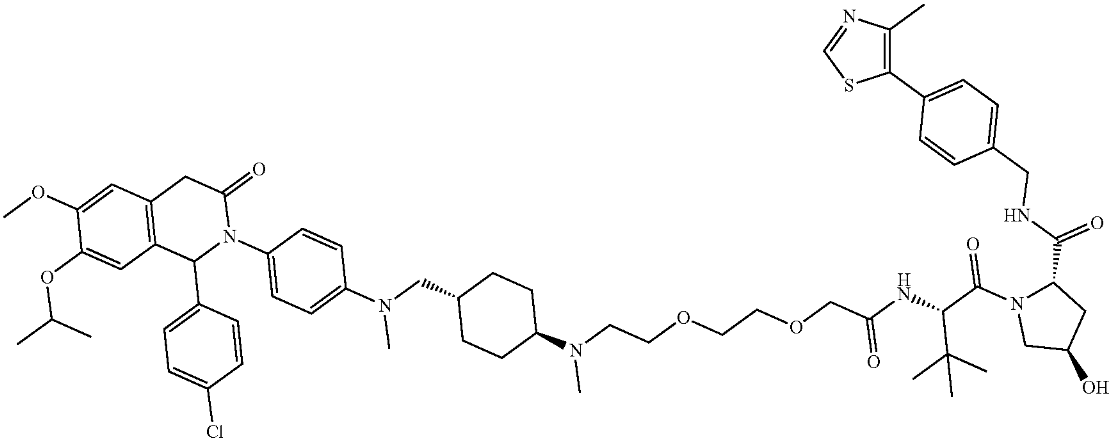 [SMILES: COc1cc2c(cc1OC(C)C)C(c1ccc(Cl)cc1)N(c1ccc(N(C)C[C@H]3CC[C@H](N(C)CCOCCOCC(=O)N[C@H](C(=O)N4C[C@H](O)C[C@H]4C(=O)NCc4ccc(-c5scnc5C)cc4)C(C)(C)C)CC3)cc1)C(=O)C2] |
| I-176 | 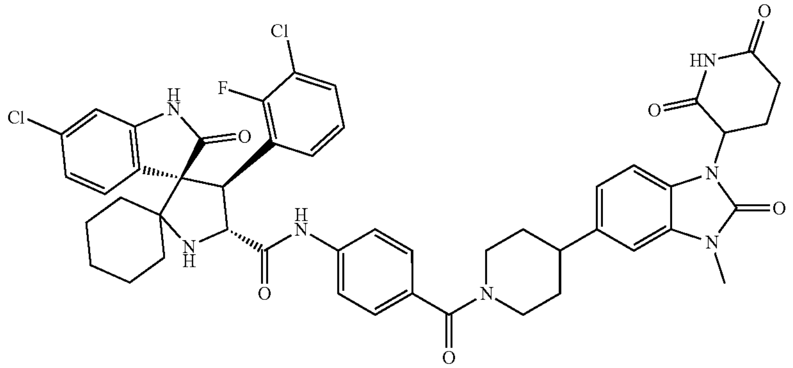 [SMILES: Cn1c(=O)n(C2CCC(=O)NC2=O)c2ccc(C3CCN(C(=O)c4ccc(NC(=O)[C@@H]5NC6(CCCCC6)[C@@]6(C(=O)Nc7cc(Cl)ccc76)[C@H]5c5cccc(Cl)c5F)cc4)CC3)cc21] |

TABLE 1-continued
| Exemplary Compounds | |
|---|---|
| I-# | Structure |
| I-177 | 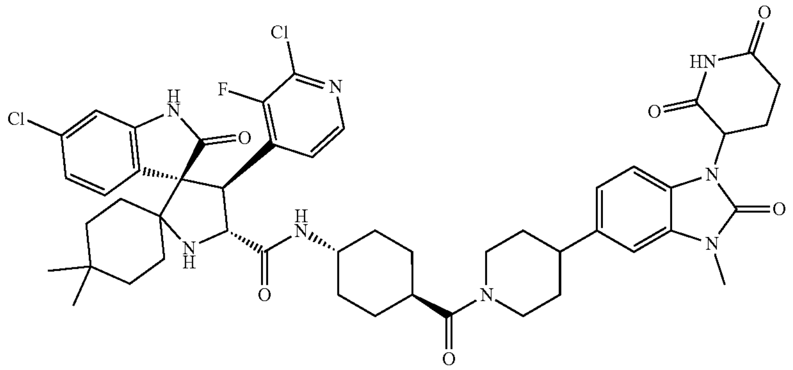 [SMILES: Cn1c(=O)n(C2CCC(=O)NC2=O)c2ccc(C3CCN(C(=O)[C@H]4CC[C@H](NC(=O)[C@@H]5NC6(CCC(C)(C)CC6)[C@@]6(C(=O)Nc7cc(Cl)ccc76)[C@H]5c5ccnc(Cl)c5F)CC4)CC3)cc21] |
| I-178 | 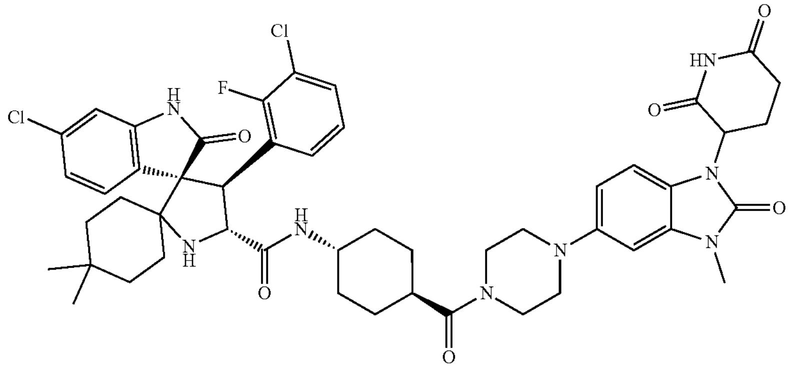 [SMILES: Cn1c(=O)n(C2CCC(=O)NC2=O)c2ccc(N3CCN(C(=O)[C@H]4CC[C@H](NC(=O)[C@@H]5NC6(CCC(C)(C)CC6)[C@@]6(C(=O)Nc7cc(Cl)ccc76)[C@H]5c5cccc(Cl)c5F)CC4)CC3)cc21] |
| I-179 | 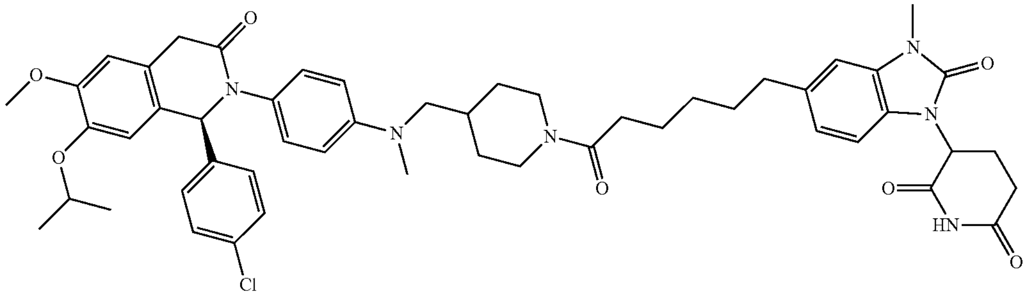 [SMILES: COc1cc2c(cc1OC(C)C)[C@H](c1ccc(Cl)cc1)N(c1ccc(N(C)CC3CCN(C(=O)CCCCCc4ccc5c(c4)n(C)c(=O)n5C4CCC(=O)NC4=O)CC3)cc1)C(=O)C2] |
| I-180 | 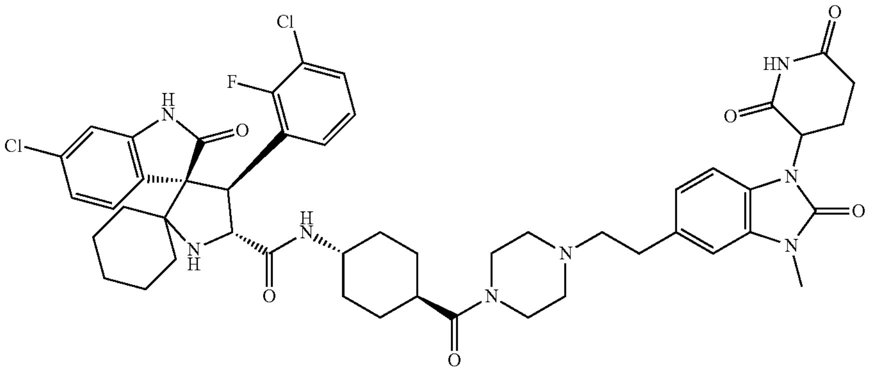 [SMILES: Cn1c(=O)n(C2CCC(=O)NC2=O)c2ccc(CCN3CCN(C(=O)[C@H]4CC[C@H](NC(=O)[C@@H]5NC6(CCCCC6)[C@@]6(C(=O)Nc7cc(Cl)ccc76)[C@H]5c5cccc(Cl)c5F)CC4)CC3)cc21] |

TABLE 1-continued
| Exemplary Compounds | |
|---|---|
| I-# | Structure |
| I-181 | 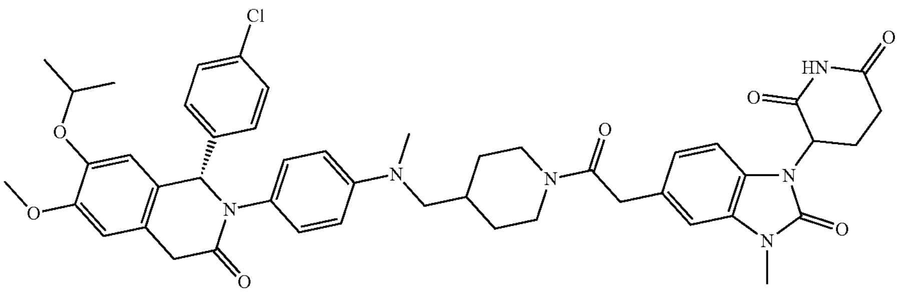 [SMILES: COc1cc2c(cc1OC(C)C)[C@H](c1ccc(Cl)cc1)N(c1ccc(N(C)CC3CCN(C(=O)Cc4ccc5c(c4)n(C)c(=O)n5C4CCC(=O)NC4=O)CC3)cc1)C(=O)C2] |
| I-182 | 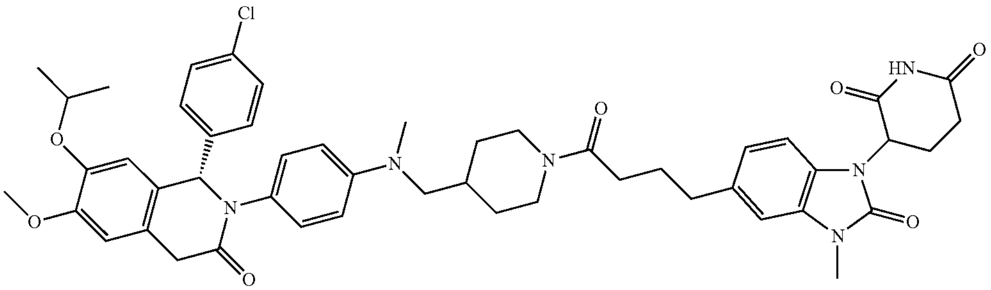 [SMILES: COc1cc2c(cc1OC(C)C)[C@H](c1ccc(Cl)cc1)N(c1ccc(N(C)CC3CCN(C(=O)CCCc4ccc5c(c4)n(C)c(=O)n5C4CCC(=O)NC4=O)CC3)cc1)C(=O)C2] |
| I-183 | 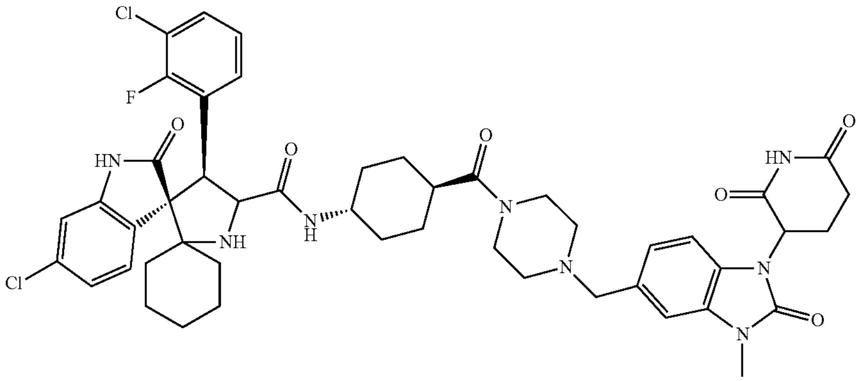 [SMILES: Cn1c(=O)n(C2CCC(=O)NC2=O)c2ccc(CN3CCN(C(=O)[C@H]4CC[C@H](NC(=O)C5NC6(CCCCC6)[C@@]6(C(=O)Nc7cc(Cl)ccc76)[C@H]5c5cccc(Cl)c5F)CC4)CC3)cc21] |
| I-184 | 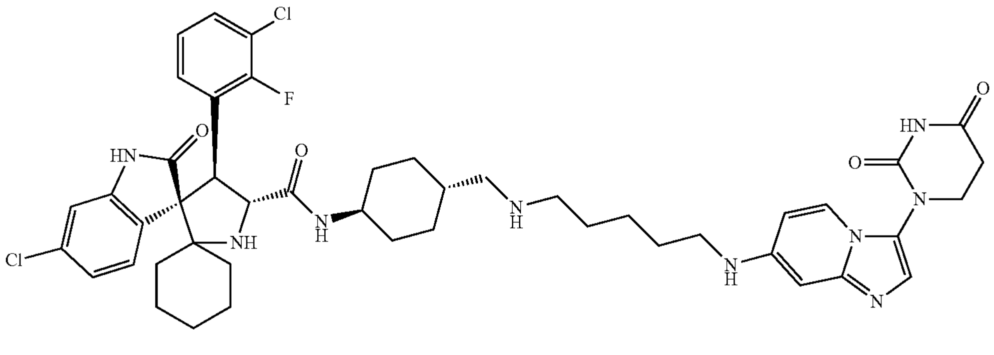 [SMILES: O=C1CCN(c2cnc3cc(NCCCCCNC[C@H]4CC[C@H](NC(=O)[C@@H]5NC6(CCCCC6)[C@@]6(C(=O)Nc7cc(Cl)ccc76)[C@H]5c5cccc(Cl)c5F)CC4)ccn23)C(=O)N1] |

TABLE 1-continued
| Exemplary Compounds | |
|---|---|
| I-# | Structure |
| I-185 | 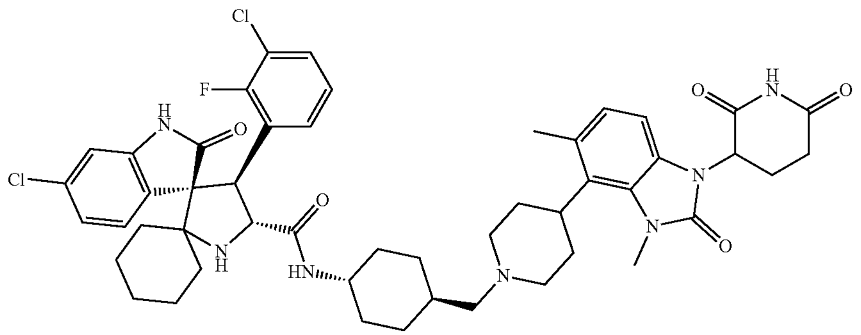 [SMILES: Cc1ccc2c(c1C1CCN(C[C@H]3CC[C@H](NC(=O)[C@@H]4NC5(CCCCC5)[C@@]5(C(=O)Nc6cc(Cl)ccc65)[C@H]4c4cccc(Cl)c4F)CC3)CC1)n(C)c(=O)n2C1CCC(=O)NC1=O] |
| I-186 | 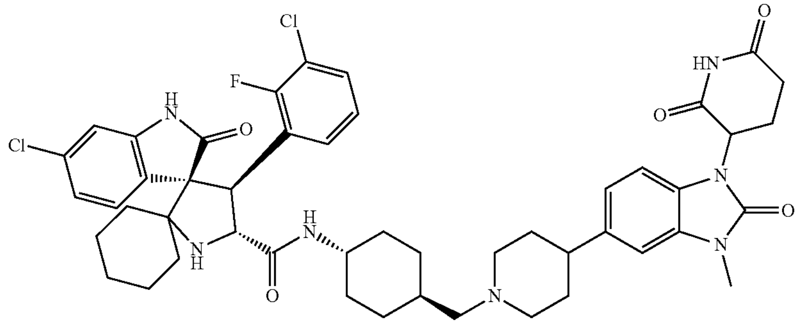 [SMILES: Cn1c(=O)n(C2CCC(=O)NC2=O)c2ccc(C3CCN(C[C@H]4CC[C@H](NC(=O)[C@@H]5NC6(CCCCC6)[C@@]6(C(=O)Nc7cc(Cl)ccc76)[C@H]5c5cccc(Cl)c5F)CC4)CC3)cc21] |
| I-187 | 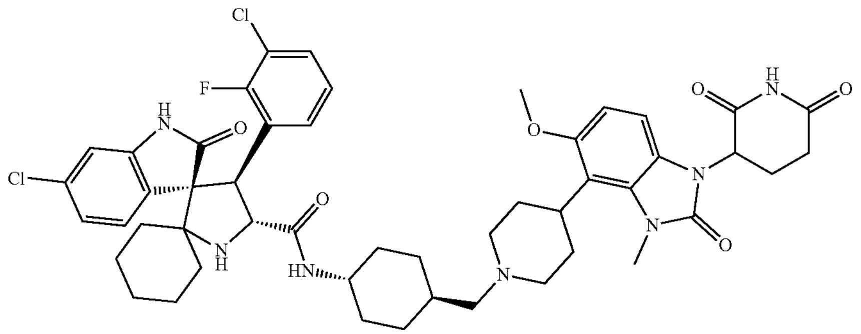 [SMILES: COc1ccc2c(c1C1CCN(C[C@H]3CC[C@H](NC(=O)[C@@H]4NC5(CCCCC5)[C@@]5(C(=O)Nc6cc(Cl)ccc65)[C@H]4c4cccc(Cl)c4F)CC3)CC1)n(C)c(=O)n2C1CCC(=O)NC1=O] |
| I-188 | 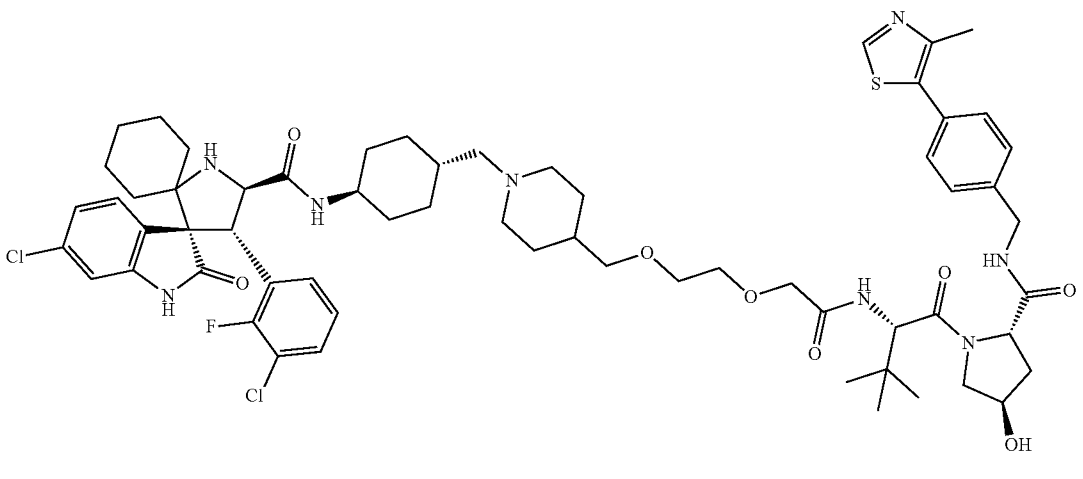 [SMILES: Cc1ncsc1-c1ccc(CNC(=O)[C@@H]2C[C@@H](O)CN2C(=O)[C@@H](NC(=O)COCCOCC2CCN(C[C@H]3CC[C@H](NC(=O)[C@@H]4NC5(CCCCC5)[C@@]5(C(=O)Nc6cc(Cl)ccc65)[C@H]4c4cccc(Cl)c4F)CC3)CC2)C(C)(C)C)cc1] |

TABLE 1-continued
| Exemplary Compounds | |
|---|---|
| I-# | Structure |
| I-189 | 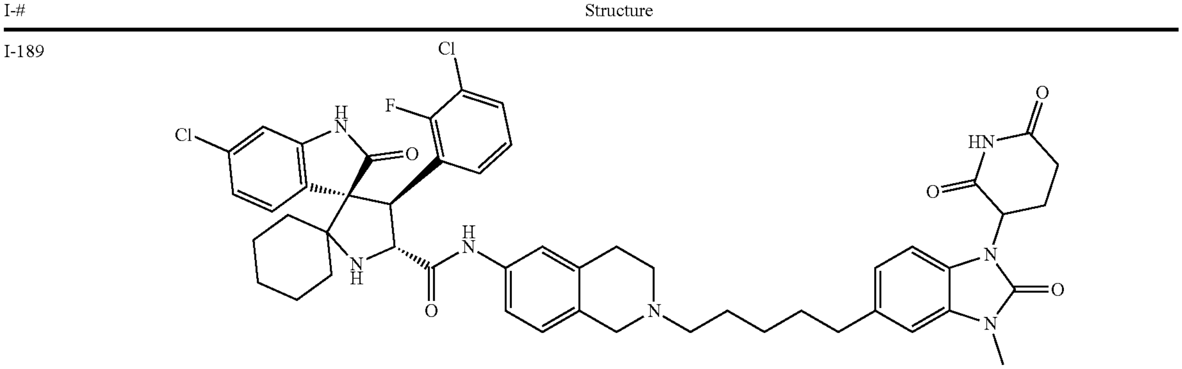 |
| I-190 | 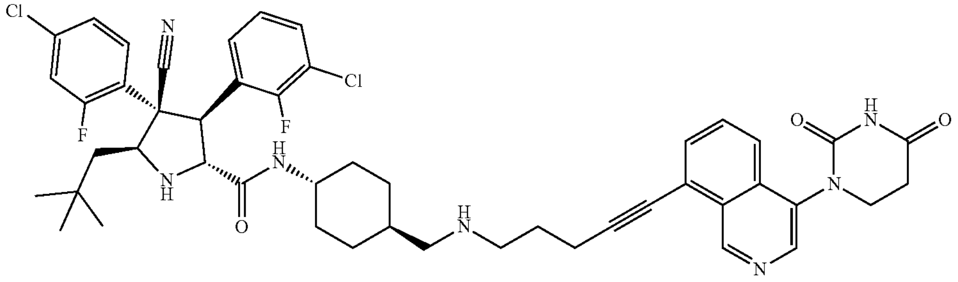 [SMILES: CC(C)(C)C[C@@H]1N[C@@H](C(=O)N[C@H]2CC[C@H](CNCCCC#Cc3cccc4c(N5CCC(=O)NC5=O)cncc34)CC2)[C@H](c2cccc(Cl)c2F)[C@@]1(C#N)c1ccc(Cl)cc1F] |
| I-191 | 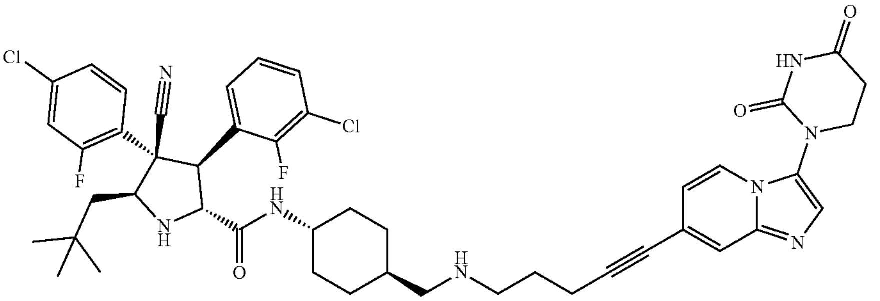 [SMILES: CC(C)(C)C[C@@H]1N[C@@H](C(=O)N[C@H]2CC[C@H](CNCCCC#Cc3ccn4c(N5CCC(=O)NC5=O)cnc4c3)CC2)[C@H](c2cccc(Cl)c2F)[C@@]1(C#N)c1ccc(Cl)cc1F] |
| I-192 | 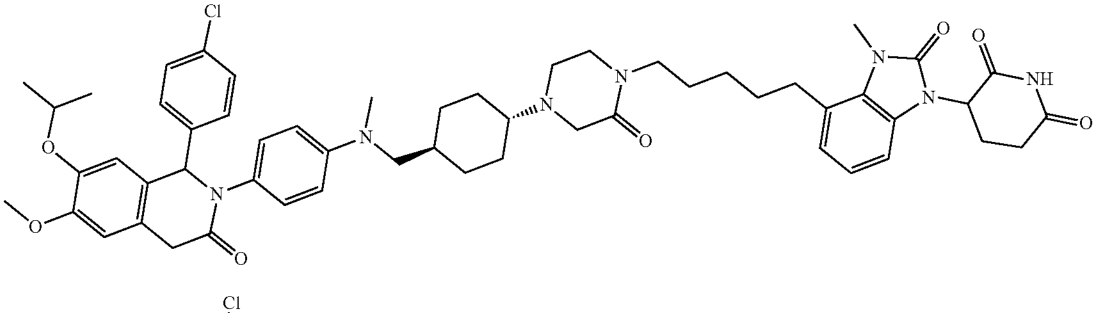 |
| I-193 | 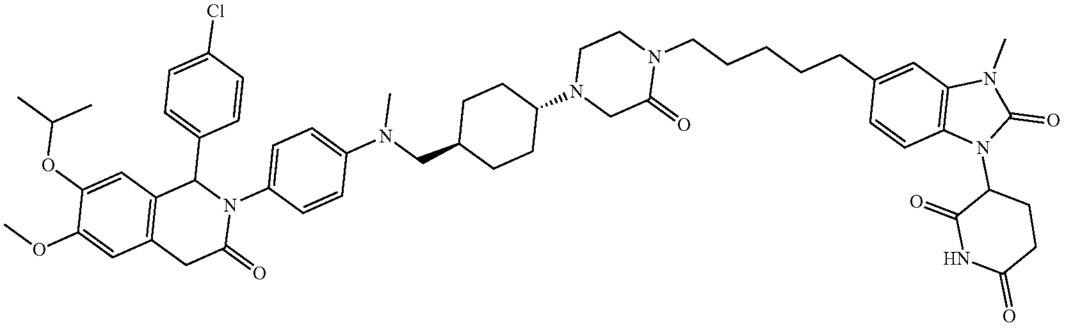 [SMILES: COc1cc2c(cc1OC(C)C)C(c1ccc(Cl)cc1)N(c1ccc(N(C)C[C@H]3CC[C@H](N4CCN(CCCCCc5ccc6c(c5)n(C)c(=O)n6C5CCC(=O)NC5=O)C(=O)C4)CC3)cc1)C(=O)C2] |

TABLE 1-continued
| Exemplary Compounds | |
|---|---|
| I-# | Structure |
| I-194 | 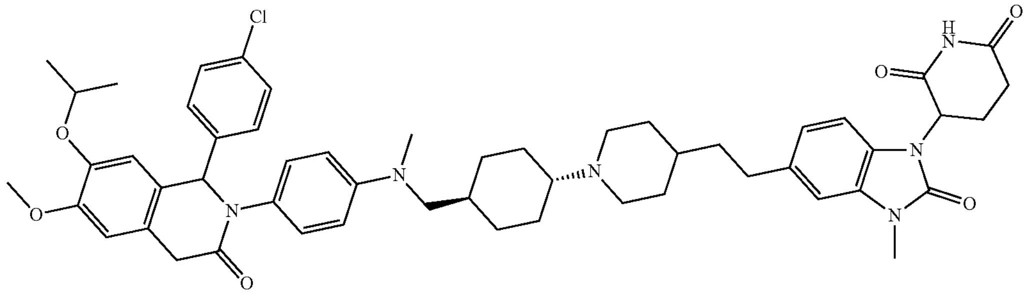 [SMILES: COc1cc2c(cc1OC(C)C)C(c1ccc(Cl)cc1)N(c1ccc(N(C)C[C@H]3CC[C@H](N4CCC(CCc5ccc6c(c5)n(C)c(=O)n6C5CCC(=O)NC5=O)CC4)CC3)cc1)C(=O)C2] |
| I-195 | 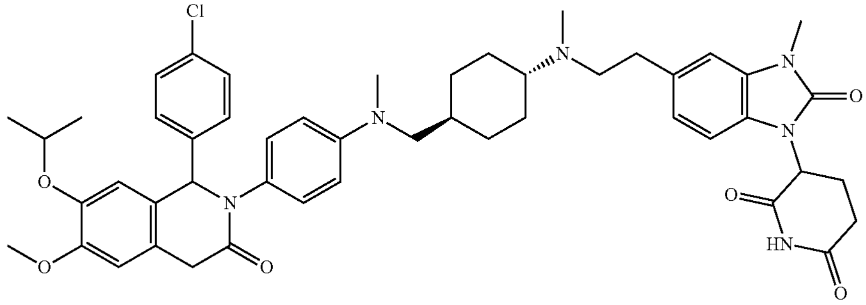 [SMILES: COc1cc2c(cc1OC(C)C)C(c1ccc(Cl)cc1)N(c1ccc(N(C)C[C@H]3CC[C@H](N(C)CCc4ccc5c(c4)n(C)c(=O)n5C4CCC(=O)NC4=O)CC3)cc1)C(=O)C2] |
| I-196 | 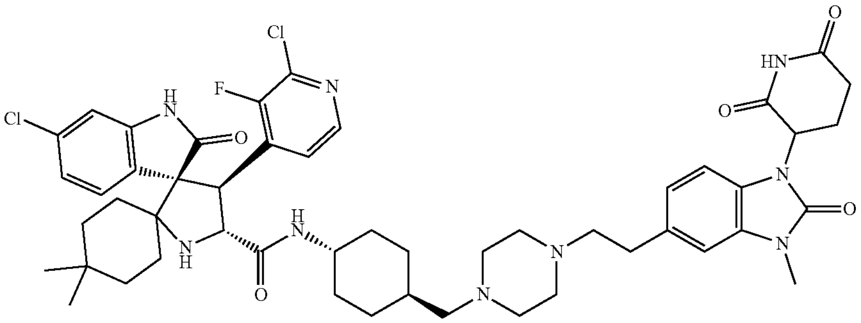 [SMILES: Cn1c(=O)n(C2CCC(=O)NC2=O)c2ccc(CCN3CCN(C[C@H]4CC[C@H](NC(=O)[C@@H]5NC6(CCC(C)(C)CC6)[C@@]6(C(=O)Nc7cc(Cl)ccc76)[C@H]5c5ccnc(Cl)c5F)CC4)CC3)cc21] |
| I-197 | 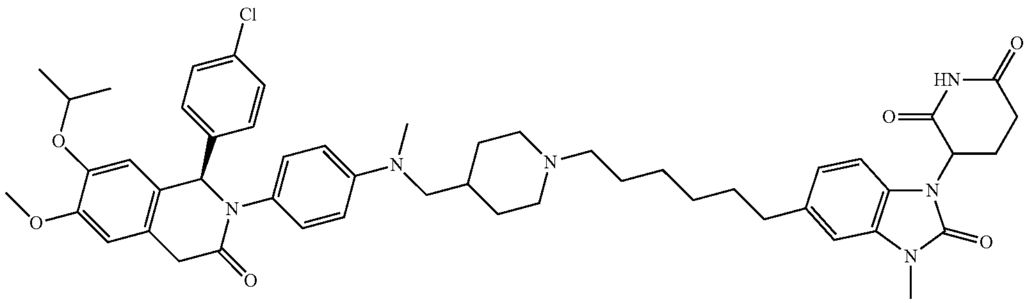 [SMILES: COc1cc2c(cc1OC(C)C)[C@@H](c1ccc(Cl)cc1)N(c1ccc(N(C)CC3CCN(CCCCCCc4ccc5c(c4)n(C)c(=O)n5C4CCC(=O)NC4=O)CC3)cc1)C(=O)C2] |

TABLE 1-continued
| Exemplary Compounds | |
|---|---|
| I-# | Structure |
| I-198 | 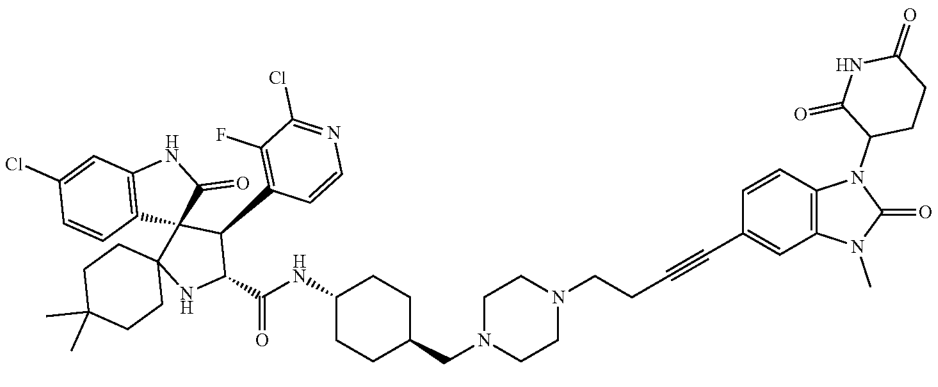 [SMILES: Cn1c(=O)n(C2CCC(=O)NC2=O)c2ccc(C#CCCN3CCN(C[C@H]4CC[C@H](NC(=O)[C@@H]5NC6(CCC(C)(C)CC6)[C@@]6(C(=O)Nc7cc(Cl)ccc76)[C@H]5c5ccnc(Cl)c5F)CC4)CC3)cc21] |
| I-199 | 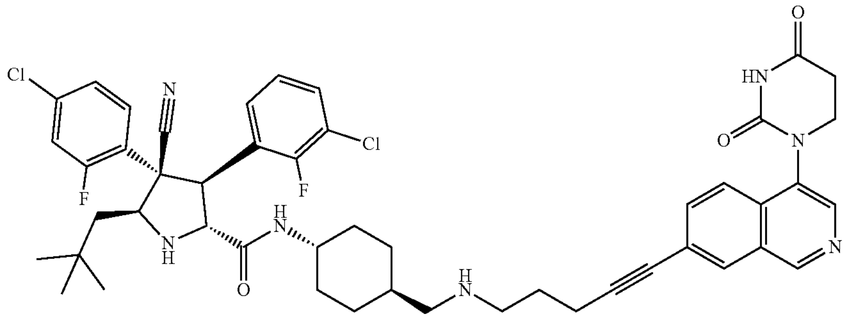 [SMILES: CC(C)(C)C[C@@H]1N[C@@H](C(=O)N[C@H]2CC[C@H](CNCCCC#Cc3ccc4c(N5CCC(=O)NC5=O)cncc4c3)CC2)[C@H](c2cccc(Cl)c2F)[C@@]1(C#N)c1ccc(Cl)cc1F] |
| I-200 | 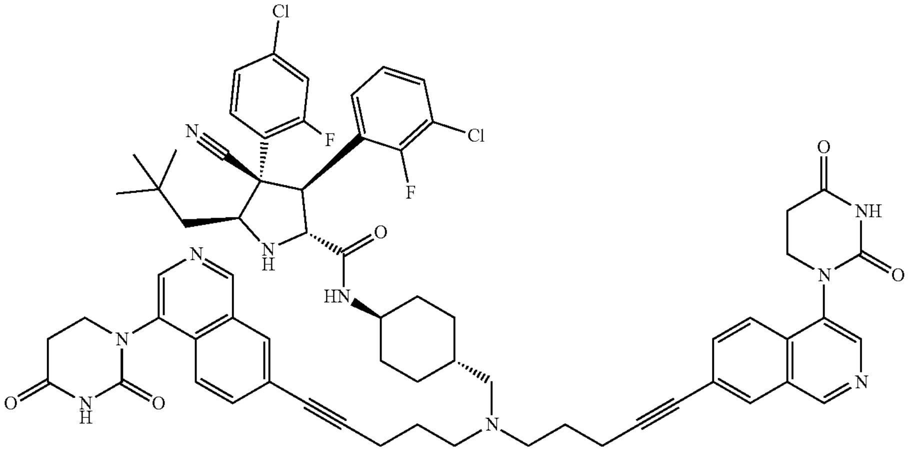 [SMILES: CC(C)(C)C[C@@H]1N[C@@H](C(=O)N[C@H]2CC[C@H](CN(CCCC#Cc3ccc4c(N5CCC(=O)NC5=O)cncc4c3)CCCC#Cc3ccc4c(N5CCC(=O)NC5=O)cncc4c3)CC2)[C@H](c2cccc(Cl)c2F)[C@@]1(C#N)c1ccc(Cl)cc1F] |
| I-201 | 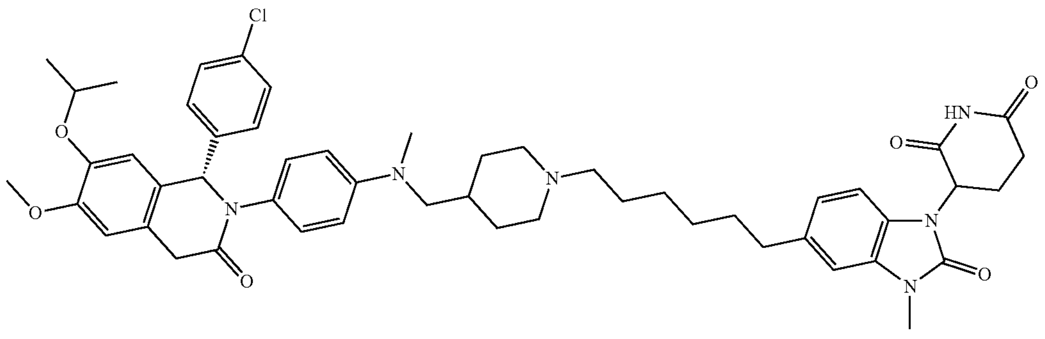 [SMILES: COc1cc2c(cc1OC(C)C)[C@H](c1ccc(Cl)cc1)N(c1ccc(N(C)CC3CCN(CCCCCCc4ccc5c(c4)n(C)c(=O)n5C4CCC(=O)NC4=O)CC3)cc1)C(=O)C2] |

TABLE 1-continued
| Exemplary Compounds | |
|---|---|
| I-# | Structure |
| I-202 | 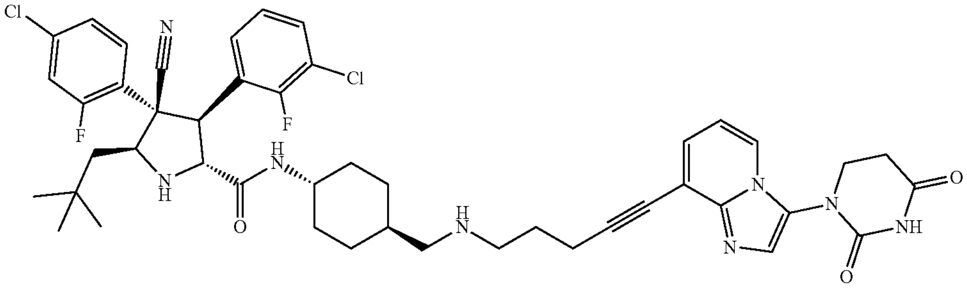 [SMILES: CC(C)(C)C[C@@H]1N[C@@H](C(=O)N[C@H]2CC[C@H](CNCCCC#Cc3cccn4c(N5CCC(=O)NC5=O)cnc34)CC2)[C@H](c2cccc(Cl)c2F)[C@@]1(C#N)c1ccc(Cl)cc1F] |
| I-203 | 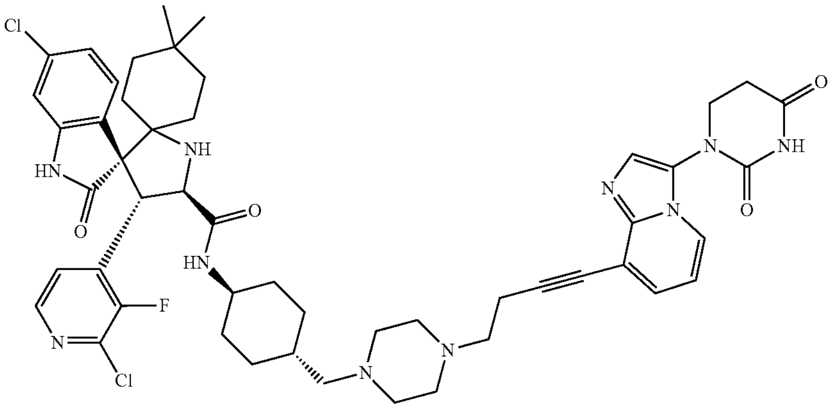 [SMILES: CC1(C)CCC2(CC1)N[C@@H](C(=O)N[C@H]1CC[C@H](CN3CCN(CCC#Cc4cccn5c(N6CCC(=O)NC6=O)cnc45)CC3)CC1)[C@H](c1ccnc(Cl)c1F)[C@]21C(=O)Nc2cc(Cl)ccc21] |
| I-204 | 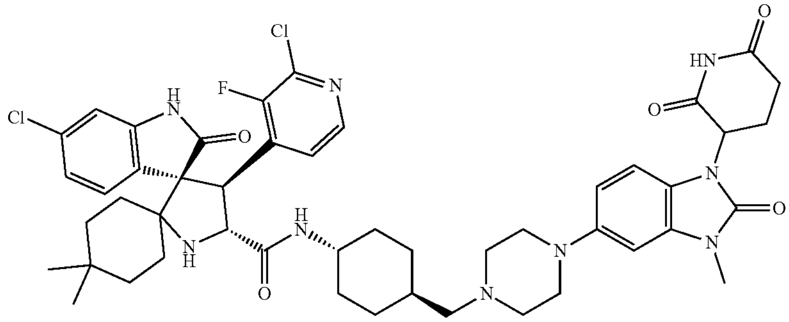 [SMILES: Cn1c(=O)n(C2CCC(=O)NC2=O)c2ccc(N3CCN(C[C@H]4CC[C@H](NC(=O)[C@@H]5NC6(CCC(C)(C)CC6)[C@@]6(C(=O)Nc7cc(Cl)ccc76)[C@H]5c5ccnc(Cl)c5F)CC4)CC3)cc21] |
| I-205 | 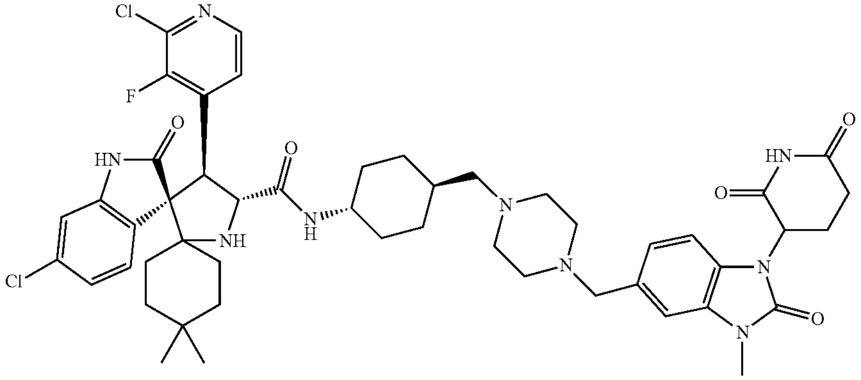 [SMILES: Cn1c(=O)n(C2CCC(=O)NC2=O)c2ccc(CN3CCN(C[C@H]4CC[C@H](NC(=O)[C@@H]5NC6(CCC(C)(C)CC6)[C@@]6(C(=O)Nc7cc(Cl)ccc76)[C@H]5c5ccnc(Cl)c5F)CC4)CC3)cc21] |

TABLE 1-continued
| Exemplary Compounds | |
|---|---|
| I-# | Structure |
| I-206 | 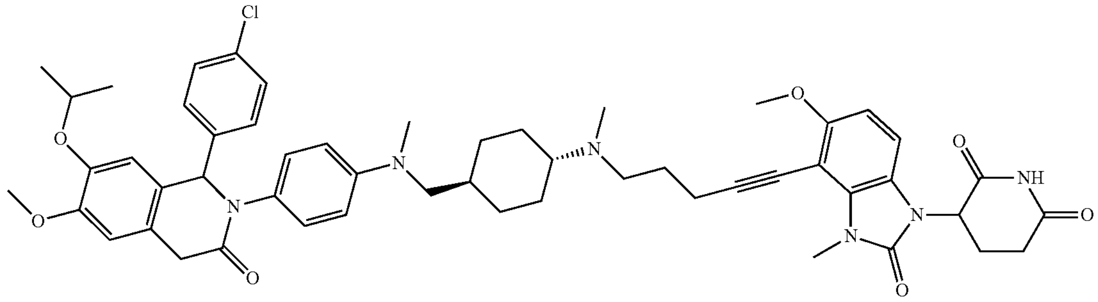 [SMILES: COc1cc2c(cc1OC(C)C)C(c1ccc(Cl)cc1)N(c1ccc(N(C)C[C@H]3CC[C@H](N(C)CCCC#Cc4c(OC)ccc5c4n(C)c(=O)n5C4CCC(=O)NC4=O)CC3)cc1)C(=O)C2] |
| I-207 | 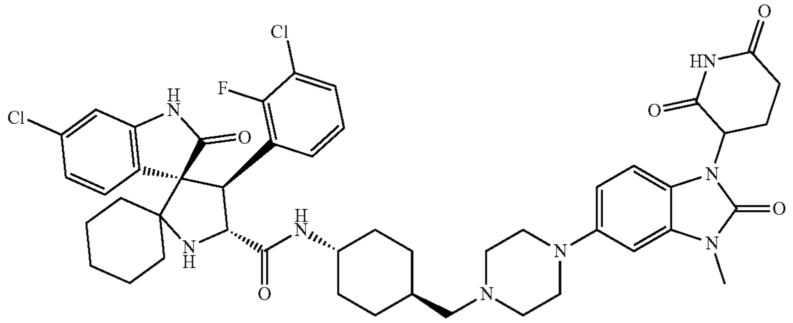 [SMILES: Cn1c(=O)n(C2CCC(=O)NC2=O)c2ccc(N3CCN(C[C@H]4CC[C@H](NC(=O)[C@@H]5NC6(CCCCC6)[C@@]6(C(=O)Nc7cc(Cl)ccc76)[C@H]5c5cccc(Cl)c5F)CC4)CC3)cc21] |
| I-208 | 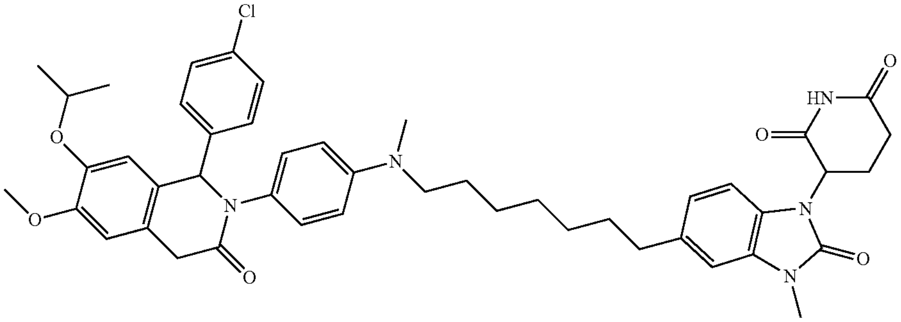 [SMILES: COc1cc2c(cc1OC(C)C)C(c1ccc(Cl)cc1)N(c1ccc(N(C)CCCCCCCc3ccc4c(c3)n(C)c(=O)n4C3CCC(=O)NC3=O)cc1)C(=O)C2] |
| I-209 | 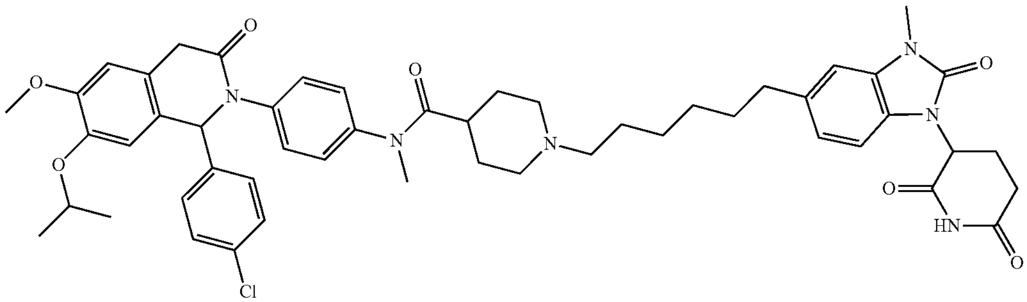 [SMILES: COc1cc2c(cc1OC(C)C)C(c1ccc(Cl)cc1)N(c1ccc(N(C)C(=O)C3CCN(CCCCCCc4ccc5c(c4)n(C)c(=O)n5C4CCC(=O)NC4=O)CC3)cc1)C(=O)C2] |

TABLE 1-continued
| Exemplary Compounds | |
|---|---|
| I-# | Structure |
| I-210 | 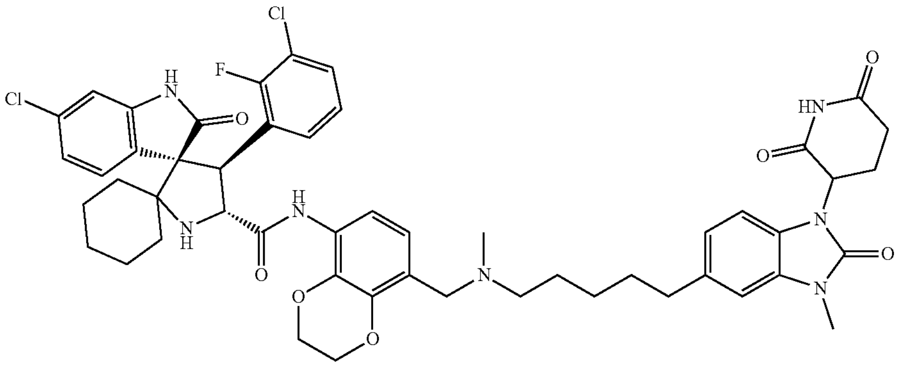 [SMILES: CN(CCCCCc1ccc2c(c1)n(C)c(=O)n2C1CCC(=O)NC1=O)Cc1ccc(NC(=O)[C@@H]2NC3(CCCCC3)[C@@]3(C(=O)Nc4cc(Cl)ccc43)[C@H]2c2cccc(Cl)c2F)c2c1OCCO2] |
| I-211 | 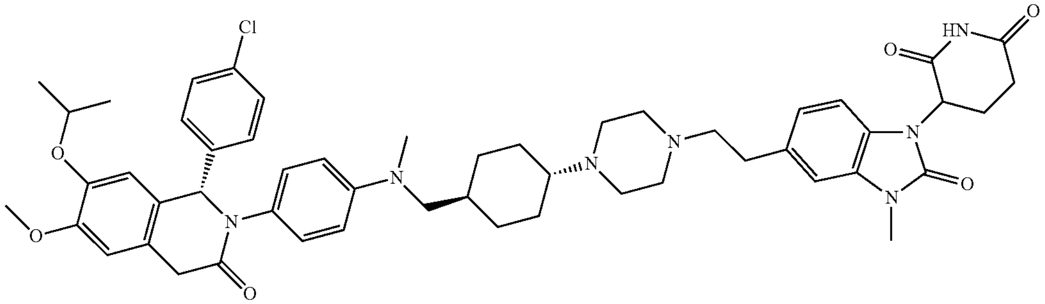 [SMILES: COc1cc2c(cc1OC(C)C)[C@H](c1ccc(Cl)cc1)N(c1ccc(N(C)C[C@H]3CC[C@H](N4CCN(CCc5ccc6c(c5)n(C)c(=O)n6C5CCC(=O)NC5=O)CC4)CC3)cc1)C(=O)C2] |
| I-212 | 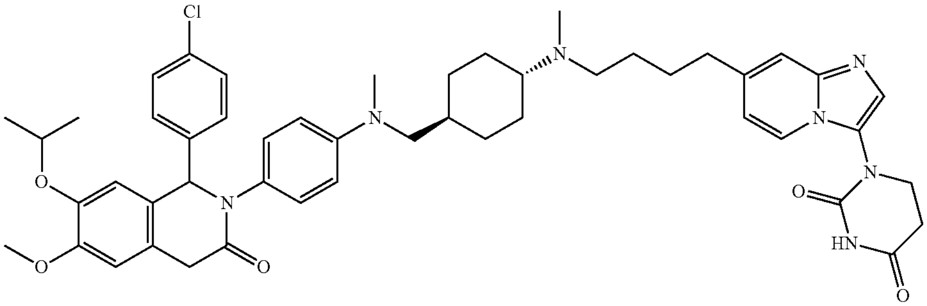 [SMILES: COc1cc2c(cc1OC(C)C)C(c1ccc(Cl)cc1)N(c1ccc(N(C)C[C@H]3CC[C@H](N(C)CCCCc4ccn5c(N6CCC(=O)NC6=O)cnc5c4)CC3)cc1)C(=O)C2] |
| I-213 | 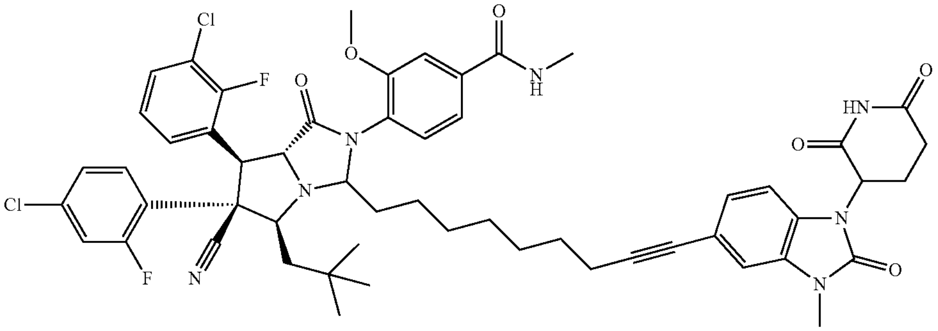 |

TABLE 1-continued
| Exemplary Compounds | |
|---|---|
| I-# | Structure |
| I-214 | 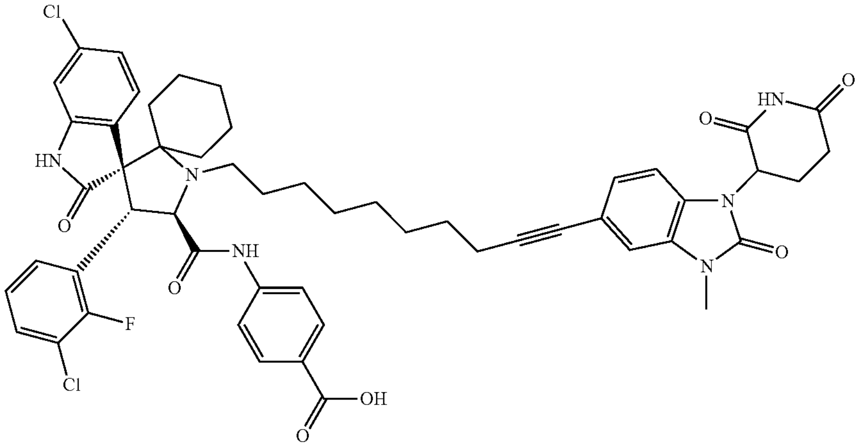 [SMILES: Cn1c(=O)n(C2CCC(=O)NC2=O)c2ccc(C#CCCCCCCCCN3[C@@H](C(=O)Nc4ccc(C(=O)O)cc4)[C@H](c4cccc(Cl)c4F)[C@]4(C(=O)Nc5cc(Cl)ccc54)C34CCCCC4)cc21] |
| I-215 | 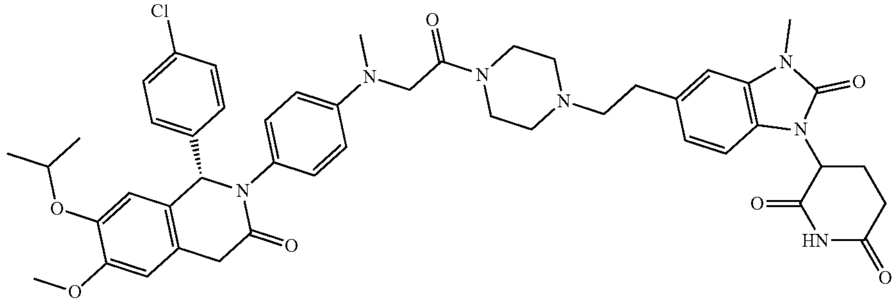 [SMILES: COc1cc2c(cc1OC(C)C)[C@H](c1ccc(Cl)cc1)N(c1ccc(N(C)CC(=O)N3CCN(CCc4ccc5c(c4)n(C)c(=O)n5C4CCC(=O)NC4=O)CC3)cc1)C(=O)C2] |
| I-216 | 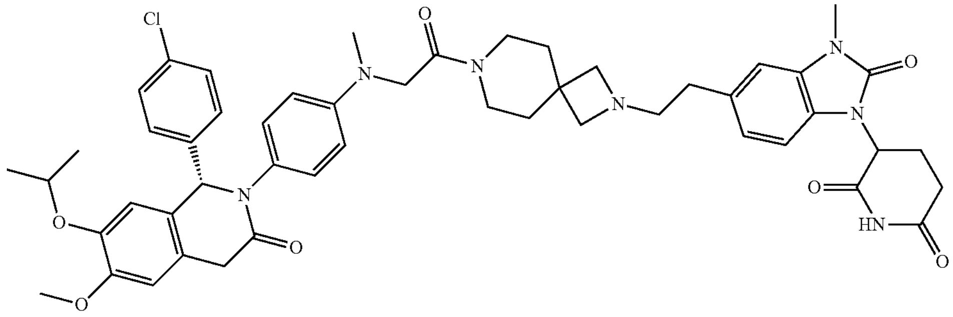 [SMILES: COc1cc2c(cc1OC(C)C)[C@H](c1ccc(Cl)cc1)N(c1ccc(N(C)CC(=O)N3CCC4(CC3)CN(CCc3ccc5c(c3)n(C)c(=O)n5C3CCC(=O)NC3=O)C4)cc1)C(=O)C2] |
| I-217 | 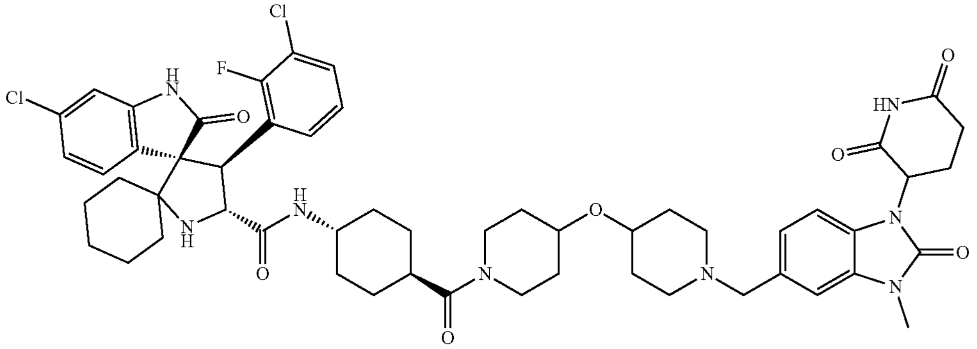 [SMILES: Cn1c(=O)n(C2CCC(=O)NC2=O)c2ccc(CN3CCC(OC4CCN(C(=O)[C@H]5CC[C@H](NC(=O)[C@@H]6NC7(CCCCC7)[C@@]7(C(=O)Nc8cc(Cl)ccc87)[C@H]6c6cccc(Cl)c6F)CC5)CC4)CC3)cc21] |

TABLE 1-continued
| Exemplary Compounds | |
|---|---|
| I-# | Structure |
| I-218 | 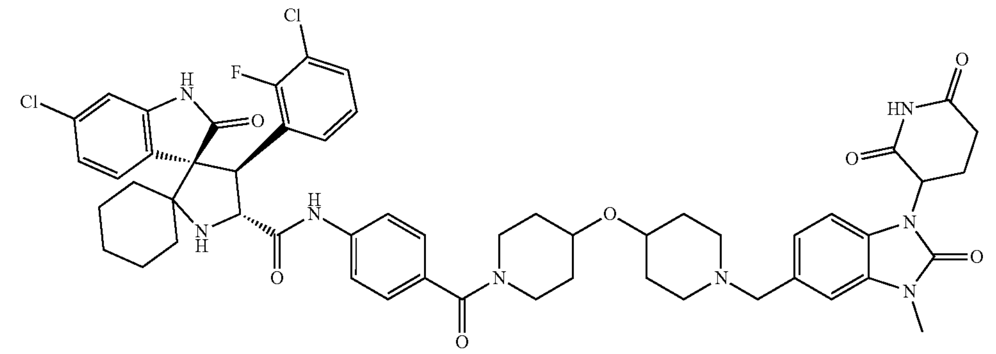 [SMILES: Cn1c(=O)n(C2CCC(=O)NC2=O)c2ccc(CN3CCC(OC4CCN(C(=O)c5ccc(NC(=O)[C@@H]6NC7(CCCCC7)[C@@]7(C(=O)Nc8cc(Cl)ccc87)[C@H]6c6cccc(Cl)c6F)cc5)CC4)CC3)cc21] |
| I-219 | 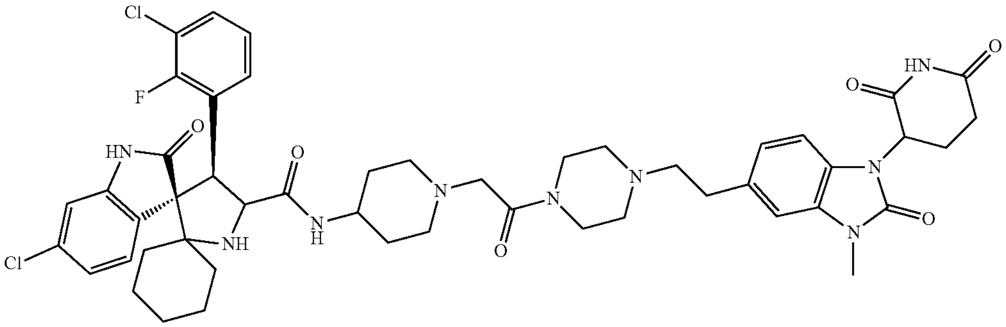 [SMILES: Cn1c(=O)n(C2CCC(=O)NC2=O)c2ccc(CCN3CCN(C(=O)CN4CCC(NC(=O)C5NC6(CCCCC6)[C@@]6(C(=O)Nc7cc(Cl)ccc76)[C@H]5c5cccc(Cl)c5F)CC4)CC3)cc21] |
| I-220 | 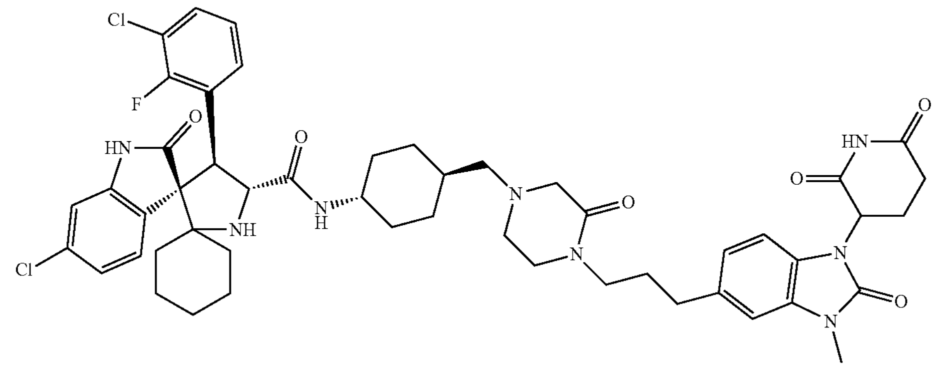 [SMILES: Cn1c(=O)n(C2CCC(=O)NC2=O)c2ccc(CCCN3CCN(C[C@H]4CC[C@H](NC(=O)[C@@H]5NC6(CCCCC6)[C@@]6(C(=O)Nc7cc(Cl)ccc76)[C@H]5c5cccc(Cl)c5F)CC4)CC3=O)cc21] |
| I-221 | 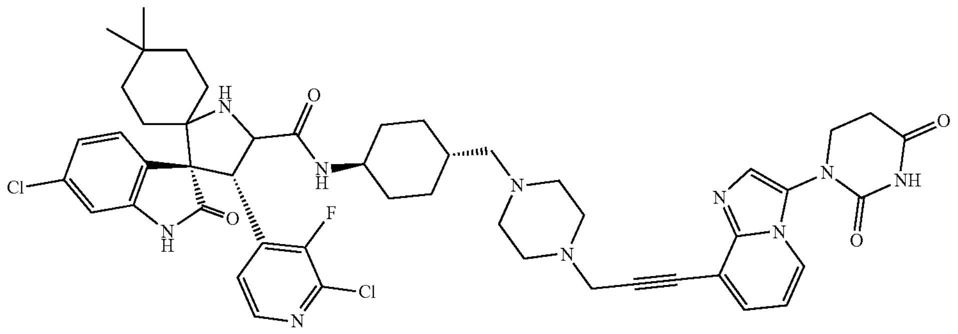 [SMILES: CC1(C)CCC2(CC1)NC(C(=O)N[C@H]1CC[C@H](CN3CCN(CC#Cc4cccn5c(N6CCC(=O)NC6=O)cnc45)CC3)CC1)[C@H](c1ccnc(Cl)c1F)[C@]21C(=O)Nc2cc(Cl)ccc21] |

TABLE 1-continued

Exemplary Compounds

| I-# | Structure |
| --- | --- |
| I-222 | 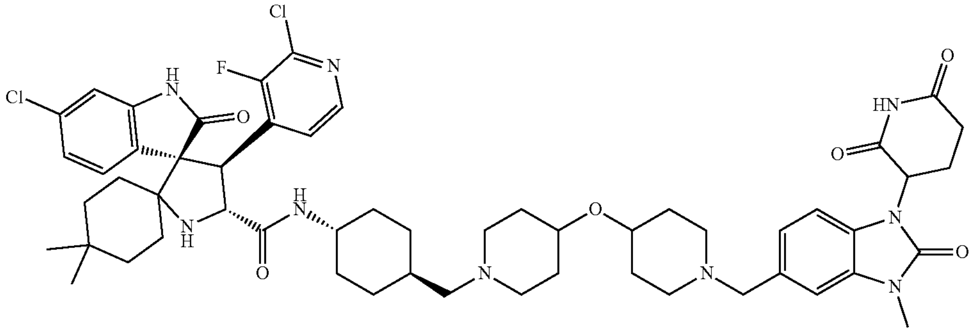 [SMILES: Cn1c(=O)n(C2CCC(=O)NC2=O)c2ccc(CN3CCC(OC4CCN(C[C@H]5CC[C@H](NC(=O)[C@@H]6NC7(CCC(C)(C)CC7)[C@@]7(C(=O)Nc8cc(Cl)ccc87)[C@H]6c6ccnc(Cl)c6F)CC5)CC4)CC3)cc21] |
| I-223 | 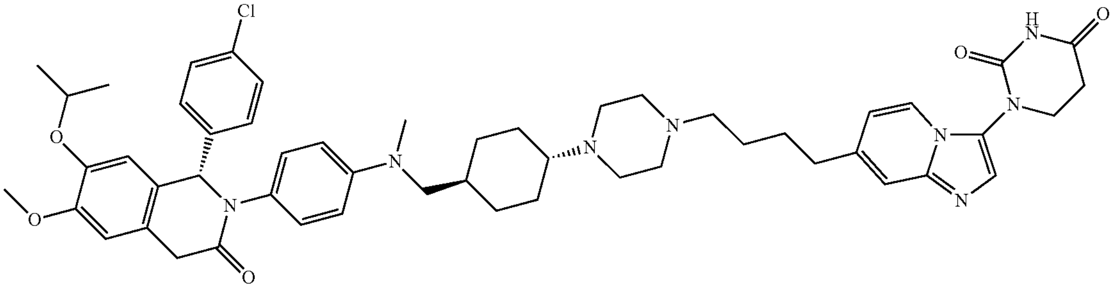 [SMILES: COc1cc2c(cc1OC(C)C)[C@H](c1ccc(Cl)cc1)N(c1ccc(N(C)C[C@H]3CC[C@H](N4CCN(CCCCc5ccn6c(N7CCC(=O)NC7=O)cnc6c5)CC4)CC3)cc1)C(=O)C2] |
| I-224 | 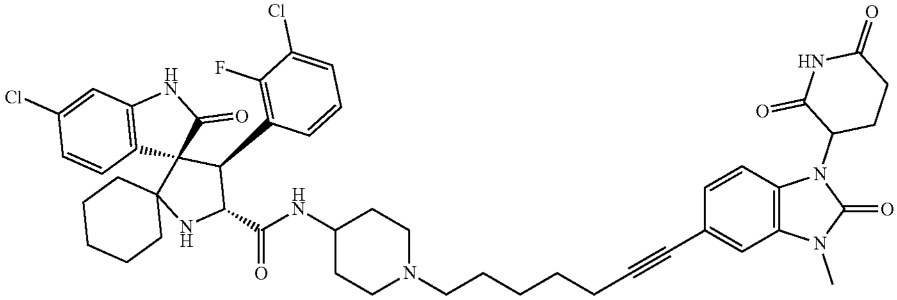 [SMILES: Cn1c(=O)n(C2CCC(=O)NC2=O)c2ccc(C#CCCCCCN3CCC(NC(=O)[C@@H]4NC5(CCCCC5)[C@@]5(C(=O)Nc6cc(Cl)ccc65)[C@H]4c4cccc(Cl)c4F)CC3)cc21] |

In some embodiments, the present invention provides a compound set forth in Table 1, above, or a pharmaceutically acceptable salt thereof.

4. General Methods of Providing the Present Compounds

The compounds of this invention may be prepared or isolated in general by synthetic and/or semi-synthetic methods known to those skilled in the art for analogous compounds and by methods described in detail in the Examples, herein.

In the Schemes below, where a particular protecting group, leaving group, or transformation condition is depicted, one of ordinary skill in the art will appreciate that other protecting groups, leaving groups, and transformation conditions are also suitable and are contemplated. Such groups and transformations are described in detail in *March's Advanced Organic Chemistry: Reactions, Mechanisms, and Structure*, M. B. Smith and J. March, 5th Edition, John Wiley & Sons, 2001, *Comprehensive Organic Transformations*, R. C. Larock, 2nd Edition, John Wiley & Sons, 1999, and *Protecting Groups in Organic Synthesis*, T. W. Greene and P. G. M. Wuts, 3rd edition, John Wiley & Sons, 1999, the entirety of each of which is hereby incorporated herein by reference.

As used herein, the phrase "oxygen protecting group" includes, for example, carbonyl protecting groups, hydroxyl protecting groups, etc. Hydroxyl protecting groups are well known in the art and include those described in detail in *Protecting Groups in Organic Synthesis*, T. W. Greene and P. G. M. Wuts, 3rd edition, John Wiley & Sons, 1999, the entirety of each of which is herein incorporated by reference. Examples of suitable hydroxyl protecting groups include, but are not limited to, esters, allyl ethers, ethers, silyl ethers, alkyl ethers, arylalkyl ethers, and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetyl), crotonate, 4-methoxy-crotonate, benzoate, p-benylbenzoate, 2,4,6-trimethylbenzoate, carbonates such as methyl, 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl.

Examples of such silyl ethers include trimethylsilyl, triethylsilyl, t-butyldimethylsilyl, t-butyldiphenylsilyl, triisopropylsilyl, and other trialkylsilyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyranyl ethers. Examples of arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, and 2- and 4-picolyl.

Amino protecting groups are well known in the art and include those described in detail in *Protecting Groups in Organic Synthesis*, T. W. Greene and P. G. M. Wuts, 3$^{rd}$ edition, John Wiley & Sons, 1999, the entirety of each of which is herein incorporated by reference. Suitable amino protecting groups include, but are not limited to, aralkylamines, carbamates, cyclic imides, allyl amines, amides, and the like. Examples of such groups include t-butyloxycarbonyl (BOC), ethyloxycarbonyl, methyloxycarbonyl, trichloroethyloxycarbonyl, allyloxycarbonyl (Alloc), benzyloxocarbonyl (CBZ), allyl, phthalimide, benzyl (Bn), fluorenylmethylcarbonyl (Fmoc), formyl, acetyl, chloroacetyl, dichloroacetyl, trichloroacetyl, phenylacetyl, trifluoroacetyl, benzoyl, and the like.

In the schemes below, where a provided compound is formed having a reactive moiety (e.g., amine, alcohol, etc.), it is not shown but it is generally appreciated and well known by those having ordinary skill in the art that the reactivity of said reactive moiety may be masked by employing a suitable protecting group that can thereafter be removed in situ or during a separate synthetic step.

In certain embodiments, compounds of the present invention are generally prepared according to Scheme 1 set forth below:

Scheme 1: Synthesis of Compounds of Formula I

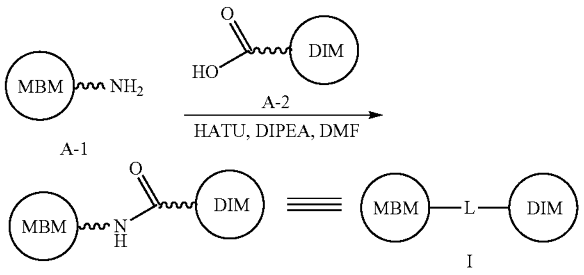

As depicted in Scheme 1, above, amine A-1 is coupled to acid A-2 using the coupling agent HATU in the presence of the base DIPEA in DMF to form a compound of formula I with a linker comprising an amide bond. The squiggly bond, , represents the portion of the linker between MBM and the terminal amino group of A-1 or the portion of the linker between DIM and the terminal carboxyl group of A-2, respectively. Additionally, an amide bond can be formed using coupling reagents known in the art such as, but not limited to DCC, DIC, EDC, HBTU, HCTU, PyAOP, PyBrOP, BOP, BOP—Cl, DEPBT, T3P, TATU, TBTU, TNTU, TOTU, TPTU, TSTU, or TDBTU.

In certain embodiments, compounds of the present invention are generally prepared according to Scheme 2 set forth below:

Scheme 2: Synthesis of Compounds of Formula I

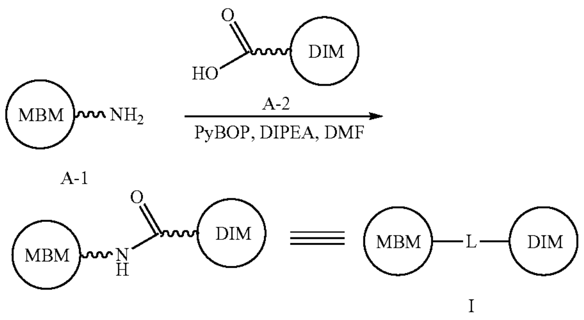

As depicted in Scheme 2, above, amine A-1 is coupled to acid A-2 using the coupling agent PyBOP in the presence of the base DIPEA in DMF to form a compound of formula I with a linker comprising an amide bond. The squiggly bond, , represents the portion of the linker between MBM and the terminal amino group of A-1 or the portion of the linker between DIM and the terminal carboxyl group of A-2, respectively. Additionally, an amide bond can be formed using coupling reagents known in the art such as, but not limited to DCC, DIC, EDC, HBTU, HCTU, PyAOP, PyBrOP, BOP, BOP—Cl, DEPBT, T3P, TATU, TBTU, TNTU, TOTU, TPTU, TSTU, or TDBTU.

In certain embodiments, compounds of the present invention are generally prepared according to Scheme 3 set forth below:

Scheme 3: Synthesis of Compounds of Formula I

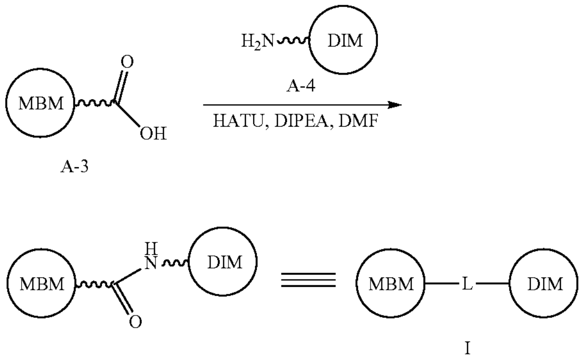

As depicted in Scheme 3, above, acid A-3 is coupled to amine A-4 using the coupling agent HATU in the presence of the base DIPEA in DMF to form a compound of formula I with a linker comprising an amide bond. The squiggly bond, , represents the portion of the linker between MBM and the terminal carboxyl group of A-3 or the portion of the linker between DIM and the terminal amino group of A-4, respectively. Additionally, an amide bond can be formed using coupling reagents known in the art such as, but not limited to DCC, DIC, EDC, HBTU, HCTU, PyAOP, PyBrOP, BOP, BOP—Cl, DEPBT, T3P, TATU, TBTU, TNTU, TOTU, TPTU, TSTU, or TDBTU.

In certain embodiments, compounds of the present invention are generally prepared according to Scheme 4 set forth below:

Scheme 4: Synthesis of Compounds of Formula I

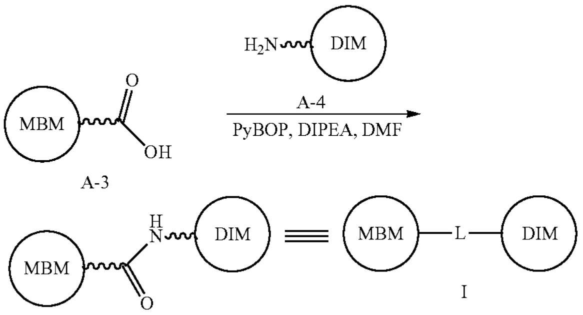

As depicted in Scheme 4, above, acid A-3 is coupled to amine A-4 using the coupling agent PyBOP in the presence of the base DIPEA in DMF to form a compound of formula I with a linker comprising an amide bond. The squiggly bond ~~~, represents the portion of the linker between MBM and the terminal carboxyl group of A-3 or the portion of the linker between DIM and the terminal amino group of A-4, respectively. Additionally, an amide bond can be formed using coupling reagents known in the art such as, but not limited to DCC, DIC, EDC, HBTU, HCTU, PyAOP, PyBrOP, BOP, BOP—Cl, DEPBT, T3P, TATU, TBTU, TNTU, TOTU, TPTU, TSTU, or TDBTU.

In certain embodiments, compounds of the present invention are generally prepared according to Scheme 5 set forth below:

Scheme 5: Synthesis of Compounds of Formula I

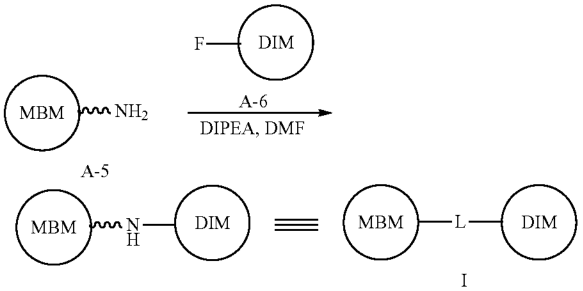

As depicted in Scheme 5, above, an $S_NAr$ displacement of fluoride A-6 by amine A-5 is effected in the presence of the base DIPEA in DMF to form a compound of formula I with a linker comprising a secondary amine. The squiggly bond, ~~~, represents the portion of the linker between MBM and the terminal amino group of A-5.

In certain embodiments, compounds of the present invention are generally prepared according to Scheme 6 set forth below:

Scheme 6: Synthesis of Compounds of Formula I

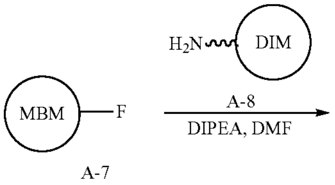

-continued

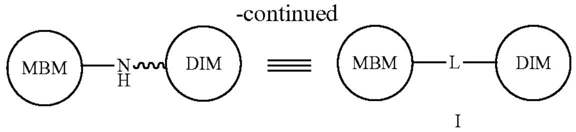

As depicted in Scheme 6, above, an $S_NAr$ displacement of fluoride A-7 by amine A-8 is effected in the presence of the base DIPEA in DMF to form a compound of formula I with a linker comprising a secondary amine. The squiggly bond, ~~~, represents the portion of the linker between DIM and the terminal amino group of A-8.

Scheme 7: Synthesis of Compounds of Formula I

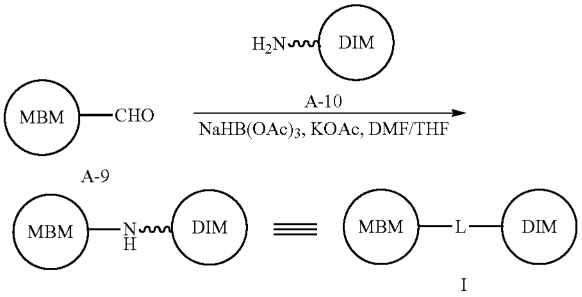

As depicted in Scheme 7, above, reductive amination of the mixture of aldehyde A-9 and amine A-10 is effected in the presence of $NaHB(OAc)_3$ and KOAc in DMF/THF to form a compound of formula I with a linker comprising a secondary amine. The squiggly bond, ~~~, represents the portion of the linker between DIM and the terminal amino group of A-8.

One of skill in the art will appreciate that various functional groups present in compounds of the invention such as aliphatic groups, alcohols, carboxylic acids, esters, amides, aldehydes, halogens and nitriles can be interconverted by techniques well known in the art including, but not limited to reduction, oxidation, esterification, hydrolysis, partial oxidation, partial reduction, halogenation, dehydration, partial hydration, and hydration. "March's Advanced Organic Chemistry", $5^{th}$ Ed., Ed.: Smith, M. B. and March, J., John Wiley & Sons, New York: 2001, the entirety of which is incorporated herein by reference. Such interconversions may require one or more of the aforementioned techniques, and certain methods for synthesizing compounds of the invention are described below in the Exemplification.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably degrade and/or inhibit a MDM2 protein, or a mutant thereof, in a biological sample or in a patient. In certain embodiments, the amount of compound in compositions of this invention is such that is effective to measurably degrade and/or inhibit a MDM2 protein, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily or degratorily active metabolite or residue thereof.

As used herein, the term "inhibitorily active metabolite or residue thereof" means that a metabolite or residue thereof is also an inhibitor of a MDM2 protein, or a mutant thereof.

As used herein, the term "degratorily active metabolite or residue thereof" means that a metabolite or residue thereof is also a degrader of a MDM2 protein, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the degradation and/or inhibition of MDM2 protein activity.

MDM2 protein that is degraded and/or inhibited by the compounds and compositions described herein and against which the methods described herein are useful include those of the mouse double minute 2 homolog (MDM2) protein or E3 ubiquitin-protein ligase MDM2 that is encoded by the MDM2 gene. MDM2 is an important negative regulator of the p53 tumor suppressor. The p53 tumor suppressor is a principal mediator of growth arrest, senescence, and apoptosis in response to a broad array of cellular damage. Rapid induction of high p53 protein levels by various stress types prevents inappropriate propagation of cells carrying potentially mutagenic, damaged DNA. p53 can kill cells via a dual transcription-dependent and transcription -independent function in the nucleus and at the mitochondria. It has been demonstrated that cellular p53 protein levels are the single most important determinant of its function. In normal unstressed cells, p53 is a very unstable protein with a half-life ranging from 5 to 30 min, which is present at very low cellular levels owing to continuous degradation largely mediated by MDM2. Conversely, a hallmark of many cellular stress pathways such as DNA damage, hypoxia, telomere shortening, and oncogene activation is the rapid stabilization of p53 via a block of its degradation. MDM2 has emerged as the principal cellular antagonist of p53 by limiting the p53 tumor suppressor function. Moll and Petrenko, *Mol. Cancer Res.* 2003, 1:1001.

MDM2 is transcriptionally activated by p53 and MDM2, in turn, inhibits p53 activity by at least three mechanisms. Wu et al., *Genes Dev.* 1993, 7:1126. First, MDM2 protein directly binds to the p53 transactivation domain and thereby inhibits p53-mediated transactivation. Second, MDM2 protein contains a nuclear export signal sequence, and upon binding to p53, induces the nuclear export of p53, preventing p53 from binding to the targeted DNAs. Third, MDM2 protein is an E3 ubiquitin ligase and upon binding to p53 is able to promote p53 degradation.

The activity of a compound utilized in this invention as a degrader and/or inhibitor of MDM2 protein or a mutant thereof, may be assayed in vitro, in vivo or in a cell line. In vitro assays include assays that determine inhibition of either the activity and/or the subsequent functional consequences of activated MDM2 protein, or a mutant thereof. Alternate in vitro assays quantitate the ability of the inhibitor to bind to a MDM2 protein. Inhibitor binding may be measured by radiolabeling the inhibitor prior to binding, isolating the inhibitor/MDM2 complex and determining the amount of radiolabel bound. Alternatively, inhibitor binding may be determined by running a competition experiment where new inhibitors are incubated with a MDM2 protein bound to known radioligands. Representative in vitro and in vivo assays useful in assaying a MDM2 inhibitor include those described and disclosed in, e.g., Zhange et al., "Fluorescence polarization assay and inhibitor design for MDM2/p53 interaction" *Anal. Biochem.* 2004, 333(1):138; Herman et al., "Discovery of Mdm2-MdmX E3 Ligase Inhibitors Using a Cell-Based Ubiquitination Assay" *Cancer Discovery.* 2011, 1(4):312. Detailed conditions for assaying a compound utilized in this invention as a degrader and/or inhibitor of STAT proteins, or a mutant thereof, are set forth in the Examples below.

Representative small molecule inhibitors that target the p53-MDM2 interaction have therapeutic potential for treating cancer and other diseases. Chene, *Nat. Rev. Cancer* 2003, 3:102 and Vassilev et al., Science 2004, 303:844. Antagonists of the p53-MDM2 interaction are described in U.S. Pat. Nos. 7,759,383; 7,737,174; 8,518,984; 8,680,132; 8,629,141; 6,617,346; 6,734,302; 7,132,421; 7,425,638; 7,579,368; 7,060,713; 7,553,833; 6,916,833; 7,495,007; 7,638,548; 7,576,082; 7,625,895; and 7,083,983; and U.S. Patent Application Publication Nos. 2005/0288287; 2009/0143364; 2009/0312310; 2006/0211718; 2010/0048593; 2005/0227932; 2008/0261917; 2009/0227542; 2008/0171723; 2006/0211757; 2005/0137137; 2002/0132977; and 2009/0030181, the entirety of each of which is herein incorporated by reference.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are degraders and/or inhibitors of MDM2 protein and are therefore useful for treating one or more disorders associated with activity of MDM2 protein. Thus, in certain embodiments, the present invention provides a method for treating a MDM2-mediated disorder comprising the step of administering to a patient in need thereof a compound of the present invention, or pharmaceutically acceptable composition thereof.

As used herein, the terms "MDM2-mediated" disorders, diseases, and/or conditions as used herein means any disease or other deleterious condition in which MDM2 protein or a mutant thereof, are known to play a role. Accordingly, another embodiment of the present invention relates to treating or lessening the severity of one or more diseases in which MDM2 protein or a mutant thereof, are known to play a role.

In some embodiments, the present invention provides a method for treating one or more disorders, diseases, and/or conditions wherein the disorder, disease, or condition is a cancer, a neurodegenerative disorder, a viral disease, an autoimmune disease, an inflammatory disorder, a hereditary disorder, a hormone-related disease, a metabolic disorder, conditions associated with organ transplantation, immunodeficiency disorders, a destructive bone disorder, a proliferative disorder, an infectious disease, a condition associated with cell death, thrombin-induced platelet aggregation, liver disease, pathologic immune conditions involving T cell activation, a cardiovascular disorder, or a CNS disorder.

Diseases and conditions treatable according to the methods of this invention include, but are not limited to, cancer (see, e.g., Vassilev, Trends in *Mol. Med.* 2007, 13(1):23), diabetes (see, e.g., Secchiero et al., *Acta Diabeto.* 2013, 50:899), cardiovascular disease, viral disease (see, e.g., Yang et al., *Protein & Cell* 2013, 4:71), autoimmune diseases such as lupus erythematosus (see, e.g., Thomasova et al., *Neoplasia* 2012, 14(12):1097), and rheumatoid arthritis (see, e.g., Zhang et al., *Int. Immunopharm.* 2016, 30:69), autoinflammatory syndromes, atherosclerosis (see, e.g., Ihling et al., *J Pathol.* 1998, 185(3):303), psoriasis (see, e.g., Assmann et al., *Rheumatol. Int.* 2010, 30:1273), allergic disorders (see, e.g., Han et al., *J. Invest. Dermatol.* 2014, 134(10):2521), inflammatory bowel disease (see, e.g., Zimmer et al., *Digestion* 2019, 81:246), inflammation (see, e.g., Ebrahim et al., *Histol. Histopathol.* 2015, 31(11):1271), acute and chronic gout and gouty arthritis, neurological disorders (see, e.g., Engel et al., *Brain* 2013, 136(2):577), metabolic syndrome, immunodeficiency disorders such as AIDS and HIV (see, e.g., Izumi et al., *Retrovirology* 2009, 6:1), destructive bone disorders (see, e.g., Jatiani et al., *Genes & Can.* 2011, 1(10):979), osteoarthritis (see, e.g., U.S. Pat. No. 9,993,472), proliferative disorders (see, e.g., U.S. Pat. No. 8,658,170), Waldenstrom's Macroglobulinemia, infectious diseases such as sepsis (see, e.g., Kleiman et al., *Am. J Surg.* 2009, 197(1):43), conditions associated with cell death, pathologic immune conditions involving T cell activation, and CNS disorders in a patient. In one embodiment, a human patient is treated with a compound of the current invention and a pharmaceutically acceptable carrier, adjuvant, or vehicle, wherein said compound is present in an amount to measurably degrade and/or inhibit MDM2 protein or a mutant thereof Compounds of the current invention are useful in the treatment of a proliferative disease selected from a benign or malignant tumor, solid tumor, liquid tumor, carcinoma of the brain, kidney, liver, adrenal gland, bladder, breast, stomach, gastric tumors, ovaries, colon, rectum, prostate, pancreas, lung, vagina, cervix, testis, genitourinary tract, esophagus, larynx, skin, bone or thyroid, sarcoma, glioblastomas, neuroblastomas, multiple myeloma, gastrointestinal cancer, especially colon carcinoma or colorectal adenoma, a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, Hodgkin's and Non-Hodgkin's, a mammary carcinoma, follicular carcinoma, undifferentiated carcinoma, papillary carcinoma, seminoma, melanoma, an IL-1 driven disorder, an MyD88 driven disorder, Smoldering of indolent multiple myeloma, or hematological malignancies (including leukemia, diffuse large B-cell lymphoma (DLBCL), ABC DLBCL, chronic lymphocytic leukemia (CLL), chronic lymphocytic lymphoma, primary effusion lymphoma, Burkitt lymphoma/leukemia, acute lymphocytic leukemia, B-cell prolymphocytic leukemia, lymphoplasmacytic lymphoma, Waldenstrom's macroglobulinemia (WM), splenic marginal zone lymphoma, multiple myeloma, plasmacytoma, intravascular large B-cell lymphoma).

In some embodiment, the present disclosure provides a method of treating a benign proliferative disorder, such as, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratosis, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

In another aspect, the present disclosure provides methods of treating a condition or disease by administering a therapeutically effective amount of a provided compound to an individual, e.g., a human, in need thereof. The disease or condition of interest is treatable by degradation of MDM2 proteins, for example, a cancer, a chronic autoimmune disorder, an inflammatory condition, a proliferative disorder, sepsis, or a viral infection. Also provided are methods of preventing the proliferation of unwanted proliferating cells, such as in cancer, in a subject comprising administering a therapeutically effective amount of a provided compound to a subject at risk of developing a condition characterized by unwanted proliferating cells. In some embodiments, a provided compound reduces the proliferation of unwanted cells by inducing apoptosis in those cells.

MDM2 hyperactivity, due to amplification/overexpression or mutational inactivation of the ARF locus, inhibits the function of wild-type p53 and can lead to the development of a wide variety of cancers. In some embodiments, the MDM2 hyperactivity which can be treated according to the methods of this invention is a human cancer. In some embodiments, the human cancer which can be treated according to the methods of this invention is selected from glioma, breast cancer, prostate cancer, head and neck squamous cell carcinoma, skin melanomas, and ovarian cancer.

In some embodiments, the cancer is selected from adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogeous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma periotonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma thyroid cancer, transitional cell carcinoma, throat cancer, urachal cancer, urogenital cancer, urothelial carcinoma, uveal melanoma, uterine cancer, verrucous carcinoma, visual pathway ghoma, vulvar cancer, vaginal cancer, Waldenstrom's macroglobulinemia, Warthin's tumor, and Wilms' tumor.

In some embodiments, the cancer is a leukaemia, for example a leukaemia selected from acute monocytic leukemia, acute myelogenous leukemia, chronic myelogenous leukemia, chronic lymphocytic leukemia and mixed lineage leukaemia (MLL). In another embodiment the cancer is NUT-midline carcinoma. In another embodiment the cancer is multiple myeloma. In another embodiment the cancer is a lung cancer such as small cell lung cancer (SCLC). In another embodiment the cancer is a neuroblastoma. In another embodiment the cancer is Burkitt's lymphoma. In another embodiment the cancer is cervical cancer. In another embodiment the cancer is esophageal cancer. In another embodiment the cancer is ovarian cancer. In another embodiment the cancer is colorectal cancer. In another embodiment, the cancer is prostate cancer. In another embodiment, the cancer is breast cancer.

In some embodiments, the present invention provides a method oftreating triple negative breast cancer in a patient in need thereof, comprising administering a compound of the present invention, or a pharmaceutically acceptable salt thereof.

In some embodiments, the present invention provides a method of treating malignant peripheral nerve sheath tumors (MPNST) in a patient in need thereof, comprising administering a compound of the present invention, or a pharmaceutically acceptable salt thereof.

In some embodiments, the present invention provides a method of treating pancreatic cancer in a patient in need thereof, comprising administering a compound of the present invention, or a pharmaceutically acceptable salt thereof.

Compounds according to the invention are useful in the treatment of inflammatory or obstructive airways diseases, resulting, for example, in reduction of tissue damage, airways inflammation, bronchial hyperreactivity, remodeling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics.

Compounds according to the invention are useful in the treatment of heteroimmune diseases. Examples of such heteroimmune diseases include, but are not limited to, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, such as therapy for or intended to restrict or abort symptomatic attack when it occurs, for example antiinflammatory or bronchodilatory. Prophylactic benefit in asthma may in particular be apparent in subjects prone to "morning dipping". "Morning dipping" is a recognized asthmatic syndrome, common to a substantial percentage of asthmatics and characterized by asthma attack, e.g. between the hours of about 4 to 6 am, i.e. at a time normally substantially distant form any previously administered symptomatic asthma therapy.

Compounds of the current invention can be used for other inflammatory or obstructive airways diseases and conditions to which the present invention is applicable and include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, but not limited to, acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

With regard to their anti-inflammatory activity, in particular in relation to inhibition of eosinophil activation, compounds of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Compounds of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, systemic lupus erythematosus, pemphigus vulgaris, pemphigus *foliaceus*, paraneoplastic pemphigus, epidermolysis bullosa acquisita, acne vulgaris, and other inflammatory or allergic conditions of the skin.

Compounds of the invention may also be used for the treatment of other diseases or conditions, such as diseases or conditions having an inflammatory component, for example, treatment of diseases and conditions of the eye such as ocular allergy, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, multiple sclerosis, primary biliary cirrhosis, uveitis (anterior and posterior), Sjogren's syndrome, keratoconjunctivitis sicca and vernal keratoconjunctivitis, interstitial lung fibrosis, psoriatic arthritis, systemic juvenile idiopathic arthritis, cryopyrin-associated periodic syndrome, nephritis, vasculitis, diverticulitis, interstitial cystitis, glomerulonephritis (with and without nephrotic syndrome, e.g. including idiopathic nephrotic syndrome or minal change nephropathy), chronic granulomatous disease, endometriosis, leptospiriosis renal disease, glaucoma, retinal disease, ageing, headache, pain, complex regional pain syndrome, cardiac hypertrophy, musclewasting, catabolic disorders, obesity, fetal growth retardation, hyperchlolesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, anaphylaxis, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, Type 1 diabetes, or Type 2 diabetes, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis.

In some embodiments the inflammatory disease which can be treated according to the methods of this invention is an disease of the skin. In some embodiments, the inflammatory disease of the skin is selected from contact dermatitis, atopic dermatitis, alopecia areata, erythema multiforma, dermatitis herpetiformis, scleroderma, vitiligo, hypersensitivity angiitis, urticaria, bullous pemphigoid, pemphigus vulgaris, pemphigus foliaceus, paraneoplastic pemphigus, epidermolysis bullosa acquisita, and other inflammatory or allergic conditions of the skin.

In some embodiments the inflammatory disease which can be treated according to the methods of this invention is selected from acute and chronic gout, chronic gouty arthritis, psoriasis, psoriatic arthritis, rheumatoid arthritis, Juvenile rheumatoid arthritis, Systemic juvenile idiopathic arthritis (SJIA), Cryopyrin Associated Periodic Syndrome (CAPS), and osteoarthritis.

In some embodiments the inflammatory disease which can be treated according to the methods of this invention is a TH17 mediated disease. In some embodiments the TH17 mediated disease is selected from Systemic lupus erythematosus, Multiple sclerosis, and inflammatory bowel disease (including Crohn's disease or ulcerative colitis).

In some embodiments the inflammatory disease which can be treated according to the methods of this invention is selected from Sjogren's syndrome, allergic disorders, osteoarthritis, conditions of the eye such as ocular allergy, conjunctivitis, keratoconjunctivitis sicca and vernal conjunctivitis, and diseases affecting the nose such as allergic rhinitis.

Cardiovascular diseases which can be treated according to the methods of this invention include, but are not limited to, restenosis, cardiomegaly, atherosclerosis, myocardial infarction, ischemic stroke, congestive heart failure, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, and deep venous thrombosis.

In some embodiments, the neurodegenerative disease which can be treated according to the methods of this invention include, but are not limited to, Alzheimer's disease, Parkinson's disease, amyotrophic lateral sclerosis, Huntington's disease, cerebral ischemia, and neurodegenerative disease caused by traumatic injury, glutamate neurotoxicity, hypoxia, epilepsy, treatment of diabetes, metabolic syndrome, obesity, organ transplantation and graft versus host disease.

In some embodiments the invention provides a method of treating, preventing or lessening the severity of Alzheimer's disease comprising administering to a patient in need thereof a provided compound or a pharmaceutically acceptable salt or composition thereof.

In some embodiments the invention provides a method of treating a disease or condition commonly occurring in connection with transplantation. In some embodiments, the disease or condition commonly occurring in connection with transplantation is selected from organ transplantation, organ transplant rejection, and graft versus host disease.

In some embodiments, the present invention provides a method of treating a metabolic disease. In some embodiments the metabolic disease is selected from Type 1 diabetes, Type 2 diabetes, metabolic syndrome, and obesity.

In some embodiments, the present invention provides a method of treating systemic inflammatory response syndromes, such as LPS-induced endotoxic shock and/or bacteria-induced sepsis by administration of an effective amount of a provided compound to a mammal, in particular a human in need of such treatment.

In some embodiments, the present invention provides a method for treating viral infections and diseases. Examples of viral infections and diseases treated using the compounds and methods described herein include episome-based DNA viruses including, but not limited to, human papillomavirus, Herpesvirus, Epstein-Barr virus, human immunodeficiency virus (HIV), hepatis B virus, and hepatitis C virus.

In some embodiments, the present invention provides a method of treating a viral disease. In some embodiments, the viral infection is HIV infection.

In some embodiments, the present invention provides a method of modulating protein methylation, gene expression, cell proliferation, cell differentiation and/or apoptosis in vivo in diseases mentioned above, in particular cancer, inflammatory disease, and/or viral disease is provided by administering a therapeutically effective amount of a provide compound to a subject in need of such therapy.

In some embodiments, the present invention provides a method of regulating endogenous or heterologous promoter activity by contacting a cell with a provided compound.

Furthermore, the invention provides the use of a compound according to the definitions herein, or a pharmaceutically acceptable salt, or a hydrate or solvate thereof for the preparation of a medicament for the treatment of a proliferative disease, an inflammatory disease, an obstructive respiratory disease, a cardiovascular disease, a metabolic disease, a neurological disease, a neurodegenerative disease, a viral disease, or a disorder commonly occurring in connection with transplantation.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

In some embodiments, the present invention provides a method of treating a disclosed disease or condition comprising administering to a patient in need thereof an effective amount of a compound disclosed herein or a pharmaceutically acceptable salt thereof and co-administering simultaneously or sequentially an effective amount of one or more additional therapeutic agents, such as those described herein. In some embodiments, the method includes co-administering one additional therapeutic agent. In some embodiments, the method includes co-administering two additional therapeutic agents. In some embodiments, the combination of the disclosed compound and the additional therapeutic agent or agents acts synergistically.

Examples of agents the combinations of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, combination therapies of the present invention, or a pharmaceutically acceptable composition thereof, are administered in combination with a monoclonal antibody or an siRNA therapeutic.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

One or more other therapeutic agent may be administered separately from a compound or composition of the invention, as part of a multiple dosage regimen. Alternatively, one or more other therapeutic agents may be part of a single dosage form, mixed together with a compound of this invention in a single composition. If administered as a multiple dosage regime, one or more other therapeutic agent and a compound or composition of the invention may be administered simultaneously, sequentially or within a period of time from one another, for example within 1, 2, 3, 4, 5, 6, 7, 8, 9, 10, 11, 12, 13, 14, 15, 16, 17, 18, 18, 20, 21, 22, 23, or 24 hours from one another. In some embodiments, one or more other therapeutic agent and a compound or composition of the invention are administered as a multiple dosage regimen within greater than 24 hours apart.

In one embodiment, the present invention provides a composition comprising a provided compound and one or more additional therapeutic agents. The therapeutic agent may be administered together with a provided compound, or may be administered prior to or following administration of a provided compound. Suitable therapeutic agents are described in further detail below. In certain embodiments, a provided compound may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a provided compound may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating an inflammatory disease, disorder or condition by administering to a patient in need thereof a provided compound and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In another embodiment, the present invention provides a method of treating gout comprising administering to a patient in need thereof a provided compound and one or more additional therapeutic agents selected from non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol and febuxostat (Uloric®).

In another embodiment, the present invention provides a method of treating rheumatoid arthritis comprising administering to a patient in need thereof a provided compound and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a provided compound and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating lupus comprising administering to a patient in need thereof a provided compound and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating inflammatory bowel disease comprising administering to a patient in need thereof a provided compound and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a provided compound and one or more additional therapeutic agents selected from Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, cromolyn sodium (Intal®), methylxanthines such as theophylline (Theo-Dur®, Theolair®, Slo-bid®, Uniphyl®, Theo-24®) and aminophylline, and IgE antibodies such as omalizumab (Xolair®).

In some embodiments, the present invention provides a method of treating COPD comprising administering to a patient in need thereof a provided compound and one or more additional therapeutic agents selected from beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophylline (Theo-Dur®, Theolair®, Slo-bid®, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, In some embodiments, the present invention provides a method of treating HIV comprising administering to a patient in need thereof a provided compound and one or more additional therapeutic agents selected from nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), and combinations thereof.

In another embodiment, the present invention provides a method of treating a hematological malignancy comprising administering to a patient in need thereof a provided compound and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a TYK2 inhibitor, a PI3K inhibitor, a SYK inhibitor, and combinations thereof.

In another embodiment, the present invention provides a method of treating a solid tumor comprising administering to a patient in need thereof a provided compound and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a TYK2 inhibitor, a PI3K inhibitor, a SYK inhibitor, and combinations thereof.

In another embodiment, the present invention provides a method of treating a hematological malignancy comprising administering to a patient in need thereof a provided compound and a Hedgehog (Hh) signaling pathway inhibitor. In some embodiments, the hematological malignancy is DLBCL (Ramirez et al "Defining causative factors contributing in the activation of hedgehog signaling in diffuse large B-cell lymphoma" Leuk. Res. (2012), published online July 17, and incorporated herein by reference in its entirety).

In another embodiment, the present invention provides a method of treating diffuse large B-cell lymphoma (DLBCL) comprising administering to a patient in need thereof a provided compound and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In another embodiment, the present invention provides a method of treating multiple myeloma comprising administering to a patient in need thereof a provided compound and one or more additional therapeutic agents selected from bortezomib (Velcade®), and dexamethasone (Decadron®), a hedgehog signaling inhibitor, a BTK inhibitor, a JAK/pan-JAK inhibitor, a TYK2 inhibitor, a PI3K inhibitor, a SYK inhibitor in combination with lenalidomide (Revlimid®).

In another embodiment, the present invention provides a method of treating Waldenstrom's macroglobulinemia comprising administering to a patient in need thereof a provided compound and one or more additional therapeutic agents selected from chlorambucil (Leukeran®), cyclophosphamide (Cytoxan®, Neosar®), fludarabine (Fludara®), cladribine (Leustatin®), rituximab (Rituxan®), a hedgehog signaling inhibitor, a BTK inhibitor, a JAK/pan-JAK inhibitor, a TYK2 inhibitor, a PI3K inhibitor, and a SYK inhibitor.

In some embodiments, one or more other therapeutic agent is an antagonist of the hedgehog pathway. Approved hedgehog pathway inhibitors which may be used in the present invention include sonidegib (Odomzo®, Sun Pharmaceuticals); and vismodegib (Erivedge®, Genentech), both for treatment of basal cell carcinoma.

In some embodiments, one or more other therapeutic agent is a Poly ADP ribose polymerase (PARP) inhibitor. In some embodiments, a PARP inhibitor is selected from olaparib (Lynparza®, AstraZeneca); rucaparib (Rubraca®, Clovis Oncology); niraparib (Zejula®, Tesaro); talazoparib (MDV3800/BMN 673/LT00673, Medivation/Pfizer/Biomarin); veliparib (ABT-888, AbbVie); and BGB-290 (BeiGene, Inc.).

In some embodiments, one or more other therapeutic agent is a histone deacetylase (HDAC) inhibitor. In some embodiments, an HDAC inhibitor is selected from vorinostat (Zolinza®, Merck); romidepsin (Istodax®, Celgene); panobinostat (Farydak®, Novartis); belinostat (Beleodaq®, Spectrum Pharmaceuticals); entinostat (SNDX-275, Syndax Pharmaceuticals) (NCT00866333); and chidamide (Epidaza®, HBI-8000, Chipscreen Biosciences, China).

In some embodiments, one or more other therapeutic agent is a CDK inhibitor, such as a CDK4/CDK6 inhibitor. In some embodiments, a CDK 4/6 inhibitor is selected from palbociclib (Ibrance®, Pfizer); ribociclib (Kisqali®, Novartis); abemaciclib (Ly2835219, Eli Lilly); and trilaciclib (G1T28, G1 Therapeutics).

In some embodiments, one or more other therapeutic agent is a folic acid inhibitor. Approved folic acid inhibitors useful in the present invention include pemetrexed (Alimta®, Eli Lilly).

In some embodiments, one or more other therapeutic agent is a CC chemokine receptor 4 (CCR4) inhibitor. CCR4 inhibitors being studied that may be useful in the present invention include mogamulizumab (Poteligeo®, Kyowa Hakko Kirin, Japan).

In some embodiments, one or more other therapeutic agent is an isocitrate dehydrogenase (IDH) inhibitor. IDH inhibitors being studied which may be used in the present invention include AG120 (Celgene; NCT02677922); AG221 (Celgene, NCT02677922; NCT02577406); BAY1436032 (Bayer, NCT02746081); IDH305 (Novartis, NCT02987010).

In some embodiments, one or more other therapeutic agent is an arginase inhibitor. Arginase inhibitors being studied which may be used in the present invention include AEB1102 (pegylated recombinant arginase, Aeglea Biotherapeutics), which is being studied in Phase 1 clinical trials for acute myeloid leukemia and myelodysplastic syndrome (NCT02732184) and solid tumors (NCT02561234); and CB-1158 (Calithera Biosciences).

In some embodiments, one or more other therapeutic agent is a glutaminase inhibitor. Glutaminase inhibitors being studied which may be used in the present invention include CB-839 (Calithera Biosciences).

In some embodiments, one or more other therapeutic agent is an antibody that binds to tumor antigens, that is, proteins expressed on the cell surface of tumor cells. Approved antibodies that bind to tumor antigens which may be used in the present invention include rituximab (Rituxan®, Genentech/BiogenIdec); ofatumumab (anti-CD20, Arzerra®, GlaxoSmithKline); obinutuzumab (anti-CD20, Gazyva®, Genentech), ibritumomab (anti-CD20 and Yttrium-90, Zevalin®, Spectrum Pharmaceuticals); daratumumab (anti-CD38, Darzalex®, Janssen Biotech), dinutuximab (anti-glycolipid GD2, Unituxin®, United Therapeutics); trastuzumab (anti-HER2, Herceptin®, Genentech); ado-trastuzumab emtansine (anti-HER2, fused to emtansine, Kadcyla®, Genentech); and pertuzumab (anti-HER2, Perjeta®, Genentech); and brentuximab vedotin (anti-CD30-drug conjugate, Adcetris®, Seattle Genetics).

In some embodiments, one or more other therapeutic agent is a topoisomerase inhibitor. Approved topoisomerase inhibitors useful in the present invention include irinotecan (Onivyde®, Merrimack Pharmaceuticals); topotecan (Hycamtin®, GlaxoSmithKline). Topoisomerase inhibitors being studied which may be used in the present invention include pixantrone (Pixuvri®, CTI Biopharma).

In some embodiments, one or more other therapeutic agent is an inhibitor of anti-apoptotic proteins, such as BCL-2. Approved anti-apoptotics which may be used in the present invention include venetoclax (Venclexta®, AbbVie/Genentech); and blinatumomab (Blincyto®, Amgen). Other therapeutic agents targeting apoptotic proteins which have undergone clinical testing and may be used in the present invention include navitoclax (ABT-263, Abbott), a BCL-2 inhibitor (NCT02079740).

In some embodiments, one or more other therapeutic agent is an androgen receptor inhibitor. Approved androgen receptor inhibitors useful in the present invention include enzalutamide (Xtandi®, Astellas/Medivation); approved inhibitors of androgen synthesis include abiraterone (Zytiga®, Centocor/Ortho); approved antagonist of gonadotropin-releasing hormone (GnRH) receptor (degaralix, Firmagon®, Ferring Pharmaceuticals).

In some embodiments, one or more other therapeutic agent is a selective estrogen receptor modulator (SERM), which interferes with the synthesis or activity of estrogens. Approved SERMs useful in the present invention include raloxifene (Evista®, Eli Lilly).

In some embodiments, one or more other therapeutic agent is an inhibitor of bone resorption. An approved therapeutic which inhibits bone resorption is Denosumab (Xgeva®, Amgen), an antibody that binds to RANKL, prevents binding to its receptor RANK, found on the surface of osteoclasts, their precursors, and osteoclast-like giant cells, which mediates bone pathology in solid tumors with osseous metastases. Other approved therapeutics that inhibit bone resorption include bisphosphonates, such as zoledronic acid (Zometa®, Novartis).

In some embodiments, one or more other therapeutic agent is an inhibitor of interaction between the two primary p53 suppressor proteins, MDMX and MDM2. Inhibitors of p53 suppression proteins being studied which may be used in the present invention include ALRN-6924 (Aileron), a stapled peptide that equipotently binds to and disrupts the interaction of MDMX and MDM2 with p53. ALRN-6924 is currently being evaluated in clinical trials for the treatment of AML, advanced myelodysplastic syndrome (MDS) and peripheral T-cell lymphoma (PTCL) (NCT02909972; NCT02264613).

In some embodiments, one or more other therapeutic agent is an inhibitor of transforming growth factor-beta (TGF-beta or TGFβ). Inhibitors of TGF-beta proteins being studied which may be used in the present invention include NIS793 (Novartis), an anti-TGF-beta antibody being tested in the clinic for treatment of various cancers, including breast, lung, hepatocellular, colorectal, pancreatic, prostate and renal cancer (NCT 02947165). In some embodiments, the inhibitor of TGF-beta proteins is fresolimumab (GC1008; Sanofi-Genzyme), which is being studied for melanoma (NCT00923169); renal cell carcinoma (NCT00356460); and non-small cell lung cancer (NCT02581787). Additionally, in some embodiments, the additional therapeutic agent is a TGF-beta trap, such as described in Connolly et al. (2012) Int'l J. Biological Sciences 8:964-978. One therapeutic compound currently in clinical trials for treatment of solid tumors is M7824 (Merck KgaA—formerly MSB0011459X), which is a bispecific, anti-PD-L1/TGFβ trap compound (NCT02699515); and (NCT02517398). M7824 is comprised of a fully human IgG1 antibody against PD-L1 fused to the extracellular domain of human TGF-beta receptor II, which functions as a TGFβ "trap."

In some embodiments, one or more other therapeutic agent is selected from glembatumumab vedotin-monomethyl auristatin E (MMAE) (Celldex), an anti-glycoprotein NMB (gpNMB) antibody (CR011) linked to the cytotoxic MMAE. gpNMB is a protein overexpressed by multiple tumor types associated with cancer cells' ability to metastasize.

In some embodiments, one or more other therapeutic agent is an antiproliferative compound. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF 1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, $AZd_6244$ from AstraZeneca, PD181461 from Pfizer and leucovorin.

In some embodiments, the present invention provides a method of treating Alzheimer's disease comprising administering to a patient in need thereof a provided compound and one or more additional therapeutic agents selected from donepezil (Aricept®), rivastigmine (Excelon®), galantamine (Razadyne®), tacrine (Cognex®), and memantine (Namenda®).

In some embodiments, one or more other therapeutic agent is a taxane compound, which causes disruption of microtubules, which are essential for cell division. In some embodiments, a taxane compound is selected from paclitaxel (Taxol®, Bristol-Myers Squibb), docetaxel (Taxotere®, Sanofi-Aventis; Docefrez®, Sun Pharmaceutical), albumin-bound paclitaxel (Abraxane®; Abraxis/Celgene), cabazitaxel (Jevtana®, Sanofi-Aventis), and SID530 (SK Chemicals, Co.) (NCT00931008).

In some embodiments, one or more other therapeutic agent is a nucleoside inhibitor, or a therapeutic agent that interferes with normal DNA synthesis, protein synthesis, cell replication, or will otherwise inhibit rapidly proliferating cells.

In some embodiments, a nucleoside inhibitor is selected from trabectedin (guanidine alkylating agent, Yondelis®, Janssen Oncology), mechlorethamine (alkylating agent, Valchlor®, Aktelion Pharmaceuticals); vincristine (Oncovin®, Eli Lilly; Vincasar®, Teva Pharmaceuticals; Marqibo®, Talon Therapeutics); temozolomide (prodrug to alkylating agent 5-(3-methyltriazen-1-yl)-imidazole-4-carboxamide (MTIC) Temodar®, Merck); cytarabine injection (ara-C, antimetabolic cytidine analog, Pfizer); lomustine (alkylating agent, CeeNU®, Bristol-Myers Squibb; Gleostine®, NextSource Biotechnology); azacitidine (pyrimidine nucleoside analog of cytidine, Vidaza®, Celgene); omacetaxine mepesuccinate (cephalotaxine ester) (protein synthesis inhibitor, Synribo®; Teva Pharmaceuticals); asparaginase *Erwinia chrysanthemi* (enzyme for depletion of asparagine, Elspar®, Lundbeck; Erwinaze®, EUSA Pharma); eribulin mesylate (microtubule inhibitor, tubulin-based antimitotic, Halaven®, Eisai); cabazitaxel (microtubule inhibitor, tubulin-based antimitotic, Jevtana®, Sanofi-Aventis); capacetrine (thymidylate synthase inhibitor, Xeloda®, Genentech); bendamustine (bifunctional mechlorethamine derivative, believed to form interstrand DNA cross-links, Treanda®, Cephalon/Teva); ixabepilone (semi-synthetic analog of epothilone B, microtubule inhibitor, tubulin-based antimitotic, Ixempra®, Bristol-Myers Squibb); nelarabine (prodrug of deoxyguanosine analog, nucleoside metabolic inhibitor, Arranon®, Novartis); clorafabine (prodrug of ribonucleotide reductase inhibitor, competitive inhibitor of deoxycytidine, Clolar®, Sanofi-Aventis); and trifluridine and tipiracil (thymidine-based nucleoside analog and thymidine phosphorylase inhibitor, Lonsurf®, Taiho Oncology).

In some embodiments, one or more other therapeutic agent is a kinase inhibitor or VEGF-R antagonist. Approved VEGF inhibitors and kinase inhibitors useful in the present invention include: bevacizumab (Avastin®, Genentech/Roche) an anti-VEGF monoclonal antibody; ramucirumab (Cyramza®, Eli Lilly), an anti-VEGFR-2 antibody and ziv-aflibercept, also known as VEGF Trap (Zaltrap®; Regeneron/Sanofi). VEGFR inhibitors, such as regorafenib (Stivarga®, Bayer); vandetanib (Caprelsa®, AstraZeneca); axitinib (Inlyta®, Pfizer); and lenvatinib (Lenvima®, Eisai); Raf inhibitors, such as sorafenib (Nexavar®, Bayer AG and Onyx); dabrafenib (Tafinlar®, Novartis); and vemurafenib (Zelboraf®, Genentech/Roche); MEK inhibitors, such as cobimetanib (Cotellic®, Exelexis/Genentech/Roche); trametinib (Mekinist®, Novartis); Bcr-Abl tyrosine kinase inhibitors, such as imatinib (Gleevec®, Novartis); nilotinib (Tasigna®, Novartis); dasatinib (Sprycel®, BristolMyersSquibb); bosutinib (Bosulif®, Pfizer); and ponatinib (Inclusig®, Ariad Pharmaceuticals); Her2 and EGFR inhibitors, such as gefitinib (Iressa®, AstraZeneca); erlotinib (Tarceeva®, Genentech/Roche/Astellas); lapatinib (Tykerb®, Novartis); afatinib (Gilotrif®, Boehringer Ingelheim); osimertinib (targeting activated EGFR, Tagrisso®, AstraZeneca); and brigatinib (Alunbrig®, Ariad Pharmaceuticals); c-Met and VEGFR2 inhibitors, such as cabozanitib (Cometriq®, Exelexis); and multikinase inhibitors, such as sunitinib (Sutent®, Pfizer); pazopanib (Votrient®, Novartis); ALK inhibitors, such as crizotinib (Xalkori®, Pfizer); ceritinib (Zykadia®, Novartis); and alectinib (Alecenza®, Genentech/Roche); Bruton's tyrosine kinase inhibitors, such as ibrutinib (Imbruvica®, Pharmacyclics/Janssen); and Flt3 receptor inhibitors, such as midostaurin (Rydapt®, Novartis).

Other kinase inhibitors and VEGF-R antagonists that are in development and may be used in the present invention include tivozanib (Aveo Pharmaceuticals); vatalanib (Bayer/Novartis); lucitanib (Clovis Oncology); dovitinib (TK1258, Novartis); Chiauanib (Chipscreen Biosciences); CEP-11981 (Cephalon); linifanib (Abbott Laboratories); neratinib (HKI-272, Puma Biotechnology); radotinib (Supect®, IY5511, Il-Yang Pharmaceuticals, S. Korea); ruxolitinib (Jakafi®, Incyte Corporation); PTC299 (PTC Therapeutics); CP-547,632 (Pfizer); foretinib (Exelexis, GlaxoSmithKline); quizartinib (Daiichi Sankyo) and motesanib (Amgen/Takeda).

In another embodiment, the present invention provides a method of treating organ transplant rejection or graft vs. host disease comprising administering to a patient in need thereof a provided compound and one or more additional therapeutic agents selected from a steroid, cyclosporin, FK506, rapamycin, a hedgehog signaling inhibitor, a BTK inhibitor, a JAK/pan-JAK inhibitor, a TYK2 inhibitor, a PI3K inhibitor, and a SYK inhibitor.

In another embodiment, the present invention provides a method of treating or lessening the severity of a disease comprising administering to a patient in need thereof a provided compound and a BTK inhibitor, wherein the disease is selected from inflammatory bowel disease, arthritis, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, also known as HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleraderma, mycosis fungoides, acute inflammatory responses (such as acute respiratory distress syndrome and ischemia/reperfusion injury), and Graves' disease.

In another embodiment, the present invention provides a method of treating or lessening the severity of a disease comprising administering to a patient in need thereof a provided compound and a PI3K inhibitor, wherein the disease is selected from a cancer, a neurodegenerative disorder, an angiogenic disorder, a viral disease, an autoimmune disease, an inflammatory disorder, a hormone-related disease, conditions associated with organ transplantation, immunodeficiency disorders, a destructive bone disorder, a proliferative disorder, an infectious disease, a condition associated with cell death, thrombin-induced platelet aggregation, chronic myelogenous leukemia (CML), chronic lymphocytic leukemia (CLL), liver disease, pathologic immune conditions involving T cell activation, a cardiovascular disorder, and a CNS disorder.

In another embodiment, the present invention provides a method of treating or lessening the severity of a disease comprising administering to a patient in need thereof a provided compound and a PI3K inhibitor, wherein the disease is selected from benign or malignant tumor, carcinoma or solid tumor of the brain, kidney (e.g., renal cell carcinoma (RCC)), liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia, diseases include Cowden syndrome, Lhermitte-Dudos disease and Bannayan-Zonana syndrome, or diseases in which the PI3K/PKB pathway is aberrantly activated, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy, bronchitis of whatever type or genesis including, but not limited to, acute, arachidic, catarrhal, croupus, chronic or phthinoid bronchitis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Loffler's syndrome, eosinophilic, pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction, psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy, restenosis, cardiomegaly, atherosclerosis, myocardial infarction, ischemic stroke and congestive heart failure, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia. In some embodiments, one or more other therapeutic agent is a phosphatidylinositol 3 kinase (PI3K) inhibitor. In some embodiments, a PI3K inhibitor is selected from idelalisib (Zydelig®, Gilead), alpelisib (BYL719, Novartis), taselisib (GDC-0032, Genentech/Roche); pictilisib (GDC-0941, Genentech/Roche); copanlisib (BAY806946, Bayer); duvelisib (formerly IPI-145, Infinity Pharmaceuticals); PQR309 (Piqur Therapeutics, Switzerland); and TGR1202 (formerly RP5230, TG Therapeutics).

The compounds and compositions, according to the method of the present invention, may be administered using any amount and any route of administration effective for treating or lessening the severity of a cancer, an autoimmune disorder, a proliferative disorder, an inflammatory disorder, a neurodegenerative or neurological disorder, schizophrenia, a bone-related disorder, liver disease, or a cardiac disorder. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting protein kinase activity or degading a protein kinase in a biological sample comprising the step of contacting said biological sample with a compound of this invention, or a composition comprising said compound.

According to another embodiment, the invention relates to a method of inhibiting or degrading MDM2, or a mutant thereof, activity in a biological sample comprising the step of contacting said biological sample with a compound of this invention, or a composition comprising said compound.

The term "biological sample", as used herein, includes, without limitation, cell cultures or extracts thereof, biopsied material obtained from a mammal or extracts thereof, and blood, saliva, urine, feces, semen, tears, or other body fluids or extracts thereof.

Inhibition and/or degradation of a MDM2 protein, or a mutant thereof, activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of degrading a protein kinase and/or inhibiting protein kinase activity in a patient comprising the step of administering to said patient a compound of the present invention, or a composition comprising said compound.

According to another embodiment, the invention relates to a method of degrading and/or inhibiting MDM2, or a mutant thereof, activity in a patient comprising the step of administering to said patient a compound of the present invention, or a composition comprising said compound. In other embodiments, the present invention provides a method for treating a disorder mediated by MDM2, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin.

The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™. Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

In some embodiments, one or more other therapeutic agent is an mTOR inhibitor, which inhibits cell proliferation, angiogenesis and glucose uptake. In some embodiments, an mTOR inhibitor is everolimus (Afinitor®, Novartis); temsirolimus (Torisel®, Pfizer); and sirolimus (Rapamune®, Pfizer).

In some embodiments, one or more other therapeutic agent is an aromatase inhibitor. In some embodiments, an aromatase inhibitor is selected from exemestane (Aromasin®, Pfizer); anastazole (Arimidex®, AstraZeneca) and letrozole (Femara®, Novartis).

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™ Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™) The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™ Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof, see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; Isis 3521; LY333531/LY379196; isochinoline compounds; FTIs; PD184352 or QAN697 (a PI3K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) compounds targeting, decreasing or inhibiting the activity of the epidermal growth factor family of receptor tyrosine kinases ($EGFR_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, C1-1033, EKB-569, GW-2016, ELI, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

Compounds which target, decrease or inhibit the activity of a protein or lipid phosphatase are e.g. inhibitors of phosphatase 1, phosphatase 2A, or CDC25, such as okadaic acid or a derivative thereof.

In some embodiments, one or more other therapeutic agent is a growth factor antagonist, such as an antagonist of platelet-derived growth factor (PDGF), or epidermal growth factor (EGF) or its receptor (EGFR). Approved PDGF antagonists which may be used in the present invention include olaratumab (Lartruvo®; Eli Lilly). Approved EGFR antagonists which may be used in the present invention include cetuximab (Erbitux®, Eli Lilly); necitumumab (Portrazza®, Eli Lilly), panitumumab (Vectibix®, Amgen); and osimertinib (targeting activated EGFR, Tagrisso®, AstraZeneca).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3KD, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zamestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™), carfilzomib (Kyprolis®, Amgen); and ixazomib (Ninlaro®, Takeda), and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., $4^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17a-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate; non-steroidal glucocorticoid receptor agonists; LTB4 antagonists such LY293111, CGS025019C, CP-195543, SC-53228, BIIL 284, ONO 4057, SB 209247; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SeICID™ CC-10004 (Celgene), VM554/UM565 (Vemalis), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, and Takeda antagonists such as N-[[4-[[[6,7-dihydro-2-(4-methylphenyl)-5H-benzo-cyclohepten-8-yl]carbonyl]amino]phenyl]-methyl]tetrahydro-N,N-dimethyl-2H-pyran-4-aminium chloride (TAK-770).

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition.

If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 μg/kg body weight/day of the additional therapeutic agent can be administered.

The amount of one or more other therapeutic agent present in the compositions of this invention may be no more than the amount that would normally be administered in a composition comprising that therapeutic agent as the only active agent. Preferably the amount of one or more other therapeutic agent in the presently disclosed compositions will range from about 50% to 100% of the amount normally present in a composition comprising that agent as the only therapeutically active agent. In some embodiments, one or more other therapeutic agent is administered at a dosage of about 50%, about 55%, about 60%, about 65%, about 70%, about 75%, about 80%, about 85%, about 90%, or about 95% of the amount normally administered for that agent. As used herein, the phrase "normally administered" means the amount an FDA approved therapeutic agent is provided for dosing per the FDA label insert.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by precoating the device with a pharmaceutically acceptable composition comprising a kinase inhibitor. Implantable devices coated with a compound of this invention are another embodiment of the present invention.

Exemplary Immuno-Oncology Agents

In some embodiments, one or more other therapeutic agent is an immuno-oncology agent. As used herein, the term "an immuno-oncology agent" refers to an agent which is effective to enhance, stimulate, and/or up-regulate immune responses in a subject. In some embodiments, the administration of an immuno-oncology agent with a compound of the invention has a synergic effect in treating a cancer.

An immuno-oncology agent can be, for example, a small molecule drug, an antibody, or a biologic or small molecule. Examples of biologic immuno-oncology agents include, but are not limited to, cancer vaccines, antibodies, and cytokines. In some embodiments, an antibody is a monoclonal antibody. In some embodiments, a monoclonal antibody is humanized or human.

In some embodiments, an immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses.

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α1β2, FAS, FASL, RELT, DR6, TROY, NGFR.

In some embodiments, an immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In some embodiments, a combination of a compound of the invention and an immuno-oncology agent can stimulate T cell responses. In some embodiments, an immuno-oncology agent is: (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIRI, TIM-1, and TIM-4; or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

In some embodiments, an immuno-oncology agent is an antagonist of inhibitory receptors on NK cells or an agonists of activating receptors on NK cells. In some embodiments, an immuno-oncology agent is an antagonists of KIR, such as lirilumab.

In some embodiments, an immuno-oncology agent is an agent that inhibits or depletes macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In some embodiments, an immuno-oncology agent is selected from agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell energy or exhaustion) and agents that trigger innate immune activation and/or inflammation at tumor sites.

In some embodiments, an immuno-oncology agent is a CTLA-4 antagonist. In some embodiments, a CTLA-4 antagonist is an antagonistic CTLA-4 antibody. In some embodiments, an antagonistic CTLA-4 antibody is YERVOY (ipilimumab) or tremelimumab.

In some embodiments, an immuno-oncology agent is a PD-1 antagonist. In some embodiments, a PD-1 antagonist is administered by infusion. In some embodiments, an immuno-oncology agent is an antibody or an antigen-binding portion thereof that binds specifically to a Programmed Death-1 (PD-1) receptor and inhibits PD-1 activity. In some embodiments, a PD-1 antagonist is an antagonistic PD-1 antibody. In some embodiments, an antagonistic PD-1 antibody is OPDIVO (nivolumab), KEYTRUDA (pembrolizumab), or MEDI-0680 (AMP-514; WO2012/145493). In some embodiments, an immuno-oncology agent may be pidilizumab (CT-011). In some embodiments, an immuno-oncology agent is a recombinant protein composed of the extracellular domain of PD-L2 (B7-DC) fused to the Fc portion of IgG1, called AMP-224.

In some embodiments, an immuno-oncology agent is a PD-L1 antagonist. In some embodiments, a PD-L1 antagonist is an antagonistic PD-L1 antibody. In some embodiments, a PD-L1 antibody is MPDL3280A (RG7446; WO2010/077634), durvalumab (MED14736), BMS-936559 (WO2007/005874), and MSB0010718C (WO2013/79174).

In some embodiments, an immuno-oncology agent is a LAG-3 antagonist. In some embodiments, a LAG-3 antagonist is an antagonistic LAG-3 antibody. In some embodiments, a LAG3 antibody is BMS-986016 (WO10/19570, WO14/08218), or IMP-731 or IMP-321 (WO08/132601, WO009/44273).

In some embodiments, an immuno-oncology agent is a CD137 (4-1BB) agonist. In some embodiments, a CD137 (4-1BB) agonist is an agonistic CD137 antibody. In some embodiments, a CD137 antibody is urelumab or PF-05082566 (WO12/32433).

In some embodiments, an immuno-oncology agent is a GITR agonist. In some embodiments, a GITR agonist is an agonistic GITR antibody. In some embodiments, a GITR antibody is BMS-986153, BMS-986156, TRX-518 (WO006/105021, WO009/009116), or MK-4166 (WO11/028683).

In some embodiments, an immuno-oncology agent is an indoleamine (2,3)-dioxygenase (IDO) antagonist. In some embodiments, an IDO antagonist is selected from epacadostat (INCB024360, Incyte); indoximod (NLG-8189, NewLink Genetics Corporation); capmanitib (INC280, Novartis); GDC-0919 (Genentech/Roche); PF-06840003 (Pfizer); BMS.F001287 (Bristol-Myers Squibb); Phy906/KD108 (Phytoceutica); an enzyme that breaks down kynurenine (Kynase, Kyn Therapeutics); and NLG-919 (WO09/73620, WO009/1156652, WO11/56652, WO12/142237).

In some embodiments, an immuno-oncology agent is an OX40 agonist. In some embodiments, an OX40 agonist is an agonistic OX40 antibody. In some embodiments, an OX40 antibody is MEDI-6383 or MEDI-6469.

In some embodiments, an immuno-oncology agent is an OX40L antagonist. In some embodiments, an OX40L antagonist is an antagonistic OX40 antibody. In some embodiments, an OX40L antagonist is RG-7888 (WO06/029879).

In some embodiments, an immuno-oncology agent is a CD40 agonist. In some embodiments, a CD40 agonist is an agonistic CD40 antibody. In some embodiments, an immuno-oncology agent is a CD40 antagonist. In some embodiments, a CD40 antagonist is an antagonistic CD40 antibody. In some embodiments, a CD40 antibody is lucatumumab or dacetuzumab.

In some embodiments, an immuno-oncology agent is a CD27 agonist. In some embodiments, a CD27 agonist is an agonistic CD27 antibody. In some embodiments, a CD27 antibody is varlilumab.

In some embodiments, an immuno-oncology agent is MGA271 (to B7H3) (WO11/109400).

In some embodiments, an immuno-oncology agent is abagovomab, adecatumumab, afutuzumab, alemtuzumab, anatumomab mafenatox, apolizumab, atezolimab, avelumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, or tremelimumab.

In some embodiments, an immuno-oncology agent is an immunostimulatory agent. For example, antibodies blocking the PD-1 and PD-L1 inhibitory axis can unleash activated tumor-reactive T cells and have been shown in clinical trials to induce durable anti-tumor responses in increasing numbers of tumor histologies, including some tumor types that conventionally have not been considered immunotherapy sensitive. See, e.g., Okazaki, T. et al. (2013) Nat. Immunol. 14, 1212-1218; Zou et al. (2016) Sci. Transl. Med. 8. The anti-PD-1 antibody nivolumab (Opdivo®, Bristol-Myers Squibb, also known as ONO-4538, MDX1106 and BMS-936558), has shown potential to improve the overall survival in patients with RCC who had experienced disease progression during or after prior anti-angiogenic therapy.

In some embodiments, the immunomodulatory therapeutic specifically induces apoptosis of tumor cells. Approved immunomodulatory therapeutics which may be used in the present invention include pomalidomide (Pomalyst®, Celgene); lenalidomide (Revlimid®, Celgene); ingenol mebutate (Picato®, LEO Pharma).

In some embodiments, an immuno-oncology agent is a cancer vaccine. In some embodiments, the cancer vaccine is selected from sipuleucel-T (Provenge®, Dendreon/Valeant Pharmaceuticals), which has been approved for treatment of asymptomatic, or minimally symptomatic metastatic castrate-resistant (hormone-refractory) prostate cancer; and talimogene laherparepvec (Imlygic®, BioVex/Amgen, previously known as T-VEC), a genetically modified oncolytic viral therapy approved for treatment of unresectable cutaneous, subcutaneous and nodal lesions in melanoma. In some embodiments, an immuno-oncology agent is selected from an oncolytic viral therapy such as pexastimogene devacirepvec (PexaVec/JX-594, SillaJen/formerly Jennerex Biotherapeutics), a thymidine kinase-(TK-) deficient vaccinia virus engineered to express GM-CSF, for hepatocellular carcinoma (NCT02562755) and melanoma (NCT00429312); pelareorep (Reolysin®, Oncolytics Biotech), a variant of respiratory enteric orphan virus (reovirus) which does not replicate in cells that are not RAS-activated, in numerous cancers, including colorectal cancer (NCT01622543); prostate cancer (NCT01619813); head and neck squamous cell cancer (NCT01166542); pancreatic adenocarcinoma (NCT00998322); and non-small cell lung cancer (NSCLC) (NCT 00861627); enadenotucirev (NG-348, PsiOxus, formerly known as ColoAdl), an adenovirus engineered to express a full length CD80 and an antibody fragment specific for the T-cell receptor CD3 protein, in ovarian cancer (NCT02028117); metastatic or advanced epithelial tumors such as in colorectal cancer, bladder cancer, head and neck squamous cell carcinoma and salivary gland cancer (NCT02636036); ONCOS-102 (Targovax/formerly Oncos), an adenovirus engineered to express GM-CSF, in melanoma (NCT03003676); and peritoneal disease, colorectal cancer or ovarian cancer (NCT02963831); GL-ONC1 (GLV-lh68/GLV-1h153, Genelux GmbH), vaccinia viruses engineered to express beta-galactosidase (beta-gal)/beta-glucoronidase or beta-gal/human sodium iodide symporter (hNIS), respectively, were studied in peritoneal carcinomatosis (NCT01443260); fallopian tube cancer, ovarian cancer (NCT 02759588); or CG0070 (Cold Genesys), an adenovirus engineered to express GM-CSF, in bladder cancer (NCT02365818).

In some embodiments, an immuno-oncology agent is selected from JX-929 (SillaJen/formerly Jennerex Biotherapeutics), a TK- and vaccinia growth factor-deficient vaccinia virus engineered to express cytosine deaminase, which is able to convert the prodrug 5-fluorocytosine to the cytotoxic drug 5-fluorouracil; TG01 and TG02 (Targovax/formerly Oncos), peptide-based immunotherapy agents targeted for difficult-to-treat RAS mutations; and TILT-123 (TILT Biotherapeutics), an engineered adenovirus designated: Ad5/3-E2F-delta24-hTNF$\alpha$-IRES-hIL20; and VSV-GP (ViraTherapeutics) a vesicular stomatitis virus (VSV) engineered to express the glycoprotein (GP) of lymphocytic choriomeningitis virus (LCMV), which can be further engineered to express antigens designed to raise an antigen-specific $CD8^+$ T cell response.

In some embodiments, an immuno-oncology agent is a T-cell engineered to express a chimeric antigen receptor, or CAR. The T-cells engineered to express such chimeric antigen receptor are referred to as a CAR-T cells.

CARs have been constructed that consist of binding domains, which may be derived from natural ligands, single chain variable fragments (scFv) derived from monoclonal antibodies specific for cell-surface antigens, fused to endodomains that are the functional end of the T-cell receptor (TCR), such as the CD3-zeta signaling domain from TCRs, which is capable of generating an activation signal in T lymphocytes. Upon antigen binding, such CARs link to endogenous signaling pathways in the effector cell and generate activating signals similar to those initiated by the TCR complex.

For example, in some embodiments the CAR-T cell is one of those described in U.S. Pat. No. 8,906,682 (June; hereby incorporated by reference in its entirety), which discloses CAR-T cells engineered to comprise an extracellular domain having an antigen binding domain (such as a domain that binds to CD19), fused to an intracellular signaling domain of the T cell antigen receptor complex zeta chain (such as CD3 zeta). When expressed in the T cell, the CAR is able to redirect antigen recognition based on the antigen binding specificity. In the case of CD19, the antigen is expressed on malignant B cells. Over 200 clinical trials are currently in progress employing CAR-T in a wide range of indications. [https://clinicaltrials.gov/ct2/results?term=chimeric+antigen+receptors&pg=1].

In some embodiments, an immunostimulatory agent is an activator of retinoic acid receptor-related orphan receptor γ (RORγt). RORγt is a transcription factor with key roles in the differentiation and maintenance of Type 17 effector subsets of CD4+(Th17) and CD8+ (Tc17) T cells, as well as the differentiation of IL-17 expressing innate immune cell subpopulations such as NK cells. In some embodiments, an activator of RORγt is LYC-55716 (Lycera), which is currently being evaluated in clinical trials for the treatment of solid tumors (NCT02929862).

In some embodiments, an immunostimulatory agent is an agonist or activator of a toll-like receptor (TLR). Suitable activators of TLRs include an agonist or activator of TLR9 such as SD-101 (Dynavax). SD-101 is an immunostimulatory CpG which is being studied for B-cell, follicular and other lymphomas (NCT02254772). Agonists or activators of TLR8 which may be used in the present invention include motolimod (VTX-2337, VentiRx Pharmaceuticals) which is being studied for squamous cell cancer of the head and neck (NCT02124850) and ovarian cancer (NCT02431559).

Other immuno-oncology agents that may be used in the present invention include urelumab (BMS-663513, Bristol-Myers Squibb), an anti-CD137 monoclonal antibody; varlilumab (CDX-1127, Celldex Therapeutics), an anti-CD27 monoclonal antibody; BMS-986178 (Bristol-Myers Squibb), an anti-OX40 monoclonal antibody; lirilumab (IPH2102/BMS-986015, Innate Pharma, Bristol-Myers Squibb), an anti-KIR monoclonal antibody; monalizumab (IPH2201, Innate Pharma, AstraZeneca) an anti-NKG2A monoclonal antibody; andecaliximab (GS-5745, Gilead Sciences), an anti-MMP9 antibody; MK-4166 (Merck & Co.), an anti-GITR monoclonal antibody.

In some embodiments, an immunostimulatory agent is selected from elotuzumab, mifamurtide, an agonist or activator of a toll-like receptor, and an activator of RORγt.

In some embodiments, an immunostimulatory therapeutic is recombinant human interleukin 15 (rhIL-15). rhIL-15 has been tested in the clinic as a therapy for melanoma and renal cell carcinoma (NCT01021059 and NCT01369888) and leukemias (NCT02689453). In some embodiments, an immunostimulatory agent is recombinant human interleukin 12 (rhIL-12). In some embodiments, an IL-15 based immunotherapeutic is heterodimeric IL-15 (hetIL-15, Novartis/Admune), a fusion complex composed of a synthetic form of endogenous IL-15 complexed to the soluble IL-15 binding protein IL-15 receptor alpha chain (IL15:sIL-15RA), which has been tested in Phase 1 clinical trials for melanoma, renal cell carcinoma, non-small cell lung cancer and head and neck squamous cell carcinoma (NCT02452268). In some embodiments, a recombinant human interleukin 12 (rhIL-12) is NM-IL-12 (Neumedicines, Inc.), NCT02544724, or NCT02542124.

In some embodiments, an immuno-oncology agent is selected from those descripted in Jerry L. Adams et al., "Big opportunities for small molecules in immuno-oncology," Cancer Therapy 2015, Vol. 14, pages 603-622, the content of which is incorporated herein by reference in its entirety. In some embodiments, an immuno-oncology agent is selected from the examples described in Table 1 of Jerry L. Adams et al. In some embodiments, an immuno-oncology agent is a small molecule targeting an immuno-oncology target selected from those listed in Table 2 of Jerry L. Adams ET. AL. In some embodiments, an immuno-oncology agent is a small molecule agent selected from those listed in Table 2 of Jerry L. Adams et al.

In some embodiments, an immuno-oncology agent is selected from the small molecule immuno-oncology agents described in Peter L. Toogood, "Small molecule immuno-oncology therapeutic agents," Bioorganic & Medicinal Chemistry Letters 2018, Vol. 28, pages 319-329, the content of which is incorporated herein by reference in its entirety. In some embodiments, an immuno-oncology agent is an agent targeting the pathways as described in Peter L. Toogood.

In some embodiments, an immuno-oncology agent is selected from those described in Sandra L. Ross et al., "Bispecific T cell engager (BiTE®) antibody constructs can mediate bystander tumor cell killing", PLoS ONE 12(8): e0183390, the contents of which is incorporated herein by reference in its entirety. In some embodiments, an immuno-oncology agent is a bispecific T cell engager (BiTE®) antibody construct. In some embodiments, a bispecific T cell engager (BiTE®) antibody construct is a CD19/CD3 bispecific antibody construct. In some embodiments, a bispecific T cell engager (BiTE®) antibody construct is an EGFR/CD3 bispecific antibody construct. In some embodiments, a bispecific T cell engager (BiTE®) antibody construct activates T cells. In some embodiments, a bispecific T cell engager (BiTE®) antibody construct activates T cells, which release cytokines inducing upregulation of intercellular adhesion molecule 1 (ICAM-1) and FAS on bystander cells. In some embodiments, a bispecific T cell engager (BiTE®) antibody construct activates T cells which result in induced bystander cell lysis. In some embodiments, the bystander cells are in solid tumors. In some embodiments, the bystander cells being lysed are in proximity to the BiTE®-activated T cells. In some embodiment, the bystander cells comprises tumor-associated antigen (TAA) negative cancer cells. In some embodiment, the bystander cells comprise EGFR-negative cancer cells. In some embodiments, an immuno-oncology agent is an antibody which blocks the PD-L1/PD1 axis and/or CTLA4. In some embodiments, an immuno-oncology agent is an ex-vivo expanded tumor-infiltrating T cell. In some embodiments, an immuno-oncology agent is a bispecific antibody construct or chimeric antigen receptors (CARs) that directly connect T cells with tumor-associated surface antigens (TAAs).

Exemplary Immune Checkpoint Inhibitors

In some embodiments, an immuno-oncology agent is an immune checkpoint inhibitor as described herein.

The term "checkpoint inhibitor" as used herein relates to agents useful in preventing cancer cells from avoiding the immune system of the patient. One of the major mechanisms of anti-tumor immunity subversion is known as "T-cell exhaustion," which results from chronic exposure to antigens that has led to up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as a checkpoint regulators. They act as molecular "gatekeepers" that allow extracellular information to dictate whether cell cycle progression and other intracellular signaling processes should proceed.

In some embodiments, an immune checkpoint inhibitor is an antibody to PD-1. PD-1 binds to the programmed cell death 1 receptor (PD-1) to prevent the receptor from binding to the inhibitory ligand PDL-1, thus overriding the ability of tumors to suppress the host anti-tumor immune response.

In one aspect, the checkpoint inhibitor is a biologic therapeutic or a small molecule. In another aspect, the checkpoint inhibitor is a monoclonal antibody, a humanized antibody, a fully human antibody, a fusion protein or a combination thereof. In a further aspect, the checkpoint inhibitor inhibits a checkpoint protein selected from CTLA-4, PDL1, PDL2, PDl, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an additional aspect, the checkpoint inhibitor interacts with a ligand of a checkpoint protein selected from CTLA-4, PDL1, PDL2, PDl, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an aspect, the checkpoint inhibitor is an immunostimulatory agent, a T cell growth factor, an interleukin, an antibody, a vaccine or a combination thereof. In a further aspect, the interleukin is IL-7 or IL-15. In a specific aspect, the interleukin is glycosylated IL-7. In an additional aspect, the vaccine is a dendritic cell (DC) vaccine.

Checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptors or antibodies that bind to and block or inhibit immune checkpoint receptor ligands. Illustrative checkpoint molecules that may be targeted for blocking or inhibition include, but are not limited to, CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, y6, and memory CD8+(ap) T cells), CD160 (also referred to as BY55), CGEN-15049, CHK 1 and CHK2 kinases, A2aR, and various B-7 family ligands. B7 family ligands include, but are not limited to, B7-1, B7-2, B7-DC, B7-H1, B7-H2, B7-H3, B7-H4, B7-H5, B7-H6 and B7-H7. Checkpoint inhibitors include antibodies, or antigen binding fragments thereof, other binding proteins, biologic therapeutics, or small molecules, that bind to and block or inhibit the activity of one or more of CTLA-4, PDL1, PDL2, PD1, BTLA, HVEM, TIM3, GAL9, LAG3, VISTA, KIR, 2B4, CD 160 and CGEN-15049. Illustrative immune checkpoint inhibitors include Tremelimumab (CTLA-4 blocking antibody), anti-OX40, PD-L1 monoclonal Antibody (Anti-B7-H1; MED14736), MK-3475 (PD-1 blocker), Nivolumab (anti-PDl antibody), CT-011 (anti-PDl antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody), and ipilimumab (anti-CTLA-4 checkpoint inhibitor). Checkpoint protein ligands include, but are not limited to PD-L1, PD-L2, B7-H3, B7-H4, CD28, CD86 and TIM-3.

In certain embodiments, the immune checkpoint inhibitor is selected from a PD-1 antagonist, a PD-L1 antagonist, and a CTLA-4 antagonist. In some embodiments, the checkpoint inhibitor is selected from the group consisting of nivolumab (Opdivo®), ipilimumab (Yervoy®), and pembrolizumab (Keytruda®). In some embodiments, the checkpoint inhibitor is selected from nivolumab (anti-PD-1 antibody, Opdivo®, Bristol-Myers Squibb); pembrolizumab (anti-PD-1 antibody, Keytruda®, Merck); ipilimumab (anti-CTLA-4 antibody, Yervoy®, Bristol-Myers Squibb); durvalumab (anti-PD-L1 antibody, Imfinzi®, AstraZeneca); and atezolizumab (anti-PD-L1 antibody, Tecentriq®, Genentech).

In some embodiments, the checkpoint inhibitor is selected from the group consisting of lambrolizumab (MK-3475), nivolumab (BMS-936558), pidilizumab (CT-011), AMP-224, MDX-1105, MEDI4736, MPDL3280A, BMS-936559, ipilimumab, lirlumab, IPH2101, pembrolizumab (Keytruda®), and tremelimumab.

In some embodiments, an immune checkpoint inhibitor is REGN2810 (Regeneron), an anti-PD-1 antibody tested in patients with basal cell carcinoma (NCT03132636); NSCLC (NCT03088540); cutaneous squamous cell carcinoma (NCT02760498); lymphoma (NCT02651662); and melanoma (NCT03002376); pidilizumab (CureTech), also known as CT-011, an antibody that binds to PD-1, in clinical trials for diffuse large B-cell lymphoma and multiple myeloma; avelumab (Bavencio®, Pfizer/Merck KGaA), also known as MSB0010718C), a fully human IgG1 anti-PD-L1 antibody, in clinical trials for non-small cell lung cancer, Merkel cell carcinoma, mesothelioma, solid tumors, renal cancer, ovarian cancer, bladder cancer, head and neck cancer, and gastric cancer; or PDR001 (Novartis), an inhibitory antibody that binds to PD-1, in clinical trials for non-small cell lung cancer, melanoma, triple negative breast cancer and advanced or metastatic solid tumors. Tremelimumab (CP-675,206; Astrazeneca) is a fully human monoclonal antibody against CTLA-4 that has been in studied in clinical trials for a number of indications, including: mesothelioma, colorectal cancer, kidney cancer, breast cancer, lung cancer and non-small cell lung cancer, pancreatic ductal adenocarcinoma, pancreatic cancer, germ cell cancer, squamous cell cancer of the head and neck, hepatocellular carcinoma, prostate cancer, endometrial cancer, metastatic cancer in the liver, liver cancer, large B-cell lymphoma, ovarian cancer, cervical cancer, metastatic anaplastic thyroid cancer, urothelial cancer, fallopian tube cancer, multiple myeloma, bladder cancer, soft tissue sarcoma, and melanoma. AGEN-1884 (Agenus) is an anti-CTLA4 antibody that is being studied in Phase 1 clinical trials for advanced solid tumors (NCT02694822).

In some embodiments, a checkpoint inhibitor is an inhibitor of T-cell immunoglobulin mucin containing protein-3 (TIM-3). TIM-3 inhibitors that may be used in the present invention include TSR-022, LY3321367 and MBG453. TSR-022 (Tesaro) is an anti-TIM-3 antibody which is being studied in solid tumors (NCT02817633). LY3321367 (Eli Lilly) is an anti-TIM-3 antibody which is being studied in solid tumors (NCT03099109). MBG453 (Novartis) is an anti-TIM-3 antibody which is being studied in advanced malignancies (NCT02608268).

In some embodiments, a checkpoint inhibitor is an inhibitor of T cell immunoreceptor with Ig and ITIM domains, or TIGIT, an immune receptor on certain T cells and NK cells. TIGIT inhibitors that may be used in the present invention include BMS-986207 (Bristol-Myers Squibb), an anti-TIGIT monoclonal antibody (NCT02913313); OMP-313M32 (Oncomed); and anti-TIGIT monoclonal antibody (NCT03119428).

In some embodiments, a checkpoint inhibitor is an inhibitor of Lymphocyte Activation Gene-3 (LAG-3). LAG-3 inhibitors that may be used in the present invention include BMS-986016 and REGN3767 and IMP321. BMS-986016 (Bristol-Myers Squibb), an anti-LAG-3 antibody, is being studied in glioblastoma and gliosarcoma (NCT02658981). REGN3767 (Regeneron), is also an anti-LAG-3 antibody, and is being studied in malignancies (NCT03005782). IMP321 (Immutep S.A.) is an LAG-3-Ig fusion protein, being studied in melanoma (NCT02676869); adenocarcinoma (NCT02614833); and metastatic breast cancer (NCT00349934).

Checkpoint inhibitors that may be used in the present invention include OX40 agonists. OX40 agonists that are being studied in clinical trials include PF-04518600/PF-8600 (Pfizer), an agonistic anti-OX40 antibody, in metastatic kidney cancer (NCT03092856) and advanced cancers and neoplasms (NCT02554812; NCT05082566); GSK3174998 (Merck), an agonistic anti-OX40 antibody, in Phase 1 cancer trials (NCT02528357); MEDI0562 (Medimmune/AstraZeneca), an agonistic anti-OX40 antibody, in advanced solid tumors (NCT02318394 and NCT02705482); MEDI6469, an agonistic anti-OX40 antibody (Medimmune/AstraZeneca), in patients with colorectal cancer (NCT02559024), breast cancer (NCT01862900), head and neck cancer (NCT02274155) and metastatic prostate cancer (NCT01303705); and BMS-986178 (Bristol-Myers Squibb) an agonistic anti-OX40 antibody, in advanced cancers (NCT02737475).

Checkpoint inhibitors that may be used in the present invention include CD137 (also called 4-1BB) agonists. CD137 agonists that are being studied in clinical trials include utomilumab (PF-05082566, Pfizer) an agonistic anti-CD137 antibody, in diffuse large B-cell lymphoma (NCT02951156) and in advanced cancers and neoplasms (NCT02554812 and NCT05082566); urelumab (BMS-663513, Bristol-Myers Squibb), an agonistic anti-CD137 antibody, in melanoma and skin cancer (NCT02652455) and glioblastoma and gliosarcoma (NCT02658981).

Checkpoint inhibitors that may be used in the present invention include CD27 agonists. CD27 agonists that are being studied in clinical trials include varlilumab (CDX-1127, Celldex Therapeutics) an agonistic anti-CD27 antibody, in squamous cell head and neck cancer, ovarian carcinoma, colorectal cancer, renal cell cancer, and glioblastoma (NCT02335918); lymphomas (NCT01460134); and glioma and astrocytoma (NCT02924038).

Checkpoint inhibitors that may be used in the present invention include glucocorticoid-induced tumor necrosis factor receptor (GITR) agonists. GITR agonists that are being studied in clinical trials include TRX518 (Leap Therapeutics), an agonistic anti-GITR antibody, in malignant melanoma and other malignant solid tumors (NCT01239134 and NCT02628574); GWN323 (Novartis), an agonistic anti-GITR antibody, in solid tumors and lymphoma (NCT 02740270); INCAGN01876 (Incyte/Agenus), an agonistic anti-GITR antibody, in advanced cancers (NCT02697591 and NCT03126110); MK-4166 (Merck), an agonistic anti-GITR antibody, in solid tumors (NCT02132754) and MEDI1873 (Medimmune/AstraZeneca), an agonistic hexameric GITR-ligand molecule with a human IgG1 Fc domain, in advanced solid tumors (NCT02583165).

Checkpoint inhibitors that may be used in the present invention include inducible T-cell co-stimulator (ICOS, also known as CD278) agonists. ICOS agonists that are being studied in clinical trials include MEDI-570 (Medimmune), an agonistic anti-ICOS antibody, in lymphomas (NCT02520791); GSK3359609 (Merck), an agonistic anti-ICOS antibody, in Phase 1 (NCT02723955); JTX-2011 (Jounce Therapeutics), an agonistic anti-ICOS antibody, in Phase 1 (NCT02904226).

Checkpoint inhibitors that may be used in the present invention include killer IgG-like receptor (KIR) inhibitors. KIR inhibitors that are being studied in clinical trials include lirilumab (IPH2102/BMS-986015, Innate Pharma/Bristol-Myers Squibb), an anti-KIR antibody, in leukemias (NCT01687387, NCT02399917, NCT02481297, NCT02599649), multiple myeloma (NCT02252263), and lymphoma (NCT01592370); IPH2101 (1-7F9, Innate Pharma) in myeloma (NCT01222286 and NCT01217203); and IPH4102 (Innate Pharma), an anti-KIR antibody that binds to three domains of the long cytoplasmic tail (KIR3DL2), in lymphoma (NCT02593045).

Checkpoint inhibitors that may be used in the present invention include CD47 inhibitors of interaction between CD47 and signal regulatory protein alpha (SIRPa). CD47/SIRPa inhibitors that are being studied in clinical trials include ALX-148 (Alexo Therapeutics), an antagonistic variant of (SIRPa) that binds to CD47 and prevents CD47/SIRPa-mediated signaling, in phase 1 (NCT03013218); TTI-621 (SIRPa-Fc, Trillium Therapeutics), a soluble recombinant fusion protein created by linking the N-terminal CD47-binding domain of SIRPa with the Fc domain of human IgG1, acts by binding human CD47, and preventing it from delivering its "do not eat" signal to macrophages, is in clinical trials in Phase 1 (NCT02890368 and NCT02663518); CC-90002 (Celgene), an anti-CD47 antibody, in leukemias (NCT02641002); and Hu5F9-G4 (Forty Seven, Inc.), in colorectal neoplasms and solid tumors (NCT02953782), acute myeloid leukemia (NCT02678338) and lymphoma (NCT02953509).

Checkpoint inhibitors that may be used in the present invention include CD73 inhibitors. CD73 inhibitors that are being studied in clinical trials include MED19447 (Medimmune), an anti-CD73 antibody, in solidtumors (NCT02503774); and BMS-986179 (Bristol-Myers Squibb), an anti-CD73 antibody, in solid tumors (NCT02754141).

Checkpoint inhibitors that may be used in the present invention include agonists of stimulator of interferon genes protein (STING, also known as transmembrane protein 173, or TMEM173). Agonists of STING that are being studied in clinical trials include MK-1454 (Merck), an agonistic synthetic cyclic dinucleotide, in lymphoma (NCT03010176); and ADU-S100 (MIW815, Aduro Biotech/Novartis), an agonistic synthetic cyclic dinucleotide, in Phase 1 (NCT02675439 and NCT03172936).

In some embodiments, MDM2 inhibition/degradation can significantly enhance CDN-induced STING signaling and antitumor immunity (Pei et al., *Can. Lett.* 2019, 450:110).

Checkpoint inhibitors that may be used in the present invention include CSF1R inhibitors. CSF1R inhibitors that are being studied in clinical trials include pexidartinib (PLX3397, Plexxikon), a CSF1R small molecule inhibitor, in colorectal cancer, pancreatic cancer, metastatic and advanced cancers (NCT02777710) and melanoma, non-small cell lung cancer, squamous cell head and neck cancer, gastrointestinal stromal tumor (GIST) and ovarian cancer (NCT02452424); and IMC-CS4 (LY3022855, Lilly), an anti-CSF-1R antibody, in pancreatic cancer (NCT03153410), melanoma (NCT03101254), and solid tumors (NCT02718911); and BLZ945 (4-[2((1R,2R)-2-hydroxycyclohexylamino)-benzothiazol-6-yloxyl]-pyridine-2-carboxylic acid methylamide, Novartis), an orally available inhibitor of CSF1R, in advanced solid tumors (NCT02829723).

Checkpoint inhibitors that may be used in the present invention include NKG2A receptor inhibitors. NKG2A receptor inhibitors that are being studied in clinical trials include monalizumab (IPH2201, Innate Pharma), an anti-NKG2A antibody, in head and neck neoplasms (NCT02643550) and chronic lymphocytic leukemia (NCT02557516).

In some embodiments, the immune checkpoint inhibitor is selected from nivolumab, pembrolizumab, ipilimumab, avelumab, durvalumab, atezolizumab, or pidilizumab.

EXEMPLIFICATION

Abbreviations

Ac: acetyl
AcOH: acetic acid
ACN: acetonitrile
Ad: adamantly
AIBN: 2,2'-azo bisisobutyronitrile
Anhyd: anhydrous
Aq: aqueous
$B_2Pin_2$: bis (pinacolato)diboron-4,4,4',4',5,5,5',5'-octamethyl-2,2'-bi(1,3,2-dioxaborolane)
BINAP: 2,2'-bis(diphenylphosphino)-1,1'-binaphthyl
$BH_3$: Borane
Bn: benzyl
Boc: tert-butoxycarbonyl
$Boc_2O$: di-tert-butyl dicarbonate
BPO: benzoyl peroxide
$^nBuOH$: n-butanol
CDI: carbonyldiimidazole
COD: cyclooctadiene
d: days
DABCO: 1,4-diazobicyclo[2.2.2]octane
DAST: diethylaminosulfur trifluoride
dba: dibenzylideneacetone
DBU: 1,8-diazobicyclo[5.4.0]undec-7-ene
DCE: 1,2-dichloroethane
DCM: dichloromethane
DEA: diethylamine
DHP: dihydropyran
DIBAL-H: diisobutylaluminum hydride
DIPA: diisopropylamine
DIPEA or DIEA: N,N-diisopropylethylamine
DMA: N,N-dimethylacetamide
DME: 1,2-dimethoxyethane
DMAP: 4-dimethylaminopyridine
DMF: N,N-dimethylformamide
DMP: Dess-Martin periodinane
DMSO-dimethyl sulfoxide
DPPA: diphenylphosphoryl azide
dppf: 1,1'-bis(diphenylphosphino)ferrocene
EDC or EDCI: 1-(3-dimethylaminopropyl)-3-ethylcarbodiimide hydrochloride
ee: enantiomeric excess
ESI: electrospray ionization
EA: ethyl acetate
EtOAc: ethyl acetate
EtOH: ethanol
FA: formic acid
h or hrs: hours
HATU: N,N,N',N'-tetramethyl-O-(7-azabenzotriazol-1-yl)uronium hexafluorophosphate
HCl: hydrochloric acid
HPLC: high performance liquid chromatography
HOAc: acetic acid
IBX: 2-iodoxybenzoic acid
IPA: isopropyl alcohol
KHMDS: potassium hexamethyldisilazide
$K_2CO_3$: potassium carbonate
LAH: lithium aluminum hydride
LDA: lithium diisopropylamide
m-CPBA: meta-chloroperbenzoic acid
M: molar
MeCN: acetonitrile
MeOH: methanol
$Me_2S$: dimethyl sulfide MeONa: sodium methylate
MeI: iodomethane
min: minutes
mL: milliliters
mM: millimolar
mmol: millimoles
MPa: mega pascal
MOMCl: methyl chloromethyl ether
MsCl: methanesulfonyl chloride
MTBE: methyl tert-butyl ether
nBuLi: n-butyllithium
$NaNO_2$: sodium nitrite
NaOH: sodium hydroxide
$Na_2SO_4$: sodium sulfate
NBS: N-bromosuccinimide
NCS: N-chlorosuccinimide
NFSI: N-Fluorobenzenesulfonimide
NMO: N-mnethvmnorpholine N-oxide
NMP: N-methylpyrrolidine
NMR: Nuclear Magnetic Resonance
° C.: degrees Celsius
Pd/C: Palladium on Carbon
$Pd(OAc)_2$: Palladium Acetate
PBS: phosphate buffered saline
PE: petroleum ether
$POCl_3$: phosphorus oxychloride
$PPh_3$: triphenylphosphine
PyBOP: (Benzotriazol-1-yloxy)tripyrrolidinophosphonium hexafluorophosphate
Rel: relative
R.T. or rt: room temperature
sat: saturated
SEMCl: chloromethyl-2-trimethylsilylethyl ether
SFC: supercritical fluid chromatography
$SOCl_2$: sulfur dichloride
tBuOK: potassium tert-butoxide
TBAB: tetrabutylammonium bromide
TBAI: tetrabutylammonium iodide
TEA: triethylamine
Tf: trifluoromethanesulfonate
TfAA, TFMSA or $Tf_2O$: trifluoromethanesulfonic anhydride
TFA: trifluoracetic acid
TIPS: triisopropylsilyl
THF: tetrahydrofuran
THP: tetrahydropyran
TLC: thin layer chromatography
TMEDA: tetramethylethylenediamine
pTSA: para-toluenesulfonic acid
wt: weight
Xantphos: 4,5-bis(diphenylphosphino)-9,9-dimethylxanthene General Synthetic Methods The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

All reactions are carried out under nitrogen or argon unless otherwise stated.

Proton NMR ($^1H$ NMR) is conducted in deuterated solvent. In certain compounds disclosed herein, one or more $^1H$ shifts overlap with residual proteo solvent signals; these signals have not been reported in the experimental provided hereinafter.

TABLE 2

| Analytical instruments | |
|---|---|
| LCMS | Shimadzu UFLC MS: LCMS-2020<br>Agilent Technologies 1200 series MS: Agilent Technologies 6110<br>Agilent Technologies 1200 series MS: LC/MSD VL |
| NMR | BRUKER AVANCE III/400; Frequency (MHz) 400.13; Nucleus: 1H; Number of Transients: 8 |
| Prep-HPLC | Gilson GX-281 systems: instruments GX-A, GX-B, GX-C, GX-D, GX-E, GX-F, GX-G and GX-H |
| GCMS | SHIMADZU GCMS-QP2010 Ultra |
| Analytical cSFC | Agilent Technologies 1290 Infinity |
| Prep-cSFC | Waters SFC Prep 80 |

For acidic LCMS data: LCMS was recorded on an Agilent 1200 Series LC/MSD or Shimadzu LCMS2020 equipped with electro-spray ionization and quadruple MS detector [ES+ve to give $MH^+$] and equipped with Chromolith Flash RP-18e 25*2.0 mm, eluting with 0.0375 vol % TFA in water (solvent A) and 0.01875 vol % TFA in acetonitrile (solvent B). Other LCMS was recorded on an Agilent 1290 Infinity RRLC attached with Agilent 6120 Mass detector. The column used was BEH C18 50*2.1 mm, 1.7 micron. Column flow was 0.55 ml/min and mobile phase were used (A) 2 mM Ammonium Acetate in 0.1% Formic Acid in Water and (B) 0.1% Formic Acid in Acetonitrile.

For basic LCMS data: LCMS was recorded on an Agilent 1200 Series LC/MSD or Shimadzu LCMS 2020 equipped with electro-spray ionization and quadruple MS detector [ES+ve to give $MH^+$] and equipped with Xbridge C18, 2.1×50 mm columns packed with 5 mm C18-coated silica or Kinetex EVO C18 2.1×30 mm columns packed with 5 mm C18-coated silica, eluting with 0.05 vol % $NH_3H_2O$ in water (solvent A) and acetonitrile (solvent B).

HPLC Analytical Method: HPLC was carried out on X Bridge C18 150*4.6 mm, 5 micron. Column flow was 1.0 ml/min and mobile phase were used (A) 0.1% Ammonia in water and (B) 0.1% Ammonia in Acetonitrile.

Prep HPLC Analytical Method: The compound was purified on Shimadzu LC-20AP and UV detector. The column used was X-BRIDGE C18 (250*19) mm, 5µ. Column flow was 16.0 ml/min. Mobile phase were used (A) 0.1% Formic Acid in Water and (B) Acetonitrile Basic method used (A) 5 mM ammonium bicarbonate and 0.1% NH3 in Water and (B) Acetonitrile or (A) 0.1% Ammonium Hydroxide in Water and (B) Acetonitrile. The UV spectra were recorded at 202 nm & 254 nm.

NMR Method: The 1H NMR spectra were recorded on a Bruker Ultra Shield Advance 400 MHz/5 mm Probe (BBFO). The chemical shifts are reported in part-per-million.

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Intermediates:

[1-[(4-Methoxyphenyl) methyl]-2,6-dioxo-3-piperidyl] trifluoromethanesulfonate (Intermediate A)

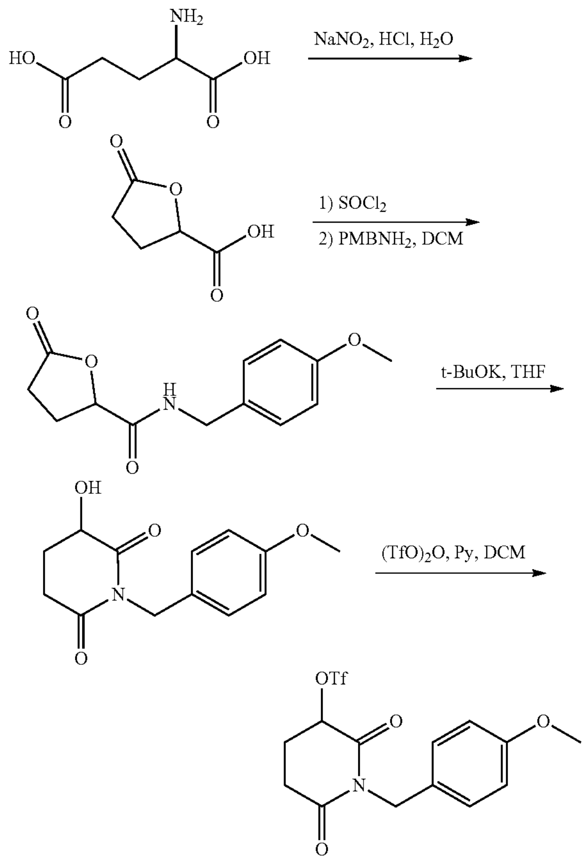

A

Step 1—5-Oxotetrahydrofuran-2-carboxylic acid

To a solution of 2-aminopentanedioic acid (210 g, 1.43 mol, CAS #617-65-2) in $H_2O$ (800 mL) and HCl (12 M, 210 mL) was added a solution of $NaNO_2$ (147 g, 2.13 mol) in $H_2O$ (400 mL) at −5° C. The mixture was stirred at 15° C. for 12 hrs. On completion, the mixture was concentrated and then dissolved in EA (500 mL) and filtered and washed with EA (3×100 mL). The filtrate and washed solution were dried over $Na_2SO_4$, filtered and concentrated in vacuo to give the title compound (200 g, crude) as yellow oil. $^1H$ NMR (400 MHz, $CDCl_3$) δ 6.43 (s, 1H), 5.02-4.95 (m, 1H), 2.67-2.38 (m, 4H)

Step 2—N-[(4-methoxyphenyl)methyl]-5-oxo-tetrahydrofuran-2-carboxamide

To 5-oxotetrahydrofuran-2-carboxylic acid (120 g, 922 mmol) was added $SOCl_2$ (246 g, 2.07 mol) at 0° C. slowly. The mixture was stirred at 85° C. for 3 hrs, and then the mixture was stirred at 15° C. for 6 hrs. The mixture was concentrated in vacuo. The residue was dissolved in dry DCM (1 L) at 0° C. under $N_2$. After that a solution of $Et_3N$ (187 g, 1.84 mol) and 4-methoxybenzylamine (101 g, 738 mmol) in DCM (400 mL) was added, then the mixture was stirred at 15° C. for 3 hrs. On completion, water (600 mL) was added and the mixture was extracted with DCM (3×300 mL). The combined organic phase was washed with 0.5 M HCl (500 mL), brine (500 mL), dried over with anhydrous sodium sulfate and filtered. The filtrate was concentrated in vacuo and the residue was purified by flash silica gel chromatography (PE:EA=1:1) to give the title compound (138 g, 60% yield) as a yellow solid. $^1H$ NMR (400 MHz, $CDCl_3$) δ 7.22-7.20 (d, J=8.0, 1H), 6.89-6.87 (d, J=8.0, 1H), 4.90-4.86 (m, 1H), 4.47-4.4.36 (m, 2H) 3.81 (s, 3H), 2.67-2.64 (m, 1H), 2.59-2.54 (m, 2H), 2.40-2.38 (m, 1H); LC-MS ($ESI^+$) m/z 272.0 $(M+Na)^+$.

Step 3—3-Hydroxy-1-[(4-methoxyphenyl)methyl]piperidine-2,6-dione

A solution of N-[(4-methoxyphenyl)methyl]-5-oxo-tetrahydrofuran-2-carboxamide (138 g, 553 mmol) in anhydrous THF (1500 mL) was cooled to −78° C. Then, t-BuOK (62.7 g, 559 mmol) in a solution of anhydrous THF (1000 mL) was added dropwise slowly at −78° C. under nitrogen atmosphere. The resulting reaction mixture was stirred at −40° C. for 1 hr. On completion, the reaction mixture was quenched with saturated $NH_4Cl$ solution (100 mL). The mixture was extracted with ethyl acetate (3×1500 mL). The combined organic layer was washed with brine (300 mL), dried over anhydrous sodium sulfate, filtered and the filtrate was concentrated in vacuo. The residue was purified by silica gel chromatography (PE:EA=1:1) to give the title compound (128 g, 92% yield) as a white solid. $^1H$ NMR (400 MHz, $CDCl_3$) δ 7.39-7.32 (m, 2H), 6.89-6.81 (m, 2H), 4.91 (s, 2H), 4.17-4.11 (m, 1H), 3.80 (s, 3H), 3.54 (s, 1H), 2.98-2.87 (m, 1H), 2.73-2.60 (m, 1H), 2.26-2.20 (m, 1H), 1.80 (dq, J=4.8, 13.1 Hz, 1H).

Step 4—[1-[(4-Methoxyphenyl) methyl]-2,6-dioxo-3-piperidyl] trifluoromethanesulfonate To a solution of 3-hydroxy-1-[(4-methoxyphenyl) methyl] piperidine-2,6-dione (43.0 g, 173 mmol) and pyridine (27.3 g, 345 mmol) in DCM (500 mL) was added trifluoromethylsulfonyl trifluoromethanesulfonate (73.0 g, 258 mmol) dropwise at 0° C. The mixture was stirred at −10° C. for 1.5 hours under $N_2$. On completion, the mixture was concentrated in vacuo. The residue was purified by column chromatography on silica gel (PE:EA=20:1/8:1) to give the title compound (45.0 g, 68% yield) as light yellow gum. $^1H$ NMR (400 MHz, $CDCl_3$) δ 7.36 (d, J=8.4 Hz, 2H), 6.85-6.82 (m, 2H), 5.32-5.28 (m, 1H), 4.91 (s, 2H), 3.79 (s, 3H), 3.02-2.97 (m, 1H), 2.79-2.74 (m, 1H), 2.41-2.35 (m, 2H).

3-(4-Bromo-3-methyl-2-oxo-2,3-dihydro-1H-benzo[d]imidazol-1-yl)piperidine-2,6-dione (Intermediate B)

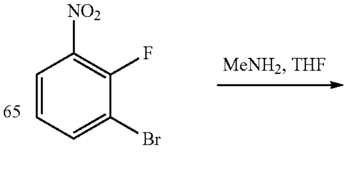

-continued

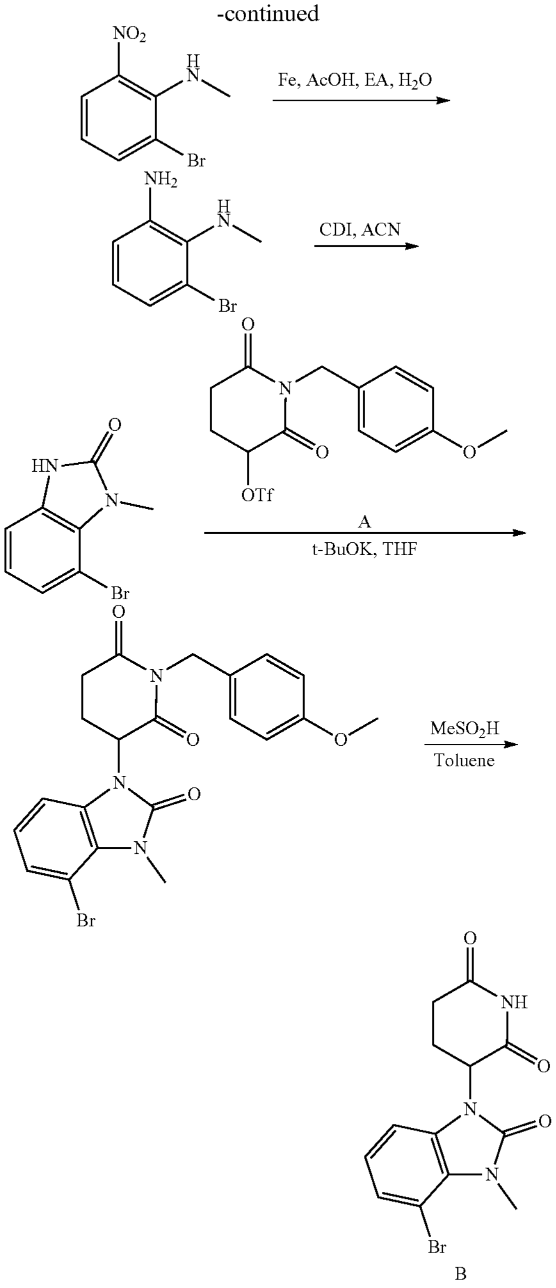

Step 1—2-Bromo-N-methyl-6-nitro-aniline

To a solution of 1-bromo-2-fluoro-3-nitro-benzene (40.0 g, 181 mmol, CAS #58534-94-4) in THF (40 mL) was added $MeNH_2$ (2 M, 400 mL). The reaction mixture was stirred at 60° C. for 12 hours. On completion, the reaction mixture was poured into sat.$NaHCO_3$ (30 mL) and extracted with EA (3×200 mL). The combined organic layers were washed with brine (2×200 mL), dried with anhydrous $Na_2SO_4$, filtered and concentrated in vacuo to give the title compound (40.0 g, 95% yield) as red oil. LC-MS ($ESI^+$) m/z 230.9 $(M+H)^+$.

Step 2—3-Bromo-N2-methyl-benzene-1,2-diamine

To a mixture of 2-bromo-N-methyl-6-nitro-aniline (23.0 g, 99.5 mmol) in EA (300 mL) and $H_2O$ (10 mL) was added AcOH (100 mL). The mixture was warmed to 50° C. Then Fe (22.2 g, 398 mmol) was added to the reaction mixture and the mixture was heated to 80° C. about 4 hours. On completion, the reaction mixture was filtered and concentrated in vacuo. The residue was diluted with water (100 mL) and extracted with EA (3×200 mL). The combined organic layers was dried over $Na_2SO_4$, filtered and concentrated in vacuo to give the title compound (20.0 g, 99% yield) as red oil. $^1H$ NMR (400 MHz, DMSO-$d_6$) δ 6.73-6.70 (m, 1H), 6.68-6.60 (m, 2H), 5.02 (s, 2H), 3.67 (s, 1H), 2.58 (s, 3H).

Step 3—4-Bromo-3-methyl-1H-benzimidazol-2-one

To a mixture of 3-bromo-N2-methyl-benzene-1,2-diamine (20.0 g, 99.4 mmol) in ACN (300 mL) was added CDI (32.2 g, 198 mmol). The reaction mixture was stirred at 85° C. for 12 hours under $N_2$ atmosphere. On completion, the reaction mixture was concentrated in vacuo. The reaction mixture was diluted with water (200 mL), where a solid precipitate was formed, which was filtered off. The solid was washed with water (1 L) and dried in vacuo to give the title compound (20.0 g, 88% yield) as white solid. $^1H$ NMR (400 MHz, DMSO-$d_6$) δ 11.17 (s, 1H), 7.14 (dd, J=1.2, 8.0 Hz, 1H), 7.00-6.95 (m, 1H), 6.93-6.87 (m, 1H), 3.55 (s, 3H).

Step 4—3-(4-Bromo-3-methyl-2-oxo-benzimidazol-1-yl)-1-[(4-methoxyphenyl)methyl]piperidine-2,6-dione To a solution of 4-bromo-3-methyl-1H-benzimidazol-2-one (12.0 g, 52.8 mmol) in THF (300 mL) was added t-BuOK (7.12 g, 63.4 mmol). The reaction mixture was stirred at 0° C. for 0.5 hr. Subsequently, [1-[(4-methoxyphenyl)methyl]-2,6-dioxo-3-piperidyl] trifluoromethanesulfonate (20.1 g, 52.8 mmol, Intermediate IQ) in a solution of THF (100 mL) was added dropwise. The resulting reaction mixture was stirred at 20° C. for 0.5 hr under $N_2$. On completion, the reaction mixture was quenched with saturated $NH_4Cl$ (100 mL), and extracted with ethyl acetate (200 mL). The combined organic layers were washed with brine (2×100 mL), dried over anhydrous sodium sulfate, filtered, the filtrate was concentrated in vacuo. The crude product was purified by reversed-phase HPLC (0.1% FA condition) to give the title compound (13.3 g, 55% yield) as a yellow solid. $^1H$ NMR (400 MHz, $CDCl_3$) δ 7.38 (d, J=8.8 Hz, 2H), 7.22 (d, J=8.0 Hz, 1H), 6.84 (d, J=8.8 Hz, 2H), 6.80 (t, J=8.0 Hz, 1H), 6.48-6.40 (d, J=8.0 Hz, 1H), 5.22 (dd, J=5.2, 12.8 Hz, 1H), 5.04-4.93 (m, 2H), 3.81 (s, 3H), 3.80 (s, 3H), 3.12-2.98 (m, 1H), 2.93-2.77 (m, 1H), 2.62 (dq, J=4.4, 13.2 Hz, 1H), 2.20-2.17 (m, 1H).

Step 5—3-(4-bromo-3-methyl-2-oxo-2,3-dihydro-1H-benzo[d]imidazol-1-yl)piperidine-2,6-dione A mixture of 3-(4-bromo-3-methyl-2-oxo-benzimidazol-1-yl)-1-[(4-methoxyphenyl)methyl]piperidine-2,6-dione (13.3 g, 29.0 mmol) in a mixed solvent of Tol. (80 mL) and methane sulfonic acid (40 mL) was degassed and purged with $N_2$ for 3 times, and then the mixture was stirred at 120° C. for 2 hrs under $N_2$ atmosphere. On completion, the reaction mixture was concentrated in vacuo to remove toluene. The residue was added 200 mL of ice water, and then white solid precipitate formed. The mixture was filtered and the filtered cake was collected and dried over in vacuo to give the title compound (7.30 g, 74% yield) as white solid. $^1H$ NMR (400 MHz, DMSO-$d_6$) δ 11.13 (s, 1H), 7.25 (d, J=8.0 Hz, 1H), 7.17 (d, J=8.0 Hz, 1H), 7.05-6.93 (m, 1H), 5.41 (dd, J=5.2, 12.8 Hz, 1H), 3.64 (s, 3H), 2.96-2.83 (m, 1H), 2.78-2.59 (m, 2H), 2.08-2.00 (m, 1H).

3-(4-bromo-1-oxoisoindolin-2-yl)piperidine-2,6-dione (Intermediate C)

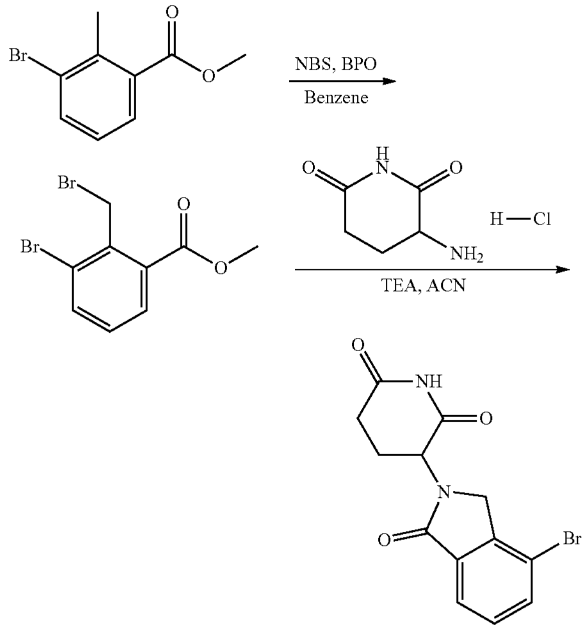

C

Step 1—3-bromo-2-(bromomethyl) benzoate

To a solution of methyl 3-bromo-2-methylbenzoate (10.0 g, 43.64 mmol, CAS #: 99548-54-6) in benzene (60 ml) were added N-bromosuccinimide (6.1 g, 52.37 mmol) and benzoyl peroxide (1.05 g, 4.36 mmol) at rt. The reaction mixture was stirred at 80° C. for 12 h. The resulting reaction mixture was poured into EtOAc (260 mL) and the organic layer was washed with water (200 ml), separated, dried over anhydrous $Na_2SO_4$ and concentrated under reduced pressure to give the residue. The crude was purified by flash chromatography (eluting at 0-2% ethyl acetate in hexane) to afford 3-bromo-2-(bromomethyl) benzoate (12.0 g, 39.33 mmol). $^1$H NMR (400 MHz, DMSO-d6) δ 7.92 (dd, J=8.0, 1.3 Hz, 1H), 7.85 (dd, J=7.8, 1.3 Hz, 1H), 7.41 (t, J=7.9 Hz, 1H), 5.02 (s, 2H), 3.87 (s, 3H).

Step 2—3-(4-bromo-1-oxoisoindolin-2-yl)piperidine-2,6-dione

To a solution of 3-bromo-2-(bromomethyl) benzoate (12.0 g, 39.33 mmol) in ACN (100 ml) were added 3-aminopiperidine-2,6-dione hydrochloride (7.76 g, 47.20 mmol, CAS #: 24666-56-6), TEA (11.95 g, 117.9 mmol) at rt. The reaction mixture was heated 80° C. for 12 h then cooled to rt. EtOAc (250 ml) was added and the organic layer was washed with water (500 ml), separated, dried over anhydrous $Na_2SO_4$ and concentrated under vacuum. The obtained crude material was purified by flash chromatography (eluting at 4-6% Methanol in DCM) to give 3-(4-bromo-1-oxoisoindolin-2-yl)piperidine-2,6-dione (5.60 g, 17.33 mmol). LCMS m/z: (ES+) 323.0 $(M+1)^+$. $^1$H NMR (400 MHz, DMSO-d6) δ 11.04 (s, 1H), 7.88 (dd, J=7.9, 0.9 Hz, 1H), 7.78 (dd, J=7.5, 0.9 Hz, 1H), 7.52 (t, J=7.7 Hz, 1H), 5.16 (dd, J=13.3, 5.1 Hz, 1H), 4.43 (d, J=17.6 Hz, 1H), 4.27 (d, J=17.7 Hz, 1H), 2.92 (ddd, J=17.2, 13.7, 5.4 Hz, 1H), 2.61 (dd, J=17.5, 4.3 Hz, 1H), 2.02 (dtd, J=12.8, 5.4, 2.3 Hz, 1H).

5-Bromo-3-methyl-1H-benzimidazol-2-one (Intermediate D)

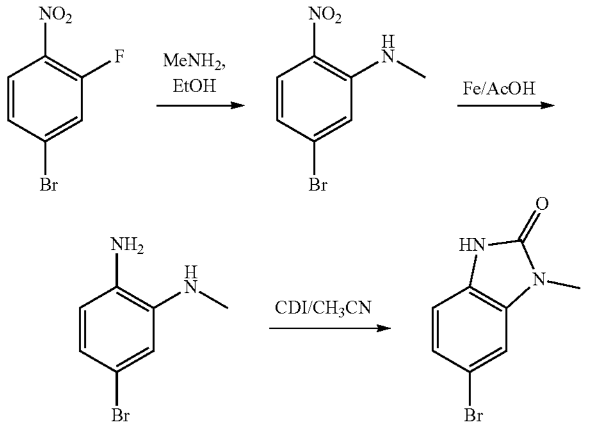

D

Step 1—5-Bromo-N-methyl-2-nitro-aniline 4-bromo-2-fluoro-1-nitro-benzene (230 g, 1.05 mol, CAS #321-23-3) was added to a solution of methylamine in tetrahydrofuran (2 M, 1.51 L). The mixture was stirred at 15° C. for 10 minutes. On completion, the mixture was diluted with $H_2O$ (250 mL) and extracted with EtOAc (3×300 mL). The combined organic layers were washed with brine (300 mL), dried over $Na_2SO_4$, filtered and concentrated in vacuo to give the title compound (200 g, 83% yield) as a yellow solid. $^1$H NMR (400 MHz, DMSO-$d_6$) δ 8.22 (s, 1H), 7.98 (d, J=9.2 Hz, 1H), 7.16 (d, J=1.6 Hz, 1H), 6.82 (dd, J=8.4, 1.6 Hz, 1H), 2.95 (d, J=4.8 Hz, 3H).

Step 2—4-Bromo-N2-methyl-benzene-1,2-diamine

To a mixture of 5-bromo-N-methyl-2-nitro-aniline (200 g, 865 mmol) in EtOAc (1 L) and $H_2O$ (500 mL) was added AcOH (1.00 L). The mixture was warmed to 50° C., and then Fe (174 g, 3.11 mol) was added to the reaction mixture. After that, the reaction mixture was stirred at 80° C. for 6 hours. On completion, the mixture was filtered through celite. The filtrate was concentrated in vacuo and the residue was diluted with $H_2O$ (250 mL) and extracted with EtOAc (3×300 mL). The combined organic layers were washed with aq.$NaHCO_3$ and brine (300 mL), dried over $Na_2SO_4$, filtered and concentrated in vacuo. The residue was purified by flash silica gel chromatography to give the title compound (130 g, 75% yield) as black oil. $^1$H NMR (400 MHz, DMSO-$d_6$) δ 6.55-6.52 (m, 1H), 6.48-6.45 (m, 1H), 6.43-6.42 (m, 1H), 4.89-4.88 (m, 1H), 4.61 (s, 2H), 2.70 (d, J=4.0 Hz, 3H).

Step 3—5-Bromo-3-methyl-1H-benzimidazol-2-one

To a solution of 4-bromo-N2-methyl-benzene-1,2-diamine (110 g, 547 mmol) in $CH_3CN$ (1.3 L) was added CDI (177 g, 1.09 mol). The mixture was stirred at 80° C. for 6 hours under $N_2$. On completion, the mixture was concentrated in vacuo. The mixture was diluted with $H_2O$ (1.0 L) and filtered. The filter cake was washed with water (3×200 mL) and dried in vacuo to give the title compound (106 g, 85% yield) as a white solid. $^1H$ NMR (400 MHz, DMSO-$d_6$) δ 11.00 (s, 1H), 7.33 (s, 1H), 7.13 (d, J=8.0 Hz, 1H), 6.92 (d, J=8.0 Hz, 1H), 3.27 (s, 3H).

3-(5-bromo-3-methyl-2-oxo-benzimidazol-1-yl)piperidine-2,6-dione (3-(5-bromo-3-methyl-2-oxo-2,3-dihydro-1H-1,3-benzodiazol-1-yl)piperidine-2,6-dione) (Intermediate E)

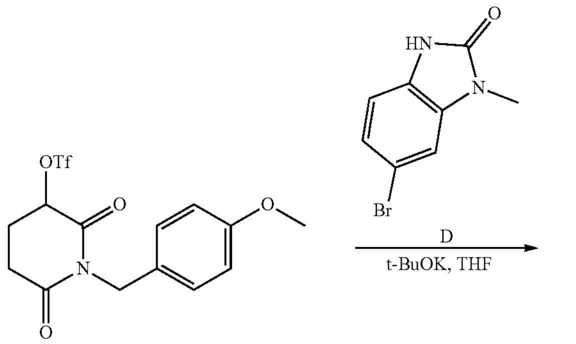

A

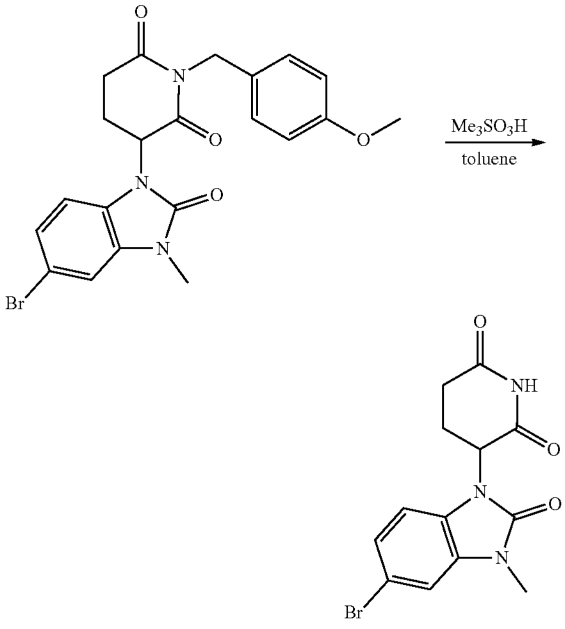

E

Step 1—3-(5-Bromo-3-methyl-2-oxo-benzimidazol-1-yl)-1-[(4-methoxyphenyl)methyl]piperidine-2,6-dione To a solution of 5-bromo-3-methyl-1H-benzimidazol-2-one (4.90 g, 21.6 mmol, Intermediate D) in THF (300 mL) was added t-BuOK (3.63 g, 32.3 mmol) at 0° C. The mixture was stirred at 0-10° C. for 1 hour under $N_2$. Then a solution of [1-[(4-methoxyphenyl) methyl]-2,6-dioxo-3-piperidyl] trifluoromethanesulfonate (9.87 g, 25.9 mmol, Intermediate A) in THF (100 mL) was added to the reaction mixture at 0-10° C. during 30 minutes. The mixture was stirred at 0-10° C. for 30 minutes under $N_2$. An additional solution of [1-[(4-methoxyphenyl) methyl]-2,6-dioxo-3-piperidyl] trifluoromethanesulfonate (2.47 g, 6.47 mmol) in THF (20 mL) was added to the reaction mixture at 0-10° C. dropwise. The mixture was then stirred at 0-10° C. for another 30 minutes under $N_2$. On completion, the reaction was quenched water (400 mL) and extracted with EA (3×200 mL). The combined organic layer was concentrated in vacuo. The residue was triturated with EA (80 mL) and filtered. The filter cake was collected and dried in vacuo to give the title compound (6.70 g, 67% yield) as light yellow solid. The filtrate was also concentrated in vacuo and the residue was purified by column chromatography to give another batch title compound (1.80 g, 18% yield) as light yellow solid. $^1H$ NMR (400 MHz, DMSO-$d_6$) δ 7.47 (d, J=1.6 Hz, 1H), 7.21-7.16 (m, 3H), 7.01 (d, J=8.0 Hz, 1H), 6.85 (d, J=8.8 Hz, 2H), 5.55-5.51 (m, 1H), 4.84-4.73 (m, 2H), 3.72 (s, 3H), 3.33 (s, 3H), 3.04-3.00 (m, 1H), 2.83-2.67 (m, 2H), 2.07-2.05 (m, 1H).

Step 2—3-(5-Bromo-3-methyl-2-oxo-benzimidazol-1-yl)piperidine-2,6-dione

To a mixture of 3-(5-bromo-3-methyl-2-oxo-benzimidazol-1-yl)-1-[(4-methoxyphenyl)methyl] piperidine-2,6-dione (8.50 g, 18.6 mmol) in toluene (50 mL) was added methanesulfonic acid (33.8 g, 351 mmol, 25 mL) at room temperature (15° C.). The mixture was stirred at 120° C. for 2 hours. On completion, the reaction mixture was cooled to room temperature and concentrated in vacuo. The residue was poured into ice/water (200 mL), and extracted with EA (3×100 mL). The combined organic layer was washed with brine (50 mL), dried over $Na_2SO_4$, filtered and concentrated in vacuo. The residue was triturated with EA (80 mL) and filtered. The filtrate cake was collected and dried in vacuo to give the title compound (4.20 g, 67% yield) as off-white solid. $^1H$ NMR (400 MHz, DMSO-$d_6$) δ 11.12 (s, 1H), 7.47 (d, J=2.0 Hz, 1H), 7.22 (d, J=8.4 Hz, 1H), 7.10 (d, J=8.4 Hz, 1H), 5.40-5.35 (m, 1H), 2.34 (s, 3H), 2.92-2.88 (m, 1H), 2.71-2.60 (m, 2H), 2.03-1.99 (m, 1H).

3-[4-(5-Aminopentyl)-3-methyl-2-oxo-1,3-benzodiazol-1-yl]piperidine-2,6-dione (Intermediate H)

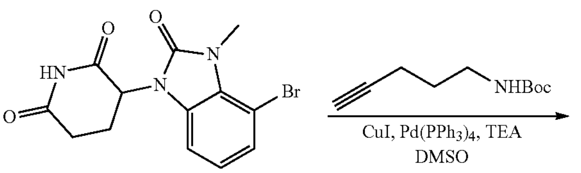

B

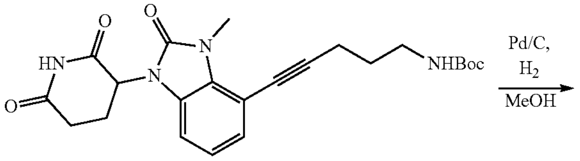

F

-continued

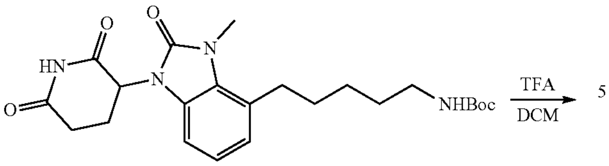

G

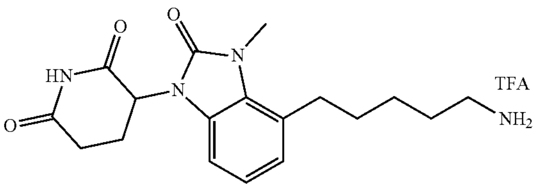

H

Step 1—Tert-butyl N-[5-[1-(2,6-dioxopiperidin-3-yl)-3-methyl-2-oxo-1,3-benzodiazol-4-yl]pent-4-yn-1-yl]carbamate (Intermediate F)

To a stirred mixture of 3-(4-bromo-3-methyl-2-oxo-1,3-benzodiazol-1-yl)piperidine-2,6-dione (10 g, 29.57 mmol, Intermediate B) and tert-butyl N-(pent-4-yn-1-yl)carbamate (8.13 g, 44.3 mmol, CAS #151978-50-6) in DMSO (100 mL) were added TEA (50 mL), CuI (0.56 g, 2.96 mmol) and $Pd(PPh_3)_4$ (3.42 g, 2.957 mmol) at room temperature. The resulting mixture was stirred for 2 h at 80 MC under nitrogen atmosphere. After cooling down to rt, the reaction mixture was diluted with water (200 mL) and extracted with EtOAc (4×200 mL). The combined organic layers were washed with brine (2×200 mL), dried over anhydrous $Na_2SO_4$ and filtered. The filtrate was concentrated under reduced pressure. The residue was purified by silica gel column chromatography (Mobile Phase: EtOAc) to afford the title compound (11 g, 84%) as a brown solid. $^1H$ NMR (400 MHz, $CD_3OD$) δ 7.15 (dd, J=7.5, 1.5 Hz, 1H), 7.10-7.01 (m, 2H), 5.34 (dd, J=12.2, 5.4 Hz, 1H), 3.78 (s, 3H), 3.23 (t, J=6.9 Hz, 2H), 3.01-2.75 (m, 3H), 2.54 (t, J=7.1 Hz, 2H), 2.19 (dp, J=10.3, 5.8, 5.2 Hz, 1H), 1.82 (p, J=7.0 Hz, 2H), 1.45 (s, 9H); LC/MS (ESI, m/z): $[(M+18)]^+$=458.2.

The intermediates in Table 3 were prepared according to Step 1 of the procedure to prepare Intermediate H.

TABLE 3

Characterization data for intermediates prepared according Step 1 using the corresponding bromides and alkynes for the coupling.

| Inter-mediate | Structure | Chemical name | Bro-mide | Alkyne | MS: $[(M+1)]^+$ | $^1H$-NMR (400 MHz) |
|---|---|---|---|---|---|---|
| 1 | 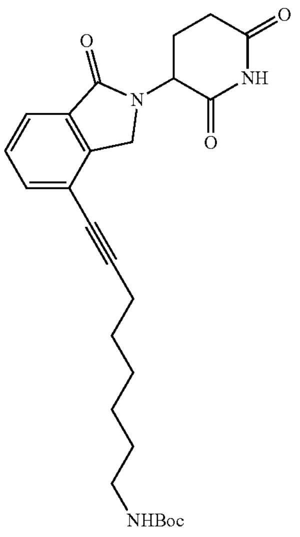 [SMILES: CC(C)(C)OC(=O)NCCCCCCC#Cc1cccc2c1CN(C1CCC(=O)NC1=O)C2=O] | tert-butyl N-[8-[2-(2,6-dioxopiperidin-3-yl)-1-oxo-3H-isoindol-4-yl]oct-7-yn-1-yl]carbamate | C | tert-butyl oct-7-yn-1-ylcarbamate (CAS# 1451262-84-2) | 468.2 | |

TABLE 3-continued

Characterization data for intermediates prepared according Step 1 using the corresponding bromides and alkynes for the coupling.

| Intermediate | Structure | Chemical name | Bromide | Alkyne | MS: [(M + 1)]$^+$ | $^1$H-NMR (400 MHz) |
|---|---|---|---|---|---|---|
| J | 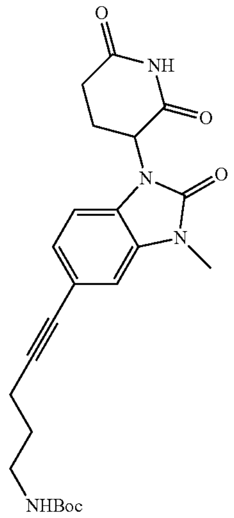 [SMILES: Cn1c(=O)n(C2CCC(=O)NC2=O)c2ccc(C#CCCCNC(=O)OC(C)(C)C)cc21] | tert-butyl N-[5-[1-(2,6-dioxopiperidin-3-yl)-3-methyl-2-oxo-1,3-benzodiazol-5-yl]pent-4-yn-1-yl]carbamate | E | tert-butyl N-(pent-4-yn-1-yl)carbamate (CAS# 151978-50-6) | $[M - 1]^- =$ 439.2 | (DMSO-$d_6$) δ 11.10 (s, 1H), 7.25 (s, 1H), 7.10 (d, J = 1.1 Hz, 2H), 6.88 (s, 1H), 5.38 (dd, J = 12.7, 5.3 Hz, 1H), 3.34 (s, 3H), 3.06 (q, J = 6.6 Hz, 2H), 3.00-2.84 (m, 1H), 2.79-2.58 (m, 2H), 2.41 (t, J = 7.1 Hz, 2H), 2.07-1.99 (m, 1H), 1.66 (p, J = 7.1 Hz, 2H), 1.39 (s, 9H) |
| K | 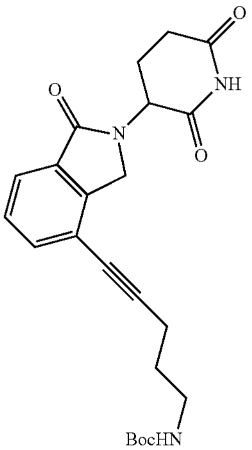 [SMILES: CC(C)(C)OC(=O)NCCCC#Cc1cccc2c1CN(C1CCC(=O)NC1=O)C2=O] | tert-butyl N-[5-[2-(2,6-dioxopiperidin-3-yl)-1-oxo-3H-isoindol-4-yl]pent-4-yn-1-yl]carbamate | C | tert-butyl N-(pent-4-yn-1-yl)carbamate (CAS# 151978-50-6) | 426.2 | ($CD_3OD$) δ 7.76 (dd, J = 7.6, 1.1 Hz, 1H), 7.70-7.66 (m, 1H), 7.64-7.62 (m, 1H), 5.19 (dd, J = 13.3, 5.2 Hz, 1H), 4.67-4.43 (m, 2H), 3.28-3.22 (m, 2H), 2.95-2.91 (m, 1H), 2.83-2.76 (m, 1H), 2.58-2.52 (m, 4H), 2.25-2.12 (m, 1H), 1.87-1.73 (m, 2H), 1.44 (s, 9H). |

TABLE 3-continued

Characterization data for intermediates prepared according Step 1 using the corresponding bromides and alkynes for the coupling.

| Inter-mediate | Structure | Chemical name | Bro-mide | Alkyne | MS: [(M + 1)]$^+$ | $^1$H-NMR (400 MHz) |
|---|---|---|---|---|---|---|
| L | 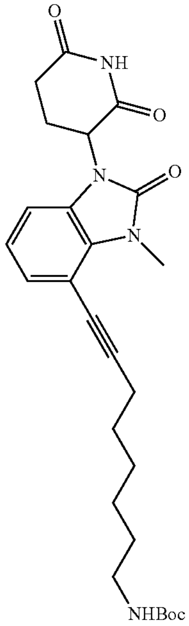 [SMILES: Cn1c(=O)n(C2CCC(=O)NC2=O)c2cccc(C#CCCCCCCNC(=O)OC(C)(C)C)c21] | tert-butyl (8-(1-(2,6-dioxopiperidin-3-yl)-3-methyl-2-oxo-2,3-dihydro-1H-benzo[d]imidazol-4-yl)oct-7-yn-1-yl)carbamate | B | tert-butyl oct-7-yn-1-ylcarbamate (CAS# 1451262-84-2) | 483.3 | ($CDCl_3$) δ 8.28 (S, 1H), 7.14-7.11 (m, 1H), 6.98-0.94 (m, 1H), 6.72 (dd, J = 8.0, 1.0 Hz, 1H), 5.22 (dd, J = 12.5, 5.3 Hz, 1H), 4.56 (br, 1H), 3.78 (s, 3H), 3.14 (q, J = 6.9 Hz, 2H), 2.93-2.90 (m, 1H), 2.92-2.75 (m, 1H), 2.73-2.70 (m, 1H), 2.46 (td, J = 7.1, 2.2 Hz, 2H), 2.27-2.16 (m, 1H), 1.68-1.61 (m, 2H), 1.53-1.46 (m, 13H), 1.43-1.33 (m, 2H) |
| M | 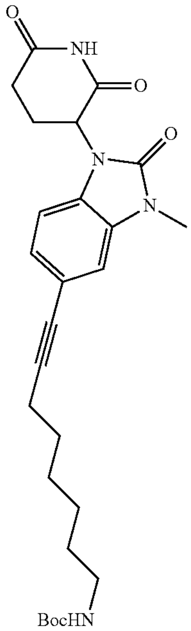 [SMILES: Cn1c(=O)n(C2CCC(=O)NC2=O)c2ccc(C#CCCCCCCNC(=O)OC(C)(C)C)cc21] | tert-butyl (8-(1-(2,6-dioxopiperidin-3-yl)-3-methyl-2-oxo-2,3-dihydro-1H-benzo[d]imidazol-5-yl)oct-7-yn-1-yl)carbamate | E | tert-butyl oct-7-yn-1-ylcarba-mate (CAS# 1451262-84-2) | M + 1 − 56]$^+$ = 427.15 | (DMSO-$d_6$) δ 11.10 (s, 1H), 7.24 (d, J = 1.1 Hz, 1H), 7.10-7.08 (m, 2H), 6.76 (s, 1H), 5.37 (dd, J = 12.8, 5.4 Hz, 1H), 3.34 (s, 3H), 2.97-2.80 (m, 3H), 3.79-2.57 (m, 2H), 2.41 (t, J = 7.0 Hz, 2H), 2.06-1.99 (m, 1H), 1.57-1.50 (m, 2H), 1.45-1.37 (m, 13H), 1.32-1.27 (m, 2H) |

Step 2—Tert-butyl N-[5-[1-(2,6-dioxopiperidin-3-yl)-3-methyl-2-oxo-1,3-benzodiazol-4-yl]pentyl] carbamate (Intermediate G)

To a stirred solution of tert-butyl N-[5-[1-(2,6-dioxopiperidin-3-yl)-3-methyl-2-oxo-1,3-benzodiazol-4-yl]pent-4-yn-1-yl]carbamate (5.50 g, 12.48 mmol, Intermediate F) in MeOH (500 mL) was added Pd/C (1.99 g, 18.73 mmol) at room temperature under nitrogen atmosphere. The resulting mixture was stirred for 16 h at rt under hydrogen atmosphere (1.5 atm). The resulting mixture was then filtered and the filter cake was washed with MeOH (3×100 mL). The filtrate was concentrated under reduced pressure to afford the title compound (5 g, 90A) as a white solid. $^1$H NMR (400 MHz, DMSO-$d_6$) δ 11.12 (s, 1H), 6.96-6.93 (m, 2H), 6.89-6.75 (m, 2H), 5.37 (dd, J=12.8, 5.2 Hz, 1H), 3.55 (s, 3H), 2.90 (dq, J=16.2, 8.3, 7.2 Hz, 6H), 2.79-2.56 (m, 2H), 2.02-1.97 (m, 2H), 1.59 (t, J=7.6 Hz, 2H), 1.45-1.42 (m, 2H), 1.37 (s, 9H); LC/MS (ESI, m/z): [(M+1)]$^+$=445.3.

The intermediates in Table 4 were prepared according to Step 2 of the procedure to prepare Intermediate H.

TABLE 4

Characterization data for intermediates prepared according to Step 2 using the corresponding alkyne intermediates for the hydrogenation.

| Intermediate | Structure | Chemical Name | Alkyne | MS: [(M + 1)]$^+$ | $^1$H-NMR (400 MHz) |
|---|---|---|---|---|---|
| N | 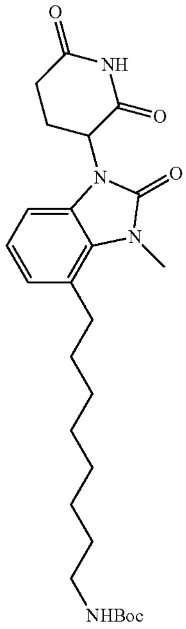 [SMILES: Cn1c(=O)n(C2CCC(=O)NC2=O)c2cccc(CCCCCCCCNC(=O)OC(C)(C)C)c21] | tert-butyl N-[8-[1-(2,6-dioxopiperidin-3-yl)-3-methyl-2-oxo-1,3-benzodiazol-4-yl]octayl]carbamate | L | 487.3 | (DMSO-$d_6$) δ 11.10 (s, 1H), 6.96 (d, J = 5.2 Hz, 2H), 6.90-6.84 (m, 1H), 6.77 (s, 1H), 5.37 (dd, J = 12.6, 5.4 Hz, 1H), 3.55 (s, 3H), 3.00-2.82 (m, 5H), 2.80-2.56 (m, 2H), 2.00 (t, J = 6.6 Hz, 1H), 1.58 (d, J = 9.5 Hz, 2H), 1.37-1.18 (m, 19H) |

TABLE 4-continued

Characterization data for intermediates prepared according to Step 2 using the corresponding alkyne intermediates for the hydrogenation.

| Intermediate | Structure | Chemical Name | Alkyne | MS: [(M + 1)]$^+$ | $^1$H-NMR (400 MHz) |
|---|---|---|---|---|---|
| O | 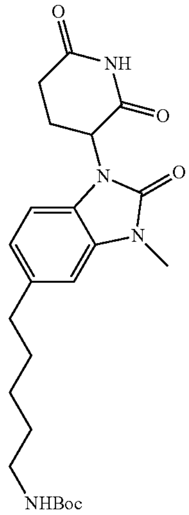 [SMILES: Cn1c(=O)n(C2CCC(=O)NC2=O)c2ccc(CCCCCNC(=O)OC(C)(C)C)cc21] | tert-butyl N-[5-[1-(2,6-dioxopiperidin-3-yl)-3-methyl-2-oxo-1,3-benzodiazol-5-yl]pentyl]carbamate | J | 445.3 | (DMSO-$d_6$) δ 11.07 (s, 1H), 7.08-6.94 (m, 2H), 6.86 (dd, J = 8.0, 1.6 Hz, 1H), 6.75 (t, J = 5.7 Hz, 1H), 5.34 (dd, J = 12.7, 5.3 Hz, 1H), 3.32 (d, J = 2.4 Hz, 4H), 2.90 (q, J = 6.8 Hz, 3H), 2.72 (td, J = 12.9, 4.4 Hz, 1H), 2.66-2.56 (m, 2H), 2.00 (ddd, J = 10.9, 5.9, 3.7 Hz, 1H), 1.60-1.56 (m, 2H), 1.39-1.35 (m, 11H), 1.30-1.26 (m, 2H). |
| P | 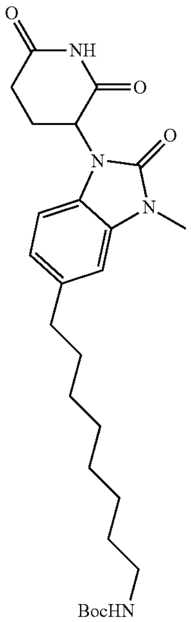 [SMILES: Cn1c(=O)n(C2CCC(=O)NC2=O)c2ccc(CCCCCCCCNC(=O)OC(C)(C)C)cc21] | tert-butyl N-[8-[1-(2,6-dioxopiperidin-3-yl)-3-methyl-2-oxo-1,3-benzodiazol-5-yl]octyl]carbamate | M | 487.3 | ($CDCl_3$) δ 6.89 (dd, J = 8.0, 1.7 Hz, 1H), 6.85 (d, J = 1.5 Hz, 1H), 6.73 (d, J = 8.0 Hz, 1H), 5.24 (dd, J = 12.6, 5.3 Hz, 1H), 3.44 (s, 3H), 3.12-3.08 (m, 2H), 3.00-2.81 (m, 2H), 2.81-2.69 (m, 1H), 2.65 (t, J = 7.7 Hz, 2H), 2.27-2.18 (m, 1H), 1.62 (h, J = 6.9 Hz, 2H), 1.46 (s, 11H), 1.32 (t, J = 4.8 Hz, 8H). |

Step 3—3-[4-(5-Aminopentyl)-3-methyl-2-oxo-1,3-benzodiazol-1-yl]piperidine-2,6-dione (Intermediate H)

To a solution of tert-butyl N-[5-[1-(2,6-dioxopiperidin-3-yl)-3-methyl-2-oxo-1,3-benzodiazol-4-yl]pentyl]carbamate (1.00 g, 2.25 mmol, Intermediate G) in DCM (10 mL) was added TFA (2 mL) at 25° C. and the solution was stirred at 25° C. for 2 h. The resulting mixture was concentrated under reduced pressure to give the crude title compound (1.00 g) as a white solid. $^1$H NMR (400 MHz, DMSO-$d_6$) δ 11.09 (s, 1H), 8.16 (s, br, 3H), 7.03-6.94 (m, 2H), 6.89 (dd, J=7.5, 1.5 Hz, 1H), 5.41 (dd, J=12.6, 5.4 Hz, 1H), 3.56 (s, 3H), 3.00-2.83 (m, 3H), 2.81-2.54 (m, 4H), 2.03-1.98 (m, 1H), 1.64-1.58 (m, 4H), 1.46-1.42 (m, 2H); LC/MS (ESI, m/z): [(M+1)]$^+$=345.3.

The intermediates in Table 5 were prepared according to Step 3 of the procedure to prepare Intermediate H.

TABLE 5

Characterization data for intermediates prepared according to Step 3 using the corresponding NHBoc-amine intermediates for the deprotection.

| Intermediate | Structure | Chemical Name | NHBoc-Amine | MS: $[(M+1)]^+$ | $^1$H-NMR (400 MHz) |
|---|---|---|---|---|---|
| Q | 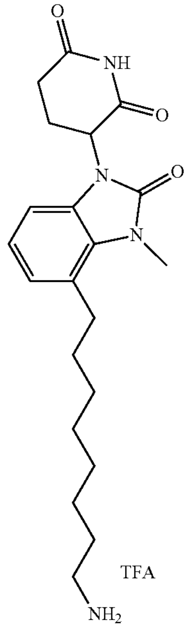 [SMILES: Cn1c(=O)n(C2CCC(=O)NC2=O)c2cccc(CCCCCCCCN)c21] | 3-[4-(8-aminooctyl)-3-methyl-2-oxo-1,3-benzodiazol-1-yl]piperidine-2,6-dione trifluoroacetate | N | 387.3 | (DMSO-$d_6$) δ 11.09 (s, 1H), 8.06 (br, 3H), 7.02-6.92 (m, 2H), 6.86 (dd, J = 7.2, 1.7 Hz, 1H), 5.40 (dd, J = 12.6, 5.4 Hz, 1H), 3.55 (s, 3H), 3.01-2.83 (m, 3H), 2.81-2.57 (m, 4H), 2.02-1.98 (m, 1H), 1.60-1.56 (m, 4H), 1.47-1.14 (m, 8H) |
| R | 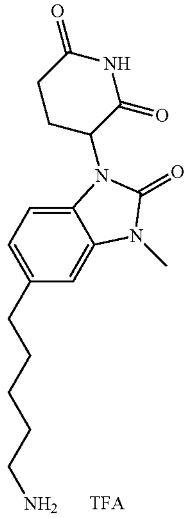 | 3-[5-(5-aminopentyl)-3-methyl-2-oxo-1,3-benzodiazol-1-yl]piperidine-2,6-dione trifluoroacetate | O | $[M-1]^-$ = 343.2 | (DMSO-$d_6$) δ 11.10 (s, 1H), 8.03 (br, 3H), 7.05 (d, J = 1.5 Hz, 1H), 7.03 (d, J = 8.0 Hz, 1H), 6.88 (dd, J = 8.1, 1.6 Hz, 1H), 5.37 (dd, J = 12.7, 5.4 Hz, 1H), 3.34 (s, 3H), 3.04-2.83 (m, 1H), 2.84-2.67 (m, 3H), 2.65-26.1 (m, 3H), 2.06-1.95 (m, 1H), 1.66-1.58 (m, 4H), 1.39-1.30 (m, 2H) |

TABLE 5-continued

Characterization data for intermediates prepared according to Step 3 using the corresponding NHBoc-amine intermediates for the deprotection.

| Inter-mediate | Structure | Chemical Name | NHBoc-Amine | MS: [(M + 1)]+ | $^1$H-NMR (400 MHz) |
|---|---|---|---|---|---|
| S | 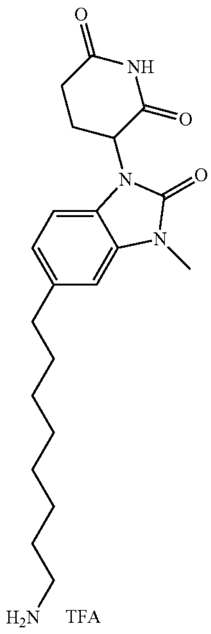 [SMILES: Cn1c(=O)n(C2CCC(=O)NC2=O)c2ccc(CCCCCCCCN)cc21] | 3-[5-(8-aminooctyl)-3-methyl-2-oxo-1,3-benzodiazol-1-yl]piperidine-2,6-dione trifluoroacetate | P | 387.3 | (DMSO-$d_6$) δ 11.08 (s, 1H), 8.05 (br, 3H), 7.05-6.99 (m, 2H), 6.86 (dd, J = 8.1, 1.6 Hz, 1H), 5.36 (dd, J = 12.7, 5.4 Hz, 1H), 3.32 (s, 3H), 3.00-2.86 (m, 1H), 2.79-2.67 (m, 3H), 2.65-2.56 (m, 3H), 2.08-1.95 (m, 1H), 1.62-1.52 (m, 4H), 1.39-1.20 (m, 8H) |
| T | 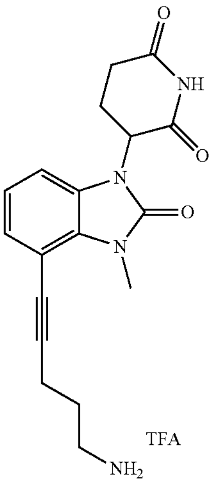 [SMILES: Cn1c(=O)n(C2CCC(=O)NC2=O)c2cccc(C#CCCCN)c21] | 3-[4-(5-aminopent-1-yn-1-yl)-3-methyl-2-oxo-1,3-benzodiazol-1-yl]piperidine-2,6-dione trifluoroacetate | F | 341.3 | ($CD_3OD$) δ 7.15 (dd, J = 7.6, 1.3 Hz, 1H), 7.13-7.09 (m, 1H), 7.05 (t, J = 7.8 Hz, 1H), 5.35 (dd, J = 12.3, 5.5 Hz, 1H), 3.77 (s, 3H), 3.21-3.08 (m, 2H), 3.00-2.88 (m, 1H), 2.87-2.73 (m, 2H), 2.68 (t, J = 7.0 Hz, 2H), 2.24-2.12 (m, 1H), 2.08-1.95 (m, 2H). |

TABLE 5-continued

Characterization data for intermediates prepared according to Step 3 using the corresponding NHBoc-amine intermediates for the deprotection.

| Inter-mediate | Structure | Chemical Name | NHBoc-Amine | MS: [(M + 1)]$^+$ | $^1$H-NMR (400 MHz) |
|---|---|---|---|---|---|
| U | 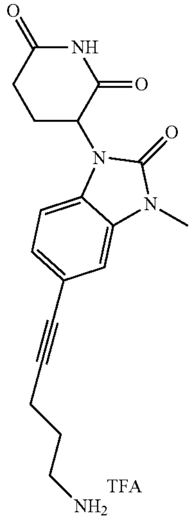 [SMILES: Cn1c(=O)n(C2CCC(=O)NC2=O)c2ccc(C#CCCCN)cc21] | 3-[5-(5-aminopent-1-yn-1-yl)-3-methyl-2-oxo-1,3-benzodiazol-1-yl]piperidine-2,6-dione trifluoroacetate | J | 341.3 | ($CD_3OD$) δ 7.21 (d, J = 1.4 Hz, 1H), 7.17 (dd, J = 8.2, 1.5 Hz, 1H), 7.07 (d, J = 8.2 Hz, 1H), 5.34 (dd, J = 12.6, 5.4 Hz, 1H), 3.41 (s, 3H), 3.14 (t, J = 7.7 Hz, 2H), 2.95-2.90 (m, 1H), 2.87-2.72 (m, 2H), 2.60 (t, J = 6.9 Hz, 2H), 2.28-2.13 (m, 1H), 2.09-1.92 (m, 2H) |
| V | 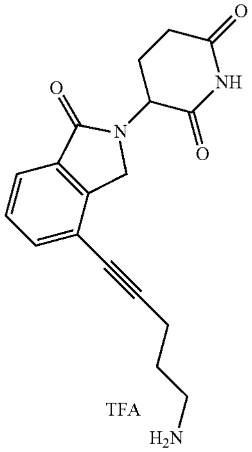 [SMILES: NCCCC#Cc1cccc2c1CN(C1CCC(=O)NC1=O)C2=O] | 3-[4-(5-aminopent-1-yn-1-yl)-1-oxo-3H-isoindol-2-yl]piperidine-2,6-dione trifluoroacetate | K | 326.1 | ($CD_3OD$) δ 7.79 (dd, J = 7.7, 1.1 Hz, 1H), 7.65 (dd, J = 7.7, 1.1 Hz, 1H), 7.54 (d, J = 7.6 Hz, 1H), 5.20 (dd, J = 13.3, 5.2 Hz, 1H), 4.62-4.46 (m, 2H), 3.14 (t, J = 7.7 Hz, 2H), 2.97-2.92 (m, 1H), 2.83-2.78 (m, 1H), 2.68 (t, J = 7.0 Hz, 2H), 2.53 (qd, J = 13.3, 4.6 Hz, 1H), 2.24-2.18 (m, 1H), 2.0.3-1.97 (m, 2H) |

TABLE 5-continued

Characterization data for intermediates prepared according to Step 3 using the corresponding NHBoc-amine intermediates for the deprotection.

| Inter-mediate | Structure | Chemical Name | NHBoc-Amine | MS: [(M + 1)]$^+$ | $^1$H-NMR (400 MHz) |
|---|---|---|---|---|---|
| W | 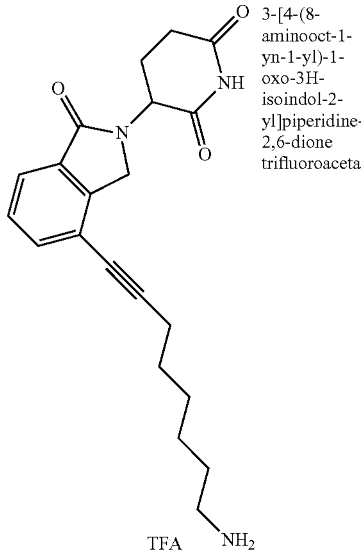 | 3-[4-(8-aminooct-1-yn-1-yl)-1-oxo-3H-isoindol-2-yl]piperidine-2,6-dione trifluoroacetate | I | 368.3 | (DMSO-$d_6$) δ 11.00 (s, 1H), 7.85 (s, 3H), 7.71 (dd, J = 7.6, 1.1 Hz, 1H), 7.63 (dd, J = 7.7, 1.1 Hz, 1H), 7.52 (t, J = 7.6 Hz, 1H), 5.15 (dd, J = 13.3, 5.1 Hz, 1H), 4.45 (d, J = 17.7 Hz, 1H), 4.32 (d, J = 17.7 Hz, 1H), 2.92 (ddd, J = 17.3, 13.6, 5.4 Hz, 1H), 2.82-2.78 (m, 2H), 2.64-2.57 (m, 1H), 2.50-2.41 (m, 2H), 2.05-2.03 (m, 1H), 1.60-1.53 (m, 4H), 1.48-1.25 (m, 4H) |

1-[2-(4-Aminobutanainido)-3,3-dimethylbutanoyl]-4-hydroxy-N-[[4-(1,3-thiazol-5-yl)phenyl]methyl] pyrrolidine-2-carboxamide (Intermediate X)

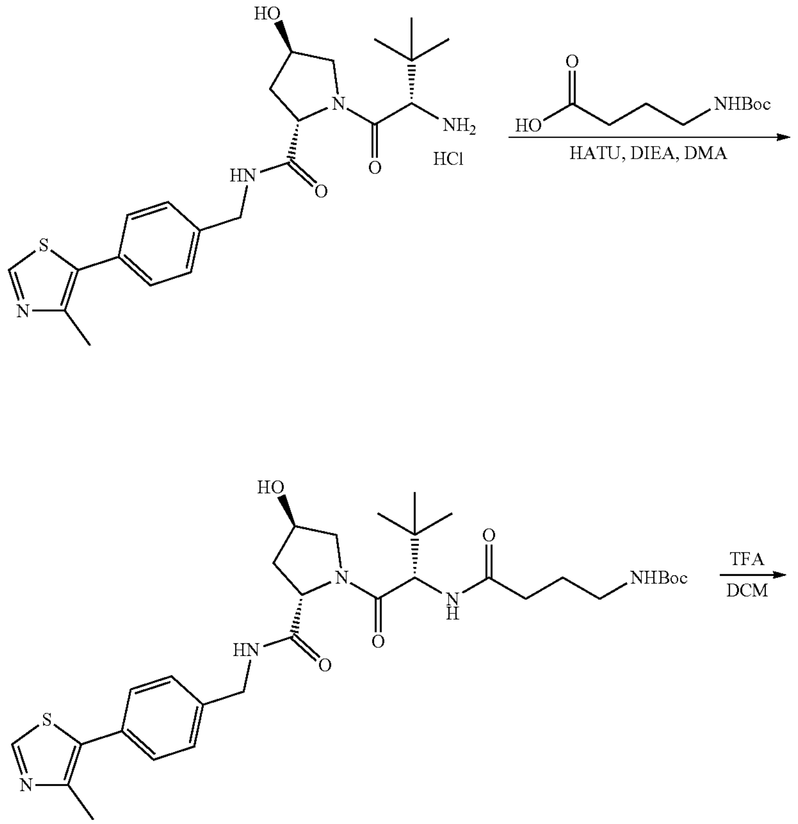

-continued

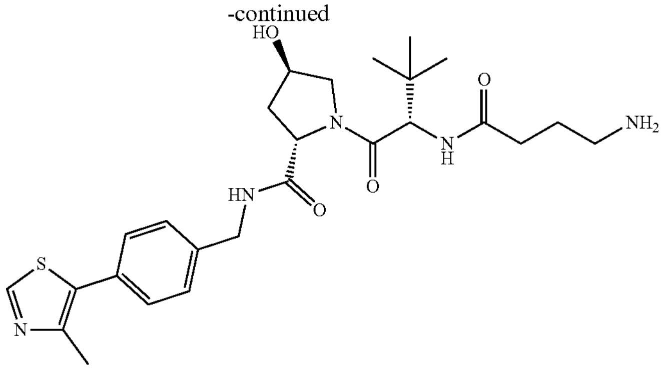

X

Step 1—Tert-butyl N-(3-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]propyl)carbamate To a stirred solution of (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide hydrochloride (5.00 g, 10.7 mmol, CAS #1448189-80-7) and 4-[(tert-butoxycarbonyl)amino]butanoic acid (2.18 g, 10.7 mmol, CAS #57294-38-9) in DMA (133 mL) was added DIEA (5.54 g, 42 mmol) at 25° C. under nitrogen atmosphere. To the above mixture was then added HATU (5.29 g, 13.9 mmol) and the resulting mixture was stirred for additional 30 min at 25° C. The resulting mixture was diluted with water (500 mL) and extracted with EtOAc (3×600 mL). The combined organic layers were washed with brine (500 mL), and dried over anhydrous $Na_2SO_4$. After filtration, the filtrate was concentrated under reduced pressure. The residue was purified by reverse phase chromatography (Column: Spherical $C^{18}$, 20~40 um, 330 g; Mobile Phase A: water (plus 10 mmol/L AcOH), Mobile Phase B: ACN; Flow rate: 80 mL/min; Gradient (B %): 30%~50%, 25 min; Detector: UV 220/254 nm; Desired fractions were collected at 48% B) and concentrated under reduced pressure to afford the title compound (3.9 g, 34%) as a yellow solid. $^{1}H$ NMR (400 MHz, DMSO-$d_6$) δ 8.98 (s, 1H), 8.56 (t, J=6.1 Hz, 1H), 7.89 (d, J=9.3 Hz, 1H), 7.40 (q, J=8.2 Hz, 4H), 6.79 (t, J=5.7 Hz, 1H), 5.12 (d, J=3.6 Hz, 1H), 4.54 (d, J=9.3 Hz, 1H), 4.47-4.42 (m, 2H), 4.40-4.33 (m, 1H), 4.22 (dd, J=15.9, 5.5 Hz, 1H), 3.77-3.57 (m, 2H), 3.00-2.81 (m, 2H), 2.45 (s, 3H), 2.28-2.22 (m, 1H), 2.17-1.98 (m, 2H), 1.93-1.89 (m, 1H), 1.72-1.50 (m, 2H), 1.37 (s, 9H), 0.94 (s, 9H); LC/MS (ESI, m/z): [(M+1)]=616.5.

Step 2. 1-[2-(4-Aminobutanamido)-3,3-dimethylbutanoyl]-4-hydroxy-N-[[4-(1,3-thiazol-5-yl)phenyl]methyl]pyrrolidine-2-carboxamide The title compound was prepared via the deprotection Step 3 of Intermediate H. $^{1}H$ NMR (400 MHz, DMSO-$d_6$) δ 8.99 (s, 1H), 8.57 (t, J=6.1 Hz, 1H), 7.98 (d, J=9.3 Hz, 1H), 7.44-7.36 (m, 4H), 4.55 (d, J=9.3 Hz, 1H), 4.47-4.39 (m, 2H), 4.38-4.34 (m, 1H), 4.23 (dd, J=15.8, 5.4 Hz, 1H), 3.73-3.59 (m, 2H), 2.72 (t, J=7.4 Hz, 2H), 2.45 (s, 3H), 2.38-2.32 (m, 1H), 2.25-2.20 (m, 1H), 2.11-1.99 (m, 1H), 1.94-1.87 (m, 1H), 1.76-1.70 (m, 2H), 0.95 (s, 9H); LC/MS (ESI, m/z): [(M+1)]=516.3.

4-Amino-N-[7-[(4-aminophenyl)formamido]heptyl]benzamide (Intermediate Y)

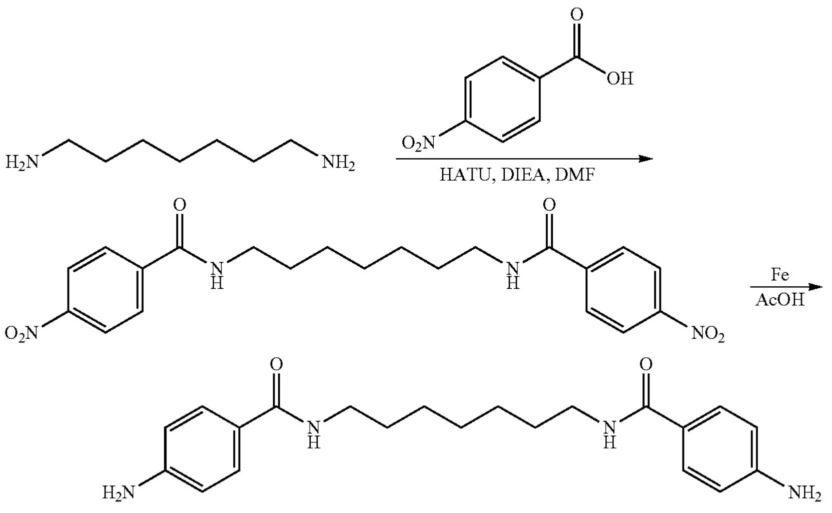

Y

Step 1—4-Nitro-N-[7-[(4-nitrophenyl)formamido]heptyl]benzamide

The title compound was prepared according to the procedure of Step 1 of Intermediate X coupling 4-nitrobenzoic acid (CAS #62-23-7) and heptane-1,7-diamine (CAS #646-19-5). $^1$H NMR (400 MHz, DMSO-$d_6$) δ 8.76 (t, J=5.6 Hz, 2H), 8.35-8.25 (m, 4H), 8.12-7.99 (m, 4H), 3.33-3.24 (m, 4H), 1.55 (p, J=6.9 Hz, 4H), 1.34 (d, J=4.0 Hz, 6H); LC/MS (ESI, m/z): [(M+1)]=429.3.

The intermediates in Table 6 were prepared according to the procedure of Step 1 of Intermediate X.

TABLE 6

Characterization data for intermediates prepared according to Step 1 of Intermediate X using the corresponding amines and 4-nitrobenzoic acid for the coupling.

| Intermediate | Structure | Chemical Name | Amine | MS: $[(M+1)]^+$ | $^1$H-NMR (400 MHz) |
|---|---|---|---|---|---|
| Z | 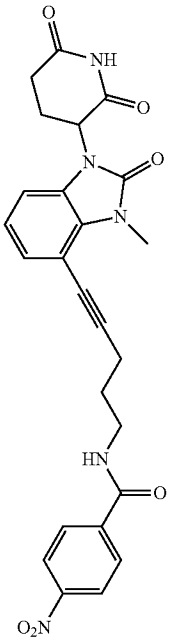 | N-[5-[1-(2,6-dioxopiperidin-3-yl)-3-methyl-2-oxo-1,3-benzodiazol-4-yl]pent-4-yn-1-yl]-4-nitrobenzamide | T | 490.2 | (DMSO-$d_6$) δ 11.10 (s, 1H), 8.86 (t, J = 5.5 Hz, 1H), 8.35-8.25 (m, 2H), 8.16-8.02 (m, 2H), 7.11 (dd, J = 7.8, 1.3 Hz, 1H), 7.05 (dd, J = 8.0, 1.3 Hz, 1H), 6.98 (t, J = 7.8 Hz, 1H), 5.38 (dd, J = 12.7, 5.3 Hz, 1H), 3.66 (s, 3H), 3.46 (q, J = 6.5 Hz, 2H), 3.01-2.82 (m, 1H), 2.78-2.64 (m, 2H), 2.59 (t, J = 7.0 Hz, 2H), 2.06-1.98 (m, 1H), 1.91-1.84 (m, 2H) |
| AA | 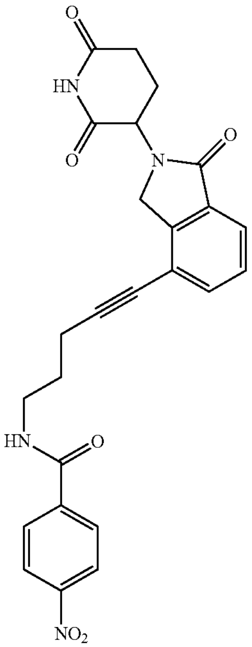 | N-[5-[2-(2,6-dioxopiperidin-3-yl)-1-oxo-3H-isoindol-4-yl]pent-4-yn-1-yl]-4-nitrobenzamide | V | 475.3 | ($CD_3OD$) δ 8.27 (d, J = 8.6 Hz, 2H), 8.01 (d, J = 8.6 Hz, 2H), 7.74 (d, J = 7.6 Hz, 1H), 7.59 (d, J = 7.6 Hz, 1H), 7.49 (t, J = 7.7 Hz, 1H), 5.20 (dd, J = 13.5, 5.2 Hz, 1H), 4.62-4.46 (m, 2H), 3.64 (t, J = 7.0 Hz, 2H), 3.04-2.88 (m, 1H), 2.82-2.75 (m, 1H), 2.66-2.62 (m, 3H), 2.21-2.17 (m, 1H), 2.01-1.95 (m, 2H) |

TABLE 6-continued

Characterization data for intermediates prepared according to Step 1 of Intermediate X using the corresponding amines and 4-nitrobenzoic acid for the coupling.

| Inter-mediate | Structure | Chemical Name | Amine | MS: [(M + 1)]+ | $^1$H-NMR (400 MHz) |
|---|---|---|---|---|---|
| AB | 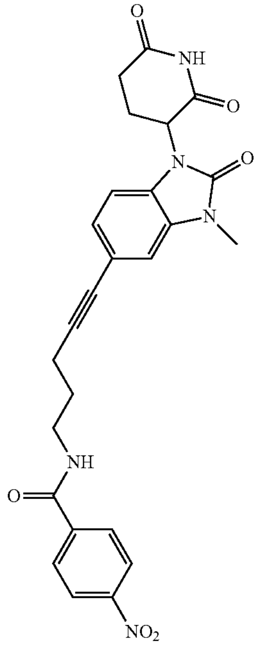 | N-[5-[1-(2,6-dioxopiperidin-3-yl)-3-methyl-2-oxo-1,3-benzodiazol-5-yl]pent-4-yn-1-yl]-4-nitrobenzamide | U | 490.2 | (DMSO-$d_6$) δ 11.04 (s, 1H), 7.66-7.61 (m, 2H), 7.42 (s, 1H), 7.16-7.07 (m, 2H), 6.86-6.67 (m, 3H), 5.24 (dd, J = 12.8, 5.4 Hz, 1H), 3.36-3.34 (m, 3H), 3.24 (s, 3H), 2.96-2.81 (m, 1H), 2.61-2.55 (m, 3H), 2.51-2.48 (m, 1H), 1.91-1.67 (m, 2H) |
| AC | 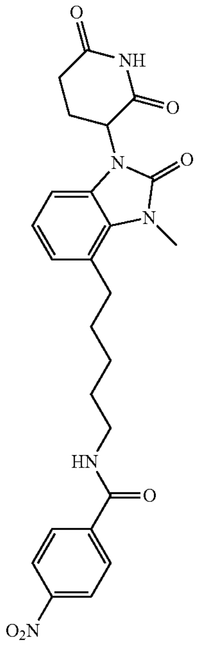 | N-[5-[1-(2,6-dioxopiperidin-3-yl)-3-methyl-2-oxo-1,3-benzodiazol-4-yl]pentyl]-4-nitorbenzamide | H | 494.2 | (DMSO-$d_6$) δ 11.08 (s, 1H), 8.78 (t, J = 5.6 Hz, 1H), 8.38-8.24 (m, 3H), 8.09-8.04 (m, 2H), 7.00-6.91 (m, 1H), 6.87 (dd, J = 6.4, 2.6 Hz, 1H), 5.36 (dd, J = 12.6, 5.3 Hz, 1H), 3.56 (s, 3H), 2.94-2.87 (m, 3H), 2.79-2.58 (m, 2H), 2.01-1.97 (m, 1H), 1.69-1.58 (m, 4H), 1.49-1.43 (m, 2H), 1.16 (t, J = 4.7 Hz, 1H), 1.06-1.04 (m, 1H) |

TABLE 6-continued

Characterization data for intermediates prepared according to Step 1 of Intermediate X using the corresponding amines and 4-nitrobenzoic acid for the coupling.

| Intermediate | Structure | Chemical Name | Amine | MS: [(M + 1)]$^+$ | $^1$H-NMR (400 MHz) |
|---|---|---|---|---|---|
| AD | 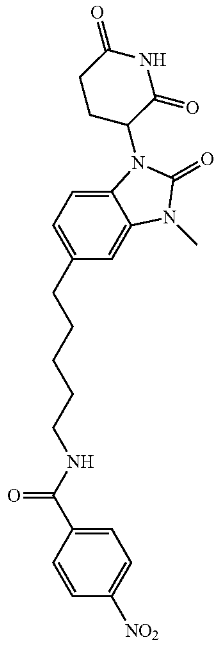 | N-[5-[1-(2,6-dioxopiperidin-3-yl)-3-methyl-2-oxo-1,3-benzodiazol-5-yl]pentyl]-4-nitrobenzamide | R | 494.2 | (DMSO-$d_6$) δ 11.08 (s, 1H), 8.77 (t, J = 5.6 Hz, 1H), 8.33-8.28 (m, 2H), 8.09-8.00 (m, 2H), 7.05-6.95 (m, 2H), 6.87 (dd, J = 8.1, 1.6 Hz, 1H), 5.33 (dd, J = 12.7, 5.3 Hz, 1H), 3.30 (s, 3H), 3.28-3.26 (m, 2H), 2.98-2.82 (m, 1H), 2.750-2.68 (m, 1H), 2.64-2.59 (m, 3H), 2.06-1.94 (m, 1H), 1.68-1.55 (m, 4H), 1.44-1.30 (m, 2H) |

Step 2—4-Amino-N-[7-[(4-aminophenyl)formamido]heptyl]benzamide

To a stirred solution of 4-nitro-N-[7-[(4-nitrophenyl)formamido]heptyl]benzamide (130 mg, 0.31 mmol) in AcOH (10 mL) was added Fe (169 mg, 3.03 mmol) in portions at room temperature under nitrogen atmosphere. The resulting mixture was stirred for 4 h at rt under nitrogen atmosphere. The resulting mixture was filtered and the filter cake was washed with THF (3×60 mL). The filtrate was concentrated under reduced pressure and the residue was purified by reverse phase flash chromatography (Column: Spherical $C^{18}$, 20-40 um, 120 g; Mobile Phase A: water (plus 10 mmol/L HOAc), Mobile Phase B: ACN; Flow rate: 45 mL/min; Gradient (B %): 22%~40%, 20 min; Detector: UV 254/220 nm desired product were collected at 31% B) to afford the title compound (100 mg, 89%) as a brown solid. $^1$H NMR (400 MHz, DMSO-$d_6$) δ 8.15 (t, J=5.4 Hz, 2H), 7.68 (d, J=7.9 Hz, 4H), 6.84 (d, J=7.9 Hz, 4H), 5.51 (s, 4H), 3.20 (q, J=6.3 Hz, 4H), 1.49 (t, J=6.8 Hz, 4H), 1.30 (d, J=4.0 Hz, 6H); LC/MS (ESI, m/z): [(M+1)]$^+$=369.3.

The intermediates in Table 7 were prepared according to Step 2 of the procedure to prepare Intermediate Y.

TABLE 7

Characterization data for intermediates prepared according to Step 2 of Intermediate Y using the corresponding nitro for the reduction.

| Inter-mediate | Structure | Chemical Name | Nitro | MS: [(M + 1)]+ | $^1$H-NMR |
|---|---|---|---|---|---|
| AE | 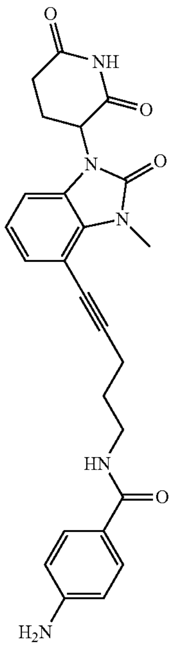 [SMILES: Cn1c(=O)n(C2CCC(=O)NC2=O)c2cccc(C#CCCCNC(=O)c3ccc([N+](=O)[O-])cc3)c21] | 4-amino-N-[5-[1-(2,6-dioxopiperidin-3-yl)-3-methyl-2-oxo-1,3-benzodiazol-4-yl]pent-4-yn-1-yl]benzamide | Z | 460.2 | $^1$H NMR (400 MHz, DMSO-$d_6$) δ 11.11 (s, 1H), 8.05 (t, J = 5.6 Hz, 1H), 7.60-7.53 (m, 2H), 7.12 (dd, J = 7.8, 1.2 Hz, 1H), 7.06 (dd, J = 7.9, 1.2 Hz, 1H), 6.99 (t, J = 7.8 Hz, 1H), 6.56-6.50 (m, 2H), 5.57 (s, 2H), 5.39 (dd, J = 12.6, 5.4 Hz, 1H), 3.66 (s, 3H), 3.38-3.30 (m, 2H), 2.99-2.81 (m, 1H), 2.78-2.59 (m, 2H), 2.56-2.51 (m, 2H), 2.08-1.98 (m, 1H), 1.85-1.78 (m, 2H) |
| AF | 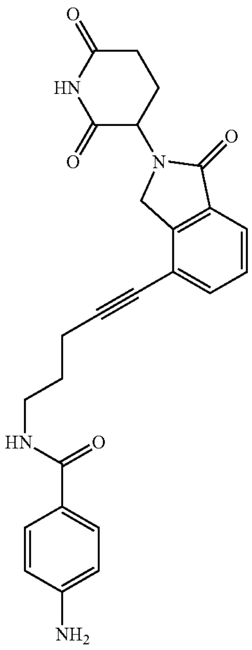 [SMILES: O=C1CCC(N2Cc3c(C#CCCCNC(=O)c4ccc([N+](=O)[O-])cc4)cccc3C2=O)C(=O)N1] | 4-amino-N-[5-[2-(2,6-dioxopiperidin-3-yl)-1-oxo-3H-isoindol-4-yl]pent-4-yn-1-yl]benzamide | AA | 445.3 | $^1$H NMR (400 MHz, $CD_3OD$) δ 7.75 (dd, J = 7.7, 1.1 Hz, 1H), 7.65-7.55 (m, 3H), 7.49 (t, J = 7.6 Hz, 1H), 6.66-6.56 (m, 2H), 5.16 (dd, J = 13.4, 5.2 Hz, 1H), 4.63-4.40 (m, 2H), 3.55 (td, J = 6.9, 1.9 Hz, 2H), 2.97-2.87 (m, 1H), 2.82-2.76 (m, 1H), 2.63-2.46 (m, 3H), 2.24-2.12 (m, 1H), 2.03-1.88 (m, 2H) |

TABLE 7-continued

Characterization data for intermediates prepared according to Step 2 of Intermediate Y using the corresponding nitro for the reduction.

| Inter-mediate | Structure | Chemical Name | Nitro | MS: [(M + 1)]$^+$ | $^1$H-NMR |
|---|---|---|---|---|---|
| AG | 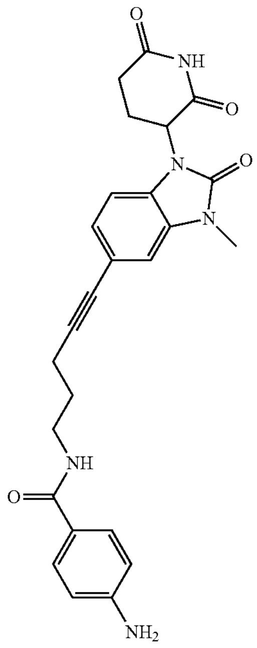 | 4-amino-N-[5-[1-(2,6-dioxopiperidin-3-yl)-3-methyl-2-oxo-1,3-benzodiazol-5-yl]pent-4-yn-1-yl]benzamide | AB | 460.2 | |
| AH | 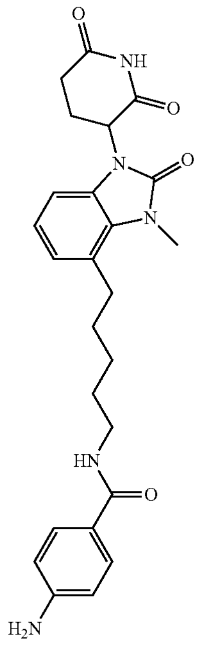 [SMILES: Cn1c(=O)n(C2CCC(=O)NC2=O)c2cccc(CCCCCNC(=O)c3ccc([N+](=O)[O-])cc3)c21] | 4-amino-N-[5-[1-(2,6-dioxopiperidin-3-yl)-3-methyl-2-oxo-1,3-benzodiazol-4-yl]pentyl]benzamide | AC | 464.2 | $^1$H NMR (400 MHz, DMSO-$d_6$) δ 11.09 (s, 1H), 7.98-7.96 (m, 1H), 7.62-7.52 (m, 2H), 6.99-6.82 (m, 3H), 6.62-6.50 (m, 2H), 5.56 (br, 2H), 5.37 (dd, J = 12.6, 5.4 Hz, 1H), 3.55 (s, 3H), 3.22 (q, J = 6.6 Hz, 2H), 2.91-2.87 (m, 2H), 2.75-2.72 (m, 2H), 2.70-2.57 (m, 1H), 2.05-1.94 (m, 1H), 1.67-1.52 (m, 4H), 1.45-1.39 (m, 2H) |

TABLE 7-continued

Characterization data for intermediates prepared according to Step 2 of Intermediate Y using the corresponding nitro for the reduction.

| Inter-mediate | Structure | Chemical Name | Nitro | MS: [(M + 1)]+ | $^1$H-NMR |
|---|---|---|---|---|---|
| AI | 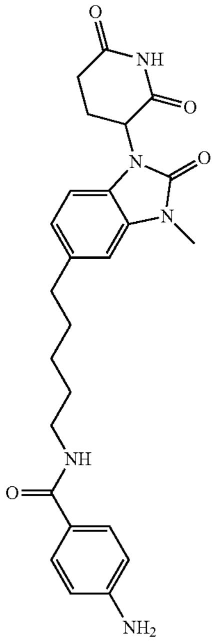 [SMILES: Cn1c(=O)n(C2CCC(=O)NC2=O)c2ccc(CCCCCNC(=O)c3ccc([N+](=O)[O-])cc3)cc21] | 4-amino-N-[5-[1-(2,6-dioxopiperidin-3-yl)-3-methyl-2-oxo-1,3-benzodiazol-5-yl]pentyl]benzamide | AD | 464.2 | $^1$H NMR (400 MHz, DMSO-$d_6$) δ 11.06 (s, 1H), 7.95 (t, J = 5.7 Hz, 1H), 7.59-7.51 (m, 2H), 7.07-6.95 (m, 2H), 6.86 (dd, J = 8.1, 1.6 Hz, 1H), 6.59-6.50 (m, 2H), 5.55 (br, 2H), 5.33 (dd, J = 12.8, 5.3 Hz, 1H), 3.45 (qt, J = 6.9, 3.5 Hz, 1H), 3.30 (s, 3H), 3.26-3.13 (m, 1H), 3.00-2.82 (m, 1H), 2.78-2.67 (m, 1H), 2.65-2.58 (m, 3H), 2.03-1.98 (m, 1H), 1.66-1.47 (m, 4H), 1.36-1.30 (m, 2H) |

(2S,4R)-1-((S)-2-(8-aminoacetamido)-3,3-dimethylbutanoyl)-4-hydroxy-N-(4-(4-methylthiazol-5-yl)benzyl)pyrrolidine-2-carboxamide (Intermediate AL)

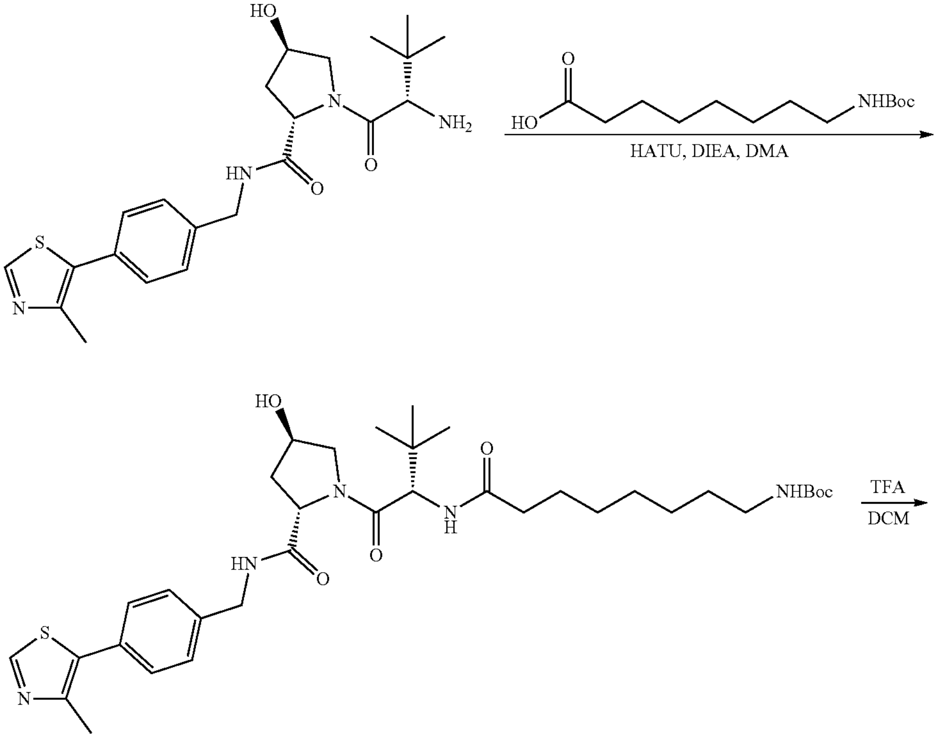

-continued

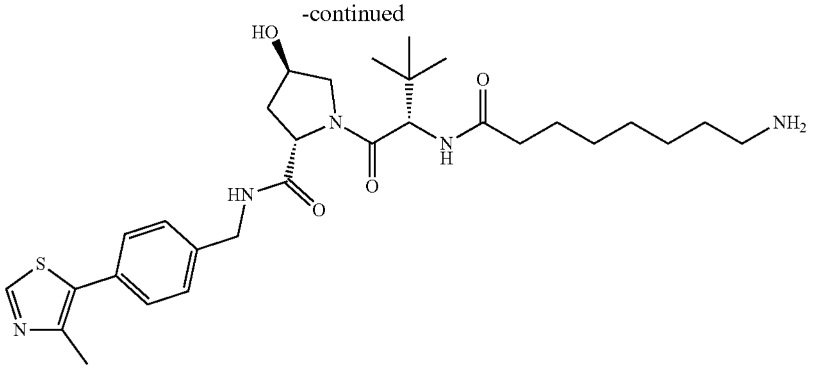

AL

Step 1—tert-butyl N-(7-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]heptyl)carbamate To a stirred solution of 8-[(tert-butoxycarbonyl)amino]octanoic acid (300 mg, 1.16 mmol, CAS #30100-16-4) and (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide (598 mg, 1.39 mmol, CAS #1448189-80-7) in DMA (2 mL) were added $Et_3N$ (351 mg, 3.47 mmol) and HATU (660 mg, 1.74 mmol) in portions at room temperature under nitrogen atmosphere. After stirring for additional 1 h at rt, the resulting mixture was purified by reverse phase flash chromatography (column, Spherical C18 Column, 20-40 um, 330 g; Mobile Phase A: Water (plus 10 mmol/L $NH_4HCO_3$), Mobile Phase B: ACN; Gradient: 35% to 45% B in 10 min; Detector: UV 254/220 nm, desired fractions were collected at 43% B) and concentrated under reduced pressure and lyophilized to afford title compound (685 mg, 88%) as a white solid. $^1H$ NMR (400 MHz, DMSO-$d_6$) δ 8.99 (s, 1H), 8.56 (t, J=6.1 Hz, 1H), 7.84 (d, J=9.3 Hz, 1H), 7.41 (q, J=8.5 Hz, 4H), 6.74 (d, J=6.1 Hz, 1H), 5.12 (d, J=3.6 Hz, 1H), 4.55 (d, J=9.4 Hz, 1H), 4.46-4.42 (m, 2H), 4.37-4.35 (m, 1H), 4.24-4.20 (m, 1H), 3.65 (t, J=8.7 Hz, 1H), 3.31 (s, 2H), 2.88 (q, J=6.7 Hz, 2H), 2.45 (s, 3H), 2.28-2.24 (m, 1H), 2.16-2.05 (m, 1H), 2.04-2.01 (m, 1H), 1.93-1.89 (m, 1H), 1.55-1.42 (m, 2H), 1.37 (s, 9H), 1.26-1.19 (m, 8H), 0.94 (s, 9H); LC/MS (ESI, m/z): $[(M+1)]^+$=672.5.

Step 2—(2S,4R)-1-[(2S)-2-(8-aminooctanamido)-3,3-dimethylbutanoyl]-4-hydroxy-N-[[4-(4-methyl-1,3-thiazol-5-yl)phenyl]methyl]pyrrolidine-2-carboxamide To a stirred solution of tert-butyl N-(7-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]heptyl)carbamate (1.70 g, 2.53 mmol) in DCM (15 mL) was added TFA (15 mL) in portions at room temperature. The resulting mixture was stirred for 2 h at rt. The resulting mixture was concentrated under reduced pressure to afford the title compound (1.4 g, 97%) as a white solid. $^1H$ NMR (400 MHz, $CD_3OD$) δ 8.96 (s, 1H), 7.52-7.41 (m, 4H), 4.66 (s, 1H), 4.64-4.49 (m, 3H), 4.43-4.29 (m, 1H), 4.02-3.79 (m, 2H), 2.93 (t, J=7.6 Hz, 2H), 2.50 (s, 3H), 2.39-2.19 (m, 3H), 2.13-2.08 (m, 1H), 1.69-1.62 (m, 4H), 1.43-1.37 (m, 6H), 1.05 (s, 9H); LC/MS (ESI, m/z): [(M+1)]=572.5.

Tert-butyl N-[3-(3-aminopropoxy)propyl]carbamate (Intermediate AQ)

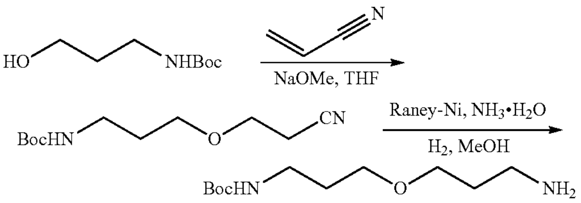

AQ

Step 1—Tert-butyl N-[3-(2-cyanoethoxy)propyl]carbamate

To a mixture of tert-butyl N-(3-hydroxypropyl)carbamate (10.0 g, 57.0 mmol, 9.80 mL, CAS #58885-58-8) and prop-2-enenitrile (6.06 g, 114 mmol, 7.57 mL, CAS #107-13-1) in THF (100 mL) was added NaOMe (308 mg, 5.71 mmol). The reaction mixture was stirred at 25° C. for 12 hours. On completion, the reaction mixture was diluted with water (100 mL) and extracted with EA (2×200 mL). The combined organic layers was dried over $Na_2SO_4$, filtered and concentrated in vacuo to give a residue. The residue was purified by column chromatography to give the title compound (9.70 g, 74% yield) as colorless oil. $^1H$ NMR (400 MHz, $CDCl_3$) δ 4.77 (s, 1H), 3.64 (t, J=6.0 Hz, 2H), 3.54 (t, J=6.0 Hz, 2H), 3.27-3.16 (m, 2H), 2.59 (t, J=6.0 Hz, 2H), 1.81-1.72 (m, 2H), 1.43 (s, 9H).

Step 2—Tert-butyl N-[3-(3-aminopropoxy)propyl]carbamate

To a mixture of tert-butyl N-[3-(2-cyanoethoxy)propyl]carbamate (9.70 g, 42.49 mmol) in MeOH (80 mL) was added $NH_3 \cdot H_2O$ (910 mg, 6.49 mmol, 1 mL, 25% solution) and Raney-Ni (3.68 g, 43.0 mmol). The reaction mixture was stirred at 25° C. for 12 hours under $H_2$ (50 Psi) atmosphere. On completion, the reaction mixture was filtered and concentrated in vacuo to give the title compound (9.00 g, 91% yield) as colorless oil. $^1H$ NMR (400 MHz, $CDCl_3$) δ 4.97 (s, 1H), 3.51-3.45 (m, 4H), 3.26-3.17 (m, 2H), 2.80 (t, J=6.8 Hz, 2H), 2.69 (t, J=6.8 Hz, 1H), 1.79-1.68 (m, 4H), 1.44 (s, 9H).

Tert-butyl N-[3-[3-[(4-aminobenzoyl)amino]propoxy]propyl]carbamate (Intermediate AR)

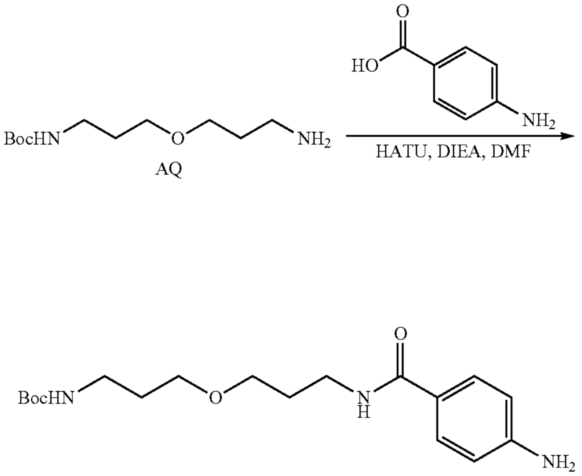

AQ

AR

To a solution of tert-butyl N-[3-(3-aminopropoxy)propyl]carbamate (300 mg, 1.29 mmol, Intermediate AQ) and 4-aminobenzoic acid (136 mg, 993 umol, CAS #150-13-0) in DMF (10 mL) was added HATU (453 mg, 1.19 mmol), and DIEA (256 mg, 1.99 mmol) at 25° C. The reaction mixture was stirred at 25° C. for 2 hrs. On completion, the reaction mixture was added 0.5 mL $H_2O$ and was concentrated in vacuo to give a residue. The residue was purified by reverse phase (0.1% TFA condition) to give the title compound (250 mg, 71% yield) as yellow solid. $^1$H NMR (400 MHz, DMSO-$d_6$) δ 7.99 (t, J=5.2 Hz, 1H), 7.57 (d, J=8.8 Hz, 2H), 6.80 (t, J=5.6 Hz, 1H), 6.58 (d, J=8.4 Hz, 2H), 3.38-3.33 (m, 6H), 3.27-3.22 (m, 2H), 2.99-2.94 (m, 2H), 1.73-1.66 (m, 2H), 1.62-156 (m, 2H), 1.37 (s, 9H); LC-MS (ESI$^+$) m/z 252.1 (M−100+H)$^+$.

2-(2,6-dioxopiperidin-3-yl)-4-fluoroisoindoline-1,3-dione (Intermediate AS)

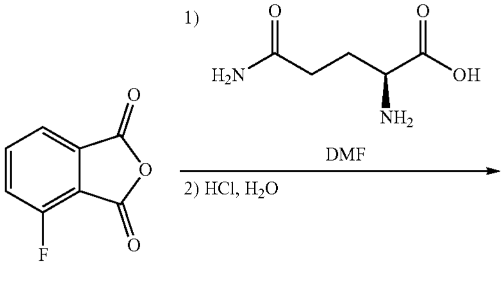

-continued

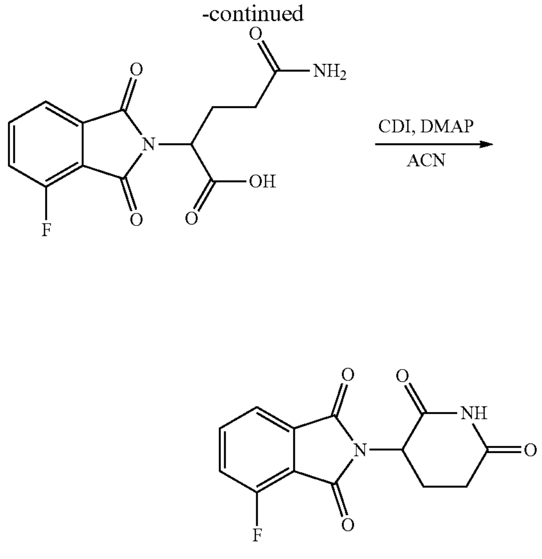

AS

Step 1—5-amino-2-(4-fluoro-1,3-dioxoisoindolin-2-yl)-5-oxopentanoic acid

To a stirred solution of 4-fluoroisobenzofuran-1,3-dione (25 g, 150 mmol, CAS #652-39-1) in DMF (100 mL) was added L-glutamine (22 g, 150 mmol) at rt. The resulting reaction mixture was heated to at 90° C. and stirred for 2 h. The reaction mixture was then evaporated under reduced pressure, transferred into 4 N aqueous HCl solution and the resulting mixture was stirred for 36 h at rt. The solid precipitate was then filtered off, washed with cold water and dried under reduced pressure to give 5-amino-2-(4-fluoro-1,3-dioxoisoindolin-2-yl)-5-oxopentanoic acid as a white solid (28 g, 63%). LC-MS (ESI$^+$) m/z 295 (M+H)$^+$.

Step 2—2-(2,6-dioxopiperidin-3-yl)-4-fluoroisoindoline-1,3-dione

To a stirred solution of 5-amino-2-(4-fluoro-1,3-dioxoisoindolin-2-yl)-5-oxopentanoic acid (28 g, 95 mmol) in acetonitrile (200 mL) was added CDI (19 g, 110 mmol) and DMAP (0.14 g, 1.1 mmol) at rt. The resulting reaction mixture then heated to 90° C. and stirred for 5 h. The reaction mixture was then evaporated under reduced pressure. The crude product was purified using silica gel column chromatography (2% MeOH-DCM) to give 2-(2,6-dioxopiperidin-3-yl)-4-fluoroisoindoline-1,3-dione as a yellow solid (12 g, 46%). $^1$H NMR (400 MHz, DMSO) δ ppm 11.16 (s, 1H), 7.98-7.93 (m, 1H), 7.80-7.76 (m, 2H), 5.19-5.14 (m, 1H), 2.94-2.85 (m, 1H), 2.63-2.54 (m, 2H), 2.09-2.04 (m, 1H).

4-[2-[2-[2-(2-Aminoethoxy)ethoxy]ethoxy]ethylamino]-2-(2,6-dioxo-3-piperidyl)isoindoline-1,3-dione (Intermediate AT)

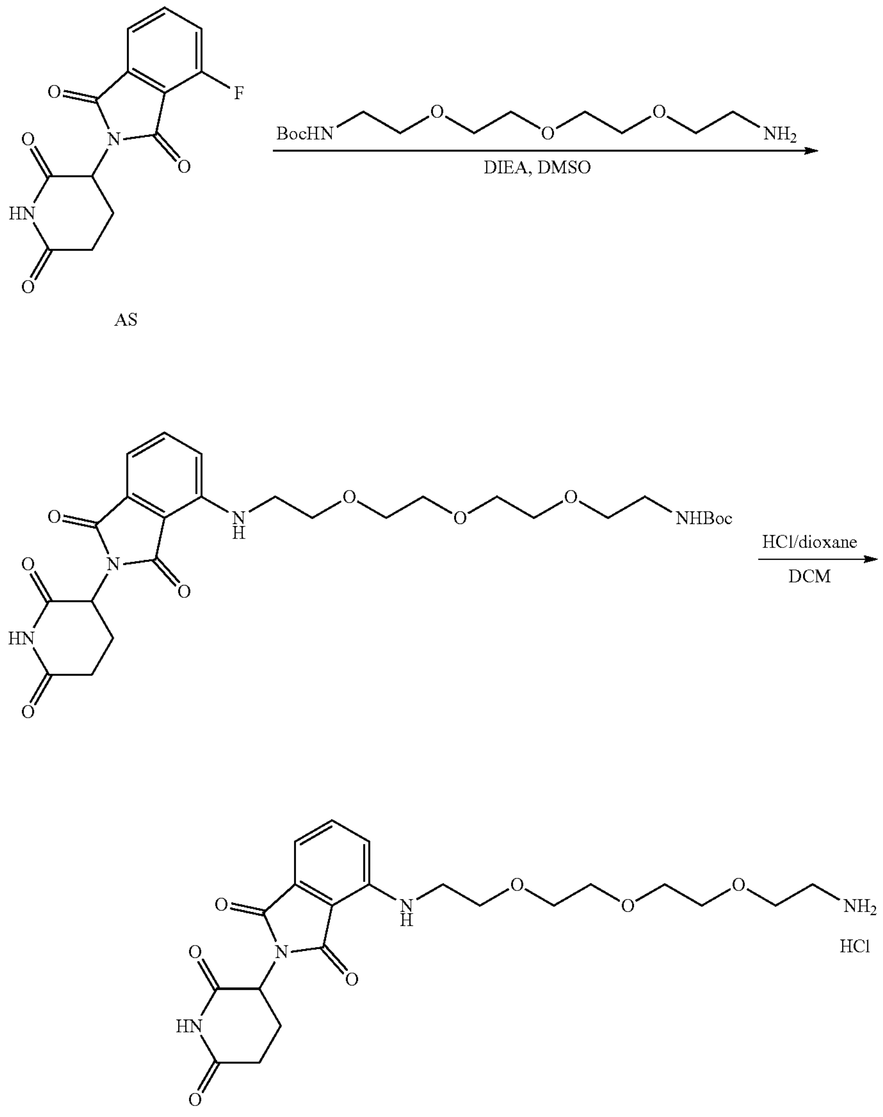

AS

AT

Step 1—Tert-butyl N-[2-[2-[2-[2-[[2-(2,6-dioxo-3-piperidyl)-1,3-dioxo-isoindolin-4-yl]amino]ethoxy]ethoxy]ethoxy]ethyl]carbamate To a solution of 2-(2,6-dioxo-3-piperidyl)-4-fluoro-isoindoline-1,3-dione (311 mg, 1.13 mmol, Intermediate AS) and tert-butyl N-[2-[2-[2-(2-aminoethoxy)ethoxy]ethoxy]ethyl]carbamate (300 mg, 1.03 mmol, CAS #101187-40-0) in DMSO (5 mL) was added DIEA (265 mg, 2.05 mmol). The reaction mixture was stirred at 130° C. for 3 hours. On completion, the reaction mixture was diluted with water (30 mL) and extracted with EA (3×50 mL). The combined organic layers were washed with brine (2×30 mL), dried over $Na_2SO_4$, filtered and the filtrate was concentrated in vacuo to give a residue. The residue was purified by reverse phase (0.1% FA) to give the title compound (400 mg, 71% yield) as yellow solid. $^1H$ NMR (400 MHz, DMSO-$d_6$) δ 11.09 (s, 1H), 7.64-7.53 (m, 1H), 7.15 (d, J=8.4 Hz, 1H), 7.04 (d, J=6.8 Hz, 1H), 6.73 (t, J=5.2 Hz, 1H), 6.60 (t, J=5.6 Hz, 1H), 5.05 (dd, J=5.6, 12.8 Hz, 1H), 3.65-3.60 (m, 2H), 3.58-3.44 (m, 10H), 3.38-3.35 (m, 2H), 3.04 (q, J=6.0 Hz, 2H), 2.95-2.82 (m, 1H), 2.63-2.52 (m, 2H), 2.05-1.97 (m, 1H), 1.36 (s, 9H).

Step 2—4-[2-[2-[2-(2-Aminoethoxy)ethoxy]ethoxy]ethylamino]-2-(2,6-dioxo-3-piperidyl)isoindoline-1,3-dione To a solution of tert-butyl N-[2-[2-[2-[2-[[2-(2,6-dioxo-3-piperidyl)-1,3-dioxo-isoindolin-4-yl]amino] ethoxy]ethoxy]ethoxy]ethyl]carbamate (400 mg, 672 umol, FA salt) in DCM (10 mL) was added HCl/dioxane (4 M, 5 mL). The reaction mixture was stirred at 20° C. for 0.5 hour. On completion, the reaction mixture was concentrated in vacuo to give the title compound (326 mg, 99% yield, HCl salt) as yellow solid. LC-MS (ESI$^+$) m/z 449.2.

4-Amino-N-[2-[2-[2-[2-[[2-(2,6-dioxo-3-piperidyl)-1,3-dioxo-isoindolin-4-yl]amino] ethoxy]ethoxy] ethoxy]ethyl]benzamide (Intermediate AU)

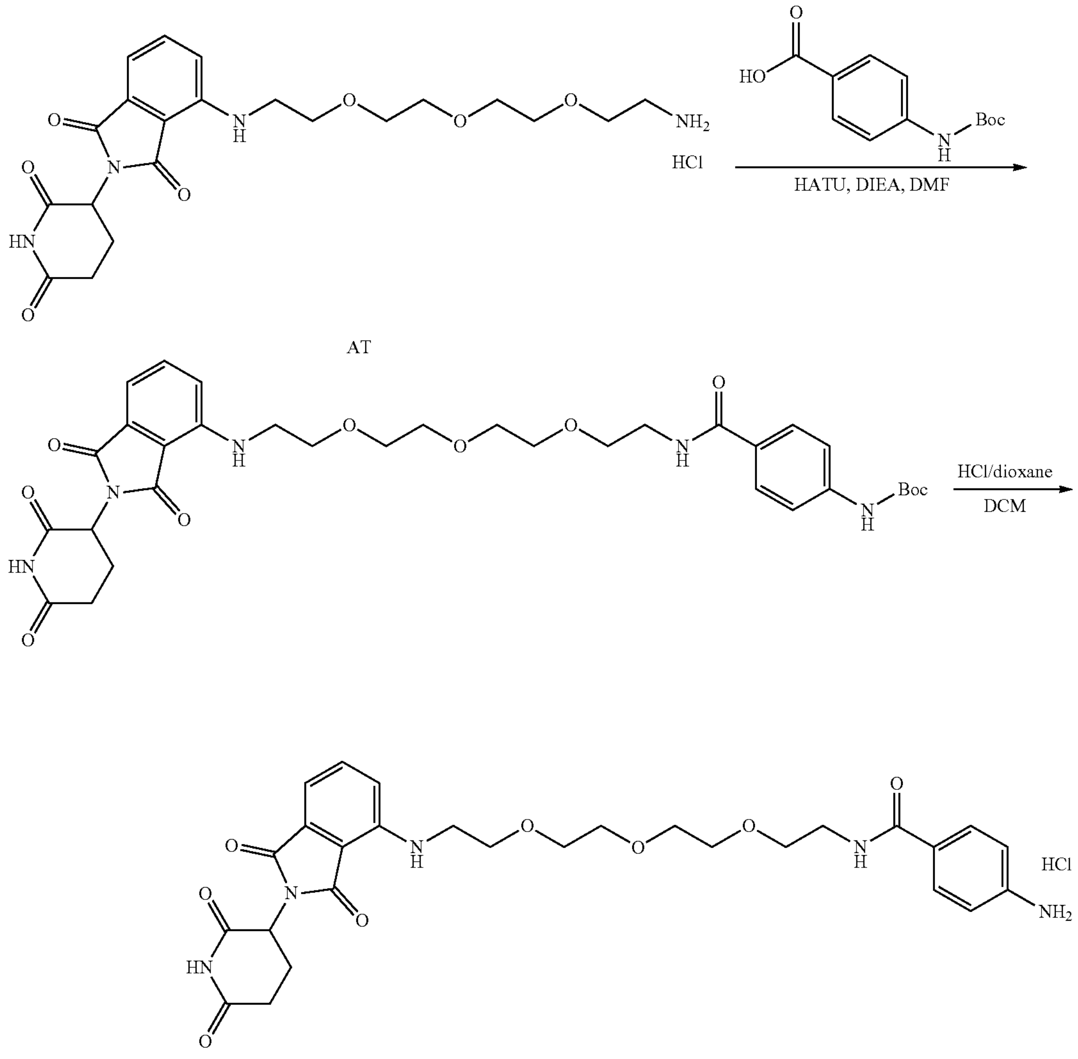

AT

AU

Step 1—Tert-butyl N-[4-[2-[2-[2-[2-[[2-(2,6-dioxo-3-piperidyl)-1,3-dioxo-isoindolin-4-yl]amino] ethoxy]ethoxy]ethoxy]ethylcarbamoyl]phenyl]carbamate To a solution of 4-(tert-butoxycarbonylamino)benzoic acid (78.2 mg, 329 umol) and HATU (163 mg, 428 umol) in DMF (2 mL) was added a solution of 4-[2-[2-[2-(2-amino-ethoxy) ethoxy] ethoxy]ethylamino]-2-(2,6-dioxo-3-piperidyl)isoindoline-1,3-dione (160 mg, 329 umol, HCl salt, Intermediate AT) and DIEA (127 mg, 989 umol) in DMF (5 mL). The reaction mixture was stirred at 20° C. for 1 hour. On completion, the reaction mixture was poured into water (25 mL) and extracted with EA (3×40 mL). The combined organic layers were washed with brine (3×20 mL), dried over $Na_2SO_4$, filtered and the filtrate was concentrated in vacuo to give a residue. The residue was purified by reverse phase (0.1% FA) to give the title compound (160 mg, 71% yield) as yellow solid. $^1H$ NMR (400 MHz, DMSO-$d_6$) δ 11.09 (s, 1H), 9.60 (s, 1H), 8.32 (t, J=5.6 Hz, 1H), 7.75 (d, J=8.8 Hz, 2H), 7.57 (dd, J=7.2, 8.4 Hz, 1H), 7.50 (d, J=8.8 Hz, 2H), 7.12 (d, J=8.8 Hz, 1H), 7.03 (d, J=7.2 Hz, 1H), 6.59 (t, J=6.0 Hz, 1H), 5.05 (dd, J=5.2, 12.8 Hz, 1H), 3.63-3.57 (m, 2H), 3.56-3.34 (m, 15H), 2.94-2.81 (m, 1H), 2.62-2.53 (m, 1H), 2.07-1.97 (m, 1H), 1.48 (s, 9H).

Step 2—4-Amino-N-[2-[2-[2-[2-[[2-(2,6-dioxo-3-piperidyl])-1,3-dioxo-isoindolin-4-yl]amino]ethoxy] ethoxy]ethoxy]ethyl]benzamide To a solution of tert-butyl N-[4-[2-[2-[2-[2-[[2-(2,6-dioxo-3-piperidyl)-1,3-dioxo-isoindolin-4-yl] amino] ethoxy] ethoxy]ethoxy]ethylcarbamoyl]phenyl]carbamate (160 mg, 239 umol) in DCM (5 mL) was added HCl/dioxane (4 M, 3 mL). The reaction mixture was stirred at 15° C. for 0.5 hour. On completion, the reaction mixture was concentrated in vacuo to give the title compound (144 mg, 91% yield, HCl salt) as yellow solid. LC-MS (ESI$^+$) m/z 568.3.

(4S,5R)-2-(4-tert-butyl-2-ethoxy-phenyl)-4,5-bis(4-chlorophenyl)-4,5-dihydroimidazole-1-carbonyl chloride (Intermediate AV)

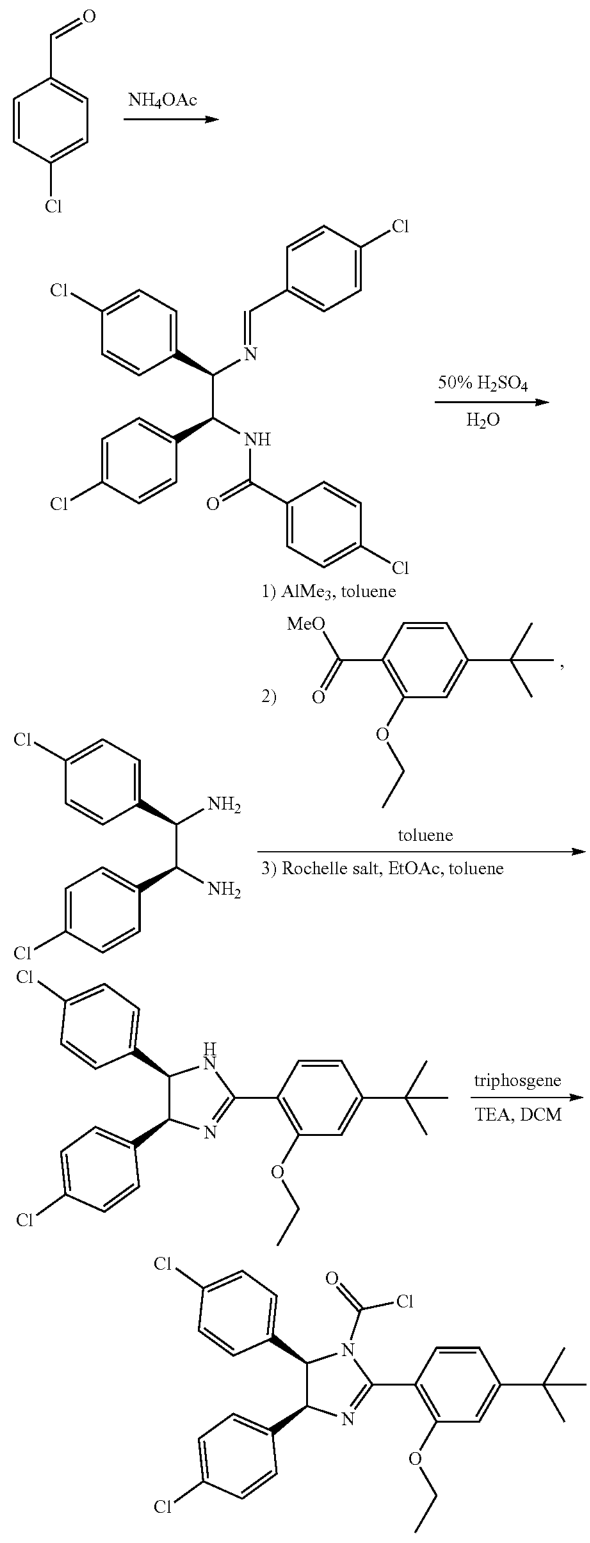

AV

Step 1—N-[1,2-bis(4-chlorophenyl)-2-[(E)-(4-chlorophenyl)methyleneamino]ethyl]-4-chloro-benzamide A mixture of 4-chlorobenzaldehyde (5 g, 35.6 mmol, CAS #104-88-1) and $NH_4OAc$ (10.4 g, 135 mmol) was stirred at 120° C. for 3 hours. On completion, the mixture was washed with 5% NaOH aqueous (50 mL), the solid was filtered and the filter cake was collected and dried in vacuo to give a crude product. The crude product was purified by triturated with PE/EA (3/1) to give the title compound (7.6 g, 39% yield) as yellow solid. LC-MS ($ESI^+$) m/z 543.1 $(M+H)^+$.

Step 2—Tert-butyl N-[(1S,2R)-2-amino-1,2-bis(4-chlorophenyl)ethyl]carbamate

A mixture of N-[1,2-bis(4-chlorophenyl)-2-[(E)-(4-chlorophenyl)methyleneamino]ethyl]-4-chloro-benzamide (3.40 g, 6.27 mmol in a mixed solvent of $H_2SO_4$ (3.0 mL) and $H_2O$ (3.0 mL) was stirred at 180° C. for 4 hours. On completion, the mixture was cooled to 25° C., and then poured into ice water (100 mL). The mixture was extracted with EA (2×15 mL), the aqueous phase was collected and basified by $NH_3$—$H_2O$ until the pH=10. After that, the mixture was extracted with DCM (3×20 mL), the combined organic phase was dried over $Na_2SO_4$, filtered and the filtrate was concentrated in vacuo to give the title compound (1.2 g, 50% yield) yellow solid. $^1H$ NMR (400 MHz, $CDCl_3$) δ 7.27-7.16 (m, 8H), 3.92 (s, 2H), 0.00 (s, 4H). LC-MS ($ESI^+$) m/z 264.0 ($M-NH_2$).

Step 3—(4S,5R)-2-(4-Tert-butyl-2-ethoxy-phenyl)-4,5-bis(4-chlorophenyl)-4,5-dihydro-1H-imidazole To a mixture of $AlMe_3$ (2 M, 2.59 mL) in toluene (5.0 mL) was added a solution of tert-butyl N-[(1S,2R)-2-amino-1,2-bis(4-chlorophenyl)ethyl]carbamate (658 mg, 1.73 mmol) in toluene (5 mL) dropwise at 0° C. under $N_2$. After the addition was completed, the mixture was stirred at 25° C. for 30 mins and then at 55° C. for 30 mins, then 85° C. for 30 mins. After cooled to 60° C., a solution of methyl 4-tert-butyl-2-ethoxy-benzoate (407 mg, 1.73 mmol, CAS #870007-39-9) in toluene (5 mL) was added. The mixture was stirred at 110° C. for 3 hours. On completion, the reaction mixture was quenched with Rochelle salt (40 mL) at 25° C. and stirred for 2 hours. Then, the mixture was extracted with EA (3×20 mL). The combined organic layers were washed with brine (10 mL), dried over $Na_2SO_4$, filtered and concentrated in vacuo to give a residue. The residue was purified by column chromatography ($SiO_2$, petroleum ether/ethyl acetate=2/1) to afford the title compound (520 mg, 64% yield) as yellow solid. $^1H$ NMR (400 MHz, $CDCl_3$) δ 8.19 (d, J=8.4 Hz, 1H), 7.14-7.10 (m, 1H), 7.06-7.00 (m, 5H), 6.95-6.88 (m, 4H), 5.37 (s, 2H), 4.27-4.19 (m, 2H), 1.42 (t, J=7.0 Hz, 3H), 1.37 (s, 9H); LC-MS ($ESI^+$) m/z 467.2 $(M+H)^+$.

Step 4—(4S,5R)-2-(4-tert-butyl-2-ethoxy-phenyl)-4,5-bis(4-chlorophenyl)-4,5-dihydroimidazole-1-carbonyl chloride To a mixture of (4S,5R)-2-(4-tert-butyl-2-ethoxy-phenyl)-4,5-bis(4-chlorophenyl)-4,5-dihydro-1H-imidazole (150 mg, 320 umol) in DCM (5 mL) was added bis(trichloromethyl) carbonate (190 mg, 641 umol) and TEA (97.4 mg, 962 umol, 134 uL). The mixture was stirred at 0° C. for 1.5 hours. On completion, the mixture was concentrated in vacuo to give the title compound (150 mg, 88% yield).

Tert-butyl 4-prop-2-ynylpiperazine-1-carboxylate (Intermediate AW)

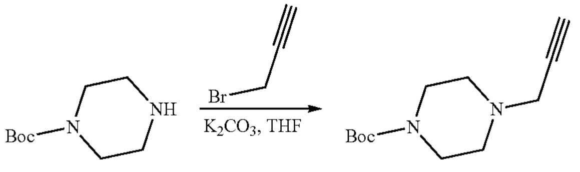

AW

To a mixture of tert-butyl piperazine-1-carboxylate (2.0 g, 10.7 mmol, CAS #57260-71-6) and 3-bromoprop-1-yne (1.53 g, 12.8 mmol, 1.11 mL) in THF (20 mL) was added $K_2CO_3$ (2.97 g, 21.5 mmol). The mixture was stirred at 25° C. for 2 hours. On completion, the reaction mixture was quenched with water (10.0 mL) at 25° C., and then extracted with DCM (3×20 mL). The combined organic layers were washed with brine (10.0 mL), dried over $Na_2SO_4$, filtered and concentrated in vacuo to give a residue. The residue was purified by column chromatography ($SiO_2$, petroleum ether/ethyl acetate=10/1) to afford the title compound (1.0 g, 41% yield) as colorless oil.

3-(4-Bromo-1-oxo-isoindolin-2-yl)piperidine-2,6-dione (Intermediate AX)

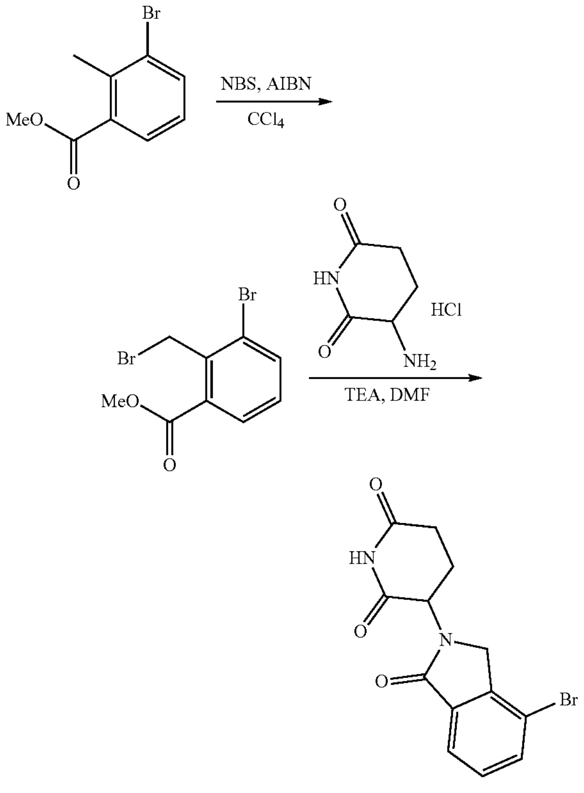

AX

Step 1—Methyl 3-bromo-2-(bromomethyl)benzoate

To a mixture of methyl 3-bromo-2-methyl-benzoate (3.00 g, 13.1 mmol, CAS #99548-54-6) in $CCl_4$ (50 mL) was added NBS (2.80 g, 15.7 mmol) and AIBN (215 mg, 1.31 mmol). The reaction mixture was stirred at 80° C. for 12 hours. On completion, the reaction mixture was concentrated in vacuo. The residue was purified by column chromatography to give the title compound (4.00 g, 99% yield) as light yellow oil. $^1H$ NMR (400 MHz, $CDCl_3$) δ 7.84-7.75 (m, 1H), 7.70-7.65 (m, 1H), 7.15 (t, J=8.0 Hz, 1H), 5.05 (s, 2H), 3.91-3.84 (m, 3H).

Step 2—3-(4-Bromo-1-oxo-isoindolin-2-yl)piperidine-2,6-dione

To a mixture of methyl 3-bromo-2-(bromomethyl)benzoate (3.82 g, 12.3 mmol) and 3-aminopiperidine-2,6-dione (1.70 g, 10.3 mmol, HCl, CAS #2353-44-8) in DMF (50 mL) was added TEA (4.18 g, 41.3 mmol, 5.75 mL). The reaction mixture was stirred at 75° C. for 12 hours. On completion, the reaction mixture was diluted with water (10 mL) and solid was formed. Then the mixture was filtered and the filter cake was collected and dried in vacuo to give the title compound (1.60 g, 47% yield) as off-white solid. $^1H$ NMR (400 MHz, DMSO-$d_6$) δ 11.03 (s, 1H), 7.89-7.73 (m, 2H), 7.51 (t, J=7.6 Hz, 1H), 5.19-5.10 (m, 1H), 4.47-4.22 (m, 2H), 3.00-2.85 (m, 1H), 2.65-2.51 (m, 2H), 2.09-1.96 (m, 1H).

3-[1-Oxo-4-(3-piperazin-1-ylprop-1-ynyl)isoindolin-2-yl]piperidine-2,6-dione (Intermediate AY

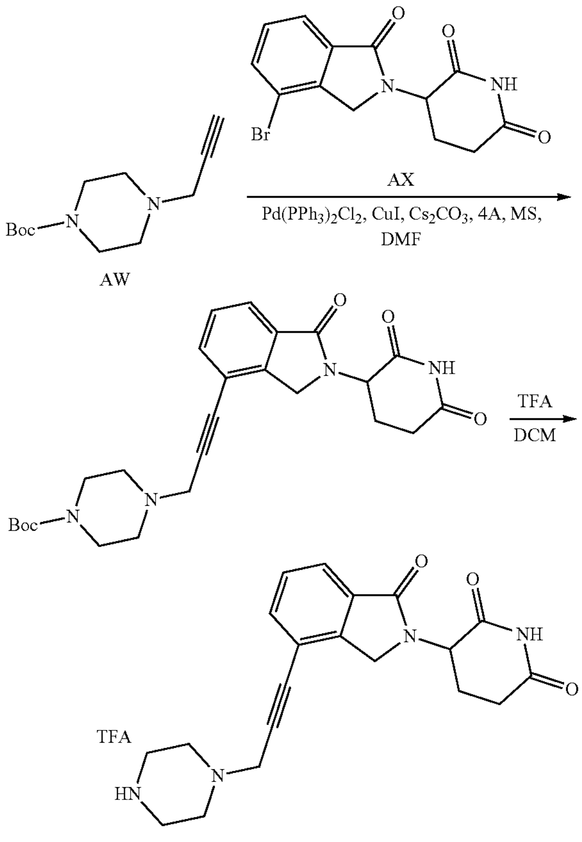

AY

Step 1—Tert-butyl 4-[3-[2-(2,6-dioxo-3-piperidyl)-1-oxo-isoindolin-4-yl]prop-2-ynyl]piperazine-1-carboxylate To a mixture of 3-(4-bromo-1-oxo-isoindolin-2-yl)piperidine-2,6-dione (200 mg, 618 umol, Intermediate AX) and tert-butyl 4-prop-2-ynylpiperazine-1-carboxylate (208 mg, 928 umol, Intermediate AW) in DMF (2.0 mL) was added $Pd(PPh_3)_2Cl_2$ (43.4 mg, 61.8 umol), CuI (11.8 mg, 61.8 umol), $Cs_2CO_3$ (403 mg, 1.24 mmol) and 4A molecular sieves (100 mg). The mixture was stirred at 80° C. for 2 hours. On completion, the mixture was quenched with $H_2O$ (0.5 mL) and then concentrated in vacuo to give a residue. The residue was purified by reverse phase (FA condition) to afford the title compound (240 mg, 83% yield) as white solid. LC-MS ($ESI^+$) m/z 467.3 $(M+H)^+$.

Step 2—3-[1-Oxo-4-(3-piperazin-1-ylprop-1-ynyl)isoindolin-2-yl]piperidine-2,6-dione To a mixture of tert-butyl 4-[3-[2-(2,6-dioxo-3-piperidyl)-1-oxo-isoindolin-4-yl]prop-2-ynyl]piperazine-1-carboxylate (120 mg, 257 umol) in DCM (1.0 mL) was added TFA (4.62 g, 40.5 mmol, 3.00 mL) at 25° C. The mixture was stirred at 25° C. for 2 hours. On completion, the mixture was concentrated in vacuo to give the title compound (90.0 mg, 95% yield) as yellow solid. LC-MS ($ESI^+$) m/z 367.2 $(M+H)^+$.

The following acids and amines were purchased from commercial suppliers: 2-((3R,5R,6S)-5-(3-chlorophenyl)-6-(4-chlorophenyl)-1-((S)-1-(isopropylsulfonyl)-3-methylbutan-2-yl)-3-methyl-2-oxopiperidin-3-yl)acetic acid (CAS #1352066-68-2) (Intermediate AJ)

AJ

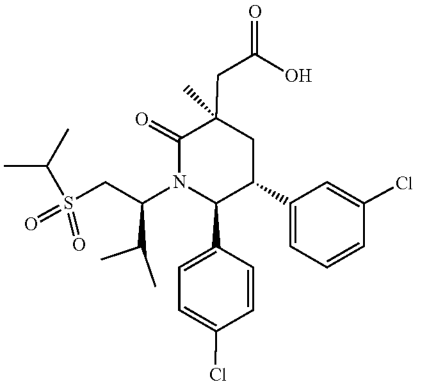

Undecane-1,11-diamine (CAS #822-08-2) (Intermediate AK)

AK

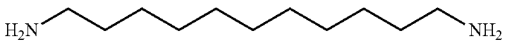

4-[(3'R,4’S,5'R)-6"-chloro-4'-(3-chloro-2-fluorophenyl)-2"-oxo-1"H-dispiro[cyclohexane-1,2'-pyrrolidine-3',3"-indol]-5'-ylamidolbenzoic acid (CAS #1410737-34-6) (Intermediate AM)

AM

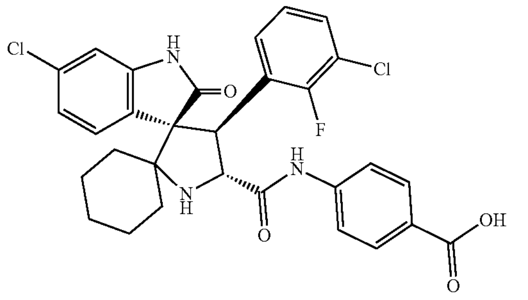

4-[(2R,3S,4R,5S)-3-(3-chloro-2-fluorophenyl)-4-(4-chloro-2-fluorophenyl)-4-cyano-5-(2,2-dimethylpropyl)pyrrolidine-2-amido]-3-methoxybenzoic acid (CAS #1229705-06-9) (Intermediate AN)

AN

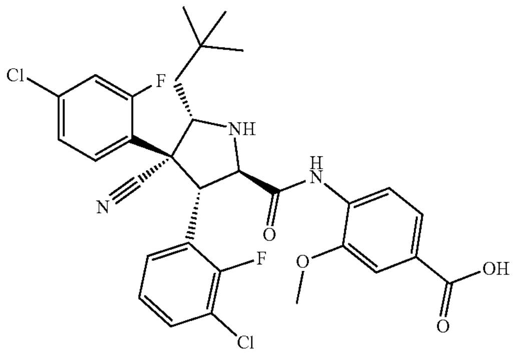

2,2'-(Ethane-1,2-diylbis(oxy))bis(ethan-1-amine) (CAS #929-59-9) (Intermediate AO)

AO

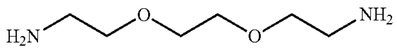

Octane-1,8-diamine (CAS #373-44-4) (Intermediate AP)

AP

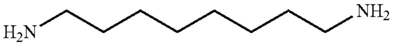

tert-butyl N-(5-aminopentyl)carbamate (CAS #51644-96-3) (Intermediate AZ)

AZ

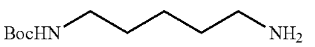

3-[3-Methyl-2-oxo-4-[3-(4-piperidyloxy)prop-1-ynyl]benzimidazol-1-yl]piperidine-2,6-dione (Intermediate BB)

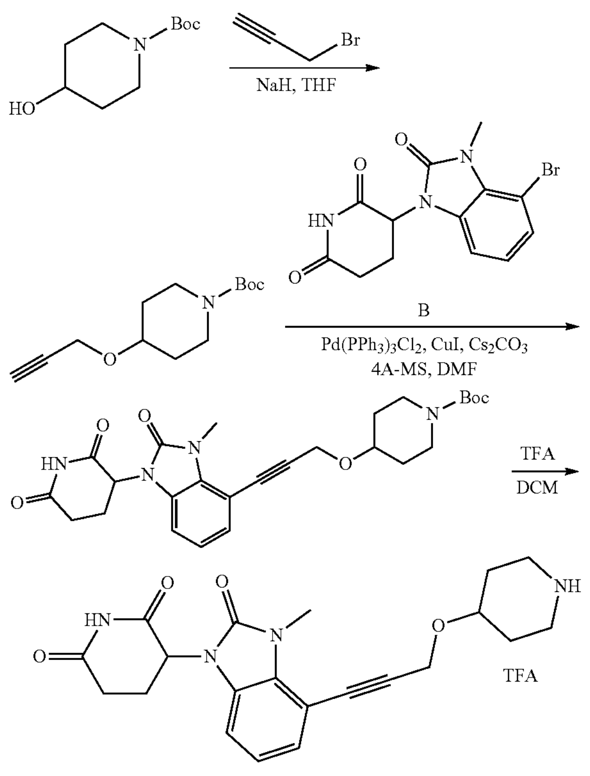

BB

Step 1—Tert-butyl 4-prop-2-ynoxypiperidine-1-carboxylate

To a solution of tert-butyl 4-hydroxypiperidine-1-carboxylate (2.00 g, 9.94 mmol, CAS #109384-19-2) in anhydrous THF (10 mL) was cooled to 0° C., and subsequently NaH (477 mg, 11.9 mmol, 60% oil dispersion) was added. The reaction mixture was stirred at 0° C. for 0.5 hr. Then, 3-bromoprop-1-yne (1.18 g, 9.94 mmol, 856 uL) was added. The resulting reaction mixture was stirred at 25° C. for 12 hrs. On completed, the reaction mixture was quenched with water (1 mL), then diluted with ethyl acetate (100 mL). The organic layers were washed with brine (20 mL), dried over anhydrous sodium sulfate, filtered and the filtrate was concentrated in vacuo. The residue was purified by column chromatography to give the title compound (2.38 g, 100% yield) as yellow oil. $^1H$ NMR (400 MHz, $CDCl_3$) δ 4.22 (d, J=2.4 Hz, 2H), 3.84-3.75 (m, 2H), 3.73-3.70 (m, 1H), 3.15-3.09 (m, 2H), 2.43 (t, J=2.4 Hz, 1H), 1.93-1.82 (m, 2H), 1.61-1.50 (m, 2H), 1.47 (s, 9H).

Step 2—Tert-butyl 4-[3-[1-(2,6-dioxo-3-piperidyl)-3-methyl-2-oxo-benzimidazol-4-yl]prop-2-ynoxy]piperidine-1-carboxylate A suspension of 3-(4-bromo-3-methyl-2-oxo-benzimidazol-1-yl)piperidine-2,6-dione (300 mg, 887 umol, Intermediate B), tert-butyl 4-prop-2-ynoxypiperidine-1-carboxylate (318 mg, 1.33 mmol), $Pd(PPh_3)_2Cl_2$ (124 mg, 177 umol), CuI (33.8 mg, 177 umol), 4A molecular sieves (400 mg) and $Cs_2CO_3$ (1.16 g, 3.55 mmol) in DMF (5 mL) was de-gassed under vacuum and purged with $N_2$ several times and then heated to 80° C. for 2 hours under $N_2$. On completion, the reaction mixture was concentrated in vacuo to remove DMF. The residue was diluted with EA (50 mL) and water (20 mL). After, the organic layer was separated and washed with brine (5 mL×2), dried over anhydrous $Na_2SO_4$, filtered and the filtrate was concentrated in vacuo to give a residue. The residue was purified by reverse phase to give the title compound (222 mg, 48% yield) as a yellow solid. $^1H$ NMR (400 MHz, $CDCl_3$) δ 8.09 (s, 1H), 7.10 (d, J=8.0 Hz, 1H), 6.92 (t, J=8.0 Hz, 1H), 6.69 (d, J=8.0 Hz, 1H), 5.13 (dd, J=5.2, 12.8 Hz, 1H), 4.39 (s, 2H), 3.76-3.66 (m, 6H), 3.09-3.03 (m, 2H), 2.94-2.84 (m, 1H), 2.82-2.71 (m, 1H), 2.71-2.59 (m, 1H), 2.22-2.11 (m, 1H), 1.83-1.78 (m, 2H), 1.57-1.49 (m, 2H), 1.39 (s, 9H), LC-MS ($ESI^+$) m/z 441.2 $(M+H-56)^+$.

Step 3—3-[3-Methyl-2-oxo-4-[3-(4-piperidyloxy)prop-1-ynyl]benzimidazol-1-yl]piperidine-2,6-dione To a mixture of tert-butyl 4-[3-[1-(2,6-dioxo-3-piperidyl)-3-methyl-2-oxo-benzimidazol-4-yl]prop-2-ynoxy]piperidine-1-carboxylate (1.50 g, 3.02 mmol) in DCM (30 mL) was added TFA (23.1 g, 202 mmol, 15 mL). The reaction mixture was stirred at 20° C. for 1 hr. On completion, the reaction mixture was concentrated in vacuo to give the title compound (1.50 g, 97% yield, TFA salt) as yellow oil. LC-MS ($ESI^+$) m/z 397.2 $(M+H)^+$.

3-(3-Methyl-2-oxo-4-(piperidin-4-yl)-2,3-dihydro-1H-benzo[d]imidazol-1-yl)piperidine-2,6-dione (Intermediate BC)

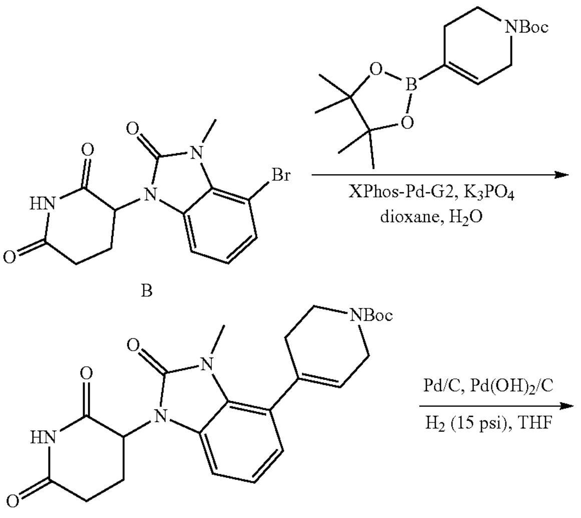

-continued

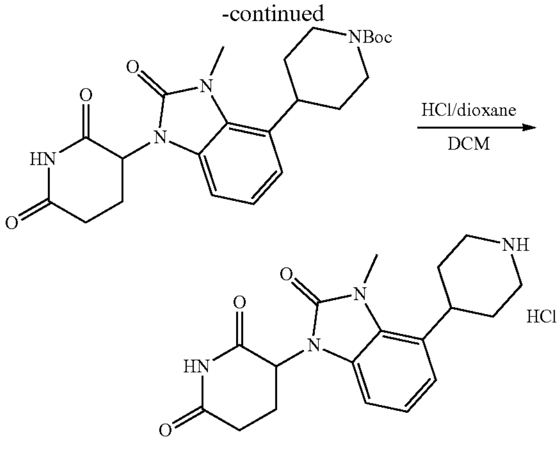

BC

Step 1—Tert-butyl 4-(1-(2,6-dioxopiperidin-3-yl)-3-methyl-2-oxo-2,3-dihydro-1H-benzo[d]imidazol-4-yl)-5,6-dihydropyridine-1(2H)-carboxylate To a solution of 3-(4-bromo-3-methyl-2-oxo-benzimidazol-1-yl)piperidine-2,6-dione (9.00 g, 26.6 mmol, Intermediate B), tert-butyl 4-(4,4,5,5-tetramethyl-1,3,2-dioxaborolan-2-yl)-3,6-dihydro-2H-pyridine-1-carboxylate (12.3 g, 39.9 mmol) and XPhos-Pd-G2 (2.09 g, 2.66 mmol) in dioxane (150 mL) and $H_2O$ (15 mL) was added $K_3PO_4$ (11.3 g, 53.2 mmol). The reaction mixture was stirred at 80° C. for 4 hours under $N_2$. On completion, the reaction mixture was filtered. The filtrate was dried with anhydrous $Na_2SO_4$ and filtered. The filtrate was concentrated in vacuo. The residue was triturated with sat. $NH_4Cl$ (2×50 mL), water (2×50 mL) and EA (2×50 mL) and filtered. The solid was dried in vacuo to give the title compound (8.00 g, 68% yield) as an off-white solid. LC-MS ($ESI^+$) m/z 441.1 $(M+H)^+$ Step 2—Tert-butyl 4-(1-(2,6-dioxopiperidin-3-yl)-3-methyl-2-oxo-2,3-dihydro-1H-benzo[d]imidazol-4-yl)piperidine-1-carboxylate To a solution of tert-butyl 4-[1-(2,6-dioxo-3-piperidyl)-3-methyl-2-oxo-benzimidazol-4-yl]-3,6-dihydro-2H-pyridine-1-carboxylate (8.00 g, 18.2 mmol) in DMF (20 mL) and THF (60 mL) was added $H_2$, Pd/C (1.00 g, 10 wt %) and $Pd(OH)_2$ (1.00 g, 3.56 mmol, 50 wt %). The mixture was degassed and purged with nitrogen 3 times, then degassed and purged with hydrogen 3 times. The mixture was stirred at 25° C. for 16 hrs under hydrogen (15 psi) atmosphere. On completion, the reaction mixture was filtered and the combined filtrates were concentrated in vacuo to give the title compound (5.60 g, 70% yield) as a white solid. 1H NMR (400 MHz, DMSO-d6) δ 11.10 (s, 1H), 7.06-6.92 (m, 3H), 5.38 (m, 1H), 4.18-3.96 (m, 2H), 3.60 (s, 3H), 3.48-3.39 (m, 1H), 2.97-2.81 (m, 3H), 2.76-2.61 (m, 2H), 2.05-1.94 (m, 1H), 1.81 (m, 2H), 1.65-1.50 (m, 2H), 1.47-1.40 (m, 9H). LC-MS ($ESI^+$) m/z 287.4 $(387.3)^+$.

Step 3—3-(3-Methyl-2-oxo-4-(piperidin-4-yl)-2,3-dihydro-1H-benzo[d]imidazol-1-yl)piperidine-2,6-dione To a solution of tert-butyl 4-[1-(2,6-dioxo-3-piperidyl)-3-methyl-2-oxo-benzimidazol-4-yl]piperidine-1-carboxylate (100 mg, 226 umol) in DCM (1 mL) was added HCl/dioxane (1 mL). The reaction mixture was stirred at 25° C. for 0.5 hr. On completion, the reaction mixture was concentrated in vacuo to give the title compound (85.0 mg, 99% yield) as a yellow solid. LC-MS ($ESI^+$) m/z 343.3 $(M+H)^+$.

1-(2,6-dioxo-3-piperidyl)-3-methyl-2-oxo-benzimidazole-4-carbaldehyde (Intermediate BD)

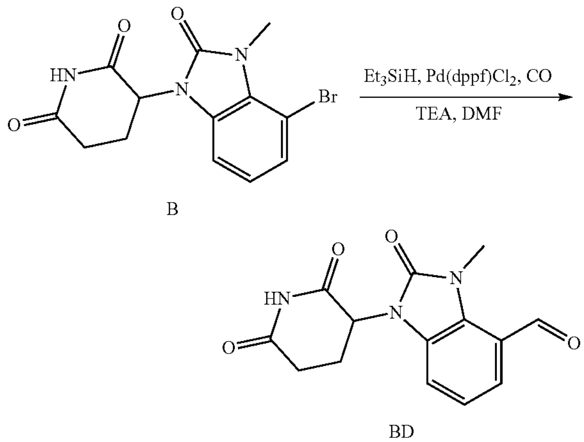

B

BD

To a solution of 3-(4-bromo-3-methyl-2-oxo-2,3-dihydro-1H-benzo[d]imidazol-1-yl)piperidine-2,6-dione (500 mg, 1.48 mmol, Intermediate HP) in DMF (20 mL) was added TEA (448 mg, 4.44 mmol), $Pd(dppf)Cl_2$ (162 mg, 221 umol) and $Et_3SiH$ (515 mg, 4.44 mmol). The reaction mixture was stirred at 80° C. for 16 hours under CO (50 Psi). On completion, the reaction mixture was concentrated in vacuo and purified by reverse phase (0.1% FA) to give the title compound (400 mg, 47% yield) as a white solid. LC-MS ($ESI^+$) m/z 288.0 $(M+H)^+$.

3-[3-Methyl-4-[[4-(methylamino)-1-piperidyl]methyl]-2-oxo-benzimidazol-1-yl]piperidine-2,6-dione (Intermediate BE)

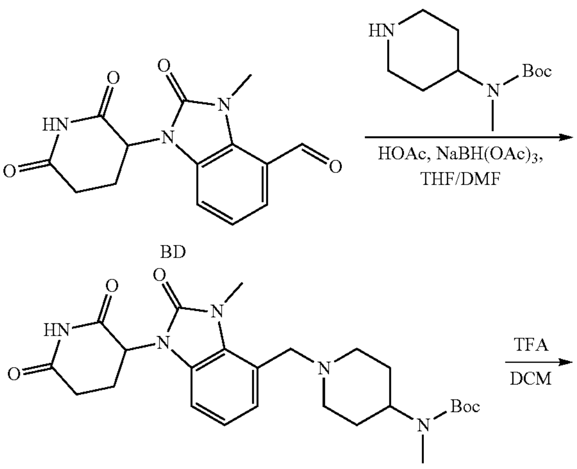

BD

-continued

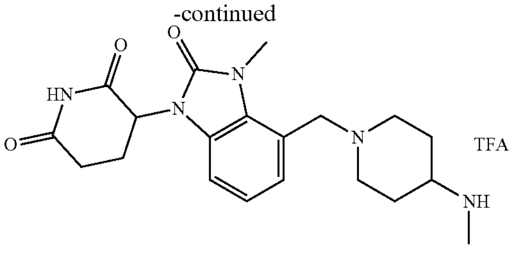

BE

Step 1—Tert-butyl N-[1-[[1-(2,6-dioxo-3-piperidyl)-3-methyl-2-oxo-benzimidazol-4-yl]methyl]-4-piperidyl]-N-methyl-carbamate To a solution of 1-(2,6-dioxo-3-piperidyl)-3-methyl-2-oxo-benzimidazole-4-carbaldehyde (160 mg, 556 umol, Intermediate BD) and tert-butyl N-methyl-N-(4-piperidyl) carbamate (119 mg, 556 μmol) in a mixed solvents of THF (3 mL) and DMF (1.5 mL) was added AcOH until the pH=5-7. After the reaction mixture was stirred at 20° C. for 3 hours. $NaBH(OAc)_3$ (177 mg, 835 umol) was added to the reaction mixture. The mixture was stirred at 20° C. for 12 hours. On completion, the reaction mixture was quenched by water (3 drops) and filtered. The filtrate was concentrated in vacuo. The residue was purified by reverse phase (FA condition) to give the title compound (220 mg, 46% yield) as white solid. LC-MS ($ESI^+$) m/z 486.2 $(M+H)^+$.

Step 2—3-[3-Methyl-4-[[4-(methylamino)-1-piperidyl]methyl]-2-oxo-benzimidazol-1-yl]piperidine-2,6-dione To a solution of tert-butyl N-[1-[[1-(2,6-dioxo-3-piperidyl)-3-methyl-2-oxo-benzimidazol-4-yl]methyl]-4-piperidyl]-N-methyl-carbamate (200 mg, 235 umol) in DCM (3 mL) was added TFA (3 mL). The reaction mixture was stirred at 15° C. for 0.5 hour. On completion, the reaction mixture was concentrated in vacuo to give the title compound (220 mg, 100% yield, TFA salt) as yellow oil. LC-MS ($ESI^+$) m/z 386.2 $(M+H)^+$.

Tert-butyl 2-(2-bromoethyl)-7-azaspiro[3.5]nonane-7-carboxylate (Intermediate BF)

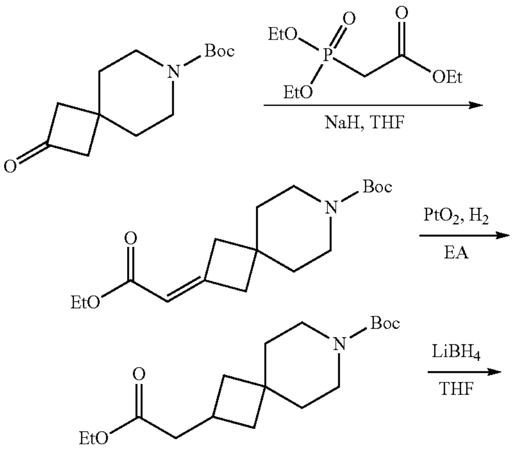

-continued

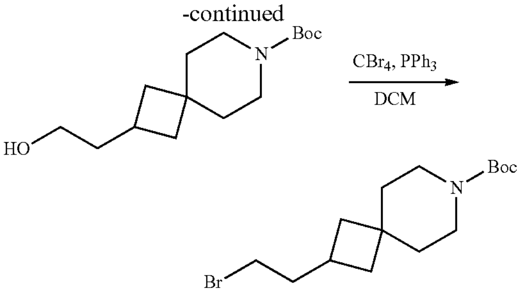

BF

Step 1—Tert-butyl 2-(2-ethoxy-2-oxoethylidene)-7-azaspiro[3.5]nonane-7-carboxylate To a solution of methyl 2-diethoxyphosphorylacetate (2.64 g, 12.5 mmol) in DMF (30 mL) was added NaH (501 mg, 12.5 mmol, 60% dispersion in mineral oil) at 0° C. with stirring for 0.5 hour. Next was added a solution of tert-butyl 2-oxo-7-azaspiro[3.5]nonane-7-carboxylate (2.00 g, 8.36 mmol, CAS #203661-69-2) in DMF (10 mL). The mixture was warmed to 25° C. with stirring for 2 hours. On completion, the mixture was poured into 150 mL saturated ammonium chloride aqueous solution and extracted with ethyl acetate (50 mL×3). The combined organic layers were washed with brine (20 mL, dried over anhydrous sodium sulfate and concentrated in vacuo. The residue was purified by silica gel column chromatography [petroleum ether:ethyl acetate=10:1 to 3:1]. The title compound (2.00 g, 80% yield) was obtained as colorless oil. $^1H$ NMR (400 MHz, $CDCl_3$) δ 5.65-5.64 (m, 1H), 3.62 (s, 3H), 3.35-3.21 (m, 4H), 2.80 (s, 2H), 2.50 (s, 2H), 1.52-1.45 (m, 2H), 1.38 (m, 9H).

Step 2—Tert-butyl 2-(2-ethoxy-2-oxoethyl)-7-azaspiro[3.5]nonane-7-carboxylate

To a solution of tert-butyl 2-(2-methoxy-2-oxo-ethylidene)-7-azaspiro[3.5]nonane-7-carboxylate (1.8 g, 6.09 mmol) in EtOH (50 mL) was added $Pd(OH)_2/C$ (100 mg, 10% wt) and Pd/C (100 mg, 10% wt) under $N_2$. The suspension was degassed under vacuum and purged with $H_2$ several times. The mixture was stirred under $H_2$ (15 psi) at 25° C. for 16 hours. On completion, the reaction mixture was filtered and the filter was concentrated. The title compound (1.7 g, 80% purity) was obtained as colorless oil. $^1H$ NMR (400 MHz, $CDCl_3$) δ 3.58 (s, 3H), 3.32-3.24 (m, 2H), 3.22-3.14 (m, 2H), 2.57 (td, J=8.0, 16.0 Hz, 1H), 2.36 (d, J=7.8 Hz, 2H), 2.03-1.92 (m, 2H), 1.52-1.47 (m, 2H), 1.43-1.34 (m, 14H).

Step 3—Ttert-butyl 2-(2-hydroxyethyl)-7-azaspiro[3.5]nonane-7-carboxylate

To a solution of tert-butyl 2-(2-methoxy-2-oxo-ethyl)-7-azaspiro[3.5]nonane-7-carboxylate (1.70 g, 5.72 mmol) in THF (30 mL) was added $LiBH_4$ (373 mg, 17.1 mmol) and the mixture was stirred at 75° C. for 4 hours. On, completion, the mixture was cooled to rt and poured into 30 mL water and extracted with ethyl acetate (50 mL×3). The combined organic layers were washed with water, brine, dried over anhydrous sodium sulfate and concentrated in vacuo. The title compound (1.50 g, 97% yield) was obtained as colorless oil. $^1H$ NMR (400 MHz, $CDCl_3$) δ 3.57-3.45 (m, 2H), 3.31-3.23 (m, 2H), 3.22-3.15 (m, 2H), 2.27 (d, J=8.0, 16.0 Hz, 1H), 1.96-1.85 (m, 2H), 1.61 (q, J=6.8 Hz, 2H), 1.52-1.45 (m, 2H), 1.41-1.30 (m, 13H).

Step 4—Tert-butyl 2-(2-bromoethyl)-7-azaspiro[3.5] nonane-7-carboxylate

To a solution of tert-butyl 2-(2-hydroxyethyl)-7-azaspiro [3.5]nonane-7-carboxylate (1.50 g, 5.57 mmol) and $PPh_3$ (4.38 g, 16.7 mmol) in DCM (30 mL) was added $CBr_4$ (5.54 g, 16.7 mmol) at 0° C. and the mixture was stirred at 25° C. for 14 hours. On completion, the mixture was filtered and concentrated. The residue was purified by silica gel column chromatography [petroleum ether:ethyl acetate=100:1 to 3:1] and the title compound (1.50 g, 81% yield) was obtained as colorless oil. $^1H$ NMR (400 MHz, $CDCl_3$) δ 3.38-3.30 (m, 4H), 3.29-3.23 (m, 2H), 2.40 (J=8.0 Hz, 1H), 2.05-1.94 (m, 4H), 1.59-1.55 (m, 2H), 1.47-1.39 (m, 13H).

3-[4-[2-(7-azaspiro[3.5]nonan-2-yl)ethyl]-3-methyl-2-oxo-benzimidazol-1-yl] piperidine-2,6-dione (Intermediate BG)

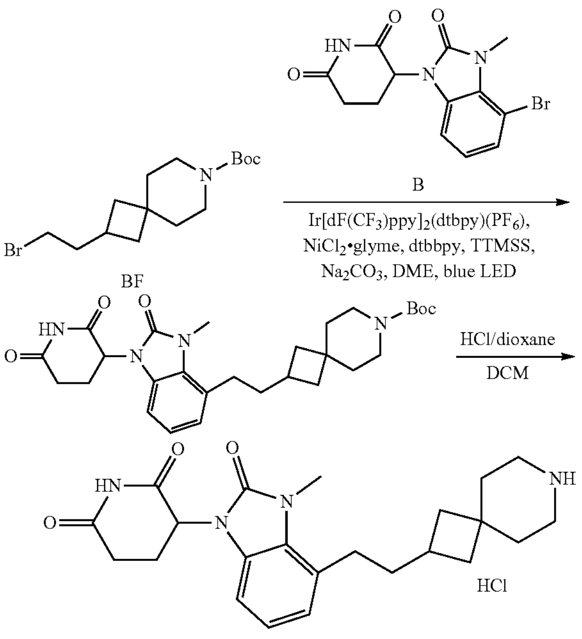

BG

Step 1—Tert-butyl 2-(2-(1-(2,6-dioxopiperidin-3-yl)-3-methyl-2-oxo-2,3-dihydro-1H-benzo[d] imidazol-4-yl)ethyl)-7-azaspiro[3.5]nonane-7-carboxylate To an 40 mL vial equipped with a stir bar was added 3-(4-bromo-3-methyl-2-oxo-benzimidazol-1-yl)piperidine-2,6-dione (1.00 g, 2.96 mmol, Intermediate B), tert-butyl 2-(2-bromoethyl)-7-azaspiro[3.5]nonane-7-carboxylate (1.08 g, 3.25 mmol, Intermediate BF), bis[3,5-difluoro-2-[5-(trifluoromethyl)-2-pyridyl] phenyl]iridium (1+); 4-tert-butyl-2-(4-tert-butyl-2-pyridyl)pyridine; hexafluorophosphate (33.1 mg, 29.5 umol), $NiCl_2$·dtbbpy (5.88 mg, 14.7 umol), TTMSS (735 mg, 2.96 mmol) and $Na_2CO_3$ (626 mg, 5.91 mmol) in DME (24 mL). The vial was sealed and placed under nitrogen was added. The reaction was stirred and irradiated with a 34 W blue LED lamp (7 cm away), with cooling fan to keep the reaction temperature at 25° C. for 4 hr. On completion, the mixture was filtered and concentrated. The residue was purified by prep-HPLC: reverse phase (condition: 0.1% FA). The title compound (400 mg, 26% yield) was obtained as red solid. LC-MS ($ESI^+$) m/z 455.2 $(M+H-56)^+$.

Step 2—3-(4-(2-(7-azaspiro[3.5]nonan-2-yl)ethyl)-3-methyl-2-oxo-2,3-dihydro-1H-benzo[d]imidazol-1-yl)piperidine-2,6-dione To a solution of tert-butyl 2-[2-[1-(2,6-dioxo-3-piperidyl)-3-methyl-2-oxo-benzimidazol-4-yl]ethyl]-7-azaspiro[3.5]nonane-7-carboxylate (140 mg, 274 umol) in DCM (3 mL) was added HCl/dioxane (4 M, 1.08 mL) and the mixture was stirred at 25° C. for 1 hour. On completion, the mixture was concentrated. The title compound (110 mg, 89% yield, HCl) was obtained as white solid. LC-MS ($ESI^+$) m/z 411.0 $(M+H)^+$.

4-Benzyloxy-3-methyl-1H-benzimidazol-2-one (Intermediate BH)

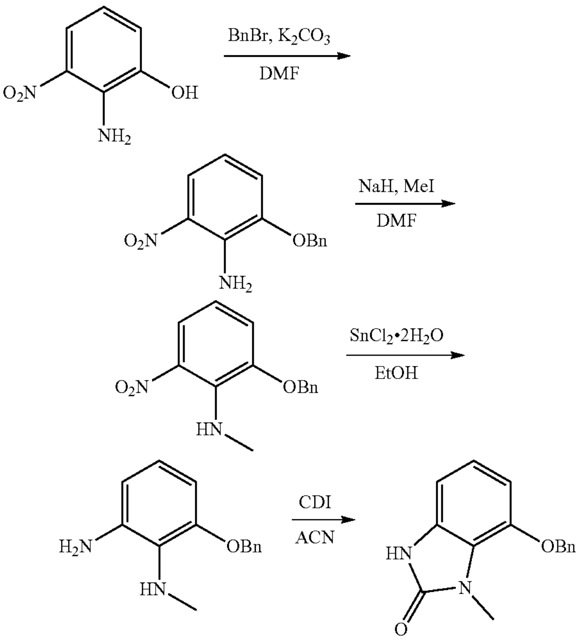

BH

Step 1—2-Benzyloxy-6-nitro-aniline

To a solution of 2-amino-3-nitro-phenol (60.0 g, 389 mmol, CAS #2835-97-4) and $K_2CO_3$ (107 g, 778 mmol) in DMF (1000 mL) was added BnBr (79.9 g, 467 mmol) at −10° C. The reaction was then warmed to 25° C. and stirred for 18 hours. On completion, the reaction mixture was quenched by addition $H_2O$ (1000 mL), and extracted with ethyl acetate (3×5000 mL). The combined organic layers were washed with brine (3×500 mL) and dried over $Na_2SO_4$, filtered and concentrated in vacuo to give a crude product. The residue was purified by silica gel column chromatography (PE:EA=3:1) to give the title compound (95.0 g, 99% yield) as brown solid. $^1$H NMR (400 MHz, $CDCl_3$) δ 7.77 (dd, J=1.2, 8.8 Hz, 1H), 7.49-7.36 (m, 5H), 7.04-6.95 (m, 1H), 6.61 (dd, J=7.6, 8.8 Hz, 1H), 6.48 (br s, 2H), 5.15 (s, 2H), LC-MS (ESI$^+$) m/z 245.6 (M+H)$^+$.

Step 2—2-Benzyloxy-N-methyl-6-nitro-aniline

To a solution of 2-benzyloxy-6-nitro-aniline (85.0 g, 348 mmol) in DMF (100 mL) was added NaH (13.9 g, 348 mmol, 60% dispersion in mineral oil) at 0° C. and stirred at 0° C. for 0.5 hr. Then MeI (49.4 g, 348 mmol, 21.6 mL) was added and the reaction mixture was stirred at 25° C. for 12 hrs. On completion, the reaction mixture was quenched by addition $H_2O$ (200 mL), and extracted with ethyl acetate (3×600 mL). The combined organic layers were washed with brine (3×100 mL) and dried over $Na_2SO_4$, filtered and concentrated in vacuo to give the title compound (100 g, 90% yield) as yellow oil. $^1$H NMR (400 MHz, $CDCl_3$) δ 7.73 (dd, J=1.6, 8.8 Hz, 1H), 7.43-7.35 (m, 5H), 7.01-6.97 (m, 1H), 6.60 (dd, J=7.6, 8.8 Hz, 1H), 5.08 (s, 2H), 3.16 (s, 3H).

Step 3—3-Benzyloxy-N2-methyl-benzene-1,2-diamine

To a solution of 2-benzyloxy-N-methyl-6-nitro-aniline (75.0 g, 290 mmol) in EtOH (1500 mL) was added $SnCl_2 \cdot 2H_2O$ (327 g, 1.45 mol). The reaction mixture was then exposed to ultrasonic radiation for approximately 30 minutes at 25° C. The reaction mixture was then basified with 1M KOH solution (5000 mL) and extracted with DCM (3×5000 mL). The combined organic layer was washed with brine (3×500 mL), dried over $NaSO_4$ and concentrated in vacuo. The residue was purified by silica gel column chromatography (PE:EA=3:1) to give the title compound (20.0 g, 30% yield) as yellow oil, $^1$H NMR (400 MHz, $CDCl_3$) δ 7.48-7.32 (m, 5H), 6.84 (t, J=8.0 Hz, 1H), 6.49-6.38 (m, 2H), 5.07 (s, 2H), 3.91 (br s, 2H), 2.70 (s, 3H), LC-MS (ESI$^+$) m/z 229.7 (M+H)$^+$.

Step 4—4-Benzyloxy-3-methyl-1H-benzimidazol-2-one

To a solution of 3-benzyloxy-N2-methyl-benzene-1,2-diamine (20.0 g, 87.6 mmol) in ACN (600 mL) was added CDI (14.2 g, 87.6 mmol), and the reaction mixture was stirred at 25° C. for 16 hours. On completion, the reaction mixture was filtered and the solid was collected to give the title compound (17.0 g, 76% yield) as white solid. $^1$H NMR (400 MHz, DMSO-$d_6$) δ 10.83 (s, 1H), 7.55-7.47 (m, 2H), 7.46-7.39 (m, 2H), 7.38-7.32 (m, 1H), 6.95-6.87 (m, 1H), 6.83-6.77 (m, 1H), 6.64 (dd, J=0.8, 7.6 Hz, 1H), 5.19 (s, 2H), 3.47 (s, 3H), LC-MS (ESI$^+$) m/z 255.0 (M+H)$^+$.

3-(4-Hydroxy-3-methyl-2-oxo-benzimidazol-1-yl) piperidine-2,6-dione (Intermediate BI)

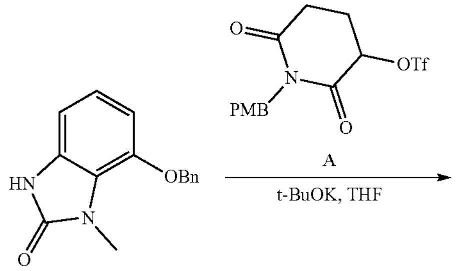

BH

-continued

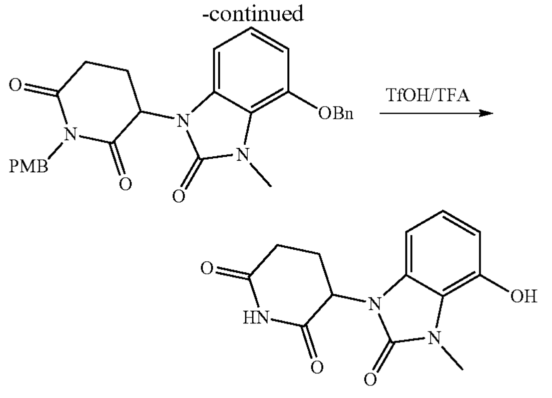

BI

Step 1—3-(4-Benzyloxy-3-methyl-2-oxo-benzimidazol-1-yl)-1-[(4-methoxyphenyl)methyl]piperidine-2,6-dione To a mixture of 4-benzyloxy-3-methyl-1H-benzimidazol-2-one (2.00 g, 7.87 mmol, Intermediate BH) in THF (60 mL) was added KOtBu (1.77 g, 15.7 mmol) at −10° C. for 0.5 hr under $N_2$. Then solution of [1-[(4-methoxyphenyl) methyl]-2,6-dioxo-3-piperidyl] trifluoromethanesulfonate (7.50 g, 19.6 mmol, Intermediate A) in THF (20 mL) was added dropwise and the mixture was stirred at −10° C. for 1 hour under $N_2$. On completion, the mixture was poured into saturated ammonium chloride aqueous solution (100 mL) and extracted with ethyl acetate (3×100 mL). The combined organic layers were washed with water, brine, dried over anhydrous sodium sulfate and concentrated in vacuo. The residue was purified by silica gel column chromatography (EA) to give the title compound (2.20 g, 57% yield) as blue solid. $^1$H NMR (400 MHz, DMSO-$d_6$) δ7.56-7.50 (m, 2H), 7.44-7.40 (m, 2H), 7.38-7.34 (m, 1H), 7.21 (d, J=8.8 Hz, 2H), 6.92-6.83 (m, 4H), 6.66 (dd, J=7.8, 13.6 Hz, 1H), 5.49 (dd, J=5.4, 12.8 Hz, 1H), 5.22 (s, 2H), 4.87-4.73 (m, 2H), 3.73 (s, 3H), 3.54 (s, 3H), 3.10-2.98 (m, 1H), 2.89-2.64 (m, 2H), 2.10-2.02 (m, 1H).

Step 2—3-(4-Hydroxy-3-methyl-2-oxo-benzimidazol-1-yl)piperidine-2,6-dione

To a mixture of 3-(4-benzyloxy-3-methyl-2-oxo-benzimidazol-1-yl)-1-[(4-methoxyphenyl)methyl]piperidine-2,6-dione (2.00 g, 4.12 mmol) in TFA (10.0 mL) was added TfOH (17.0 g, 113 mmol). The reaction mixture was heated to 60° C. and stirred for 1 hour. On completion, the mixture was concentrated in vacuo to remove TFA. The residue was poured into water (100 mL), neutralized with saturated $NaHCO_3$ aqueous solution until the pH=5, and concentrated in vacuo. The residue was purified by reverse phase: (0.1% FA) to give the title compound (500 mg, 43% yield) as off-white solid. $^1$H NMR (400 MHz, DMSO-$d_6$) δ 11.07 (s, 1H), 9.81 (s, 1H), 6.87-6.79 (m, 1H), 6.60-6.54 (m, 2H), 5.30 (dd, J=5.4, 12.8 Hz, 1H), 3.53 (s, 3H), 2.97-2.83 (m, 1H), 2.75-2.60 (m, 2H), 2.05-1.95 (m, 1H).

Tert-butyl 2-methylsulfonyloxy-7-azaspiro[3.5] nonane-7-carboxylate (Intermediate BJ)

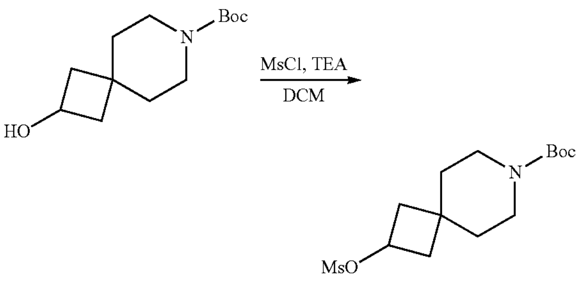

BJ

To a solution of tert-butyl 2-hydroxy-7-azaspiro[3.5] nonane-7-carboxylate (2.00 g, 8.29 mmol, CAS #240401-28-9) and TEA (2.10 g, 20.7 mmol) in DCM (30 mL) was added MsCl (1.14 g, 9.95 mmol) dropwise at 0° C. Then the reaction mixture was stirred at 20° C. for 2 hrs. On completion, the mixture was quenched with water (50 mL), then extracted with DCM (2×50 mL). The organic layer was washed with citric acid (100 ml), brine (2×100 mL), dried with $Na_2SO_4$, filtered and the filtrate was concentrated in vacuo to give the title compound (2.60 g, 98% yield) as a yellowish oil. $^1$H NMR (400 MHz, $CDCl_3$) δ 5.04 (t, J=7.2 Hz, 1H), 3.38-3.28 (m, 4H), 2.99 (s, 3H), 2.48-2.36 (m, 2H), 2.14-2.04 (m, 2H), 1.58-1.51 (m, 4H), 1.45 (s, 9H).

3-[4-(7-Azaspiro[3.5]nonan-2-yloxy)-3-methyl-2-oxo-benzimidazol-1-yl]piperidine-2,6-dione (Intermediate BK)

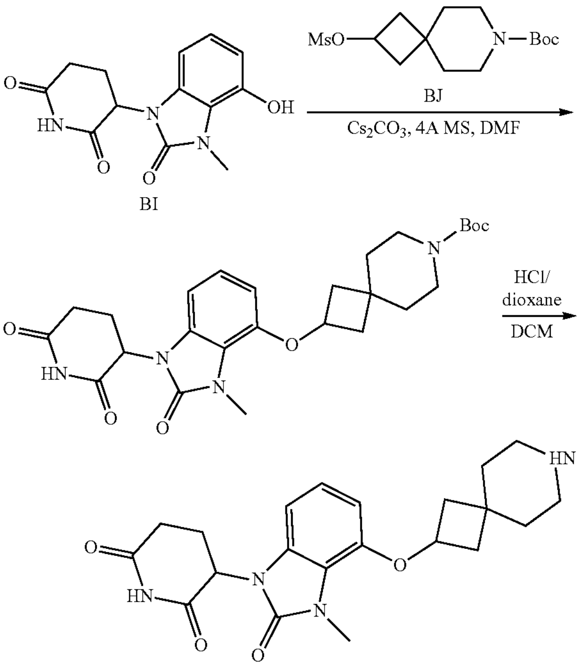

BI

BK

Step 1—Tert-butyl 2-[1-(2,6-dioxo-3-piperidyl)-3-methyl-2-oxo-benzimidazol-4-yl]oxy-7-azaspiro [3.5] nonane-7-carboxylate To a mixture of 3-(4-hydroxy-3-methyl-2-oxo-benzimidazol-1-yl)piperidine-2,6-dione (250 mg, 908 umol, Intermediate BI) and 4A molecular sieves (250 mg) in DMF (4.00 mL) was added $Cs_2CO_3$ (887 mg, 2.72 mmol) and tert-butyl 2-methylsulfonyloxy-7-azaspiro[3.5]nonane-7-carboxylate (870 mg, 2.72 mmol, Intermediate BJ) and the mixture was stirred at 80° C. for 16 hours. On completion, mixture was filtered. The filtrate was acidified with formic acid (0.05 mL) and concentrated in vacuo. The residue was purified by reverse phase (0.1% FA) to give the title compound (70.0 mg, 15% yield) as white solid. $^1$H NMR (400 MHz, DMSO-$d_6$) δ 11.07 (br s, 1H), 7.00-6.86 (m, 1H), 6.75 (d, J=8.0 Hz, 1H), 6.57 (d, J=8.4 Hz, 1H), 5.34 (dd, J=5.2, 12.8 Hz, 1H), 4.86 (q, J=6.4 Hz, 1H), 3.55 (s, 3H), 3.33-3.20 (m, 4H), 2.96-2.84 (m, 1H), 2.77-2.58 (m, 2H), 2.47-2.30 (m, 3H), 2.06-1.85 (m, 4H), 1.59-1.45 (m, 2H), 1.39 (s, 9H).

Step 2—3-[4-(7-Azaspiro[3.5]nonan-2-yloxy)-3-methyl-2-oxo-benzimidazol-1-yl]piperidine-2,6-dione To a mixture of tert-butyl 2-[1-(2,6-dioxo-3-piperidyl)-3-methyl-2-oxo-benzimidazol-4-yl]oxy-7-azaspiro[3.5] nonane-7-carboxylate (70.0 mg, 140 umol) in DCM (3.00 mL) was added HCl/dioxane (4.00 M, 1.00 mL), and the mixture was stirred at 25° C. for 1 hour. On completion, the mixture was concentrated in vacuo to give the title compound (60.0 mg, 98% yield, HCl) as white solid. LC-MS ($ESI^+$) m/z 399.2 $(M+H)^+$.

4-(1-(2,6-Dioxopiperidin-3-yl)-3-methyl-2-oxo-2,3-dihydro-1H-benzo[d]imidazol-4-yl) butanoic acid (Intermediate BL)

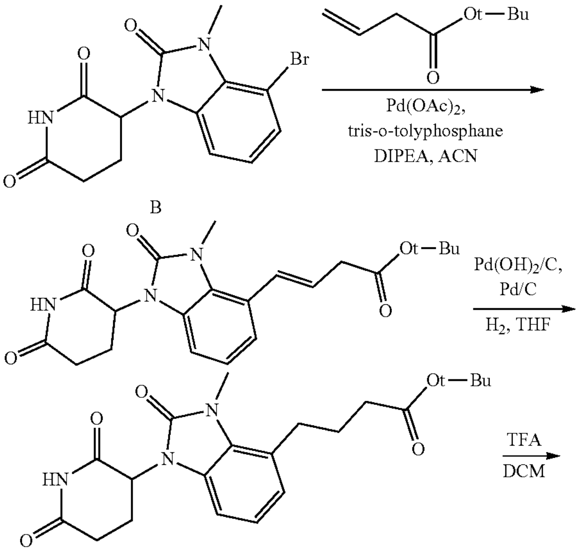

B

-continued

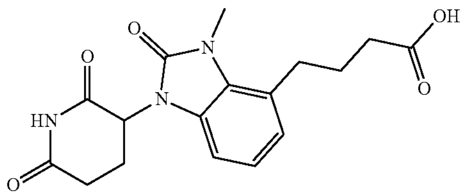

BL

Step 1—(E)-tert-butyl 4-(1-(2,6-dioxopiperidin-3-yl)-3-methyl-2-oxo-2,3-dihydro-1H-benzo[d] imidazol-4-yl)but-3-enoate A mixture of 3-(4-bromo-3-methyl-2-oxo-benzimidazol-1-yl)piperidine-2,6-dione (3.00 g, 8.87 mmol, Intermediate B), tert-butyl but-3-enoate (2.52 g, 17.74 mmol, CAS #14036-55-6), DIPEA (2.29 g, 17.7 mmol), tris-o-tolylphosphane (8.10 g, 26.6 mmol) and $Pd(OAc)_2$ (199 mg, 887 umol) in ACN (50 mL) was heated to 100° C. with stirring for 16 hours under $N_2$. On completion, the mixture was filtered and concentrated. The residue was purified by prep-HPLC: reverse phase (condition: 0.1% FA) to give the title compound (2.00 g, 56% yield) as yellow solid. $^1H$ NMR (400 MHz, DMSO-$d_6$) δ 11.10 (s, 1H), 7.14-6.95 (m, 3H), 6.24-6.03 (m, 1H), 5.58-5.48 (m, 1H), 5.38 (d, J=5.2, 12.0 Hz, 1H), 3.88 (d, J=4.4 Hz, 1H), 3.62-3.47 (m, 3H), 3.26 (d, J=6.4 Hz, 1H), 2.99-2.84 (m, 1H), 2.79-2.63 (m, 2H), 2.06-1.94 (m, 1H), 1.44 (s, 4H), 1.41 (s, 3H), 1.25 (s, 1H). LC-MS ($ESI^+$) m/z 400.1 $(M+H)^+$.

Step 2—Tert-butyl 4-(1-(2,6-dioxopiperidin-3-yl)-3-methyl-2-oxo-2,3-dihydro-1H-benzo[d]imidazol-4-Yl)butanoate To a solution of tert-butyl (E)-4-[1-(2,6-dioxo-3-piperidyl)-3-methyl-2-oxo-benzimidazol-4-yl] but-3-enoate (500 mg, 1.25 mmol) in THF (50 mL) was added Pd/C (100 mg, 10% wt) and $Pd(OH)_2$/C (100 mg, 10% wt) under $N_2$. The suspension was degassed under vacuum and purged with $H_2$ gas several times. The mixture was stirred under $H_2$ (15 psi) at 20° C. for 2 hours. On completion, the mixture was filtered and concentrated. The title compound (400 mg, 79% yield) was obtained as white solid. $^1H$ NMR (400 MHz, DMSO-$d_6$) δ 11.09 (s, 1H), 7.02-6.95 (m, 2H), 6.89-6.81 (m, 1H), 5.37 (dd, J=5.2, 12.4 Hz, 1H), 3.56 (s, 3H), 2.95-2.89 (m, 2H), 2.73-2.61 (m, 2H), 2.31 (t, J=7.2 Hz, 2H), 2.05-1.94 (m, 1H), 1.87-1.74 (m, 3H), 1.41 (s, 9H).

Step 3—4-(1-(2,6-Dioxopiperidin-3-yl)-3-methyl-2-oxo-2,3-dihydro-1H-benzo[d]imidazol-4-yl) butanoic acid To a solution of tert-butyl 4-[1-(2,6-dioxo-3-piperidyl)-3-methyl-2-oxo-benzimidazol-4-yl]butanoate (400 mg, 996 umol) in DCM (10 mL) was added TFA (4.62 g, 40.5 mmol, 3.0 mL) and the mixture was stirred at 25° C. for 2 hours. On completion, the mixture was concentrated. The title compound (250 mg, 72% yield) was obtained as colorless oil. LC-MS ($ESI^+$) m/z 346.0 $(M+H)^+$.

3-(3-Methyl-2-oxo-4-(4-oxo-4-(piperazin-1-yl) butyl)-2,3-dihydro-1H-benzo[d]imidazol-1-yl) piperidine-2,6-dione (Intermediate BM)

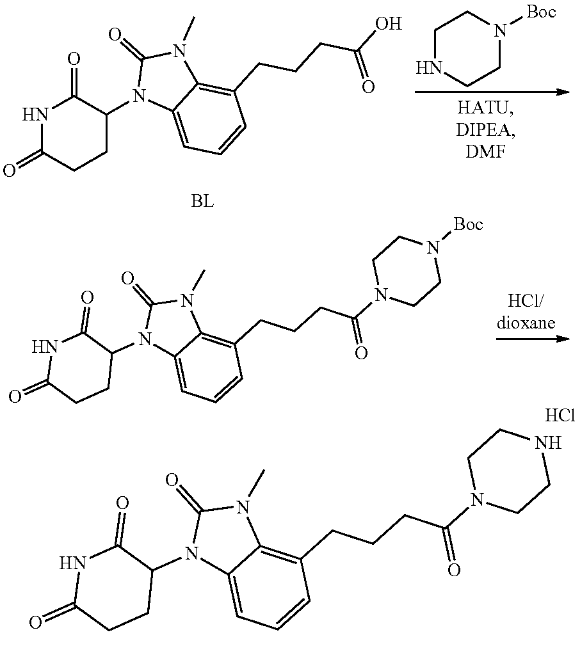

BM

Step 1—Tert-butyl 4-(4-(1-(2,6-dioxopiperidin-3-yl)-3-methyl-2-oxo-2,3-dihydro-1H-benzo[d] imidazol-4-yl)butanoyl)piperazine-1-carboxylate A mixture of 4-[1-(2,6-dioxo-3-piperidyl)-3-methyl-2-oxo-benzimidazol-4-yl]butanoic acid (150 mg, 434 umol, Intermediate BL) and HATU (247 mg, 651 umol), DIPEA (280 mg, 2.17 mmol) in DMF (1.0 mL) was stirred at 25° C. for 10 min and then tert-butyl piperazine-1-carboxylate (161 mg, 868 μmol) was added. The mixture was stirred at 25° C. for 1 hour. On completion, the mixture was quenched with water (0.1 mL) and concentrated. The residue was purified by reverse phase (condition: 0.1% FA) to give the title compound (60.0 mg, 26% yield) as yellow solid. LC-MS ($ESI^+$) m/z 414.2 $(M-100+H)^+$.

Step 2—3-(3-Methyl-2-oxo-4-(4-oxo-4-(piperazin-1-yl)butyl)-2,3-dihydro-1H-benzo[d]imidazol-1-yl) piperidine-2,6-dione To a solution of tert-butyl 4-[4-[1-(2,6-dioxo-3-piperidyl)-3-methyl-2-oxo-benzimidazol-4-yl]butanoyl]piperazine-1-carboxylate (50 mg, 97.3 umol) in DCM (3.0 mL) was added HCl/dioxane (4 M, 1.0 mL) and the mixture was stirred at 25° C. for 1 hour. On completion, the mixture was concentrated to give the title compound (40.0 mg, 91% yield, HCl) as white solid. LC-MS ($ESI^+$) m/z 414.2 $(M+H)^+$.

Benzyl N-[2-(aminomethyl)spiro[3.5]nonan-7-yl]-N-methyl-carbamate (Intermediate BN)

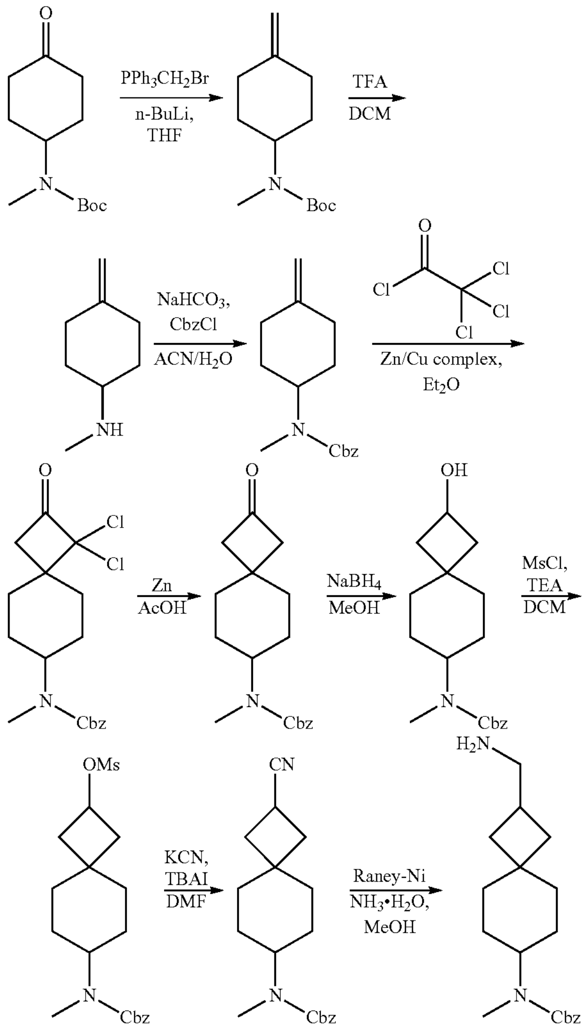

BN

Step 1—Tert-butyl N-methyl-N-(4-methylenecyclohexyl)carbamate

A solution of n-BuLi (2.5 M, 66.0 mL) was added to a mixture of methyltriphenylphosphonium bromide (58.9 g, 165 mmol) in tetrahydrofuran (200 mL) at −10° C. After stirring for 30 min at −10° C., the yellow suspension was cooled to −78° C. and a solution of tert-butyl N-methyl-N-(4-oxocyclohexyl)carbamate (25.0 g, 110 mmol, CAS #400899-84-5) in tetrahydrofuran (100 mL) was added. After stirring for 10 min at −78° C., the reaction mixture was warmed to 25° C. slowly and stirred for 3 hrs. On completion, the reaction mixture was quenched with saturated ammonium chloride (20 mL), then extracted with ethyl acetate (3×100 mL). The combined organic layers were washed with brine (100 mL), dried over anhydrous sodium sulfate, filtered and the filtrate was concentrated in vacuo. The residue was purified by column chromatography (Petroleum ether/Ethyl acetate=40/1) to give the title compound (23.7 g, 96% yield) as a white solid. $^1$H NMR (400 MHz, $CDCl_3$) δ 4.66 (s, 2H), 4.33-3.94 (m, 1H), 2.72 (s, 3H), 2.47-2.32 (m, 2H), 2.24-2.10 (m, 2H), 1.84-1.75 (m, 2H), 1.54-1.49 (m, 2H), 1.48 (m, 9H).

Step 2—N-methyl-4-methylene-cyclohexanamine

To a solution of tert-butyl N-methyl-N-(4-methylenecyclohexyl)carbamate (5.00 g, 22.2 mmol) in DCM (10 mL) was added tertfluoroacetic acid (7.70 g, 67.5 mmol, 5.00 mL). The reaction mixture was stirred at 20° C. for 2 hrs. On completion, the reaction mixture was concentrated in vacuo to give the title compound (5.31 g, 100% yield, TFA salt) as colorless oil. The product was unstable which was used for the next step without purification. $^1$H NMR (400 MHz, $CDCl_3$) δ 4.77 (s, 2H), 3.27-3.06 (m, 1H), 2.76-2.73 (m, 3H), 2.50-2.42 (m, 2H), 2.22-2.05 (m, 4H), 1.58-1.50 (m, 2H).

Step 3—Benzyl N-methyl-N-(4-methylenecyclohexyl)carbamate

To a solution of N-methyl-4-methylene-cyclohexanamine (5.31 g, 22.2 mmol, TFA salt) and $NaHCO_3$ (6.53 g, 77.7 mmol, 3.02 mL) in a mixed solvent of ACN (50 mL) and $H_2O$ (50 mL) was added CbzCl (5.68 g, 33.3 mmol, 4.73 mL). The reaction mixture was stirred at 25° C. for 12 hrs. On completion, the reaction mixture was concentrated in vacuo to remove ACN, and extracted with ethyl acetate (2×100 mL). The combined organic layer was washed with brine (20 mL), dried over anhydrous sodium sulfate, filtered and concentrated in vacuo. The residue was purified by silica gel chromatography (petroleum ether: ethyl acetate=50:1) to give the title compound (4.00 g, 68% yield) as a colorless oil. $^1$H NMR (400 MHz, $CDCl_3$) δ 7.42-7.28 (m, 5H), 5.15 (s, 2H), 4.66 (t, J=1.6 Hz, 2H), 4.33-4.01 (m, 1H), 2.79 (s, 3H), 2.37-2.34 (m, 2H), 2.18-2.15 (m, 2H), 1.87-1.73 (m, 2H), 1.57-1.48 (m, 2H). LC-MS ($ESI^+$) m/z 260.2 $(M+H)^+$.

Step 4—Benzyl N-(3,3-dichloro-2-oxo-spiro[3.5]nonan-7-yl)-N-methyl-carbamate

To a solution of benzyl N-methyl-N-(4-methylenecyclohexyl)carbamate (3.50 g, 13.5 mmol) in diethyl ether (70 mL) was added Zn/Cu complex (7 g). Then a mixture of 2,2,2-trichloroacetyl chloride (7.36 g, 40.5 mmol, 4.52 mL) in diethyl ether (140 mL) was added dropwise. The reaction mixture was stirred at 30° C. for 16 hrs. On completion, the reaction mixture was poured into saturated $NaHCO_3$ aqueous solution (100 mL) and filtered through a pad of Celite and the filtrate was collected. The organic layer was dried over anhydrous $Na_2SO_4$ and concentrated in vacuo to get a residue. The residue was purified by silica gel chromatography (petroleum ether/ethyl acetate=5/1) to give the title compound (3.80 g, 76% yield) as a white solid. $^1$H NMR (400 MHz, $CDCl_3$) δ 7.35-7.21 (m, 5H), 5.08 (s, 2H), 4.19-4.02 (m, 1H), 2.93 (s, 2H), 2.76 (s, 3H), 2.37-2.26 (m, 2H), 1.86-1.62 (m, 6H). LC-MS ($ESI^+$) m/z 370.0 $(M+H)^+$.

Step 5—Benzyl N-methyl-N-(2-oxospiro[3.5]nonan-7-yl)carbamate

To a solution of benzyl N-(3,3-dichloro-2-oxo-spiro[3.5]nonan-7-yl)-N-methyl-carbamate (3.30 g, 8.91 mmol) in acetic acid (10 mL) was added Zn (2.33 g, 35.6 mmol) at 15° C. The reaction mixture was stirred at 80° C. for 3 hrs. On completion, the reaction mixture was filtered and the filtrate was diluted with water (50 mL), then extracted with ethyl acetate (3×50 mL). The combined organic layers were washed saturated $NaHCO_3$ (30 mL) and brine (30 mL), dried over anhydrous sodium sulfate, filtered and concentrated in vacuo to give the title compound (2.40 g, 89% yield) as a gum oil. $^1H$ NMR (400 MHz, $CDCl_3$) δ 7.46-7.28 (m, 5H), 5.15 (s, 2H), 4.20-3.84 (m, 1H), 2.90-2.68 (m, 7H), 1.86-1.68 (m, 6H), 1.55-1.42 (m, 2H); LC-MS ($ESI^+$) m/z 302.2 $(M+H)^+$.

Step 6—Benzyl N-(2-hydroxyspiro[3.5]nonan-7-yl)-N-methyl-carbamate

To a solution of benzyl N-methyl-N-(2-oxospiro[3.5]nonan-7-yl)carbamate (1.00 g, 3.32 mmol) in MeOH (10 mL) was added $NaBH_4$ (151 mg, 3.98 mmol) at 0° C., and the mixture was stirred at 25° C. for 1 h. On completion, the reaction mixture was quenched with water (5 mL). The mixture was concentrated in vacuo to remove methanol, then the solution was extracted with ethyl acetate (3×20 mL). The combined organic layers were washed with brine (10 mL), dried over anhydrous sodium sulfate, filtered and the filtrate was concentrated in vacuo to give the title compound (1.00 g, 99% yield) as a yellow oil. $^1H$ NMR (400 MHz, $CDCl_3$) δ 7.44-7.28 (m, 5H), 5.14 (s, 2H), 4.28 (q, J=7.2 Hz, 1H), 4.05-3.75 (m, 1H), 2.79 (s, 3H), 2.40-2.27 (m, 1H), 2.22-2.11 (m, 1H), 1.71-1.64 (m, 3H), 1.62-1.51 (m, 4H), 1.48-1.46 (m, 3H); LC-MS ($ESI^+$) m/z 304.1 $(M+H)^+$.

Step 7—[7-[Benzyloxycarbonyl(methyl)amino]spiro[3.5]nonan-2-yl] methanesulfonate To a solution of benzyl N-(2-hydroxyspiro[3.5]nonan-7-yl)-N-methyl-carbamate (1.00 g, 3.30 mmol) in DCM (20 mL) was added TEA (1.00 g, 9.89 mmol, 1.38 mL) and MsCl (566 mg, 4.94 mmol, 383 uL) at 0° C. The reaction mixture was stirred at 20° C. for 3 hrs. On completion, the reaction mixture was quenched with water (10 mL). The organic layer was separated and washed with brine (50 mL), dried over anhydrous sodium sulfate, filtered and concentrated in vacuo to give the title compound (1.26 g, 100% yield) as yellow oil. $^1H$ NMR (400 MHz, $CDCl_3$) δ 7.42-7.28 (m, 5H), 5.13 (s, 2H), 5.01-4.97 (m, 1H), 4.05-3.74 (m, 1H), 2.98 (s, 3H), 2.78 (s, 3H), 2.45 (m, 1H), 2.34-2.21 (m, 1H), 2.11-2.06 (m, 1H), 2.02-1.97 (m, 1H), 1.74-1.67 (m, 2H), 1.59-1.36 (m, 6H). LC-MS ($ESI^+$) m/z 382.1 $(M+H)^+$.

Step 8—Benzyl N-(2-cyanospiro[3.5]nonan-7-yl)-N-methyl-carbamate

To a solution of [7-[benzyloxycarbonyl(methyl)amino]spiro[3.5]nonan-2-yl] methanesulfonate (1.26 g, 3.30 mmol) in DMF (10 mL) was added KCN (430 mg, 6.61 mmol, 283 uL) and TBAI (122 mg, 330 umol). The reaction mixture was heated to 120° C. for 16 hrs. On completion, the reaction mixture was diluted with water (10 mL), and extracted with ethyl acetate (3×50 mL). The combined organic layers were wash with brine (30 mL), dried over anhydrous sodium sulfate, filtered and the filtrate was concentrated in vacuo. The residue was purified by silica gel chromatography (petroleum ether/ethyl acetate=4/1) to give the title compound (570 mg, 55% yield) as a yellow oil. $^1H$ NMR (400 MHz, $CDCl_3$) δ 7.45-7.28 (m, 5H), 5.13 (s, 2H), 4.07-3.73 (m, 1H), 3.06-2.98 (m, 1H), 2.78 (s, 3H), 2.32-2.22 (m, 1H), 2.20-2.06 (m, 3H), 1.96-1.87 (m, 1H), 1.82-1.78 (m, 1H), 1.62-1.59 (m, 2H), 1.54-1.36 (m, 4H). LC-MS ($ESI^+$) m/z 313.1 $(M+H)^+$.

Step 9—Benzyl N-[2-(aminomethyl)spiro[3.5]nonan-7-yl]-N-methyl-carbamate

To a solution of benzyl N-(2-cyanospiro[3.5]nonan-7-yl)-N-methyl-carbamate (370 mg, 1.18 mmol) in MeOH (5 mL) was added Raney-Ni (101 mg, 1.18 mmol), $NH_3H_2O$ (3.37 g, 31.7 mmol, 3.70 mL, 33% solution) under $N_2$. The suspension was degassed under vacuum and purged with $H_2$ several times. The mixture was stirred under $H_2$ (50 psi) at 25° C. for 4 hours. On completion, the reaction mixture was filtered and concentrated in vacuo to give the title compound (300 mg, 84% yield) as colorless oil. $^1H$ NMR (400 MHz, $CDCl_3$) δ 7.47-7.29 (m, 5H), 5.15 (s, 2H), 4.89-4.50 (m, 2H), 4.04-3.78 (m, 1H), 2.79 (s, 3H), 2.69 (d, J=7.2 Hz, 2H), 2.28-2.20 (m, 1H), 2.02-1.73 (m, 6H), 1.48-1.31 (m, 6H); LC-MS ($ESI^+$) m/z 317.1 $(M+H)^+$.

Benzyl methyl(2-methylenespiro[3.5]nonan-7-yl)carbamate (Intermediate BO)

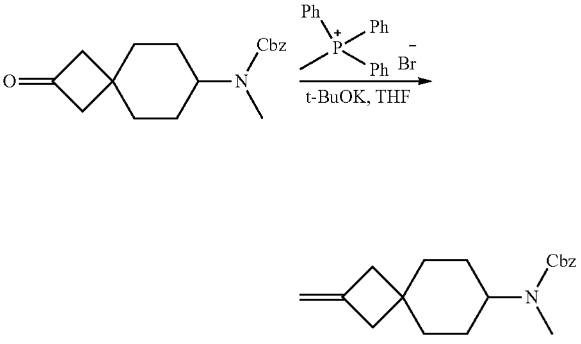

BO

To a solution of methyl(triphenyl)phosphonium; bromide (1.69 g, 4.74 mmol) in THF (15 mL) was added t-BuOK (532 mg, 4.74 mmol) at 0° C., then the mixture was warmed to 40° C. and stirred for 3 hrs. Then benzyl N-methyl-N-(2-oxospiro[3.5]nonan-7-yl)carbamate (650 mg, 2.16 mmol, synthesized via Steps 1-5 of Intermediate BN) in THF (5 mL) was added at 0° C. and the mixture was warmed to 40° C. for 1 hr. On completion, the reaction was quenched with $NH_4Cl$ aqueous (10 mL). The aqueous was extracted with EA (3×20 mL). The combined organic layer was washed with brine, dried over $Na_2SO_4$ and concentrated in vacuo. The residue was purified by column chromatography (PE:EA=100:1) to give the title compound (400 mg, 62% yield) as a colorless oil. $^1H$ NMR (400 MHz, $CDCl_3$) δ 7.42-7.28 (m, 5H), 5.14 (s, 2H), 4.89-4.76 (m, 2H), 4.09-3.76 (m, 1H), 2.79 (s, 3H), 2.41-2.37 (m, 4H), 1.79-1.76 (m, 2H), 1.64-1.58 (m, 2H), 1.53-1.38 (m, 4H).

3-(3-Methyl-4-((7-(methylamino)spiro[3.5]nonan-2-yl)methyl)-2-oxo-2,3-dihydro-1H-benzo[d]imidazol-1-yl)piperidine-2,6-dione (Intermediate BP)

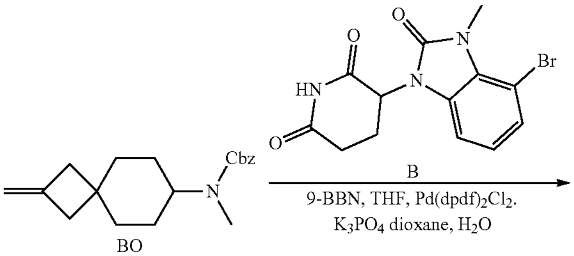

BO

-continued

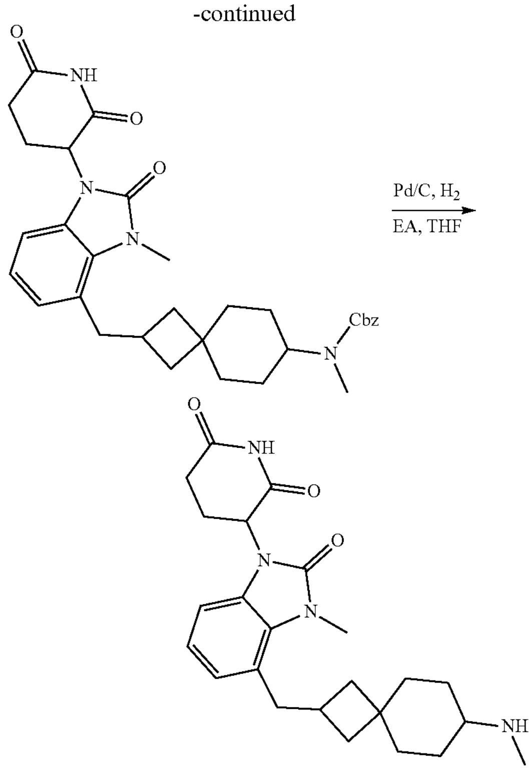

BP

Step 1—Benzyl (2-((1-(2,6-dioxopiperidin-3-yl)-3-methyl-2-oxo-2,3-dihydro-1H-benzo[d]imidazol-4-yl)methyl)spiro[3.5]nonan-7-yl)(methyl)carbamate A mixture of benzyl N-methyl-N-(2-methylenespiro[3.5]nonan-7-yl)carbamate (1.30 g, 4.34 mmol, Intermediate BO) and 9-BBN (0.5 M, 8.68 mL, CAS #280-64-8) in THF (10 mL) was stirred at 25° C. for 3 hrs. The above mixture was added to a mixture of 3-(4-bromo-3-methyl-2-oxo-benzimidazol-1-yl)piperidine-2,6-dione (2.20 g, 6.51 mmol, Intermediate B), ditert-butyl(cyclopentyl)phosphane; dichloropalladium; iron (282 mg, 434 umol) and $K_3PO_4$ (2.30 g, 10.8 mmol) in a mixture of dioxane (20 mL) and $H_2O$ (2 mL). Then the mixture was stirred at 80° C. for 4 hrs under $N_2$ atmosphere. On completion, the reaction was filtered. The filtrate was purified by reverse phase (FA) to give the title compound (1.10 g, 45% yield) as a yellow solid. $^1H$ NMR (400 MHz, $CDCl_3$) δ=8.52 (s, 1H), 7.49-7.28 (m, 5H), 7.04-6.91 (m, 1H), 6.85 (d, J=7.6 Hz, 1H), 6.67 (d, J=7.6 Hz, 1H), 5.22 (dd, J=4.8, 12.0 Hz, 1H), 5.13 (s, 2H), 3.73-3.46 (m, 3H), 3.20-2.74 (m, 7H), 2.60-2.35 (m, 2H), 2.25-2.16 (m, 1H), 2.06-1.98 (m, 1H), 1.92-1.74 (m, 3H), 1.68-1.38 (m, 9H).

Step 2—3-(3-Methyl-4-((7-(methylamino)spiro[3.5]nonan-2-yl)methyl)-2-oxo-2,3-dihydro-1H-benzo[d]imidazol-1-yl)piperidine-2,6-dione To a solution of benzyl N-[2-[[1-(2,6-dioxo-3-piperidyl)-3-methyl-2-oxo-benzimidazol-4-yl]methyl] spiro[3.5]nonan-7-yl]-N-methyl-carbamate (1.00 g, 1.79 mmol) in EA (10 mL) and THF (10 mL) was added Pd/C (200 mg, 10 wt %) under $N_2$ atmosphere. The suspension was degassed and purged with $H_2$ gas 3 times. The mixture was stirred at 25° C. for 4 hrs under $H_2$ (15 psi) atmosphere. On completion, the reaction was filtered. The filtrate was concentrated to give the title compound (700 mg, 92% yield, 90% purity) as a white solid. $^1H$ NMR (400 MHz, $CDCl_3$) δ 7.00-6.92 (m, 1H), 6.85 (d, J=7.6 Hz, 1H), 6.66 (d, J=7.6 Hz, 1H), 5.30-5.15 (m, 1H), 3.66 (s, 3H), 3.02 (d, J=7.2 Hz, 1H), 2.97-2.90 (m, 2H), 2.83-2.74 (m, 2H), 2.58-2.45 (m, 1H), 2.41 (s, 3H), 2.32-2.18 (m, 2H), 2.04-1.97 (m, 1H), 1.93-1.67 (m, 4H), 1.63-1.42 (m, 4H), 1.40-1.28 (m, 2H), 1.20-1.02 (m, 2H).

3-[4-(3-Aminoprop-1-ynyl)-3-methyl-2-oxo-benzimidazol-1-yl]piperidine-2,6-dione (Intermediate BQ)

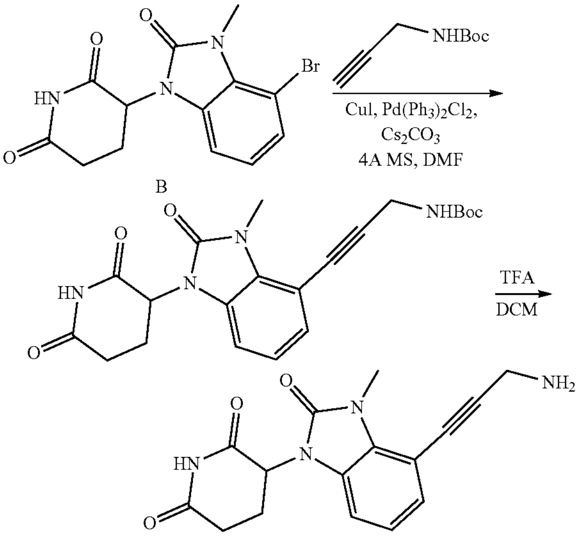

BQ

Step 1—Tert-butyl N-[3-[1-(2,6-dioxo-3-piperidyl)-3-methyl-2-oxo-benzimidazol-4-yl]prop-2-ynyl]carbamate To a mixture of 3-(4-bromo-3-methyl-2-oxo-benzimidazol-1-yl)piperidine-2,6-dione (500 mg, 1.48 mmol, Intermediate B), CuI (28.1 mg, 147 umol), $Cs_2CO_3$ (1.45 g, 4.44 mmol), 4A molecular sieves (50.0 mg), and dichloropalladium; triphenylphosphane (103 mg, 147 umol) in DMF (5.00 mL) at $N_2$ atmosphere. Then a solution of tert-butyl N-prop-2-ynylcarbamate (344 mg, 2.22 mmol, CAS #92136-39-5) in DMF (5.00 mL) was added to the above solution. The reaction mixture was stirred at 80° C. for 2 hrs. On completion, the mixture was concentrated in vacuo. The residue was diluted with water (15 mL) and exacted with EA (3×15 mL). The organic phase was dried over anhydrous sodium sulfate and concentrated in vacuo. The residue was purified by prep-HPLC (column: Phenomenex luna C18 150*40 mm*15 um; mobile phase: [water (0.225% FA)-ACN]; B %: 22%-52%, 9 min) to give the title compound (290 mg, 37% yield) as light yellow solid. $^1H$ NMR (400 MHz, DMSO-$d_6$) δ 11.18 (s, 1H), 7.60-7.54 (m, 1H), 7.20-7.10 (m, 1H), 7.10-7.04 (m, 1H), 5.50-5.40 (m, 1H), 4.00 (d, J=5.7 Hz, 2H), 3.62 (s, 3H), 2.99-2.82 (m, 1H), 2.79-2.60 (m, 2H), 2.55-2.50 (m, 1H), 2.11-1.94 (m, 1H), 1.41 (s, 9H).

Step 2—3-[4-(3-Aminoprop-1-ynyl)-3-methyl-2-oxo-benzimidazol-1-yl]piperidine-2,6-dione To a solution of tert-butyl N-[3-[1-(2,6-dioxo-3-piperidyl)-3-methyl-2-oxo-benzimidazol-4-yl]prop-2-ynyl]carbamate (30.0 mg, 72.7 umol) in DCM (1.00 mL) was added TFA (308 mg, 2.70 mmol) and the mixture was stirred at 25° C. for 0.5 hr. On completion, the mixture was concentrated in vacuo to give the title compound (31 mg, 99% yield, TFA) as yellow solid. LC-MS ($ESI^+$) m/z 335.1 $(M+Na)^+$.

3-[3-Methyl-4-[2-[(2R)-morpholin-2-yl]ethynyl]-2-oxo-benzimidazol-1-yl]piperidine-2,6-dione (Intermediate BR)

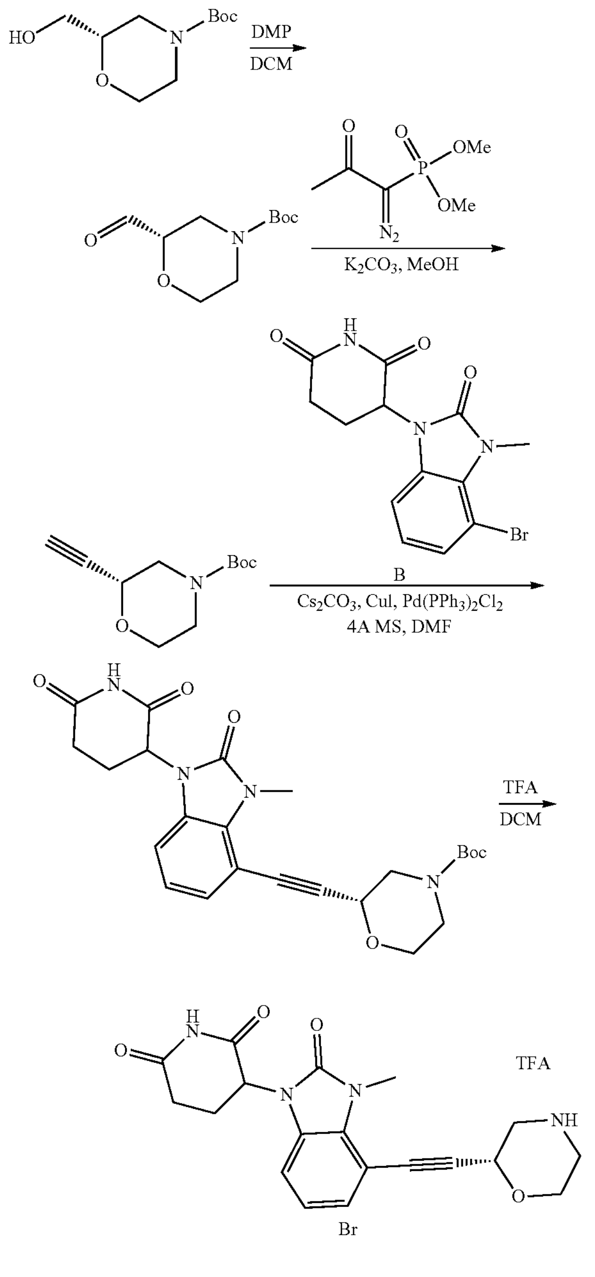

Step 1—Tert-butyl (2S)-2-formylmorpholine-4-carboxylate

To a solution of tert-butyl (2S)-2-(hydroxymethyl)morpholine-4-carboxylate (1.00 g, 4.60 mmol, CAS #135065-76-8) in DCM (10 mL) was added DMP (2.15 g, 5.06 mmol) at 0° C. Then the mixture was warmed to 25° C. and stirred for 16 hours. On completion, the mixture was quenched with saturated sodium thiosulfate solution (50 mL) and adjusted pH to 7-8 with sodium bicarbonate saturated solution (20 mL), and then extracted with ethyl acetate (50 mL×3). The combined organic layers were washed with sodium chloride solution (25 mL), dried over anhydrous sodium sulfate, filtered and concentrated in vacuo to give the title compound (1.5 g, crude) as a yellow gum. $^1H$ NMR (400 MHz, DMSO-$d_6$) δ 9.56 (s, 1H), 3.83-3.69 (m, 4H), 3.56-3.54 (m, 2H), 3.50-3.40 (m, 2H), 0.98 (s, 9H).

Step 2—Tert-butyl (2R)-2-ethynylmorpholine-4-carboxylate

To a solution of tert-butyl (2S)-2-formylmorpholine-4-carboxylate (1.50 g, 6.97 mmol) and $K_2CO_3$ (2.89 g, 20.9 mmol) in MeOH (10 mL) was added 1-diazo-1-dimethoxyphosphoryl-propan-2-one (1.34 g, 6.97 mmol) dropwise at 0° C. Then mixture was stirred at 25° C. and stirred for 16 hrs. On completion, the reaction mixture was filtered and concentrated in vacuo. The residue was purified by silica gel chromatography (petroleum ether:ethyl acetate=1:0 to 50:1) to give the title compound (630 mg, 42% yield) as white solid. $^1H$ NMR (400 MHz, DMSO-$d_6$) δ 4.40-4.31 (m, 1H), 3.90-3.80 (m, 1H), 3.75-3.52 (m, 2H), 3.50-3.31 (m, 2H), 3.30-3.15 (m, 2H), 1.40 (s, 9H).

Step 3—Tert-butyl (2R)-2-[2-[1-(2,6-dioxo-3-piperidyl)-3-methyl-2-oxo-benzimidazol-4-yl]ethynyl]morpholine-4-carboxylate To a solution of 3-(4-bromo-3-methyl-2-oxo-benzimidazol-1-yl)piperidine-2,6-dione (1.01 g, 2.98 mmol, Intermediate B), $Cs_2CO_3$ (2.91 g, 8.95 mmol), CuI (56.8 mg, 298 umol), $Pd(PPh_3)_2Cl_2$ (209 mg, 298 umol) and 4A molecular sieves (2.98 mmol) in DMF (5 mL) was degassed and purged with nitrogen for 3 times, then added a solution of tert-butyl (2R)-2-ethynylmorpholine-4-carboxylate (630 mg, 2.98 mmol) in DMF (5 mL) was added. Then the mixture was stirred at 80° C. for 3 hrs under nitrogen atmosphere. On completion, the reaction mixture was filtered and was concentrated in vacuo. The residue was purified by silica gel chromatography (petroleum ether:ethyl acetate=20:1 to 1:2) to give the title compound (700 mg, 46% yield, 93% purity) as yellow solid. LC-MS ($ESI^+$) m/z 413.3 $(M-56)^+$.

Step 4—3-[3-Methyl-4-[2-[(2R)-morpholin-2-yl]ethynyl]-2-oxo-benzimidazol-1-yl]piperidine-2,6-dione To a solution of tert-butyl (2R)-2-[2-[1-(2,6-dioxo-3-piperidyl)-3-methyl-2-oxo-benzimidazol-4-yl]ethynyl]morpholine-4-carboxylate (40.0 mg, 85.3 umol) in DCM (1 mL) was added TFA (4.05 mmol, 0.3 mL) at 25° C. Then the reaction mixture was stirred at 25° C. for 1 hr. On completion, the reaction mixture was concentrated in vacuo to give the title compound (40.0 mg, 97% yield, TFA salt) as yellow oil. LC-MS ($ESI^+$) m/z 369.2 $(M+H)^+$.

3-[5-(4-aminobut-1-ynyl)-3-methyl-2-oxo-benzimidazol-1-yl]piperidine-2,6-dione (Intermediate BS)

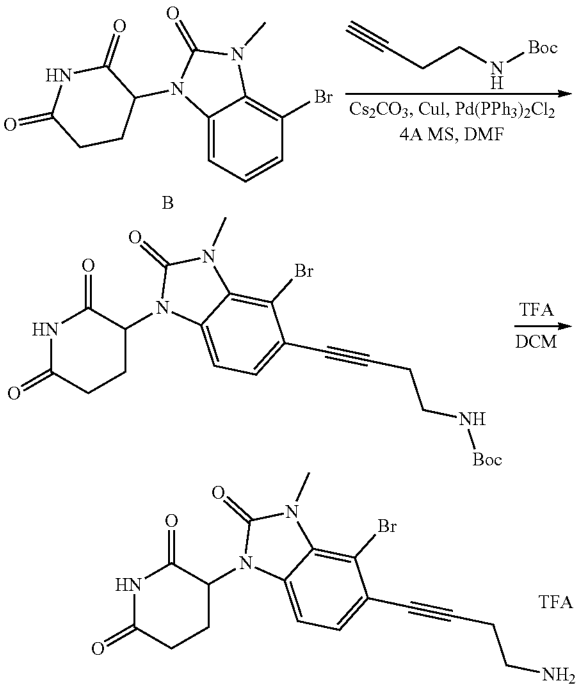

B

BS

Step 1—Tert-butyl N-[4-[1-(2,6-dioxo-3-piperidyl)-3-methyl-2-oxo-benzimidazol-5-yl]but-3-ynyl] carbamate A solution of 3-(5-bromo-3-methyl-2-oxo-benzimidazol-1-yl)piperidine-2,6-dione (400 mg, 1.18 mmol, Intermediate B), $Cs_2CO_3$ (1.16 g, 3.55 mmol), CuI (22.5 mg, 118 umol), $Pd(PPh_3)_2Cl_2$ (83.0 mg, 118 umol) and 4A molecular sieves (1.18 mmol) in DMF (4 mL) was degassed and purged with nitrogen three times. Next, a solution of tert-butyl Nbut-3-ynylcarbamate (240 mg, 1.42 mmol) in DMF (1 mL) was added, and then the mixture was stirred at 80° C. for 3 hrs. On completion, the reaction mixture was filtered and was concentrated in vacuo. The residue was purified by reverse phase (0.1% FA condition) to give the title compound (300 mg, 41% yield) as a green solid. $^1$H NMR (400 MHz, DMSO-$d_6$) δ 11.10 (s, 1H), 7.26 (s, 1H), 7.09 (s, 1H), 7.01 (t, J=5.6 Hz, 1H), 3.40-3.17 (m, 1H), 3.15 (s, 3H), 2.88-2.71 (m, 2H), 2.66-2.52 (m, 2H), 2.03-2.01 (m, 1H), 1.42-1.36 (m, 1H), 1.35 (s, 9H); LC-MS (ESI$^+$) m/z 427.3 $(M+H)^+$.

Step 2—3-[5-(4-aminobut-1-ynyl)-3-methyl-2-oxo-benzimidazol-1-yl]piperidine-2,6-dione To a solution of tert-butyl N-[4-[1-(2,6-dioxo-3-piperidyl)-3-methyl-2-oxo-benzimidazol-5-yl]but-3-ynyl]carbamate (40.0 mg, 93.7 umol) in DCM (1 mL) was added TFA (5.94 mmol, 439 uL) at 25° C. Then the reaction mixture was stirred at 25° C. for 1 hr. On completion, the reaction mixture was concentrated in vacuo to give the title compound (40.0 mg, 96% yield, TFA salt) as yellow oil. LC-MS (ESI$^+$) m/z 327.1 $(M+H)^+$.

3-[4-(5-aminopent-1-ynyl)-3-methyl-2-oxo-benzimidazol-1-yl]piperidine-2,6-dione (Intermediate BT)

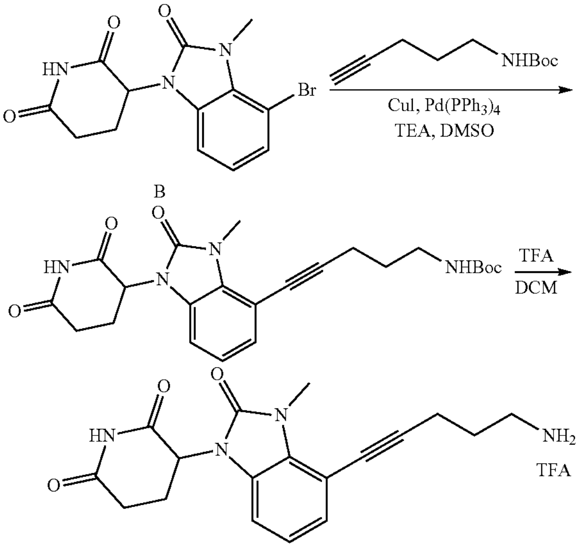

B

BT

Step 1—tert-butyl N-[5-[1-(2,6-dioxopiperidin-3-yl)-3-methyl-2-oxo-1,3-benzodiazol-4-yl]pent-4-yn-1-yl]carbamate To a stirred solution of 3-(4-bromo-3-methyl-2-oxo-1,3-benzodiazol-1-yl)piperidine-2,6-dione (10.00 g, 29.57 mmol, Intermediate B) in DMSO (100 mL) were added tert-butyl N-(pent-4-yn-1-yl)carbamate (8.13 g, 44.36 mmol, CAS #151978-50-6), TEA (50 mL), CuI (0.56 g, 2.96 mmol) and $Pd(PPh_3)_4$ (3.42 g, 2.96 mmol) at rt. The resulting mixture was stirred for 3 h at 80° C. under a nitrogen atmosphere. Upon completion, the resulting mixture was cooled down to rt and filtered. The filtered cake was washed with EtOAc (3×20 mL). The filtrate was diluted with EtOAc (600 mL) and washed with brine (8×100 mL), and dried over anhydrous $Na_2SO_4$. After filtration, the filtrate was concentrated under reduced pressure. The residue was purified by silica gel column chromatography, eluted with 80% EtOAc in petroleum ether, to afford the title compound (11 g, 85%) as a brown solid. $^1$H NMR (400 MHz, $CD_3OD$) δ 7.15 (dd, J=1.5, 7.5 Hz, 1H), 7.10-7.01 (m, 2H), 5.34 (dd, J=5.4, 12.2 Hz, 1H), 3.78 (s, 3H), 3.23 (t, J=6.9 Hz, 2H), 2.99-2.75 (m, 3H), 2.54 (t, J=7.1 Hz, 2H), 2.21-2.17 (m, 1H), 1.84-1.80 (m, 2H), 1.45 (s, 9H).

Step 2—3-[4-(5-aminopent-1-yn-1-yl)-3-methyl-2-oxo-1,3-benzodiazol-1-yl]piperidine-2,6-dione trifluoroacetate

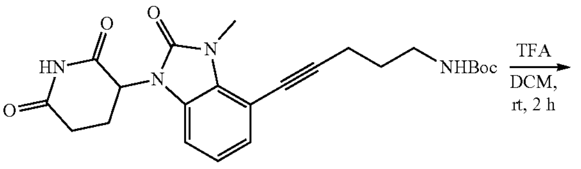

3

-continued

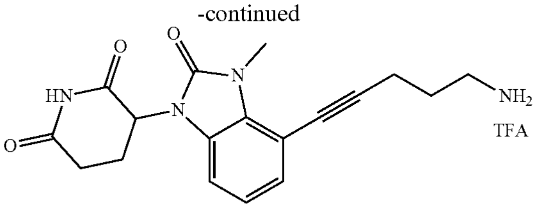

4

To a stirred solution of tert-butyl N-[5-[1-(2,6-dioxopiperidin-3-yl)-3-methyl-2-oxo-1,3-benzodiazol-4-yl]pent-4-yn-1-yl]carbamate (5.50 g, 12.47 mmol) in DCM (50 mL) was added TFA (10 mL) dropwise at rt. The resulting mixture was stirred for 2 h at rt. Upon completion, the resulting mixture was concentrated under reduced pressure, and the residue was triturated with $Et_2O$ to afford the title compound (5.70 g) as a yellow semi-solid. $^1H$ NMR (400 MHz, $CD_3OD$) δ 7.16-7.07 (m, 2H), 7.05-7.01 (m, 1H), 5.33 (dd, J=5.5, 12.3 Hz, 1H), 3.75 (s, 3H), 3.15-3.07 (m, 2H), 2.99-2.84 (m, 1H), 2.87-2.71 (m, 2H), 2.66 (t, J=7.0 Hz, 2H), 2.21-2.11 (m, 1H), 2.03-1.95 (m, 2H); LC/MS (ESI, m/z): $[(M+1)]^+$=341.1.

Tert-butyl N-methyl-N-(3-prop-2-ynoxypropyl)carbamate (Intermediate BU)

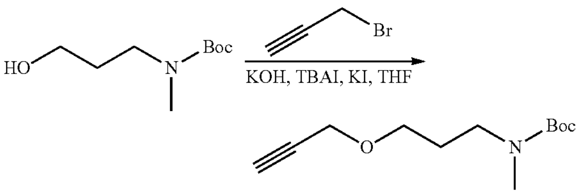

BU

To a solution of 3-bromoprop-1-yne (1.32 g, 11.1 mmol, CAS #106-96-7) and tert-butyl N-(3-hydroxypropyl)-N-methyl-carbamate (2.00 g, 10.6 mmol, CAS #98642-44-5) in THF (20 mL) was added TBAI (234 mg, 634 umol) and KI (263 mg, 1.59 mmol). Then KOH (698 mg, 10.6 mmol, 85% purity) was added into the above mixture. The reaction mixture was stirred at 25° C. for 12 hrs. On completion, the mixture was concentrated in vacuo to remove the solvent, the residue was diluted with water (30 mL), then extracted with EA (3×40 mL). The organic phase was dried over $Na_2SO_4$, filtered and the filtrate was concentrated in vacuo. The residue was purified by silica gel chromatography ($SiO_2$) to give the title compound (1.15 g, 48% yield) as colorless oil. $^1H$ NMR (400 MHz, $CDCl_3$) δ 4.15-4.11 (m, 2H), 3.57-3.49 (m, 2H), 3.29 (t, J=6.8 Hz, 2H), 2.86 (s, 3H), 2.42 (t, J=2.4 Hz, 1H), 1.85-1.76 (m, 2H), 1.46 (s, 9H).

3-[3-Methyl-4-[3-[3-(methylamino)propoxy]propyl-2-oxo-benzimidazol-1-yl]piperidine-2,6-dione (Intermediate BV)

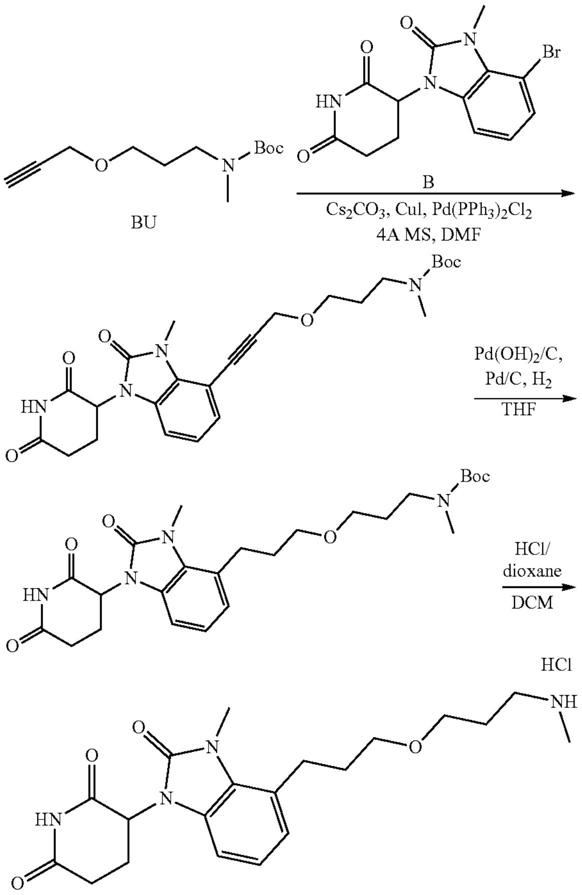

BV

Step 1—Tert-butyl N-[3-[3-[1-(2,6-dioxo-3-piperidyl)-3-methyl-2-oxo-benzimidazol-4-yl]prop-2-ynoxy]propyl]-N-methyl-carbamate 3-(4-bromo-3-methyl-2-oxo-benzimidazol-1-yl)piperidine-2,6-dione (300 mg, 887 umol, Intermediate B), tert-butyl N-methyl-N-(3-prop-2-ynoxypropyl)carbamate (504 mg, 2.22 mmol, Intermediate BU), $Pd(PPh_3)_2Cl_2$ (125 mg, 177 umol), $Cs_2CO_3$ (1.45 g, 4.44 mmol), CuI (33.8 mg, 177 umol) and 4A molecular sieves (150 mg) in DMF (8 mL) was heated at 80° C. for 2 hrs under $N_2$. On completion, the mixture was concentrated in vacuo. The residue was purified by reverse phase (0.1% FA condition) to give the title compound (200 mg, 40% yield) as a yellow solid. LC-MS ($ESI^+$) m/z 507.3 $(M+Na)^+$.

Step 2—Tert-butyl N-[3-[3-[1-(2,6-dioxo-3-piperidyl)-3-methyl-2-oxo-benzimidazol-4-yl]propoxy]propyl-N-methyl-carbamate To a solution of tert-butyl N-[3-[3-[1-(2,6-dioxo-3-piperidyl)-3-methyl-2-oxo-benzimidazol-4-yl] prop-2-ynoxy]propyl]-N-methyl-carbamate (200 mg, 351 umol) in THF (6 mL) was added Pd/C (0.100 g, 10% wt) and $Pd(OH)_2$/C (0.100 g, 10% wt). The reaction mixture was stirred at 25° C. for 10 hrs under $H_2$ (15 Psi) atmosphere. On completion, the mixture was filtered and the filtrate was concentrated in vacuo to give the title compound (200 mg, 930% yield) as a yellow solid. $^1$H NMR (400 MHz, DMSO-$d_6$) δ 11.10 (s, 1H), 7.00-6.92 (m, 2H), 6.90-6.84 (m, 1H), 5.44-5.24 (m, 1H), 3.56 (s, 3H), 3.44-3.40 (m, 4H), 3.22 (t, J=7.2 Hz, 2H), 2.99-2.92 (m, 2H), 2.76 (s, 3H), 2.74-2.69 (m, 1H), 2.65-2.58 (m, 2H), 2.04-1.96 (m, 1H), 1.87-1.79 (m, 2H), 1.74-1.65 (m, 2H), 1.38 (s, 9H); LC-MS (ESI$^+$) m/z 511.3 $(M+Na)^+$.

Step 3—3-[3-Methyl-4-[3-[3-(methylamino) propoxy]propyl-2-oxo-benzimidazol-1-yl]piperidine-2,6-dione To a solution of tert-butyl N-[3-[3-[1-(2,6-dioxo-3-piperidyl)-3-methyl-2-oxo-benzimidazol-4-yl] propoxy]propyl]-N-methyl-carbamate (200 mg, 327 umol) in DCM (4 mL) was added HCl/dioxane (4 M, 3.20 mL). The reaction mixture was stirred at 25° C. for 2 hrs. On completion, the mixture was concentrated in vacuo to give the title compound (160 mg, 100% yield, HCl) as a white solid. $^1$H NMR (400 MHz, DMSO-$d_6$) δ 11.08 (s, 1H), 7.02-6.92 (m, 2H), 6.90-6.83 (m, 1H), 5.44-5.24 (dd, J=5.6, 12.4 Hz, 1H), 3.57 (s, 3H), 3.49-3.43 (m, 4H), 3.00-2.91 (m, 4H), 2.74-2.53 (m, 6H), 2.04-1.94 (m, 1H), 1.90-1.81 (m, 4H); LC-MS (ESI$^+$) m/z 389.2 $(M+H)^+$.

3-(7-bromo-2-oxo-1,3-benzoxazol-3-yl)piperidine-2,6-dione (Intermediate BW)

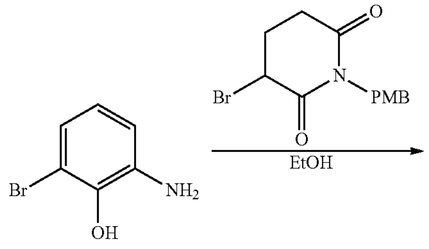

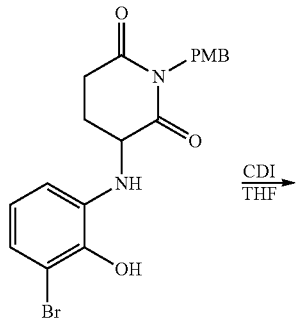

-continued

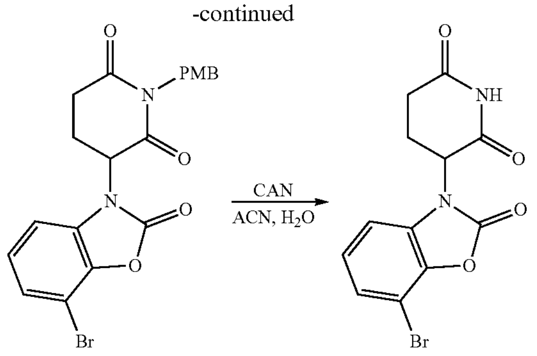

BW

Step 1—3-(3-bromo-2-hydroxyphenylamino)-1-(4-methoxybenzyl)piperidine-2,6-dione

To a solution of 3-bromo-1-(4-methoxybenzyl)piperidine-2,6-dione (145 mg, 0.77 mmol) in EtOH (10 mL) was added 2-amino-6-bromophenol (200 mg, 0.64 mmol) and at r.t.. The reaction mixture was heated and stirred under microwave irradiation at 140° C. for 25 mins. The reaction mixture was concentrated under reduced pressure. The residue was purified via reverse phase column chromatography ($ACN/H_2O$ with 0.1% TFA) to give title compound (80 mg, 30% yield) as a colorless oil. $^1$H NMR (400 MHz, DMSO-$d_6$) δ 8.94 (s, 1H), 7.18 (d, J=8.6 Hz, 2H), 6.85 (d, J=8.7 Hz, 2H), 6.75 (dd, J=6.9, 2.6 Hz, 1H), 6.67-6.59 (m, 2H), 5.48 (d, J=7.1 Hz, 1H), 4.76 (q, J=14.3 Hz, 2H), 4.58-4.40 (m, 1H), 3.71 (s, 3H), 3.05-2.89 (m, 1H), 2.83-2.61 (m, 1H), 2.25-2.10 (m, 1H), 2.02-1.97 (m, 1H). LC-MS (ESI$^+$): m/z 421.1 $(M+H)^+$.

Step 2—3-(7-bromo-2-oxobenzo[d]oxazol-3(2H)-yl)-1-(4-methoxybenzyl)piperidine-2,6-dione To a solution of 3-(3-bromo-2-hydroxyphenylamino)-1-(4-methoxybenzyl)piperidine-2,6-dione (80 mg, 0.19 mmol) in THF (5 mL) was added a solution of CDI (46 mg, 0.284 mmol) in THF (5 mL) at r.t. under $N_2$. The reaction mixture was stirred at 35° C. for 12 h. The reaction mixture was then concentrated under reduced pressure and the residue was purified via column chromatography (Petroleum ether/EtOAc=2/1) to give title compound (70 mg, 74% yield) as a white solid. $^1$H NMR (400 MHz, DMSO-$d_6$) δ 7.39 (dd, J=8.0, 1.1 Hz, 1H), 7.23-7.16 (m, 4H), 6.86 (d, J=8.7 Hz, 2H), 5.56 (dd, J=13.3, 5.3 Hz, 1H), 4.89-4.70 (m, 2H), 3.72 (s, 3H), 3.04-3.01 (m, 1H), 2.87-2.83 (m, 1H), 2.71-2.65 (m, 1H), 2.27-2.18 (m, 1H). LC-MS (ESI$^+$): m/z 445.1 $(M+H)^+$.

Step 3—3-(7-bromo-2-oxobenzo[d]oxazol-3(2H)-yl) piperidine-2,6-dione

To a solution of 3-(7-bromo-2-oxobenzo[d]oxazol-3(2H)-yl)-1-(4-methoxybenzyl)piperidine-2,6-dione (80 mg, 0.180 mmol) in $CH_3CN$ (2 mL) was added a solution of CAN (690 mg, 1.26 mmol) in 0.5 mL of water dropwise at r.t.. The reaction mixture was stirred at r.t. for 2 hours. The reaction mixture was then extracted with EtOAc (15 mL×2), the organic layer washed with brine, dried over anhydrous $Na_2SO_4$ and concentrated under reduced pressure. The residue was purified via Pre-TLC (Petroleum ether/EtOAc=1/1) to give the title compound (9.7 mg, 17% yield) as a pale yellow solid. $^1$H NMR (400 MHz, DMSO-$d_6$) δ 11.26 (s, 1H), 7.39 (dd, J=8.2, 0.8 Hz, 1H), 7.33-7.27 (m, 1H), 7.19 (t, J=8.1 Hz, 1H), 5.42-5.38 (m, 1H), 2.97-2.79 (m, 1H), 2.75-2.60 (m, 2H), 2.27-2.12 (m, 1H). LC-MS ($ESI^+$): m/z 325.1 $(M+H)^+$.

3-[2-Oxo-7-[3-(4-piperidyloxy)propyl]-1,3-benzoxazol-3-yl]piperidine-2,6-dione (Intermediate BX)

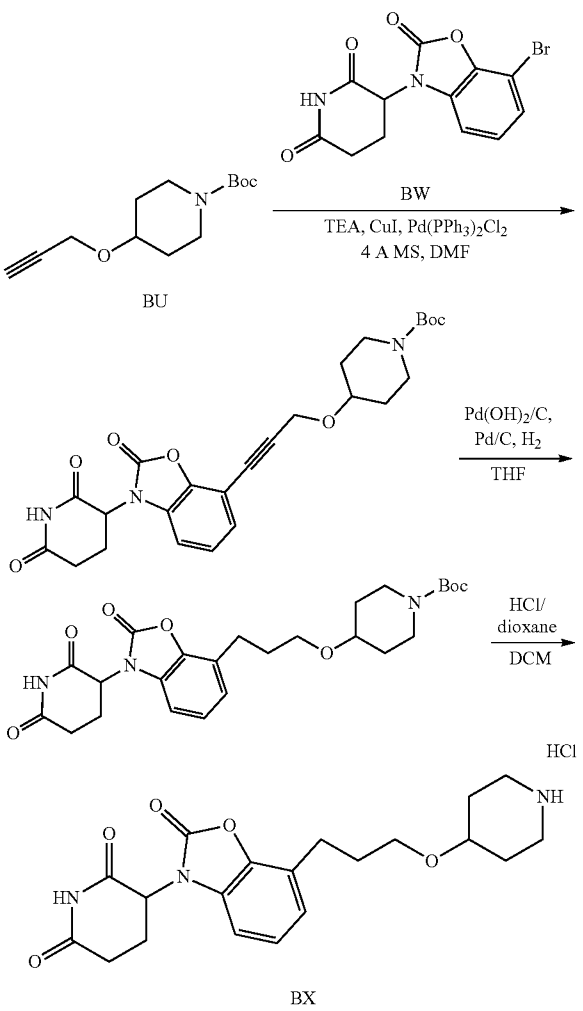

Step 1—Tert-butyl 4-[3-[3-(2,6-dioxo-3-piperidyl)-2-oxo-1,3-benzoxazol-7-yl]prop-2-vnoxy] piperidine-1-carboxylate To a solution of 3-(7-bromo-2-oxo-1,3-benzoxazol-3-yl) piperidine-2,6-dione (500 mg, 1.54 mmol, Intermediate BW) and tert-butyl 4-prop-2-ynoxypiperidine-1-carboxylate (441 mg, 1.85 mmol, synthesized via Step 1 of Intermediate BB) in DMF (10 mL) was added TEA (1.56 g, 15.3 mmol, 2.14 mL), CuI (29.3 mg, 153 umol) 4A molecular sieves (100 mg) and $Pd(PPh_3)_2Cl_2$ (107 mg, 153 umol). The reaction mixture was stirred at 80° C. for 2 hr under $N_2$. On completion, the mixture was diluted with $H_2O$ (20 mL), then extracted with EA (2×50 mL). The organic phase was dried over by $Na_2SO_4$, then filtered and the filtrate was concentrated in vacuo to give a residue. The residue was purified by reverse phase (0.1% FA condition) to give the title compound (260 mg, 34.9% yield) as a yellow solid. $^1H$ NMR (400 MHz, DMSO-$d_6$) δ11.23 (s, 1H), 7.31 (dd, J=2.0, 6.8 Hz, 1H), 7.27-7.19 (m, 2H), 5.39 (dd, J=5.2, 12.8 Hz, 1H), 4.51 (s, 2H), 3.77-3.70 (m, 1H), 3.68-3.60 (m, 2H), 3.13-2.99 (m, 2H), 2.93-2.83 (m, 1H), 2.74-2.68 (m, 1H), 2.67-2.61 (m, 1H), 2.22-2.13 (m, 1H), 1.90-1.81 (m, 2H), 1.47-1.40 (m, 2H), 1.39 (s, 9H); LC-MS ($ESI^+$) m/z 506.2 $(M+Na)^+$.

Step 2—Tert-butyl 4-[3-[3-(2,6-dioxo-3-piperidyl)-2-oxo-1,3-benzoxazol-7-yl]propoxy]piperidine-1-carboxylate To a solution of tert-butyl 4-[3-[3-(2,6-dioxo-3-piperidyl)-2-oxo-1,3-benzoxazol-7-yl]prop-2-ynoxy] piperidine-1-carboxylate (240 mg, 496 umol) in THF (10 mL) was added Pd/C (100 mg, 605 umol, 10 wt %) and $Pd(OH)_2/C$ (100 mg, 10 wt %). The reaction mixture was stirred at 20° C. for 2 hr under $H_2$ (15 psi). On completion, the mixture was filtered, and the filtrate was concentrated in vacuo to give the title compound (220 mg, 91% yield) as a white solid. $^1H$ NMR (400 MHz, DMSO-$d_6$) δ 11.20 (s, 1H), 7.17-7.06 (m, 2H), 7.02 (d, J=7.2 Hz, 1H), 5.35 (dd, J=5.2, 12.8 Hz, 1H), 3.64-3.57 (m, 2H), 3.45-3.42 (m, 2H), 3.41-3.38 (m, 1H), 3.00 (t, J=9.0 Hz, 2H), 2.93-2.85 (m, 1H), 2.76 (t, J=7.6 Hz, 2H), 2.70-2.63 (m, 2H), 2.19-2.12 (m, 1H), 1.89-1.81 (m, 2H), 1.79-1.72 (m, 2H), 1.39 (s, 9H), 1.34-1.27 (m, 2H); LC-MS ($ESI^+$) m/z 510.1 $(M+Na)^+$.

Step 3—3-[2-Oxo-7-[3-(4-piperidyloxy)propyl]-1,3-benzoxazol-3-yl]piperidine-2,6-dione To a solution of tert-butyl 4-[3-[3-(2,6-dioxo-3-piperidyl)-2-oxo-1,3-benzoxazol-7-yl]propoxy] piperidine-1-carboxylate (220 mg, 451 umol) in DCM (4 mL) was added HCl/dioxane (4 M, 2 mL). The reaction mixture was stirred at 20° C. for 2 hrs. On completion, the mixture was concentrated in vacuo to give the title compound (190 mg, 99% yield, HCl) as a yellow solid. $^1H$ NMR (400 MHz, DMSO-$d_6$) δ11.22 (s, 1H), 7.18-7.10 (m, 2H), 7.03 (dd, J=2.0, 6.8 Hz, 1H), 5.39 (dd, J=5.2, 12.8 Hz, 1H), 3.56-3.50 (m, 1H), 3.45 (t, J=6.0 Hz, 2H), 3.18-3.06 (m, 2H), 2.99-2.88 (m, 3H), 2.77 (t, J=7.6 Hz, 2H), 2.71-2.62 (m, 2H), 2.20-2.12 (m, 1H), 1.99-1.91 (m, 2H), 1.91-1.83 (m, 2H), 1.73-1.63 (m, 2H); LC-MS ($ESI^+$) m/z 388.2 $(M+H)^+$.

3-[4-(3,9-diazaspiro[5.5]undecan-3-yl)-3-methyl-2-oxo-benzimidazol-1-yl] piperidine-2,6-dione (Intermediate BY)

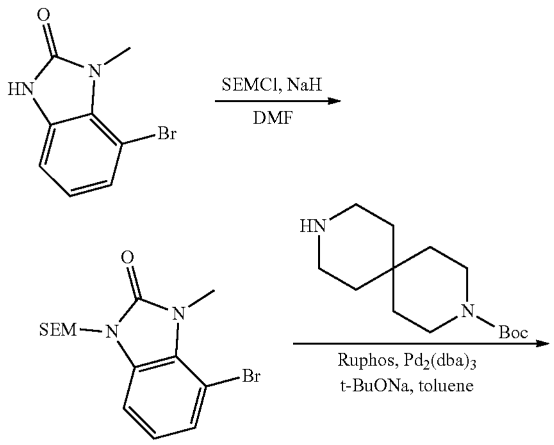

-continued

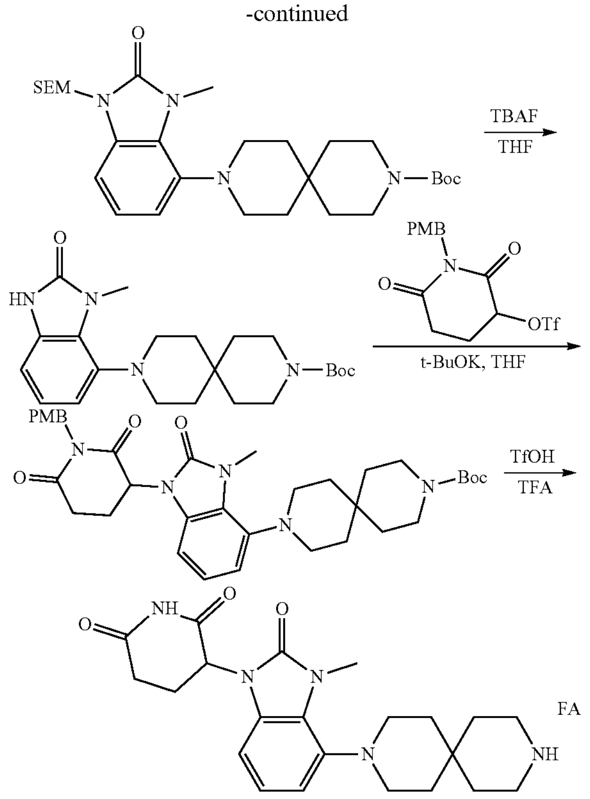

BY

Step 1—4-Bromo-3-methyl-1-(2-trimethylsilylethoxymethyl)benzimidazol-2-one

To a mixture of 4-bromo-3-methyl-1H-benzimidazol-2-one (50.0 g, 220 mmol, synthesized via Steps 1-3 of Intermediate B) in DMF (500 mL) was added NaH (13.2 g, 330 mmol, 60% dispersion in mineral oil) at 0° C. and the reaction mixture was stirred for 30 min. Then SEMCl (44.0 g, 264 mmol) was added dropwise at 0° C. and the reaction mixture was stirred for 16 hours. On completion, the mixture was poured into water (500 mL). The mixture was extracted by DCM (3×200 mL) and the combined organic layer was dried over by $Ns_2SO_4$. The mixture was filtered and the filtrate was concentrated in vacuo. The residue was purified by column chromatography (petroleum ether/ethyl acetate=20/1) to give the title compound (60.0 g, 76% yield) as yellow oil. $^1$H NMR (400 MHz, DMSO-$d_6$) δ 7.34-7.21 (m, 2H), 7.01-6.97 (m, 1H), 5.24 (s, 2H), 3.61 (s, 3H), 3.55-3.51 (m, 2H), 0.85-0.81 (m, 2H), 0.07 (s, 9H).

Step 2—Tert-butyl 9-[3-methyl-2-oxo-1-(2-trimethylsilylethoxymethyl)benzimidazol-4-yl]-3,9-diazaspiro[5.5]undecane-3-carboxylate To a solution of 4-bromo-3-methyl-1-(2-trimethylsilylethoxymethyl)benzimidazol-2-one (5.0 g, 13.9 mmol) and tert-butyl 3,9-diazaspiro[5.5]undecane-3-carboxylate (3.74 g, 14.6 mmol, CAS #173405-78-2) in toluene (50 mL) was added RuPhos (1.31 g, 2.80 mmol), $Pd_2(dba)_3$ (1.28 g, 1.40 mmol), t-BuONa (3.36 g, 34.9 mmol), and the reaction mixture was stirred at 80° C. for 2 hours. On completion, the reaction mixture was filtered, and the filtrate was concentrated in vacuo to give a residue. The residue was purified by reverse phase (0.1% FA condition) to give the title compound (4.4 g, 59% yield) as yellow oil. LC-MS (ESI$^+$) m/z 531.5 $(M+1)^+$.

Step 3—Tert-butyl 9-(3-methyl-2-oxo-1H-benzimidazol-4-yl)-3,9-diazaspiro[5.5]undecane-3-carboxylate To a solution of tert-butyl 9-[3-methyl-2-oxo-1-(2-trimethylsilylethoxymethyl)benzimidazol-4-yl]-3,9-diazaspiro[5.5]undecane-3-carboxylate (4.4 g, 8.29 mmol) in THF (40 mL) was added TBAF (10.8 g, 41.4 mmol), and the reaction mixture was stirred at 75° C. for 24 hours. On completion, the reaction mixture was diluted with $H_2O$ (20 mL), and then extracted with EA (2×100 mL), washed with brine (2×200 mL), dried over $Na_2SO_4$, filtered and concentrated in vacuo to give a residue. The residue was purified by column chromatography ($SiO_2$, petroleum ether/ethyl acetate=10/1 to 2/1, PE/EA=1/1) to give the title compound (2.3 g, 69% yield) as a white solid. $^1$H NMR (400 MHz, $CDCl_3$) δ 10.21 (s, 1H), 7.00-6.96 (m, 1H), 6.94-6.85 (m, 2H), 3.76 (s, 3H), 3.47-3.40 (m, 4H), 3.04-2.86 (m, 4H), 1.79-1.58 (m, 6H), 1.48 (s, 9H), 1.46-1.35 (m, 2H); LC-MS (ESI$^+$) m/z 401.2 $(M+1)^+$.

Step 4—Tert-butyl 9-[1-[1-[(4-methoxyphenyl)methyl]-2,6-dioxo-3-piperidyl]-3-methyl-2-oxo-benzimidazol-4-yl]-3,9-diazaspiro[5.5]undecane-3-carboxylate To a solution of tert-butyl 9-(3-methyl-2-oxo-1H-benzimidazol-4-yl)-3,9-diazaspiro[5.5]undecane-3-carboxylate (2.2 g, 5.49 mmol) in THF (20 mL) was added t-BuOK (924 mg, 8.24 mmol) at 0° C., the mixture was stirred at 0° C. for 0.5 hour. Then a solution of [1-[(4-methoxyphenyl)methyl]-2,6-dioxo-3-piperidyl] trifluoromethanesulfonate (2.30 g, 6.04 mmol, Intermediate A) in THF (20 mL) was added dropwise to the mixture, and the reaction mixture was stirred at 20° C. for 16 hours. On completion, the mixture was acidified with HCOOH to pH=3-5, diluted with water (100 mL), then extracted with EA (2×100 mL). The organic layer was washed with brine (100 mL), and then concentrated in vacuo to give a residue. The residue was purified by reverse phase (0.1% FA condition) to give the title compound (2.3 mg, 66% yield) as a yellow solid. $^1$H NMR (400 MHz, $CDCl_3$) δ 7.40-7.34 (m, 2H), 6.94-6.85 (m, 2H), 6.84-6.81 (m, 2H), 6.28 (d, J=7.6 Hz, 1H), 5.21 (dd, J=5.2, 12.8 Hz, 1H), 5.03-4.92 (m, 2H), 3.80 (s, 3H), 3.76 (s, 3H), 3.50-3.38 (m, 4H), 3.04-2.97 (m, 1H), 2.97-2.88 (m, 4H), 2.87-2.77 (m, 1H), 2.68-2.55 (m, 1H), 2.19-2.12 (m, 1H), 1.81-1.72 (m, 2H), 1.70-1.61 (m, 4H), 1.48 (s, 9H), 1.46-1.37 (m, 2H); LC-MS (ESI$^+$) m/z 632.5 $(M+1)^+$.

Step 5—3-[4-(3,9-diazaspiro[5.5]undecan-3-yl)-3-methyl-2-oxo-benzimidazol-1-yl]piperidine-2,6-dione To a solution of tert-butyl 9-[1-[1-[(4-methoxyphenyl)methyl]-2,6-dioxo-3-piperidyl]-3-methyl-2-oxo-benzimidazol-4-yl]-3,9-diazaspiro[5.5]undecane-3-carboxylate (500 mg, 791 umol) in TFA (2.4 mL) was added TfOH (850 mg, 5.66 mmol, 500 uL), and the reaction mixture was stirred at 65° C. for 12 hours. On completion, the reaction mixture concentrated in vacuo to give a residue. The residue was purified by reverse phase (0.1% FA condition) to give the title compound (250 mg, 69% yield, FA salt) as a yellow solid. $^1$H NMR (400 MHz, DMSO-$d_6$) δ 10.95 (s, 1H), 9.39

(s, 1H), 7.01-6.94 (m, 2H), 6.91-6.83 (m, 1H), 5.35 (dd, J=5.2, 12.8 Hz, 1H), 3.62 (s, 3H), 3.07-2.97 (m, 4H), 2.95-2.81 (m, 5H), 2.72-2.57 (m, 2H), 2.05-1.93 (m, 1H), 1.85-1.66 (m, 4H), 1.63-1.45 (m, 4H).

3-(3-Methyl-2-oxo-4-vinyl-benzimidazol-1-yl)piperidine-2,6-dione (Intermediate BZ)

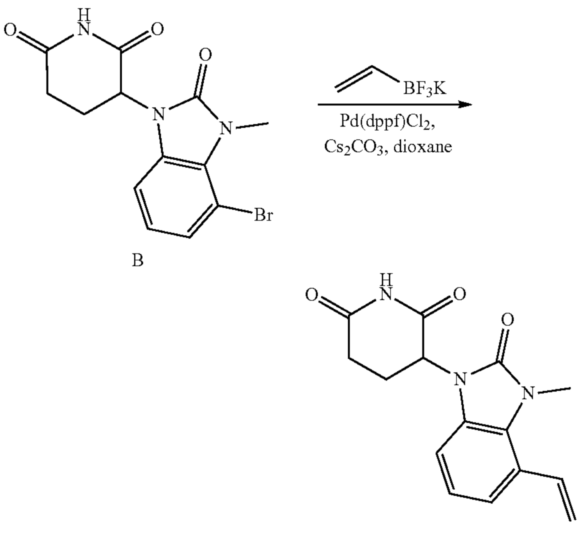

B

BZ

A mixture of 3-(4-bromo-3-methyl-2-oxo-benzimidazol-1-yl)piperidine-2,6-dione (10.0 g, 29.5 mmol, Intermediate B), potassium; trifluoro(vinyl)boranuide (11.8 g, 88.7 mmol, CAS #13682-77-4), $Cs_2CO_3$ (2 M in water, 29.5 mL) and $Pd(dppf)Cl_2 \cdot CH_2Cl_2$ (1.69 g, 2.07 mmol) in dioxane (300 mL) was stirred at 90° C. for 2 hrs under nitrogen. On completion, the reaction mixture was filtered and the filtrated was concentrated in vacuo. The residue was purified by silica gel chromatography (petroleum ether:ethyl acetate=1:2) to give the title compound (5.70 g, 67% yield) as yellow solid. $^1H$ NMR (400 MHz, DMSO-$d_6$) δ 11.10 (s, 1H), 7.40 (dd, J=10.8, 17.2 Hz, 1H), 7.18 (d, J=7.2 Hz, 1H), 7.10-6.98 (m, 2H), 5.72 (d, J=17.2 Hz, 1H), 5.47-5.31 (m, 2H), 3.54 (s, 3H), 2.96-2.82 (m, 1H), 2.79-2.57 (m, 2H), 2.06-1.94 (m, 1H).

2-[1-(2,6-Dioxo-3-piperidyl)-3-methyl-2-oxo-benzimidazol-4-yl]acetaldehyde (Intermediate CA)

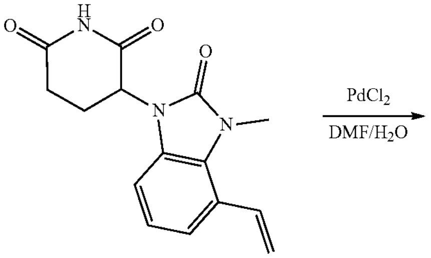

BZ

-continued

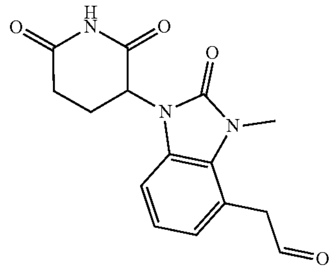
CA

To a solution of 3-(3-methyl-2-oxo-4-vinyl-benzimidazol-1-yl)piperidine-2,6-dione (1.00 g, 3.51 mmol, Intermediate BZ) in a mixed solvent of DMF (20 mL) and $H_2O$ (2 mL) was added $PdCl_2$ (1.24 g, 7.01 mmol, CAS #7647-10-1) at 25° C. under $N_2$. The mixture was stirred at 25° C. for 18 hours. On completion, the reaction mixture was concentrated under reduced pressure to remove solvent. The residue was diluted with water (20 mL) and extracted with EA (3×20 mL). The combined organic layers were dried over $Na_2SO_4$, filtered and concentrated in vacuo to give the title compound (260 mg, 24% yield) as black brown oil. LC-MS (ESI$^+$) m/z 301.9 $(M+H)^+$.

3-[4-[2-(2,7-Diazaspiro[3.5]nonan-2-yl)ethyl]-3-methyl-2-oxo-benzimidazol-1-yl]piperidine-2,6-dione (Intermediate CB)

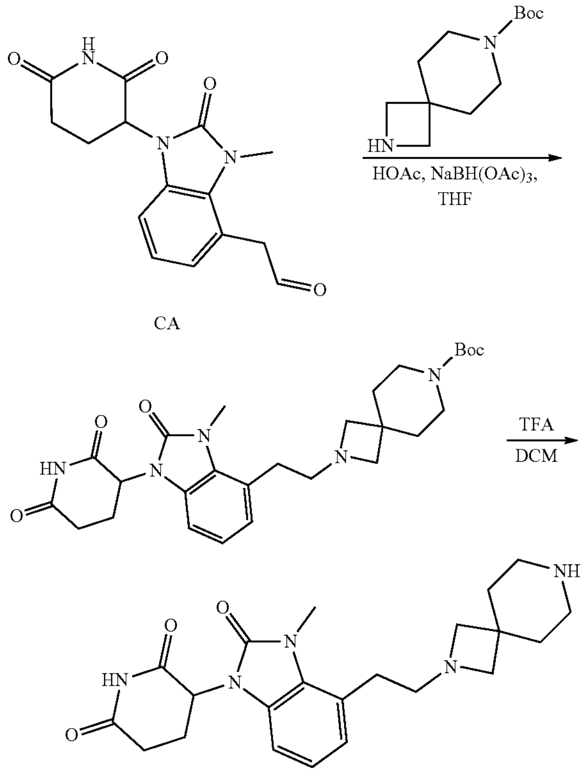

CA

CB

Step 1—Tert-butyl 2-[2-[1-(2,6-dioxo-3-piperidyl)-3-methyl-2-oxo-benzimidazol-4-yl]ethyl]-2,7-diazaspiro[3.5]nonane-7-carboxylate To a mixture of 2-[1-(2,6-dioxo-3-piperidyl)-3-methyl-2-oxo-benzimidazol-4-yl]acetaldehyde (200 mg, 663 umol, Intermediate CA) and tert-butyl 2,7-diazaspiro[3.5]nonane-7-carboxylate (187 mg, 663 umol, CAS #896464-16-7) in THF (5 mL) was added HOAc (39.8 mg, 663 umol) in one portion at 25° C. The mixture was stirred at 25° C. for 0.5 hour. Then $NaBH(OAc)_3$ (281 mg, 1.33 mmol) was added to the mixture. The mixture was stirred at 25° C. for 1.5 hours. On completion, the reaction mixture was quenched with water (0.5 mL) at 25° C., and then concentrated in vacuo to give a residue. The residue was purified by prep-HPLC (column: Shim-pack C18 150*25*10 um; mobile phase: [water (0.225% FA)–ACN]; B %: 6%-36%, 10 min) to give the title compound (35.0 mg, 10% yield) as a white solid. LC-MS ($ESI^+$) m/z 512.4 $(M+H)^+$.

Step 2—3-[4-[2-(2,7-Diazaspiro[3.5]nonan-2-yl)ethyl]-3-methyl-2-oxo-benzimidazol-1-yl]piperidine-2,6-dione To a mixture of tert-butyl 2-[2-[1-(2,6-dioxo-3-piperidyl)-3-methyl-2-oxo-benzimidazol-4-yl] ethyl]-2,7-diazaspiro[3.5]nonane-7-carboxylate (15.0 mg, 29.3 umol) in DCM (3 mL) was added TFA (3.00 mL) at 25° C. The mixture was stirred at 25° C. for 2 hours. On completion, the reaction mixture was concentrated in vacuo to give the title compound (15.0 mg, 97% yield, FA salt) as yellow solid. LC-MS ($ESI^+$) m/z 412.3 $(M+H)^+$.

3-[4-(2,7-Diazaspiro[3.5]nonan-7-ylmethyl)-3-methyl-2-oxo-benzimidazol-1-yl]piperidine-2,6-dione (Intermediate CC)

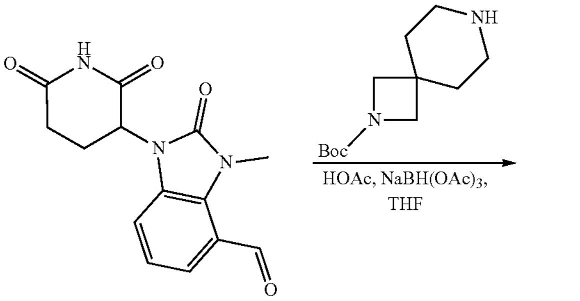

BD

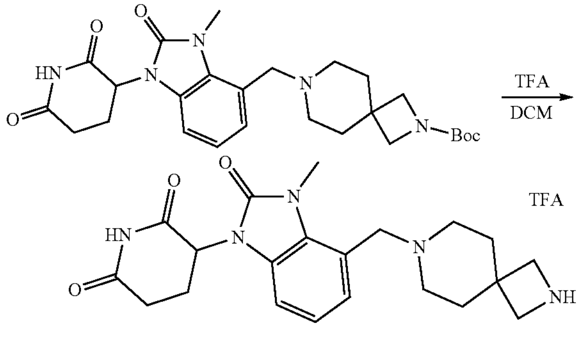

CC

Step 1—Tert-butyl 7-[[1-(2,6-dioxo-3-piperidyl)-3-methyl-2-oxo-benzimidazol-4-yl]methyl]-2,7-diazaspiro[3.5]nonane-2-carboxylate To a solution of tert-butyl 2,7-diazaspiro[3.5]nonane-2-carboxylate (133 mg, 591 umol, CAS #236406-55-6) in THF (15 mL) and DMF (3 mL) was added HOAc (591 umol, 33.8 uL) and 1-(2,6-dioxo-3-piperidyl)-3-methyl-2-oxo-benzimidazole-4-carbaldehyde (170 mg, 591 umol, Intermediate BD). The reaction mixture was stirred at 80° C. for 20 minutes, then $NaBH(OAc)_3$ (250 mg, 1.18 mmol) was added to the mixture at 0° C. The reaction mixture was stirred at 25° C. for 45 hrs. On completion, the reaction mixture was quenched with 1 mL $H_2O$ and concentrated in vacuo to give a residue. The residue was purified by reverse phase (0.1% FA condition) to give the title compound (115 mg, 39% yield) as a white solid. $^1H$ NMR (400 MHz, DMSO-$d_6$) δ 11.10 (s, 1H), 7.06 (d, J=7.6 Hz, 1H), 6.95 (t, J=7.6 Hz, 1H), 6.86 (d, J=8.0 Hz, 1H), 5.44-5.29 (m, 1H), 3.66 (s, 3H), 3.59 (s, 2H), 3.51 (s, 6H), 2.96-2.82 (m, 1H), 2.75-2.69 (m, 1H), 2.65-2.55 (m, 2H), 2.05-1.97 (m, 1H), 1.63 (s, 5H), 1.37 (s, 9H); LC-MS ($ESI^+$) m/z 498.3 $(M+H)^+$.

Step 2—3-[4-(2,7-Diazaspiro[3.5]nonan-7-ylmethyl)-3-methyl-2-oxo-benzimidazol-1-yl]piperidine-2,6-dione To a solution of tert-butyl 7-[[1-(2,6-dioxo-3-piperidyl)-3-methyl-2-oxo-benzimidazol-4-yl]methyl]-2,7-diazaspiro[3.5]nonane-2-carboxylate (50.0 mg, 100 umol) in DCM (5 mL) was added TFA (54.0 mmol, 4 mL) at 25° C. The reaction mixture was stirred at 25° C. for 1 hr. On completion, the reaction mixture was concentrated in vacuo to give the title compound (38 mg, 95% yield) as colorless oil. LC-MS ($ESI^+$) m/z 398.2 $(M+H)^+$.

3-(4-amino-3-methyl-2-oxo-benzimidazol-1-yl)piperidine-2,6-dione (Intermediate CD)

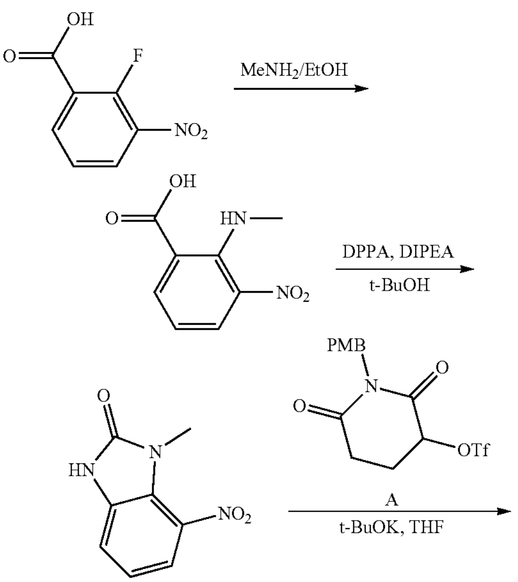

-continued

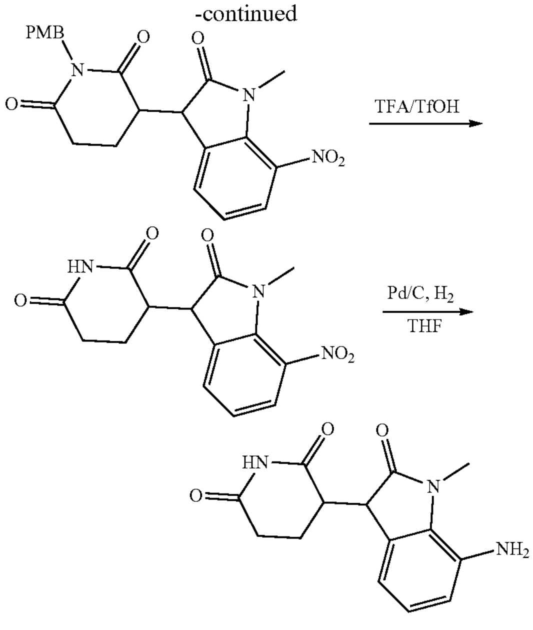

CD

Step 1—2-(Methylamino)-3-nitro-benzoic acid

To a solution of $MeNH_2$/EtOH (54.0 mmol, 200 mL, 30% solution) was added 2-fluoro-3-nitro-benzoic acid (10.0 g, 54.0 mmol) in portions at 0° C. Then the reaction mixture was stirred at 20° C. for 2 hrs. On completion, the mixture was concentrated in vacuo. The residue was diluted with water (100 mL), acidified with citric acid to pH=3-5, stirred and filtered. The filter cake was dried in vacuo to give the title compound (9.60 g, 91% yield) as a yellow solid. $^1H$ NMR (400 MHz, DMSO-$d_6$) δ 13.41 (s, 1H), 8.62 (s, 1H), 8.04 (dd, J=1.6, 8.0 Hz, 1H), 7.97 (dd, J=1.6, 8.0 Hz, 1H), 6.72 (t, J=8.0 Hz, 1H), 2.70 (s, 3H).

Step 2—3-Methyl-4-nitro-1H-benzimidazol-2-one

To a solution of 2-(methylamino)-3-nitro-benzoic acid (8.60 g, 43.8 mmol) and DIPEA (17.0 g, 132 mmol) in t-BuOH (200 mL) was added DPPA (12.1 g, 43.8 mmol) dropwise at 0° C. Then the reaction mixture was stirred at 85° C. for 12 hours. On completion, the mixture was diluted with MeOH (100 mL), cooled to 10-20° C., filtered and the filter cake was dried in vacuo to give the title compound (6.80 g, 80% yield) as a yellow solid. $^1H$ NMR (400 MHz, DMSO-$d_6$) δ 11.61 (s, 1H), 7.58 (dd, J=0.8, 8.0 Hz, 1H), 7.30 (dd, J=0.8, 8.0 Hz, 1H), 7.18-7.07 (m, 1H), 3.34 (s, 3H).

Step 3—1-[(4-Methoxyphenyl)methyl]-3-(3-methyl-4-nitro-2-oxo-benzimidazol-1-yl)piperidine-2,6-dione To a solution of 3-methyl-4-nitro-1H-benzimidazol-2-one (7.20 g, 37.3 mmol) in THF (70 mL) was added t-BuOK (8.37 g, 74.6 mmol) at −10-0° C. One hour later, a solution of [1-[(4-methoxyphenyl)methyl]-2,6-dioxo-3-piperidyl] trifluoromethanesulfonate (21.3 g, 55.9 mmol, Intermediate A) in THF (50 mL) was added into the above mixture and the reaction mixture was stirred at 0-20° C. for 12 hrs. On completion, the mixture was acidified with FA to pH=3-5, diluted with water (300 mL), and extracted with EA (2×300 mL). The organic layer was washed with brine (200 mL), then concentrated in vacuo. The residue was purified by reverse phase (0.1% FA condition) to give the title compound (5.80 g, 37% yield) as a yellow solid. $^1H$ NMR (400 MHz, DMSO-$d_6$) δ 7.69 (dd, J=0.8, 8.0 Hz, 1H), 7.46 (d, J=8.0 Hz, 1H), 7.27-7.17 (m, 3H), 6.93-6.78 (m, 2H), 5.67 (dd, J=5.2, 12.8 Hz, 1H), 4.94-4.62 (m, 2H), 3.72 (s, 3H), 3.41 (s, 3H), 3.11-2.98 (m, 1H), 2.89-2.70 (m, 2H), 2.17-2.08 (m, 1H).

Step 4—3-(3-Methyl-4-nitro-2-oxo-benzimidazol-1-yl)piperidine-2,6-dione

To a solution of 1-[(4-methoxyphenyl)methyl]-3-(3-methyl-4-nitro-2-oxo-benzimidazol-1-yl) piperidine-2,6-dione (2.00 g, 4.71 mmol) in TFA (20 mL) was added TfOH (2 mL). The reaction mixture was stirred at 60° C. for 12 hours. On completion, the mixture was concentrated in vacuo. The residue was purified by reverse phase (0.1% FA condition) to give the title compound (900 mg, 63% yield) as a yellow solid. $^1H$ NMR (400 MHz, DMSO-$d_6$) δ 11.19 (s, 1H), 7.68 (dd, J=0.8, 8.0 Hz, 1H), 7.55 (d, J=8.0 Hz, 1H), 7.23 (t, J=8.0 Hz, 1H), 5.51 (dd, J=5.2, 12.8 Hz, 1H), 3.41 (s, 3H), 2.95-2.85 (m, 1H), 2.80-2.60 (m, 2H), 2.13-2.06 (m, 1H).

Step 5—3-(4-Amino-3-methyl-2-oxo-benzimidazol-1-yl)piperidine-2,6-dione

To a solution of 3-(3-methyl-4-nitro-2-oxo-benzimidazol-1-yl)piperidine-2,6-dione (850 mg, 2.79 mmol) in THF (50 mL) was added Pd/C (200 mg, 10% wt). The reaction mixture was stirred at 20° C. for 12 hrs under $H_2$ (15 Psi) atmosphere. On completion, the mixture was filtered and the filtrate was concentrated in vacuo to give the title compound (0.70 g, 91% yield) as a pink solid. LC-MS (ESI$^+$) m/z 275.1 $(M+H)^+$.

3-[4-(2-Azaspiro[3.3]heptan-6-ylmethylamino)-3-methyl-2-oxo-benzimidazol-1-yl]piperidine-2,6-dione (Intermediate CE)

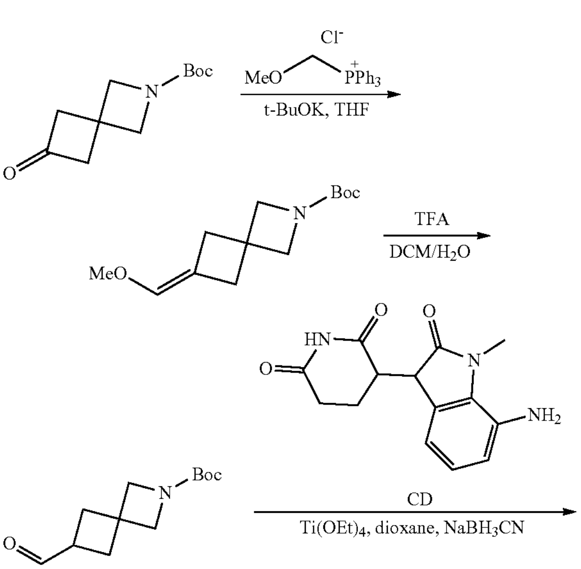

-continued

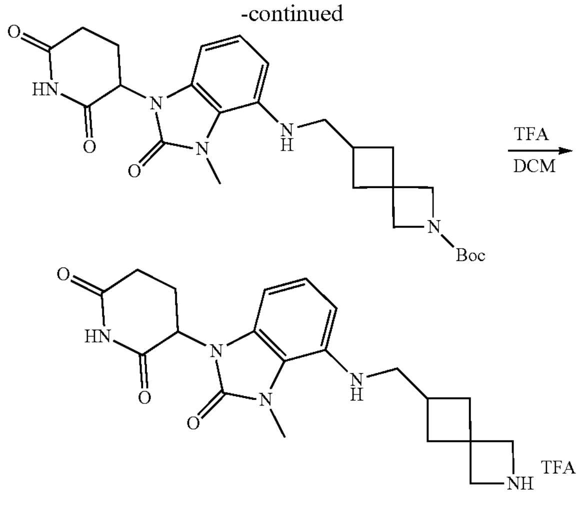

CE

Step 1—Tert-butyl 6-(methoxymethylene)-2-azaspiro[3.3]heptane-2-carboxylate

To a suspension of chloro-(methoxymethyl)-triphenyl-phosphane (6.33 g, 18.4 mmol, CAS #1181816-12-5) in toluene (45 mL) was added t-BuOK (2 g, 18.4 mmol) at 0° C. The mixture was stirred at 10° C. for 0.5 hour. To the mixture was added a solution of tert-butyl 6-oxo-2-azaspiro[3.3]heptane-2-carboxylate (3.00 g, 14.2 mmol, CAS #4009-98-7) in toluene (35 mL) at 10° C. The mixture was then stirred at 70° C. for 4 hours. The reaction was then quenched with sat. aq. $NH_4Cl$ (10 mL). The residue was diluted with water (20 mL), and extracted with EA (3×50 mL). The combined organic layer was washed with brine (20 mL), dried over $Na_2SO_4$, filtered and concentrated in vacuo. The residue was purified by column chromatography on silica gel (PE:EA=50:1-15:1) to give the title compound as light yellow oil (1.20 g, 35% yield)$^1$H NMR (400 MHz, $CDCl_3$) δ 5.81 (J=2.4 Hz, 1H), 3.92 (s, 4H), 3.56 (s, 3H), 2.87 (d, J=2.4 Hz, 2H), 2.79 (d, J=1.6 Hz, 2H), 1.44 (s, 9H).

Step 2—Tert-butyl 6-formyl-2-azaspiro[3.3]heptane-2-carboxylate

To a solution of tert-butyl 6-(methoxymethylene)-2-azaspiro [3.3]heptane-2-carboxylate (400 mg, 1.67 mmol) in DCM (4 mL) and $H_2O$ (2 mL) was added TFA (1.0 mL) at 25° C. The mixture was stirred at 25° C. for 2 hours. On completion, the reaction was quenched with sat. aq. $NaHCO_3$ (10 mL). The mixture was concentrated in vacuo, and diluted with water (10 mL), then extracted with EA (3×45 mL). The combined organic layer was washed with brine (15 mL), dried over $Na_2SO_4$, filtered and concentrated in vacuo. The crude product was purified by column chromatography on silica gel (PE:EA=50:1-15:1) to give the title compound (137 mg, 36% yield) as light yellow solid. $^1$H NMR (400 MHz, $CDCl_3$) δ 9.73 (d, J=1.6 Hz, 1H), 3.95 (s, 2H), 3.84 (s, 2H), 3.16-3.04 (m, 1H), 2.46-2.33 (m, 4H), 1.43 (s, 9H).

Step 3—Tert-butyl 6-[[[1-(2,6-dioxo-3-piperidyl)-3-methyl-2-oxo-benzimidazol-4-yl]amino]methyl]-2-azaspiro[3.3]heptane-2-carboxylate To a solution of tert-butyl 6-formyl-2-azaspiro[3.3]heptane-2-carboxylate (80.0 mg, 355 μmol), 3-(4-amino-3-methyl-2-oxo-benzimidazol-1-yl)piperidine-2,6-dione (97.4 mg, 355 umol, Intermediate CD) in dioxane (4.5 mL) was added $Ti(OEt)_4$ (162 mg, 710.22 umol) at 25° C. for 16 hours. Then to the mixture was added $NaBH_3CN$ (44.6 mg, 710 umol) and the mixture was stirred at 25° C. for 1 hour. On completion, the reaction was quenched with water (20 mL), and extracted with EA (3×60 mL). The combined organic layer was dried over $Na_2SO_4$, filtered and concentrated in vacuo to give the title compound (137 mg, 79% yield) as light yellow solid $^1$H NMR (400 MHz, $CDCl_3$) δ 8.16 (s, 1H), 6.98-6.91 (m, 1H), 6.45 (d, J=8.0 Hz, 1H), 6.32 (d, J=7.6 Hz, 1H), 5.20-5.11 (m, 1H), 3.96 (s, 2H), 3.85 (s, 2H), 3.73 (s, 3H), 3.57 (d, J=6.4 Hz, 1H), 3.13 (d, J=7.2 Hz, 2H), 2.96 (s, 1H), 2.89 (s, 1H), 2.40-2.33 (m, 3H), 2.29-2.24 (m, 1H), 2.24-2.16 (m, 2H), 2.05 (s, 4H), 1.98-1.91 (m, 3H), 1.44 (s, 9H), 0.08 (s, 1H); LC-MS (ESI$^+$) m/z 384.2 $(M+H)^+$.

Step 4—3-[4-(2-Azaspiro[3.3]heptan-6-ylmethyl-amino)-3-methyl-2-oxo-benzimidazol-1-yl]piperidine-2,6-dione To a solution of tert-butyl 6-[[[1-(2,6-dioxo-3-piperidyl)-3-methyl-2-oxo-benzimidazol-4-yl]amino] methyl]-2-azaspiro[3.3]heptane-2-carboxylate (70.0 mg, 145 umol) in DCM (1.5 mL) was added TFA (1.5 mL) at 25° C. The mixture was stirred at 25° C. for 1 hour. On completion, the mixture was concentrated in vacuo to give the title compound as white solid (70.0 mg, 97% yield, TFA salt). $^1$H NMR (400 MHz, DMSO-$d_6$) δ 11.06 (s, 1H), 8.58 (d, J=2.4 Hz, 2H), 6.86 (t, J=8.0 Hz, 1H), 6.52 (d, J=7.6 Hz, 2H), 6.42 (d, J=8.2 Hz, 2H), 5.28 (dd, J=5.6, 12.4 Hz, 1H), 3.98 (t, J=6.0 Hz, 2H), 3.89 (t, J=6.0 Hz, 2H), 3.60 (s, 3H), 3.04 (d, J=7.2 Hz, 2H), 2.93-2.81 (m, 1H), 2.70-2.56 (m, 2H), 2.50 (d, J=1.6, 3.5 Hz, 11H), 2.46-2.39 (m, 1H), 2.36-2.28 (m, 2H), 2.04-1.90 (m, 3H), 1.53 (s, 1H).

3-(3-Methyl-4-(4-(methylamino)but-1-yn-1-yl)-2-oxo-2,3-dihydro-1H-benzo[d]imidazol-1-yl)piperidine-2,6-dione (Intermediate CF)

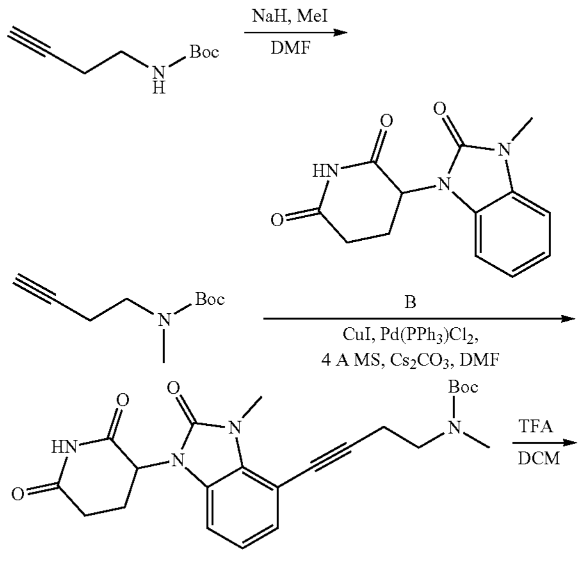

-continued

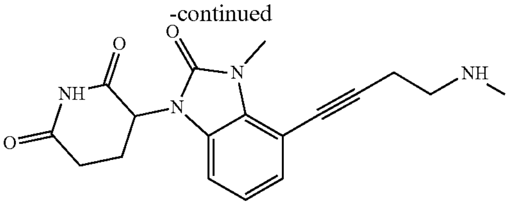

CF

Step 1—Tert-butyl but-3-yn-1-yl(methyl)carbamate

To a solution of tert-butyl N-but-3-ynylcarbamate (7 g, 41.4 mmol, CAS #149990-27-2) in THF (50 mL) was added NaH (1.99 g, 49.6 mmol, 60% dispersion in mineral oil) at 0° C. The mixture was stirred at 0° C. for 0.5 hr, then MeI (11.7 g, 82.7 mmol) was added and the mixture was stirred at 40° C. for 15.5 hrs. On completion, the reaction mixture was quenched by saturated ammonium chloride aqueous solution (250 mL) and extracted with ethyl acetate (3×200 mL). The combined organic layers were washed with sodium chloride solution (25 mL), dried over anhydrous sodium sulfate, filtered and concentrated in vacuo to give a residue. The residue was purified by silica gel chromatography (petroleum ether:ethyl acetate=100:1) to give the title compound (4.5 g, 59% yield) as colorless oil. $^{1}H$ NMR (400 MHz, $CDCl_3$) δ 3.38 (m, 2H), 2.92 (s, 3H), 2.45-2.37 (m, 2H), 1.97 (t, J=2.8 Hz, 1H), 1.46 (s, 9H).

Step 2—Tert-butyl (4-(1-(2,6-dioxopiperidin-3-yl)-3-methyl-2-oxo-2,3-dihydro-1H-benzo[d]imidazol-4-yl)but-3-yn-1-yl)(methyl)carbamate To a solution of 3-(4-bromo-3-methyl-2-oxo-benzimidazol-1-yl)piperidine-2,6-dione (1.54 g, 4.55 mmol, Intermediate B), $Cs_2CO_3$ (4.45 g, 13.7 mmol), CuI (86.6 mg, 455 umol), $Pd(PPh_3)_2Cl_2$ (319 mg, 455 umol) and 4A molecular sieves (500 mg) in DMF (10 mL) was degassed and purged with nitrogen for 3 times, then a solution of tert-butyl N-but-3-ynyl-N-methyl-carbamate (1 g, 5.46 mmol) in DMF (5 mL) was added. The mixture was stirred at 80° C. for 3 hrs under nitrogen atmosphere. On completion, the reaction mixture was filtered and concentrated in vacuo to give a residue. The residue was purified by reversed-phase HPLC (FA condition) to give the title compound (1.40 g, 61% yield) as a green solid. $^{1}H$ NMR (400 MHz, $CDCl_3$) δ 8.28 (s, 1H), 7.13 (d, J=8.0 Hz, 1H), 6.97 (t, J=8.0 Hz, 1H), 6.73 (d, J=7.6 Hz, 1H), 5.21 (dd, J=12.8, 5.6 Hz, 1H), 3.53-3.49 (m, 2H), 3.77 (s, 3H), 2.97 (s, 3H), 2.94-2.63 (m, 6H), 2.27-2.18 (m, 1H), 1.47 (s, 9H). LC-MS ($ESI^+$) m/z 341.1 $(M+H-Boc)^+$.

Step 3—3-(3-Methyl-4-(4-(methylamino)but-1-yn-1-yl)-2-oxo-2,3-dihydro-1H-benzo[d]imidazol-1-yl)piperidine-2,6-dione To a solution of tert-butyl N-[4-[1-(2,6-dioxo-3-piperidyl)-3-methyl-2-oxo-benzimidazol-4-yl]but-3-ynyl]-N-methyl-carbamate (100 mg, 227 umol) in DCM (1 mL) was added TFA (0.1 mL). The mixture was stirred at 25° C. for 0.5 hr. On completion, the reaction mixture was concentrated in vacuo to give the title compound (100 mg, 96% yield) as yellow oil. LC-MS ($ESI^+$) m/z 341.3 $(M+H)^+$.

3-[5-(5-aminopentyl)-3-methyl-2-oxo-benzimidazol-1-yl]-1-methyl-piperidine-2,6-dione (Intermediate CG)

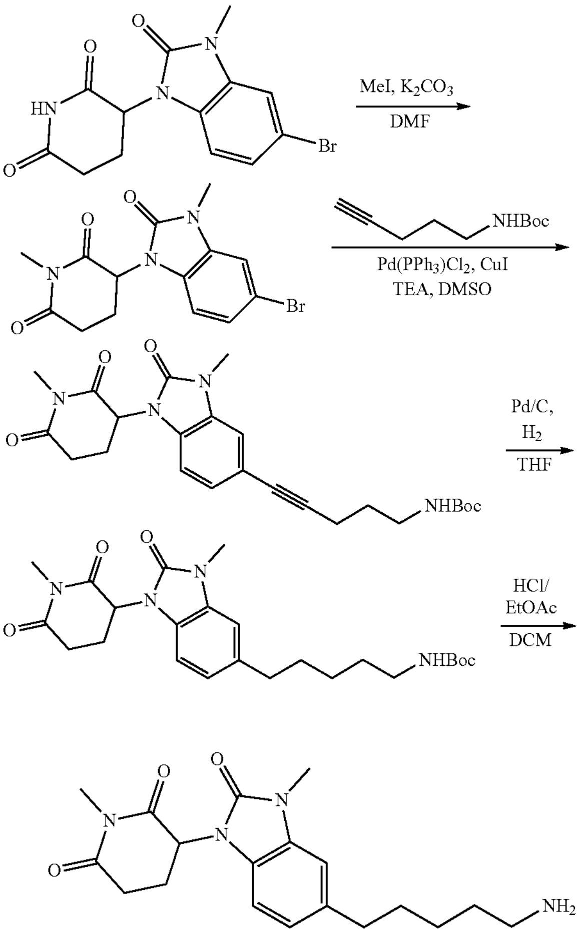

CG

Step 1: 3-(5-bromo-3-methyl-2-oxo-benzimidazol-1-yl)-1-methyl-piperidine-2,6-dione To a solution of 3-(5-bromo-3-methyl-2-oxo-benzimidazol-1-yl) piperidine-2,6-dione (1 g, 2.96 mmol, Intermediate E) in DMF (30 mL) was added MeI (848 mg, 5.97 mmol, 371 uL) and $K_2CO_3$ (2.05 g, 14.8 mmol) and the reaction mixture was stirred at 25° C. for 12 h under nitrogen atmosphere. On completion, the reaction mixture was partitioned between EtOAc (100×2 mL) and water (50 mL), and the separated organic layer was washed with brine (50 mL). The organic layer was dried over $MgSO_4$, filtered and evaporated to dryness. The residue was purified by column ($SiO_2$, petroleum ether:ethyl acetate=10:1 to 3:7) to give the title compound (518 mg, 1.47 mmol, 50% yield) as a light yellow solid. $^{1}H$ NMR (400 MHz, $CHCl_3$) δ ppm 7.21 (d, J=1.6 Hz, 1H), 7.19-7.16 (m, 1H), 6.65 (d, J=8.4 Hz, 1H), 5.15 (dd, J=13.2, 5.6 Hz, 1H), 3.25 (s, 3H), 3.43 (s, 3H), 3.00-3.08 (m, 1H), 2.87-2.79 (m, 1H), 2.69 (qd, J=13.2, 4.4 Hz, 1H), 2.21 (dtd, J=12.8, 5.2, 5.2, 2.8 Hz, 1H).

Step 2: tert-butylN-[5-[3-methyl-1-(1-methyl-2,6-dioxo-3-piperidyl)-2-oxo-benzimidazol-5-yl]pent-4-ynyl]carbamate To a solution of 3-(5-bromo-3-methyl-2-oxo-benzimidazol-1-yl)-1-methyl-piperidine-2,6-dione (0.3 g, 851 umol) and tert-butyl N-pent-4-ynylcarbamate (240.00 mg, 1.31 mmol, CAS #151978-50-6) in DMSO (5 mL) was added $Pd(PPh_3)_4$ (110 mg, 95.2 umol), CuI (20 mg, 105 umol) and TEA (872.40 mg, 8.62 mmol, 1.20 mL) in portions at 25° C. under nitrogen atmosphere. The resulting mixture was stirred for 6 h at 80° C. under nitrogen atmosphere. On completion, the reaction was partitioned between ethyl acetate (100 mL×2) and water (50 mL). The separated organic layer was washed with brine (20 mL), dried over $MgSO_4$, filtered and evaporated to dryness. The residue was purified by column ($SiO_2$, petroleum ether:ethyl acetate=5:1 to 1:1) to give the title compound (290 mg, 638 umol, 75% yield) as a light red solid. $^1H$ NMR (400 MHz, $CHCl_3$) δ ppm 7.73-7.66 (m, 1H), 7.15 (d, J=8.0 Hz, 1H), 7.08 (s, 1H), 6.70 (d, J=8.0 Hz, 1H), 5.16 (dd, J=12.8, 5.2 Hz, 1H), 3.44 (s, 3H), 3.27 (s, 3H), 3.10-2.97 (m, 1H), 2.93-2.80 (m, 1H), 2.72 (qd, J=13.2, 4.4 Hz, 1H), 2.49 (t, J=6.8 Hz, 2H), 2.27-2.18 (m, 1H), 1.82 (q, J=6.8 Hz, 2H), 1.58 (s, 2H), 1.47 (s, 9H).

Step 3: tert-butyl N-[5-[3-methyl-1-(1-methyl-2,6-dioxo-3-piperidyl)-2-oxo-benzimidazol-5-yl]pentyl] carbamate To a solution of tert-butylN-[5-[3-methyl-1-(1-methyl-2,6-dioxo-3-piperidyl)-2-oxo-benzimidazol-5-yl]pent-4-ynyl] carbamate (120 mg, 264 umol) in THF (5 mL) was added Pd/C (300.00 mg, 253.31 umol, 10 wt %) under $N_2$. The suspension was degassed under vacuum and purged with $H_2$ several times. The resulting mixture was stirred for 12 h at 25° C. under $H_2$ atmosphere. On completion, the residue was washed with MeOH, filtered and evaporated to dryness. The crude product was purified by Prep-TLC ($SiO_2$, dichloromethane:methanol=10:1) to give the title compound (110 mg, 240 umol, 91% yield) as a light yellow solid. LC-MS (ESI+) m/z: 459.3 $(M+H)^+$.

Step 4: 3-[5-(5-aminopentyl)-3-methyl-2-oxo-benzimidazol-1-yl]-1-methyl-piperidine-2,6-dione To a solution of tert-butyl N-[5-[3-methyl-1-(1-methyl-2,6-dioxo-3-piperidyl)-2-oxo-benzimidazol-5-yl]pentyl]carbamate (110 mg, 240 umol) in DCM (1 mL) was added TFA (308 mg, 2.70 mmol, 0.2 mL) slowly in one portion, and the resulting solution was stirred at 25° C. for 12 h under nitrogen atmosphere. On completion, the reaction mixture was concentrated under reduced pressure to remove DCM and TFA. The residue was purified by prep-HPLC (column: Phenomenex Luna C18 150*30 mm*5 um; mobile phase: [water (0.1% TFA)-ACN]; B %: 1%-45%, 8 min) to give the title compound (60 mg, 167.39 umol, 69.78% yield) as light yellow oil. LC-MS (ESI+) m/z: 359.2 $(M+H)^+$.

3-[5-[2-[1-(3-aminocyclobutanecarbonyl)azetidin-3-yl]ethynyl]-3-methyl-2-oxo-benzimidazol-1-yl]piperidine-2,6-dione (Intermediate CH)

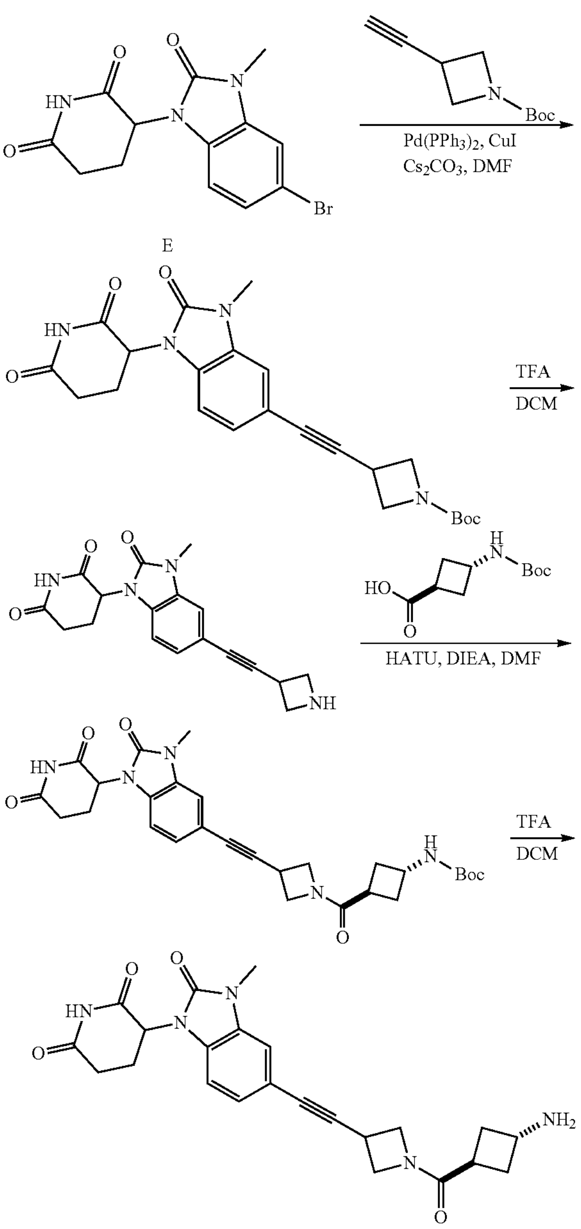

CH

Step 1—tert-butyl 3-[2-[1-(2,6-dioxo-3-piperidyl)-3-methyl-2-oxo-benzimidazol-5-yl]ethynyl] azetidine-1-carboxylate A mixture of 3-(5-bromo-3-methyl-2-oxo-benzimidazol-1-yl)piperidine-2,6-dione (800 mg, 2.37 mmol, Intermediate E), tert-butyl 3-ethynylazetidine-1-carboxylate (857 mg, 4.73 mmol CAS #287093-01-5), $Pd(PPh_3)_2Cl_2$ (166 mg, 236 umol), CuI (22.5 mg, 118 umol) and $Cs_2CO_3$ (2.31 g, 7.10 mmol) in DMF (16 mL) was degassed and purged with $N_2$ three times, and then the mixture was stirred at 80° C. for 6 hr under $N_2$ atmosphere. On completion, the reaction mixture was concentrated in vacuo to give a residue. The residue was purified by column chromatography ($SiO_2$, ethyl acetate) to give the title compound (900 mg, 78% yield) as brown solid. $^1H$ NMR (400 MHz, DMSO-d6) δ=11.11 (s, 1H), 8.00-7.96 (m, 1H), 7.32 (s, 1H), 7.16-7.12 (m, 1H), 5.38 (dd, J=5.2, 12.8 Hz, 1H), 4.22-4.17 (m, 1H), 3.85 (t, J=6.4 Hz, 2H), 3.66 (tt, J=6.1, 8.6 Hz, 1H), 3.27 (d, J=5.6 Hz, 3H), 2.86 (d, J=5.6 Hz, 1H), 2.71-2.63 (m, 2H), 2.59 (d, J=18.8 Hz, 1H), 2.07-1.98 (m, 1H), 1.43-1.38 (m, 9H).

Step 2—3-[5-[2-(azetidin-3-yl)ethynyl]-3-methyl-2-oxo-benzimidazol-1-yl]piperidine-2,6-dione To a solution of tert-butyl 3-[2-[1-(2,6-dioxo-3-piperidyl)-3-methyl-2-oxo-benzimidazol-5-yl]ethynyl] azetidine-1-carboxylate (500 mg, 1.14 mmol) in DCM (5 mL) was added TFA (1.54 g, 13.1 mmol, 1 mL) and the mixture was stirred at 25° C. for 2 hr. On completion, the reaction mixture was concentrated in vacuo to give a residue to give the title compound (360 mg, crude) as brown oil. LC-MS ($ESI^+$) m/z 339.1 (M+H).

Step 3—tert-butyl N-[3-[3-[2-[1-(2,6-dioxo-3-piperidyl)-3-methyl-2-oxo-benzimidazol-5-yl]ethynyl] azetidine-1-carbonyl]cyclobutyl]carbamate To a solution of HATU (525 mg, 1.38 mmol), 3-(tert-butoxycarbonylamino)cyclobutanecarboxylic acid (229 mg, 1.06 mmol CAS #1008773-79-2), DIEA (687 mg, 5.32 mmol) in DMF (4 mL) was added 3-[5-[2-(azetidin-3-yl) ethynyl]-3-methyl-2-oxo-benzimidazol-1-yl]piperidine-2,6-dione (360 mg, 1.06 mmol) and the mixture was stirred at 25° C. for 2 hr. On completion, the reaction mixture was concentrated in vacuo to give a residue. The residue was purified by column chromatography ($SiO_2$, petroleum ether: ethyl acetate=3:1) to give the title compound (100 mg, 17% yield) as yellow solid. $^1H$ NMR (400 MHz, DMSO-d6) δ=11.14-10.84 (m, 1H), 7.72-7.65 (m, 1H), 7.22 (s, 1H), 7.10-7.03 (m, 3H), 5.29 (dd, J=5.2, 12.8 Hz, 1H), 4.26 (t, J=8.4 Hz, 1H), 4.12 (t, J=9.2 Hz, 1H), 4.02-3.88 (m, 4H), 3.76 (dd, J=6.4, 8.8 Hz, 1H), 3.06 (J=4.0, 7.2 Hz, 1H), 2.87-2.75 (m, 4H), 2.66-2.58 (m, 2H), 2.00-1.92 (m, 4H), 1.28 (s, 9H).

Step 4—3-[5-[2-[1-(3-aminocyclobutanecarbonyl) azetidin-3-yl]ethynyl]-3-methyl-2-oxo-benzimidazol-1-yl]piperidine-2,6-dione To a solution of tert-butyl N-[3-[3-[2-[1-(2,6-dioxo-3-piperidyl)-3-methyl-2-oxo-benzimidazol-5-yl] ethynyl]azetidine-1-carbonyl]cyclobutyl]carbamate (100 mg, 186 umol) in DCM (2 mL) was added TFA (616 mg, 5.40 mmol) and the mixture was stirred at 25° C. for 1 hr. On completion, the reaction mixture was concentrated in vacuo to give a residue to give the title compound (80 mg, 95% yield) as yellow oil. LC-MS ($ESI^+$) m/z 436.2 (M+H).

Chloro-(3-chloro-2-fluoro-phenyl)-oxo-dispiro[BLAH] carboxylic acid (Intermediate CI)

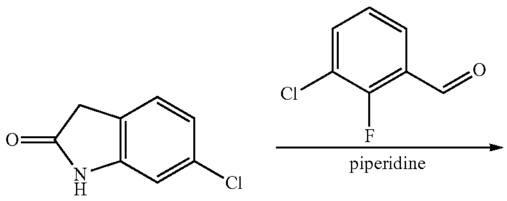

-continued

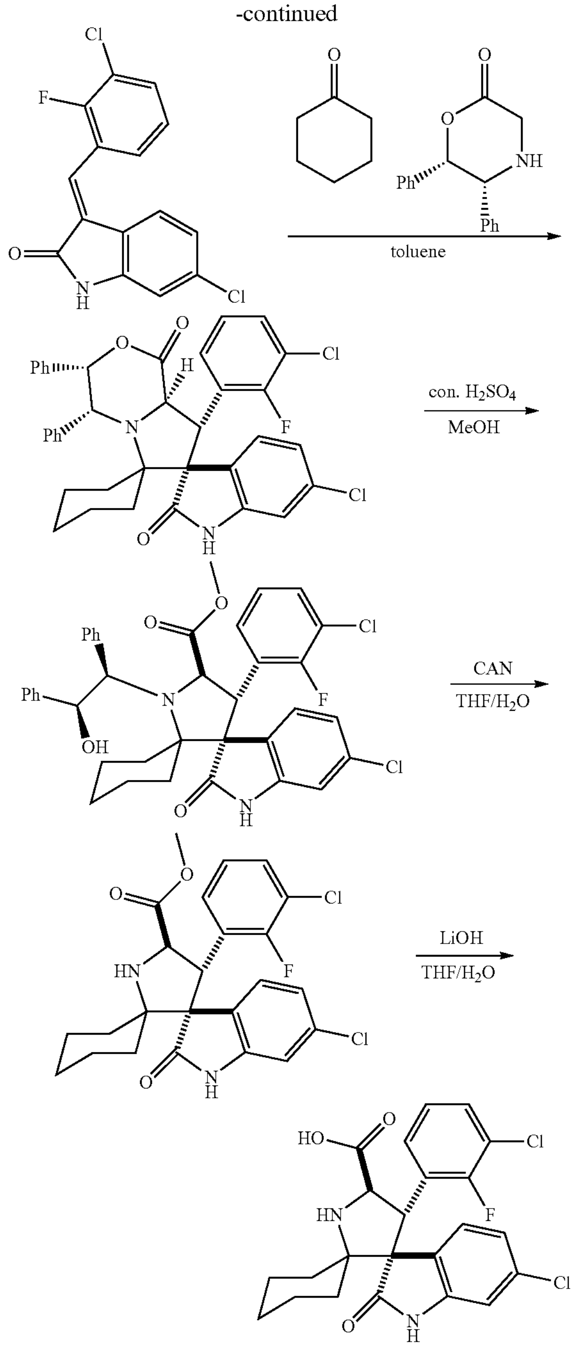

CI

Step 1—(3E)-6-chloro-3-[(3-chloro-2-fluoro-phenyl) methylene]indolin-2-one

A 500 mL 3-necked round bottom flask was charged with 6-chloroindolin-2-one (89.6 g, 535 mmol, CAS #56341-37-8), 3-chloro-2-fluoro-benzaldehyde (84.8 g, 535 mmol, CAS #85070-48-0), MeOH (1700 mL) and piperidine (9.11 g, 107 mmol). The mixture was stirred at 65° C. for 5 h, then at 25° C. for 12 h. On completion, the reaction mixture was filtered and the filter cake was dried under reduced pressure to give title product (160 g, 94% yield). $^1H$ NMR (400 MHz, DMSO-$d_6$) δ=10.87 (s, 1H), 7.82-7.63 (m, 2H), 7.56 (s, 1H), 7.39 (t, J=8.0 Hz, 1H), 7.18 (d, J=8.0 Hz, 1H), 7.03-6.77 (m, 2H).

Step 2—chloro-(3-chloro-2-fluoro-phenyl)-diphenyl-dispiro[BLAH]dione (3E)-6-chloro-3-[(3-chloro-2-fluoro-phenyl)methylene]indolin-2-one (50 g, 162 mmol), (5R,6S)-5,6-diphenylmorpholin-2-one (49.3 g, 194 mmol, CAS #282735-66-4), and cyclohexanone (31.8 g, 324 mmol, 33.6 mL) were dissolved in THF (75 mL) and toluene (750 mL) and 140° C. for 12 hours. On completion, the reaction mixture was concentrated in vacuo to give a residue. The residue was purified by column chromatography ($SiO_2$, petroleum ether/ethyl acetate=8/1 to 5/1) to give the title compound (160 g 97% purity). $^1H$ NMR (400 MHz, DMSO-$d_6$) δ=10.79 (s, 1H), 7.95 (t, J=6.8 Hz, 1H), 7.45-7.37 (m, 1H), 7.33-7.20 (m, 4H), 7.18-7.09 (m, 4H), 7.07-6.98 (m, 2H), 6.86-6.75 (m, 3H), 6.66 (dd, J=2.0, 8.4 Hz, 1H), 6.35 (d, J=8.4 Hz, 1H), 5.44 (d, J=11.2 Hz, 1H), 4.90 (d, J=2.8 Hz, 1H), 4.58 (d, J=11.2 Hz, 1H), 2.39 (d, J=12.8 Hz, 1H), 2.24-2.09 (m, 1H), 1.42-1.18 (m, 4H), 1.10-0.78 (m, 1H).

Step 3—methyl chloro-(3-chloro-2-fluoro-phenyl)-[(1R,2S)-2-hydroxy-1,2-diphenyl-ethyl]-oxo-dispiro[BLAH]carboxylate $H_2SO_4$ (9.07 g, 92.5 mmol, 4.93 mL) was added to a solution of intermediate chloro-(3-chloro-2-fluoro-phenyl)-diphenyl-dispiro[BLAH]dione (9.0 g, 14.03 mmol) dissolved in MeOH (70 mL) and the resulting solution was heated to 50° C. for 5 hours. On completion, the reaction mixture was cooled to 0° C. and slowly neutralized with a solution of saturated sodium bicarbonate. The aqueous solution was extracted with ethyl acetate, and the organic layer was dried over sodium sulfate, filtered, concentrated to give the residue. The residue was purified by reverse phase flash [ACN/(0.1% FA in water), 0% to 90%] to give title compound (7.0 g 84.2% purity). $^1H$ NMR (400 MHz, DMSO-$d_6$) δ=7.74-7.68 (m, 1H), 7.57 (s, 1H), 7.51 (d, J=8.4 Hz, 1H), 7.41 (d, J=7.2 Hz, 4H), 7.25 (d, J=7.6 Hz, 6H), 7.19-7.11 (m, 6H), 7.10-6.98 (m, 4H), 6.94-6.88 (m, 1H), 6.65-6.58 (m, 1H), 5.39-5.27 (m, 1H), 4.89-4.75 (m, 1H), 4.42-4.29 (m, 2H), 4.04 (q, J=6.8 Hz, 1H), 3.63-3.53 (m, 2H), 3.40 (s, 3H), 2.22-2.12 (m, 1H), 2.05-1.94 (m, 3H), 1.40-1.32 (m, 2H), 1.28-1.13 (m, 3H).

Step 4—methyl chloro-(3-chloro-2-fluoro-phenyl)-oxo-dispiro[BLAH]carboxylate

The resulting intermediate methyl chloro-(3-chloro-2-fluoro-phenyl)-[(1R,2S)-2-hydroxy-1,2-diphenyl-ethyl]-oxo-dispiro[BLAH]carboxylate (7.0 g, 10.3 mmol) was dissolved in ACN (78 mL), then CAN (11.3 g, 20.7 mmol) was added, followed by the addition of $H_2O$ (78 mL). The reaction was stirred at 25° C. for 30 min. On completion, the reaction mixture was quenched by adding the mixture to a cold saturated aqueous $NaHCO_3$ solution (50 mL). The aqueous layer was extracted with ethyl acetate (20 mL×3). The organic layer was separated, dried over anhydrous $Na_2SO_4$, filtered and concentrated under reduced pressure to give the residue. The residue was purified by column chromatography ($SiO_2$, petroleum ether/ethyl acetate=50/1 to 5/1) to give title compound (1.58 g, 31% purity). LC-MS ($ESI^+$) m/z 477.2 $(M+H)^+$.

Step 5—chloro-(3-chloro-2-fluoro-phenyl)-oxo-dispiro[BLAH]carboxylic acid

Methyl chloro-(3-chloro-2-fluoro-phenyl)-oxo-dispiro[BLAH]carboxylate (2.00 g, 4.19 mmol) was dissolved in THF (14 mL) and $LiOH{\cdot}H_2O$ (527 mg, 12.5 mmol) was added followed by water (14 mL) and MeOH (2 mL) and the reaction was stirred at 25° C. for 15 min. On completion, water (20 mL) was added and the reaction was slowly neutralized with 2M HCl and the suspension was stirred for 15 min. The resulting precipitate was filtered, washed with water to give title compound (1.50 g, 70% yield). $^1H$ NMR (400 MHz, DMSO-$d_6$) δ=10.75-10.57 (m, 1H), 10.55 (s, 1H), 7.61-7.54 (m, 1H), 7.50-7.44 (m, 1H), 7.41-7.34 (m, 1H), 7.18-7.12 (m, 1H), 7.08-7.02 (m, 1H), 6.72-6.66 (m, 1H), 4.72-4.65 (m, 1H), 4.54-4.47 (m, 1H), 3.18-3.15 (m, 1H), 2.22-2.13 (m, 1H), 1.83-1.70 (m, 2H), 1.64-1.52 (m, 3H), 1.51-1.43 (m, 2H), 1.42-1.34 (m, 1H), 1.04-0.92 (m, 1H), 0.89-0.77 (m, 1H). LC-MS ($ESI^+$) m/z 463.2 $(M+H)^+$.

Tert-butyl N-[(15)-1-[[(2S)-1-[(3S)-7-(2-aminoethoxy)-3-[[(1R)-1,2,3,4-tetrahydronaphthalen-1-yl]carbamoyl]-3,4-dihydro-1H-isoquinolin-2-yl]-3,3-dimethyl-1-oxobutan-2-yl]carbamoyl]ethyl]-N-methylcarbamate (Intermediate CJ)

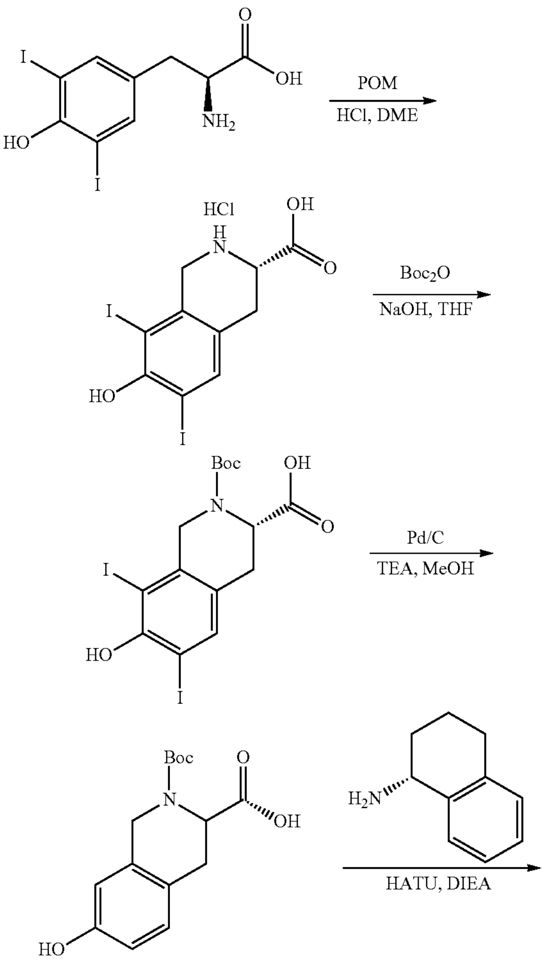

-continued

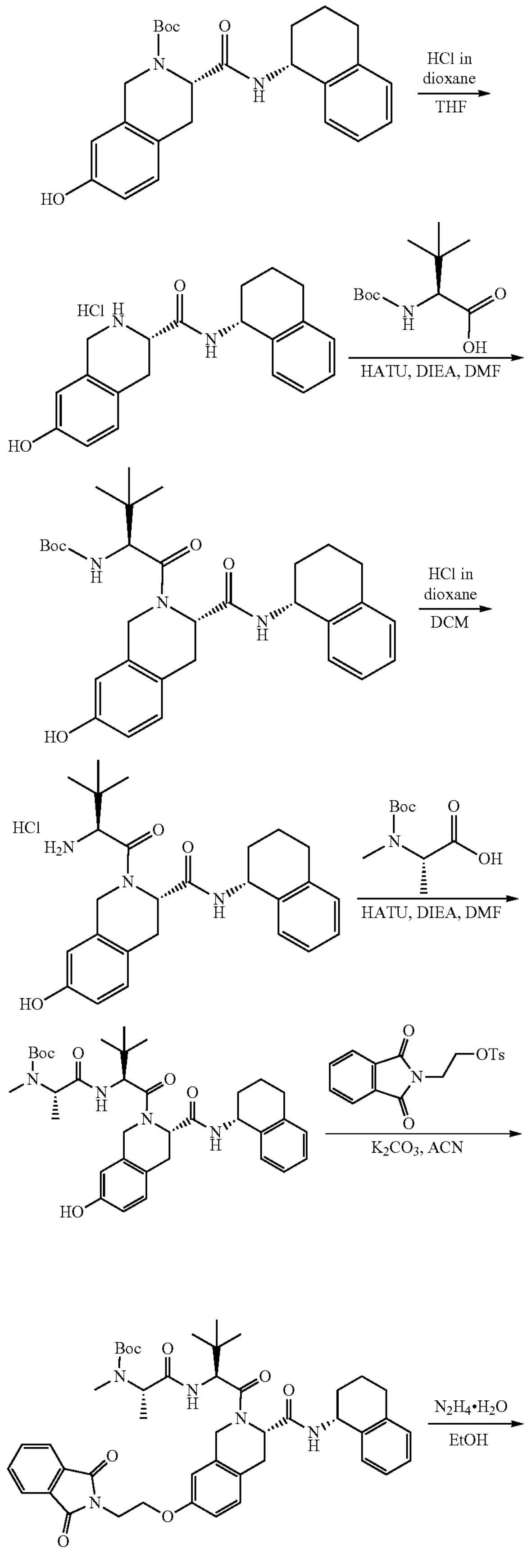

-continued

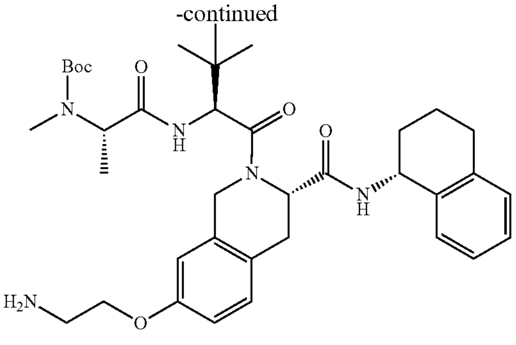

CJ

Step 1—(S)-7-hydroxy-6,8-diiodo-1,2,3,4-tetrahydroisoquinoline-3-carboxylic acid hydrochloride To a stirred solution of 3,5-diiodotyrosine (264 g, 609.72 mmol, CAS #18835-59-1) in conc. HCl (3 L) were added DME (300 mL), polyformaldehyde (329 g, 3658.38 mmol) in portions at 0° C. under a nitrogen atmosphere. The resulting mixture was stirred for 16 h at 70° C. under a nitrogen atmosphere. After cooling down to 0° C., solids were precipitated and collected by filtration. The filtered cake was washed with DME (3×100 mL) and dried under vacuum to afford the title compound (170 g, 63% yield) as a white solid. $^1$H NMR (400 MHz, DMSO-d4) δ 14.04 (s, 1H), 10.23 (s, 2H), 7.71 (s, 1H), 4.31 (dd, J=4.9, 11.0 Hz, 1H), 4.10-3.99 (m, 2H), 3.26-3.16 (m, 1H), 3.10-3.04 (m, 1H); LC/MS (ESI, m/z): [(M+1)]+=445.8.

Step 2—(S)-2-(tert-butoxycarbonyl)-7-hydroxy-6,8-diiodo-1,2,3,4-tetrahydroisoquinoline-3-carboxylic acid To a stirred solution of (3S)-7-hydroxy-6,8-diiodo-1,2,3,4-tetrahydroisoquinoline-3-carboxylic acid hydrochloride (300 g, 623.12 mmol) in 1 N NaOH (2.00 L) was added a solution of di-tert-butyl dicarbonate (149 g, 685.41 mmol) in THF (500 mL) at 0° C. under a nitrogen atmosphere. After stirring for 6 h at rt, the mixture was acidified to pH 4 with HCl (aq.). The precipitated solids were collected by filtration and washed with water (3×20 mL). The water layer was extracted with EtOAc (3×500 mL). The combined organic layers were washed with brine (2×300 mL) and dried over anhydrous $MgSO_4$. After filtration, the filtrate was concentrated under reduced pressure. This residue was combined with the solid from the filtered cake and recovered from water layer to afford the title compound (320 g, 94% yield) as a light yellow solid; $^1$H NMR (400 MHz, DMSO-$d_6$) δ 12.49 (s, 1H), 9.35 (s, 1H), 7.59 (s, 1H), 4.72 (ddd, J=3.0, 6.2, 50.7 Hz, 1H), 4.44 (dd, J=17.3, 20.0 Hz, 1H), 4.20 (dd, J=10.4, 17.3 Hz, 1H), 3.13-2.90 (m, 2H), 1.43 (d, J=23.8 Hz, 9H); LC/MS (ESI, m/z): $[(M-1)]^-$=543.9.

Step 3—(S)-2-(tert-butoxycarbonyl)-7-hydroxy-1,2,3,4-tetrahydroisoquinoline-3-carboxylic acid To a solution of (3S)-2-(tert-butoxycarbonyl)-7-hydroxy-6,8-diiodo-3,4-dihydro-1H-isoquinoline-3-carboxylic acid (320 g, 587.03 mmol) in MeOH (800 mL) were added TEA (131 g, 1291.43 mmol) and Pd/C (62.47 g, 10 wt %) under a nitrogen atmosphere. The mixture was hydrogenated at rt for 24 h under a hydrogen atmosphere using a hydrogen balloon. After completion, the reaction mixture was filtered through a celite pad and concentrated under reduced pressure. The residue was diluted with water (1.5 L) and the mixture was acidified to pH 4 with HCl (aq.). The precipitated solids were collected by filtration and washed with water (3×50 mL). The solid was dried under vacuum to afford the title compound (150 g, 87% yield) as a light yellow solid. $^1$H NMR (400 MHz, DMSO-$d_6$) δ 12.49 (s, 1H), 9.26 (s, 1H), 6.97 (d, J=7.9 Hz, 1H), 6.62-6.50 (m, 2H), 4.87-4.22 (m, 3H), 3.10-2.90 (m, 2H), 1.43 (d, J=26.0 Hz, 9H); LC/MS (ESI, m/z): $[(M-1)]^-$=292.1.

Step 4: tert-butyl (S)-7-hydroxy-3-(((R)-1,2,3,4-tetrahydronaphthalen-1-yl)carbamoyl)-3,4-dihydroisoquinoline-2(1H)-carboxylate To a stirred mixture of (3S)-2-(tert-butoxycarbonyl)-7-hydroxy-3,4-dihydro-1H-isoquinoline-3-carboxylic acid (150 g, 511.39 mmol) and (1R)-1,2,3,4-tetrahydronaphthalen-1-amine (90.34 g, 613.67 mmol, CAS #23357-46-2) in DMF (1.5 L) were added DIEA (198 g, 1.53 mol) and HATU (233 g, 613.67 mmol) in portions at 0° C. The resulting mixture was stirred for 2 h at rt. The resulting mixture was quenched with water (3 L) and extracted with $Et_2O$ (5×200 mL). The combined organic layers were washed with water (5×1 L) and dried over anhydrous $Na_2SO_4$. After filtration, the filtrate was concentrated under reduced pressure. The crude product was purified by silica gel column chromatography with 2%~30% ethyl acetate in petroleum ether to afford the title compound (190 g, 88% yield) as a white solid. $^1$H NMR (400 MHz, $CD_3OD$) δ 7.69-7.63 (m, 1H), 7.12-6.98 (m, 4H), 6.76 (d, J=8.7 Hz, 1H), 6.63 (s, 1H), 4.93 (d, J=8.2 Hz, 1H), 4.78-4.60 (m, 1H), 4.53 (d, J=15.2 Hz, 1H), 3.14-3.06 (m, 2H), 2.86-2.64 (m, 3H), 2.04-1.83 (m, 2H), 1.74-1.67 (m, 2H), 1.51 (s, 9H); LC/MS (ESI, m/z): [(M+1)]=423.3.

Step 5—(S)-7-hydroxy-N—((R)-1,2,3,4-tetrahydronaphthalen-1-yl)-1,23,4-tetrahydroisoquinoline-3-carboxamide hydrochloride To a stirred solution of tert-butyl (3S)-7-hydroxy-3-[[(1R)-1,2,3,4-tetrahydronaphthalen-1-yl]carbamoyl]-3,4-dihydro-1H-isoquinoline-2-carboxylate (190 g, 450 mmol) in THF (500 mL) was added HCl (gas) in 1,4-dioxane (250 Ml, 4 M) dropwise at 0° C. The reaction mixture was stirred for 16 h at rt. On completion, the mixture was concentrated under reduced pressure. LC/MS (ESI, m/z): $[(M+1)]^+$=232.3.

Step 6—tert-butyl ((S)-1-((S)-7-hydroxy-3-(((R)-1,2,3,4-tetrahydronaphthalen-1-yl)carbamoyl)-3,4-dihydroisoquinolin-2(1H)-yl)-3,3-dimethyl-1-oxobutan-2-yl)carbamate To a stirred mixture of (2S)-2-[(tert-butoxycarbonyl)amino]-3,3-dimethylbutanoic acid (182 g, 786.13 mmol) and (3S)-7-hydroxy-N-[(1R)-1,2,3,4-tetrahydronaphthalen-1-yl]-1,2,3,4-tetrahydroisoquinoline-3-carboxamide hydrochloride (235 g, 655.11 mmol) in DMF (1 L) were added DIEA (254 g, 1.96 mol) and HATU (299 g, 786.13 mmol) in portions at 0° C. The resulting mixture was stirred for 2 h at rt. On completion, the reaction was quenched with water (3 L), and extracted with ethyl acetate (3×1 L). The combined organic layers were washed with water (2×2 L) and brine (2×500 mL), then dried over anhydrous $Na_2SO_4$. After filtration, the filtrate was concentrated under reduced pressure. The crude product was purified by silica gel column chromatography, eluting with 1%-30% ethyl acetate in petroleum ether to afford the title compound (154.5 g, 44% yield) as a white solid. LC/MS (ESI, m/z): [(M+1)]=536.3.

Step 7—tert-butyl ((S)-1-(((S)-1-((S)-7-((2,2-dimethyl-3,3-diphenyl-4,7,10-trioxa-3-siladodecan-12-yl)oxy)-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate To a stirred solution of tert-butyl N-[(2S)-1-[(3S)-7-hydroxy-3-[[(1R)-1,2,3,4-tetrahydronaphthalen-1-yl]carbamoyl]-3,4-dihydro-1H-isoquinolin-2-yl]-3,3-dimethyl-1-oxobutan-2-yl]carbamate (154 g, 288.23 mmol) in dioxane (700 mL) and DCM (200 mL) was added 4 M HCl (gas) in 1,4-dioxane (350 mL) dropwise at 0° C. The resulting mixture was stirred for 16 h at rt. On completion, the mixture was concentrated under reduced pressure to give the title compound. $^1$H NMR (400 MHz, $CD_3OD$) δ 7.33 (dd, J=2.1, 7.1 Hz, 1H), 7.16-7.05 (m, 5H), 6.87 (d, J=2.5 Hz, 1H), 6.72 (dd, J=2.5, 8.1 Hz, 1H), 5.03 (dd, J=4.8, 7.7 Hz, 1H), 4.95 (d, J=14.6 Hz, 1H), 4.67 (dd, J=5.8, 9.1 Hz, 1H), 4.63-4.58 (m, 2H), 3.37 (s, 4H), 3.15 (dd, J=5.9, 15.0 Hz, 1H), 3.04 (dd, J=9.2, 15.0 Hz, 1H), 2.88-2.71 (m, 2H), 1.96 (ddt, J=4.3, 10.8, 13.3 Hz, 2H), 1.85-1.71 (m, 2H), 1.26 (s, 9H), 1.15 (d, J=10.2 Hz, 2H); LC/MS (ESI, m/z): [(M+1)]=436.3.

Step 8—tert-butyl ((S)-1-(((S)-1-((S)-7-hydroxy-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate To a stirred mixture of (3S)-2-[(2S)-2-amino-3,3-dimethylbutanoyl]-7-hydroxy-N-[(1R)-1,2,3,4-tetrahydronaphthalen-1-yl]-3,4-dihydro-1H-isoquinoline-3-carboxamide hydrochloride (145 g, 307.18 mmol) and (2S)-2-[(tert-butoxycarbonyl)(methyl)amino]propanoic acid (74.92 g, 368.62 mmol) in DMF (1.5 L) were added DIEA (119 g, 921.55 mmol) and HATU (140 g, 368.62 mmol) in portions at 0° C. The resulting mixture was stirred for 2 h at rt. On completion, the reaction was quenched with water (5 L), and extracted with ethyl acetate (3×1 L). The combined organic layers were washed with water (2×2 L), brine (2×500 mL), and dried over anhydrous $Na_2SO_4$. After filtration, the filtrate was concentrated under reduced pressure. The crude product was purified by silica gel column chromatography, eluted with the 1%~50% ethyl acetate in petroleum ether to afford the title compound (110 g, 58% yield) as a yellow solid. LC/MS (ESI, m/z): $[(M+1)]^+$=621.4.

Step 9—tert-butyl N-[(1S)-1-[[(2S)-1-[(3S)-7-[2-(1,3-dioxoisoindol-2-yl)ethoxy]-3-[[(1R)-1,2,3,4-tetrahydronaphthalen-1-yl]carbamoyl]-3,4-dihydro-1H-isoquinolin-2-yl]-3,3-dimethyl-1-oxobutan-2-yl]carbamoyl]ethyl]-N-methylcarbamate To a stirred mixture of tert-butyl N-[(1S)-1-[[(2S)-1-[(3S)-7-hydroxy-3-[[(1R)-1,2,3,4-tetrahydronaphthalen-1-yl]carbamoyl]-3,4-dihydro-1H-isoquinolin-2-yl]-3,3-dimethyl-1-oxobutan-2-yl]carbamoyl]ethyl]-N-methylcarbamate (10.00 g, 16.11 mmol) and 2-(1,3-dioxoisoindol-2-yl)ethyl 4-methylbenzenesulfonate (8.35 g, 24.16 mmol) in acetonitrile (200 mL) was added $K_2CO_3$ (4.45 g, 32.22 mmol) in portions at rt. The resulting mixture was stirred for 16 h at 80° C. The resulting mixture was concentrated under reduced pressure. The crude product was purified by silica gel column chromatography, eluted with the 1%~50% ethyl acetate in petroleum ether to afford the title compound (11 g, 86% yield) as a white solid. $^1$H NMR (400 MHz, $CD_3OD$) δ 8.00-7.67 (m, 4H), 7.33-7.00 (m, 4H), 6.99-6.58 (m, 3H), 5.13-4.90 (m, 2H), 4.70-4.50 (m, 3H), 4.34-4.26 (m, 2H), 4.13-4.09 (m, 2H), 3.82-3.73 (m, 2H), 3.10-2.98 (m, 2H), 2.93-2.68 (m, 4H), 1.95-1.55 (m, 4H), 1.58-1.40 (m, 10H), 1.32-1.28 (m, 2H), 1.09 (s, 9H); LC/MS (ESI, m/z): $[(M+1)]^+$=794.4.

Step 10—tert-butyl N-[(1S)-1-[[(2S)-1-[(3S)-7-(2-aminoethoxy)-3-[[(1R)-1,2,3,4-tetrahydronaphthalen-1-yl]carbamoyl]-3,4-dihydro-1H-isoquinolin-2-yl]-3,3-dimethyl-1-oxobutan-2-yl]carbamoyl]ethyl]-N-methylcarbamate A solution of tert-butyl N-[(1S)-1-[[(2S)-1-[(3S)-7-[2-(1,3-dioxoisoindol-2-yl)ethoxy]-3-[[(1R)-1,2,3,4-tetrahydronaphthalen-1-yl]carbamoyl]-3,4-dihydro-1H-isoquinolin-2-yl]-3,3-dimethyl-1-oxobutan-2-yl]carbamoyl]ethyl]-N-methylcarbamate (11.00 g, 13.86 mmol) and $NH_2NH_2$—$H_2O$ (5.00 mL, 102.87 mmol) in EtOH (150.00 mL) was stirred for 2 h at rt. The resulting mixture was filtered and the filter cake was washed with ethanol (3×20 mL). The filtrate was concentrated under reduced pressure. The crude product was purified by reverse phase flash chromatography (Column: Spherical C18 Column, 20-40 um, 330 g; Mobile Phase A: Water (plus 10 mM FA); Mobile Phase B: ACN; Flow rate: 60 mL/min; Gradient: 30% B to 50% B in 25 min; Detector: UV 254/220 nm, the fractions containing the desired product were collected at 43% B) and concentrated under reduced pressure to afford the title compound (6.7 g, 73% yield) as a yellow solid. $^1$H NMR (300 MHz, $CD_3OD$) δ 7.28-7.25 (m, 1H), 7.17-7.00 (m, 4H), 6.97-6.79 (m, 2H), 5.50 (s, 1H), 5.23-4.90 (m, 2H), 4.78-4.50 (m, 3H), 4.31-4.03 (m, 2H), 3.33-3.17 (m, 2H), 3.15-3.07 (m, 2H), 2.88-2.77 (m, 5H), 2.01-1.59 (m, 4H), 1.50-1.47 (m, 10H), 1.37-1.23 (m, 2H), 1.11-1.08 (m, 9H); LC/MS (ESI, m/z): $[(M+1)]^+$=664.4.

4-[[2-[(3R,5R,6S)-5-(3-chlorophenyl)-6-(4-chlorophenyl)-1-[(1S)-1-(isopropylsulfonylmethyl)-2-methyl-propyl]-3-methyl-2-oxo-3-piperidyl]acetyl]amino]benzoic acid (Intermediate CK)

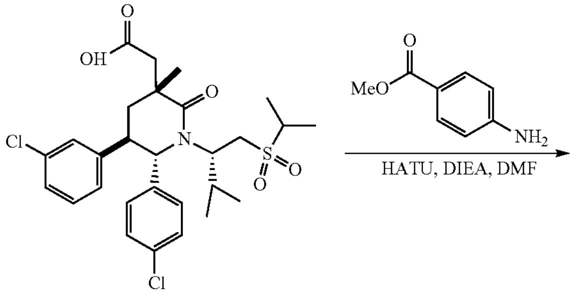

-continued

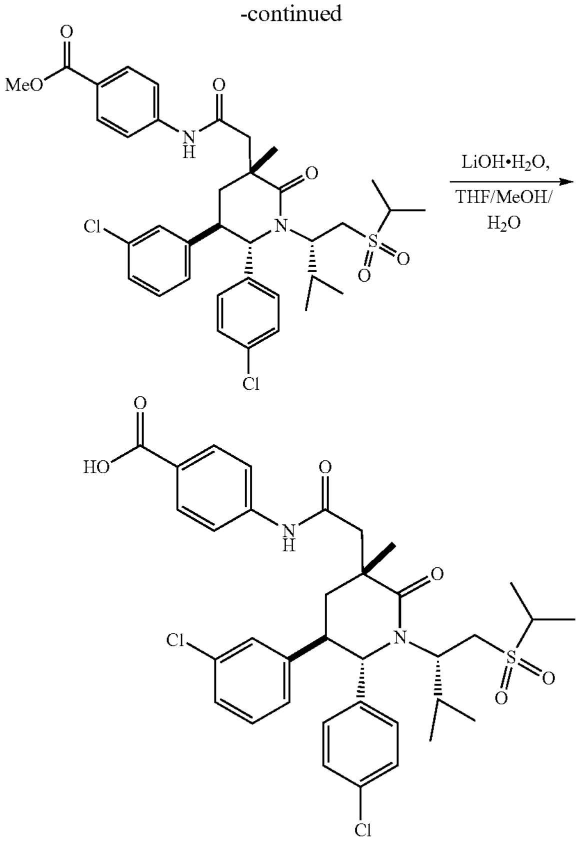

CK

Step 1—Methyl 4-[[2-[(3R,5R,6S)-5-(3-chlorophenyl)-6-(4-chlorophenyl)-1-[(1S)-1-(isopropyl sulfonylmethyl)-2-methyl-propyl]-3-methyl-2-oxo-3-piperidyl]acetyl]amino]benzoate To a mixture of 2-[(3R,5R,6S)-5-(3-chlorophenyl)-6-(4-chlorophenyl)-1-[(1S)-1-(isopropylsulfonyl methyl)-2-methyl-propyl]-3-methyl-2-oxo-3-piperidyl]acetic acid (250 mg, 439 umol, CAS #1352066-68-2), 1-methylimidazole (126 mg, 1.54 mmol, 122 uL) and [chloro(dimethylamino) methylene]-dimethyl-ammonium; hexafluorophosphate (148 mg, 527 umol) in ACN (2 mL) was added methyl 4-aminobenzoate (79.7 mg, 527 umol, CAS #619-45-4). The reaction mixture was stirred at 25° C. for 5 hr. On completion, the reaction mixture was diluted with water (10 mL) where a white solid precipitated which was filtered to give the title compound (300 mg, 97% yield) as light yellow solid. LC-MS ($ESI^+$) m/z 723.4 $(M+Na)^+$.

Step 2—4-[[2-[(3R,5R,6S)-5-(3-chlorophenyl)-6-(4-chlorophenyl)-1-[(1S)-1-(isopropylsulfonyl methyl)-2-methyl-propyl]-3-methyl-2-oxo-3-piperidyl]acetyl]amino]benzoic acid To a mixture of methyl 4-[[2-[(3R,5R,6S)-5-(3-chlorophenyl)-6-(4-chlorophenyl)-1-[(1S)-1-(isopropylsulfonylmethyl)-2-methyl-propyl]-3-methyl-2-oxo-3-piperidyl]acetyl]amino]benzoate (280 mg, 399 umol) in THF (4 mL) and $H_2O$ (0.5 mL) was added LiOH—$H_2O$ (83.7 mg, 2.00 mmol) and the reaction mixture was stirred at 25° C. for 2 hour. On completion, the reaction mixture was diluted with water (10 mL) and acidified with HCl (1N) until the pH=5-6, then the residue was extracted with EA (2×10 mL). The combined organic layer was dried over $Na_2SO_4$, filtered and concentrated in vacuo to give the title compound (350 mg, 90% yield) as light yellow solid. $^1H$ NMR (400 MHz, DMSO-$d_6$) δ 12.69 (s, 1H), 10.49 (s, 1H), 7.98-7.62 (m, 5H), 7.52-6.97 (m, 5H), 6.92-6.82 (m, 2H), 5.03 (d, J=11.2 Hz, 1H), 3.90-3.81 (m, 1H), 3.62-3.51 (m, 1H), 3.44-3.35 (m, 1H), 3.18 (d, J=13.2 Hz, 1H), 3.13-3.03 (m, 2H), 2.65 (d, J=13.6 Hz, 1H), 2.21-2.04 (m, 3H), 0.87 (t, J=7.6 Hz, 9H), 0.57 (d, J=6.4 Hz, 3H), 0.44 (d, J=6.8 Hz, 3H).

Tert-butyl N-[1-[1-[1-[(4-methoxyphenyl)methyl]-2,6-dioxo-3-piperidyl]-3,5-dimethyl-2-oxo-benzimidazol-4-yl]-4-piperidyl]-N-methyl-carbamate (Intermediate CL)

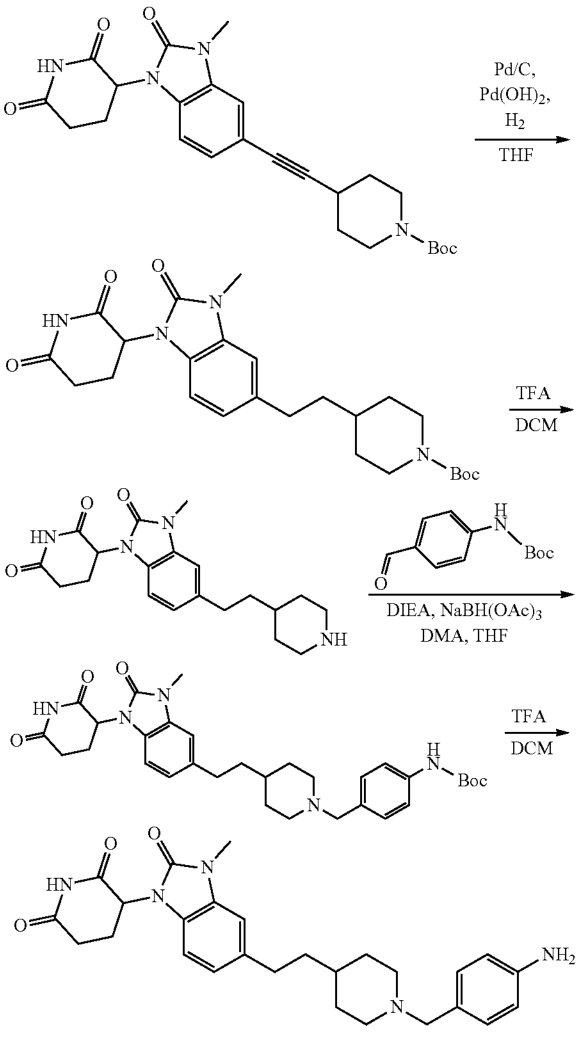

CL

Step 1—Tert-butyl 4-[2-[1-(2,6-dioxo-3-piperidyl)-3-methyl-2-oxo-benzimidazol-5-yl]ethyl] piperidine-1-carboxylate To a solution of tert-butyl 4-[2-[1-(2,6-dioxo-3-piperidyl)-3-methyl-2-oxo-benzimidazol-5-yl] ethynyl]piperidine-1-carboxylate (800 mg, 1.71 mmol, synthesized via Step 1 of Intermediate CT) in THF (50 mL) was added Pd/C (408 mg, 171 umol, 10 wt %) and $Pd(OH)_2$ (120 mg, 171 umol, 20 wt %) under $N_2$ atmosphere. The suspension was degassed and purged with $H_2$ three times and the mixture was stirred under $H_2$ (15 psi) at 25° C. for 16 hours. On completion, the mixture was filtered and concentrated in vacuo to give the title compound (730 mg, 1.55 mmol, 90% yield) as a yellow oil. LC-MS (ESI$^+$) m/z 371.1 (M−100)$^+$.

Step 2—3-[3-Methyl-2-oxo-5-[2-(4-piperidyl)ethyl] benzimidazol-1-yl]piperidine-2,6-dione To a solution of tert-butyl 4-[2-[1-(2,6-dioxo-3-piperidyl)-3-methyl-2-oxo-benzimidazol-5-yl]ethyl] piperidine-1-carboxylate (700 mg, 1.49 mmol) was added TFA (508 mg, 4.46 mmol) and DCM (28 mL) and the mixture was stirred at 25° C. for 1.5 hours. On completion, the reaction mixture was concentrated in vacuo to give the title compound (950 mg, TFA) as a yellow oil. LC-MS (ESI$^+$) m/z 371.0 (M+H)$^+$.

Step 3—Tert-butyl N-[4-[[4-[2-[1-(2,6-dioxo-3-piperidyl)-3-methyl-2-oxo-benzimidazol-5-yl]ethyl]-1-piperidyl]methyl]phenyl]carbamate To a solution of 3-[3-methyl-2-oxo-5-[2-(4-piperidyl) ethyl]benzimidazol-1-yl]piperidine-2,6-dione (430 mg, 887 umol TFA) and 4A molecular sieves (87.0 mg, 21.7 mmol) in DMA (12 mL) and THF (6 mL) was added DIEA (114 mg, 887 umol). The resulting mixture was stirred for 0.25 hour. Then AcOH (53.3 mg, 887 umol) was added, and tert-butyl N-(4-formylphenyl)carbamate (1.96 g, 8.88 mmol) was added to adjust the pH to 6. The mixture was stirred at 25° C. for 0.25 hour. Next, $NaBH(OAc)_3$ (940 mg, 4.44 mmol) was added to the mixture at 0° C. and stirred for 7.5 hours at 60° C. On completion, the mixture was quenched with water (5 mL) and extracted with DCM (3×5 mL). The combined organic phase was dried over anhydrous sodium sulfate, filtered and concentrated to give a residue. The residue was purified by column chromatography ($SiO_2$, DCM/Methanol=10:1) to give the title compound (70.0 mg, 13% yield) as a yellow oil. LC-MS (ESI$^+$) m/z 576.4 (M+H)$^+$.

Step 4—Tert-butyl N-[1-[1-[1-[(4-methoxyphenyl) methyl]-2,6-dioxo-3-piperidyl]-3,5-dimethyl-2-oxo-benzimidazol-4-yl]-4-piperidyl]-N-methyl-carbamate To a solution of tert-butyl N-[4-[[4-[2-[1-(2,6-dioxo-3-piperidyl)-3-methyl-2-oxo-benzimidazol-5-yl]ethyl]-1-piperidyl]methyl]phenyl]carbamate (70.0 mg, 121 umol) in DCM (2 mL) was added TFA (41.5 mg, 364 umol). The mixture was stirred at 25° C. for 1 hour. On completion, the mixture was concentrated in vacuo to give the title compound (100 mg, TFA) as a brown oil. LC-MS (ESI$^+$) m/z 476.3 (M+H)$^+$.

4-Amino-N-[5-[1-(2,6-dioxo-3-piperidyl)-3-methyl-2-oxo-benzimidazol-5-yl]pentyl]cyclohexanecarboxamide (Intermediate CM)

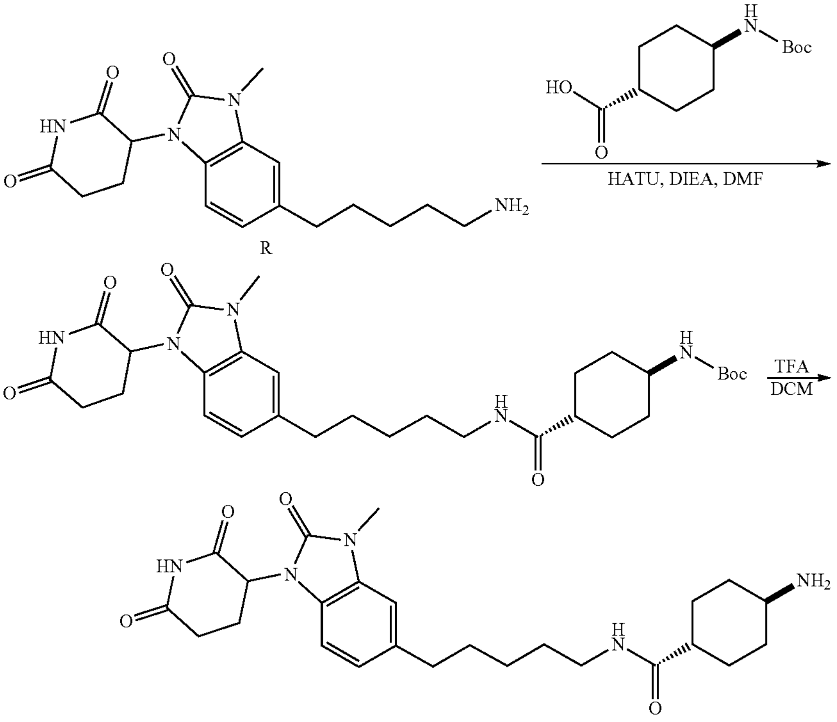

R

CM

Step 1—Tert-butyl N-[4-[5-[1-(2,6-dioxo-3-piperidyl)-3-methyl-2-oxo-benzimidazol-5-yl]pentylcarbamoyl]cyclohexyl]carbamate To a solution of 4-(tert-butoxycarbonylamino)cyclohexanecarboxylic acid (76.6 mg, 315 μmol, CAS #53292-89-0) and 3-[5-(5-aminopentyl)-3-methyl-2-oxo-benzimidazol-1-yl]piperidine-2,6-dione (100 mg, 262 umol, HCl salt, Intermediate R) in DMF (2.0 mL) was added HATU (129 mg, 341 μmol) and DIEA (169 mg, 1.31 mmol) at 25° C. The reaction solution was stirred at 25° C. for 2 hours. On completion, the reaction mixture was concentrated in vacuo to give a residue. The residue was purified by reverse phase flash [ACN/(0.1% FA in water), 0% to 90%] to give the title compound (80.0 mg, 50% yield) as white solid. $^1$H NMR (400 MHz, DMSO-$d_6$) δ 11.07 (s, 1H), 7.64 (t, J=5.6 Hz, 1H), 7.06-6.93 (m, 2H), 6.86 (d, J=8.8 Hz, 1H), 6.68 (d, J=7.6 Hz, 1H), 5.33 (dd, J=5.6, 12.8 Hz, 1H), 3.14 (dd, J=2.8, 8.0 Hz, 1H), 3.00 (q, J=6.8 Hz, 2H), 2.95-2.85 (m, 1H), 2.77-2.57 (m, 4H), 2.07-1.89 (m, 2H), 1.77 (d, J=10.0 Hz, 2H), 1.70-1.52 (m, 4H), 1.43-1.35 (m, 11H), 1.32-1.21 (m, 3H), 1.19-1.03 (m, 2H). LC-MS (ESI$^+$) m/z 570.4 $(M+H)^+$.

Step 2—4-Amino-N-[5-[1-(2,6-dioxo-3-piperidyl)-3-methyl-2-oxo-benzimidazol-5-yl]pentyl] cyclohexanecarboxamide To a mixture of tert-butyl N-[4-[5-[1-(2,6-dioxo-3-piperidyl)-3-methyl-2-oxo-benzimidazol-5-yl]pentylcarbamoyl]cyclohexyl]carbamate (30.0 mg, 52.6 umol) in DCM (1.0 mL) was added HCl/dioxane (4 M, 0.2 mL) at 25° C. under $N_2$ and the mixture was stirred at 25° C. for 30 min. On completion, the reaction mixture was concentrated in vacuo to give the title compound (25 mg, 99% yield) as yellow solid. LC-MS (ESI$^+$) m/z 470.2 $(M+H)^+$.

Chloro-(3-chloro-2-fluoro-phenyl)-dimethyl-oxo-dispiro[BLAH]carboxylic acid (Intermediate CN)

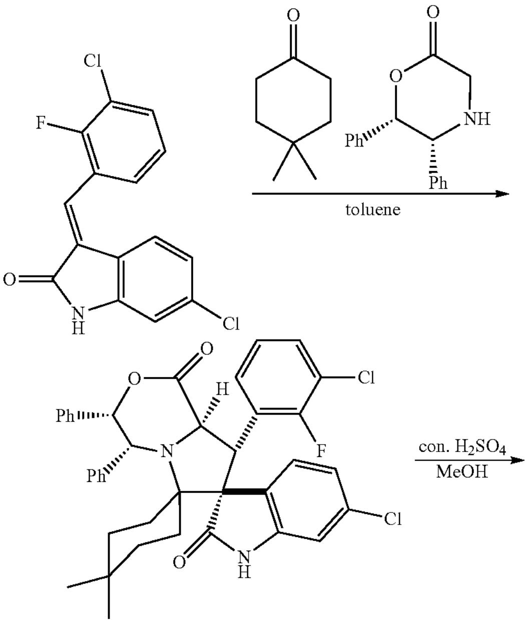

-continued

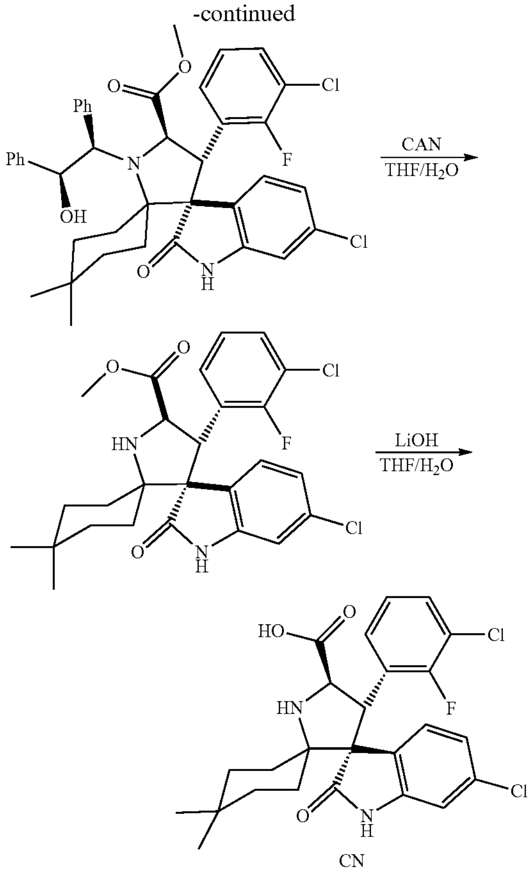

CN

Step 1—chloro-(3-chloro-2-fluoro-phenyl)-dimethyl-diphenyl-dispiro [BLAH]dione

To a solution of (3E)-6-chloro-3-[(3-chloro-2-fluoro-phenyl)methylene]indolin-2-one (1.00 g, 3.25 mmol, synthesized via Step 1 of Intermediate CI) in THF (2 mL) and toluene (20 mL) was added 4,4-dimethylcyclohexanone (819 mg, 6.49 mmol) and (5R,6S)-5,6-diphenylmorpholin-2-one (986 mg, 3.89 mmol, CAS #282735-66-4). The mixture was then stirred at 140° C. for 3 hrs. On completion, the mixture was diluted by ethyl acetate (25 mL) and washed with brine (25 mL). The organic layer was dried by sodium sulfate, filtered and concentrated in vacuo to give the residue. The residue was purified by column chromatography ($SiO_2$, petroleum ether:ethyl acetate=3:1) to give the title compound (1.00 g, 34% yield) as yellow solid. LC-MS ($ESI^+$) m/z 689 $(M+H)^+$.

Step 2—methylchloro-(3-chloro-2-fluoro-phenyl)-[(1R,2S)-2-hydroxy-1,2-diphenyl-ethyl]-dimethy 1-oxo-dispiro[BLAH] carboxylate To a solution of chloro-(3-chloro-2-fluoro-phenyl)-dimethyl-diphenyl-dispiro[BLAH]dione (1.00 g, 1.49 mmol) in MeOH (12 mL) was added $H_2SO_4$ (1.10 g, 11.2 mmol, 0.6 mL) and the mixture was stirred at 50° C. for 12 hrs. On completion, to the mixture was added sodium bicarbonate to adjust the pH<7 and then the mixture was extracted with ethyl acetate (200 mL). The organic layer was dried by sodium sulfate, filtered and concentrated in vacuo to give the residue. The residue was purified by column chromatography ($SiO_2$, petroleum ether:ethyl acetate=2:1) to give the title compound (400 mg, 32% yield) as yellow solid. $^1H$ NMR (400 MHz, DMSO-$d_6$) δ 10.43 (s, 1H), 7.52 (d, J=2.4, 8.0 Hz, 1H), 7.40 (d, J=6.4 Hz, 2H), 7.34-7.25 (m, 1H), 7.23-7.10 (m, 9H), 7.08-6.97 (m, 3H), 6.95-6.88 (m, 1H), 6.63 (d, J=2.0 Hz, 1H), 5.50 (d, J=1.8 Hz, 1H), 5.33 (s, 1H), 4.75 (d, J=3.6 Hz, 1H), 4.40 (s, 2H), 3.43 (s, 3H), 1.99 (s, 1H), 1.31-1.12 (m, 3H), 1.01-0.92 (m, 4H), 0.88-0.82 (m, 3H), 0.80-0.75 (m, 1H), 0.52 (s, 3H); LC-MS ($ESI^+$) m/z 701 $(M+H)^+$.

Step 3—methyl chloro-(3-chloro-2-fluoro-phenyl)-dimethyl-oxo-dispiro [BLAH]carboxylate To a solution of methyl chloro-(3-chloro-2-fluoro-phenyl)-[(1R,2S)-2-hydroxy-1,2-diphenyl-ethyl]-dimethyl-oxo-dispiro [BLAH]carboxylate (350 mg, 498 umol) in $H_2O$ (2.0 mL) and ACN (2.0 mL) was added CAN (546 mg, 997 umol) and the mixture was stirred at 25° C. for 15 hrs. On completion, the mixture was poured to the water (50 mL) and extracted with ethyl acetate (30 mL×2). The organic layer was dried by sodium sulfate and concentrated in vacuo to give the residue. The residue was purified by column chromatography ($SiO_2$, petroleum ether:ethyl acetate=2:1) to give the title compound (140 mg, 56% yield) as yellow solid. $^1H$ NMR (400 MHz, DMSO-$d_6$) δ 10.56 (s, 1H), 7.56 (t, J=6.4 Hz, 1H), 7.46 (d, J=2.0, 8.0 Hz, 1H), 7.40-7.30 (m, 1H), 7.14 (d, J=8.0 Hz, 1H), 7.05 (d, J=2.0, 8.1 Hz, 1H), 6.69 (d, J=2.0 Hz, 1H), 4.76 (d, J=9.6 Hz, 1H), 4.56 (d, J=9.6 Hz, 1H), 4.04 (m, J=8.0 Hz, 1H), 3.58 (s, 3H), 1.99 (s, 1H), 1.92-1.75 (m, 2H), 1.57-1.37 (m, 3H), 1.25-1.03 (m, 4H), 1.01-0.93 (m, 1H), 0.86 (s, 3H), 0.61 (s, 3H).

Step 4—chloro-(3-chloro-2-fluoro-phenyl)-dimethyl-oxo-dispiro[BLAH]carboxylic acid To a solution of methyl chloro-(3-chloro-2-fluoro-phenyl)-dimethyl-oxo-dispiro[BLAH]carboxylate (140 mg, 277 umol) in THF (3.0 mL) and $H_2O$ (3.0 mL) was added LiOH—$H_2O$ (23.3 mg, 554 umol) and the mixture was stirred at 25° C. for 12 hrs. On completion, the mixture was added hydrochloride to adjust the pH to 6. The mixture was then filtered and concentrated in vacuo to give the title compound (100 mg, 66% yield) as a yellow solid. $^1H$ NMR (400 MHz, DMSO-$d_6$) δ 10.71-10.43 (m, 1H), 7.63-7.43 (m, 2H), 7.40-7.33 (m, 1H), 7.20-7.05 (m, 2H), 6.87-6.62 (m, 2H), 4.69 (d, J=9.6 Hz, 1H), 4.56-4.47 (m, 1H), 4.39-4.38 (m, 1H), 1.69-1.41 (m, 4H), 1.38-1.13 (m, 4H), 0.87 (d, J=10.4 Hz, 3H), 0.63 (d, J=8.0 Hz, 3H); LC-MS ($ESI^+$) m/z 491 $(M+H)^+$.

3-[5-[2-[1-[(4-Aminocyclohexyl)methyl]-4-piperidyl]ethynyl]-3-methyl-2-oxo-benzimidazol-1-yl]piperidine-2,6-dione (Intermediate CO)

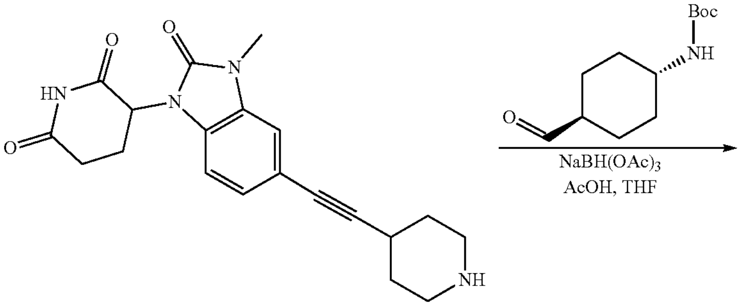

CT

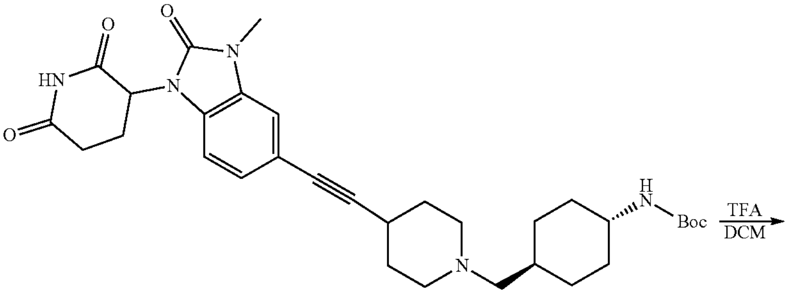

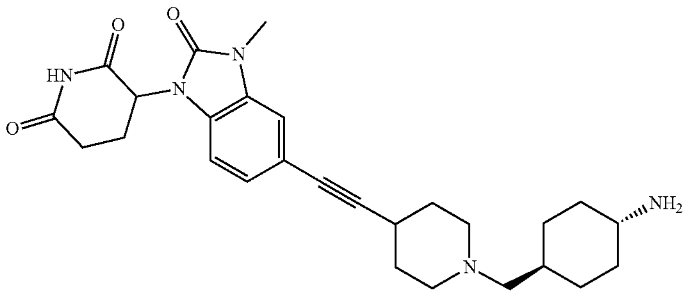

CO

Step 1—Tert-butyl N-[4-[[4-[2-[1-(2,6-dioxo-3-piperidyl)-3-methyl-2-oxo-benzimidazol-5-yl]ethynyl]-1-piperidyl]methyl]cyclohexyl]carbamate To a solution of 3-[3-methyl-2-oxo-5-[2-(4-piperidyl)ethynyl]benzimidazol-1-yl]piperidine-2,6-dione (200 mg, 545 umol, Intermediate CT) in THF (3 mL) was added tert-butyl N-(4-formylcyclohexyl)carbamate (124 mg, 546 umol, CAS #181308-56-5), AcOH (65.06 mg, 1.09 mmol) and $NaBH(OAc)_3$ (173 mg, 819 umol) in turn. The mixture was stirred at 25° C. for 2 hrs. On completion, the mixture was quenched with $NH_4Cl$ (2 mL) and brine (4 mL), then extracted with EA (20 mL). The organic layer was dried over $Na_2SO_4$, filtered and concentrated in vacuo to afford the crude product. The residue was purified by silica gel column chromatography to give the title compound (110 mg, 34% yield) as light yellow powder. LC-MS ($ESI^+$) m/z 578.2 $(M+H)^+$.

Step 2—3-[5-[2-[1-[(4-Aminocyclohexyl)methyl]-4-piperidyl]ethynyl]-3-methyl-2-oxo-benzimidazol-1-yl]piperidine-2,6-dione To a solution of tert-butyl N-[4-[[4-[2-[1-(2,6-dioxo-3-piperidyl)-3-methyl-2-oxo-benzimidazol-5-yl]ethynyl]-1-piperidyl]methyl]cyclohexyl]carbamate (60.0 mg, 104 umol) in DCM (0.5 mL) was added TFA (385 mg, 3.38 mmol) and the mixture was stirred at 25° C. for 1 hr. On completion, the mixture was concentrated to give the title compound (40.0 mg, 68% yield) as a red solid. LC-MS ($ESI^+$) m/z 478.3 $(M+H)^+$.

3-[5-[2-[1-(4-Aminocyclohexanecarbonyl)-4-piperidyl]ethynyl]-3-methyl-2-oxo-benzimidazol-1-yl]piperidine-2,6-dione (Intermediate CP)

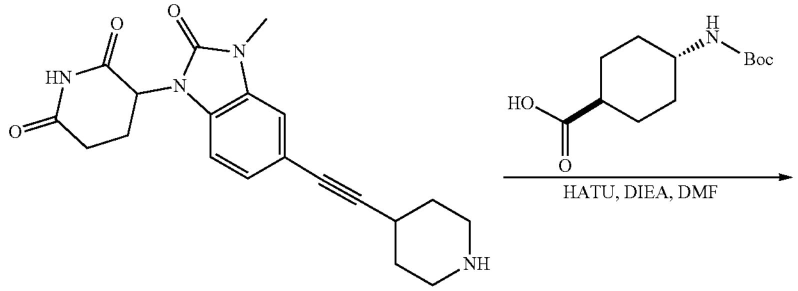

CT

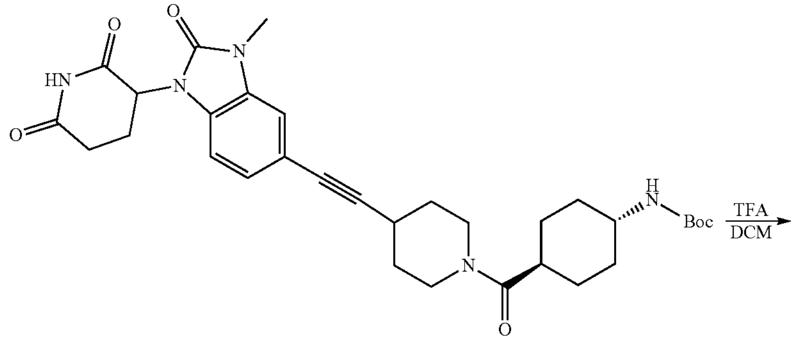

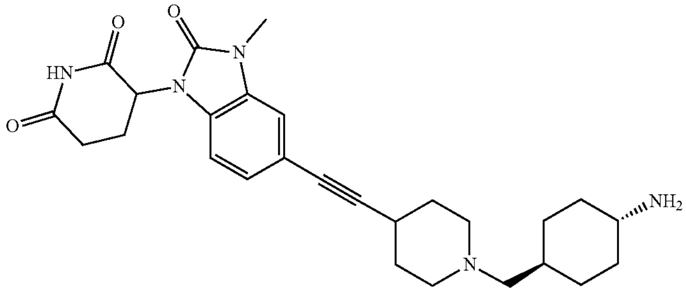

CP

Step 1—Tert-butylN-[4-[4-[2-[1-(2,6-dioxo-3-piperidyl)-3-methyl-2-oxo-benzimidazol-5-yl]ethynyl]piperidine-1-carbonyl]cyclohexyl]carbamate The mixture of 3-[3-methyl-2-oxo-5-[2-(4-piperidyl)ethynyl]benzimidazol-1-yl]piperidine-2,6-dione (70.0 mg, 145 umol, TFA salt, Intermediate CT) and DIEA (94.1 mg, 728 umol) in DMF (1.5 mL), 4-(tert-butoxycarbonylamino)cyclohexanecarboxylic acid (35.5 mg, 145.7 umol, CAS #130309-46-5) and HATU (66.5 mg, 175 umol) was added into the mixture in turn. The mixture was then stirred at 25° C. for 1 hr. On completion, the mixture was quenched with brine (10 mL), then extracted with EtOAc (20 mL). The organic layer was dried over $Na_2SO_4$, and concentrated in vacuo to afford the crude. The crude was purified by Pre-TLC (DCM:MeOH=20:1) to give the title compound (70.0 mg, 79% yield) as white powder. $^1H$ NMR (400 MHz, $CDCl_3$) δ 8.19-8.04 (m, 1H), 7.17-7.12 (m, 1H), 7.06 (d, J=1.2 Hz, 1H), 6.74 (d, J=8.0 Hz, 1H), 4.45-4.31 (m, 1H), 4.04-3.89 (m, 1H), 3.80-3.66 (m, 2H), 3.45-3.42 (m, 3H), 3.34 (s, 2H), 3.00-2.66 (m, 4H), 2.51-2.37 (m, 1H), 2.29-2.20 (m, 1H), 2.05 (s, 2H), 1.90 (dd, J=2.4, 12.8 Hz, 2H), 1.82-1.64 (m, 6H), 1.45 (s, 11H), 1.19-1.08 (m, 2H); LC-MS (ESI−) m/z 536.3 $(M-C4H9)^+$.

Step 2—3-[5-[2-[1-(4-Aminocyclohexanecarbonyl)-4-piperidyl]ethynyl]-3-methyl-2-oxo-benzimidazol-1-yl]piperidine-2,6-dione To a solution of tert-butyl N-[4-[4-[2-[1-(2,6-dioxo-3-piperidyl)-3-methyl-2-oxo-benzimidazol-5-yl] ethynyl] piperidine-1-carbonyl]cyclohexyl]carbamate (70.0 mg, 118 umol) in DCM (0.5 mL) was added TFA (385 mg, 3.38 mmol) and the mixture was stirred at 25° C. for 1 hr. On completion, the mixture was concentrated to give the title compound (50.0 mg, 56% yield) as yellow solid. LC-MS $(ESI^+)$ m/z 492.4 $(M+H)^+$.

C4-amino-N-[5-[1-(2,6-dioxo-3-piperidyl)-3-methyl-2-oxo-benzimidazol-5-yl]pentyl] benzamide (Intermediate CQ)

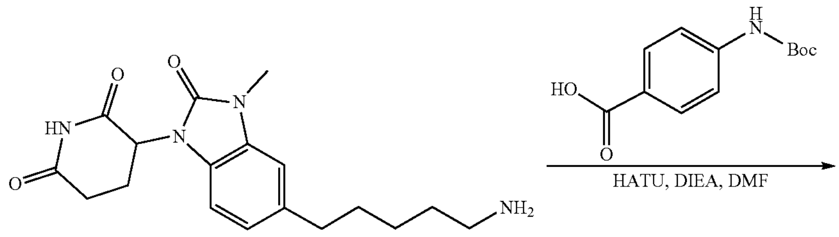

R

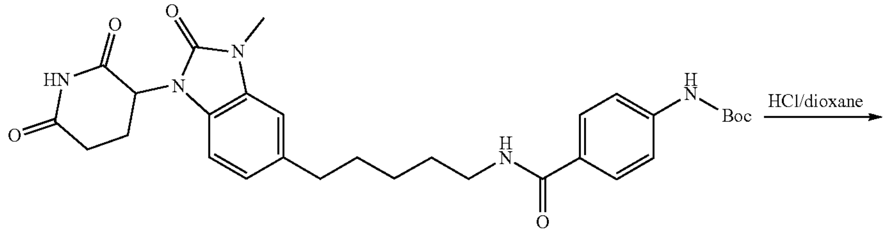

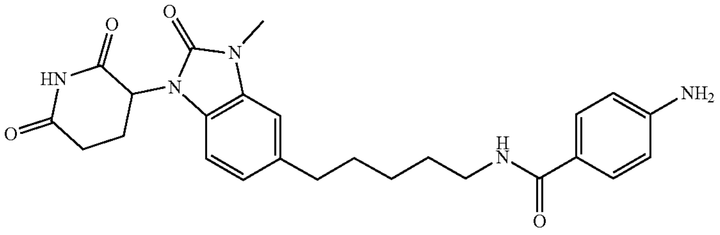

CQ

Step 1-tert-butylN-[4-[5-[1-(2,6-dioxo-3-piperidyl)-3-methyl-2-oxo-benzimidazol-5-yl]pentylcarbamoyl]phenyl]carbamate To a solution of 3-[5-(5-aminopentyl)-3-methyl-2-oxo-benzimidazol-1-yl]piperidine-2,6-dione (450 mg, 1.31 mmol, Intermediate R) and 4-(tert-butoxycarbonylamino)benzoic acid (281 mg, 1.19 mmol) in DMF (10 mL) was added DIEA (767 mg, 5.94 mmol) and HATU (587 mg, 1.54 mmol). The mixture was stirred at 25° C. for 1 hr. On completion, the reaction mixture was filtered, concentrated in vacuo to give the residue. The crude product was purified by reversed-phase HPLC (0.1% FA condition) to give the title compound (380 mg, 48% yield). $^1$H NMR (400 MHz, DMSO-$d_6$) δ11.08 (s, 1H), 9.59 (s, 1H), 8.27 (m, J=5.6 Hz, 1H), 7.74 (d, J=8.8 Hz, 2H), 7.50 (d, J=8.8 Hz, 2H), 7.11-6.95 (m, 2H), 6.87 (J=1.2, 8.0 Hz, 1H), 5.33 (d, J=5.6, 12.8 Hz, 1H), 3.31 (s, 3H), 3.26-3.18 (m, 2H), 2.97-2.84 (m, 1H), 2.75-2.54 (m, 4H), 2.05-1.95 (m, 1H), 1.70-1.58 (m, 4H), 1.49 (s, 9H), 1.39-1.32 (m, 2H). LC-MS (ESI$^+$) m/z 564.2 (M+H)$^+$.

Step 2—C4-amino-N-[5-[1-(2,6-diox o-3-piperidyl)-3-methyl-2-oxo-benzimidazol-5-yl]pentyl]benzamide To a solution of tert-butyl N-[4-[5-[1-(2.6-dioxo-3-piperidyl)-3-methyl-2-oxo-benzimidazol-5-yl] pentylcarbamoyl] phenyl] carbamate (80.0 mg, 141 umol) in DCM (2.0 mL) was added HCl/dioxane (4 M, 1.60 mL) and the mixture was stirred at 25° C. for 1 hr. On completion, the reaction mixture was concentrated in vacuo to give the title compound (50 mg, 60% yield). LC-MS (ESI$^+$) m/z 464.2 (M+H)$^+$.

3-[5-[2-[1-[(4-aminophenyl)methyl]-4-piperidyl]ethynyl]-3-methyl-2-oxo-benzimidazol-1-yl]piperidine-2,6-dione (Intermediate CR)

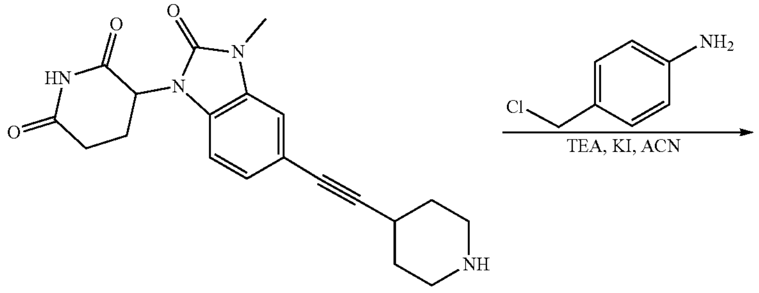

CT

-continued

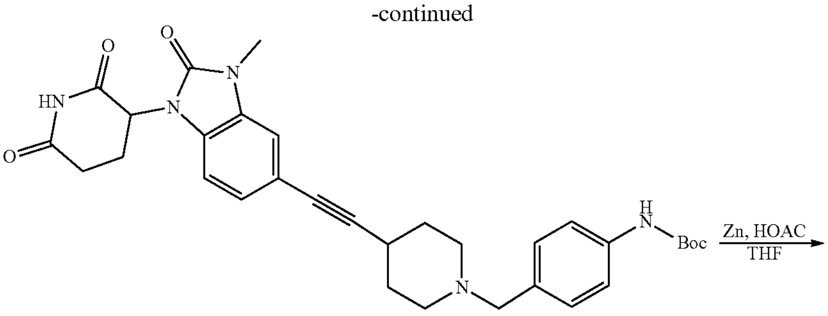

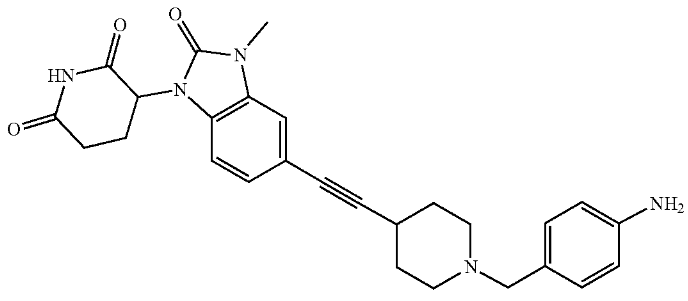

CR

Step 1—3-[3-methyl-5-[2-[1-[(4-nitrophenyl) methyl]-4-piperidyl]ethynyl]-2-oxo-benzimidazol-1-yl]piperidine-2,6-dione To a solution of 3-[3-methyl-2-oxo-5-[2-(4-piperidyl) ethynyl]benzimidazol-1-yl]piperidine-2,6-dione (1.00 g, 2.08 mmol, TFA) in ACN (15 mL) was added TEA (421 mg, 4.16 mmol), KI (34.5 mg, 208 umol) and 1-(chloromethyl)-4-nitro-benzene (357 mg, 2.08 mmol). The mixture was stirred at 25° C. for 12 hours. On completion, the mixture was concentrated to give the residue. The residue was purified by column chromatography ($SiO_2$, dichloromethane:methanol=1:0 to 10:1) to give the title compound (712 mg, 60% yield) as a yellow solid. LC-MS ($ESI^+$) m/z 602.2 $(M+H)^+$.

Step 2—3-[5-[2-[1-[(4-aminophenyl)methyl]-4-piperidyl]ethynyl]-3-methyl-2-oxo-benzimidazol-1-yl] piperidine-2,6-dione To a solution of 3-[3-methyl-5-[2-[1-[(4-nitrophenyl) methyl]-4-piperidyl]ethynyl]-2-oxo-benzimidazol-1-yl]piperidine-2,6-dione (20.0 mg, 39.8 umol) in AcOH (0.5 mL) and THF (2.5 mL) was added Zn (26.0 mg, 398 umol) and the mixture was stirred at 25° C. for 2 hours. The mixture was filtered, and the filtrate was concentrated to give title compound (20.0 mg, 94% yield) as a white solid. LC-MS ($ESI^+$) m/z 472.1 $(M+H)^+$.

3-[5-[2-[1-(5-Aminotetrahydropyran-2-carbonyl)-4-piperidyl]ethynyl]-3-methyl-2-oxo-benzimidazol-1-yl]piperidine-2,6-dione (Intermediate CS)

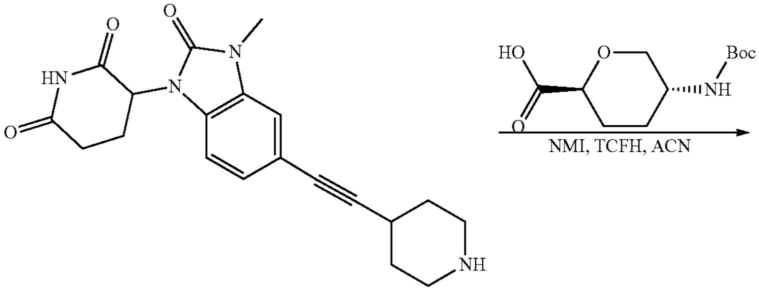

CT

-continued

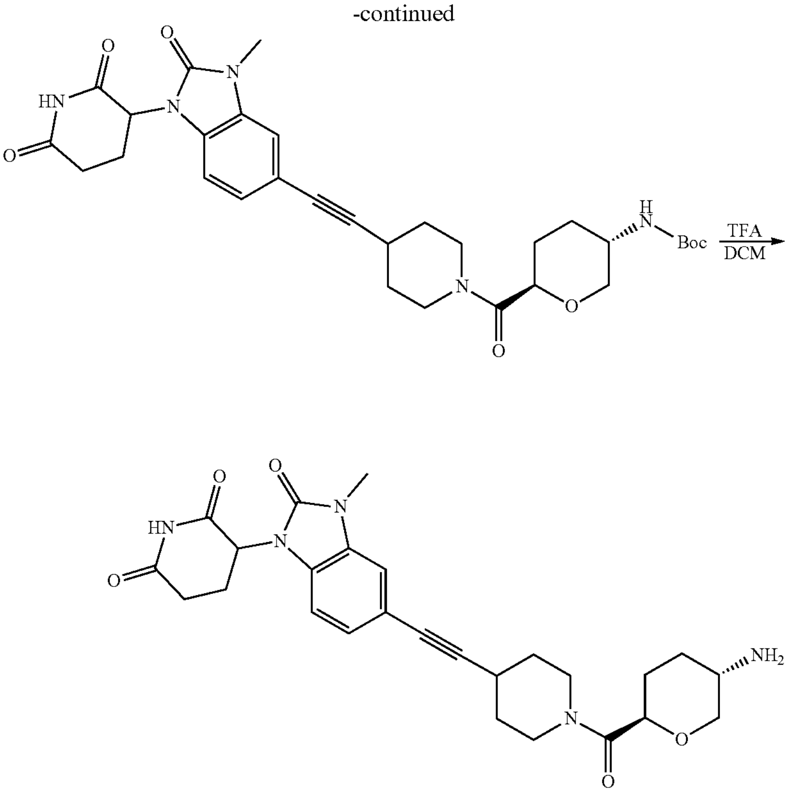

CS

Step 1—Tert-butyl N-[6-[4-[2-[1-(2,6-dioxo-3-piperidyl)-3-methyl-2-oxo-benzimidazol-5-yl]ethynyl]piperidine-1-carbonyl]tetrahydropyran-3-ylcarbamate To a solution of 3-[3-methyl-2-oxo-5-[2-(4-piperidyl)ethynyl]benzimidazol-1-yl]piperidine-2,6-dione (300 mg, 624 umol, Intermediate CT) and (2S,5R)-5-(tert-butoxycarbonylamino)tetrahydropyran-2-carboxylic acid (128 mg, 520 umol, CAS #603130-13-8) in ACN (6 mL) was adjusted to pH=8 with 1-methylimidazole (214 mg, 2.60 mmol) and then [chloro (dimethylamino)methylene]-dimethyl-ammonium; hexafluorophosphate (438 mg, 1.56 mmol) was added. The mixture was stirred at 25° C. for 0.5 hr. On completion, the mixture was quenched with water (10 mL), and extracted with EA (2×20 mL). Then the organic layer was washed with brine (2×10 mL), dried over $Na_2SO_4$, concentrated in vacuo to afford the crude product. The residue was purified by silica gel column chromatography (EA, eluted ~100%) to give the title compound (120 mg, 36% yield) as light yellow solid. LC-MS ($ESI^+$) m/z 594.4 $(M+H)^+$.

Step 2—3-[5-[2-[1-(5-Aminotetrahydropyran-2-carbonyl)-4-piperidyl]ethynyl]-3-methyl-2-oxo-benzimidazol-1-yl]piperidine-2,6-dione To a solution of tert-butyl N-[6-[4-[2-[1-(2,6-dioxo-3-piperidyl)-3-methyl-2-oxo-benzimidazol-5-yl]ethynyl]piperidine-1-carbonyl]tetrahydropyran-3-yl]carbamate (50 mg, 84.2 umol) in DCM (0.5 mL) was added TFA (154 mg, 1.35 mmol) and the mixture was stirred at 0° C. for 1 hr. On completion, the mixture was concentrated to give the title compound (50 mg, 98% yield) as a red solid. LC-MS (ESI−) m/z 494.2 $(M+H)^+$.

Ethyl 3-[3-methyl-2-oxo-5-[2-(4-piperidyl)ethynyl]benzimidazol-1-yl]piperidine-2,6-dione (Intermediate CT)

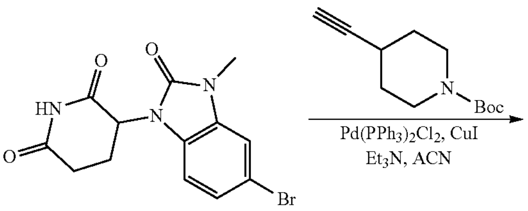

E

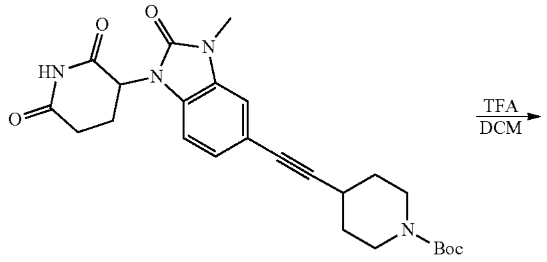

-continued

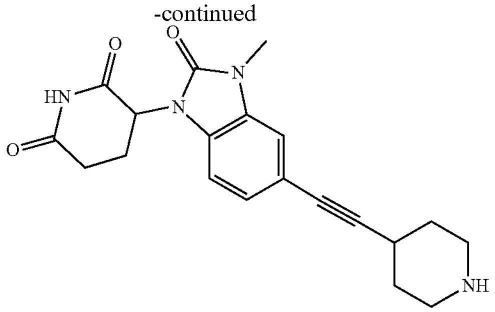

CT

Step 1—Ethyl tert-butyl 4-[2-[1-(2,6-dioxo-3-piperidyl)-3-methyl-2-oxo-benzimidazol-5-yl]ethynyl]piperidine-1-carboxylate To a solution of 3-(5-bromo-3-methyl-2-oxo-benzimidazol-1-yl)piperidine-2,6-dione (3.00 g, 8.87 mmol, Intermediate E) and tert-butyl 4-ethynylpiperidine-1-carboxylate (2.23 g, 10.6 mmol, CAS #287192-97-6) in ACN (30 mL) was added TEA (4.49 g, 44.4 mmol), $Pd(PPh_3)_2Cl_2$ (622 mg, 887 umol) and CuI (84.4 mg, 443 umol) was degassed and purged with $N_2$ three times, and then the mixture was stirred at 80° C. for 16 hrs under $N_2$ atmosphere. The mixture was filtered and concentrated to give a residue. The residue was purified by column chromatography ($SiO_2$, petroleum ether/ethyl acetate=5:1 to 1:1.5) to give the title compound (2.70 g, 65% yield) as a yellow solid. $^1H$ NMR (400 MHz, $CDCl_3$) δ 8.04 (s, 1H), 7.15 (dd, J=1.2, 8.0 Hz, 1H), 7.07 (d, J=1.2 Hz, 1H), 6.73 (d, J=8.0 Hz, 1H), 5.19 (dd, J=5.2, 12.8 Hz, 1H), 3.82-3.70 (m, 2H), 3.43 (s, 3H), 3.26 (ddd, J=3.2, 8.4, 13.2 Hz, 2H), 3.00-2.92 (m, 1H), 2.85-2.78 (m, 2H), 2.73 (dd, J=4.4, 13.2 Hz, 1H), 2.32-2.19 (m, 1H), 1.95-1.83 (m, 2H), 1.69 (tdd, J=4.0, 8.4, 12.8 Hz, 2H), 1.48 (s, 9H).

Step 2—Ethyl 3-[3-methyl-2-oxo-5-[2-(4-piperidyl)ethynyl]benzimidazol-1-yl]piperidine-2,6-dione To a solution of tert-butyl 4-[2-[1-(2,6-dioxo-3-piperidyl)-3-methyl-2-oxo-benzimidazol-5-yl]ethynyl]piperidine-1-carboxylate (500 mg, 1.07 mmol) in DCM (12 mL) was added TFA (6.16 g, 54.02 mmol). The mixture was stirred at 25° C. for 6 hrs. On completion, the mixture was concentrated to give the title compound (490 mg, 100% yield) as a yellow solid. LC-MS (ESI$^+$) m/z 367.1 (M+H)$^+$.

Ethyl 3-[5-[2-[1-(4-aminobenzoyl)-4-piperidyl]ethynyl]-3-methyl-2-oxo-benzimidazol-1-yl]piperidine-2,6-dione (Intermediate CU)

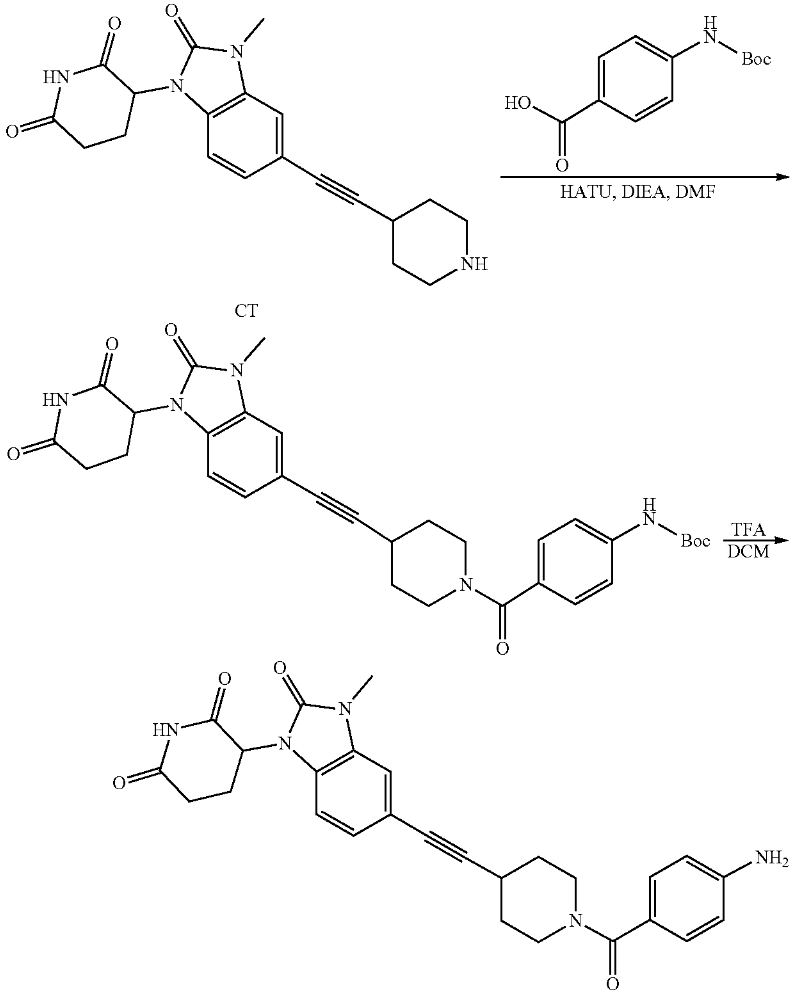

CU

Step 1—Ethyl tert-butyl N-[4-[4-[2-[1-(2,6-dioxo-3-piperidyl)-3-methyl-2-oxo-benzimidazol-5-yl]ethynyl]piperidine-1-carbonyl]phenyl]carbamate To a solution of 4-(tert-butoxycarbonylamino)benzoic acid (222 mg, 936 umol, CAS #66493-39-8) in DMF (3 mL) was added DIEA (484 mg, 3.75 mmol) and HATU (356.14 mg, 936.65 umol). The reaction mixture was stirred for 30 minutes then 3-[3-methyl-2-oxo-5-[2-(4-piperidyl)ethynyl]benzimidazol-1-yl]piperidine-2,6-dione (300 mg, 624 umol, TFA, Intermediate CT) was added and the mixture was stirred at 25° C. for 2 hrs. On completion, the mixture was quenched with water (10 mL), and extracted with ethyl acetate (3×20 mL). The organic layer was dried over $Na_2SO_4$, and concentrated in vacuo to afford crude. The residue was purified by column chromatography ($SiO_2$, dichloromethane:methanol=100:1 to 20:1) to give the compound (300 mg, 57% yield) as a yellow oil. LC-MS ($ESI^+$) m/z 586.2 $(M+H)^+$.

Step 2—Ethyl 3-[5-[2-[1-(4-aminobenzoyl)-4-piperidyl]ethynyl]-3-methyl-2-oxo-benzimidazol-1-yl]piperidine-2,6-dione A solution of tert-butyl N-[4-[4-[2-[1-(2,6-dioxo-3-piperidyl)-3-methyl-2-oxo-benzimidazol-5-yl] ethynyl]piperidine-1-carbonyl]phenyl]carbamate (100 mg, 170 umol) in TFA (1 mL) and DCM (5 mL) was stirred at 25° C. for 1 hr. On completion, the mixture was concentrated to give the compound (100 mg, 97% yield, TFA) as a yellow oil. LC-MS ($ESI^+$) m/z 486.2 $(M+H)^+$.

3-[3-Methyl-2-oxo-4-[[4-(4-piperidyloxy)-1-piperidyl]methyl]benzimidazol-1-yl]piperidine-2,6-dione (Intermediate CV)

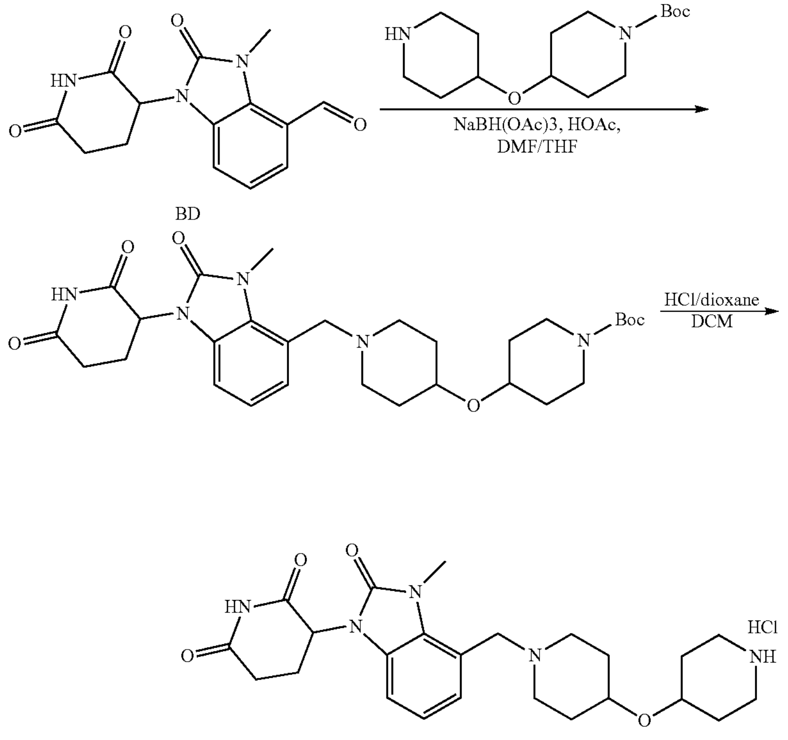

CV

Step 1—Tert-butyl 4-[[1-[[1-(2,6-dioxo-3-piperidyl)-3-methyl-2-oxo-benzimidazol-4-yl]methyl]-4-piperidyl]oxy]piperidine-1-carboxylate To a solution of 1-(2,6-dioxo-3-piperidyl)-3-methyl-2-oxo-benzimidazole-4-carbaldehyde (200 mg, 696 umol, Intermediate BD), tertbutyl 4-(4-piperidyloxy)piperidine-1-carboxylate (218 mg, 766 μmol, CAS #845305-83-1) in DMF (2.00 mL) and THF (2.00 mL) was added HOAc (83.6 mg, 1.39 mmol). The mixture was stirred at 80° C. for 0.5 hr. Then $NaBH(OAc)_3$ (295 mg, 1.39 mmol) was added, then the mixture was stirred at 20° C. for 16 hrs. On completion, the reaction was quenched by addition water (0.5 mL), and concentrated in vacuo to give a residue. The residue was purified by reverse phase (0.1% FA) to give the title compound (180 mg, 46% yield) as a yellow solid. LC-MS ($ESI^+$) m/z 556.3 $(M+H)^+$ Step 2—3-[3-Methyl-2-oxo-4-[[4-(4-piperidyloxy)-1-piperidyl]methyl]benzimidazol-1-yl]piperidine-2,6-dione To a solution of tert-butyl 4-[[1-[[1-(2,6-dioxo-3-piperidyl)-3-methyl-2-oxo-benzimidazol-4-yl]methyl]-4-piperidyl]oxy]piperidine-1-carboxylate (150 mg, 270 umol) in DCM (3.00 mL) was added HCl/dioxane (4 M, 3.00 mL), then the mixture was stirred at 20° C. for 1 hr. On completion, the reaction mixture was concentrated in vacuo to give a residue. The residue was purified by reverse phase (0.1% FA condition) to give the title compound (100 mg, 75% yield, HCl) as a white solid. $^1H$ NMR (400 MHz, DMSO-$d_6$) δ 11.12 (s, 1H), 9.36-9.07 (m, 1H), 7.51-7.33 (m, 1H), 7.24 (s, 1H), 7.09 (s, 1H), 5.45 (dd, J=4.6, 12.0 Hz, 1H), 4.70-4.47 (m, 1H), 4.02-3.68 (m, 2H), 3.66 (s, 3H), 3.43-

3.38 (m, 2H), 3.27-3.22 (m, 2H), 3.15-3.04 (m, 2H), 2.99-2.91 (m, 2H), 2.88 (d, J=5.8 Hz, 1H), 2.78-2.68 (m, 1H), 2.68-2.57 (m, 1H), 2.14-1.91 (m, 5H), 1.91-1.75 (m, 2H), 1.75-1.58 (m, 2H).

Tert-butyl N-methyl-N-[[(2R)-4-prop-2-ynylmorpholin-2-yl]methyl]carbamate (Intermediate CW)

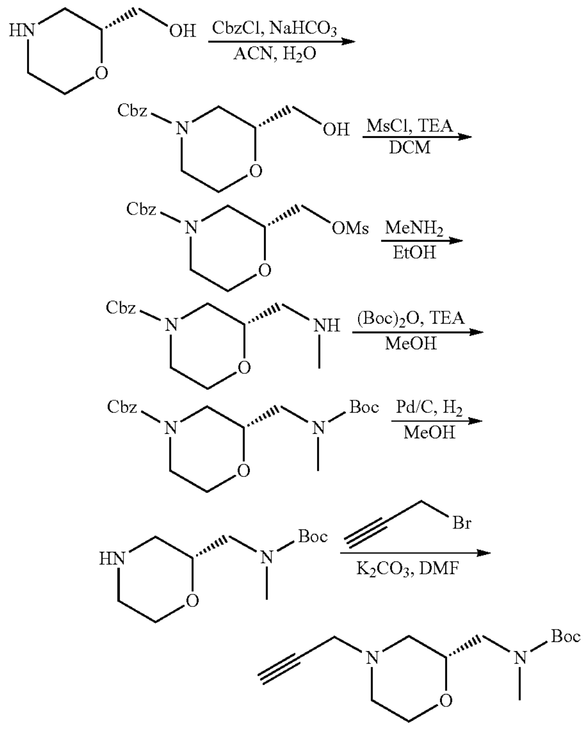

CW

Step 1—Benzyl (2R)-2-(hydroxymethyl)morpholine-4-carboxylate

To a solution of [(2R)-morpholin-2-yl]methanol (2.50 g, 16.2 mmol, HCl, CAS #156925-22-3), $NaHCO_3$ (4.10 g, 48.8 mmol) in a mixed solvent of ACN (80.0 mL) and $H_2O$ (80.0 mL) was added CbzCl (4.16 g, 24.4 mmol, 3.47 mL) at 0° C. dropwise. The mixture was then stirred at 25° C. for 16 hrs. On completion, the mixture was concentrated in vacuo to remove ACN. Then the mixture was extracted with EA (2×20 mL), and the combined organic layers were concentrated in vacuo. The residue was purified by silica gel column (PE:EA=1:1) to give the title compound (3.7 g, 90% yield) as colorless oil. $^1H$ NMR (400 MHz, $CDCl_3$) δ 7.42-7.33 (m, 5H), 5.17 (d, J 2.0 Hz, 2H), 4.08-3.88 (m, 3H), 3.77-3.65 (m, 1H), 3.63-3.46 (m, 3H), 3.13-2.73 (m, 2H), 2.07-1.96 (m, 1H).

Step 2—Benzyl (2R)-2-(methylsulfonyloxymethyl) morpholine-4-carboxylate

To a solution of benzyl (2R)-2-(hydroxymethyl)morpholine-4-carboxylate (3.70 g, 14.7 mmol), and TEA (4.47 g, 44.1 mmol) in DCM (40.0 mL) was added MsCl (2.53 g, 22.0 mmol) at 0° C., then the mixture was stirred at 25° C. for 1 hr. On completion, the mixture was diluted with DCM (20 mL) and washed with $H_2O$ (3×30 mL). The organic layer was dried over anhydrous $Na_2SO_4$, filtered and concentrated in vacuo to give the title compound (4.85 g, 100% yield) as yellow oil. $^1H$ NMR (400 MHz, $CDCl_3$) δ 7.43-7.33 (m, 5H), 5.20-5.15 (m, 2H), 4.26 (d, J 4.8 Hz, 2H), 4.10-3.83 (m, 3H), 3.80-3.65 (m, 1H), 3.63-3.48 (m, 1H), 3.08 (s, 3H), 3.07-2.75 (m, 2H).

Step 3—Benzyl (2S)-2-(methylaminomethyl)morpholine-4-carboxylate

To a solution of benzyl (2R)-2-(methylsulfonyloxymethyl)morpholine-4-carboxylate (4.3 g, 13.0 mmol) in EtOH (10.0 mL) was added $MeNH_2$ (40.5 g, 391 mmol, 30% solution in ethanol), and the mixture was stirred at 80° C. for 16 hrs in a 100 mL of autoclave. On completion, the mixture was concentrated in vacuo to give the title compound (3.45 g, 100% yield) as yellow oil. LC-MS ($ESI^+$) m/z 265.1 $(M+H)^+$.

Step 4—Benzyl (2S)-2-[[tert-butoxycarbonyl (methyl)amino]methyl]morpholine-4-carboxylate To a solution of benzyl (2S)-2-(methylaminomethyl)morpholine-4-carboxylate (3.45 g, 13.0 mmol) in MeOH (50.0 mL) was added TEA (1.58 g, 15.6 mmol, 2.18 mL). Then $(Boc)_2O$ (4.27 g, 19.5 mmol, 4.50 mL) was added into the above mixture dropwise. The mixture was stirred at 25° C. for 2 hrs. On completion, the mixture was concentrated in vacuo. The residue was purified by silica gel column (PE: EA=5:1) to give the title compound (4.10 g, 86% yield) as yellow oil. $^1H$ NMR (400 MHz, $CDCl_3$) δ 7.43-7.30 (m, 5H), 5.24-5.09 (m, 2H), 4.11-3.83 (m, 3H), 3.68-3.34 (m, 3H), 3.30-3.14 (m, 1H), 3.09-2.97 (m, 1H), 2.94 (s, 3H), 2.80-2.62 (m, 1H), 1.47 (s, 9H).

Step 5—Tert-butyl N-methyl-N-[[(2R)-morpholin-2-yl]methyl]carbamate

To a solution of benzyl (2S)-2-[[tert-butoxycarbonyl (methyl)amino]methyl]morpholine-4-carboxylate (4.10 g, 11.2 mmol) in MeOH (40.0 mL) was added Pd/C (1.00 g, 10% wt), and the mixture was stirred at 25° C. for 16 hrs under $H_2$ (15 psi). On completion, the mixture was filtered and the filtrate was concentrated in vacuo to give the title compound (2.54 g, 98% yield) as colorless oil. $^1H$ NMR (400 MHz, DMSO-$d_6$) δ 3.75-3.65 (m, 1H), 3.50-3.42 (m, 1H), 3.41-3.37 (m, 1H), 3.24-3.13 (m, 1H), 3.10-3.03 (m, 1H), 2.85-2.75 (m, 3H), 2.70-2.53 (m, 4H), 2.37-2.23 (m, 1H), 1.39 (s, 9H).

Step 6—Tert-butyl N-methyl-N-[[(2R)-4-prop-2-ynylmorpholin-2-yl]methyl]carbamate To a solution of tert-butyl N-methyl-N-[[(2R)-morpholin-2-yl]methyl]carbamate (1.00 g, 4.34 mmol), 3-bromoprop-1-yne (516 mg, 4.34 mmol, CAS #106-96-7) in DMF (10.0 mL) was added $K_2CO_3$ (3.00 g, 21.7 mmol). The mixture was stirred at 25° C. for 2 hrs. On completion, the mixture was diluted with $H_2O$ (20 mL), then extracted with EA (2×20 mL). The combined organic layers were washed with brine (2×20 mL), dried over anhydrous $Na_2SO_4$, filtered and the filtrate was concentrated in vacuo. The residue was purified by silica gel column (PE:EA=5:1) to give the title compound (960 mg, 82% yield) as yellow oil. $^1H$ NMR (400 MHz, DMSO-$d_6$) δ 3.85-3.76 (m, 1H), 3.63-3.52 (m, 1H), 3.50-3.40 (m, 1H), 3.30-3.24 (m, 2H), 3.20-3.14 (m, 2H), 2.84-2.78 (m, 3H), 2.68-2.55 (m, 2H), 2.54-2.52 (m, 1H), 2.30-2.16 (m, 1H), 2.03-1.90 (m, 1H), 1.39 (s, 9H).

3-[3-Methyl-5-[3-[(2S)-2-(methylaminomethyl)morpholin-4-yl]prop-1-ynyl]-2-oxo-benzimidazol-1-yl] piperidine-2,6-dione (Intermediate CX)

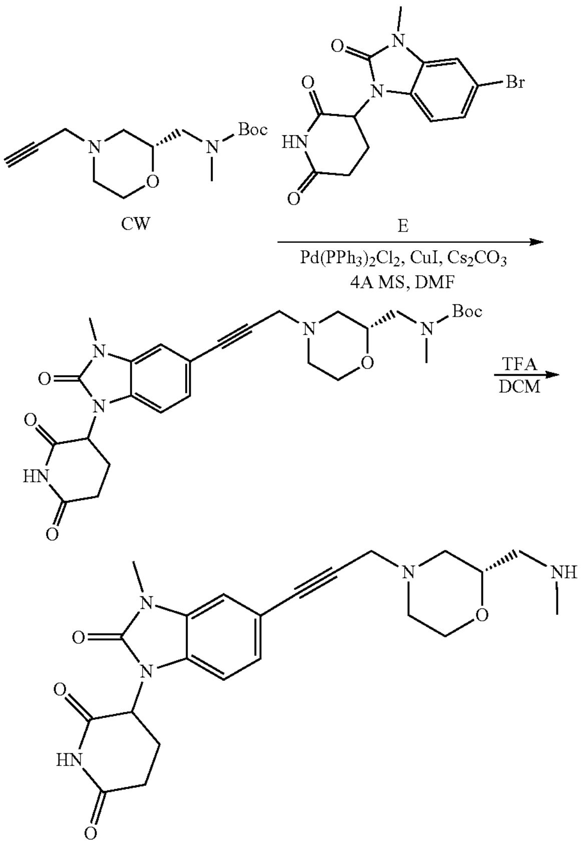

CX

Step 1—Tert-butyl N-[[(2R)-4-[3-[1-(2,6-dioxo-3-piperidyl)-3-methyl-2-oxo-benzimidazol-5-yl] prop-2-ynyl]morpholin-2-yl]methyl]-Nmethyl-carbamate To a solution of tert-butyl N-methyl-N-[[(2R)-4-prop-2-ynylmorpholin-2-yl]methyl]carbamate (571 mg, 2.13 mmol, Intermediate CW), 3-(5-bromo-3-methyl-2-oxo-benzimidazol-1-yl)piperidine-2,6-dione (400 mg, 1.18 mmol, Intermediate E) in DMF (15.0 mL) was added $Pd(PPh_3)_2Cl_2$ (83.0 mg, 118 umol), 4A molecular sieves (50.0 mg), $Cs_2CO_3$ (1.93 g, 5.91 mmol) and CuI (22.5 mg, 118 μmol). The mixture was stirred at 80° C. for 2 hrs under $N_2$. On completion, the mixture was filtered and the filtrate was concentrated in vacuo. The residue was purified by reverse phase (0.1% FA) to give the title compound (400 mg, 64% yield) as yellow solid. $^1H$ NMR (400 MHz, $CDCl_3$) δ 8.28 (s, 1H), 7.17 (d, J 8.0 Hz, 1H), 7.10 (s, 1H), 6.74 (d, J 8.0 Hz, 1H), 5.25-5.14 (m, 1H), 3.99-3.90 (m, 1H), 3.82-3.65 (m, 2H), 3.57-3.47 (m, 2H), 3.43 (s, 3H), 3.25-3.14 (m, 1H), 3.00-2.94 (m, 1H), 2.94 (s, 3H), 2.89-2.82 (m, 2H), 2.82-2.74 (m, 2H), 2.74-2.63 (m, 1H), 2.50-2.38 (m, 1H), 2.30-2.21 (m, 1H), 2.20-2.13 (m, 1H), 1.45 (s, 9H).

Step 2—3-[3-Methyl-5-[3-[(2S)-2-(methylaminomethyl)morpholin-4-yl]prop-1-ynyl]-2-oxo-benzimidazol-1-yl]piperidine-2,6-dione To a solution of tert-butyl N-[[(2R)-4-[3-[1-(2,6-dioxo-3-piperidyl)-3-methyl-2-oxo-benzimidazol-5-yl] prop-2-ynyl] morpholin-2-yl]methyl]-N-methyl-carbamate (150 mg, 285 umol) in DCM (5.00 mL) was added TFA (7.70 g, 67.5 mmol, 5.00 mL). The mixture was stirred at 20° C. for 1 hr. On completion, the mixture was concentrated in vacuo to give the title compound (150 mg, 97% yield, TFA salt) as yellow solid. $^1H$ NMR (400 MHz, DMSO-$d_6$) δ 11.15 (s, 1H), 8.83 (s, 1H), 7.37 (d, J 1.2 Hz, 1H), 7.27-7.22 (m, 1H), 7.22-7.17 (m, 1H), 5.47-5.37 (m, 1H), 4.39-4.21 (m, 3H), 4.18-4.14 (m, 1H), 4.09-4.03 (m, 1H), 3.84-3.73 (m, 1H), 3.58-3.44 (m, 2H), 3.36 (s, 3H), 3.27-3.17 (m, 1H), 3.12-3.02 (m, 2H), 2.95-2.84 (m, 2H), 2.68-2.62 (m, 1H), 2.60-2.57 (m, 3H), 2.09-2.00 (m, 1H).

5-(3-(2-(2-aminoethoxy)ethoxy)propyl)-2-(2,6-dioxopiperidin-3-yl)isoindoline-1,3-dione (Intermediate CY)

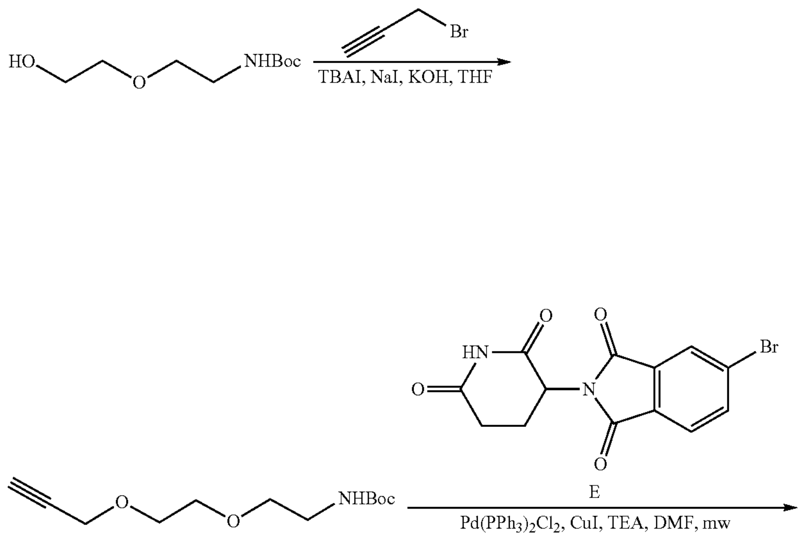

-continued

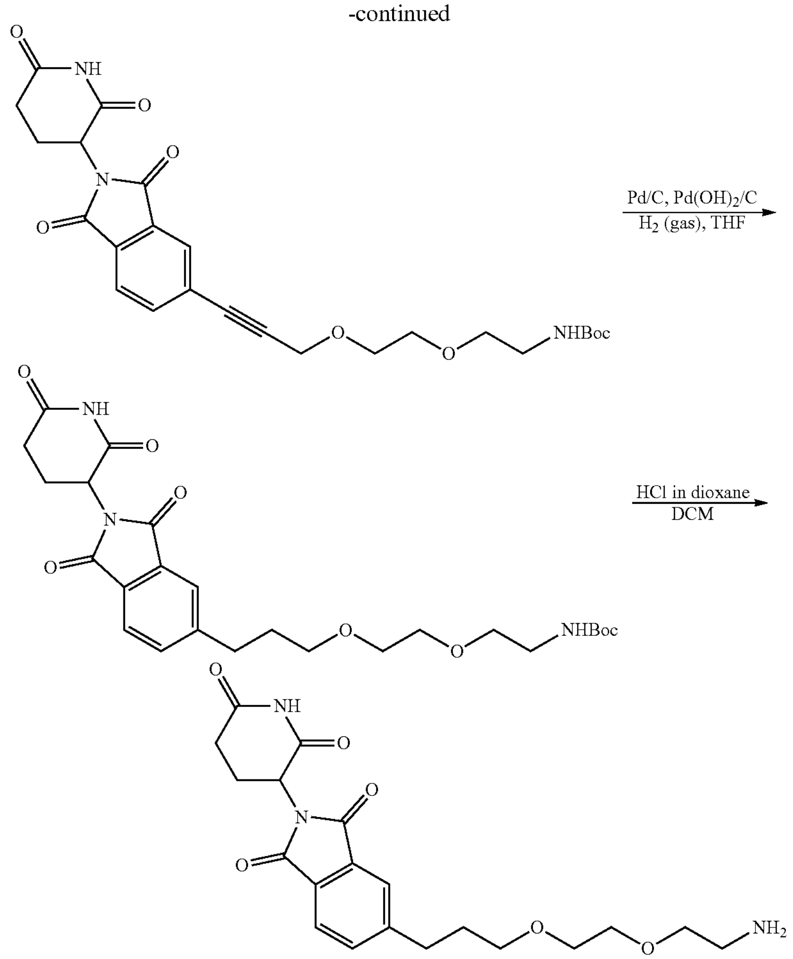

CY

Step 1—Tert-butyl N-[2-(2-prop-2-ynoxyethoxy) ethyl]carbamate

To a solution of tert-butyl N-[2-(2-hydroxyethoxy)ethyl] carbamate (5.00 g, 24.4 mmol, CAS #139115-91-6) and 3-bromoprop-1-yne (2.90 g, 24.4 mmol, 2.10 mL) in THF (40 mL) was added TBAI (540 mg, 1.46 mmol), KI (606 mg, 3.65 mmol) and KOH (1.61 g, 24.4 mmol, 85% wt %). The reaction mixture was stirred at rt for 16 h. On completion, the mixture was filtered, and the filtrate was concentrated in vacuo to give a residue. The residue was diluted with $H_2O$ (20 mL) and extracted with EA (2×50 mL). The organic phase was concentrated in vacuo to give a residue. The residue was purified by column chromatography ($SiO_2$, petroleum ether:ethyl acetate=5:1) to give the title compound (4.00 g, 67% yield) as a yellow oil. $^1H$ NMR (400 MHz, $CDCl_3$) δ 5.02 (s, 1H), 4.17 (d, J=2.4 Hz, 2H), 3.68-3.63 (m, 2H), 3.62-3.58 (m, 2H), 3.51 (t, J=5.2 Hz, 2H), 3.28 (q, J=5.2 Hz, 2H), 2.43 (t, J=2.4 Hz, 1H), 1.43 (s, 9H).

Step 2—Tert-butyl (2-(2-((3-(2-(2,6-dioxopiperidin-3-yl)-1,3-dioxoisoindolin-5-yl)prop-2-yn-1-yl)oxy) ethoxy)ethyl)carbamate To a solution of 5-bromo-2-(2,6-dioxopiperidin-3-yl) isoindoline-1,3-dione (300 mg, 890 μmol, Intermediate CO) and tert-butyl N-[2-(2-prop-2-ynoxyethoxy)ethyl]carbamate (433 mg, 1.78 mmol) in DMF (8 mL) was added $Pd(PPh_3)_2Cl_2$ (62.5 mg, 88.9 umol), TEA (1.62 g, 16.0 mmol, 2.23 mL) and CuI (16.9 mg, 88.9 umol). The reaction mixture was heated at 80° C. for 30 minutes under microwave. On completion, the mixture was concentrated in vacuo to give a residue. The residue was purified by column chromatography ($SiO_2$, Petroleum ether: Ethyl acetate=5:1 to 1:0) to give the title compound (440 mg, 89% yield) as a yellow solid. LC-MS ($ESI^+$) m/z 400.1 $(M+H-100)^+$.

Step 3—Tert-butyl (2-(2-(3-(2-(2,6-dioxopiperidin-3-yl)-1,3-dioxoisoindolin-5-yl)propoxy)ethoxy) ethyl)carbamate To a solution of tert-butyl N-[2-[2-[3-[2-(2,6-dioxo-3-piperidyl)-1,3-dioxo-isoindolin-4-yl]prop-2-ynoxy] ethoxy] ethyl]carbamate (580 mg, 1.16 mmol) in THF (10 mL) was added Pd/C (300 mg, 10 wt %) and $Pd(OH)_2/C$ (300 mg, 10 wt %). The reaction mixture was stirred at rt under hydrogen atmosphere (15 psi pressure) for 12 h. On completion, the residue was filtered and the filter was concentrated in vacuo to give the title compound (500 mg, 85% yield) as a yellow oil. LC-MS ($ESI^+$) m/z 526.1 $(M+Na)^+$.

Step 4—5-(3-(2-(2-aminoethoxy)ethoxy)propyl)-2-(2,6-dioxopiperidin-3-yl)isoindoline-1,3-dione To a solution of tert-butyl N-[2-[2-[3-[2-(2,6-dioxo-3-piperidyl)-1,3-dioxo-isoindolin-4-yl]propoxy] ethoxy]ethyl] carbamate (200 mg, 397 umol) in DCM (2 mL) was added HCl in dioxane (4 M, 2.00 mL), and the reaction mixture was stirred at rt for 20 minutes. On completion, the mixture was concentrated in vacuo to give the title compound (160 mg, 99% yield) as a yellow solid. LC-MS (ESI$^+$) m/z 404.0 $(M+H)^+$.

6-Bromo-3H-1,3-benzoxazol-2-one (Intermediate CZ)

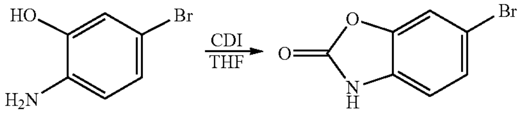

CZ

To a solution of 2-amino-5-bromo-phenol (4.50 g, 23.9 mmol, CAS #38191-34-3) in THF (120 mL) was added CDI (4.66 g, 28.7 mmol). The reaction mixture was stirred at 70° C. for 2 hours. On completion, the reaction mixture was added to water (240 mL) and the mixture was adjusted pH=6~ 7 with 2.0 M aq. HCl, then ethyl acetate (150 mL) was added. The organic layer was separated and washed with a saturated sodium chloride solution (20 mL), dried over anhydrous sodium sulfate, filtered, and concentrated in vacuo. The residue was recrystallized in toluene (60 mL) to give the title compound (3.75 g, 90% yield) as an off-white solid. $^1$H NMR (400 MHz, DMSO-$d_6$) δ 7.58 (d, J=1.6 Hz, 1H), 7.32 (dd, J=1.8, 8.4 Hz, 1H), 7.06 (s, 1H), 7.04-7.01 (m, 1H). LC-MS (ESI$^+$) m/z 216.0 & 214.0 $(M+Na)^+$.

3-(6-Bromo-2-oxo-1,3-benzoxazol-3-yl)piperidine-2,6-dione (Intermediate DA)

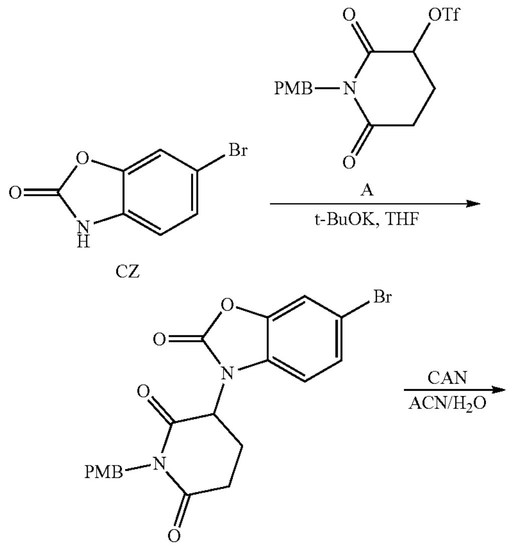

-continued

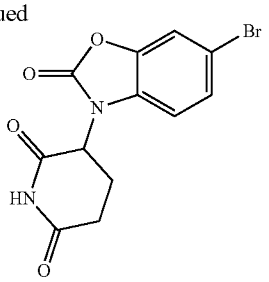

DA

Step 1—3-(6-Bromo-2-oxo-1,3-benzoxazol-3-yl)-1-[(4-methoxyphenyl)methyl]piperidine-2,6-dione To a solution of 6-bromo-3H-1,3-benzoxazol-2-one (2.00 g, 9.35 mmol, Intermediate OY) in THF (50 mL) was added t-BuOK (1.26 g, 11.2 mmol). The reaction mixture was stirred at 0° C. for 0.5 hour. Subsequently, [1-[(4-methoxyphenyl)methyl]-2,6-dioxo-3-piperidyl] trifluoromethanesulfonate (4.81 g, 12.6 mmol, Intermediate A) in a solution of THF (30 mL) was added dropwise. The resulting reaction mixture was stirred at 20° C. for 0.5 hour under $N_2$. On completion, the reaction mixture was quenched with saturated $NH_4Cl$ (100 mL), and extracted with ethyl acetate (100 mL). The combined organic layer was washed with brine (2×100 mL), dried over anhydrous sodium sulfate and filtered. The filtrate was concentrated in vacuo. The residue was purified by silica gel chromatography (PE:EA:DCM=5:1:2) to give the title compound (3.75 g, 90% yield) as a yellow solid. $^1$H NMR (400 MHz, $CDCl_3$) δ 7.22-7.20 (d, J=8.0 Hz, 1H), 6.89-6.87 (d, J=8.0 Hz, 1H), 4.90-4.86 (m, 1H), 4.47-4.36 (m, 2H) 3.81 (s, 3H), 2.67-2.64 (m, 1H), 2.59-2.54 (m, 2H), 2.40-2.38 (m, 1H). LC-MS (ESI$^+$) m/z 466.9 & 468.9 $(M+Na)^+$.

Step 2—3-(6-Bromo-2-oxo-1,3-benzoxazol-3-yl) piperidine-2,6-dione

To a mixture of 3-(6-bromo-2-oxo-1,3-benzoxazol-3-yl)-1-[(4-methoxyphenyl)methyl]piperidine-2,6-dione (2.00 g, 4.49 mmol) in ACN (60 mL) was added CAN (7.39 g, 13.4 mmol) in solution of $H_2O$ (20 mL), and the reaction mixture was degassed and purged with $N_2$ for 3 times. Then the mixture was stirred at 20° C. for 3 hours under $N_2$ atmosphere. On completion, the reaction mixture was filtered. The filtered cake was collected and dried in vacuo to give the title compound (900 mg, 61% yield) as a white solid. $^1$H NMR (400 MHz, DMSO-$d_6$) δ 11.24 (s, 1H), 7.74 (d, J=1.6 Hz, 1H), 7.48-7.41 (m, 1H), 7.27 (d, J=8.4 Hz, 1H), 5.39 (dd, J=5.2, 12.8 Hz, 1H), 3.00-2.80 (m, 1H), 2.76-2.60 (m, 2H), 2.18-2.15 (m Hz, 1H). LC-MS (ESI$^+$) m/z 325.0 &327.0 $(M+H)^+$.

2-3-[6-[3-[2-(2-Aminoethoxy)ethoxy]propyl]-2-oxo-1,3-benzoxazol-3-yl]piperidine-2,6-dione (Intermediate DB)

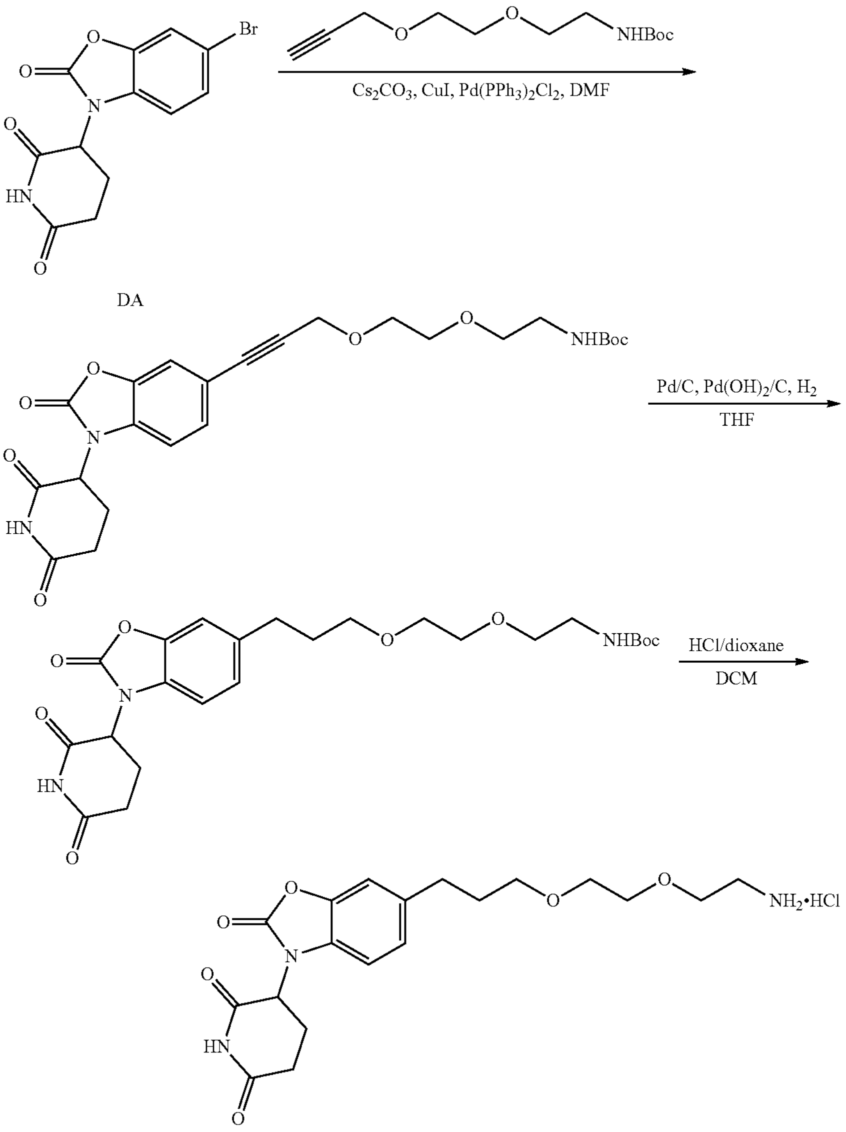

DA

DB

Step 1—Tert-butyl N-[2-[2-[3-[3-(2,6-dioxo-3-piperidyl)-2-oxo-1,3-benzoxazol-6-yl]propoxy]ethoxy]ethyl]carbamate 3-(6-bromo-2-oxo-1,3-benzoxazol-3-yl)piperidine-2,6-dione (400 mg, 1.23 mmol, Intermediate DA), tert-butylN-[2-(2-prop-2-ynoxyethoxy)ethyl]carbamate (898 mg, 3.69 mmol, synthesized via Step 1 of Intermediate CY), $Pd(PPh_3)_2Cl_2$ (86.3 mg, 123 umol), CuI (23.4 mg, 123 umol), 4A MS (400 mg, 307 umol) and $Cs_2CO_3$ (2.00 g, 6.15 mmol) in DMF (6 mL) was stirred at 80° C. for 2 hours under $N_2$. On completion, the reaction mixture was filtered and the filtrate was concentrated in vacuo. The residue was purified by column chromatography (ACN) to give an impure product. The impure product was re-purified by reverse phase (0.1% FA condition) to give the title compound (340 mg, 54% yield) as yellow oil. $^1$H NMR (400 MHz, DMSO-$d_6$) δ 11.23 (s, 1H), 7.53 (s, 1H), 7.37-7.33 (m, 1H), 7.31-7.27 (m, 1H), 6.82-6.75 (m, 1H), 5.40 (dd, J=5.2, 12.8 Hz, 1H), 4.39 (s, 2H), 3.65-3.60 (m, 2H), 3.57-3.53 (m, 2H), 3.41-3.38 (m, 2H), 3.07-3.02 (m, 2H), 2.93-2.81 (m, 1H), 2.72-2.61 (m, 2H), 2.18-2.16 (m, 1H), 1.37 (s, 9H), 1.37-1.36 (m, 1H). LC-MS (ESI$^+$) m/z 510.2 (M+Na)$^+$.

Step 2—Tert-butyl N-[2-[2-[3-[3-(2,6-dioxo-3-piperidyl)-2-oxo-1,3-benzoxazol-6-yl]propoxy]ethoxy]ethyl]carbamate To a solution of tert-butyl N-[2-[2-[3-[3-(2,6-dioxo-3-piperidyl)-2-oxo-1,3-benzoxazol-6-yl]prop-2-ynoxy]ethoxy]ethyl]carbamate (420 mg, 861 umol) in THF (30 mL) was added Pd/C (0.1 g, 10% wt) and $Pd(OH)_2$/C (0.1 g, 10% wt) under $N_2$. The suspension was degassed under vacuum and purged with $H_2$ gas several times. The mixture was stirred under $H_2$ (15 psi) at 20° C. for 12 hours. On completion, the reaction mixture was filtered and the filtrate was concentrated in vacuo to give the title compound (440 mg, 93% yield) as yellow oil. $^1H$ NMR (400 MHz, DMSO-$d_6$) δ 11.25 (s, 1H), 7.32 (s, 1H), 7.22 (d, J=8.0 Hz, 1H), 7.11 (d, J=8.0 Hz, 1H), 6.79 (s, 1H), 5.40 (dd, J=5.2, 12.8 Hz, 1H), 3.57-3.53 (m, 4H), 3.46-3.43 (m, 4H), 3.13 (d, J=6.0 Hz, 2H), 3.00-2.89 (m, 1H), 3.00-2.89 (m, 1H), 2.80-2.67 (m, 4H), 2.25-2.20 (m, 1H), 1.88-1.83 (m, 2H), 1.43-1.42 (m, 9H). LC-MS (ESI$^+$) m/z 514.2 $(M+Na)^+$.

Step 3—2-3-[6-[3-[2-(2-Aminoethoxy)ethoxy]propyl]-2-oxo-1,3-benzoxazol-3-yl]piperidine-2,6-dione To a solution of tert-butyl N-[2-[2-[3-[3-(2,6-dioxo-3-piperidyl)-2-oxo-1,3-benzoxazol-6-yl]propoxy] ethoxy]ethyl]carbamate (150 mg, 305 umol) in DCM (5 mL) was added HCl/dioxane (4 M, 7.50 mL). The reaction mixture was stirred at 20° C. for 1 hour. On completion, the reaction mixture was concentrated in vacuo to give the title compound (130 mg, 99% yield, HCl salt) as a white solid. LC-MS (ESI$^+$) m/z 392.2 $(M+H)^+$.

Tert-butyl 7-prop-2-ynyl-2,7-diazaspiro[3.5]nonane-2-carboxylate (Intermediate DC)

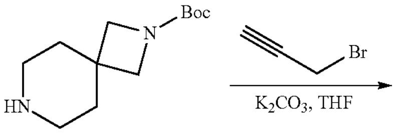

-continued

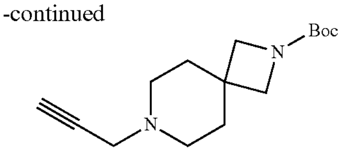

DC

To a solution of tert-butyl 2,7-diazaspiro[3.5]nonane-2-carboxylate (200 mg, 884 umol, CAS #236406-55-6) and 3-bromoprop-1-yne (158 mg, 1.06 mmol) in the THF (5 mL) was added $K_2CO_3$ (244 mg, 1.77 mmol). The reaction mixture was stirred at 20° C. for 5 hrs. On completion, the reaction was filtered and concentrated in vacuo. The residue was diluted with ethyl acetate (20 mL) and washed with water (20 mL). The organic layer was dried over $Na_2SO_4$, filtered and concentrated in vacuo to give colorless oil (200 mg, 86% yield). $^1H$ NMR (400 MHz, $CDCl_3$) δ 3.62 (s, 4H), 3.28 (d, J=2.5 Hz, 2H), 2.47 (br s, 4H), 2.24 (t, J=2.4 Hz, 1H), 1.79 (t, J=5.5 Hz, 4H), 1.45 (s, 9H).

3-[4-[3-(2,7-diazaspiro[3.5]nonan-7-yl)propyl]-3-methyl-2-oxo-benzimidazol-1-yl]piperidine-2,6-dione (Intermediate DD)

B

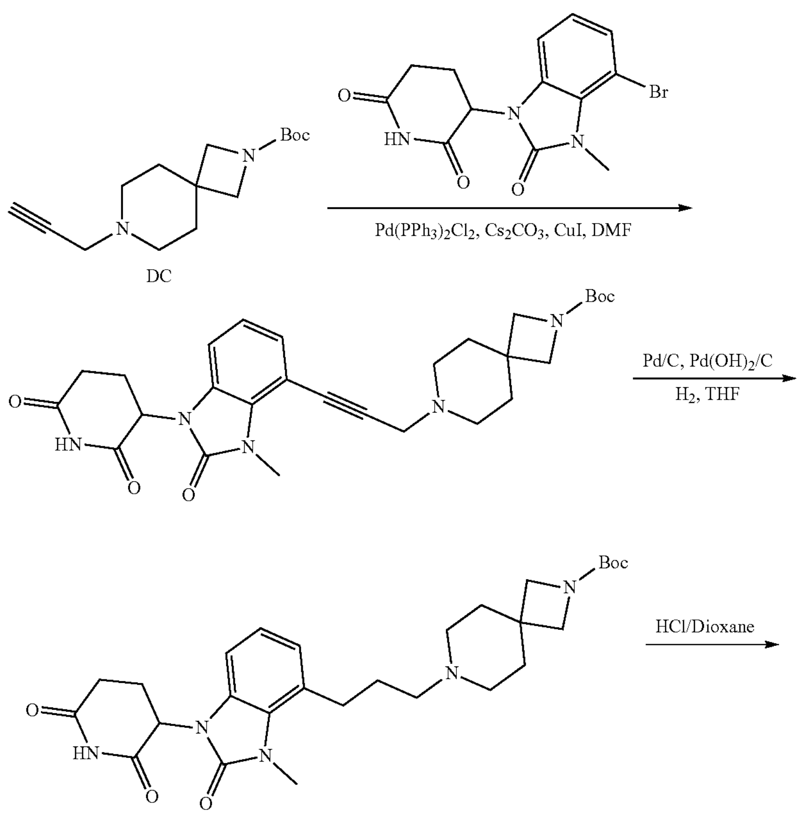

-continued

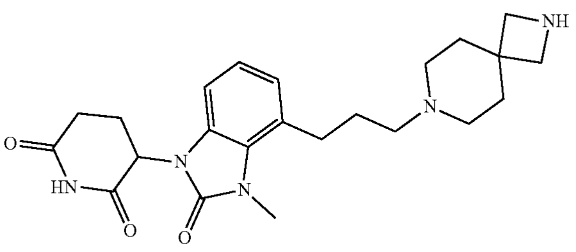

DD

Step 1—Tert-butyl 7-[3-[1-(2,6-dioxo-3-piperidyl)-3-methyl-2-oxo-benzimidazol-4-yl]prop-2-ynyl]-2,7-diazaspiro[3.5]nonane-2-carboxylate To a solution of tert-butyl 7-prop-2-ynyl-2,7-diazaspiro[3.5]nonane-2-carboxylate (300 mg, 1.13 mmol, Intermediate DC) and 3-(4-bromo-3-methyl-2-oxo-benzimidazol-1-yl)piperidine-2,6-dione (384 mg, 1.13 mmol, Intermediate B) in the DMF (6 mL) was added $Pd(PPh_3)_2Cl_2$ (79.7 mg, 113 μmol), $Cs_2CO_3$ (1.48 g, 4.54 mmol) and CuI (21.6 mg, 113 umol) under $N_2$. The resulting mixture was stirred at 80° C. for 2 hrs. On completion, the mixture was filtered and purified by reversed phase (0.1% FA) to give the title compound (450 mg, 76% yield) as yellow solid. $^1H$ NMR (400 MHz, $CDCl_3$) δ 8.35 (br s, 1H), 7.16 (dd, J=0.8, 8.0 Hz, 1H), 7.00 (t, J=8.0 Hz, 1H), 6.80-6.74 (m, 1H), 5.21 (dd, J=5.6, 12.6 Hz, 1H), 3.76 (s, 3H), 3.66 (s, 4H), 3.00-2.91 (m, 1H), 2.89-2.82 (m, 1H), 2.82-2.76 (m, 1H), 2.76-2.66 (m, 4H), 2.62-2.54 (m, 1H), 2.28-2.19 (m, 1H), 1.90 (t, J=5.6 Hz, 4H), 1.84 (t, J=5.6 Hz, 1H), 1.44 (s, 9H); LC-MS ($ESI^+$) m/z 522.4 $(M+H)^+$.

Step 2—Tert-butyl 7-[3-[1-(2,6-dioxo-3-piperidyl)-3-methyl-2-oxo-benzimidazol-4-yl]propyl]-2,7-diazaspiro[3.5]nonane-2-carboxylate To a solution of tert-butyl 7-[3-[1-(2,6-dioxo-3-piperidyl)-3-methyl-2-oxo-benzimidazol-4-yl] prop-2-ynyl]-2,7-diazaspiro[3.5]nonane-2-carboxylate (150 mg, 288 umol) in the THF (3 mL) was added Pd/C (50 mg, 10 wt %) and $Pd(OH)_2/C$ (50 mg, 10 wt %). The resulting mixture was stirred at 20° C. for 12 hrs under $H_2$ (15 Psi). On completion, the reaction mixture was filtered and concentrated in vacuo to give the title compound (150 mg, 99% yield) as brown solid. LC-MS ($ESI^+$) m/z 526.4 $(M+H)^+$.

Step 3—3-[4-[3-(2,7-diazaspiro[3.5]nonan-7-yl)propyl]-3-methyl-2-oxo-benzimidazol-1-yl]piperidine-2,6-dione A solution of tert-butyl 7-[3-[1-(2,6-dioxo-3-piperidyl)-3-methyl-2-oxo-benzimidazol-4-yl]propyl]-2,7-diazaspiro[3.5]nonane-2-carboxylate (150 mg, 285 umol) in the HCl/dioxane (1 mL) was stirred at 20° C. for 1 hr. On completion, the reaction mixture was concentrated in vacuo to give the title compound (120 mg, 99% yield) as brown solid. LC-MS ($ESI^+$) m/z 426.4 $(M+H)^+$.

1-3-[4-[3-(2,7-Diazaspiro[3.5]nonan-7-yl)prop-1-ynyl]-3-methyl-2-oxo-benzimidazol-1-yl]piperidine-2,6-dione (Intermediate DE)

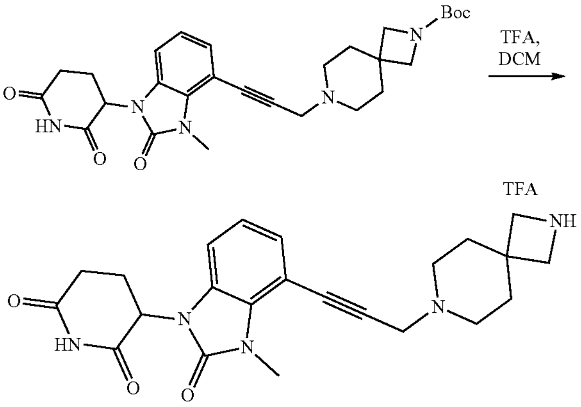

DE

To a solution of tert-butyl 7-[3-[1-(2,6-dioxo-3-piperidyl)-3-methyl-2-oxo-benzimidazol-4-yl]prop-2-ynyl]-2,7-diazaspiro[3.5]nonane-2-carboxylate (50.0 mg, 95.8 umol, synthesized via Step 1 of Intermediate DD) in DCM (1 mL) was added TFA (109 mg, 958 umol). The mixture was stirred at 25° C. for 1 hr. On completion, the reaction mixture was concentrated in vacuo to give the title compound (46.0 mg, 95% yield, TFA) as yellow oil. LC-MS ($ESI^+$) m/z 422.1 $(M+H)^+$.

Step 1—Tert-butyl 4-prop-2-ynoxypiperidine-1-carboxylate (Intermediate DF)

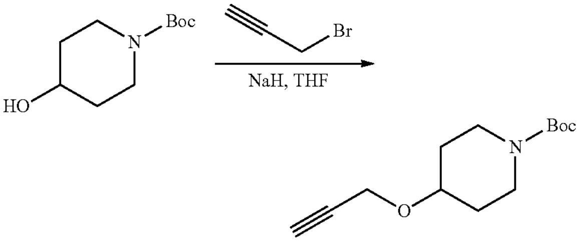

DF

To a solution of tert-butyl 4-hydroxypiperidine-1-carboxylate (2.00 g, 9.94 mmol, CAS #109384-19-2) in anhydrous THF (10 mL) was cooled to 0° C., and subsequently NaH (477 mg, 11.9 mmol, 60% oil dispersion) was added. The reaction mixture was stirred at 0° C. for 0.5 hr. Then, 3-bromoprop-1-yne (1.18 g, 9.94 mmol, 856 uL) was added. The resulting reaction mixture was stirred at 25° C. for 12 hrs. On completed, the reaction mixture was quenched with water (1 mL), then diluted with ethyl acetate (100 mL). The organic layers were washed with brine (20 mL), dried over anhydrous sodium sulfate, filtered and the filtrate was concentrated in vacuo. The residue was purified by column chromatography to give the title compound (2.38 g, 100% yield) as yellow oil. $^1$H NMR (400 MHz, $CDCl_3$) δ 4.22 (d, J=2.4 Hz, 2H), 3.84-3.75 (m, 2H), 3.73-3.70 (m, 1H), 3.15-3.09 (m, 2H), 2.43 (t, J=2.4 Hz, 1H), 1.93-1.82 (m, 2H), 1.61-1.50 (m, 2H), 1.47 (s, 9H).

3-[3-Methyl-2-oxo-4-[3-(4-piperidyloxy)propyl]benzimidazol-1-yl]piperidine-2,6-dione (Intermediate DG)

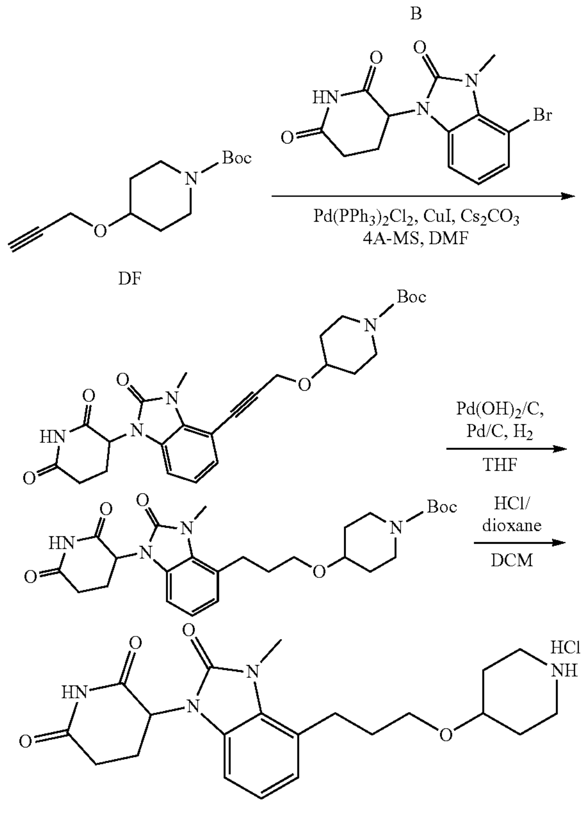

DG

Step 1—Tert-butyl 4-[3-[1-(2,6-dioxo-3-piperidyl)-3-methyl-2-oxo-benzimidazol-4-yl]prop-2-ynoxy]piperidine-1-carboxylate A suspension of 3-(4-bromo-3-methyl-2-oxo-benzimidazol-1-yl)piperidine-2,6-dione (300 mg, 887 umol, Intermediate B), tert-butyl 4-prop-2-ynoxypiperidine-1-carboxylate (318 mg, 1.33 mmol, Intermediate DF), $Pd(PPh_3)_2Cl_2$ (124 mg, 177 umol), CuI (33.8 mg, 177 umol), 4 Å molecular sieves (400 mg) and $Cs_2CO_3$ (1.16 g, 3.55 mmol) in DMF (5 mL) was de-gassed under vacuum and purged with $N_2$ several times and then heated to 80° C. for 2 hours under $N_2$. On completion, the reaction mixture was concentrated in vacuo to remove DMF. The residue was diluted with EA (50 mL) and water (20 mL). After, the organic layer was separated and washed with brine (5 mL×2), dried over anhydrous $Na_2SO_4$, filtered and the filtrate was concentrated in vacuo to give a residue. The residue was purified by reverse phase to give the title compound (222 mg, 48% yield) as a yellow solid. $^1$H NMR (400 MHz, $CDCl_3$) δ 8.09 (s, 1H), 7.10 (d, J=8.0 Hz, 1H), 6.92 (t, J=8.0 Hz, 1H), 6.69 (d, J=8.0 Hz, 1H), 5.13 (dd, J=5.2, 12.8 Hz, 1H), 4.39 (s, 2H), 3.76-3.66 (m, 6H), 3.09-3.03 (m, 2H), 2.94-2.84 (m, 1H), 2.82-2.71 (m, 1H), 2.71-2.59 (m, 1H), 2.22-2.11 (m, 1H), 1.83-1.78 (m, 2H), 1.57-1.49 (m, 2H), 1.39 (s, 9H), LC-MS (ESI$^+$) m/z 441.2 (M+H−56)$^+$.

Step 2—Tert-butyl4-[3-[1-(2,6-dioxo-3-piperidyl)-3-methyl-2-oxo-benzimidazol-4-yl]propoxy] piperidine-1-carboxylate To a solution of tert-butyl 4-[3-[1-(2,6-dioxo-3-piperidyl)-3-methyl-2-oxo-benzimidazol-4-yl]prop-2-ynoxy] piperidine-1-carboxylate (370 mg, 745 umol) in THF (10 mL) was added Pd/C (0.1 g, 10% wt) and $Pd(OH)_2/C$ (0.1 g, 10% wt). The suspension was degassed under vacuum and purged with $H_2$ several times. The mixture was stirred under $H_2$ (15 psi) at 25° C. for 12 hours. On completion, the reaction mixture was filtered and the filtrate was concentrated in vacuo to give the title compound (330 mg, 88% yield) as a white solid. $^1$H NMR (400 MHz, $CDCl_3$) δ 8.03 (s, 1H), 6.91 (d, J=8.0 Hz, 1H), 6.83 (d, J=8.0 Hz, 1H), 6.59 (t, J=8.0 Hz, 1H), 5.20-5.09 (m, 1H), 3.70-3.64 (m, 2H), 3.62 (s, 3H), 3.44 (t, J=5.6 Hz, 2H), 3.41-3.34 (m, 1H), 3.06-3.04 (m, 2H), 2.98-2.93 (m, 2H), 2.91-2.80 (m, 1H), 2.79-2.63 (m, 2H), 2.19-2.10 (m, 1H), 1.89-1.81 (m, 2H), 1.80-1.73 (m, 2H), 1.47-1.39 (m, 2H), 1.39 (s, 9H); LC-MS (ESI$^+$) m/z 523.1 (M+Na)$^+$.

Step 3—3-[3-Methyl-2-oxo-4-[3-(4-piperidyloxy)propyl]benzimidazol-1-yl]piperidine-2,6-dione To a solution of tert-butyl 4-[3-[1-(2,6-dioxo-3-piperidyl)-3-methyl-2-oxo-benzimidazol-4-yl]propoxy] piperidine-1-carboxylate (100 mg, 199 umol) in DCM (4 mL) was added HCl/dioxane (4 M, 2 mL). The reaction mixture was stirred at 25° C. for 0.5 hr. On completion, the reaction mixture was concentrated in vacuo to give the title compound (87.0 mg, 100% yield, HCl salt) as a white solid. LC-MS (ESI$^+$) m/z 401.1 (M+H)$^+$.

Tert-butyl N-methyl-N-pent-4-ynyl-carbamate (Intermediate DH)

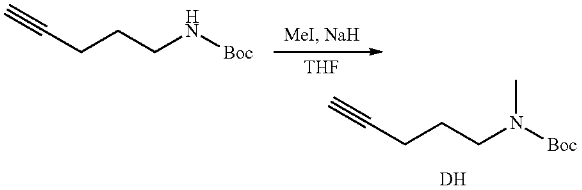

DH

A mixture of tert-butyl N-pent-4-ynylcarbamate (200 mg, 1.09 mmol, CAS #151978-50-6) in THF (5.50 mL) was cooled with an ice/water bath. Then NaH (52.3 mg, 1.31 mmol, 60% dispersion in mineral oil) was added in 3 portions and the resulting mixture stirred at 25° C. for 20 minutes. Next, MeI (929 mg, 6.55 mmol) was slowly added and the resulting mixture stirred for 72 hrs. On completion, the reaction mixture was concentrated in vacuo to give a residue. The residue was purified by column chromatography ($SiO_2$, petroleum ether/ethyl acetate=10/1 to 5/1) to give the title compound (200 mg, 93.0% yield) as white solid. $^1H$ NMR (400 MHz, DMSO-$d_6$) δ=3.29 (s, 3H), 3.13-3.11 (m, 1H), 2.89-2.85 (m, 1H), 2.70-2.67 (m, 1H), 2.06-2.02 (m, 2H), 1.55-1.52 (m, 2H), 1.30 (s, 9H).

3-[3-methyl-5-[5-(methylamino)pentyl]-2-oxo-benzimidazol-1-yl]piperidine-2,6-dione (Intermediate DI)

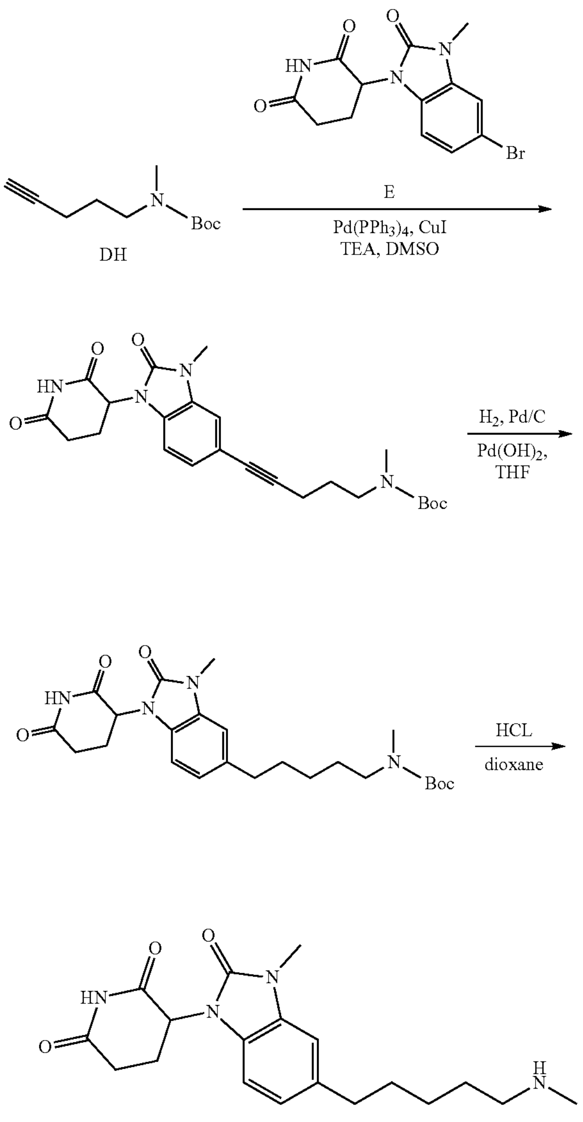

DI

Step 1 tert-butyl N-[5-[1-(2,6-dioxo-3-piperidyl)-3-methyl-2-oxo-benzimidazol-5-yl]pent-4-ynyl]-N-methyl-carbamate To a solution of tert-butyl N-methyl-N-pent-4-ynyl-carbamate (175 mg, 887 umol, Intermediate DH), 3-(5-bromo-3-methyl-2-oxo-benzimidazol-1-yl)piperidine-2,6-dione (200 mg, 591 umol, Intermediate E) in DMSO (5 mL) was added TEA (581 mg, 5.75 mmol). The solution was purged with nitrogen for 5 min, then CuI (11.2 mg, 59.1 umol), and $Pd(PPh_3)_4$ (68.3 mg, 59.1 umol) was added. The resulting solution was stirred at 80° C. for 12 hrs. On completion, the reaction mixture was quenched by adding the mixture to a cold saturated aqueous $H_2O$ solution (3 ml). The aqueous layer was extracted with ethyl acetate (5 ml×2) and the organic layer was separated. The residue was purified by reverse phase flash [ACN/(0.1% FA in water), 0% to 90%] to give the title compound (60.0 mg, 21% yield) as white solid. $^1H$ NMR (400 MHz, DMSO-$d_6$) δ=11.11 (s, 1H), 7.30-7.00 (m, 3H), 5.38 (dd, J=5.6, 12.4 Hz, 1H), 3.28-3.22 (m, 3H), 2.81 (s, 4H), 2.73-2.63 (m, 3H), 2.41 (t, J=6.8 Hz, 3H), 2.33 (d, J=1.6 Hz, 1H), 2.07-1.98 (m, 1H), 1.74 (t, J=7.2 Hz, 2H), 1.40 (s, 9H).

Step 2 tert-butylN-[5-[1-(2,6-dioxo-3-piperidyl)-3-methyl-2-oxo-benzimidazol-5-yl]pentyl]-N-methyl-carbamate To a solution of tert-butyl N-[5-[1-(2,6-dioxo-3-piperidyl)-3-methyl-2-oxo-benzimidazol-5-yl] pent-4-ynyl]-N-methyl-carbamate (60.0 mg, 132 umol) in THF (15 mL) was added Pd/C (10 mg, 132 μmol, 10 wt %) and $Pd(OH)_2$ (31.2 mg, 222 umol) at 25° C. under $N_2$. The reaction solution was stirred at 40° C. for 4 hrs under $H_2$ (15 psi). On completion, the reaction mixture was filtered and the filtrate was concentrated under reduced pressure to give the title compound (50.0 mg, 73% yield). $^1H$ NMR (400 MHz, DMSO-$d_6$) δ=11.18 (s, 1H), 7.14-7.08 (m, 2H), 7.00-6.94 (m, 2H), 5.44 (dd, J=5.2, 12.8 Hz, 1H), 3.71 (t, J=6.4 Hz, 1H), 3.40 (s, 3H), 3.24 (t, J=7.2 Hz, 2H), 3.04-2.96 (m, 1H), 2.88-2.82 (m, 3H), 2.76-2.69 (m, 2H), 2.76-2.68 (m, 1H), 2.60-2.60 (m, 1H), 2.60-2.55 (m, 1H), 2.29 (s, 1H), 2.15-2.07 (m, 1H), 1.87 (td, J=3.2, 6.4 Hz, 1H), 1.72 (t, J=7.2 Hz, 2H), 1.39-1.31 (m, 3H).

Step 3 3-[3-methyl-5-[5-(methylamino)pentyl]-2-oxo-benzimidazol-1-yl]piperidine-2,6-dione To a mixture of tert-butyl tert-butyl N-[5-[1-(2,6-dioxo-3-piperidyl)-3-methyl-2-oxo-benzimidazol-5-yl]pentyl]-N-methyl-carbamate (50.0 mg, 109 umol) in DCM (1.5 mL) was added HCl/dioxane (4 M, 0.3 mL) in one portion at 25° C. under $N_2$ and the mixture was stirred at 25° C. for 30 min. On completion, the reaction mixture was concentrated in vacuo to give the title compound (40.0 mg, 99% crude yield, TFA). LC-MS ($ESI^+$) m/z 359.2 $(M+H)^+$.

Tert-butyl (1-(3,5-dimethyl-2-oxo-1-((2-(trimethylsilyl)ethoxy)methyl)-2,3-dihydro-1H-benzo[d]imidazol-4-yl)piperidin-4-yl)(methyl)carbamate (Intermediate DJ)

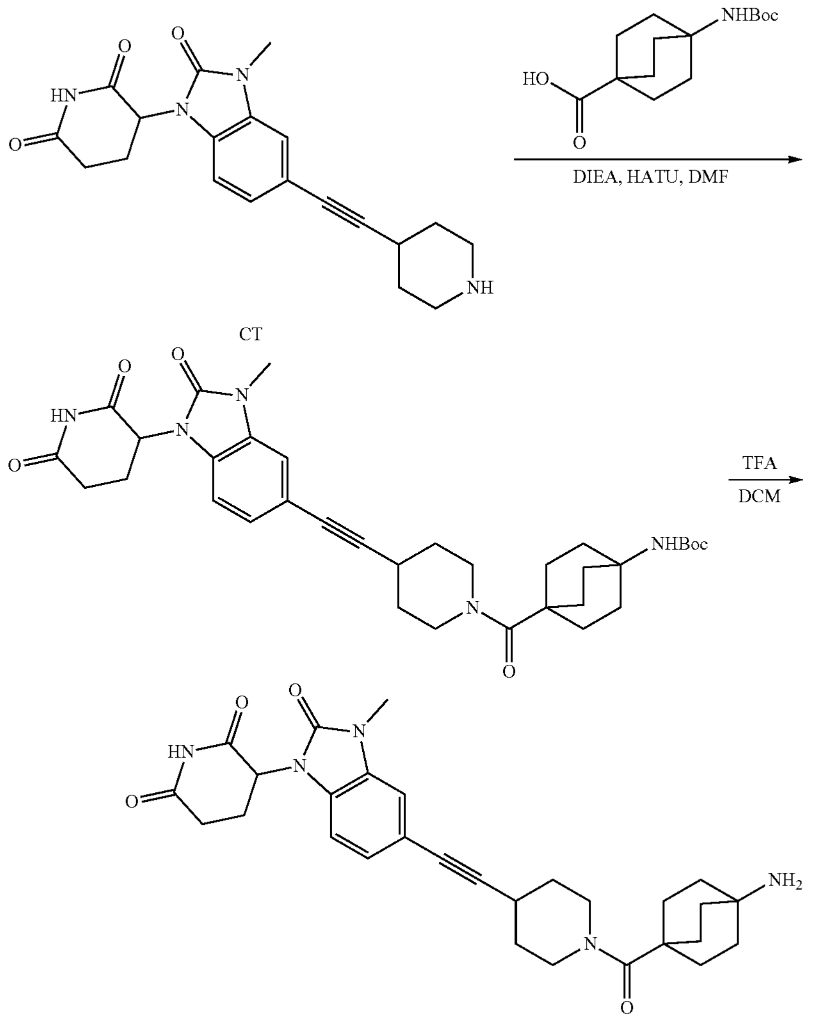

DJ

Step 1—Tert-butyl N-[4-[4-[2-[1-(2,6-dioxo-3-piperidyl)-3-methyl-2-oxo-benzimidazol-5-yl]ethynyl]piperidine-1-carbonyl]-1-bicyclo[2.2.2]octanyl]carbamate To a solution of 3-[3-methyl-2-oxo-5-[2-(4-piperidyl)ethynyl]benzimidazol-1-yl]piperidine-2,6-dione (1.00 g, 2.08 mmol, TFA salt, Intermediate CT) in DMF (20 mL) was added DIEA (1.08 g, 8.33 mmol) to adjust the pH to 8, then 4-(tert-butoxycarbonylamino)bicyclo[2.2.2]octane-1-carboxylic acid (560 mg, 2.08 mmol, CAS #863304-76-1) and HATU (1.58 g, 4.16 mmol) were added. The mixture was stirred at 25° C. for 1 hr. On completion, the mixture was added into the water (100 mL) and filtered. The residue was purified by column chromatography ($SiO_2$, DCM/Ethyl acetate=1:0 to 1:4) to give the title compound (300 mg, 485 umol, 23% yield) as a white solid. $^1H$ NMR (400 MHz, $CDCl_3$) δ 8.24-8.05 (m, 1H), 7.19-7.10 (m, 1H), 7.09-7.03 (m, 1H), 6.76-6.68 (m, 1H), 5.28-5.11 (m, 1H), 4.41-4.34 (m, 1H), 4.43-4.32 (m, 1H), 4.01-3.90 (m, 2H), 3.46-3.37 (m, 5H), 2.91-2.70 (m, 3H), 2.02-1.84 (m, 16H), 1.74-1.64 (m, 2H), 1.46-1.41 (m, 9H).

Step 2—Tert-butyl (1-(3,5-dimethyl-2-oxo-1-((2-(trimethylsilyl)ethoxy)methyl)-2,3-dihydro-1H-benzo[d]imidazol-4-yl)piperidin-4-yl)(methyl)carbamate To a solution of tert-butyl N-[4-[4-[2-[1-(2,6-dioxo-3-piperidyl)-3-methyl-2-oxo-benzimidazol-5-yl] ethynyl]piperidine-1-carbonyl]-1-bicyclo[2.2.2]octanyl]carbamate (200 mg, 273 umol, TFA) in DCM (2 mL) was added TFA (520 mg, 4.56 mmol). The mixture was stirred at 25° C. for 0.5 hr. On completion, the mixture was concentrated in vacuo to give the title compound (170 mg, 99% crude yield, TFA salt) as a brown oil. LC-MS ($ESI^+$) m/z 518.4 $(M+H)^+$.

4-[[chloro-(3-chloro-2-fluoro-phenyl)-ethyl-oxo-dispiro[BLAH]carbonyl]amino]bicycle[2.2.2]octane-1-carboxylic acid (CAS #1818393-16-6) (Intermediate DK)

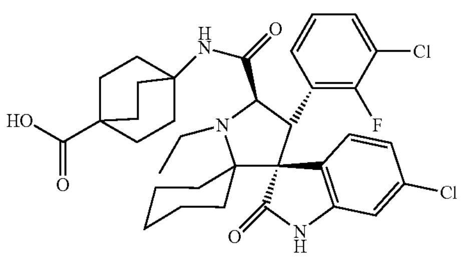

DK 3-amino-N-[5-[1-(2,6-dioxo-3-piperidyl)-3-methyl-2-oxo-benzimidazol-5-yl]pentyl]benzamide (Intermediate DL)

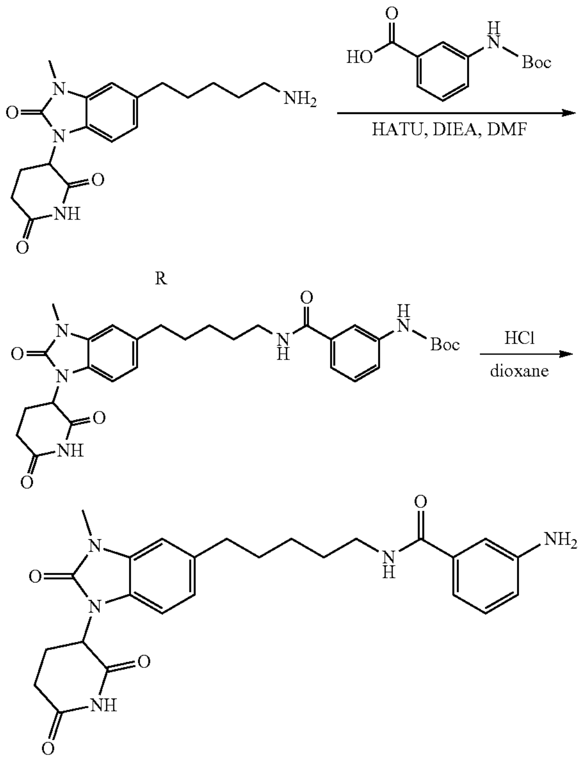

DL

Step 1—tert-butyl N-[3-[5-[1-(2,6-dioxo-3-piperidyl)-3-methyl-2-oxo-benzimidazol-5-yl]pentylcarbamoyl]phenyl]carbamate To a solution of 3-[5-(5-aminopentyl)-3-methyl-2-oxo-benzimidazol-1-yl]piperidine-2,6-dione (120 mg, 348 umol, Intermediate R), 3-(tert-butoxycarbonylamino)benzoic acid (100 mg, 421 umol, CAS #51524-84-6) and DIEA (185 mg, 1.44 mmol, 250 uL) in DMF (2.0 mL) was added HATU (180 mg, 473 umol) and the reaction was stirred at 20° C. for 12 hours. The reaction mixture was diluted with $H_2O$ (20 mL) and extracted with EtOAc (10 mL×3). The combined organic layers were washed with brine (10 mL×2), dried over $Na_2SO_4$, filtered and concentrated under reduced pressure to give a residue. The residue was purified by Prep-TLC (petroleum ether:ethyl acetate=0:1) to give the title compound (80.0 mg, 39% yield) as a white solid. $^1H$ NMR (400 MHz, DMSO-$d_6$) δ=11.07 (s, 1H), 9.44 (s, 1H), 8.34 (t, J=5.6 Hz, 1H), 7.93 (s, 1H), 7.54-7.48 (m, 1H), 7.39-7.34 (m, 1H), 7.32-7.26 (m, 1H), 7.03-7.01 (m, 1H), 6.99-6.95 (m, 1H), 6.88-6.83 (m, 1H), 5.32 (dd, J=5.6, 12.8 Hz, 1H), 3.31-3.30 (m, 3H), 3.25-3.20 (m, 2H), 2.66 (d, J=4.4 Hz, 4H), 1.98 (s, 2H), 1.67-1.50 (m, 4H), 1.48 (s, 9H), 1.32 (d, J=7.6 Hz, 2H).

Step 2—3-amino-N-[5-[1-(2,6-dioxo-3-piperidyl)-3-methyl-2-oxo-benzimidazol-5-yl]pentyl]benzamide To a solution of tert-butyl N-[3-[5-[1-(2,6-dioxo-3-piperidyl)-3-methyl-2-oxo-benzimidazol-5-yl] pentylcarbamoyl]phenyl]carbamate (80.0 mg, 142 umol) in DCM (1.5 mL) was added TFA (0.5 mL) and the reaction was stirred at 20° C. for 1 hour. The reaction mixture was concentrated to give the title compound (90 mg, 99% yield, TFA) as a brown solid. LC-MS ($ESI^+$) m/z 464.5 $(M+H)^+$.

Chloro-(3-chloro-2-fluoro-phenyl)-methyl-oxo-dispiro[BLAH]carboxylic acid (Intermediate DM)

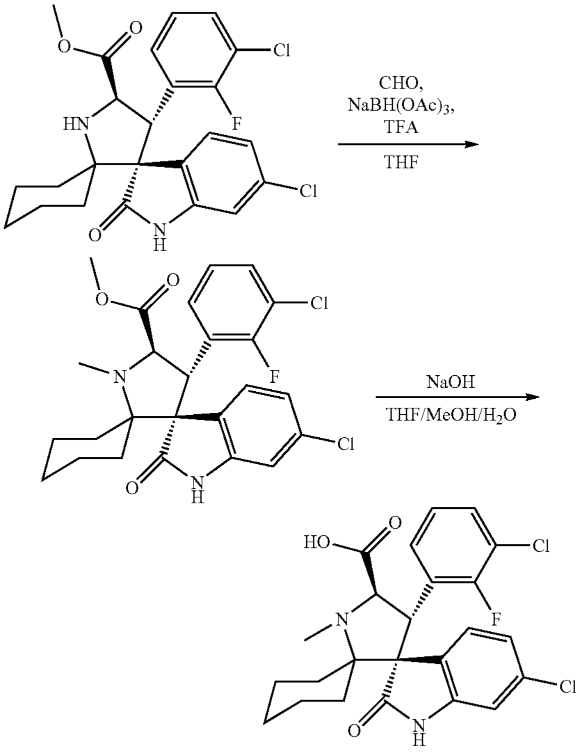

DM

Step 1—Methyl chloro-(3-chloro-2-fluoro-phenyl)-methyl-oxo-dispiro[BLAH]carboxylate To a solution of methyl chloro-(3-chloro-2-fluoro-phenyl)-oxo-dispiro[BLAH]carboxylate (2.00 g, 4.19 mmol, synthesized via Steps 1-4 of Intermediate CI) in THF (40 mL) was added $NaBH_3CN$ (1.32 g, 20.9 mmol) paraformaldehyde (4.00 g, 41.9 mmol), and TFA (3.26 g, 28.6 mmol). The mixture was stirred at 25° C. for 12 hrs. On completion, sodium bicarbonate was added to the reaction mixture to adjust the pH to 8. The mixture was then extracted with ethyl acetate (25 mL×3), filtered and concentrated to give a residue. The residue was purified by column chromatography ($SiO_2$, petroleum ether/ethyl acetate=10:1 to 5:1) to give the title compound (800 mg, 38% yield) as yellow oil. $^1H$ NMR (400 MHz, $CDCl_3$) δ 4.25 (q, J=7.2 Hz, 2H), 4.01-3.95 (m, 4H), 2.27-2.13 (m, 1H), 2.13-1.99 (m, 3H), 1.96-1.85 (m, 2H), 1.77-1.65 (m, 2H), 1.30 (t, J=7.2 Hz, 3H).

Step 2—Chloro-(3-chloro-2-fluoro-phenyl)-methyl-oxo-dispiro[BLAH]carboxylic acid To a solution of methyl chloro-(3-chloro-2-fluoro-phenyl)-methyl-oxo-dispiro[BLAH]carboxylate (800 mg, 1.63 mmol) in THF (8 mL) and $H_2O$ (8 mL) was added LiOH—$H_2O$ (136 mg, 3.26 mmol) and the mixture was stirred at 25° C. for 12 hrs. On completion, the mixture was adjusted to pH=6 with hydrochloride, and then filtered and concentrated in vacuo to give the residue. The mixture was purified by reversed-phase HPLC (water (0.225% FA)-ACN) to give the title compound (100 mg, 11% yield) as a yellow solid. $^1H$ NMR (400 MHz, DMSO-$d_6$) δ 10.60-10.52 (m, 1H), 7.60-7.52 (m, 1H), 7.47-7.41 (m, 1H), 7.40-7.34 (m, 1H), 7.17-7.11 (m, 1H), 7.06-7.00 (m, 1H), 6.64 (d, J=2.0 Hz, 1H), 4.65-4.56 (m, 1H), 4.32-4.21 (m, 1H), 2.87 (s, 3H), 2.09-1.88 (m, 2H), 1.60-1.34 (m, 6H), 1.06-0.89 (m, 2H).

Chloro-(3-chloro-2-fluoro-phenyl)-trimethyl-oxo-dispiro[BLAH]carboxylic acid (Intermediate DN)

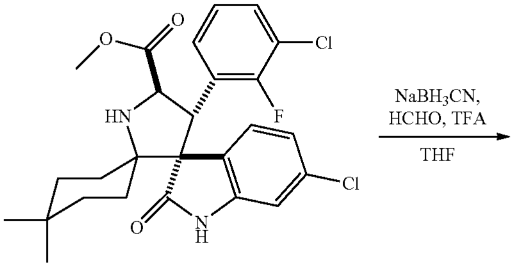

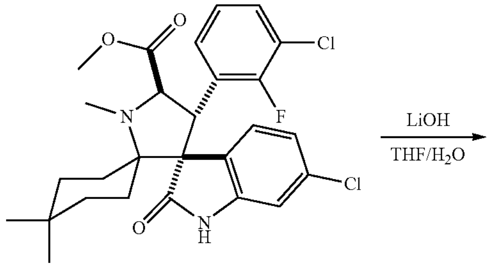

-continued

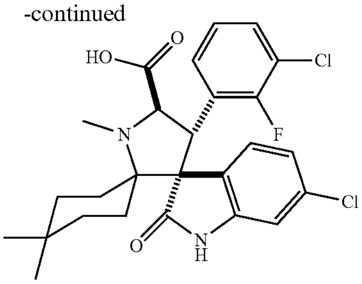

DN

Step 1—methyl chloro-(3-chloro-2-fluoro-phenyl)-trimethyl-oxo-dispiro[BLAH]carboxylate To a solution of methyl chloro-(3-chloro-2-fluoro-phenyl)-dimethyl-oxo-dispiro[BLAH]carboxylate (1 g, 1.98 mmol, synthesized via Steps 1-4 of Intermediate CN) in THF (20 mL) was added $NaBH_3CN$ (621 mg, 9.89 mmol), paraformaldehyde (2.0 g) and TFA (1.54 g, 13.5 mmol). The mixture was stirred at 25° C. for 12 hrs. On completion, sodium bicarbonate solution was added to the mixture to adjust pH>7, and then the solution was extracted with ethyl acetate (30 mL×3). The organic layer was dried with sodium sulfate and concentrated in vacuo to give the residue. The residue was purified by column chromatography ($SiO_2$, petroleum ether:ethyl acetate=3:1) to give the title compound (220 mg, 17% yield) as a yellow solid. $^1H$ NMR (400 MHz, DMSO-d6) δ 10.61 (s, 1H), 7.60 (m, J=6.4 Hz, 1H), 7.53-7.50 (m, 1H), 7.47-7.37 (m, 1H), 7.24-7.15 (m, 1H), 7.09 (d, J=2.0, 8.0 Hz, 1H), 6.71 (d, J=2.0 Hz, 1H), 4.71 (d, J=10.8 Hz, 1H), 4.38 (d, J=10.4 Hz, 1H), 3.68-3.59 (m, 3H), 2.90 (s, 3H), 1.94-1.75 (m, 2H), 1.63-1.37 (m, 2H), 1.31-1.24 (m, 2H), 1.10 (dt, J=4.8, 13.4 Hz, 2H), 0.92 (s, 4H), 0.61 (s, 3H); LC-MS ($ESI^+$) m/z 519 $(M+H)^+$.

Step 2—chloro-(3-chloro-2-fluoro-phenyl)-trimethyl-oxo-dispiro[BLAH]carboxylic acid To a solution of methyl chloro-(3-chloro-2-fluoro-phenyl)-trimethyl-oxo-dispiro[BLAH]carboxylate (200 mg, 385 umol) in THF (2 mL) and $H_2O$ (2 mL) was added LiOH—$H_2O$ (32.1 mg, 770 umol) and the mixture was stirred at 25° C. for 12 hrs. On completion, the reaction mixture was filtered, and the filter cake was dried in vacuo. The crude product was purified by reversed-phase HPLC (0.1% FA condition) to give the title compound (70.0 mg, 110 umol, 28% yield) as a yellow solid. $^1H$ NMR (400 MHz, DMSO-d6) δ 10.65-10.37 (m, 1H), 7.56 (m, J=6.8 Hz, 1H), 7.46 (d, J=7.6 Hz, 1H), 7.37 (d, J=7.2 Hz, 1H), 7.14 (m, J=7.6 Hz, 1H), 7.04 (d, J=7.8 Hz, 1H), 6.66 (s, 1H), 4.61 (d, J=10.4 Hz, 1H), 4.25 (d, J=10.4 Hz, 1H), 2.87 (s, 3H), 1.82-1.52 (m, 4H), 1.30-1.11 (m, 4H), 0.91-0.78 (m, 3H), 0.57 (s, 3H). LC-MS ($ESI^+$) m/z 505.2 $(M+H)^+$.

4-amino-N-[5-[1-(2,6-dioxo-3-piperidyl)-3-methyl-2-oxo-benzimidazol-5-yl]pent-4-ynyl cyclohexanecarboxamide (Intermediate DO)

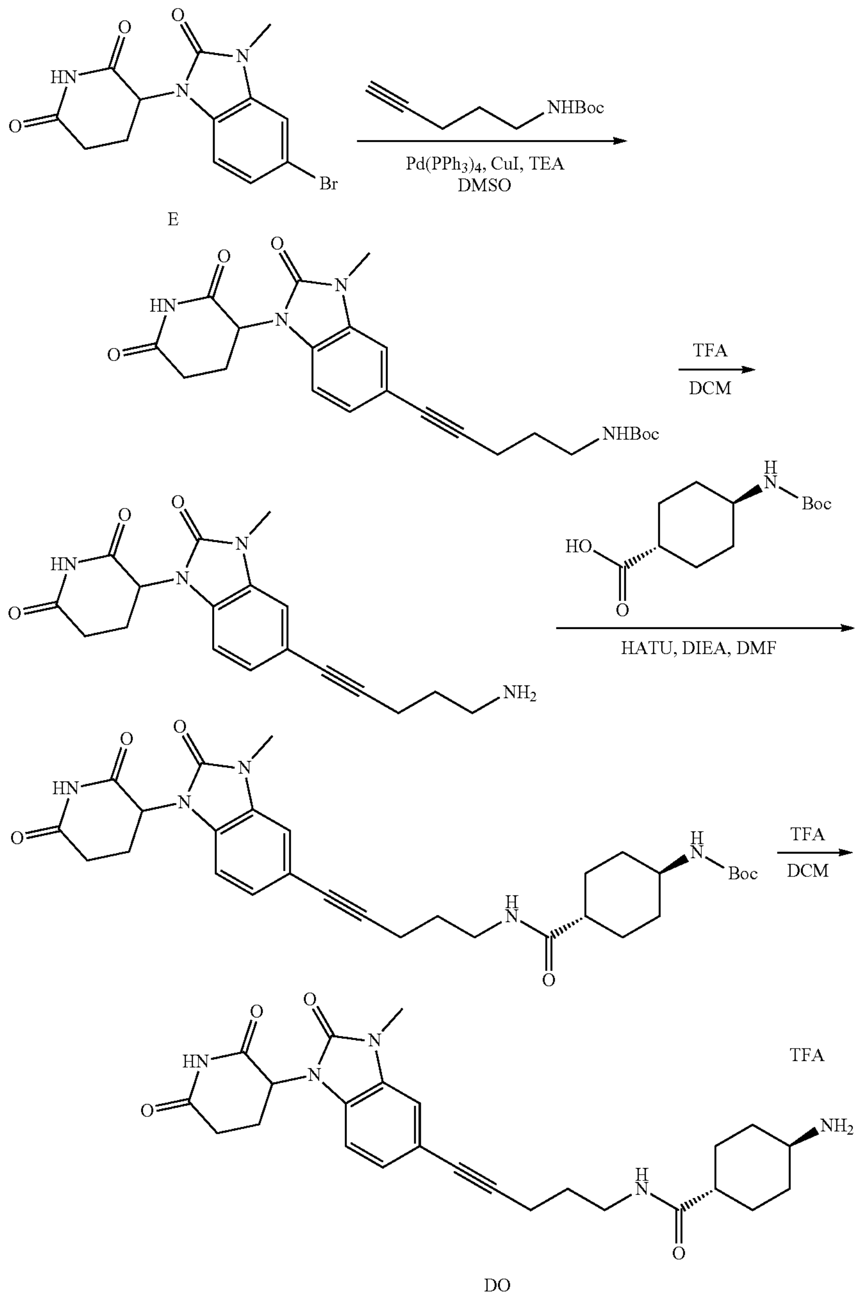

DO

Step 1—tert-butyl N-[5-[1-(2,6-dioxo-3-piperidyl)-3-methyl-2-oxo-benzimidazol-5-yl]pent-4-ynyl]carbamate To a mixture of 3-(5-bromo-3-methyl-2-oxo-benzimidazol-1-yl)piperidine-2,6-dione (5.00 g, 14.8 mmol, Intermediate E), tert-butyl N-pent-4-ynylcarbamate (4.06 g, 22.2 mmol, CAS #151975-50-6), CuI (282 mg, 1.48 mmol) and $Pd(PPh_3)_4$ (1.71 g, 1.48 mmol) was added DMSO (90 mL). The solution was purged with nitrogen for 5 min, then TEA (14.5 g, 144 mmol, 20 mL) was added and the resulting solution was stirred at 80° C. for 12 hrs. On completion, water (100 mL) was added to the reaction mixture. The aqueous layer was extracted with ethyl acetate (50 ml×5). The organic layer was separated and concentrated under reduced pressure to give the crude. The crude product was purified by silica gel chromatography eluted with PE:EtOAc (1:9), then triturated twice with EtOAc (20 mL×2) at 25° C. to give the title compound (6.00 g, 78% yield) as a white solid. 1H NMR (400 MHz, DMSO-$d_6$) δ=11.11 (s, 1H), 7.25 (s, 1H), 7.10-7.08 (d, 1H), 6.89-6.77 (d, 1H), 5.40-5.35 (dd, J=5.2, 8.8 Hz, 1H), 3.31 (s, 1H), 3.08-3.05 (m, 2H), 3.03-3.02 (m, 1H), 2.71-2.65 (m, 2H), 2.43-2.39 (m, 2H), 2.00-

2.02 (m, 1H), 1.68-1.64 (m, 2H), 1.39 (s, 9H). LC-MS ($ESI^+$) m/z 385.1 $(M+H-56)^+$.

Step 2—3-[5-(5-aminopent-1-ynyl)-3-methyl-2-oxo-benzimidazol-1-yl]piperidine-2,6-dione To tert-butyl N-[5-[1-(2,6-dioxo-3-piperidyl)-3-methyl-2-oxo-benzimidazol-5-ylpent-4-ynyl] carbamate (400 mg, 908 umol) in DCM (4 mL) was added TFA (1.23 g, 10.8 mmol, 0.8 mL) and the solution was stirred at 25° C. for 2 hrs. On completion, the solution was concentrated under reduced pressure to give the title compound (400 mg 68% yield, TFA) as green oil. LC-MS ($ESI^+$) m/z 341.1 $(M+H)^+$.

Step 3—tert-butylN-[4-[5-[1-(2,6-dioxo-3-piperidyl)-3-methyl-2-oxo-benzimidazol-5-yl]pent-4-ynylcarbamoyl]cyclohexyl]carbamate To a mixture of 3-[5-(5-aminopent-1-ynyl)-3-methyl-2-oxo-benzimidazol-1-yl]piperidine-2,6-dione (400 mg, 880.28 umol, TFA), 4-(tert-butoxycarbonylamino)cyclohexanecarboxylic acid (321 mg, 1.32 mmol, CAS #130309-46-5), and DIEA (569 mg, 4.40 mmol, 0.77 mL) was added in DMF (6 mL). The mixture was stirred 2 minutes, then added HATU (435 mg, 1.14 mmol) and the mixture was stirred at 25° C. for 12 hrs. On completion, water (20 mL) was added dropwise to the reaction mixture. Then the mixture was filtered and the filter cake was washed with 5 mL of ACN, then dried in vacuo to afford the title compound (220 mg, 38% yield) as a green solid. 1H NMR (400 MHz, DMSO-$d_6$) δ=11.14 (s, 1H), 7.77-7.76 (d, J=4.4 Hz, 1H), 7.24 (s, 1H), 7.10 (s, 1H), 6.72-6.68 (m, 1H), 5.37 (br dd, J=5.6, 12.8 Hz, 1H), 3.42 (s, 3H), 3.16-3.13 (m, 2H), 3.00-2.84 (m, 1H), 2.82-2.57 (m, 2H), 2.41 (brt, J=7.2 Hz, 1H), 2.14-1.93 (m, 2H), 1.92-1.52 (m, 5H), 1.38 (s, 9H), 1.14-1.13 (m, 2H). LC-MS ($ESI^+$) m/z 510.2 $(M+H-56)^+$.

Step 4—4-amino-N-[5-[1-(2,6-dioxo-3-piperidyl)-3-methyl-2-oxo-benzimidazol-5-yl]pent-4-ynyl] cyclohexanecarboxamide A solution of tert-butylN-[4-[5-[1-(2,6-dioxo-3-piperidyl)-3-methyl-2-oxo-benzimidazol-5-yl]pent-4-ynylcarbamoyl]cyclohexyl]carbamate (70.0 mg, 124 umol) in DCM (3 mL) was added TFA (924 mg, 8.10 mmol, 0.6 mL) and the solution was stirred at 25° C. for 40 min. On completion, the reaction mixture was concentrated under reduced pressure to remove DCM and TFA to give the title compound (71.5 mg, 85% yield, TFA) as red oil. LC-MS ($ESI^+$) m/z 466.2 $(M+H)^+$.

2-[2-(2-bromoethoxy)ethyl]isoindole-1,3-dione (Intermediate DP)

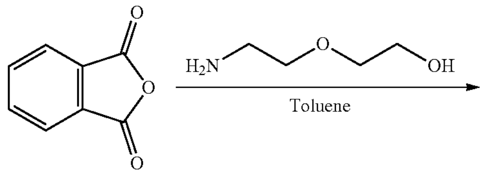

-continued

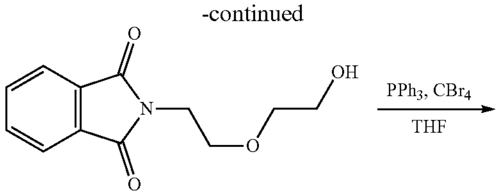

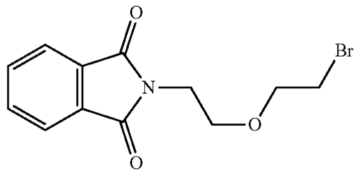

DP

Step 1—2-[2-(2-hydroxyethoxy)ethyl]isoindole-1,3-dione

To a stirred solution of phthalic anhydride (133 g, 897.94 mmol) in toluene (1 L) was added 2-(2-aminoethoxy)ethanol (94.41 g, 897.94 mmol) at rt under a nitrogen atmosphere. The resulting mixture was refluxed overnight under a nitrogen atmosphere. On completion, the mixture was cooled to rt, then the resulting mixture was concentrated under reduced pressure. The mixture was then diluted with ethyl acetate (3 L), washed with brine (3×1 L), and dried over anhydrous $Na_2SO_4$. After filtration, the filtrate was concentrated under reduced pressure to the title compound (200 g, 95% yield) as a light yellow solid. $^1H$ NMR (400 MHz, $CDCl_3$) δ 7.78 (dd, J=3.1, 5.5 Hz, 2H), 7.67 (dd, J=3.1, 5.5 Hz, 2H), 3.85 (t, J=5.5 Hz, 2H), 3.70 (t, J=5.5 Hz, 2H), 3.63 (dd, J=3.7, 5.2 Hz, 2H), 3.55 (dd, J=3.7, 5.2 Hz, 2H); LC/MS (ESI, m/z): $[(M+1)]^+$=236.1.

Step 2—2-[2-(2-bromoethoxy)ethyl]isoindole-1,3-dione

To a stirred solution of 2-[2-(2-hydroxyethoxy)ethyl] isoindole-1,3-dione (100 g, 425 mmol) and $CBr_4$ (211 g, 637 mmol) in THF (1 L) was added $PPh_3$ (167 g, 637 mmol) in portions at 0° C. under a nitrogen atmosphere. The resulting mixture was stirred overnight at rt under a nitrogen atmosphere. The resulting mixture was concentrated under reduced pressure. The residue was purified by silica gel column chromatography (eluted with 20% ethyl acetate in petroleum ether) to afford the title compound (110 g, 87% yield) as a white solid. $^1H$ NMR (400 MHz, $CDCl_3$) δ 7.85 (dd, J=3.1, 5.5, Hz, 2H), 7.72 (dd, J=3.1, 5.5 Hz, 2H), 3.92 (t, J=5.7 Hz, 2H), 3.81-3.76 (m, 4H), 3.41 (t, J=6.2 Hz, 2H); LC/MS (ESI, m/z): $[(M+1)]^+$=298.0, 300.0.

Tert-butyl N-[(1S)-1-[[(2S)-1-[(3S)-7-[2-(2-amino-ethoxy)ethoxy]-3-[[(1R)-1,2,3,4-tetrahydronaphthalen-1-yl]carbamoyl]-3,4-dihydro-1H-isoquinolin-2-yl]-3,3-dimethyl-1-oxobutan-2-yl]carbamoyl]ethyl]-N-methylcarbamate (Intermediate DQ)

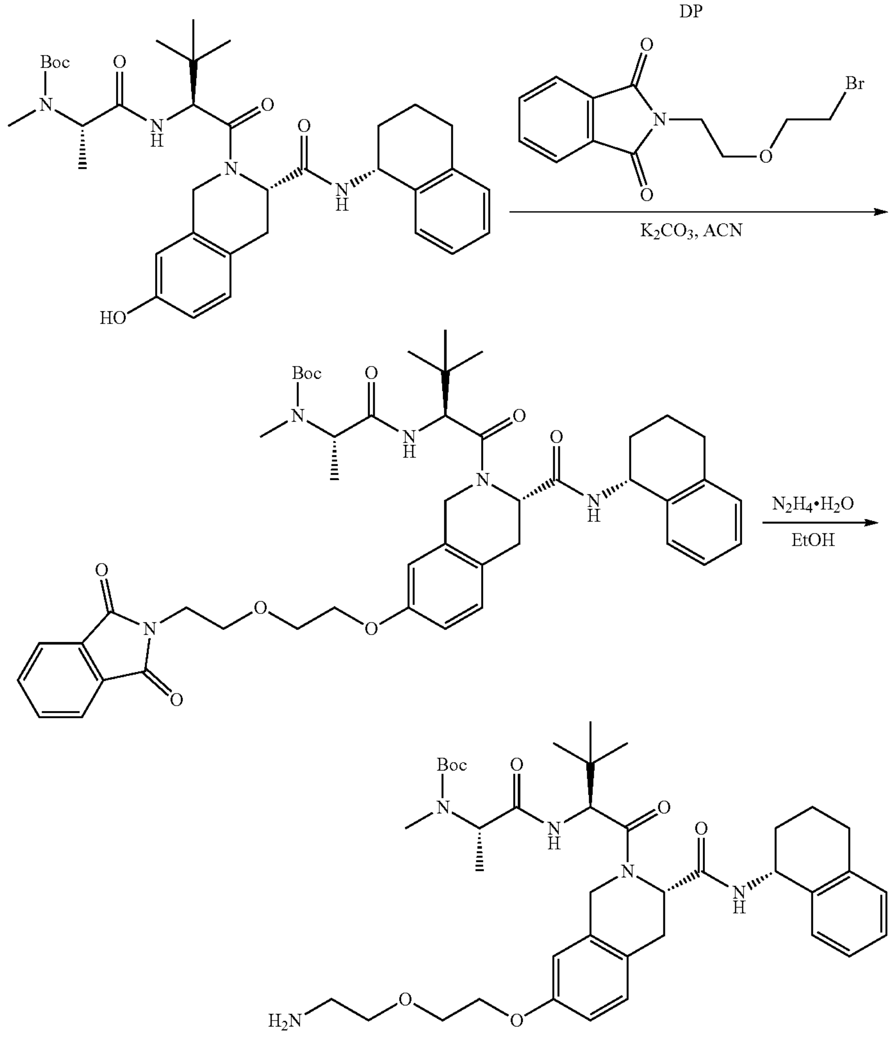

DQ

Step 1—Tert-butyl N-[(1S)-1-[[(25)-1-[(3S)-7-[2-[2-(1,3-dioxoisoindol-2-yl)ethoxy]ethoxy]-3-[[(1R)-1,2,3,4-tetrahydronaphthalen-1-yl]carbamoyl]-3,4-dihydro-1H-isoquinolin-2-yl]-3,3-dimethyl-1-oxobutan-2-yl]carbamoyl]ethyl]-N-methylcarbamate To a stirred mixture of tert-butyl N-[(1S)-1-[[(2S)-1-[(3S)-7-hydroxy-3-[[(1R)-1,2,3,4-tetrahydronaphthalen-1-yl]carbamoyl]-3,4-dihydro-1H-isoquinolin-2-yl]-3,3-dimethyl-1-oxobutan-2-yl]carbamoyl]ethyl]-N-methylcarbamate (10.00 g, 16.11 mmol, synthesized via Steps 1-8 of Intermediate CJ) and 2-[2-(2-bromoethoxy)ethyl]isoindole-1,3-dione (7.18 g, 24.16 mmol, Intermediate DP) in acetonitrile (200 mL) was added $K_2CO_3$ (4.45 g, 32.22 mmol) in portions at rt. The resulting mixture was stirred for 16 h at 80° C. On completion, the resulting mixture was concentrated under reduced pressure. The crude product was purified by silica gel column chromatography (Mobile Phase A: DCM, Mobile Phase B: MeOH; Gradient: 20% B to 50% B in 50 min; Detector: UV 254 nm; the fractions containing the desired product were collected at 49% B) and concentrated under reduced pressure to afford the title compound (12 g, 92% yield) as a white solid. LC/MS (ESI, m/z): [(M+1)]=838.4.

Step 2—Tert-butyl N-[(1S)-1-[[(2S)-1-[(3S)-7-[2-(2-aminoethoxy)ethoxy]-3-[[(1R)-1,2,3,4-tetrahydronaphthalen-1-yl]carbamoyl]-3,4-dihydro-1H-isoquinolin-2-yl]-3,3-dimethyl-1-oxobutan-2-yl]carbamoyl]ethyl]-N-methylcarbamate To a solution of tert-butyl N-[(1S)-1-[[(2S)-1-[(3S)-7-[2-[2-(1,3-dioxoisoindol-2-yl)ethoxy]ethoxy]-3-[[(1R)-1,2,3,4-tetrahydronaphthalen-1-yl]carbamoyl]-3,4-dihydro-1H-isoquinolin-2-yl]-3,3-dimethyl-1-oxobutan-2-yl]carbamoyl]ethyl]-N-methylcarbamate (12.00 g, 14.32 mmol) in ethanol (150 mL) was added $NH_2NH_2 \cdot H_2O$ (7.00 mL, 82% in water). The resulting mixture was stirred for 2 h at 70° C. On completion, the reaction mixture was cooled down to room temperature and filtered. The filtered cake was washed with ethanol (3×20 mL). The filtrate was concentrated under reduced pressure. The crude product was purified by reverse phase flash chromatography (Column: Spherical C18 Column, 20-40 μm, 330 g; Mobile Phase A: Water (plus 10 mm formic acid); Mobile Phase B: ACN; Flow rate: 100 mL/min; Gradient: 25% B to 50% B in 25 min; Detector: UV 254 nm; the fractions containing the desired product were collected at 42% B) and concentrated under reduced pressure and lyophilized to afford the title compound (10 g, 99% yield) as a yellow solid. $^1H$ NMR (300 MHz, $CD_3OD$) δ 7.28-7.25 (m, 1H), 7.17-7.00 (m, 4H), 6.97-6.79 (m, 2H), 5.50 (s, 1H), 5.23-4.90 (m, 2H), 4.78-4.50 (m, 3H), 4.31-4.03 (m, 2H), 3.93-3.87 (m, 2H), 3.86-3.82 (m, 2H), 3.33-3.17 (m, 2H), 3.16-3.08 (m, 2H), 2.86-2.77 (m, 5H), 2.02-1.58 (m, 4H), 1.51-1.48 (m, 10H), 1.38-1.24 (m, 2H), 1.12-1.09 (m, 9H); LC/MS (ESI, m/z): $[(M+1)]^+$=708.4.

Tert-butyl N-methyl-N-pent-4-ynyl-carbamate (Intermediate DR)

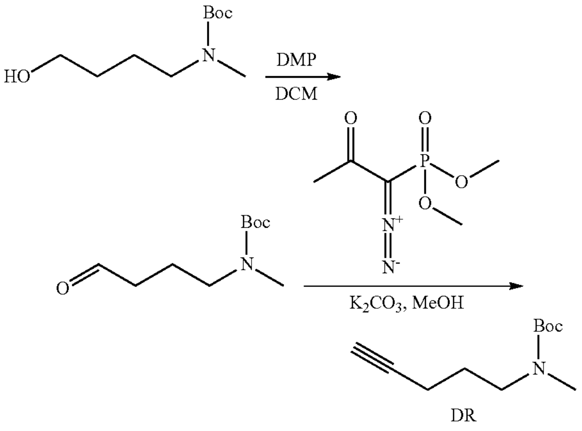

Step 1—Tert-butyl N-methyl-N-(4-oxobutyl) carbamate

To a solution of tert-butyl N-(4-hydroxybutyl)-N-methyl-carbamate (1.16 g, 5.71 mmol, CAS #99207-32-6) in DCM (10 mL) and THF (10 mL) was added DMP (3.63 g, 8.56 mmol, CAS #87413-09-0). The mixture was stirred at 25° C. for 16 hr. On completion, the mixture was quenched with the solution of sodium thiosulfate (20 mL) and extracted with dichloromethane (25 mL×3). The combined organic phase was dried over anhydrous sodium sulfate, filtered and concentrated to give a residue. The residue was purified by column chromatography ($SiO_2$, petroleum ether/ethyl acetate=1:0 to 1:1) to give the compound (1.00 g, 87% yield) as yellow oil. $^1H$ NMR (400 MHz, $CDCl_3$) δ 9.80 (s, 1H), 3.26 (t, J=6.8 Hz, 2H), 2.84 (s, 3H), 2.48 (t, J=7.2 Hz, 2H), 1.86 (d, J=7.2 Hz, 2H), 1.46 (s, 9H).

Step 2—Tert-butyl N-methyl-N-pent-4-ynyl-carbamate

To a solution of tert-butyl N-methyl-N-(4-oxobutyl)carbamate (2.13 g, 10.6 mmol) in MeOH (60 mL) was added $K_2CO_3$ (4.39 g, 31.8 mmol) and 1-diazo-1-dimethoxyphosphoryl-propan-2-one (2.44 g, 12.7 mmol, CAS #90965-06-3). The mixture was stirred at 25° C. for 14 hrs. On completion, the mixture was quenched with water (30 mL) and extracted with dichloromethane (3×25 mL). The combined organic phase was dried over anhydrous sodium sulfate, filtered and concentrated to give a residue. The residue was purified by column chromatography ($SiO_2$, petroleum ether/ethyl acetate=1:0 to 10:1) to give the title compound (608 mg, 29% yield) as colorless oil. $^1H$ NMR (400 MHz, $CDCl_3$) δ 3.32 (t, J=7.2 Hz, 2H), 2.86 (s, 3H), 2.20 (dt, J=2.8, 7.2 Hz, 2H), 1.96 (t, J=2.8 Hz, 1H), 1.76-1.74 (m, 2H), 1.46 (s, 9H).

3-[5-[5-[(4-Aminocyclohexyl)methyl-methyl-amino]pentyl]-3-methyl-2-oxo-benzimidazol-1-yl]piperidine-2,6-dione (Intermediate DS)

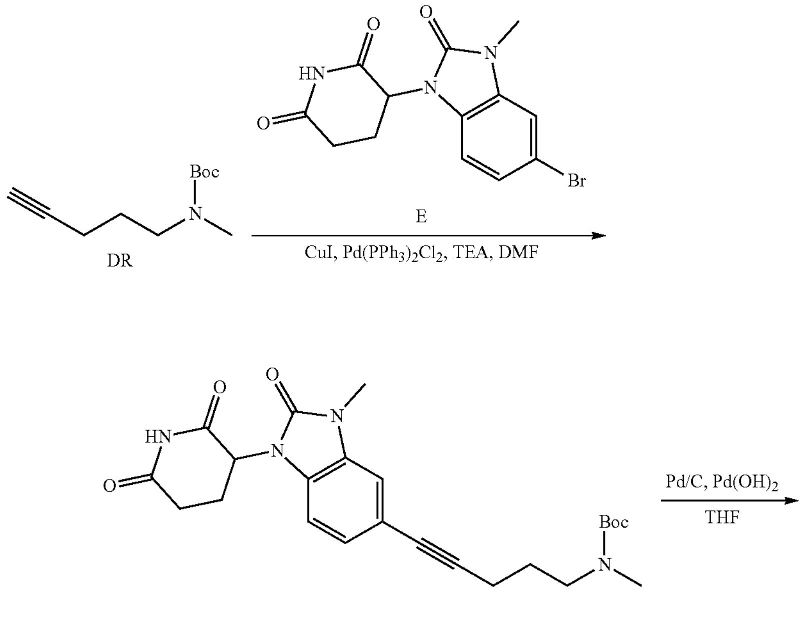

-continued

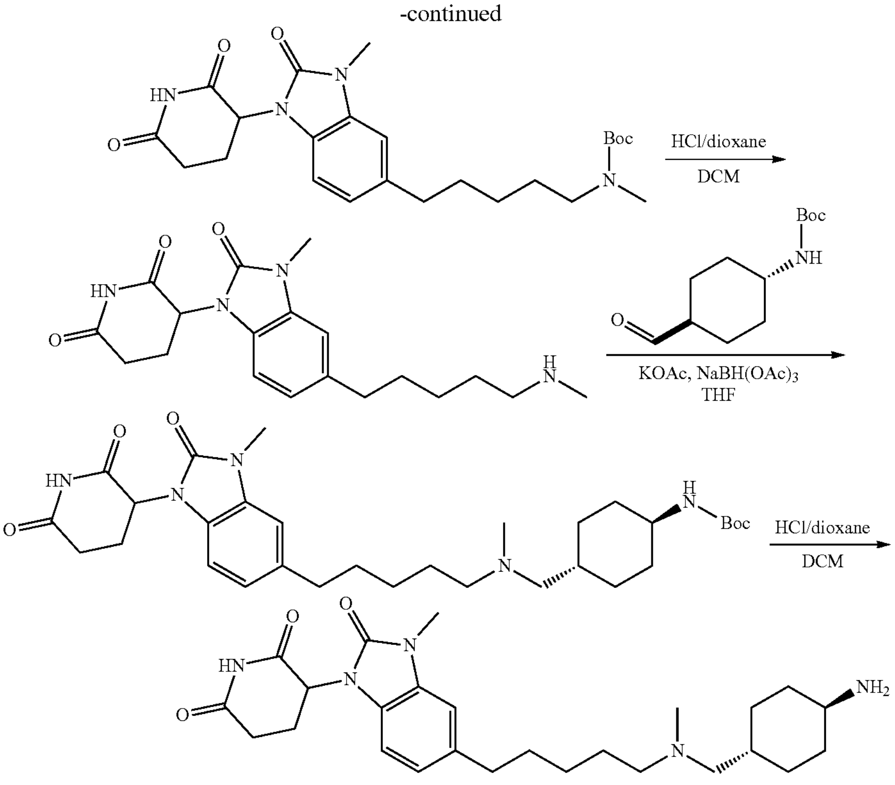

DS

Step 1—Tert-butyl N-[5-[1-(2,6-dioxo-3-piperidyl)-3-methyl-2-oxo-benzimidazol-5-yl]pent-4-ynyl]-N-methyl-carbamate A mixture of 3-(5-bromo-3-methyl-2-oxo-benzimidazol-1-yl)piperidine-2,6-dione (357 mg, 1.06 mmol, Intermediate E), tert-butyl N-methyl-N-pent-4-ynyl-carbamate (250 mg, 1.27 mmol, Intermediate DR), CuI (10.0 mg, 52.8 umol), $Pd(PPh_3)_2Cl_2$ (74.1 mg, 105 umol) and TEA (534 mg, 5.28 mmol) in DMF (17 mL) was degassed and purged with $N_2$ three times, and then the mixture was stirred at 80° C. for 3 hrs under $N_2$ atmosphere. On completion, the mixture was quenched with water (20 mL) and extracted with ethyl acetate (3×25 mL). The combined organic phase was dried over anhydrous sodium sulfate, filtered and concentrated to give a residue. The residue was purified first by column chromatography ($SiO_2$, petroleum ether/ethyl acetate=1:0 to 1:2) then by prep. HPLC (column: Phenomenex Luna C18 150*25 mm*10 um; mobile phase: [water (0.225% FA)-ACN]; B %: 37%-67%, 11 min) to give the title compound (67.0 mg, 147 umol, 14% yield) as a white solid. 1H NMR (400 MHz, DMSO-d6) δ 9.52 (d, J=6.0 Hz, 1H), 8.80 (d, J=7.6 Hz, 1H), 8.40 (d, J=4.4 Hz, 1H), 8.24 (d, J=5.6 Hz, 1H), 7.84 (t, J=5.6 Hz, 1H), 7.28-6.96 (m, 1H), 6.92-6.40 (m, 1H), 5.32-5.04 (m, 1H), 4.76 (d, J=16.8 Hz, 1H), 4.32-4.16 (m, 1H), 3.84-3.80 (m, 1H), 3.76 (d, J=7.6 Hz, 1H), 3.64-3.56 (m, 3H), 3.54-3.48 (m, 6H), 3.48-3.44 (m, 2H), 3.44-3.34 (m, 4H), 3.20 (d, J=5.6 Hz, 2H), 2.20 (tt, J=3.2, 12.0 Hz, 1H), 2.08-2.02 (m, 2H), 2.02-1.91 (m, 2H), 1.84 (d, J=11.2 Hz, 2H), 1.80-1.64 (m, 4H), 1.60-1.52 (m, 2H), 1.52-1.44 (m, 2H), 1.44-1.36 (m, 2H), 1.34-1.26 (m, 2H); LC-MS ($ESI^+$) m/z 399.2 $(M+H)^+$.

Step 2—Tert-butyl N-[5-[1-(2,6-dioxo-3-piperidyl)-3-methyl-2-oxo-benzimidazol-5-yl]pentyl]-N-methyl-carbamate To a solution of tert-butyl N-[5-[1-(2,6-dioxo-3-piperidyl)-3-methyl-2-oxo-benzimidazol-5-yl] pent-4-ynyl]-N-methyl-carbamate (52.0 mg, 114 umol) in THF (10 mL) was added Pd/C (2.73 mg, 11.4 umol) and $Pd(OH)_2$ (1.61 mg, 11.4 umol) under argon. The suspension was degassed under vacuum and purged with $H_2$ several times. The mixture was stirred under $H_2$ (15 psi) at 25° C. for 16 hours. On completion, the mixture was concentrated to give a residue to give the compound (52.0 mg, 99% yield) as white oil. LC-MS ($ESI^+$) m/z 481.2 $(M+Na)^+$.

Step 3—3-[3-methyl-5-[5-(methylamino) pentyl]-2-oxo-benzimidazol-1-yl] piperidine-2,6-dione To a solution of tert-butyl N-[5-[1-(2,6-dioxo-3-piperidyl)-3-methyl-2-oxo-benzimidazol-5-yl] pentyl]-N-methyl-carbamate (250 mg, 545 umol) in DCM (10 mL) was added HCl/dioxane (4 M, 1.4 mL) and the mixture was stirred at 25° C. for 1 hr. On completion, the mixture was concentrated to give a residue to give the compound (195 mg, 99% yield) as a white solid. LC-MS ($ESI^+$) m/z 359.1 $(M+H)^+$.

Step 4—Tert-butyl N-[4-[[5-[1-(2,6-dioxo-3-piperidyl)-3-methyl-2-oxo-benzimidazol-5-yl]pentyl-methyl-amino]methyl]cyclohexyl]carbamate To a solution of 3-[3-methyl-5-[5-(methylamino) pentyl]-2-oxo-benzimidazol-1-yl]piperidine-2,6-dione (195 mg, 493 umol) in THF (10 mL) was added KOAc (242 mg, 2.47 mmol) until the pH 5-6 at 25° C. for 0.5 hour. Then tert-butyl N-(4-formylcyclohexyl) carbamate (112 mg, 493 umol, CAS #181308-56-5) and $NaBH(OAc)_3$ (156 mg, 740 umol) was added at 0° C. for 0.5 hours. Then the mixture was stirred at 25° C. for 1 hour. On completion, the mixture was quenched with water (20 mL) and extracted with DCM (3×20 mL). The combined organic phase was dried over anhydrous sodium sulfate, filtered and concentrated to give a residue to give the compound (200 mg, 71% yield) as a yellow solid. $^1H$ NMR (400 MHz, DMSO-$d_6$) δ 11.07 (s, 1H), 7.04-6.96 (m, 2H), 6.85 (d, J=9.1 Hz, 1H), 6.70-6.62 (m, 1H), 5.37-5.29 (m, 1H), 3.66-3.53 (m, 1H), 2.72-2.64 (m, 2H), 2.59 (s, 2H), 2.26-2.16 (m, 5H), 2.05-1.95 (m, 5H), 1.91 (d, J=2.6 Hz, 6H), 1.78-1.67 (m, 7H), 1.64-1.52 (m, 4H), 1.37 (s, 9H); LC-MS ($ESI^+$) m/z 570.5 $(M+H)^+$.

Step 5—3-[5-[5-[(4-Aminocyclohexyl) methyl-methyl-amino] pentyl]-3-methyl-2-oxo-benzimidazol-1-yl] piperidine-2,6-dione To a solution of tert-butyl N-[4-[[5-[1-(2,6-dioxo-3-piperidyl)-3-methyl-2-oxo-benzimidazol-5-yl] pentyl methyl-amino]methyl]cyclohexyl]carbamate (50.0 mg, 87.7 umol) in DCM (5 mL) was added HCl/dioxane (4 M, 175 uL). The mixture was stirred at 25° C. for 1 hr. On completion, the mixture was concentrated to give the title compound (41.2 mg, 93% yield, HCl salt) as a white solid. LC-MS ($ESI^+$) m/z 470.4 $(M+H)^+$.

tert-butyl N-[(1S)-1-[[(1S)-1-cyclohexyl-2-[(2S)-2-[4-(3-hydroxybenzoyl)-1,3-thiazol-2-yl]pyrrolidin-1-yl]-2-oxoethyl]carbamoyl]ethyl]-N-methylcarbamate (Intermediate DT)

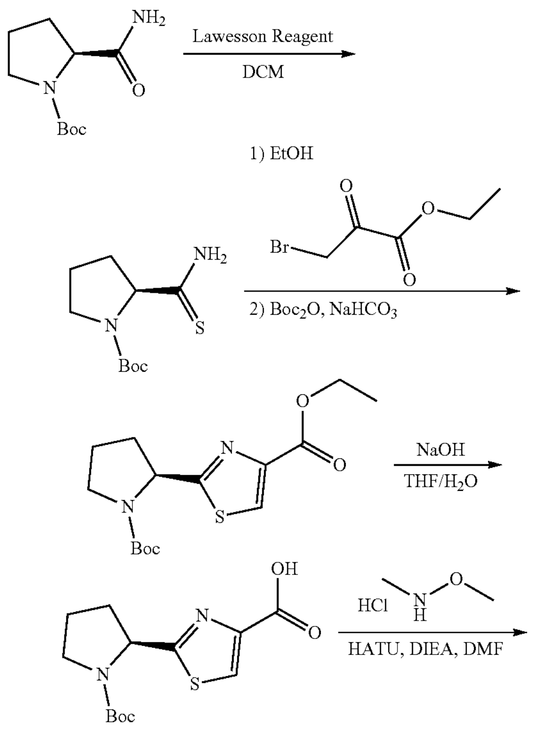

-continued

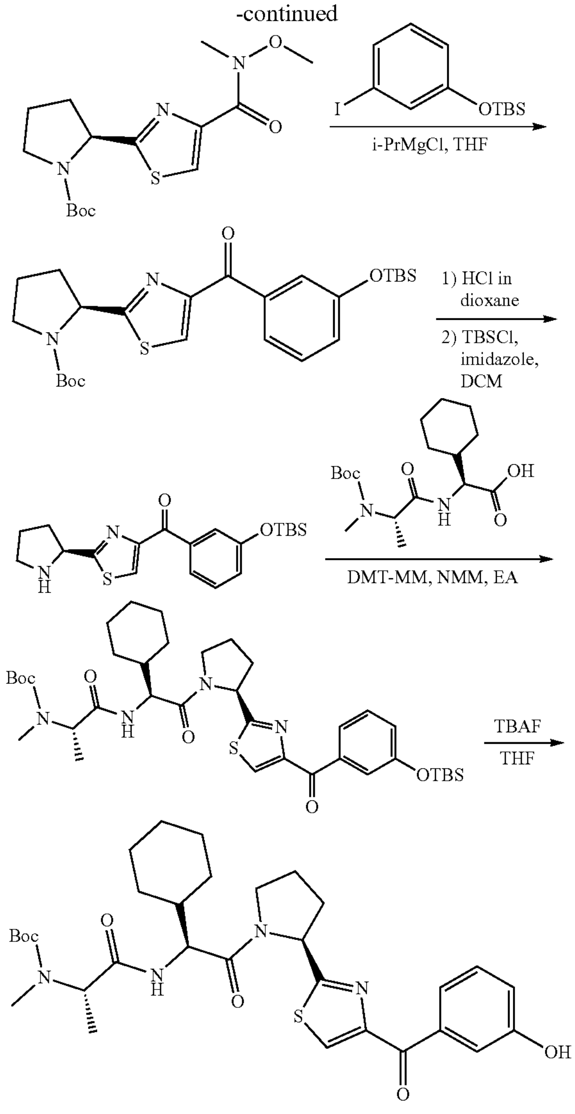

DT

Step 1—Tert-butyl (2S)-2-carbamothioylpyrrolidine-1-carboxylate

To a solution of tert-butyl (2S)-2-carbamoylpyrrolidine-1-carboxylate (500 g, 2.33 mol) in DCM (2.50 L) was added Lawesson's Reagent (566.31 g, 1.40 mol) at 0° C. in portions. The mixture was then stirred at rt for 16 h. The reaction was quenched by the addition of sat. $NaHCO_3$ (aq.) (2 L) at 0° C. The precipitated solids were collected by filtration and washed with DCM (3×200 mL). The filtrate was washed with brine (2×500 mL) and dried over anhydrous $Na_2SO_4$. After filtration, the filtrate was concentrated under reduced pressure. The residue was triturated with diethyl ether (500 mL) for 30 min. The precipitated solids were collected by filtration to afford the title compound (410 g, 76% yield) as a white solid. $^1H$ NMR (400 MHz, DMSO-$d_6$) (9.49 (s, 1H), 9.08-9.06 (m, 1H), 4.42 (dd, J=8.7, 3.5 Hz, 1H), 3.51-3.41 (m, 1H), 3.37-3.27 (m, 1H), 2.25-2.12 (m, 1H), 1.96-1.77 (m, 2H), 1.76-1.73 (m, 1H), 1.39-1.36 (m, 9H); LC/MS (ESI, m/z): $[(M+H-56)]^+$=175.1.

Step 2—Ethyl 2-[(2S)-1-(tert-butoxycarbonyl)pyrrolidin-2-yl]-1,3-thiazole-4-carboxylate To a solution of tert-butyl (2S)-2-carbamothioylpyrrolidine-1-carboxylate (400 g, 1.74 mol) in EtOH (2 L) was added ethyl 3-bromo-2-oxopropanoate (474 g, 2.43 mol) at 25° C. The mixture was then stirred at 60° C. for 3 h. The resulting mixture was concentrated under reduced pressure. The residue was dissolved in THF (1 L) then a solution of $NaHCO_3$ (295 g, 3.47 mol) in $H_2O$ (1 L) was added, followed by the addition of $Boc_2O$ (568 g, 2.61 mol) dropwise at 0° C. The mixture was stirred at rt for 16 h. On completion, the mixture was concentrated under reduce pressure to remove THF. The mixture was extracted with ethyl acetate (3×1 L). The combined organic layers were washed with brine (3×1 L) and dried over anhydrous $Na_2SO_4$. After filtration, the filtrate was concentrated under reduced pressure. The residue was triturated with petroleum ether (2 L) for 30 min. The precipitated solids were collected by filtration and washed with petroleum ether (2×500 mL) to afford the title compound (370 g, 66% yield) as a light solid. $^1H$ NMR (400 MHz, $CD_3OD$) δ 8.32 (s, 1H), 5.19-5.16 (m, 1H), 4.40 (q, J=7.1 Hz, 2H), 3.63 (dt, J=11.4, 5.9 Hz, 1H), 3.51 (dd, J=10.4, 7.8 Hz, 1H), 2.46-2.42 (m, 1H), 2.19-2.15 (m, 1H), 2.05-1.92 (m, 2H), 1.52-1.48 (m, 9H), 1.40 (t, J=7.1 Hz, 3H); LC/MS (ESI, m/z): $[(M+H)]^+$=327.2.

Step 3—2-[(2S)-1-(tert-butoxycarbonyl)pyrrolidin-2-yl]-1,3-thiazole-4-carboxylic acid To a solution of ethyl 2-[(2S)-1-(tert-butoxycarbonyl)pyrrolidin-2-yl]-1,3-thiazole-4-carboxylate (460 g, 1.41 mol) in THF (2.3 L) was added dropwise a solution of NaOH (169 g, 4.23 mol) in $H_2O$ (2.30 L) at 0° C. The mixture was stirred at rt for 2 h. On completion, the mixture was concentrated under reduce pressure to remove THF. The aqueous layer was acidified to pH 3-5 with 0.5 N HCl (aq.). The mixture was extracted with dichloromethane (3×1.5 L). The combined organic layers were washed with brine (3×1 L) and dried over anhydrous $Na_2SO_4$. After filtration, the filtrate was concentrated under reduced pressure to afford the title compound (420 g, 100% yield) as a yellow solid. $^1H$ NMR (400 MHz, DMSO-$d_6$) δ 13.03 (s, 1H), 8.32 (s, 1H), 5.09-5.06 (m, 1H), 3.51-3.42 (m, 2H), 2.35-2.32-2.30 (m, 1H), 2.07-2.04 (m, 1H), 1.94-1.82 (m, 2H), 1.42-1.26 (m, 9H); LC/MS (ESI, m/z): $[(M+H)]^+$=299.2.

Step 4—Tert-butyl (2S)-2-[4-[methoxy(methyl)carbamoyl]-1,3-thiazol-2-yl]pyrrolidine-1-carboxylate To a solution of 2-[(2S)-1-(tert-butoxycarbonyl)pyrrolidin-2-yl]-1,3-thiazole-4-carboxylic acid (400 g, 1.34 mol) in DMF (2 L) were added methoxy(methyl)amine hydrochloride (196 g, 2.01 mol), DIEA (518 g, 4.01 mol) and HATU (661 g, 1.74 mmol) at 0° C. The mixture was then stirred at rt for 2 h. The resulting mixture was diluted with ethyl acetate (5 L) and washed with brine (10×1 L). The organic layers were dried over anhydrous $Na_2SO_4$. After filtration, the filtrate was concentrated under reduced pressure. The residue was purified by silica gel column chromatography, eluted with 25% ethyl acetate in petroleum ether, to afford the title compound (400 g, 88% yield) as a light yellow solid. $^1H$ NMR (400 MHz, DMSO-$d_6$) δ 8.10 (s, 1H), 5.09-5.06 (m, 1H), 3.71 (s, 3H), 3.50-3.44 (m, 1H), 3.41-3.35 (m, 1H), 3.28 (s, 3H), 2.35-2.28 (m, 1H), 2.08-2.04 (m, 1H), 1.92-1.85 (m, 2H), 1.41-1.25 (m, 9H); LC/MS (ESI, m/z): $[(M+H)]^+$=342.2.

Step 5—Tert-butyl (2S)-2-[4-[methoxy(methyl)carbamoyl]-1,3-thiazol-2-yl]pyrrolidine-1-carboxylate To a solution of tert-butyl(3-iodophenoxy)dimethylsilane (352 g, 1.05 mol) in THF (500 mL) was added isopropylmagnesium chloride (539 mL, 1.08 mol, 2M) dropwise at −10° C. under a $N_2$ atmosphere. The reaction mixture was stirred at 0° C. for 30 min. Then a solution of tert-butyl (2S)-2-[4-[methoxy(methyl)carbamoyl]-1,3-thiazol-2-yl] pyrrolidine-1-carboxylate (200 g, 585.77 mmol) in THF (1 L) was added at 0° C. The mixture was stirred at 0° C. for 30 min then warmed to rt and stirred for 4 h. After completion of reaction, the mixture was then cooled to −5° C. and quenched with saturated ammonium chloride solution (2 L). The mixture was partitioned between water (3 L) and ethyl acetate (1 L). The organic phase was separated and the aqueous phase was further extracted with ethyl acetate (3×2 L). The organic phases were combined, washed with brine (2 L) and dried over anhydrous sodium sulfate. The dried solution was filtered and concentrated under reduced pressure. The crude product was purified by silica gel column chromatography, eluting with 3%~10% ethyl acetate in hexanes, to afford the title compound (176 g, 62% yield) as a yellow oil: $^1H$ NMR (400 MHz, $CDCl_3$) δ 8.12 (s, 1H), 7.78 (dt, J=7.7, 1.4 Hz, 1H), 7.71 (dd, J=2.5, 1.5 Hz, 1H), 7.36 (t, J=7.9 Hz, 1H), 7.12-7.05 (m, 1H), 5.24-5.21 (m, 1H), 3.66-3.64 (m, 1H), 3.63-3.54 (m, 1H), 3.52-3.49 (m, 1H), 2.44-2.41 (m, 1H), 2.02-1.98 (m, 2H), 1.47 (s, 9H), 1.02 (s, 9H), 0.28 (s, 6H); LC/MS (ESI, m/z): $[(M+H)]^+$ =489.3.

Step 6—4-[3-[(tert-butyldimethylsilyl)oxy]benzoyl]-2-[(2S)-pyrrolidin-2-yl]-1,3-thiazole To a solution of tert-butyl (2S)-2-(4-[3-[(tert-butyldimethylsilyl)oxy]benzoyl]-1,3-thiazol-2-yl)pyrrolidine-1-carboxylate (176 g, 360.12 mmol) in dioxane (500 mL) was added dropwise 4 M HCl in 1,4-dioxane (500 mL) at 0° C. The resulting mixture was stirred at rt for 4 h. The resulting mixture was concentrated under reduced pressure. The residue was re-dissolved into dichloromethane (1.50 L), followed by the addition of imidazole (123 g, 1.80 mol) and tert butyldimethylsilyl chloride (70 g, 468 mmol). The resulting mixture was stirred at rt for 16 h. On completion, the reaction mixture was quenched with $H_2O$ (1 L) and was extracted with dichloromethane (3×1 L). The combined organic layers were washed with brine (3×1 L) and dried over anhydrous $Na_2SO_4$. After filtration, the filtrate was concentrated under reduced pressure. The residue was purified by silica gel column chromatography, eluted with 20%~100% ethyl acetate in petroleum ether, to afford the title compound (100 g, 72% yield) as a yellow oil. $^1H$ NMR (400 MHz, DMSO-$d_6$) δ 8.38 (s, 1H), 7.72-7.65 (m, 2H), 7.44 (t, J=7.8 Hz, 1H), 7.18-7.11 (m, 1H), 4.52 (dd, J=8.4, 4.9 Hz, 1H), 3.56 (br s, 1H), 3.05-2.93 (m, 2H), 2.24-2.19 (m, 1H), 1.91-1.87 (m, 1H), 1.80-1.63 (m, 2H), 0.98 (s, 9H), 0.24 (s, 6H); LC/MS (ESI, m/z): $[(M+H)]^+$=389.2.

Step 7—Tert-butyl N-[(1S)-1-[[(1S)-2-[(2S)-2-(4-[3-[(tert-butyldimethylsilyl)oxy]benzoyl]-1,3-thiazol-2-yl)pyrrolidin-1-yl]-1-cyclohexyl-2-oxoethyl]carbamoyl]ethyl]-N-methylcarbamate To a solution of 4-[3-[(tert-butyldimethylsilyl)oxy]benzoyl]-2-[(2S)-pyrrolidin-2-yl]-1,3-thiazole (137 g, 353 mmol) in ethyl acetate (2 L) were added (S)-[(2S)-2-[(tert-butoxycarbonyl)(methyl)amino]propanamido](cyclohexyl) acetic acid (157 g, 458 mmol, CAS #894789-27-6), N-methyl morpholine (71.32 g, 705.1 mmol) and 4-(4,6-dimethoxy[1.3.5]triazin-2-yl)-4-methylmorpholinium chloride (127 g, 458 mmol) at 0° C. The mixture was stirred at rt for 4 h. The precipitated solids were removed by filtration. The filtrate was washed with brine (3×1 L) and dried over anhydrous $Na_2SO_4$. After filtration, the filtrate was concentrated under reduced pressure. The residue was purified by silica gel column chromatography, eluted with 15%~50% ethyl acetate in petroleum ether, to afford the title compound (250 g, 99% yield) as a yellow oil. $^1H$ NMR (400 MHz, $CD_3OD$) δ 8.35 (s, 1H), 7.79-7.77 (m, 1H), 7.72-7.69 (m, 1H), 7.42 (d, J=7.9 Hz, 1H), 7.15 (dd, J=8.1, 2.4 Hz, 1H), 5.52-5.49 (m, 1H), 5.54-5.47 (m, 1H), 4.63-4.59 (m, 1H), 4.56-4.52 (m, 1H), 4.03-3.88 (m, 2H), 2.88 (s, 3H), 2.43-2.28 (m, 2H), 2.19-2.15 (m, 1H), 1.77-1.65 (m, 4H), 1.64-1.54 (m, 4H), 1.48 (s, 9H), 1.39-1.29 (m, 3H), 1.23-1.18 (m, 3H), 1.04 (s, 9H), 0.27 (s, 6H); LC/MS (ESI, m/z): $[(M+H)]^+$=713.3.

Step 8—Tert-butyl N-[(1S)-1-[[(1S)-1-cyclohexyl-2-[(2S)-2-[4-(3-hydroxybenzoyl)-1,3-thiazol-2-yl]pyrrolidin-1-yl]-2-oxoethyl]carbamoyl]ethyl]-N-methylcarbamate A solution of tert-butyl N-[(1S)-1-[[(1S)-2-[(2S)-2-(4-[3-[(tert-butyldimethylsilyl)oxy]benzoyl]-1,3-thiazol-2-yl)pyrrolidin-1-yl]-1-cyclohexyl-2-oxoethyl]carbamoyl]ethyl]-N-methylcarbamate (250 g, 350.62 mmol) in THF (2 L) was treated with tetrabutylammonium fluoride (110 g, 420.75 mmol) at rt for 2 h. The resulting mixture was concentrated under reduced pressure. The residue was dissolved into ethyl acetate (1 L), washed with brine (5×1 L) and dried over anhydrous $Na_2SO_4$. After filtration, the filtrate was concentrated under reduced pressure. The residue was purified by silica gel column chromatography, eluted with 15%-50% ethyl acetate in petroleum ether, to afford the title compound (200 g, 95% yield) as a light yellow solid. $^1H$ NMR (400 MHz, $CDCl_3$) δ 8.08 (s, 1H), 7.71-7.52 (m, 2H), 7.38-7.24 (m, 1H), 7.11-7.08 (m, 1H), 5.62-5.58 (m, 1H), 4.63-4.58 (m, 1H), 4.01-3.89 (m, 2H), 2.81 (s, 3H), 2.76 (s, 1H), 2.53-2.07 (m, 4H), 1.67-1.56 (m, 6H), 1.47 (s, 9H), 1.42-1.35 (m, 3H), 1.21-0.94 (m, 5H); LC/MS (ESI, m/z): $[(M+1)]^+$=599.4.

Tert-butyl N-[(15)-1-[[(1S)-2-[(25)-2-[4-(3-[2-[2-(2-aminoethoxy)ethoxy]ethoxy]benzoyl)-1,3-thiazol-2-yl]pyrrolidin-1-yl]-1-cyclohexyl-2-oxoethyl]carbamoyl]ethyl]-N-methylcarbamate (Intermediate DU)

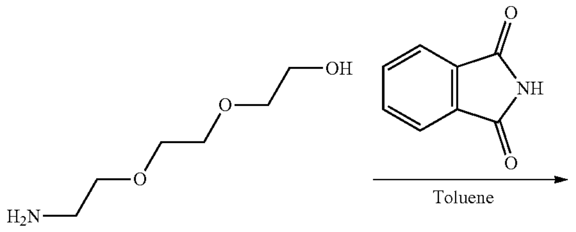

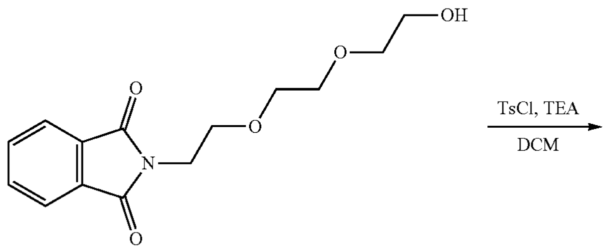

-continued
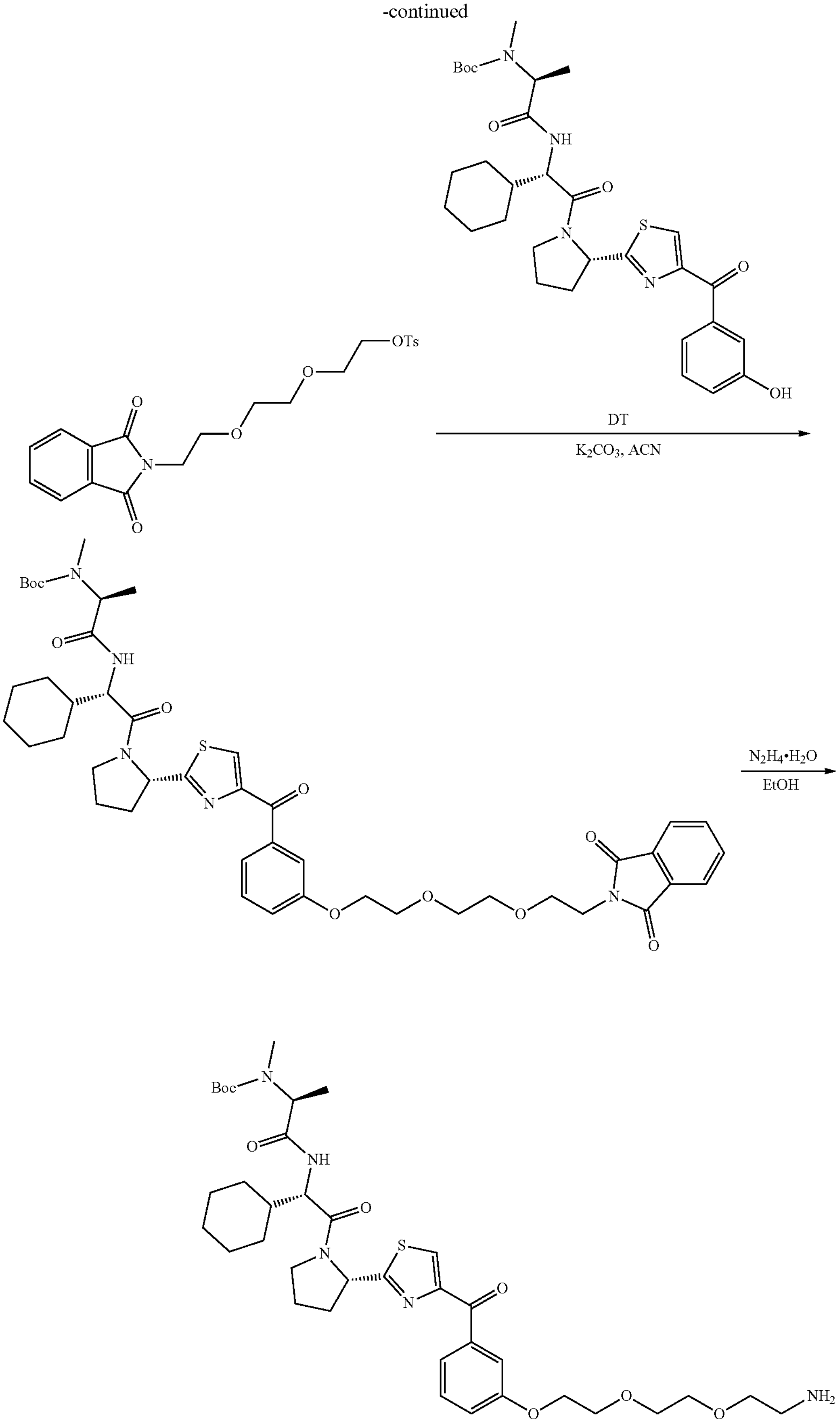
DU

Step 1—2-[2-[2-(2-hydroxyethoxy)ethoxy]ethyl] isoindole-1,3-dione

A mixture of 2-[2-(2-aminoethoxy)ethoxy]ethanol (35 g, 234.60 mmol) and phthalic anhydride (34.75 g, 234.60 mmol) in toluene (400 mL) was stirred for 16 h at 100° C. Upon completion, the resulting mixture was concentrated under reduced pressure. The residue was dissolved into ethyl acetate (1500 mL) and washed with water (3×300 mL), then dried over anhydrous $Na_2SO_4$. After filtration, the filtrate was concentrated under reduced pressure. This crude product was triturated with diethyl ether (200 mL) to afford the title compound (59 g, 90% yield) as a yellow solid. $^1$H NMR (400 MHz, $CD_3OD$) δ 7.92-7.77 (m, 4H), 3.89 (t, J=5.7 Hz, 2H), 3.76 (t, J=5.7 Hz, 2H), 3.66 (dd, J=5.7, 3.2 Hz, 2H), 3.61-3.57 (m, 4H), 3.49 (dd, J=5.6, 3.2 Hz, 2H); LC/MS (ESI, m/z): $[(M+1)]^+$=280.2.

Step 2—2-[2-[2-(1,3-dioxoisoindol-2-yl)ethoxy] ethoxy]ethyl 4-methylbenzenesulfonate To a solution of 2-[2-[2-(2-hydroxyethoxy)ethoxy]ethyl] isoindole-1,3-dione (41 g, 146.80 mmol) in DCM (200 mL) were added TEA (29.71 g, 293.60 mmol) and TsCl (30.79 g, 161.48 mmol) in portions at 0° C. The resulting mixture was stirred at rt for 16 h. On completion, the mixture was diluted with water (500 mL) and the mixture was extracted with DCM (3×300 mL). The combined organic layers were washed with brine (3×300 mL), then dried over anhydrous $Na_2SO_4$. After filtration, the filtrate was concentrated under reduced pressure to afford the title compound (57 g, 89% yield) as a yellow solid. LC/MS (ESI, m/z): $[(M+NH_4)]^+$=451.2.

Step 3—tert-butyl N-[(1S)-1-[[(15)-1-cyclohexyl-2-[(25)-2-[4-[3-(2-[2-[2-(1,3-dioxoisoindol-2-yl) ethoxy]ethoxy]ethoxy)benzoyl]-1,3-thiazol-2-yl] pyrrolidin-1-yl]-2-oxoethyl]carbamoyl]ethyl]-N-methylcarbamate To a solution of tert-butyl N-[(1S)-1-[[(1S)-1-cyclohexyl-2-[(25)-2-[4-(3-hydroxybenzoyl)-1,3-thiazol-2-yl]pyrrolidin-1-yl]-2-oxoethyl]carbamoyl]ethyl]-N-methylcarbamate (10 g, 16.70 mmol, Intermediate DT) in acetonitrile (150 mL) were added 2-[2-[2-(1,3-dioxoisoindol-2-yl)ethoxy] ethoxy]ethyl 4-methylbenzenesulfonate (10.86 g, 20.05 mmol) and $K_2CO_3$ (4.62 g, 33.40 mmol) at rt. The resulting mixture was stirred for 16 h at 80° C. Upon completion, the reaction mixture was cooled to rt and filtered. The filtered cake was wash with acetonitrile (3×20 mL) and the filtrate was concentrated under reduced pressure. The residue was purified by silica gel column chromatography (eluted with the following conditions: Mobile Phase A: petroleum ether; Mobile Phase B: ethyl acetate; Gradient: 50% B to 80% B in 25 min; Detector: UV 254/220 nm; the fractions containing the desired product were collected at 75% B) and concentrated under reduced pressure to afford the title compound (13 g, 90% yield) as a yellow solid. $^1$H NMR (400 MHz, $CD_3OD$) δ 8.33 (s, 1H), 7.83-7.76 (m, 2H), 7.76-7.70 (m, 3H), 7.70-7.64 (m, 1H), 7.40 (t, J=8.0 Hz, 1H), 7.17-7.14 (m, 1H), 5.49 (td, J=7.7, 4.0 Hz, 1H), 4.57-4.52 (m, 1H), 4.10-4.03 (m, 2H), 4.01-3.88 (m, 1H), 3.86 (t, J=5.7 Hz, 2H), 3.81-3.70 (m, 4H), 3.67-3.56 (m, 5H), 2.86 (s, 3H), 2.45-2.09 (m, 4H), 1.83-1.55 (m, 4H), 1.49-1.43 (m, 12H), 1.40-1.31 (m, 2H), 1.21-0.98 (m, 6H); LC/MS (ESI, m/z): $[(M+H)]^+$=860.4.

Step 4—Tert-butyl N-[(1S)-1-[[(1S)-2-[(25)-2-[4-(3-[2-[2-(2-aminoethoxy)ethoxy]ethoxy]benzoyl)-1,3-thiazol-2-yl]pyrrolidin-1-yl]-1-cyclohexyl-2-oxo-ethyl]carbamoyl]ethyl]-N-methylcarbamate A mixture of tert-butyl N-[(15)-1-[[(1S)-1-cyclohexyl-2-[(2S)-2-[4-[3-(2-[2-[2-(1,3-dioxoisoindol-2-yl)ethoxy] ethoxy]ethoxy)benzoyl]-1,3-thiazol-2-yl]pyrrolidin-1-yl]-2-oxoethyl]carbamoyl]ethyl]-N-methylcarbamate (13.00 g, 15.12 mmol) and a 80% aqueous $NH_2NH_2$—$H_2O$ (6.00 mL) in EtOH (150 mL) was stirred for 2 h at 70° C. Upon completion, the resulting mixture cooled to rt and filtered. The filtered cake was washed with ethanol (5×10 mL) and the filtrate was concentrated under reduced pressure. The crude product was purified by reverse phase flash chromatography (Column: Spherical C18 Column, 20-40 um, 330 g; Mobile Phase A: Water (plus 10 mmol/L FA); Mobile Phase B: ACN; Flow rate: 100 mL/min; Gradient: 25% B to 45% B in 25 min detector: UV 254/220 nm; the fractions containing the desired product were collected at 33% B), concentrated and lyophilized to afford the title compound (10.1 g, 92% yield) as a yellow solid. $^1$H NMR (400 MHz, $CD_3OD$) δ 8.35 (s, 1H), 7.78-7.71 (m, 2H), 7.47 (t, J=8.0 Hz, 1H), 7.27-7.24 (m, 1H), 5.61-5.45 (m, 1H), 4.65-4.49 (m, 1H), 4.28-4.20 (m, 2H), 4.18-4.14 (m, 1H), 3.97-3.84 (m, 4H), 3.79-3.63 (m, 4H), 3.16-3.13 (m, 2H), 2.87 (s, 3H), 2.52-2.02 (m, 4H), 1.88-1.54 (m, 4H), 1.53-1.42 (m, 12H), 1.41-1.28 (m, 2H), 1.21-0.98 (m, 8H); LC/MS (ESI, m/z): $[(M+H)]^+$=730.4.

2-[4-[(4-Aminocyclohexyl) methyl-methyl-amino] phenyl]-1-(4-chlorophenyl)-7-isopropoxy-6-methoxy-1,4-dihydroisoquinolin-3-one (Intermediate DW)

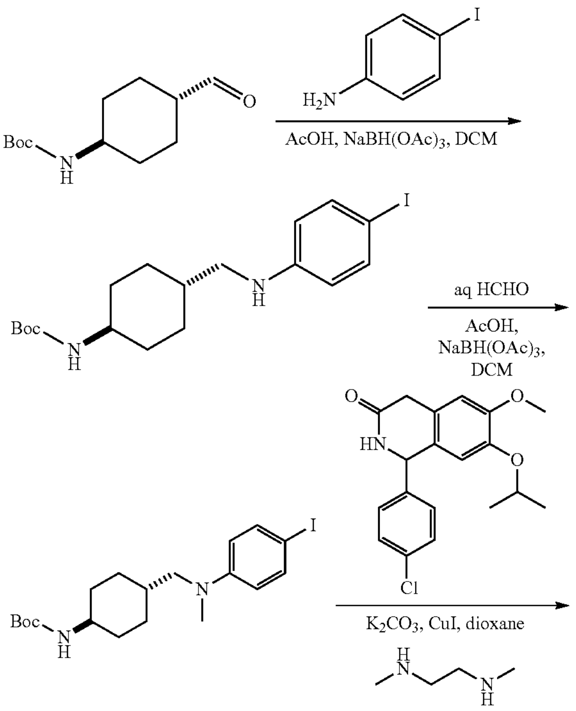

-continued

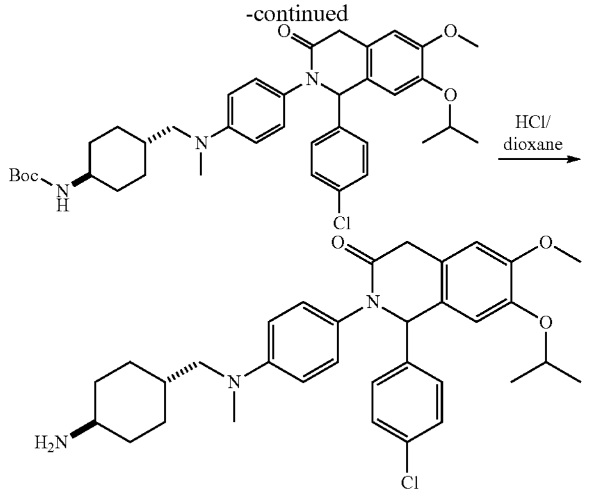

DW

Step 1—Tert-butyl N-[4-[(4-iodoanilino)methyl] cyclohexyl]carbamate

To a solution of 4-iodoaniline (3.07 g, 14.0 mmol, CAS #540-37-4) in DCM (88 mL) was added AcOH (1.68 g, 28.0 mmol), tert-butyl N-(4-formylcyclohexyl)carbamate (3.50 g, 15.4 mmol, CAS #181308-57-6) and $NaBH(OAc)_3$ (5.93 g, 28.0 mmol). The mixture was stirred at 25° C. for 1 hour. On completion, the reaction mixture was poured into water (50 mL) and extracted with DCM (3×15 mL). The combined organic phases were dried with anhydrous $Na_2SO_4$, filtered and concentrated in vacuo to give the title compound (5.80 g, 96% yield) as a white solid. $^1H$ NMR (400 MHz, $CDCl_3$) δ 7.40 (d, J=8.8 Hz, 2H), 6.37 (d, J=8.8 Hz, 2H), 4.41 (s, 1H), 3.40 (s, 1H), 2.93 (d, J=6.8 Hz, 2H), 2.10-2.02 (m, 2H), 1.89-1.81 (m, 2H), 1.56-1.48 (m, 1H), 1.45 (s, 9H), 1.12-1.03 (m, 4H). LC-MS ($ESI^+$) m/z 374.9 $(M-56)^+$.

Step 2—Tert-butyl N-[4-[(4-iodo-N-methyl-anilino) methyl]cyclohexyl]carbamate

To a solution of tert-butyl N-[4-[(4-iodoanilino)methyl] cyclohexyl]carbamate (5.80 g, 13.4 mmol) in DCM (50 mL) was added AcOH (1.62 g, 26.9 mmol, 1.5 mL) and formaldehyde (809 mg, 26.9 mmol) and $NaBH(OAc)_3$ (5.71 g, 26.9 mmol). The mixture was stirred at 25° C. for 16 hours. On completion, the reaction mixture was diluted with DCM (50 mL) and washed with a 2M aqueous $Na_2CO_3$ solution (2×50 mL). The residue was purified by column chromatography ($SiO_2$, Petroleum ether/Ethyl acetate=100:1 to 85:15) to give the title compound (4.40 g, 73% yield) as a white solid. $^1H$ NMR (400 MHz, DMSO-$d_6$) δ 7.38 (d, J=9.2 Hz, 2H), 6.49 (d, J=9.2 Hz, 2H), 3.32 (s, 1H), 3.11 (d, J=7.2 Hz, 2H), 2.86 (s, 3H), 1.74 (d, J=10.9 Hz, 2H), 1.61 (d, J=12.4 Hz, 2H), 1.56-1.49 (m, 1H), 1.36 (s, 9H), 1.09-0.93 (m, 4H). LC-MS ($ESI^+$) m/z 444.8 $(M+H)^+$.

Step 3—Tert-butyl N-[4-[[4-[1-(4-chlorophenyl)-7-isopropoxy-6-methoxy-3-oxo-1,4-dihydroisoquinolin-2-yl]-N-methyl-anilino]methyl]cyclohexyl]carbamate To a solution of 1-(4-chlorophenyl)-7-isopropoxy-6-methoxy-2,4-dihydro-1H-isoquinolin-3-one (500 mg, 1.45 mmol, CAS #1313366-29-8) in dioxane (10 mL) was added tert-butyl N-[4-[(4-iodo-N-methyl-anilino)methyl]cyclohexyl]carbamate (770 mg, 1.74 mmol), N,N'-dimethylethane-1,2-diamine (12.7 mg, 144 umol), CuI (13.7 mg, 72.2 umol) and $K_2CO_3$ (399 mg, 2.89 mmol) and the mixture was stirred at 120° C. for 16 hours. On completion, the reaction mixture was poured into water (20 mL) and extracted with ethyl acetate (3×15 mL). The combined organic phases were dried with anhydrous $Na_2SO_4$, filtered and concentrated in vacuo. The residue was purified by column chromatography ($SiO_2$, Petroleum ether/Ethyl acetate=1:0 to 10:1) to give the title compound (250 mg, 26% yield) as a yellow solid. $^1H$ NMR (400 MHz, DMSO-$d_6$) δ 7.35 (s, 4H), 7.04 (s, 1H), 6.89 (d, J=9.2 Hz, 2H), 6.83 (s, 1H), 6.65 (d, J=8.0 Hz, 1H), 6.55 (d, J=9.2 Hz, 2H), 5.94 (s, 1H), 4.45 (quin, J=6.0 Hz, 1H), 3.88 (d, J=19.6 Hz, 1H), 3.72 (s, 3H), 3.56 (d, J=20.0 Hz, 1H), 3.16-3.07 (m, 3H), 2.87 (s, 3H), 1.78-1.70 (m, 2H), 1.64 (d, J=11.6 Hz, 2H), 1.57-1.49 (m, 1H), 1.36 (s, 9H), 1.23 (d, J=6.0 Hz, 3H), 1.18 (d, J=5.6 Hz, 3H), 1.09-0.94 (m, 4H); LC-MS ($ESI^+$) m/z 662.2 $(M+H)^+$.

Step 4—2-[4-[(4-Aminocyclohexyl) methyl-methyl-amino]phenyl]-1-(4-chlorophenyl)-7-isopropoxy-6-methoxy-1,4-dihydroisoquinolin-3-one To tert-butyl N-[4-[[4-[1-(4-chlorophenyl)-7-isopropoxy-6-methoxy-3-oxo-1,4-dihydroisoquinolin-2-yl]-N-methyl-anilino]methyl]cyclohexyl]carbamate (240 mg, 362 umol) was added HCl/dioxane (1.0 mL) and the mixture was stirred at 25° C. for 1 hour. On completion, the mixture was concentrated in vacuo to give the title compound (200 mg, 334 umol, 92% yield, HCl) as a yellow solid. LC-MS ($ESI^+$) m/z 562.2 $(M+H)^+$.

2-Chloro-N-[5-[1-(2,6-dioxo-3-piperidyl)-3-methyl-2-oxo-benzimidazol-5-yl]pentyl]acetamide (Intermediate DX)

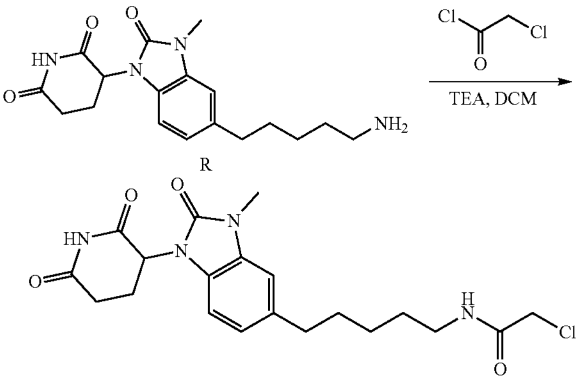

DX

3-[5-(5-aminopentyl)-3-methyl-2-oxo-benzimidazol-1-yl]piperidine-2,6-dione (250 mg, 656 umol, HCl, Intermediate R) was dissolved in DCM (3 mL). Then 2-chloroacetyl chloride (222 mg, 1.97 mmol, CAS #79-04-9) was added to TEA (199 mg, 1.97 mmol, 16.3 uL) and this mixture was added to the 3-[5-(5-aminopentyl)-3-methyl-2-oxo-benzimidazol-1-yl]piperidine-2,6-dione solution. Then the mixture was stirred at 25° C. for 3 hours. On completion, the reaction mixture was poured into water (5 mL) and extracted with DCM (3×5 mL). The combined organic phases were dried with anhydrous $Na_2SO_4$, filtered and concentrated in vacuo to give the title compound (250 mg) as a brown oil. $^1$H NMR (400 MHz, $CDCl_3$) δ 8.14 (s, 1H), 6.89 (dd, J=1.6, 8.0 Hz, 1H), 6.85 (s, 1H), 6.72 (d, J=8.0 Hz, 1H), 6.57 (s, 1H), 5.21 (dd, J=5.2, 12.4 Hz, 1H), 4.05 (s, 2H), 3.44 (s, 3H), 2.67 (t, J=7.6 Hz, 2H), 1.74-1.53 (m, 10H), 1.43-1.36 (m, 2H). LC-MS ($ESI^+$) m/z 421.3 $(M+H)^+$.

5-[1-(2,6-dioxo-3-piperidyl)-3-methyl-2-oxo-benzimidazol-5-yl]pentanal (Intermediate DY)

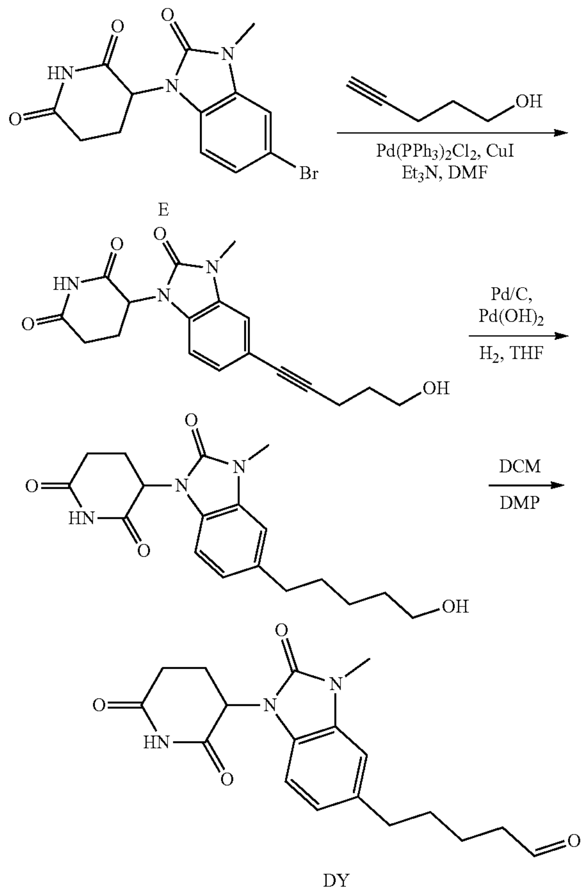

DY

Step 1—3-[5-(5-Hydroxypent-1-ynyl)-3-methyl-2-oxo-benzimidazol-1-yl] piperidine-2,6-dione A mixture of 3-(5-bromo-3-methyl-2-oxo-2,3-dihydro-1H-benzo[d]imidazol-1-yl)piperidine-2,6-dione (1.00 g, 2.96 mmol, Intermediate E), pent-4-yn-1-ol (1.24 g, 14.8 mmol), $Pd(PPh_3)_2Cl_2$ (208 mg, 296 umol), CuI (28.2 mg, 148 umol) and $Et_3N$ (1.50 g, 14.8 mmol) in DMF (15 mL) was degassed and purged with $N_2$ three times. Then the mixture was stirred at 100° C. for 16 hours under $N_2$ atmosphere. The mixture was quenched with brine (20 mL) and extracted with dichloromethane (20 mL×3). The combined organic phases were dried over anhydrous sodium sulfate, filtered and concentrated to give a residue. The residue was purified by column chromatography ($SiO_2$, petroleum ether/ethyl acetate=1:0 to 0:1) to give the title compound (533 mg, 50% yield) as a yellow oil. LC-MS ($ESI^+$) m/z 342.0 $(M+H)^+$.

Step 2—3-[5-(5-Hydroxypentyl)-3-methyl-2-oxo-benzimidazol-1-yl]piperidine-2,6-dione To a solution of 3-[5-(5-hydroxypent-1-ynyl)-3-methyl-2-oxo-benzimidazol-1-yl]piperidine-2,6-dione (830 mg, 2.43 mmol) in THF (20 mL) was added Pd/C (579 mg, 243 umol, 10 wt %) and $Pd(OH)_2$ (171 mg, 20 wt %) under Argon. The suspension was degassed under vacuum and purged with $H_2$ three times. The mixture was stirred under $H_2$ (15 psi) at 25° C. for 16 hours. On completion, the mixture was concentrated and the residue was purified by column chromatography ($SiO_2$, petroleum ether/ethyl acetate=1:0 to 10:1) to give the title compound (500 mg, 90% yield) as a white solid. LC-MS ($ESI^+$) m/z 346.1 $(M+H)^+$.

Step 3—5-[1-(2,6-Dioxo-3-piperidyl)-3-methyl-2-oxo-benzimidazol-5-yl]pentanal

To a solution of 3-[5-(5-hydroxypentyl)-3-methyl-2-oxo-benzimidazol-1-yl]piperidine-2,6-dione (100 mg, 289 umol) in DCM (0.5 mL) was added DMP (184 mg, 434 umol) and the mixture was stirred at 25° C. for 2 hours. The mixture was quenched with saturated sodium thiosulfate (10 mL), then extracted with dichloromethane (20 mL×3). The organic layer was dried over $Na_2SO_4$, and concentrated in vacuo to give the compound (90.0 mg, 91% yield) as a yellow oil. $^1$H NMR (400 MHz, $CDCl_3$) δ 9.75-9.70 (m, 1H), 6.89-6.77 (m, 2H), 6.73-6.67 (m, 1H), 3.38 (s, 3H), 2.77-2.70 (m, 1H), 2.67-2.62 (m, 2H), 2.47-2.40 (m, 3H), 2.21-2.12 (m, 2H), 1.70-1.53 (m, 6H).

1-(4-Chlorophenyl)-7-isopropoxy-6-methoxy-2-[4-[methyl-[[4-(methylamino)cyclohexyl]methyl]amino]phenyl]-1,4-dihydroisoquinolin-3-one (Intermediate DZ)

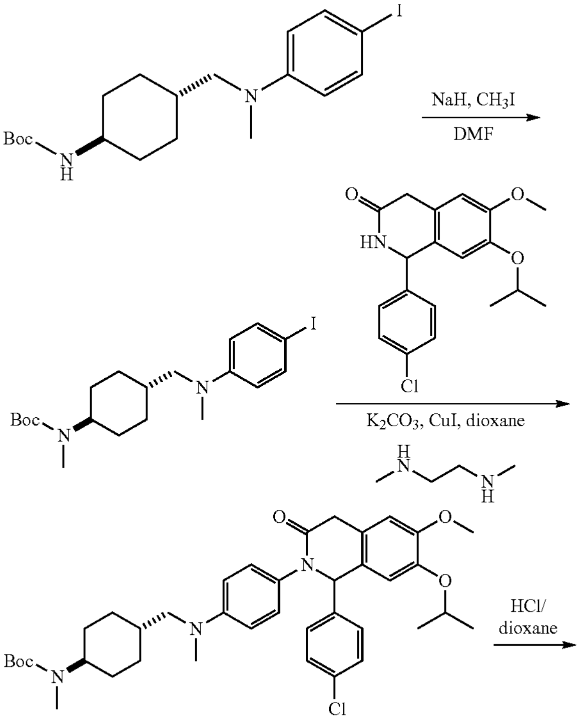

-continued

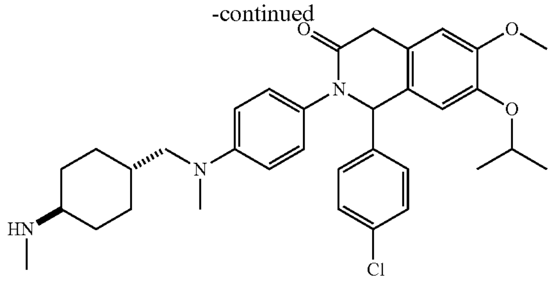

DZ

Step 1—tert-butyl N-[4-[(4-iodo-N-methyl-anilino) methyl]cyclohexyl]-N-methyl-carbamate To a solution of tert-butyl N-[4-[(4-iodo-N-methyl-anilino)methyl]cyclohexyl]carbamate (500 mg, 1.13 mmol, synthesized via Steps 1-2 of Intermediate DW) in DMF (5 mL) was added NaH (135 mg, 3.38 mmol, 60% dispersion in mineral oil) at 0° C. stirred for 30 minutes. Then $CH_3I$ (798 mg, 5.63 mmol, 350 uL) was added and the mixture was stirred at 25° C. for 16 hours. On completion, the reaction mixture was concentrated in vacuo to give a residue. The crude product was purified by reversed-phase (TFA condition) to give the title compound (260 mg, 49% yield) as a white solid. $^1H$ NMR (400 MHz, DMSO-$d_6$) δ 7.44-7.32 (m, 2H), 6.55-6.46 (m, 2H), 3.29 (s, 1H), 3.14 (d, J=7.2 Hz, 2H), 2.87 (s, 3H), 2.62 (s, 3H), 2.50 (td, J=1.6, 3.6 Hz, 4H), 1.69 (d, J=12.8 Hz, 2H), 1.63-1.48 (m, 1H), 1.46-1.40 (m, 1H), 1.38 (s, 9H), 1.11-0.98 (m, 1H). LC-MS (ESI$^+$) m/z 459.3 $(M+H)^+$.

Step 2—tert-butyl N-[4-[[4-[1-(4-chlorophenyl)-7-isopropoxy-6-methoxy-3-oxo-1A-dihydroisoquinolin-2-yl]-N-methyl-anilino]methyl]cyclohexyl]-N-methyl-carbamate To a solution of 1-(4-chlorophenyl)-7-isopropoxy-6-methoxy-2,4-dihydro-1H-isoquinolin-3-one (138 mg, 399 umol, CAS #1313366-29-8) in dioxane (4 mL) was added tert-butyl N-[4-[(4-iodo-N-methyl-anilino)methyl]cyclohexyl]-N-methyl-carbamate (220 mg, 479 umol), N,N'-dimethylethane-1,2-diamine (3.53 mg, 40.0 umol, 4.30 uL), CuI (3.81 mg, 20.0 umol) and $K_2CO_3$ (110 mg, 799 umol). The mixture was stirred at 120° C. for 16 hours. On completion, the reaction mixture was concentrated in vacuo to give a residue. The crude product was purified by reversed-phase HPLC (0.1% TFA condition) to give the title compound (110 mg, 39 yield) as a white solid. LC-MS (ESI$^+$) m/z 676.2 $(M+H)^+$.

Step 3—1-(4-Chlorophenyl)-7-isopropoxy-6-methoxy-2-[4-[methyl-[[4-(methylamino)cyclohexyl] methyl]amino]phenyl]-1,4-dihydroisoquinolin-3-one To a mixture of tert-butyl tert-butyl N-[4-[[4-[1-(4-chlorophenyl)-7-isopropoxy-6-methoxy-3-oxo-1,4-dihydroisoquinolin-2-yl]-N-methyl-anilino]methyl]cyclohexyl]-N-methyl-carbamate (30.0 mg, 44.3 umol) in DCM (1.0 mL) was added HCl/dioxane (4 M, 1.0 mL) at 25° C. under $N_2$. The mixture was stirred at 25° C. for 30 minutes. On completion, the reaction mixture was concentrated in vacuo to give a residue. The residue was purified by prep-HPLC (column: Phenomenex luna C18 150*25 mm*10 um; mobile phase: [water (0.225% FA)–ACN]; B %: 22%-52%, 11.5 min) to give the title compound (6.09 mg, 18% yield, FA salt) as white solid. $^1H$ NMR (400 MHz, DMSO-$d_6$) δ 7.35 (s, 4H), 7.04 (s, 1H), 6.89 (d, J=8.8 Hz, 2H), 6.83 (s, 1H), 6.56 (d, J=9.2 Hz, 2H), 5.94 (s, 1H), 4.45 (td, J=6.0, 12.0 Hz, 1H), 3.94-3.86 (m, 1H), 3.73 (s, 3H), 3.59 (s, 2H), 3.11 (d, J=5.2 Hz, 2H), 2.87 (s, 3H), 2.37 (s, 3H), 1.94 (d, J=10.0 Hz, 2H), 1.69 (d, J=12.0 Hz, 3H), 1.23 (d, J=6.4 Hz, 3H), 1.18 (d, J=6.2 Hz, 3H), 1.11-0.92 (m, 4H). LC-MS (ESI$^+$) m/z 576.5 $(M+H)^+$.

6-[1-(2,6-Dioxo-3-piperidyl)-3-methyl-2-oxo-benzimidazol-5-yl]hexanal (Intermediate EA)

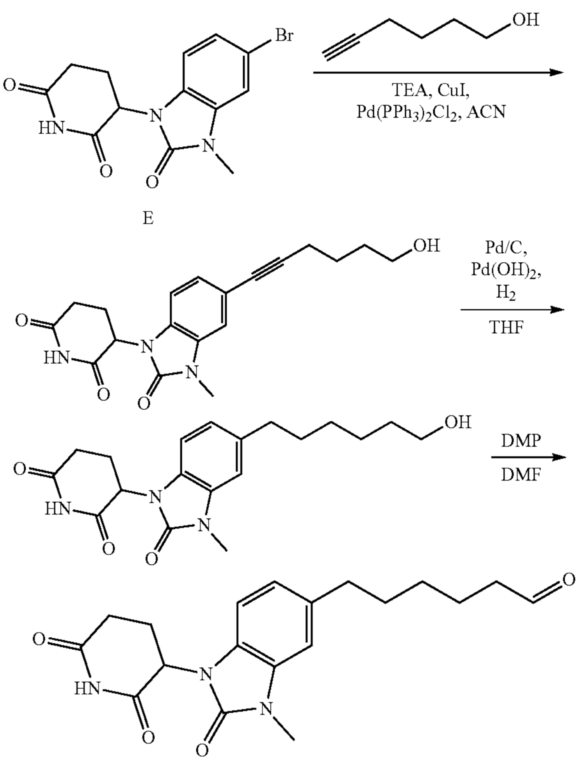

EA

Step 1—3-[5-(6-Hydroxyhex-1-ynyl)-3-methyl-2-oxo-benzimidazol-1-yl]piperidine-2,6-dione To a mixture of 3-(5-bromo-3-methyl-2-oxo-benzimidazol-1-yl)piperidine-2,6-dione (1.00 g, 2.96 mmol, Intermediate E) and hex-5-yn-1-ol (348.27 mg, 3.55 mmol, CAS #928-90-5) in ACN (10 mL) was added TEA (1.50 g, 14.8 mmol), CuI (28.2 mg, 148 umol) and $Pd(PPh_3)_2Cl_2$ (208 mg, 296 umol). The mixture was degassed and purged with $N_2$ 3 times, and then the mixture was stirred at 80° C. for 16 hours under $N_2$ atmosphere. On completion, the mixture was concentrated to give a residue. The residue was purified by column chromatography ($SiO_2$, dichloromethane:ethyl acetate=1:0 to 1:2) to give the title compound (760 mg, 72% yield) as a yellow solid. LC-MS (ESI$^+$) m/z 356.1 $(M+H)^+$. $^1H$ NMR (400 MHz, $CDCl_3$) δ 8.01 (s, 1H), 7.15 (dd, J=1.2, 8.0 Hz, 1H), 7.07 (s, 1H), 6.73 (d, J=8.0 Hz, 1H), 5.19 (dd, J=5.2, 12.8 Hz, 1H), 3.74 (t, J=6.0 Hz, 2H), 3.43 (s, 3H), 3.00-2.65 (m, 4H), 2.48 (t, J=6.8 Hz, 2H), 2.28-2.21 (m, 1H), 1.79-1.70 (m, 4H).

Step 2—3-[5-(6-Hydroxyhexyl)-3-methyl-2-oxo-benzimidazol-1-yl]piperidine-2,6-dione To a solution of 3-[5-(6-hydroxyhex-1-ynyl)-3-methyl-2-oxo-benzimidazol-1-yl]piperidine-2,6-dione (600 mg, 1.69 mmol) in THF (18 mL) was added Pd/C (600 mg, 1.69 mmol, 10 wt %) and $Pd(OH)_2$ (600 mg, 854 umol, 20 wt %) under $N_2$. The suspension was degassed under vacuum and purged with $H_2$ several times. The mixture was stirred under $H_2$ (15 psi) at 25° C. for 16 hours. On completion, the mixture was filtered and concentrated to give the title compound (500 mg, 82% yield) as a white oil. LC-MS ($ESI^+$) m/z 360.3 $(M+H)^+$.

Step 3—6-[1-(2,6-Dioxo-3-piperidyl)-3-methyl-2-oxo-benzimidazol-5-yl]hexanal To a solution of 3-[5-(6-hydroxyhexyl)-3-methyl-2-oxo-benzimidazol-1-yl]piperidine-2,6-dione (60.0 mg, 167 umol) in DMF (0.5 mL) was added DMP (106 mg, 250 umol). The mixture was stirred at 25° C. for 2 hours. On completion, the mixture was quenched with $Na_2SO_3$ aqueous (4 mL) and extracted with dichloromethane (3 mL×3). The combined organic phases were dried over anhydrous sodium sulfate, filtered and concentrated to give the title compound (59.0 mg, 98% yield) as a white oil. LC-MS ($ESI^+$) m/z 358.3 $(M+H)^+$.

1-(4-Chlorophenyl)-7-isopropoxy-6-methoxy-2-[4-[methyl(4-piperidylmethyl)amino]phenyl]-1,4-dihydroisoquinolin-3-one (Intermediate EC)

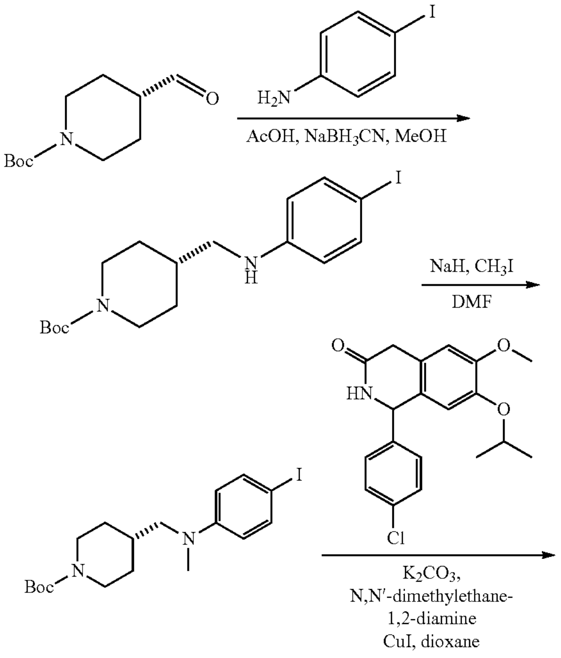

-continued

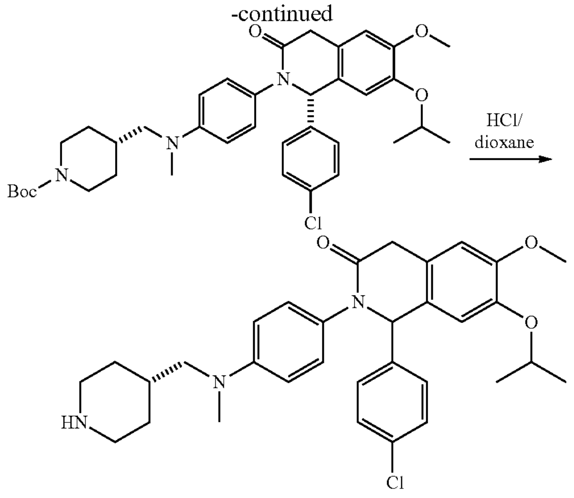

EC

Step 1—Tert-butyl 4-[(4-iodoanilino)methyl]piperidine-1-carboxylate

To a solution of 4-iodoaniline (3.91 g, 17.9 mmol, CAS #540-37-4) in MeOH (30 mL) was added tert-butyl 4-formylpiperidine-1-carboxylate (3.91 g, 17.9 mmol, CAS #137076-22-3) and AcOH (1.07 g, 17.9 mmol). The mixture was stirred at 25° C. for 3 hours. Then sodium cyanoborohydride (1.12 g, 17.9 mmol) was added in portions slowly at 0° C., then the solution was stirred at 25° C. for 13 hours. The compound precipitated out of solution. On completion, the mixture was filtered to give the title compound (5.4 g, 62% yield) as a white solid. LC-MS ($ESI^+$) m/z 361.3 $(M+H-56)^+$. $^1H$ NMR (400 MHz, $CDCl_3$) δ 7.46-7.40 (m, 2H), 6.43 (d, J=8.4 Hz, 2H), 4.12 (s, 2H), 3.00 (d, J=6.4 Hz, 2H), 2.69 (t, J=12.4 Hz, 2H), 1.79-1.70 (m, 3H), 1.46 (s, 9H), 1.24-1.09 (m, 2H).

Step 2—Tert-butyl 4-[(4-iodo-N-methyl-anilino)methyl]piperidine-1-carboxylate To a solution of tert-butyl 4-[(4-iodoanilino)methyl]piperidine-1-carboxylate (2.00 g, 4.80 mmol) in DMF (20 mL) was added NaH (961 mg, 24.0 mmol, 60% dispersion in mineral oil) in batches, then the mixture was stirred at 0° C. for 0.5 hour. Next, $CH_3I$ (3.41 g, 24.0 mmol) was added to the mixture at 25° C. and the mixture was stirred at 25° C. for 14 hours. On completion, the mixture was quenched with water (80 mL) and extracted with ethyl acetate (25 mL×3). The combined organic phases were dried over anhydrous sodium sulfate, filtered and concentrated to give a residue. The residue was purified by column chromatography ($SiO_2$, petroleum ether/ethyl acetate=1:0 to 8:1) to give the title compound (1.75 g, 79% yield) as a white solid. LC-MS ($ESI^+$) m/z 375.0 $(M+H-56)^+$.

Step 3—Tert-butyl 4-[[4-[1-(4-chlorophenyl)-7-isopropoxy-6-methoxy-3-oxo-1,4-dihydroisoquinolin-2-yl]-N-methyl-anilino]methyl]piperidine-1-carboxylate To a solution of 1-(4-chlorophenyl)-7-isopropoxy-6-methoxy-2,4-dihydro-1H-isoquinolin-3-one (386 mg, 1.12 mmol, CAS #1313366-29-8)) in dioxane (10 mL) was added tert-butyl 4-[(4-iodo-N-methyl-anilino)methyl]piperidine-1-carboxylate (1.20 g, 2.79 mmol), N,N'-dimethylethane-1,2-diamine (9.83 mg, 111 umol), CuI (10.6 mg, 55.8 umol) and $K_2CO_3$ (308 mg, 2.23 mmol). The mixture was degassed and purged with $N_2$ three times, and then the mixture was stirred at 120° C. for 20 hours under $N_2$ atmosphere. On completion, the mixture was quenched with water (20 mL) and extracted with ethyl acetate (15 mL×3). The combined organic phases were dried over anhydrous sodium sulfate, filtered and concentrated to give a residue. The residue was purified by column chromatography ($SiO_2$, petroleum ether/ethyl acetate=1:0 to 1:1) to give the title compound (219 mg, 30% yield) as a brown oil. LC-MS ($ESI^+$) m/z 592.2 $(M+H-56)^+$.

Step 4—1-(4-Chlorophenyl)-7-isopropoxy-6-methoxy-2-[4-[methyl(4-piperidylmethyl)amino]phenyl]-1,4-dihydroisoquinolin-3-one To a solution of tert-butyl 4-[[4-[1-(4-chlorophenyl)-7-isopropoxy-6-methoxy-3-oxo-1,4-dihydroisoquinolin-2-yl]-N-methyl-anilino]methyl]piperidine-1-carboxylate (60.0 mg, 92.6 umol) in DCM (2.0 mL) was added HCl/dioxane (33.8 mg, 4 M). The mixture was stirred at 25° C. for 1 hour. On completion, the mixture was concentrated to give the title compound (54.0 mg, 99% yield, HCl) as a red solid. LC-MS ($ESI^+$) m/z 548.5 $(M+H)^+$.

6-[1-(2,6-Dioxo-3-piperidyl)-3-methyl-2-oxo-benzimidazol-4-yl]hexanal (Intermediate ED)

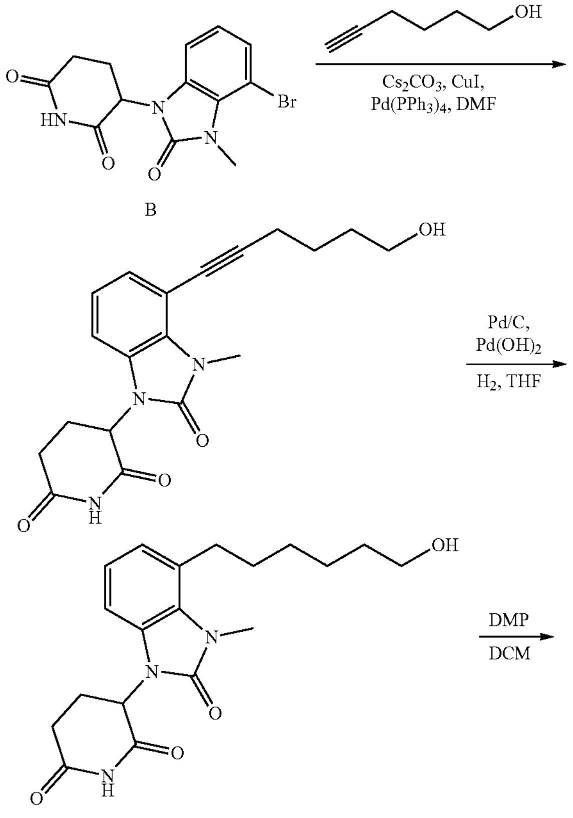

-continued

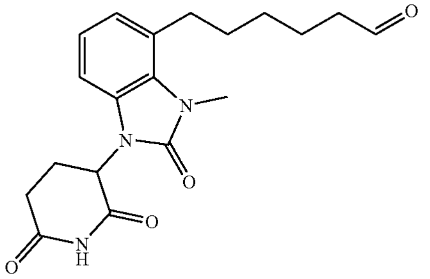

ED

Step 1—3-[4-(6-Hydroxyhex-1-ynyl)-3-methyl-2-oxo-benzimidazol-1-yl]piperidine-2,6-dione To a mixture of 3-(4-bromo-3-methyl-2-oxo-benzimidazol-1-yl)piperidine-2,6-dione (400 mg, 1.18 mmol, Intermediate B)) and hex-5-yn-1-ol (139 mg, 1.42 mmol, CAS #928-90-5) in ACN (8.0 mL) was added TEA (598 mg, 5.91 mmol), $Pd(PPh_3)_2Cl_2$ (83.0 mg, 118 umol) and CuI (11.3 mg, 59.1 μmol). Then the mixture was stirred at 80° C. for 16 hours under $N_2$ atmosphere. On completion, the mixture was concentrated in vacuo and purified by column chromatography ($SiO_2$, petroleum ether/ethyl acetate=10:1 to 1:1) to afford title compound (270 mg, 66% yield) as an off-white solid. LC-MS ($ESI^+$) m/z 356.3 $(M+H)^+$.

Step 2-3-[4-(6-Hydroxyhexyl)-3-methyl-2-oxo-benzimidazol-1-yl]piperidine-2,6-dione To a solution of 3-[4-(6-hydroxyhex-1-ynyl)-3-methyl-2-oxo-benzimidazol-1-yl]piperidine-2,6-dione (250 mg, 703 umol) in THF (5 mL) was added Pd/C (250 mg, 703 umol) and $Pd(OH)_2$ (250 mg, 356 umol). The resulting mixture was stirred at 25° C. for 1 hour under $H_2$ (15 psi). On completion, the mixture was filtered and concentrated to give title compound (294 mg, crude) as a colorless oil. LC-MS ($ESI^+$) m/z 360.2 $(M+H)^+$.

Step 3—6-[1-(2,6-Dioxo-3-piperidyl)-3-methyl-2-oxo-benzimidazol-4-yl]hexanal

To a solution of 3-[4-(6-hydroxyhexyl)-3-methyl-2-oxo-benzimidazol-1-yl]piperidine-2,6-dione (42.0 mg, 116 umol) in DMF (0.5 mL) was added DMP (74.3 mg, 175 umol), and the resulting mixture was stirred at 25° C. for 0.5 hour. On completion, the mixture was quenched with $H_2O$ (2.0 mL) and extracted with ethyl acetate (1.5 mL×3). The combined organic phase was dried over anhydrous sodium sulfate, filtered and concentrated to give title compound (42.0 mg, crude) as a yellow oil. LC-MS ($ESI^+$) m/z 358.1 $(M+H)^+$.

5-[1-(2,6-dioxo-3-piperidyl)-3-methyl-2-oxo-benzimidazol-4-yl]pentanal (Intermediate EE)

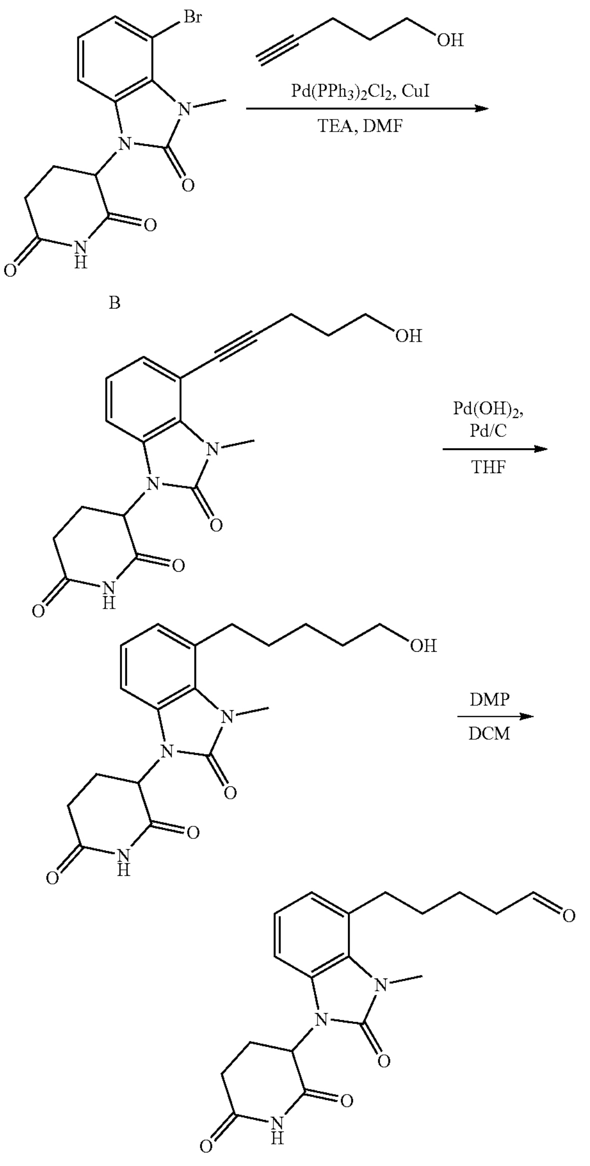

EE

Step 1—3-[4-(5-hydroxypent-1-ynyl)-3-methyl-2-oxo-benzimidazol-1-Yl]piperidine-2,6-dione A mixture of 3-(4-bromo-3-methyl-2-oxo-benzimidazol-1-yl)piperidine-2,6-dione (2.00 g, 5.91 mmol, Intermediate B), pent-4-yn-1-ol (2.49 g, 29.5 mmol, CAS #5390-04-5), $Pd(PPh_3)_2Cl_2$ (415 mg, 591 umol), CuI (56.3 mg, 295 umol,) and $Et_3N$ (2.99 g, 29.5 mmol) in DMF (20 mL) was degassed and purged with $N_2$ three times. Then the mixture was stirred at 100° C. for 16 hours under $N_2$ atmosphere. On completion, the reaction mixture was concentrated in vacuo to give a residue. The residue was purified by column chromatography ($SiO_2$, DCM/IPA=30/1 to 20/1) and then triturated with EA at 25° C. for 5 minutes to give the title compound (1.45 g, 71% yield) as a yellow solid. $^1H$ NMR (400 MHz, DMSO-$d_6$) δ 11.10 (s, 1H), 7.12 (d, J=7.6 Hz, 1H), 7.07-7.02 (m, 1H), 7.01-6.95 (m, 1H), 5.40 (dd, J=5.2, 12.4 Hz, 1H), 4.56 (s, 1H), 3.63 (s, 3H), 3.56-3.47 (m, 2H), 2.96-2.83 (m, 1H), 2.77-2.56 (m, 2H), 2.55-2.51 (m, 2H), 2.11-1.91 (m, 1H), 1.72 (q, J=6.4 Hz, 2H). LC-MS ($ESI^+$) m/z 342.3 $(M+H)^+$.

Step 2—3-[4-(5-hydroxypentyl)-3-methyl-2-oxo-benzimidazol-1-yl]piperidine-2,6-dione To a solution of 3-[4-(5-hydroxypent-1-ynyl)-3-methyl-2-oxo-benzimidazol-1-yl]piperidine-2,6-dione (300 mg, 878 umol) in THF (30 mL) was added Pd/C (50 mg, 10 wt %) and $Pd(OH)_2$ (50.5 mg, 72.0 umol, 20 wt %) under Argon. The suspension was degassed under vacuum and purged with $H_2$ several times. The mixture was stirred under $H_2$ (15 psi) at 25° C. for 16 hours. On completion, the reaction mixture was concentrated in vacuo to give a residue. The crude product was purified by reversed-phase (0.1% TFA condition) to give the title compound (205 mg, 67% yield) as a white solid. LC-MS ($ESI^+$) m/z 346.1 $(M+H)^+$.

Step 3—5-[1-(2,6-dioxo-3-piperidyl)-3-methyl-2-oxo-benzimidazol-4-yl]pentanal

To a solution of 3-[4-(5-hydroxypentyl)-3-methyl-2-oxo-benzimidazol-1-yl]piperidine-2,6-dione (85.0 mg, 246 umol) in DCM (1 mL) was added DMP (156 mg, 369 umol). The mixture was stirred at 25° C. for 2 hours. On completion, the mixture was quenched with saturated sodium thiosulfate (5 mL), then extracted with dichloromethane (5 mL×3). The organic layer was dried over $Na_2SO_4$, and concentrated in vacuo to afford crude title compound (85.0 mg 80% yield) as a white solid. LC-MS ($ESI^+$) m/z 481.3 $(M+H)^+$.

1-(4-chlorophenyl)-7-isopropoxy-6-methoxy-2-(4-piperazin-1-ylphenyl)-1,4-dihydroisoquinolin-3-one (Intermediate EF)

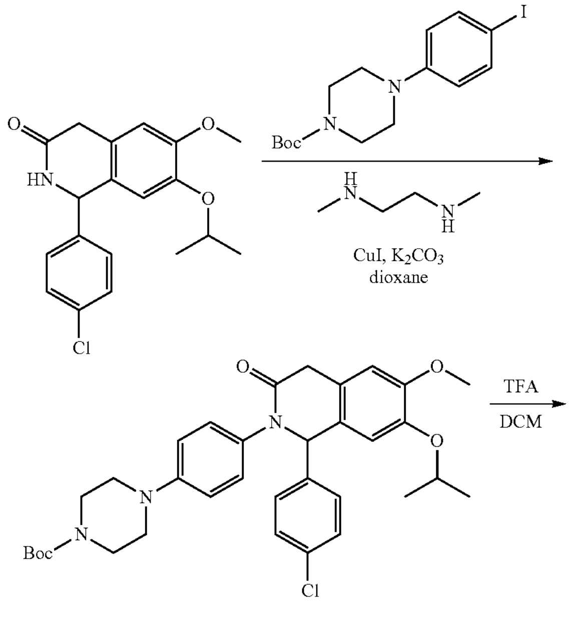

-continued

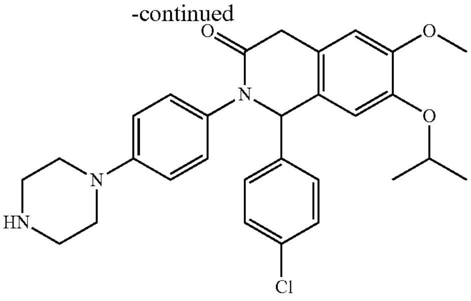

EF

Step 1—Tert-butyl 4-[4-[1-(4-chlorophenyl)-7-isopropoxy-6-methoxy-3-oxo-1,4-dihydroisoquinolin-2-yl]phenyl]piperazine-1-carboxylate 1-(4-chlorophenyl)-7-isopropoxy-6-methoxy-2,4-dihydro-1H-isoquinolin-3-one (200 mg, 578 umol, CAS #1313366-29-8), tert-butyl 4-(4-iodophenyl)piperazine-1-carboxylate (269 mg, 694 umol, CAS #151978-66-4), $K_2CO_3$ (160 mg, 1.16 mmol,) and CuI (5.51 mg, 28.9 umol), N,N'-dimethylethane-1,2-diamine (5.10 mg, 57.8 umol) in dioxane (2.0 mL) was de-gassed and then heated to 120° C. for 12 hours under $N_2$. On completion, the reaction mixture was concentrated in vacuo to give a residue. The residue was purified by column chromatography ($SiO_2$, petroleum ether/ethyl acetate=1/1 to 0/1) to give the title compound (150 mg, 37% yield) as yellow solid. $^1H$ NMR (400 MHz, chloroform-d) δ 7.17 (d, J=8.4 Hz, 3H), 7.04-6.90 (m, 5H), 6.61 (d, J=5.2 Hz, 2H), 5.62 (s, 1H), 4.43-4.30 (m, 1H), 3.80-3.78 (m, 3H), 3.77-3.49 (m, 6H), 3.10 (d, J=1.2 Hz, 4H), 1.50 (s, 6H), 1.41 (s, 9H).

Step 2—1-(4-chlorophenyl)-7-isopropoxy-6-methoxy-2-(4-piperazin-1-ylphenyl)-1,4-dihydroisoquinolin-3-one To a mixture of tert-butyl 4-[4-[1-(4-chlorophenyl)-7-isopropoxy-6-methoxy-3-oxo-1,4-dihydroisoquinolin-2-yl]phenyl]piperazine-1-carboxylate (20.0 mg, 33.0 umol) in DCM (1.0 mL) was added HCl/dioxane (4 M, 0.3 mL) at 25° C. under $N_2$. The mixture was stirred at 25° C. for 30 minutes. On completion, the reaction mixture was concentrated in vacuo to give the title compound (20.0 mg, 80% yield) as a yellow solid. LC-MS ($ESI^+$) m/z 506.2 $(M+H)^+$.

(2S,5R)-5-amino-N-[5-[1-(2,6-dioxo-3-piperidyl)-3-methyl-2-oxo-benzimidazol-5-yl]pentyl]tetrahydropyran-2-carboxamide (Intermediate EH)

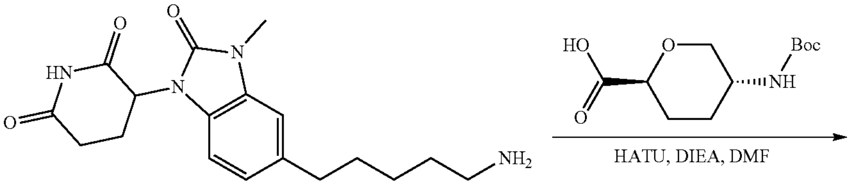

R

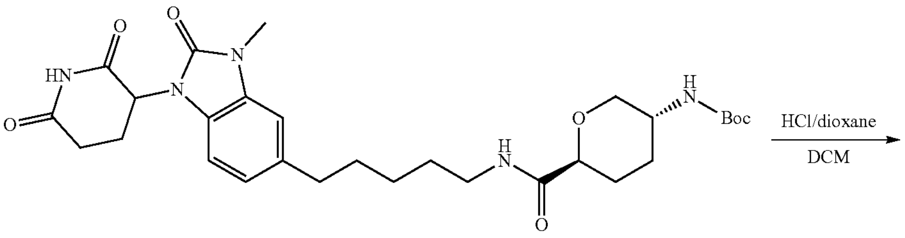

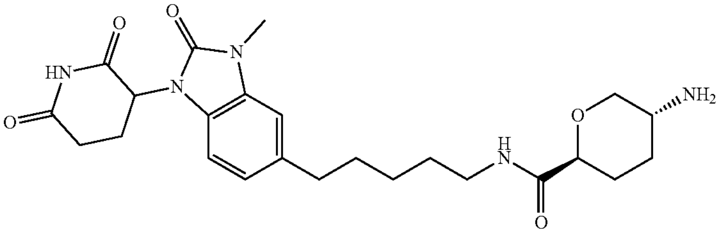

EH

Step 1—tert-butylN-[(3R,6S)-6-[5-[1-(2,6-dioxo-3-piperidyl)-3-methyl-2-oxo-benzimidazol-5-yl] pentylcarbamoyl]tetrahydropyran-3-yl]carbamate To a mixture of 3-[5-(5-aminopentyl)-3-methyl-2-oxo-benzimidazol-1-yl]piperidine-2,6-dione (200 mg, 525 umol, Intermediate R), (2S,5R)-5-(tert-butoxycarbonylamino)tetrahydropyran-2-carboxylic acid (154 mg, 630 umol, CAS #603130-13-8) and DIEA (339 mg, 2.63 mmol, 0.5 mL) in DMF (1.5 mL) was added HATU (259 mg, 683 umol). The mixture was stirred at 25° C. for 5 minutes. On completion, reaction mixture was directly purified by reversed phase flash (0.1% FA condition) to give the title compound (200 mg, 63% yield) as a white solid. $^1$H NMR (400 MHz, DMSO-d6) δ11.08 (s, 1H), 7.60 (s, 1H), 7.12-6.72 (m, 4H), 5.46-5.20 (m, 1H), 4.01-3.74 (m, 1H), 3.58 (s, 1H), 3.31 (s, 3H), 3.04 (s, 4H), 2.60 (s, 4H), 2.07-1.81 (m, 3H), 1.58 (t, J=7.2 Hz, 2H), 1.49-1.18 (m, 15H). LC-MS (ESI$^+$) m/z 572.3 (M+H)$^+$.

Step 2—(2S,5R)-5-amino-N-[5-[1-(2,6-dioxo-3-piperidyl)-3-methyl-2-oxo-benzimidazol-5-yl] pentyl]tetrahydropyran-2-carboxamide To a mixture of tert-butyl N-[(3R,6S)-6-[5-[1-(2,6-dioxo-3-piperidyl)-3-methyl-2-oxo-benzimidazol-5-yl]pentylcarbamoyl]tetrahydropyran-3-yl]carbamate (65.0 mg, 113 umol) in DCM (1.0 mL) was added HCl/dioxane (4 M, 0.2 mL). The mixture was stirred at 25° C. for 1 hour. On completion, the reaction mixture was concentrated under reduced pressure to remove DCM and HCl/dioxane to give the title compound (57.0 mg, 90% yield) as a yellow solid. LC-MS (ESI$^+$) m/z 472.4 (M+H)$^+$.

3-[5-[5-[(4-Aminophenyl)methyl-methyl-amino] pentyl]-3-methyl-2-oxo-benzimidazol-1-yl]piperidine-2,6-dione (Intermediate E1)

Step 1—Tert-butylN-[4-[[5-[1-(2,6-dioxo-3-piperidyl)-3-methyl-2-oxo-benzimidazol-5-yl]pentyl-methyl-amino]methyl]phenyl]carbamate (HCl)

To a solution of 3-[3-methyl-5-[5-(methylamino)pentyl]-2-oxo-benzimidazol-1-yl]piperidine-2,6-dione (80.0 mg, 202 umol, HCl, Intermediate DI) in THF (2 mL), KOAc (99.4 mg, 1.01 mmol) was added and the resulting mixture was stirred for 0.25 hour. Then tert-butyl N-(4-formylphenyl)carbamate (67.2 mg, 303 umol, CAS #144072-30-0) was added and the mixture was stirred at 25° C. for 0.25 hour. Then NaBH(OAc)$_3$ (85.8 mg, 405 umol) was added to the reaction mixture, which was then stirred for 7.5 hours at 80° C. On completion, the mixture was quenched with water (5 mL) and extracted with DCM (5×3 mL). The combined organic phase was dried over anhydrous sodium sulfate, filtered and concentrated to give a residue The residue was purified by column chromatography (SiO$_2$, Petroleum ether/Ethyl acetate=1:1 to 0:1) and concentrated in vacuo to give the title compound (120 mg, crude) as a yellow oil. $^1$H NMR (400 MHz, CHLOROFORM-d) δ=7.39-7.32 (m, 2H), 7.25 (s, 1H), 7.06 (s, 1H), 6.84-6.79 (m, 2H), 6.71 (d, J=8.0 Hz, 1H), 5.20 (dd, J=5.6, 12.4 Hz, 1H), 3.75 (s, 2H), 3.39 (s, 3H), 2.93-2.79 (m, 2H), 2.59 (td, J=7.6, 18.8 Hz, 4H), 2.38 (s, 3H), 2.24-2.14 (m, 1H), 1.72-1.56 (m, 4H), 1.51-1.47 (m, 9H), 1.35-1.25 (m, 2H). LC-MS (ESI$^+$) m/z 564.3 (M+H)$^+$.

Step 2—3-[5-[5-[(4-Aminophenyl)methyl-methyl-amino]pentyl]-3-methyl-2-oxo-benzimidazol-1-yl] piperidine-2,6-dione To a solution of tert-butyl N-[4-[[5-[1-(2,6-dioxo-3-piperidyl)-3-methyl-2-oxo-benzimidazol-5-yl]pentyl-methyl-amino]methyl]phenyl]carbamate (70.0 mg, 124 umol), in DCM (2 mL) was added HCl/dioxane (4 M, 31.0 uL) at 25° C. The mixture was stirred at 25° C. for 2 hours. On

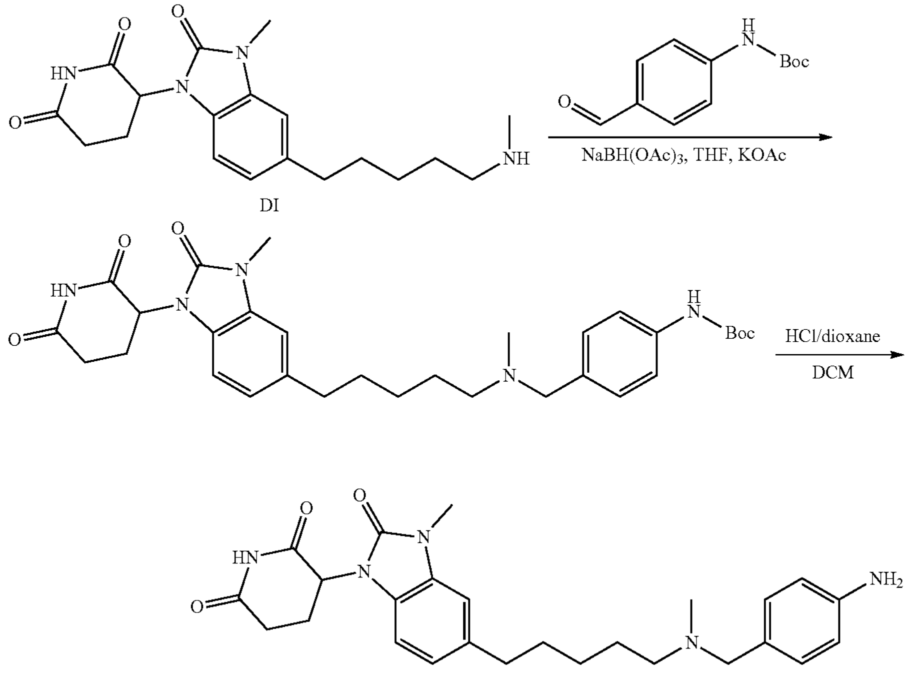

DI

EI completion, the reaction mixture was concentrated in vacuo to give the title compound (50.0 mg, 80% yield) as a yellow solid. LC-MS (ESI+) m/z 464.3 $(M+H)^+$.

Ethyl N-[4-(aminomethyl)cyclohexyl]-chloro-(3-chloro-2-fluoro-phenyl)-oxo-dispiro[BLAH]carboxamide (Intermediate EK)

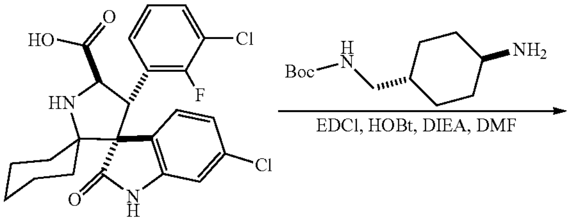

CI

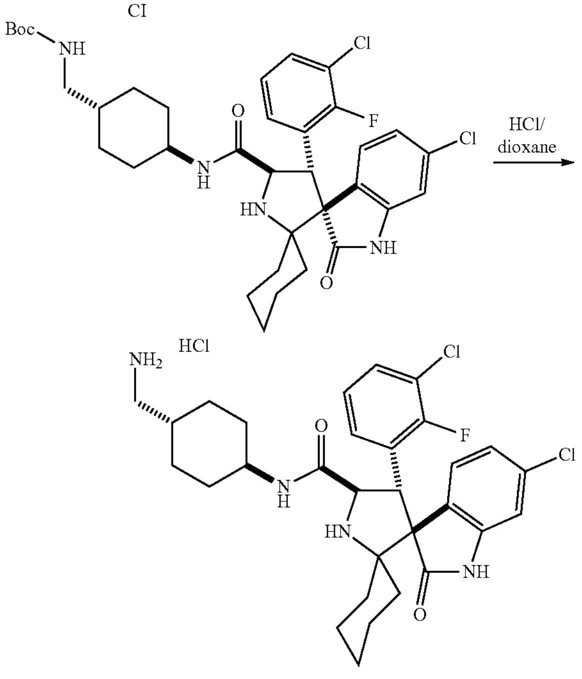

EK

Step 1—Tert-butyl N-[[4-[[chloro-(3-chloro-2-fluoro-phenyl)-oxodispiro[BLAH]carbonyl]amino]cyclohexyl]methyl]carbamate Chloro-(3-chloro-2-fluoro-phenyl)-oxo-dispiro[BLAH] carboxylic acid (150 mg, 324 umol, Intermediate CI) was dissolved in DMF (9 mL). Then EDCI (93.1 mg, 486 umol), HOBt (65.6 mg, 486 umol) and DIEA (209 mg, 1.62 mmol) was added. The mixture was stirred at 25° C. for 0.5 hour, then tert-butyl N-[(4-aminocyclohexyl)methyl]carbamate (148 mg, 647 umol) was added. The mixture was stirred at 25° C. for 14 hours. On completion, the mixture was quenched with brine (20 mL) and extracted with ethyl acetate (20 mL×3). The combined organic phase was dried over anhydrous sodium sulfate, filtered and concentrated to give a residue. The residue was purified by column chromatography ($SiO_2$, petroleum ether/ethyl acetate=30:1 to 1:1) to give the title compound (175 umol, 54% yield) as a white solid. LC-MS (ESI+) m/z 673.3 $(M+H)^+$.

Step 2—Ethyl N-[4-(aminomethyl)cyclohexyl]-chloro-(3-chloro-2-fluoro-phenyl)-oxo-dispiro [BLAH] carboxamide To a solution of tert-butylN-[[4-[[chloro-(3-chloro-2-fluoro-phenyl)-oxo-dispiro[BLAH]carbonyl] amino]cyclohexyl]methyl]carbamate (50.0 mg, 74.2 umol) in DCM (1.0 mL) was added HCl/dioxane (4 M, 186 uL). The mixture was stirred at 25° C. for 1 hour. On completion, the mixture was concentrated to give the title compound (40.0 mg, 88% yield, HCl) as a white solid. LC-MS (ESI+) m/z 573.0 $(M+H)^+$.

3-(3-Methyl-2-oxo-4-(piperidin-4-yl)-2,3-dihydro-1H-benzo[d]imidazol-1-yl)piperidine-2,6-dione (Intermediate EL)

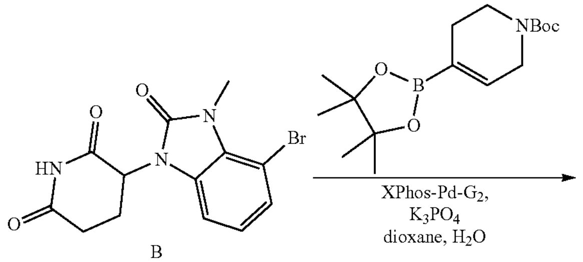

B

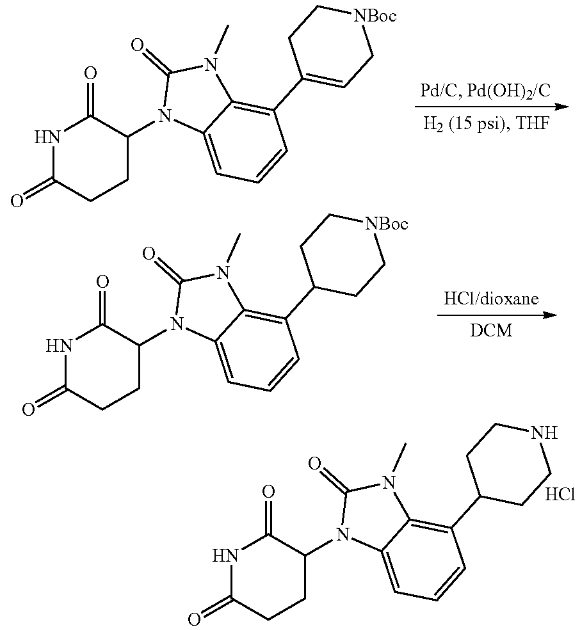

EL

Step 1—Tert-butyl 4-(1-(2,6-dioxopiperidin-3-yl)-3-methyl-2-oxo-2,3-dihydro-1H-benzo[d]imidazol-4-yl)-5,6-dihydropyridine-1(2H)-carboxylate To a solution of 3-(4-bromo-3-methyl-2-oxo-benzimidazol-1-yl)piperidine-2,6-dione (9.00 g, 26.6 mmol, Intermediate B), tert-butyl 4-(4,4,5,5-tetramethyl-1,3,2-dioxaborolan-2-yl)-3,6-dihydro-2H-pyridine-1-carboxylate (12.3 g, 39.9 mmol, CAS #286961-14-6) and XPhos-Pd-G2 (2.09 g, 2.66 mmol) in dioxane (150 mL) and $H_2O$ (15 mL) was added $K_3PO_4$ (11.3 g, 53.2 mmol). The reaction mixture was stirred at 80° C. for 4 hours under $N_2$. On completion, the reaction mixture was filtered. The filtrate was dried with anhydrous $Na_2SO_4$ and filtered. The filtrate was concentrated in vacuo. The residue was triturated with sat. $NH_4Cl$ (2×50 mL), water (2×50 mL) and EA (2×50 mL) and filtered. The solid was dried in vacuo to give the title compound (8.00 g, 68% yield) as an off-white solid. LC-MS ($ESI^+$) m/z 441.1 $(M+H)^+$ Step 2—Tert-butyl 4-(1-(2,6-dioxopiperidin-3-yl)-3-methyl-2-oxo-2,3-dihydro-1H-benzo[d]imidazol-4-yl)piperidine-1-carboxylate To a solution of tert-butyl 4-[1-(2,6-dioxo-3-piperidyl)-3-methyl-2-oxo-benzimidazol-4-yl]-3,6-dihydro-2H-pyridine-1-carboxylate (8.00 g, 18.2 mmol) in DMF (20 mL) and THF (60 mL) was added $H_2$, Pd/C (1.00 g, 10 wt %) and $Pd(OH)_2$ (1.00 g, 3.56 mmol, 50 wt %). The mixture was degassed and purged with nitrogen 3 times, then degassed and purged with hydrogen 3 times. The mixture was stirred at 25° C. for 16 hrs under hydrogen (15 psi) atmosphere. On completion, the reaction mixture was filtered and the combined filtrates were concentrated in vacuo to give the title compound (5.60 g, 70% yield) as a white solid. $^1H$ NMR (400 MHz, DMSO-$d_6$) δ 11.10 (s, 1H), 7.06-6.92 (m, 3H), 5.38 (m, 1H), 4.18-3.96 (m, 2H), 3.60 (s, 3H), 3.48-3.39 (m, 1H), 2.97-2.81 (m, 3H), 2.76-2.61 (m, 2H), 2.05-1.94 (m, 1H), 1.81 (m, 2H), 1.65-1.50 (m, 2H), 1.47-1.40 (m, 9H). LC-MS ($ESI^+$) m/z 287.4 $(387.3)^+$.

Step 3—3-(3-Methyl-2-oxo-4-(piperidin-4-yl)-2,3-dihydro-1H-benzo[d]imidazol-1-yl)piperidine-2,6-dione To a solution of tert-butyl 4-[1-(2,6-dioxo-3-piperidyl)-3-methyl-2-oxo-benzimidazol-4-yl]piperidine-1-carboxylate (100 mg, 226 umol) in DCM (1 mL) was added HCl/dioxane (1 mL). The reaction mixture was stirred at 25° C. for 0.5 hr. On completion, the reaction mixture was concentrated in vacuo to give the title compound (85.0 mg, 99% yield) as a yellow solid. LC-MS ($ESI^+$) m/z 343.3 $(M+H)^+$.

3-[4-[1-[4-aminocyclohexyl)methyl]-4-piperidyl]-3-methyl-2-oxo-benzimidazol-1-yl]piperidine-2,6-dione (Intermediate EM)

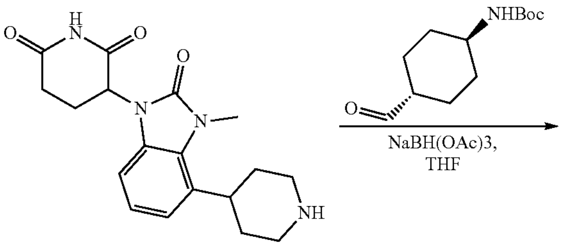

EL

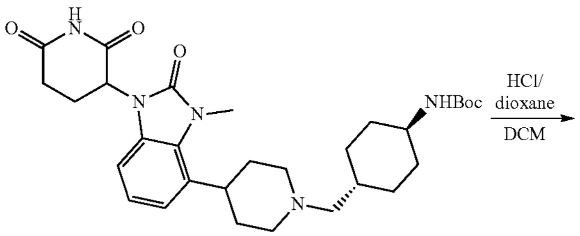

-continued

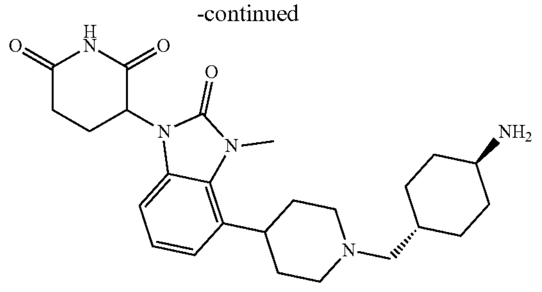

EM

Step 1—Tert-butyl N-[4-[[4-[1-(2,6-dioxo-3-piperidyl)-3-methyl-2-oxo-benzimidazol-4-yl]-1-piperidyl] methyl]cyclohexyl]carbamate To a solution of 3-[3-methyl-2-oxo-4-(4-piperidyl)benzimidazol-1-yl]piperidine-2,6-dione (75.0 mg, 219 umol, Intermediate EL) in THF (2.0 mL) and DMF (0.5 mL) was added DIEA (56.6 mg, 438 μmol), AcOH (39.4 mg, 657 umol) and tert-butyl N-(4-formylcyclohexyl)carbamate (44.8 mg, 197 umol, CAS #181308-57-6) at −10° C. The reaction liquid was stirred at −10° C. for 1 hour. Then $NaBH(OAc)_3$ (139 mg, 657 umol) was added to the reaction mixture at −10° C. The mixture was stirred at −10° C. for 5 hours. On completion, the reaction mixture was concentrated under reduced pressure to give a residue. The residue was purified by prep-HPLC (Column: Phenomenex luna C18 150*25 mm*10 um; mobile phase: [water (0.225% FA)–ACN]; B %: 10%-40%, 10 min) to give the title compound (100 mg, 82% yield) as a white solid. $^1H$ NMR (400 MHz, DMSO-$d_6$) δ=11.09 (s, 1H), 7.06-6.95 (m, 3H), 6.72 (d, J=8.0 Hz, 1H), 5.37 (dd, J=5.2, 12 Hz, 1H), 3.58 (s, 3H), 3.23-3.06 (m, 5H), 2.94-2.84 (m, 1H), 2.72-2.59 (m, 2H), 2.42 (s, 3H), 1.96-2.01 (m, 1H), 1.85 (s, 4H), 1.78 (d, J=10.8 Hz, 4H), 1.55-1.47 (m, 1H), 1.37 (s, 9H), 1.19-1.10 (m, 2H), 0.99-0.88 (m, 2H). LC-MS ($ESI^+$) m/z 554.5 $(M+H)^+$.

Step 2—3-[4-[1-[(4-aminocyclohexyl)methyl]-4-piperidyl]-3-methyl-2-oxo-benzimidazol-1-yl] piperidine-2,6-dione To a solution of tert-butyl N-[4-[[4-[1-(2,6-dioxo-3-piperidyl)-3-methyl-2-oxo-benzimidazol-4-yl]-1-piperidyl] methyl]cyclohexyl]carbamate (70.0 mg, 126 umol) in DCM (3 mL) was added HCl/dioxane (4 M, 2.0 mL) and the mixture was stirred at 25° C. for 4 hours. On completion, the reaction mixture was concentrated under reduced pressure to give the title compound (50.0 mg, 80% yield, HCl salt) as a white solid. LC-MS ($ESI^+$) m/z 454.4 $(M+H)^+$.

N-[4-[4-[1-(2,6-dioxo-3-piperidyl)-3-methyl-2-oxo-benzimidazol-4-yl] piperidine-1-carbonyl]cyclohexyl]carbamate (Intermediate EN)

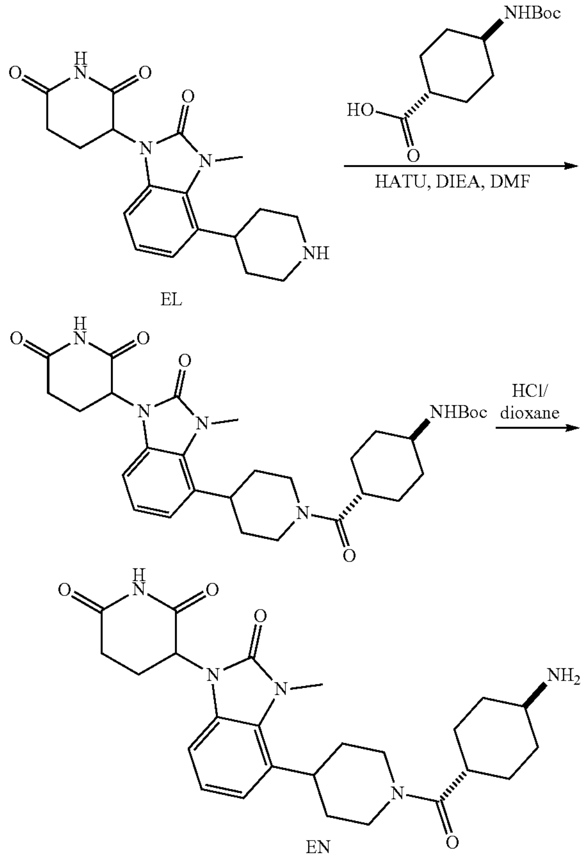

EL

EN

Step 1—3-[3-Methyl-2-oxo-4-(4-piperidyl)benzimidazol-1-yl]piperidine-2,6-dione

To a mixture of 3-[3-methyl-2-oxo-4-(4-piperidyl)benzimidazol-1-yl]piperidine-2,6-dione (30 mg, 87.62 umol, Intermediate EL), 4-(tert-butoxycarbonylamino)cyclohexanecarboxylic acid (21.3 mg, 87.6 umol) in DMF (3 mL) was added DIEA (11.3 mg, 87.6 umol) at 0° C. until the pH=13 and the mixture was stirred for 0.5 hour. Next, HATU (39.9 mg, 105 umol) was added and the mixture was stirred at 0° C. for 1 hour. On completion, the reaction mixture was filtered and was purified by reversed-phase HPLC (0.1% FA condition) to give the title compound (30.0 mg, 60% yield) as a white solid. LC-MS (ESI$^+$) m/z 568.5 (M+H)$^+$.

Step 2—N-[4-[4-[1-(2,6-dioxo-3-piperidyl)-3-methyl-2-oxo-benzimidazol-4-yl]piperidine-1-carbonyl]cyclohexyl]carbamate To a solution of tert-butyl N-[4-[4-[1-(2,6-dioxo-3-piperidyl)-3-methyl-2-oxo-benzimidazol-4-yl] piperidine-1-carbonyl]cyclohexyl]carbamate (10 mg, 17.6 umol) in DCM (3 mL) was added HCl/dioxane (4 M, 0.5 mL). The mixture was stirred at 25° C. for 1 hour. On completion, the reaction mixture was concentrated in vacuo to give the title compound (8.00 mg, 97% yield) as a white solid. LC-MS (ESI$^+$) m/z 468.2 (M+H)$^+$.

Chloro-(3-chloro-2-fluoro-phenyl)-N-(4-formylphenyl)-oxo-dispiro[BLAH]carboxamide (Intermediate EO)

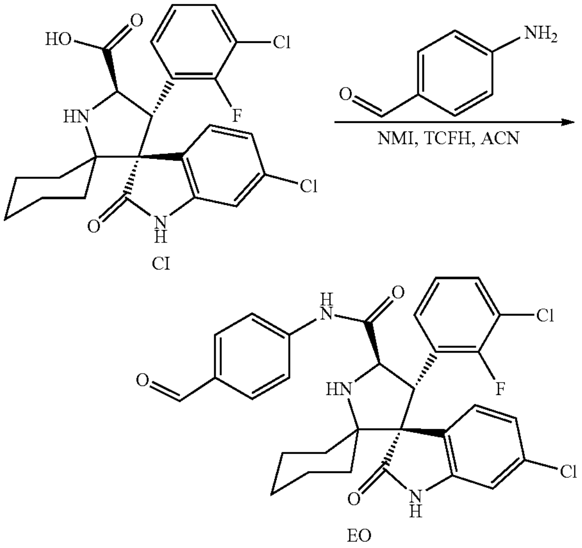

CI

EO

To a mixture of chloro-(3-chloro-2-fluoro-phenyl)-oxo-dispiro[BLAH]carboxylic acid (300 mg, 647 umol, Intermediate CI), 4-aminobenzaldehyde (78.4 mg, 647 umol, CAS #556-18-3) and [chloro (dimethylamino)methylene]-dimethyl-ammonium; hexafluorophosphate (218 mg, 777 umol) in ACN (6 mL) was added 1-methylimidazole (186 mg, 2.27 mmol). The mixture was stirred at 25° C. for 0.5 hour. On completion, the mixture was quenched with water (30 mL) and extracted with ethyl acetate (3×30 mL). The combined organic phase was dried over anhydrous sodium sulfate, filtered and concentrated to give a residue. The residue was purified by reversed-phase HPLC (0.1% FA condition) to give the title compound (365 mg, 99% yield) as a white solid. $^1$H NMR (400 MHz, DMSO-d6) δ 10.60 (s, 1H), 10.44 (s, 1H), 9.88 (s, 1H), 9.56 (s, 1H), 7.86 (d, J=5.6 Hz, 2H), 7.56 (s, 2H), 7.52 (s, 2H), 7.08 (s, 1H), 6.86 (s, 1H), 6.60 (s, 1H), 6.28 (s, 1H), 4.84-4.76 (m, 1H), 4.72 (d, J=9.2 Hz, 1H), 2.14-1.96 (m, 2H), 1.70-1.48 (m, 6H), 1.02 (d, J=2.0 Hz, 1H), 0.88-0.80 (m, 1H); LC-MS (ESI$^+$) m/z 556.4 (M+H)$^+$.

4-[Tert-butoxycarbonyl(methyl)amino]cyclohexanecarboxylic acid (Intermediate EP)

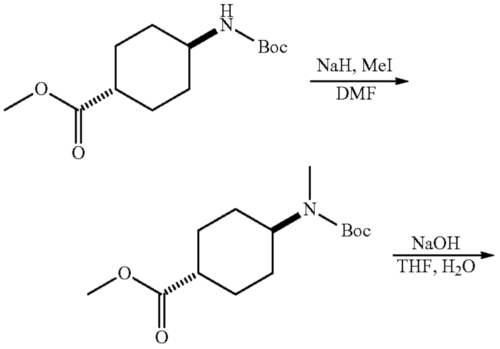

-continued

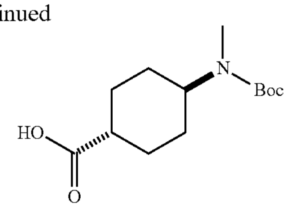

EP

Step 1—Methyl 4-[tert-butoxycarbonyl(methyl) amino]cyclohexanecarboxylate

To a solution of methyl 4-(tert-butoxycarbonylamino) cyclohexanecarboxylate (200 mg, 777 umol, CAS #146307-51-9) in DMF (3 mL) at 0° C. was added NaH (93.2 mg, 2.33 mmol) and the mixture was stirred at 25° C. for 1 hour. The mixture was cooled to 0° C., then treated with $CH_3I$ (132 mg, 932 umol) and the reaction mixture was stirred at 25° C. for 12 hours. On completion, the mixture was poured into a saturated $NH_4Cl$ aqueous and extracted with ethyl acetate. The combined organic phase was washed with water and brine, dried over anhydrous $Na_2SO_4$ and concentrated under reduced pressure. The residue was purified by column chromatography on silica gel ($SiO_2$, petroleum ether:ethyl acetate=100 1) to give the title compound (100 mg, 47% yield) as a brown solid. $^1H$ NMR (400 MHz, DMSO-$d_6$) δ 3.82-3.68 (m, 1H), 3.59 (s, 3H), 2.78-2.59 (m, 4H), 2.26 (m, 1H), 2.01-1.89 (m, 2H), 1.63-1.50 (m, 4H), 1.44-1.35 (m, 9H).

Step 2—4-[Tert-butoxycarbonyl(methyl)amino]cyclohexanecarboxylic acid

To a solution of methyl 4-[tert-butoxycarbonyl(methyl) amino]cyclohexanecarboxylate (180 mg, 663 umol) in THF (5 mL) and $H_2O$ (5 mL) was added NaOH (53.1 mg, 1.33 mmol). The mixture was stirred at 25° C. for 2 hours. On completion, the solvent was concentrated, and the residue taken in water and acidified with 1N HCl, then extracted with ethyl acetate. The organic layer was separated, dried over anhydrous $Na_2SO_4$, filtered and concentrated under reduced pressure to give the title compound (150 mg, 50% yield) as a yellow solid. LC-MS (ESI$^+$) m/z 202.1 (M+H−56)$^+$.

N-[5-[1-(2,6-dioxo-3-piperidyl)-3-methyl-2-oxo-benzimidazol-5-yl]pentyl]-4-(methylamino)cyclohexanecarboxamide (Intermediate EQ)

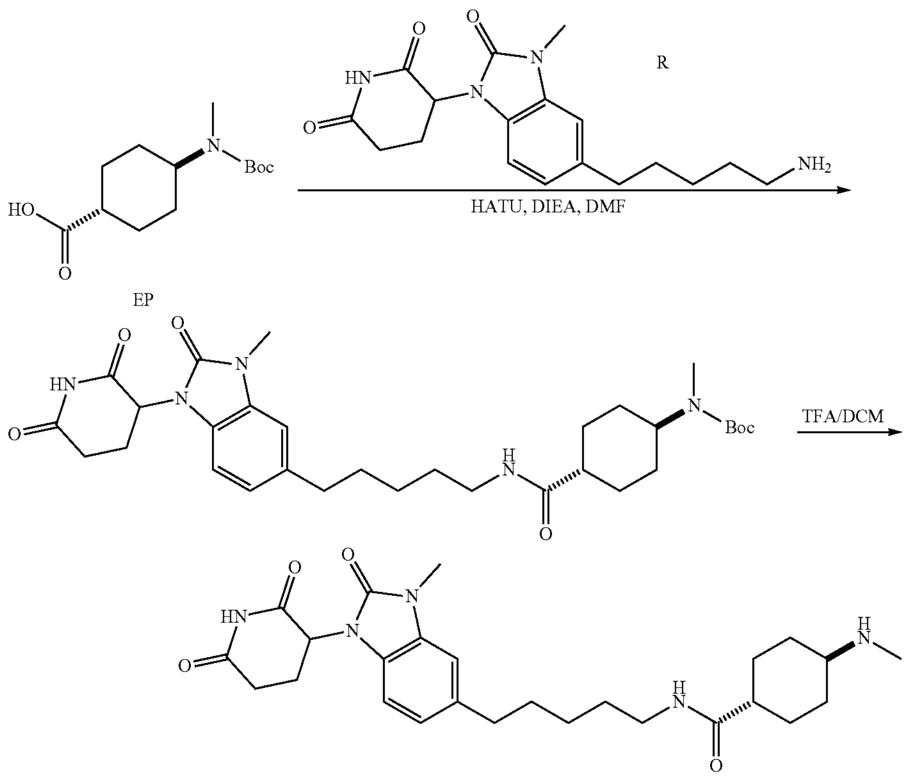

EQ

Step 1—Tert-butyl N-[4-[5-[1-(2,6-dioxo-3-piperidyl)-3-methyl-2-oxo-benzimidazol-5-yl]pentylcarbamoyl]cyclohexyl]-N-methyl-carbamate To a solution of 4-[tert-butoxycarbonyl(methyl)amino] cyclohexanecarboxylic acid (100 mg, 388 umol, Intermediate EP) 3-[5-(5-aminopentyl)-3-methyl-2-oxo-benzimidazol-1-yl]piperidine-2,6-dione (133 mg, 388 umol, Intermediate R) in DMF (1 mL) was added HATU (192 mg, 505 umol) and DIEA (150 mg, 1.17 mmol). The mixture was stirred at 25° C. for 2 hours. On completion, the reaction mixture was concentrated in vacuo to give a residue. The crude product was purified by reversed-phase flash (0.1% FA condition) to give the title compound (60.0 mg, 24% yield) as a white solid. $^1$H NMR (400 MHz, DMSO-$d_6$) δ 11.08 (s, 1H), 7.68 (t, J=5.6 Hz, 1H), 7.07-6.94 (m, 2H), 6.89-6.71 (m, 1H), 5.34 (dd, J=5.6, 12.8 Hz, 1H), 3.75-3.47 (m, 1H), 3.32-3.30 (m, 3H), 3.01 (d, J=6.0 Hz, 2H), 2.94-2.81 (m, 1H), 2.65 (s, 3H), 2.60 (d, J=1.6 Hz, 3H), 1.99 (d, J=4.4 Hz, 2H), 1.73 (d, J=10.0 Hz, 2H), 1.65-1.52 (m, 4H), 1.42 (s, 4H), 1.40 (s, 12H), 1.32-1.17 (m, 2H). LC-MS (ESI$^+$) m/z 584.3 (M+H)$^+$.

Step 2—N-[5-[1-(2,6-dioxo-3-piperidyl)-3-methyl-2-oxo-benzimidazol-5-yl]pentyl]-4-(methylamino) cyclohexanecarboxamide To a mixture of tert-butyl N-[4-[5-[1-(2,6-dioxo-3-piperidyl)-3-methyl-2-oxo-benzimidazol-5-yl] pentylcarbamoyl]cyclohexyl]-N-methyl-carbamate (40.0 mg, 68.5 umol) in DCM (1 mL) was added HCl/dioxane (4 M, 0.5 mL) at 25° C. under $N_2$. The mixture was stirred at 25° C. for 2 hours. On completion, the reaction mixture was concentrated in vacuo to give the title compound (33.0 mg, 91% yield) as a white solid. LC-MS (ESI$^+$) m/z 484.3 (M+H)$^+$.

3-[(4-methoxyphenyl)methyl]hexahydropyrimidine-2,4-dione (Intermediate EJ)

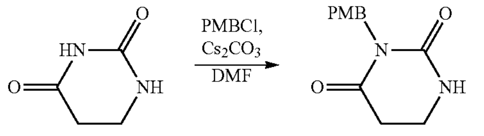

EJ

To the solution of hexahydropyrimidine-2,4-dione (3.0 g, 26.3 mmol, CAS #504-07-4) in DMF (60 mL) was added $Cs_2CO_3$ (17.1 g, 52.6 mmol) at 25° C., then 1-(chloromethyl)-4-methoxybenzene (3.71 g, 23.6 mmol) was dropwise added to the mixture slowly at 25° C. The mixture was stirred at 25° C. for 2 hours. On completion, the reaction was filtered and the filter cake was washed by EA (30 mL×2). The filtrate was poured into water (150 mL) and extracted with EA (100 mL×2). The combined organic layer was washed with water (100 mL) and saturated brine (100 mL). The organic layer was dried over $Na_2SO_4$, filtered and concentrated to give the crude product. The crude product was suspended in EA/PE (1/1, 80 mL) and stirred for 0.5 hour. The suspension was filtered, the filter cake was dried to give compound (2.80 g, 45% yield) as a white solid. $^1$H NMR (400 MHz, CHLOROFORM-d) δ 7.42-7.30 (m, 2H), 6.90-6.62 (m, 2H), 6.15 (s, 1H), 4.88 (s, 2H), 3.78 (s, 3H), 3.37 (dt, J=2.4, 6.8 Hz, 2H), 2.71 (t, J=6.8 Hz, 2H).

1-(7-Bromoimidazo[1,2-a]pyridin-3-yl)hexahydropyrimidine-2,4-dione (Intermediate ER)

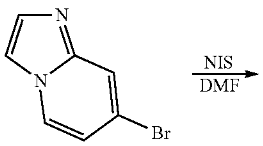

-continued

EJ

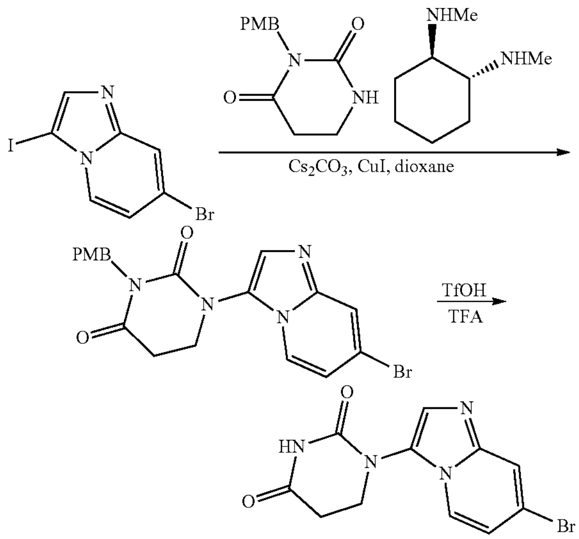

ER

Step 1—7-bromo-3-iodo-imidazo[1,2-a]pyridine

To a solution of 7-bromoimidazo[1,2-a]pyridine (9.50 g, 48.2 mmol, CAS #808744-34-5) in DMF (150 mL) was added NIS (13.0 g, 57.8 mmol) at 25° C. The mixture was stirred at 100° C. for 1 hour. On completion, the reaction mixture was poured into 400 mL of water and extracted with EtOAc (200 mL×2). The organic layer was washed with water (200 mL) and saturated brine (200 mL), then dried over $Na_2SO_4$, filtered and concentrated to give the crude product. The crude product was purified by flash silica gel chromatography (120 g Column, Eluent of 0~5% ethyl acetate/petroleum ether gradient @ 150 mL/min) to give the compound (11.6 g, 74% yield) as a black brown solid. $^1$H NMR (400 MHz, CHLOROFORM-d) δ 8.00 (d, J=7.2 Hz, 1H), 7.82 (d, J=1.2 Hz, 1H), 7.67 (s, 1H), 7.04 (dd, J=2.0, 7.3 Hz, 1H).

Step 2—1-(7-bromoimidazo[1,2-a]pyridin-3-yl)-3-[(4-methoxyphenyl)methyl]hexahydropyrimidine-2,4-dione To a solution of 3-[(4-methoxyphenyl)methyl]hexahydropyrimidine-2,4-dione (4 g, 17.08 mmol, Intermediate EJ), 7-bromo-3-iodo-imidazo[1,2-a]pyridine (6.62 g, 20.49 mmol) in 1,4-dioxane (100 mL) was added $Cs_2CO_3$ (11.1 g, 34.1 mmol), CuI (650 mg, 3.42 mmol) and (1R,2R)—N1,N2-Dimethylcyclohexane-1,2-diamine (485 mg, 3.42 mmol, CAS #68737-65-5) at 25° C. under $N_2$. Then the mixture was stirred at 80° C. for 16 hours. On completion, the reaction mixture was poured into 200 mL of water and extracted with EtOAc (100 mL×2). The combined organic layers were washed with water (200 mL) and saturated brine (200 mL), then dried over $Na_2SO_4$, filtered and concentrated to give a crude product. The crude product was purified by silica gel chromatography (eluted with petroleum ether/ethyl acetate=10/1 to 0/1 to give the title compound (2.00 g, 27% yield) as a yellow solid.

Step 3—1-(7-Bromoimidazo[1,2-a]pyridin-3-yl) hexahydropyrimidine-2,4-dione

A solution of 1-(7-bromoimidazo[1,2-a]pyridin-3-yl)-3-[(4-methoxyphenyl)methyl]hexahydropyrimidine-2,4-dione (2.30 g, 5.36 mmol) in TfOH (1.5 mL) was stirred at 65° C. for 4 hours. On completion, the mixture was concentrated to give residue, then the residue was adjusted pH to 6-7 with TEA at 0° C. Then the mixture was concentrated to give a residue. The residue was suspended in EtOAc (30 mL) and stirred for 0.5 hour. Next, the suspension was filtered and the filter cake was concentrated to give the title compound (1.55 g, 84% yield) as a white solid. $^1$H NMR (400 MHz, DMSO-$d_6$) δ 10.69 (s, 1H), 8.32 (d, J=7.2 Hz, 1H), 7.93 (d, J=1.2 Hz, 1H), 7.59 (s, 1H), 7.15 (dd, J=2.0, 7.2 Hz, 1H), 3.81 (t, J=6.8 Hz, 2H), 2.83 (t, J=6.4 Hz, 2H).

1-[7-[3-(4-Piperidyloxy)prop-1-ynyl]imidazo[1,2-a]pyridin-3-yl]hexahydropyrimidine-2,4-dione (Intermediate ES)

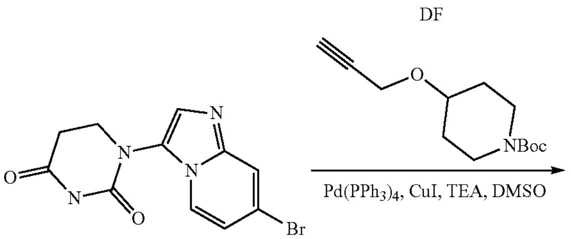

ER

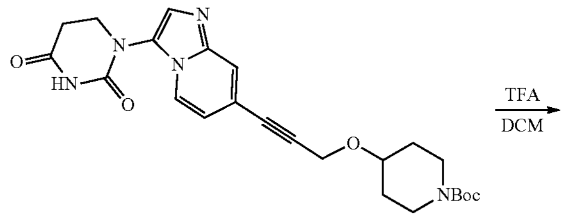

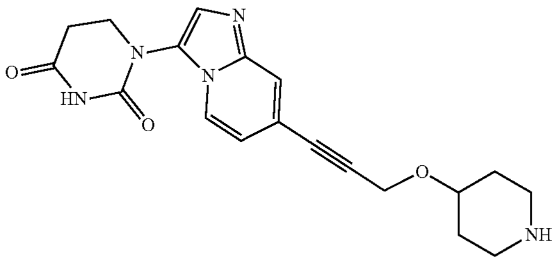

ES

Step 1—Tert-butyl 4-[3-[3-(2,4-dioxohexahydropyrimidin-1-yl)imidazo[1,2-a]pyridin-7-yl]prop-2-ynoxy]piperidine-1-carboxylate To a mixture of 1-(7-bromoimidazo[1,2-a]pyridin-3-yl) hexahydropyrimidine-2,4-dione (500 mg, 1.62 mmol, Intermediate ER), tert-butyl 4-prop-2-ynoxypiperidine-1-carboxylate (580 mg, 2.43 mmol, Intermediate DF), CuI (30.8 mg, 161 umol) and Pd(PPh$_3$)$_4$ (186 mg, 161 umol) in DMSO (5 mL) was added TEA (1.59 g, 15.7 mmol). The mixture was stirred at 80° C. for 5 hours. On completion, to the reaction mixture was added water (100 mL) and the aqueous layer was extracted with ethyl acetate (20 mL×5). The organic layer was separated and concentrated under reduced pressure to give the crude. The crude product was purified by silica gel chromatography eluted with PE:EA=1:1 to 0:1, and then triturated twice with EtOAc (20 mL) to give the title compound (500 mg, 56% yield) as a white solid. $^1$H NMR (400 MHz, DMSO-$d_6$) δ 10.70 (s, 1H), 8.34 (d, J=6.8 Hz, 1H), 7.74 (s, 2H), 6.97 (d, J=7.2 Hz, 1H), 4.48 (s, 2H), 3.81 (t, J=6.8 Hz, 2H), 3.76-3.61 (m, 3H), 3.06 (t, J=9.6 Hz, 2H), 2.83 (t, J=6.8 Hz, 2H), 1.94-1.77 (m, 2H), 1.40 (m, 11H). LC-MS (ESI$^+$) m/z 468.2 (M+H)$^+$.

Step 2—1-[7-[3-(4-Piperidyloxy)prop-1-ynyl]imidazo[1,2-a]pyridin-3-yl]hexahydropyrimidine-2,4-dione To a mixture of tert-butyl 4-[3-[3-(2,4-dioxohexahydropyrimidin-1-yl)imidazo[1,2-a]pyridin-7-yl] prop-2-ynoxy] piperidine-1-carboxylate (200 mg, 427 umol) in DCM (2 mL) was added TFA (616 mg, 5.40 mmol) and the mixture was stirred at 25° C. for 30 minutes. On completion, the reaction mixture was concentrated under reduced pressure to give the title compound (200 mg, 87% yield, TFA salt) as a yellow solid. LC-MS (ESI$^+$) m/z 368.0 (M+H)$^+$.

1-[7-[3-[[1-(4-Aminobenzoyl)-4-piperidyl]oxy] prop-1-ynyl]imidazo[1,2-al pyridin-3-yl]hexahydropyrimidine-2,4-dione (Intermediate ET)

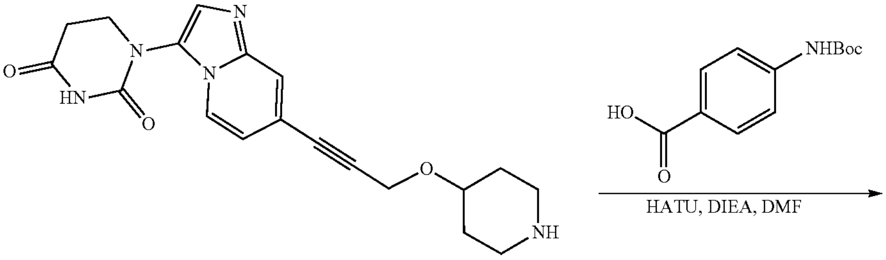

ES

-continued

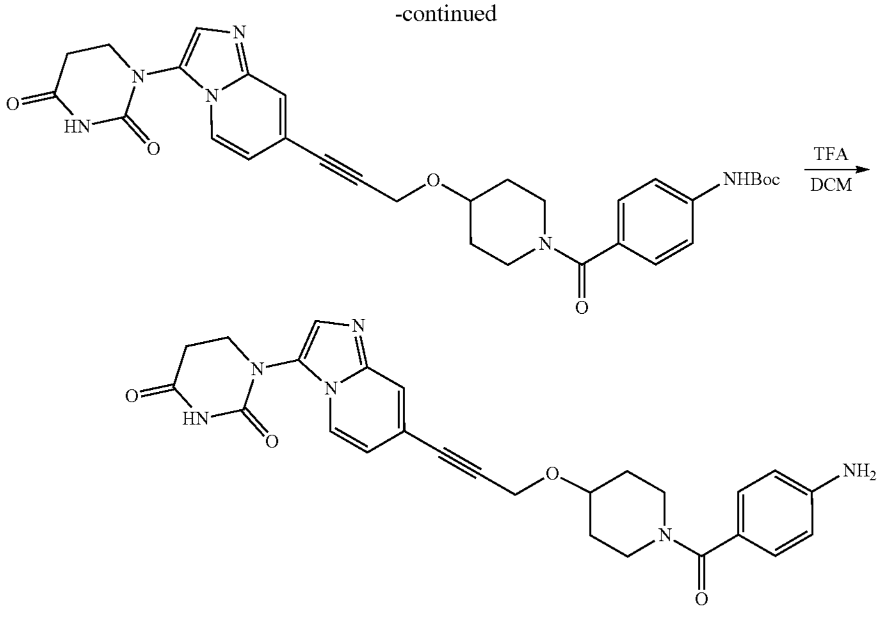

ET

Step 1—Tert-butyl N-[4-[4-[3-[3-(2,4-dioxohexahydropyrimidin-1-yl) imidazo[1,2-a]pyridin-7-yl] prop-2-ynoxy]piperidine-1-carbonyl]phenyl]carbamate To a mixture of 1-[7-[3-(4-piperidyloxy) prop-1-ynyl] imidazo[1,2-a] pyridin-3-yl]hexahydropyrimidine-2,4-dione (200 mg, 415 umol, TFA salt, Intermediate ES), 4-(tert-butoxycarbonylamino)benzoic acid (118 mg, 498 umol, CAS #66493-39-8) and DIEA (268 mg, 2.08 mmol) in DMF (2 mL) was added HATU (205 mg, 540 umol). The mixture was stirred at 25° C. for 10 minutes. On completion, the reaction was directly purified by reversed phase (0.1% FA condition) to give the title compound (125 mg, 50% yield) as a green solid. $^{1}H$ NMR (400 MHz, DMSO-$d_6$) δ 10.73 (s, 1H), 9.55 (s, 1H), 8.49 (s, 1H), 8.06-7.64 (m, 1H), 7.51 (d, J=8.4 Hz, 2H), 7.31 (d, J=8.4 Hz, 2H), 7.09 (d, J=7.2 Hz, 1H), 4.51 (s, 2H), 4.1-3.4 (m, 7H), 2.84 (t, J=6.4 Hz, 2H), 1.92 (m, 2H), 1.49 (m, 11H). LC-MS (ESI$^+$) m/z 587.4 $(M+H)^+$.

Step 2—1-[7-[3-[[1-(4-Aminobenzoyl)-4-piperidyl] oxy] prop-1-ynyl]imidazo[1,2-a]pyridin-3-yl] hexahydropyrimidine-2,4-dione To a mixture of tert-butyl N-[4-[4-[3-[3-(2,4-dioxohexahydropyrimidin-1-yl)imidazo[1,2-a] pyridin-7-yl]prop-2-ynoxy]piperidine-1-carbonyl]phenyl]carbamate (92.0 mg, 156 umol) in DCM (1.0 mL) was added TFA (308 mg, 2.70 mmol). The mixture was stirred 25° C. for 30 min. On completion, the reaction mixture was concentrated under reduced pressure to give the title compound (94.0 mg, 97% yield, TFA salt) as a yellow oil. LC-MS (ESI$^+$) m/z 487.1 $(M+H)^+$.

3-[3-Methyl-2-oxo-4-[2-(4-piperidyl)ethynyl]benzimidazol-1-yl]piperidine-2,6-dione (Intermediate EU)

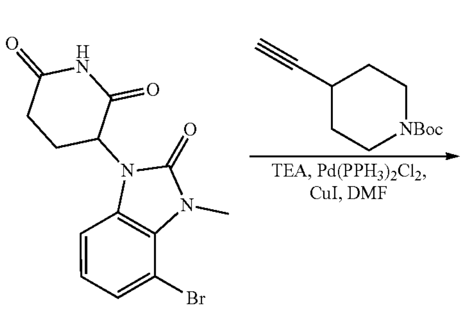

B

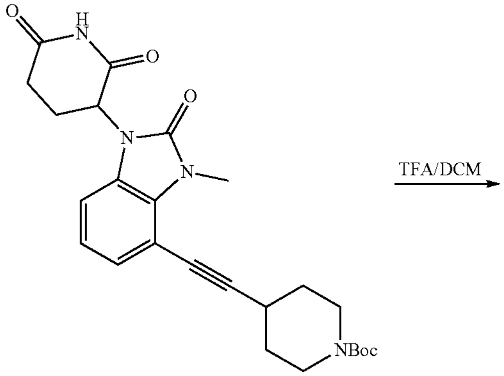

-continued

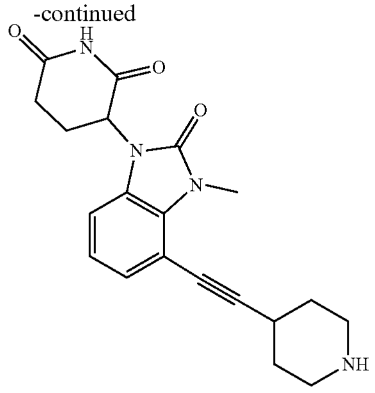

EU

Step 1—Tert-butyl 4-[2-[1-(2,6-dioxo-3-piperidyl)-3-methyl-2-oxo-benzimidazol-4-yl]ethynyl] piperidine-1-carboxylate To a mixture of 3-(4-bromo-3-methyl-2-oxo-benzimidazol-1-yl)piperidine-2,6-dione (3.00 g, 8.87 mmol, Intermediate B) and tert-butyl 4-ethynylpiperidine-1-carboxylate (2.23 g, 10.6 mmol, CAS #287192-97-6) in ACN (30 mL) was added TEA (4.49 g, 44.4 mmol), $Pd(PPh_3)_2Cl_2$ (622 mg, 887 umol) and CuI (84.5 mg, 444 umol). The mixture was degassed and purged with $N_2$ three times, then the mixture was stirred at 80° C. for 16 hours under $N_2$ atmosphere. On completion, the mixture was filtered and concentrated to give a residue. The residue was purified by column chromatography ($SiO_2$, dichloromethane:ethyl acetate=1:0 to 2:1) to give the title compound (1.97 g, 47% yield) as a yellow solid. LC-MS ($ESI^+$) m/z 411.0 $(M+H-55)^+$.

Step 2—3-[3-Methyl-2-oxo-4-[2-(4-piperidyl)ethynyl]benzimidazol-1-yl]piperidine-2,6-dione To a solution of tert-butyl 4-[2-[1-(2,6-dioxo-3-piperidyl)-3-methyl-2-oxo-benzimidazol-4-yl]ethynyl] piperidine-1-carboxylate (500 mg, 1.07 mmol) in DCM (5 mL) was added TFA (1.0 mL). The mixture was stirred at 0° C. for 1 hour. On completion, the mixture was concentrated to give the title compound (514 mg, 99% yield, TFA) as a yellow solid. LC-MS ($ESI^+$) m/z 367.0 $(M+H)^+$.

3-[4-[2-[1-[(4-aminocyclohexyl)methyl]-4-piperidyl] ethynyl]-3-methyl-2-oxo-benzimidazol-1-yl]piperidine-2,6-dione

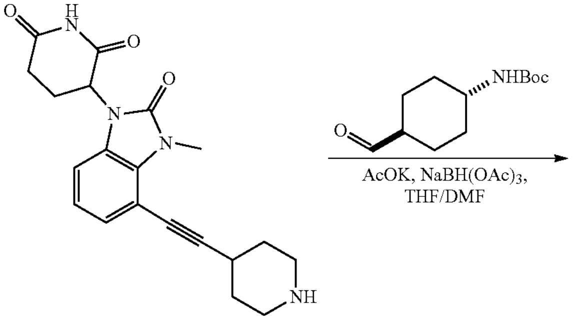

EU

-continued

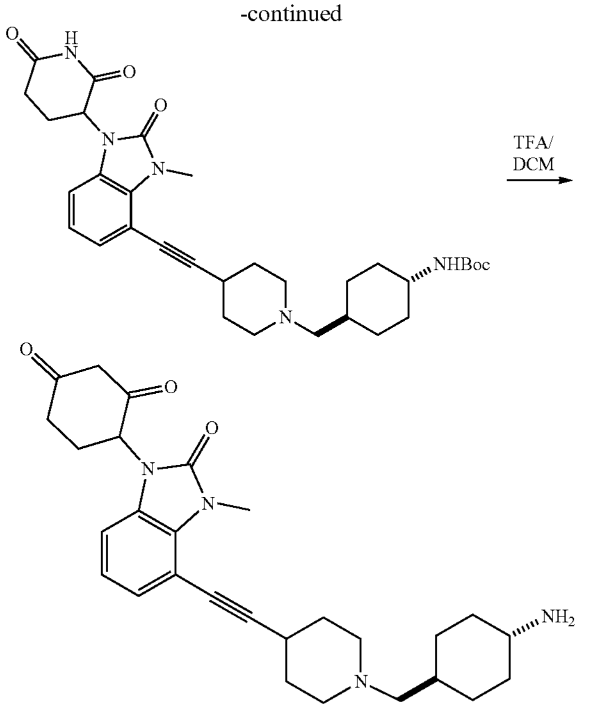

EV

Step 1—Tert-butyl N-[4-[[4-[2-[1-(2,6-dioxo-3-piperidyl)-3-methyl-2-oxo-benzimidazol-4-yl]ethynyl]-1-piperidyl]methyl]cyclohexyl]carbamate To a solution of 3-[3-methyl-2-oxo-4-[2-(4-piperidyl) ethynyl]benzimidazol-1-yl]piperidine-2,6-dione (510 mg, 1.06 mmol, TFA, Intermediate EU) in THF (6 mL) and DMF (2 mL) was added AcOK (1.04 g, 10.6 mmol), then the mixture was stirred at 25° C. for 10 minutes. Next, tert-butyl N-(4-formylcyclohexyl)carbamate (289 mg, 1.27 mmol, CAS #181308-56-5) was added to the mixture and the mixture was stirred at 25° C. for 5 minutes. Finally, NaBH $(OAc)_3$ (270 mg, 1.27 mmol) was added to the mixture at 25° C. and the reaction mixture was stirred at 25° C. for 14 hours. On completion, the mixture was concentrated to give a residue. The residue was purified by reversed-phase CC (0.1% TFA condition) to give the title compound (347 mg, 56% yield) as a brown solid. $^1H$ NMR (400 MHz, $CDCl_3$) δ=8.13 (d, J=5.6 Hz, 1H), 7.13 (d, J=7.6 Hz, 1H), 7.04-6.90 (m, 1H), 6.77 (dd, J=7.6, 18.0 Hz, 1H), 5.25-5.17 (m, 1H), 3.80 (s, 1H), 3.79-3.71 (m, 3H), 3.61 (d, J=12.4 Hz, 1H), 3.44-3.26 (m, 1H), 3.13-3.01 (m, 1H), 3.00-2.92 (m, 1H), 2.92-2.81 (m, 3H), 2.81-2.67 (m, 2H), 2.65-2.55 (m, 1H), 2.29-2.21 (m, 2H), 2.10-1.94 (m, 5H), 1.45 (s, 9H), 1.30-1.08 (m, 4H). LC-MS ($ESI^+$) m/z 578.2 $(M+H)^+$.

Step 2—3-[4-[2-[1-[(4-aminocyclohexyl)methyl]-4-piperidyl]ethynyl]-3-methyl-2-oxo-benzimidazol-1-yl]piperidine-2,6-dione To a solution of tert-butyl N-[4-[[4-[2-[1-(2,6-dioxo-3-piperidyl)-3-methyl-2-oxo-benzimidazol-4-yl] ethynyl]-1-piperidyl]methyl]cyclohexyl]carbamate (100 mg, 173 umol) in DCM (1.0 mL) was added TFA (0.2 mL). The mixture was stirred at 0° C. for 1 hour. On completion, the mixture was concentrated to give the title compound (102 mg, 99% yield, TFA) as a yellow solid. LC-MS ($ESI^+$) m/z 478.2 $(M+H)^+$.

Chloro-(3-chloro-2-fluoro-phenyl)-diphenyl-dispiro [BLAH]dione (Intermediate EW)

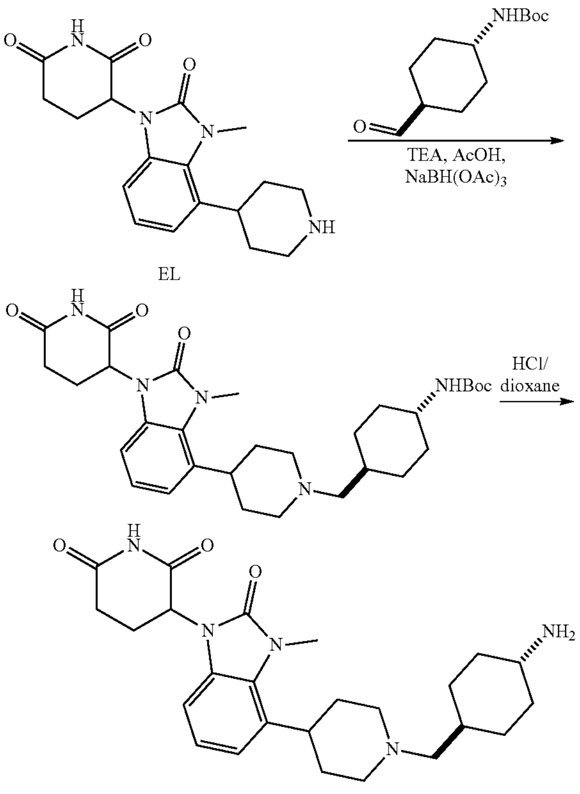

EL

EW

Step 1—(3E)-6-chloro-3-[(3-chloro-2-fluoro-phenyl) methylene]indolin-2-one

To a solution of 3-[3-methyl-2-oxo-4-(4-piperidyl)benzimidazol-1-yl]piperidine-2,6-dione (300 mg, 876 umol, Intermediate EL) in THF (3 mL) was added TEA (88.6 mg, 876 umol) until the pH=8-9, then AcOH (52.6 mg, 876 umol) was added until pH=5-7. Next, tert-butyl N-(4-formylcyclohexyl) carbamate (199 mg, 876 umol, CAS #181308-56-5) was added and the reaction mixture was stirred at 0° C. for 1 hour. Finally, $NaBH(OAc)_3$ (278 mg, 1.31 mmol) was added and the reaction mixture was stirred at 25° C. for 2 hours. On completion, the reaction mixture was concentrated in vacuo to give a residue. The crude product was purified by reversed-phase (0.1% TFA condition) to give the title compound (135 mg, 26% yield). LC-MS ($ESI^+$) m/z 554.5 $(M+H)^+$.

Step 2—Chloro-(3-chloro-2-fluoro-phenyl)-diphenyl-dispiro[BLAH]dione

To a mixture of tert-butyl tert-butyl N-[4-[[4-[1-(2,6-dioxo-3-piperidyl)-3-methyl-2-oxo-benzimidazol-4-yl]-1-piperidyl]methyl]cyclohexyl]carbamate (135 mg, 243 umol) in DCM (1.0 mL) was added HCl/dioxane (4 M, 0.3 mL) at 25° C. under $N_2$. The mixture was stirred at 25° C. for 30 minutes. On completion, the reaction mixture was concentrated in vacuo to give the title compound (135 mg, 100% yield). LC-MS ($ESI^+$) m/z 454.4 $(M+H)^+$.

3-[5-[3-[4-[(4-Aminophenyl)methyl]piperazin-1-yl]prop-1-ynyl]-3-methyl-2-oxo-benzimidazol-1-yl]piperidine-2,6-dione (Intermediate EX)

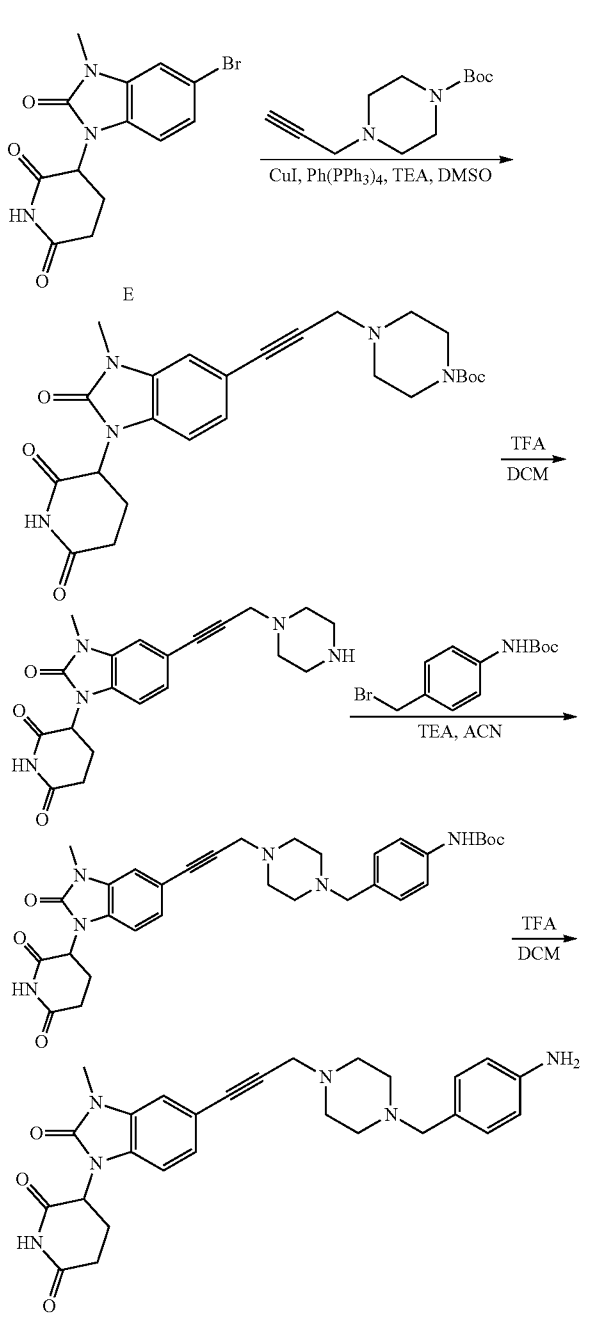

E

EX

Step 1—Tert-butyl 4-[3-[1-(2,6-dioxo-3-piperidyl)-3-methyl-2-oxo-benzimidazol-5-yl]prop-2-ynyl]piperazine-1-carboxylate A mixture of 3-(5-bromo-3-methyl-2-oxo-benzimidazol-1-yl)piperidine-2,6-dione (1.00 g, 2.96 mmol, Intermediate E), tert-butyl 4-prop-2-ynylpiperazine-1-carboxylate (994 mg, 4.44 mmol, CAS #199538-99-3), CuI (56.3 mg, 295 umol), TEA (2.91 g, 28.74 mmol) and $Pd(PPh_3)_4$ (341 mg, 295 μmol) in DMSO (12 mL) was degassed and purged with $N_2$ three times. Then the mixture was stirred at 80° C. for 12 hours under $N_2$ atmosphere. On completion, the reaction mixture was concentrated in vacuo to give a residue. The residue was purified by column chromatography ($SiO_2$, petroleum ether:ethyl acetate=0:1) to give the title compound (1.20 g, 67% yield) as a brown solid. $^1H$ NMR (400 MHz, DMSO-$d_6$) δ 7.73-7.59 (m, 2H), 7.36 (s, 1H), 7.13 (d, J=1.6 Hz, 1H), 5.39 (dd, J=5.2, 12.8 Hz, 1H), 3.54 (s, 2H), 3.31-3.22 (m, 3H), 2.91-2.81 (m, 1H), 2.75-2.58 (m, 2H), 2.55 (s, 2H), 2.48 (d, J=4.8 Hz, 3H), 2.42-2.22 (m, 3H), 2.12-1.98 (m, 1H), 1.40 (s, 9H).

Step 2—3-[3-Methyl-2-oxo-5-(3-piperazin-1-ylprop-1-ynyl)benzimidazol-1-yl]piperidine-2,6-dione To a mixture of tert-butyl 4-[3-[1-(2,6-dioxo-3-piperidyl)-3-methyl-2-oxo-benzimidazol-5-yl]prop-2-ynyl]piperazine-1-carboxylate (500 mg, 1.04 mmol) in DCM (1.0 mL) was added TFA (0.2 ml) in one portion at 25° C. under $N_2$. The mixture was stirred at 25° C. for 2 hours. On completion, the reaction mixture was concentrated in vacuo to give the title compound (390 mg, 90% yield) as a brown oil. LC-MS (ESI$^+$) m/z 382.0 (M+H)$^+$.

Step 3—Tert-butyl N-[4-[[4-[3-[1-(2,6-dioxo-3-piperidyl)-3-methyl-2-oxo-benzimidazol-5-yl]prop-2-ynyl]piperazin-1-yl]methyl]phenyl]carbamate To a solution of 3-[3-methyl-2-oxo-5-(3-piperazin-1-yl-prop-1-ynyl)benzimidazol-1-yl]piperidine-2,6-dione (220 mg, 576 umol), tert-butyl N-[4-(bromomethyl)phenyl]carbamate (198 mg, 692 μmol) in ACN (2 mL) was added TEA (175 mg, 1.73 mmol). The mixture was stirred at 40° C. for 10 minutes. On completion, the reaction mixture was concentrated in vacuo to give a residue. The crude product was purified by reversed-phase flash (0.1% TFA condition) to give the title compound (120 mg, 34% yield) as a yellow solid. $^1H$ NMR (400 MHz, DMSO-$d_6$) δ 11.13 (s, 1H), 9.53 (s, 1H), 7.53 (d, J=8.4 Hz, 2H), 7.36 (d, J=8.0 Hz, 2H), 7.29 (s, 1H), 7.22-7.19 (m, 2H), 5.39 (dd, J=5.2, 13.2 Hz, 1H), 4.30-4.14 (m, 2H), 3.87-3.78 (m, 3H), 3.38-3.30 (m, 6H), 2.75-2.62 (m, 7H), 1.48 (s, 9H). LC-MS (ESI$^+$) m/z 587.5 (M+H)$^+$.

Step 4—3-[5-[3-[4-[(4-Aminophenyl)methyl]piperazin-1-yl]prop-1-ynyl]-3-methyl-2-oxo-benzimidazol-1-yl]piperidine-2,6-dione To a mixture of tert-butyl N-[4-[[4-[3-[1-(2,6-dioxo-3-piperidyl)-3-methyl-2-oxo-benzimidazol-5-yl]prop-2-ynyl]piperazin-1-yl]methyl]phenyl]carbamate (100 mg, 170 umol) in DCM (1.0 mL) was added TFA (0.2 ml) in one portion at 25° C. under $N_2$. The mixture was stirred at 25° C. for 1 hour. On completion, the reaction mixture was concentrated in vacuo to give a residue to give the title compound (80 mg, 83% yield) as a yellow oil. LC-MS (ESI$^+$) m/z 487.4 (M+H)$^+$.

3-[4-[[4-[[1-[(4-Aminocyclohexyl)methyl]-4-piperidyl]oxy]-1-piperidyl]methyl]-3-methyl-2-oxo-benzimidazol-1-yl]piperidine-2,6-dione (Intermediate EY)

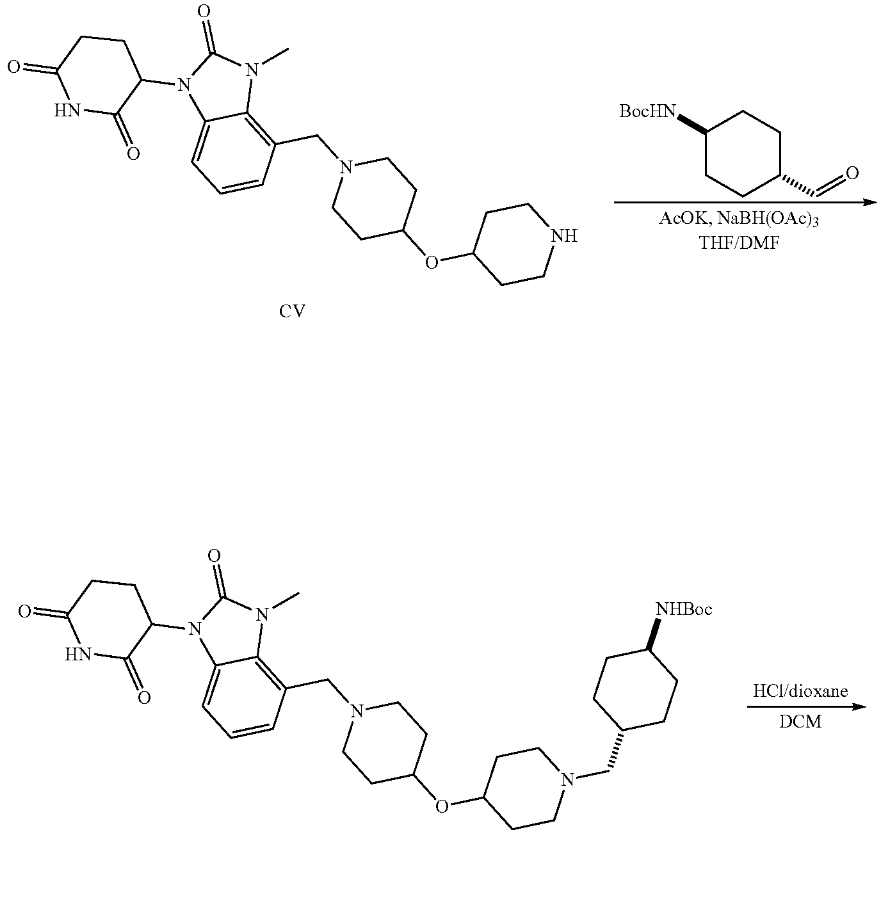

CV

-continued

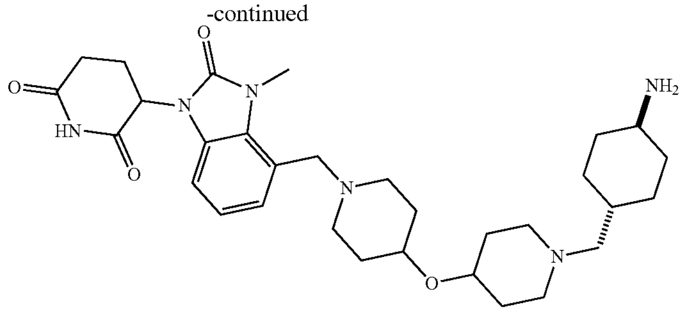

EY

Step 1—Tert-butyl N-[4-[[4-[[1-[[1-(2,6-dioxo-3-piperidyl)-3-methyl-2-oxo-benzimidazol-4-yl] methyl]-4-piperidyl] oxyl-1-piperidyl] methyl]cyclohexyl]carbamate To a solution of 3-[3-methyl-2-oxo-4-[[4-(4-piperidyloxy)-1-piperidyl]methyl]benzimidazol-1-yl] piperidine-2,6-dione (250 mg, 549 umol, Intermediate CV) in THF (12 mL) and DMF (4 mL) was added AcOK (323 mg, 3.29 mmol), then the mixture was stirred at 25° C. for 10 minutes. Next, tert-butyl N-(4-formylcyclohexyl) carbamate (150 mg, 659 umol, CAS #181308-56-5) was added to the mixture and stirred at 25° C. for 5 minutes. Finally, NaBH$(OAc)_3$ (349 mg, 1.65 mmol) was added to the mixture at 25° C. The reaction mixture was stirred at 25° C. for 14 hours. On completion, the mixture was concentrated to give a residue. The residue was purified by reversed-phase column chromatography (0.5% HCl condition) to give the title compound (267 mg, 55% yield) as a yellow solid. $^1$H NMR (400 MHz, DMSO-$d_6$) δ 11.12 (s, 1H), 8.08 (d, J=3.2 Hz, 2H), 7.38-7.29 (m, 1H), 7.17-7.05 (m, 1H), 5.49-5.41 (m, 1H), 4.66-4.54 (m, 2H), 3.80 (s, 1H), 3.65 (t, J=3.6 Hz, 5H), 3.45 (dd, J=10.0, 12.0 Hz, 3H), 3.29 (s, 3H), 3.17-3.03 (m, 2H), 2.98-2.80 (m, 7H), 2.76-2.68 (m, 1H), 2.67-2.58 (m, 1H), 2.18-2.04 (m, 3H), 2.01-1.87 (m, 9H), 1.85-1.65 (m, 4H), 1.42-1.27 (m, 3H), 1.04 (s, 3H). LC-MS (ESI$^+$) m/z 667.3 (M+H)$^+$.

Step 2—3-[4-[[4-[[1-[(4-Aminocyclohexyl)methyl]-4-piperidyl] oxy]-1-piperidyl] methyl]-3-methyl-2-oxo-benzimidazol-1-yl]piperidine-2,6-dione To a solution of tert-butyl N-[4-[[4-[[1-[[1-(2,6-dioxo-3-piperidyl)-3-methyl-2-oxo-benzimidazol-4-yl] methyl]-4-piperidyl]oxy]-1-piperidyl]methyl]cyclohexyl]carbamate (200 mg, 300 μmol) in DCM (4 mL) was added HCl/dioxane (4 M, 1.3 mL). The mixture was stirred at 25° C. for 1 hour. On completion, the mixture was concentrated to give the title compound (180 mg, 99% yield, HCl) as a yellow solid. LC-MS (ESI$^+$) m/z 567.4 (M+H)$^+$.

3-[4-[2-[7-[(4-Aminocyclohexyl) methyl]-7-azaspiro[3.5]nonan-2-yl]ethyl]-3-methyl-2-oxo-benzimidazol-1-yl]piperidine-2,6-dione (Intermediate EZ)

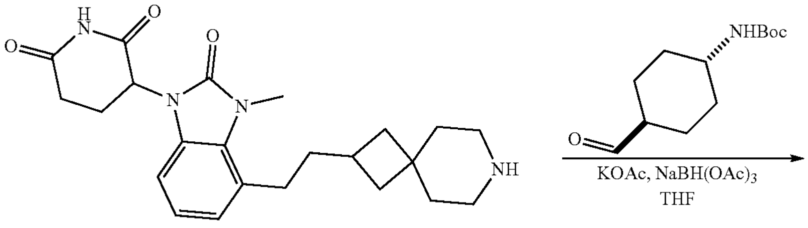

BG

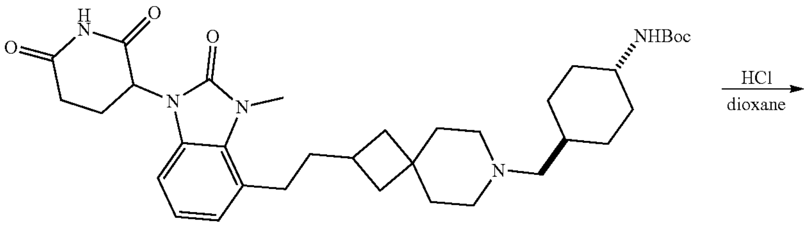

-continued

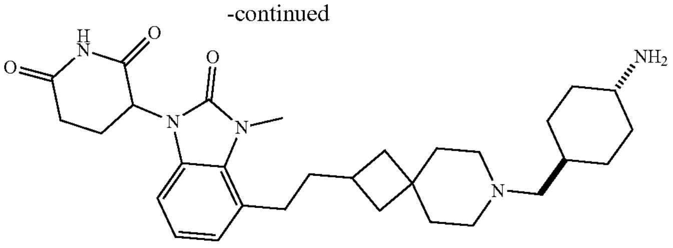

EZ

Step 1—Tert-butyl N-[4-[[2-[2-[1-(2,6-dioxo-3-piperidyl)-3-methyl-2-oxo-benzimidazol-4-yl]ethyl]-7-azaspiro[3.5]nonan-7-yl]methyl]cyclohexyl]carbamate To a solution of 3-[4-[2-(7-azaspiro[3.5]nonan-2-yl) ethyl]-3-methyl-2-oxo-benzimidazol-1-yl] piperidine-2,6-dione (80.0 mg, 195 umol, Intermediate BG) in THF (2.0 mL) was added KOAc (115 mg, 1.17 mmol) stirred for 10 minutes, then tert-butyl N-(4-formylcyclohexyl)carbamate (53.2 mg, 233 μmol, CAS #181308-56-5) was added stirred for 5 minutes. Next, $NaBH(OAc)_3$ (61.9 mg, 292 umol) was added and the mixture was stirred at 25° C. for 0.5 hour. On completion, the mixture was quenched with water (5 mL) and extracted with DCM (5 mL×3). The combined organic phase was dried over anhydrous sodium sulfate, concentrated to give the title compound (120 mg, 99% yield) as a yellow oil. LC-MS ($ESI^+$) m/z 622.5 $(M+H)^+$.

Step 2—3-[4-[2-[7-[(4-Aminocyclohexyl) methyl]-7-azaspiro[3.5]nonan-2-yl]ethyl]-3-methyl-2-oxo-benzimidazol-1-yl]piperidine-2,6-dione To a solution of tert-butyl N-[4-[[2-[2-[1-(2,6-dioxo-3-piperidyl)-3-methyl-2-oxo-benzimidazol-4-yl] ethyl]-7-azaspiro[3.5]nonan-7-yl]methyl]cyclohexyl]carbamate (80.0 mg, 129 umol) in DCM (1.0 mL) was added HCl/dioxane (4 M, 2.0 mL). The mixture was stirred at 25° C. for 0.5 hour. On completion, the mixture was concentrated to give the title compound (67.0 mg, 93% yield, HCl) as a yellow solid. LC-MS ($ESI^+$) m/z 522.5 $(M+H)^+$.

4-[[chloro-(3-chloro-2-fluoro-phenyl)-oxo-dispiro [BLAH]carbonyl]-methyl-amino]benzoic acid (Intermediate FA)

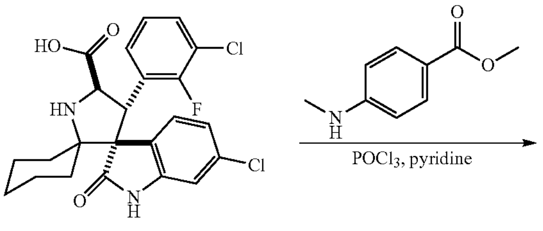

CI

-continued

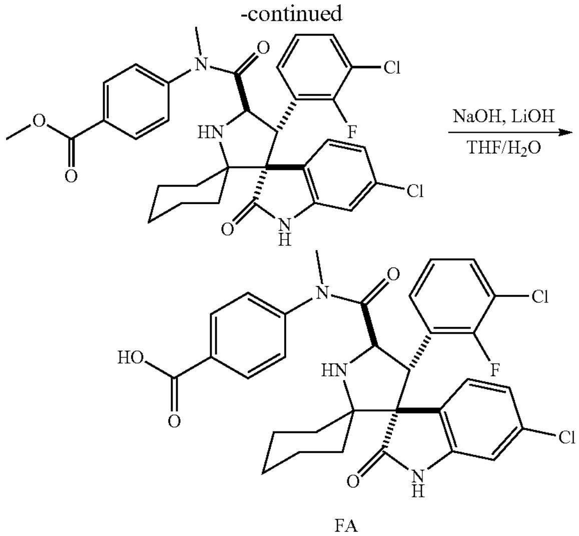

FA

Step 1—methyl 4-[[chloro-(3-chloro-2-fluoro-phenyl)-oxo-dispiro[BLAH]carbonyl]-methyl-amino] benzoate To a solution of chloro-(3-chloro-2-fluoro-phenyl)-oxo-dispiro[BLAH]carboxylic acid (150 mg, 323 umol, Intermediate CI) and methyl 4-(methylamino)benzoate (106 mg, 647 umol) in pyridine (2.0 mL) was added $POCl_3$ (148 mg, 971 umol) at 25° C. The reaction solution was stirred at 25° C. for 30 min. On completion, 5.0 ml MeOH was added and stirred 10 mins, then the reaction mixture was concentrated in vacuo to give a residue. The crude product was purified by reversed-phase HPLC (0.1% FA condition) to give the title compound (160 mg, 63% yield). LC-MS ($ESI^+$) m/z 610.4 $(M+H)^+$.

Step 2—4-[[chloro-(3-chloro-2-fluoro-phenyl)-oxo-dispiro[BLAH]carbonyl]-methyl-amino]benzoic acid Methyl 4-[[chloro-(3-chloro-2-fluoro-phenyl)-oxo-dispiro[BLAH]carbonyl]-methyl-amino]benzoate (85.0 mg, 139 umol) was dissolved in MeOH (0.4 mL); then LiOH—$H_2O$ (35.0 mg, 835 μmol), NaOH (33.4 mg, 835 umol) in THF (0.4 mL) and $H_2O$ (0.2 mL) were added. The mixture was stirred for 30 min at 25° C. On completion, the reaction mixture was concentrated in vacuo to give a residue. The residue was purified by prep-HPLC (TFA condition) to give the title compound (45.0 mg, 58% yield). LC-MS ($ESI^+$) m/z 596.3 $(M+H)^+$.

3-[3-Methyl-2-oxo-5-(3-piperazin-1-ylpropyl)benzimidazol-1-yl]piperidine-2,6-dione (Intermediate FB)

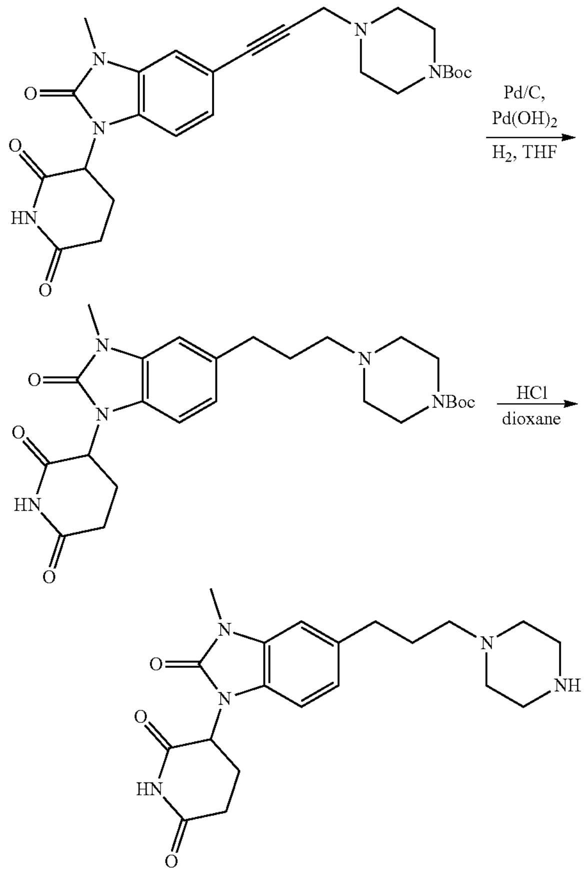

FB

Step 1—Tert-butyl 4-[3-[1-(2,6-dioxo-3-piperidyl)-3-methyl-2-oxo-benzimidazol-5-yl]propyl] piperazine-1-carboxylate To a mixture of tert-butyl 4-[3-[1-(2,6-dioxo-3-piperidyl)-3-methyl-2-oxo-benzimidazol-5-yl] prop-2-ynyl]piperazine-1-carboxylate (760 mg, 1.58 mmol, synthesized via Step 1 of Intermediate EX) in THF (50 mL) was added Pd/C (200 mg, 10 wt %) and $Pd(OH)_2$ (200 mg, 20 wt %) under $N_2$. The mixture was stirred at 25° C. for 24 hours under $H_2$ (15 psi). The reaction mixture was filtered and the filtrate concentrated under reduced pressure to give the title compound (500 mg, 45% yield,) as a yellow solid. $^1H$ NMR (400 MHz, DMSO-$d_6$) δ 11.13 (s, 1H), 7.12-7.02 (m, 2H), 6.95-6.89 (m, 1H), 5.39 (dd, J=5.2, 12.8 Hz, 1H), 3.70-3.62 (m, 1H), 3.48-3.39 (m, 1H), 3.36 (s, 3H), 3.02-2.89 (m, 1H), 2.82-2.71 (m, 1H), 2.71-2.61 (m, 3H), 2.39-2.30 (m, 5H), 2.10-2.00 (m, 1H), 1.86-1.75 (m, 3H), 1.44 (m, 10H), 1.00-0.88 (m, 1H). LC-MS ($ESI^+$) m/z 486.4 $(M+H)^+$.

Step 2—3-[3-Methyl-2-oxo-5-(3-piperazin-1-ylpropyl)benzimidazol-1-yl]piperidine-2,6-dione To a mixture of tert-butyl 4-[3-[1-(2,6-dioxo-3-piperidyl)-3-methyl-2-oxo-benzimidazol-5-yl] propyl]piperazine-1-carboxylate (300 mg, 617 umol) in DCM (3.0 mL) was added HCl/dioxane (4 M, 1.0 mL). The mixture was stirred at 25° C. for 30 minutes. On completion, the reaction mixture was concentrated under reduced pressure to give the title compound (350 mg 100% yield, HCl salt) as a yellow solid. LC-MS ($ESI^+$) m/z 386.4 $(M+H)^+$.

3-[5-[3-[4-(4-Aminocyclohexanecarbonyl)piperazin-1-yl]propyl]-3-methyl-2-oxo-benzimid-azol-1-yl]piperidine-2,6-dione (Intermediate FC)

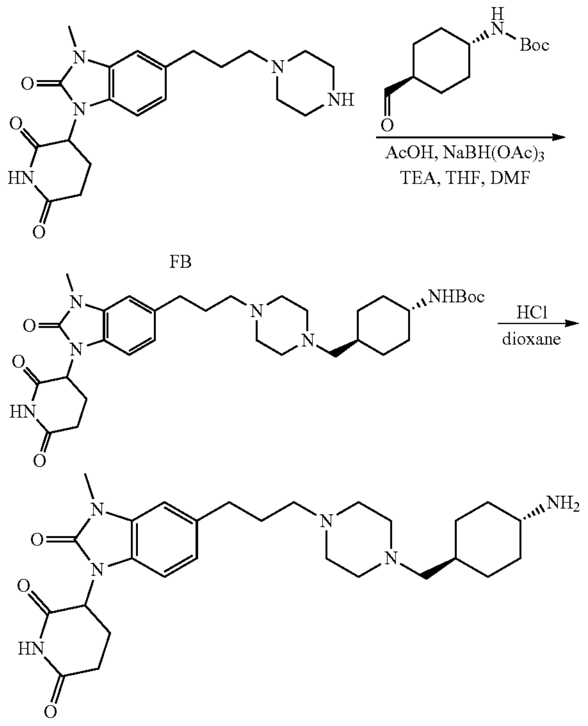

FC

Step 1—Tert-butyl N-[4-[[4-[3-[1-(2,6-dioxo-3-piperidyl)-3-methyl-2-oxo-benzimidazol-5-yl]propyl] piperazin-1-yl]methyl]cyclohexyl]carbamate To a solution of 3-[3-methyl-2-oxo-5-(3-piperazin-1-yl-propyl)benzimidazol-1-yl]piperidine-2,6-dione (280 mg, 663 umol, HCl salt, Intermediate FB) in THF (2.5 mL) and DMF (2.5 mL) was added TEA (67.1 mg, 663 umol, 92.4 uL) until the pH=8-9. Then AcOH (39.8 mg, 663 umol, 37.9 uL) was added until the pH=5-7 at 0° C. Next, tert-butyl N-(4-formylcyclohexyl) carbamate (150 mg, 663 umol, CAS #181308-56-5) was added at 0° C. with stirring for 1 hour, then $NaBH(OAc)_3$ (210 mg, 995 umol) was added. The reaction mixture was stirred at 25° C. for 2 hours. On completion, the reaction mixture was directly purified by reversed phase (0.1% TFA condition) to give the title compound (180 mg, 40% yield) as a white solid. $^1H$ NMR (400 MHz, DMSO-$d_6$) δ 11.10 (s, 1H), 7.10-7.00 (m, 2H), 6.91 (dd, J=1.2, 8.0 Hz, 1H), 6.74 (d, J=8.0 Hz, 1H), 5.36 (dd, J=5.2, 12.8 Hz, 1H), 4.55-3.75 (m, 6H), 3.55-3.38 (m, 2H), 3.23-2.82 (m, 7H), 2.78-2.58 (m, 5H), 2.07-1.86 (m, 3H), 1.76 (s, 4H), 1.58-1.43 (m, 2H), 1.40-1.35 (m, 9H), 1.24-1.05 (m, 2H), 1.02-0.84 (m, 2H). LC-MS ($ESI^+$) m/z 597.4 $(M+H)^+$.

Step 2—3-[5-[3-[4-(4-Aminocyclohexanecarbonyl)piperazin-1-yl]propyl]-3-methyl-2-oxo-benzimidazol-1-yl]piperidine-2,6-dione To a mixture of tert-butyl N-[4-[[4-[3-[1-(2,6-dioxo-3-piperidyl)-3-methyl-2-oxo-benzimidazol-5-yl] propyl]piperazin-1-yl]methyl]cyclohexyl]carbamate (80.0 mg, 134 umol) in DCM (1.0 mL) was added HCl/dioxane (4 M, 0.50 mL). The mixture was stirred at 25° C. for 30 minutes. On completion, the reaction mixture was concentrated under reduced pressure to give the title compound (75.0 mg 100% yield, HCl salt) as a white solid. LC-MS ($ESI^+$) m/z 497.3 $(M+H)^+$.

Dec-9-ynal (Intermediate FD)

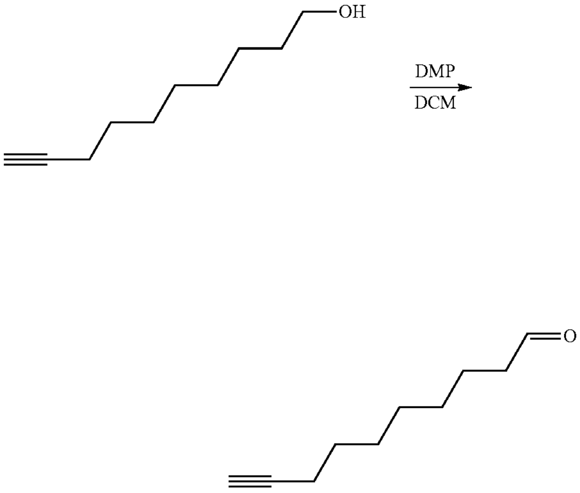

FD

To a solution of dec-9-yn-1-ol (500 mg, 3.24 mmol, CAS #17643-36-6) in DCM (15 mL) was added DMP (1.65 g, 3.89 mmol) at 0° C. The mixture was stirred at 25° C. for 1 hour. On completion, the reaction mixture was quenched with saturated sodium thiosulfate (20 mL) and separated the organic layer. Then the organic layer was washed with saturated sodium hydrogen carbonate (2×10 mL), washed with brine (10 mL), dried over anhydrous sodium sulfate, filtered and concentrated under reduced pressure to give the title compound (490 mg, 99% yield) as a yellow solid. $^1H$ NMR (400 MHz, $CDCl_3$) δ 9.78 (t, J=1.6 Hz, 1H), 2.46-2.41 (m, 2H), 2.22-2.16 (m, 2H), 1.95 (t, J=2.8 Hz, 1H), 1.67-1.61 (m, 2H), 1.55-1.51 (m, 2H), 1.39-1.30 (m, 6H).

(2R,3S,4R,5S)-3-(3-chloro-2-fluoro-phenyl)-4-(4-chloro-2-fluoro-phenyl)-4-cyano-5-(2,2-dimethylpropyl)-N-[2-methoxy-4-(methylcarbamoyl)phenyl]pyrrolidine-2-carboxamide (Intermediate FE)

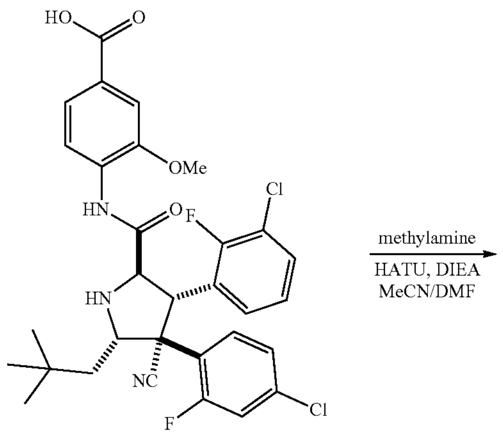

AN

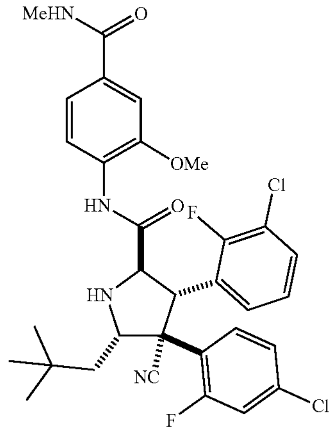

FE

To a solution of 4-[[3-(3-chloro-2-fluoro-phenyl)-4-(4-chloro-2-fluoro-phenyl)-4-cyano-5-(2,2-dimethylpropyl)pyrrolidine-2-carbonyl]amino]-3-methoxy-benzoic acid (40.0 mg, 64.8 umol, Intermediate AN) in MeCN (2 mL) was added $MeNH_2$ (10.0 mg, 148 umol, 2.28 eq, HCl), HATU (25.0 mg, 65.7 umol), DMF (0.4 mL) and DIEA (37.1 mg, 287 umol). The reaction was stirred at 20° C. for 12 hours. On completion, the reaction mixture was concentrated under reduce pressure to give the residue. The residue was triturated with petroleum ether/MeOH=20:1 for 5 minutes to give the title compound (31.0 mg, 75% yield) as a white solid. LC-MS ($ESI^+$) m/z 629.3 $(M+H)^+$.

3-[4-[1-[(4-Aminophenyl)methyl]-4-piperidyl]-3-methyl-2-oxo-benzimidazol-1-yl]piperidine-2,6-dione (Intermediate FF)

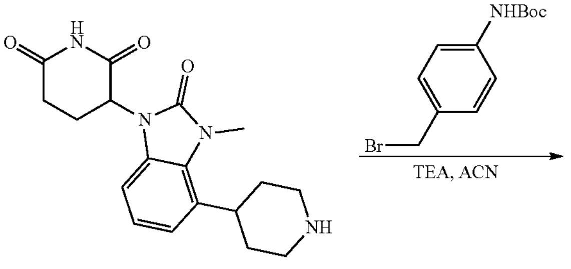

EL

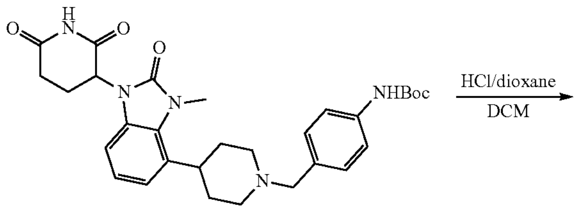

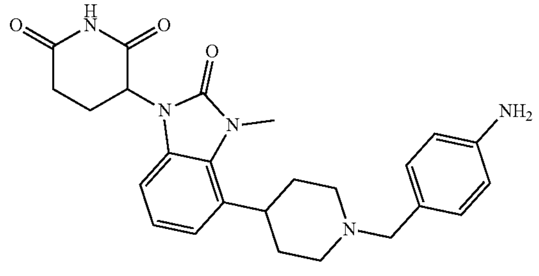

FF

Step 1—Tert-butyl N-[4-[[4-[1-(2,6-dioxo-3-piperidyl)-3-methyl-2-oxo-benzimidazol-4-yl]-1-piperidyl]methyl]phenyl]carbamate To a mixture of tert-butyl 3-[3-methyl-2-oxo-4-(4-piperidyl)benzimidazol-1-yl]piperidine-2,6-dione (300 mg, 876 umol, Intermediate EL) and tert-butyl N-[4-(bromomethyl)phenyl]carbamate (250 mg, 876 umol CAS #239074-27-2) in ACN (2 mL) was added TEA (88.6 mg, 876 umol) at 0° C. under $N_2$. The mixture was stirred at 40° C. for 10 minutes. On completion, the reaction mixture was concentrated in vacuo to give a residue. The crude product was purified by reversed-phase (TFA condition) to give the title compound (70.0 mg, 13% yield). 1H NMR (400 MHz, DMSO-$d_6$) δ 11.10 (s, 1H), 9.67-9.53 (m, 1H), 7.60-7.51 (m, 3H), 7.45-7.35 (m, 3H), 7.11-6.98 (m, 2H), 6.92 (d, J=7.6 Hz, 1H), 5.38 (dd, J=5.6, 12.4 Hz, 1H), 4.39 (d, J=11.2 Hz, 1H), 4.27 (d, J=3.6 Hz, 2H), 3.66-3.57 (m, 5H), 3.22-3.10 (m, 4H), 2.94-2.83 (m, 1H), 2.77-2.57 (m, 3H), 2.11-1.87 (m, 5H), 1.29 (t, J=7.2 Hz, 4H). LC-MS (ESI$^+$) m/z 548.5 $(M+H)^+$.

Step 2—3-[4-[1-[(4-Aminophenyl)methyl]-4-piperidyl]-3-methyl-2-oxo-benzimidazol-1-yl] piperidine-2,6-dione To a mixture of tert-butyl tert-butyl N-[4-[[4-[1-(2,6-dioxo-3-piperidyl)-3-methyl-2-oxo-benzimidazol-4-yl]-1-piperidyl]methyl]phenyl]carbamate (70.0 mg, 128 umol) in DCM (1.0 mL) was added HCl/dioxane (4 M, 0.3 mL) at 25° C. under $N_2$. The mixture was stirred at 25° C. for 30 minutes. On completion, the reaction mixture was concentrated in vacuo to give the title compound (50.0 mg, 88% yield). LC-MS (ESI$^+$) m/z 448.2 $(M+H)^+$.

3-[4-[2-[1-[[4-(Aminomethyl)phenyl]methyl]-4-piperidyl] ethynyl]-3-methyl-2-oxo-benzimidazol-1-yl]piperidine-2,6-dione (Intermediate FG)

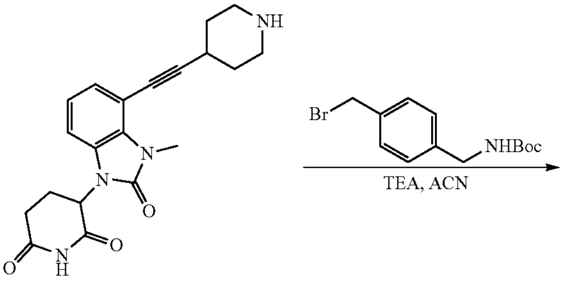

EU

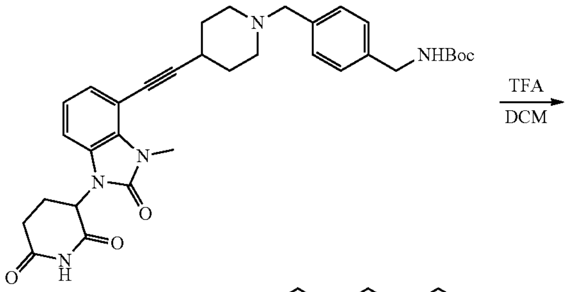

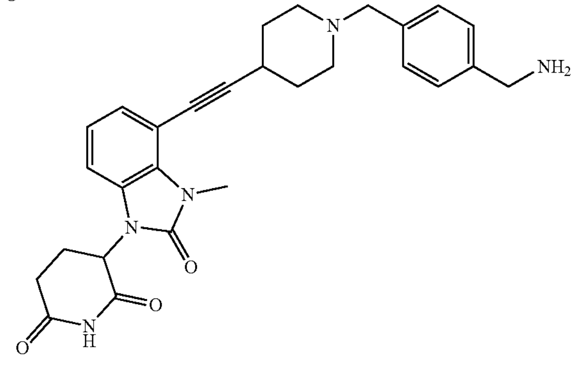

FG

Step 1—Tert-butyl N-[[4-[[4-[2-[1-(2,6-dioxo-3-piperidyl)-3-methyl-2-oxo-benzimidazol-4-yl]ethynyl]-1-piperidyl]methyl]phenyl]methyl]carbamate To a mixture of 3-[3-methyl-2-oxo-4-[2-(4-piperidyl)ethynyl]benzimidazol-1-yl]piperidine-2,6-dione (510 mg, 1.39 mmol, Intermediate EU) and tert-butyl N-[[4-(bromomethyl)phenyl]methyl]carbamate (836 mg, 2.78 mmol, CAS #187283-17-6) in ACN (5 mL) was added TEA (422 mg, 4.18 mmol). The mixture was stirred at 80° C. for 2 hours. On completion, the mixture was concentrated to give a residue. The residue was purified by reversed-phase CC (0.1% FA condition) to give the title compound (254 mg, 28% yield) as a yellow solid. $^1H$ NMR (400 MHz, DMSO- $d_6$) δ 11.16-11.07 (m, 1H), 9.74 (s, 1H), 7.56-7.42 (m, 3H), 7.32 (d, J=7.6 Hz, 2H), 7.19-7.11 (m, 1H), 7.03 (t, J=7.6 Hz, 1H), 5.38 (dd, J=5.2, 12.8 Hz, 1H), 4.38-4.26 (m, 2H), 4.16 (d, J=6.0 Hz, 2H), 3.62 (s, 3H), 3.44-3.25 (m, 3H), 3.15 (d, J=6.0 Hz, 1H), 3.04-2.82 (m, 3H), 2.77-2.58 (m, 2H), 2.20 (d, J=13.2 Hz, 1H), 2.02 (d, J=5.2 Hz, 2H), 1.91-1.79 (m, 1H), 1.39 (s, 9H). LC-MS (ESI$^+$) m/z 586.3 (M+H)$^+$.

Step 2—3-[4-[2-[1-[[4-(Aminomethyl)phenyl] methyl]-4-piperidyl]ethynyl]-3-methyl-2-oxo-benz-imidazol-1-yl]piperidine-2,6-dione To a solution of tert-butyl N-[[4-[[4-[2-[1-(2,6-dioxo-3-piperidyl)-3-methyl-2-oxo-benzimidazol-4-yl] ethynyl]-1-piperidyl]methyl]phenyl]methyl]carbamate (180 mg, 307 umol) in DCM (2 mL) was added TFA (701 mg, 6.15 mmol). The mixture was stirred at 0° C. for 1 hour. On completion, the mixture was concentrated to give the title compound (184 mg, 99% yield, TFA) as a yellow oil. LC-MS (ESI$^+$) m/z 486.3 (M+H)$^+$.

1-(2,6-Dioxo-3-piperidyl)-3-methyl-2-oxo-benzimi-dazole-5-carbaldehyde (Intermediate FH)

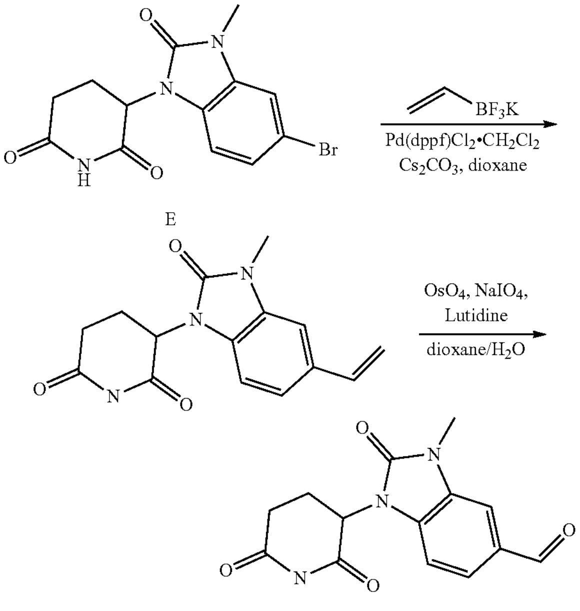

E

FH

Step 1—3-(3-Methyl-2-oxo-5-vinyl-benzimidazol-1-yl)piperidine-2,6-dione

A mixture of 3-(5-bromo-3-methyl-2-oxo-benzimidazol-1-yl)piperidine-2,6-dione (2.00 g, 5.91 mmol, Intermediate E), trifluoro-potassio-vinyl-boron (2.38 g, 17.74 mmol, CAS #13682-77-4), $Pd(dppf)Cl_2{\cdot}CH_2Cl_2$ (483 mg, 591 umol), $Cs_2CO_3$ (5.78 g, 17.7 mmol) in dioxane (30 mL) was degassed and purged with $N_2$ three times. Then the mixture was stirred at 120° C. for 16 hours under $N_2$ atmosphere. On completion, the mixture was quenched with the solution of sodium thiosulfate (20 mL) and extracted with dichloromethane (25 mL×3). The combined organic phase was dried over anhydrous sodium sulfate, filtered and concentrated to give a residue. The residue was purified by column chromatography ($SiO_2$, petroleum ether/ethyl acetate=1:0 to 0:1) to give the title compound (1.00 g, 59% yield) as a yellow solid. LC-MS (ESI$^+$) m/z 286.2 (M+H)$^+$.

Step 2—1-(2,6-Dioxo-3-piperidyl)-3-methyl-2-oxo-benzimidazole-5-carbaldehyde

A mixture of 3-(3-methyl-2-oxo-5-vinyl-benzimidazol-1-yl)piperidine-2,6-dione (1.00 g, 3.51 mmol), $OsO_4$ (26.7 mg, 105 umol), $NaIO_4$ (3.00 g, 14.0 mmol) and 2,6-lutidine (751 mg, 7.01 mmol) in a mixed solvents of dioxane (10 mL) and $H_2O$ (10 mL) was stirred at 0° C. for 1 hour. On completion, the mixture was quenched with water (30 mL) and extracted with dichloromethane (25 mL×3). The combined organic phase was dried over anhydrous sodium sulfate, filtered and concentrated to give a residue. The crude product was triturated with $Na_2S_2O_3$ (25 mL) at 25° C. for 10 minutes to give the title compound (320 mg, 31% yield) as a white solid. $^1H$ NMR (400 MHz, DMSO-$d_6$) δ 11.16 (s, 1H), 9.94 (s, 1H), 7.72-7.68 (m, 2H), 7.38-7.34 (m, 1H), 5.48 (dd, J=5.2, 12.8 Hz, 1H), 3.42 (s, 3H), 2.96-2.84 (m, 1H), 2.80-2.70 (m, 1H), 2.69-2.60 (m, 1H), 2.12-2.02 (m, 1H).

3-[3-Methyl-2-oxo-5-[[4-(4-piperidyloxy)-1-pip-eridyl]methyl]benzimidazol-1-yl]piperidine-2,6-dione (Intermediate FI)

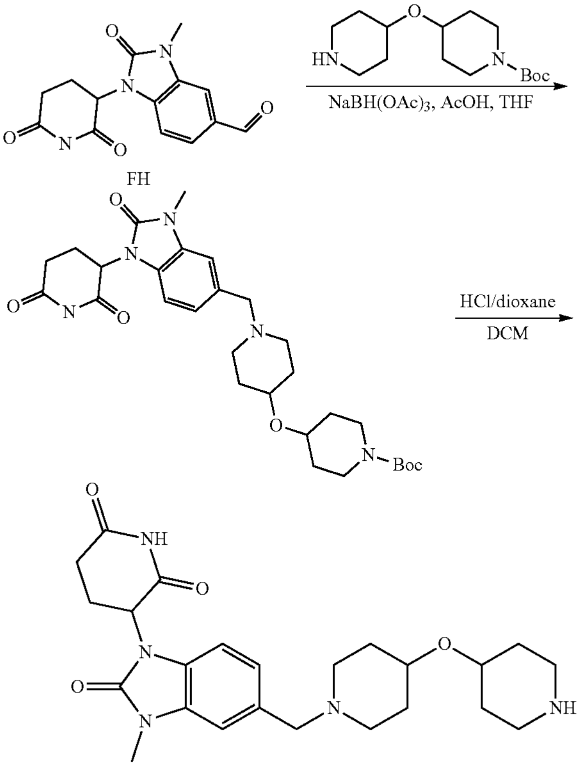

FH

FI

Step 1—Tert-butyl 4-[[1-[[1-(2,6-dioxo-3-pip-eridyl)-3-methyl-2-oxo-benzimidazol-5-yl]methyl]-4-piperidyl]oxy]piperidine-1-carboxylate Tert-butyl 4-(4-piperidyloxy)piperidine-1-carboxylate (348 mg, 1.23 mmol, CAS #845305-83-1) was dissolved in THF (5 mL) and DMF (5 mL). Then AcOH (2 mL) was added to reaction mixture until the pH 5-6 at 25° C. for 0.5 hour. Next, 1-(2,6-dioxo-3-piperidyl)-3-methyl-2-oxo-benzimidazole-5-carbaldehyde (320 mg, 1.11 mmol, Intermediate FH) and $NaBH(OAc)_3$ (472 mg, 2.23 mmol) was added to the mixture at 0° C. and the mixture was stirred for 0.5 hour. The mixture was then stirred at 25° C. for 1 hour. On completion, the mixture was quenched with water (20 mL) and extracted with ethyl acetate (25 mL×3). The combined organic phases were dried over anhydrous sodium sulfate, filtered and concentrated to give a residue. The residue was purified by reversed-phase HPLC (0.1% FA condition) to give the title compound (189 mg, 30% yield) as a white solid. $^1H$ NMR (400 MHz, DMSO-$d_6$) δ 11.12 (s, 1H), 9.36-9.08 (m, 1H), 7.32 (d, J=14.8 Hz, 1H), 7.24-7.12 (m, 2H), 5.40 (dd, J=5.2, 12.8 Hz, 1H), 4.32 (dd, J=4.4, 11.6 Hz, 2H), 3.68-3.54 (m, 4H), 3.36 (s, 4H), 3.28-3.16 (m, 3H), 3.16-2.84 (m, 7H), 2.84-2.58 (m, 3H), 2.16-1.96 (m, 6H), 1.94-1.86 (m, 1H), 1.84-1.64 (m, 4H), 1.58-1.46 (m, 1H), 1.39-1.36 (m, 10H), 1.36-1.20 (m, 3H); LC-MS (ESI$^+$) m/z 556.5 $(M+H)^+$.

Step 2—3-[3-Methyl-2-oxo-5-[[4-(4-piperidyloxy)-1-piperidyl]methyl]benzimidazol-1-yl]piperidine-2,6-dione To a solution of tert-butyl 4-[[1-[[1-(2,6-dioxo-3-piperidyl)-3-methyl-2-oxo-benzimidazol-5-yl]methyl]-4-piperidyl]oxy]piperidine-1-carboxylate (189 mg, 340 umol) in DCM (5 mL) was added HCl/dioxane (4 M, 850 uL). The mixture was stirred at 25° C. for 1 hour. On completion, the mixture was concentrated to give a residue to give the title compound (167 mg, 99% yield, HCl) as a white solid. LC-MS (ESI$^+$) m/z 456.5 $(M+H)^+$ 3-[5-[[4-[[1-[(4-Aminocyclohexyl)methyl]-4-piperidyl] oxyl-1-piperidyl] methyl]-3-methyl-2-oxo-benzimidazol-1-yl]piperidine-2,6-dione (Intermediate FJ)

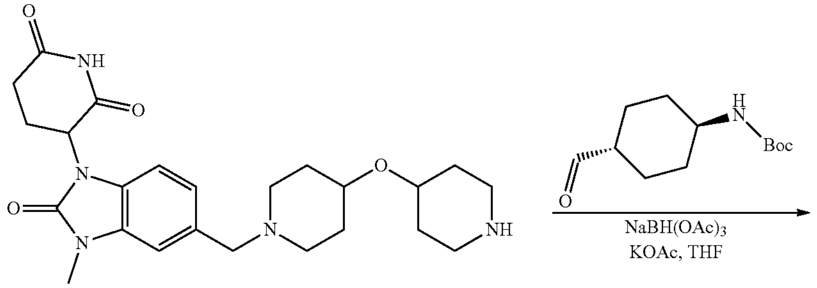

FI

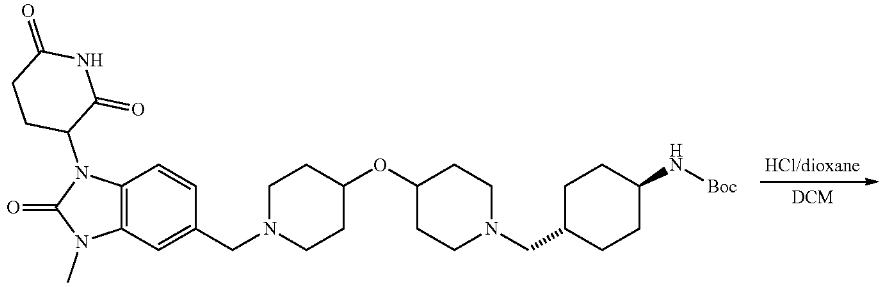

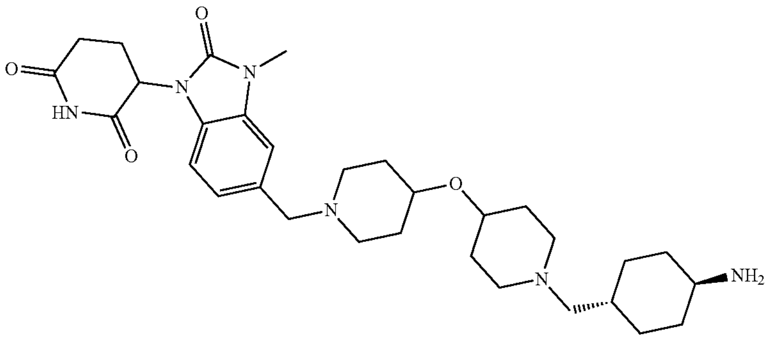

FJ

Step 1—Tert-butyl N-[4-[[4-[[1-[[1-(2,6-dioxo-3-piperidyl)-3-methyl-2-oxo-benzimidazol-5-yl]methyl]-4-piperidyl]oxy]-1-piperidyl]methyl]cyclohexyl]carbamate 3-[3-Methyl-2-oxo-5-[[4-(4-piperidyloxy)-1-piperidyl]methyl]benzimidazol-1-yl]piperidine-2,6-dione (167 mg, 339 umol, HCl, Intermediate FI) was dissolved in THF (8 mL). Next, KOAc (333 mg, 3.39 mmol) was added to solution until the pH 5-6, then the mixture was stirred at 25° C. for 0.5 hour. Then tert-butyl N-(4-formylcyclohexyl) carbamate (77.2 mg, 339 umol) and $NaBH(OAc)_3$ (216 mg, 1.02 mmol) was added at 25° C. over 0.5 hour. Then the mixture was stirred at 25° C. for 1 hour. On completion, the mixture was quenched with water (20 mL) and extracted with ethyl acetate (25 mL×3), The combined organic phase was dried over anhydrous sodium sulfate, filtered and concentrated to give a residue. The residue was purified by reversed-phase HPLC (0.5% FA condition) to give the title compound (75.0 mg, 33% yield) as a yellow solid. $^1$H NMR (400 MHz, $CDCl_3$) δ 8.42 (s, 1H), 7.30 (s, 1H), 7.24-7.14 (m, 2H), 5.42 (dd, J=5.2, 13.2 Hz, 1H), 4.24-4.06 (m, 2H), 3.88-3.72 (m, 2H), 3.44 (s, 3H), 3.32-3.17 (m, 4H), 3.12-2.60 (m, 9H), 2.26 (dd, J=4.8, 6.0 Hz, 1H), 2.12-1.96 (m, 4H), 1.96-1.72 (m, 10H), 1.38 (s, 9H), 1.32-1.00 (m, 5H); LC-MS ($ESI^+$) m/z 667.6 $(M+H)^+$.

Step 2—3-[5-[[4-[[1-[(4-Aminocyclohexyl)methyl]-4-piperidyl]oxy]-1-piperidyl]methyl]-3-methyl-2-oxo-benzimidazol-1-yl]piperidine-2,6-dione To a solution of tert-butyl N-[4-[[4-[[1-[[1-(2,6-dioxo-3-piperidyl)-3-methyl-2-oxo-benzimidazol-5-yl]methyl]-4-piperidyl]oxy]-1-piperidyl]methyl]cyclohexyl]carbamate (75.0 mg, 112 umol) in DCM (4 mL) was added HCl/dioxane (4 M, 28 uL). The mixture was stirred at 25° C. for 0.5 hour. On completion, the mixture was filtered and concentrated to give the title compound (67.0 mg, 111 umol, 99% yield, HCl) as a white solid. LC-MS ($ESI^+$) m/z 567.6 $(M+H)^+$.

9-Iodonon-1-yne (Intermediate FK)

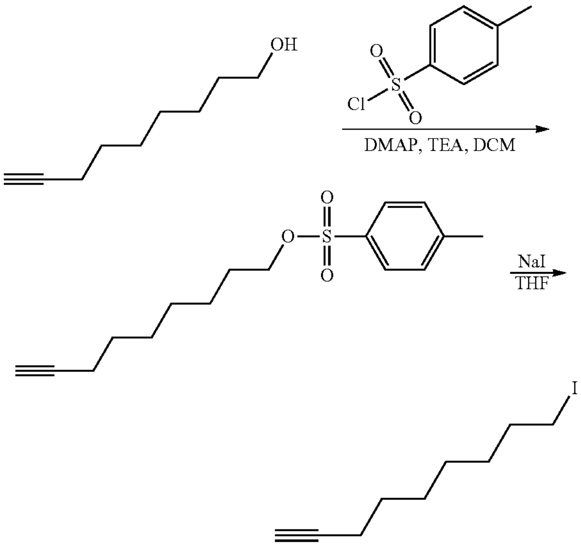

FK

Step 1—Non-8-ynyl 4-methylbenzenesulfonate

To a solution of non-8-yn-1-ol (1.00 g, 7.13 mmol, CAS #10160-28-8) in DCM (10 mL) was added DMAP (87.1 mg, 713 umol), TEA (2.16 g, 21.3 mmol) and 4-methylbenzenesulfonyl chloride (1.63 g, 8.56 mmol, CAS #98-59-9). The mixture was stirred at 25° C. for 2 hours. On completion, the reaction mixture was poured into water (10 mL) and extracted with ethyl acetate (15 mL×3). The combined organic phase was dried with anhydrous $Na_2SO_4$, filtered and concentrated in vacuo to give the title compound (2.00 g, 6.79 mmol, 95% yield) as a brown oil.

Step 2—9-Iodonon-1-yne

To a solution of non-8-ynyl 4-methylbenzenesulfonate (1.00 g, 3.40 mmol) in THF (15 mL) was added NaI (610 mg, 4.08 mmol, CAS #7681-82-5). The mixture was stirred at 60° C. for 12 hours. On completion, the mixture was concentrated in vacuo to give a residue. The residue was purified by column chromatography ($SiO_2$, petroleum ether/ethyl acetate=1:0 to 99:1) to give the title compound (700 mg, 2.80 mmol, 82% yield) as a colorless oil. $^1$H NMR (400 MHz, $CDCl_3$-d) δ=3.22-3.15 (m, 1H), 3.19 (t, J=7.2 Hz, 1H), 2.21-2.15 (m, 2H), 1.94 (t, J=2.8 Hz, 1H), 1.87-1.78 (m, 2H), 1.59-1.48 (m, 2H), 1.45-1.38 (m, 4H), 1.36-1.30 (m, 2H).

3-[4-[2-[1-[[4-(Aminomethyl)cyclohexyl]methyl]-4-piperidyl]vinyl-3-methyl-2-oxo-benzimidazol-1-yl]piperidine-2,6-dione (Intermediate FL)

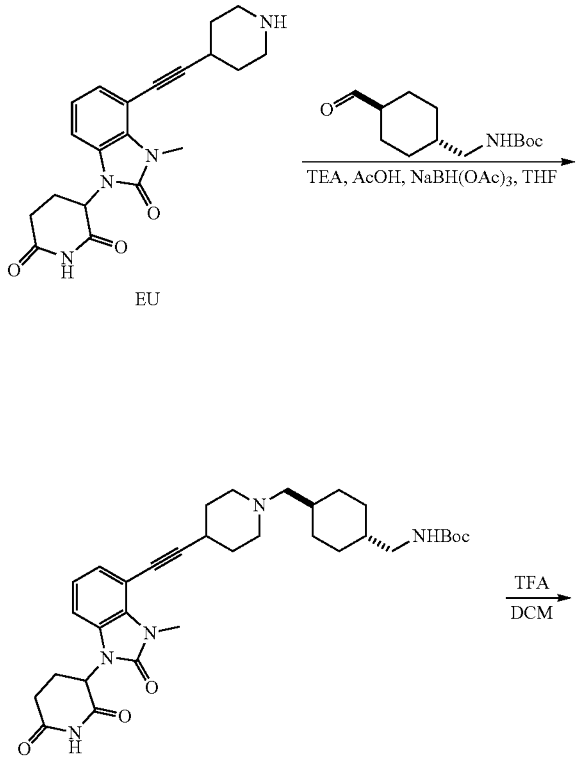

-continued

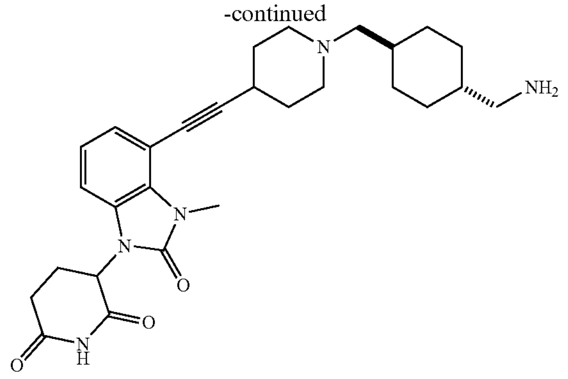

FL

Step 1—Tert-butyl N-[[4-[[4-[2-[1-(2,6-dioxo-3-piperidyl)-3-methyl-2-oxo-benzimidazol-4-yl]vinyl]-1-piperidyl]methyl]cyclohexyl]methyl]carbamate To a solution of 3-[3-methyl-2-oxo-4-[2-(4-piperidyl)ethynyl]benzimidazol-1-yl]piperidine-2,6-dione (473 mg, 1.29 mmol, TFA, Intermediate EU) in DMF (3 mL) and THF (9 mL) was added AcOK (1.27 g, 12.9 mmol), then the mixture was stirred at 25° C. for 10 minutes. Next, tert-butyl N-[(4-formylcyclohexyl) methyl]carbamate (467 mg, 1.94 mmol, CAS #181308-56-5) was added to the mixture and stirred at 25° C. for 5 minutes. Finally, $NaBH(OAc)_3$ (1.37 g, 6.45 mmol) was added to the mixture at 25° C. and the reaction mixture was stirred at 25° C. for 14 hours. On completion, the mixture was concentrated to give a residue. The residue was purified by reversed-phase CC (0.1% TFA condition) to give the title compound (473 mg, 59% yield) as a brown solid. $^1H$ NMR (400 MHz, $CDCl_3$) δ 11.23 (s, 1H), 8.29 (s, 1H), 7.03-6.98 (m, 1H), 6.83 (d, J=11.2 Hz, 1H), 6.75 (d, J=8.0 Hz, 2H), 5.73 (dd, J=10.0, 11.2 Hz, 1H), 5.29-5.18 (m, 1H), 4.60 (s, 1H), 3.75-3.72 (m, 1H), 3.67-3.60 (m, 2H), 3.56 (s, 3H), 3.46 (d, J=3.6 Hz, 3H), 3.01-2.91 (m, 4H), 2.91-2.83 (m, 2H), 2.82-2.70 (m, 4H), 2.61-2.46 (m, 3H), 2.27-2.22 (m, 1H), 2.15-2.09 (m, 1H), 2.02-1.66 (m, 9H). LC-MS ($ESI^+$) m/z 594.4 $(M+H)^+$.

Step 2—3-[4-[2-[1-[[4-(Aminomethyl)cyclohexyl]methyl]-4-piperidyl]vinyl]-3-methyl-2-oxo-benzimidazol-1-yl]piperidine-2,6-dione To a solution of tert-butyl N-[[4-[[4-[2-[1-(2,6-dioxo-3-piperidyl)-3-methyl-2-oxo-benzimidazol-4-yl] vinyl]-1-piperidyl]methyl]cyclohexyl]methyl]carbamate (201 mg, 338 umol) in DCM (2 mL) was added TFA (617 mg, 5.41 mmol) and the mixture was stirred at 0° C. for 2 hours. On completion, the mixture was concentrated to give the title compound (205 mg, 99% yield, TFA) as a white oil. LC-MS ($ESI^+$) m/z 494.2 $(M+H)^+$.

1-[7-[2-(4-Piperidyl)ethynyl] imidazo[1,2-a]pyridin-3-yl]hexahydropyrimidine-2,4-dione (Intermediate FM)

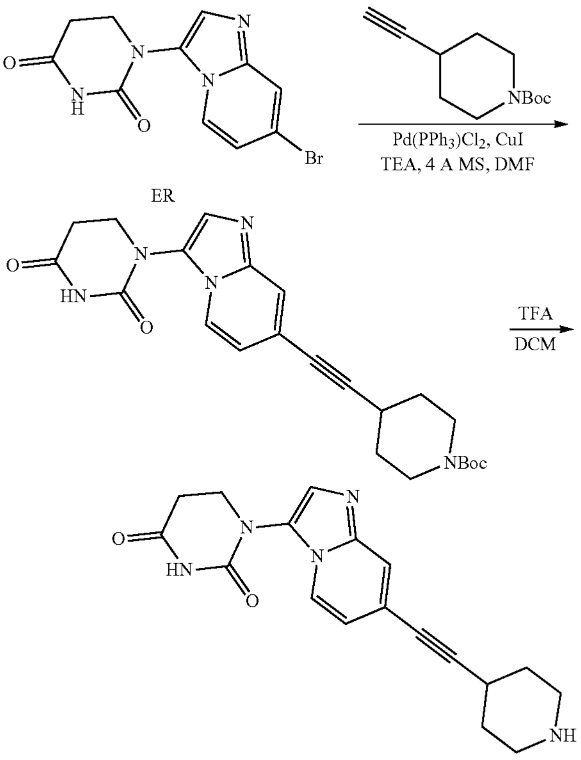

ER

FM

Step 1—Tert-butyl 4-[2-[3-(2,4-dioxohexahydropyrimidin-1-yl)imidazo[1,2-a]pyridin-7-yl]ethynyl]piperidine-1-carboxylate To a solution of 1-(7-bromoimidazo[1,2-a]pyridin-3-yl)hexahydropyrimidine-2,4-dione (400 mg, 1.29 mmol, Intermediate ER) and tert-butyl 4-ethynylpiperidine-1-carboxylate (269 mg, 1.29 mmol CAS #287192-97-6), 4 Å molecular sieves (100 mg) in DMF (5 mL), $Pd(PPh_3)Cl_2$ (90.3 mg, 129 μmol), CuI (24.5 mg, 129 umol), TEA (1.31 g, 12.9 mmol) was added. The mixture was stirred at 80° C. for 8 hours under $N_2$ atmosphere. On completion, the mixture was concentrated in vacuo. The mixture was purified by reversed-phase HPLC (0.1% TFA condition) to give the title compound (400 mg, 70% yield) as a yellow oil. LC-MS ($ESI^+$) m/z 438.3 $(M+H)^+$.

Step 2—1-[7-[2-(4-Piperidyl)ethynyl]imidazo[1,2-a]pyridin-3-yl]hexahydropyrimidine-2,4-dione (TFA)

To a solution of e tert-butyl 4-[2-[3-(2,4-dioxohexahydropyrimidin-1-yl)imidazo[1,2-a]pyridin-7-yl]ethynyl]piperidine-1-carboxylate (150 mg, 342 umol), DCM (2 mL), TFA (39.0 mg, 342 μmol) was stirred at 25° C. for 2 hours. On completion, the mixture was concentrated in vacuo to give the title compound (120 mg, 77% yield) as brown oil. LC-MS ($ESI^+$) m/z 338.3 $(M+H)^+$.

1-[7-[2-[1-[(4-Aminocyclohexyl)methyl]-4-piperidyl] ethynyl] imidazo[1,2-a]pyridin-3-yl]hexahydropyrimidine-2,4-dione (Intermediate FN)

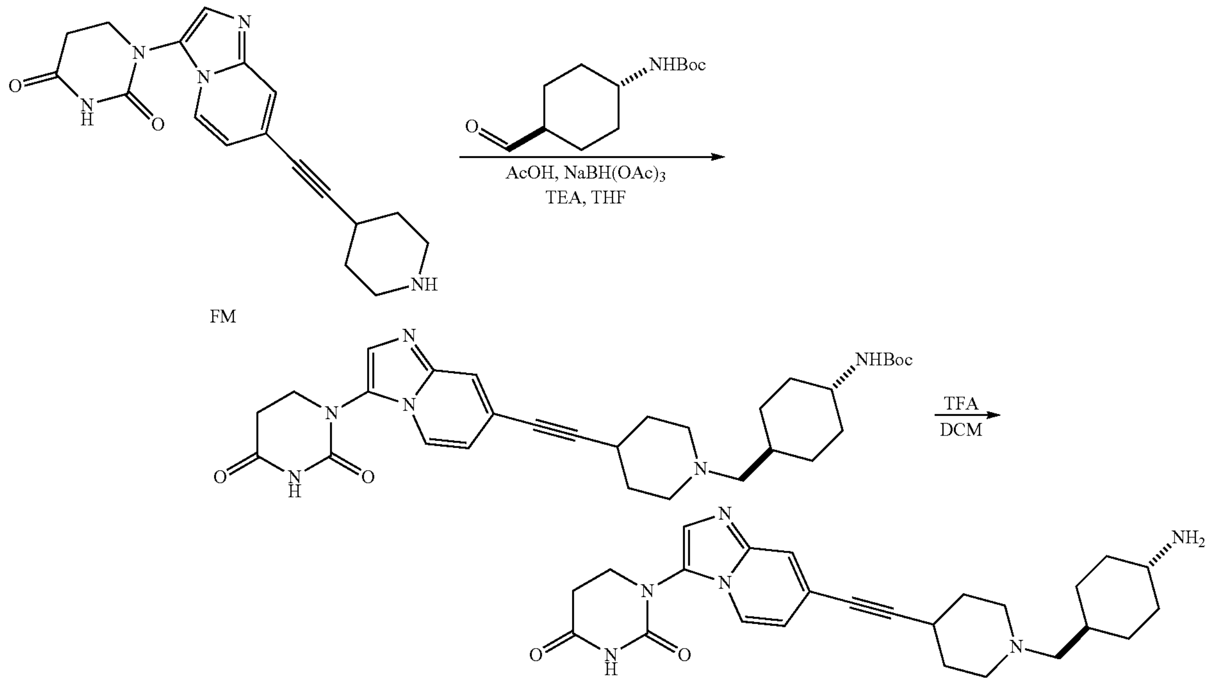

FM

FN

Step 1—Tert-butyl N-[4-[[4-[2-[3-(2,4-dioxohexahydropyrimidin-1-yl)imidazo[1,2-a]pyridin-7-yl] ethynyl]-1-piperidyl]methyl]cyclohexyl]carbamate To a solution of 1-[7-[2-(4-piperidyl)ethynyl]imidazo[1,2-a]pyridin-3-yl]hexahydropyrimidine-2,4-dione (120 mg, 265 umol, TFA, Intermediate FM) in THF (2 mL), TEA (26.9 mg, 265 umol) was added. The resulting mixture was stirred for 0.25 hour. Then AcOH (15.9 mg, 265 umol) was added to adjust the pH to 6. Next, tert-butyl N-(4-formylcyclohexyl)carbamate (60.4 mg, 265 umol, CAS #181308-56-5) was added and he mixture was stirred at 0° C. for 0.25 hour. Finally, $NaBH(OAc)_3$ (112 mg, 531 umol) was added to the reaction mixture at 0° C., and then stirred for 3.5 hours at 25° C. On completion, the mixture was concentrated in vacuo. The residue was purified by reversed-phase HPLC (0.1% FA) to give the title compound (100 mg, 68% yield) as a white solid. LC-MS ($ESI^+$) m/z 549.5 $(M+H)^+$.

Step 2—1-[7-[2-[1-[(4-Aminocyclohexyl)methyl]-4-piperidyl]ethynyl]imidazo[1,2-a]pyridin-3-yl]hexahydropyrimidine-2,4-dione (TFA)

To a solution of tert-butyl N-[4-[[4-[2-[3-(2,4-dioxohexahydropyrimidin-1-yl)imidazo[1,2-a]pyridin-7-yl]ethynyl]-1-piperidyl]methyl]cyclohexyl]carbamate (75.0 mg, 136 umol), DCM (1 mL), TFA (15.5 mg, 136 umol) was stirred at 25° C. for 1 hour. On completion, the mixture was concentrated in vacuo to give the title compound (60.0 mg, 78% yield, TFA) as a brown oil. LC-MS ($ESI^+$) m/z 449.3 $(M+H)^+$.

Methyl 4-(methylamino)cyclohexanecarboxylate (Intermediate FO)

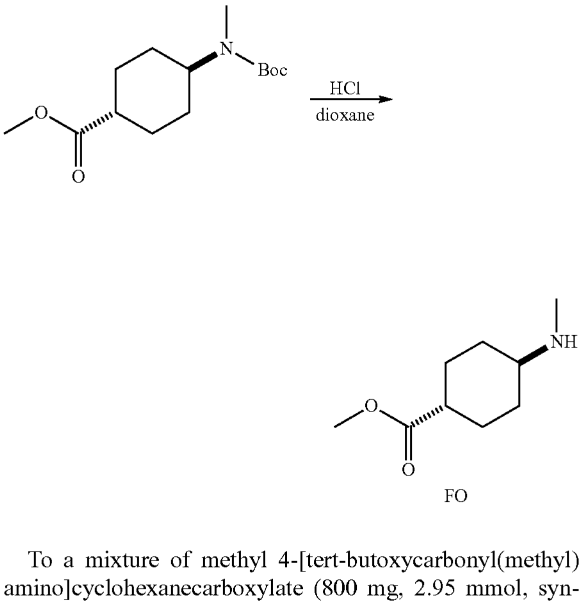

FO

To a mixture of methyl 4-[tert-butoxycarbonyl(methyl)amino]cyclohexanecarboxylate (800 mg, 2.95 mmol, synthesized via Step 1 of Intermediate EP) in DCM (4 mL) was added HCl/dioxane (2 ml) at 25° C. under $N_2$. The mixture was stirred at 25° C. for 1 hour. On completion, the reaction mixture was concentrated in vacuo to give the title compound (500 mg, 100% crude yield) as white solid. LC-MS ($ESI^+$) m/z 172.1 $(M+H)^+$.

4-[Chloro-(3-chloro-2-fluoro-phenyl)-oxo-dispiro[BLAH]carbonyl]-methyl-amino]cyclohexanecarboxylic acid (Intermediate FP)

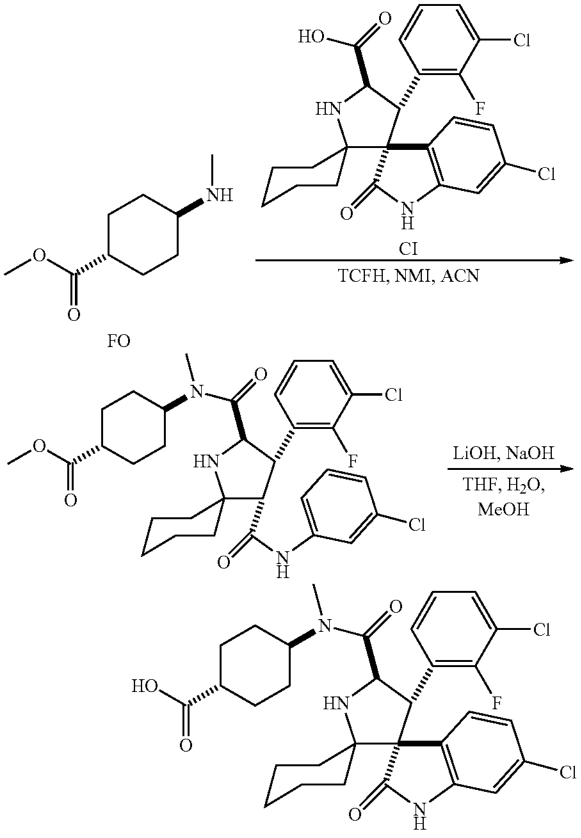

FO

FP

Step 1-Methyl 4-[[chloro-(3-chloro-2-fluoro-phenyl)-oxo-dispiro[BLAH]carbonyl]-methyl-amino] cyclohexanecarboxylate To a solution of chloro-(3-chloro-2-fluoro-phenyl)-oxo-dispiro[BLAH]carboxylic acid (300 mg, 647 umol, Intermediate CI), methyl 4-(methylamino)cyclohexanecarboxylate (400 mg, 2.34 mmol, Intermediate FO) in ACN (4 mL) was added [chloro(dimethylamino)methylene]-dimethyl-ammonium; hexafluorophosphate (454 mg, 1.62 mmol) and 1-methylimidazole (1.70 g, 20.7 mmol). The mixture was stirred at 25° C. for 5 minutes. On completion, the reaction mixture was concentrated in vacuo to give a residue. The residue was purified by reversed-phase (0.1% TFA condition) to give the title compound (200 mg, 46% yield) as a yellow oil. $^1$H NMR (400 MHz, DMSO-$d_6$) δ 7.71-7.38 (m, 3H), 7.33-7.17 (m, 1H), 7.11 (d, J=8.4 Hz, 1H), 6.75 (s, 1H), 5.00-4.62 (m, 1H), 4.28-3.85 (m, 1H), 3.77 (d, J=5.2 Hz, 3H), 3.64 (s, 4H), 2.78-2.71 (m, 3H), 2.08 (s, 1H), 1.94-1.93 (m, 3H), 1.64-1.58 (m, 12H), 1.27-1.10 (m, 2H). LC-MS (ESI$^+$) m/z 616.3 (M+H)$^+$.

Step 2—4-[Chloro-(3-chloro-2-fluoro-phenyl)-oxo-dispiro[BLAH]carbonyl]-methyl-amino] cyclohexanecarboxylic acid To a solution of methyl 4-[[chloro-(3-chloro-2-fluoro-phenyl)-oxo-dispiro[BLAH]carbonyl]-methyl-amino]cyclohexanecarboxylate (200 mg, 324 umol) in THF (3 mL), $H_2O$ (1.5 mL) and MeOH (3 mL) was added LiOH—$H_2O$ (81.6 mg, 1.95 mmol) and NaOH (77.8 mg, 1.95 mmol). The mixture was stirred at 25° C. for 2 hours. On completion, the reaction mixture was concentrated in vacuo to give a residue. The crude product was purified by reversed-phase flash (0.1% TFA condition) to give the title compound (53.0 mg, 27% yield) as a white solid. $^1$H NMR (400 MHz, DMSO-$d_6$) δ 11.31-10.88 (m, 1H), 7.70-7.60 (m, 1H), 7.58-7.44 (m, 2H), 7.31-7.17 (m, 1H), 7.11 (dd, J=1.6, 8.4 Hz, 1H), 6.75 (s, 1H), 5.69-5.18 (m, 1H), 4.96-4.72 (m, 1H), 4.24-4.10 (m, 1H), 4.04-3.74 (m, 2H), 2.78-2.61 (m, 4H), 2.15-2.07 (m, 1H), 2.00-1.86 (m, 3H), 1.72-1.31 (m, 12H), 1.06 (d, J=3.2 Hz, 2H).

3-[5-[3-[4-[(4-Aminophenyl)methyl]piperazin-1-yl]propyl]-3-methyl-2-oxo-benzimidazol-1-yl]piperidine-2,6-dione (Intermediate FQ)

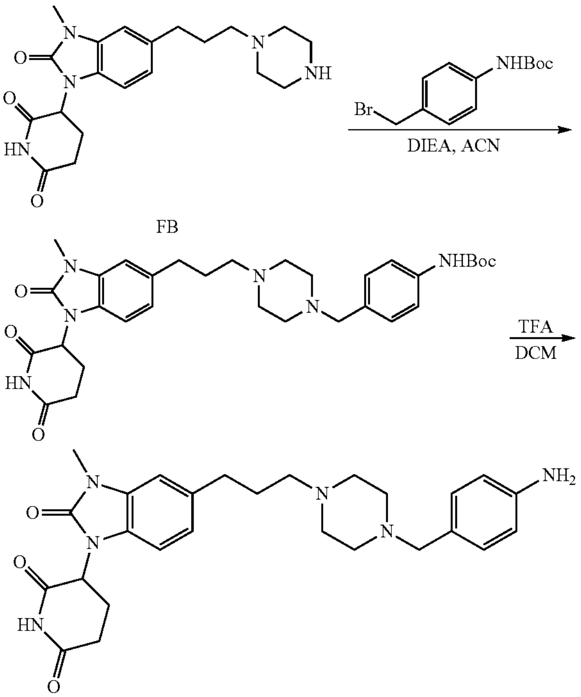

FB

FQ

Step 1—Tert-butyl N-[4-[[4-[3-[1-(2,6-dioxo-3-piperidyl)-3-methyl-2-oxo-benzimidazol-5-yl] propyl]piperazin-1-yl]methyl]phenyl]carbamate To a solution of 3-[3-methyl-2-oxo-5-(3-piperazin-1-yl-propyl)benzimidazol-1-yl]piperidine-2,6-dione (290 mg, 752 umol, Intermediate FB), tert-butyl N-[4-(bromomethyl)phenyl]carbamate (215 mg, 75.0 umol, CAS #239074-27-2) in ACN (6 mL) was added DIEA (291 mg, 2.26 mmol). The mixture was stirred at 25° C. for 20 minutes. On completion, the reaction mixture was concentrated in vacuo to give a residue. The crude product was purified by reversed-phase flash (0.10% TFA condition) to give the title compound (200 mg, 40% yield) as a yellow solid. $^1$H NMR (400 MHz, DMSO-$d_6$) δ 11.09 (s, 1H), 9.47 (s, 1H), 7.48 (d, 1H), 7.37-7.30 (d, 2H), 7.19 (s, 1H), 7.11-6.99 (m, 2H), 6.90 (dd, J=1.2, 8.4 Hz, 1H), 5.35 (dd, J=5.6, 12.8 Hz, 1H), 4.18-3.87 (s, 2H), 3.68-3.46 (m, 2H), 3.33 (s, 3H), 3.27-3.13 (m, 2H), 3.05 (s, 3H), 2.97-2.83 (m, 2H), 2.76-2.65 (m, 3H), 2.06-1.90 (m, 3H), 1.48 (s, 9H). LC-MS (ESI$^+$) m/z 591.7 $(M+H)^+$.

Step 2—3-[5-[3-[4-[(4-Aminophenyl)methyl]piperazin-1-yl]propyl]-3-methyl-2-oxo-benzimidazol-1-yl]piperidine-2,6-dione To a mixture of tert-butyl N-[4-[[4-[3-[1-(2,6-dioxo-3-piperidyl)-3-methyl-2-oxo-benzimidazol-5-yl] propyl]piperazin-1-yl]methyl]phenyl]carbamate (150 mg, 253 umol) in DCM (2 mL) was added TFA (0.4 ml) at 25° C. under $N_2$. The mixture was stirred at 25° C. for 2 hours. On completion, the reaction mixture was concentrated in vacuo to give the title compound (110 mg, 90% yield) as a yellow oil. LC-MS (ESI$^+$) m/z 491.1 $(M+H)^+$.

3-[5-[2-[1-(4-Aminobicyclo[2.2.2]octane-1-carbonyl)-4-piperidyl] ethynyl]-3-methyl-2-oxo-benzimidazol-1-yl]piperidine-2,6-dione (Intermediate FR)

Step 1—Tert-butyl N-[4-[4-[2-[1-(2,6-dioxo-3-piperidyl)-3-methyl-2-oxo-benzimidazol-5-yl]ethynyl] piperidine-1-carbonyl]-1-bicyclo[2.2.2]octanyl]carbamate To a solution of 3-[3-methyl-2-oxo-5-[2-(4-piperidyl) ethynyl]benzimidazol-1-yl]piperidine-2,6-dione (500 mg, 1.04 mmol, TFA, Intermediate CT) and 4-(tert-butoxycarbonylamino)bicyclo[2.2.2]octane-1-carboxylic acid (280 mg, 1.04 mmol, CAS #863304-76-1) in DMF (12 mL) was adjusted to pH=8 with DIEA (538 mg, 4.16 mmol), then HATU (399 mg, 1.05 mmol) was added into the mixture. The mixture was stirred at 25° C. for 1 hour. On completion, the mixture was poured into the water (60 ml) and many precipitated were emerged. The precipitates were collected by filtration and were purified by column chromatography ($SiO_2$, DCM/EA=1:0 to 1:2) to give the title compound (549 mg, 85% yield) as a yellow solid. $^1H$ NMR (400 MHz, $CDCl_3$) δ 8.03 (s, 1H), 7.10-7.05 (m, 1H), 6.66 (d, J=8.4 Hz, 1H), 5.15-5.09 (m, 1H), 4.35-4.26 (m, 1H), 3.95-3.80 (m, 2H), 3.36 (s, 3H), 2.23-2.14 (m, 1H), 1.95-1.88 (m, 6H), 1.86-1.77 (m, 9H), 1.67-1.61 (m, 2H), 1.58 (s, 6H), 1.36 (s, 9H).

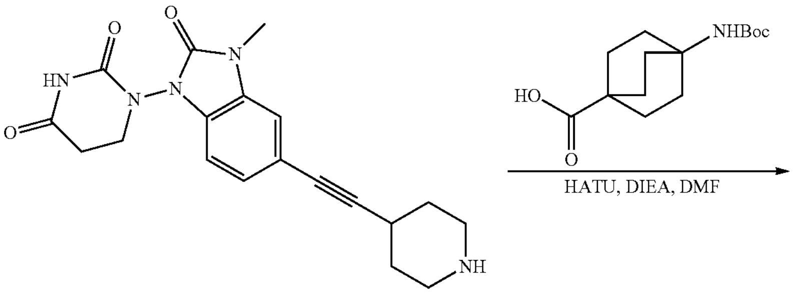

CT

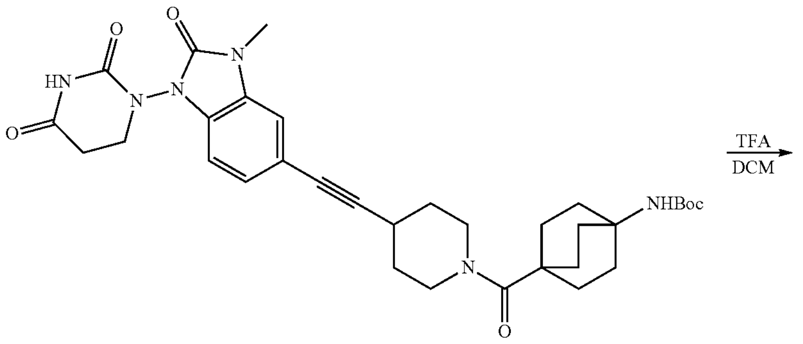

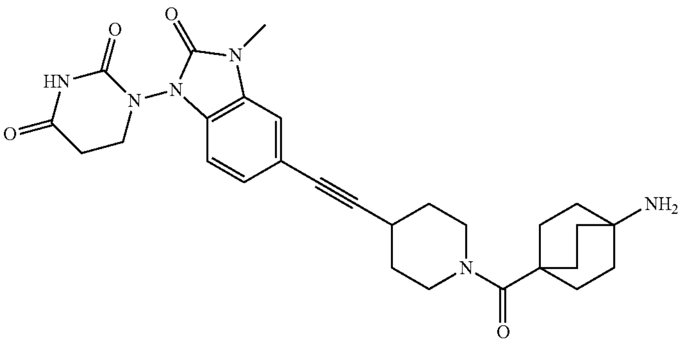

FR

Step 2—3-[5-[2-[1-(4-Aminobicyclo[2.2.2]octane-1-carbonyl)-4-piperidyl] ethynyl]-3-methyl-2-oxo-benzimidazol-1-yl]piperidine-2,6-dione To a mixture of tert-butyl N-[4-[4-[2-[1-(2,6-dioxo-3-piperidyl)-3-methyl-2-oxo-benzimidazol-5-yl]ethynyl]piperidine-1-carbonyl]-1-bicyclo[2.2.2]octanyl]carbamate (300 mg, 486 umol) in DCM (6 mL) was added TFA (3.08 g, 27.0 mmol). The mixture was stirred at 0° C. for 0.5 hour. On completion, the mixture was concentrated to give the title compound (306 mg, 99% yield, TFA) as a yellow semi-solid. LC-MS (ESI$^+$) m/z 518.4 (M+H)$^+$.

3-[5-[2-[1-[(3-Aminocyclobutyl)methyl]azetidin-3-yl]ethynyl]-3-methyl-2-oxo-benzimidazol-1-yl]piperidine-2,6-dione (Intermediate FS)

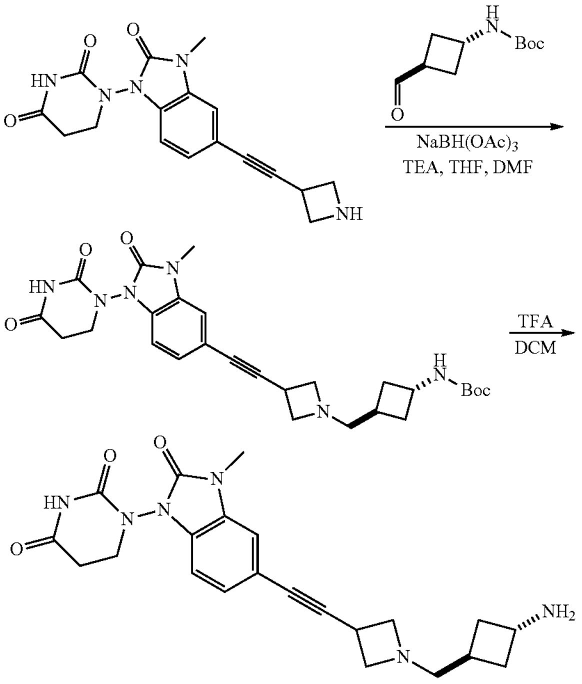

FS

Step 1—Tert-butyl N-[3-[[3-[2-[1-(2,6-dioxo-3-piperidyl)-3-methyl-2-oxo-benzimidazol-5-yl]ethynyl]azetidin-1-yl]methyl]cyclobutyl]carbamate To a solution of 3-[5-[2-(azetidin-3-yl)ethynyl]-3-methyl-2-oxo-benzimidazol-1-yl]piperidine-2,6-dione (220 mg, 650 umol, synthesized via Steps 1-2 of Intermediate CH) in a mixed solvents of DMF (1.0 mL) and THF (3.0 mL) was added TEA (197 mg, 1.95 mmol) until the pH=8-9. Next, AcOH (117 mg, 1.95 mmol) was added until pH=5-7. Then tert-butyl N-(3-formylcyclobutyl) carbamate (259 mg, 1.30 mmol) was added. The reaction mixture was stirred at 0° C. for 0.5 hours, then NaBH(OAc)$_3$ (206 mg, 975 umol) was added in portions. Then the reaction mixture was then stirred at 0° C. for 2 hours. On completion, the reaction mixture was concentrated in vacuo to give a residue. The crude product was purified by reversed-phase flash (0.1% TFA condition) to give the title compound (30.0 mg, 8% yield) as a white solid. $^1$H NMR (400 MHz, DMSO-d$_6$) δ 11.18-11.10 (m, 1H), 7.33-7.25 (m, 1H), 7.21-7.08 (m, 3H), 5.46-5.33 (m, 1H), 4.49-4.25 (m, 2H), 3.88-3.70 (m, 2H), 3.35 (s, 4H), 3.21 (d, J=5.6 Hz, 1H), 2.90 (s, 1H), 2.74-2.63 (m, 2H), 2.35-2.27 (m, 3H), 2.12-1.95 (m, 4H), 1.72-1.66 (m, 1H), 1.37 (s, 9H). LC-MS (ESI$^+$) m/z 522.1 (M+H)$^+$.

Step 2—3-[5-[2-[1-[(3-Aminocyclobutyl)methyl] azetidin-3-yl]ethynyl]-3-methyl-2-oxo-benzimidazol-1-yl]piperidine-2,6-dione To a mixture of tert-butyl N-[3-[[3-[2-[1-(2,6-dioxo-3-piperidyl)-3-methyl-2-oxo-benzimidazol-5-yl]ethynyl]azetidin-1-yl]methyl]cyclobutyl]carbamate (30.0 mg, 57.5 umol) in DCM (1.0 mL) was added TFA (0.3 ml) at 25° C. under $N_2$. The mixture was stirred at 25° C. for 1 hour. On completion, the reaction mixture was concentrated in vacuo to give the title compound (22 mg) as a yellow oil. LC-MS (ESI$^+$) m/z 422.4 (M+H)$^+$.

Tert-butyl N-(4-formyl-1-bicyclo[2.2.2]octanyl)carbamate (Intermediate FT)

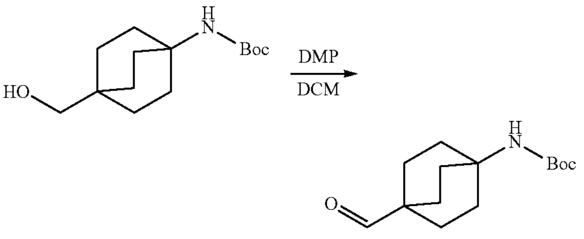

FT

To a solution of tert-butyl N-[4-(hydroxymethyl)-1-bicyclo[2.2.2]octanyl]carbamate (0.50 g, 1.96 mmol, CAS #1333384-43-2) in DCM (1 mL) was added DMP (913 mg, 2.15 mmol). The mixture was stirred at 0° C. for 0.5 hour. On completion, the mixture was quenched with water (5 mL) and extracted with ethyl acetate (5 mL×3). The combined organic phases were dried over anhydrous sodium sulfate, filtered and concentrated to give the title compound (450 mg, 90% yield) as a white solid. $^1$H NMR (400 MHz, CDCl3) δ 9.37 (s, 1H), 1.83-1.79 (m, 6H), 1.67-1.35 (m, 6H), 1.35 (s, 1H).

3-[5-[5-[(4-Amino-1-bicyclo[2.2.2]octanyl])methyl-methyl-amino]pentyl]-3-methyl-2-oxo-benzimidazol-1-yl]piperidine-2,6-dione (Intermediate FU)

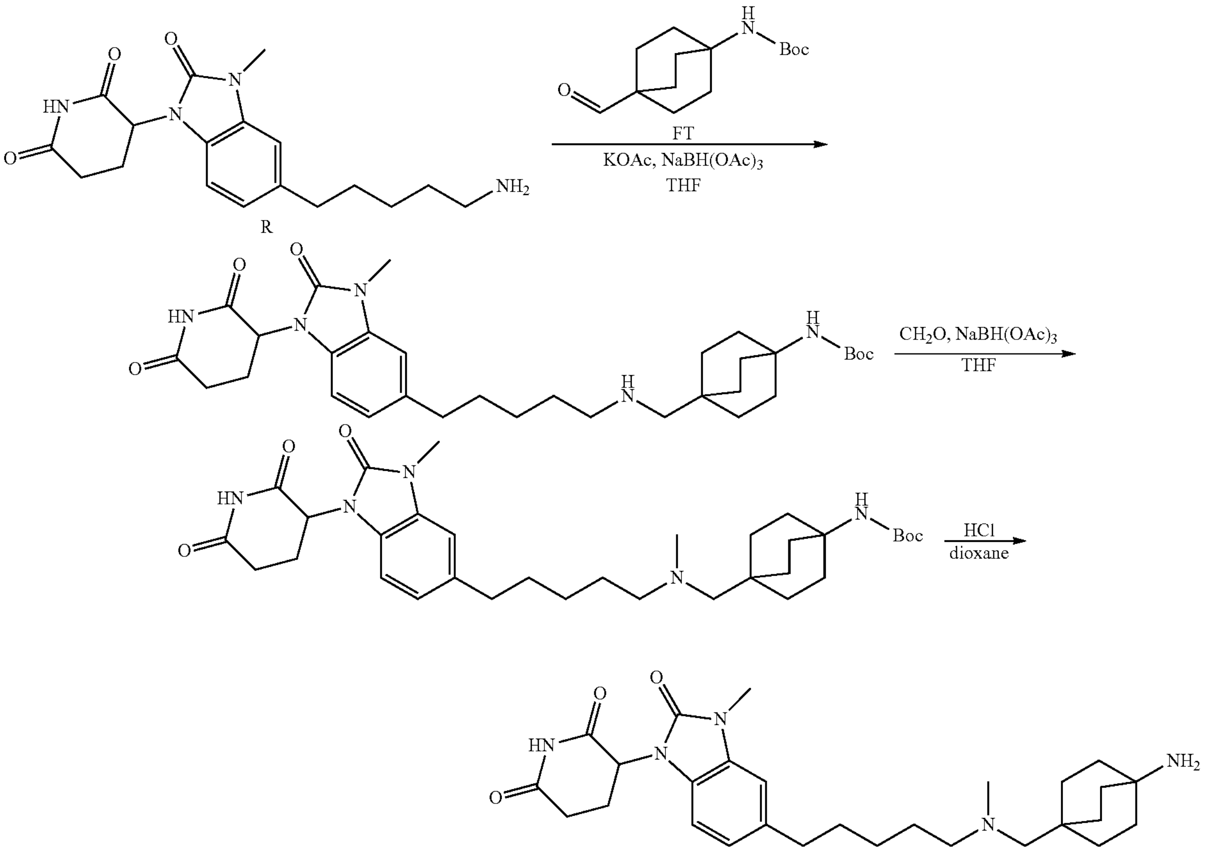

FU

Step 1—Tert-butyl N-[4-[[5-[1-(2,6-dioxo-3-piperidyl)-3-methyl-2-oxo-benzimidazol-5-yl] pentylamino]methyl]-1-bicyclo[2.2.2]octanyl]carbamate To a mixture of 3-[5-(5-aminopentyl)-3-methyl-2-oxo-benzimidazol-1-yl]piperidine-2,6-dione (257 mg, 674 umol, HCl salt, Intermediate R), tert-butyl N-(4-formyl-1-bicyclo[2.2.2]octanyl)carbamate (170 mg, 674 umol, Intermediate FT) and KOAc (397 mg, 4.05 mmol) in THF (2 mL) was added $NaBH(OAc)_3$ (286 mg, 1.35 mmol) at 20° C. The mixture was stirred at 20° C. for 3 hours. On completion, the mixture was quenched with $H_2O$ (10 mL), then extracted with EtOAc (3×10 mL). The EtOAc solution was dried over $Na_2SO_4$, filtered, and concentrated in vacuo to give the title compound (320 mg, 81% yield) as a white solid. $^1H$ NMR (400 MHz, $CDCl_3$) δ 8.28 (s, 1H), 6.86-6.77 (m, 2H), 6.75-6.66 (m, 1H), 5.26-5.20 (m, 1H), 4.53-4.33 (m, 1H), 3.48-3.36 (m, 3H), 2.91 (d, J=9.2 Hz, 3H), 2.84-2.77 (m, 1H), 2.77-2.55 (m, 5H), 2.32-2.13 (m, 1H), 1.82 (s, 8H), 1.62 (s, 8H), 1.42 (s, 9H), 1.33 (d, J=6.4 Hz, 2H).

Step 2—Tert-butyl N-[4-[[5-[1-(2,6-dioxo-3-piperidyl)-3-methyl-2-oxo-benzimidazol-5-yl]pentyl-methyl-amino]methyl]-1-bicyclo[2.2.2]octanyl]carbamate To a mixture of tert-butyl N-[4-[[5-[1-(2,6-dioxo-3-piperidyl)-3-methyl-2-oxo-benzimidazol-5-yl] pentylamino]methyl]-1-bicyclo[2.2.2]octanyl]carbamate (150 mg, 257 umol), and KOAc (75.9 mg, 773 umol) in THF (2 mL) was added paraformaldehyde (150 mg) and $NaBH(OAc)_3$ (81.9 mg, 386 umol) at 20° C. The mixture was stirred at 20° C. for 3 hours. On completion, the mixture was quenched with $H_2O$ (10 mL), then extracted with EtOAc (3×10 mL). The EtOAc solution was dried over $Na_2SO_4$, filtered, and concentrated in vacuo to give the title compound (110 mg, 71% yield) as a white solid. LC-MS ($ESI^+$) m/z 596.3 $(M+H)^+$.

Step 3—3-[5-[5-[(4-Amino-1-bicyclo[2.2.2]octanyl) methyl-methyl-amino]pentyl]-3-methyl-2-oxo-benzimidazol-1-yl]piperidine-2,6-dione To a mixture of tert-butyl N-[4-[[5-[1-(2,6-dioxo-3-piperidyl)-3-methyl-2-oxo-benzimidazol-5-yl]pentyl-methyl-amino]methyl]-1-bicyclo[2.2.2]octanyl]carbamate (90.0 mg, 151 umol,) in DCM (2 mL) was added HCl/dioxane (4 M, 188 uL) at 20° C. The mixture was stirred at 20° C. for 3 hours. On completion, the mixture was concentrated to give the title compound (80 mg, 99% yield, HCl salt) as a white solid. LC-MS ($ESI^+$) m/z 496.5 $(M+H)^+$.

Chloro-(3-chloro-2-fluoro-phenyl)-trimethyl-oxo-dispiro[BLAH]carboxylic acid (Intermediate FV)

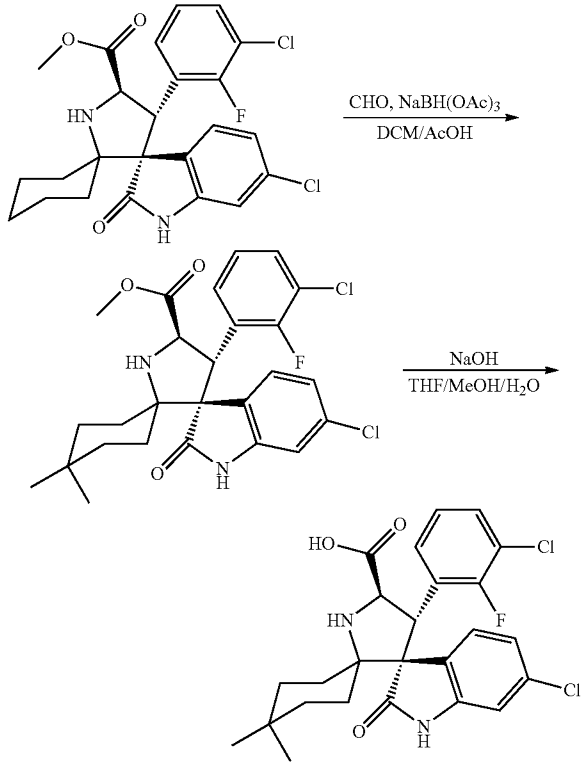

FV

Step 1—Methyl chloro-(3-chloro-2-fluoro-phenyl)-trimethyl-oxo-dispiro[BLAH]carboxylate To a mixture of methyl chloro-(3-chloro-2-fluoro-phenyl)-dimethyl-oxo-dispiro[BLAH]carboxylate (300 mg, 593 umol, synthesized via Steps 1-3 of Intermediate CN) in DCM (5 mL), AcOH (5 mL) was added paraformaldehyde (300 mg, 5.94 mmol) and $NaBH(OAc)_3$ (1.26 g, 5.94 mmol). The mixture was stirred at 50° C. for 2 hours. On completion, the mixture was extracted with ethyl acetate (3×10 mL). The organic phase was dried over $Na_2SO_4$, filtered, and concentrated in vacuo to give the title compound (300 mg, 97% yield) as a white solid. LC-MS ($ESI^+$) m/z 519.4 $(M+H)^+$.

Step 2—Chloro-(3-chloro-2-fluoro-phenyl)-trimethyl-oxo-dispiro[BLAH]carboxylic acid To a mixture of methyl chloro-(3-chloro-2-fluoro-phenyl)-trimethyl-oxo-dispiro[BLAH]carboxylate (300 mg, 577 umol) in $H_2O$ (5 mL), THF (5 mL) and MeOH (5 mL) was added NaOH (115 mg, 2.89 mmol). The mixture was stirred at 50° C. for 2 hours. On completion, the mixture was adjusted to pH=3-4 with HCl (1 N HCl) and extracted with DCM (3×10 mL). The organic phase was dried over $Na_2SO_4$, filtered, and concentrated in vacuo to give the title compound (180 mg, 61% yield) as a yellow solid. LC-MS ($ESI^+$) m/z 505.1 $(M+H)^+$.

1-[7-(3-aminopropylamino)imidazo[1,2-a]pyridin-3-yl]hexahydropyrimidine-2,4-dione (Intermediate FW)

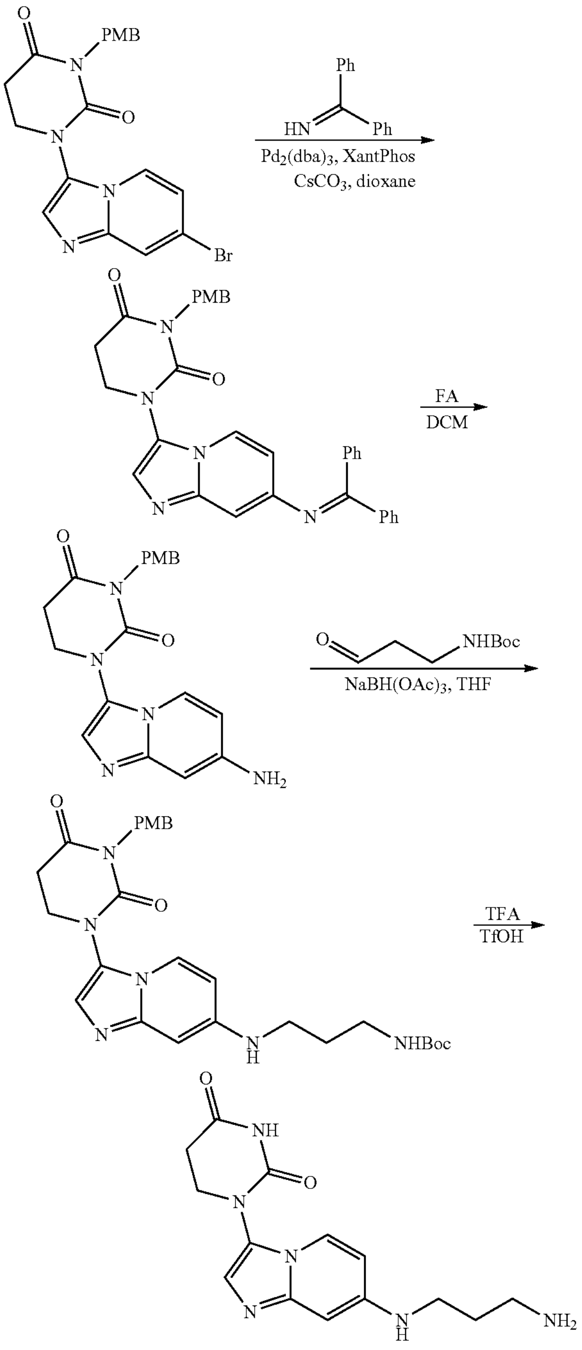

FW

Step 1—Ethyl 8-fluoro-1,4-dioxaspiro[4.5]decane-8-carboxylate

To a solution of 1-(7-bromoimidazo[1,2-a]pyridin-3-yl)-3-[(4-methoxyphenyl)methyl]hexahydropyrimidine-2,4-dione (1.30 g, 3.03 mmol, synthesized via Steps 1-2 of Intermediate ER), diphenylmethanimine (1.10 g, 6.06 mmol, CAS #1013-88-3), $Pd_2(dba)_3$ (277 mg, 303 μmol), XantPhos (350 mg, 605 umol) and $Cs_2CO_3$ (2.96 g, 9.09 mmol) in dioxane (25 mL) was degassed and purged with $N_2$ three times. Then the mixture was stirred at 100° C. for 16 hours under $N_2$ atmosphere. On completion, the mixture was quenched with saturated $NH_4Cl$ (800 mL) and with water (20 mL), then extracted with DCM (25×3 mL). The combined organic phase was dried over anhydrous sodium sulfate, then the residue concentrated in vacuo. The mixture was purified by column chromatography ($SiO_2$, DCM/methanol=1:0 to 0:1) to give the title compound (1.30 g, 81% yield)) as a black solid. LC-MS ($ESI^+$) m/z 530.2 $(M+H)^+$.

Step 2—1-(7-Aminoimidazo [1,2-a]pyridin-3-yl)-3-[(4-methoxyphenyl)methyl]hexahydropyrimidine-2,4-dione To a solution of 1-[7-(benzhydrylideneamino)imidazo[1,2-a]pyridin-3-yl]-3-[(4-methoxyphenyl) methyl]hexahydropyrimidine-2,4-dione (1.20 g, 2.27 mmol) in DCM (10 mL) formic acid (108 mg, 2.27 mmol) was added. Then the mixture was stirred at 25° C. for 1 hour. On completion, the mixture was concentrated in vacuo. The mixture was purified by reversed-phase HPLC (0.1% FA) to give the title compound (600 mg, 52% yield) as green solid. $^1H$ NMR (400 MHz, DMSO-$d_6$) δ=8.32 (d, J=7.6 Hz, 1H), 7.79 (s, 1H), 7.25 (d, J=8.4 Hz, 3H), 7.13 (d, J=6.4 Hz, 2H), 6.87 (d, J=8.8 Hz, 2H), 6.62 (d, J=2.0 Hz, 1H), 4.81 (s, 2H), 3.83 (t, J=6.8 Hz, 2H), 3.73 (s, 3H), 3.02 (s, 2H), LC-MS ($ESI^+$) m/z 366.0 $(M+H)^+$.

Step 3—Tert-butyl N-[3-[[3-[3-[(4-methoxyphenyl) methyl]-2,4-dioxo-hexahydropyrimidin-1-yl]imidazo [1,2-a]pyridin-7-yl]amino]propyl]carbamate To a solution of 1-(7-aminoimidazo[1,2-a]pyridin-3-yl)-3-[(4-methoxyphenyl)methyl]hexahydropyrimidine-2,4-dione (300 mg, 821 umol), tert-butyl N-(3-oxopropyl)carbamate (213 mg, 1.23 mmol) in dioxane (5 mL), was added tetraisopropoxytitanium (233 mg, 821 umol). The resulting mixture was stirred at 80° C. for 11.5 hours. Then $NaBH_3CN$ (103 mg, 1.64 mmol) was added and the resulting mixture was stirred at 25° C. for 0.5 hour. On completion, the mixture was partitioned between DMF (5 mL) and $H_2O$ (5 mL). The separated organic layer was washed with aqueous DCM (5 mL×3), dried over $Na_2SO_4$, filtered and concentrated in vacuo. The mixture was purified by reversed-phase HPLC (0.1% TFA ) to give the title compound (65.0 mg, 15% yield) as a white solid, LC-MS ($ESI^+$) m/z 523.4 $(M+H)^+$.

Step 4—1-[7-(3-Aminopropylamino)imidazo[1,2-a] pyridin-3-yl]hexahydropyrimidine-2,4-dione A solution of tert-butyl N-[3-[[3-[3-[(4-methoxyphenyl) methyl]-2,4-dioxo-hexahydropyrimidin-1-yl] imidazo[1,2-a]pyridin-7-yl]amino]propyl]carbamate (20.0 mg, 38.2 umol), TFA (87.2 mg, 765 umol), and TfOH (5.74 mg, 38.2 umol) was stirred at 25° C. for 1 hour. On completion, the mixture was concentrated in vacuo. The residue was purified by pre-HPLC (column: Waters Xbridge 150×25 mm 10 um; mobile phase: [water (10 mM $NH_4HCO_3$)-ACN]; B %: 0%-15%, 11 min) to give the title compound (6.75 mg, 57% yield) as a white solid. $^1H$ NMR (400 MHz, DMSO-$d_6$) δ=11.99-10.82 (m, 1H), 6.48 (d, J=7.6 Hz, 1H), 5.73 (s, 1H), 5.08-5.02 (m, 1H), 4.83-4.75 (m, 2H), 2.32 (t, J=6.8 Hz, 4H), 1.66 (s, 4H), 1.39 (t, J=6.4 Hz, 2H), 0.36-0.27 (m, 2H). LC-MS ($ESI^+$) m/z 303.1 $(M+H)^+$.

3-amino-1-methyl-cyclobutanol (Intermediate FX) (CAS #1363381-26-3)

FX

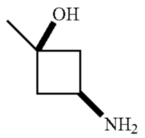

3-[5-[2-[1-(2-Aminoethyl)-4-piperidyl]ethyl]-3-methyl-2-oxo-benzimidazol-1-yl]piperidine-2,6-dione (Intermediate FY)

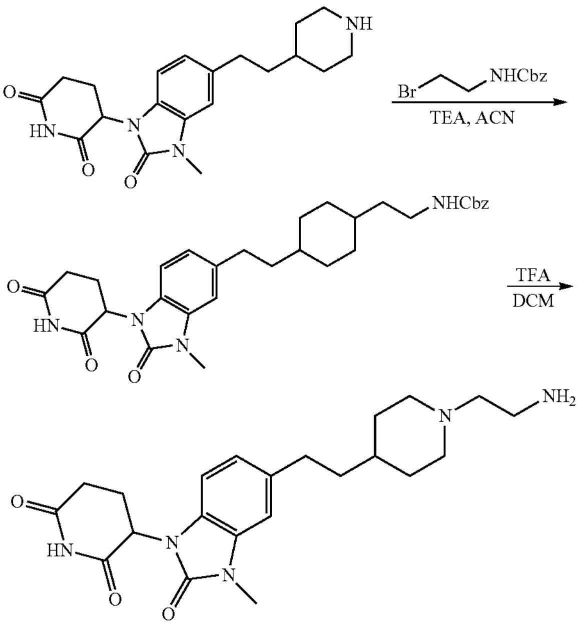

FY

Step 1—Benzyl N-[2-[4-[2-[1-(2,6-dioxo-3-piperidyl)-3-methyl-2-oxo-benzimidazol-5-yl]ethyl]-1-piperidyl]ethyl]carbamate To a solution of benzyl N-(2-bromoethyl)carbamate (227 mg, 881 umol, CAS #53844-02-3), 3-[3-methyl-2-oxo-5-[2-(4-piperidyl)ethyl]benzimidazol-1-yl]piperidine-2,6-dione (395 mg, 734 umol, TFA, synthesized via Steps 1-2 of Intermediate CL) in ACN (15 mL) was added TEA (743 mg, 7.34 mmol). Then the mixture was stirred at 80° C. for 16 hours. On completion, the mixture was concentrated to give a residue. The mixture was purified by reversed-phase HPLC (0.1% FA condition) to give the title compound (180 mg, 45% yield) as a white solid. $^1H$ NMR (400 MHz, CHLOROFORM-d) δ=12.19-11.96 (m, 1H), 8.31-8.14 (m, 1H), 7.42-7.31 (m, 5H), 6.92-6.80 (m, 2H), 6.74 (br d, J=7.6 Hz, 1H), 6.62-6.52 (m, 1H), 5.27-5.18 (m, 1H), 5.17-5.08 (m, 2H), 3.80-3.52 (m, 4H), 3.45 (s, 3H), 3.24-3.04 (m, 2H), 3.03-2.54 (m, 8H), 2.32-2.17 (m, 1H), 1.90-1.76 (m, 5H), 1.74-1.62 (m, 2H), 1.56-1.41 (m, 1H).

Step 2—3-[5-[2-[1-(2-Aminoethyl)-4-piperidyl] ethyl]-3-methyl-2-oxo-benzimidazol-1-yl]piperidine-2,6-dione To a solution of benzyl N-[2-[4-[2-[1-(2,6-dioxo-3-piperidyl)-3-methyl-2-oxo-benzimidazol-5-yl] ethyl]-1-piperidyl]ethyl]carbamate (120 mg, 219 umol) in DCM (3.0 mL) was added HBr/HOAC (219 umol, 3.0 mL). Then the mixture was stirred at 25° C. for 12 hours. On completion, the mixture was concentrated to give a residue. The mixture was purified by reversed-phase HPLC (0.1% FA condition) to give the title compound (113 mg, 100% yield) as a yellow oil. LC-MS (ESI+) m/z 414.3 $(M+H)^+$.

3-[4-[[4-[[1-[(4-Aminophenyl)methyl]-4-piperidyl] oxy]-1-piperidyl]methyl]-3-methyl-2-oxo-benzimidazol-1-yl]piperidine-2,6-dione (Intermediate FZ)

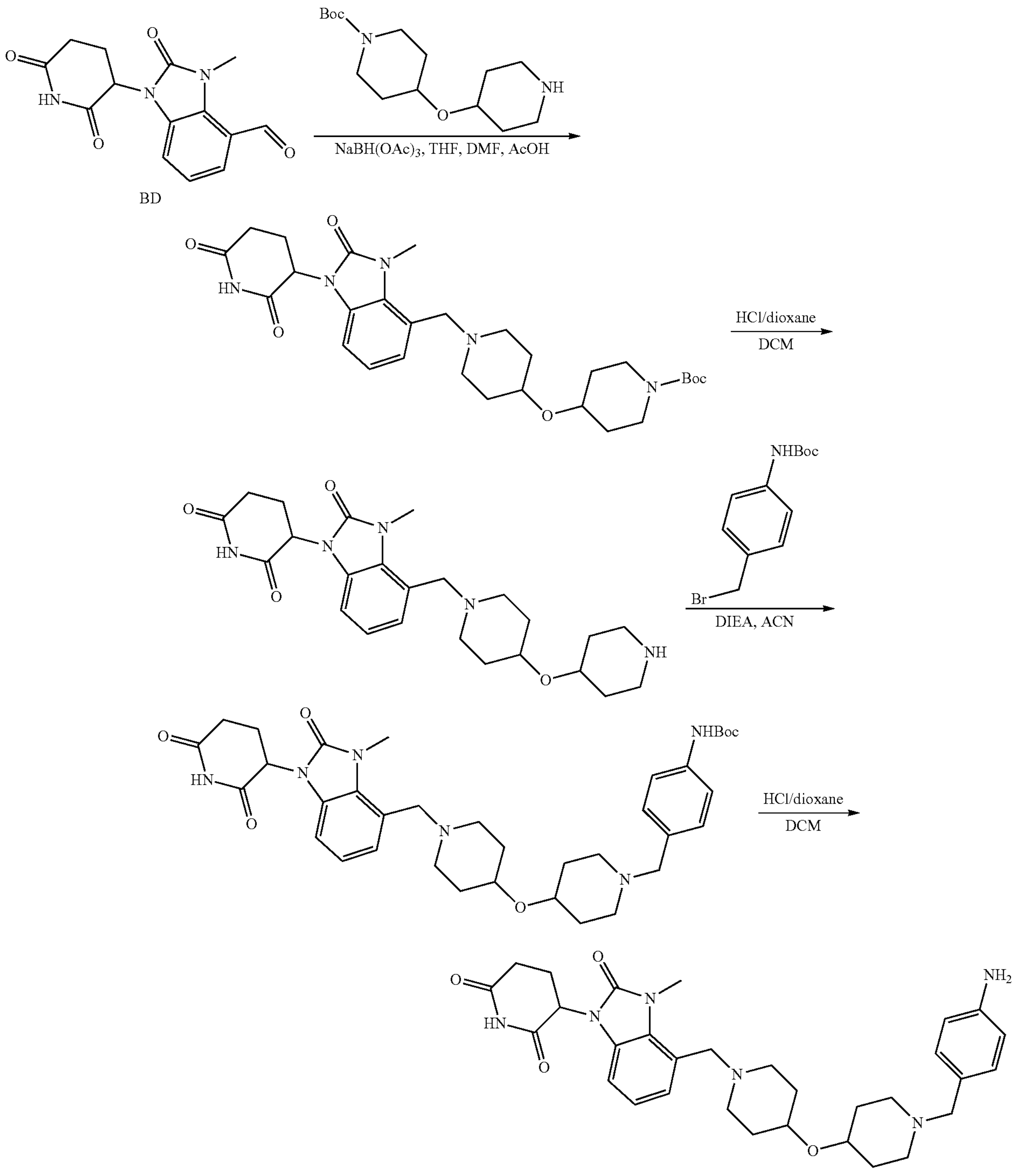

BD

FZ

Step 1—Tert-butyl 4-[[1-[[1-(2,6-dioxo-3-piperidyl)-3-methyl-2-oxo-benzimidazol-4-yl]methyl]-4-piperidyl]oxy]piperidine-1-carboxylate To a solution of 1-(2,6-dioxo-3-piperidyl)-3-methyl-2-oxo-benzimidazole-4-carbaldehyde (1.00 g, 3.48 mmol, Intermediate BD) and tert-butyl 4-(4-piperidyloxy)piperidine-1-carboxylate (990 mg, 3.48 mmol, CAS #845305-83-1) in THF (5 mL), DMF (5 mL) and HOAc (3 mL) at 80° C. for 1 hour. Next, $NaBH(OAc)_3$ (1.48 g, 6.96 mmol) was added at 25° C., then the mixture was stirred at 80° C. for 16 hours. On completion, the mixture was quenched with the solution of sodium thiosulfate (20 mL) and extracted with dichloromethane (25 mL×3). The combined organic phases were dried over anhydrous sodium sulfate, filtered and concentrated to give a residue. The residue was purified by reversed-phase HPLC (0.5% FA condition) to give the title compound (500 mg, 26% yield) as a yellow oil. LC-MS ($ESI^+$) m/z 556.3 $(M+H)^+$.

Step 2—3-[3-Methyl-2-oxo-4-[[4-(4-piperidyloxy)-1-piperidyl]methyl]benzimidazol-1-yl]piperidine-2,6-dione To a solution of tert-butyl 4-[[1-[[1-(2,6-dioxo-3-piperidyl)-3-methyl-2-oxo-benzimidazol-4-yl] methyl]-4-piperidyl]oxy]piperidine-1-carboxylate (250 mg, 450 umol) in DCM (6 mL) was added HCl/dioxane (4 M, 112 uL). The mixture was stirred at 25° C. for 0.5 hour. On completion, the mixture was filtered and concentrated to give the title compound (220 mg, 99% yield, HCl salt) as a white solid. LC-MS ($ESI^+$) m/z 456.3 $(M+H)^+$.

Step 3—Tert-butyl N-[4-[[4-[[1-[[1-(2,6-dioxo-3-piperidyl)-3-methyl-2-oxo-benzimidazol-4-yl] methyl]-4-piperidyl]oxy]-1-piperidyl]methyl]phenyl] carbamate To a solution of tert-butyl N-[4-(bromomethyl)phenyl] carbamate (78.5 mg, 274 umol, CAS #239074-27-2) and 3-[3-methyl-2-oxo-4-[[4-(4-piperidyloxy)-1-piperidyl] methyl]benzimidazol-1-yl]piperidine-2,6-dione (150 mg, 305 umol, HCl) in ACN (8 mL) was added DIEA (39.4 mg, 305 umol) at 25° C. The mixture was stirred at 25° C. for 16 hours. On completion, the mixture was filtered and concentrated to give a residue. The residue was purified by reversed-phase HPLC (0.5% FA condition) to give the title compound (30.0 mg, 15% yield) as a white solid. LC-MS ($ESI^+$) m/z 661.4 $(M+H)^+$.

Step 4—3-[4-[[4-[[1-[(4-Aminophenyl)methyl]-4-piperidyl]oxy]-1-piperidyl]methyl]-3-methyl-2-oxo-benzimidazol-1-yl]piperidine-2,6-dione To a solution of tert-butyl N-[4-[[4-[[1-[[1-(2,6-dioxo-3-piperidyl)-3-methyl-2-oxo-benzimidazol-4-yl] methyl]-4-piperidyl]oxy]-1-piperidyl]methyl]phenyl]carbamate (30.0 mg, 45.4 umol) in DCM (4 mL) was added HCl/dioxane (4M, 100 uL). The mixture was stirred at 25° C. for 0.5 hour. On completion, the mixture was concentrated to give the title compound (27.0 mg, 99% yield, HCl salt) as a yellow solid. LC-MS ($ESI^+$) m/z 561.4 $(M+H)^+$.

3-[3-Methyl-2-oxo-4-(3-piperazin-1-ylpropyl)benzimidazol-1-yl]piperidine-2,6-dione (Intermediate GA)

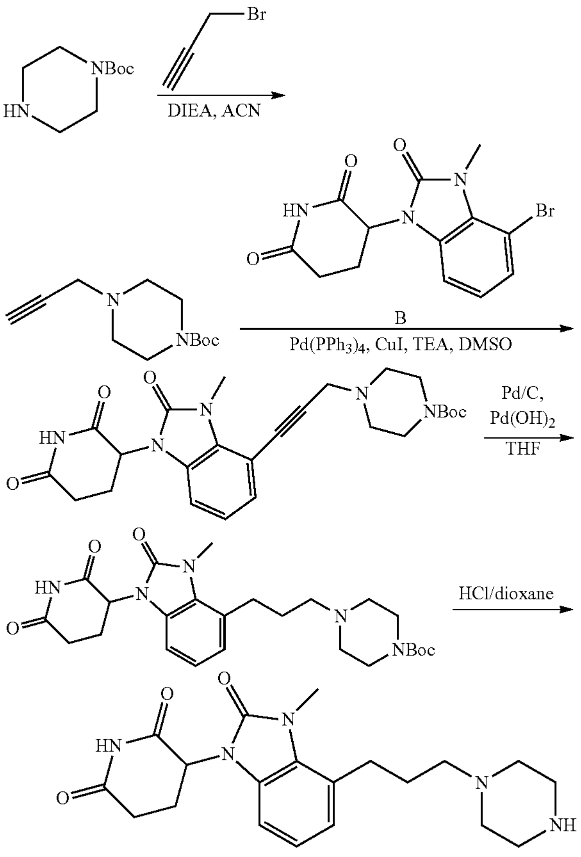

GA

Step 1—Tert-butyl 4-prop-2-ynylpiperazine-1-carboxylate

To a mixture of 3-bromoprop-1-yne (1.28 g, 10.7 mmol, CAS #106-96-7), tert-butyl piperazine-1-carboxylate; hydrochloride (2.39 g, 10.7 mmol, CAS #57260-71-6) and DIEA (2.50 g, 19.3 mmol) in ACN (20 mL) was stirred at 25° C. for 2 hours. On completion, the reaction mixture was added water (100 mL). The aqueous layer was extracted with ethyl acetate (50 ml×5). The organic layer was separated and concentrated under reduced pressure to give the crude product. The crude product was purified by column chromatography ($SiO_2$, Petroleum ether/Ethyl acetate=I/O to 2/1), concentrated under reduced pressure to give product (1.90 g, 85% yield) as a yellow oil. $^1H$ NMR (400 MHz, DMSO-$d_6$) δ 3.37-3.29 (m, 4H), 3.28 (d, J=2.4 Hz, 2H), 3.13 (t, J=2.4 Hz, 1H), 2.42-2.35 (m, 4H), 1.39 (s, 9H).

Step 2—Tert-butyl 4-[3-[1-(2,6-dioxo-3-piperidyl)-3-methyl-2-oxo-benzimidazol-4-yl]prop-2-ynyl]piperazine-1-carboxylate To a mixture of 3-(4-bromo-3-methyl-2-oxo-benzimidazol-1-yl)piperidine-2,6-dione (2.15 g, 6.36 mmol, Intermediate B), CuI (121 mg, 635 umol) and $Pd(PPh_3)_4$ (734 mg, 635 umol) in DMSO (10 mL) was added tert-butyl 4-prop-2-ynylpiperazine-1-carboxylate (1.71 g, 7.63 mmol) and TEA (6.25 g, 61.8 mmol) under $N_2$. The mixture was stirred at 80° C. for 2 hours. On completion, the reaction mixture was added water (300 mL). The aqueous layer was extracted with ethyl acetate (180 mL×5). The organic layer was separated and concentrated under reduced pressure to give the crude product. The crude product was purified by column chromatography ($SiO_2$, Petroleum ether/Ethyl acetate=I/O to 0/1), concentrated under reduced pressure to give product (2.50 g, 80% yield) as a yellow solid. $^1H$ NMR (400 MHz, DMSO-$d_6$) δ 11.18 (s, 1H), 7.80-7.50 (m, 1H), 7.25-7.14 (m, 2H), 7.11-7.04 (m, 1H), 5.45 (dd, J=5.2, 12.4 Hz, 1H), 3.72-3.64 (s, 2H), 3.46-3.40 (m, 4H), 3.37 (s, 1H), 3.01-2.87 (m, 1H), 2.84-2.66 (m, 2H), 2.54 (s, 2H), 2.13-2.06 (m, 1H), 1.50-1.41 (m, 12H); LC-MS (ESI$^+$) m/z 482.2 (M+H)$^+$.

Step 3—Tert-butyl 4-[3-[1-(2,6-dioxo-3-piperidyl)-3-methyl-2-oxo-benzimidazol-4-yl propyl] piperazine-1-carboxylate To a mixture of tert-butyl 4-[3-[1-(2,6-dioxo-3-piperidyl)-3-methyl-2-oxo-benzimidazol-4-yl] prop-2-ynyl]piperazine-1-carboxylate (1.00 g, 2.08 mmol) in THF (80 mL) was added Pd/C (250 mg, 10 wt %) and $Pd(OH)_2$ (250 mg, 356 umol, 20 wt %) under $N_2$. The mixture was stirred at 25° C.

for 24 hours under $H_2$ (15 Psi). On completion, the reaction mixture was filtered and the filtrate concentrated under reduced pressure. The crude product was purified with reversed phase flash (0.1% TFA condition). The residual aqueous solution was lyophilized to give title compound (600 mg, 53% yield) as a white solid. $^1H$ NMR (400 MHz, DMSO-$d_6$) δ 11.10 (s, 1H), 7.04-6.98 (m, 2H), 6.91 (dd, J=2.4, 6.4 Hz, 1H), 5.38 (dd, J=5.2, 12.8 Hz, 1H), 4.08-3.94 (m, 2H), 3.58 (s, 3H), 3.55-3.42 (m, 3H), 3.15-2.88 (m, 7H), 2.75-2.59 (m, 2H), 2.08-1.95 (m, 3H), 1.47-1.37 (m, 10H); LC-MS (ESI$^+$) m/z 486.2 (M+H)$^+$.

Step 4—3-[3-Methyl-2-oxo-4-(3-piperazin-1-ylpropyl)benzimidazol-1-yl]piperidine-2,6-dione To a mixture of tert-butyl 4-[3-[1-(2,6-dioxo-3-piperidyl)-3-methyl-2-oxo-benzimidazol-4-yl] propyl]piperazine-1-carboxylate (400 mg, 823 umol) in DCM (16 mL) was added HCl/dioxane (4 M, 3 mL). The mixture was stirred at 25° C. for 30 minutes. On completion, the reaction mixture was concentrated under reduced pressure to remove DCM and HCL/dioxane. The title compound (350 mg, 90% yield, HCl salt) was obtained as a white solid. LC-MS (ESI$^+$) m/z 386.3 (M+H)$^+$.

3-[4-[3-[4-(3-Aminopropyl)piperazin-1-yl]propyl]-3-methyl-2-oxo-benzimidazol-1-yl]piperidine-2,6-dione (Intermediate GB)

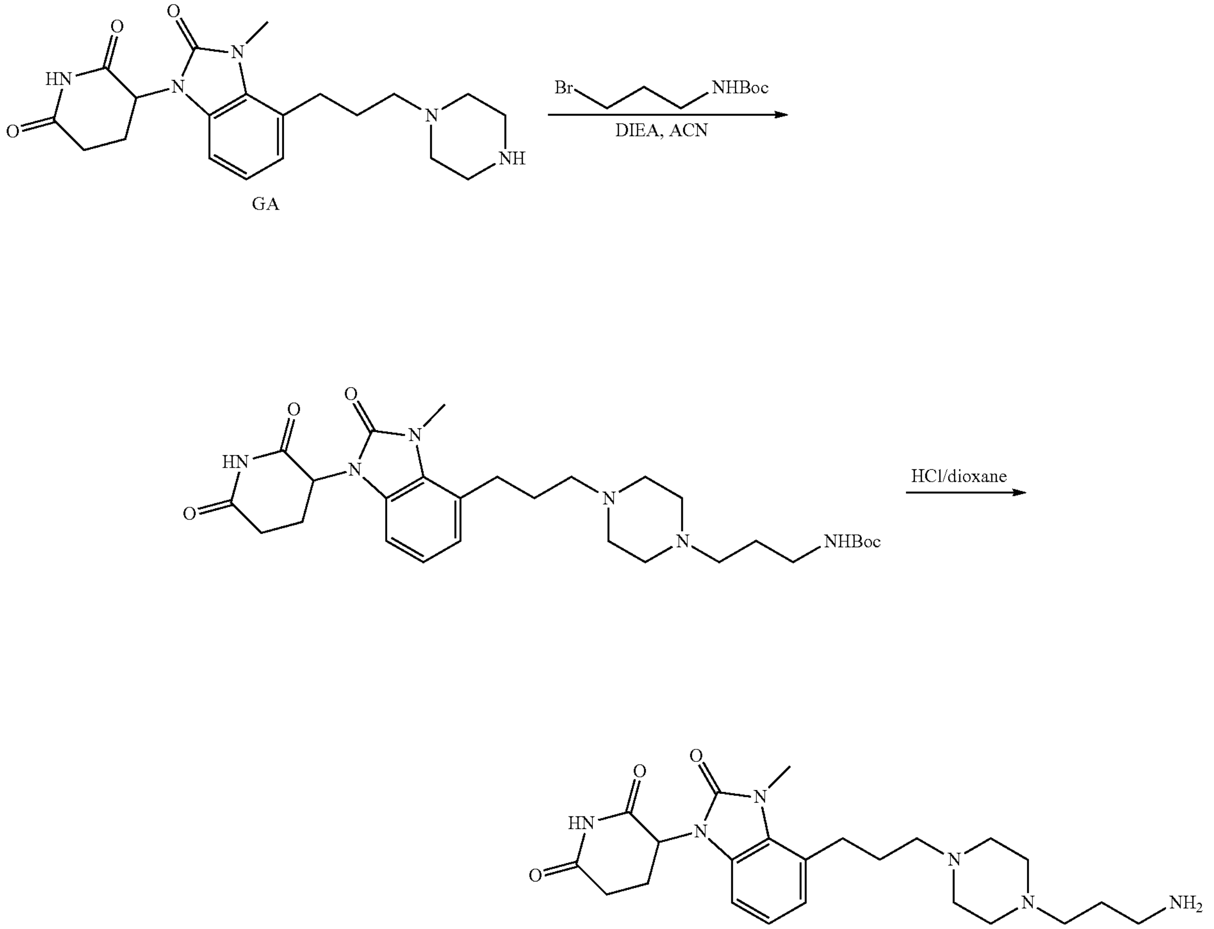

GA

GB

Step 1—Tert-butyl N-[3-[4-[3-[1-(2,6-dioxo-3-piperidyl)-3-methyl-2-oxo-benzimidazol-4-yl]propyl]piperazin-1-yl]propyl]carbamate To a solution of 3-[3-methyl-2-oxo-4-(3-piperazin-1-yl-propyl)benzimidazol-1-yl]piperidine-2,6-dione (350 mg, 829 umol, HCl salt, Intermediate GA) in ACN (10 mL) was added DIEA (107 mg, 829 umol, 144 uL) until the pH=8-9 at 25° C. Then tert-butyl N-(3-bromopropyl)carbamate (296 mg, 1.24 mmol, CAS #83948-53-2) was added in one portion, and the reaction was stirred at 40° C. for 12 hours. On completion, the reaction mixture was directly purified by reversed phase flash chromatography (0.1% TFA condition). The residual aqueous solution was lyophilized to give title compound (300 mg, 56% yield) as a yellow solid. $^1H$ NMR (400 MHz, DMSO-$d_6$) δ 11.18 (s, 1H), 9.28-8.67 (s, 1H), 7.13-7.05 (m, 2H), 7.03-6.95 (m, 1H), 5.46 (dd, J=5.2, 12.8 Hz, 1H), 3.89-3.47 (m, 7H), 3.17-2.89 (m, 8H), 2.86-2.71 (m, 2H), 2.06 (dd, J=5.4, 10.4 Hz, 3H), 1.89-1.74 (m, 2H), 1.60 (d, J=7.2 Hz, 1H), 1.46 (s, 9H), 1.38-1.29 (m, 4H). LC-MS (ESI$^+$) m/z 543.4 (M+H)$^+$.

Step 2—3-[4-[3-[4-(3-Aminopropyl)piperazin-1-yl]propyl]-3-methyl-2-oxo-benzimidazol-1-yl]piperidine-2,6-dione To a solution of tert-butyl N-[3-[4-[3-[1-(2,6-dioxo-3-piperidyl)-3-methyl-2-oxo-benzimidazol-4-yl] propyl]piperazin-1-yl]propyl]carbamate (150 mg, 276 umol) in DCM (2.0 mL) was added HCl/dioxane (4 M, 0.60 mL). Then the mixture was stirred at 25° C. for 1 hour. On completion, the reaction mixture was concentrated under reduced pressure to remove DCM and HCl/dioxane. The title compound (130 mg, 88% yield, HCl salt) was obtained as a white solid. LC-MS (ESI$^+$) m/z 443.4 (M+H)$^+$.

4-[[Chloro-(3-chloro-2-fluoro-phenyl)-oxo-dispiro[BLAH]carbonyl]amino]cyclohexanecarboxylic acid (Intermediate GC)

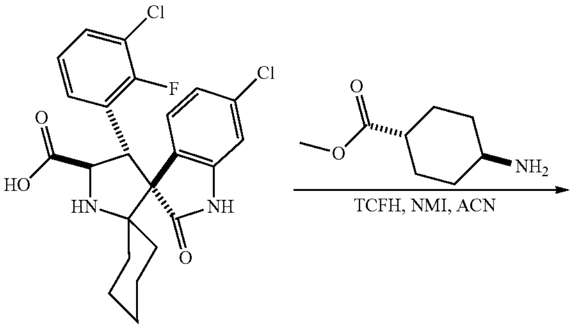

CI

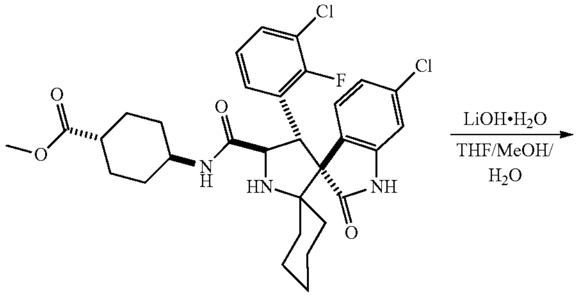

-continued

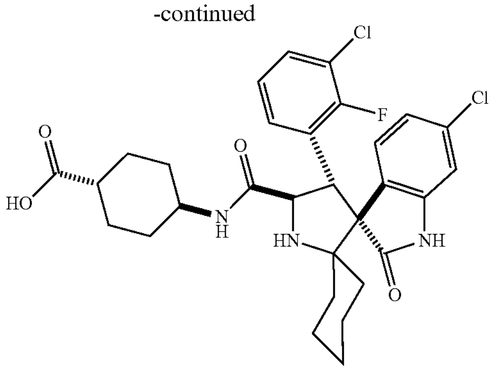

GC

Step 1—Methyl 4-[[chloro-(3-chloro-2-fluoro-phenyl)-oxo-dispiro[BLAH]carbonyl]amino] cyclohexanecarboxylate To a mixture of methyl 4-aminocyclohexanecarboxylate (209 mg, 1.08 mmol, CAS #62456-15-9) and chloro-(3-chloro-2-fluoro-phenyl)-oxo-dispiro[BLAH]carboxylic acid (500 mg, 1.08 mmol, from Intermediate CI) in ACN (10 mL) was added 1-methylimidazole (265 mg, 3.24 mmol) and [chloro(dimethylamino)methylene]-dimethyl-ammonium; hexafluorophosphate (605 mg, 2.16 mmol). The mixture was stirred at 25° C. for 1 hour. On completion, the mixture was filtered and concentrated to give a residue. The crude product was purified by reversed-phase (TFA condition) to give the title compound (900 mg, 100% yield, TFA salt) as a white solid. LC-MS (ESI$^+$) m/z 602.3 (M+H)$^+$.

Step 2—4-[[Chloro-(3-chloro-2-fluoro-phenyl)-oxo-dispiro[BLAH]carbonyl]amino]cyclohexanecarboxylic acid To a solution of methyl 4-[[chloro-(3-chloro-2-fluoro-phenyl)-oxo-dispiro[BLAH]carbonyl]amino] cyclohexanecarboxylate (900 mg, 1.49 mmol, TFA salt) in THF (9 mL) MeOH (9 mL) and $H_2O$ (9 mL) was added LiOH—$H_2O$ (313 mg, 7.47 mmol). The mixture was stirred at 50° C. for 5 hours. On completion, the mixture was adjusted to pH=4-5 with diluted hydrochloric acid and then extracted with ethyl acetate (3×10 mL). The ethyl acetate solution was dried over $Na_2SO_4$, filtered, and concentrated in vacuo to give the title compound (480 mg, 54% yield) as a white solid. $^1H$ NMR (400 MHz, DMSO-$d_6$) δ 10.52 (s, 1H), 7.77 (d, J=8.4 Hz, 1H), 7.58 (t, J=6.8 Hz, 1H), 7.40 (dd, J=1.6, 8.0 Hz, 1H), 7.31 (t, J=6.8 Hz, 1H), 7.10 (t, J=8.0 Hz, 1H), 7.02 (dd, J=1.6, 8.0 Hz, 1H), 6.66 (d, J=2.0 Hz, 1H), 4.56 (d, J=9.2 Hz, 1H), 4.36 (d, J=9.2 Hz, 1H), 4.03 (d, J=7.2 Hz, 1H), 3.55-3.39 (m, 1H), 1.97-1.62 (m, 8H), 1.62-1.29 (m, 10H), 1.03-0.90 (m, 1H), 0.85-0.71 (m, 1H).

3-[1-Oxo-4-[2-(4-piperidyl)ethynyl]isoindolin-2-yl]piperidine-2,6-dione (Intermediate GD)

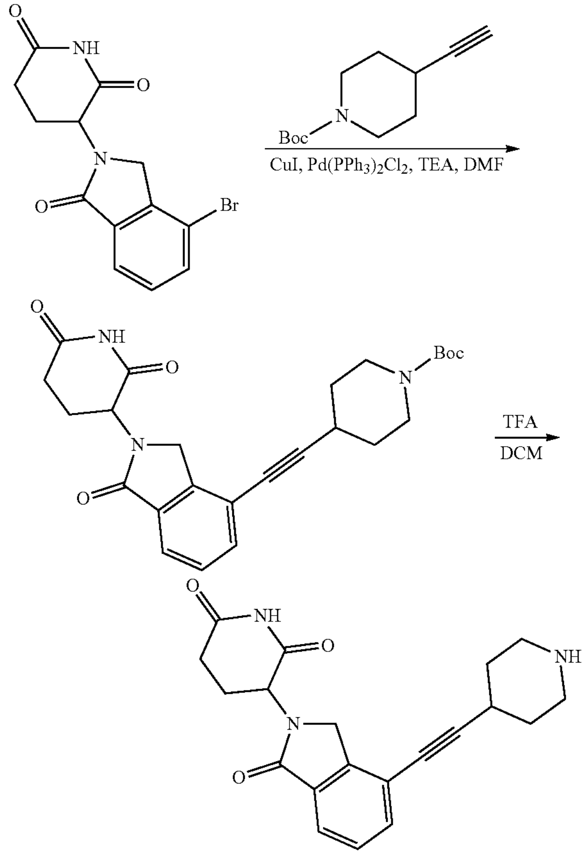

GD

Step 1—Tert-butyl 4-[2-[2-(2,6-dioxo-3-piperidyl)-1-oxo-isoindolin-4-yl]ethynyl]piperidine-1-carboxylate A mixture of 3-(4-bromo-1-oxo-isoindolin-2-yl)piperidine-2,6-dione (950 mg, 2.94 mmol, CAS #2093387-36-9) and tert-butyl 4-ethynylpiperidine-1-carboxylate (922 mg, 4.41 mmol, CAS #287192-97-6) in DMF (25 mL) was added $Pd(PPh_3)_2Cl_2$ (206 mg, 293 umol), CuI (111 mg, 587 umol) and TEA (5.95 g, 58.8 mmol) under $N_2$. The mixture and stirred at 80° C. for 12 hours. On completion, the mixture was poured into the water (80 mL), then the aqueous phase was extracted with ethyl acetate (20 mL×3). The combined organic phase was washed with brine (20 mL×3), dried with anhydrous $Na_2SO_4$, filtered and concentrated in vacuo to give the residue. The residue was purified by column chromatography ($SiO_2$, Petroleum ether/Ethyl acetate=3:1 to 0:1) to give the title compound (1.20 g, 90% yield) as a brown solid. $^1$H NMR (400 MHz, $CDCl_3$) δ 8.16 (s, 1H), 7.82 (d, J=7.2 Hz, 1H), 7.58 (d, J=7.2 Hz, 1H), 7.52-7.41 (m, 2H), 5.29-5.22 (m, 1H), 4.53-4.45 (m, 1H), 4.37-4.30 (m, 1H), 3.81-3.72 (m, 2H), 3.28-3.19 (m, 2H), 2.94-2.79 (m, 3H), 2.29-2.19 (m, 1H), 1.96-1.83 (m, 2H), 1.73-1.64 (m, 2H), 1.47 (s, 9H).

Step 2—3-[1-Oxo-4-[2-(4-piperidyl)ethynyl]isoindolin-2-yl]piperidine-2,6-dione

To a mixture of tert-butyl 4-[2-[2-(2,6-dioxo-3-piperidyl)-1-oxo-isoindolin-4-yl]ethynyl]piperidine-1-carboxylate (150 mg, 332 umol) in DCM (5 mL) was added TFA (189 mg, 1.66 mmol). Then the mixture was stirred at 0° C. for 0.5 hour. On completion, the mixture was concentrated to give the title compound (154 mg, 99% yield, TFA salt) as a white solid. LC-MS (ESI$^+$) m/z 351.9 $(M+H)^+$.

3-[4-[2-[1-(4-Aminobicyclo[2.2.2]octane-1-carbonyl)-4-piperidyl]ethynyl]-1-oxo-isoindolin-2-yl]piperidine-2,6-dione (Intermediate GE)

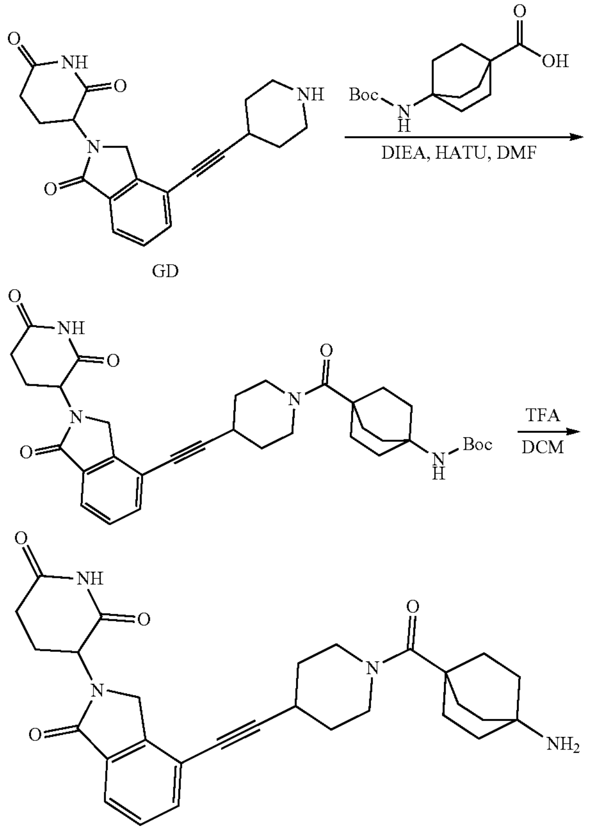

GE

Step 1—Tert-butyl N-[4-[4-[2-[2-(2,6-dioxo-3-piperidyl)-1-oxo-isoindolin-4-yl]ethynyl]piperidine-1-carbonyl]-1-bicyclo[2.2.2]octanyl]carbamate To a mixture of 4-(tert-butoxycarbonylamino)bicyclo[2.2.2]octane-1-carboxylic acid (298 mg, 1.11 mmol, CAS #863304-76-1) in DMF (10 mL) was added DIEA (429 mg, 3.32 mmol) and HATU (462 mg, 1.22 mmo). Then 3-[1-oxo-4-[2-(4-piperidyl)ethynyl]isoindolin-2-yl]piperidine-2,6-dione (515 mg, 1.11 mmol, Intermediate GD) was added into the mixture and stirred at 20° C. for 1 hour. On completion, the mixture was poured into the water (30 mL) and filtered to give the filter cake. The filter cake was dried to give the title compound (520 mg, 77% yield) as a brown solid. $^1$H NMR (400 MHz, DMSO-$d_6$) δ 11.00 (s, 1H), 7.72

(d, J=7.6 Hz, 1H), 7.66 (d, J=7.6 Hz, 1H), 7.55-7.50 (m, 1H), 6.43 (s, 1H), 5.17-5.07 (m, 1H), 4.49-4.42 (m, 1H), 4.38-4.25 (m, 1H), 3.92 (d, J=13.2 Hz, 2H), 3.02-2.94 (m, 1H), 2.94-2.87 (m, 1H), 2.60 (d, J=17.6 Hz, 1H), 2.49-2.42 (m, 1H), 2.07-1.98 (m, 1H), 1.94-1.65 (m, 16H), 1.60-1.47 (m, 2H), 1.36 (s, 9H).

Step 2—3-[4-[2-[1-(4-Aminobicyclo[2.2.2]octane-1-carbonyl)-4-piperidyl]ethynyl]-1-oxo-isoindolin-2-yl]piperidine-2,6-dione To a mixture of tert-butyl N-[4-[4-[2-[2-(2,6-dioxo-3-piperidyl)-1-oxo-isoindolin-4-yl]ethynyl]piperidine-1-carbonyl]-1-bicyclo[2.2.2]octanyl]carbamate (150 mg, 248 umol) in DCM (2 mL) was added TFA (141 mg, 1.24 mmol). The mixture was stirred at 0° C. for 0.5 hour. On completion, the mixture was concentrated in vacuo to give the title compound (153 mg, 99% yield, TFA salt) as a brown oil. LC-MS (ESI$^+$) m/z 503.1 (M+H)$^+$.

(2R,3S,4R,5S)-3-(3-chloro-2-fluoro-phenyl)-4-(4-chloro-2-fluoro-phenyl)-4-cyano-5-(2,2-dimethylpropyl)pyrrolidine-2-carboxylic acid (Intermediate GF) and (2S,3R,4S,5R)-3-(3-chloro-2-fluoro-phenyl)-4-(4-chloro-2-fluoro-phenyl)-4-cyano-5-(2,2-dimethylpropyl)pyrrolidine-2-carboxylic acid (Intermediate JN)

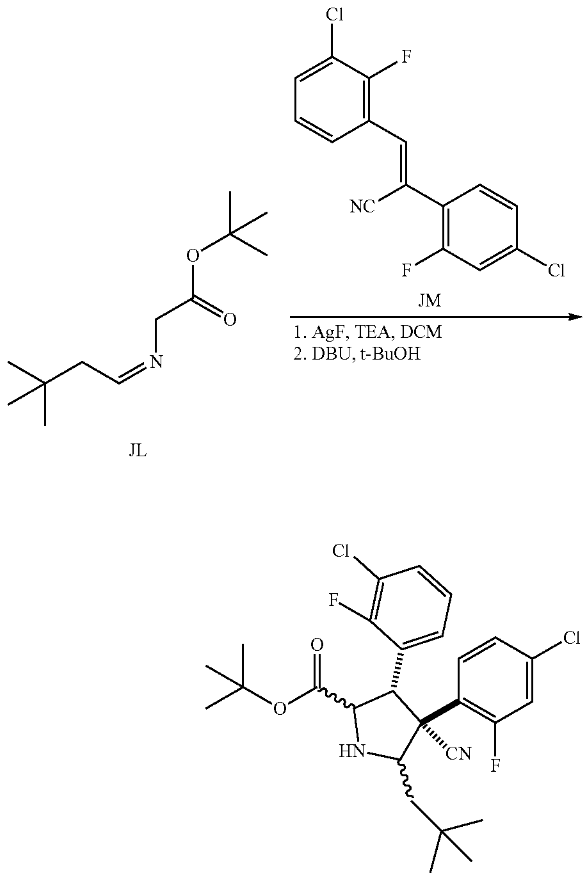

Racemic

-continued

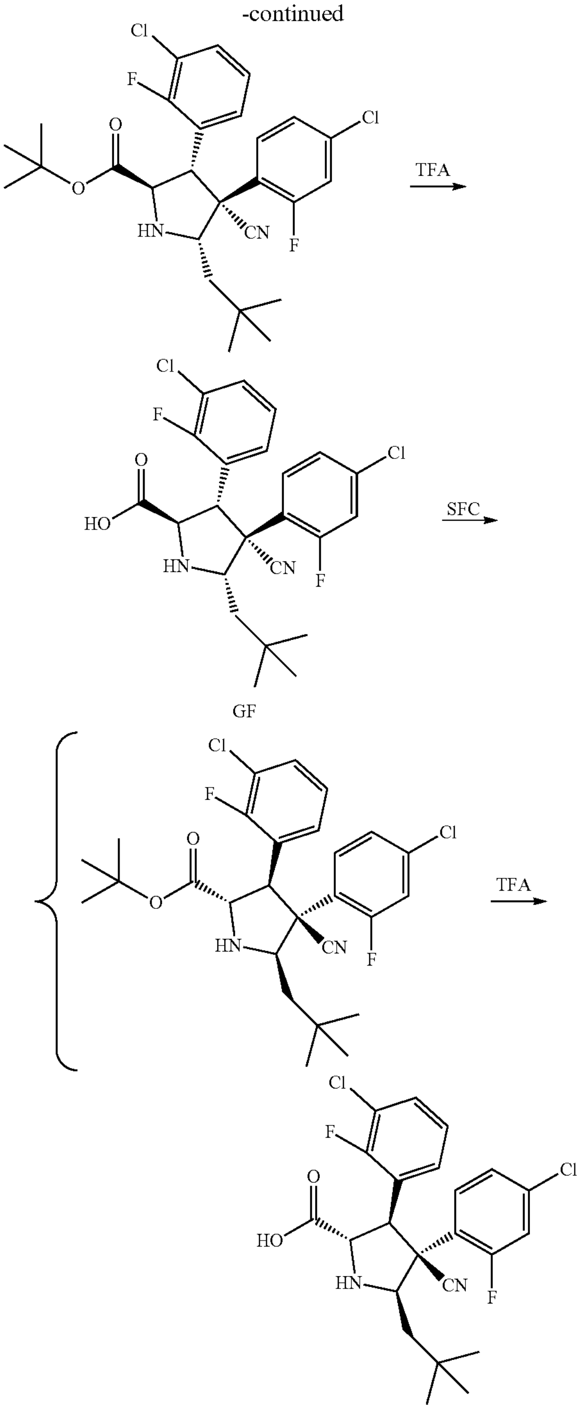

JN

Step 1—Tert-butyl (2R,3S,4R,5S)-3-(3-chloro-2-fluoro-phenyl)-4-(4-chloro-2-fluoro-phenyl)-4-cyano-5-(2,2-dimethylpropyl)pyrrolidine-2-carboxylate and tert-butyl (2S,3R,4S,5R)-3-(3-chloro-2-fluoro-phenyl)-4-(4-chloro-2-fluoro-phenyl)-4-cyano-5-(2,2-dimethylpropyl)pyrrolidine-2-carboxylate To a solution of tert-butyl 2-[(Z)-3,3-dimethylbutylideneamino]acetate (14.0 g, 65.6 mmol, Intermediate JL) and (Z)-3-(3-chloro-2-fluoro-phenyl)-2-(4-chloro-2-fluoro-phenyl)prop-2-enenitrile (14.8 g, 47.9 mmol, Intermediate JM) in DCM (1000 mL) was added TEA (17.2 g, 170 mmol) and AgF (4.16 g, 32.8 mmol). The mixture was then stirred at 25° C. for 18 hours. On completion, the mixture was concentrated and the residue was partitioned between ethyl acetate and brine. The organic layer was separated, dried over $Na_2SO_4$, and concentrated. The residue was dissolved into tert-butanol (70 mL), and DBU (70.7 g, 464 mmol) was added. The mixture was heated at 100° C. for 2 hours. On completion, the reaction mixture was concentrated under reduced pressure to remove tert-butanol. Then the residue was partitioned between ethyl acetate and water. The organic layer was separated, dried over $Na_2SO_4$, and concentrated. The crude product was pre-purified by column chromatography on silica gel eluted with petroleum ether/ethyl acetate ($SiO_2$, Petroleum ether/Ethyl acetate=I/O to 15/1) to give product racemic product. Then the racemic product was further separated by SFC (column: REGIS(S,S)WHELK-O1 (250 mm*25 mm, 10 μm); mobile phase: [0.1% $NH_3H_2O$ IPA]; B %: 8%-8%, 2.5; 60 min). Tert-butyl (2R,3S,4R,5S)-3-(3-chloro-2-fluoro-phenyl)-4-(4-chloro-2-fluoro-phenyl)-4-cyano-5-(2,2-dimethylpropyl)pyrrolidine-2-carboxylate (7.00 g, 19% yield) was obtained as white solid. $^1H$ NMR (400 MHz, DMSO-$d_6$) δ 7.74-7.63 (m, 2H), 7.54 (t, J=7.6 Hz, 1H), 7.38-7.30 (m, 3H), 4.60 (d, J=7.2 Hz, 1H), 4.26 (t, J=6.8 Hz, 1H), 3.99 (t, J=9.2 Hz, 1H), 3.50 (dd, J=6.8, 8.8 Hz, 1H), 1.50 (dd, J=9.2, 14.0 Hz, 1H), 1.35 (s, 9H), 1.20 (d, J=14.0 Hz, 1H), 0.86 (s, 9H). LC-MS (ESI$^+$) m/z 524.6 (M+H)$^+$. tert-butyl (2S,3R,4S,5R)-3-(3-chloro-2-fluoro-phenyl)-4-(4-chloro-2-fluoro-phenyl)-4-cyano-5-(2,2-dimethylpropyl)pyrrolidine-2-carboxylate (7.00 g, 19% yield) was obtained as a white solid. $^1H$ NMR (400 MHz, DMSO-$d_6$) δ 7.74-7.62 (m, 2H), 7.53 (t, J=7.2 Hz, 1H), 7.38-7.30 (m, 3H), 4.60 (d, J=7.2 Hz, 1H), 4.26 (t, J=6.8 Hz, 1H), 3.99 (t, J=9.2 Hz, 1H), 3.50 (dd, J=6.8, 8.8 Hz, 1H), 1.50 (dd, J=9.2, 14.0 Hz, 1H), 1.35 (s, 9H), 1.25-1.19 (m, 1H), 0.86 (s, 9H). LC-MS (ESI$^+$) m/z 524.6 (M+H)$^+$.

Step 2—(2R,3S,4R,5S)-3-(3-chloro-2-fluoro-phenyl)-4-(4-chloro-2-fluoro-phenyl)-4-cyano-5-(2,2-dimethylpropyl)pyrrolidine-2-carboxylic acid To a solution of tert-butyl (2R,3S,4R,5S)-3-(3-chloro-2-fluoro-phenyl)-4-(4-chloro-2-fluoro-phenyl)-4-cyano-5-(2,2-dimethylpropyl)pyrrolidine-2-carboxylate (200 mg, 382 umol) in TFA (1.0 mL) was stirred at 25° C. for 8 hours. On completion, the reaction mixture was concentrated to give the crude product. The crude was further purified by SFC (column: DAICEL CHIRALPAK IC (250 mm*30 mm, 10 μm); mobile phase: [0.1% $NH_3H_2O$ IPA]; B %: 20%-20%, 1.6; 60 min). The residual aqueous solution was lyophilized to give the title compound a white solid (18.5 mg, 9.1% yield). $^1H$ NMR (400 MHz, DMSO-$d_6$) δ 7.72-7.61 (m, 2H), 7.56-7.50 (m, 1H), 7.38-7.29 (m, 3H), 4.65 (d, J=7.6 Hz, 1H), 4.34 (d, J=7.6 Hz, 1H), 4.01 (d, J=8.8 Hz, 1H), 1.52 (dd, J=9.2, 14 Hz, 1H), 1.21 (d, J=14 Hz, 1H), 0.85 (s, 9H). LC-MS (ESI$^+$) m/z 467.3 (M+H)$^+$. Peak 1 of SFC ee=100%.

Step 3—(2S,3R,4S,5R)-3-(3-chloro-2-fluoro-phenyl)-4-(4-chloro-2-fluoro-phenyl)-4-cyano-5-(2,2-dimethylpropyl)pyrrolidine-2-carboxylic acid To a solution of tert-butyl (2S,3R,4S,5R)-3-(3-chloro-2-fluoro-phenyl)-4-(4-chloro-2-fluoro-phenyl)-4-cyano-5-(2,2-dimethylpropyl)pyrrolidine-2-carboxylate (200 mg, 382 umol) in TFA (1.0 mL) was stirred at 25° C. for 8 hours. On completion, the reaction mixture was concentrated under reduced pressure to remove TFA. The compound was purified by prep-HPLC (column: Welch Xtimate C18 150*25 mm*5 um; mobile phase: [water (0.05% HCl)–ACN]; B %: 48%-78%, 10 min). The residual aqueous solution was lyophilized to give the title compound as a white solid (23.5 mg, 12% yield). $^1H$ NMR (400 MHz, DMSO-$d_6$) δ 7.74-7.67 (m, 2H), 7.57-7.51 (m, 1H), 7.37-7.30 (m, 3H), 4.67 (d, J=8.4 Hz, 1H), 4.58-4.46 (m, 1H), 4.21-4.08 (m, 1H), 1.73-1.57 (m, 1H), 1.24 (d, J=14.4 Hz, 1H), 0.86 (s, 9H). LC-MS (ESI$^+$) m/z 467.0 (M+H)$^+$. Peak 2 of SFC ee=99%.

1-[7-(4-Piperidyl)imidazo[1,2-a]pyridin-3-yl]hexahydropyrimidine-2,4-dione (Intermediate GG)

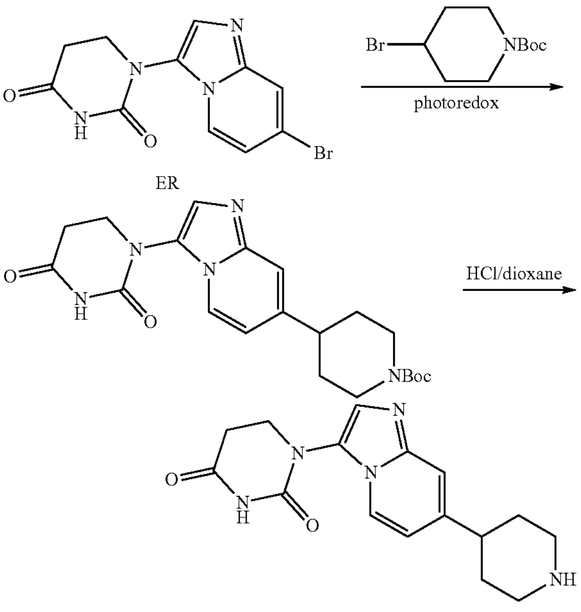

GG

Step 1—Tert-butyl 4-[3-(2,4-dioxohexahydropyrimidin-1-yl)imidazo[1,2-a]pyridin-7-yl]piperidine-1-carboxylate To an 8 mL vial equipped with a stir bar was added 1-(7-bromoimidazo[1,2-a] pyridin-3-yl)hexahydropyrimidine-2,4-dione (400 mg, 1.29 mmol, Intermediate ER), tert-butyl 4-bromopiperidine-1-carboxylate (444 mg, 1.68 mmol, CAS #180695-79-8), Ir[dF(CF3)ppy]2(dtbpy)(PF6) (14.5 mg, 12.9 μmol), $NiCl_2$·dtbbpy (2.58 mg, 6.47 umol), TTMSS (321 mg, 1.29 mmol), 2,6-dimethylpyridine (277 mg, 2.59 mmol) and DME (7 mL). The vial was sealed and placed under nitrogen was added. The reaction was stirred and irradiated with a 34 W blue LED lamp (7 cm away), with cooling fan to keep the reaction temperature at 25° C. for 14 hours. On completion, the filtrate was concentrated in vacuo. The crude product was purified by reversed-phase HPLC (0.1% FA condition) to give the title compound (300 mg, 52% yield) as a white solid. LC-MS (ESI$^+$) m/z 414.4 (M+H)$^+$.

Step 2—1-[7-(4-Piperidyl)imidazo[1,2-a]pyridin-3-yl]hexahydropyrimidine-2,4-dione To a solution of tert-butyl 4-[3-(2,4-dioxohexahydropyrimidin-1-yl)imidazo[1,2-a]pyridin-7-yl] piperidine-1-carboxylate (300 mg, 725 umol) in DCM (5 mL) was added HCl/dioxane (4 M, 5 mL). Then the mixture was stirred at 25° C. for 1 hour. On completion, the mixture was concentrated in vacuo to give the title compound (160 mg, 63% yield) as a yellow solid. $^1$H NMR (400 MHz, DMSO-d6) δ 10.92-10.86 (m, 1H), 8.93-8.68 (m, 1H), 8.40-8.23 (m, 1H), 7.84-7.66 (m, 1H), 7.65-7.45 (m, 1H), 3.90-3.82 (m, 3H), 3.45-3.39 (m, 2H), 3.33-3.23 (m, 2H), 3.07-2.98 (m, 1H), 2.90-2.82 (m, 2H), 2.75-2.66 (m, 1H), 2.09-1.98 (m, 2H), 1.91 (s, 1H).

1-[7-[1-(4-Aminobenzoyl)-4-piperidyl]imidazo[1,2-a]pyridin-3-yl]hexahydropyrimidine-2,4-dione (Intermediate GH)

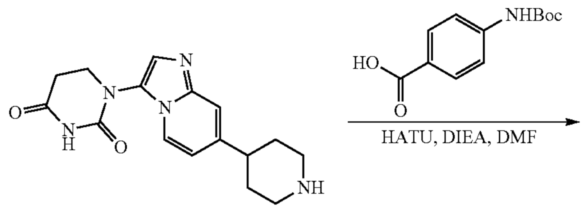

GG

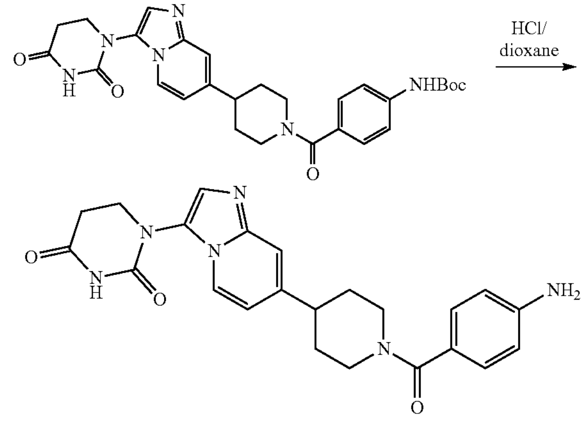

GH

Step 1—Tert-butyl N-[4-[4-[3-(2,4-dioxohexahydropyrimidin-1-yl)imidazo[1,2-a]pyridin-7-yl] piperidine-1-carbonyl]phenyl]carbamate To a mixture of 1-[7-(4-piperidyl)imidazo[1,2-a]pyridin-3-yl]hexahydropyrimidine-2,4-dione (150 mg, 478 umol, Intermediate GG), 4-(tert-butoxycarbonylamino)benzoic acid (113 mg, 478 μmol, CAS #66493-39-8) and DIEA (185 mg, 1.44 mmol) in DMF (2 mL) was stirred 10 minutes. The mixture was added HATU (218 mg, 574 umol) and stirred at 25° C. for 1 hour. On completion, the mixture was concentrated in vacuo. The crude product was purified by reversed-phase HPLC (0.1% HCl condition ) to give the title compound (60.0 mg, 21% yield) as a brown solid. LC-MS (ESI[+]) m/z 533.2 (M+H)[+].

Step 2—1-[7-[1-(4-Aminobenzoyl)-4-piperidyl]imidazo[1,2-a]pyridin-3-yl]hexahydropyrimidine-2,4-dione To a solution of tert-butyl N-[4-[4-[3-(2,4-dioxohexahydropyrimidin-1-yl)imidazo[1,2-a]pyridin-7-yl] piperidine-1-carbonyl]phenyl]carbamate (60.0 mg, 112 umol) in DCM (4 mL) was added HCl/dioxane (4 M, 6.00 mL). The mixture was then stirred at 25° C. for 1 hour. On completion, the filtrate was concentrated in vacuo to give the title compound (40.0 mg, 66% yield) as a yellow solid. $^1$H NMR (400 MHz, DMSO-d6) δ 10.91-10.88 (m, 1H), 8.84 (d, J=7.2 Hz, 1H), 8.81-8.71 (m, 1H), 8.26 (s, 1H), 7.97-7.88 (m, 1H), 7.84 (s, 1H), 7.71 (s, 1H), 7.63 (d, J=7.2 Hz, 1H), 7.43-7.38 (m, 2H), 3.86 (t, J=6.2 Hz, 3H), 3.39 (s, 2H), 3.15-3.08 (m, 2H), 2.89 (s, 1H), 2.74-2.66 (m, 3H), 1.92-1.85 (m, 2H), 1.59 (s, 1H).

Chloro-(2-chloro-3-fluoro-4-pyridyl)-dimethyl-oxo-dispiro[BLAH]carboxylic acid (Intermediate GI)

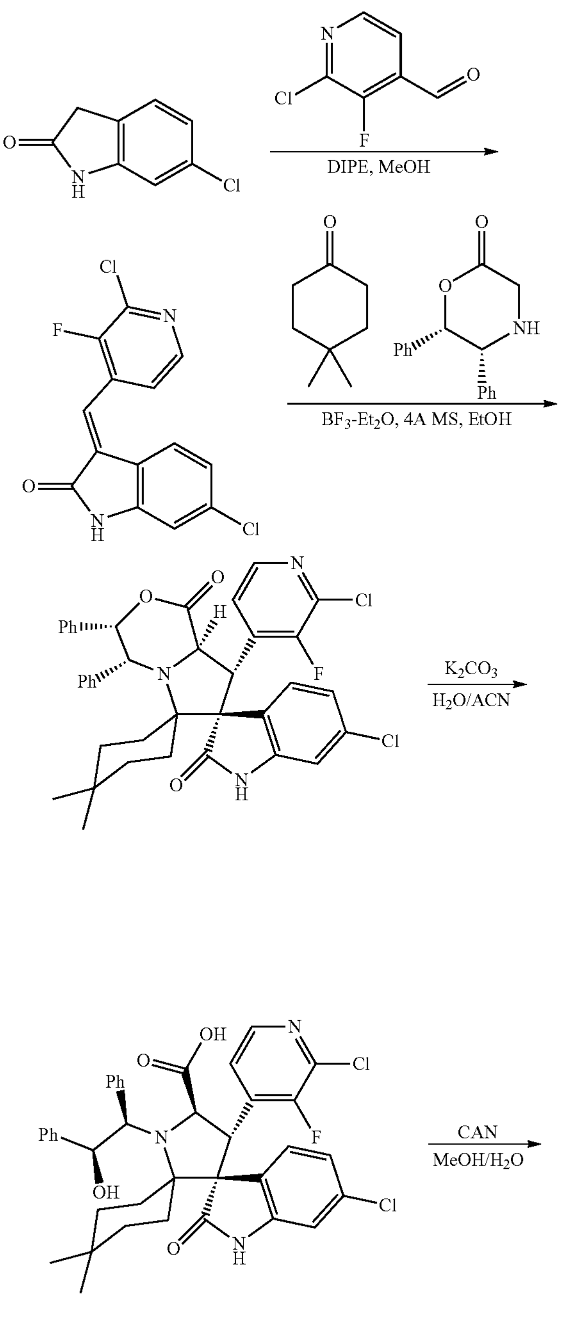

-continued

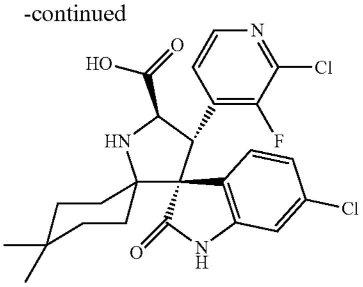

GI

Step 1—(3E)-6-Chloro-3-[(2-chloro-3-fluoro-4-pyridyl)methylene]indolin-2-one

To a solution of 6-chloroindolin-2-one (10.0 g, 59.6 mmol, CAS #56341-37-8) in MeOH (600 mL) was added DIEA (1.54 g, 11.9 mmol, 2.0 mL) and 2-chloro-3-fluoro-pyridine-4-carbaldehyde (10.0 g, 62.6 mmol, CAS #329794-28-7). The mixture was stirred at 70° C. for 16 hours. On completion, the precipitate was collected by filtration to give the title compound (16.6 g, 53.7 mmol, 90% yield) as a brown solid. 1H NMR (400 MHz, DMSO-d6) δ=10.92 (s, 1H), 8.39 (d, J=4.8 Hz, 1H), 7.79-7.76 (m, 1H), 7.48 (s, 1H), 7.14 (d, J=8.0 Hz, 1H), 6.95-6.87 (m, 2H). LC-MS ($ESI^+$) m/z 308.8 $(M+H)^+$.

Step 2—Chloro-(2-chloro-3-fluoro-4-pyridyl)-dimethyl-diphenyl-dispiro[BLAH]dione To a solution of (3E)-6-chloro-3-[(2-chloro-3-fluoro-4-pyridyl)methylene]indolin-2-one (8.00 g, 25.8 mmol) in 2-methyltetrahydrofuran (130 mL) was added (5R,6S)-5,6-diphenylmorpholin-2-one (7.21 g, 28.4 mmol, CAS #282735-66-4), 4,4-dimethylcyclohexanone (3.59 g, 28.4 mmol, CAS #4255-62-3), $BF_3Et_2O$ (734 mg, 5.18 mmol, 638 uL) and 4 Å molecular sieves (14.3 g). The mixture was stirred at 70° C. for 16 hours under $N_2$ atmosphere. On completion, the mixture was concentrated in vacuo to give a residue. The residue was purified by column chromatography ($SiO_2$, Petroleum ether/Ethyl acetate=1:0 to 4:1) to give the title compound (15.5 g, 89% yield) as a white solid. $^1$H NMR (400 MHz, CHLOROFORM-d) 8=8.30 (d, J=5.2 Hz, 1H), 8.17 (s, 1H), 7.80 (t, J=4.8 Hz, 1H), 7.25-7.19 (m, 3H), 7.16-7.06 (m, 6H), 6.94 (d, J=2.0 Hz, 1H), 6.75 (d, J=6.8 Hz, 2H), 6.67 (dd, J=2.0, 8.4 Hz, 1H), 6.27 (d, J=8.4 Hz, 1H), 5.32 (d, J=11.2 Hz, 1H), 4.87 (d, J=3.2 Hz, 1H), 4.59 (d, J=11.2 Hz, 1H), 2.29 (dd, J=2.8, 14.2 Hz, 1H), 1.78 (d, J=10.4 Hz, 1H), 1.43-1.31 (m, 3H), 1.30-1.24 (m, 3H), 1.06-0.90 (m, 3H), 0.53 (s, 3H), 0.22 (s, 3H). LC-MS ($ESI^+$) m/z 670.5 $(M+H)^+$.

Step 3—Chloro-(2-chloro-3-fluoro-4-pyridyl)-[(1R,2S)-2-hydroxy-1,2-diphenyl-ethyl]-dimethyl-oxo-dispiro[BLAH]carboxylic acid To a solution of chloro-(2-chloro-3-fluoro-4-pyridyl)-dimethyl-diphenyl-dispiro[BLAH]dione (15.4 g, 22.9 mmol) in ACN (300 mL) and $H_2O$ (120 mL) was added $K_2CO_3$ (3.81 g, 27.5 mmol). The mixture was stirred at 85° C. for 16 hours. On completion, $MgSO_4$ (2.76 g, 22.9 mmol) was added and the mixture was stirred at 25° C. for 0.5 hour. Then, the reaction mixture was extracted with ethyl acetate (100 mL×3). The combined organic phase was dried with anhydrous $Na_2SO_4$, filtered and concentrated in vacuo to give the title compound (19.0 g) as a yellow solid. $^1$H NMR (400 MHz, METHANOL-d4) δ=7.71 (d, J=5.2 Hz, 1H), 7.62-7.50 (m, 4H), 7.23 (d, J=7.6 Hz, 1H), 7.17 (d, J=7.6 Hz, 2H), 7.13-7.09 (m, 3H), 7.07-6.99 (m, 5H), 6.97 (d, J=7.2 Hz, 1H), 6.86 (t, J=5.2 Hz, 1H), 6.71 (d, J=2.0 Hz, 1H), 5.63-5.55 (m, 1H), 4.95 (d, J=3.2 Hz, 1H), 4.91 (d, J=3.2 Hz, 1H), 4.76 (d, J=10.0 Hz, 1H), 4.66-4.61 (m, 1H), 4.16 (d, J=8.8 Hz, 1H), 1.93 (s, 1H), 1.77 (s, 1H), 1.49-1.38 (m, 1H), 1.21-1.15 (m, 1H), 1.09 (s, 1H), 1.05 (s, 3H), 0.87 (s, 1H), 0.65 (s, 3H). LC-MS ($ESI^+$) m/z 688.3 $(M+H)^+$.

Step 4—Chloro-(2-chloro-3-fluoro-4-pyridyl)-dimethyl-oxo-dispiro[BLAH]carboxylic acid To a solution of chloro-(2-chloro-3-fluoro-4-pyridyl)-[(1R,2S)-2-hydroxy-1,2-diphenyl-ethyl]-dimethyl-oxo-dispiro[BLAH]carboxylic acid (15.0 g, 21.7 mmol) in MeOH (600 mL) and $H_2O$ (160 mL) was added CAN (35.8 g, 65.3 mmol, CAS #16774-21-3). The mixture was stirred at 0° C. for 1 hour. On completion, $K_2CO_3$ (18.0 g, 131 mmol) was added at 0° C. and stirred for 1 hour. Next, the mixture was concentrated in vacuo to give a residue. The residue was poured into water (100 mL) and extracted with ethyl acetate (50 mL×3). The combined organic phases were dried with anhydrous $Na_2SO_4$, filtered and concentrated in vacuo. The residue was purified by column chromatography ($SiO_2$, Dichloromethane/Methanol=1:0 to 9:1) to give the title compound (4.60 g, 9.34 mmol, 42% yield) as a yellow solid. $^1$H NMR (400 MHz, METHANOL-$d_4$) 6=8.12 (d, J=5.2 Hz, 1H), 7.66 (t, J=5.2 Hz, 1H), 7.59 (dd, J=2.4, 8.4 Hz, 1H), 7.12 (dd, J=2.0, 8.0 Hz, 1H), 6.78 (d, J=2.0 Hz, 1H), 4.98 (d, J=10.4 Hz, 1H), 2.36 (dd, J=2.4, 14.0 Hz, 1H), 2.07 (dt, J=4.0, 14.0 Hz, 1H), 1.96-1.88 (m, 1H), 1.76 (dt, J=3.2, 14.0 Hz, 1H), 1.58 (d, J=15.2 Hz, 1H), 1.47 (dd, J=3.6, 14.0 Hz, 1H), 1.43-1.36 (m, 1H), 1.30 (dt, J=4.4, 14.0 Hz, 1H), 0.98 (s, 3H), 0.72 (s, 3H). LC-MS ($ESI^+$) m/z 492.0 $(M+H)^+$.

(3R,4'S,5'R)-6-chloro-4'-(3-chloro-2-fluorophenyl)-2-oxo-2",3",5",6"-tetrahydrodispiro[indoline-3,3'-pyrrolidine-2',4"-pyran]-5'-carboxylic acid (Intermediate GJ)

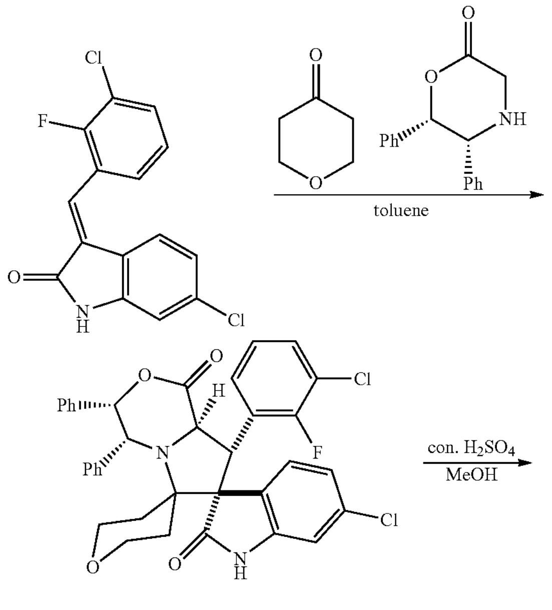

-continued

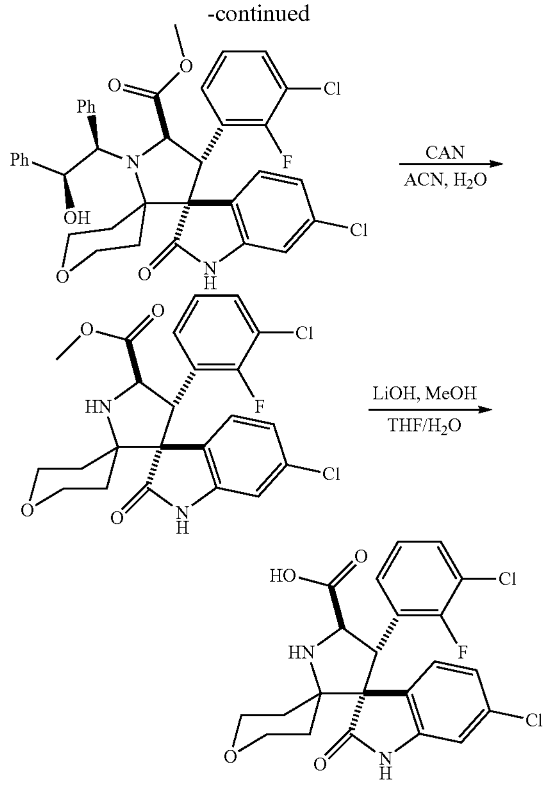

GJ

Step 1—Chloro-(3-chloro-2-fluoro-phenyl)-diphenyl-dispiro[BLAH]dione (3E)-6-chloro-3-[(3-chloro-2-fluoro-phenyl)methylene] indolin-2-one (5.00 g, 16.2 mmol, synthesized via Step 1 of Intermediate CI), tetrahydropyran-4-one (3.25 g, 32.4 mmol, 3 mL, CAS #143562-54-3) and (5R,6S)-5,6-diphenylmorpholin-2-one (4.93 g, 19.4 mmol CAS #282735-66-4) were dissolved in THF (8 mL) and toluene (75 mL) at the reaction mixture was stirred at 140° C. for 5 hours. On completion, the reaction mixture was concentrated in vacuo to give a residue. The residue was purified by column chromatography ($SiO_2$, Petroleum ether/Ethyl acetate=20/1 to 1/1) to give the title compound (6.69 g, 64% yield) as a yellow solid. $^1H$ NMR (400 MHz, DMSO-$d_6$) δ 10.85 (s, 1H), 7.95 (t, J=6.8 Hz, 1H), 7.47-7.34 (m, 1H), 7.29-7.20 (m, 4H), 7.19-7.11 (m, 3H), 7.08 (d, J=2.4 Hz, 1H), 7.03 (dd, J=2.8, 6.4 Hz, 2H), 6.88-6.81 (m, 3H), 6.68 (dd, J=2.1, 8.0 Hz, 1H), 6.35 (d, J=8.4 Hz, 1H), 5.51 (d, J=11.2 Hz, 1H), 4.95 (d, J=2.8 Hz, 1H), 4.63 (d, J=11.2 Hz, 1H), 3.46-3.39 (m, 1H), 3.36-3.20 (m, 2H), 3.04 (t, J=10.8 Hz, 1H), 2.43-2.33 (m, 1H), 2.11 (d, J=12.8 Hz, 1H), 1.52-1.38 (m, 1H), 1.32-1.21 (m, 1H). LC-MS ($ESI^+$) m/z 643.4 $(M+H)^+$.

Step 2—Methyl chloro-(3-chloro-2-fluoro-phenyl)-[(1R,2S)-2-hydroxy-12-diphenyl-ethyl]-oxo-dispiro [BLAH]carboxylate To a solution of chloro-(3-chloro-2-fluoro-phenyl)-diphenyl-dispiro[BLAH]dione (5.92 g, 9.20 mmol) dissolved in MeOH (80 mL) was added $H_2SO_4$ (5.95 g, 60.7 mmol, 3 mL), and the resulting solution was heated to 50° C. for 5 hours. On completion, the reaction mixture was cooled to 0° C. and slowly neutralized with a solution of saturated sodium bicarbonate. The aqueous solution was extracted with ethyl acetate. The ethyl acetate solution was dried over sodium sulfate, filtered, and concentrated to give the title compound (8.09 g, 67% yield) as a yellow solid. LC-MS ($ESI^+$) m/z 675.4 $(M+H)^+$.

Step 3—Methyl chloro-(3-chloro-2-fluoro-phenyl)-oxo-dispiro[BLAH]carboxylate

Methyl chloro-(3-chloro-2-fluoro-phenyl)-[(1R,2S)-2-hydroxy-1,2-diphenyl-ethyl]-oxo-dispiro[BLAH]carboxylate (6.21 g, 9.19 mmol) was dissolved in ACN (70 mL), then CAN (10.0 g, 18.3 mmol) was added and the reaction was stirred for 5 min, then followed by the addition of $H_2O$ (70 mL). The reaction was stirred at 25° C. for 30 minutes. On completion, the reaction mixture was concentrated in vacuo to give a residue. The crude product was purified by reversed-phase (0.1% TFA condition) to give title compound (2.00 g, 32% yield) as a yellow solid. $^1H$ NMR (400 MHz, DMSO-$d_6$) δ 10.72 (s, 1H), 7.60-7.53 (m, 1H), 7.50 (dd, J=1.7, 8.0 Hz, 1H), 7.43-7.37 (m, 1H), 7.17 (t, J=8.0 Hz, 1H), 7.09 (dd, J=1.9, 8.0 Hz, 1H), 6.72 (d, J=2.0 Hz, 1H), 4.82-4.71 (m, 3H), 3.90-3.80 (m, 1H), 3.77-3.71 (m, 1H), 3.61 (s, 3H), 3.60 (s, 1H), 3.57-3.50 (m, 1H), 2.03 (d, J=11.8 Hz, 1H), 1.76-1.66 (m, 1H), 1.53 (d, J=14.0 Hz, 1H), 1.19-1.09 (m, 1H). LC-MS ($ESI^+$) m/z 481.3 $(M+H)^+$.

Step 4—Chloro-(3-chloro-2-fluoro-phenyl)-oxo-dispiro[BLAH]carboxylic acid

Methyl chloro-(3-chloro-2-fluoro-phenyl)-oxo-dispiro [BLAH]carboxylate (880 mg, 1.84 mmol) was dissolved in THF (7 mL) and LiOH·$H_2O$ (231 mg, 5.51 mmol) was added followed by $H_2O$ (7 mL) and MeOH (1 mL). The reaction was stirred at 25° C. for 15 minutes. On completion, water (20 mL) was added and the reaction was slowly neutralized with 2M HCl and the suspension was stirred for 15 minutes. The resulting precipitates were filtered, and washed with water. The crude product was purified by reversed-phase (0.1% TFA condition) to give title compound (360 mg, 41% yield) as a white solid. $^1H$ NMR (400 MHz, METHANOL-$d_4$) δ 7.67 (t, J=6.8 Hz, 1H), 7.60 (dd, J=2.4, 8.4 Hz, 1H), 7.38 (t, J=7.2 Hz, 1H), 7.16 (ddd, J=2.8, 4.9, 8.0 Hz, 2H), 6.82 (d, J=1.6 Hz, 1H), 5.25 (d, J=10.4 Hz, 1H), 4.07 (d, J=7.6 Hz, 2H), 3.91-3.83 (m, 1H), 3.78-3.69 (m, 1H), 2.49 (d, J=14.0 Hz, 1H), 2.26 (td, J=8.5, 14.4 Hz, 1H), 2.06-1.97 (m, 1H), 1.51 (dt, J=5.3, 13.2 Hz, 1H). LC-MS ($ESI^+$) m/z 465.2 $(M+H)^+$.

3-(4-Methoxybenzyl)dihydropyrimidine-2,4(1H, 3H)-dione (Intermediate GK)

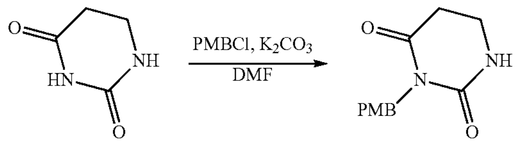

GK

To a mixture of dihydropyrimidine-2,4(1H,3H)-dione (10.0 g, 87.6 mmol, CAS #504-07-4) in DMF (100 mL) was added PMB-Cl (13.7 g, 87.6 mmol, 11.9 mL), $Cs_2CO_3$ (28.5 g, 87.6 mmol) at 25° C. The mixture was then stirred at 50°

C. for 3 hours. On completion, the reaction mixture was quenched with of water (100 mL), and extracted with EtOAc (3×50 mL). The organic layer was dried over anhydrous $Na_2SO_4$, filtered and concentrated in vacuo. The crude product was purified by re-crystallization from EA/PE (20 mL, v/v=1/1) at 25° C. to give the title compound (9.40 g, 45% yield) as a white solid. $^1$H NMR (400 MHz, $CDCl_3$) δ 7.81 (s, 1H), 7.18 (d, J=8.4 Hz, 2H), 6.83 (d, J=8.4 Hz, 2H), 4.72 (s, 2H), 3.72 (s, 3H), 3.23-3.20 (m, 2H), 2.63 (t, J=6.8 Hz, 2H).

1-(8-Bromoimidazo[1,2-a]pyridin-3-yl)hexahydro-pyrimidine-2,4-dione (Intermediate GL)

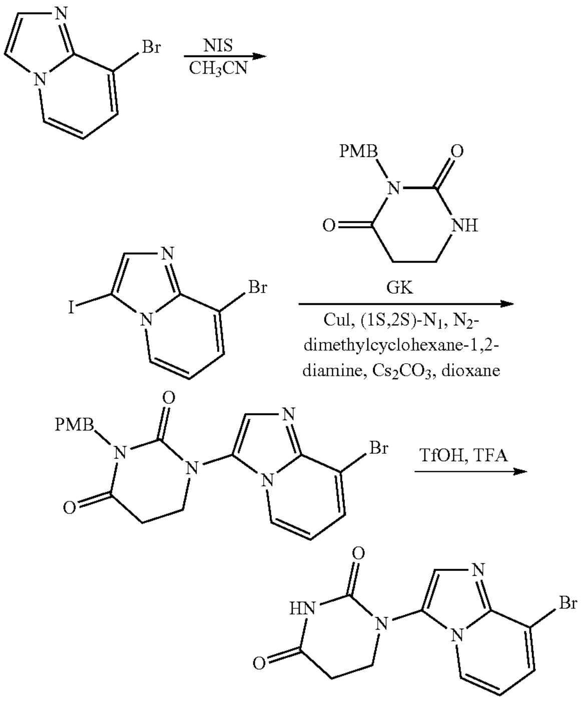

GL

Step 1—8-Bromo-3-iodoimidazo[1,2-a]pyridine

To a solution of 8-bromoimidazo[1,2-a]pyridine (5.00 g, 25.3 mmol, CAS #850349-02-9) in $CH_3CN$ (30 mL) was added NIS (5.71 g, 25.3 mmol) at 25° C. The mixture was stirred at 25° C. for 0.5 hour. On completion, the mixture was concentrated in vacuo. The mixture was purified by silica gel column to give the title compound (7.30 g, 89% yield) as a greenish solid. $^1$H NMR (400 MHz, $CDCl_3$) δ 8.38 (d, J=6.8 Hz, 1H), 7.80 (s, 1H), 7.70 (d, J=7.2 Hz, 1H), 7.00 (t, J=7.2 Hz, 1H).

Step 2—1-(8-Bromoimidazo[1,2-a]pyridin-3-yl)-3-(4-methoxybenzyl)dihydropyrimidine-2,4(1H,3H) dione A mixture of 8-bromo-3-iodo-imidazo[1,2-a]pyridine (500 mg, 1.55 mmol) and 3-(4-methoxybenzyl) dihydropyrimidine-2,4(1H,3H)-dione (362 mg, 1.55 mmol, Intermediate GK), CuI (58.9 mg, 309 umol), $Cs_2CO_3$ (1.01 g, 3.10 mmol), and (1S,2S)—N1,N2-dimethylcyclohexane-1,2-diamine (44.0 mg, 309 umol) in dioxane (10 mL) was stirred at 60° C. for 6 hours under $N_2$. On completion, the mixture was filtered through celite and the filtrate was concentrated in vacuo. The residue was purified by reversed phase flash (120 g Flash Column, Welch Ultimate XB_C18, 20-40 um; 120 A, 5% to 35% MeCN in $H_2O$, 0.5% FA in $H_2O$) and then further purified by prep-HPLC (column: Waters xbridge, 150 mm*25 mm*10 um; mobile phase: [water (10 mM $NH_4HCO_3$)-MeCN]; B %: 22%-52%, 10 min) to give the title compound (200 mg, 10% yield) as a yellow solid. $^1$H NMR (400 MHz, DMSO-$d_6$) δ 8.35 (dd, J=0.8, 6.8 Hz, 1H), 7.69-7.67 (m, 1H), 7.67 (s, 1H), 7.24 (d, J=7.6 Hz, 2H), 6.91 (t, J=7.2 Hz, 1H), 6.87-6.84 (m, 2H), 4.81 (s, 2H), 3.84 (t, J=6.4 Hz, 2H), 3.72 (s, 3H), 3.02 (s, 2H).

Step 3—1-(8-Bromoimidazo[1,2-a]pyridin-3-yl) dihydropyrimidine-2,4(1H,3H)-dione

A solution of 1-(8-bromoimidazo[1,2-a]pyridin-3-yl)-3-(4-methoxybenzyl)dihydropyrimidine-2,4 (1H,3H)-dione (50.0 mg, 116 umol) in TFA (0.5 mL) and TfOH (0.01 mL) was stirred at 70° C. for 2.5 hours. On completion, the mixture was concentrated in vacuo. The residue was purified by prep-HPLC (Waters xbridge, 150 mm*25 mm*10 μm, water (10 mM $NH_4HCO_3$)-MeCN, 1% to 30% MeCN in $H_2O$, 11 min) and then further purified by prep-HPLC (column: Phenomenex Luna C18, 150 mm*25 mm*10 um; mobile phase: [water (0.225% FA)-MeCN]; MeCN %: 0%-20%, 11 min) to give the title compound (3.19 mg, 77% yield) as a white solid. $^1$H NMR (400 MHz, DMSO-$d_6$) δ 10.70 (s, 1H), 8.38 (d, J=6.0 Hz, 1H), 7.67-7.65 (m, 2H), 6.91 (t, J=6.8 Hz, 1H), 3.81 (t, J=6.8 Hz, 2H), 2.84 (t, J=5.2 Hz, 2H); LC-MS (ESI$^+$) m/z 308.9 (M+H)$^+$.

1-[8-[2-(4-Piperidyl)ethynyl]imidazo[1,2-a]pyridin-3-yl]hexahydropyrimidine-2,4-dione (Intermediate GM)

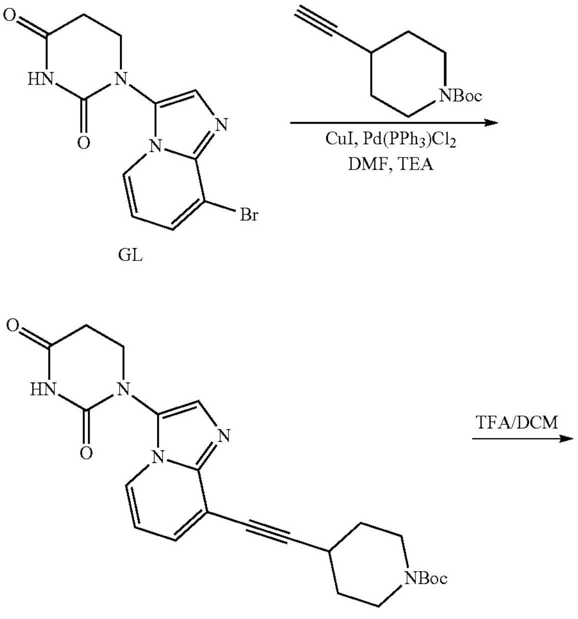

-continued

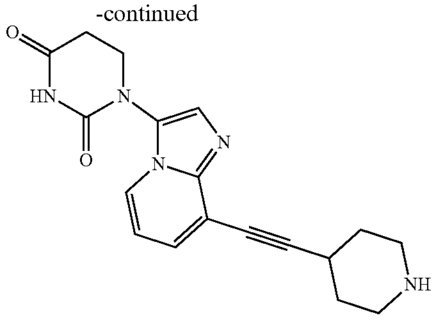

GM

Step 1—Tert-butyl 4-[2-[3-(2,4-dioxohexahydropyrimidin-1-yl)imidazo[1,2-a]pyridin-8-yl]ethynyl]piperidine-1-carboxylate A mixture of 1-(8-bromoimidazo[1,2-a]pyridin-3-yl)hexahydropyrimidine-2,4-dione (300 mg, 970 umol, Intermediate GL), tert-butyl 4-ethynylpiperidine-1-carboxylate (243 mg, 1.16 mmol, CAS #287192-97-6) in DMF (3 mL), was added TEA (491 mg, 4.85 mmol), dichloropalladium; triphenylphosphane (68.1 mg, 97.0 umol), CuI (9.24 mg, 48.5 umol) and DMF (3 mL). The reaction was degassed and purged with $N_2$ for three, and then the mixture was stirred at 80° C. for 12 hours under $N_2$ atmosphere. The mixture was quenched with water (10 mL), and extracted with ethyl acetate (20 mL). The organic layer was dried over $Na_2SO_4$, and concentrated in vacuo to afford the crude product. The crude product was purified by reversed-phase (0.1% TFA condition) to give the title compound (100 mg, 23% yield) as a white solid. LC-MS ($ESI^+$) m/z 438.2 $(M+H)^+$.

Step 2—1-[8-[2-(4-Piperidyl)ethynyl]imidazo[1,2-a]pyridin-3-yl]hexahydropyrimidine-2A-dione To a solution of tert-butyl 4-[2-[3-(2,4-dioxohexahydropyrimidin-1-yl)imidazo[1,2-a]pyridin-8-yl] ethynyl]piperidine-1-carboxylate (400 mg, 914 umol) in DCM (5 mL) at 25° C. was added TFA (1 mL) at 0° C. The mixture was stirred at 0° C. for 0.5 hour. The mixture was concentrated to give the title compound (400 mg, 96% yield, TFA salt) as a yellow oil. LC-MS ($ESI^+$) m/z 338.1 $(M+H)^+$.

1-[8-[2-[1-[(4-Aminocyclohexyl)methyl]-4-piperidyl]ethynyl]imidazo[1,2-a]pyridin-3-yl]hexahydropyrimidine-2,4-dione (Intermediate GN)

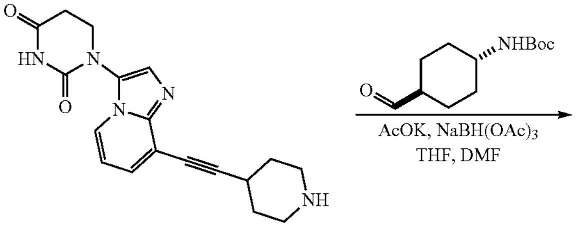

GM

-continued

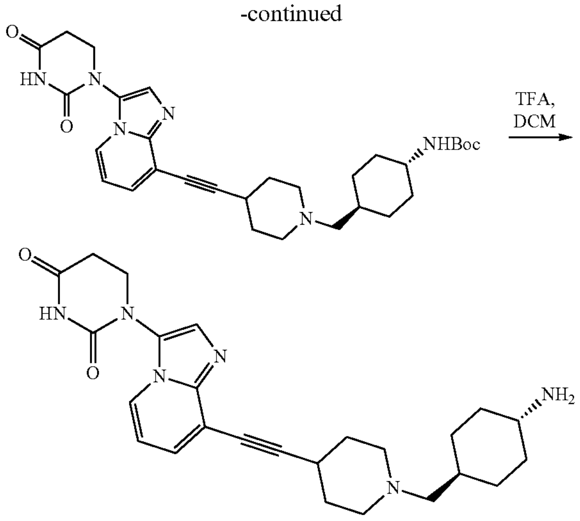

GN

Step 1—Tert-butyl N-[4-[[4-[2-[3-(2,4-dioxohexahydropyrimidin-1-yl)imidazo[1,2-a]pyridin-8-yl]ethynyl]-1-piperidyl]methyl]cyclohexyl]carbamate To a solution of 1-[8-[2-(4-piperidyl)ethynyl]imidazo[1,2-a]pyridin-3-yl]hexahydropyrimidine-2,4-dione (400 mg, 886 umol, TFA salt, Intermediate GM) in THF (6 mL) and DMF (2 mL) was added AcOK (869 mg, 8.86 mmol), then the mixture was stirred at 25° C. for 10 minutes. Next, tert-butyl N-(4-formylcyclohexyl) carbamate (201 mg, 886 umol, CAS #181308-57-6) was added to the mixture and stirred at 25° C. for 5 minutes. Finally, $NaBH(OAc)_3$ (281 mg, 1.33 mmol) was added to the mixture at 25° C. and the reaction mixture was stirred at 25° C. for 14 hours. On completion, the mixture was quenched with water (20 mL) and extracted with ethyl acetate (25 mL×3). The combined organic phase was dried over anhydrous sodium sulfate, filtered and concentrated to give a residue. The crude product was purified by reversed-phase (0.1% TFA condition) to give the title compound (200 mg, 41% yield) as a white solid. $^1H$ NMR (400 MHz, DMSO-$d_6$) δ 10.75 (s, 1H), 8.50 (d, J=1.2 Hz, 1H), 7.83 (s, 1H), 7.68-7.60 (m, 1H), 7.13 (s, 1H), 6.78 (d, J=7.6 Hz, 1H), 3.55 (d, J=12.4 Hz, 3H), 3.30 (s, 1H), 3.18 (d, J=7.2 Hz, 1H), 3.05-2.90 (m, 4H), 2.84 (s, 2H), 2.21 (d, J=13.2 Hz, 1H), 2.17-2.06 (m, 1H), 2.04-1.88 (m, 2H), 1.85-1.66 (m, 6H), 1.37 (s, 9H), 1.23-1.12 (m, 2H), 1.08-0.94 (m, 2H). LC-MS ($ESI^+$) m/z 549.4 $(M+H)^+$.

Step 2—1-[8-[2-[1-[(4-Aminocyclohexyl)methyl]-4-piperidyl]ethynyl]imidazo[1,2-a]pyridin-3-yl]hexahydropyrimidine-2,4-dione To a solution of tert-butyl N-[4-[[4-[2-[3-(2,4-dioxohexahydropyrimidin-1-yl)imidazo[1,2-a]pyridin-8-yl]ethynyl]-1-piperidyl]methyl]cyclohexyl]carbamate (150 mg, 273 umol) in DCM (2.5 mL) at 25° C. was added TFA (0.5 mL) at 0° C. The mixture was stirred at 0° C. for 1 hour. On completion, the mixture was filtered and concentrated to give the title compound (150 mg, 97% yield, TFA salt) as a yellow oil. LC-MS ($ESI^+$) m/z 449.4 $(M+H)^+$.

3-[3-methyl-2-oxo-5-[2-(4-piperidyl)ethyl]benzimidazol-1-yl]piperidine-2,6-dione (Intermediate GO)

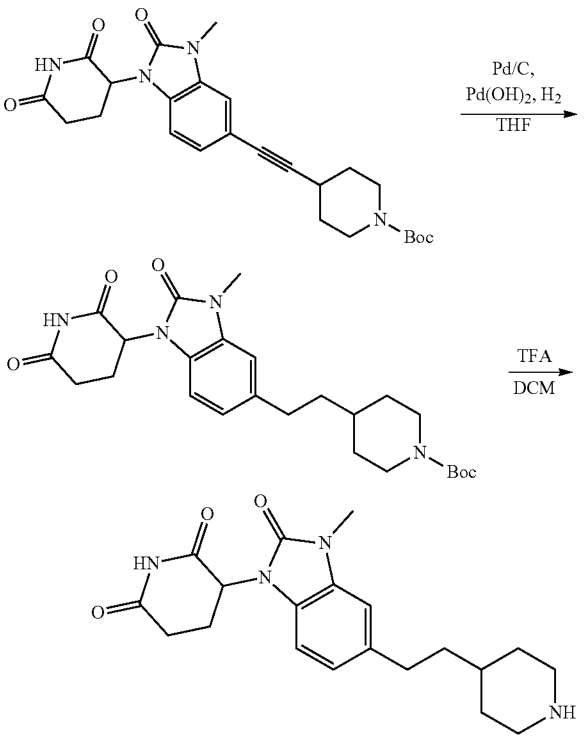

GO

The title compound was synthesized via Steps 1-2 of Intermediate CL.

Chloro-(3-chloro-2-fluoro-phenyl)-(chloromethyl)-methyl-dispiro[BLAH]one (Intermediate GP)

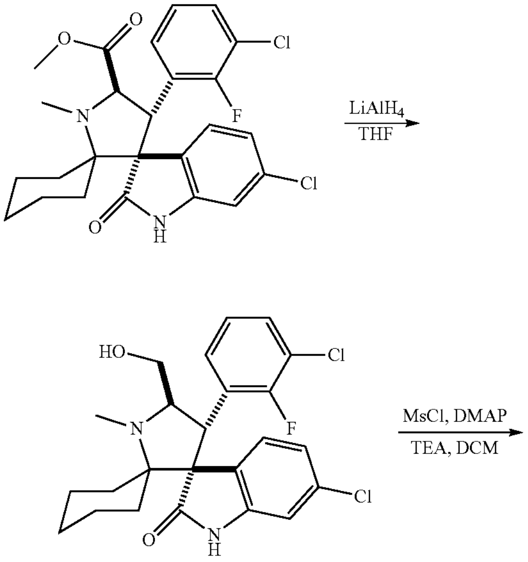

-continued

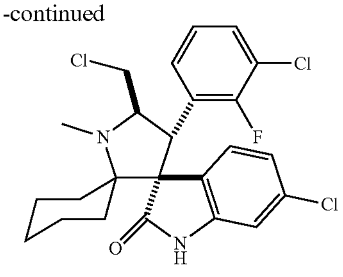

GP

Step 1—Chloro-(3-chloro-2-fluoro-phenyl)-(hydroxymethyl)-methyl-dispiro[BLAH]one To a mixture of methyl chloro-(3-chloro-2-fluoro-phenyl)-methyl-oxo-dispiro[BLAH]carboxylate (800 mg, 1.63 mmol, synthesized via Step 1 of Intermediate DM) in THF (10 mL) was added $LiAlH_4$ (247 mg, 6.51 mmol) at 0° C. under $N_2$. The mixture was stirred at 25° C. for 30 minutes. On completion, the reaction mixture was quenched with addition $H_2O$ (0.24 mL), 15% NaOH (0.24 mL) and $H_2O$ (0.72 mL) at 0° C. Then the reaction mixture was filtered and the filtrate was concentrated under reduced pressure to give a residue. The residue was purified by reverse phase flash [ACN/(0.1% FA in water), 0% to 90%] to give the title compound (400 mg, 47% yield) as white solid. $^1H$ NMR (400 MHz, DMSO-$d_6$) δ 10.48-10.33 (m, 1H), 7.58-7.48 (m, 1H), 7.39-7.27 (m, 2H), 7.10 (t, J=8.0 Hz, 1H), 7.00 (dd, J=2.0, 8.0 Hz, 1H), 6.61 (d, J=2.0 Hz, 1H), 4.25 (d, J=10.4 Hz, 1H), 3.81-3.75 (m, 1H), 3.43 (dd, J=4.4, 11.2 Hz, 1H), 3.26 (dd, J=4.0, 11.2 Hz, 1H), 2.80 (s, 3H), 1.97 (d, J=12.8 Hz, 2H), 1.64-1.41 (m, 6H), 1.00-0.88 (m, 2H). LC-MS ($ESI^+$) m/z 464.3 $(M+H)^+$.

Step 2—chloro-(3-chloro-2-fluoro-phenyl)-(chloromethyl)-methyl-dispiro[BLAH]one

MsCl (96.4 mg, 842 umol) was added dropwise to a solution of chloro-(3-chloro-2-fluoro-phenyl)-(hydroxymethyl)-methyl-dispiro[BLAH]one (300 mg, 647 umol), TEA (131 mg, 1.29 mmol) and DMAP (6.33 mg, 51.8 umol) in DCM (3.0 mL). The mixture was stirred at 0° C. for 30 minutes. On completion, the reaction mixture was quenched by pouring the mixture into a cold saturated sodium carbonate aqueous solution (5.0 ml). The aqueous layer was extracted with DCM (3.0 ml×2). The organic layer was separated, dried over anhydrous $Na_2SO_4$, filtered and concentrated under reduced pressure to give the title compound 4 (400 mg, 70% yield) as a yellow solid. LC-MS ($ESI^+$) m/z 480.9 $(M+H)^+$.

4-[[Chloro-(3-chloro-2-fluoro-phenyl)-methyl-oxo-dispiro[BLAH]yl]methylamino]cyclohexanecarboxylic acid (Intermediate GQ)

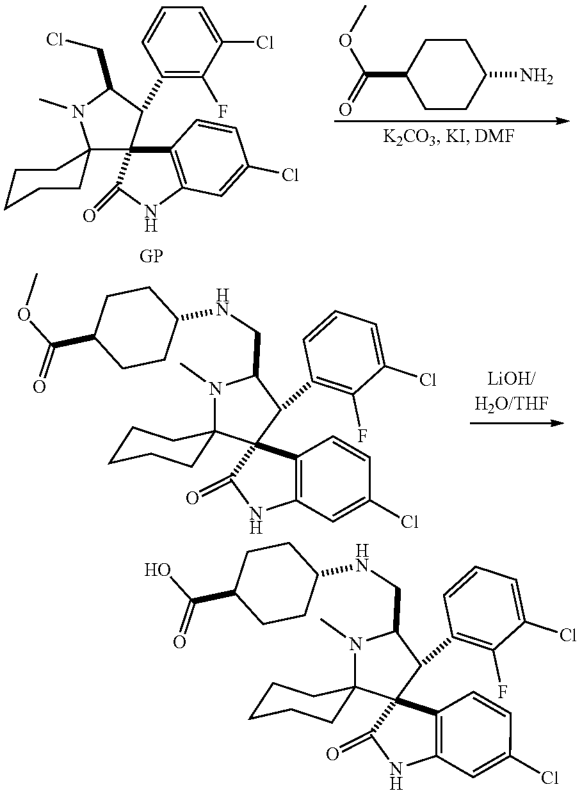

GP

GQ

Step 1—Methyl 4-[[chloro-(3-chloro-2-fluoro-phenyl)-methyl-oxo-dispiro[BLAH]yl]methylamino] cyclohexanecarboxylate A mixture of chloro-(3-chloro-2-fluoro-phenyl)-(chloromethyl)-methyl-dispiro[BLAH]one (250 mg, 519 umol, Intermediate GP), methyl 4-aminocyclohexanecarboxylate (301 mg, 1.56 mmol, CAS #61367-07-5), $K_2CO_3$ (143 mg, 1.04 mmol), and KI (8.61 mg, 51.9 umol) in DMF (4.0 mL) was degassed and purged with $N_2$ three times. Then the mixture was stirred at 60° C. for 12 hours under $N_2$ atmosphere. On completion, the reaction mixture was concentrated in vacuo to give a residue. The residue was purified by reverse phase flash [ACN/(0.1% TFA in water), 0% to 90%] to give the title compound (60 mg, 20% yield) as a yellow solid. LC-MS ($ESI^+$) m/z 602.2 $(M+H)^+$.

Step 2—4-[[Chloro-(3-chloro-2-fluoro-phenyl)-methyl-oxo-dispiro[BLAH]yl]methylamino] cyclohexanecarboxylic acid A mixture of methyl 4-[[chloro-(3-chloro-2-fluoro-phenyl)-methyl-oxo-dispiro[BLAH]yl]methylamino]cyclohexanecarboxylate (50.0 mg, 83.0 umol), $LiOH{\cdot}H_2O$ (20.9 mg, 498 umol), and NaOH (19.9 mg, 498 umol) in MeOH (0.4 mL), $H_2O$ (0.2 mL) and THF (0.4 mL) was stirred at 25° C. for 12 hours under $N_2$ atmosphere. On completion, 2N HCl was added to the reaction mixture to adjust the pH=6. Then the reaction was concentrated in vacuo to give a residue. The residue was purified by reverse phase flash [ACN/(0.1% TFA in water), 0% to 90%] to give the title compound (40 mg, 65% yield) as a yellow solid. LC-MS ($ESI^+$) m/z 588.2 $(M+H)^+$.

2-[1-(2,6-Dioxo-3-piperidyl)-3-methyl-2-oxo-benzimidazol-5-yl]acetaldehyde (Intermediate GR)

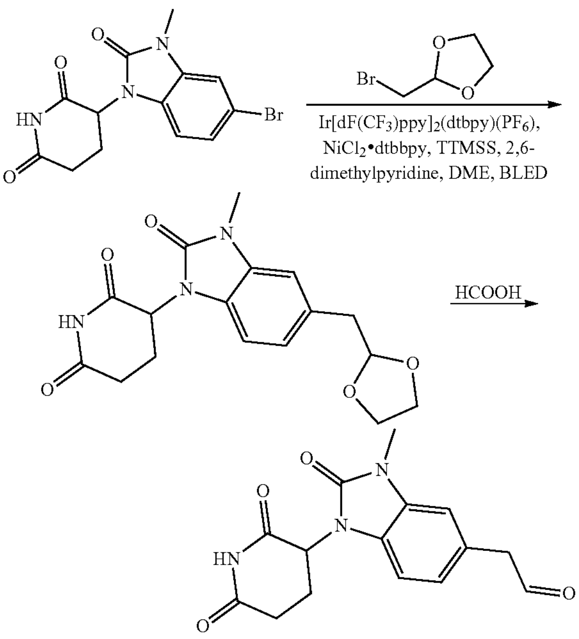

GR

Step 1—3-[5-(1,3-Dioxolan-2-ylmethyl)-3-methyl-2-oxo-benzimidazol-1-yl]piperidine-2,6-dione To an 40 mL vial equipped with a stir bar was added 3-(5-bromo-3-methyl-2-oxo-benzimidazol-1-yl)piperidine-2,6-dione (3.00 g, 8.87 mmol, Intermediate E), 2-(bromomethyl)-1,3-dioxolane (1.93 g, 11.5 mmol, CAS #4360-63-8), $Ir[dF(CF_3)ppy]_2(dtbpy)(PF_6)$ (99.5 mg, 88.7 umol), $NiCl_2{\cdot}dtbbpy$ (17.6 mg, 44.3 umol), TTMSS (2.21 g, 8.87 mmol), 2,6-dimethylpyridine (1.90 g, 17.7 mmol) in DME (87 mL). The vial was sealed and placed under nitrogen was added. The reaction was stirred and irradiated with a 40 W [455 nm] blue LED lamp (7 cm away), with cooling fan to keep the reaction temperature at 25° C. for 14 hours. On completion, the reaction mixture was concentrated under reduced pressure to remove the DME. The residue was purified by column chromatography ($SiO_2$, Dichloromethane/Ethyl acetate=0/1 to 1/1), concentrated under reduced pressure to give title compound (1.90 g, 47% yield) as a yellow solid. $^1H$ NMR (400 MHz, DMSO-$d_6$) δ 10.96 (s, 1H), 6.99-6.92 (m, 1H), 6.92-6.85 (m, 1H), 6.80 (d, J=8.0 Hz, 1H), 5.22 (dd, J=4.8, 11.6 Hz, 1H), 4.84 (t, J=4.4 Hz, 1H), 3.84-3.70 (m, 2H), 3.70-3.59 (m, 2H), 3.19 (s, 3H), 2.85-2.71 (m, 3H), 2.64-2.45 (m, 2H), 1.95-1.83 (m, 1H). LC-MS ($ESI^+$) m/z 346.3 $(M+H)^+$.

Step 2—2-[1-(2,6-Dioxo-3-piperidyl)-3-methyl-2-oxo-benzimidazol-5-yl]acetaldehyde To 3-[5-(1,3-dioxolan-2-ylmethyl)-3-methyl-2-oxo-benzimidazol-1-yl]piperidine-2,6-dione (500 mg, 1.45 mmol)

was added HCOOH (25 mL) and the mixture was stirred at 25° C. for 15 minutes. On completion, the reaction mixture was concentrated under reduced pressure to remove HCOOH. The title compound (430 mg, 69% yield) was obtained as a yellow oil. LC-MS ($ESI^+$) m/z 302.3 $(M+H)^+$.

3-[5-[2-(2,7-Diazaspiro[3.5]nonan-2-yl)ethyl]-3-methyl-2-oxo-benzimidazol-1-yl]piperidine-2,6-dione (Intermediate GS)

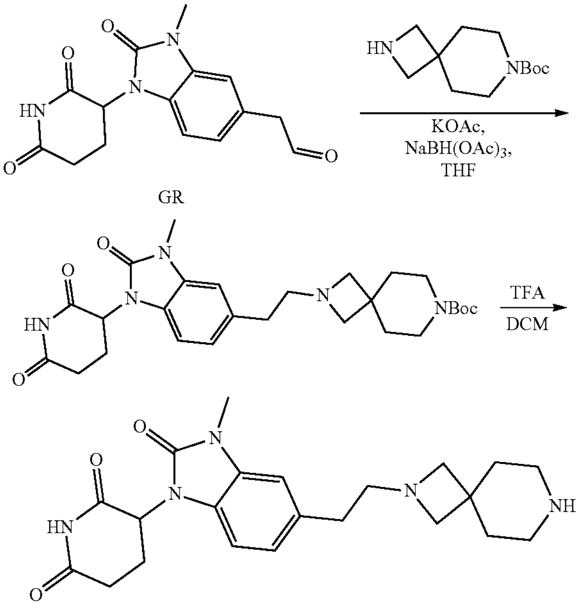

GR

GS

Step 1—Tert-butyl 2-[2-[1-(2,6-dioxo-3-piperidyl)-3-methyl-2-oxo-benzimidazol-5-yl]ethyl]-2,7-diazaspiro[3.5]nonane-7-carboxylate To a solution of 2-[1-(2,6-dioxo-3-piperidyl)-3-methyl-2-oxo-benzimidazol-5-yl]acetaldehyde (430 mg, 1.43 mmol, Intermediate GR), tert-butyl-2,7-diazaspiro[3.5]nonane-7-carboxylate (322 mg, 1.43 mmol, CAS #896464-16-7) and KOAc (840 mg, 8.56 mmol) in THF (50 mL) was added $NaBH(OAc)_3$ (907 mg, 4.28 mmol). The mixture was stirred at 25° C. for 1 hour. On completion, the reaction mixture was concentrated under reduced pressure to remove THF. The crude product was purified with reversed phase flash (0.1% FA condition). The residual aqueous solution was lyophilized to give title compound (730 mg, 89% yield) as a white solid. $^1H$ NMR (400 MHz, DMSO-$d_6$) 11.09 (s, 1H), 7.04 (s, 1H), 7.00 (d, J=8.0 Hz, 1H), 6.87 (dd, J=0.8, 8.4 Hz, 1H), 5.34 (dd, J=5.2, 12.8 Hz, 1H), 3.90-3.54 (m, 5H), 3.24 (s, 4H), 3.00 (s, 4H), 2.70-2.63 (m, 3H), 2.60 (d, J=6.4 Hz, 2H), 2.06-1.95 (m, 1H), 1.65-1.52 (m, 4H), 1.39 (s, 9H). LC-MS ($ESI^+$) m/z 512.4 $(M+H)^+$.

Step 2—3-[5-[2-(2,7-Diazaspiro[3.5]nonan-2-yl)ethyl]-3-methyl-2-oxo-benzimidazol-1-yl]piperidine-2,6-dione To a solution of tert-butyl 2-[2-[1-(2,6-dioxo-3-piperidyl)-3-methyl-2-oxo-benzimidazol-5-yl]ethyl]-2,7-diazaspiro[3.5]nonane-7-carboxylate (350 mg, 684 umol) in DCM (7 mL) was added TFA (1.4 mL). The mixture was stirred at 25° C. for 40 minutes. On completion, the reaction mixture was concentrated under reduced pressure to remove TFA and DCM. The title compound (359 mg, 79% yield, TFA salt) was obtained as a yellow oil. LC-MS ($ESI^+$) m/z 412.2 $(M+H)^+$.

3-[5-[2-[7-[(4-Aminocyclohexyl)methyl]-2,7-diazaspiro[3.5]nonan-2-yl]ethyl]-3-methyl-2-oxo-benzimidazol-1-yl]piperidine-2,6-dione (Intermediate GT)

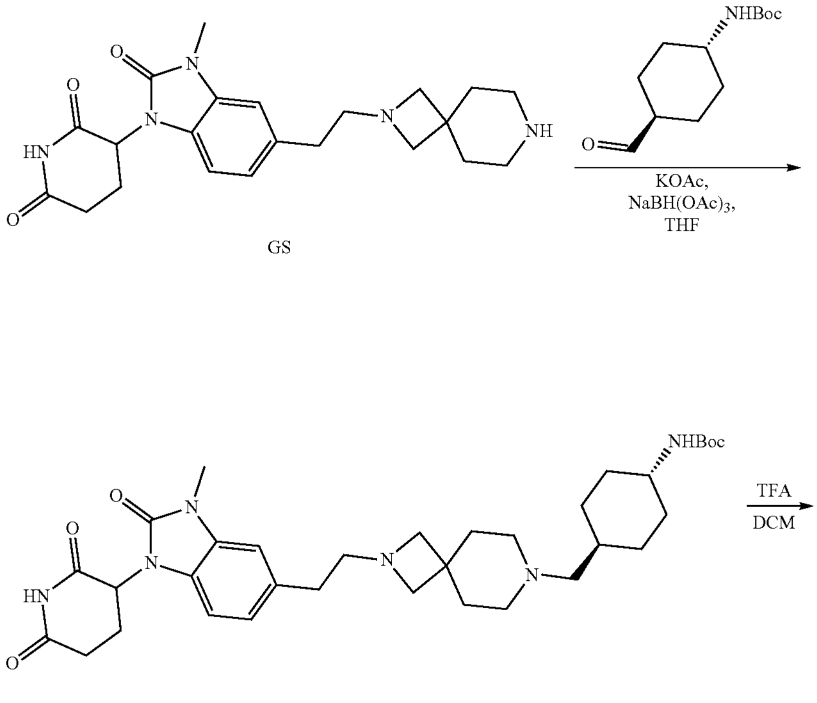

GS

-continued

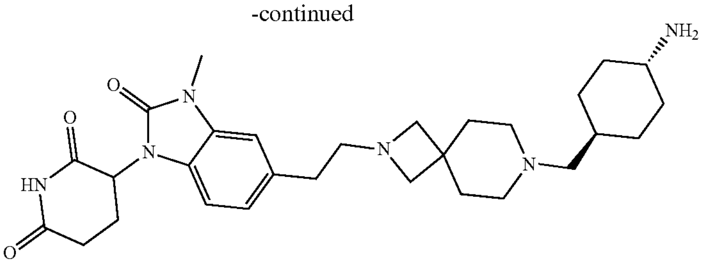

GT

Step 1—Tert-butyl N-[4-[[2-[2-[1-(2,6-dioxo-3-piperidyl)-3-methyl-2-oxo-benzimidazol-5-yl]ethyl]-2,7-diazaspiro[3.5]nonan-7-yl]methyl]cyclohexyl] carbamate To a solution of 3-[5-[2-(2,7-diazaspiro[3.5]nonan-2-yl) ethyl]-3-methyl-2-oxo-benzimidazol-1-yl] piperidine-2,6-dione (359 mg, 683 umol, TFA salt, Intermediate GS), tert-butyl N-(4-formylcyclohexyl)carbamate (232 mg, 1.02 mmol, CAS #181308-57-6) and KOAc (402 mg, 4.10 mmol) in THF (7 mL) was added $NaBH(OAc)_3$ (434 mg, 2.05 mmol). The mixture was then stirred at 25° C. for 20 minutes. On completion, the reaction mixture was concentrated under reduced pressure to remove THF. The crude product combined with reversed phase flash (0.10% FA condition). The residual aqueous solution was lyophilized to give title compound (300 mg, 66% yield) as a white solid. $^1H$ NMR (400 MHz, DMSO-$d_6$) δ 11.10 (s, 1H), 7.11 (s, 1H), 7.07 (d, J=8.0 Hz, 1H), 6.94 (d, J=8.0 Hz, 1H), 6.72 (d, J=8.0 Hz, 1H), 5.36 (dd, J=5.2, 12.8 Hz, 1H), 3.73 (s, 4H), 3.33-3.24 (m, 6H), 3.19-3.08 (m, 2H), 2.97-2.85 (m, 1H), 2.83-2.74 (m, 2H), 2.74-2.67 (m, 1H), 2.63 (d, J=17.2 Hz, 2H), 2.35-2.21 (m, 2H), 2.05-1.96 (m, 1H), 1.88-1.79 (m, 4H), 1.77-1.66 (t, J=13.2 Hz, 4H), 1.51-1.42 (m, 1H), 1.40-1.30 (m, 10H), 1.16-1.04 (m, 2H), 0.96-0.81 (m, 2H). LC-MS (ESI$^+$) m/z 623.6 $(M+H)^+$.

Step 2—3-[5-[2-[7-[(4-Aminocyclohexyl)methyl]-2,7-diazaspiro[3.5]nonan-2-yl]ethyl]-3-methyl-2-oxo-benzimidazol-1-yl]piperidine-2,6-dione To a solution of tert-butyl N-[4-[[2-[2-[1-(2,6-dioxo-3-piperidyl)-3-methyl-2-oxo-benzimidazol-5-yl] ethyl]-2,7-diazaspiro[3.5]nonan-7-yl]methyl]cyclohexyl]carbamate (50.0 mg, 80.2 μmol) in DCM (1.0 mL) was added TFA (770 mg, 6.75 mmol, 0.50 mL). The mixture was stirred at 25° C. for 1 hour. On completion, the reaction mixture was concentrated under reduced pressure to remove DCM and TFA. The title compound (50.0 mg, 88% yield, TFA salt) was obtained as yellow oil. LC-MS (ESI$^+$) m/z 523.6 $(M+H)^+$.

3-[4-[2-[7-[(4-Aminocyclohexyl)methyl]-2,7-diazaspiro[3.5]nonan-2-yl]ethyl]-3-methyl-2-oxo-benzimidazol-1-yl]piperidine-2,6-dione (Intermediate GU)

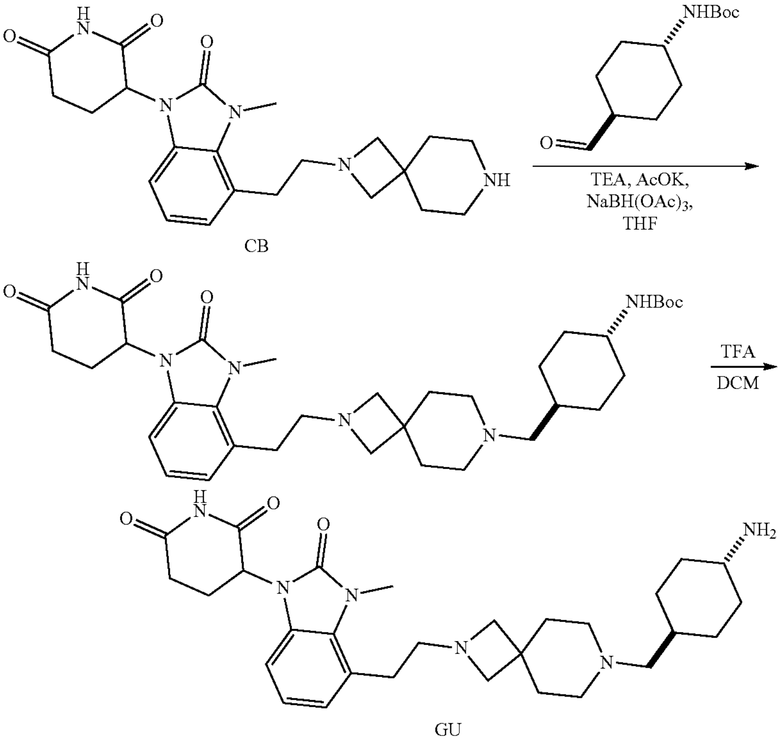

CB

GU

Step 1—N-[4-[[2-[2-[1-(2,6-dioxo-3-piperidyl)-3-methyl-2-oxo-benzimidazol-4-yl]ethyl]-2,7-diazaspiro[3.5]nonan-7-yl]methyl]cyclohexyl]carbamate The mixture 3-[4-[2-(2,7-diazaspiro[3.5]nonan-2-yl)ethyl]-3-methyl-2-oxo-benzimidazol-1-yl] piperidine-2,6-dione (100 mg, 190 umol, TFA salt, Intermediate CB) in THF (5 mL) was added AcOK (112.1 mg, 1.14 mmol). The mixture was stirred at 25° C. for 15 minutes, then tert-butyl N-(4-formylcyclohexyl)carbamate (43.3 mg, 190 umol, CAS #181308-56-5) was added to the mixture and the mixture was stirred at 25° C. for 15 minutes. Next, NaBH$(OAc)_3$ (121 mg, 571 umol) was added to the mixture at 25° C. and the mixture was stirred for 0.5 hour. On completion, the mixture was concentrated to give a residue. The crude product was purified by reversed-phase HPLC (0.1% TFA condition) to give the title compound (80.0 mg, 63% yield) as a white solid. LC-MS ($ESI^+$) m/z 623.6 $(M+H)^+$.

Step 2—3-[4-[2-[7-[(4-Aminocyclohexyl)methyl]-2,7-diazaspiro[3.5]nonan-2-yl]ethyl]-3-methyl-2-oxo-benzimidazol-1-yl]piperidine-2,6-dione To a solution of tert-butyl N-[4-[[2-[2-[1-(2,6-dioxo-3-piperidyl)-3-methyl-2-oxo-benzimidazol-4-yl] ethyl]-2,7-diazaspiro[3.5]nonan-7-yl]methyl]cyclohexyl]carbamate (80.0 mg, 128 μmol) in DCM (2.5 mL) was added TFA (0.5 mL), then the mixture was stirred at 25° C. for 1 hour. On completion, the mixture was concentrated to give a residue. The title compound (80.0 mg, 126 umol, 97.8% yield, TFA salt) was obtained as a yellow oil. LC-MS ($ESI^+$) m/z 523.3 $(M+H)^+$.

1-[7-(5-Aminopentylamino)imidazo[1,2-a]pyridin-3-yl]hexahydropyrimidine-2,4-dione (Intermediate GV)

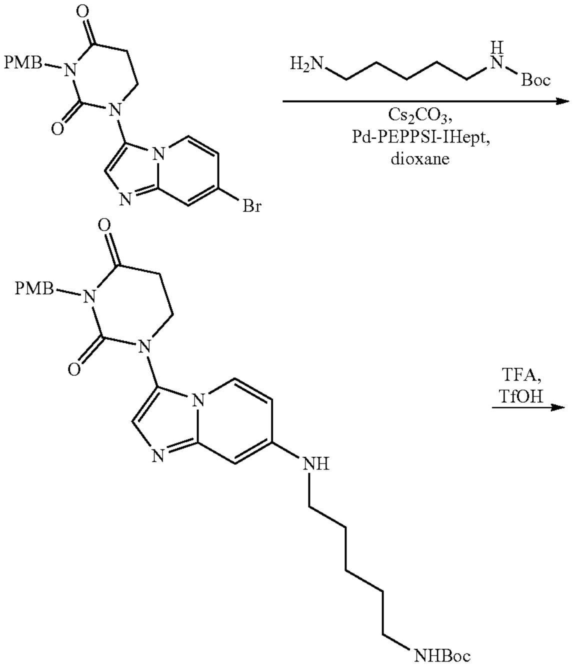

-continued

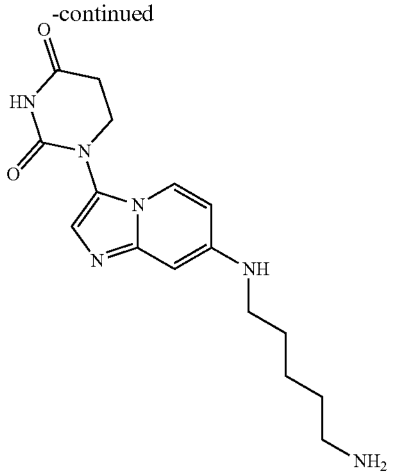

GV

Step 1—Tert-butyl N-[5-[[3-[3-[(4-methoxyphenyl)methyl]-2,4-dioxo-hexahydropyrimidin-1-yl]imidazo[1,2-a]pyridin-7-yl]amino]pentyl]carbamate A mixture of 1-(7-bromoimidazo[1,2-a]pyridin-3-yl)-3-[(4-methoxyphenyl)methyl]hexahydropyrimidine-2,4-dione (400 mg, 931 umol, synthesized via Steps 1-2 of Intermediate ER), tert-butylN-(5-aminopentyl) carbamate (377 mg, 1.86 mmol, CAS #51644-96-3), $Cs_2CO_3$ (607 mg, 1.86 mmol) and Pd-PEPPSI-IHept (70.0 mg, 18.4 umol) in dioxane (20 mL) was degassed and purged with $N_2$ three times. Then the mixture was stirred at 110° C. for 16 hours under $N_2$ atmosphere. On completion, the mixture was quenched with water (20 mL) and extracted with ethyl acetate (25 mL×3). The combined organic phase was dried over anhydrous sodium sulfate, filtered and concentrated to give a residue. The residue was purified by reversed-phase HPLC (0.1% TFA condition) to give the title compound (476 mg, 58% yield) as a yellow solid. $^1H$ NMR (400 MHz, DMSO-d6) δ 12.90 (s, 1H), 8.29 (d, J=7.6 Hz, 1H), 7.79 (s, 1H), 7.60 (t, J=5.2 Hz, 1H), 7.24 (d, J=8.4 Hz, 2H), 6.86 (d, J=8.4 Hz, 3H), 6.79 (t, J=5.2 Hz, 1H), 6.45 (s, 1H), 4.80 (s, 2H), 3.82 (t, J=6.8 Hz, 2H), 3.72 (s, 3H), 3.18-3.13 (m, 2H), 3.01 (s, 2H), 2.92 (q, J=6.4 Hz, 3H), 1.63-1.55 (m, 2H), 1.43 (d, J=4.0 Hz, 2H), 1.36 (s, 9H); LC-MS (ESI+) m/z 551.4 $(M+H)^+$.

Step 2—1-[7-(5-Aminopentylamino)imidazo[1,2-a]pyridin-3-yl]hexahydropyrimidine-2A-dione To a solution of tert-butyl N-[5-[[3-[3-[(4-methoxyphenyl)methyl]-2,4-dioxo-hexahydropyrimidin-1-yl]imidazo[1,2-a]pyridin-7-yl]amino]pentyl]carbamate (456 mg, 828 umol) in TFA (1.89 g, 16.5 mmol) was added TfOH (124 mg, 828 umol). Then the mixture was stirred at 80° C. for 1 hour. On completion, the mixture was filtered and concentrated to give the crude product (400 mg, 100% yield, TfOH salt) as a black oil. LC-MS (ESI+) m/z 331.2 $(M+H)^+$.

Chloro-(3-chloro-2-fluoro-phenyl)-N-(4-formylcyclohexyl)-oxo-dispiro[BLAH]carboxamide (Intermediate GW)

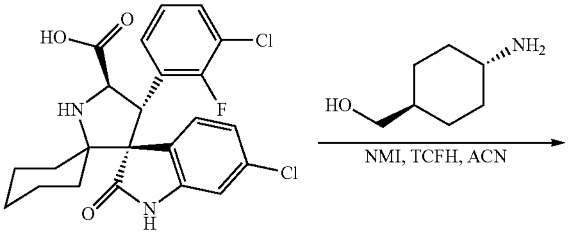

CI

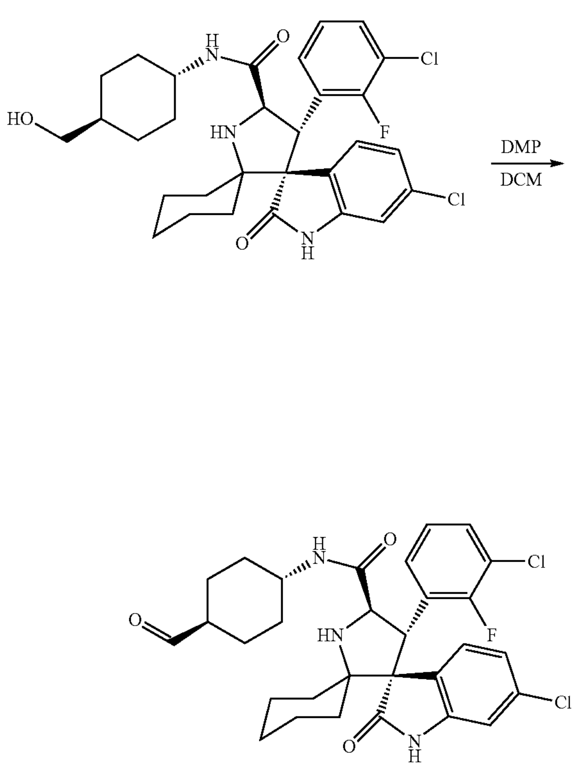

GW

Step 1—Chloro-(3-chloro-2-fluoro-phenyl)-N-[4-(hydroxymethyl)cyclohexyl]-oxo-dispiro[BLAH] carboxamide To a mixture of (4-aminocyclohexyl)methanol (139 mg, 1.08 mmol, CAS #1467-84-1), chloro-(3-chloro-2-fluoro-phenyl)-oxo-dispiro[BLAH]carboxylic acid (500 mg, 1.08 mmol, Intermediate CI) and [chloro (dimethylamino)methylene]-dimethyl-ammonium; hexafluorophosphate (302 mg, 1.08 mmol) in ACN (20 mL) was added 1-methylimidazole (2.66 g, 32.4 mmol). Then the mixture was stirred at 25° C. for 1 hour. On completion, the mixture was quenched with water (20 mL) and extracted with ethyl acetate (25 mL×3). The combined organic phase was dried over anhydrous sodium sulfate, filtered and concentrated to give a residue. The residue was purified by reversed-phase HPLC (0.1% TFA condition) to give the title compound (600 mg, 96% yield) as a white solid. $^1$H NMR (400 MHz, DMSO-d6) δ 10.89 (s, 1H), 9.04 (s, 1H), 7.68 (d, J=11.6 Hz, 1H), 7.62-7.54 (m, 1H), 7.53-7.40 (m, 2H), 7.20 (t, J=8.0 Hz, 1H), 7.13-7.04 (m, 1H), 6.78-6.67 (m, 1H), 4.96-4.73 (m, 1H), 4.62 (d, J=9.6 Hz, 1H), 3.86 (s, 1H), 3.51-3.37 (m, 2H), 3.17 (d, J=6.0 Hz, 2H), 1.97-1.83 (m, 2H), 1.82-1.77 (m, 1H), 1.73 (d, J=13.2 Hz, 1H), 1.66-1.48 (m, 6H), 1.29-1.18 (m, 1H), 1.16-1.09 (m, 1H), 1.07-0.95 (m, 2H), 0.94-0.84 (m, 2H); LC-MS (ESI+) m/z 576.4 $(M+H)^+$.

Step 2—Chloro-(3-chloro-2-fluoro-phenyl)-N-(4-formylcyclohexyl)-oxo-dispiro[BLAH]carboxamide To a solution of chloro-(3-chloro-2-fluoro-phenyl)-N-[4-(hydroxymethyl)cyclohexyl]-oxo-dispiro [BLAH]carboxamide (600 mg, 1.04 mmol) in DCM (3 mL) was added DMP (531 mg, 1.25 mmol). Then the mixture was stirred at 25° C. for 0.5 hour. On completion, the mixture was quenched with water (20 mL) and extracted with ethyl acetate (25 mL×3). The combined organic phase was dried over anhydrous sodium sulfate, filtered and concentrated to give a residue. The residue was purified by prep-HPLC (column: Phenomenex Luna C18 150*25 mm*10 um; mobile phase: [water (0.225% FA)-ACN]; B %: 36%-66%) to give a residue to give the title compound (70.0 mg, 12% yield) as white oil. $^1$H NMR (400 MHz, DMSO-d6) δ 10.52 (s, 1H), 9.57 (d, J=0.8 Hz, 1H), 7.81 (d, J=8.4 Hz, 1H), 7.59 (t, J=6.4 Hz, 1H), 7.41 (dd, J=2.0, 8.0 Hz, 1H), 7.35-7.29 (m, 1H), 7.11 (t, J=8.0 Hz, 1H), 7.03 (dd, J=2.0, 8.0 Hz, 1H), 6.67 (d, J=2.0 Hz, 1H), 4.57 (d, J=9.2 Hz, 1H), 4.42-4.34 (m, 1H), 3.54-3.41 (m, 1H), 2.30-2.21 (m, 1H), 1.97-1.69 (m, 6H), 1.64-1.40 (m, 6H), 1.39-1.21 (m, 5H), 1.04-0.87 (m, 1H), 0.84-0.74 (m, 1H); LC-MS $(ESI^+)$ m/z 572.1 $(M+H)^+$.

3-[5-[5-[(4-Amino-3-methoxy-phenyl)methyl-methyl-amino]pentyl]-3-methyl-2-oxo-benzimidazol-1-yl]piperidine-2,6-dione (Intermediate GX)

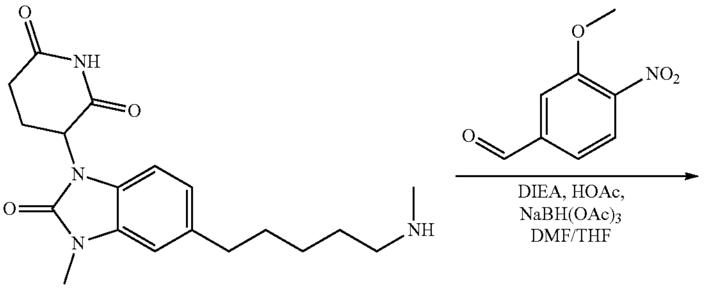

DI

-continued

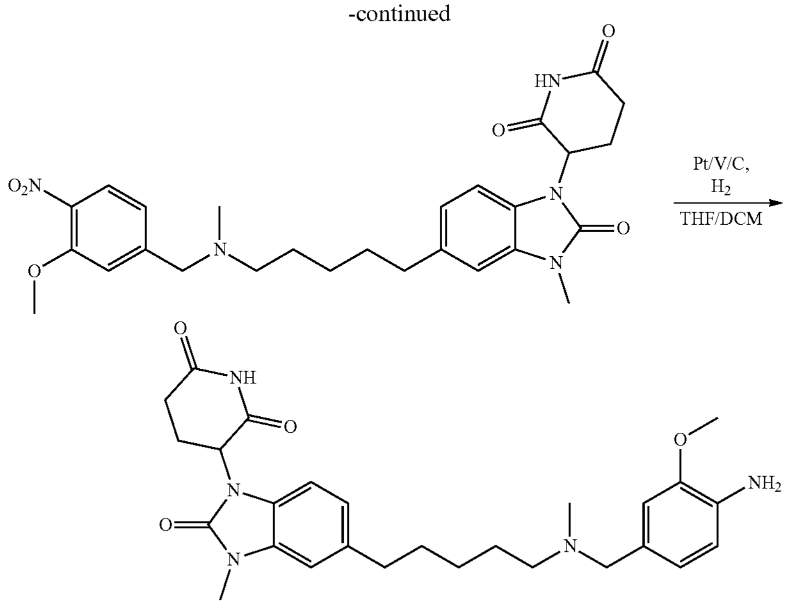

GX

Step 1—3-[5-[5-[(3-Methoxy-4-nitro-phenyl) methyl-methyl-amino]pentyl]-3-methyl-2-oxo-benz-imidazol-1-yl]piperidine-2,6-dione To a mixture of 3-methoxy-4-nitro-benzaldehyde (227 mg, 1.26 mmol, CAS #80410-57-7) in a mixed solvent of THF (10 mL) and DMF (2 mL) was added DIEA (162 mg, 1.26 mmol) until the pH=8. The mixture was stirred for 10 minutes, then AcOH (75.4 mg, 1.26 mmol) was added at until the pH=6. The mixture was stirred for 10 minutes. Subsequently, 3-[3-methyl-5-[5-(methylamino) pentyl]-2-oxo-benzimidazol-1-yl] piperidine-2,6-dione (450 mg, 1.26 mmol, Intermediate DI) was added to the reaction mixture. Next, $NaBH(OAc)_3$ (532 mg, 2.51 mmol) was added in one portion and the resulting reaction mixture was stirred at 25° C. for 3 hours. On completion, the filtrate was concentrated in vacuo. The crude product was purified by reversed-phase HPLC (0.1% FA condition) to give the title compound (290 mg, 42% yield) as a white solid. LC-MS ($ESI^+$) m/z 524.3 $(M+H)^+$.

Step 2—3-[5-[5-[(4-Amino-3-methoxy-phenyl) methyl-methyl-amino]pentyl]-3-methyl-2-oxo-benz-imidazol-1-yl]piperidine-2,6-dione A solution of 3-[5-[5-[(3-methoxy-4-nitro-phenyl) methyl-methyl-amino]pentyl]-3-methyl-2-oxo-benzimidazol-1-yl]piperidine-2,6-dione (290 mg, 553 umol) in a mixed solvent of THF (10 mL) and DCM (10 mL) was added Pt/V/C (101 mg, 387 umol). The mixture was purged with $H_2$ three times, and then the mixture was stirred at 25° C. for 2 hour under $H_2$ atmosphere (15 psi). On completion, the reaction mixture was filtered and the filter cake washed with DCM (30 mL). The filtrate was concentrated in vacuo to give the title compound (230 mg, 84% yield) as light yellow solid. LC-MS ($ESI^+$) m/z 494.3 $(M+H)^+$.

3-[5-[5-[(4-Amino-3-fluoro-phenyl)methyl-methyl-amino]pentyl]-3-methyl-2-oxo-benzimidazol-1-yl] piperidine-2,6-dione (Intermediate GY)

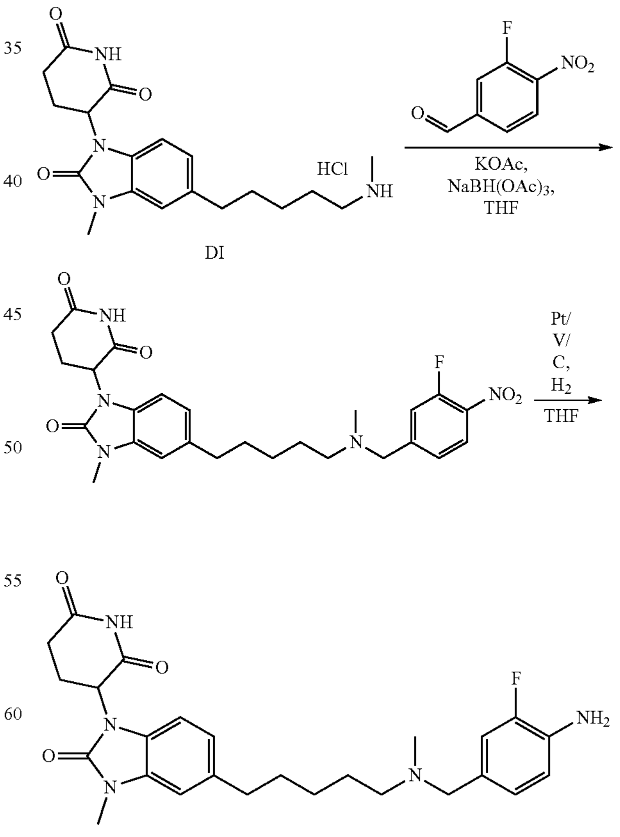

GY

Step 1—3-[5-[5-[(3-Fluoro-4-nitro-phenyl)methyl-methyl-amino]pentyl]-3-methyl-2-oxo-benzimidazol-1-yl]piperidine-2,6-dione To a solution of 3-[3-methyl-5-[5-(methylamino)pentyl]-2-oxo-benzimidazol-1-yl]piperidine-2,6-dione (200 mg, 557 umol, Intermediate DI) in THF (5.0 mL) and DMF (0.5 mL), KOAc (273 mg, 2.79 mmol) was added. The resulting mixture was stirred for 0.25 hour, then 3-fluoro-4-nitro-benzaldehyde (94.3 mg, 557 umol, CAS #160538-51-2) was added. The mixture was stirred at 25° C. for 0.25 hour. Next, $NaBH(OAc)_3$ (236 mg, 1.12 mmol) was added to the reaction mixture then stirred for 2 hours at 25° C. On completion, the mixture was concentrated in vacuo. The mixture was purified by reversed-phase HPLC (0.1% TFA condition) to give the title compound (160 mg, 56% yield) as a yellow oil. $^1H$ NMR (400 MHz, DMSO-$d_6$) δ=11.08 (s, 1H), 8.28 (t, J=7.4 Hz, 1H), 7.82-7.72 (m, 1H), 7.58 (d, J=6.6 Hz, 1H), 7.04-6.98 (m, 2H), 6.88 (d, J=9.0 Hz, 1H), 5.40-5.28 (m, 1H), 3.64-3.58 (m, 1H), 3.34 (s, 6H), 3.12 (dq, J=4.8, 7.2 Hz, 4H), 2.06-1.96 (m, 2H), 1.78 (td, J=3.4, 6.8 Hz, 2H), 1.66-1.58 (m, 2H), 1.36-1.22 (m, 6H), 1.18 (t, J=7.3 Hz, 3H); LC-MS (ESI$^+$) m/z 512.3 (M+H)$^+$.

Step 2—3-[5-[5-[(4-Amino-3-fluoro-phenyl)methyl-methyl-amino]pentyl]-3-methyl-2-oxo-benzimidazol-1-yl]piperidine-2,6-dione A solution of 3-[5-[5-[(3-fluoro-4-nitro-phenyl)methyl-methyl-amino]pentyl]-3-methyl-2-oxo-benzimidazol-1-yl]piperidine-2,6-dione (80.0 mg, 156 umol), Pt/V/C (15.4 mg, 156 umol) in THF (0.5 mL) stirred at 25° C. for 2 hours under $H_2$ (15 psi). On completion, the mixture was concentrated in vacuo to give the title compound (60.0 mg, 79% yield) as a yellow oil. LC-MS (ESI$^+$) m/z 482.4 (M+H)$^+$.

3-[5-[5-[(6-Amino-3-pyridyl)methyl-methyl-amino]pentyl]-3-methyl-2-oxo-benzimidazol-1-yl]piperidine-2,6-dione (Intermediate GZ)

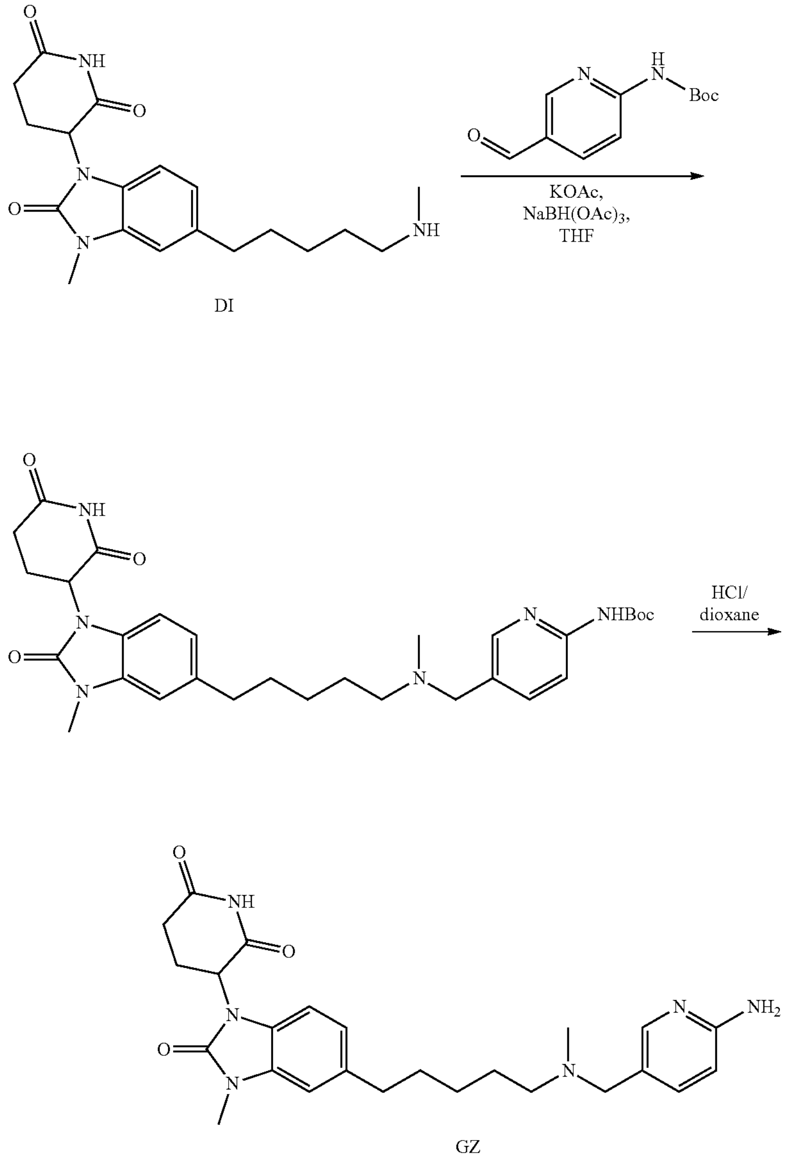

DI

GZ

Step 1—Tert-butyl N-[5-[[5-[1-(2,6-dioxo-3-piperidyl)-3-methyl-2-oxo-benzimidazol-5-yl]pentyl-methyl-amino]methyl]-2-pyridyl] carbamate To a solution of 3-[3-methyl-5-[5-(methylamino)pentyl]-2-oxo-benzimidazol-1-yl]piperidine-2,6-dione (230 mg, 641 umol, Intermediate DI) in DMF (1.0 mL) and THF (5.0 mL), was added KOAc (314 mg, 3.21 mmol). The resulting mixture was stirred for 0.25 hour. Then tert-butylN-(5-formyl-2-pyridyl)carbamate (142 mg, 641 umol, CAS #199296-40-7) was added. The mixture was then stirred at 25° C. for 0.25 hour. Next, $NaBH(OAc)_3$ (272 mg, 1.28 mmol) was added to the reaction mixture which was then stirred for 7.5 hours at 25° C. On completion, the mixture was concentrated in vacuo. The crude product was purified by reversed-phase HPLC (0.1% TFA) to give the title compound (200 mg, 55% yield) as a yellow oil. LC-MS ($ESI^+$) m/z 565.5 $(M+H)^+$.

Step 2—3-[5-[5-[(6-Amino-3-pyridyl)methyl-methyl-amino]pentyl]-3-methyl-2-oxo-benzimidazol-1-yl]piperidine-2,6-dione (HCl)

To a solution of tert-butyl N-[5-[[5-[1-(2,6-dioxo-3-piperidyl)-3-methyl-2-oxo-benzimidazol-5-yl] pentyl-methyl-amino]methyl]-2-pyridyl]carbamate (55.0 mg, 97.4 umol) in DCM (5.0 mL) was added HCl/dioxane (1 mL, 4M) and stirred at 25° C. for 2 hours. On completion, the mixture was concentrated in vacuo to give the title compound (48.0 mg, 98% yield, HCl salt) as a yellow solid. LC-MS ($ESI^+$) m/z 465.3 $(M+H)^+$.

5-(Tert-butoxycarbonylamino)-2,3-dihydro-1,4-benzodioxine-8-carboxylic acid (Intermediate HA)

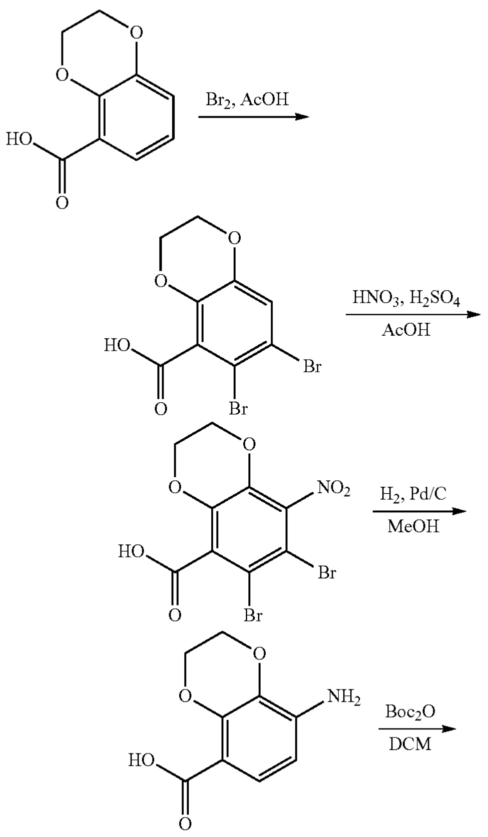

-continued

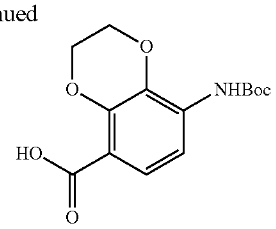

HA

Step 1—6,7-Dibromo-2,3-dihydro-1,4-benzodioxine-5-carboxylic acid

To a solution of 2,3-dihydro-1,4-benzodioxine-5-carboxylic acid (5.00 g, 27.7 mmol, CAS #4442-53-9) in AcOH (50 mL) was added $Br_2$ (13.3 g, 83.2 mmol) dropwise at 25° C. The mixture was stirred at 80° C. for 16 hours. On completion, the mixture was quenched with water (20 mL) and extracted with ethyl acetate (25 mL×3). The combined organic phase was dried over anhydrous sodium sulfate, filtered and concentrated to give a residue. The residue was purified by reversed-phase HPLC (0.1% TFA condition) to give the title compound (2.00 g, 21% yield) as a white solid. $^1H$ NMR (400 MHz, DMSO-d6) δ 13.85-13.55 (m, 1H), 7.36 (s, 1H), 4.30 (s, 4H); LC-MS ($ESI^+$) m/z 336.7 $(M+H)^+$.

Step 2—6,7-Dibromo-5-nitro-2,3-dihydro-1,4-benzodioxine-8-carboxylic acid

To a solution of 6,7-dibromo-2,3-dihydro-1,4-benzodioxine-5-carboxylic acid (1.80 g, 5.33 mmol) in AcOH (27 mL) was added $H_2SO_4$ (18 mL) at 0° C. Then $HNO_3$ (671 mg, 10.6 mmol) was added dropwise at 0° C. Then the mixture was warmed to 25° C. for 2 hours. On completion, the mixture was concentrated to give the title compound (1.90 g, 93% yield) as a white solid. $^1H$ NMR (400 MHz, DMSO-d6) δ 7.03 (d, J=8.4 Hz, 1H), 6.01 (dd, J=2.4, 8.0 Hz, 2H).

Step 3—5-Amino-2,3-dihydro-1,4-benzodioxine-8-carboxylic acid

To a solution of 6,7-dibromo-5-nitro-2,3-dihydro-1,4-benzodioxine-8-carboxylic acid (900 mg, 2.35 mmol) in $H_2O$ (10 mL) was added Pd/C (300 mg, 10 wt %) and $Na_2CO_3$ (124 mg, 1.18 mmol) under $N_2$ atmosphere. The suspension was degassed and purged with $H_2$ gas three times. The mixture was stirred under $H_2$ (1 MPa) at 50° C. for 16 hours. On completion, the mixture was quenched with water (20 mL) and extracted with ethyl acetate (25 mL×3). The combined organic phase was dried over anhydrous sodium sulfate, filtered and concentrated to give the title compound (300 mg, 65% yield) as a white solid; LC-MS ($ESI^+$) m/z 196.0 $(M+H)^+$.

Step 4—5-(tert-butoxycarbonylamino)-2,3-dihydro-1,4-benzodioxine-8-carboxylic acid To a solution of 5-amino-2,3-dihydro-1,4-benzodioxine-8-carboxylic acid (300 mg, 1.54 mmol) in DCM (12 mL) was added $Boc_2O$ (503 mg, 2.31 mmol) and TEA (466 mg, 4.61 mmol). The mixture was stirred at 25° C. for 16 hours. On completion, the mixture was concentrated to give a residue. The residue was purified by reversed-phase HPLC (0.1% FA condition) to give the title compound (120 mg, 26% yield) as a white solid. 1H NMR (400 MHz, DMSO-d6) δ 7.22 (d, J=8.8 Hz, 1H), 6.28 (d, J=8.8 Hz, 1H), 6.02 (s, 2H), 4.33-4.23 (m, 4H), 1.47 (s, 9H).

5-Amino-N-[5-[1-(2,6-dioxo-3-piperidyl)-3-methyl-2-oxo-benzimidazol-5-yl]pentyl]-2,3-dihydro-1,4-benzodioxine-8-carboxamide (Intermediate HB)

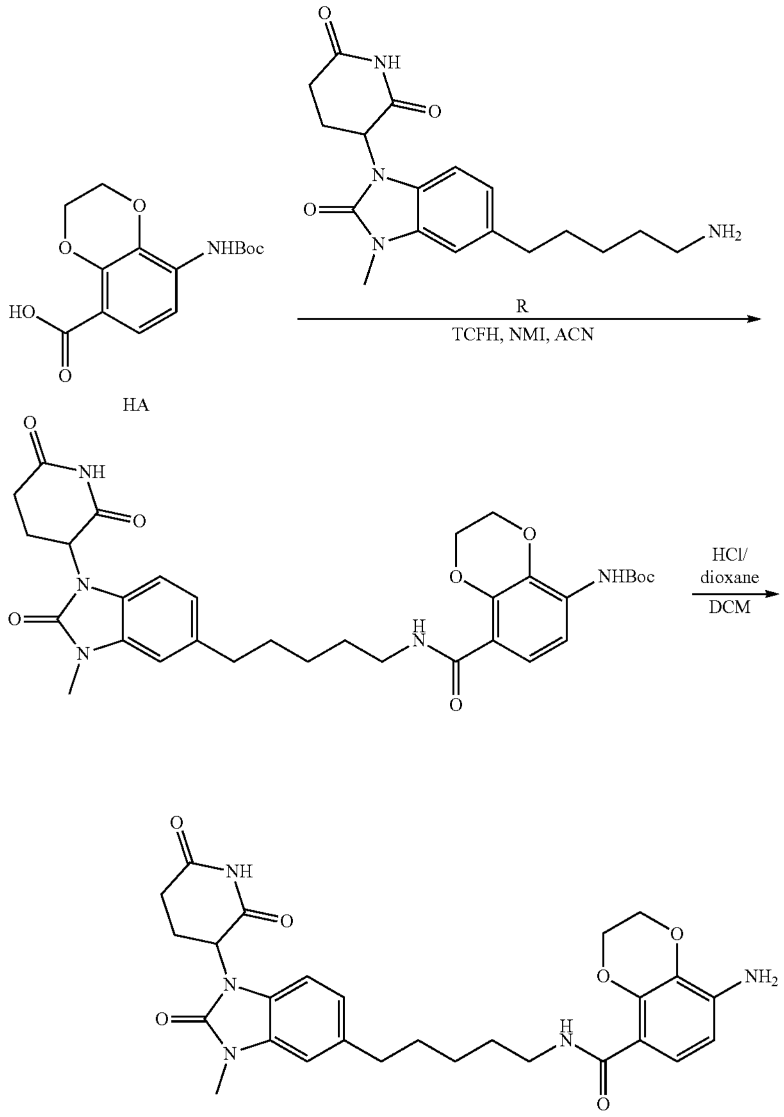

HA

HB

Step 1—Tert-butyl N-[8-[5-[1-(2,6-dioxo-3-piperidyl)-3-methyl-2-oxo-benzimidazol-5-yl]pentylcarbamoyl]-2,3-dihydro-1,4-benzodioxin-5-yl]carbamate To a solution of 5-(tert-butoxycarbonylamino)-2,3-dihydro-1,4-benzodioxine-8-carboxylic acid (100 mg, 338 umol, Intermediate HA) and 3-[5-(5-aminopentyl)-3-methyl-2-oxo-benzimidazol-1-yl]piperidine-2,6-dione (128 mg, 338 umol, HCl, Intermediate R) in ACN (10 mL) was added 1-methylimidazole (834 mg, 10.2 mmol) and [chloro (dimethylamino)methylene]-dimethyl-ammonium; hexafluorophosphate (190 mg, 677 umol). The mixture was stirred at 25° C. for 1 hours. On completion, the mixture was quenched with water (20 mL) and extracted with ethyl acetate (25 mL×3). The combined organic phase was dried over anhydrous sodium sulfate, filtered and concentrated to give a residue. The residue was purified by reversed-phase HPLC (0.1% FA condition) to give the title compound (80 mg, 38% yield) as a white solid. LC-MS (ESI$^+$) m/z 522.2 (M+H)$^+$.

Step 2—5-Amino-N-[5-[1-(2,6-dioxo-3-piperidyl)-3-methyl-2-oxo-benzimidazol-5-yl]pentyl]-2,3-dihydro-1,4-benzodioxine-8-carboxamide To a solution of tert-butyl N-[8-[5-[1-(2,6-dioxo-3-piperidyl)-3-methyl-2-oxo-benzimidazol-5-yl] pentylcarbamoyl]-2,3-dihydro-1,4-benzodioxin-5-yl]carbamate (70.0 mg, 112 umol) in DCM (3 mL) was added HCl/dioxane (4 M). The mixture was stirred at 25° C. for 0.5 hour. On completion, the mixture was concentrated to give the title compound (60 mg, 95% yield, HCl salt) as a white solid; LC-MS (ESI$^+$) m/z 522.2 (M+H)$^+$.

3-[5-chloro-3-methyl-2-oxo-4-(4-piperidyl)benzimidazol-1-yl]piperidine-2,6-dione (Intermediate HC

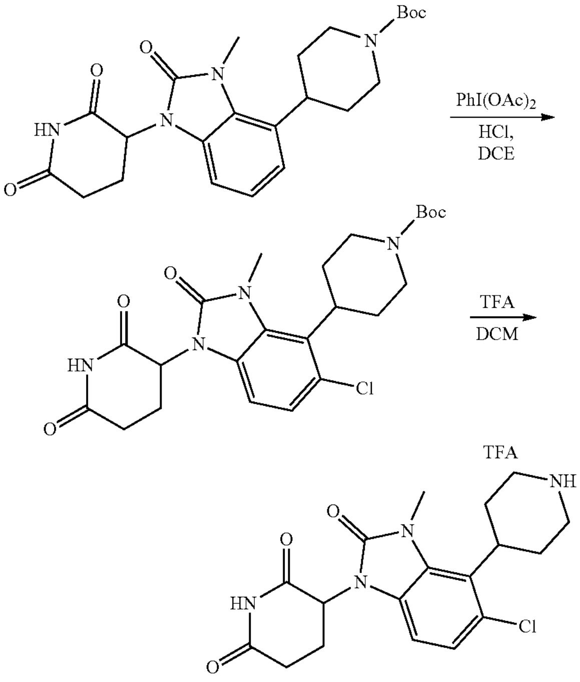

HC

Step 1—Tert-butyl 4-[5-chloro-1-(2,6-dioxo-3-piperidyl)-3-methyl-2-oxo-benzimidazol-4-yl] piperidine-1-carboxylate To a solution of tert-butyl 4-[1-(2,6-dioxo-3-piperidyl)-3-methyl-2-oxo-benzimidazol-4-yl] piperidine-1-carboxylate (1.00 g, 2.26 mmol, synthesized via Steps 1-2 of Intermediate BC) in DCE (50.0 mL) was added $PhI(OAc)_2$ (727 mg, 2.26 mmol) and HCl (1 M, 11.30 mL). The mixture was stirred at 50° C. for 12 hrs. On completion, the reaction mixture was washed with saturated solution of $NaHCO_3$ (2×50 mL) and saturated solution of $Na_2S_2O_3$ (2×50 mL). The organic layer was washed with brine (2×50 mL), then dried over anhydrous $Na_2SO_4$, filtered and concentrated in vacuo to give a residue. The residue was purified by reversed phase (0.1% FA condition) to give the crude product. The crude product was re-purified by prep-HPLC (column: Welch Ultimate XB—SiOH 250*50*10 um; mobile phase: [Hexane-EtOH]; B %: 1%-40%, 15 min) to give the title compound (250 mg, 23% yield) as a white solid. $^1H$ NMR (400 MHz, $CDCl_3$-d) δ 8.20 (s, 1H), 7.07 (d, J=8.4 Hz, 1H), 6.61 (d, J=8.4 Hz, 1H), 5.18 (dd, J=4.4, 12.0 Hz, 1H), 4.42-4.16 (m, 2H), 3.71 (s, 3H), 3.67-3.57 (m, 1H), 3.02-2.91 (m, 1H), 2.90-2.65 (m, 6H), 2.27-2.18 (m, 1H), 1.50 (s, 9H).

Step 2—3-[5-Chloro-3-methyl-2-oxo-4-(4-piperidyl) benzimidazol-1-yl]piperidine-2,6-dione To a solution of tert-butyl 4-[5-chloro-1-(2,6-dioxo-3-piperidyl)-3-methyl-2-oxo-benzimidazol-4-yl] piperidine-1-carboxylate (30.0 mg, 62.9 umol) in DCM (2.00 mL) was added TFA (770 mg, 6.75 mmol, 0.50 mL). The mixture was stirred at 25° C. for 0.5 hr. On completion, the reaction mixture was concentrated in vacuo to give the title compound (30.0 mg, 97% yield, TFA) as a white solid. LC-MS ($ESI^+$) m/z 377.3 $(M+H)^+$.

3-[3,5-Dimethyl-2-oxo-4-(4-piperidyl)benzimidazol-1-yl]piperidine-2,6-dione (Intermediate HD)

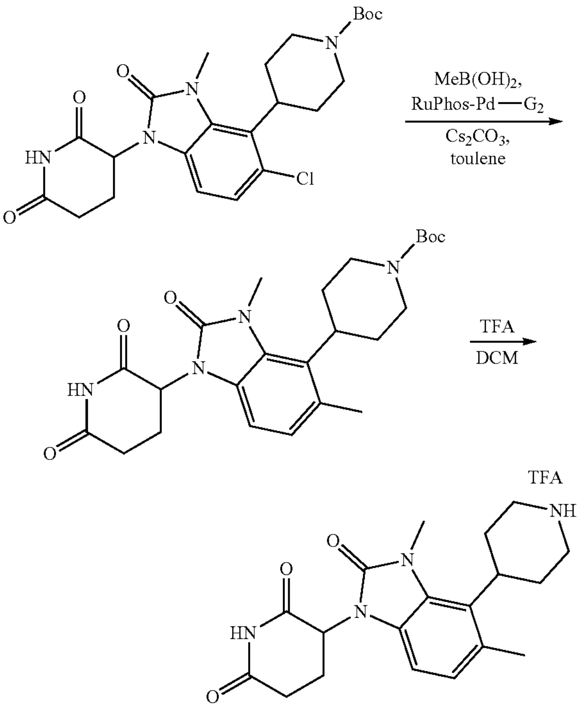

HD

Step 1—Tert-butyl 4-[1-(2,6-dioxo-3-piperidyl)-3,5-dimethyl-2-oxo-benzimidazol-4-yl]piperidine-1-carboxylate To a mixture of tert-butyl 4-[5-chloro-1-(2,6-dioxo-3-piperidyl)-3-methyl-2-oxo-benzimidazol-4-yl] piperidine-1-carboxylate (95.0 mg, 199 umol, synthesized via Step 1 of Intermediate HC) in toluene (4 mL) was added $MeB(OH)_2$ (238 mg, 3.98 mmol), $Cs_2CO_3$ (194 mg, 597 umol) and [2-(2-aminophenyl)phenyl]-chloro-palladium; dicyclohexyl-[2-(2,6-diisopropoxyphenyl)phenyl]phosphane (15.4 mg, 19.9 umol). Then the reaction mixture was stirred at 100° C. for 12 hours. On completion, the reaction mixture was filtered and concentrated in vacuo. The residue was purified by prep-HPLC (Column Phenomenex luna C18 150*25 mm*10 μm, Condition: water (0.225% FA)–ACN) to give the title compound (20.0 mg, 21% yield) as white solid. LC-MS ($ESI^+$) m/z 479.1 $(M+Na)^+$.

Step 2—3-[3,5-Dimethyl-2-oxo-4-(4-piperidyl)benzimidazol-1-yl]piperidine-2,6-dione To a mixture of tert-butyl 4-[1-(2,6-dioxo-3-piperidyl)-3,5-dimethyl-2-oxo-benzimidazol-4-yl] piperidine-1-carboxylate (20.0 mg, 43.8 umol) in DCM (3 mL) was added TFA (770 mg, 6.75 mmol, 0.5 mL) then the reaction mixture was stirred at 25° C. for 0.5 hour. On completion, the reaction mixture was concentrated in vacuo to give title compound (20.0 mg, 97% yield, TFA) as red oil. LC-MS ($ESI^+$) m/z 357.0 $(M+H)^+$.

3-[3-Methyl-2-oxo-5-(4-piperidyl)benzimidazol-1-yl]piperidine-2,6-dione (Intermediate HE)

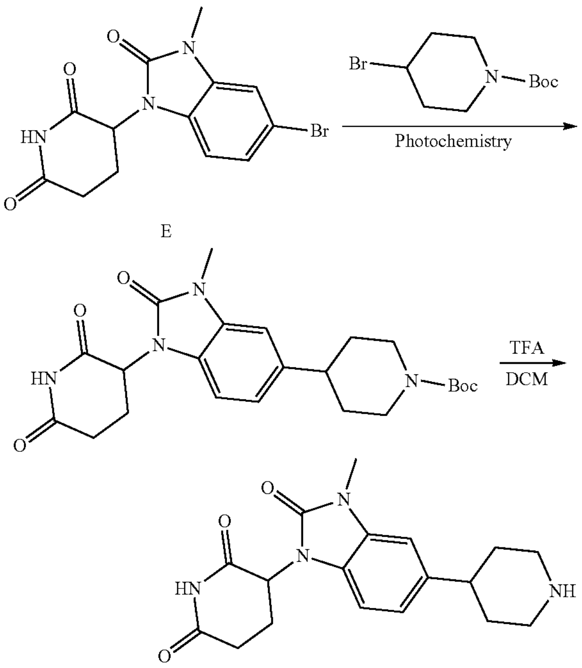

E

HE

Step 1—Tert-butyl 4-[1-(2,6-dioxo-3-piperidyl)-3-methyl-2-oxo-benzimidazol-5-yl]piperidine-1-carboxylate To an 40 mL vial equipped with a stir bar was added 3-(5-bromo-3-methyl-2-oxo-benzimidazol-1-yl)piperidine-2,6-dione (1.00 g, 2.96 mmol, Intermediate E), tert-butyl 4-bromopiperidine-1-carboxylate (1.02 g, 3.84 mmol, CAS #180695-79-8), $Ir[dF(CF_3)ppy]_2(dtbpy)(PF_6)$ (33.18 mg, 29.57 μmol), $NiCl_2 \cdot dtbbpy$ (5.88 mg, 14.7 umol), TTMSS (735 mg, 2.96 mmol), 2,6-dimethylpyridine (633.75 mg, 5.91 mmol) in DME (15 mL). The vial was sealed and placed under nitrogen. The reaction was stirred and irradiated with a 50W [455 nm] blue LED lamp (3 cm away), with cooling water to keep the reaction temperature at 25° C. for 14 hours. On completion, the mixture was filtered and concentrated to give a residue. The residue was purified by column chromatography ($SiO_2$, DCM/Ethyl acetate=1:0 to 1:1) to give the title compound (1.13 g, 86% yield) as a yellow solid. $^1H$ NMR (400 MHz, DMSO-d6) δ 11.18-10.94 (m, 1H), 7.11 (s, 1H), 7.01 (d, J=8.0 Hz, 1H), 6.91 (dd, J=0.8, 8.0 Hz, 1H), 5.75 (s, 1H), 5.33 (dd, J=5.6, 12.8 Hz, 1H), 4.09 (d, J=11.2 Hz, 2H), 3.33 (s, 3H), 2.95-2.83 (m, 2H), 2.76-2.57 (m, 4H), 1.75 (d, J=12.0 Hz, 2H), 1.55 (dq, J=4.0, 12.4 Hz, 2H), 1.42 (s, 9H); LC-MS ($ESI^+$) m/z 443.2 $(M+H)^+$.

Step 2—3-[3-Methyl-2-oxo-5-(4-piperidyl)benzimidazol-1-yl]piperidine-2,6-dione

To a solution of tert-butyl 4-[1-(2,6-dioxo-3-piperidyl)-3-methyl-2-oxo-benzimidazol-5-yl]piperidine-1-carboxylate (150 mg, 338 umol) in DCM (3 mL) was added TFA (773 mg, 6.78 mmol). The mixture was stirred at 25° C. for 0.5 hour. On completion, the mixture was concentrated to give the title compound (150 mg, 96.95% yield, TFA salt) as a colorless oil; LC-MS ($ESI^+$) m/z 343.1 $(M+H)^+$.

2-[Chloro-(3-chloro-2-fluoro-phenyl)-oxo-dispiro[BLAH]yl]oxazole-4-carboxylic acid (Intermediate HF)

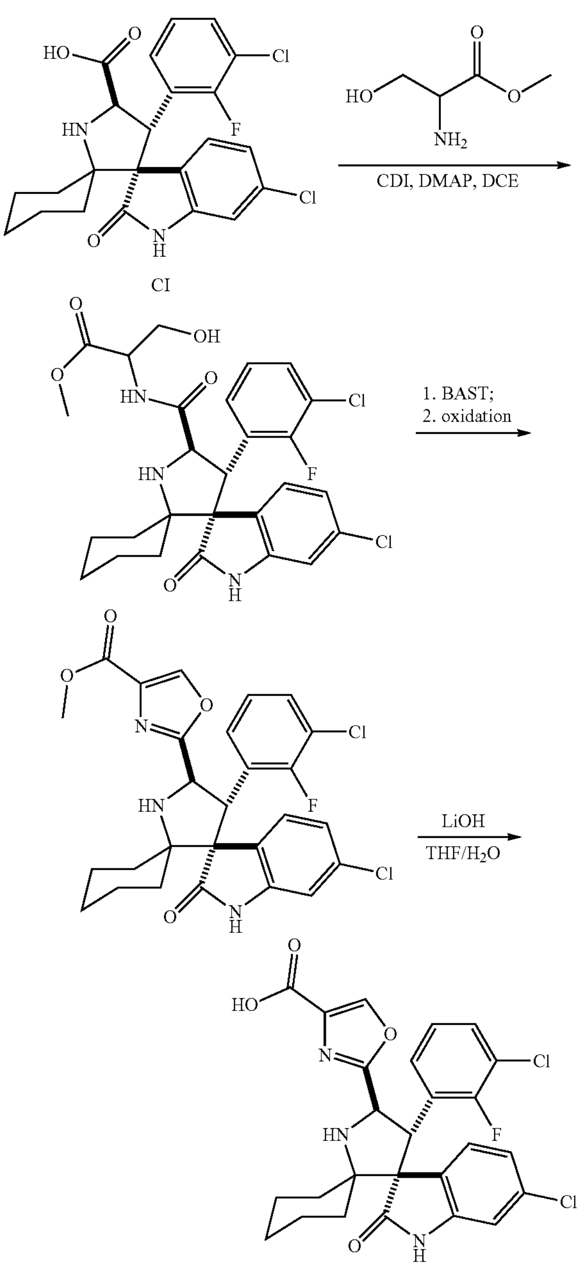

CI

HF

Step 1—Methyl 2-[[chloro-(3-chloro-2-fluoro-phenyl)-oxo-dispiro[BLAH]carbonyl]amino]-3-hydroxy-propanoate A solution of CDI (1.05 g, 6.47 mmol), DMAP (263 mg, 2.16 mmol), and IEA (1.39 g, 10.7 mmol) were added to a suspension of chloro-(3-chloro-2-fluoro-phenyl)-oxo-dispiro[BLAH]carboxylic acid (1 g, 2.16 mmol, Intermediate CI) in DCE (20 ml) at 50° C. After 30 minutes, the methyl (2R)-2-amino-3-hydroxy-propanoate; hydrochloride (1.68 g, 10.7 mmol) was added and the reaction was refluxed 12 hours. On completion, the reaction mixture was concentrated in vacuo to give a residue. The crude product was purified by reversed-phase HPLC (0.1% FA condition) to give the title compound (600 mg, 46% yield) as a white solid. $^1$H NMR (400 MHz, DMSO-d6) δ 10.55 (s, 1H), 8.36 (d, J=8.0 Hz, 1H), 7.77-7.60 (m, 2H), 7.43-7.29 (m, 1H), 7.12 (t, J=8.0 Hz, 1H), 7.03 (dd, J=1.9, 8.1 Hz, 1H), 6.70-6.62 (m, 1H), 5.76 (s, 3H), 5.20 (s, 1H), 4.61-4.37 (m, 4H), 4.19-3.97 (m, 2H), 1.76-1.42 (m, 6H), 1.36-1.10 (m, 3H), 1.04-0.89 (m, 1H).

Step 2—Methyl 2-[chloro-(3-chloro-2-fluoro-phenyl)-oxo-dispiro[BLAH]yl]oxazole-4-carboxylate At −20° C., 2-methoxy-N-(2-methoxyethyl)-N-(trifluoro-λ4-sulfanyl)ethanamine (303 mg, 1.37 mmol) was added to a solution of methyl 2-[[chloro-(3-chloro-2-fluoro-phenyl)-oxo-dispiro [BLAH]carbonyl]amino]-3-hydroxy-propanoate (300 mg, 531 umol) in THF (6 mL). After 30 minutes bromo(trichloro)methane (6.03 g, 30.4 mmol) and 2,3,4,6,7,8,9,10-octahydropyrimido[1,2-a]azepine (2.42 g, 15.9 mmol) were added and the reaction was allowed to warm to 25° C. The mixture was stirred at 25° C. for 1 hour. On completion, the reaction mixture was concentrated in vacuo to give a residue. The crude product was purified by reversed-phase HPLC (0.1% FA condition) to give the title compound (25 mg, 6.9% yield) as a white solid. LC-MS (ESI$^+$) m/z 544.1 (M+H)$^+$.

Step 3—2-[Chloro-(3-chloro-2-fluoro-phenyl)-oxo-dispiro[BLAH]yl]oxazole-4-carboxylic acid To a solution of methyl 2-[chloro-(3-chloro-2-fluoro-phenyl)-oxo-dispiro[BLAH]yl]oxazole-4-carboxylate (20.0 mg, 36.7 umol) in THF (1.5 mL) and $H_2O$ (1.5 mL) was added LiOH—$H_2O$ (40.0 mg, 953 umol). The mixture was stirred at 25° C. for 2 hours. On completion, the reaction mixture was concentrated in vacuo to give a residue. The crude product was purified by reversed-phase HPLC (0.1% FA condition) to give the title compound (10.0 mg, 43.6% yield) as a white solid. LC-MS (ESI$^+$) m/z 530.2 (M+H)$^+$.

3-(5-methoxy-3-methyl-2-oxo-4-(piperidin-4-yl)-2,3-dihydro-1H-benzo[d]imidazol-1-yl) piperidine-2,6-dione (Intermediate HG)

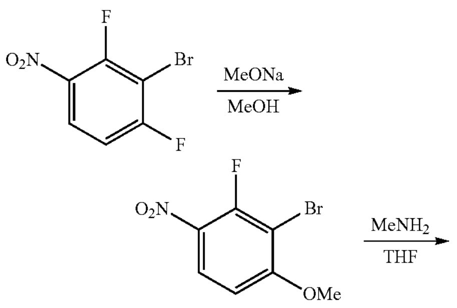

-continued

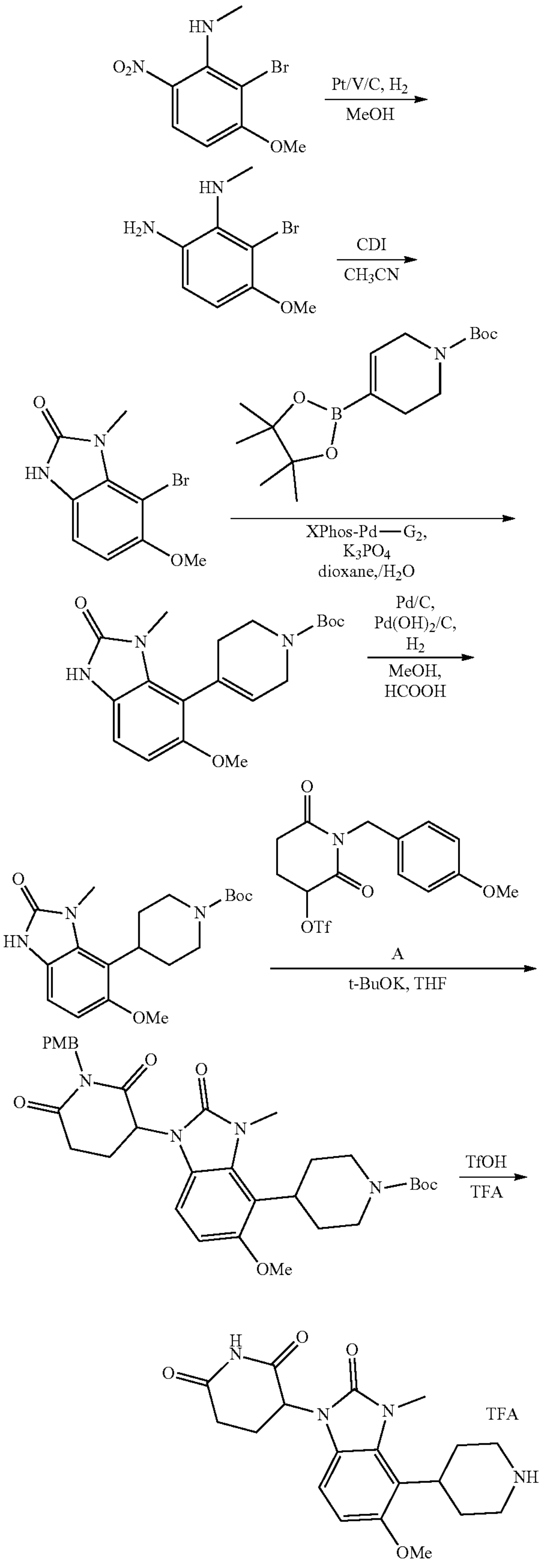

HG

Step 1—2-bromo-3-fluoro-1-methoxy-4-nitrobenzene

To a solution of 2-bromo-1,3-difluoro-4-nitro-benzene (1 g, 4.20 mmol, from CAS #103977-78-2) in MeOH (10 mL) was added MeONa (226 mg, 4.20 mmol) at 0° C. The mixture was warmed to 20° C. and stirred for 2 hrs. On completion, the mixture was poured into the water (10 mL) and the aqueous phase was extracted with ethyl acetate (2×50 mL). The combined organic phase was separated, dried with anhydrous $Na_2SO_4$, filtered and the filtrate was concentrated in vacuo to give the crude product. The crude product was triturated with PE:EA=20:1 (20 mL) to give the title compound (130 mg, 12% yield) as white solid. $^1H$ NMR (400 MHz, $CDCl_3$) δ 8.13 (t, J=8.8 Hz, 1H), 6.80 (dd, J=1.6, 9.2 Hz, 1H), 4.03 (s, 3H).

Step 2—2-bromo-3-methoxy-N-methyl-6-nitroaniline

To a solution of 2-bromo-3-fluoro-1-methoxy-4-nitro-benzene (3 g, 12.00 mmol) in THF (10 mL) was added 30% $MeNH_2$ (1.86 g, 18.00 mmol) in EtOH and the reaction was stirred at 25° C. for 2 hrs. On completion, the reaction was concentrated in vacuo. The residue was purified by column chromatography ($SiO_2$, petroleum ether/ethyl acetate=50/1 to 10/1) to give the title compound (3 g, 95% yield) as yellow solid. $^1H$ NMR (400 MHz, $CDCl_3$) δ 8.08 (d, J=9.2 Hz, 1H), 6.45 (d, J=9.6 Hz, 1H), 3.99 (s, 3H), 3.13-3.09 (m, 3H).

Step 3—6-bromo-5-methoxy-N1-methylbenzene-1,2-diamine

To a solution of 2-bromo-3-methoxy-N-methyl-6-nitroaniline (100 mg, 383 umol) in MeOH (5 mL) was added Pt/V/C (30.0 mg, 10 wt %). The reaction mixture was stirred at 25° C. under $H_2$ (15 psi) for 2 hrs. On completion, the reaction mixture was filtered and the filtrate was concentrated in vacuo to give the title compound (80 mg, 90% yield) as brown oil. $^1H$ NMR (400 MHz, $CDCl_3$) δ 6.58 (d, J=8.6 Hz, 1H), 6.46 (d, J=8.6 Hz, 1H), 3.74 (s, 3H), 2.65 (s, 3H).

Step 4—7-bromo-6-methoxy-1-methyl-1H-benzo[d]imidazol-2(3H)-one

To a solution of 3-bromo-4-methoxy-N2-methyl-benzene-1,2-diamine (1.7 g, 7.36 mmol) in $CH_3CN$ (30 mL) was added CDI (1.79 g, 11.03 mmol) and the mixture was stirred at 90° C. for 3 hrs. On completion, the mixture was concentrated in vacuo to remove MeCN, then $H_2O$ (20 mL) was added. The mixture was filtered to give the filter cake. The filter cake was triturated with PE:EA=3:1 (40 mL) to give the title compound (1.7 g, 90% yield) as yellow solid. $^1H$ NMR (400 MHz, DMSO-$d_6$) δ 10.94 (s, 1H), 6.91 (d, J=8.4 Hz, 1H), 6.75 (d, J=8.4 Hz, 1H), 3.79 (s, 3H), 3.57 (s, 3H).

Step 5—Tert-butyl 4-(5-methoxy-3-methyl-2-oxo-2,3-dihydro-1H-benzo[d]imidazol-4-yl)-5,6-dihydropyridine-1(2H)-carboxylate A solution of 4-bromo-5-methoxy-3-methyl-1H-benzimidazol-2-one (300 mg, 1.17 mmol), tert-butyl 4-(4,4,5,5-tetramethyl-1,3,2-dioxaborolan-2-yl)-3,6-dihydro-2H-pyridine-1-carboxylate (541 mg, 1.75 mmol, CAS #286961-14-6), Xphos-PD-G2 (91.8 mg, 116 umol) and $K_3PO_4$ (495 mg, 2.33 mmol) in dioxane (10 mL) and $H_2O$ (1 mL) was stirred at 80° C. for 16 hrs under $N_2$. On completion, the reaction mixture was extracted with EtOAc (2×40 mL). The combined organic layers were washed with water (2×30 mL), dried over $Na_2SO_4$ and concentrated in vacuo. The residue was purified by reversed-phase HPLC (0.1% FA condition) to give the title compound (130 mg, 31% yield) as yellow solid. $^1H$ NMR (400 MHz, MeOD) δ 6.94 (d, J=8.4 Hz, 1H), 6.73 (d, J=8.4 Hz, 1H), 5.64 (s, 1H), 4.22-4.12 (m, 1H), 4.09-3.97 (m, 1H), 3.80-3.73 (m, 4H), 3.65-3.53 (m, 1H), 3.36 (s, 3H), 3.34-3.31 (m, 2H), 2.60 (d, J=16.8 Hz, 1H), 2.29-2.19 (m, 1H), 1.52 (s, 10H).

Step 6—Tert-butyl 4-(5-methoxy-3-methyl-2-oxo-2,3-dihydro-1H-benzo[d]imidazol-4-yl)piperidine-1-carboxylate To a solution of tert-butyl 4-(5-methoxy-3-methyl-2-oxo-1H-benzimidazol-4-yl)-3,6-dihydro-2H-pyridine-1-carboxylate (100 mg, 278 umol) in HCOOH (0.05 mL) and MeOH (50 mL) was added Pd/C (50 mg, 10 wt %) and $Pd(OH)_2/C$(50 mg, 10 wt %). The reaction mixture was stirred at 60° C. for 48 hrs under $H_2$ (50 psi). On completion, the reaction mixture was filtered and the filtrate was concentrated in vacuo to give the title compound (80 mg, 79% yield) as white solid. $^1H$ NMR (400 MHz, $CDCl_3$) δ 6.89 (d, J=8.4 Hz, 1H), 6.74 (d, J=8.4 Hz, 1H), 4.19 (d, J=13.2 Hz, 2H), 3.80 (s, 3H), 3.65 (s, 3H), 3.62-3.51 (m, 2H), 2.90 (s, 1H), 2.48-2.41 (m, 2H), 1.97-1.84 (m, 2H), 1.52 (s, 9H).

Step 7—Tert-butyl 4-(5-methoxy-1-(1-(4-methoxybenzyl)-2,6-dioxopiperidin-3-yl)-3-methyl-2-oxo-2,3-dihydro-1H-benzo[d]imidazol-4-ylpiperidine-1-carboxylate To a solution of tert-butyl 4-(5-methoxy-3-methyl-2-oxo-1H-benzimidazol-4-yl)piperidine-1-carboxylate (70.0 mg, 193 umol) and t-BuOK (43.4 mg, 387 umol) in THF (5 mL) was added a solution of [1-[(4-methoxyphenyl)methyl]-2,6-dioxo-3-piperidyl] trifluoromethanesulfonate (147 mg, 387 umol, Intermediate A) in THF (0.5 mL) at 0° C. The reaction mixture was stirred at 0° C. for 2 h. On completion, the reaction was quenched with saturated $NH_4Cl$ solution (0.5 mL), then diluted with EtOAc (50 mL). The organic layer was washed with brine (2×20 mL), dried over $Na_2SO_4$ and concentrated in vacuo. The residue was purified by prep-TLC (PE:EA=3:2, Rf=0.3) to give the title compound (70.0 mg, 60% yield). $^1H$ NMR (400 MHz, $CDCl_3$) δ 7.30 (d, J=8.8 Hz, 2H), 6.75 (d, J=7.6 Hz, 2H), 6.40 (d, J=8.8 Hz, 1H), 6.19 (d, J=8.8 Hz, 1H), 5.15-5.05 (m, 1H), 4.89 (s, 2H), 4.20-4.14 (m, 1H), 3.72 (s, 3H), 3.69 (s, 3H), 3.59 (s, 3H), 3.39-3.30 (m, 1H), 2.97-2.89 (m, 1H), 2.86-2.66 (m, 4H), 2.62-2.47 (m, 2H), 2.41-2.22 (m, 3H), 2.11-2.03 (m, 1H), 1.43 (s, 9H).

Step 8—3-(5-methoxy-3-methyl-2-oxo-4-(piperidin-4-yl)-2,3-dihydro-1H-benzo[d]imidazol-1-yl) piperidine-2,6-dione A solution of tert-butyl 4-[5-methoxy-1-[1-[(4-methoxyphenyl) methyl]-2,6-dioxo-3-piperidyl]-3-methyl-2-oxo-benzimidazol-4-yl] piperidine-1-carboxylate (60 mg, 101 umol) in TFA (1 mL) and TfOH (0.2 mL) was stirred at 70° C. for 1h. On completion, the reaction mixture was concentrated in vacuo. The residue was purified by prep-HPLC (column: Phenomenex Luna C18 150*25 mm*10 um;

mobile phase: [water (0.1% TFA) ACN]; B %: 2%-32%, 10 min) to give the title compound (25 mg, 66% yield) as yellow solid. LC-MS ($ESI^+$) m/z 373.0 $(M+H)^+$.

2-[2-[(1-Tert-butoxycarbonyl-4-piperidyl)methoxy]ethoxy]acetic acid (Intermediate HH)

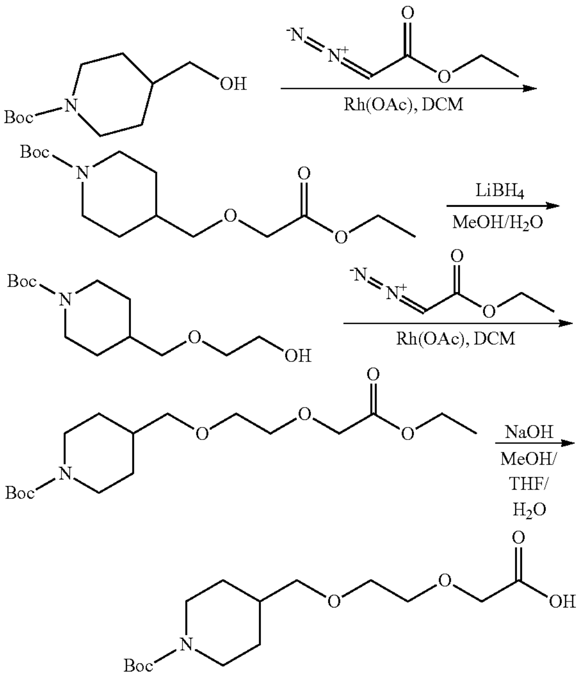

HH

Step 1—Tert-butyl 4-[(2-ethoxy-2-oxo-ethoxy)methyl]piperidine-1-carboxylate

To a solution of tert-butyl 4-(hydroxymethyl)piperidine-1-carboxylate (10.0 g, 46.4 mmol, CAS #123855-51-6) and $Rh(OAc)_2$ (513 mg, 2.32 mmol) in DCM (80 ml) was added drop-wise a solution of ethyl 2-diazoacetate (7.95 g, 69.6 mmol, CAS #623-73-4) in DCM (30 ml) at 0° C. The mixture was warmed to 20° C. and stirred at 12 hours. On completion, the mixture was poured into the water (80 ml), and the aqueous phase was extracted with ethyl acetate (20 ml×3). The combined organic phase was washed with brine (20 mL×3), dried with anhydrous $Na_2SO_4$, filtered and concentrated in vacuo to give the residue. The residue was purified by column chromatography to give the title compound (13.0 g, 92% yield) as a brown oil. $^1H$ NMR (400 MHz, DMSO-$d_6$) δ 4.25-4.15 (m, 1H), 4.14-4.08 (m, 2H), 4.06 (s, 2H), 3.92 (d, J=11.2 Hz, 2H), 2.69 (s, 2H), 1.78-1.67 (m, 1H), 1.63 (d, J=13.2 Hz, 2H), 1.38 (s, 9H), 1.28-1.22 (m, 1H), 1.19 (t, J=7.2 Hz, 3H), 1.08-0.96 (m, 2H).

Step 2 Tert-butyl 4-(2-hydroxyethoxymethyl)piperidine-1-carboxylate

To a solution of tert-butyl 4-[(2-ethoxy-2-oxo-ethoxy)methyl]piperidine-1-carboxylate (1.00 g, 3.32 mmol) in MeOH (10 ml) and $H_2O$ (1.0 ml) was added $LiBH_4$ (216 mg, 9.95 mmol) at 0° C. The mixture was then allowed to warm to 20° C. and stirred at 2 hours. On completion, the mixture was poured into the water (40 ml), and the aqueous phase was extracted with ethyl acetate (20 ml×3). The combined organic phase was washed with brine (20 ml×3), dried with anhydrous $Na_2SO_4$, filtered and concentrated in vacuo to give the residue to give the title compound (720 mg, 83% yield) as a brown oil. $^1H$ NMR (400 MHz, DMSO-$d_6$) δ 4.55 (t, J=5.6 Hz, 1H), 3.93 (d, J=12.0 Hz, 2H), 3.52-3.44 (m, 2H), 3.40-3.36 (m, 2H), 3.24 (d, J=6.4 Hz, 2H), 2.68 (s, 2H), 1.75-1.66 (m, 1H), 1.64 (d, J=13.2 Hz, 2H), 1.39 (s, 9H), 1.07-0.92 (m, 2H).

Step 3—Tert-butyl 4-[2-(2-ethoxy-2-oxo-ethoxy)ethoxymethyl]piperidine-1-carboxylate To a solution of tert-butyl 4-(2-hydroxyethoxymethyl)piperidine-1-carboxylate (700 mg, 2.70 mmol) and $Rh(OAc)_2$ (59 mg, 269 umol) in DCM (10 ml) was added dropwise a solution of ethyl 2-diazoacetate (461 mg, 4.05 mmol) in DCM (10 ml) at 0° C. The mixture was warmed to 20° C. and stirred at 12 hours. On completion, the mixture was poured into the water (80 mL), and the aqueous phase was extracted with ethyl acetate (20 ml×3). The combined organic phase was washed with brine (20 ml×3), dried with anhydrous $Na_2SO_4$, filtered and concentrated in vacuo to give the residue. The residue was purified by column chromatography to give the title compound (623 mg, 66% yield) as a brown oil. $^1H$ NMR (400 MHz, $CDCl_3$) δ 4.26-4.19 (m, 3H), 4.15 (s, 2H), 4.13-4.06 (m, 2H), 3.75-3.70 (m, 2H), 3.65-3.60 (m, 2H), 3.32 (d, J=6.4 Hz, 2H), 2.74-2.65 (m, 2H), 1.72 (d, J=12.8 Hz, 2H), 1.46 (s, 9H), 1.31-1.27 (m, 3H), 1.19-1.06 (m, 2H).

Step 4—2-[2-[(1-Tert-butoxycarbonyl-4-piperidyl)methoxy]ethoxy]acetic acid

To a solution of tert-butyl 4-[2-(2-ethoxy-2-oxo-ethoxy)ethoxymethyl]piperidine-1-carboxylate (550 mg, 1.59 mmol) in THF (5.0 ml), MeOH (5.0 mL) and $H_2O$ (2.0 mL) was added NaOH (318 mg, 7.96 mmol) and stirred at 50° C. for 2 hours. On completion, the mixture was cooled to 20° C. and adjusted to pH=5-6, then the mixture was extracted with ethyl acetate (3×10 ml). The combined organic phase was washed with brine (3×20 ml), dried with anhydrous $Na_2SO_4$, filtered and concentrated in vacuo to give the title compound (425 mg, 84% yield) as a brown oil. $^1H$ NMR (400 MHz, $CDCl_3$) δ 8.99-7.57 (m, 1H), 4.15 (s, 2H), 4.13-4.02 (m, 2H), 3.80-3.71 (m, 2H), 3.69-3.54 (m, 2H), 3.35 (d, J=6.4 Hz, 2H), 2.70 (t, J=12.0 Hz, 2H), 1.85-1.75 (m, 1H), 1.71 (d, J=13.6 Hz, 2H), 1.45 (s, 9H), 1.19-1.07 (m, 2H).

(2S,4R)-1-[(2S)-3,3-Dimethyl-2-[[2-[2-(4-piperidylmethoxy)ethoxy]acetyl]amino]butanoyl]-4-hydroxy-N-[[4-(4-methylthiazol-5-yl)phenyl]methyl]pyrrolidine-2-carboxamide (Intermediate HI)

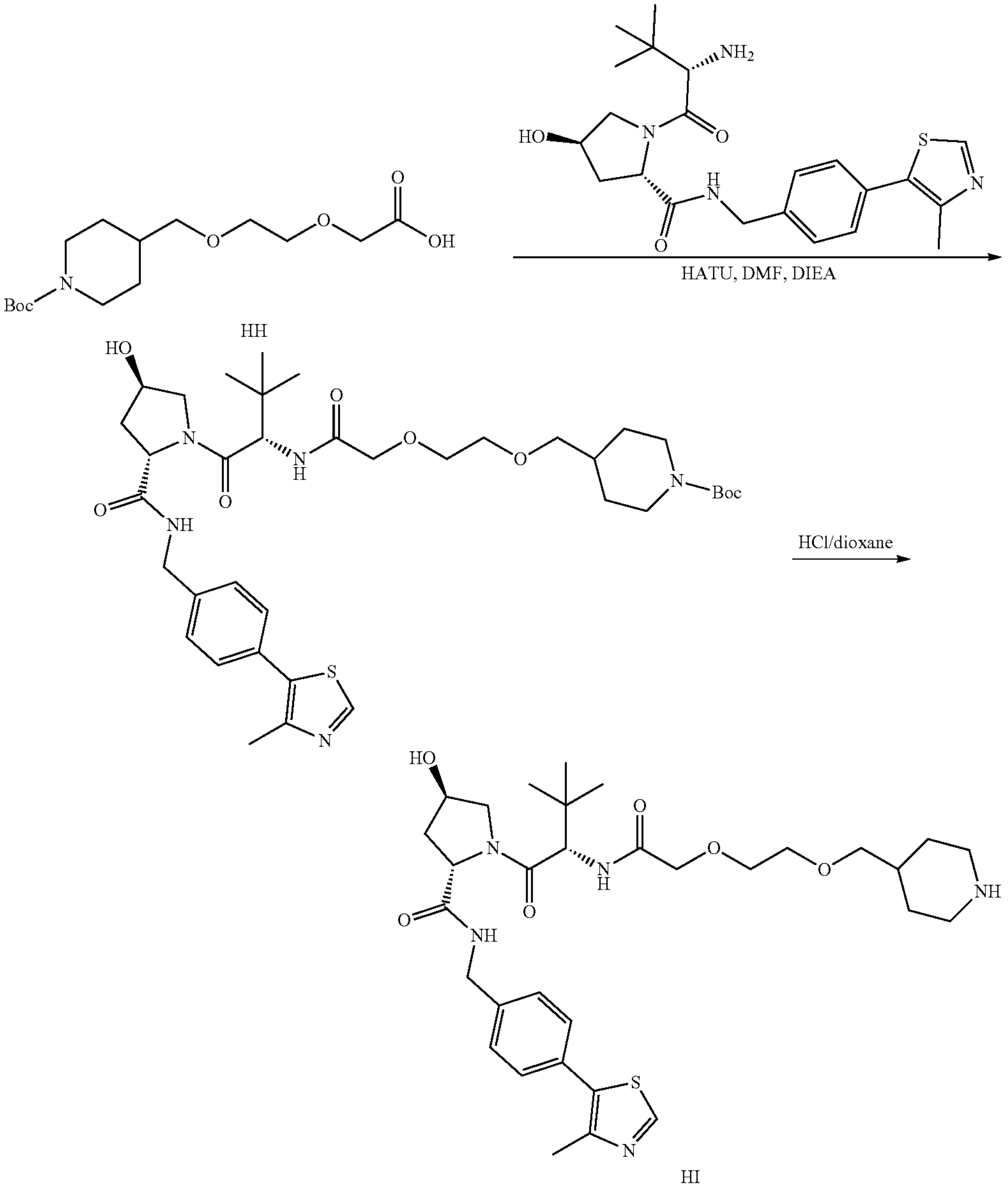

HI

Step 1—Tert-butyl 4-[2-[2-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-2-oxo-ethoxy]ethoxymethyl]piperidine-1-carboxylate To a solution of 2-[2-[(1-tert-butoxycarbonyl-4-piperidyl)methoxy]ethoxy]acetic acid (200 mg, 630 umol, Intermediate HH), and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide (271 mg, 630 umol) in DMF (5.0 mL). Then DIEA (407 mg, 3.15 mmol) and HATU (263 mg, 693 umol) were added and the mixture was stirred at 25° C. for 1 hour. On completion, the mixture was quenched with water (15 mL) and extracted with EA (15 mL×3). The combined organic phase was dried over anhydrous sodium sulfate, filtered and concentrated to give a residue. The residue was purified by column chromatography to give the title compound (340 mg, 73% yield) as a yellow oil. LC-MS (ESI$^+$) m/z 730.6 $(M+H)^+$.

Step 2—(2S,4R)-1-[(2S)-3,3-Dimethyl-2-[[2-[2-(4-piperidylmethoxy)ethoxy]acetyl]amino]butanoyl]-4-hydroxy-N-[[4-(4-methylthiazol-5-yl)phenyl]methyl]pyrrolidine-2-carboxamide To a solution of tert-butyl 4-[2-[2-[[(1S)-1-[(2S,4R)-4-hydroxy-2[[4-(4-methylthiazol-5-yl)phenyl] methylcarbamoyl]pyrrolidine-1-carbonyl]-2,2-dimethyl-propyl]amino]-2-oxo-ethoxy]ethoxymethyl]piperidine-1-carboxylate (100 mg, 137 umol) in DCM (2.0 mL) was added HCl/dioxane (4 M, 0.1 mL). The mixture was stirred at 25° C. for 1 hr. On completion, the mixture was concentrated in vacuo to give the title compound (90.0 mg, 98% yield, HCl salt) as a yellow oil. LC-MS (ESI+) m/z 630.6 $(M+H)^+$.

5-[1-(2,6-dioxo-3-piperidyl)-3-methyl-2-oxo-benzimidazol-5-yl]pentanoic acid (Intermediate HJ)

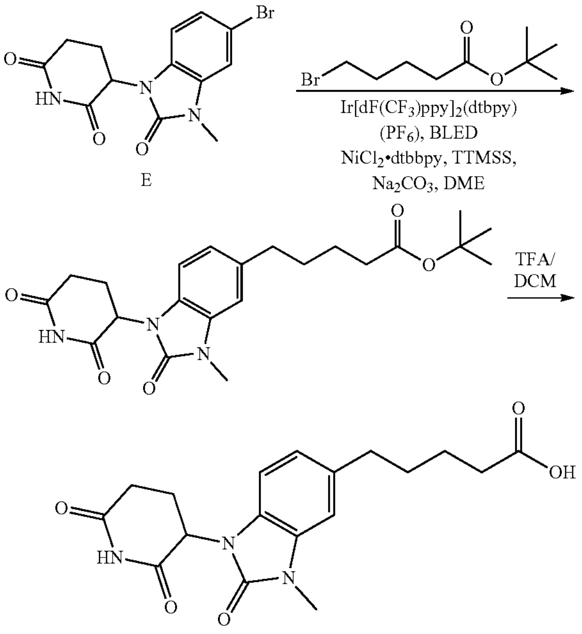

HJ

Step 1—tert-butyl 5-[1-(2,6-dioxo-3-piperidyl)-3-methyl-2-oxo-benzimidazol-5-yl]pentanoate To an 40 mL vial equipped with a stir bar was 3-(5-bromo-3-methyl-2-oxo-benzimidazol-1-yl)piperidine-2,6-dione (500 mg, 1.48 mmol, Intermediate E), tert-butyl 5-bromopentanoate (455 mg, 1.92 mmol, CAS #88987-42-2), bis[3,5-difluoro-2-[5-(trifluoromethyl)-2-pyridyl]phenyl] iridium(1+); 4-tert-butyl-2-(4-tert-butyl-2-pyridyl)pyridine; hexafluorophosphate (16.5 mg, 14.7 umol), 4-tert-butyl-2-(4-tert-butyl-2-pyridyl)pyridine; dichloronickel (2.94 mg, 7.39 umol), bis(trimethylsilyl)silyl-trimethyl-silane (367 mg, 1.48 mmol, 456 uL), 2,6-dimethylpyridine (316 mg, 2.96 mmol, 344 uL) in DME (15 mL). The vial was sealed and placed under nitrogen was added. The reaction was stirred and irradiated with a 50 W blue LED lamp (3 cm away), with cooling water to keep the reaction temperature at 25° C. for 14 hours. On completion, the reaction mixture was concentrated in vacuo to give a residue. The residue was purified by column chromatography ($SiO_2$, Petroleum ether/Ethyl acetate=20/1 to 0/1) to give the title compound (470 mg, 76% yield) as a white solid. $^1H$ NMR (400 MHz, DMSO-d6) δ 11.07 (s, 1H), 7.03-6.96 (m, 2H), 6.85 (dd, J=1.2, 8.0 Hz, 1H), 5.33 (dd, J=5.2, 12.8 Hz, 1H), 3.40 (s, 5H), 3.31 (s, 3H), 2.95-2.82 (m, 1H), 2.77-2.65 (m, 1H), 2.60 (s, 3H), 2.23-2.18 (m, 2H), 2.04-1.94 (m, 1H), 1.63-1.46 (m, 4H), 1.37 (s, 4H). LC-MS (ESI+) m/z 831.3 $(M*2+H)^+$.

Step 2—5-[1-(2,6-dioxo-3-piperidyl)-3-methyl-2-oxo-benzimidazol-5-yl]pentanoic acid To a mixture of tert-butyl tert-butyl 5-[1-(2,6-dioxo-3-piperidyl)-3-methyl-2-oxo-benzimidazol-5-yl] pentanoate (200 mg, 481 umol) in DCM (2 mL) was added TFA (1.08 g, 9.45 mmol, 0.7 mL) in one portion at 25° C. under $N_2$. The mixture was stirred at 25° C. for 30 minutes. On completion, the reaction mixture was concentrated in vacuo to give the title compound (300 mg) as a white solid. LC-MS (ESI+) m/z 676.2 $(M+H)^+$.

345-[4-(4-Amino-1-piperidyl) but-1-ynyl]-3-methyl-2-oxo-benzimidazol-1-yl]piperidine-2,6-dione (Intermediate HK)

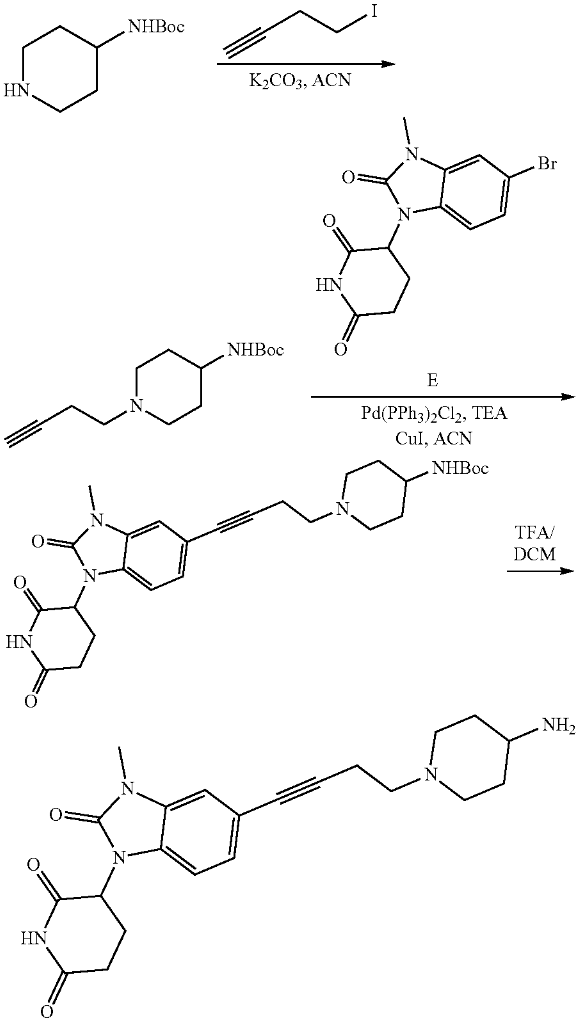

HK

Step 1—Tert-butyl N-(1-but-3-ynyl-4-piperidyl)carbamate

To a solution of tert-butyl N-(4-piperidyl) carbamate (1.00 g, 4.99 mmol, CAS #73874-95-0) in ACN (10 mL) was added $K_2CO_3$ (2.07 g, 14.9 mmol) and 4-iodobut-1-yne (898 mg, 4.99 mmol, CAS #43001-2-8). The mixture was then stirred at 25° C. for 12 hours. On completion, the mixture was concentrated in vacuo to give a residue. The residue was purified by column chromatography ($SiO_2$, DCM/MeOH=1:0 to 95:1) to give the title compound (500 mg, 1.98 mmol, 39% yield) as a white solid. $^1H$ NMR (400 MHz, $CDCl_3$-d) δ=4.42 (s, 1H), 3.46 (s, 1H), 2.84 (d, J=11.2 Hz, 2H), 2.65-2.55 (m, 2H), 2.42-2.31 (m, 2H), 2.14 (t, J=11.2 Hz, 2H), 1.97 (d, J=0.8 Hz, 1H), 1.93 (d, J=12.0 Hz, 2H), 1.45 (s, 9H), 1.43-1.36 (m, 2H).

Step 2—Tert-butylN-[1-[4-[1-(2,6-dioxo-3-piperidyl)-3-methyl-2-oxo-benzimidazol-5-yl]but-3-ynyl-4-piperidyl]carbamate To a solution of tert-butyl N-(1-but-3-ynyl-4-piperidyl) carbamate (450 mg, 1.78 mmol) in ACN (10 mL) was added CuI (16.9 mg, 89.1 umol) and $Pd(PPh_3)_2Cl_2$ (125 mg, 178 umol), TEA (902 mg, 8.92 mmol) and 3-(5-bromo-3-methyl-2-oxo-benzimidazol-1-yl)piperidine-2,6-dione (603 mg, 1.78 mmol, Intermediate E). The mixture was then stirred at 80° C. for 16 hours under $N_2$ atmosphere. On completion, insoluble matter was removed by filtration and the filtrate was concentrated in vacuo. The residue was purified by reverse phase CC (water (0.1% FA)–ACN) to give the title compound (160 mg, 313 umol, 17% yield) as a white solid. LC-MS ($ESI^+$) m/z 510.4 $(M+H)^+$.

Step 3—3-[5-[4-(4-Amino-1-piperidyl) but-1-ynyl]-3-methyl-2-oxo-benzimidazol-1-yl]piperidine-2,6-dione To a solution of tert-butyl N-[1-[4-[1-(2,6-dioxo-3-piperidyl)-3-methyl-2-oxo-benzimidazol-5-yl] but-3-ynyl]-4-piperidyl]carbamate (160 mg, 313 umol) in DCM (2.5 mL) was added TFA (0.5 mL). Then the mixture was stirred at 25° C. for 1 hour. On completion, the mixture was filtered and concentrated to give the title compound (160 mg, 97% yield, TFA salt) as a yellow oil. LC-MS ($ESI^+$) m/z 410.3 $(M+H)^+$.

3-[3-methyl-2-oxo-5-[5-(4-piperidyloxy)pentyl]benzimidazol-1-yl]piperidine-2,6-dione (Intermediate HL)

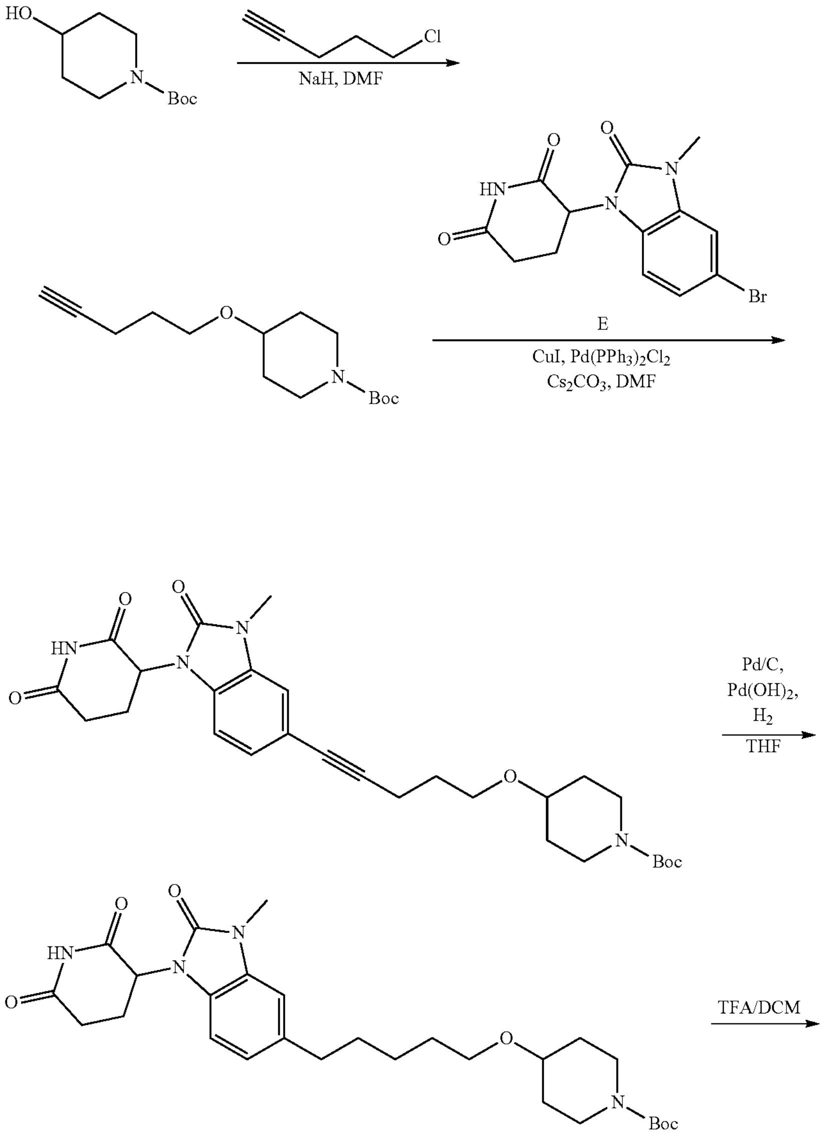

-continued

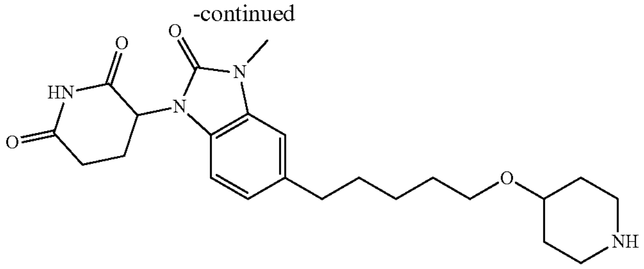

HL

Step 1—Tert-butyl 4-pent-4-ynoxypiperidine-1-carboxylate

To a solution of tert-butyl 4-hydroxypiperidine-1-carboxylate (2.0 g, 9.94 mmol, CAS #109384-19-2) in DMF (20 mL) was added NaH (795 mg, 19.9 mmol) in batches at 0° C., then the mixture was stirred at 0° C. for 0.5 hours. Next, 5-chloropent-1-yne (1.53 g, 14.9 mmol, CAS #14267-92-6) was added to the mixture at 25° C. The mixture was stirred at 25° C. for 2 hours. On completion, the mixture was quenched with water (20 mL) and extracted with ethyl acetate (25 mL×3). The combined organic phase was dried over anhydrous sodium sulfate, filtered and concentrated to give a residue. The residue was purified by column chromatography ($SiO_2$, Petroleum ether/Ethyl acetate=1:0 to 20:1) to give the title compound (416 mg, 15% yield) as a colorless oil. $^1$H NMR (400 MHz, DMSO-$d_6$) δ 3.61-3.58 (m, 2H), 3.48-3.46 (m, 2H), 3.45-3.41 (m, 1H), 3.12-2.91 (m, 2H), 2.76-2.74 (m, 1H), 2.22-2.18 (m, 2H), 1.73-1.66 (m, 2H), 1.64-1.63 (m, 2H), 1.38 (s, 9H), 1.34-1.30 (m, 2H).

Step 2—tert-butyl 4-[5-[1-(2,6-dioxo-3-piperidyl)-3-methyl-2-oxo-benzimidazol-5-yl]pent-4-ynoxy]piperidine-1-carboxylate A mixture of tert-butyl 4-pent-4-ynoxypiperidine-1-carboxylate (400 mg, 1.50 mmol), 3-(5-bromo-3-methyl-2-oxobenzimidazol-yl)piperidine-2,6-dione (505 mg, 1.50 mmol, Intermediate E), CuI (28.4 mg, 149 umol), $Cs_2CO_3$ (1.46 g, 4.49 mmol) and $Pd(PPh_3)_2Cl_2$ (105 mg, 149 umol) in ACN (9 mL) was degassed and purged with $N_2$ three times, and then the mixture was stirred at 80° C. for 12 hours under $N_2$ atmosphere. On completion, the reaction mixture was concentrated in vacuo to give a residue. The crude product was purified by column chromatography on silica gel eluted with petroleum ether/ethyl acetate (DCM/EA=1:0 to 2:1). to give the title compound (500 mg, 50% yield) as a yellow solid. LC-MS (ESI$^+$) m/z 469.2 (M+H−56)$^+$.

Step 3—Tert-butyl 4-[5-[1-(2,6-dioxo-3-piperidyl)-3-methyl-2-oxo-benzimidazol-5-yl]pentoxy]piperidine-1-carboxylate To a mixture of tert-butyl 4-[5-[1-(2,6-dioxo-3-piperidyl)-3-methyl-2-oxo-benzimidazol-5-yl]pent-4-ynoxy]piperidine-1-carboxylate (500 mg, 953 umol) in THF (10 mL) was added Pd/C (100 mg, 953 umol) and $Pd(OH)_2$ (669 mg, 953 umol) under $N_2$. The mixture was stirred at 25° C. for 12 hours under $H_2$ (15 psi). On completion, the reaction mixture was concentrated in vacuo to give a residue. The crude product was purified by reversed-phase HPLC (0.1% FA condition) to give the title compound (120 mg, 23% yield) as a yellow solid. $^1$H NMR (400 MHz, DMSO-d6) δ 11.08 (s, 1H), 7.09-6.96 (m, 2H), 6.86 (d, J=8.0 Hz, 1H), 5.34 (dd, J=5.6, 12.8 Hz, 1H), 3.65-3.52 (m, 5H), 3.39 (t, J=6.4 Hz, 3H), 3.09-2.83 (m, 3H), 2.76-2.56 (m, 4H), 2.00 (td, J=5.2, 10.6 Hz, 1H), 1.82-1.70 (m, 2H), 1.66-1.47 (m, 4H), 1.41-1.26 (m, 13H).

Step 4—3-[3-methyl-2-oxo-5-[5-(4-piperidyloxy)pentyl]benzimidazol-1-yl]piperidine-2,6-dione To a mixture of tert-butyl 4-[5-[1-(2,6-dioxo-3-piperidyl)-3-methyl-2-oxo-benzimidazol-5-yl] pentoxy]piperidine-1-carboxylate (30.0 mg, 56.7 umol) in DCM (0.5 mL) was added TFA (0.1 ml) in one portion at 25° C. under $N_2$. The mixture was then stirred at 25° C. for 2 hours. On completion, the reaction mixture was concentrated in vacuo to give the title compound (24.0 mg, 99% yield) as a yellow oil. LC-MS (ESI$^+$) m/z 429.3 (M+H)$^+$.

1-(4-chlorophenyl)-7-isopropoxy-6-methoxy-2-[4-(methylamino)phenyl]-1,4-dihydroisoquinolin-3-one (Intermediate HM)

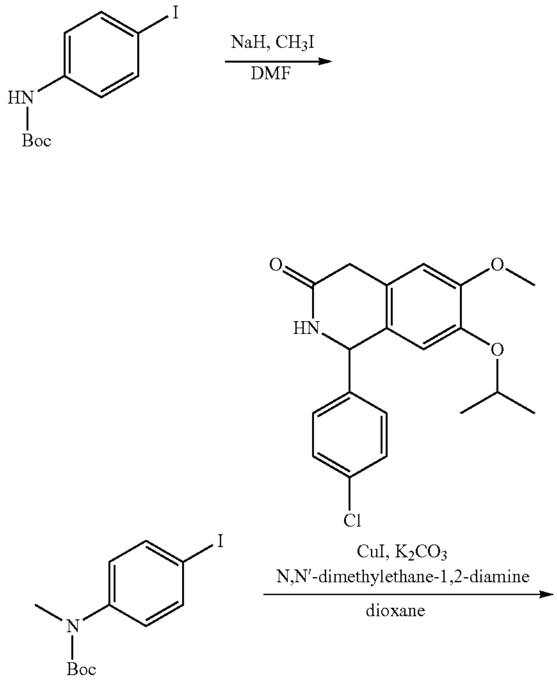

-continued

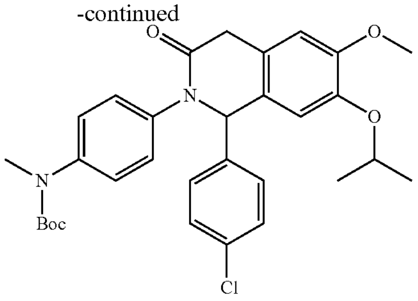

HM

Step 1—Tert-butyl N-[4-[1-(4-chlorophenyl)-7-isopropoxy-6-methoxy-3-oxo-1,4-dihydroisoquinolin-2-yl]phenyl]-N-methylcarbamate To a solution of tert-butyl N-(4-iodophenyl)carbamate (1.00 g, 3.13 mmol, CAS #159217-89-7) in DMF (10 mL) was added NaH (376 mg, 9.40 mmol, 60% dispersion in mineral oil) at 0° C. stirred for 30 mins, and $CH_3I$ (2.22 g, 15.7 mmol) was added. Then the mixture was stirred at 25° C. for 2 hours. On completion, the reaction mixture was poured into the $H_2O$ (10 mL), then extracted with EtOAc (6.0 mL×3). The organic layer was separated, dried over anhydrous $Na_2SO_4$, filtered and concentrated under reduced pressure to give the residue. The residue was purified by column chromatography ($SiO_2$, Petroleum ether/Ethyl acetate=10/1 to 2/3) to give the title compound (840 mg, 75% yield) as a white solid. LC-MS ($ESI^+$) m/z 278.2 $(M+H-56)^+$.

Step 2—Tert-butyl N-[4-[1-(4-chlorophenyl)-7-isopropoxy-6-methoxy-3-oxo-1,4-dihydroisoquinolin-2-yl]phenyl]-N-methylcarbamate To a solution of tert-butyl N-(4-iodophenyl)-N-methylcarbamate (840 mg, 2.52 mmol) in dioxane (15 mL) was added 1-(4-chlorophenyl)-7-isopropoxy-6-methoxy-2,4-dihydro-1H-isoquinolin-3-one (726 mg, 2.10 mmol, CAS #1313366-29-8), N,N'-dimethylethane-1,2-diamine (18.5 mg, 210 umol), CuI (20.0 mg, 105 umol), and $K_2CO_3$ (581 mg, 4.20 mmol), then the mixture was stirred at 120° C. for 16 hours. On completion, the reaction mixture was concentrated in vacuo to give a residue. The residue was purified by column chromatography ($SiO_2$, Petroleum ether/Ethyl acetate=5/1 to 1/1) to give the title compound (420 mg, 32% yield) as yellow solid. $^1H$ NMR (400 MHz, DMSO-$d_6$) δ 8.50 (d, J=3.6 Hz, 1H), 7.35 (s, 4H), 7.24 (d, J=8.4 Hz, 2H), 7.13 (d, J=8.8 Hz, 2H), 7.07 (s, 1H), 6.90-6.84 (m, 1H), 6.09 (s, 1H), 4.52-4.35 (m, 1H), 3.90 (d, J=20.0 Hz, 1H), 3.73 (s, 3H), 3.62 (d, J=20.0 Hz, 1H), 3.15 (s, 3H), 1.38 (s, 9H), 1.24 (d, J=6.0 Hz, 3H), 1.19 (d, J=6.0 Hz, 3H). LC-MS ($ESI^+$) m/z 551.2 $(M+H)^+$.

Step 3—1-(4-Chlorophenyl)-7-isopropoxy-6-methoxy-2-[4-(methylamino)phenyl]-1,4-dihydroisoquinolin-3-one To a mixture of tert-butyl N-[4-[1-(4-chlorophenyl)-7-isopropoxy-6-methoxy-3-oxo-1,4-dihydroisoquinolin-2-yl]phenyl]-N-methyl-carbamate (120 mg, 218 umol) in DCM (1.0 mL) was added HCl/dioxane (4 M, 0.5 mL) at 25° C. under $N_2$. The mixture was stirred at 25° C. for 30 min. On completion, the reaction mixture was concentrated in vacuo to give title compound (100 mg, 80% yield). LC-MS ($ESI^+$) m/z 451.1 $(M+H)^+$.

Tert-butyl 3-oxo-4-pent-4-ynyl-piperazine-1-carboxylate (Intermediate HN)

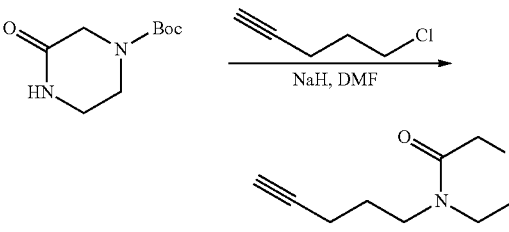

HN

To a solution of tert-butyl 3-oxopiperazine-1-carboxylate (10.0 g, 49.9 mmol, CAS #76003-29-7) in DMF (100 mL) was added dropwise NaH (3.00 g, 74.9 mmol) at 0° C. After addition, the mixture was stirred at this temperature for 30 minutes, and then 5-chloropent-1-yne (5.12 g, 49.9 mmol, CAS #14267-92-6) was added at 25° C. The resulting mixture was stirred at 25° C. for 12 hours. On completion, the reaction mixture was poured into water (50 mL) and extracted with ethyl acetate (3×50 mL). The combined organic phase was dried with anhydrous $Na_2SO_4$, filtered and concentrated in vacuo. The residue was purified by reverse phase column chromatography (water (0.1% $NH_3H_2O$–ACN) to give the title compound (5.00 g, 18.7 mmol, 37% yield) as a colorless oil. LC-MS ($ESI^+$) m/z 533.3 $(2M+H)^+$.

3-[3-Methyl-2-oxo-4-[5-(2-oxopiperazin-1-yl)pentyl]benzimidazol-1-yl]piperidine-2,6-dione (Intermediate HO)

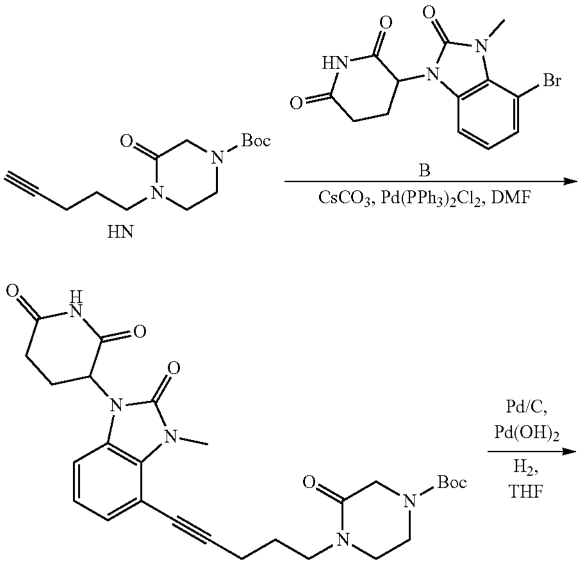

-continued

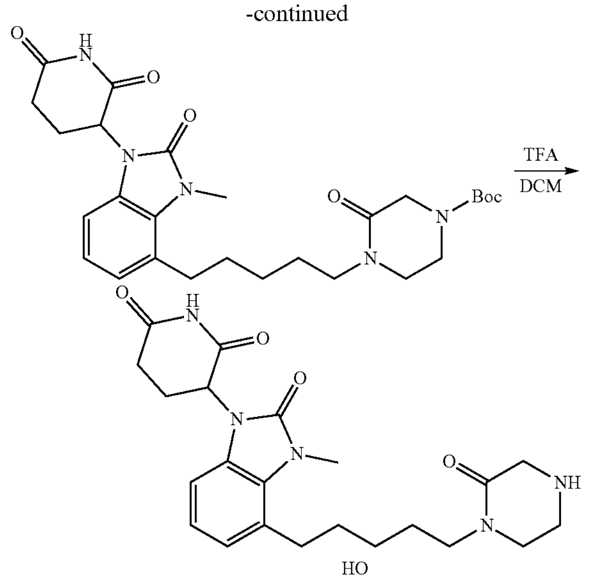

Step 1—Tert-butyl 3-oxo-4-pent-4-ynyl-piperazine-1-carboxylate

To a solution of tert-butyl 3-oxo-4-pent-4-ynyl-piperazine-1-carboxylate (1 g, 3.75 mmol, Intermediate HN) in DMF (15 mL) was added $Cs_2CO_3$ (6.12 g, 18.7 mmol), XPhos-Pd-G3 (317 mg, 375 μmol) and 3-(4-bromo-3-methyl-2-oxo-benzimidazol-1-yl)piperidine-2,6-dione (1.27 g, 3.75 mmol, Intermediate B). The mixture was stirred at 80° C. for 14 hours under $N_2$ atmosphere. The reaction mixture was poured into water (20 ml) and extracted with ethyl acetate (3×15 ml). The combined organic phases were dried with anhydrous $Na_2SO_4$, filtered and concentrated in vacuo. The residue was purified by reverse phase column chromatography (water (0.1% FA)–ACN) to give the title compound (1.00 g, 44% yield) as a yellow soil. $^1H$ NMR (400 MHz, DMSO-d6) δ 11.17 (s, 1H), 7.20-7.16 (m, 1H), 7.14-7.11 (m, 1H), 7.08-7.02 (m, 1H), 5.48-5.41 (m, 1H), 3.97-3.93 (m, 2H), 3.74-3.68 (m, 3H), 3.64-3.58 (m, 2H), 3.54-3.48 (m, 2H), 3.45-3.39 (m, 5H), 2.99-2.89 (m, 1H), 2.82-2.69 (m, 2H), 2.59-2.54 (m, 9H). LC-MS (ESI$^+$) m/z 424.2 (M+H)$^+$.

Step 2—3-[3-Methyl-2-oxo-5-(3-piperazin-1-ylpropyl)benzimidazol-1-yl]piperidine-2,6-dione To a mixture of tert-butyl 4-[5-[1-(2,6-dioxo-3-piperidyl)-3-methyl-2-oxo-benzimidazol-4-yl] pent-4-ynyl]-3-oxo-piperazine-1-carboxylate (1.00 g, 1.91 mmol) in THF (4.0 mL) was added Pd/C (100 mg, 1.91 mmol) and $Pd(OH)_2$ (100 mg, 142 umol) under $N_2$. The mixture was stirred at 25° C. for 12 hours under $H_2$ (15 psi). The reaction mixture was filtered through a pad of celite and the filtrate was concentrated in vacuo to give a residue. The title compound (700 mg, 59% yield) was isolated as a yellow solid. LC-MS (ESI$^+$) m/z 582.2 (M+H)$^+$.

Step 3—3-[3-Methyl-2-oxo-4-[5-(2-oxopiperazin-1-yl)pentyl]benzimidazol-1-yl]piperidine-2,6-dione To a solution of tert-butyl 4-[5-[1-(2,6-dioxo-3-piperidyl)-3-methyl-2-oxo-benzimidazol-4-yl] pentyl]-3-oxo-piperazine-1-carboxylate (280 mg, 530 umol) in TFA (1.08 g, 9.45 mmol, 0.7 mL) and DCM (4 mL). Then the mixture was stirred at 25° C. for 2 hours. On completion, the reaction mixture was filtered and concentrated in vacuo to give the title compound (220 mg, 96% yield, TFA salt) as a brown oil. LC-MS (ESI$^+$) m/z 428.2 (M+H)$^+$.

4-[4-[5-[1-(2,6-Dioxo-3-piperidyl)-3-methyl-2-oxo-benzimidazol-5-yl]pentyl]-3-oxo-piperazin-1-yl] cyclohexanecarbaldehyde (Intermediate HP)

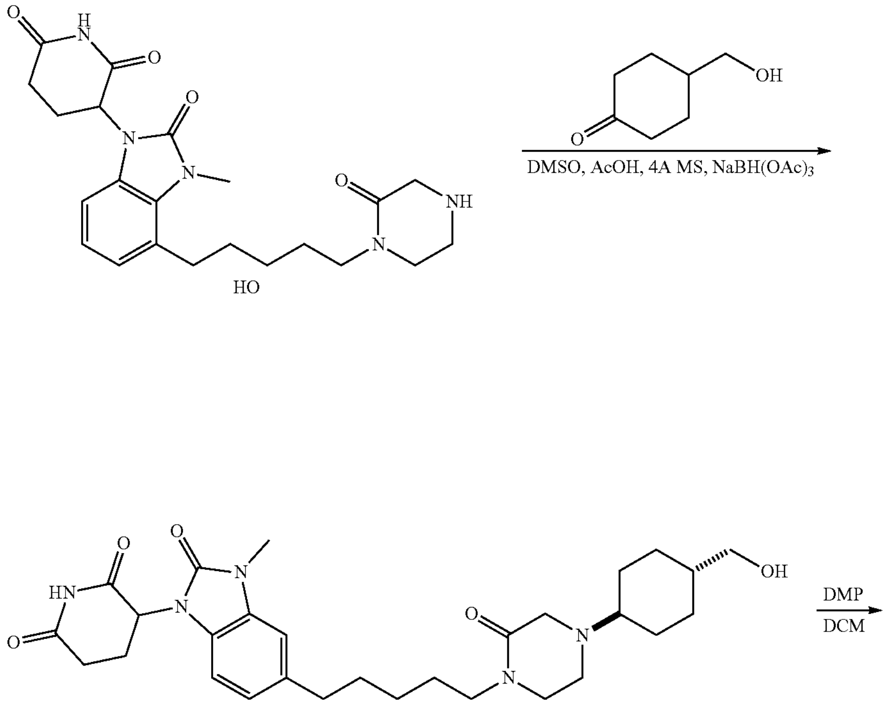

-continued

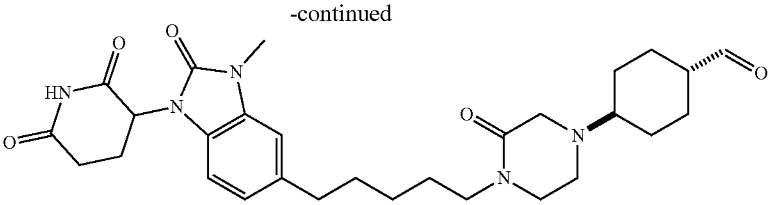

HP

Step 1—3-[5-[5-[4-[4-(Hydroxymethyl)cyclohexyl]-2-oxo-piperazin-1-yl]pentyl]-3-methyl-2-oxo-benzimidazol-1-yl]piperidine-2,6-dione To a solution of 3-[3-methyl-2-oxo-4-[5-(2-oxopiperazin-1-yl)pentyl]benzimidazol-1-yl]piperidine-2,6-dione (220 mg, 514 umol, Intermediate HO) in DMSO (1.0 mL) and THF (4.0 mL) was added 4 Å molecular sieves (60 mg, 514 umol) to adjust pH to 5-6. After addition, to the mixture was added 4-(hydroxymethyl)cyclohexanone (65.9 mg, 514 mmol) and $NaBH(OAc)_3$ (218 mg, 1.03 mmol), then the mixture was stirred at 40° C. for 12 hours. Next, AcOK (392 mg, 4.00 mmol) was added at 25° C. and the resulting mixture was stirred at 25° C. for 2 hours. On completion, the reaction mixture was concentrated in vacuo and the crude product was purified by reversed-phase HPLC (0.1% FA condition) to give the title compound (230 mg, 49% yield) as a brown solid. $^1H$ NMR (400 MHz, DMSO-d6) δ=11.10 (s, 1H), 7.12-6.74 (m, 3H), 5.37 (dd, J=5.6, 12.8 Hz, 1H), 3.87 (s, 3H), 3.56 (s, 3H), 3.45-3.13 (m, 8H), 2.95-2.83 (m, 3H), 2.77-2.58 (m, 2H), 2.08-1.95 (m, 2H), 1.89-1.54 (m, 8H), 1.50-1.27 (m, 5H), 0.96 (d, J=11.2 Hz, 1H). LC-MS ($ESI^+$) m/z 540.5 $(M+H)^+$.

Step 2—4-[4-[5-[1-(2,6-Dioxo-3-piperidyl)-3-methyl-2-oxo-benzimidazol-5-yl]pentyl]-3-oxo-piperazin-1-yl]cyclohexanecarbaldehyde To a solution of 3-[5-[5-[4-[4-(hydroxymethyl)cyclohexyl]-2-oxo-piperazin-1-yl] pentyl]-3-methyl-2-oxo-benzimidazol-1-yl] piperidine-2,6-dione (50.0 mg, 92.0 umol) in DCM (1.0 mL) was added DMP (39.3 mg, 92.6 umol). The mixture was stirred at 25° C. for 2 hours. On completion, the reaction mixture was quenched with saturated $NaS_2O_3$ aqueous (5.0 mL) at 25° C., and extracted with DCM (3×10 mL). The combined organic layers were washed with $NaHCO_3$ mL (3×5 mL), then concentrated in vacuo to give the title compound (30.0 mg, 48% yield) as a yellow solid. LC-MS ($ESI^+$) m/z 538.1 (M+H).

3-[3-Methyl-2-oxo-5-[5-(2-oxopiperazin-1-yl)pentyl]benzimidazol-1-yl]piperidine-2,6-dione (Intermediate HQ)

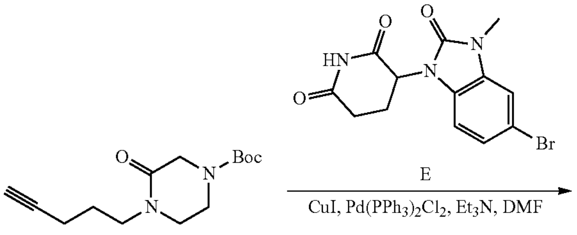

HN

-continued

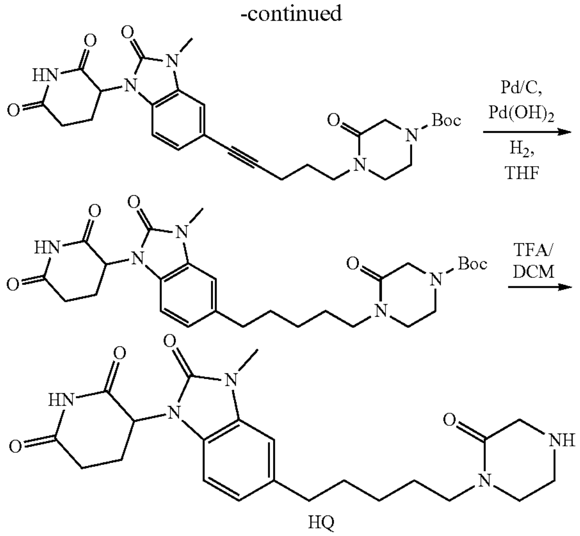

HQ

Step 1—Tert-butyl 4-[5-[1-(2,6-dioxo-3-piperidyl)-3-methyl-2-oxo-benzimidazol-5-yl]pent-4-ynyl]-3-oxo-piperazine-1-carboxylate To a solution of tert-butyl 3-oxo-4-pent-4-ynyl-piperazine-1-carboxylate (2.00 g, 7.51 mmol, Intermediate HN) in DMF (36 mL) was added $Cs_2CO_3$ (12.2 g, 37.5 mmol) and XPhos-Pd-$G_3$ (635 mg, 750 umol) and 3-(5-bromo-3-methyl-2-oxo-benzimidazol-1-yl)piperidine-2,6-dione (2.54 g, 7.51 mmol, Intermediate E). The mixture was stirred at 80° C. for 14 hours under $N_2$ atmosphere. On completion, the reaction mixture was poured into water (20 mL) and extracted with ethyl acetate (3×15 mL). The combined organic phases were dried with anhydrous $Na_2SO_4$, filtered and concentrated in vacuo. The residue was purified by reverse phase column chromatography (water (0.1% FA)-ACN) to give the title compound (1.55 g, 2.96 mmol, 39% yield) as a brown oil. LC-MS ($ESI^+$) m/z 524.4 $(M+H)^+$.

Step 2—Tert-butyl 4-[5-[1-(2,6-dioxo-3-piperidyl)-3-methyl-2-oxo-benzimidazol-5-yl]pentyl]-3-oxo-piperazine-1-carboxylate To a solution of tert-butyl 4-[5-[1-(2,6-dioxo-3-piperidyl)-3-methyl-2-oxo-benzimidazol-5-yl] pent-4-ynyl]-3-oxo-piperazine-1-carboxylate (1.55 g, 2.96 mmol) in THF (20 mL) was added Pd/C (705 mg, 296 umol) and $Pd(OH)_2$ (207 mg, 296 umol) under $N_2$ atmosphere. The suspension was degassed and purged with $H_2$ gas three times. The mixture was stirred under $H_2$ (15 psi) at 25° C. for 16 hours. On completion, insoluble matter was removed by filtration and the filtrate was concentrated in vacuo to give the title compound (1.60 g) as a brown oil. LC-MS ($ESI^+$) m/z 528.3 $(M+H)^+$.

Step 3—3-[3-Methyl-2-oxo-5-[5-(2-oxopiperazin-1-yl)pentyl]benzimidazol-1-yl]piperidine-2,6-dione To a solution of tert-butyl 4-[5-[1-(2,6-dioxo-3-piperidyl)-3-methyl-2-oxo-benzimidazol-5-yl]pentyl]-3-oxo-piperazine-1-carboxylate (2.50 g, 4.74 mmol) in DCM (25 mL) was added TFA (7.70 g, 67.5 mmol, 5 mL). The mixture was stirred at 25° C. for 0.5 hour. On completion, the mixture was concentrated in vacuo to give the title compound (2.50 g, TFA salt) as a brown oil. LC-MS (ESI$^+$) m/z 428.5 (M+H)$^+$.

4-[4-[5-[1-(2,6-dioxo-3-piperidyl)-3-methyl-2-oxo-benzimidazol-5-yl]pentyl]-3-oxo-piperazin-1-yl] cyclohexanecarbaldehyde (Intermediate HR)

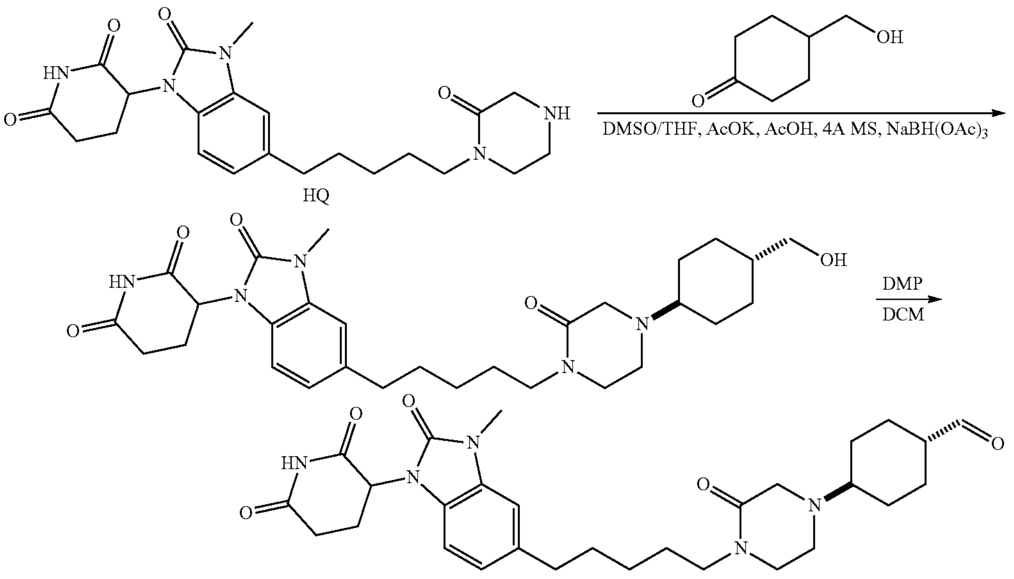

HQ

HR

Step 1—3-[5-[5-[4-[4-(hydroxymethyl)cyclohexyl]-2-oxo-piperazin-1-yl]pentyl]-3-methyl-2-oxo-benzimidazol-1-yl]piperidine-2,6-dione To a solution of 3-[3-methyl-2-oxo-5-[5-(2-oxopiperazin-1-yl) pentyl] benzimidazol-1-yl]piperidine-2,6-dione (2.50 g, 4.62 mmol, Intermediate HQ) in THF (25 mL) and DMSO (5 mL) was added AcOK (1.36 g, 13.8 mmol) and 4 Å molecular sieves (100 mg). Then AcOH (277 mg, 4.62 mmol, 264 uL) was added to adjust pH to 6. After addition, to the mixture was added 4-(hydroxymethyl)cyclohexanone (591 mg, 4.62 mmol, CAS #38580-68-6) and stirred at 40° C. for 16 hours. Next, $NaBH(OAc)_3$ (1.96 g, 9.23 mmol) was added at 25° C. and the resulting mixture was stirred at 25° C. for 2 hours. On completion, the mixture was concentrated in vacuo to give a residue. The residue was purified by reverse phase column chromatography (water (0.1% FA)-ACN) to give the title compound (900 mg, 1.67 mmol, 36% yield) as a white solid. $^1$H NMR (400 MHz, $CDCl_3$-d) 6=8.23 (d, J=17.6 Hz, 1H), 6.92-6.82 (m, 2H), 6.71 (d, J=8.0 Hz, 1H), 5.28-5.17 (m, 1H), 3.56 (d, J=6.8 Hz, 1H), 3.48 (d, J=6.0 Hz, 1H), 3.44 (s, 3H), 3.41-3.32 (m, 4H), 2.99-2.91 (m, 2H), 2.89-2.70 (m, 4H), 2.68-2.63 (m, 2H), 2.29-2.19 (m, 2H), 2.01 (d, J=11.6 Hz, 1H), 1.93 (d, J=12.8 Hz, 1H), 1.76-1.54 (m, 9H), 1.53-1.45 (m, 2H), 1.39-1.27 (m, 3H), 1.10-1.00 (m, 1H). LC-MS (ESI$^+$) m/z 540.2 (M+H)$^+$.

Step 2—4-[4-[5-[1-(2,6-dioxo-3-piperidyl)-3-methyl-2-oxo-benzimidazol-5-yl]pentyl]-3-oxo-piperazin-1-yl]cyclohexanecarbaldehyde To a solution of 3-[5-[5-[4-[4-(hydroxymethyl) cyclohexyl]-2-oxo-piperazin-1-yl]pentyl]-3-methyl-2-oxo-benzimidazol-1-yl]piperidine-2,6-dione (200 mg, 370 umol) in DCM (2.0 mL) was added DMP (314 mg, 741 umol, 229 uL). The mixture was stirred at 25° C. for 2 hours. On completion, the mixture was quenched by sodium thiosulfate solution (5.0 mL). Then the pH of the residue was adjusted to 8 by sodium bicarbonate solution. The mixture was extracted by DCM (3×10 mL). The combined organic layers were concentrated in vacuo to give the title compound (130 mg, 241 umol, 65% yield) as a yellow solid. $^1$H NMR (400 MHz, CHLOROFORM-d) 6=9.69-9.62 (m, 1H), 8.21-7.94 (m, 1H), 6.88 (d, J=8.0 Hz, 1H), 6.84 (s, 1H), 6.71 (d, J=8.0 Hz, 1H), 5.21 (dd, J=5.4, 12.4 Hz, 1H), 3.44 (s, 3H), 3.39-3.31 (m, 2H), 3.30-3.18 (m, 3H), 2.99-2.91 (m, 1H), 2.89-2.60 (m, 6H), 2.43-1.97 (m, 6H), 1.71-1.51 (m, 8H), 1.38-1.26 (m, 4H). LC-MS (ESI$^+$) m/z 538.5 (M+H)$^+$.

4-[4-[2-[1-(2,6-Dioxo-3-piperidyl)-3-methyl-2-oxo-benzimidazol-5-yl]ethyl]-1-piperidyl]cyclohexanecarbaldehyde (Intermediate HS)

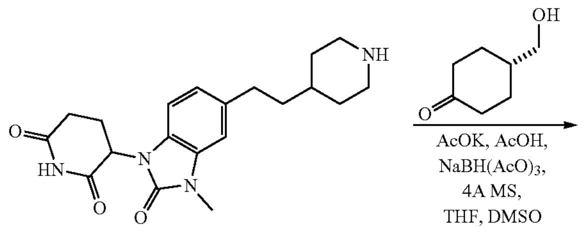

GO

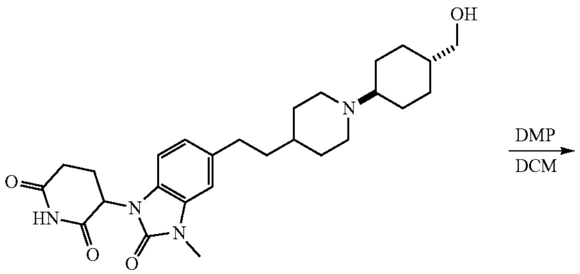

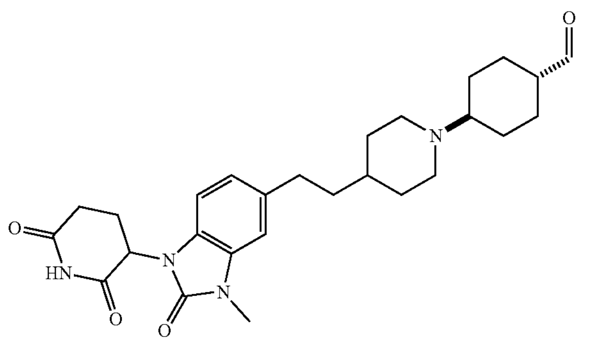

HS

Step 1—3-[5-[2-[1-[4-(Hydroxymethyl)cyclohexyl]-4-piperidyl]ethyl]-3-methyl-2-oxo-benzimidazol-1-yl]piperidine-2,6-dione To a solution of 3-[3-methyl-2-oxo-5-[2-(4-piperidyl)ethyl]benzimidazol-1-yl]piperidine-2,6-dione (500 mg, 1.35 mmol, Intermediate GO) in THF (10 mL) and DMSO (2 mL) was added KOAc (662 mg, 6.75 mmol) and HOAc (81.0 mg, 1.35 mmol), 4 Å molecular sieves (1.35 mmol), and 4-(hydroxymethyl)cyclohexanone (345 mg, 2.70 mmol, CAS #38580-68-6). The mixture was stirred at 40° C. for 14 hours. Then $NaBH(OAc)_3$ (572 mg, 2.70 mmol) was added, and the mixture was stirred at 25° C. for 2 hours. On completion, the reaction mixture was filtered and concentrated in vacuo. The crude product was purified by reversed-phase HPLC (0.1% TFA) to give the title compound (200 mg, 31% yield) as a white solid. LC-MS ($ESI^+$) m/z 483.1 $(M+H)^+$.

Step 2—4-[4-[2-[1-(2,6-Dioxo-3-piperidyl)-3-methyl-2-oxo-benzimidazol-5-yl]ethyl]-1-piperidyl]cyclohexanecarbaldehyde To a solution of 3-[5-[2-[1-[4-(hydroxymethyl)cyclohexyl]-4-piperidyl]ethyl]-3-methyl-2-oxo-benzimidazo 1-1-yl]piperidine-2,6-dione (80.0 mg, 165 umol) in DCM (3.0 mL) was added DMP (140 mg, 331 umol). The mixture was stirred at 25° C. for 1 hour. On completion, the mixture was quenched with water (5.0 mL) and extracted with EA (8 mL×3). The combined organic phase was dried over anhydrous sodium sulfate, filtered and concentrated to give the title compound (70.0 mg, 88% yield) as a yellow oil. LC-MS ($ESI^+$) m/z 481.4 $(M+H)^+$.

Tert-butyl 2-[2-[2-(sulfanylethoxy)ethoxy]ethoxy]acetate (Intermediate HT)

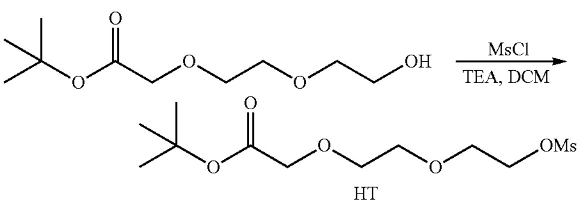

HT

To a solution of tert-butyl 2-[2-(2-hydroxyethoxy)ethoxy]acetate (300 mg, 1.36 mmol, CAS #149299-82-1) in DCM (6 mL) was added TEA (413 mg, 4.09 mmol) to adjust the pH=8, then MsCl (470 mg, 4.10 mmol) was added at 0° C. The mixture was then stirred at 0-25° C. for 0.5 hour. On completion, the mixture was quenched with water (20 mL) and extracted with DCM (25 mL×3). The combined organic phase was dried over anhydrous sodium sulfate, filtered and concentrated to give the title compound (360 mg, 99% yield) as a yellow oil.

2-[2-[2-[[4-[[4-[1-(4-Chlorophenyl)-7-isopropoxy-6-methoxy-3-oxo-1,4-dihydroisoquinolin-2-yl]-N-methyl-anilino]methyl]cyclohexyl]-methyl-amino]ethoxy]ethoxy]acetic acid (Intermediate HU)
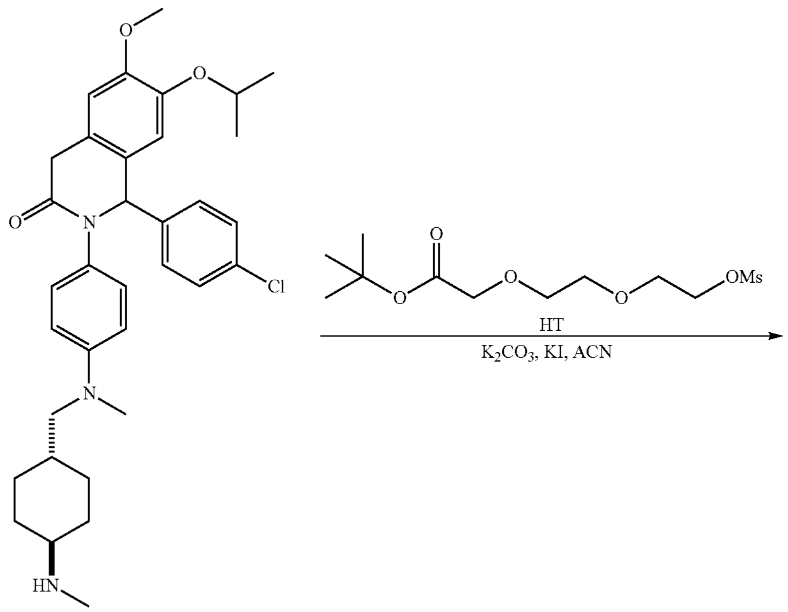
DZ
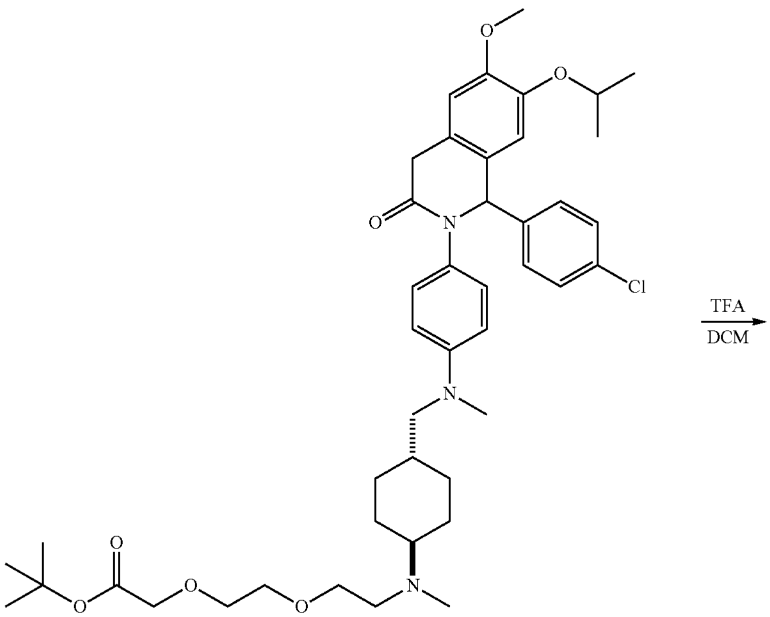

-continued

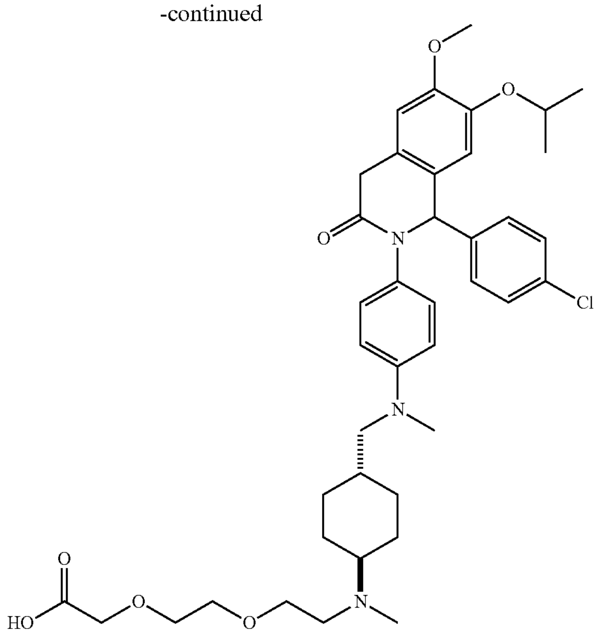

HU

Step 1—Tert-butyl 2-[2-[2-[[4-[[4-[1-(4-chlorophenyl)-7-isopropoxy-6-methoxy-3-oxo-1,4-dihydroisoquinolin-2-yl]-N-methyl-anilino]methyl]cyclohexyl]-methyl-amino]ethoxy]ethoxy]acetate To a solution of tert-butyl 2-[2-[2-(sulfanylmethoxy)ethoxy]ethoxy]acetate (58.6 mg, 220 μmol, Intermediate HT) and 1-(4-chlorophenyl)-7-isopropoxy-6-methoxy-2-[4-[methyl-[[4-(methylamino)cyclohexyl]methyl]amino]phenyl]-1,4-dihydroisoquinolin-3-one (90.0 mg, 146 umol, Intermediate DZ) in ACN (2.0 mL) was added $K_2CO_3$ (60.9 mg, 440 umol) and KI (2.44 mg, 14.6 umol). The mixture was stirred at 60° C. for 12 hours. On completion, the mixture was quenched with water (1 mL) concentrated to give a residue. The mixture was purified by reversed-phase HPLC (0.1% TFA condition) to give the title compound (70 mg, 61% yield) as a white solid. LC-MS ($ESI^+$) m/z 778.4 $(M+H)^+$.

Step 2—2-[2-[2-[[4-[[4-[1-(4-Chlorophenyl)-7-isopropoxy-6-methoxy-3-oxo-1,4-dihydroisoquinolin-2-yl]-N-methyl-anilino]methyl]cyclohexyl]-methyl-amino]ethoxy]ethoxy]acetic acid To a solution of tert-butyl 2-[2-[2-[[4-[[4-[1-(4-chlorophenyl)-7-isopropoxy-6-methoxy-3-oxo-1,4-dihydroisoquinolin-2-yl]-N-methyl-anilino]methyl]cyclohexyl]-methyl-amino]ethoxy]ethoxy]acetate (70.0 mg, 89.9 umol) in DCM (1.5 mL) was added TFA (770 mg, 6.75 mmol, 0.5 mL). Then the mixture was stirred at 25° C. for 1 hour. On completion, the mixture was concentrated to give the title compound (70.0 mg, 93% yield) as a yellow oil.

Dec-9-ynal (Intermediate HV)

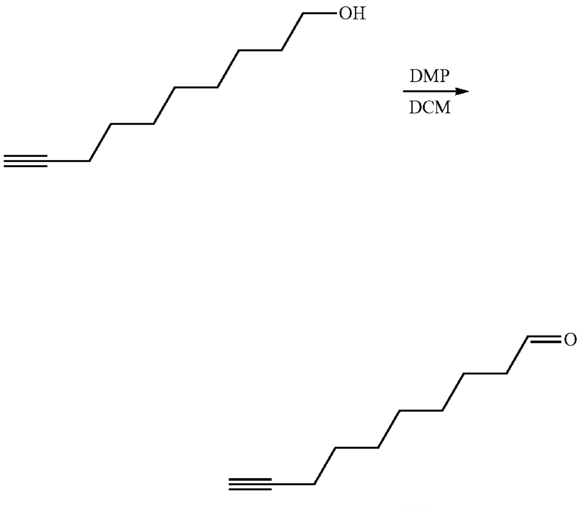

HV

To a mixture of dec-9-yn-1-ol (540 mg, 3.50 mmol, CAS #17643-36-6) in DCM (2 mL) was added DMP (1.78 g, 4.20 mmol). The mixture was stirred at 20° C. for 1 hour. On completion, the mixture was quenched with saturated sodium thiosulfate solution (10 mL) and aqueous solution of sodium bicarbonate (10 mL), then the mixture was stirred for 10 minutes, and the mixture was extracted with EtOAc (3×10 mL). The organic phase was dried over $Na_2SO_4$, filtered, and concentrated in vacuo to give the title compound (450 mg, 84% yield) as a brown solid. $^1H$ NMR (400 MHz, $CDCl_3$) δ 9.76 (t, J=1.6 Hz, 1H), 2.46-2.40 (m, 2H), 2.21-2.15 (m, 2H), 1.94 (t, J=2.4 Hz, 1H), 1.64 (t, J=7.2 Hz, 2H), 1.55-1.50 (m, 2H), 1.44-1.38 (m, 2H), 1.35-1.31 (m, 4H).

4-[[chloro-(3-chloro-2-fluoro-phenyl)-oxo-dispiro[BLAH]carbonyl]amino]benzoic acid (Intermediate HW)

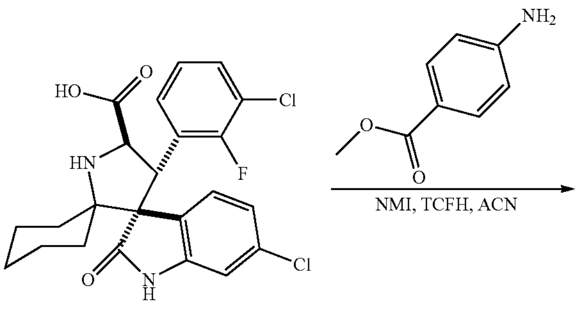

CI

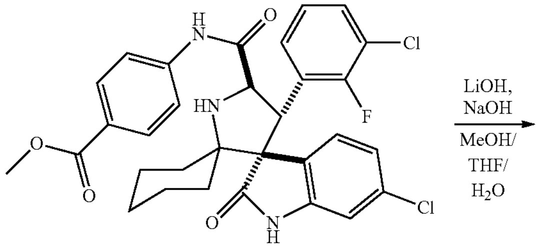

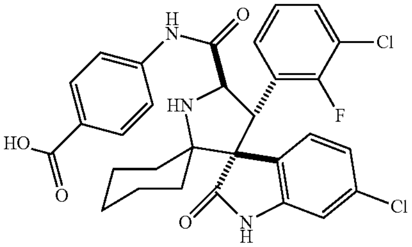

HW

Step 1—methyl 4-[[chloro-(3-chloro-2-fluoro-phenyl)-oxo-dispiro[BLAH]carbonyl]amino]benzoate To a solution of chloro-(3-chloro-2-fluoro-phenyl)-oxo-dispiro[BLAH]carboxylic acid (440 mg, 949 umol, Intermediate CI) and methyl 4-aminobenzoate (143 mg, 949 umol, CAS #619-45-4) in ACN (8 mL) was added 1-methylimidazole (2.34 g, 28.4 mmol, 2.27 mL) and [chloro(dimethylamino)methylene]-dimethyl-ammonium; hexafluorophosphate (666 mg, 2.37 mmol) at 25° C. The reaction solution was stirred at 25° C. for 30 mins. On completion, the mixture was poured into water (30 mL) and the suspension was filtered. Then the filter cake was washed with water (5 mL×3), and dried in vacuo to give the title compound (560 mg 24% yield). LC-MS (ESI$^+$) m/z 596.1 $(M+H)^+$.

Step 2—4-[[chloro-(3-chloro-2-fluoro-phenyl)-oxo-dispiro[BLAH]carbonyl]amino]benzoic acid Methyl 4-[[chloro-(3-chloro-2-fluoro-phenyl)-oxo-dispiro[BLAH]carbonyl]amino]benzoate (500 mg, 838 umol) was dissolved in THF (2.0 mL), then LiOH—$H_2O$ (211 mg, 5.03 mmol) and NaOH (201 mg, 5.03 mmol) in a mixture of $H_2O$ (1 mL) and MeOH (2 mL) was added. The mixture was stirred for 30 mins at 25° C. On completion, the reaction mixture was quenched by adding it to a cold saturated aqueous $H_2O$ solution (5.0 ml). The aqueous layer was extracted with ethyl acetate (10 ml×3). The organic layer was separated, dried over anhydrous $Na_2SO_4$, filtered and concentrated under reduced pressure to give the residue. The residue was purified by reverse phase flash [ACN/(0.1% FA in water), 0% to 90%] to give the title compound (15 mg, 20% yield). $^1H$ NMR (400 MHz, DMSO-$d_6$) δ 12.95-12.49 (m, 1H), 10.59 (s, 1H), 10.32 (s, 1H), 7.90 (d, J=8.8 Hz, 2H), 7.74 (d, J=8.8 Hz, 2H), 7.68-7.58 (m, 1H), 7.46 (d, J=7.8 Hz, 1H), 7.40-7.33 (m, 1H), 7.15 (t, J=8.0 Hz, 1H), 7.04 (dd, J=1.6, 8.0 Hz, 1H), 6.69 (d, J=2.0 Hz, 1H), 4.82-4.75 (m, 1H), 4.75-4.67 (m, 1H), 2.10-2.03 (m, 1H), 1.88-1.77 (m, 1H), 1.75-1.43 (m, 6H), 1.42-1.33 (m, 1H), 1.03-0.79 (m, 2H). LC-MS (ESI$^+$) m/z 582.0 $(M+H)^+$.

4-[[Chloro-(3-chloro-2-fluoro-phenyl)-dec-9-ynyl-oxo-dispiro[BLAH]carbonyl]amino]benzoic acid (Intermediate HX)

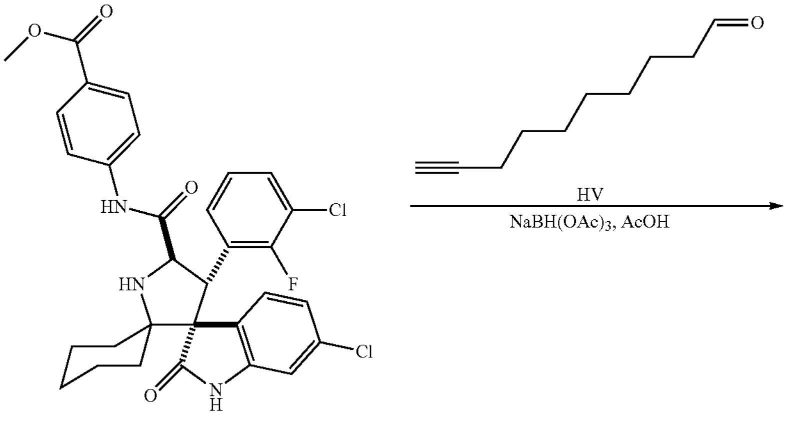

-continued

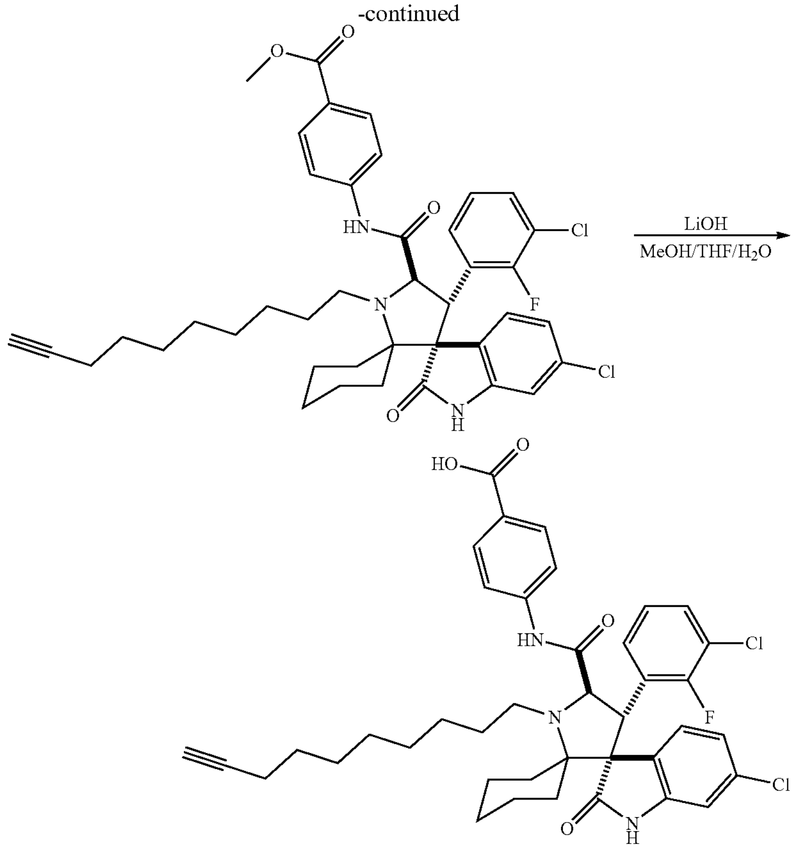

HX

Step 1—Methyl 4-[[chloro-(3-chloro-2-fluoro-phenyl)-dec-9-ynyl-oxo-dispiro[BLAH]carbonyl] amino]benzoate A mixture of methyl 4-[[chloro-(3-chloro-2-fluoro-phenyl)-oxo-dispiro[BLAH]carbonyl]amino]benzoate (500 mg, 838 umol, synthesized via Step 1 of Intermediate HW) and dec-9-ynal (127 mg, 838 umol, Intermediate HV) in HOAc (5 mL) stirred at 20° C. for 1 hour. Then the mixture was cooled to 20° C. Next, $NaBH(OAc)_3$ (266 mg, 1.26 mmol) was added into the mixture and stirred at 20° C. for 12 hours. On completion, the mixture was poured into the water (20 mL) and extracted with ethyl acetate (3×10 mL). The combined organic phase was washed with brine (3×20 mL), dried with anhydrous $Na_2SO_4$, filtered and concentrated in vacuo to give the crude compound. The crude compound was purified by column chromatography ($SiO_2$, Petroleum ether/Ethyl acetate=10:1 to 5:1) to give the title compound (60.0 mg, 9.7% yield) as a brown solid. $^1H$ NMR (400 MHz, $CDCl_3$) δ 9.79 (s, 1H), 8.03 (d, J=8.0 Hz, 2H), 7.69 (t, J=6.8 Hz, 1H), 7.62 (d, J=8.4 Hz, 2H), 7.30 (s, 2H), 7.17 (t, J=7.2 Hz, 1H), 7.07-6.94 (m, 2H), 6.67 (s, 1H), 4.55 (d, J=10.0 Hz, 1H), 4.40 (d, J=10.4 Hz, 1H), 3.91 (s, 3H), 3.51-3.26 (m, 2H), 2.20-2.09 (m, 4H), 1.96-1.87 (m, 2H), 1.86-1.77 (m, 2H), 1.74-1.61 (m, 4H), 1.52-1.43 (m, 3H), 1.36 (d, J=4.4 Hz, 4H), 1.28 (s, 4H), 1.20-1.08 (m, 1H), 1.06-0.95 (m, 1H).

Step 2—4-[[Chloro-(3-chloro-2-fluoro-phenyl)-dec-9-ynyl-oxo-dispiro[BLAH]carbonyl]amino] benzoic acid A mixture of methyl 4-[[chloro-(3-chloro-2-fluoro-phenyl)-dec-9-ynyl-oxo-dispiro[BLAH] carbonyl]amino]benzoate (150 mg, 204 umol) and LiOH (24.5 mg, 1.02 mmol) in MeOH (1.0 mL), THF (1.0 mL) and $H_2O$ (1.0 mL). The mixture was then stirred at 50° C. for 1 hour. On completion, the mixture was adjusted to pH=3-4 with HCl (1N), and extracted with EtOAc (3×10 mL). The organic phase was dried over $Na_2SO_4$, filtered, and concentrated in vacuo to give the title compound (130 mg, 88% yield) as a brown solid. LC-MS ($ESI^+$) m/z 718.0 $(M+H)^+$.

(5-Amino-2,3-dihydro-1,4-benzodioxin-8-yl)methanol (Intermediate HY)

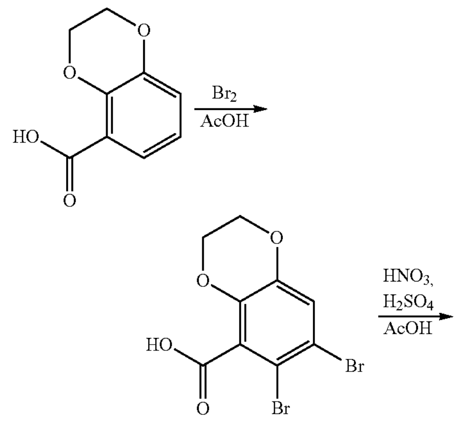

-continued

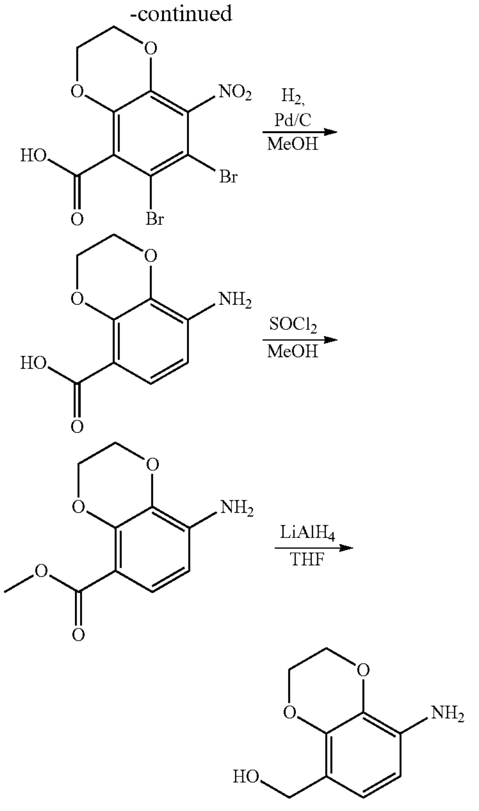

HY

Step 1—6,7-Dibromo-2,3-dihydro-1,4-benzodioxine-5-carboxylic acid

To a solution of 2,3-dihydro-1,4-benzodioxine-5-carboxylic acid (4.40 g, 24.4 mmol, CAS #4442-53-9) in AcOH (27 mL) was added $Br_2$ (11.7 g, 73.2 mmol) dropwise at 25° C. The mixture was stirred at 80° C. for 16 hours. On completion, the mixture was quenched with water (20 mL) and extracted with ethyl acetate (25 mL×3). The combined organic phase was washed with a solution of $NaHCO_3$ and was dried over anhydrous sodium sulfate, filtered and concentrated to give the title compound (10.5 g, 100% yield) as a brown solid. $^1H$ NMR (400 MHz, DMSO-d6) δ 14.43-12.43 (m, 1H), 7.35 (s, 1H), 4.31-4.28 (m, 4H).

Step 2—6,7-Dibromo-5-nitro-2,3-dihydro-1,4-benzodioxine-8-carboxylic acid

To a solution of 6,7-dibromo-2,3-dihydro-1,4-benzodioxine-5-carboxylic acid (10.5 g, 31.0 mmol) in AcOH (100 mL) and $H_2SO_4$ (30 mL) at 0° C. Then $HNO_3$ (3.92 g, 62.1 mmol) was added dropwise at 0° C. The mixture was warmed to 40° C. for 16 hours. On completion, the crude product was triturated with $H_2O$ (200 mL) at 0° C. for 5 minutes. Then the mixture was filtered and the filter cake to give the title compound (8.00 g, 67% yield) as a colorless oil. $^1H$ NMR (400 MHz, DMSO-d6) δ 14.82-13.43 (m, 1H), 4.45 (s, 4H).

Step 3—5-Amino-2,3-dihydro-1,4-benzodioxine-8-carboxylic acid

To a solution of 6,7-dibromo-5-nitro-2,3-dihydro-1,4-benzodioxine-8-carboxylic acid (2.00 g, 5.22 mmol) in $H_2O$ (25 mL) was added Pd/C (400 mg, 10 wt %) and $Na_2CO_3$ (276 mg, 2.61 mmol) under $N_2$ atmosphere. The suspension was degassed and purged with $H_2$ three times. The mixture was stirred under $H_2$ (1 MPa) at 50° C. for 16 hours. On completion, the mixture was quenched with water (20 mL) and extracted with ethyl acetate (25 mL×3). The combined organic phase was dried over anhydrous sodium sulfate, filtered and concentrated to give the title compound (520 mg, 51% yield) as a white solid. $^1H$ NMR (400 MHz, DMSO-d6) δ 11.96-11.08 (m, 1H), 7.17 (d, J=8.4 Hz, 1H), 6.52-6.46 (m, 1H), 6.20 (d, J=7.2 Hz, 2H), 4.22-4.16 (m, 4H).

Step 4—Methyl 5-amino-2,3-dihydro-1,4-benzodioxine-8-carboxylate

To a solution of 5-amino-2,3-dihydro-1,4-benzodioxine-8-carboxylic acid (400 mg, 2.05 mmol) in MeOH (8 mL) was added $SOCl_2$ (487 mg, 4.10 mmol) dropwise at 0° C. The mixture was stirred at 60° C. for 0.5 hour. On completion, the mixture was filtered and concentrated to give a residue. The residue was purified by reversed-phase HPLC (0.1% FA condition) to give the title compound (200 mg, 46% yield) as a yellow solid. $^1H$ NMR (400 MHz, DMSO-d6) δ 7.17 (d, J=8.8 Hz, 1H), 6.23 (d, J=8.4 Hz, 1H), 5.52 (s, 2H), 4.26-4.23 (m, 4H), 3.67 (s, 3H); LC-MS ($ESI^+$) m/z 210.0 $(M+H)^+$.

Step 5—(5-Amino-2,3-dihydro-1,4-benzodioxin-8-yl)methanol

To a solution of methyl 5-amino-2,3-dihydro-1,4-benzodioxine-8-carboxylate (200 mg, 956 umol) in THF (6 mL) was added $LiAlH_4$ (72.5 mg, 1.91 mmol) at 0° C. The mixture was stirred at 25° C. for 1 hour. On completion, the mixture was quenched with water (0.4 mL), 15% NaOH (0.4 mL) and water (1.2 mL), the mixture was concentrated to give the title compound (150 mg, 86% yield) as a brown solid; LC-MS ($ESI^+$) m/z 182.1 $(M+H)^+$.

Chloro-(3-chloro-2-fluoro-phenyl)-N-(8-formyl-2,3-dihydro-1,4-benzodioxin-5-yl)-oxo-dispiro[BLAH] carboxamide (Intermediate HZ)

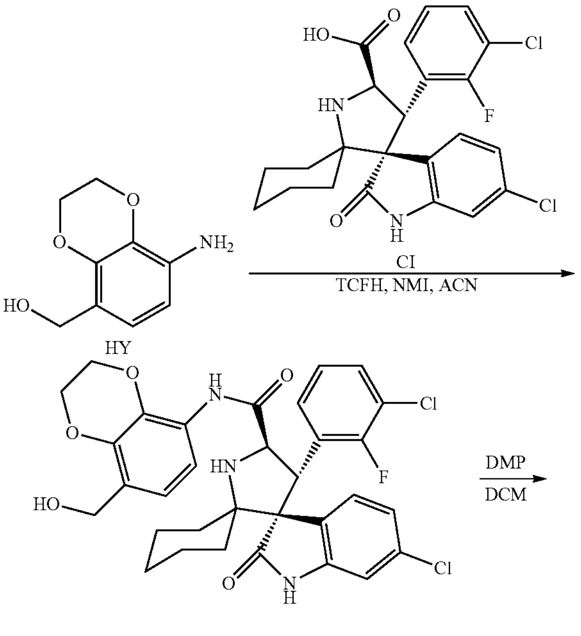

-continued

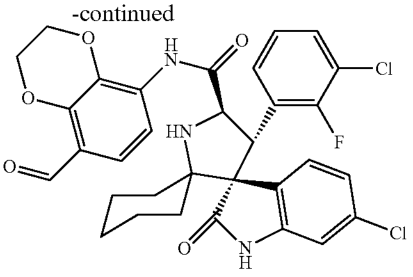

HZ

Step 1—Chloro-(3-chloro-2-fluoro-phenyl)-N-[8-(hydroxymethyl)-2,3-dihydro-1,4-benzodioxin-5-yl]-oxo-dispiro[BLAH]carboxamide To a solution of (5-amino-2,3-dihydro-1,4-benzodioxin-8-yl)methanol (100 mg, 551 umol, Intermediate HY) and chloro-(3-chloro-2-fluoro-phenyl)-oxo-dispiro[BLAH]carboxylic acid (255 mg, 551 μmol, Intermediate CI) in ACN (4 mL) was added 1-methylimidazole (1.36 g, 16.5 mmol) and [chloro(dimethylamino)methylene]-dimethyl-ammonium; hexafluorophosphate (309 mg, 1.10 mmol). The mixture was stirred at 25° C. for 1 hour. On completion, the mixture was filtered and concentrated to give a residue. The residue was purified by reversed-phase HPLC (0.1% FA condition) to give the title compound (100 mg, 29% yield) as a yellow oil. $^1H$ NMR (400 MHz, DMSO-d6) δ 10.57 (s, 1H), 10.14 (s, 1H), 7.73 (d, J=8.4 Hz, 1H), 7.67-7.60 (m, 1H), 7.47-7.42 (m, 1H), 7.38-7.31 (m, 1H), 7.18-7.11 (m, 1H), 7.04-6.98 (m, 1H), 6.83 (d, J=8.4 Hz, 1H), 6.67 (d, J=2.0 Hz, 1H), 4.96-4.89 (m, 1H), 4.54 (d, J=10.0 Hz, 1H), 4.41 (d, J=5.2 Hz, 2H), 4.33-4.25 (m, 3H), 2.09-2.02 (m, 1H), 1.99 (s, 2H), 1.71 (d, J=13.2 Hz, 1H), 1.64-1.58 (m, 2H), 1.52 (s, 1H), 1.42-1.35 (m, 1H), 1.23 (s, 2H), 1.02-0.94 (m, 1H), 0.87-0.79 (m, 2H); LC-MS (ESI$^+$) m/z 626.1 $(M+H)^+$.

Step 2—Chloro-(3-chloro-2-fluoro-phenyl)-N-(8-formyl-2,3-dihydro-1,4-benzodioxin-5-yl)-oxo-dispiro[BLAH]carboxamide To a solution of chloro-(3-chloro-2-fluoro-phenyl)-N-[8-(hydroxymethyl)-2,3-dihydro-1,4-benzodioxin-5-yl]-oxo-dispiro[BLAH]carboxamide (50.0 mg, 79.8 umol) in DCM (2 mL) was added DMP (40.6 mg, 95.7 umol). The mixture was stirred at 25° C. for 0.25 hour. On completion, the mixture was quenched with saturated $Na_2SO_3$ (20 mL) and extracted with DCM (25 mL×3). The combined organic phase was dried over anhydrous sodium sulfate, filtered and concentrated to give the title compound (40.0 mg, 80.26% yield) as a yellow solid. LC-MS (ESI$^+$) m/z 624.3 $(M+H)^+$.

Tert-butyl 4-(4-formylcyclohexyl)piperazine-1-carboxylate (Intermediate IA)

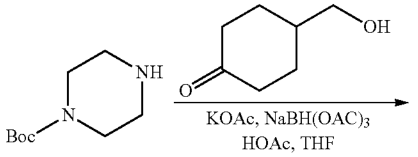

-continued

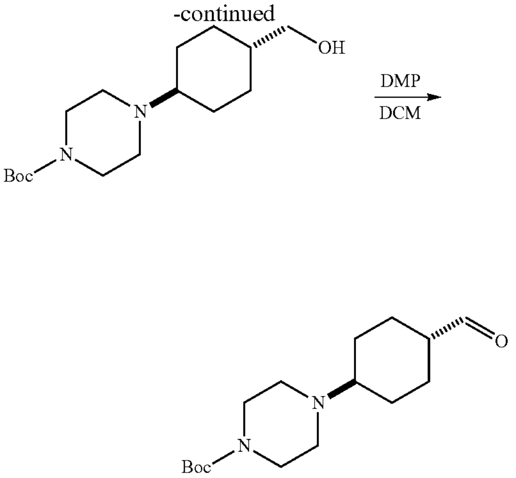

IA

Step 1—Tert-butyl 4-[4-(hydroxymethyl)cyclohexyl]piperazine-1-carboxylate

To a solution of tert-butyl piperazine-1-carboxylate (1.50 g, 8.05 mmol, CAS #143238-38-4) in DCM (10 mL) was added $K_2CO_3$ (5.39 g, 39.0 mmol) for 0.25 hour. Next, HOAc (5.0 mL), and 4-(hydroxymethyl)cyclohexanone (500 mg, 3.90 mmol, CAS #38580-68-6) was added to the mixture which was then stirred for 0.25 hour. Then NaBH$(OAc)_3$ (1.65 g, 7.80 mmol) was added and the mixture was stirred at 25° C. for 2.5 hours. On completion, the mixture was quenched with water (20 mL) and extracted with DCM (25 mL×3). The combined organic phases were dried over anhydrous sodium sulfate, filtered and concentrated to give a residue. The residue was purified by column chromatography to give the title compound (300 mg, 26% yield) as a white solid. $^1H$ NMR (400 MHz, CHLOROFORM-d) 6=3.60 (d, J=6.5 Hz, 2H), 3.56 (s, 2H), 3.51-3.42 (m, 1H), 3.47 (d, J=6.3 Hz, 1H), 2.81-2.57 (m, 4H), 1.86-1.59 (m, 6H), 1.56-1.33 (m, 13H).

Step 2 Tert-butyl 4-(4-formylcyclohexyl)piperazine-1-carboxylate

To a solution of tert-butyl 4-[4-(hydroxymethyl)cyclohexyl]piperazine-1-carboxylate (250 mg, 837 umol) in DCM (4.0 mL) was added DMP (532 mg, 1.26 mmol). The mixture was stirred at 25° C. for 1 hour. On completion, the mixture was quenched with water (5.0 mL) and extracted with DCM (5.0 mL×3). The combined organic phase was dried over anhydrous sodium sulfate, filtered and concentrated to give the title compound (240 mg, 97% yield) as a yellow oil. LC-MS (ESI$^+$) m/z 297.4 $(M+H)^+$.

(1S)-1-(4-chlorophenyl)-7-isopropoxy-6-methoxy-2-[4-(methylamino)phenyl]-1,4-dihydroisoquinolin-3-one (Intermediate IB)

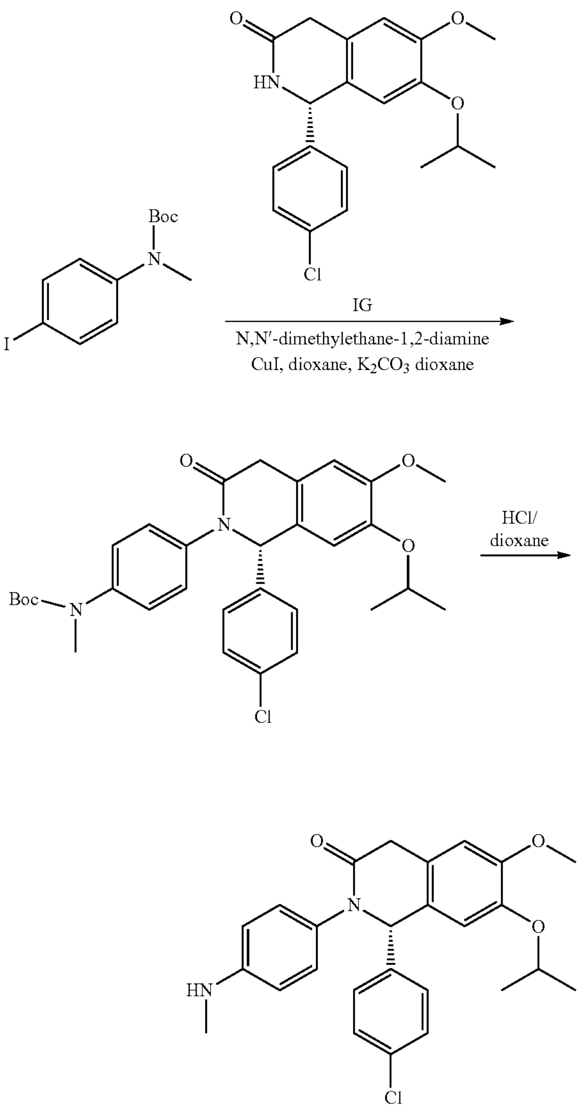

IB

Step 1—Tert-butyl N-[4-[(1S)-1-(4-chlorophenyl)-7-isopropoxy-6-methoxy-3-oxo-1,4-dihydroisoquinolin-2-yl]phenyl]-Nmethyl-carbamate To a solution of (1S)-1-(4-chlorophenyl)-7-isopropoxy-6-methoxy-2,4-dihydro-1H-isoquinolin-3-one (800 mg, 2.31 mmol, Intermediate IG) in dioxane (15.0 mL) was added tert-butyl N-(4-iodophenyl)-N-methyl-carbamate (1.60 g, 4.81 mmol, synthesized via Steps 1-2 of Intermediate HM), CuI (44.0 mg, 231 umol), $K_2CO_3$ (639 mg, 4.63 mmol) and N,N'-dimethylethane-1,2-diamine (20.3 mg, 231 umol). The mixture was stirred at 120° C. for 16 hours under $N_2$ atmosphere. On completion, the mixture was filtered and concentrated to give a residue. The residue was purified by column chromatography to give the title compound (591 mg, 46% yield) as yellow oil. LC-MS ($ESI^+$) m/z 551.2 $(M+H)^+$.

Step 2—(1S)-1-(4-Chlorophenyl)-7-isopropoxy-6-methoxy-2-[4-(methylamino)phenyl]-1,4-dihydroisoquinolin-3-one To a solution of tert-butyl N-[4-[(1S)-1-(4-chlorophenyl)-7-isopropoxy-6-methoxy-3-oxo-1,4-dihydroisoquinolin-2-yl]phenyl]-N-methyl-carbamate (80.0 mg, 145 umol) in DCM (3.0 mL) was added HCl/dioxane (4 M, 36 uL). The mixture was stirred at 25° C. for 2 hours. On completion, the mixture was filtered and concentrated to give the title compound (70.0 mg, 98% yield, HCl) as yellow oil. LC-MS ($ESI^+$) m/z 451.4 $(M+H)^+$.

(1S)-1-(4-Chlorophenyl)-7-isopropoxy-6-methoxy-2-[4-[methyl-[(4-piperazin-1-ylcyclohexyl)methyl]amino]phenyl]-1,4-dihydroisoquinolin-3-one (Intermediate IC)

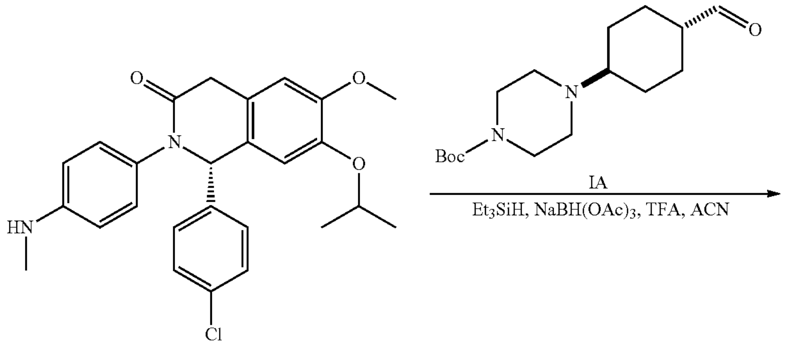

IB

-continued

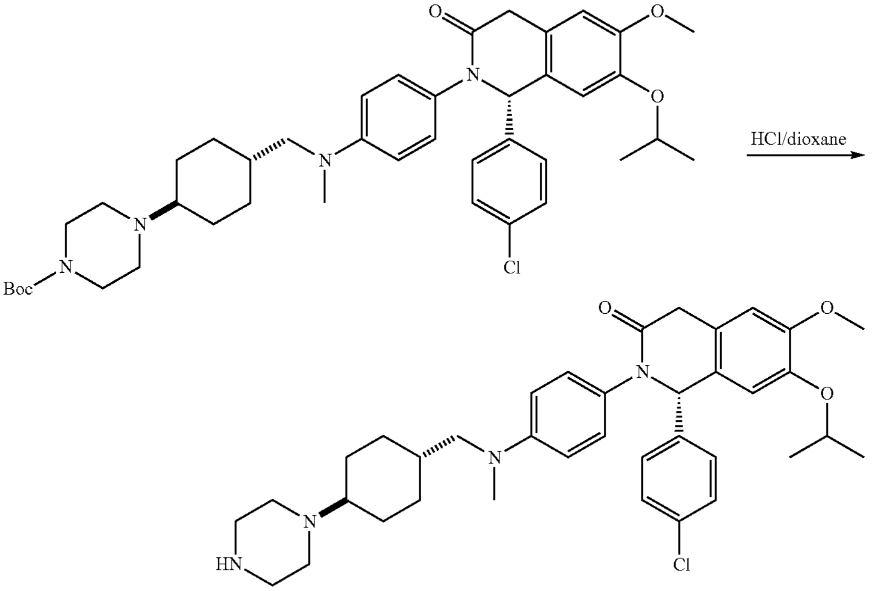

IC

Step 1—Tert-butyl 4-[4-[[4-[(1S)-1-(4-chlorophenyl)-7-isopropoxy-6-methoxy-3-oxo-1,4-dihydroisoquinolin-2-yl]-N-methyl-anilino]methyl]cyclohexyl] piperazine-1-carboxylate To a solution of (1S)-1-(4-chlorophenyl)-7-isopropoxy-6-methoxy-2-[4-(methylamino)phenyl]-1,4-dihydroisoquinolin-3-one (70.0 mg, 155 umol, Intermediate IB) in ACN (2.0 mL) was added TFA (276 mg, 2.43 mmol) tert-butyl 4-(4-formylcyclohexyl)piperazine-1-carboxylate (240 mg, 809 umol, Intermediate IA), $Et_3SiH$ (282 mg, 2.43 mmol), $NaBH(OAc)_3$ (343 mg, 1.62 mmol). The mixture was stirred at 25° C. for 2 hours. On completion, the mixture was filtered and concentrated in vacuo. The crude product was purified by reversed-phase HPLC (0.1% FA) to give the title compound (80.0 mg, 13.5% yield) as a white solid. LC-MS ($ESI^+$) m/z 731.2 $(M+H)^+$.

Step 2—(1S)-1-(4-Chlorophenyl)-7-isopropoxy-6-methoxy-2-[4-[methyl-[(4-piperazin-1-ylcyclohexyl)methyl]amino]phenyl]-1,4-dihydroisoquinolin-3-one To a solution of tert-butyl 4-[4-[[4-[(1S)-1-(4-chlorophenyl)-7-isopropoxy-6-methoxy-3-oxo-1,4-dihydroisoquinolin-2-yl]-N-methyl-anilino]methyl]cyclohexyl]piperazine-1-carboxylate (40.0 mg, 54.6 umol) in DCM (1.0 mL) was added HCl/dioxane (4 M, 0.1 mL). The mixture was stirred at 25° C. for 1 hour. On completion, the mixture was concentrated in vacuo to give the title compound (34.0 mg, 98% yield) as a yellow oil. LC-MS ($ESI^+$) m/z 631.7 $(M+H)^+$.

Tert-butyl 4-[[4-[1-(4-chlorophenyl)-7-isopropoxy-6-methoxy-3-oxo-1,4-dihydroisoquinolin-2-yl]phenyl]-methyl-carbamoyl]piperidine-1-carboxylate (Intermediate ID)

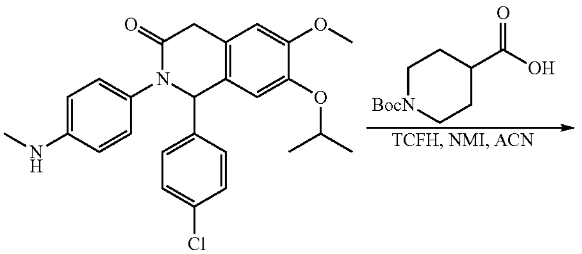

HM

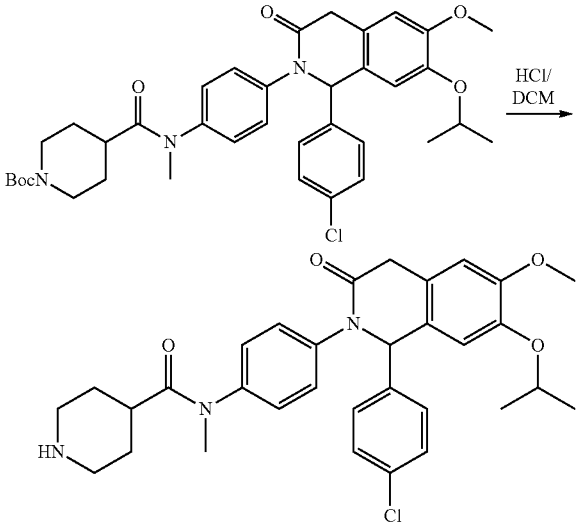

ID

Step 1—tert-butyl 4-[[4-[1-(4-chlorophenyl)-7-isopropoxy-6-methoxy-3-oxo-1,4-dihydroisoquinolin-2-yl]phenyl]-methyl-carbamoyl]piperidine-1-carboxylate To a solution of 1-(4-chlorophenyl)-7-isopropoxy-6-methoxy-2-[4-(methylamino)phenyl]-1,4-dihydroisoquinolin-3-one (90 mg, 199.58 umol, Intermediate HM) and 1-tert-butoxycarbonylpiperidine-4-carboxylic acid (68.64 mg, 299.36 umol, CAS #174286-31-8) in ACN (3 mL) was added [chloro(dimethylamino)methylene]-dimethyl-ammonium; hexafluorophosphate (1.79 g, 6.39 mmol) and 1-methylimidazole (40.9 mg, 499 umol, 39.8 uL). The mixture was stirred at 20° C. for 15 minutes. On completion, the reaction mixture was concentrated in vacuo to give a residue. The crude product was purified by reversed-phase (0.1% FA condition) to give the title compound (60.0 mg, 45% yield) as a white solid. $^1$H NMR (400 MHz, DMSO-$d_6$) δ=7.37-7.33 (m, 1H), 7.41-7.29 (m, 1H), 7.39-7.19 (m, 6H), 6.99 (br s, 1H), 6.88 (s, 1H), 8.38-6.07 (m, 1H), 3.97-3.90 (m, 1H), 3.70-3.61 (m, 1H), 3.11 (br s, 3H), 2.61-2.39 (m, 36H), 1.61-1.31 (m, 1H), 1.59-1.29 (m, 1H), 1.57-1.29 (m, 13H), 1.62-1.29 (m, 1H), 1.21 (dd, J=6.0, 17.4 Hz, 5H). LC-MS (ESI$^+$) m/z 662.3 (M+H)$^+$.

Step 2—tert-butyl 4-[[4-[1-(4-chlorophenyl)-7-isopropoxy-6-methoxy-3-oxo-1,4-dihydroisoquinolin-2-yl]phenyl]-methyl-carbamoyl]piperidine-1-carboxylate To a solution of tert-butyl 4-[[4-[1-(4-chlorophenyl)-7-isopropoxy-6-methoxy-3-oxo-1,4-dihydroisoquinolin-2-yl]phenyl]-methyl-carbamoyl]piperidine-1-carboxylate (20.0 mg, 30.20 umol) was added HCl/dioxane (4 M, 0.1 mL). The mixture was stirred at 20° C. for 30 minutes. On completion, the reaction mixture was concentrated in vacuo to give the title compound (22.0 mg, crude, 90% yield) as a white solid. LC-MS (ESI$^+$) m/z 562.3 (M+H)$^+$.

3-[3-Methyl-2-oxo-5-(piperazin-1-ylmethyl)benzimidazol-1-yl]piperidine-2,6-dione (Intermediate IE)

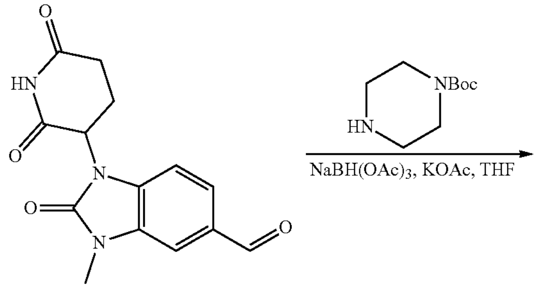

HF

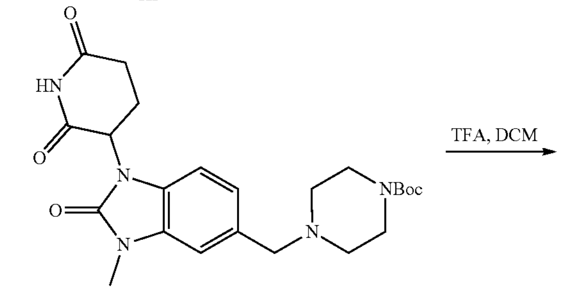

-continued

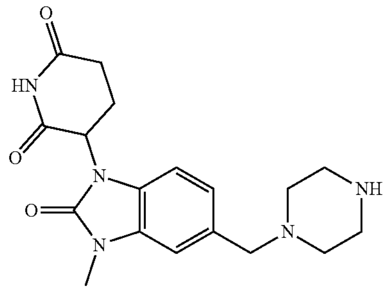

IE

Step 1—Tert-butyl 4-[[1-(2,6-dioxo-3-piperidyl)-3-methyl-2-oxo-benzimidazol-5-yl]methyl]piperazine-1-carboxylate To a solution of 1-(2,6-dioxo-3-piperidyl)-3-methyl-2-oxo-benzimidazole-5-carbaldehyde (100 mg, 348 umol, Intermediate FH), and tert-butyl piperazine-1-carboxylate (97.2 mg, 522 umol, CAS #143238-38-4) in THF (3.0 mL) was added KOAc (204 mg, 2.09 mmol) and NaBH(OAc)$_3$ (110 mg, 522 μmol). The mixture was stirred at 25° C. for 2 hours. On completion, the reaction mixture was concentrated in vacuo to give a residue. The crude product was purified by reversed-phase HPLC (0.1% FA condition) to give the title compound (120 mg, 67% yield) as a yellow solid. LC-MS (ESI$^+$) m/z 458.0 (M+H)$^+$.

Step 2—3-[3-Methyl-2-oxo-5-(piperazin-1-ylmethyl)benzimidazol-1-yl]piperidine-2,6-dione To a mixture of tert-butyl 4-[[1-(2,6-dioxo-3-piperidyl)-3-methyl-2-oxo-benzimidazol-5-yl] methyl]piperazine-1-carboxylate (80.0 mg, 174 umol) in DCM (0.5 mL) was added TFA (616 mg, 5.40 mmol) in one portion at 25° C. under $N_2$. The mixture was stirred at 25° C. for 2 hours. On completion, the reaction mixture was concentrated in vacuo to give the title compound (60 mg, 76.8% yield, TFA salt) as a yellow oil. LC-MS (ESI$^+$) m/z 358.2 (M+H)$^+$.

tert-butyl 4-[(4-iodo-N-methyl-anilino)methyl]piperidine-1-carboxylate (Intermediate IF)

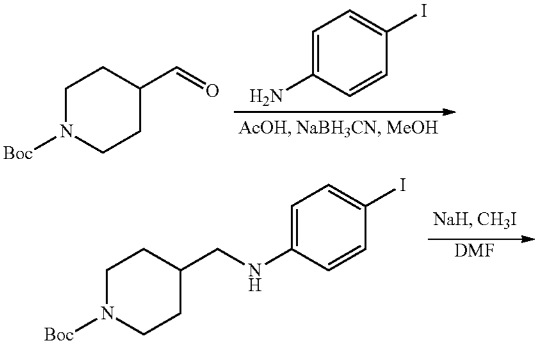

-continued

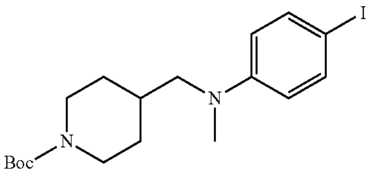

IF

Step 1—Tert-butyl 4-[(4-iodoanilino)methyl]piperidine-1-carboxylate

To a solution of 4-iodoaniline (3.91 g, 17.9 mmol, CAS #540-37-4) in MeOH (30 mL) was added tert-butyl 4-formylpiperidine-1-carboxylate (3.91 g, 17.9 mmol, CAS #137076-22-3) and AcOH (1.07 g, 17.9 mmol). The mixture was stirred at 25° C. for 3 hours. Then sodium cyanoborohydride (1.12 g, 17.9 mmol) was added in portions slowly at 0° C., and the reaction mixture was stirred at 25° C. for 13 hours. Many precipitates were emerged. On completion, the mixture was filtered to give the title compound (5.4 g, 62% yield) as a white solid. LC-MS ($ESI^+$) m/z 361.3 $(M+H-56)^+$. $^1H$ NMR (400 MHz, $CDCl_3$) δ 7.46-7.40 (m, 2H), 6.43 (d, J=8.4 Hz, 2H), 4.12 (s, 2H), 3.00 (d, J=6.4 Hz, 2H), 2.69 (t, J=12.4 Hz, 2H), 1.79-1.70 (m, 3H), 1.46 (s, 9H), 1.24-1.09 (m, 2H).

Step 2—Tert-butyl 4-[(4-iodoanilino)methyl]piperidine-1-carboxylate

To a solution of tert-butyl 4-[(4-iodoanilino)methyl]piperidine-1-carboxylate (1.80 g, 4.32 mmol) in DMF (20 mL) was added NaH (864 mg, 21.6 mmol, 60% dispersion in mineral oil) at 0° C. stirred for 30 minutes. Then MeI (3.07 g, 21.6 mmol was added and the mixture was stirred at 25° C. for 2 hours. On completion, the reaction mixture was concentrated in vacuo to give a residue. The residue was purified by column chromatography ($SiO_2$, Petroleum ether/Ethyl acetate=10/1 to 0/1) to give the title compound (1.86 g, 67% yield) as a white solid. LC-MS ($ESI^+$) m/z 430.9 $(M+H)^+$.

(1S)-1-(4-chlorophenyl)-7-isopropoxy-6-methoxy-2,4-dihydro-1H-isoquinolin-3-one (Intermediate IG) and (1R)-1-(4-chlorophenyl)-7-isopropoxy-6-methoxy-2,4-dihydro-1H-isoquinolin-3-one (Intermediate JO)

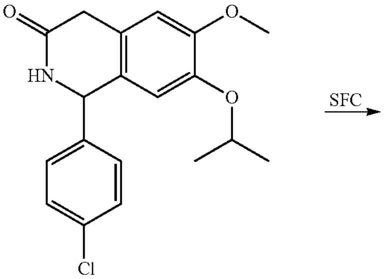

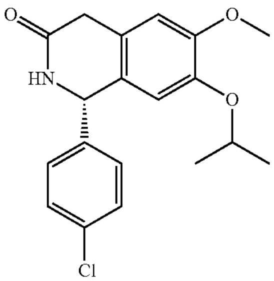

IG

+

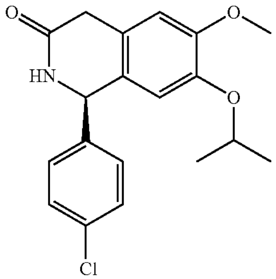

JO 1-(4-chlorophenyl)-7-isopropoxy-6-methoxy-2,4-dihydro-1H-isoquinolin-3-one (500 mg, 1.45 mmol, CAS #1313366-29-8) was purified by SFC to give (1R)-1-(4-chlorophenyl)-7-isopropoxy-6-methoxy-2,4-dihydro-1H-isoquinolin-3-one (180 mg, 36% yield) as yellow solid and (1S)-1-(4-chlorophenyl)-7-isopropoxy-6-methoxy-2,4-dihydro-1H-isoquinolin-3-one (230 mg, 45% yield) as yellow solid.

(1S)-1-(4-chlorophenyl)-7-isopropoxy-6-methoxy-2-[4-[methyl(4-piperidylmethyl)amino]phenyl]-1,4-dihydroisoquinolin-3-one (Intermediate IH)

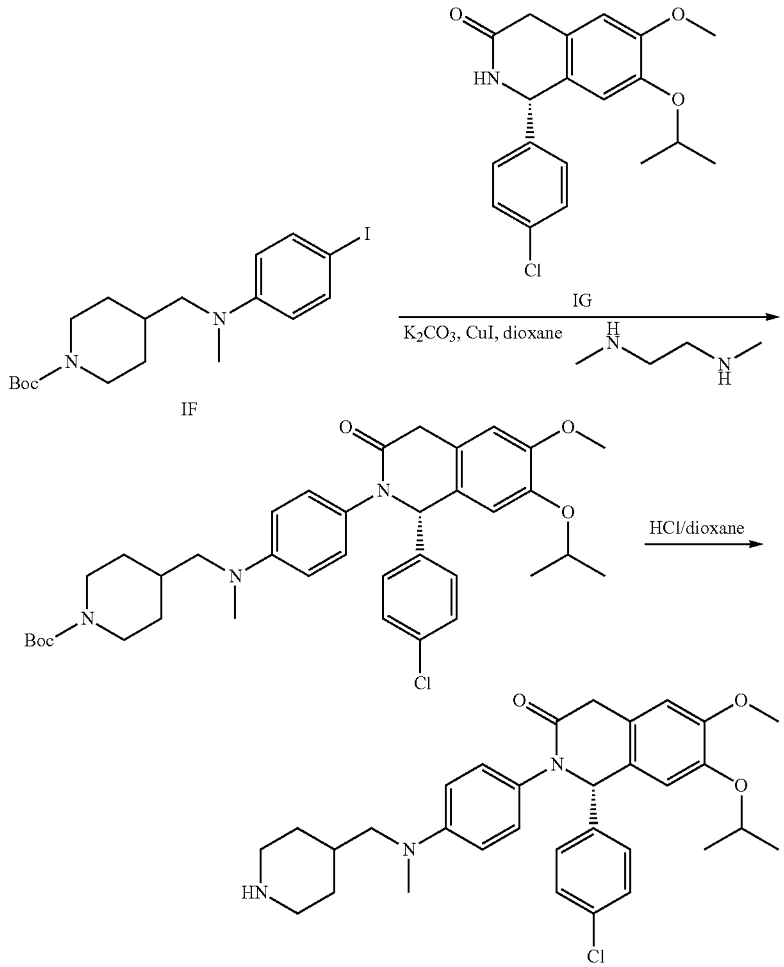

IG

IF

IH

Step 1—Tert-butyl 4-[[4-[(1S)-1-(4-chlorophenyl)-7-isopropoxy-6-methoxy-3-oxo-1,4-dihydroisoquinolin-2-yl]-N-methyl-anilino]methyl]piperidine-1-carboxylate To a solution of tert-butyl 4-[(4-iodo-N-methyl-anilino)methyl]piperidine-1-carboxylate (253 mg, 589 umol, Intermediate IF), (1S)-1-(4-chlorophenyl)-7-isopropoxy-6-methoxy-2,4-dihydro-1H-isoquinolin-3-one (170 mg, 491 umol, Intermediate IG) was added dioxane (5.0 mL). Then N,N'-dimethylethane-1,2-diamine (4.33 mg, 49.1 umol), potassium carbonate (135 mg, 983 umol) and CuI (4.68 mg, 24.5 umol) were added and the mixture was stirred at 120° C. for 16 hours. On completion, the reaction mixture was concentrated in vacuo to give a residue. The residue was purified or by prep-TLC ($SiO_2$, PE:EA=0:1) to give the title compound (120 mg, 34% yield) as a yellow solid. LC-MS (ESI$^+$) m/z 648.3 $(M+H)^+$.

Step 2—(IS)-1-(4-chlorophenyl)-7-isopropoxy-6-methoxy-2-[4-[methyl(4-piperidylmethyl)amino]phenyl]-1,4-dihydroisoquinolin-3-one To a mixture of tert-butyl 4-[[4-[(1S)-1-(4-chlorophenyl)-7-isopropoxy-6-methoxy-3-oxo-1,4-dihydroisoquinolin-2-yl]-N-methyl-anilino]methyl]piperidine-1-carboxylate (70.0 mg, 107 umol) in DCM (1.0 mL) was added HCl/dioxane (4 M, 1.0 mL) in one portion at 25° C. under $N_2$. The mixture was stirred at 25° C. for 2 hours. On completion, the reaction mixture was concentrated in vacuo to give the title compound (59.0 mg, 89% yield) as a yellow oil. $^1$H NMR (400 MHz, DMSO-d6) δ 7.42 (s, 4H), 7.10 (s, 1H), 6.97 (d, J=9.2 Hz, 2H), 6.90 (s, 1H), 6.64 (d, J=9.2 Hz, 2H), 6.01 (s, 1H), 4.51 (td, J=6.0, 12.0 Hz, 1H), 3.95 (d, J=19.6 Hz, 1H), 3.79 (s, 3H), 3.65 (s, 1H), 3.23-3.11 (m, 4H), 2.95 (s, 3H), 2.68-2.61 (m, 1H), 1.95-1.81 (m, 1H), 1.70 (d, J=12.4 Hz, 2H), 1.27 (dd, J=6.0, 19.6 Hz, 8H); LC-MS (ESI$^+$) m/z 548.5 $(M+H)^+$.

4-[1-(2,6-Dioxo-3-piperidyl)-3-methyl-2-oxo-benzimidazol-5-yl]butanoic acid (Intermediate II)

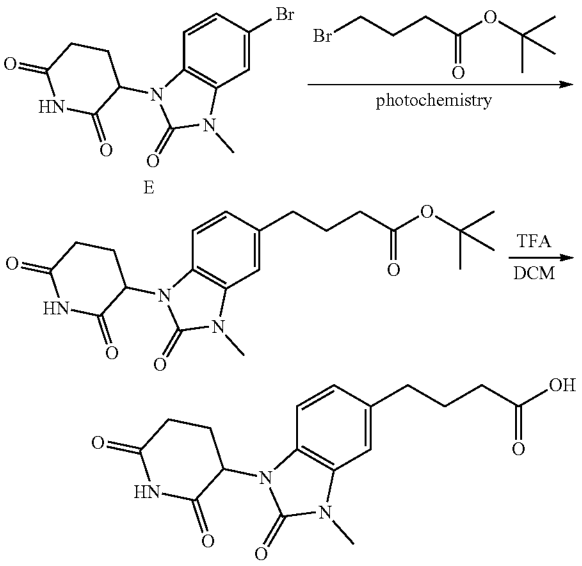

E, II

Step 1—Tert-butyl 4-[1-(2,6-dioxo-3-piperidyl)-3-methyl-2-oxo-benzimidazol-5-yl]butanoate To an 40 mL vial equipped with a stir bar was added 3-(5-bromo-3-methyl-2-oxo-benzimidazol-1-yl)piperidine-2,6-dione (500 mg, 1.48 mmol, Intermediate E), tert-butyl 4-bromobutanoate (428 mg, 1.92 mmol, CAS #1100611-91-1), bis[3,5-difluoro-2-[5-(trifluoromethyl)-2-pyridyl]phenyl]iridium(1+); 4-tert-butyl-2-(4-tert-butyl-2-pyridyl)pyridine; hexafluorophosphate (16.5 mg, 14.7 umol), $NiCl_2$·dtbbpy (2.94 mg, 7.39 umol), TTMSS (367 mg, 1.48 mmol), 2,6-dimethylpyridine (316 mg, 2.96 mmol) in DME (15 mL). The vial was sealed and placed under nitrogen. The reaction was stirred and irradiated with a 40 W blue LED lamp (3 cm away), with cooling water to keep the reaction temperature at 25° C. for 14 hours. On completion, the mixture was filtered and concentrated to give a residue. The residue was purified by column chromatography ($SiO_2$, DCM/Ethyl acetate=1:0 to 0:1) to give the title compound (1.00 g, 84% yield) as a yellow solid. $^1H$ NMR (400 MHz, DMSO-d6) δ 11.11-11.05 (m, 1H), 7.04-6.99 (m, 2H), 6.85 (d, J=8.0 Hz, 1H), 5.37-5.31 (m, 1H), 3.32 (s, 3H), 2.92-2.85 (m, 1H), 2.68 (s, 1H), 2.66-2.57 (m, 4H), 2.23-2.15 (m, 2H), 1.84-1.75 (m, 2H), 1.40 (s, 9H); LC-MS ($ESI^+$) m/z 402.1 $(M+H)^+$.

Step 2—4-[1-(2,6-Dioxo-3-piperidyl)-3-methyl-2-oxo-benzimidazol-5-yl]butanoic acid To a solution of tert-butyl 4-[1-(2,6-dioxo-3-piperidyl)-3-methyl-2-oxo-benzimidazol-5-yl]butanoate (35.0 mg, 87.1 umol) in DCM (2 mL) was added TFA (198 mg, 1.74 mmol). The mixture was stirred at 25° C. for 0.5 hour. On completion, the mixture was filtered and concentrated to give the title compound (40.0 mg, 99% yield, TFA salt) as a colorless oil; LC-MS ($ESI^+$) m/z 346.1 $(M+H)^+$.

2-[1-(2,6-Dioxo-3-piperidyl)-3-methyl-2-oxo-benzimidazol-5-yl]acetic acid (Intermediate IJ)

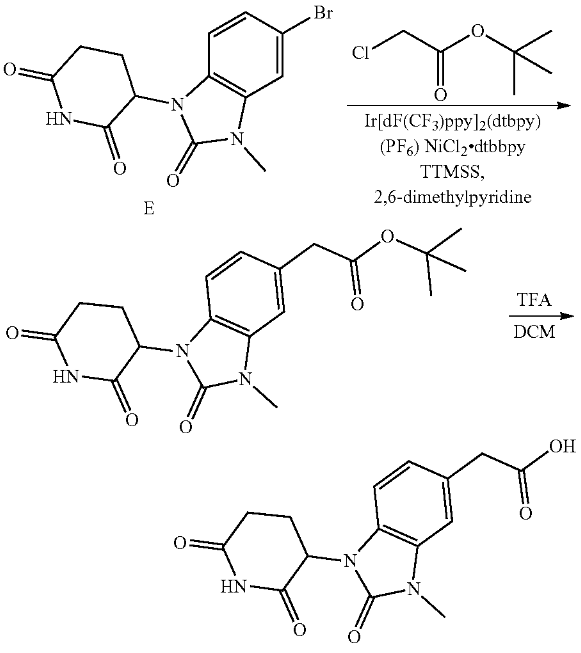

E, IJ

Step 1—Tert-butyl 2-[1-(2,6-dioxo-3-piperidyl)-3-methyl-2-oxo-benzimidazol-5-yl]acetate To an 40 mL vial equipped with a stir bar was added 3-(5-bromo-3-methyl-2-oxo-benzimidazol-1-yl)piperidine-2,6-dione (500 mg, 1.48 mmol, Intermediate E), tert-butyl 2-chloroacetate (334 mg, 2.22 mmol), $Ir[dF(CF_3)ppy]_2(dtbpy)(PF_6)$ (16.5 mg, 14.7 umol), $NiCl_2$·dtbbpy (29.4 mg, 73.9 μmol), TTMSS (551 mg, 2.22 mmol), and 2,6-dimethylpyridine (396 mg, 3.70 mmol) in DME (15 mL). The vial was sealed and placed under nitrogen. The reaction was stirred and irradiated with a 50 W blue LED lamp (3 cm away), with cooling water to keep the reaction temperature at 25° C. for 14 hours. On completion, the insoluble matter was removed by filtration and the filtrate was washed with brine and then dried over $Na_2SO_4$, filtered and concentrated in vacuo. The residue was purified by reverse phase column chromatography (water (0.1% FA)–ACN) to give the title compound (200 mg, 36% yield) as a white solid. $^1H$ NMR (400 MHz, CHLOROFORM-d) δ=8.09 (s, 1H), 7.01-6.95 (m, 2H), 6.76 (d, J=8.4 Hz, 1H), 5.21 (dd, J=5.2, 12.4 Hz, 1H), 3.57 (s, 2H), 3.44 (s, 3H), 2.99-2.68 (m, 3H), 2.28-2.19 (m, 1H), 1.46 (s, 9H). LC-MS ($ESI^+$) m/z 374.0 $(M+H)^+$.

Step 2—2-[1-(2,6-Dioxo-3-piperidyl)-3-methyl-2-oxo-benzimidazol-5-yl]acetic acid To a solution of tert-butyl 2-[1-(2,6-dioxo-3-piperidyl)-3-methyl-2-oxo-benzimidazol-5-yl]acetate (100 mg, 267 umol) in DCM (2.0 mL) was added TFA (0.4 mL). The mixture was stirred at 25° C. for 1 hour. On completion, the mixture was concentrated in vacuo to give the title compound (100 mg, 86% yield, TFA salt) as a brown oil. LC-MS ($ESI^+$) m/z 318.3 $(M+H)^+$.

3-[5-(7-Hydroxyheptyl)-3-methyl-2-oxo-benzimidazol-1-yl]piperidine-2,6-dione (Intermediate IK)

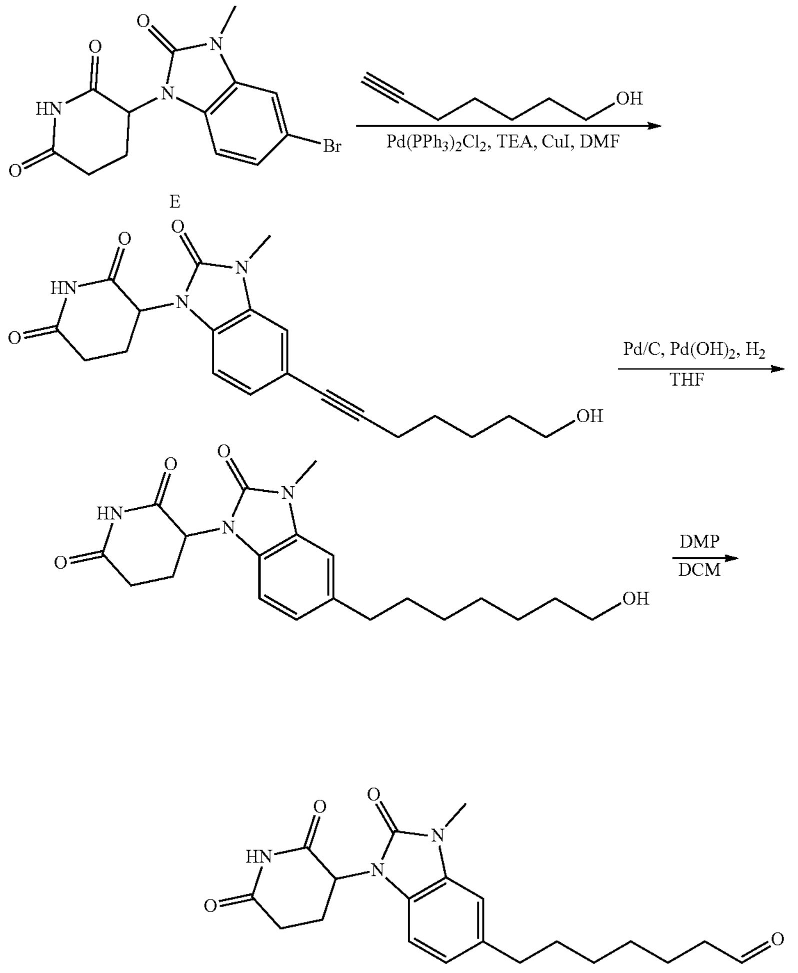

IK

Step 1—3-[5-(7-Hydroxyhept-1-ynyl)-3-methyl-2-oxo-benzimidazol-1-yl]piperidine-2,6-dione A mixture of 3-(5-bromo-3-methyl-2-oxo-benzimidazol-1-yl)piperidine-2,6-dione (1.00 g, 2.96 mmol, Intermediate E), hept-6-yn-1-ol (398 mg, 3.55 mmol), $Pd(PPh_3)_2Cl_2$ (103 mg, 147 umol), TEA (2.99 g, 29.5 mmol) and CuI (56.3 mg, 295 umol) in DMF (10 mL) was degassed and purged with $N_2$ three times, and then the mixture was stirred at 85° C. for 12 hours under $N_2$ atmosphere. On completion, the mixture was concentrated to give the residue. The residue was purified by reverse phase column chromatography (water (0.1% FA)-ACN) to give the title compound (600 mg, 54% yield) as a yellow oil. $^1H$ NMR (400 MHz, CHLOROFORM-d) δ=8.22-8.02 (m, 1H), 7.14 (d, J=8.0 Hz, 1H), 7.07 (s, 1H), 6.72 (d, J=8.0 Hz, 1H), 5.19 (dd, J=5.2, 12.8 Hz, 1H), 3.72-3.67 (m, 2H), 3.66-3.61 (m, 1H), 3.42 (s, 3H), 3.00-2.90 (m, 2H), 2.89-2.65 (m, 4H), 2.44 (t, J=6.8 Hz, 2H), 1.67-1.62 (m, 4H). LCMS ($ESI^+$) m/z 370.2 $(M+H)^+$.

Step 2—3-[5-(7-Hydroxyheptyl)-3-methyl-2-oxo-benzimidazol-1-yl] piperidine-2,6-dione To a solution of 3-[5-(7-hydroxyhept-1-ynyl)-3-methyl-2-oxo-benzimidazol-1-yl]piperidine-2,6-dione (200 mg, 378 umol) in THF (4 mL) was added Pd/C (90.2 mg, 37.9 umol, 10 wt %) and $Pd(OH)_2$ (26.6 mg, 37.9 umol, 20 wt %) under $N_2$ atmosphere. The suspension was degassed and purged with $H_2$ gas three times. The mixture was stirred under $H_2$ (15 psi) at 25° C. for 16 hours. On completion, the mixture was concentrated in vacuo to give the title compound (80.0 mg, 56% yield) as a colorless oil. LCMS ($ESI^+$) m/z 374.4 $(M+H)^+$.

Step 3—3-[5-(7-Hydroxyheptyl)-3-methyl-2-oxo-benzimidazol-1-yl]piperidine-2,6-dione To a solution of 3-[5-(7-hydroxyheptyl)-3-methyl-2-oxo-benzimidazol-1-yl]piperidine-2,6-dione (50.0 mg, 133 umol) in DCM (0.5 mL) was added DMP (85.1 mg, 200 umol. The mixture was stirred at 25° C. for 2 hours. On completion, the mixture was concentrated to give the residue. The residue was purified by reverse phase column chromatography (water (0.10% FA)-ACN) to give the title compound (40.0 mg, 80% yield) as a yellow oil. LCMS ($ESI^+$) m/z 372.2 $(M+H)^+$.

4-[[Chloro-(3-chloro-2-fluoro-phenyl)-oxo-dispiro[BLAH]carbonyl]amino]cyclohexanecarboxylic acid (Intermediate IL)

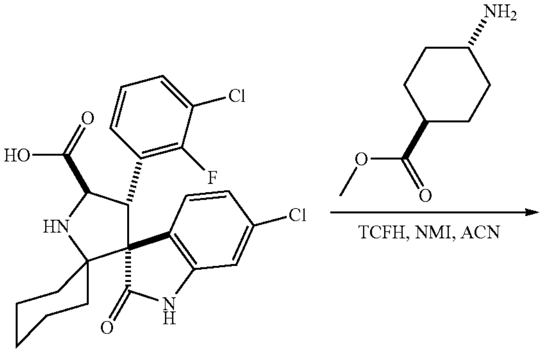

CI

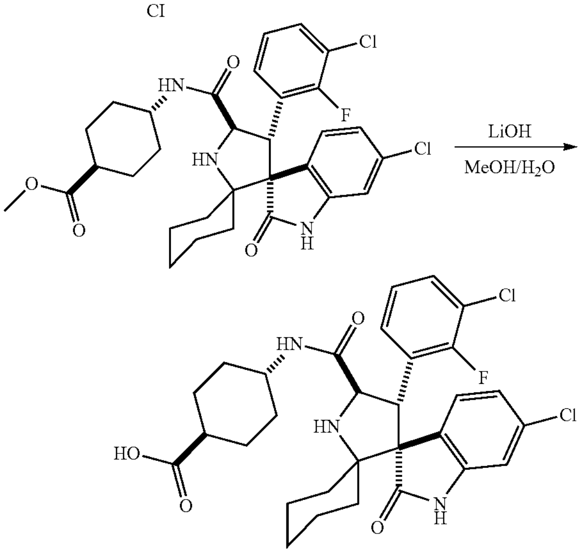

IL

Step 1—Methyl 4-[[chloro-(3-chloro-2-fluoro-phenyl)-oxo-dispiro[BLAH]carbonyl]amino]cyclohexanecarboxylate To a solution of methyl 4-aminocyclohexanecarboxylate (407 mg, 2.59 mmol, CAS #175867-59-1), chloro-(3-chloro-2-fluoro-phenyl)-oxo-dispiro[BLAH]carboxylic acid (1.00 g, 2.16 mmol, Intermediate CI) in ACN (20.0 mL) was added [chloro(dimethylamino)methylene]-dimethyl-ammonium; hexafluorophosphate (1.52 g, 5.40 mmol) and 1-methylimidazole (5.68 g, 69.1 mmol). The mixture was then stirred at 25° C. for 10 minutes. On completion, the reaction mixture was concentrated in vacuo to give a residue. The crude product was purified by reversed-phase HPLC (0.10% HCl condition) to give the title compound (800 mg, 49% yield) as a yellow solid. $^1$H NMR (400 MHz, DMSO-d6) δ 10.67 (s, 1H), 7.59 (t, J=7.2 Hz, 1H), 7.40 (d, J=8.0 Hz, 1H), 7.32 (t, J=7.2 Hz, 1H), 7.19 (s, 1H), 7.11 (t, J=8.0 Hz, 1H), 7.02 (d, J=8.4 Hz, 1H), 4.56 (d, J=9.2 Hz, 1H), 4.37 (d, J=9.0 Hz, 1H), 3.68 (s, 3H), 2.69 (s, 1H), 2.35-2.25 (m, 1H), 1.98-1.72 (m, 6H), 1.64-1.18 (m, 10H), 1.02-0.88 (m, 1H), 0.84-0.72 (m, 1H).

Step 2—4-[[Chloro-(3-chloro-2-fluoro-phenyl)-oxo-dispiro[BLAH]carbonyl]amino]cyclohexanecarboxylic acid To a solution of methyl 4-[[chloro-(3-chloro-2-fluoro-phenyl)-oxo-dispiro[BLAH]carbonyl]amino] cyclohexanecarboxylate (500 mg, 829 umol) in $H_2O$ (2.0 mL), MeOH (4.0 mL), THF (4.0 mL) was added LiOH—$H_2O$ (208 mg, 4.98 mmo) and NaOH (199 mg, 4.98 mmol). The mixture was stirred at 25° C. for 2 hours. On completion, the mixture was poured into water (20 mL) and the suspension was filtered. The filter cake was washed with ACN (5 mL×3), and dried in vacuo to give the title compound (200 mg, 41% yield) as a white solid. LC-MS (ESI$^+$) m/z 588.2 (M+H)$^+$.

3-[3-Methyl-2-oxo-5-(2-piperazin-1-ylethyl)benzimidazol-1-yl]piperidine-2,6-dione (Intermediate IM)

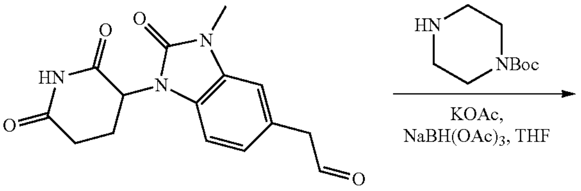

GR

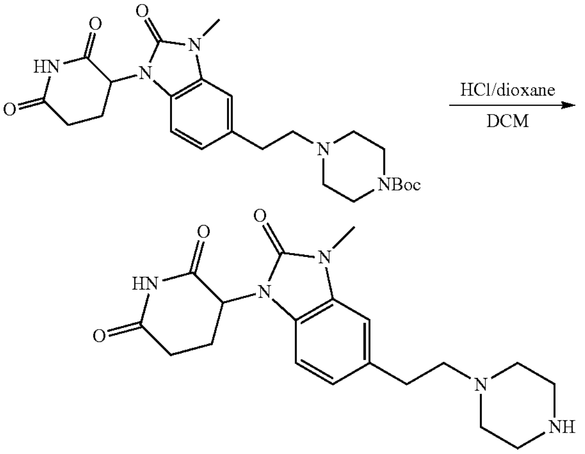

IM

Step 1—Tert-butyl 4-[2-[1-(2,6-dioxo-3-piperidyl)-3-methyl-2-oxo-benzimidazol-5-yl]ethyl] piperazine-1-carboxylate To a solution of 2-[1-(2,6-dioxo-3-piperidyl)-3-methyl-2-oxo-benzimidazol-5-yl]acetaldehyde (260 mg, 862 umol, Intermediate GR) and tert-butyl piperazine-1-carboxylate; hydrochloride (230 mg, 1.04 mmol, CAS #57260-71-6) in THF (20 mL) was added KOAc (508 mg, 5.18 mmol). Then NaBH(OAc)$_3$ (548 mg, 2.59 mmol) was added and the mixture was stirred at 25° C. for 1 hour. On completion, the reaction mixture was concentrated under reduced pressure to remove THF. The crude product was purified by reversed phase flash (0.1% FA condition) to give the title compound (200 mg, 39% yield) as a white solid. $^1$H NMR (400 MHz, DMSO-d$_6$) δ 11.08 (s, 1H), 7.07 (s, 1H), 7.01 (d, J=8.0 Hz, 1H), 6.90 (d, J=8.0 Hz, 1H), 5.34 (dd, J=5.2, 12.8 Hz, 1H), 4.49-3.44 (m, 3H), 3.34 (s, 3H), 2.95-2.85 (m, 1H), 2.80-2.74 (m, 2H), 2.73-2.62 (m, 4H), 2.40 (t, J=4.8 Hz, 5H), 2.05-1.95 (m, 1H), 1.40 (s, 9H). LC-MS ($ESI^+$) m/z 472.3 $(M+H)^+$.

Step 2—3-[3-Methyl-2-oxo-5-(2-piperazin-1-yl-ethyl)benzimidazol-1-yl]piperidine-2,6-dione To a solution of tert-butyl 4-[2-[1-(2,6-dioxo-3-piperidyl)-3-methyl-2-oxo-benzimidazol-5-yl]ethyl] piperazine-1-carboxylate (30.0 mg, 63.6 umol) in DCM (1.0 mL) was added HCl/dioxane (4 M, 1.0 mL). On completion, the mixture was stirred at 25° C. for 3 hours. The reaction mixture was concentrated under reduced pressure to remove HCl/dioxane and DCM and to give the title compound (26.0 mg, crude, HCl salt) was obtained as a white solid. LC-MS ($ESI^+$) m/z 372.1 $(M+H)^+$.

6-[1-(2,6-dioxo-3-piperidyl)-3-methyl-2-oxo-benzimidazol-5-yl]hexanoic acid (Intermediate IO)

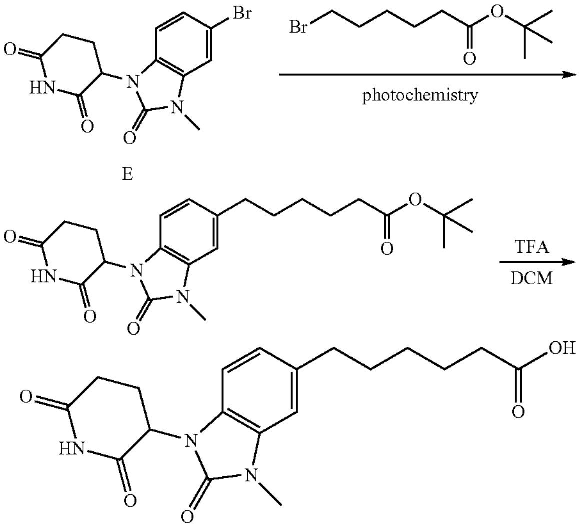

E

IO

Step 1—tert-butyl 6-[1-(2,6-dioxo-3-piperidyl)-3-methyl-2-oxo-benzimidazol-5-yl]hexanoate To an 40 mL vial equipped with a stir bar was added 3-(5-bromo-3-methyl-2-oxo-benzimidazol-1-yl)piperidine-2,6-dione (500 mg, 1.48 mmol, Intermediate E), tert-butyl 6-bromohexanoate (482 mg, 1.92 mmol, CAS #65868-63-5), Ir[dF(CF3)ppy]2(dtbpy)(PF6) (16.5 mg, 14.7 umol), $NiCl_2$·dtbbpy (2.94 mg, 7.39 umol), TTMSS (367 mg, 1.48 mmol), and 2,6-dimethylpyridine (316 mg, 2.96 mmol) in DME (15 mL). The vial was sealed and placed under nitrogen was added. The reaction was stirred and irradiated with a 50 W blue LED lamp (3 cm away), with cooling water to keep the reaction temperature at 25° C. for 14 hours. On completion, the reaction mixture was concentrated in vacuo to give a residue. The residue was purified by prep-HPLC (TFA condition) to give the title compound (280 mg, 40% yield) as a white solid. LC-MS ($ESI^+$) m/z 37402 $(M-56+H)^+$.

Step 2—6-[1-(2,6-dioxo-3-piperidyl)-3-methyl-2-oxo-benzimidazol-5-yl]hexanoic acid To a mixture of tert-butyl tert-butyl 6-[1-(2,6-dioxo-3-piperidyl)-3-methyl-2-oxo-benzimidazol-5-yl]hexanoate (100 mg, 232 umol) in DCM (2 mL) was added TFA (1.08 g, 9.45 mmol) in one portion at 25° C. under $N_2$. The mixture was stirred at 25° C. for 30 minutes. On completion, the reaction mixture was concentrated in vacuo to give the title compound (100 mg) as a white solid. LC-MS ($ESI^+$) m/z 374.1 $(M+H)^+$.

Tert-butyl 4-but-3-ynylpiperazine-1-carboxylate (Intermediate IP)

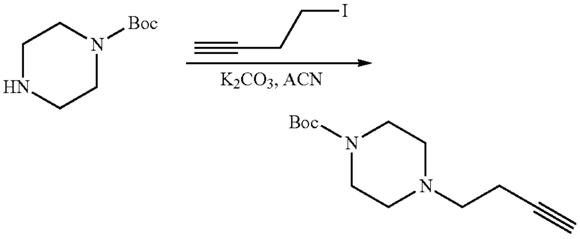

IP

A solution of 4-iodobut-1-yne (1.45 g, 8.05 mmol, CAS #43001-25-8) and tert-butyl piperazine-1-carboxylate (1.50 g, 8.05 mmol, CAS #143238-38-4) in ACN (10 mL), $K_2CO_3$ (3.34 g, 24.1 mmol) was added. The mixture was stirred at 25° C. for 2 hours. On completion, the reaction mixture was filtered and concentrated in vacuo. The residue was purified by column chromatography to give the title compound (1.00 g, 52.1% yield) as a yellow oil. $^1$H NMR (400 MHz, CHLOROFORM-d) δ=7.27 (s, 1H), 3.48-3.38 (m, 4H), 2.66-2.56 (m, 2H), 2.48-2.40 (m, 4H), 2.40-2.32 (m, 2H), 1.98 (t, J=2.6 Hz, 1H), 1.44 (s, 8H), 1.48-1.42 (m, 1H).

3-[3-Methyl-2-oxo-5-(4-piperazin-1-ylbut-1-ynyl) benzimidazol-1-yl]piperidine-2,6-dione (Intermediate IQ)

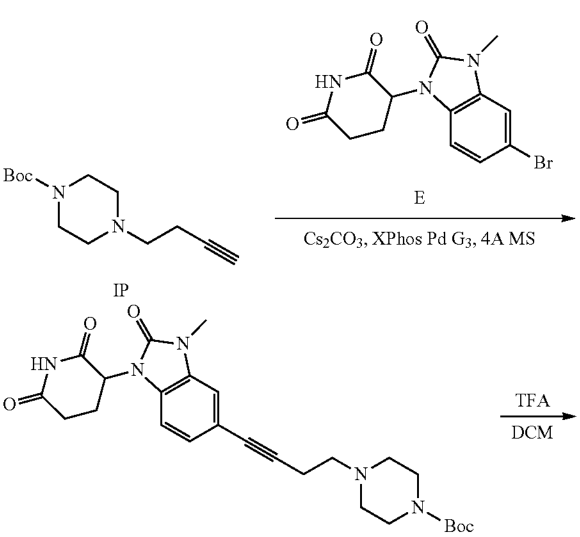

E

IP

-continued

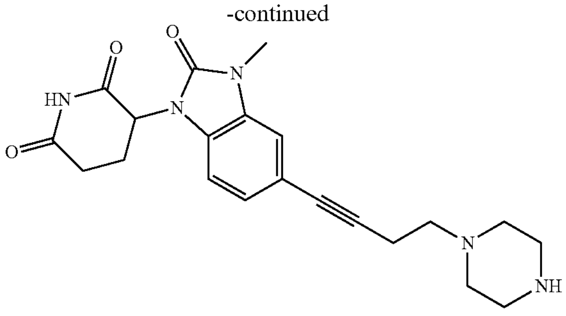

IQ

Step 1—Tert-butyl 4-[4-[1-(2,6-dioxo-3-piperidyl)-3-methyl-2-oxo-benzimidazol-5-yl]but-3-ynyl]piperazine-1-carboxylate To a mixture of 3-(5-bromo-3-methyl-2-oxo-benzimidazol-1-yl)piperidine-2,6-dione (300 mg, 887 umol, Intermediate E) and tert-butyl 4-but-3-ynylpiperazine-1-carboxylate (422 mg, 1.77 mmol, Intermediate IP) in DMF (10 mL) was added 4 Å molecular sieves (50.0 mg, 887 umol), $Cs_2CO_3$ (867 mg, 2.66 mmol), and XPhos Pd $G_3$ (75.0 mg, 88.7 umol). The mixture was stirred at 80° C. for 8 hours under $N_2$ atmosphere. On completion, the mixture was filtered and concentrated in vacuo. The crude product was purified by reversed-phase HPLC (0.1% FA condition) to give the title compound (200 mg, 45% yield) as a brown solid. LC-MS ($ESI^+$) m/z 496.5 $(M+H)^+$.

Step 2—3-[3-Methyl-2-oxo-5-(4-piperazin-1-ylbut-1-ynyl)benzimidazol-1-yl]piperidine-2,6-dione (TFA)

To a solution of tert-butyl 4-[4-[1-(2,6-dioxo-3-piperidyl)-3-methyl-2-oxo-benzimidazol-5-yl] but-3-ynyl]piperazine-1-carboxylate (50.0 mg, 100 umol) in DCM (2.0 mL) was added TFA (115 mg, 1.01 mmol). The mixture was stirred at 25° C. for 1 hour. On completion, the mixture was filtered and concentrated in vacuo to give the title compound (50.0 mg, 97% yield, TFA salt) as a yellow oil. LC-MS ($ESI^+$) m/z 396.4 $(M+H)^+$.

3-(3-Methyl-2-oxo-5-piperazin-1-yl-benzimidazol-1-yl)piperidine-2,6-dione (Intermediate IR)

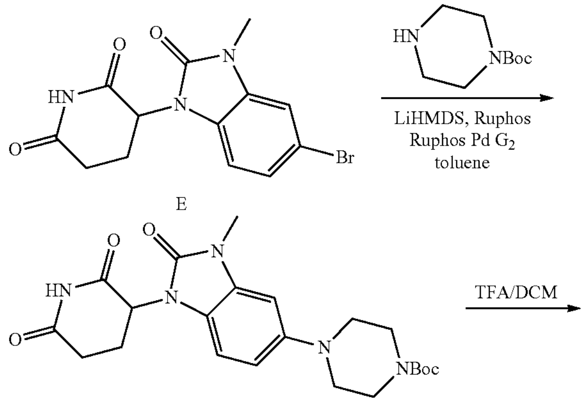

-continued

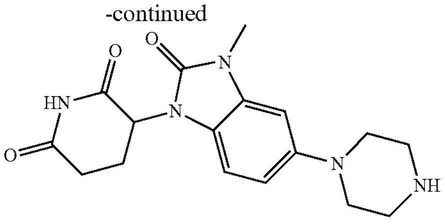

IR

Step 1—Tert-butyl 4-[1-(2,6-dioxo-3-piperidyl)-3-methyl-2-oxo-benzimidazol-5-yl]piperazine-1-carboxylate A mixture of 3-(5-bromo-3-methyl-2-oxo-benzimidazol-1-yl)piperidine-2,6-dione (2.00 g, 5.91 mmol, Intermediate E), tert-butyl piperazine-1-carboxylate (1.97 g, 8.87 mmol, CAS #143238-38-4), [2-(2-aminophenyl)phenyl]-chloro-palladium; dicyclohexyl-[2-(2,6-diisopropoxyphenyl)phenyl]phosphane (918 mg, 1.18 mmol), 4A MS (400 mg), RuPhos (551 mg, 1.18 mmol) and LiHMDS (1 M, 35 mL) in toluene (20 mL) was degassed and purged with $N_2$ for three times. Then the mixture was stirred at 100° C. for 16 hours under $N_2$ atmosphere. On completion, the mixture was acidified with FA to pH=3-5, filtered and the filtrate was concentrated in vacuo. The residue was purified by reverse phase column chromatography (water (0.1% FA)-ACN) to give the title compound (440 mg, 16% yield) as a brown solid. $^1$H NMR (400 MHz, CHLOROFORM-d) δ=8.07 (s, 1H), 6.76-6.57 (m, 3H), 5.20 (dd, J=5.2, 12.8 Hz, 1H), 3.63 (s, 4H), 3.42 (s, 3H), 3.09 (s, 4H), 2.99-2.63 (m, 4H), 1.50 (s, 9H). LC-MS ($ESI^+$) m/z 444.3 $(M+H)^+$.

Step 2—3-(3-Methyl-2-oxo-5-piperazin-1-yl-benzimidazol-1-yl)piperidine-2,6-dione To a solution of tert-butyl 4-[1-(2,6-dioxo-3-piperidyl)-3-methyl-2-oxo-benzimidazol-5-yl]piperazine-1-carboxylate (100 mg, 225 umol) in DCM (1.0 mL) was added TFA (0.2 mL). The mixture was stirred at 25° C. for 1 hour. On completion, the mixture was concentrated in vacuo to give the tilte compound (100 mg, 218 umol, 97% yield, TFA salt) as a brown oil. LC-MS ($ESI^+$) m/z 344.1 $(M+H)^+$.

3-(4-bromo-5-methoxy-3-methyl-2-oxo-benzimidazol-1-yl)piperidine-2,6-dione (Intermediate IS)

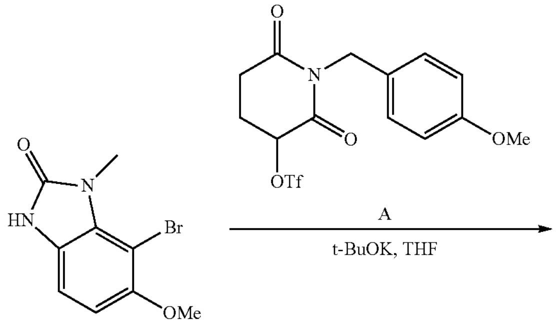

-continued

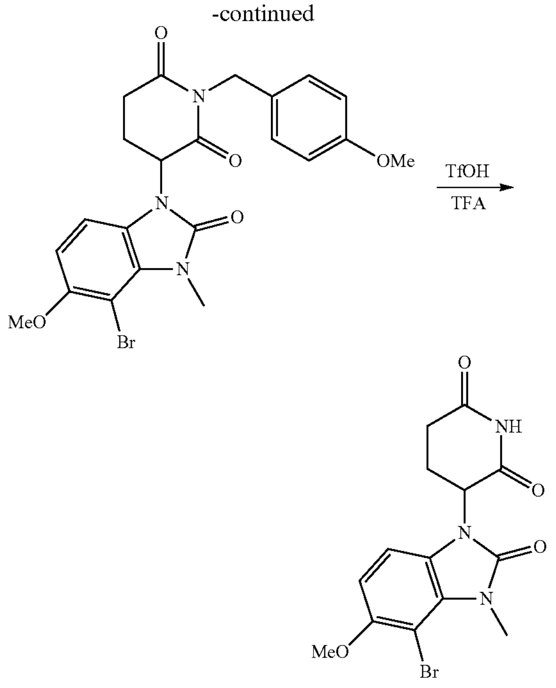

IS

Step 1—3-(4-Bromo-5-methoxy-3-methyl-2-oxo-benzimidazol-1-yl)-1-[(4-methoxyphenyl)methyl]piperidine-2,6-dione To a mixture of [1-[(4-methoxyphenyl)methyl]-2,6-dioxo-3-piperidyl]trifluoromethanesulfonate (2.22 g, 5.83 mmol, Intermediate A) and t-BuOK (654 mg, 5.83 mmol) in THF (20 mL) was added 4-bromo-5-methoxy-3-methyl-1H-benzimidazol-2-one (1.00 g, 3.89 mmol, synthesized via Steps 1-4 of Intermediate HG) at 0° C. Then the mixture was warmed to rt and stirred for 12 hours. On completion, the mixture was poured into the water (30 mL) and extracted with ethyl acetate (2×20 mL). The combined organic phase was washed with brine (2×30 mL), dried with anhydrous $Na_2SO_4$, filtered and concentrated in vacuo to give the title compound (1.50 g, 78% yield) as a brown solid. $^1$H NMR (400 MHz, $CDCl_3$) δ 7.39-7.33 (m, 2H), 6.85-6.82 (m, 2H), 6.50 (d, J=8.4 Hz, 1H), 6.32 (d, J=8.4 Hz, 1H), 5.19 (dd, J=5.6, 13.2 Hz, 1H), 4.96 (s, 2H), 3.86 (s, 3H), 3.80 (s, 6H), 3.05-2.96 (m, 1H), 2.88-2.76 (m, 1H), 2.58 (dd, J=4.4, 13.2 Hz, 1H), 2.19-2.15 (m, 1H).

Step 2—3-(4-bromo-5-methoxy-3-methyl-2-oxo-benzimidazol-1-yl)piperidine-2,6-dione To a solution of 3-(4-bromo-5-methoxy-3-methyl-2-oxo-benzimidazol-1-yl)-1-[(4-methoxyphenyl)methyl]piperidine-2,6-dione (3.00 g, 6.14 mmol) in TFA (36 mL) was added TfOH (1.8 mL). The mixture was then stirred at 65° C. for 3 hours. On completion, the mixture was concentrated to give a residue, then the residue was adjusted pH to 6-7 by TEA at 0° C. The mixture was concentrated to give a residue. The crude product was purified by reversed-phase HPLC (0.1% FA condition) to give the title (600 mg, 26% yield) as a gray solid. H NMR (400 MHz, DMSO-$d_6$) δ=11.11 (s, 1H), 7.97-7.89 (m, 1H), 7.14-7.06 (m, 1H), 7.05-7.01 (m, 1H), 6.82 (d, J=8.6 Hz, 1H), 5.45-5.26 (m, 1H), 3.64 (s, 4H), 2.97-2.81 (m, 2H), 2.39-2.29 (m, 1H), 2.06-1.97 (m, 1H). LC-MS ($ESI^+$) m/z 370.0 $(M+H)^+$.

5-[1-(2,6-dioxo-3-piperidyl)-5-methoxy-3-methyl-2-oxo-benzimidazol-4-yl]pent-4-ynal (Intermediate IT)

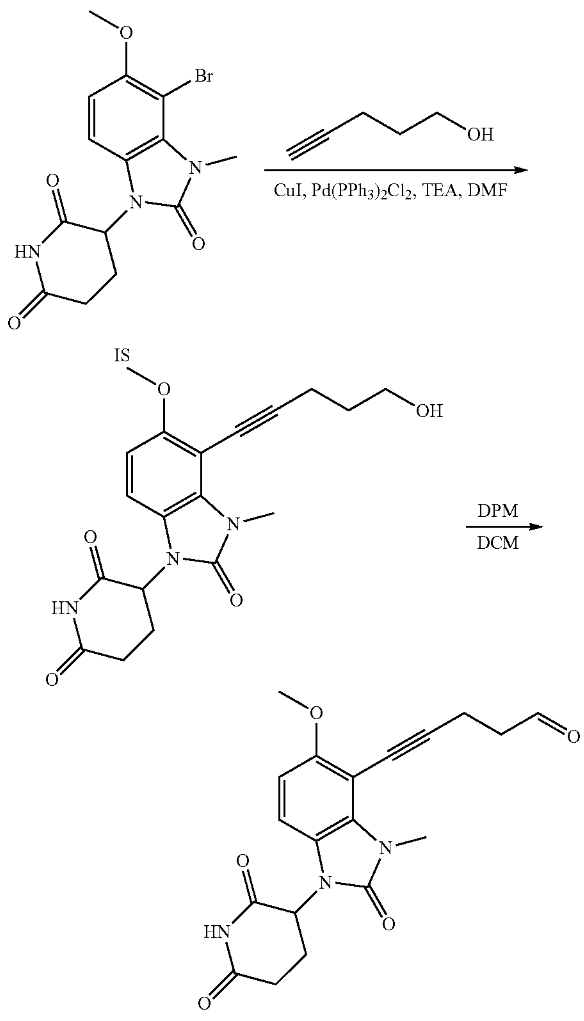

IS

IT

Step 1—3-[4-(5-hydroxypent-1-ynyl)-5-methoxy-3-methyl-2-oxo-benzimidazol-1-yl]piperidine-2,6-dione A mixture of 3-(4-bromo-5-methoxy-3-methyl-2-oxo-benzimidazol-1-yl)piperidine-2,6-dione (500 mg, 1.36 mmol, Intermediate IS), pent-4-yn-1-ol (342.69 mg, 4.07 mmol), $Cs_2CO_3$ (1.33 g, 4.07 mmol,), and XPhos Pd G3 (115 mg, 136 umol) in DMF (5 mL) was degassed and purged with $N_2$ three times. Then the mixture was stirred at 80° C. for 12 hours under $N_2$ atmosphere. The mixture was filtered and concentrated to give a residue. The crude product was purified by reversed-phase HPLC (0.1% FA condition) to give the title compound (200 mg, 35% yield, FA salt) as a yellow solid. LC-MS ($ESI^+$) m/z 372.2 $(M+H)^+$.

Step 2—5-[1-(2,6-dioxo-3-piperidyl)-5-methoxy-3-methyl-2-oxo-benzimidazol-4-yl]pent-4-ynal To a solution of 3-[4-(5-hydroxypent-1-ynyl)-5-methoxy-3-methyl-2-oxo-benzimidazol-1-yl]piperi dine-2,6-dione (180 mg, 484 umol) in DCM (2 mL) was added DMP (308 mg, 727 umol. The mixture was stirred at 25° C. for 0.5 hour. On completion, the mixture was quenched with hypo solution (5 mL) and saturated sodium bicarbonate solution, then extracted with DCM (10 mL). The organic layer was dried over $Na_2SO_4$, concentrated in vacuo to afford the title compound (140 mg, 78% yield) as a yellow solid. LC-MS ($ESI^+$) m/z 370.2 $(M+H)^+$.

4-[[chloro-(2-chloro-3-fluoro-4-pyridyl)-dimethyl-oxo-dispiro[BLAH]carbonyl]amino]cyclohexanecarboxylic acid (Intermediate IU)

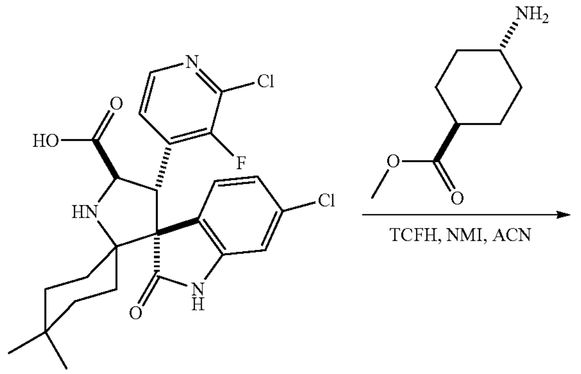

GI

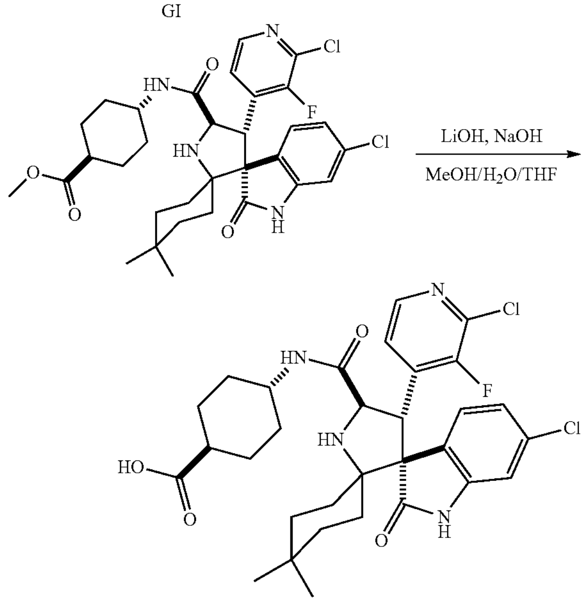

IU

Step 1—methyl 4-[[chloro-(2-chloro-3-fluoro-4-pyridyl)-dimethyl-oxo-dispiro[BLAH]carbonyl]amino]cyclohexanecarboxylate To a solution of chloro-(2-chloro-3-fluoro-4-pyridyl)-dimethyl-oxo-dispiro[BLAH]carboxylic acid (1.00 g, 2.03 mmol, Intermediate GI) and methyl 4-aminocyclohexanecarboxylate (319 mg, 2.03 mmol, CAS #3685-25-4) in ACN (15 mL) was added [chloro(dimethylamino)methylene]-dimethyl-ammonium hexafluorophosphate (1.42 g, 5.08 mmol) and 1-methylimidazole (5.34 g, 64.9 mmol) at 25° C. The reaction solution was stirred at 25° C. for 30 minutes. On completion, the reaction mixture was concentrated in vacuo to give a residue. The residue was purified by prep-HPLC (FA condition) to give the title compound (500 mg, 36% yield) as a white solid. LC-MS ($ESI^+$) m/z 631.4 $(M+H)^+$.

Step 2—4-[[chloro-(2-chloro-3-fluoro-4-pyridyl)-dimethyl-oxo-dispiro[BLAH]carbonyl]amino]cyclohexanecarboxylic acid Methyl 4-[[chloro-(2-chloro-3-fluoro-4-pyridyl)-dimethyl-oxo-dispiro[BLAH]carbonyl]amino]cyclohexanecarboxylate (100 mg, 158 umol) was dissolved in MeOH (0.4 mL) then LiOH—$H_2O$ (39.8 mg, 950 umol), NaOH (38.00 mg, 950 umol) and THF (0.4 mL) were added. Then $H_2O$ (0.2 mL) was added and stirred for 30 minutes at 25° C. On completion, water (5 mL) was added and the reaction was slowly neutralized with 2M HCl aqueous and the suspension was stirred for 15 minutes. The resulting precipitate was filtered, washed with water, then dried to give the title compound (50.0 mg, 45% yield) as a yellow solid. LC-MS ($ESI^+$) m/z 617.4 $(M+H)^+$.

Chloro-(2-chloro-3-fluoro-4-pyridyl)-N-(4-formylcyclohexyl)-dimethyl-oxo-dispiro[BLAH]carboxamide (Intermediate IV)

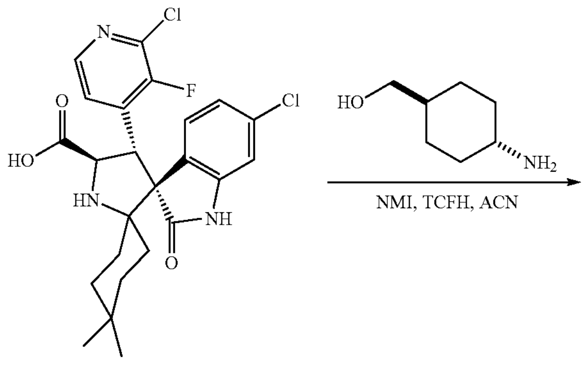

GI

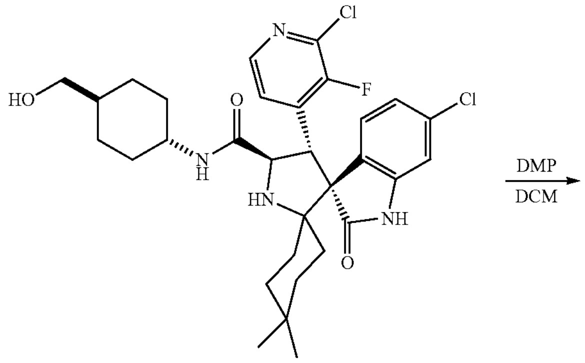

-continued

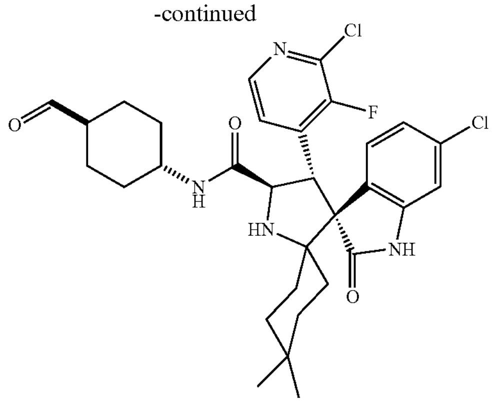

IV

Step 1-chloro-(2-chloro-3-fluoro-4-pyridyl)-N-[4-(hydroxymethyl)cyclohexyl]-dimethyl-oxo-dispiro[BLAH]carboxamide To a solution of chloro-(2-chloro-3-fluoro-4-pyridyl)-dimethyl-oxo-dispiro[BLAH]carboxylic acid (3.00 g, 6.09 mmol, Intermediate GI) and (4-aminocyclohexyl)methanol (787 mg, 6.09 mmol) in ACN (40 mL) was added 1-methylimidazole (1.50 g, 18.3 mmol) and [chloro(dimethylamino) methylene]-dimethyl-ammonium; hexafluorophosphate (3.42 g, 12.2 mmol). The mixture was stirred at 25° C. for 1 hour. The mixture was quenched with water (10 mL), and extracted with ethyl acelate (20 mL). The organic layer was dried over $Na_2SO_4$, concentrated in vacuo to afford crude. The residue was purified by column chromatography ($SiO_2$, Petroleum ether/Ethyl acetate=1:0 to 0:1) to give the title compound (1.70 g, 46% yield) as a yellow oil. $^1H$ NMR (400 MHz, DMSO-$d_6$) δ 10.60 (s, 1H), 8.16 (d, J=5.2 Hz, 1H), 7.72 (d, J=8.4 Hz, 1H), 7.64 (t, J=5.2 Hz, 1H), 7.52 (dd, J=2.0, 8.4 Hz, 1H), 7.04 (dd, J=2.0, 8.0 Hz, 1H), 6.72 (d, J=2.0 Hz, 1H), 4.56 (d, J=9.0 Hz, 1H), 4.48-4.40 (m, 1H), 4.36 (t, J=5.2 Hz, 1H), 3.52 (d, J=10.4 Hz, 1H), 3.48-3.40 (m, 1H), 3.20 (t, J=5.8 Hz, 2H), 1.88-1.64 (m, 8H), 1.60-1.52 (m, 1H), 1.52-1.40 (m, 2H), 1.36-1.28 (m, 2H), 1.24 (d, J=10.4 Hz, 2H), 1.16-1.08 (m, 2H), 0.88 (s, 3H), 0.60 (s, 3H); LC-MS ($ESI^+$) m/z 603.2 $(M+H)^+$.

Step 2-chloro-(2-chloro-3-fluoro-4-pyridyl)-N-(4-formylcyclohexyl)-dimethyl-oxo-dispiro[BLAH]carboxamide To a solution of chloro-(2-chloro-3-fluoro-4-pyridyl)-N-[4-(hydroxymethyl)cyclohexyl]-dimethyl-oxo-dispiro[BLAH]carboxamide (1.20 g, 1.99 mmol) in DCM (10 mL) was added DMP (1.26 g, 2.98 mmol) at 0° C. The mixture was stirred at 25° C. for 0.5 hour. The mixture was quenched with saturated sodium thiosulfate aqueous (10 mL) and sodium bicarbonate aqueous, then extracted with DCM (20 mL). The organic layer was dried over $Na_2SO_4$, and concentrated in vacuo to afford crude. The residue was purified by column chromatography ($SiO_2$, Petroleum ether/Ethyl acetate=1:0 to 1:4) to give the title compound (600 mg, 997 umol, 50% yield) as a yellow solid. $^1H$ NMR (400 MHz, DMSO-$d_6$) δ 10.60 (s, 1H), 9.56 (s, 1H), 8.18 (d, J=5.2 Hz, 1H), 7.80 (d, J=8.4 Hz, 1H), 7.64 (t, J=5.0 Hz, 1H), 7.48 (d, J=6.9 Hz, 1H), 7.04 (dd, J=1.6, 8.4 Hz, 1H), 6.72 (d, J=1.6 Hz, 1H), 4.60-4.52 (m, 1H), 4.48-4.40 (m, 1H), 3.60-3.44 (m, 2H), 1.88-1.68 (m, 5H), 1.60-1.40 (m, 4H), 1.36-1.08 (m, 8H), 0.88 (s, 3H), 0.60 (s, 3H); LC-MS ($ESI^+$) m/z 601.4 $(M+H)^+$.

1-[8-(4-Piperazin-1-ylbut-1-ynyl)imidazo[1,2-a]pyridin-3-yl]hexahydropyrimidine-2,4-dione (Intermediate IW)

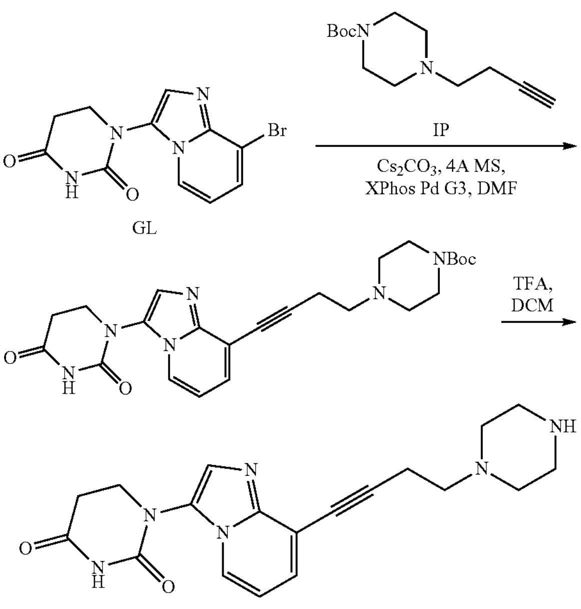

IW

Step 1—Tert-butyl 4-[4-[3-(2,4-dioxohexahydropyrimidin-1-yl)imidazo[1,2-a]pyridin-8-yl]but-3-ynyl]piperazine-1-carboxylate To a solution of 1-(8-bromoimidazo[1,2-a]pyridin-3-yl)hexahydropyrimidine-2,4-dione (140 mg, 452 umol, Intermediate GL) and tert-butyl 4-but-3-ynylpiperazine-1-carboxylate (323 mg, 1.36 mmol, Intermediate IP) in DMF (6 mL) was added 4 Å molecular sieves (50 mg), [2-(2-aminophenyl)phenyl] palladium (1+); dicyclohexyl-[2-(2,4,6-triisopropylphenyl)phenyl]phosphane; methanesulfonate (38.3 mg, 45.2 umol) and $Cs_2CO_3$ (442 mg, 1.36 mmol). The mixture was stirred at 80° C. for 16 hours. On completion, the mixture was quenched with water (20 mL) and extracted with DCM (25 mL×3). The combined organic phase was dried over anhydrous sodium sulfate, filtered and concentrated to give a residue. The residue was purified by reversed-phase HPLC (0.1% TFA condition) to give the title compound (200 mg, 94% yield) as a colorless oil. $^1H$ NMR (400 MHz, DMSO-d6) δ 10.73 (s, 1H), 8.47 (d, J=6.8 Hz, 1H), 7.77 (s, 1H), 7.59 (d, J=7.2 Hz, 1H), 7.14-7.02 (m, 1H), 3.85-3.78 (m, 2H), 3.49-3.44 (m, 2H), 3.32-3.26 (m, 4H), 3.13-3.10 (m, 2H), 3.10-3.05 (m, 2H), 2.88-2.80 (m, 1H), 2.72-2.62 (m, 3H), 1.41 (s, 9H); LC-MS ($ESI^+$) m/z 467.3 $(M+H)^+$.

Step 2—1-[8-(4-Piperazin-1-ylbut-1-ynyl)imidazo[1,2-a]pyridin-3-yl]hexahydropyrimidine-2,4-dione To a solution of tert-butyl 4-[4-[3-(2,4-dioxohexahydropyrimidin-1-yl)imidazo[1,2-a]pyridin-8-yl] but-3-ynyl]piperazine-1-carboxylate (47.0 mg, 100 umol) in DCM (3 mL) was added TFA (114 mg, 1.01 mmol). The mixture was stirred at 25° C. for 0.5 hour. On completion, the mixture was filtered and concentrated to give the title compound (48 mg, 99% yield, TFA salt) as a yellow oil. LC-MS (ESI$^+$) m/z 367.1 (M+H)$^+$.

5-[3-(2,4-Dioxohexahydropyrimidin-1-yl)imidazo[1,2-a]pyridin-8-yl]pent-4-ynal (Intermediate IX)

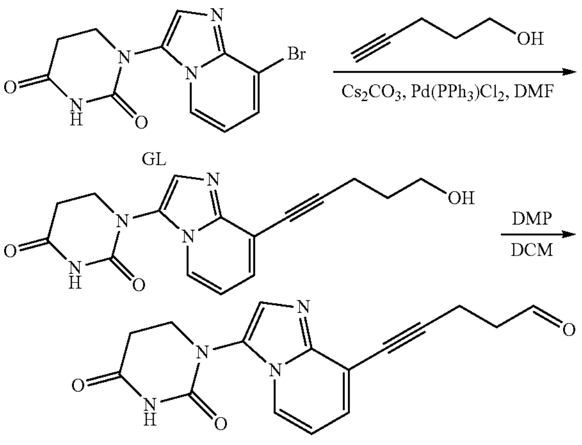

GL

IX

Step 1—1-[8-(5-Hydroxypent-1-ynyl)imidazo[1,2-a]pyridin-3-yl]hexahydropyrimidine-2,4-dione To a mixture of 1-(8-bromoimidazo[1,2-a]pyridin-3-yl)hexahydropyrimidine-2,4-dione (500 mg, 1.62 mmol, Intermediate GL), CuI (15.4 mg, 80.9 umol), and $Pd(PPh_3)_2Cl_2$ (114 mg, 162 umol) in DMF (2.0 mL) was added pent-4-yn-1-ol (544 mg, 6.47 mmol, CAS #5390-04-5) and TEA (819 mg, 8.09 mmol) under $N_2$. The mixture was stirred at 100° C. for 5 hours. On completion, the reaction mixture was concentrated under reduced pressure to give the residue. The residue was purified by column chromatography ($SiO_2$, DCM/I—PrOH=15/1 to 10/1) to give the title compound (150 mg, 30% yield) as a yellow solid. LC-MS (ESI$^+$) m/z 309.0 (M+H)$^+$. $^1$H NMR (400 MHz, DMSO-$d_6$) δ 11.08 (s, 1H), 7.07 (s, 1H), 7.01 (d, J=8.0 Hz, 1H), 6.90 (d, J=8.0 Hz, 1H), 5.34 (dd, J=5.4, 12.7 Hz, 1H), 3.32 (s, 3H), 2.97-2.84 (m, 1H), 2.82-2.73 (m, 2H), 2.73-2.59 (m, 2H), 2.55 (m, 5H), 2.40 (m, 5H), 2.05-1.95 (m, 1H), 1.40 (s, 9H).

Step 2—5-[3-(2,4-Dioxohexahydropyrimidin-1-yl)imidazo[1,2-a]pyridin-8-yl]pent-4-ynal A mixture of 1-[8-(5-hydroxypent-1-ynyl)imidazo[1,2-a]pyridin-3-yl]hexahydropyrimidine-2,4-dione (60.0 mg, 192 umol), and DMP (122 mg, 288 umol) in DCM (2.0 mL) was degassed and purged with $N_2$ three times, and then the mixture was stirred at 25° C. for 2 hours under $N_2$ atmosphere. On completion, the reaction mixture was quenched by adding saturated aqueous $Na_2S_2O_3$ solution (2.0 mL). The aqueous layer was extracted with DCM (2.0 mL×2). The organic layer was washed with saturated aqueous $NaHCO_3$ (5 mL×3), the organic layer was separated, dried over anhydrous $Na_2SO_4$, filtered and concentrated under reduced pressure to give the title product (60.0 mg) as a yellow solid. LC-MS (ESI$^+$) m/z 311.1 (M+H)$^+$.

N-[4-(aminomethyl)cyclohexyl]-3-(3-chloro-2-fluoro-phenyl)-4-(4-chloro-2-fluoro-phenyl)-4-cyano-5-(2,2-dimethylpropyl)pyrrolidine-2-carboxamide (Intermediate IY)

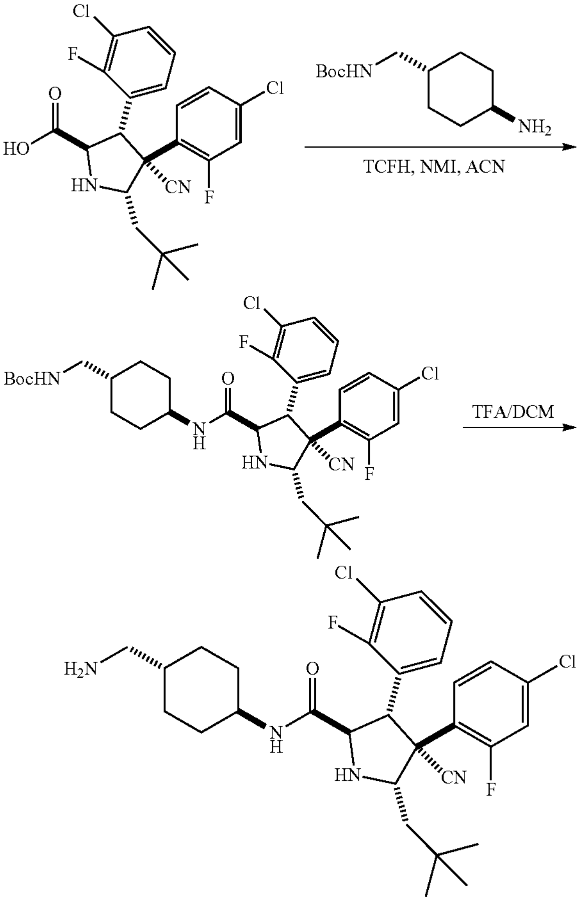

IY

Step 1—Tert-butyl N-[[4-[[3-(3-chloro-2-fluoro-phenyl)-4-(4-chloro-2-fluoro-phenyl)-4-cyano-5-(2,2-dimethylpropyl)pyrrolidine-2-carbonyl]amino]cyclohexyl]methyl]carbamate To a solution of 3-(3-chloro-2-fluoro-phenyl)-4-(4-chloro-2-fluoro-phenyl)-4-cyano-5-(2,2-dimethylpropyl)pyrrolidine-2-carboxylic acid (400 mg, 855 umol, Intermediate GF), tert-butylN-[(4-aminocyclohexyl)methyl]carbamate (293 mg, 1.28 mmol, CAS #192323-07-2) in DMF (5 mL) was added HATU (423 mg, 1.11 mmol) and DIEA (553 mg, 4.28 mmol). The mixture was stirred at 25° C. for 5 minutes. On completion, the reaction mixture was concentrated in vacuo to give a residue. The crude product was purified by reversed-phase HPLC (0.1% FA condition) to give title compound (400 mg, 66% yield) as a white solid. LC-MS (ESI$^+$) m/z 677.5 (M+H)$^+$.

Step 2—N-[4-(aminomethyl)cyclohexyl]-3-(3-chloro-2-fluoro-phenyl)-4-(4-chloro-2-fluoro-phenyl)-4-cyano-5-(2,2-dimethylpropyl)pyrrolidine-2-carboxamide To a mixture of tert-butyl N-[[4-[[3-(3-chloro-2-fluoro-phenyl)-4-(4-chloro-2-fluoro-phenyl)-4-cyano-5-(2,2-dimethylpropyl)pyrrolidine-2-carbonyl]amino]cyclohexyl]methyl]carbamate (50.0 mg, 73.7 umol) in DCM (0.5 mL) was added TFA (0.1 ml) in one portion at 25° C. under $N_2$. The mixture was stirred at 25° C. for 2 hours. On completion, the reaction mixture was concentrated in vacuo to give a Compound (40.0 mg, 84% yield, TFA salt) was obtained as a white solid. LC-MS ($ESI^+$) m/z 577.5 $(M+H)^+$.

5-[3-(2,4-dioxohexahydropyrimidin-1-yl)imidazo[1,2-a]pyridin-7-yl]pent-4-ynal (Intermediate IZ)

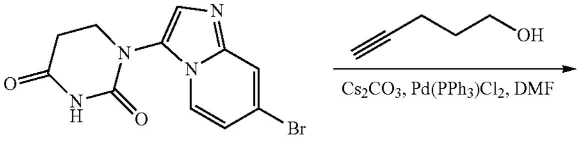

ER

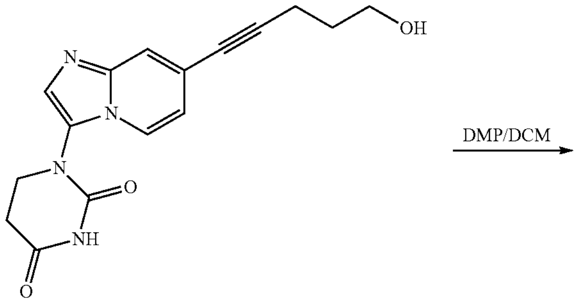

-continued

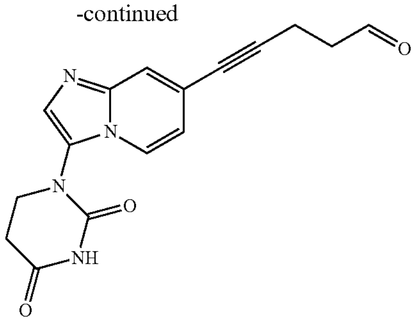

IZ

Step 1—1-[7-(5-Hydroxypent-1-ynyl)imidazo[1,2-a]pyridin-3-yl]hexahydropyrimidine-2,4-dione A mixture of 1-(7-bromoimidazo[1,2-a]pyridin-3-yl)hexahydropyrimidine-2,4-dione (1.20 g, 3.88 mmol, Intermediate ER), pent-4-yn-1-ol (1.31 g, 15.5 mmol), CuI (36.9 mg, 194 umol), TEA (1.96 g, 19.4 mmol) and $Pd(PPh_3)_2Cl_2$ (272 mg, 388 umol) in DMF (8 mL) was degassed and purged with $N_2$ for three times. Then the mixture was stirred at 100° C. for 12 hours under $N_2$ atmosphere. The reaction mixture was concentrated in vacuo to give a residue. The residue was purified by column chromatography ($SiO_2$, Petroleum ether:THF:IPA=8:8:1) to give the title compound (700 mg, 51% yield) as a yellow solid. $^1H$ NMR (400 MHz, DMSO-d6) δ 10.68 (s, 1H), 8.85-8.18 (m, 1H), 8.14-7.10 (m, 2H), 6.92 (d, J=6.4 Hz, 1H), 4.57 (t, J=5.2 Hz, 1H), 3.80 (s, 2H), 3.61-3.48 (m, 2H), 2.82 (s, 2H), 2.50-2.38 (m, 2H), 1.79-1.68 (m, 2H).

Step 2—5-[3-(2,4-dioxohexahydropyrimidin-1-yl)imidazo[1,2-a]pyridin-7-yl]pent-4-ynal A mixture of 1-[7-(5-hydroxypent-1-ynyl)imidazo[1,2-a]pyridin-3-yl]hexahydropyrimidine-2,4-dione (50.0 mg, 160 umol), and DMP (101 mg, 240 umol) in DMF (2.0 mL) was degassed and purged with $N_2$ three times, and then the mixture was stirred at 25° C. for 2 hours under $N_2$ atmosphere. On completion, the reaction mixture was quenched by adding saturated aqueous $Na_2S_2O_3$ solution (2 ml). The aqueous layer was extracted with DCM (5 ml×2). The organic layer was washed by saturated aqueous $NaHCO_3$ (5 ml×2), was separated, dried over anhydrous $Na_2SO_4$, filtered and concentrated under reduced pressure to give the title compound (30.0 mg) as a yellow solid. LC-MS ($ESI^+$) m/z 386.4 $(M+H)^+$.

(1R)-1-(4-chlorophenyl)-7-isopropoxy-6-methoxy-2-[4-[methyl(4-piperidylmethyl)amino]phenyl]-1,4-dihydroisoquinolin-3-one (Intermediate JA)

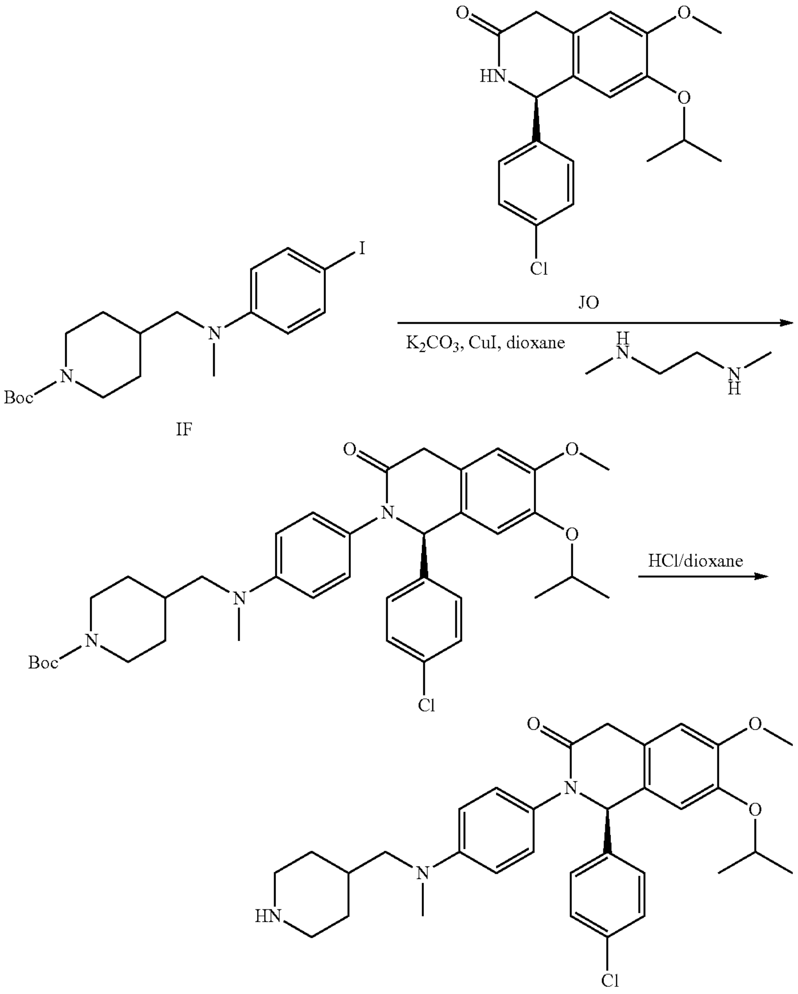

JA

Step 1—Tert-butyl 4-[[4-[(1R)-1-(4-chlorophenyl)-7-isopropoxy-6-methoxy-3-oxo-1,4-dihydroisoquinolin-2-yl]-N-methyl-anilino]methyl]piperidine-1-carboxylate To a solution of tert-butyl 4-[(4-iodo-N-methyl-anilino)methyl]piperidine-1-carboxylate (253 mg, 589 umol, Intermediate IF), (1S)-1-(4-chlorophenyl)-7-isopropoxy-6-methoxy-2,4-dihydro-1H-isoquinolin-3-one (170 mg, 491 umol, Intermediate JO) in dioxane (5 mL) was added CuI (4.68 mg, 24.5 μmol), then N,N'-dimethylethane-1,2-diamine (4.33 mg, 49.1 umol), and potassium carbonate (135 mg, 983 μmol). The mixture was stirred at 120° C. for 16 hours. On completion. The reaction mixture was concentrated in vacuo to give a residue. The residue was purified by column chromatography ($SiO_2$, Petroleum ether/Ethyl acetate=20/1 to 0/1) to give the title compound (130 mg, 37% yield) as a white solid. LC-MS ($ESI^+$) m/z 648.2 $(M+H)^+$.

Step 2—(1R)-1-(4-chlorophenyl)-7-isopropoxy-6-methoxy-2-[4-[methyl(4-piperidylmethyl)amino]phenyl]-1,4-dihydroisoquinolin-3-one To a mixture of tert-butyl tert-butyl 4-[[4-[(1S)-1-(4-chlorophenyl)-7-isopropoxy-6-methoxy-3-oxo-1,4-dihydroisoquinolin-2-yl]-N-methyl-anilino]methyl]piperidine-1-carboxylate (10.0 mg, 15.4 umol) in DCM (1.0 mL) was added HCl/dioxane (4 M, 0. mL) in one portion at 25° C. under $N_2$. The mixture was stirred at 25° C. for 30 minutes. On completion, the reaction mixture was concentrated in vacuo to give a residue. The residue was purified by prep-HPLC (column: Phenomenex Luna C18 150*25 mm*10 um; mobile phase: [water (0.225% FA)-ACN]; B %: 23%-53%, 11.5 min). Give title compound (4.17 mg, 48% yield) as a white solid. $^1H$ NMR (400 MHz, DMSO-$d_6$) δ 7.35 (s, 4H), 7.04 (s, 1H), 6.90 (d, J=9.2 Hz, 2H), 6.83-6.83 (m, 1H), 6.83 (s, 2H), 6.57 (d, J=9.2 Hz, 1H), 5.94 (s, 1H), 4.45 (td, J=6.0, 12.0 Hz, 1H), 3.89-3.85 (m, 1H), 3.73 (s, 3H), 3.59 (s, 0.5H), 3.54 (s, 0.5H), 3.29-3.26 (m, 2H), 3.15 (d, J=6.8 Hz, 2H), 3.07-3.00 (m, 2H), 2.89 (s, 3H), 2.59-2.53 (m, 1H), 1.65-1.57 (m, 2H), 1.23 (d, J=6.0 Hz, 3H), 1.18 (d, J=6.0 Hz, 3H), 1.17-1.10 (m, 2H); LC-MS ($ESI^+$) m/z 548.3 $(M+H)^+$.

1-(7-Chloroisoquinolin-4-yl)dihydropyrimidine-2,4 (1H,3H)-dione (Intermediate JB)

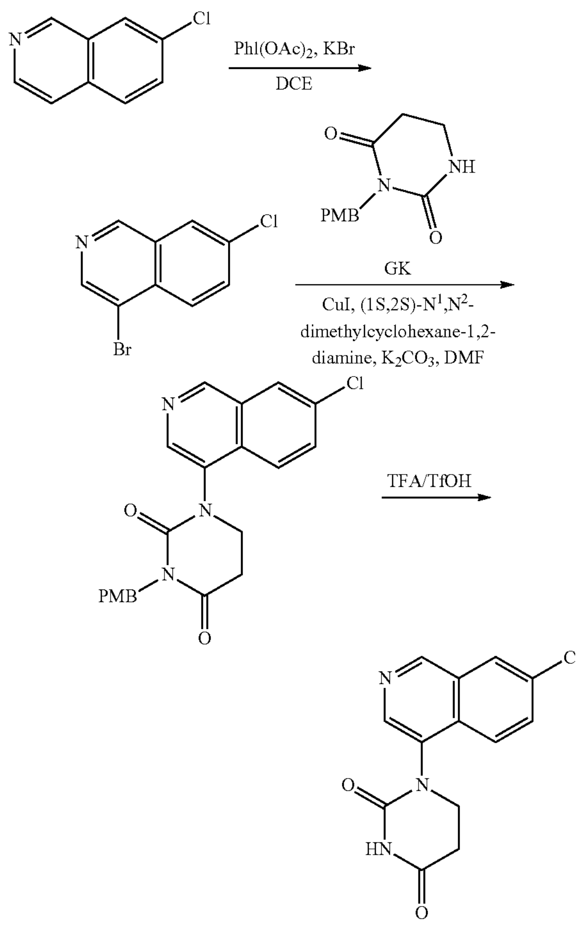

JB

Step 1—4-Bromo-7-chloroisoquinoline

To a solution of 7-chloroisoquinoline (5.00 g, 30.5 mmol, CAS #34784-06-0) in DCE (50 mL) was added $PhI(OAc)_2$ (14.7 g, 45.8 mmol) and KBr (18.1 g, 152 mmol) and the mixture was stirred at 50° C. for 16 hours. On completion, the mixture was poured into water (100 mL), and extracted with EA (300 mL). The organic layer was washed with brine (2×100 mL), dried over anhydrous $Na_2SO_4$, filtered and concentrated in vacuo. The mixture was purified by silica gel column to give the title compound (5.50 g, 65% yield) as a white solid. $^1$H NMR (400 MHz, $CDCl_3$) δ 9.13 (s, 1H), 8.74 (s, 1H), 8.13 (d, J=9.2 Hz, 1H), 7.99 (d, J=2.0 Hz, 1H), 7.77 (dd, J=2.0, 9.2 Hz, 1H).

Step 2—1-(7-Chloro-4-isoquinolyl)-3-[(4-methoxy-phenyl)methyl]hexahydropyrimidine-2A-dione To a solution of 4-bromo-7-chloroisoquinoline (2.00 g, 8.25 mmol) and 3-(4-methoxybenzyl) dihydropyrimidine-2,4(1H,3H)-dione (1.93 g, 8.25 mmol, Intermediate GK) in DMF (20 mL) was added (1S,2S)—N1,N2-dimethylcyclohexane-1,2-diamine (234 mg, 1.65 mmol), CuI (314 mg, 1.65 mmol) and $K_2CO_3$ (3.42 g, 24.7 mmol). Then the mixture was stirred at 100° C. for 16 hours under $N_2$. On completion, the reaction solution was diluted with water (100 mL) and then extracted with ethyl acetate (3×100 mL). The combined organic layers were washed with brine (2×100 mL), dried over anhydrous sodium sulfate, filtered and concentrated under vacuum. The mixture was purified by reversed phase flash: (C18, 10% to 40% MeCN in $H_2O$, contained 0.1% FA in $H_2O$) to give the title compound (200 mg, 5% yield) as a light yellow solid. $^1$H NMR (400 MHz, DMSO-$d_6$) δ 9.31 (s, 1H), 8.60 (s, 1H), 8.39 (d, J=2.0 Hz, 1H), 8.00 (d, J=9.2 Hz, 1H), 7.83 (dd, J=2.0, 8.8 Hz, 1H), 7.25 (d, J=8.8 Hz, 2H), 6.90-6.86 (m, 2H), 4.83 (s, 2H), 4.00-3.94 (m, 1H), 3.79-3.76 (m, 1H), 3.73 (s, 3H), 3.19-3.11 (m, 1H), 2.99-2.92 (m, 1H).

Step 3—1-(7-Chloroisoquinolin-4-yl)dihydropyrimidine-2,4(1H,3H)-dione 1-(7-Chloroisoquinolin-4-yl)-3-(4-methoxybenzyl)dihydropyrimidine-2,4(1H,3H)-dione (50.0 mg, 126 umol) was added into TFA (0.5 mL) and TfOH (0.01 mL) and the mixture was stirred at 60° C. for 2 hours. On completion, the reaction solution was diluted with water (5 mL) and then extracted with ethyl acetate (3×5 mL). The combined organic layers were washed with brine (2×5 mL), dried over anhydrous sodium sulfate, filtered and concentrated in vacuo. The residue was further purified by prep-HPLC (Column: [Phenomenex luna C18, 150 mm*25 mm*10 um]; mobile phase: (water (0.225% FA)-MeCN, MeCN %: 8%-38%); 11 min) to give the title compound (5.18 mg, 14% yield) as a yellow solid. $^1$H NMR (400 MHz, DMSO-$d_6$) δ 10.56 (s, 1H), 9.31 (s, 1H), 8.59 (s, 1H), 8.38 (d, J=2.0 Hz, 1H), 8.06 (d, J=9.2 Hz, 1H), 7.84 (dd, J=2.4, 8.8 Hz, 1H), 4.00-3.93 (m, 1H), 3.75-3.69 (m, 1H), 3.02-2.94 (m, 1H), 2.78-2.71 (m, 1H). LC-MS ($ESI^+$) m/z 275.9 $(M+H)^+$.

5-[4-(2,4-dioxohexahydropyrimidin-1-yl)-7-isoquinolyl]pent-4-ynal (Intermediate JC)

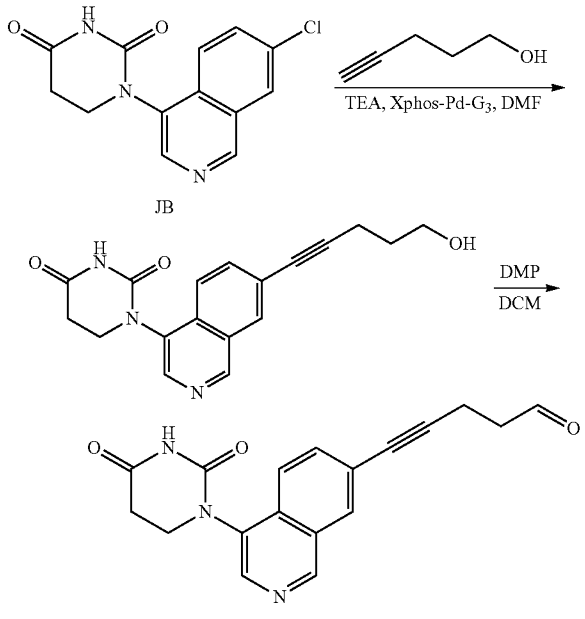

JC

Step 1—1-[7-(5-hydroxypent-1-ynyl)-4-isoquinolyl]hexahydropyrimidine-2,4-dione

A mixture of 1-(7-chloro-4-isoquinolyl)hexahydropyrimidine-2,4-dione (50.0 mg, 181 μmol, Intermediate JB), pent-4-yn-1-ol (18.3 mg, 217 umol), XPhos-Pd-G3 (15.3 mg, 18.1 umol), TEA (55.0 mg, 544 umol) in DMF (2 mL) was degassed and purged with $N_2$ three times. Then the mixture was stirred at 80° C. for 3 hours under $N_2$ atmosphere. On completion, the reaction mixture was concentrated in vacuo to give a residue. The residue was purified by column chromatography ($SiO_2$, Petroleum ether/Ethyl acetate=0/1) to give the title compound (50.0 mg, 68% yield) as a yellow solid. LC-MS (ESI$^+$) m/z 324.1 (M+H)$^+$.

Step 2—5-[4-(2,4-dioxohexahydropyrimidin-1-yl)-7-isoquinolyl]pent-4-ynal

A mixture of 1-[7-(5-hydroxypent-1-ynyl)-4-isoquinolyl]hexahydropyrimidine-2,4-dione (50.0 mg, 154 umol) and DMP (98.4 mg, 231 umol) in DCM (2 mL) was degassed and purged with $N_2$ three times, and then the mixture was stirred at 25° C. for 2 hours under $N_2$ atmosphere. On completion, the reaction mixture was quenched by adding saturated aqueous $Na_2S_2O_3$ solution (5 ml) and the aqueous layer was extracted with DCM (5 ml×2). The organic layer was washed by saturated aqueous $NaHCO_3$ (5 ml×3), the organic layer was separated, dried over anhydrous $Na_2SO_4$, filtered and concentrated under reduced pressure to give the title compound (50.0 mg, 80% yield) as a yellow solid. LC-MS (ESI$^+$) m/z 322.2 (M+H)$^+$.

3-[5-[2-[4-(4-Amino-1-piperidyl)cyclohexyl]ethyl]-3-methyl-2-oxo-benzimidazol-1-yl]piperidine-2,6-dione (Intermediate JD)

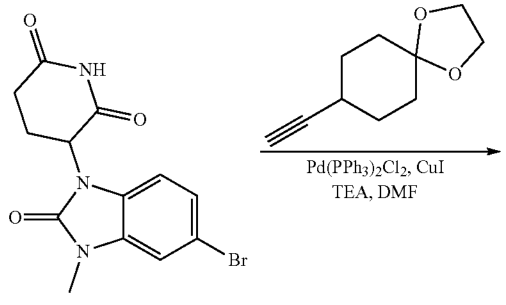

E

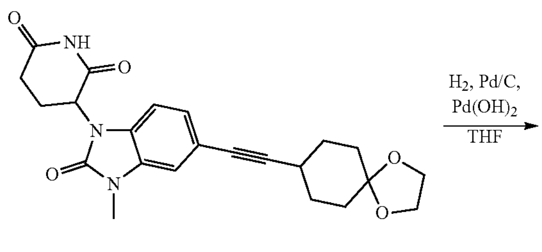

-continued

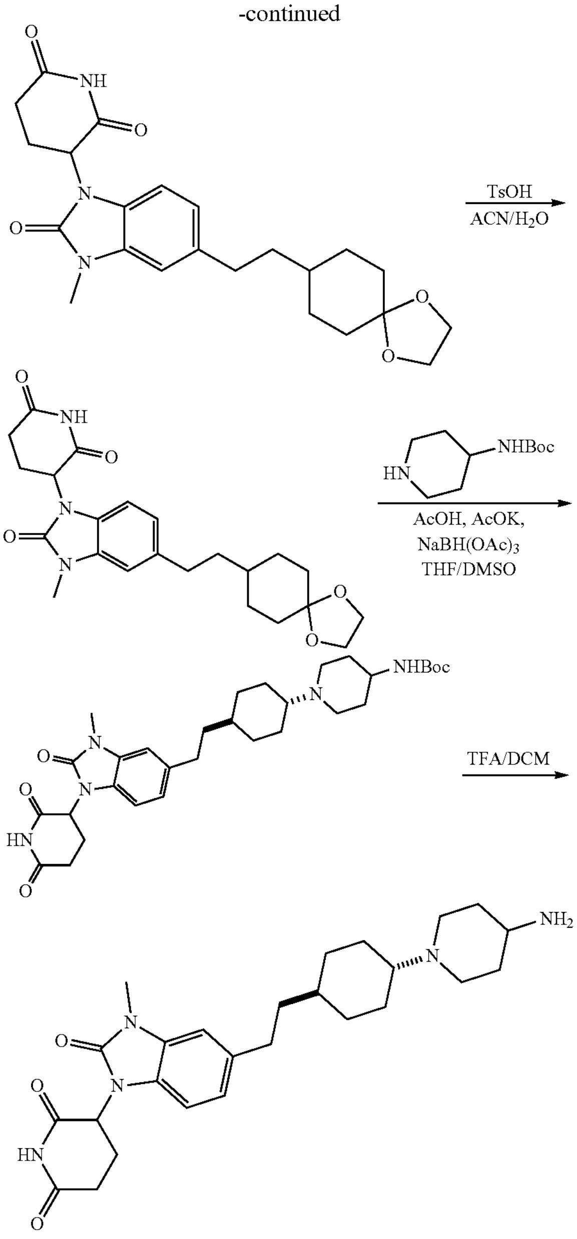

JD

Step 1—3-[5-[2-(1,4-Dioxaspiro[4.5]decan-8-yl)ethynyl]-3-methyl-2-oxo-benzimidazol-1-yl]piperidine-2,6-dione A mixture of 3-(5-bromo-3-methyl-2-oxo-benzimidazol-1-yl)piperidine-2,6-dione (500 mg, 1.48 mmol, Intermediate E) 8-ethynyl-1,4-dioxaspiro[4.5]decane (368 mg, 2.22 mmol, CAS #96184-86-0), CuI (28.16 mg, 148 umol), $Pd(PPh_3)_2Cl_2$ (103 mg, 147 umol) and TEA (1.50 g, 14.7 mmol) in DMF (5 mL), and then the mixture was stirred at 80° C. for 12 hours under $N_2$ atmosphere. On completion, the mixture was quenched with water (20 mL) and extracted with ethyl acetate (25 mL×3). The combined organic phase was dried over anhydrous sodium sulfate, filtered and concentrated to give a residue. The residue was purified by column chromatography ($SiO_2$, Petroleum ether/Ethyl acetate=20:1 to 1:9) to give the title compound (255 mg, 40% yield) as a yellow solid. LC-MS (ESI+) m/z 425.2 (M+H)+.

Step 2—3-[5-[2-(1,4-Dioxaspiro[4.5]decan-8-yl) ethyl]-3-methyl-2-oxo-benzimidazol-1-yl]piperidine-2,6-dione To a solution of 3-[5-[2-(1,4-dioxaspiro[4.5]decan-8-yl) ethynyl]-3-methyl-2-oxo-benzimidazol-1-yl] piperidine-2,6-dione (230 mg, 543 umol) in THF (5.0 mL) was added Pd/C (50 mg, 10 wt %) and $Pd(OH)_2$ (50 mg, 71.2 umol, 20 wt %) under $N_2$ atmosphere. The suspension was degassed and purged with $H_2$ gas three times. The mixture was stirred under $H_2$ (15 Psi) at 25° C. for 4 hours. On completion, the mixture was concentrated to give the title compound (220 mg, 94% yield) as a yellow oil. LC-MS (ESI+) m/z 428.5 (M+H)+.

Step 3—3-[3-Methyl-2-oxo-5-[2-(4-oxocyclohexyl) ethyl]benzimidazol-1-yl]piperidine-2,6-dione To a solution of 3-[5-[2-(1,4-dioxaspiro[4.5]decan-8-yl) ethyl]-3-methyl-2-oxo-benzimidazol-1-yl] piperidine-2,6-dione (200 mg, 467 umol) in ACN (2.0 mL) and $H_2O$ (2.0 mL) was added 4-methylbenzenesulfonic acid (161 mg, 935 umol). The mixture was stirred at 25° C. for 1 hr. On completion, the mixture was quenched with water (20 mL) and extracted with ethyl acetate (25 mL×3). The combined organic phase was dried over anhydrous sodium sulfate, filtered and concentrated to give a residue. The mixture was purified by column chromatography ($SiO_2$, Petroleum ether/Ethyl acetate=1:0 to 1:1) to give the title compound (120 mg, 66% yield) as a yellow oil. $^1$H NMR (400 MHz, $CDCl_3$) δ 6.93-6.88 (m, 1H), 6.86 (s, 1H), 6.73 (d, J=7.6 Hz, 1H), 5.27-5.17 (m, 1H), 3.44 (s, 3H), 2.99-2.91 (m, 1H), 2.89-2.77 (m, 1H), 2.77-2.69 (m, 3H), 2.48-2.31 (m, 4H), 2.28-2.19 (m, 1H), 2.17-2.08 (m, 2H), 1.83-1.72 (m, 1H), 1.70-1.63 (m, 2H), 1.54-1.42 (m, 2H); LC-MS (ESI+) m/z 384.1 (M+H)+.

Step 4—Tert-butyl N-[1-[4-[2-[1-(2,6-dioxo-3-piperidyl)-3-methyl-2-oxo-benzimidazol-5-yl]ethyl] cyclohexyl]-4-piperidyl]carbamate To a solution of 3-[3-methyl-2-oxo-5-[2-(4-oxocyclohexyl)ethyl]benzimidazol-1-yl]piperidine-2,6-dione (100 mg, 260 umol) in THF (2.0 mL) and DMSO (0.4 mL) was added AcOK (76.7 mg, 782 umol) and 4 Å molecular sieves (5.00 mg). Then AcOH (15.6 mg, 260 umol) was added into the mixture. Next, tert-butyl N-(4-piperidyl)carbamate (52.2 mg, 260 umol) was added and the mixture was stirred at 40° C. for 12 hours. Finally, $NaBH(OAc)_3$ (55.2 mg, 260 umol) was added at 0° C. and the resulting mixture was stirred at 25° C. for 4 hours. On completion, the mixture was quenched with water (0.4 mL) and concentrated to give a residue. The mixture was purified by reversed-phase HPLC (0.1% TFA condition) to give the title compound (40.0 mg, 27% yield) as a white solid. LC-MS (ESI+) m/z 568.5 (M+H)+.

Step 5 3-[5-[2-[4-(4-Amino-1-piperidyl)cyclohexyl] ethyl]-3-methyl-2-oxo-benzimidazol-1-yl]piperidine-2,6-dione To a solution of tert-butyl N-[1-[4-[2-[1-(2,6-dioxo-3-piperidyl)-3-methyl-2-oxo-benzimidazol-5-yl] ethyl]cyclohexyl]-4-piperidyl]carbamate (40.0 mg, 70.4 umol) in DCM (1.0 mL) was added TFA (462 mg, 4.05 mmol). The mixture was then stirred at 25° C. for 0.5 hour. On completion, the mixture was concentrated to give the title compound (40.0 mg, 97% yield) as a yellow oil. LC-MS (ESI+) m/z 468.4 (M+H)+.

Chloro-(3-chloro-2-fluoro-phenyl)-oxo-N-(1,2,3,4-tetrahydroisoquinolin-6-yl)dispiro [BLAH]carboxamide (Intermediate JE)

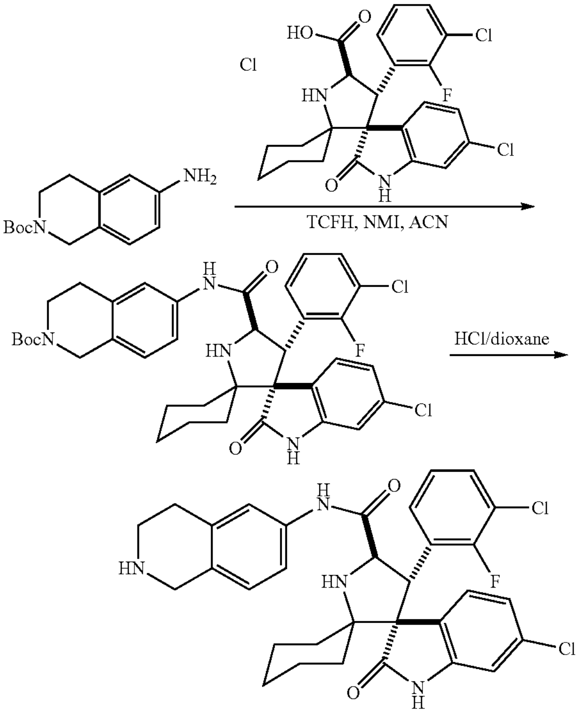

JE

Step 1—Tert-butyl 6-[[chloro-(3-chloro-2-fluoro-phenyl)-oxo-dispiro[BLAH]carbonyl]amino]-3,4-dihydro-1H-isoquinoline-2-carboxylate To a solution of tert-butyl 6-amino-3,4-dihydro-1H-isoquinoline-2-carboxylate (300 mg, 1.21 mmol, CAS #164148-92-9) in ACN (8 mL) was added 1-methylimidazole (495 mg, 6.04 mmol), [chloro(dimethylamino)methylene]-dimethyl-ammonium; hexafluorophosphate (1.02 g, 3.62 mmol) and chloro-(3-chloro-2-fluoro-phenyl)-oxo-dispiro[BLAH]carboxylic acid (559 mg, 1.21 mmol, Intermediate CI). The mixture was stirred at 25° C. for 1 hour. On completion, the mixture was concentrated in vacuo to give a residue. The residue was purified by column chromatography ($SiO_2$, Petroleum ether/Ethyl acetate=1:0 to 3:1) to give the title compound (500 mg, 576 umol, 47% yield) as a yellow oil. $^1$H NMR (400 MHz, DMSO-$d_6$) δ=10.62 (s, 1H), 9.99 (s, 1H), 7.63 (t, J=6.8 Hz, 1H), 7.52 (s, 1H), 7.45 (dd, J=2.0, 8.4 Hz, 1H), 7.37-7.31 (m, 2H), 7.17-7.11 (m, 2H), 7.03 (dd, J=2.0, 8.0 Hz, 1H), 6.69 (d, J=2.0 Hz, 1H), 4.77-4.71 (m, 1H), 4.68-4.61 (m, 1H), 4.43 (s, 2H), 3.56-3.51 (m, 2H), 2.73 (t, J=6.0 Hz, 2H), 2.04 (d, J=13.2 Hz, 1H), 1.68-1.48 (m, 6H), 1.42 (s, 9H), 1.07-0.90 (m, 2H), 0.89-0.77 (m, 2H); LC-MS (ESI+) m/z 693.5 (M+H)+.

Step 2—Chloro-(3-chloro-2-fluoro-phenyl)-oxo-N-(1,2,3,4-tetrahydroisoquinolin-6-yl)dispiro [BLAH] carboxamide To tert-butyl 6-[[chloro-(3-chloro-2-fluoro-phenyl)-oxo-dispiro[BLAH]carbonyl] amino]-3,4-dihydro-1H-isoquinoline-2-carboxylate (250 mg, 288 umol) was added HCl/dioxane (2.0 mL). The mixture was stirred at 25° C. for 1 hour. On completion, the mixture was concentrated in vacuo to give the title compound (180 mg, 285 umol, 99% yield, HCl salt) as a brown solid. LC-MS ($ESI^+$) m/z 593.2 $(M+H)^+$.

1-(8-Chloro-4-isoquinolyl)hexahydropyrimidine-2,4-dione (Intermediate JF)

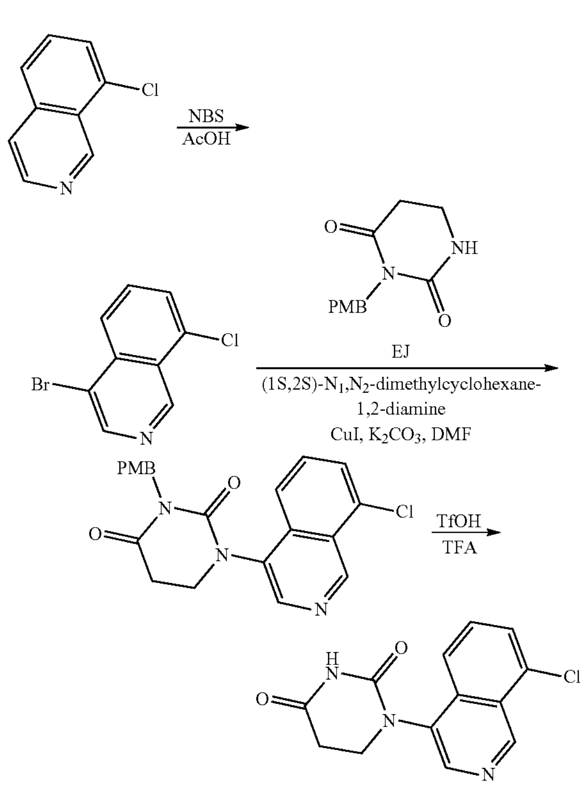

JF

Step 1—4-Bromo-8-chloro-isoquinoline

To a solution of 8-chloroisoquinoline (5.00 g, 30.5 mmol, CAS #34784-07-1) in AcOH (50 mL) was added NBS (7.07 g, 39.7 mmol), then the reaction mixture was stirred at 50° C. for 40 min. On completion, the reaction mixture was diluted with water (100 mL), then extracted with EA (3×80 mL). The combined organic layer was basified with $NaHCO_3$ until the pH=6-7, then the mixture was extracted with EA (2×60 mL). The combined organic layers was dried over $Na_2SO_4$, filtered and concentrated in vacuo to give a residue. The residue was purified by column chromatography ($SiO_2$, PE:EA=100:1 to PE:EA=50:1, PE:EA=10:1, P1:$R_f$=0.74) to give the title compound (1.00 g, 37% yield) as yellow solid. $^1H$ NMR (400 MHz, $CDCl_3$) δ 9.56 (s, 1H), 8.78 (s, 1H), 8.10-8.03 (m, 1H), 7.73-7.64 (m, 2H). LC-MS ($ESI^+$) m/z 241.9 $(M+H)^+$.

Step 2—1-(8-Chloro-4-isoquinolyl)-3-[(4-methoxyphenyl)methyl]hexahydropyrimidine-24-dione To a solution of 4-bromo-8-chloro-isoquinoline (100 mg, 412 umol) and 3-[(4-methoxyphenyl)methyl]hexahydropyrimidine-2,4-dione (96.6 mg, 412.37 umol, Intermediate EJ) in DMF (1 mL) was added CuI (7.85 mg, 41.2 umol), (1S,2S)—$N_1$,$N_2$-dimethylcyclohexane-1,2-diamine (5.87 mg, 41.2 umol) and $K_3PO_4$ (175 mg, 824 umol), then the mixture was stirred at 110° C. for 8 hr. On completion, the reaction mixture was filtered and concentrated in vacuo to give the residue. The residue was diluted with water (50 mL) and extracted with EA (5×30 mL). Then the combined organic layers was dried over anhydrous $Na_2SO_4$, filtered and concentrated in vacuo to give a residue. The residue was purified by reverse-phase (0.1% FA) to give the title compound (15 mg, 3.06% yield) as yellow solid. $^1H$ NMR (400 MHz, DMSO-$d_6$) δ 9.89-9.56 (br s, 1H), 8.59 (br s, 1H), 7.73-7.68 (m, 1H), 7.64 (t, J=8.0 Hz, 1H), 7.60-7.55 (m, 1H), 7.43 (d, J=8.4 Hz, 2H), 6.85 (d, J=8.4 Hz, 2H), 5.00 (s, 2H), 3.95-3.86 (m, 1H), 3.80 (s, 3H), 3.78-3.69 (m, 1H), 3.07-2.99 (m, 2H); LC-MS ($ESI^+$) m/z 396.1 $(M+H)^+$.

Step 3—1-(8-Chloro-4-isoquinolyl)hexahydropyrimidine-2,4-dione

To a solution of 1-(8-chloro-4-isoquinolyl)-3-[(4-methoxyphenyl)methyl]hexahydropyrimidine-2,4-dione (40.0 mg, 101 umol) in TFA (0.49 mL) and TfOH (0.01 mL), then the mixture was stirred at 60° C. for 2 hours. On completion, the mixture was concentrated to give the residue and purified by prep-HPLC (0.1% FA) to give the title compound (3 mg, 10.77% yield) as yellow solid. $^1H$ NMR (400 MHz, DMSO-$d_6$) δ=10.59 (s, 1H), 9.56 (s, 1H), 8.71 (s, 1H), 8.03 (d, J=8.4 Hz, 1H), 7.92-7.87 (m, 1H), 7.85-7.78 (m, 1H), 4.00-3.93 (m, 1H), 3.75-3.69 (m 1H), 3.03-2.95 (m, 1H), 2.79-2.72 (m, 1H). LC-MS ($ESI^+$) m/z 276.0 $(M+H)^+$.

1-[8-[2-(4-piperidyl)ethynyl]-4-isoquinolyl]hexahydropyrimidine-2,4-dione (Intermediate JG)

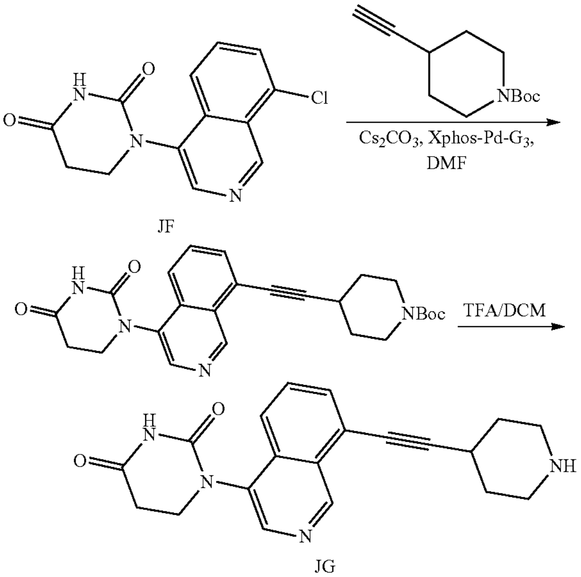

JG

Step 1—tert-butyl 4-[2-[4-(2,4-dioxohexahydropyrimidin-1-yl)-8-isoquinolyl]ethynyl]piperidine-1-carboxylate To a mixture of 1-(8-chloro-4-isoquinolyl)hexahydropyrimidine-2,4-dione (400 mg, 1.45 mmol, Intermediate JF) and tert-butyl 4-ethynylpiperidine-1-carboxylate (455 mg, 2.18 mmol, CAS #287192-97-6) in DMF (12 mL) was added $Cs_2CO_3$ (2.36 g, 7.25 mmol,) and XPhos-Pd-$G_3$ (122 mg, 145 μmol). Then the resulting mixture was stirred at 80° C. for 3 hours. On completion, the mixture was quenched with water (50 mL) and extracted with ethyl acetate (15 mL×3). The combined organic phase was dried over anhydrous sodium sulfate, filtered and concentrated to give a residue. The residue was purified by column chromatography ($SiO_2$, Dichloromethane:Ethyl acetate=1:0 to 1:4) to give the title compound (550 mg, 84% yield) as a brown solid. LC-MS ($ESI^+$) m/z 449.3 $(M+H)^+$.

Step 2—1-[8-[2-(4-piperidyl)ethynyl]-4-isoquinolyl]hexahydropyrimidine-2,4-dione To a solution of tert-butyl 4-[2-[4-(2,4-dioxohexahydropyrimidin-1-yl)-8-isoquinolyl]ethynyl] piperidine-1-carboxylate (500 mg, 1.11 mmol) in DCM (10 mL) was added TFA (5.39 g, 47.3 mmol), then the resulting mixture was stirred at 25° C. for 30 minutes. On completion, the mixture was concentrated to give the title compound (520 mg, TFA salt) as a green oil. LC-MS ($ESI^+$) m/z 349.1 $(M+H)^+$.

1-[8-[2-[1-[(4-Aminocyclohexyl)methyl]-4-piperidyl]ethynyl]-4-isoquinolyl]hexahydropyrimidine-2,4-dione (Intermediate JH)

Step 1—Tert-butyl N-[4-[[4-[2-[4-(2,4-dioxohexahydropyrimidin-1-yl)-8-isoquinolyl]ethynyl]-1-piperidyl]methyl]cyclohexyl]carbamate To a mixture of 1-[8-[2-(4-piperidyl)ethynyl]-4-isoquinolyl]hexahydropyrimidine-2,4-dione (520 mg, 1.12 mmol, Intermediate JG) in THF (10 mL) was added AcOK (1.10 g, 11.2 mmol) and stirred for 15 minutes at 25° C. Then tert-butyl N-(4-formylcyclohexyl)carbamate (306 mg, 1.35 mmol, CAS #181308-57-6) was added and the mixture was stirred for 20 minutes. Finally, $NaBH(OAc)_3$ (1.19 g, 5.62 mmol) was added to the mixture and stirred for 12 hours at 25° C. On completion, the mixture was concentrated to give a residue. The crude product was purified by reversed-phase (0.1% FA condition) to give the title compound (200 mg, 31% yield) as a white solid. LC-MS ($ESI^+$) m/z 560.5 (M+H)*; $^1H$ NMR (400 MHz, DMSO-$d_6$) δ 10.58 (s, 1H), 9.56 (s, 1H), 8.65 (s, 1H), 8.02 (d, J=8.4 Hz, 1H), 7.86-7.76 (m, 2H), 6.74 (d, J=8.0 Hz, 1H), 4.02-3.91 (m, 1H), 3.76-3.66 (m, 1H), 3.23-2.93 (m, 6H), 2.82-2.71 (m, 2H), 2.19-1.84 (m, 5H), 1.78 (d, J=10.8 Hz, 5H), 1.54 (s, 1H), 1.38 (s, 9H), 1.21-1.12 (m, 1H), 1.11 (s, 1H), 1.01-0.90 (m, 2H).

Step 2—1-[8-[2-[1-[(4-Aminocyclohexyl)methyl]-4-piperidyl]ethynyl]-4-isoquinolyl]hexahydropyrimidine-2,4-dione To a solution of tert-butyl N-[4-[[4-[2-[4-(2,4-dioxohexahydropyrimidin-1-yl)-8-isoquinolyl]ethynyl]-1-piperidyl] methyl]cyclohexyl]carbamate (112 mg, 200 umol) in DCM (1.0 mL) was added TFA (456 mg, 4.00 mmol), then the resulting mixture was stirred at 25° C. for 30 minutes. On

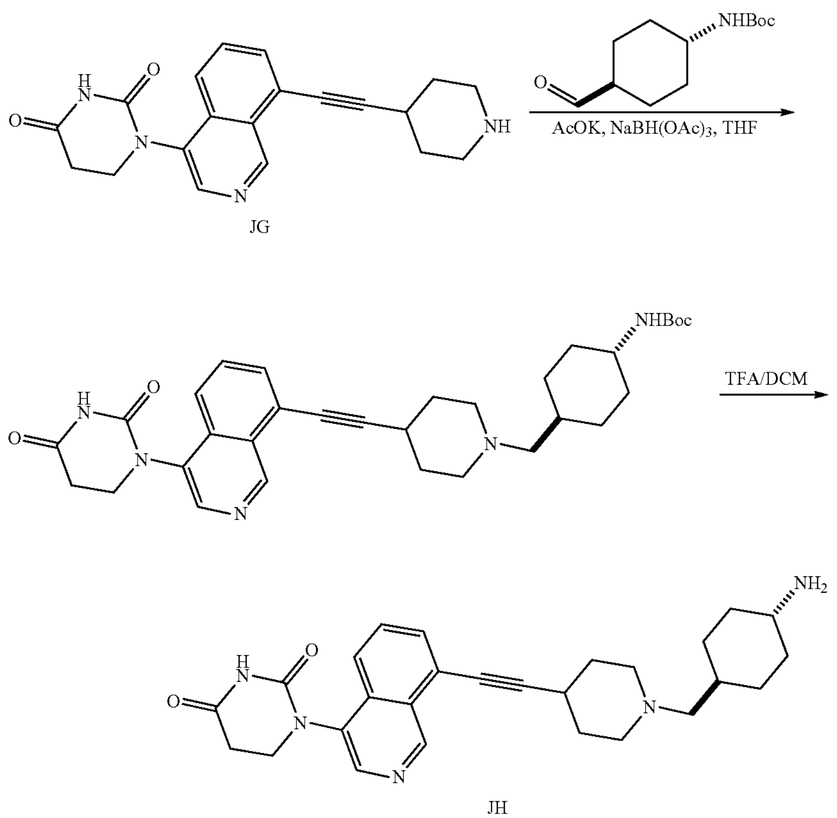

JG

JH completion, the mixture was concentrated to give the title compound (114 mg, 99% yield, TFA salt) as a brown oil. LC-MS ($ESI^+$) m/z 460.3 $(M+H)^+$.

1-[7-[2-(4-Piperidyl)ethynyl]-4-isoquinolyl]hexahydropyrimidine-2,4-dione (Intermediate JI)

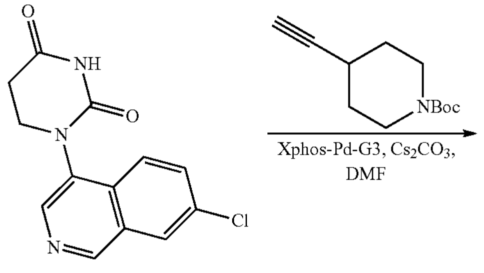

JB

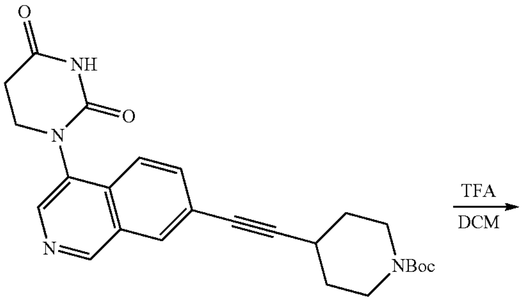

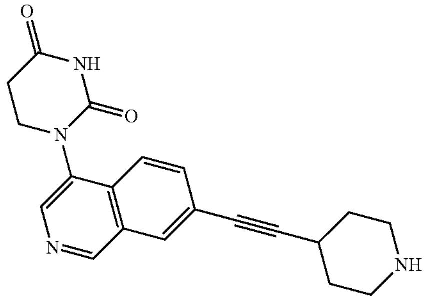

JI

Step 1—Tert-butyl 4-[2-[4-(2,4-dioxohexahydropyrimidin-1-yl)-7-isoquinolyl]ethynyl]piperidine-1-carboxylate To a mixture of 1-(7-chloro-4-isoquinolyl)hexahydropyrimidine-2,4-dione (300 mg, 1.09 mmol, Intermediate JB) and tert-butyl 4-ethynylpiperidine-1-carboxylate (342 mg, 1.63 mmol, CAS #287192-97-6) in DMF (12 mL) was added XPhos-Pd-$G_3$ (92.1 mg, 109 umol) and $Cs_2CO_3$ (1.77 g, 5.44 mmol), then the mixture was stirred at 80° C. for 3 hours under $N_2$ atmosphere. On completion, the mixture was quenched with water (50 mL) and extracted with ethyl acetate (15.0 mL×3). The combined organic phase was dried over anhydrous sodium sulfate, filtered and concentrated to give a residue. The residue was purified by column chromatography ($SiO_2$, Dichloromethane:Ethyl acetate=1:0 to 1:4) to give the title compound (402 mg, 68% yield) as a brown solid. LC-MS ($ESI^+$) m/z 449.2 $(M+H)^+$; $^1H$ NMR (400 MHz, $CDCl_3$) δ 9.23 (s, 1H), 8.53 (s, 1H), 8.15 (s, 1H), 7.85-7.70 (m, 3H), 4.07-3.98 (m, 1H), 3.89-3.76 (m, 3H), 3.30-3.23 (m, 2H), 3.03-2.96 (m, 2H), 2.87 (tt, J=4.0, 8.4 Hz, 1H), 1.92 (ddd, J=3.2, 6.4, 9.6 Hz, 2H), 1.78-1.68 (m, 2H), 1.48 (s, 9H).

Step 2—1-[7-[2-(4-Piperidyl)ethynyl]-4-isoquinolyl]hexahydropyrimidine-2,4-dione To a solution of tert-butyl 4-[2-[4-(2,4-dioxohexahydropyrimidin-1-yl)-7-isoquinolyl]ethynyl] piperidine-1-carboxylate (400 mg, 892 umol) in DCM (4.0 mL) was added TFA (1.22 g, 10.7 mmol). The mixture was stirred at 0° C. for 1 hour. On completion, the mixture was concentrated to give the title compound (412 mg, 99% yield, TFA salt) as a brown oil. LC-MS ($ESI^+$) m/z 349.3 $(M+H)^+$.

1-[7-[2-[1-[(4-Aminocyclohexyl)methyl]-4-piperidyl]ethynyl]-4-isoquinolyl]hexahydropyrimidine-2,4-dione (Intermediate JJ)

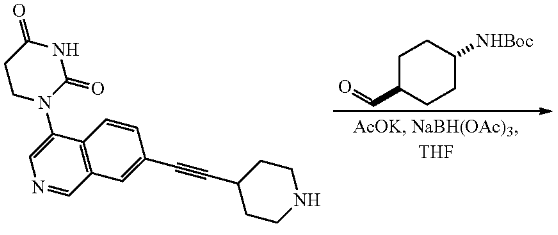

JI

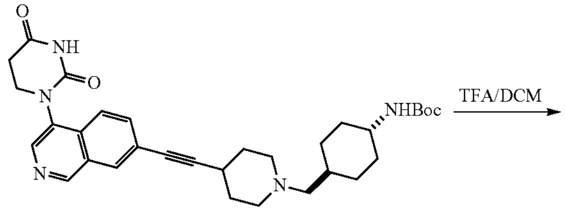

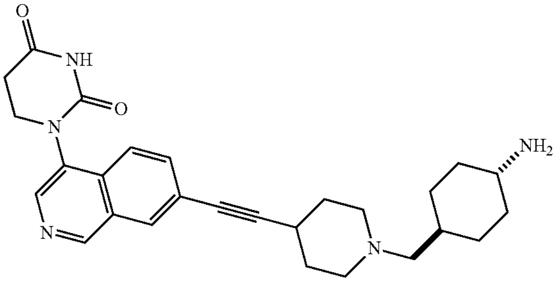

JJ

Step 1—Tert-butyl N-[4-[[4-[2-[4-(2,4-dioxohexahydropyrimidin-1-yl)-7-isoquinolyl]ethynyl]-1-piperidyl 1methyl]cyclohexyl]carbamate To a solution of 1-[7-[2-(4-piperidyl)ethynyl]-4-isoquinolyl]hexahydropyrimidine-2,4-dione (412 mg, 891 umol, TFA salt, Intermediate JI) in THF (9 mL) was added AcOK (874 mg, 8.91 mmol), then the mixture was stirred at 25° C. for 10 minutes. Next, tert-butyl N-(4-formylcyclohexyl) carbamate (243 mg, 1.07 mmol, CAS #181308-57-6) was added to the mixture and the mixture was stirred at 25° C. for 5 minutes. Then $NaBH(OAc)_3$ (378 mg, 1.78 mmol) was added to the mixture at 0° C. The reaction mixture was stirred at 25° C. for 2 hours. On completion, the mixture was concentrated to give a residue. The crude product was purified by reversed-phase (0.1% FA condition) to give the title compound (363 mg, 72% yield) as a white solid. LC-MS ($ESI^+$) m/z 560.4 $(M+H)^+$; 1H NMR (400 MHz, DMSO-d6) δ 10.56 (s, 1H), 9.29 (s, 1H), 8.57 (s, 1H), 8.32 (s, 1H), 7.97 (d, J=8.8 Hz, 1H), 7.76 (d, J=8.0 Hz, 1H), 6.79-6.70 (m, 1H), 3.96 (ddd, J=5.2, 10.0, 12.0 Hz, 1H), 3.71 (td, J=6.0, 12.0 Hz, 1H), 3.16 (dd, J=4.4, 6.8 Hz, 2H), 2.97 (ddd, J=6.0, 10.0, 16.4 Hz, 2H), 2.76 (td, J=5.2, 16.8 Hz, 2H), 2.13-1.97 (m, 2H), 1.77 (d, J=9.2 Hz, 7H), 1.66-1.50 (m, 1H), 1.37 (s, 9H), 1.30-0.78 (m, 6H).

Step 2—1-[7-[2-[1-[(4-Aminocyclohexyl)methyl]-4-piperidyl]ethynyl]-4-isoquinolyl]hexahydropyrimidine-2,4-dione To a solution of tert-butyl N-[4-[[4-[2-[4-(2,4-dioxohexahydropyrimidin-1-yl)-7-isoquinolyl]ethynyl]-1-piperidyl]methyl]cyclohexyl]carbamate (100 mg, 179 umol) in DCM (1.0 mL) was added TFA (306 mg, 2.68 mmol). The mixture was stirred at 0° C. for 1 hour. On completion, the mixture was concentrated to give the title compound (102 mg, 99% yield, TFA salt) as a white oil. LC-MS ($ESI^+$) m/z 460.3 $(M+H)^+$.

4-[3-(2,4-dioxohexahydropyrimidin-1-yl)imidazo[1,2-a]pyridin-7-yl]butanal (Intermediate JK)

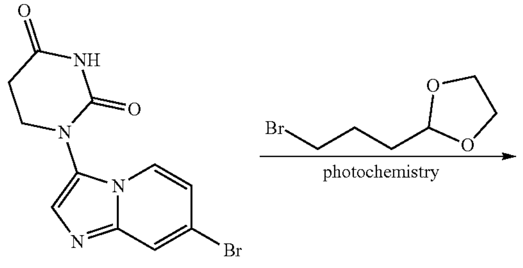

ER

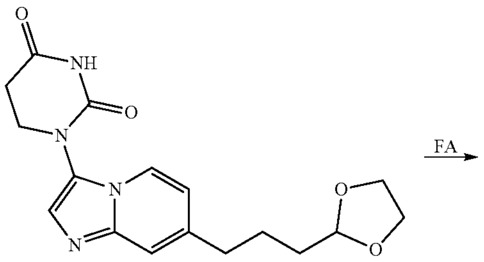

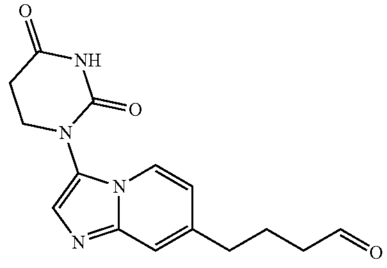

JK

Step 1—1-[7-[3-(1,3-dioxolan-2-yl)propyl]imidazo[1,2-a]pyridin-3-yl]hexahydropyrimidine-2,4-dione To a 40 mL vial equipped with a stir bar was added 1-(7-bromoimidazo[1,2-a]pyridin-3-yl) hexahydropyrimidine-2,4-dione (500 mg, 1.62 mmol, Intermediate ER), 2-(3-bromopropyl)-1,3-dioxolane (315.50 mg, 1.62 mmol), Ir[dF(CF3)ppy]2(dtbpy)(PF6) (18.2 mg, 16.2 umol), $NiCl_2$·dtbbpy (3.22 mg, 8.09 umol), TTMSS (402 mg, 1.62 mmol, 0.5 mL) in DME (8 mL). The vial was sealed and placed under nitrogen. The reaction was stirred and irradiated with a 50 W blue LED lamp (3 cm away), with cooling water to keep the reaction temperature at 25° C. for 14 hours. On completion, the reaction mixture was concentrated in vacuo to give a residue. The residue was purified by column chromatography ($SiO_2$, DCM/isopropanol=10/1 to 3/1) to give the compound (150 mg, 30% yield) as a yellow oil. $^1H$ NMR (400 MHz, DMSO-$d_6$) δ=10.77 (s, 1H), 8.69 (t, J=7.6 Hz, 2H), 8.09 (s, 1H), 7.69 (s, 1H), 7.61 (dd, J=1.7, 7.2 Hz, 1H), 7.39 (dd, J=1.2, 6.9 Hz, 1H), 4.70 (t, J=4.6 Hz, 1H), 3.73-3.70 (m, 2H), 3.67-3.62 (m, 2H), 1.71-1.57 (m, 2H), 1.55-1.43 (m, 2H); LC-MS ($ESI^+$) m/z 345.0 $(M+H)^+$.

Step 2—4-[3-(2,4-dioxohexahydropyrimidin-1-yl)imidazo[1,2-a]pyridin-7-yl]butanal A mixture of 1-[7-[3-(1,3-dioxolan-2-yl)propyl]imidazo[1,2-a]pyridin-3-yl]hexahydropyrimidine-2,4-dione (100 mg, 290 umol) in HCOOH (1.5 mL) was stirred at 20° C. for 40 minutes. On completion, the reaction mixture was concentrated in vacuo to give a compound (87.0 mg, 80% yield) as a brown solid. LC-MS ($ESI^+$) m/z 301.0 $(M+H)^+$.

Tert-butyl 2-[(Z)-3,3-dimethylbutylideneamino]acetate (Intermediate JL)

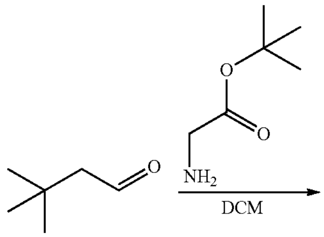

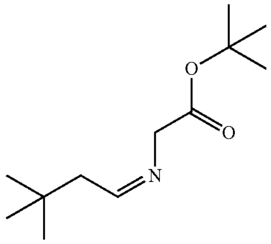

JL

A solution of tert-butyl 2-aminoacetate (10.0 g, 76.2 mmol, CAS #6456-74-2) and 3,3-dimethylbutanal (8.02 g, 80.0 mmol, 10 mL, CAS #2987-16-8) in DCM (150 mL) was stirred at 25° C. for 12 hours. On completion, the reaction mixture was concentrated under reduced pressure to remove DCM. The title compound (16.0 g, 83% yield) was obtained as a green oil. $^1H$ NMR (400 MHz, DMSO-$d_6$) δ 7.75-7.68 (m, 1H), 4.05 (s, 2H), 2.10 (d, J=5.6 Hz, 2H), 1.41 (s, 9H), 0.95 (s, 9H).

(Z)-3-(3-Chloro-2-fluoro-phenyl)-2-(4-chloro-2-fluoro-phenyl)prop-2-enenitrile (Intermediate JM)

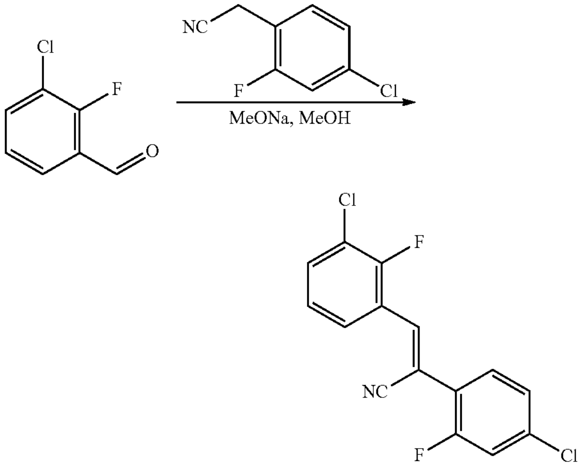

JM

To a mixture of 3-chloro-2-fluoro-benzaldehyde (10.0 g, 63.1 mmol, CAS #85070-48-0) and 2-(4-chloro-2-fluoro-phenyl) acetonitrile (10.0 g, 58.9 mmol, CAS #75279-53-7) in MeOH (250 mL) was slowly added NaOMe/MeOH reagent (5.4 M, 32.7 mL). The mixture was stirred at 45° C. for 12 hours. On completion, the reaction mixture was filtered and the filter cake was washed with $H_2O$ (6 mL) and MeOH (10 mL), and dried in vacuum to afford the title compound (18.0 g, 88% yield) as a white solid. $^1H$ NMR (400 MHz, chloroform-d) δ 8.09-8.02 (m, 1H), 7.72 (s, 1H), 7.53-7.41 (m, 2H), 7.20-7.14 (m, 3H).

Chloro-(3-chloro-2-fluoro-phenyl)-oxo-N-(4-piperidyl)dispiro[BLAH]carboxamide (Intermediate JP)

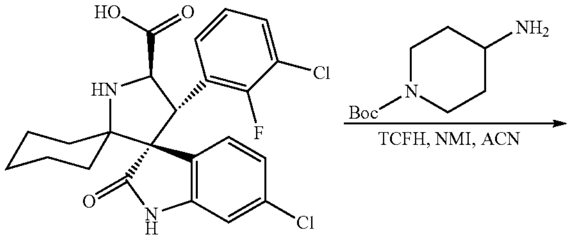

Cl

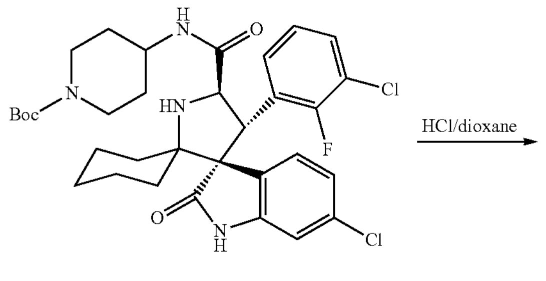

-continued

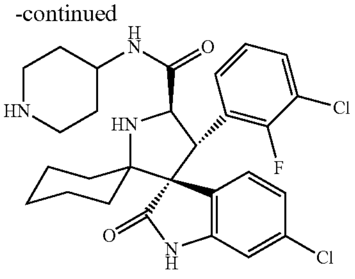

JP

Step 1—tert-butyl 4-[[chloro-(3-chloro-2-fluoro-phenyl)-oxo-dispiro [BLAH]carbonyl]amino]piperidine-1-carboxylate To a solution of chloro-(3-chloro-2-fluoro-phenyl)-oxo-dispiro[BLAH]carboxylic acid (300 mg, 647 umol, Intermediate CI) and tert-butyl 4-aminopiperidine-1-carboxylate (129 mg, 647 umol, CAS #502482-34-0) in ACN (2 mL) was added 1-methylimidazole (1.70 g, 20.7 mmol) and [chloro(dimethylamino)methylene]-dimethyl-ammonium; hexafluorophosphate (454 mg, 1.62 mmol) at 25° C. The reaction solution was stirred at 25° C. for 30 minutes. On completion, the reaction mixture was concentrated in vacuo to give a residue. The crude product was purified by reversed-phase (0.1% FA condition) to give the title compound (380 mg, 81% yield) as a white solid. LC-MS (ESI$^+$) m/z 645.2 (M+H)$^+$.

Step 2—Chloro-(3-chloro-2-fluoro-phenyl)-oxo-N-(4-piperidyl)dispiro[BLAH]carboxamide To a mixture of tert-butyl tert-butyl 4-[[chloro-(3-chloro-2-fluoro-phenyl)-oxo-dispiro[BLAH]carbonyl]amino]piperidine-1-carboxylate (50.0 mg, 77.4 umol) in DCM (0.5 mL) was added HCl/dioxane (4 M, 0.1 mL) in one portion at 25° C. under $N_2$. The mixture was stirred at 25° C. for 30 minutes. On completion, the reaction mixture was concentrated in vacuo to give the title compound (50.0 mg) as a white solid. LC-MS (ESI$^+$) m/z 545.2 (M+H)$^+$.

7-[1-(2,6-dioxo-3-piperidyl)-3-methyl-2-oxo-benzimidazol-5-yl]hept-6-ynal (Intermediate JO)

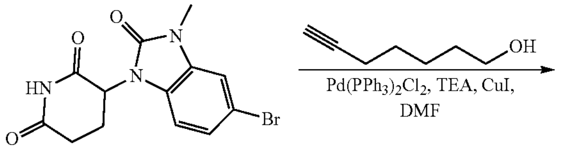

E

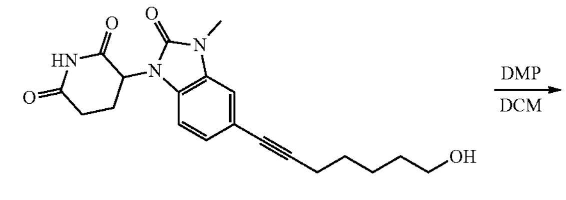

-continued

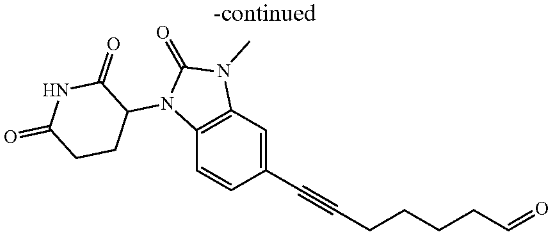

JQ

Step 1—3-[5-(7-hydroxyhept-1-ynyl)-3-methyl-2-oxo-benzimidazol-1-yl]piperidine-2,6-dione To a solution of 3-(5-bromo-3-methyl-2-oxo-benzimidazol-1-yl)piperidine-2,6-dione (300 mg, 887 umol, Intermediate E), hept-6-yn-1-ol (119 mg, 1.06 mmol) in DMF (5 mL) was added CuI (8.45 mg, 44.3 umol), TEA (897 mg, 8.87 mmol), and $Pd(PPh_3)_2Cl_2$ (62.2 mg, 88.7 umol), The mixture was stirred at 80° C. for 5 hours. On completion, the reaction mixture was concentrated in vacuo to give a residue. The residue was purified by column chromatography ($SiO_2$, Petroleum ether/Ethyl acetate=10/1 to 0/1) to give the title compound (380 mg, 81% yield) as a white solid. LC-MS ($ESI^+$) m/z 370.1 $(M+H)^+$.

Step 2—7-[1-(2,6-dioxo-3-piperidyl)-3-methyl-2-oxo-benzimidazol-5-yl]hept-6-ynal To a solution of 3-[5-(7-hydroxyhept-1-ynyl)-3-methyl-2-oxo-benzimidazol-1-yl]piperidine-2,6-dione (40.0 mg, 108 umol) in DCM (1 mL) was added DMP (68.8 mg, 162 umol). The reaction was stirred at 25° C. for 30 minutes. On completion, the mixture was quenched with sodium thiosufate (2 mL) and $NaHCO_3$ (2 ml), then extracted with dichloromethane (5 mL×3). The organic layer was dried over $Na_2SO_4$, and concentrated in vacuo to afford the title compound (35.0 mg) as white solid. LC-MS ($ESI^+$) m/z 368.2 $(M+H)^+$.

3-[3-Methyl-2-oxo-5-[3-(2-oxopiperazin-1-yl)propyl]benzimidazol-1-yl]piperidine-2,6-dione (Intermediate JR)

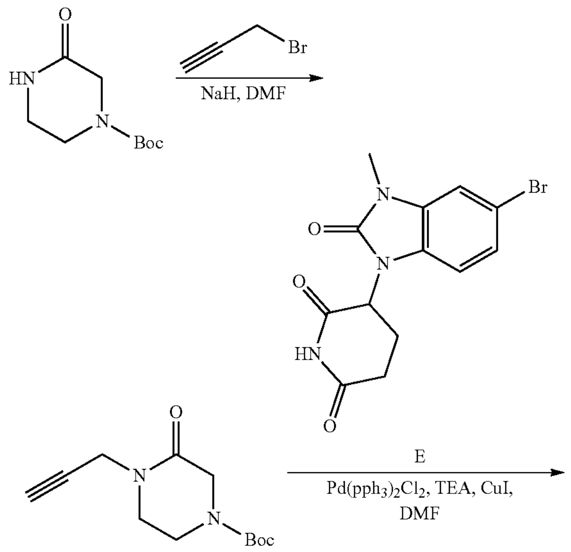

-continued

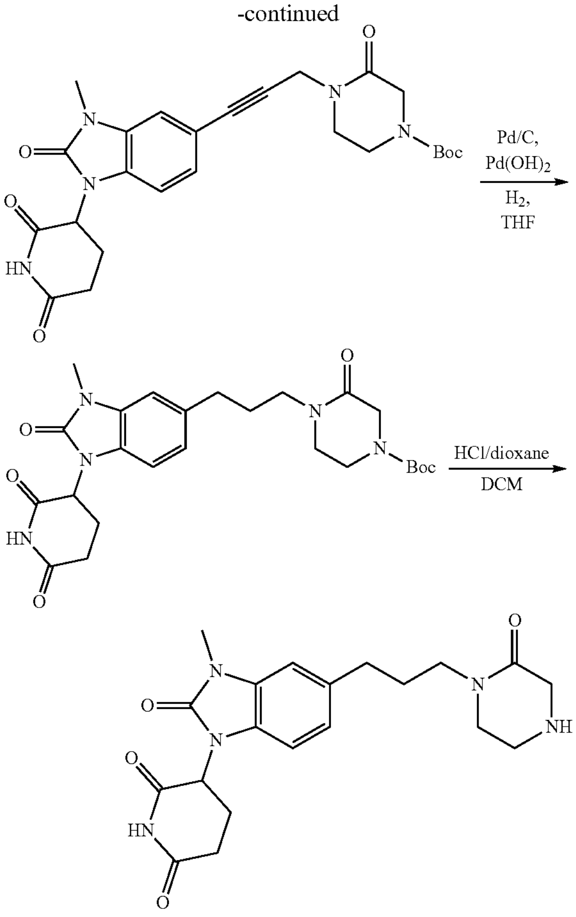

JR

Step 1—Tert-butyl 3-oxo-4-prop-2-ynyl-piperazine-1-carboxylate

To a solution of tert-butyl 3-oxopiperazine-1-carboxylate (3.00 g, 14.9 mmol, CAS #76003-29-7) in THF (25 mL) was added NaH (1.00 g, 25.0 mmol, 60% dispersion in mineral oil) for 25° C. under $N_2$ atmosphere, then the mixture was stirred at 1 hour for 25° C. Next, 3-bromoprop-1-yne (1.96 g, 16.4 mmol, CAS #106-96-7) was added at 25° C. and the mixture was stirred at 25° C. for 0.5 hour. On completion, the mixture was quenched with water (200 mL) and extracted with ethyl acetate (100 mL×3). The combined organic phase was washed with the solution of saturated sodium chloride and was dried over anhydrous sodium sulfate, filtered and concentrated to give a residue. The residue was purified by column chromatography ($SiO_2$, Petroleum ether/Ethyl acetate=1:0 to 0:1) to give the title compound (3.06 g, 86% yield) as a colorless oil. $^1H$ NMR (400 MHz, $CDCl_3$-d) δ 4.29 (d, J=2.4 Hz, 2H), 4.11 (s, 2H), 3.72-3.66 (m, 2H), 3.51-3.45 (m, 2H), 2.27-2.24 (m, 1H), 1.47 (s, 9H).

Step 2—Tert-butyl 4-[3-[1-(2,6-dioxo-3-piperidyl)-3-methyl-2-oxo-benzimidazol-5-yl]prop-2-ynyl]-3-oxo-piperazine-1-carboxylate A mixture of tert-butyl 3-oxo-4-prop-2-ynyl-piperazine-1-carboxylate (1.50 g, 6.30 mmol), 3-(5-bromo-3-methyl-2-oxo-benzimidazol-1-yl)piperidine-2,6-dione (1.06 g, 3.15 mmol, Intermediate E), $Pd(PPh_3)_2Cl_2$ (220 mg, 314 umol), TEA (3.18 g, 31.4 mmol) and CuI (119 mg, 629 umol) in DMF (15 mL) was degassed and purged with $N_2$ three times. Then the mixture was stirred at 80° C. for 16 hours under $N_2$ atmosphere. On completion, the mixture was quenched with water (20 mL) and extracted with ethyl acetate (25 mL×3). The combined organic phase was dried over anhydrous sodium sulfate, filtered and concentrated to give a residue. The residue was purified by reversed-phase HPLC (0.1% FA condition) to give the title compound (700 mg, 45% yield, FA salt) as a yellow solid. $^1H$ NMR (400 MHz, DMSO-d6) δ 11.11 (s, 1H), 7.32 (d, J=0.8 Hz, 1H), 7.23-7.16 (m, 1H), 7.16-7.13 (m, 1H), 5.41-5.35 (m, 1H), 4.46 (s, 2H), 3.97 (s, 2H), 3.66-3.59 (m, 2H), 3.51-3.46 (m, 2H), 3.34 (s, 3H), 2.95-2.83 (m, 2H), 2.76-2.65 (m, 2H), 1.41 (s, 9H); LC-MS ($ESI^+$) m/z 496.2 $(M+H)^+$.

Step 3—Tert-butyl 4-[3-[1-(2,6-dioxo-3-piperidyl)-3-methyl-2-oxo-benzimidazol-5-yl]propyl]-3-oxo-piperazine-1-carboxylate To a solution of tert-butyl 4-[3-[1-(2,6-dioxo-3-piperidyl)-3-methyl-2-oxo-benzimidazol-5-yl]prop-2-ynyl]-3-oxo-piperazine-1-carboxylate (300 mg, 605 umol) in THF (5 mL) was added Pd/C (80.0 mg, 10 wt %) and $Pd(OH)_2$ (80 mg) under $N_2$ atmosphere. The suspension was degassed and purged with $H_2$ three times. The mixture was stirred under $H_2$ (15 Psi) at 25° C. for 16 hours. On completion, the mixture was filtered and concentrated to give the title compound (290 mg, 96% yield, TFA salt) as a yellow solid. LC-MS ($ESI^+$) m/z 444.5 $(M-56)^+$.

Step 4—3-[3-Methyl-2-oxo-5-[3-(2-oxopiperazin-1-yl)propyl]benzimidazol-1-yl]piperidine-2,6-dione To a solution of tert-butyl 4-[3-[1-(2,6-dioxo-3-piperidyl)-3-methyl-2-oxo-benzimidazol-5-yl] propyl]-3-oxo-piperazine-1-carboxylate (50.0 mg, 100 umol) in DCM (2 mL) was added HCl/dioxane (4 M). The mixture was stirred at 25° C. for 0.5 hour. On completion, the mixture was filtered and concentrated to give the title compound (38.0 mg, 87% yield, HCl salt) as a yellow solid. LC-MS ($ESI^+$) m/z 400.2 $(M+H)^+$.

1-[8-(3-Piperazin-1-ylprop-1-ynyl)imidazo[1,2-a]pyridin-3-yl]hexahydropyrimidine-2,4-dione (Intermediate JS)

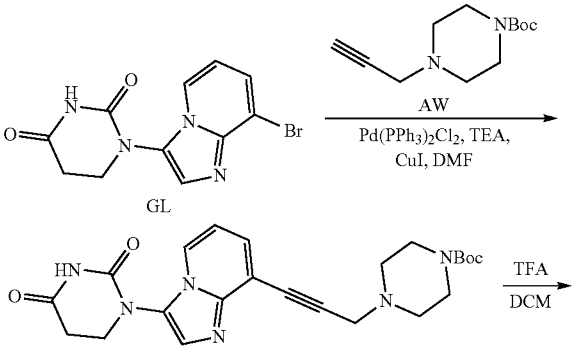

-continued

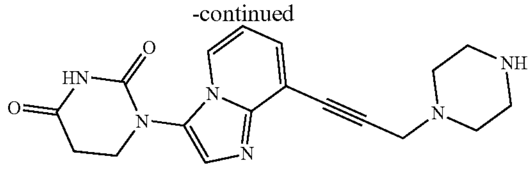

JS

Step 1—Tert-butyl 4-[3-[3-(2,4-dioxohexahydropyrimidin-1-yl)imidazo[1,2-a]pyridin-8-yl]prop-2-ynyl]piperazine-1-carboxylate A mixture of 1-(8-bromoimidazo[1,2-a]pyridin-3-yl)hexahydropyrimidine-2,4-dione (185 mg, 598 umol, Intermediate GL), tert-butyl 4-prop-2-ynylpiperazine-1-carboxylate (268 mg, 1.20 mmol, Intermediate AW), $Pd(PPh_3)_2Cl_2$ (42.0 mg, 59.8 umol), TEA (605 mg, 5.98 mmol) and CuI (22.8 mg, 119 μmol) in DMF (12 mL) was degassed and purged with $N_2$ three times. Then the mixture was stirred at 80° C. for 16 hours under $N_2$ atmosphere. On completion, the mixture was quenched with water (20 mL) and extracted with ethyl acetate (25 mL×3). The combined organic phase was dried over anhydrous sodium sulfate, filtered and concentrated to give a residue. The residue was purified by reversed-phase HPLC (0.1% FA condition), to give the title compound (230 mg, 85% yield, FA salt) as a yellow solid. $^1H$ NMR (400 MHz, DMSO-d6) δ 10.72 (s, 1H), 8.84 (s, 1H), 8.53 (s, 1H), 7.70 (d, J=6.8 Hz, 1H), 7.13 (s, 1H), 4.43 (s, 1H), 3.86-3.78 (m, 2H), 3.60 (s, 2H), 3.53-3.47 (m, 2H), 3.29 (s, 3H), 3.12-3.04 (m, 2H), 2.90-2.80 (m, 2H), 1.41 (d, J=2.0 Hz, 9H); LC-MS ($ESI^+$) m/z 453.2 $(M+H)^+$.

Step 2—1-[8-(3-Piperazin-1-ylprop-1-ynyl)imidazo[1,2-a]pyridin-3-yl]hexahydropyrimidine-2,4-dione To a solution of tert-butyl 4-[3-[3-(2,4-dioxohexahydropyrimidin-1-yl)imidazo[1,2-a]pyridin-8-yl]prop-2-ynyl] piperazine-1-carboxylate (60.0 mg, 132 umol) in DCM (1 mL) was added TFA (151 mg, 1.33 mmol). The mixture was stirred at 25° C. for 0.5 hour. On completion, the mixture was filtered and concentrated to give the title compound (60.0 mg, 97% yield, TFA salt) as a yellow oil. LC-MS ($ESI^+$) m/z 353.2 $(M+H)^+$.

2-[4-[(1S)-1-(4-chlorophenyl)-7-isopropoxy-6-methoxy-3-oxo-1,4-dihydroisoquinolin-2-yl]-N-methyl-anilino]acetic acid (Intermediate JT)

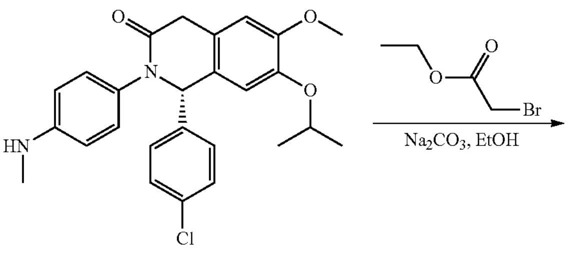

IB

-continued

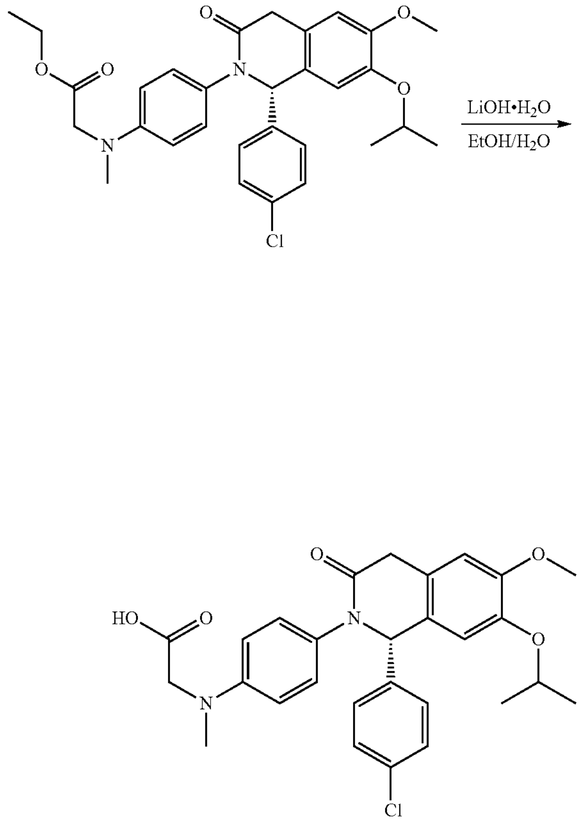

JT

Step 1—ethyl 2-[4-[(1S)-1-(4-chlorophenyl)-7-isopropoxy-6-methoxy-3-oxo-1,4-dihydroisoquinolin-2-yl]-N-methyl-anilino]acetate To a mixture of tert-butyl (1S)-1-(4-chlorophenyl)-7-isopropoxy-6-methoxy-2-[4-(methylamino) phenyl]-1,4-dihydroisoquinolin-3-one (80.0 mg, 177 umol, Intermediate IB), ethyl 2-bromoacetate (88.8 mg, 532 umol) in EtOH (2 mL) was added $Na_2CO_3$ (56.4 mg, 532 umol) in one portion at 80° C. under $N_2$. The mixture was then stirred at 80° C. for 14 hours. On completion, the reaction mixture was concentrated in vacuo to give the title compound (90.0 mg, 93% yield) as a white solid. LC-MS ($ESI^+$) m/z 537.2 $(M+H)^+$.

Step 2—2-[4-[(1S)-1-(4-chlorophenyl)-7-isopropoxy-6-methoxy-3-oxo-1,4-dihydroisoquinolin-2-yl]-N-methyl-anilino]acetic acid To a mixture of tert-butyl ethyl 2-[4-[(1S)-1-(4-chlorophenyl)-7-isopropoxy-6-methoxy-3-oxo-1,4-dihydroisoquinolin-2-yl]-N-methyl-anilino]acetate (80.0 mg, 148 umol) in EtOH (2 mL) and $H_2O$ (2 mL) was added LiOH aqueous (1 M, 1.0 mL) in one portion at 25° C. under $N_2$. Then the mixture was stirred at 25° C. for 3 hours. On completion, the mixture was extracted with EA (5 mL×3). The organic layer was dried over $Na_2SO_4$, and concentrated in vacuo to give the title compound (70.0 mg 87% yield) as a white solid. LC-MS ($ESI^+$) m/z 509.2 $(M+H)^+$.

2-[4-[[chloro-(3-chloro-2-fluoro-phenyl)-oxo-dispiro[BLAH]carbonyl]amino]-1-piperidyl]acetic acid (Intermediate JU)

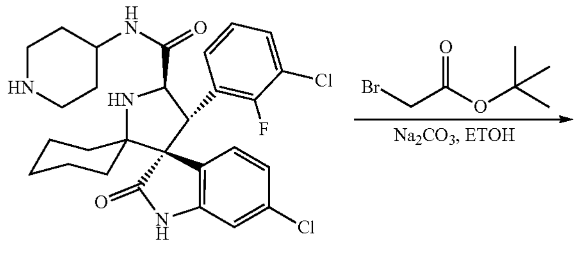

JP

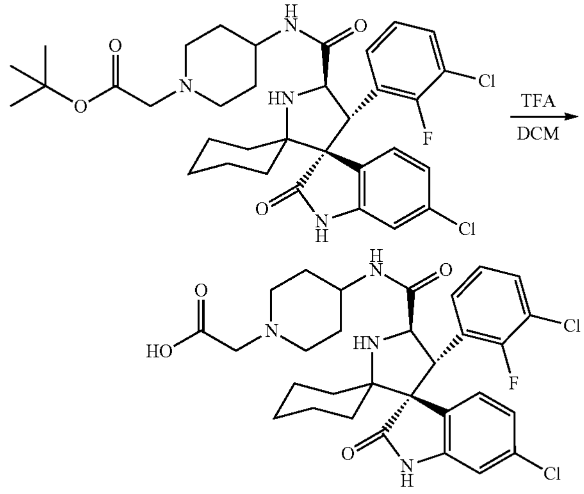

JU

Step 1—tert-butyl 2-[4-[[chloro-(3-chloro-2-fluoro-phenyl)-oxo-dispiro[BLAH]carbonyl]amino]-1-piperidyl]acetate To a mixture of tert-butyl tert-butyl 2-bromoacetate (160 mg, 824 umol, CAS #5292-43-3), chloro-(3-chloro-2-fluoro-phenyl)-oxo-N-(4-piperidyl)dispiro[BLAH]carboxamide (90.0 mg, 164 μmol, Intermediate JP) in EtOH (1 mL) was added $Na_2CO_3$ (52.4 mg, 494 umol) in one portion at 25° C. under $N_2$. Then the mixture was stirred at 25° C. for 3 hours. On completion, the mixture was concentrated to give a residue. The residue was poured into water (10 mL) and extracted with ethyl acetate (3×10 mL). The combined organic phase was washed with brine dried with anhydrous $Na_2SO_4$, filtered and concentrated in vacuo to give the title compound (90.0 mg) as a white solid. LC-MS ($ESI^+$) m/z 689.3 $(M+H)^+$.

Step 2—2-[4-[[chloro-(3-chloro-2-fluoro-phenyl)-oxo-dispiro[BLAH]carbonyl]amino]-1-piperidyl] acetic acid To a mixture of tert-butyl tert-butyl 2-[4-[[chloro-(3-chloro-2-fluoro-phenyl)-oxo-dispiro[BLAH]carbonyl] amino]-1-piperidyl]acetate (70.0 mg, 106 umol) in DCM (1 mL) was added TFA (12.1 mg, 106 umol) in one portion at 25° C. under $N_2$. The mixture was stirred at 25° C. for 12 hours.. On completion, the reaction mixture was concentrated in vacuo to give the title compound (60.0 mg) as a white solid. LC-MS (ESI+) m/z 603.6 (M+H)+.

1-(4-Chlorophenyl)-7-isopropoxy-6-methoxy-2-[4-[methyl(4-piperidylmethyl)amino]phenyl]-1,4-dihydroisoquinolin-3-one (Intermediate JV)

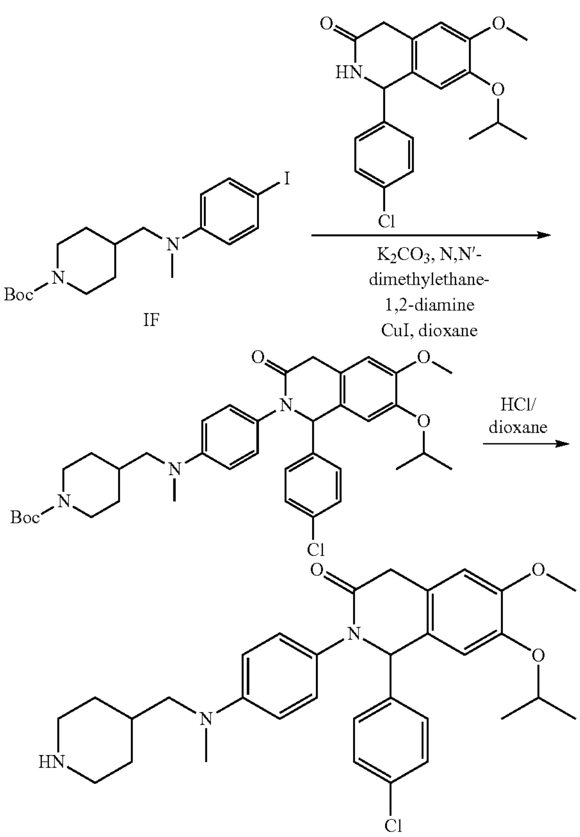

IF

JV

Step 1—Tert-butyl 4-[[4-[1-(4-chlorophenyl)-7-isopropoxy-6-methoxy-3-oxo-1,4-dihydroisoquinolin-2-yl]-N-methyl-anilino]methyl]piperidine-1-carboxylate To a solution of 1-(4-chlorophenyl)-7-isopropoxy-6-methoxy-2,4-dihydro-1H-isoquinolin-3-one (386 mg, 1.12 mmol, CAS #1313366-29-8) in dioxane (10 mL) was added tert-butyl 4-[(4-iodo-N-methyl-anilino)methyl]piperidine-1-carboxylate (1.20 g, 2.79 mmol, Intermediate IF), N,N'-dimethylethane-1,2-diamine (9.83 mg, 111 umol), CuI (10.6 mg, 55.8 umol) and $K_2CO_3$ (308 mg, 2.23 mmol). The mixture was degassed and purged with $N_2$ three times, and then the mixture was stirred at 120° C. for 20 hours under $N_2$ atmosphere. On completion, the mixture was quenched with water (20 mL) and extracted with ethyl acetate (15 mL×3). The combined organic phases were dried over anhydrous sodium sulfate, filtered and concentrated to give a residue. The residue was purified by column chromatography ($SiO_2$, Petroleum ether/Ethyl acetate=1:0 to 1:1) to give the title compound (219 mg, 30% yield) as a brown oil. LC-MS (ESI+) m/z 592.2 (M+H−56)+.

Step 2—1-(4-Chlorophenyl)-7-isopropoxy-6-methoxy-2-[4-[methyl(4-piperidylmethyl)amino]phenyl]-1,4-dihydroisoquinolin-3-one To a solution of tert-butyl 4-[[4-[1-(4-chlorophenyl)-7-isopropoxy-6-methoxy-3-oxo-1,4-dihydroisoquinolin-2-yl]-N-methyl-anilino]methyl]piperidine-1-carboxylate (60.0 mg, 92.6 umol) in DCM (2.0 mL) was added HCl/dioxane (33.8 mg, 4 M). The mixture was stirred at 25° C. for 1 hour. On completion, the mixture was concentrated to give the title compound (54.0 mg, 99% yield, HCl) as a red solid. LC-MS (ESI+) m/z 548.5 (M+H)+.

Chloro-(2-chloro-3-fluoro-4-pyridyl)-dimethyl-oxo-N-(4-piperidyl)dispiro [BLAH]carboxamide (Intermediate JW)

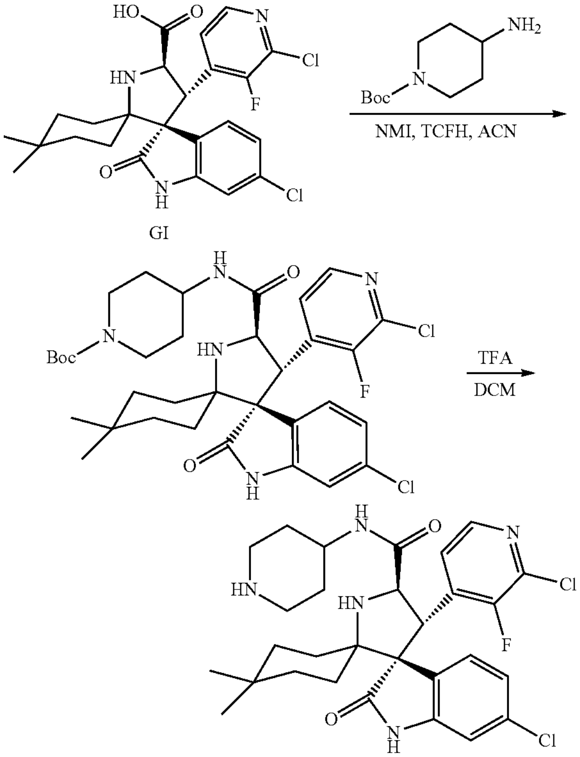

GI

JW

Step 1—Tert-butyl 4-[[chloro-(2-chloro-3-fluoro-4-pyridyl)-dimethyl-oxo-dispiro[BLAH]carbonyl]amino]piperidine-1-carboxylate To a solution of chloro-(2-chloro-3-fluoro-4-pyridyl)-dimethyl-oxo-dispiro[BLAH]carboxylic acid (1.00 g, 2.03 mmol, Intermediate GI) and tert butyl 4-aminopiperidine-1-carboxylate (406 mg, 2.03 mmol, CAS #502482-34-0) in ACN (10 mL) was added 1-methylimidazole (1.67 g, 20.3 mmol) and [chloro(dimethylamino)methylene]-dimethyl-ammonium; hexafluorophosphate (1.99 g, 7.11 mmol). The mixture was stirred at 25° C. for 2 hours. On completion, the mixture was concentrated to give a residue. The residue was purified by reverse phase column chromatography (water (0.1% FA)–ACN) to give the title compound (570 mg, 28% yield) as a yellow solid. $^1H$ NMR (400 MHz, DMSO-$d_6$) δ=10.62 (s, 1H), 8.17 (d, J=5.2 Hz, 1H), 7.89 (d, J=8.4 Hz, 1H), 7.63 (t, J=5.2 Hz, 1H), 7.49 (dd, J=1.6, 8.0 Hz, 1H), 7.06 (dd, J=2.0, 8.0 Hz, 1H), 6.71 (d, J=2.0 Hz, 1H), 4.57 (d, J=9.2 Hz, 1H), 4.45 (t, J=9.2 Hz, 1H), 3.91-3.78 (m, 2H), 3.75-3.63 (m, 1H), 3.50 (d, J=10.4 Hz, 1H), 2.84 (d, J=2.4 Hz, 2H), 2.07 (s, 1H), 1.70 (d, J=11.6 Hz, 4H), 1.64-1.48 (m, 2H), 1.40 (s, 9H), 1.33 (dd, J=3.2, 10.8 Hz, 1H), 1.25-1.07 (m, 3H), 1.02-0.93 (m, 1H), 0.88 (s, 3H), 0.59 (s, 3H); LC-MS ($ESI^+$) m/z 674.3 $(M+H)^+$.

Step 2—Chloro-(2-chloro-3-fluoro-4-pyridyl)-dimethyl-oxo-N-(4-piperidyl)dispiro [BLAH]carboxamide To a solution of tert-butyl 4-[[chloro-(2-chloro-3-fluoro-4-pyridyl)-dimethyl-oxo-dispiro [BLAH] carbonyl] amino] piperidine-1-carboxylate (150 mg, 222 umol) in DCM (1.0 mL) was added TFA (924 mg, 8.10 mmol). The mixture was stirred at 25° C. for 30 minutes. On completion, the mixture was concentrated to give the title compound (120 mg, 93% yield, TFA salt) as a yellow oil. LC-MS ($ESI^+$) m/z 574.6 $(M+H)^+$.

2-[4-[[Chloro-(2-chloro-3-fluoro-4-pyridyl)-dimethyl-oxo-dispiro[BLAH]carbonyl]amino]-1-piperidyl]acetic acid (Intermediate JX)

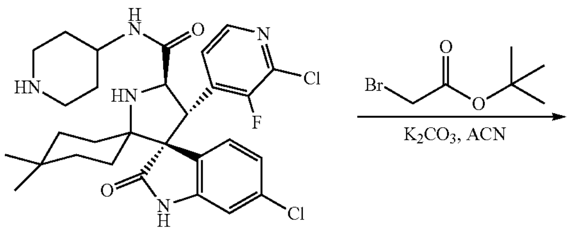

JW

-continued

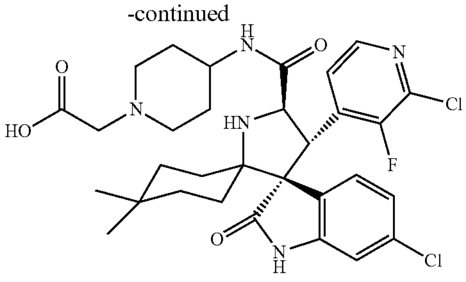

JX

Step 1—Tert-butyl 2-[4-[[chloro-(2-chloro-3-fluoro-4-pyridyl)-dimethyl-oxo-dispiro [BLAH]carbonyl] amino]-1-piperidyl]acetate To a solution of chloro-(2-chloro-3-fluoro-4-pyridyl)-dimethyl-oxo-N-(4-piperidyl)dispiro [BLAH]carboxamide (120 mg, 174 umol, TFA salt, Intermediate JW) in ACN (2.0 mL) was added $K_2CO_3$ (240 mg, 1.74 mmol) and tert-butyl 2-bromoacetate (40.7 mg, 209 umol, CAS #5292-43-3). The mixture was stirred at 25° C. for 2 hours. On completion, the mixture was concentrated to give a residue. The residue was poured into water (10 mL) and extracted with ethyl acetate (3×10 mL).The combined organic phase was washed with brine dried with anhydrous $Na_2SO_4$, filtered and concentrated in vacuo to give the title compound (180 mg, 99% yield) as a yellow oil. LC-MS ($ESI^+$) m/z 688.3 $(M+H)^+$.

Step 2—2-[4-[[Chloro-(2-chloro-3-fluoro-4-pyridyl)-dimethyl-oxo-dispiro[BLAH]carbonyl] amino]-1-piperidyl]acetic acid

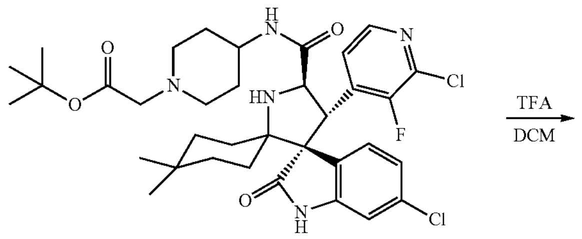

To a solution of tert-butyl 2-[4-[[chloro-(2-chloro-3-fluoro-4-pyridyl)-dimethyl-oxo-dispiro[BLAH] carbonyl] amino]-1-piperidyl]acetate (90.0 mg, 130 umol) in DCM (1.0 mL) was added TFA (231 mg, 2.03 mmol). The mixture was stirred at 25° C. for 12 hours. On completion, the mixture was concentrated in vacuo to give the title compound (90.0 mg, 92% yield, TFA salt) as a brown oil. LC-MS ($ESI^+$) m/z 632.3 $(M+H)^+$.

Example 1 (Method 1): Synthesis of 4-[2-[(3R,5R,6S)-5-(3-chlorophenyl)-6-(4-chlorophenyl)-3-methyl-1-[(2S)-3-methyl-1-(propane-2-sulfonyl)butan-2-yl]-2-oxopiperidin-3-yl]acetamido]-N-[7-[(4-[2-[(3R,5R,6S)-5-(3-chlorophenyl)-6-(4-chlorophenyl)-3-methyl-1-[(2S)-3-methyl-1-(propane-2-sulfonyl)butan-2-yl]-2-oxopiperidin-3-yl]acetamido]phenyl)formamido]heptyl]benzamide (I-8)

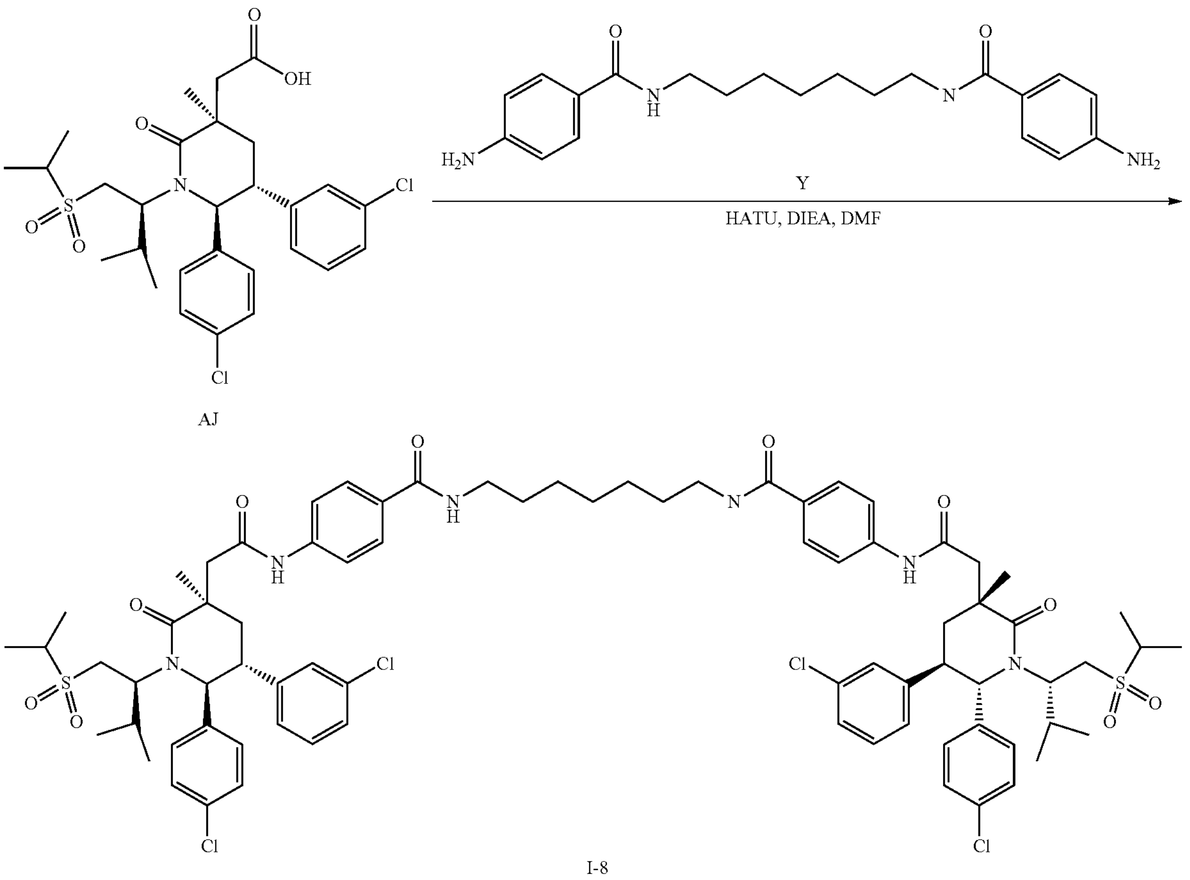

To a stirred solution of 4-amino-N-[7-[(4-aminophenyl) formamido]heptyl] benzamide (30 mg, 0.081 mmol, Intermediate Y) and [(3R,5R,6S)-5-(3-chlorophenyl)-6-(4-chlorophenyl)-3-methyl-1-[(2S)-3-methyl-1-(propane-2-sulfonyl)butan-2-yl]-2-oxopiperidin-3-yl]acetic acid (93 mg, 0.16 mmol, Intermediate AJ) in DMF (2 mL) were added DIEA (42 mg, 0.33 mmol) and HATU (43 mg, 0.12 mmol) at room temperature. The resulting mixture was stirred for overnight at rt and then purified by Prep-HPLC (Column: XBridge Shield RP18 OBD Column, 30×150 mm, 5 um; Mobile Phase A: Water (plus 10 mmol/L FA); Mobile Phase B: $CH_3CN$; Flow rate: 60 mL/min; Gradient: 65% B to 85% B in 7 min; Detector: UV 254/220 nm; Desired fractions were collected at 6.3 min) and concentrated under reduced pressure and lyophilized to afford title compound (7.9 mg, 7%) as a white solid. $^1$H NMR (400 MHz, $CD_3OD$) δ 7.91-7.76 (m, 8H), 7.30-7.20 (m, 8H), 7.11-7.00 (m, 4H), 6.88-6.84 (m, 4H), 5.12 (d, J=11.0 Hz, 2H), 4.03 (dd, J=13.9, 10.5 Hz, 2H), 3.56-3.46 (m, 2H), 3.41-3.32 (m, 6H), 3.18-3.09 (m, 2H), 3.07 (d, J=13.3 Hz, 2H), 2.63 (d, J=13.3 Hz, 2H), 2.34 (t, J=13.7 Hz, 2H), 2.25-2.21 (m, 2H), 2.16 (dd, J=13.7, 3.1 Hz, 2H), 1.67-1.64 (m, 4H), 1.51-1.25 (m, 26H), 0.70 (d, J=6.6 Hz, 6H), 0.58 (d, J=6.9 Hz, 6H); LC/MS (ESI, m/z): $[(M+1)]^+$=1468.9.

TABLE 8

Compounds synthesized via Method 1 using the corresponding amines and acids for the coupling.

| I-# | Amine | Acid | LCMS (ESI, m/z): $[(M + 1)]^+$ | $^1$H NMR (400 MHz) δ |
|---|---|---|---|---|
| I-2[b] | AZ | AN | 700.3 | (DMSO-$d_6$) 10.40 (s, 1H), 8.48-8.43 (m, 1H), 8.31 (d, J = 8.4 Hz, 1H), 7.73 (t, J = 6.8 Hz, 1H), 7.62-7.51 (m, 3H), 7.50-7.45 (m, 1H), 7.42-7.31 (m, 3H), 4.63-4.54 (m, |

TABLE 8-continued

Compounds synthesized via Method 1 using the corresponding amines and acids for the coupling.

| I-# | Amine | Acid | LCMS (ESI, m/z): $[(M + 1)]^+$ | $^1H$ NMR (400 MHz) δ |
|---|---|---|---|---|
| | | | | 2H), 4.43-4.34 (m, 1H), 3.96 (d, J = 10.8 Hz, 1H), 3.92 (s, 3H), 3.31-3.21 (m, 3H), 2.71 (t, J = 7.6 Hz, 2H), 2.53-2.51 (m, 1H), 1.70-1.61 (m, 1H), 1.58-1.48 (m, 4H), 1.39-1.31 (m, 2H), 1.27 (d, J = 13.6 Hz, 1H), 0.98 (s, 9H) |
| I-3[b] | AZ | AJ | 652.3 | (DMSO-$d_6$) 8.46 (s, 1H), 8.24 (t, J = 5.6 Hz, 1H), 7.45-7.25 (m, 2H), 7.26-7.19 (m, 1H), 7.18-7.13 (m, 1H), 7.01-6.94 (m, 2H), 5.00 (d, J = 11.2Hz, 1H), 3.90-3.79 (m, 1H), 3.64-3.54 (m, 1H), 3.44-3.33 (m, 1H), 3.24-2.94 (m, 5H), 2.82 (d, J = 13.2Hz, 1H), 2.63 (t, J = 7.6Hz, 2H), 2.53-2.51 (m, 1H), 2.34 (d, J = 13.2Hz, 1H), 2.18-2.07 (m, 1H), 2.05-1.95 (m, 2H), 1.50-1.33 (m, 4H), 1.33-1.23 (m, 9H), 1.22 (s, 3H), 0.55 (d, J = 6.4Hz, 3H), 0.40 (d, J = 6.8 Hz, 3H) |
| I-7[a] | AQ | AN | 730.4 | (DMSO-$d_6$) 10.40 (s, 1H), 8.48 (t, J = 5.6 Hz, 1H), 8.44 (s, 1H), 8.31 (d, J = 8.4 Hz, 1H), 7.73 (t, J = 6.8 Hz, 1H), 7.61-7.51 (m, 3H), 7.50-7.46 (m, 1H), 7.42-7.32 (m, 3H), 4.62-4.56 (m, 2H), 4.43-4.34 (m, 1H), 3.96 (d, J = 11.2 Hz, 2H), 3.92 (s, 3H), 3.41 (s, 2H), 3.30 (s, 2H), 2.77 (t, J = 7.2 Hz, 2H), 1.81-1.69 (m, 4H), 1.68-1.59 (m, 1H), 1.27 (d, J = 13.6 Hz, 1H), 0.97 (s, 9H). |
| I-9 | R | AM | 910.4 | ($CD_3OD$) 7.79 (d, J = 8.5 Hz, 2H), 7.73-7.64 (m, 3H), 7.46 (dd, J= 8.2, 2.4 Hz, 1H), 7.26 (t, J = 7.5 Hz, 1H), 7.11-7.02 (m, 2H), 7.00 (d, J = 7.6 Hz, 1H), 6.95 (dd, J = 8.5, 2.3 Hz, 2H), 6.75 (d, J = 1.9 Hz, 1H), 5.35-5.31 (m, 1H), 4.85 (d, J = 9.4 Hz, 1H), 4.75 (d, J = 9.3 Hz, 1H), 3.66 (s, 3H), 3.40 (t, J = 6.9 Hz, 2H), 3.01 (t, J = 7.7 Hz, 2H), 2.94- 2.72 (m, 2H), 2.12 (d, J = 13.3 Hz, 2H), 1.99 (d, J = 14.0 Hz, 1H), 1.87-1.47 (m, 13H), 1.17-0.86 (m, 2H) |
| I-10 | AL | AJ | 1121.9 | ($CD_3OD$) 8.89 (s, 1H), 7.52-7.42 (m, 4H), 7.34-7.26 (m, 4H), 7.16-7.06 (m, 2H), 7.05- 6.99 (m, 2H), 5.11 (d, J = 11.1 Hz, 1H), 4.70-4.61 (m, 1H), 4.60-5.56 (m, 1H), 4.53-4.46 (m, 1H), 4.38 (d, J = 15.5 Hz, 1H), 4.05-3.97 (m, 1H), 3.92 (d, J = 10.9 Hz, 1H), 3.82 (dd, J = 11.0, 3.9 Hz, 1H), 3.68-3.46 (m, 1H), 3.32-3.18 (m, 5H), 3.15-3.09 (m, 1H), 2.89 (d, J = 13.4 Hz, 1H), 2.52-2.48 (m, 4H), 2.35-2.15 (m, 4H), 2.15-2.01 (m, 2H), 1.72-1.47 (m, 2H), 1.42 (d, J = 6.8 Hz, 7H), 1.38-1.34 (m, 11H), 1.05 (s, 9H), 0.68 (d, J = 6.6 Hz, 3H), 0.54 (d, J = 6.9 Hz, 3H) |
| I-11 | X | AJ | 1067.2 | ($CD_3OD$) 8.89 (s, 1H), 7.54-7.38 (m, 4H), 7.35-7.26 (m, 4H), 7.17-6.92 (m, 4H), 5.11 (d, J= 11.0 Hz, 1H), 4.66-4.56 (m, 2H), 4.55-4.46 (m, 2H), 4.38 (d, J = 15.5 Hz, 1H), 4.02 (dd, J = 13.9, 10.4 Hz, 1H), 3.93 (d, J = 11.0 Hz, 1H), 3.83 (dd, J = 11.0, 3.9 Hz, 1H), 3.59 (q, J = 14.4, 12.1 Hz, 1H), 3.31-3.17 (m, 5H), 3.15-3.04 (m, 1H), 2.89 (d, J = 13.4 Hz, 1H), 2.52-2.48 (m, 4H), 2.42 -2.14 (m, 4H), 2.10 (tq, J = 10.5, 3.5, 2.5 Hz, 2H), 1.86-1.82 (m, 2H), 1.42 (dd, J = 6.8, 1.2 Hz, 6H), 1.35 (s, 3H), 1.05 (s, 9H), 0.68 (d, J = 6.5 Hz, 3H), 0.52 (d, J = 6.9 Hz, 3H) |
| I-12 | AL | AM | 1135.9 | ($CD_3OD$) 8.89 (s, 1H), 7.87-7.76 (m, 2H), 7.74-7.65 (m, 3H), 7.55-7.38 (m, 5H), 7.33-7.21 (m, 1H), 7.13-7.00 (m, 2H), 6.75 (d, J = 1.9 Hz, 1H), 4.82 (d, J = 9.4 Hz, 1H), 4.73 (d, J = 9.3 Hz, 1H), 4.65 (s, 1H), 4.63-4.46 (m, 3H), 4.37 (d, J = 15.5 Hz, 1H), 3.92 (d, J = 11.0 Hz, 1H), 3.81 (dd, J = 11.0, 3.9 Hz, 1H), 3.41-3.35 (m, 2H), 2.49 (s, 3H), 2.39-2.18 (m, 3H), 2.17-1.88 (m, 3H), 1.87-1.52 (m, 10H), 1.41-1.37 (m, 6H), 1.05-1.02 (m, 11H) |
| I-13 | X | AM | 1079.8 | ($CD_3OD$) 8.88 (s, 1H), 7.91-7.80 (m, 2H), 7.75-7.61 (m, 3H), 7.55-7.36 (m, 5H), 7.25 (td, J = 7.5, 6.9, 1.6 Hz, 1H), 7.14-7.02 (m, 2H), 6.75 (d, J = 2.0 Hz, 1H), 4.83 (d, J = 9.4 Hz, 1H), 4.74 (d, J = 9.3 Hz, 1H), 4.65-4.52 (m, 4H), 4.36 (d, J = 15.5 Hz, 1H), 3.94 (d, J = 11.0 Hz, 1H), 3.82 (dd, J = 11.0, 4.0 Hz, 1H), 3.44-3.40 (m, 2H), 2.48 (s, 3H), 2.39 (td, J = 7.4, 2.1 Hz, 2H), 2.28-2.18 (m, 1H), 2.12-2.07 (m, 2H), 1.95-1.92 (m, 3H), 1.80-1.76 (m, 4H), 1.62-1.58 (m, 2H), 1.08-1.05 (m, 11H) |
| I-14 | AI | AJ | 1013 | ($CD_3OD$) 7.84-7.73 (m, 4H), 7.37-7.18 (m, 4H), 7.12-7.04 (m, 2H), 7.01 (s, 1H), 6.99-6.93 (m, 2H), 6.87 (t, J = 3.8 Hz, 2H), 5.30 (dt, J = 12.4, 5.0 Hz, 1H), 5.12 (d, J = 11.0 Hz, 1H), 4.03 (dd, J = 13.9, 10.5 Hz, 1H), 3.56-3.46 (m, 1H), 3.40-3.35 (m, 5H), 3.32-3.29 (m, 3H), 3.19-3.04 (m, 2H), 2.99-2.85 (m, 1H), 2.84-2.57 (m, 4H), 2.34 (t, J = 13.6 Hz, 1H), 2.27-2.10 (m, 3H), 1.77-1.65 (m, 4H), 1.50-1.29 (m, 11H), 0.70 (d, J = 6.6 Hz, 3H), 0.58 (d, J = 7.0 Hz, 3H) |

TABLE 8-continued

Compounds synthesized via Method 1 using the corresponding amines and acids for the coupling.

| I-# | Amine | Acid | LCMS (ESI, m/z): $[(M + 1)]^+$ | $^1H$ NMR (400 MHz) δ |
|---|---|---|---|---|
| I-15 | Q | AJ | 938.1 | ($CD_3OD$) 8.19 (s, 1H), 7.33-7.23 (m, 4H), 7.13 (t, J = 7.8 Hz, 1H), 7.09-6.99 (m, 3H), 6.97 (d, J = 7.6 Hz, 1H), 6.92 (d, J = 7.4 Hz, 1H), 5.34 (dd, J= 12.4, 5.4 Hz, 1H), 5.11 (d, J = 11.0 Hz, 1H), 4.02 (dd, J = 13.9, 10.5 Hz, 1H), 3.63 (d, J = 3.7 Hz, 3H), 3.55 (t, J = 12.6 Hz, 1H), 3.33-3.19 (m, 5H), 3.11 (d, J = 13.8 Hz, 1H), 3.00-2.73 (m, 6H), 2.47 (d, J = 13.4 Hz, 1H), 2.37-2.11 (m, 2H), 2.05 (d, J = 13.4 Hz, 1H), 1.72-1.46 (m, 4H), 1.43-1.33 (m, 17H), 0.68 (d, J = 6.6 Hz, 3H), 0.54 (d, J = 6.9 Hz, 3H) |
| I-16 | R | AN | 942.5 | (DMSO-$d_6$) 11.07 (s, 1H), 10.41 (s, 1H), 8.40 (t, J = 5.7 Hz, 1H), 8.34-8.27 (m, 1H), 7.78-7.67 (m, 1H), 7.64-7.51 (m, 3H), 7.47 (dt, J = 8.5, 1.7 Hz, 1H), 7.42-7.31 (m, 3H), 7.02 (s, 1H), 6.99 (d, J = 8.0 Hz, 1H), 6.87 (dd, J = 8.1, 1.6 Hz, 1H), 5.33 (dd, J = 12.7, 5.4 Hz, 1H), 4.64-4.51 (m, 2H), 4.43-4.27 (m, 1H), 4.02-3.93 (m, 1H), 3.92 (s, 3H), 3.26 (q, J = 6.7 Hz, 2H), 2.97-2.81 (m, 1H), 2.77-2.57 (m, 4H), 2.05-1.95 (m, 1H), 1.72-1.50 (m, 5H), 1.48-1.21 (m, 3H), 0.98 (s, 9H) |
| I-17 | U | AN | 938.6 | ($CD_3OD$) 8.25 (dd, J = 8.4, 3.9 Hz, 1H), 7.76 (s, 1H), 7.53 (dd, J = 5.7, 1.9 Hz, 1H), 7.47-7.33 (m, 4H), 7.27 (ddd, J = 10.6, 8.4, 3.1 Hz, 2H), 7.13 (dt, J = 8.2, 1.4 Hz, 1H), 7.05-6.96 (m, 2H), 5.38-5.26 (m, 1H), 4.78 (dd, J = 7.3, 1.9 Hz, 1H), 4.66 (d, J = 8.2 Hz, 1H), 4.07 (d, J = 9.9 Hz, 1H), 3.95 (d, J = 5.7 Hz, 3H), 3.67-3.53 (m, 2H), 3.35 (s, 3H), 3.01-2.69 (m, 3H), 2.56 (t, J = 6.7 Hz, 2H), 2.21-2.10 (m, 1H), 1.95 (p, J = 6.7 Hz, 2H), 1.72 (dd, J = 14.4, 9.9 Hz, 1H), 1.50-1.27 (m, 2H), 1.05 (s, 9H) |
| I-18 | U | AM | 904.2 | ($CD_3OD$) 7.82 (d, J = 8.5 Hz, 2H), 7.73-7.61 (m, 3H), 7.45 (d, J = 8.3 Hz, 1H), 7.26 (t, J = 7.3 Hz, 1H), 7.15-6.93 (m, 6H), 6.75 (d, J = 1.9 Hz, 1H), 5.32 (dd, J = 10.1, 3.7 Hz, 1H), 4.83 (d, J = 9.4 Hz, 1H), 4.74 (d, J = 9.3 Hz, 1H), 3.76 (d, J = 2.7 Hz, 3H), 3.58 (t, J = 6.7 Hz, 2H), 2.99-2.70 (m, 2H), 2.62 (t, J = 6.9 Hz, 2H), 2.25-2.07 (m, 2H), 2.01-1.96 (m, 3H), 1.82-1.76 (m, 4H), 1.68-1.54 (m, 2H), 1.22-0.92 (m, 2H) |
| I-19 | AL | AN | 1169.9 | ($CD_3OD$) 8.88 (s, 1H), 8.37 (d, J = 8.4 Hz, 1H), 7.82 (d, J = 9.0 Hz, 1H), 7.75 (t, J = 6.9 Hz, 1H), 7.54 (d, J = 1.9 Hz, 1H), 7.50-7.40 (m, 5H), 7.39-7.32 (m, 2H), 7.28-7.24 (m, 2H), 4.78 (d, J = 8.3 Hz, 1H), 4.65 (dd, J = 8.7, 3.8 Hz, 2H), 4.62-4.55 (m, 1H), 4.52 (d, J = 10.5 Hz, 2H), 4.39-4.36 (m, 1H), 4.09 (d, J = 9.6 Hz, 1H), 3.99 (s, 3H), 3.92 (d, J = 11.0 Hz, 1H), 3.81 (dd, J = 10.9, 3.9 Hz, 1H), 3.39 (t, J = 6.5 Hz, 2H), 2.49 (s, 3H), 2.30-2.25 (m, 3H), 2.10-2.08 (m, 1H), 1.72-1.59 (m, 5H), 1.40-1.36 (m, 7H), 1.05 (d, J = 6.2 Hz, 18H) |
| I-20 | X | AN | 1113.8 | ($CD_3OD$) 8.88 (s, 1H), 8.38 (d, J = 8.4 Hz, 1H), 7.98 (d, J = 8.8 Hz, 1H), 7.75 (t, J = 7.2 Hz, 1H), 7.57 (d, J = 1.9 Hz, 1H), 7.50-7.39 (m, 5H), 7.39-7.33 (m, 2H), 7.32-7.22 (m, 2H), 4.81-4.74 (m, 1H), 4.69-4.55 (m, 3H), 4.52 (d, J = 7.5 Hz, 2H), 4.36 (d, J = 15.4 Hz, 1H), 4.09 (d, J = 9.6 Hz, 1H), 4.00 (s, 3H), 3.93 (d, J = 11.0 Hz, 1H), 3.82 (dd, J = 11.0, 4.0 Hz, 1H), 3.52-3.36 (m, 2H), 2.48 (s, 3H), 2.39 (td, J = 7.6, 7.2, 2.4 Hz, 2H), 2.23 (dd, J = 13.2, 7.7 Hz, 1H), 2.10 (ddd, J = 13.3, 9.1, 4.5 Hz, 1H), 1.93 (dq, J = 13.7, 6.9 Hz, 2H), 1.72 (dd, J = 14.2, 10.0 Hz, 1H), 1.38 (d, J = 14.3 Hz, 1H), 1.06 (d, J = 2.1 Hz, 18H) |
| I-21 | S | AJ | 938.1 | ($CD_3OD$) 8.19 (s, 1H), 7.33-7.25 (m, 4H), 7.16-7.06 (m, 2H), 7.05-6.98 (m, 4H), 6.96-6.90 (m, 1H), 5.33 (dd, J = 12.4, 5.4 Hz, 1H), 5.11 (d, J = 11.0 Hz, 1H), 4.02 (dd, J = 13.9, 10.4 Hz, 1H), 3.62-3.47 (m, 1H), 3.42 (s, 3H), 3.32-3.18 (m, 4H), 3.13-3.08 (m, 1H), 3.02-2.74 (m, 4H), 2.67 (t, J = 7.6 Hz, 2H), 2.46 (d, J = 13.4 Hz, 1H), 2.38-2.13 (m, 3H), 2.10-2.02 (m, 1H), 1.76-1.47 (m, 4H), 1.42 (d, J = 6.9 Hz, 6H), 1.36-1.31 (m, 11H), 0.68 (d, J = 6.6 Hz, 3H), 0.54 (d, J = 6.9 Hz, 3H) |
| I-22 | AG | AJ | 1009.7 | ($CD_3OD$) 7.30-7.13 (m, 5H), 7.10-7.05 (m, 5H), 7.00-6.93 (m, 2H), 6.86-6.80 (m, 3H), 5.35-5.16 (m, 1H), 5.09 (d, J = 10.9 Hz, 1H), 4.59 (s, 2H), 4.10-3.96 (m, 1H), 3.63-3.40 (m, 3H), 3.19-3.07 (m, 2H), 2.99 (d, J = 13.2 Hz, 1H), 2.93-2.61 (m, 5H), 2.54 (dd, J = 13.5, 8.6 Hz, 1H), 2.35-2.02 (m, 5H), 1.99-1.95 (m, 2H), 1.49-1.27 (m, 10H), 0.69 (d, J = 6.6 Hz, 3H), 0.53 (d, J = 6.9 Hz, 3H) |

TABLE 8-continued

| Compounds synthesized via Method 1 using the corresponding amines and acids for the coupling. | | | | |
|---|---|---|---|---|
| I-# | Amine | Acid | LCMS (ESI, m/z): $[(M + 1)]^+$ | $^1$H NMR (400 MHz) δ |
| I-23 | AK | AJ | 1287.3 | ($CDCl_3$) 7.30-7.21 (m, 8 H), 7.14-7.04 (m, 4H), 7.04 (d, J = 2.1 Hz, 2H), 6.97 (t, J = 4.2 Hz, 2H), 6.31 (s, 2H), 5.12 (d, J = 11.0 Hz, 2H), 4.07 (dd, J = 13.5, 10.3 Hz, 2H), 3.51 (t, J = 12.3 Hz, 2H), 3.39-3.22 (m, 6H), 3.13 (p, J = 6.9 Hz, 2H), 2.93-2.77 (m, 4H), 2.58 (d, J = 14.0 Hz, 2H), 2.33 (t, J = 13.6 Hz, 2H), 2.23 (dt, J = 13.7, 6.9 Hz, 2H), 2.11 (dd, J = 13.5, 3.2 Hz, 2H), 1.66-1.50 (m, 6H), 1.47 (dd, J = 6.9, 1.3 Hz, 12H), 1.38-1.28 (m, 18H), 0.68 (d, J = 6.6 Hz, 6H), 0.51 (d, J = 6.9 Hz, 6H) |
| I-24 | AH | AJ | 1013.2 | ($CD_3OD$) 7.92-7.76 (m, 4H), 7.30-7.21 (m, 4H), 7.11-7.04 (m, 2H), 7.00 (d, J = 7.2 Hz, 1H), 6.97-6.92 (m, 2H), 6.86 (dd, J = 5.8, 3.9 Hz, 2H), 5.45-5.28 (m, 1H), 5.12 (d, J = 11.0 Hz, 1H), 4.03 (dd, J = 13.9, 10.5 Hz, 1H), 3.66 (s, 3H), 3.57-3.47 (m, 1H), 3.42 (t, J = 6.9 Hz, 2H), 3.35-3.32 (m, 2H), 3.17-2.96 (m, 4H), 2.95-2.87 (m, 1H), 2.86-2.72 (m, 2H), 2.63 (d, J = 13.3 Hz, 1H), 2.34 (t, J = 13.7 Hz, 1H), 2.28-2.08 (m, 3H), 1.79-1.68 (m, 4H), 1.57-1.49 (m, 2H), 1.48-1.36 (m, 11H), 0.70 (d, J = 6.6 Hz, 3H), 0.58 (d, J = 6.9 Hz, 3H) |
| I-25 | AE | AJ | 1009.2 | ($CD_3OD$) 7.86 (d, J = 3.3 Hz, 1H), 7.84 (d, J = 3.3 Hz, 2H), 7.75-7.71 (m, 2H), 7.27-7.21 (m, 2H), 7.14-6.97 (m, 6H), 6.92-6.85 (m, 2H), 5.34 (dd, J = 12.5, 5.4 Hz, 1H), 5.12 (d, J = 10.9 Hz, 1H), 4.10-3.96 (m, 1H), 3.76 (d, J = 1.4 Hz, 3H), 3.59 (t, J = 6.8 Hz, 2H), 3.55-3.46 (m, 1H), 3.19-3.09 (m, 1H), 3.09-3.03 (m, 1H), 2.94-2.90 (m, 1H), 2.86-2.77 (m, 2H), 2.67-2.59 (m, 3H), 2.34 (t, J = 13.7 Hz, 1H), 2.24-2.18 (m, 3H), 2.03-1.97 (m, 2H), 1.46-1.39 (m, 11H), 0.70 (d, J = 6.6 Hz, 3H), 0.57 (d, J = 6.9 Hz, 3H) |
| I-26 | W | AJ | 917 | ($CD_3OD$) 7.75 (dd, J = 7.6, 1.1 Hz, 1H), 7.60 (d, J = 7.6 Hz, 1H), 7.50 (t, J = 7.6 Hz, 1H), 7.34-7.26 (m, 4H), 7.14 (t, J = 7.6 Hz, 1H), 7.08 (dq, J= 8.1, 1.7 Hz, 1H), 7.05-6.97 (m, 2H), 5.18 (ddd, J = 13.3, 5.2, 2.4 Hz, 1H), 5.10 (d, J = 11.0 Hz, 1H), 4.58-4.41 (m, 2H), 4.01 (dd, J = 13.9, 10.4 Hz, 1H), 3.65-3.47 (m, 1H), 3.35-3.21 (m, 5H), 3.16-3.05 (m, 1H), 2.99-2.86 (m, 2H), 2.84-2.78 (m, 1H), 2.60-2.39 (m, 4H), 2.34-2.12 (m, 3H), 2.10-1.98 (m, 1H), 1.68-1.45 (m, 6H), 1.46-1.27 (m, 11H), 0.68 (d, J = 6.6 Hz, 3H), 0.56-0.48 (m, 3H) |
| I-27 | AF | AJ | 995.7 | (DMSO-$d_6$) 11.00 (s, 1H), 10.39 (s, 1H), 8.43 (t, J = 5.6 Hz, 1H), 7.88-7.80 (m, 2H), 7.74-7.67 (m, 3H), 7.63 (dd, J = 7.7, 1.1 Hz, 1H), 7.52 (t, J = 7.6 Hz, 1H), 7.40-7.33 (m, 4H), 7.20 (t, J = 8.0 Hz, 1H), 7.17-7.11 (m, 1H), 6.92 (dd, J = 4.1, 2.2 Hz, 2H), 5.16 (dd, J = 13.2, 5.1 Hz, 1H), 5.04 (d, J = 11.0 Hz, 1H), 4.51 (d, J = 17.9 Hz, 1H), 4.36 (d, J = 17.9 Hz, 1H), 3.87 (t, J = 12.1 Hz, 1H), 3.60 (t, J = 13.0 Hz, 1H), 3.41 (dt, J = 13.7, 6.8 Hz, 3H), 3.19 (d, J = 13.9 Hz, 1H), 3.08 (d, J = 13.8 Hz, 2H), 2.93 (t, J = 14.0 Hz, 1H), 2.70-2.65 (m, 1H), 2.64-2.53 (m, 3H), 2.24-2.06 (m, 3H), 2.05-1.94 (m, 1H), 1.83 (p, J = 7.0 Hz, 2H), 1.39-1.21 (m, 10H), 0.58 (d, J = 6.6 Hz, 3H), 0.44 (d, J = 6.9 Hz, 3H) |
| I-28 | H | AN | 942.7 | ($CD_3OD$) 8.36 (dd, J = 8.4, 1.1 Hz, 1H), 7.75 (t, J = 7.1 Hz, 1H), 7.54 (t, J = 1.9 Hz, 1H), 7.47-7.32 (m, 4H), 7.33-7.24 (m, 2H), 7.07-6.91 (m, 3H), 5.36-5.27 (m, 1H), 4.78 (d, J = 8.5 Hz, 1H), 4.66 (d, J = 8.4 Hz, 1H), 4.10 (d, J = 9.6 Hz, 1H), 4.00 (s, 3H), 3.67 (s, 3H), 3.41 (t, J = 7.0 Hz, 2H), 3.02 (t, J = 7.7 Hz, 2H), 2.92-2.71 (m, 3H), 2.17-2.13 (m, 1H), 1.75 (td, J = 15.2, 7.8 Hz, 6H), 1.54 (d, J = 7.9 Hz, 2H), 1.44-1.26 (m, 1H), 1.06 (s, 9H) |
| I-29 | V | AM | 891 | ($CD_3OD$) 7.83-7.68 (m, 4H), 7.63-7.55 (m, 3H), 7.55-7.44 (m, 2H), 7.26 (t, J = 7.4 Hz, 1H), 7.12-7.00 (m, 2H), 6.75 (d, J = 1.9 Hz, 1H), 5.15 (dt, J = 13.4, 4.7 Hz, 1H), 4.83-4.81 (m, 1H), 4.75 (dd, J = 9.3, 2.6 Hz, 1H), 4.49-4.35 (m, 2H), 3.61 (d, J = 7.0 Hz, 2H), 3.01-2.73 (m, 2H), 2.62 (t, J = 6.6 Hz, 2H), 2.57-2.45 (m, 1H), 2.27-2.07 (m, 2H), 1.99-1.94 (m, 3H), 1.88-1.69 (m, 4H), 1.64-1.60 (m, 2H), 1.22-0.91 (m, 2H) |
| I-30 | T | AN | 938.6 | ($CD_3OD$) 8.30 (dd, J = 8.4, 7.2 Hz, 1H), 7.75 (t, J = 7.1 Hz, 1H), 7.55 (t, J = 1.6 Hz, 1H), 7.50-7.34 (m, 4H), 7.29-7.21 (m, 2H), 7.18-6.95 (m, 3H), 5.30 (dq, J = 11.8, 5.5 Hz, 1H), 4.78 (d, J = 8.4 Hz, 1H), 4.65 (d, J = 8.3 Hz, 1H), 4.09 (d, J = 9.7 Hz, 1H), 3.97 (d, J = 1.0 Hz, 3H), 3.77 (d, J = 0.9 |

TABLE 8-continued

Compounds synthesized via Method 1 using the corresponding amines and acids for the coupling.

| I-# | Amine | Acid | LCMS (ESI, m/z): $[(M + 1)]^+$ | $^1H$ NMR (400 MHz) δ |
|---|---|---|---|---|
| | | | | Hz, 3H), 3.58 (d, J = 7.4 Hz, 2H), 3.01-2.70 (m, 3H), 2.63 (t, J = 6.9 Hz, 2H), 2.15-2.11 (m, 1H), 1.99 (p, J = 7.0 Hz, 2H), 1.72 (dd, J = 14.4, 9.8 Hz, 1H), 1.38 (d, J = 14.3 Hz, 1H), 1.06 (s, 9H) |
| I-31 | V | AN | 923.6 | ($CD_3OD$) 8.41-8.24 (m, 1H), 7.83-7.66 (m, 3H), 7.55 (d, J = 7.7 Hz, 1H), 7.49-7.32 (m, 6H), 7.29-7.26 (m, 2H), 5.17-5.14 (m, 1H), 4.79 (t, J = 8.8 Hz, 1H), 4.71-4.62 (m, 1H), 4.40 (d, J = 10.5 Hz, 2H), 4.16-4.11 (m, 1H), 3.90 (d, J = 8.4 Hz, 3H), 3.73-3.52 (m, 2H), 2.98-2.71 (m, 2H), 2.63 (t, J = 6.7 Hz, 2H), 2.58-2.54 (m, 1 H), 2.22-2.19 (m, 1H), 1.97 (d, J = 6.9 Hz, 2H), 1.74-1.71 (m, 1H), 1.42-1.38 (m, 1H), 1.08 (d, J = 7.0 Hz, 9H) |
| I-32 | AP | AN | 1341.7 | ($CDCl_3$) 10.38 (s, 2H), 8.45 (d, J = 8.3 Hz, 2H), 7.55-7.52 (m, 4H), 7.34 (t, J = 7.3 Hz, 2H), 7.16 (dd, J = 22.4, 10.3 Hz, 10H), 6.19-6.17 (m, 2H), 4.79 (d, J = 8.3 Hz, 2H), 4.57 (d, J = 8.3 Hz, 2H), 4.12 ((d, J = 9.6 Hz, 2H), 3.96 (s, 6H), 3.47-3.45 (m, 4H), 2.82 (s, 1H), 1.65-1.58 (m, 2H), 1.48-1.19 (m, 12H), 1.03 (s, 18H) |
| I-33 | AO | AN | 1345.6 | ($CDCl_3$) 10.42 (s, 1H), 8.45 (d, J = 8.3 Hz, 2H), 7.58-7.45 (m, 4H), 7.34 (t, J = 7.2 Hz, 2H), 7.28-7.09 (m, 10H), 6.64 (s, 2H), 4.77 (d, J = 8.5 Hz, 2H), 4.54 (d, J = 8.7 Hz, 2H), 4.11 (d, J = 9.6 Hz, 2H), 3.95 (s, 6H), 3.69-3.64 (m, 12H), 1.59 (dd, J = 14.5, 9.8 Hz, 2H), 1.39 (d, J = 14.4 Hz, 2H), 1.28 (s, 1H), 1.02 (s, 18H) |
| I-34[c] | CJ | AN | 1161.5 | ($CD_3OD$) 8.48-8.04 (m, 2H), 7.75 (t, J = 7.2 Hz, 1H), 7.58 (d, J = 1.6 Hz, 1H), 7.49-7.33 (m, 4H), 7.30-6.83 (m, 9H), 5.15-5.10 (m, 1H), 5.08-4.90 (m, 2H), 4.78 (d, J = 8.4 Hz, 1H), 4.73-4.63 (m, 3H), 4.23-4.16 (m, 2H), 4.10 (d, J = 9.6 Hz, 1H), 4.04-3.98 (m, 3H), 3.92 (q, J = 7.4 Hz, 1H), 3.79 (t, J = 5.6 Hz, 2H), 3.28-3.06 (m, 2H), 2.88-2.70 (m, 2H), 2.69-2.63 (m, 3H), 1.99-1.87 (m, 1H), 1.85-1.66 (m, 3H), 1.48 (d, J = 6.8 Hz, 1H), 1.43-1.35 (m, 3H), 1.20-1.02 (m, 18H) |
| I-35 | CG | AM | 922.3 | ($CD_3OD$) (7.76-7.68 (m, 4H), 7.66-7.52 (m, 4H), 7.38 (s, 1H), 7.23-7.10 (m, 2H), 7.01-6.93 (m, 4H), 6.81 (s, 1H), 5.32 (dd, 13.2, 5.2 Hz, 2H), 4.99 (d, J = 12.0 Hz, 1H), 3.37 (s, 3H), 3.20 (s, 3H), 3.02-2.90 (m, 3H), 2.72 (t, J = 7.2 Hz, 3H), 2.21-2.10 (m, 2H), 1.98 (s, 3H), 1.85-1.57 (m, 9H), 1.47-1.35 (m, 3H), 1.25 (s, 2H) |
| I-36[c] | DU | AN | 615.0 | ($CD_3OD$) 8.23-8.33 (m, 2H), 7.62-7.82 (m, 3H), 7.35-7.54 (m, 6 H), 7.26-7.32 (m, 2H), 7.17 (d, J = 8.4 Hz, 1H), 5.48 (d, J = 7.2, 3.2 Hz, 1H), 4.75-4.85 (m, 2H), 4.53-4.62 (m, 1H), 4.22 (d, J = 7.6 Hz, 1H) , 4.13-4.17 (m, 2H), 3.81-4.02 (m, 8H) , 3.76 (d, J = 5.2 Hz, 2H), 3.68-3.73 (m, 4H), 3.56-3.62 (m, 2H), 3.37 (s, 1H), 2.66-2.70 (m, 3H), 2.03-2.41 (m, 4H), 1.77 (d, J = 14.4 Hz, 5H), 1.56-1.68 (m, 2H), 1.50 (d, J = 7.2 Hz, 2H), 1.39-1.48 (m, 2H), 1.29 (d, J = 6.8 Hz, 1H), 1.08-1.20 (m, 3H), 1.03 (s, 9H) |
| I-37[c] | DQ | AN | 1205.5 | ($CDCl_3$) 10.35 (d, J = 6.8 Hz, 1H) 8.32-8.48 (m, 1H) 7.73-7.86 (m, 1H) 7.46-7.57 (m, 2H) 7.32-7.37 (m, 1H) 6.96-7.26 (m, 8H) 6.85-6.95 (m, 1H) 6.79 (dd, J = 8.0, 2.57 Hz, 1H) 6.72 (d, J = 2.4 Hz, 1H) 6.58-6.65 (m, 1H) 6.18-6.45 (m, 1H) 5.07-5.15 (m, 1H) 4.98-5.05 (m, 1H) 4.88-4.96 (m, 1H) 4.65-4.79 (m, 1H) 4.47-4.57 (m, 1H) 4.27-4.41 (m, 1H) 4.05-4.17 (m, 3H) 3.93 (d, J = 4.8 Hz, 3H) 3.87 (s, 2H) 3.66-3.80 (m, 4H) 3.52 (d, J = 14.8 Hz, 1H) 2.87-3.25 (m, 2H) 2.62-2.84 (m, 3H) 2.27 (d, J = 11.6 Hz, 3H) 1.83-2.01 (m, 2H) 1.49-1.81 (m, 6H) 1.40 (br d, J = 14.8 Hz, 1H) 1.27 (d, J = 6.8 Hz, 2H) 1.20 (d, J = 6.8 Hz, 1H) 0.95-1.08 (m, 18H) |
| I-38[c] | CJ | CK | 1234.4 | (DMSO-$d_6$) 10.41 (s, 1H), 8.65-8.57 (m, 1H), 8.20-8.07 (m, 2H), 7.86 (d, J = 8.8 Hz, 2H), 7.72 (d, J = 8.4 Hz, 2H), 7.52-7.27 (m, 2H), 7.27-6.95 (m, 8H), 6.94-6.87 (m, 3H), 6.86-6.69 (m, 2H), 5.03 (d, J = 10.8 Hz, 1H), 4.98-4.90 (m, 1H), 4.89-4.83 (m, 1H), 4.76-4.61 (m, 2H), 4.08 (t, J = 6.0 Hz, 2H), 3.80-3.90 (m, 1H), 3.65-3.55 (m, 3H), 3.24-3.16 (m, 3H), 3.11-3.05 (m, 2H), 3.01-2.89 (m, 2H), 2.73-2.60 (m, 3H), 2.28-2.04 (m, 7H), 1.92-1.45 (m, 5H), 1.32-1.26 (m, 9H), 1.15-1.10 (m, 3H), 1.04 (s, 6H), 0.95 (s, 3H), 0.57 (d, J = 6.4 Hz, 3H), 0.43 (d, J = 6.8 Hz, 3H) |

TABLE 8-continued

Compounds synthesized via Method 1 using the corresponding amines and acids for the coupling.

| I-# | Amine | Acid | LCMS (ESI, m/z): $[(M + 1)]^+$ | $^1H$ NMR (400 MHz) δ |
| --- | --- | --- | --- | --- |
| I-39 | octane-1,8-diamine (CAS# 373-44-4) | AM | 1273.4 | (DMSO-$d_6$) 10.60 (s, 2H), 10.22 (s, 2H), 8.33 (t, J = 5.6 Hz, 2H), 7.81 (d, J = 8.4 Hz, 4H), 7.69-7.60 (m, 6H), 7.53-7.41 (m, 2H), 7.40-6.31 (m, 2H), 7.19-6.10 (m, 2H), 7.09-6.99 (m, 2H), 6.69 (s, 2H), 4.89-4.54 (m, 4H), 3.68 (s, 1H), 3.2-3.18 (m, 4H), 2.04-1.97 (m, 2H), 1.83-1.78 (m, 2H), 1.60-1.58 (m, 8H), 1.53-1.40 (m, 8H), 1.29 (s, 8H), 0.99-0.95 (m, 2H), 0.85-0.83 (m, 2H) |
| I-40 | DI | AM | 922.3 | (DMSO-$d_6$) 10.19 (s, 1H), 7.70-7.59 (m, 3H), 7.46 (dd, J = 1.6, 8.0 Hz, 1H), 7.39-7.28 (m, 3H), 7.23 (d, J = 7.2 Hz, 1H), 7.15 (t, J = 8.0 Hz, 1H), 7.07-6.96 (m, 3H), 6.94-6.81 (m, 1H), 6.70 (d, J = 2.0 Hz, 1H), 5.33 (dd, J = 5.2, 12.8 Hz, 1H), 4.81-4.63 (m, 2H), 3.30 (s, 9H), 2.90 (s, 3H), 2.94-2.82 (m, 1H), 2.08 (s, 5H), 1.92-1.78 (m, 1H), 1.71-1.44 (m, 9H), 1.24 (s, 1H), 0.97 (d, J = 13.2 Hz, 1H), 0.90-0.80 (m, 1H) |
| I-41 | 2-[2-(2-amino-ethoxy) ethoxy] ethan-amine (CAS# 929-59-9) | AM | 1278.3 | (DMSO-$d_6$) 10.57 (s, 2H), 10.28-10.17 (m, 2H), 8.40 (t, J = 5.2 Hz, 2H), 7.82 (d, J = 8.8 Hz, 4H), 7.71-7.60 (m, 6H), 7.46 (d, J = 7.2 Hz, 2H), 7.34 (d, J = 6.8 Hz, 2H), 7.15 (t, J = 8.0 Hz, 2H), 7.03 (d, J = 6.8 Hz, 2H), 6.69 (s, 2H), 4.81-4.62 (m, 4H), 3.80-3.60 (m, 1H), 3.53-3.47 (m, 4H), 3.42-3.37 (m, 4H), 3.17 (s, 4H), 1.99 (s, 4H), 1.81 (d, J = 1.2 Hz, 4H), 1.60 (d, J = 11.6 Hz, 10H), 1.36 (s, 2H), 1.23 (s, 4H) |
| I-42 | R | DK | 968.3 | (DMSO-$d_6$) 11.08 (s, 1H), 10.51 (s, 1H), 7.62 (t, J = 7.2 Hz, 1 H), 7.22-7.47 (m, 4H), 7.12 (t, J = 8.4 Hz, 1H), 6.93-7.05 (m, 3H), 6.80-6.88 (m, 1H), 6.64 (d, J = 2.0 Hz, 1H), 5.32 (dd, J = 12.8, 5.32 Hz, 1H), 4.29 (d, J = 9.2 Hz, 1H), 3.92 (d, J = 8.8 Hz, 1H), 3.32 (s, 3H), 2.97-3.04 (m, 2 H), 2.83-2.91 (m, 1 H), 2.54-2.74 (m, 6 H), 1.97-2.11 (m, 2H), 1.91 (d, J = 13.6 Hz, 1H), 1.67-1.78 (m, 10H), 1.55 (dt, J = 14.8, 7.2 Hz, 6H), 1.35-1.43 (m, 2H), 1.20-1.28 (m, 2H), 1.03-1.06 (m, 8H), 0.72-0.87 (m, 1H) |
| I-134[d] | GD | GC | 923.3 | 11.00 (s, 1H), 10.52 (s, 1H), 8.14 (s, 1H), 7.77 (d, J = 8.4 Hz, 1H), 7.72 (d, J = 7.6 Hz, 1H), 7.66 (d, J = 7.6 Hz, 1H), 7.59 (t, J = 6.4 Hz, 1H), 7.56-7.51 (m, 1H), 7.45-7.38 (m, 1H), 7.32 (t, J = 7.2 Hz, 1H), 7.11 (t, J = 8.0 Hz, 1H), 7.06-7.00 (m, 1H), 6.67 (d, J = 2.0 Hz, 1H), 5.17-5.10 (m, 1H), 4.56 (d, J = 9.2 Hz, 1H), 4.50-4.43 (m, 1H), 4.40-4.29 (m, 2H), 3.95-3.72 (m, 2H), 3.52-3.42 (m, 1H), 3.19 (d, J = 8.4 Hz, 1H), 3.04-2.95 (m, 1H), 2.94-2.85 (m, 1H), 2.65-2.55 (m, 2H), 2.46 (d, J = 4.4 Hz, 1H), 2.07-1.98 (m, 1H), 1.94 (d, J = 11.2 Hz, 2H), 1.85 (d, J = 11.2 Hz, 2H), 1.81-1.67 (m, 4H), 1.67-1.52 (m, 6H), 1.52-1.20 (m, 8H), 1.03-0.90 (m, 1H), 0.87-0.74 (m, 1H) |
| I-135 | FN | GF | 897.6 | 10.67 (s, 1H), 8.27 (d, J = 7.2 Hz, 1H), 7.71-7.64 (m, 2H), 7.62 (s, 2H), 7.50 (t, J = 7.6 Hz, 1H), 7.37-7.26 (m, 3H), 6.89 (d, J = 7.2 Hz, 1H), 4.61 (d, J = 7.2 Hz, 1H), 4.32-4.20 (m, 1H), 4.00-3.89 (m, 1H), 3.80 (t, J = 6.4 Hz, 3H), 3.48 (d, J = 8.0 Hz, 1H), 2.82 (t, J = 6.4 Hz, 2H), 2.79-2.68 (m, 2H), 2.26-2.03 (m, 4H), 1.96-1.72 (m, 7H), 1.71-1.60 (m, 2H), 1.59-1.47 (m, 2H), 1.27-1.07 (m, 4H), 1.03-0.89 (m, 2H), 0.86 (s, 9H) |
| I-136 | IQ | IL | 965.4 | 11.15-11.05 (m, 1H), 10.54 (s, 1H), 8.46 (s, 1H), 7.81-7.70 (m, 1H), 7.58 (t, J = 6.8 Hz, 1H), 7.40 (d, J = 8.4 Hz, 1H), 7.32 (t, J = 6.8 Hz, 1H), 7.24 (s, 1H), 7.14-7.06 (m, 3H), 7.05-6.99 (m, 1H), 6.66 (d, J = 1.6 Hz, 1H), 5.41-5.33 (m, 1H), 4.55 (d, J = 9.2 Hz, 1H), 4.42-4.29 (m, 1H), 3.52-3.42 (m, 6H), 3.32-3.32 (m, 3H), 2.95-2.81 (m, 1H), 2.80-2.69 (m, 1H), 2.64-2.56 (m, 5H), 2.09-1.98 (m, 2H), 1.97-1.91 (m, 1H), 1.87-1.81 (m, 1H), 1.79-1.67 (m, 4H), 1.62-1.54 (m, 4H), 1.50-1.20 (m, 9H), 1.01-0.90 (m, 1H), 0.86-0.72 (m, 1H) |
| I-215 | IM | JT | 862.3 | 11.08 (s, 1H), 7.35 (s, 4H), 7.08 (d, J = 1.2 Hz, 1H), 7.05-6.98 (m, 2H), 6.92-6.81 (m, 2H), 6.53 (d, J = 9.2 Hz, 2H), 5.94 (s, 1H), 5.33 (dd, J = 5.2, 12.8 Hz, 1H), 4.45 (td, J = 6.0, 12.0 Hz, 1H), 4.22 (d, J = 5.2 Hz, 2H), 3.91 (s, 1H), 3.72 (s, 3H), 3.59 (s, 1H), 3.44 (d, J = 6.8 Hz, 4H), 3.36-3.35 (m, 3H), 2.90 (s, 5H), 2.82-2.74 (m, 4H), 2.70-2.63 (m, 5H), 2.05-1.94 (m, 1H), 1.23 (d, J = 6.0 Hz, 3H), 1.18 (d, J = 6.0 Hz, 3H) |

TABLE 8-continued

Compounds synthesized via Method 1 using the corresponding amines and acids for the coupling.

| I-# | Amine | Acid | LCMS (ESI, m/z): $[(M + 1)]^+$ | $^1H$ NMR (400 MHz) δ |
|---|---|---|---|---|
| I-216 | GS | JT | 902.4 | 11.09 (s, 1H), 7.35 (s, 4H), 7.10-6.96 (m, 3H), 6.94-6.80 (m, 4H), 6.52 (d, J = 9.2 Hz, 2H), 5.94 (s, 1H), 5.42-5.33 (m, 1H), 4.45 (td, J = 6.0, 12.0 Hz, 1H), 4.26-4.18 (m, 2H), 3.92 (s, 1H), 3.73 (s, 3H), 3.59 (s, 1H), 3.25-3.22 (m, 3H), 2.97-2.81 (m, 8H), 2.78-2.60 (m, 10H), 2.07-2.00 (m, 1H), 1.80-1.71 (m, 2H), 1.62 (s, 2H), 1.24 (d, J = 6.0 Hz, 3H), 1.19 (d, J = 6.0 Hz, 3H) |

[a]The product of Step 1 of Method 1 was further deprotected using TFA in DCM at rt for 30 min. The final product was purified via prep-HPLC.
[b]After Step 1, the product was deprotected with HCl/dioxane(4M) in DCM at rt for 1 hr. The final product was purified by prep-HPLC.
[c]The product of the coupling was further deprotected with TFA in DCM for 0.5-2 hr at rt. The final product was purified by prep-HPLC.
[d]LCMS reported as $(M + 3H)^+$ ion.

Example 2. Synthesis of (3'R,4'S,5'R)—N-(4-((5-aminopentyl)carbamoyl)phenyl)-6"-chloro-4'-(3-chloro-2-fluorophenyl)-2"-oxodispiro[cyclohexane-1,2'-pyrrolidine-3',3"-indoline]-5'-carboxamide (I-1)

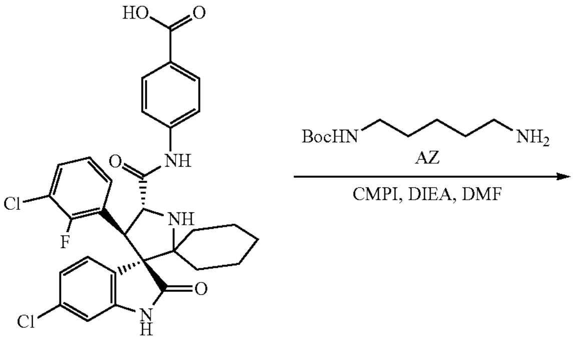

AM

-continued

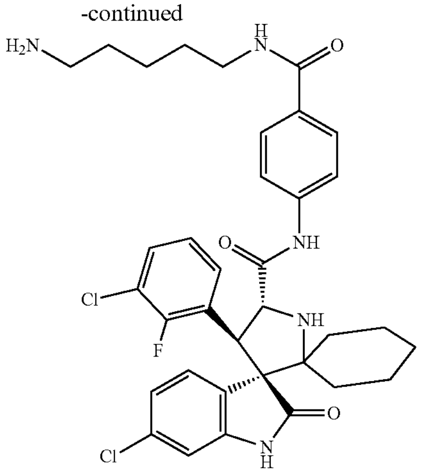

I-1

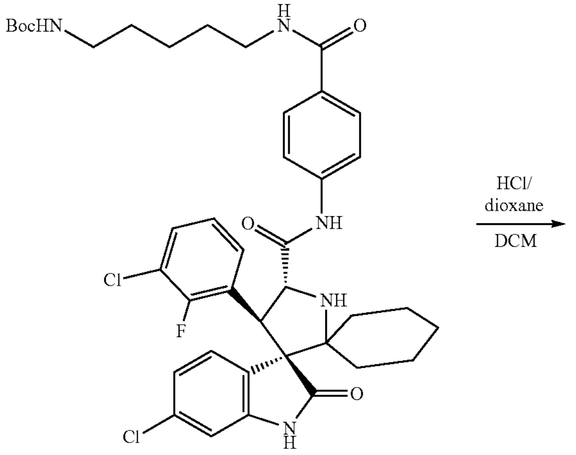

Step 1—tert-butyl (5-(4-((3'R,4'S,5'R)-6"-chloro-4'-(3-chloro-2-fluorophenyl)-2"-oxodispiro[cyclohexane-1,2'-pyrrolidine-3',3"-indoline]-5'-carboxamido)benzamido)pentyl)carbamate To a solution of tert-butyl N-(5-aminopentyl)carbamate (20.8 mg, 103 umol, 21.4 uL, Intermediate AZ) in DMF (2 mL) was added DIEA (39.9 mg, 309 umol, 53.8 uL) and 2-chloro-1-methyl-pyridin-1-ium; iodide (31.58 mg, 123 umol, CAS #51644-96-3). The mixture was stirred at 25° C. for 30 minutes, then 4-[[chloro-(3-chloro-2-fluoro-phenyl)-oxo-dispiro[BLAH]carbonyl] amino]benzoic acid (60.0 mg, 103 umol, Intermediate AM) was added, the reaction mixture was stirred at 25° C. for 1 hour. On completion, the reaction mixture was concentrated in vacuo to give a residue. The residue was purified by prep-HPLC (column: Phenomenex Synergi C18 150*25*10 um; mobile phase: [water (0.225% FA)-ACN]; B %: 56%-86%, 10 min) to give the title compound (50.0 mg, 63% yield) as a white solid. LC-MS ($ESI^+$) m/z 766.1 $(M+1)^+$.

Step 2—(3'R,4'S,5'R)—N-(4-((5-aminopentyl)carbamoyl)phenyl)-6"-chloro-4'-(3-chloro-2-fluorophenyl)-2"-oxodispiro[cyclohexane-1,2'-pyrrolidine-3',3"-indoline]-5'-carboxamide (I-1)

To a solution of tert-butyl (5-(4-((3'R,4'S,5'R)-6"-chloro-4'-(3-chloro-2-fluorophenyl)-2"-oxodispiro[cyclohexane-1, 2'-pyrrolidine-3',3"-indoline]-5'-carboxamido)benzamido) pentyl carbamate (45.0 mg, 58.6 umol) in DCM (2 mL) was added HCl/dioxane (4 M, 1 mL). The reaction mixture was stirred at 25° C. for 0.5 hr. On completion, the reaction mixture was concentrated in vacuo to give the residue. The residue was purified by prep-HPLC (column: Phenomenex Synergi C18 150*25*10 um; mobile phase: [water (0.225% FA)–ACN]; B %:19%-49%, 10 min) to give the title compound (25.8 mg, 66% yield) as a white solid. $^{1}$H NMR (400 MHz, DMSO-$d_6$) δ 10.24 (s, 1H), 8.46 (s, 1H), 8.37 (t, J=5.2 Hz, 1H), 7.81 (d, J=8.8 Hz, 2H), 7.68 (d, J=8.8 Hz, 2H), 7.63 (t, J=6.8 Hz, 1H), 7.45 (dd, J=2.0, 8.0 Hz, 1H), 7.40-7.31 (m, 1H), 7.15 (t, J=8.0 Hz, 1H), 7.03 (dd, J=2.0, 8.4 Hz, 1H), 6.70 (d, J=2.0 Hz, 1H), 4.80-4.73 (m, 1H), 4.72-4.64 (m, 1H), 3.26-3.20 (m, 5H), 2.71-2.65 (m, 2H), 2.04 (d, J=10.8 Hz, 1H), 1.90-1.76 (m, 1H), 1.71-1.44 (m, 9H), 1.42-1.28 (m, 3H), 1.05-0.90 (m, 1H), 0.90-0.78 (m, 1H); LC-MS (ESI$^+$) m/z 666.3 (M+1)$^+$.

Example 3. Synthesis of 3-[4-[3-[4-[(4S,5R)-2-(4-tert-butyl-2-ethoxy-phenyl)-4,5-bis(4-chlorophenyl)-4,5-dihydro imidazole-1-carbonyl]piperazin-1-yl]prop-1-ynyl]-1-oxo-isoindolin-2-yl]piperidine-2,6-dione (I-4)

To a mixture of 3-[1-oxo-4-(3-piperazin-1-ylprop-1-ynyl) isoindolin-2-yl]piperidine-2,6-dione (150 mg, 312 umol, TFA salt, Intermediate AY) and (4S,5R)-2-(4-tert-butyl-2-ethoxy-phenyl)-4,5-bis(4-chlorophenyl)-4,5-dihydroimidazole-1-carbonyl chloride (165 mg, 312 umol, Intermediate AV) in DCM (10.0 mL) was added DIEA (121 mg, 936 umol, 163 uL) at 0° C. The mixture was stirred at 25° C. for 2 hours. On completion, the reaction mixture was quenched with $H_2O$ (10.0 mL) at 25° C., and then extracted with DCM (3×30 mL). The combined organic layers were washed with brine (10 mL), dried over $Na_2SO_4$, filtered and concentrated in vacuo to give a residue. The residue was purified by prep-HPLC (column: Shim-pack C18 150*25*10 um; mobile phase: [water (0.225% FA)–ACN]; B %: 37%-67%, 10 min) to afford the title compound (20.0 mg, 7% yield) as white solid. $^{1}$H NMR (400 MHz, DMSO-$d_6$) δ 11.04-11.00 (m, 1H), 7.78-7.74 (m, 1H), 7.67-7.62 (m, 1H), 7.58-7.51 (m, 2H), 7.16 (d, J=8.4 Hz, 2H), 7.09 (d, J=8.2 Hz, 1H), 7.07-7.00 (m, 5H), 6.96 (d, J=8.0 Hz, 2H), 5.71-5.66 (m, 1H), 5.57-5.52 (m, 1H), 5.18-5.11 (m, 1H), 4.46-4.23 (m, 2H), 4.09 (d, J=7.0 Hz, 2H), 3.05 (s, 4H), 2.98-2.86 (m, 2H), 2.62-2.53 (m, 5H), 2.43-2.38 (m, 1H), 2.07-2.01 (m, 3H), 1.35-1.28 (m, 12H). LC-MS (ESI$^+$) m/z 861.5 (M+H)$^+$.

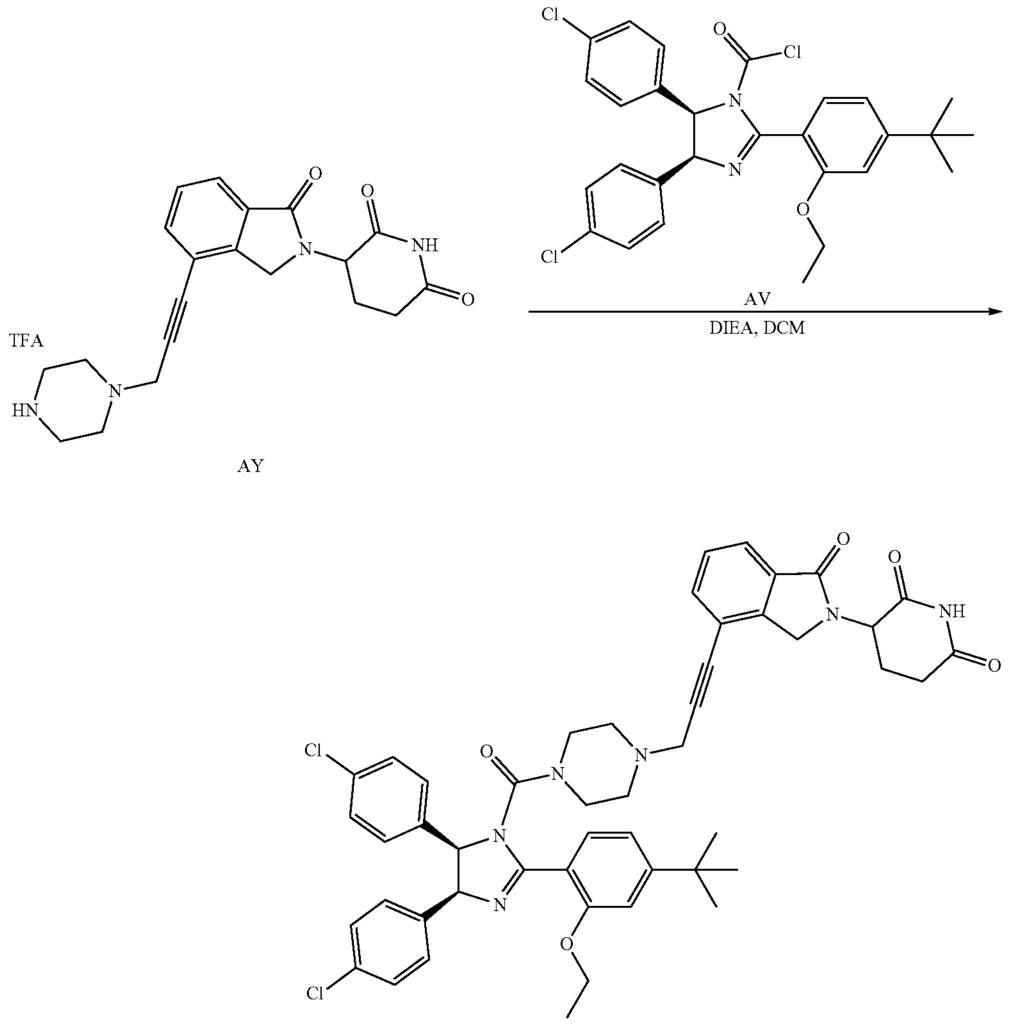

I-4

Example 4. Synthesis of N-[3-(3-aminopropoxy)propyl]-4-[[2-[(3R,5R,6S)-5-(3-chlorophenyl)-6-(4-chlorophenyl)-1-[(1S)-1-(isopropylsulfonylmethyl)-2-methyl-propyl]-3-methyl-2-oxo-3-piperidyl]acetyl]amino]benzamide (I-5)
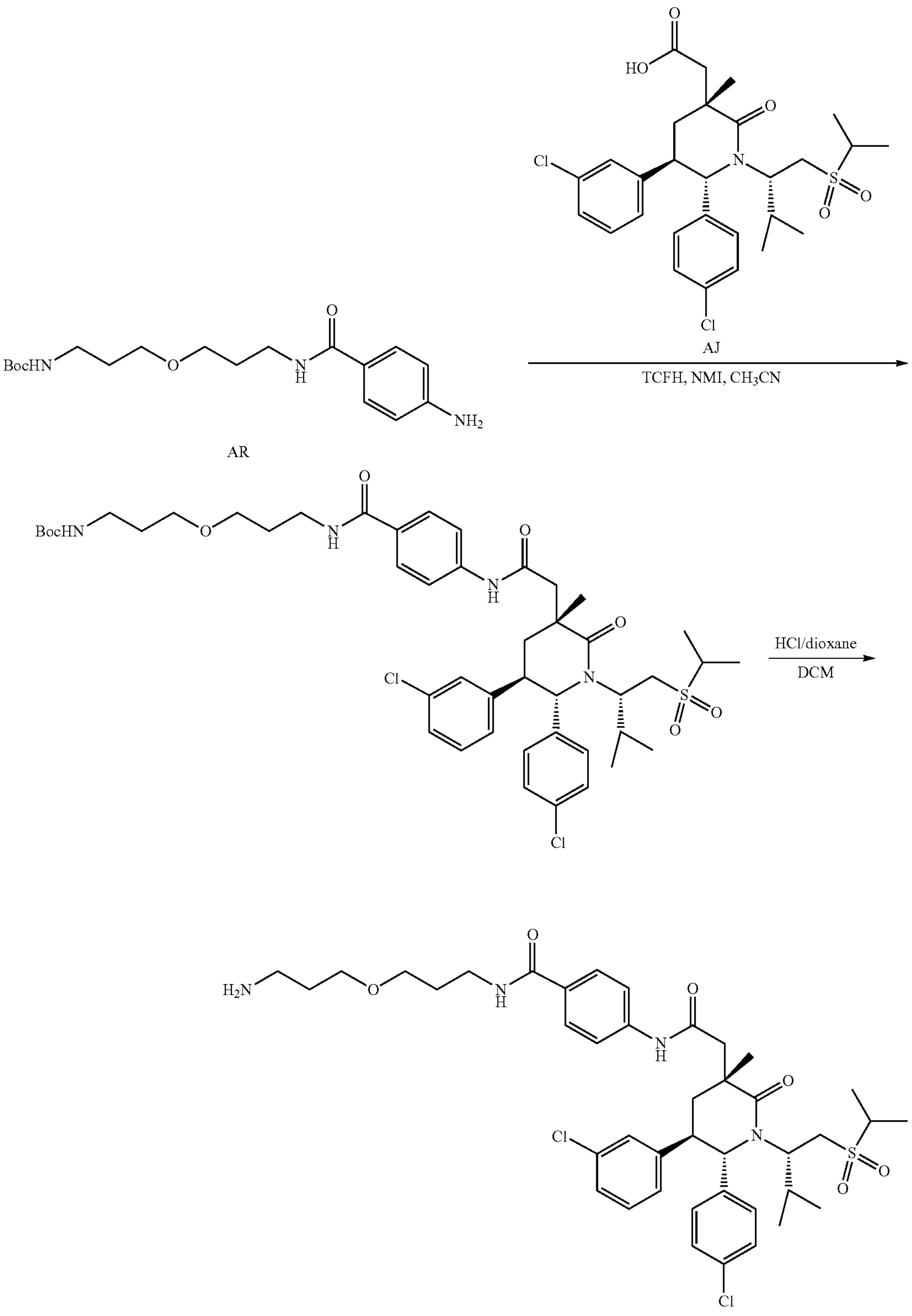
AJ
AR
I-5

Step 1—Tert-butyl N-[3-[3-[[4-[[2-[(3R,5R,6S)-5-(3-chlorophenyl)-6-(4-chlorophenyl)-1-[(1S)-1-(isopropylsulfonylmethyl)-2-methyl-propyl]-3-methyl-2-oxo-3-piperidyl]acetyl]amino]benzoyl]amino]propoxy]propyl]carbamate To a solution of 2-[(3R,5R,6S)-5-(3-chlorophenyl)-6-(4-chlorophenyl)-1-[(1S)-1-(isopropylsulfonyl methyl)-2-methyl-propyl]-3-methyl-2-oxo-3-piperidyl]acetic acid (50.0 mg, 87.9 umol, Intermediate AJ) in ACN (2 mL) was added 1-chloro-N,N,2-trimethyl-prop-1-en-1-amine (14.1 mg, 105 μmol) at 25° C. and the mixture was stirred for 0.5 hour. Then tert-butyl N-[3-[3-[(4-aminobenzoyl)amino]propoxy] propyl]carbamate (53.2 mg, 114 umol, TFA salt, Intermediate AR) and N,N-dimethylpyridin-2-amine (32.2 mg, 263 umol) in ACN (2 mL) was added to the reaction mixture at 25° C. and the reaction mixture was stirred for 2.5 hrs. On completion, the mixture was added 0.5 mL $H_2O$ and was concentrated in vacuo to give a residue. The residue was purified by prep-HPLC (column: Waters Xbridge 150*25 mm*5 um; mobile phase: [water (10 mM NH4HCO3)-ACN]; B %: 51%-81%, 10 min) to give the title compound (31.0 mg, 39% yield) as white solid. LC-MS ($ESI^+$) m/z 901.2 $(M+H)^+$.

Step 2—N-[3-(3-aminopropoxy)propyl]-4-[[2-[(3R,5R,6S)-5-(3-chlorophenyl)-6-(4-chlorophenyl)-1-[(1S)-1-(isopropylsulfonylmethyl)-2-methyl-propyl]-3-methyl-2-oxo-3-piperidyl]acetyl]amino]benzamide (I-5)

To a solution of tert-butyl N-[3-[3-[[4-[[2-[(3R,5R,6S)-5-(3-chlorophenyl)-6-(4-chlorophenyl)-1-[(1S)-1-(isopropylsulfonylmethyl)-2-methyl-propyl]-3-methyl-2-oxo-3-piperidyl]acetyl]amino]benzoyl]amino]propoxy]propyl]carbamate (20.0 mg, 22.1 umol) in DCM (0.5 mL) was added HCl/dioxane (4 M, 2.50 mL) at 25° C. and the mixture was stirred at 25° C. for 2 hrs. On completion, the mixture was concentrated in vacuo the residue. The residue was purified by prep-HPLC (column: Phenomenex Synergi C18 150*25*10 um; mobile phase: [water (0.225% FA)-ACN]; B %: 25%-55%, 10 min) to give the title compound (16.2 mg, 86% yield, FA salt) as white solid. $^1H$ NMR (400 MHz, DMSO-$d_6$) δ 10.44 (s, 1H), 8.44 (s, 1H), 8.39-8.34 (m, 1H), 7.82 (d, J=8.8 Hz, 2H), 7.71 (d, J=8.8 Hz, 2H), 7.48-7.26 (m, 2H), 7.22-7.16 (m, 1H), 7.15-7.11 (m, 1H), 6.93-6.87 (m, 2H), 5.03 (d, J=10.8 Hz, 1H), 3.90-3.81 (m, 1H), 3.62-3.55 (m, 2H), 3.44-3.40 (m, 8H), 3.13-3.02 (m, 3H), 2.75 (t, J=7.6 Hz, 2H), 2.66-2.58 (m, 1H), 2.21-2.05 (m, 4H), 1.78-1.67 (m, 4H), 1.32-1.26 (m, 9H), 0.57 (d, J=6.8 Hz, 3H), 0.43 (d, J=6.4 Hz, 3H); LC-MS ($ESI^+$) m/z 801.2 $(M+H)^+$.

Example 5. Synthesis of 4-[[2-[(3R,5R,6S)-5-(3-chlorophenyl)-6-(4-chlorophenyl)-1-[(1S)-1-(isopropylsulfonyl methyl)-2-methyl-propyl]-3-methyl-2-oxo-3-piperidyl]acetyl]amino]-N-[2-[2-[2-[2-[[2-(2,6-dioxo-3-piperidyl)-1,3-dioxo-isoindolin-4-yl]amino]ethoxy]ethoxy]ethoxy]ethyl]benzamide (I-6)

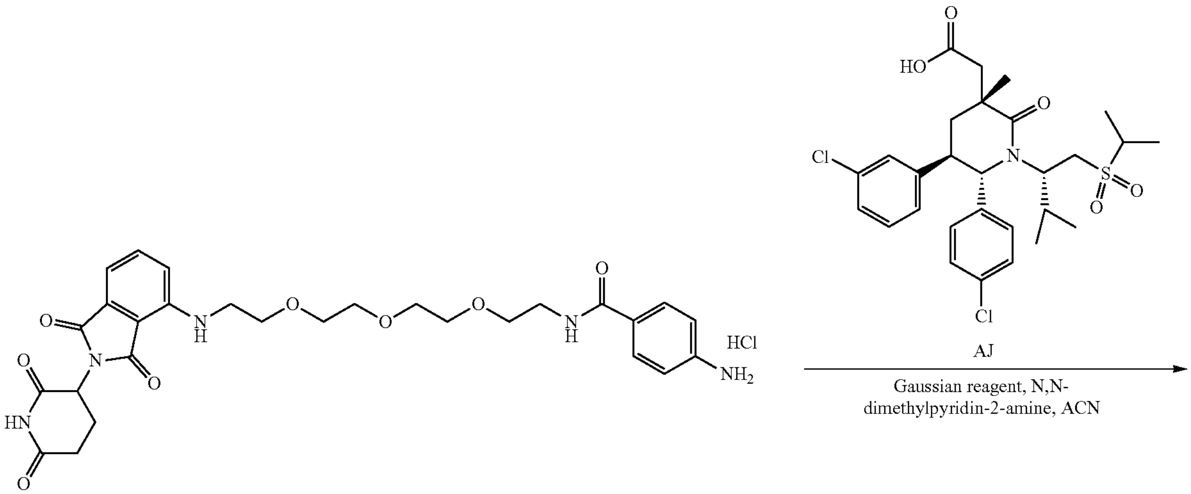

AU

-continued

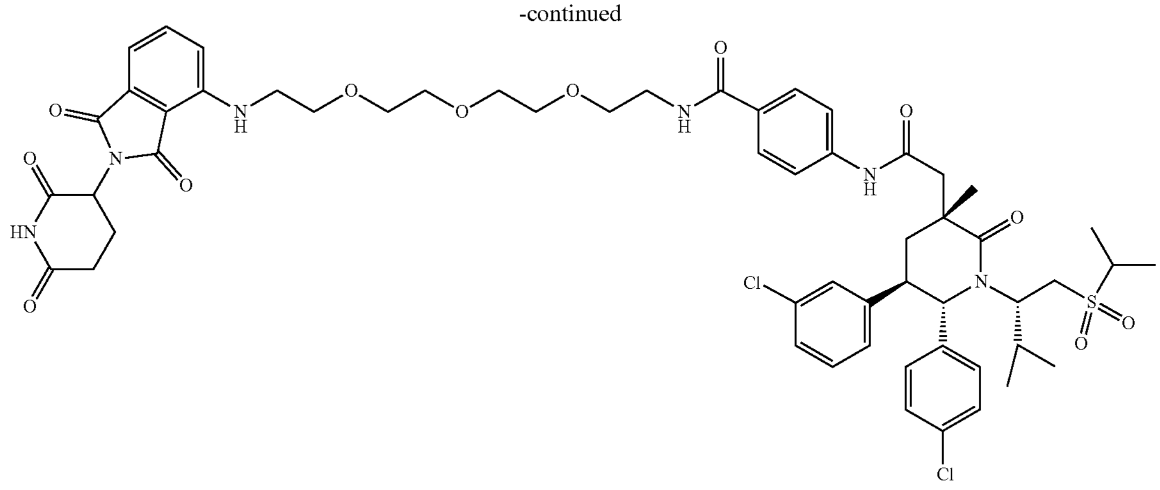

I-6

To a solution of 2-[(3R,5R,6S)-5-(3-chlorophenyl)-6-(4-chlorophenyl)-1-[(1S)-1-(isopropylsulfonyl methyl)-2-methyl-propyl]-3-methyl-2-oxo-3-piperidyl]acetic acid (20.0 mg, 35.1 umol, Intermediate AJ) in ACN (0.5 mL) was added 1-chloro-N,N,2-trimethyl-prop-1-en-1-amine (5.64 mg, 42.2 μmol), and the reaction mixture was stirred at 20° C. for 1 hour. Then the above solution was added to the solution of 4-amino-N-[2-[2-[2-[2-[[2-(2,6-dioxo-3-piperidyl)-1,3-dioxo-isoindolin-4-yl] amino] ethoxy]ethoxy] ethoxy]ethyl]benzamide (21.2 mg, 35.1 umol, HCl salt, Intermediate AU) and N,N-dimethylpyridin-2-amine (12.8 mg, 105 umol) in ACN (0.5 mL). The reaction mixture was stirred at 20° C. for 1 hour. On completion, the reaction mixture was quenched by water (0.1 mL) and concentrated in vacuo to give a residue. The residue was purified by Prep-HPLC (column: Shim-pack C18 150*25*10 um; mobile phase: [water (0.225% FA)–ACN]) to give the impure product. The impure product was purified by Prep-HPLC (column: Waters Xbridge 150*25 mm*5 um; mobile phase: [water (10 mM $NH_4HCO_3$)–ACN]) to give the title compound (15.5 mg, 38% yield) as yellow solid. $^1H$ NMR (400 MHz, DMSO-$d_6$) δ 11.23-10.64 (m, 1H), 10.41 (s, 1H), 8.39 (t, J=5.6 Hz, 1H), 7.87-7.66 (m, 5H), 7.56 (dd, J=7.6, 8.4 Hz, 1H), 7.48-7.25 (m, 2H), 7.22-7.00 (m, 5H), 6.94-6.85 (m, 2H), 6.59 (t, J=5.6 Hz, 1H), 5.11-4.97 (m, 2H), 3.85 (dd, J=10.4, 14.4 Hz, 1H), 3.64-3.56 (m, 3H), 3.56-3.52 (m, 4H), 3.52-3.50 (m, 4H), 3.50-3.48 (m, 2H), 3.46-3.41 (m, 2H), 3.40-3.37 (m, 2H), 3.26-3.16 (m, 1H), 3.12-3.02 (m, 2H), 2.96-2.81 (m, 1H), 2.66-2.58 (m, 2H), 2.57-2.53 (m, 2H), 2.21-1.96 (m, 4H), 1.32-1.25 (m, 9H), 0.57 (d, J=6.4 Hz, 3H), 0.43 (d, J=6.8 Hz, 3H). LC-MS ($ESI^+$) m/z 1117.6 $(M+H)^+$.

Example 6 (Method 2): Synthesis of (3'R,4'S,5'R)-6"-chloro-4'-(3-chloro-2-fluorophenyl)-N-(4-(4-((3-(1-(2,6-dioxopiperidin-3-yl)-3-methyl-2-oxo-2,3-dihydro-1H-benzo[d]imidazol-4-yl)prop-2-yn-1-yl)oxy)piperidine-1-carbonyl)phenyl)-2"-oxodispiro[cyclohexane-1,2'-pyrrolidine-3',3"-indoline]-5'-carboxamide (I-43)

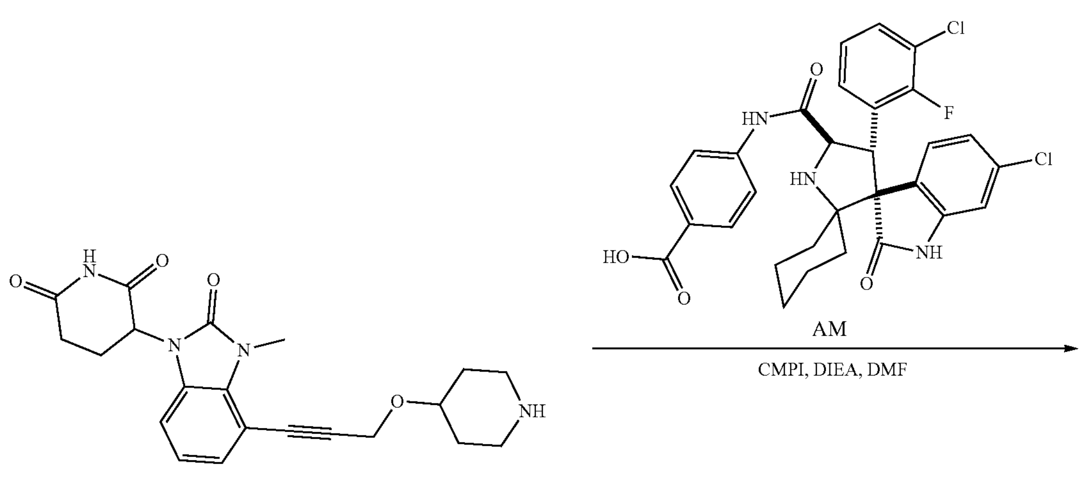

BB

-continued

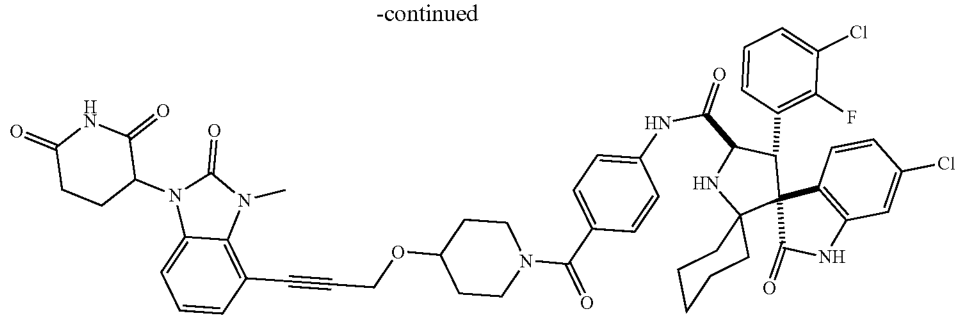

To a solution of 3-[3-methyl-2-oxo-4-[3-(4-piperidyloxy) prop-1-ynyl]benzimidazol-1-yl]piperidine-2,6-dione (40 mg, 78.3 umol, TFA, Intermediate BB) and 4-[[chloro-(3-chloro-2-fluoro-phenyl)-oxo-dispiro[BLAH]carbonyl] amino]benzoic acid (45.6 mg, 78.3 umol, Intermediate AM) in DMF (1 mL) was added DIEA (50.6 mg, 391 umol, 68.2 uL) and CMPI (24.0 mg, 94.0 umol), and the reaction mixture was stirred at 25° C. for 30 mins. On completion, the reaction mixture was concentrated in vacuo to give a residue. The residue was purified by prep-HPLC (column: Phenomenex Gemini-NX C18 75*30 mm*3 um; mobile phase: [water (10 mM NH4HCO3)-ACN]; B %: 42%-72%, 8 min) to give the title compound (7.86 mg, 10% yield) as a white solid. $^1$H NMR (400 MHz, DMSO-$d_6$) δ 11.43-10.35 (m, 1H), 10.21 (s, 1H), 7.74-7.60 (m, 3H), 7.49-7.42 (m, 1H), 7.41-7.32 (m, 3H), 7.21-7.09 (m, 3H), 7.08-6.98 (m, 2H), 6.69 (d, J=2.0 Hz, 1H), 5.39 (dd, J=4.8, 12.4 Hz, 1H), 4.79-4.72 (m, 1H), 4.71-4.64 (m, 1H), 4.52 (s, 2H), 4.10-3.78 (m, 2H), 3.69 (d, J=10.8 Hz, 1H), 3.64 (s, 3H), 3.28-3.18 (m, 3H), 2.93-2.83 (m, 1H), 2.77-2.63 (m, 2H), 2.11-1.99 (m, 2H), 1.98-1.78 (m, 3H), 1.69-1.43 (m, 7H), 1.42-1.32 (m, 1H), 1.09-0.90 (m, 1H), 0.89-0.77 (m, 1H); LC-MS (ESI$^+$) m/z 960.3 (M+H)$^+$.

TABLE 9

Compounds synthesized via Method 2 using the corresponding amines and acids for the coupling.

| I-#[a] | Amine | Acid | (ESI, m/z): [(M + 1)]$^+$ | $^1$H NMR (400 MHz, DMSO) δ |
|---|---|---|---|---|
| I-44 | BK | AM | 962.5 | 11.17-10.96 (m, 1H), 10.70-10.48 (m, 1H), 10.20 (s, 1H), 7.69-7.60 (m, 3H), 7.48-7.41 (m, 1H), 7.38-7.31 (m, 3H), 7.15 (t, J = 8.0 Hz, 1H), 7.06-7.00 (m, 1H), 6.96-6.89 (m, 1H), 6.73 (d, J = 8.4 Hz, 1H), 6.69 (d, J = 2.0 Hz, 1H), 6.58 (d, J = 8.0 Hz, 1H), 5.37-5.29 (m, 1H), 4.95-4.82 (m, 1H), 4.78-4.65 (m, 2H), 3.78-3.60 (m, 1H), 3.56-3.52 (m, 3H), 3.49-3.39 (m, 3H), 2.94-2.83 (m, 1H), 2.75-2.68 (m, 1H), 2.65-2.57 (m, 1H), 2.55-2.52 (m, 1H), 2.40 (s, 1H), 2.10-2.04 (m, 1H), 2.03-1.96 (m, 1H), 1.95-1.87 (m, 2H), 1.87-1.77 (m, 1H), 1.71-1.53 (m, 8H), 1.52-1.44 (m, 1H), 1.41-1.30 (m, 1H), 1.04-0.91 (m, 1H), 0.91-0.79 (m, 1H) |
| I-45 | BP | AM | 988.6 | 11.09 (s, 1H), 10.59 (s, 1H), 10.19 (s, 1H), 7.88-7.58 (m, 3H), 7.50-7.42 (m, 1H), 7.40-7.24 (m, 3H), 7.15 (t, J = 8.0 Hz, 1H), 7.07-7.01 (m, 1H), 6.99-6.90 (m, 2H), 6.88-6.80 (m, 1H), 6.69 (d, J = 2.0 Hz, 1H), 5.40-5.30 (m, 1H), 4.80-4.73 (m, 1H), 4.71-4.64 (m, 1H), 3.75-3.61 (m, 1H), 3.54 (s, 3H), 3.39 (s, 3H), 3.10-2.96 (m, 2H), 2.93-2.83 (m, 1H), 2.79-2.70 (m, 3H), 2.65-2.60 (m, 1H), 2.14-1.92 (m, 3H), 1.91-1.77 (m, 2H), 1.70-1.26 (m, 14H), 1.23-0.71 (m, 4H) |
| I-46 | BQ | AM | 876.4 | 11.10 (s, 1H), 10.60 (s, 1H), 10.27 (s, 1H), 8.98 (t, J = 5.2 Hz, 1H), 7.86 (d, J = 8.8 Hz, 2H), 7.72 (d, J = 8.8 Hz, 2H), 7.67-7.59 (m, 1H), 7.50-7.42 (m, 1H), 7.40-7.31 (m, 1H), 7.20-7.11 (m, 2H), 7.10-6.97 (m, 3H), 6.69 (d, J = 2.0 Hz, 1H), 5.43-5.33 (m, 1H), 4.81-4.64 (m, 2H), 4.36-4.30 (m, 2H), 3.79-3.64 (m, 1H), 3.60 (s, 3H), 2.96-2.82 (m, 1H), 2.76-2.67 (m, 1H), 2.65-2.58 (m, 1H), 2.13-1.96 (m, 2H), 1.92-1.75 (m, 1H), 1.71-1.54 (m, 4H), 1.53-1.32 (m, 2H), 1.04-0.79 (m, 2H) |
| I-47 | BR | AM | 932.4 | 11.13 (s, 1H), 10.58 (s, 1H), 10.22 (d, J = 6.4 Hz, 1H), 7.70-7.60 (m, 3H), 7.49-7.31 (m, 5H), 7.21-7.10 (m, 3H), 7.07-7.01 (m, 2H), 6.68 (d, J = 2.0 Hz, 1H), 5.44-5.35 (m, 1H), 4.83-4.65 (m, 3H), 4.00-3.90 (m, 1H), 3.71-3.62 (m, 3H), 3.58-3.48 (m, 4H), 2.94-2.83 (m, 1H), 2.65-2.59 (m, 2H), 2.10-2.01 (m, 2H), 1.89-1.77 (m, 1H), 1.70-1.46 (m, 6H), 1.41-1.31 (m, 1H), 1.04-0.92 (m, 1H), 0.88-0.76 (m, 1H) |
| I-48 | BS | AM | 890.5 | 11.15-11.06 (m, 1H), 10.59 (s, 1H), 10.25 (s, 1H), 8.63 (t, J = 5.6 Hz, 1H), 7.85 (d, J = 8.8 Hz, 2H), 7.73-7.68 (m, 2H), 7.63 (t, J = 6.8 Hz, 1H), 7.48-7.43 (m, 1H), 7.36 (t, J = 7.6 Hz, 1H), 7.23 (s, 1H), 7.17-7.12 (m, 1H), 7.09 (s, 2H), 7.04 (dd, J = 1.6, 8.0 Hz, 1H), |

TABLE 9-continued

Compounds synthesized via Method 2 using the corresponding amines and acids for the coupling.

| I-#[a] | Amine | Acid | (ESI, m/z): $[(M + 1)]^+$ | $^1H$ NMR (400 MHz, DMSO) δ |
|---|---|---|---|---|
| | | | | 6.71-6.66 (m, 1H), 5.42-5.32 (m, 1H), 4.79-4.66 (m, 2H), 3.76-3.59 (m, 2H), 3.48-3.45 (m, 2H), 3.31 (s, 3H), 2.91-2.84 (m, 1H), 2.69-2.66 (m, 2H), 2.09-2.00 (m, 2H), 1.89-1.80 (m, 1H), 1.70-1.47 (m, 6H), 1.42-1.33 (m, 1H), 1.04-0.92 (m, 1H), 0.89-0.78 (m, 1H) |
| I-49 | CV | AM | 1021.3 $(M + 3)^+$ | 11.10 (s, 1H), 10.60 (s, 1H), 10.20 (s, 1H), 7.69-7.60 (m, 3H), 7.46 (dd, J = 2.0, 8.0 Hz, 1H), 7.40-7.31 (m, 3H), 7.15 (t, J = 8.4 Hz, 1H), 7.09-7.02 (m, 2H), 6.96 (t, J = 7.6 Hz, 1H), 6.90-6.85 (m, 1H), 6.69 (d, J = 2.0 Hz, 1H), 5.41-5.35 (m, 1H), 4.79-4.73 (m, 1H), 4.71-4.65 (m, 1H), 3.74-3.65 (m, 5H), 3.62 (s, 3H), 2.94-2.84 (m, 1H), 2.67 (br s, 2H), 2.67-2.58 (m, 2H), 2.20-1.94 (m, 5H), 1.93-1.71 (m, 6H), 1.71-1.32 (m, 12H), 1.07-0.79 (m, 2H) |
| I-50 | BM | AM | 977.6 | 11.36-10.28 (m, 2H), 10.22 (s, 1H), 7.69 (d, J = 8.4 Hz, 2H), 7.66-7.61 (m, 1H), 7.47-7.43 (m, 1H), 7.40 (d, J = 8.4 Hz, 2H), 7.38-7.32 (m, 1H), 7.15 (t, J = 8.0 Hz, 1H), 7.05-7.01 (m, 1H), 6.97 (d, J = 4.4 Hz, 2H), 6.89-6.85 (m, 1H), 6.69 (d, J = 2.0 Hz, 1H), 5.39-5.33 (m, 1H), 4.78-4.73 (m, 1H), 4.72-4.65 (m, 1H), 3.69 (d, J = 10.0 Hz, 1H), 3.57 (s, 3H), 3.50 (s, 5H), 3.44 (d, J = 7.2 Hz, 1H), 2.95-2.89 (m, 2H), 2.85 (d, J = 6.0 Hz, 1H), 2.73-2.58 (m, 2H), 2.46 (s, 2H), 2.09-1.95 (m, 2H), 1.88-1.77 (m, 3H), 1.70-1.53 (m, 5H), 1.53-1.45 (m, 1H), 1.43-1.32 (m, 1H), 1.02-0.93 (m, 1H), 0.89-0.79 (m, 1H) |
| I-51 | BT | AM | 904.4 | 11.14-11.09 (m, 1H), 10.66-10.48 (m, 1H), 10.32-10.17 (m, 1H), 8.49-8.41 (m, 1H), 7.83 (d, J = 8.4 Hz, 2H), 7.73-7.62 (m, 3H), 7.48-7.29 (m, 2H), 7.13-6.95 (m, 5H), 6.75-6.65 (m, 1H), 5.38 (dd, J = 5.2, 12.8 Hz, 1H), 4.84-4.63 (m, 2H), 3.65 (s, 3H), 3.39 (d, J = 6.4 Hz, 2H), 2.93-2.85 (m, 1H), 2.71-2.69 (m, 1H), 2.76-2.68 (m, 1H), 2.65-2.59 (m, 2H), 2.06-1.98 (m, 2H), 1.87-1.80 (m, 3H), 1.68-1.56 (m, 4H), 1.50-1.35 (m, 2H), 1.25-1.15 (m, 1H), 1.02-0.93 (m, 1H), 0.90-0.82 (m, 1H) |
| I-52 | BV | AM | 952.5 | 11.16-11.03 (m, 1H), 10.68-10.56 (m, 1H), 10.30-10.05 (m, 1H), 7.70-7.59 (m, 3H), 7.50-7.39 (m, 1H), 7.39-7.32 (m, 3H), 7.18-7.11 (m, 1H), 7.04 (dd, J = 2.0, 8.4 Hz, 1H), 6.99-6.91 (m, 2H), 6.89-6.76 (m, 1H), 6.69 (d, J = 2.0 Hz, 1H), 5.36 (dd, J = 5.2, 12.4 Hz, 1H), 4.82-4.59 (m, 2H), 3.56-3.46 (m, 5H), 3.36 (s, 3H), 2.97-2.79 (m, 6H), 2.76-2.68 (m, 1H), 2.65-2.59 (m, 1H), 2.54 (s, 1H), 2.05-1.93 (m, 2H), 1.88-1.44 (m, 11H), 1.40-1.26 (m, 1H), 1.02-0.90 (m, 1H), 0.89-0.76 (m, 1H) |
| I-53 | BG | AM | 974.5 | 11.09 (s, 1H), 10.59 (s, 1H), 10.20 (s, 1H), 7.70-7.58 (m, 3H), 7.45 (d, J = 8.0 Hz, 1H), 7.40-7.28 (m, 3H), 7.15 (t, J = 8.0 Hz, 1H), 7.04 (d, J = 8.0 Hz, 1H), 6.95 (d, J = 4.4 Hz, 2H), 6.88-6.80 (m, 1H), 6.69 (s, 1H), 5.35 (dd, J = 5.2, 12.4 Hz, 1H), 4.80-4.72 (m, 1H), 4.72-4.63 (m, 1H), 3.54 (s, 3H), 3.51-3.38 (m, 2H), 3.29-3.08 (m, 2H), 2.94-2.61 (m, 5H), 2.32-2.23 (m, 1H), 2.11-1.95 (m, 4H), 1.92-1.26 (m, 16H), 1.02-0.90 (m, 1H), 0.90-0.80 (m, 1H) |
| I-54 | BX | AM | 951.6 | 11.21 (s, 1H), 10.59 (s, 1H), 10.20 (s, 1H), 7.71-7.59 (m, 3H), 7.50-7.42 (m, 1H), 7.40-7.31 (m, 3H), 7.20-7.06 (m, 3H), 7.06-6.99 (m, 2H), 6.66 (d, J = 5.6 Hz, 1H), 5.40-5.30 (m, 1H), 4.81-4.72 (m, 1H), 4.70-4.63 (m, 1H), 4.01-3.71 (m, 2H), 3.55-3.50 (m, 2H), 3.47-3.44 (m, 2H), 3.24-3.17 (m, 2H), 2.96-2.81 (m, 1H), 2.80-2.73 (m, 2H), 2.72-2.63 (m, 2H), 2.20-2.10 (m, 1H), 2.10-2.00 (m, 1H), 1.93-1.72 (m, 5H), 1.70-1.54 (m, 4H), 1.53-1.33 (m, 4H), 1.02-0.80 (m, 2H) |
| I-55 | BY | AM | 975.6 | 11.11 (s, 1H), 10.64 (s, 1H), 10.23 (s, 1H), 7.74-7.56 (m, 3H), 7.50-7.30 (m, 4H), 7.22-7.10 (m, 1H), 7.08-7.01 (m, 1H), 7.01-6.92 (m, 2H), 6.91-6.83 (m, 1H), 6.76-6.66 (m, 1H), 5.46-5.27 (m, 1H), 4.87-4.60 (m, 2H), 3.95-3.58 (m, 7H), 2.98-2.81 (m, 5H), 2.75-2.65 (m, 2H), 2.11-1.93 (m, 2H), 1.91-1.75 (m, 3H), 1.72-1.31 (m, 12H), 1.29-1.09 (m, 1H), 1.07-0.78 (m, 2H) |
| I-56 | CX | AM | 989.2 | 11.13 (s, 1H), 10.64 (s, 1H), 10.20 (s, 1H), 7.69-7.58 (m, 3H), 7.45 (d, J = 7.6 Hz, 1H), 7.35 (d, J = 8.8 Hz, 3H), 7.28 (s, 1H), 7.21-7.08 (m, 3H), 7.04 (br d, J = 8.4 Hz, 1H), 6.69 (d, J = 2.0 Hz, 1H), 5.43-5.34 (m, 1H), 4.79-4.71 (m, 1H), 4.71-4.63 (m, 1H), 3.93-3.41 (m, 11H), 2.97 (s, 3H), 2.93-2.78 (m, 2H), 2.76-2.56 (m, 4H), 2.18-1.95 (m, 3H), 1.90-1.75 (m, 1H), 1.70-1.43 (m, 5H), 1.41-1.29 (m, 1H), 1.02-0.90 (m, 1H), 0.89-0.77 (m, 1H) |
| I-57 | DB | AM | 955.5 | 11.22 (s, 1H), 10.62 (s, 1H), 10.25 (s, 1H), 8.44 (t, J = 5.2 Hz, 1H), 7.83 (d, J = 8.8 Hz, 2H), 7.69 (d, J = 8.8 Hz, 2H), 7.63 (t, J = 6.8 Hz, 1H), 7.46 (dd, J = 2.0, 8.4 Hz, 1H), 7.40-7.31 (m, 1H), 7.24 (s, 1H), 7.19-7.12 (m, 2H), 7.07-7.00 (m, 2H), 6.70 (d, J = 2.0 Hz, 1H), |

TABLE 9-continued

Compounds synthesized via Method 2 using the corresponding amines and acids for the coupling.

| I-#[a] | Amine | Acid | (ESI, m/z): [(M + 1)]$^+$ | $^1$H NMR (400 MHz, DMSO) δ |
|---|---|---|---|---|
| | | | | 5.39-5.30 (m, 1H), 4.80-4.74 (m, 1H), 4.73-4.66 (m, 1H), 3.58-3.51 (m, 4H), 3.51-3.47 (m, 2H), 3.42 (s, 6H), 2.95-2.82 (m, 1H), 2.75-2.59 (m, 4H), 2.20-2.10 (m, 1H), 2.09-2.01 (m, 1H), 1.87-1.71 (m, 3H), 1.70-1.53 (m, 4H), 1.49 (d, J = 10.8 Hz, 1H), 1.42-1.13 (m, 3H), 1.05-0.91 (m, 1H), 0.90-0.78 (m, 1H) |
| I-58 | BC | AM | 906.4 | 11.10 (s, 1H), 10.59 (s, 1H), 10.2 (s, 1H), 7.68 (d, J = 7.6 Hz, 4H), 7.47-7.40 (m, 3H), 7.35 (t, J = 6.4 Hz, 1H), 7.17-7.12 (m, 1H), 7.09-6.98 (m, 4H), 6.69 (s, 1H), 5.41-5.33 (m, 1H), 4.75 (d, J = 8.7 Hz, 1H), 4.71-4.67 (m, 1H), 4.39 (s, 2H), 4.13 (d, J = 3.2 Hz, 2H), 3.71-3.66 (m, 2H), 3.61 (s, 3H), 3.16 (d, J = 3.2 Hz, 2H), 2.95-2.82 (m, 1H), 2.76-2.61 (m, 2H), 2.08-1.97 (m, 2H), 1.89-1.80 (m, 2H), 1.76-1.68 (m, 2H), 1.64-1.59 (m, 2H), 1.52-1.44 (m, 1H), 1.41-1.32 (m, 1H), 1.00-0.92 (m, 1H), 0.88-0.80 (m, 1H) |
| I-59 | CE | AM | 947.4 | 11.27-10.86 (m, 1H), 10.76-10.39 (m, 1H), 10.24 (s, 1H), 7.71-7.56 (m, 5H), 7.45 (dd, J = 2.4, 8.0 Hz, 1H), 7.39-7.32 (m, 1H), 7.14 (t, J = 8.0 Hz, 1H), 7.03 (dd, J = 2.0, 8.4 Hz, 1H), 6.85 (t, J = 8.0 Hz, 1H), 6.69 (d, J = 2.0 Hz, 1H), 6.49 (d, J = 8.0 Hz, 1H), 6.40 (d, J = 8.0 Hz, 1H), 5.27 (dd, J = 5.2, 12.8 Hz, 1H), 5.02-4.92 (m, 1H), 4.80-4.73 (m, 1H), 4.72-4.63 (m, 1H), 4.39-4.21 (m, 2H), 4.11-3.93 (m, 2H), 3.68 (d, J = 9.6 Hz, 1H), 3.59 (s, 3H), 3.09-3.08 (m, 2H), 2.92-2.82 (m, 1H), 2.66-2.56 (m, 3H), 2.31-2.28 (m, 1H), 2.08-2.02 (m, 1H), 2.02-1.94 (m, 3H), 1.88-1.77 (m, 1H), 1.74-1.42 (m, 6H), 1.41-1.31 (m, 1H), 1.03-0.91 (m, 1H), 0.88-0.80 (m, 1H) |
| I-60 | DE | AM | 985.4 | 11.12 (s, 1H), 10.67-10.57 (m, 1H), 10.25 (s, 1H), 7.70-7.60 (m, 5H), 7.45 (dd, J = 2.4, 8.0 Hz, 1H), 7.38-7.32 (m, 1H), 7.18-7.07 (m, 3H), 7.06-6.98 (m, 2H), 6.69 (d, J = 2.0 Hz, 1H), 5.39 (dd, J = 5.2, 12.8 Hz, 1H), 4.79-4.72 (m, 1H), 4.71-4.65 (m, 1H), 4.02 (s, 2H), 3.72 (s, 2H), 3.64 (s, 4H), 3.55 (s, 2H), 2.94-2.83 (m, 1H), 2.74-2.62 (m, 2H), 2.55-2.47 (m, 3H), 2.09-1.97 (m, 2H), 1.87-1.71 (m, 5H), 1.70-1.44 (m, 6H), 1.40-1.31 (m, 1H), 1.01-0.90 (m, 1H), 0.89-0.80 (m, 1H) |
| I-61 | CB | AM | 975.6 | 11.10 (s, 1H), 10.61 (s, 1H), 10.20 (s, 1H), 8.29 (s, 1H), 7.68-7.59 (m, 3H), 7.45 (dd, J = 2.0, 8.4 Hz, 1H), 7.38-7.29 (m, 3H), 7.15 (t, J = 8.0 Hz, 1H), 7.04 (dd, J = 2.0, 8.0 Hz, 1H), 6.99-6.91 (m, 2H), 6.87 (dd, J = 2.4, 6.4 Hz, 1H), 6.69 (d, J = 2.0 Hz, 1H), 5.38-5.33 (m, 1H), 4.79-4.64 (m, 2H), 3.56 (s, 3H), 2.99 (s, 4H), 2.93-2.82 (m, 3H), 2.77-2.60 (m, 4H), 2.55-2.51 (m, 3H), 2.07-1.95 (m, 2H), 1.91-1.80 (m, 1H), 1.74-1.44 (m, 10H), 1.42-1.31 (m, 1H), 1.04-0.92 (m, 1H), 0.90-0.79 (m, 1H) |
| I-62 | CF | AM | 904.3 | 11.11 (s, 1H), 10.59 (s, 1H), 10.20 (s, 1H), 7.71-7.55 (m, 3H), 7.46 (d, J = 8.0 Hz, 1H), 7.41-7.27 (m, 3H), 7.19-7.09 (m, 2H), 7.08-6.95 (m, 3H), 6.69 (d, J = 2.0 Hz, 1H), 5.43-5.33 (m, 1H), 4.79-4.72 (m, 1H), 4.72-4.62 (m, 1H), 3.80-3.48 (m, 6H), 3.01 (s, 3H), 2.93-2.70 (m, 4H), 2.65-2.58 (m, 1H), 2.10-1.97 (m, 2H), 1.89-1.78 (m, 1H), 1.69-1.53 (m, 4H), 1.52-1.44 (m, 1H), 1.41-1.31 (m, 1H), 1.04-0.90 (m, 1H), 0.89-0.77 (m, 1H) |
| I-63 | BE | AM | 949.2 | 11.25-10.95 (m, 1H), 10.63 (s, 1H), 10.21 (s, 1H), 7.70-7.59 (m, 3H), 7.46 (dd, J = 1.2, 8.0 Hz, 1H), 7.39-7.29 (m, 3H), 7.15 (t, J = 7.8 Hz, 1H), 7.10-7.00 (m, 2H), 6.94 (t, J = 7.6 Hz, 1H), 6.90-6.79 (m, 1H), 6.70 (d, J = 1.8 Hz, 1H), 5.37 (dd, J = 5.8, 12.5 Hz, 1H), 4.84-4.73 (m, 1H), 4.72-4.60 (m, 1H), 3.67 (s, 3H), 3.63-3.53 (m, 2H), 3.02-2.90 (m, 1H), 2.91-2.83 (m, 2H), 2.78 (s, 3H), 2.73-2.66 (m, 1H), 2.65-2.56 (m, 1H), 2.56-2.51 (m, 2H), 2.11-1.96 (m, 3H), 1.89-1.70 (m, 4H), 1.68-1.54 (m, 6H), 1.54-1.44 (m, 1H), 1.41-1.33 (m, 1H), 1.04-0.92 (m, 1H), 0.90-0.80 (m, 1H) |
| I-64 | DG | AM | 964.5 | 11.09 (s, 1H), 10.72-10.37 (m, 1H), 9.34-8.93 (m, 1H), 7.72-7.42 (m, 4H), 7.38 (d, J = 8.4 Hz, 2H), 7.31-7.18 (m, 1H), 7.15-7.04 (m, 1H), 7.00-6.92 (m, 2H), 6.91-6.84 (m, 1H), 6.80-6.70 (m, 1H), 5.37 (dd, J = 5.2, 12.8 Hz, 1H), 4.93-4.77 (m, 1H), 4.05-3.78 (m, 1H), 3.57 (s, 4H), 3.49 (t, J = 5.6 Hz, 2H), 3.03-2.92 (m, 2H), 2.91-2.83 (m, 1H), 2.77-2.58 (m, 3H), 2.55-2.52 (m, 10H), 1.98 (dd, J = 5.2, 10.0 Hz, 1H), 1.88-1.78 (m, 4H), 1.69-1.38 (m, 6H), 1.18-0.91 (m, 2H) |
| I-65 | CC | AM | 947.5 | 11.09 (d, J = 3.2 Hz, 1H), 10.59 (s, 1H), 10.26 (s, 1H), 7.76-7.59 (m, 5H), 7.46 (d, J = 7.6 Hz, 1H), 7.36 (t, J = 7.6 Hz, 1H), 7.15 (t, J = 7.6 Hz, 1H), 7.04 (d, J = 8.4 Hz, 1H), 7.01-6.82 (m, 3H), 6.69 (s, 1H), 5.35-5.32 (m, 1H), 4.81-4.73 (m, 1H), 4.73-4.64 (m, 1H), 4.16 (s, 1H), 4.05 (s, 1H), 3.87 (d, J = 2.8 Hz, 1H), 3.81-3.74 (m, 1H), 3.70-3.68 (m, 1H), 3.62 (s, 3H), 3.28-3.21 (m, 1H), 3.07-2.83 (m, 2H), 2.76-2.68 (m, 1H), 2.12-1.78 (m, 9H), 1.71-1.46 (m, 6H), 1.41-1.31 (m, 1H), 1.01-0.80 (m, 2H) |

TABLE 9-continued

Compounds synthesized via Method 2 using the corresponding amines and acids for the coupling.

| I-#[a] | Amine | Acid | (ESI, m/z): $[(M + 1)]^+$ | $^1H$ NMR (400 MHz, DMSO) δ |
|---|---|---|---|---|
| I-66 | DS | CN | 944.6 | 11.08 (s, 1H), 10.53 (s, 1H), 8.22 (s, 1H), 7.72 (d, J = 8.4 Hz, 1H), 7.58 (t, J = 6.8 Hz, 1H), 7.44 (d, J = 8.0 Hz, 1H), 7.37-7.27 (m, 1H), 7.11 (t, J = 8.0 Hz, 1H), 7.04 (dd, J = 2.0, 8.0 Hz, 1H), 7.02 (s, 1H), 6.99 (d, J = 8.0 Hz, 1H), 6.85 (d, J = 7.6 Hz, 1H), 6.68 (d, J = 2.0 Hz, 1H), 5.33 (dd, J = 5.2, 12.8 Hz, 1H), 4.60-4.51 (m, 1H), 4.39-4.32 (m, 1H), 3.32 (s, 3H), 2.93-2.84 (m, 1H), 2.71 (d, J = 4.4 Hz, 1H), 2.65-2.57 (m, 3H), 2.24 (s, 2H), 2.10 (s, 3H), 2.07-1.96 (m, 3H), 1.85-1.67 (m, 6H), 1.64-1.54 (m, 3H), 1.51-1.36 (m, 5H), 1.34-1.04 (m, 8H), 1.00-0.80 (m, 6H), 0.59 (s, 3H) |
| I-93 | DS | CI | 914.6 | 11.06 (s, 1H), 10.52 (s, 1H), 8.32 (d, J = 3.2 Hz, 2H), 7.73 (d, J = 8.4 Hz, 1H), 7.63-7.53 (m, 1H), 7.45-7.36 (m, 1H), 7.35-7.26 (m, 1H), 7.10 (t, J = 8.0 Hz, 1H), 7.06-6.95 (m, 3H), 6.85 (d, J = 8.0 Hz, 1H), 6.66 (d, J = 1.6 Hz, 1H), 5.32 (dd, J = 5.6, 12.4 Hz, 1H), 4.58-4.51 (m, 1H), 4.36 (d, J = 9.2 Hz, 1H), 3.17 (s, 3H), 2.95-2.81 (m, 2H), 2.65-2.55 (m, 4H), 2.22 (t, J = 6.8 Hz, 2H), 2.08 (s, 3H), 2.05-1.87 (m, 5H), 1.80-1.69 (m, 5H), 1.65-1.50 (m, 6H), 1.40 (dd, J = 7.8, 13.8 Hz, 4H), 1.32-1.22 (m, 4H), 0.90-0.74 (m, 3H |
| I-94[b] | CP | CI | 954.6 | 11.15 (s, 1H), 11.09-10.89 (m, 1H), 8.61-8.21 (m, 1H), 7.81-7.73 (m, 2H), 7.59 (t, J = 7.2 Hz, 1H), 7.55-7.42 (m, 2H), 7.29-7.16 (m, 2H), 7.09 (d, J = 6.8 Hz, 1H), 6.75 (s, 1H), 5.46 (dd, J = 5.2, 12.8 Hz, 1H), 4.64 (d, J = 10.0 Hz, 1H), 4.34 (d, J = 13.2 Hz, 1H), 3.95-3.82 (m, 1H), 3.49 (s, 3H), 3.03-2.93 (m, 3H), 2.90 (dd, J = 5.3, 16.8 Hz, 1H), 2.80-2.60 (m, 3H), 2.20-1.87 (m, 5H), 1.80-1.25 (m, 15H), 1.76-1.23 (m, 1H), 1.17-1 |
| I-95 | FW | AM | 866.4 | 12.89-12.78 (m, 1H), 10.8 (s, 1H), 10.59 (s, 1H), 10.24 (s, 1H), 8.48-8.41 (m, 1H), 8.38-8.28 (m, 1H), 7.87-7.76 (m, 3H), 7.73-7.58 (m, 5H), 7.46 (d, J = 7.2 Hz, 1H), 7.41-7.32 (m, 1H), 7.21-7.12 (m, 1H), 7.09-7.00 (m, 1H), 6.88 (d, J = 7.6 Hz, 1H), 6.70 (s, 1H), 6.50-6.40 (m, 1H), 4.83-4.60 (m, 2H), 3.85-3.80 (m, 2H), 1.92-1.84 (m, 4H), 1.70-1.54 (m, 6H), 1.29-1.20 (m, 3H), 1.17-1.14 (m, 2H), 0.98-0.80 (m, 4H) |

[a]The reaction was run anywhere from 0.5-2 hrs at rt. The final products were isolated under standard purification techniques including reverse HPLC and prep-TLC with appropriate solvent conditions.

[b]This reduced compound was formed during the coupling.

Example 8 (Method 3): Synthesis of (3'R,4'S,5'R)-6"-chloro-4'-(3-chloro-2-fluorophenyl)-N-((1r,4R)-4-((5-(1-(2,6-dioxopiperidin-3-yl)-3-methyl-2-oxo-2,3-dihydro-1H-benzo[d]imidazol-5-yl)pentyl)carbamoyl)cyclohexyl)-2"-oxodispiro[cyclohexane-1,2'-pyrrolidine-3',3"-indoline]-5'-carboxamide (1-67)

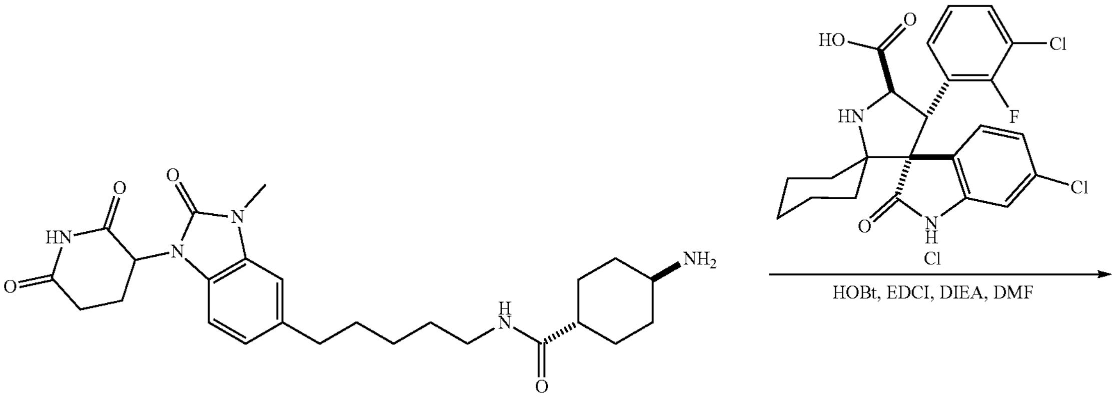

CM

-continued

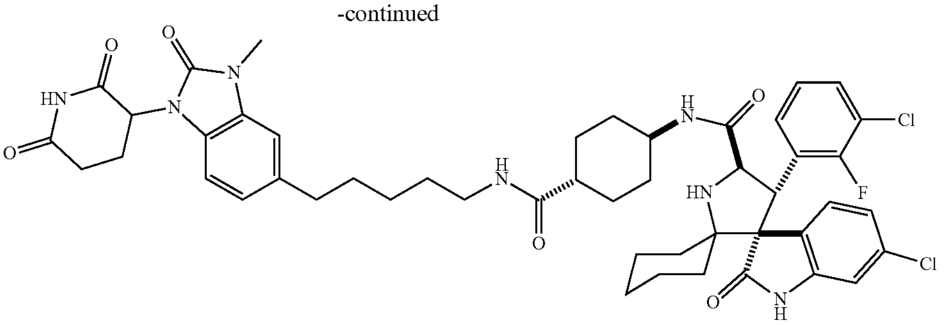

To a mixture of chloro-(3-chloro-2-fluoro-phenyl)-oxo-dispiro[BLAH]carboxylic acid (20.0 mg, 43.2 umol, Intermediate CI) and HOBt (8.75 mg, 64.7 umol) in DMF (0.5 mL) was added EDCI (12.4 mg, 64.8 umol) and DIEA (27.9 mg, 214 umol) at 25° C. under $N_2$. The mixture was stirred at 25° C. for 10 min, then 4-amino-N-[5-[1-(2,6-dioxo-3-piperidyl)-3-methyl-2-oxo-benzimidazol-5-yl]pentyl]cyclohexanecarboxamide (20.3 mg, 43.2 umol, Intermediate CM) was added and the mixture was stirred at 25° C. for 30 min. On completion, the reaction mixture was concentrated in vacuo to give a residue. The residue was purified by Prep-HPLC [column: Phenomenex luna C18 150*25 mm*10 um; mobile phase: [water (0.225% FA)-ACN]; B %: 30%-60%, 11.5 min] to give the title compound (6.80 mg, 17% yield) as white solid. $^1$H NMR (400 MHz, DMSO-$d_6$) δ 11.08 (s, 1H), 10.52 (s, 1H), 7.78 (d, J=8.8 Hz, 1H), 7.67 (t, J=4.8 Hz, 1H), 7.59 (t, J=6.8 Hz, 1H), 7.45-7.37 (m, 1H), 7.33 (t, J=6.8 Hz, 1H), 7.11 (t, J=8.0 Hz, 1H), 7.07-6.91 (m, 3H), 6.86 (d, J=8.0 Hz, 1H), 6.67 (d, J=2.0 Hz, 1H), 5.33 (dd, J=5.6, 12.8 Hz, 1H), 4.63-4.51 (m, 1H), 4.43-4.31 (m, 1H), 3.52 (d, J=10.8 Hz, 1H), 3.31 (s, 3H), 3.01 (q, J=6.0 Hz, 2H), 2.94-2.84 (m, 1H), 2.66 (d, J=16.0 Hz, 2H), 2.62-2.57 (m, 2H), 2.08-1.85 (m, 4H), 1.78-1.68 (m, 3H), 1.64-1.51 (m, 6H), 1.42-1.33 (m, 4H), 1.31-1.19 (m, 8H), 0.83-0.75 (m, 1H). LC-MS (ESI$^+$) m/z 914.3 (M+H)$^+$.

TABLE 10

Compounds synthesized via Method 3 using the corresponding amines and acids for the coupling.

| I-#[a] | Amine | Acid | LCMS (ESI, m/z): $[(M + 1)]^+$ | $^1$H NMR (400 MHz, DMSO) δ |
|---|---|---|---|---|
| I-68 | CO | CN | 950.5 | 11.14-11.08 (m, 1H), 10.56-10.48 (m, 1H), 7.77-7.69 (m, 1H), 7.65-7.54 (m, 1H), 7.47-7.39 (m, 1H), 7.36-7.28 (m, 1H), 7.24-7.19 (m, 1H), 7.11-7.01 (m, 4H), 5.43-5.28 (m, 1H), 4.60-4.49 (m, 1H), 4.41-4.29 (m, 1H), 3.42 (s, 2H), 3.29 (s, 4H), 2.68-2.66 (m, 2H), 2.13-2.01 (m, 6H), 1.91-1.71 (m, 10H), 1.64-1.54 (m, 4H), 1.51-1.39 (m, 4H), 1.26-1.09 (m, 6H), 0.89 (s, 3H), 0.61-0.57 (m, 3H) |
| I-69 | CP | CI | 936.4 | 11.32-10.89 (m, 1H), 10.66-10.32 (m, 1H), 7.77 (d, J = 8.4 Hz, 1H), 7.58 (t, J = 6.8 Hz, 1H), 7.40 (dd, J = 2.0, 8.4 Hz, 1H), 7.35-7.29 (m, 1H), 7.26 (s, 1H), 7.13-7.07 (m, 3H), 7.02 (dd, J = 2.0, 8.0 Hz, 1H), 6.67 (d, J = 2.0 Hz, 1H), 5.37 (dd, J = 5.2, 12.8 Hz, 1H), 4.55 (d, J = 9.0 Hz, 1H), 4.45-4.29 (m, 1H), 3.98-3.69 (m, 2H), 3.41 (s, 3H), 3.22-3.02 (m, 3H), 2.96-2.83 (m, 2H), 2.62-2.57 (m, 1H), 2.06-1.77 (m, 6H), 1.58 (d, J = 8.8 Hz, 8H), 1.50-1.22 (m, 8H), 1.03-0.72 (m, 2H) |
| I-70 | CO | CI | 922.4 | 11.11 (s, 1H), 10.52 (s, 1H), 7.75 (d, J = 8.4 Hz, 1H), 7.58 (s, 1H), 7.40 (dd, J = 2.0, 8.4 Hz, 1H), 7.31 (d, J = 8.4 Hz, 1H), 7.22 (s, 1H), 7.13-7.10 (m, 1H), 7.09-7.07 (m, 2H), 7.02 (dd, J = 2.0, 8.0 Hz, 1H), 6.66 (d, J = 2.0 Hz, 1H), 5.37 (dd, J = 5.2, 12.8 Hz, 1H), 4.55 (d, J = 9.2 Hz, 1H), 4.40-4.33 (m, 1H), 3.58-3.48 (m, 2H), 3.18-3.03 (m, 3H), 2.96-2.82 (m, 2H), 2.94-2.81 (m, 2H), 2.65-2.63 (m, 2H), 2.61-2.58 (m, 2H), 2.08 (d, J = 5.6 Hz, 4H), 1.88-1.72 (m, 8H), 1.60-1.43 (m, 8H), 1.30-1.08 (m, 5H), 0.94-0.77 (m, 4H) |
| I-71 | CP | CN | 964.5 | 11.23-11.11 (m, 1H), 10.64-10.51 (m, 1H), 7.86-7.75 (m, 1H), 7.69-7.60 (m, 1H), 7.53-7.46 (m, 1H), 7.42-7.35 (m, 1H), 7.33-7.30 (m, 1H), 7.21-7.14 (m, 3H), 7.13-7.06 (m, 2H), 6.76-6.70 (m, 1H), 5.44 (dd, J = 4.8, 12.8 Hz, 1H), 4.62 (d, J = 9.6 Hz, 1H), 4.49-4.38 (m, 1H), 4.03-3.76 (m, 2H), 3.36-3.32 (m, 3H), 3.01-2.91 (m, 2H), 2.80-2.69 (m, 2H), 2.14-2.03 (m, 2H), 1.92-1.73 (m, 8H), 1.69-1.61 (m, 2H), 1.57-1.43 (m, 6H), 1.39-1.27 (m, 4H), 1.24-1.14 (m, 2H), 1.03 (s, 1H), 0.96 (s, 3H), 0.69-0.64 (m, 3H) |
| I-72 | CM | CN | 942.3 | 11.08 (s, 1H), 10.54 (s, 1H), 7.74 -7.81 (d J = 8.2, 1H), 7.80-7.78 (m, 1H), 7.61-7.50 (m, 1H), 7.48-7.41 (m, 1H), 7.35-7.28 (m, 1H), 7.13-7.08 (m, 1H), 7.06-6.96 (m, 3H), 6.89-6.83 (m, 1H), 6.71-6.66 (m, 1H), 5.36-5.28 (m, 1H), 4.60-4.53 (dd, J = 0.2, J = 9.2, 1H), 4.32-4.40 (d, J = 9.2, 1H), 3.32 (s, 3H), 3.15-3.10 (m, 2H), 2.98-2.82 (m, 2H), 2.75-2.57 (m, 4H), 2.12-1.95 (m, 2H), 1.90-1.70 (m, 6H) 1.52-1.50 (m, 4H), 1.40-1.29 (m, 5H), 1.20-1.00 (m, 7H), 1.00-0.89 (m, 4H), 0.60 (s, 3H) |

TABLE 10-continued

Compounds synthesized via Method 3 using the corresponding amines and acids for the coupling.

| I-#[a] | Amine | Acid | LCMS (ESI, m/z): $[(M + 1)]^+$ | $^1H$ NMR (400 MHz, DMSO) δ |
|---|---|---|---|---|
| I-73 | CT | DK | 990.3 | 10.90-11.19 (m, 1H), 10.51 (dd, J = 4.0, 2.0 Hz, 1H), 8.23 (s, 1H), 7.58-7.65 (m, 1H), 7.31-7.39 (m, 2H), 7.21-7.28 (m, 2H), 7.06-7.14 (m, 3H), 7.01 (dd, J = 8.4, 2.00 Hz, 1H), 6.63 (d, J = 2.00 Hz, 1H), 5.30-5.40 (m, 1H), 4.29 (d, J = 10.0 Hz, 1H), 3.82-4.01 (m, 4H), 3.33 (s, 3H), 2.81-2.97 (m, 4H), 2.69-2.74 (m, 1H), 2.62-2.68 (m, 2H), 2.07 (s, 2H), 1.85 (s, 2H), 1.41-1.67 (m, 8H), 1.23 (s, 2H), 1.14 (t, J = 7.2 Hz, 1H), 1.07 (t, J = 7.2 Hz, 3H), 0.78-0.87 (m, 1 H) |
| I-96[b] | R | FA | 922.6 | 11.08 (s, 1H), 10.48 (s, 1H), 8.56 (s, 1H), 7.90 (d, J = 7.2 Hz, 2H), 7.47-7.16 (m, 4H), 7.12-6.96 (m, 4H), 6.88 (d, J = 8.4 Hz, 1H), 6.72-6.57 (m, 1H), 5.33 (dd, J = 5.2, 12.8 Hz, 1H), 5.17-4.95 (m, 1H), 4.68-4.46 (m, 1H), 3.31 (s, 6H), 3.30-3.24 (m, 2H), 3.23-3.07 (m, 2H), 2.98-2.82 (m, 1H), 2.77-2.59 (m, 4H), 2.36-2.18 (m, 1H), 2.06-1.94 (m, 1H), 1.91-1.71 (m, 1H), 1.70-1.46 (m, 6H), 1.38 (d, J = 6.4 Hz, 4H), 1.30-1.19 (m, 1H), 0.99-0.81 (m, 1H), 0.80-0.66 (m, 1H) |

[a]The reaction was run anywhere from 0.5-16 hrs at rt. The final products were isolated under standard purification techniques including reverse HPLC and prep-TLC with appropriate solvent conditions.
[b]EDCI with DMAP in pyridine was used for the coupling at rt for 30 min.

Example 9 (Method 4): Synthesis of (3'R,4'S,5'R)-6"-chloro-4'-(3-chloro-2-fluorophenyl)-N-(4-((5-(1-(2,6-dioxopiperidin-3-yl)-3-methyl-2-oxo-2,3-dihydro-1H-benzo[d]imidazol-5-yl)pentyl)carbamoyl)phenyl)-4,4-dimethyl-2"-oxodispiro[cyclohexane-1,2'-pyrrolidine-3',3"-indoline]-5'-carboxamide (I-74)

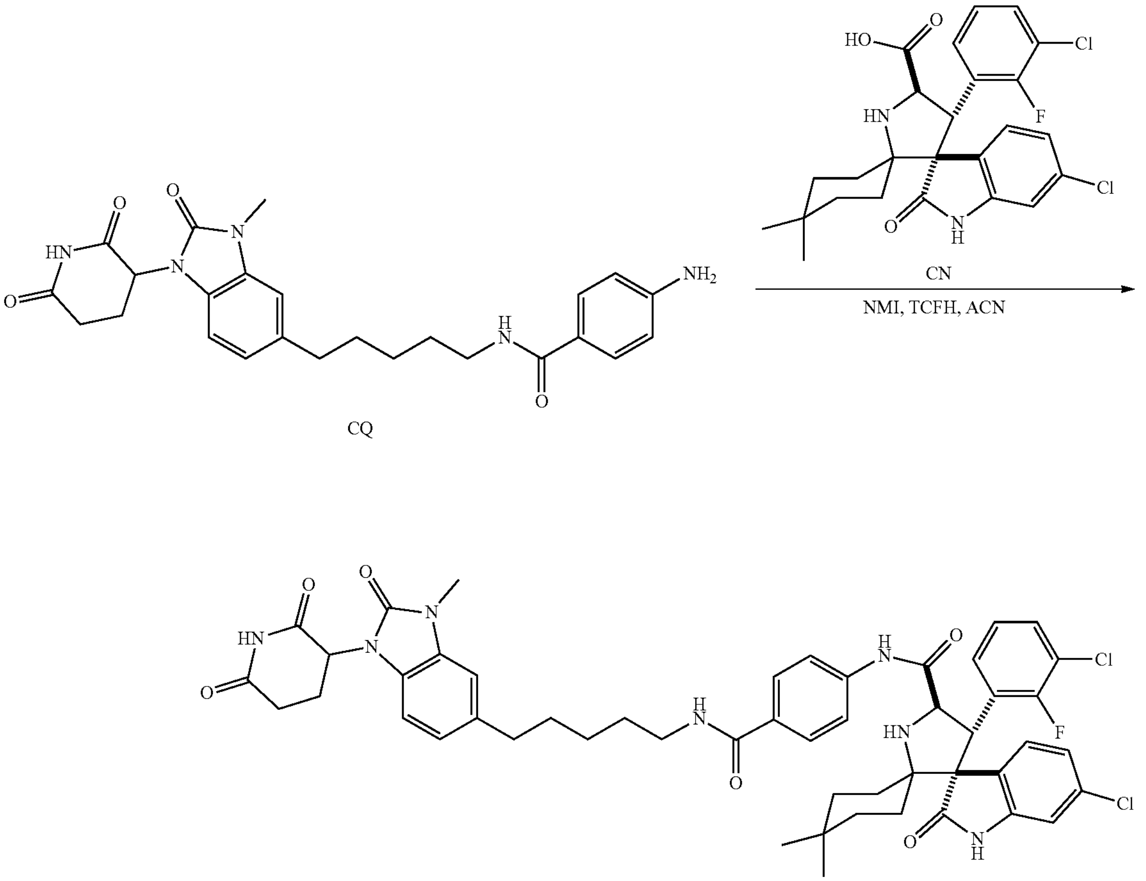

CQ

CN

To a solution of 4-amino-N-[5-[1-(2,6-dioxo-3-piperidyl)-3-methyl-2-oxo-benzimidazol-5-yl]pentyl] benzamide (35.0 mg, 75.5 umol, Intermediate CQ) and chloro-(3-chloro-2-fluoro-phenyl)-dimethyl-oxo-dispiro [BLAH] carboxylic acid (40.8 mg, 83.0 umol, Intermediate CN) in ACN (1.0 mL) was added TCFH (5.44 mg, 151 umol) and 1-methylimidazole (61.9 mg, 755 umol) and the mixture was stirred at 25° C. for 12 hrs. On completion, the reaction mixture was filtered and concentrated in vacuo. The residue was purified by prep-HPLC (column: Phenomenex Luna C18 150*25 mm*10 um; mobile phase: [water (0.225% FA)–ACN]; B %: 54%-84% 11 min) to give the title compound (12.93 mg, 18% yield) as yellow solid. Ad: NMR (400 MHz, DMSO-$d_6$) δ 11.08 (s, 1H), 10.60 (d, J=1.6 Hz, 1H), 10.38-10.04 (m, 1H), 10.34-10.03 (m, 1H), 8.35 (s, 1H), 7.82 (d, J=8.4 Hz, 2H), 7.73-7.59 (m, 3H), 7.52 (d, J=9.0 Hz, 1H), 7.37 (s, 1H), 7.24-7.11 (n, 12H), 7.08 (s, 1), 7.03-6.94 (m, 2), 6.86 (d, JH 8.8 Hz, 1H), 6.72 (s, 1H), 5.33 (n, J=5.2, 12.0 Hz, 1H), 4.92-4.50 (m, 21), 3.31 (s, 3H), 3.26-3.20 (m, 2H), 2.93-2.83 (m, 1H), 2.67 (s, 2H), 2.64-2.60 (m, 2H), 2.04-1.96 (m, 1H), 1.94-1.74 (n, 2H), 1.73-1.50 (m, 6H), 1.50-1.21 (m, 41), 1.20-0.97 (n, 2H), 0.92 (s, 3H), 0.62 (s, 3H). LC-MS (ESI$^+$) m/z 936.2 (M+H)$^+$.

TABLE 11

Compounds synthesized via Method 4 using the corresponding amines and acids for the coupling.

| I-#[a] | Amine | Acid | LCMS (ESI, m/z): [(M + 1)]$^+$ | $^1$H NMR (400 MHz, DMSO) δ |
|---|---|---|---|---|
| I-75 | DJ | CI | 962.3 | 11.16-11.06 (m, 1H), 10.62-10.45 (m, 1H), 7.66-7.50 (m, 2H), 6.74-6.61 (m, 1H), 5.44-5.29 (m, 1H), 4.55-4.45 (m, 1H), 4.37-4.19 (m, 1H), 3.99-3.82 (m, 2H), 3.29-3.19 (m, 3H), 2.97-2.80 (m, 2H), 2.09-1.96 (m, 2H), 1.95-1.74 (m, 15H), 1.72-1.40 (m, 10H), 1.05-0.69 (m, 2H) |
| I-76 | CU | CN | 958.3 | 11.19-10.99 (m, 1H), 10.02-9.86 (m, 1H), 9.94 (s, 1H), 8.08-7.96 (m, 1H), 7.71-7.58 (m, 3H), 7.57-7.48 (m, 1H), 7.46-7.34 (m, 3H), 7.33-7.15 (m, 3H), 7.14-7.03 (m, 3H), 6.77-6.67 (m, 1H), 5.44-5.29 (m, 1H), 4.90-4.74 (m, 1H), 3.21-3.15 (m, 3H), 2.90-2.81 (m, 2H), 2.10-1.77 (m, 6H), 1.74-1.43 (m, 6H), 1.41-1.01 (m, 6H), 0.96-0.87 (m, 3H), 0.67-0.56 (m, 3H) |
| I-77 | CL | CI | 934.4 | 11.06 (s, 1H), 10.52 (s, 1H), 9.95 (s, 1H), 7.69-7.66 (m, 1H), 7.55-7.53 (m, 2H), 7.46-7.44 (m, 1H), 7.36-7.32 (m, 1H), 7.24-7.22 (m, 2H), 7.16-7.12 (m, 1H), 7.02-6.97 (m, 3H), 6.86-6.84 (m,\ 1H), 6.64 (m, 1H), 5.33-5.30 (m, 1H), 4.56-4.53 (m, 1H), 4.44-4.41 (m, 1H), 3.52-3.49 (m, 2H), 2.89 (s, 3H), 2.70-2.59 (m, 6H), 2.16-1.97 (m, 8H), 1.71-1.49 (m, 11H), 1.23-1.15 (m, 4H), 1.04-0.98 (m, 2H); |
| I-78 | DL | CI | 908.5 | 11.07 (s, 1H), 10.70-10.37 (m, 1H), 10.33-9.96 (m, 1H), 8.49-8.36 (m, 1H), 8.09-7.89 (m, 1H), 7.77-7.70 (m, 1H), 7.68-7.61 (m, 1H), 7.39 (t, J = 7.6 Hz, 2H), 7.59-7.29 (m, 2H), 7.25-7.03 (m, 2H), 7.02-7.00 (m, 1H), 6.99-6.94 (m, 1H), 6.85 (d, J = 8.0 Hz, 1H), 6.78-6.61 (m, 1H), 5.36-5.28 (m, 1H), 5.09-4.41 (m, 2H), 3.30 (s, 3H), 3.27-3.20 (m, 2H), 2.97-2.83 (m, 1H), 2.74-2.55 (m, 4H), 2.10-1.93 (m, 2H), 1.90-1.78 (m, 1H), 1.76-1.41 (m, 9H), 1.40-1.21 (m, 3H), 1.14-0.80 (m, 2H) |
| I-79 | CR | CI | 916.3 | 11.07-11.14 (m, 1H), 10.52-10.61 (m, 1H), 10.52-10.61 (m, 1H), 10.52-10.61 (m, 1H), 10.02-10.14 (m, 1H), 8.12-8.14 (m, 1 H), 7.55-7.67 (m, 3 H), 7.44 (d, J = 6.4 Hz, 1H), 7.28-7.39 (m, 3H), 7.21-7.24 (m, 1H), 7.06-7.18 (m, 3H), 7.00-7.06 (m, 1H), 6.67-6.71 (m, 1H), 5.38 (s, 1H), 4.60-4.78 (m, 2H), 3.16-3.26 (m, 3H), 2.80-2.98 (m, 4H), 2.57-2.74 (m, 4H), 1.89-2.13 (m, 5H), 1.79-1.87 (m, 1H), 1.53-1.75 (m, 7H), 1.45-1.52 (m, 1H), 1.32-1.41 (m, 1H), 1.11-1.26 (m, 2H), 0.75-1.08 (m, 3H) |
| I-80 | CU | DM | 944.3 | 11.33-10.91 (m, 1H), 10.82-10.41 (m, 1H), 10.16-9.88 (m, 1H), 7.74-7.63 (m, 3H), 7.52-7.44 (m, 1H), 7.40-7.32 (m, 3H), 7.30-7.23 (m, 1H), 7.19-7.08 (m, 3H), 7.07-7.01 (m, 1H), 6.67-6.61 (m, 1H), 5.43-5.34 (m, 1H), 4.61-4.54 (m, 1H), 4.52-4.43 (m, 1H), 3.01-2.83 (m, 6H), 2.74-2.62 (m, 3H), 2.21-2.13 (m, 1H), 2.07 (s, 2H), 2.04-1.95 (m, 3H), 1.93-1.83 (m, 2H), 1.73-1.42 (m, 9H), 1.08-0.95 (m, 2H), 0.90-0.80 (m, 1H) |
| I-81 | CQ | DN | 952.2 | 11.08 (s, 1H), 10.55 (s, 1H), 10.14 (s, 1H), 8.34 (s, 1H), 7.80 (d, J = 8.6 Hz, 2H), 7.74-7.61 (m, 3H), 7.50 (dd, J = 2.8, 8.2 Hz, 1H), 7.40-7.31 (m, 1H), 7.16 (t, J = 8.0 Hz, 1H), 7.09-6.95 (m, 3H), 6.90-6.83 (m, 1H), 6.67 (d, J = 2.0 Hz, 1H), 5.33 (dd, J = 5.6, 12.5 Hz, 1H), 4.60 (br d, J = 10.4 Hz, 1H), 4.48 (d, J = 10.4 Hz, 1H), 3.31 (br s, 9H), 3.23 (br d, J = 6.0 Hz, 2H), 2.96-2.82 (m, 4H), 2.75-2.67 (m, 1H), 2.64-2.58 (m, 3H), 2.06-1.97 (m, 2H), 1.96-1.89 (m, 1H), 1.86-1.80 (m, 1H), 1.67-1.59 (m, 3H), 1.58-1.49 (m, 3H), 1.38-1.30 (m, 2H), 1.26-1.18 (m, 2H), 1.10 (br s, 1H), 0.93 (s, 3H), 0.59 (s, 3H) |

TABLE 11-continued

Compounds synthesized via Method 4 using the corresponding amines and acids for the coupling.

| I-#[a] | Amine | Acid | LCMS (ESI, m/z): $[(M + 1)]^+$ | $^1$H NMR (400 MHz, DMSO) δ |
|---|---|---|---|---|
| I-82 | DO | CI | 910.4 | 11.11 (s, 1H), 10.53 (br s, 1H), 7.80-7.79 (m, 2H), 7.59-7.57 (m, 1H), 7.33-7.25 (m, 2H), 7.12 (s, 1H), 7.10-7.02 (m, 4H), 6.67 (s, 1H), 5.38 (dd, J = 5.2, 12.4, 1H), 4.57 (d, J = 9.2 Hz, 1H), 4.37-4.36 (m, 1H), 3.51-3.46 (m, 1H), 3.42 (s, 3H), 3.17-3.14 (m, 2H), 2.86-2.82 (m, 1H), 2.74-2.64 (m, 2H), 2.44-2.40 (m, 2H), 2.09-1.95 (m, 3H), 1.84-1.72 (m, 5H), 1.66-1.52 (m, 5H), 1.47-1.34 (m, 5H), 1.30-1.11 (m, 3H), 1.01-0.91 (m, 1H), 0.86-0.76 (m, 1H) |
| I-83 | CS | CN | 968.7 $(M + 3)^+$ | 11.10 (s, 1H), 10.47-10.57 (m, 1H), 10.47-10.57 (m, 1H), 7.73-7.91 (m, 1H), 7.57 ( t, J=6.88 Hz, 1H), 7.40-7.50 (m, 1H), 7.29-7.37 (m, 1H), 7.25 (s, 1H), 7.10 (s, 3H), 7.01-7.07 (m, 1H), 6.69 ( s, 1H), 5.31-5.42 (m, 1H), 4.50-4.64 (m, 1H), 4.35-4.47 (m, 1H), 4.06-4.21 (m, 1H), 3.61-3.78 (m, 3H), 3.26 (s, 3H), 2.81-2.89 (m 3H), 2.55-2.56 (m, 2 H), 1.92 (s 3H), 1.78-1.89 (m 3H), 1.68-1.78 (m, 4H), 1.43-1.62 (m, 6H), 1.07-1.31 (m, 4H), 0.87-0.92 (m, 3H), 0.57-0.63 (m, 3H) |
| I-97 | CQ | CI | 910.4 | 11.44-11.11 (m, 1H), 11.08 (s, 1H), 10.85-10.04 (m, 1H), 9.47-8.96 (m, 1H), 8.39 (t, J = 5.2 Hz, 1H), 7.83 (d, J = 8.8 Hz, 2H), 7.74-7.63 (m, 3H), 7.58 (d, J = 1.6 Hz, 1H), 7.45 (d, J = 6.0 Hz, 1H), 7.24 (t, J = 7.2 Hz, 1H), 7.12 (d, J = 8.0 Hz, 1H), 7.04-6.95 (m, 2H), 6.91-6.84 (m, 1H), 6.77 (s, 1H), 5.69-4.99 (m, 2H), 4.93-4.74 (m, 1H), 3.31 (s, 3H), 3.23 (q, J = 6.4 Hz, 2H), 2.94-2.85 (m, 1H), 2.74-2.67 (m, 1H), 2.65-2.58 (m, 3H), 2.08-1.82 (m, 3H), 1.81-1.66 (m, 2H), 1.65-1.44 (m, 8H), 1.38-1.28 (m, 2H), 1.18-0.98 (m, 2H) |
| I-98 | EH | CN | 944.4 | 11.08 (s, 1H), 10.53 (s, 1H), 7.96-7.72 (m, 1H), 7.68-7.54 (m, 2H), 7.47 (s, 1H), 7.40-7.26 (m, 1H), 7.19-6.95 (m, 4H), 6.85 (d, J = 7.6 Hz, 1H), 6.74-6.57 (m, 1H), 5.33 (dd, J = 5.2, 12.8 Hz, 1H), 4.69-4.52 (m, 1H), 4.51-4.29 (m, 1H), 3.86-3.60 (m, 3H), 3.32-3.31 (m, 3H), 3.21-3.09 (m, 1H), 3.08-2.85 (m, 3H), 2.75-2.58 (m, 4H), 2.03-1.71 (m, 5H), 1.65-1.54 (m, 3H), 1.65-1.33 (m, 5H), 1.32-0.99 (m, 5H), 0.91 (s, 3H), 0.61 (s, 3H) |
| I-99 | EI | CI | 908.4 | 11.08 (s, 1H), 10.58 (s, 1H), 10.01 (s, 1H), 8.19 (s, 1H), 7.70-7.61 (m, 1H), 7.54 (d, J = 8.4 Hz, 2H), 7.48-7.42 (m, 1H), 7.39-7.32 (m, 1H), 7.21 (d, J = 8.4 Hz, 2H), 7.16 (d, J = 8.0 Hz, 1H), 7.06-6.97 (m, 3H), 6.86 (d, J = 8.8 Hz, 1H), 6.69 (d, J = 2.0 Hz, 1H), 5.33 (dd, J = 5.2, 12.4 Hz, 1H), 4.77-4.63 (m, 2H), 3.38 (s, 3H), 2.95-2.84 (m, 1H), 2.65-2.60 (m, 2H), 2.34-2.26 (m, 3H), 2.07 (s, 3H), 2.03-1.94 (m, 2H), 1.89-1.77 (m, 2H), 1.65-1.51 (m, 7H), 1.49-1.38 (m, 4H), 1.36-1.19 (m, 4H) |
| I-100 | CH | CN | 908.2 | 11.5-11.0 (s, 1H), 10.7-10.5 (s, 1H), 8.22 (d, J = 8.0 Hz, 1H), 7.57 (t, J = 6.8 Hz, 1H), 7.45 (dd, J = 2.0, 7.6 Hz, 1H), 7.38-7.10 (m, 2H), 7.19-7.06 (m, 3H), 7.05-6.94 (m, 1H), 6.68 (d, J = 1.6 Hz, 1H), 5.41-5.34 (m, 1H), 4.60 (d, J = 9.2 Hz, 1H), 4.43-4.33 (m, 2H), 4.29-4.17 (m, 2H), 4.10-4.03 (m, 1H), 3.88-3.82 (m, 1H), 3.71 (m, 1H), 3.30-3.09 (m, 3H), 3.08-2.77 (m, 2H), 2.72-2.54 (m, 3H), 2.38-2.31 (m, 2H), 2.24-2.10 (m, 2H), 2.05-1.98 (m, 1H), 1.85-1.68 (m, 2H), 1.60-1.37 (m, 3H), 1.23-1.20 (m, 1H), 1.16-1.08 (m, 1H), 1.05-0.94 (m, 1H), 0.93 (s, 3H), 0.65 (s, 3H) |
| I-101 | CQ | DM | 922.4 | 11.08 (s, 1H), 10.55 (s, 1H), 10.14 (s, 1H), 8.34 (t, J = 5.6 Hz, 1H), 7.80 (d, J = 8.4 Hz, 2H), 7.73-7.62 (m, 3H), 7.48 (dd, J = 2.4, 8.0 Hz, 1H), 7.40-7.32 (m, 1H), 7.15 (t, J = 8.0 Hz, 1H), 7.07-6.96 (m, 3H), 6.86 (d, J = 8.4 Hz, 1H), 6.65 (d, J = 2.0 Hz, 1H), 5.33 (dd, J = 5.6, 12.8 Hz, 1H), 4.62-4.54 (m, 1H), 4.51-4.44 (m, 1H), 3.31 (s, 3H), 3.23 (d, J = 6.4 Hz, 2H), 2.96-2.83 (m, 4H), 2.76-2.67 (m, 1H), 2.66-2.57 (m, 3H), 2.17 (d, J = 8.4 Hz, 1H), 2.06-1.94 (m, 2H), 1.76-1.42 (m, 10H), 1.41-1.28 (m, 3H), 1.02 (m, 2H) |
| I-102[b] | CL | CI | 920.3 | 11.07 (s, 1H), 10.56 (s, 1H), 10.01 (s, 1H), 7.62 (t, J = 6.4 Hz, 1H), 7.53 (d, J = 8.4 Hz, 2H), 7.44 (dd, J = 2.0, 8.0 Hz, 1H), 7.37-7.32 (m, 1H), 7.21 (d, J = 8.0 Hz, 2H), 7.14 (t, J = 8.1 Hz, 1H), 7.07-6.94 (m, 3H), 6.84 (d, J = 8.1 Hz, 1H), 6.68 (d, J = 2.0 Hz, 1H), 5.32 (dd, J = 5.3, 12.8 Hz, 1H), 4.76-4.68 (m, 1H), 4.68-4.58 (m, 1H), 3.73-3.61 (m, 1H), 3.30-3.29 (m, 3H), 2.95-2.83 (m, 2H), 2.81-2.74 (m, 2H), 2.68-2.65 (m, 3H), 2.35-2.29 (m, 3H), 2.08-1.95 (m, 3H), 1.71-1.57 (m, 6H), 1.55-1.44 (m, 4H), 1.41-1.32 (m, 1H), 1.25-1.13 (m, 4H), 0.88-0.79 (m, 1H) |

TABLE 11-continued

Compounds synthesized via Method 4 using the corresponding amines and acids for the coupling.

| I-#[a] | Amine | Acid | LCMS (ESI, m/z): $[(M + 1)]^+$ | $^1H$ NMR (400 MHz, DMSO) δ |
|---|---|---|---|---|
| I-103 | EM | CN | 926.5 | 11.09 (s, 1H), 10.53 (s, 1H), 7.74 (d, J = 8.8 Hz, 1H), 7.58 (t, J = 6.8 Hz, 1H), 7.48-7.41 (m, 1H), 7.32 (t, J = 7.2 Hz, 1H), 7.11 (t, J = 8.0 Hz, 1H), 7.06-6.99 (m, 3H), 6.99-6.95 (m, 1H), 6.68 (d, J = 2.0 Hz, 1H), 5.36 (dd, J = 5.2, 11.2 Hz, 1H), 4.56 (d, J = 9.2 Hz, 1H), 4.36 (d, J = 8.8 Hz, 1H), 3.57 (s, 3H), 2.97-2.84 (m, 4H), 2.75-2.68 (m, 1H), 2.65-2.58 (m, 1H), 2.13 (d, J = 6.8 Hz, 2H), 2.05-1.96 (m, 3H), 1.85-1.64 (m, 11H), 1.62-1.38 (m, 5H), 1.27-1.07 (m, 5H), 0.91-0.94 (m, 2H), 0.89 (s, 3H), 0.60 (s, 3H) |
| I-104 | EN | CI | 912.5 | 11.10 (s, 1H), 10.53 (s, 1H), 7.78 ( d, J = 7.2 Hz, 1H), 7.59 (t, J = 7.2 Hz, 1H), 7.42 ( d, J = 8.4 Hz, 1H), 7.33 ( t, J = 7.2 Hz, 1H), 7.12 ( t, J = 7.2 Hz, 1H), 7.07-6.93 (m, 4H), 6.67 (s, 1H), 5.38 ( dd, J = 5.2, 12.8 Hz, 1H), 4.66-4.52 (m, 2H), 4.43-4.32 (m, 1H), 4.19-4.02 (m, 1H), 3.63 (s, 3H), 3.57-3.47 (m, 2H), 3.25-3.16 (m, 1H), 2.95-2.85 (m, 1H), 2.77-2.69 (m, 1H), 2.68-2.58 (m, 3H), 2.05-1.67 (m, 10H), 1.62-1.58 (m, 4H), 1.54-1.27 (m, 8H), 1.04-0.92 (m, 1H), 0.86-0.73 (m, 1H) |
| I-105 | EQ | CI | 928.3 | 11.37-11.19 (m, 1H), 11.08 (s, 1H), 10.59-10.23 (m, 1H), 8.96-8.62 (m, 1H), 7.75-7.57 (m, 3H), 7.55-7.48 (m, 1H), 7.33-7.23 (m, 1H), 7.12 (d, J = 7.6 Hz, 1H), 7.05-6.97 (m, 2H), 6.92-6.82 (m, 1H), 6.78 (s, 1H), 5.60-5.28 (m, 2H), 4.93-4.75 (m, 1H), 4.28-4.02 (m, 1H), 3.33 (s, 3H), 3.05-2.97 (m, 2H), 2.92-2.86 (m, 1H), 2.79-2.72 (m, 3H), 2.71-2.60 (m, 6H), 2.09-1.91 (m, 4H), 1.79-1.67 (m, 4H), 1.65-1.53 (m, 6H), 1.50-1.36 (m, 5H), 1.32-1.19 (m, 3H), 1.18-0.99 (m, 3H) |
| I-106 | ET | CI | 931.3 | 10.74-10.57 (m, 2H), 10.23 (s, 1H), 8.34 (d, J = 6.8 Hz, 1H), 7.75 (s, 1H), 7.72-7.59 (m, 4H), 7.47 (dd, J = 2.0, 8.0 Hz, 1H), 7.41-7.33 (m, 3H), 7.16 (t, J = 8.0 Hz, 1H), 7.05 (dd, J = 2.0, 8.0 Hz, 1H), 6.99 (d, J = 7.2 Hz, 1H), 6.70 (d, J = 2.0 Hz, 1H), 4.85-4.64 (m, 2H), 4.50 (s, 2H), 4.02-3.62 (m, 5H), 3.61-3.47 (m, 1H), 3.28-3.16 (m, 2H), 2.83 ( t, J = 6.4 Hz, 2H), 2.18-2.04 (m, 1H), 2.01-1.79 (m, 3H), 1.73-1.47 (m, 7H), 1.39 (m, 1H), 0.99 (d, J = 12.8 Hz, 1H), 0.93-0.76 (m, 1H) |
| I-107 | CR | DM | 930.3 | 11.13-11.08 (m, 1H), 10.48-10.46 (m, 1H), 9.96-9.90 (m, 1H), 7.68 (t, J = 6.8 Hz, 1H), 7.53 (d, J = 8.4 Hz, 2H), 7.46 (dd, J = 2.0, 8.4 Hz, 1H), 7.35 (t, J = 7.2 Hz, 1H), 7.26-7.20 (m, 3H), 7.14 (t, J = 8.0 Hz, 1H), 7.08 (s, 2H), 7.02 (dd, J = 1.6, 8.4 Hz, 1H), 6.64 (d, J = 2.0 Hz, 1H), 5.46-5.28 (m, 1H), 4.57-4.53 (m, 1H), 3.40 (s, 2H), 3.34-3.33 (m, 1H), 3.33 (s, 2H), 2.89 (s, 3H), 2.35-2.30 (m, 1H), 2.07-1.94 (m, 3H), 1.92-1.74 (m, 3H) |
| I-108 | EV | CI | 922.4 | 11.11 (s, 1H), 10.52 (s, 1H), 8.14 (s, 1H), 7.76 (d, J = 8.4 Hz, 1H), 7.58 (t, J = 6.4 Hz, 1H), 7.40 (dd, J = 2.2, 8.0 Hz, 1H), 7.34-7.29 (m, 1H), 7.12 (d, J = 8.0 Hz, 2H), 7.08-6.96 (m, 4H), 6.66 (d, J = 2.0 Hz, 1H), 5.42-5.35 (m, 1H), 4.55 (d, J = 9.2 Hz, 1H), 4.36 (d, J = 9.2 Hz, 1H), 3.66-3.64 (m, 3H), 3.09-3.00 (m, 1H), 2.94-2.86 (m, 1H), 2.76-2.70 (m, 3H), 2.25-2.12 (m, 4H), 1.91 (s, 4H), 1.85-1.67 (m, 8H), 1.63-1.45 (m, 8H), 1.39-1.33 (m, 1H), 1.27-1.20 (m, 2H), 0.92 (d, J = 12.4 Hz, 2H), 0.83-0.77 (m, 1H) |
| I-109 | EW | CI | 898.6 | 11.09 (s, 1H), 10.52 (s, 1H), 7.76 ( d, J = 8.4 Hz, 1H), 7.63-7.53 (m, 1H), 7.41 (dd, J = 2.0, 8.4 Hz, 1H), 7.35-7.29 (m, 1H), 7.11 (t, J = 8.0 Hz, 1H), 7.06-6.85 (m, 4H), 6.66 (d, J = 2.0 Hz, 1H), 5.37 (dd, J = 5.2, 12.4 Hz, 1H), 4.55 (d, J = 9.2 Hz, 1H), 4.36 (d, J = 9.2 Hz, 1H), 3.64 (s, 1H), 3.58 (s, 3H), 3.51-3.42 (m, 2H), 3.28-3.20 (m, 2H), 2.98 (d, J = 9.6 Hz, 2H), 2.92-2.82 (m, 1H), 2.76-2.59 (m, 2H), 2.13-2.12 (m, 2H), 2.12-1.88 (m, 4H), 1.87-1.71 (m, 8H), 1.62-1.44 (m, 5H), 1.29-1.14 (m, 3H), 1.03-0.83 (m, 3H), 0.83-0.74 (m, 1H) |
| I-110 | EX | CI | 931.3 | 11.12 (s, 1H), 10.58 (s, 1H), 10.02 (s, 1H), 8.25 (s, 1H), 7.63 (m, 3H), 7.45 (d, J = 7.6 Hz, 1H), 7.40-7.20 (m, 4H), 7.18-7.10 (m, 2H), 7.08-6.98 (m, 1H), 6.69 (d, J = 1.6 Hz, 1H), 5.46-5.33 (m, 1H), 4.79-4.58 (m, 2H), 3.55-3.43 (m, 4H), 3.35 (s, 3H), 3.30-3.19 (m, 4H), 3.00-2.85 (m, 2H), 2.77-2.60 (m, 3H), 2.10-1.98 (m, 3H), 1.87-1.73 (m, 2H), 1.69-1.47 (m, 5H), 1.44-1.29 (m, 2H), 1.00-0.82 (m, 2H) |
| I-111 | EY | CN | 1039.6 | 11.12-11.06 (m, 1H), 10.55-10.50 (m, 1H), 8.20 (s, 1H), 7.72 (br d, J = 8.3 Hz, 1H), 7.57 (s, 1H), 7.46-7.40 (m, 1H), 7.34-7.29 (m, 1H), 7.10 (s, 1H), 7.04 (br d, J = 2.0 Hz, 2H), |

TABLE 11-continued

Compounds synthesized via Method 4 using the corresponding amines and acids for the coupling.

| I-#[a] | Amine | Acid | LCMS (ESI, m/z): [(M + 1)]+ | $^1$H NMR (400 MHz, DMSO) δ |
|---|---|---|---|---|
| | | | | 6.95 (t, J = 7.8 Hz, 1H), 6.86 (d, J = 7.3 Hz, 1H), 6.67 (d, J = 1.9 Hz, 1H), 5.37 (br dd, J = 5.9, 12.7 Hz, 1H), 4.55 (d, J = 9.3 Hz, 1H), 4.35 (d, J = 9.1 Hz, 1H), 3.67 (s, 3H), 3.61 (s, 2H), 2.94-2.84 (m, 1H), 2.73-2.58 (m, 6H), 2.16-1.92 (m, 8H), 1.82-1.55 (m, 12H), 1.51-1.30 (m, 8H), 1.27-1.08 (m, 5H), 0.92-0.83 (m, 5H), 0.59 (s, 3H) |
| I-112 | EZ | CI | 967.4 | 11.12-11.03 (m, 1H), 10.53 (s, 1H), 8.33 (d, J = 9.2 Hz, 1H), 7.75 (d, J = 8.0 Hz, 1H), 7.61-7.54 (m, 1H), 7.43-7.38 (m, 1H), 7.35-7.27 (m, 1H), 7.11 (t, J = 7.6 Hz, 1H), 7.05-7.01 (m, 1H), 6.96 (d, J = 4.8 Hz, 2H), 6.84 (t, J = 6.8 Hz, 1H), 6.67 (d, J = 1.6 Hz, 1H), 5.41-5.26 (m, 1H), 4.55 (d, J = 9.6 Hz, 1H), 4.36 (d, J = 9.6 Hz, 1H), 3.55 (s, 3H), 2.92-2.73 (m, 6H), 2.30-2.09 (m, 4H), 2.06-1.88 (m, 6H), 1.83-1.66 (m, 8H), 1.64-1.43 (m, 11H), 1.40-1.32 (m, 3H), 1.27-1.09 (m, 3H), 0.95-0.81 (m, 3H) |
| I-113 | EY | CI | 1013.5 | 11.10 (s, 1H), 10.52 (s, 1H), 8.14 (s, 1H), 7.75 (d, J = 8.4 Hz, 1H), 7.58 (t, J = 6.8 Hz, 1H), 7.39 (dd, J = 2.0, 8.4 Hz, 1H), 7.34-7.29 (m, 1H), 7.10 (t, J = 8.0 Hz, 1H), 7.07-7.00 (m, 2H), 6.95 (t, J = 7.6 Hz, 1H), 6.87 (d, J = 7.2 Hz, 1H), 6.66 (d, J = 2.0 Hz, 1H), 5.37 (dd, J = 5.2, 12.4 Hz, 1H), 4.55 (d, J = 9.2 Hz, 1H), 4.40-4.33 (m, 1H), 3.67 (s, 3H), 3.61 (s, 2H), 3.51-3.38 (m, 4H), 2.95-2.85 (m, 1H), 2.81-2.75 (m, 1H), 2.74-2.62 (m, 4H), 2.36-2.22 (m, 3H), 2.20-2.06 (m, 3H), 2.00 (dd, J = 5.2, 10.4 Hz, 1H), 1.93 (d, J = 12.8 Hz, 1H), 1.85-1.69 (m, 10H), 1.61-1.54 (m, 3H), 1.49 (d, J = 17.6 Hz, 4H), 1.41-1.31 (m, 3H), 1.25-1.15 (m, 2H), 1.00-0.84 (m, 3H), 0.79 (d, J = 4.0 Hz, 1H), 0.10--0.01 (m, 1H) |
| I-114 | FC | CI | 941.5 | 11.08 (s, 1H), 10.52 (s, 1H), 7.75 (d, J = 8.4 Hz, 1H), 7.62-7.55 (m, 1H), 7.41 (dd, J = 2.0, 8.0 Hz, 1H), 7.36-7.29 (m, 1H), 7.11 (t, J = 8.0 Hz, 1H), 7.07-6.97 (m, 3H), 6.87 (dd, J = 1.2, 8.0 Hz, 1H), 6.67 (d, J = 2.0 Hz, 1H), 5.34 (dd, J = 5.2, 12.8 Hz, 1H), 4.55 (d, J = 9.2 Hz, 1H), 4.36 (d, J = 9.2 Hz, 1H), 3.33 (s, 3H), 2.94-2.86 (m, 1H), 2.77-2.68 (m, 1H), 2.65-2.58 (m, 3H), 2.45-2.27 (m, 10H), 2.08 (d, J = 7.2 Hz, 2H), 2.03-1.98 (m, 1H), 1.93 (d, J = 12.4 Hz, 1H), 1.86-1.66 (m, 8H), 1.66-1.53 (m, 4H), 1.53-1.40 (m, 3H), 1.39-1.29 (m, 1H), 1.25-1.14 (m, 2H), 1.03-0.90 (m, 2H), 0.88-0.73 (m, 2H) |
| I-115 | FF | CI | 892.5 | 11.09 (s, 1H), 10.58 (s, 1H), 10.03 (s, 1H), 7.64 (t, J = 7.2 Hz, 1H), 7.57 (d, J = 8.4 Hz, 2H), 7.46 (dd, J = 2.0, 8.0 Hz, 1H), 7.39-7.33 (m, 1H), 7.27 (d, J = 8.0 Hz, 2H), 7.15 (t, J = 8.0 Hz, 1H), 7.06-6.99 (m, 3H), 6.99-6.95 (m, 1H), 6.69 (d, J = 2.0 Hz, 1H), 5.37 (dd, J = 5.6, 12.4 Hz, 1H), 4.77-4.71 (m, 1H), 4.70-4.63 (m, 1H), 3.74-3.63 (m, 1H), 3.57 (s, 3H), 3.48 (s, 2H), 3.29-3.19 (m, 2H), 2.97-2.83 (m, 3H), 2.71-2.57 (m, 2H), 2.15-2.04 (m, 3H), 2.02-1.97 (m, 1H), 1.77 (s, 4H), 1.68-1.57 (m, 4H), 1.53-1.46 (m, 1H), 1.28-1.22 (m, 1H), 1.06-0.94 (m, 1H), 0.91-0.81 (m, 1H) |
| I-116 | FG | CI | 930.4 | 11.11 (s, 1H), 10.52 (s, 1H), 8.40 (t, J = 6.4 Hz, 1H), 8.15 (s, 1H), 7.61 (t, J = 6.4 Hz, 1H), 7.41 (dd, J = 2.0, 8.0 Hz, 1H), 7.36-7.30 (m, 1H), 7.26-7.22 (m, 2H), 7.20-7.16 (m, 2H), 7.12 (td, J = 4.0, 7.6 Hz, 2H), 7.06-6.96 (m, 3H), 6.67 (d, J = 2.0 Hz, 1H), 5.39 (dd, J = 5.2, 12.4 Hz, 1H), 4.63 (d, J = 9.2 Hz, 1H), 4.50 (d, J = 9.2 Hz, 1H), 4.36 (dd, J = 7.2, 14.8 Hz, 1H), 4.21 (dd, J = 5.6, 14.8 Hz, 1H), 3.63 (s, 3H), 3.46 (s, 2H), 2.94-2.86 (m, 1H), 2.72 (d, J = 4.4 Hz, 4H), 2.24-2.09 (m, 2H), 2.07-1.99 (m, 1H), 1.97-1.79 (m, 4H), 1.77-1.60 (m, 4H), 1.54-1.47 (m, 2H), 1.46-1.36 (m, 2H), 1.33-1.26 (m, 1H), 0.96-0.73 (m, 2H) |
| I-117 | FJ | CI | 1013.6 | 11.12-11.04 (m, 1H), 10.52 (s, 1H), 8.22 (s, 2H), 7.74 (d, J = 8.4 Hz, 1H), 7.60-7.54 (m, 1H), 7.42-7.36 (m, 1H), 7.36-7.28 (m, 1H), 7.12-7.08 (m, 1H), 7.06-7.00 (m, 2H), 6.96 (d, J = 7.6 Hz, 1H), 6.66 (d, J = 2.0 Hz, 1H), 5.36 (dd, J = 5.2, 12.8 Hz, 1H), 4.54 (d, J = 9.2 Hz, 1H), 4.36 (d, J = 9.6 Hz, 1H), 3.46 (s, 3H), 2.94-2.84 (m, 2H), 2.64-2.58 (m, 3H), 2.12-1.88 (m, 10H), 1.84-1.68 (m, 10H), 1.64-1.54 (m, 4H), 1.48-1.32 (m, 8H), 1.24-1.06 (m, 4H), 1.00-0.72 (m, 5H) |
| I-118 | FL | CI | 938.4 | 11.16 (s, 1H), 10.57-10.48 (m, 1H), 8.17-8.09 (m, 1H), 7.92 (t, J = 6.0 Hz, 1H), 7.58 (t, J = 7.2 Hz, 1H), 7.39 (dd, J = 2.0, 8.0 Hz, 1H), 7.34-7.28 (m, 1H), 7.13-7.07 (m, 1H), 7.06-6.98 (m, 3H), 6.86-6.76 (m, 2H), 6.66 (d, J = 2.0 Hz, 1H), 5.68 (t, J = 10.8 Hz, 1H), 5.37 (dd, J = 5.2, 12.4 Hz, 1H), 4.55 (d, J = 9.6 Hz, 1H), 4.42 (d, J = 9.6 Hz, 1H), 3.65 (s, 1H), 3.46 |

TABLE 11-continued

| Compounds synthesized via Method 4 using the corresponding amines and acids for the coupling. | | | | |
|---|---|---|---|---|
| I-#[a] | Amine | Acid | LCMS (ESI, m/z): $[(M + 1)]^+$ | $^1H$ NMR (400 MHz, DMSO) δ |
| | | | | (s, 3H), 3.05-2.96 (m, 2H), 2.94-2.82 (m, 4H), 2.77-2.59 (m, 3H), 2.37-2.30 (m, 1H), 2.25-2.17 (m, 2H), 2.07-1.92 (m, 4H), 1.83-1.70 (m, 3H), 1.62 (s, 5H), 1.56-1.43 (m, 6H), 1.38-1.30 (m, 2H), 1.03-0.90 (m, 1H), 0.85-0.76 (m, 4H) |
| I-119 | FN | CI | 893.5 | 10.68 (s, 1H), 10.52 (s, 1H), 8.28 (d, J = 7.6 Hz, 1H), 8.14 (s, 1H), 7.77 (d, J = 8.4 Hz, 1H), 7.63-7.57 (m, 3H), 7.41 (dd, J = 2.0, 8.4 Hz, 1H), 7.32 (t, J = 6.8 Hz, 1H), 7.11 (t, J = 8.0 Hz, 1H), 7.03 (dd, J = 2.0, 8.0 Hz, 1H), 6.90 (dd, J = 1.6, 7.2 Hz, 1H), 6.67 (d, J = 2.0 Hz, 1H), 4.56 (d, J = 9.2 Hz, 1H), 4.36 (d, J = 8.8 Hz, 1H), 3.80 (s, 1H), 2.83 (s, 1H), 2.24-2.16 (m, 4H), 1.97-1.89 (m, 4H), 1.83-1.73 (m, 6H), 1.67-1.56 (m, 6H), 1.53-1.46 (m, 3H), 1.39-1.18 (m, 6H), 0.99-0.90 (m, 3H), 0.82-0.77 (m, 1H) |
| I-120 | 3-[5-(5-aminopent-1-ynyl)-3-methyl-2-OXO-benzimidazol-1-yl] piperidine-2,6-dione[c] | FP | 924.5 | 11.35-11.02 (m, 1H), 10.67-10.40 (m, 1H), 7.92-7.75 (m, 1H), 7.64 (td, J = 7.2, 14.8 Hz, 1H), 7.45-7.31 (m, 2H), 7.28 (d, J = 4.4 Hz, 1H), 7.17-7.05 (m, 4H), 6.71 (t, J = 2.4 Hz, 1H), 5.48-5.31 (m, 2H), 4.82-4.53 (m, 1H), 4.11-3.99 (m, 1H), 3.33 (s, 3H), 3.20 (dd, J = 5.6, 12.8 Hz, 2H), 3.03-2.88 (m, 3H), 2.78-2.64 (m, 4H), 2.49-2.43 (m, 2H), 2.12-1.98 (m, 4H), 1.80 (d, J = 6.0 Hz, 2H), 1.75-1.65 (m, 4H), 1.59-1.39 (m, 10H), 1.07 (d, J = 6.0 Hz, 1H), 0.99-0.91 (m, 1H), 0.85-0.78 (m, 1H) |
| I-121 | FQ | CI | 935.6 | 11.09 (s, 2H), 10.89-10.28 (m, 1H), 7.76-7.62 (m, 3H), 7.60-7.38 (m, 4H), 7.27-7.18 (m, 1H), 7.12-7.02 (m, 3H), 6.90 (d, J = 8.4 Hz, 1H), 6.77 (s, 1H), 5.35 (dd, J = 5.6, 12.8 Hz, 2H), 4.93-4.75 (m, 1H), 4.41-4.10 (m, 1H), 3.72-3.54 (m, 2H), 3.33 (s, 3H), 3.26-3.02 (m, 6H), 2.95-2.82 (m, 2H), 2.76-2.62 (m, 5H), 2.16-1.92 (m, 6H), 1.91-1.82 (m, 1H), 1.77-1.65 (m, 2H), 1.62-1.48 (m, 4H), 1.14-1.00 (m, 2H) |
| I-122 | FS | CN | 894.6 | 11.16 (d, J = 2.0 Hz, 1H), 10.58 (s, 1H), 8.12 (d, J = 8.0 Hz, 1H), 7.62 (t, J = 6.4 Hz, 1H), 7.51 (dd, J = 1.6, 8.4 Hz, 1H), 7.38 (t, J = 6.8 Hz, 1H), 7.32 (s, 1H), 7.21-7.12 (m, 3H), 7.09 (dd, J = 2.0, 8.0 Hz, 1H), 6.74 (d, J = 1.6 Hz, 1H), 5.43 (dd, J = 5.2, 12.4 Hz, 1H), 4.64 (d, J = 8.9 Hz, 1H), 4.45-4.32 (m, 1H), 4.13-4.00 (m, 1H), 3.61 (t, J = 6.4 Hz, 2H), 3.50-3.46 (m, 1H), 3.37-3.35 (m, 3H), 3.06 (t, J = 5.6 Hz, 2H), 3.00-2.89 (m, 1H), 2.79-2.68 (m, 2H), 2.50-2.44 (m, 2H), 2.31-2.24 (m, 1H), 2.13-2.05 (m, 2H), 2.02-1.97 (m, 1H), 1.85-1.75 (m, 2H), 1.65-1.59 (m, 2H), 1.49 (d, J = 13.6 Hz, 2H), 1.22-1.13 (m, 2H), 1.07-1.02 (m, 1H), 0.98 (s, 3H), 0.90 (s, 1H), 0.66 (s, 3H) |
| I-123 | CO | FV | 964.4 | 11.18-10.98 (m, 1H), 10.51 (s, 1H), 8.31 (s, 1H), 7.69 (d, J = 8.0 Hz, 1H), 7.61 (t, J = 6.8 Hz, 1H), 7.47-7.41 (m, 1H), 7.37-7.30 (m, 1H), 7.23 (s, 1H), 7.14-7.06 (m, 3H), 7.06-7.01 (m, 1H), 6.65 (d, J = 2.0 Hz, 1H), 5.41-5.34 (m, 1H), 4.36 (d, J = 10.4 Hz, 1H), 4.15 (d, J = 10.4 Hz, 1H), 3.34 (s, 3H), 2.93-2.83 (m, 1H), 2.79 (s, 3H), 2.66-2.57 (m, 3H), 2.16-1.97 (m, 6H), 1.91-1.73 (m, 8H), 1.73-1.56 (m, 4H), 1.54-1.39 (m, 3H), 1.25-1.01 (m, 6H), 0.91 (s, 3H), 0.89-0.82 (m, 2H), 0.58 (s, 3H) |
| I-124 | FX | I-132 | 939.7 | 11.11 (s, 1H), 8.13 (s, 1H), 7.61-7.45 (m, 2H), 7.36-7.28 (m, 1H), 7.22 (s, 1H), 7.14-6.99 (m, 5H), 5.37 (dd, J = 5.2, 13.2 Hz, 1H), 4.37 (d, J = 10.4 Hz, 1H), 3.75-3.65 (m, 1H), 3.47 ( d, J = 6.0 Hz, 3H), 2.95-2.85 (m, 2H), 2.81 (s, 3H), 2.39 (s, 3H), 2.28-2.10 (m, 6H), 2.05-1.95 (m, 3H), 1.90 (dd, J = 9.2, 10.4 Hz, 2H), 1.85-1.79 (m, 2H), 1.54-1.44 (m, 4H), 1.35-1.23 (m, 6H), 1.18 (s, 6H), 1.00 (d, J = 6.0 Hz, 4H) |
| I-137 | EN | CN | 940.2 | 11.10 (s, 1H), 10.54 (d, J = 2.4 Hz, 1H), 8.15 (s, 1H), 7.78-7.73 (m, 1H), 7.64-7.56 (m, 1H), 7.47-7.42 (m, 1H), 7.36-7.31 (m, 1H), 7.12 (s, 1H), 7.05 (dd, J = 2.0, 8.0 Hz, 1H), 7.00 (s, 2H), 6.69 (s, 1H), 5.43-5.35 (m, 1H), 4.57 (d, J = 12.0 Hz, 1H), 4.38 (d, J = 9.2 Hz, 1H), 4.15-4.06 (m, 1H), 3.63 (s, 3H), 3.55-3.43 (m, 2H), 2.94-2.85 (m, 1H), 2.66-2.57 (m, 2H), 2.06-1.95 (m, 2H), 1.93-1.64 (m, 11H), 1.55-1.39 (m, 6H), 1.35-1.22 (m, 4H), 1.16-1.08 (m, 2H), 0.90 (s, 3H), 0.61 (s, 3H) |
| I-138 | FY | CI | 858.3 | 11.08 (s, 1H), 10.71-10.24 (m, 1H), 7.61-7.53 (m, 1H), 7.53-7.29 (m, 1H), 7.24 (s, 4H), 6.91 (s, 1H), 6.81-6.61 (m, 1H), 5.37-5.30 (m, 1H), 4.76-4.58 (m, 1H), 4.56-4.32 (m, 1H), 3.49-3.46 (m, 4H), 3.12-3.00 (m, 3H), 2.91-2.86 (m, 1H), 2.76-2.69 (m, 2H), 2.65-2.58 (m, 6H), 2.05-1.94 (m, 2H), 1.91-1.74 (m, 3H), 1.68-1.19 (m, 14H), 1.15-0.89 (m, 2H) |

TABLE 11-continued

Compounds synthesized via Method 4 using the corresponding amines and acids for the coupling.

| I-#[a] | Amine | Acid | LCMS (ESI, m/z): $[(M + 1)]^+$ | $^1H$ NMR (400 MHz, DMSO) δ |
|---|---|---|---|---|
| I-139 | FZ | CI | 1005.7 | 11.14-11.04 (m, 1H), 10.56 (s, 1H), 10.00 (s, 1H), 7.64 (t, J = 7.2 Hz, 1H), 7.52 (d, J = 8.6 Hz, 2H), 7.44 (dd, J = 2.0, 8.4 Hz, 1H), 7.38-7.32 (m, 1H), 7.20 (d, J = 8.4 Hz, 2H), 7.18-7.12 (m, 1H), 7.08-7.00 (m, 2H), 6.96-6.92 (m, 1H), 6.86 (d, J = 7.6 Hz, 1H), 6.68 (d, J = 2.0 Hz, 1H), 5.44-5.28 (m, 1H), 4.76-4.68 (m, 1H), 4.68-4.60 (m, 1H), 3.66 (s, 3H), 3.62-3.56 (m, 2H), 2.66-2.56 (m, 3H), 2.16-1.94 (m, 10H), 1.80-1.68 (m, 5H), 1.66-1.52 (m, 5H), 1.52-1.44 (m, 2H), 1.44-1.32 (m, 6H), 1.28-1.20 (m, 2H), 0.94-0.80 (m, 2H) |
| I-140 | FL | CI | 936.6 | 11.11 (s, 1H), 10.51 (s, 1H), 8.16 (s, 1H), 7.95-7.89 (m, 1H), 7.58 (t, J = 7.2 Hz, 1H), 7.42-7.37 (m, 1H), 7.31 (t, J = 7.2 Hz, 1H), 7.14-7.08 (m, 2H), 7.06-6.96 (m, 3H), 6.66 (d, J = 2.0 Hz, 1H), 5.38 (dd, J = 5.2, 12.4 Hz, 1H), 4.55 (d, J = 9.6 Hz, 1H), 4.45-4.39 (m, 1H), 3.65 (s, 3H), 3.06-2.95 (m, 1H), 2.92-2.81 (m, 2H), 2.70-2.62 (m, 4H), 2.32 (d, J = 1.6 Hz, 1H), 2.11-2.03 (m, 4H), 1.95-1.84 (m, 3H), 1.81-1.70 (m, 3H), 1.63 (dd, J = 10.4, 13.2 Hz, 6H), 1.56-1.50 (m, 2H), 1.48-1.29 (m, 5H), 0.97-0.73 (m, 6H) |
| I-141 | GB | CI | 887.6 | 12.28-11.76 (m, 1H), 11.10 (s, 2H), 10.66-10.26 (m, 1H), 9.05-8.76 (m, 1H), 7.62 (t, J = 6.8 Hz, 1H), 7.56 (d, J = 7.6 Hz, 1H), 7.48 (t, J = 6.4 Hz, 1H), 7.24 (t, J = 7.8 Hz, 1H), 7.14-7.08 (m, 1H), 7.05-6.96 (m, 2H), 6.92 (dd, J = 1.6, 7.2 Hz, 1H), 6.77 (d, J = 1.6 Hz, 1H), 5.39 (dd, J = 5.2, 12.8 Hz, 1H), 5.31-4.88 (m, 1H), 4.69 (d, J = 10.8 Hz, 1H), 3.85-3.66 (m, 2H), 3.60 (s, 5H), 3.35-3.17 (m, 6H), 3.17-3.07 (m, 2H), 3.04-2.84 (m, 5H), 2.78-2.60 (m, 3H), 2.07 (s, 2H), 2.04-1.92 (m, 3H), 1.80 (d, J = 5.2 Hz, 2H), 1.72-1.61 (m, 2H), 1.60-1.48 (m, 3H), 1.08 (dd, J = 1.6, 5.2 Hz, 2H) |
| I-142 | JJ | CI | 904.4 | 10.54 (d, J = 16.0 Hz, 2H), 9.29 (s, 1H), 8.56 (s, 1H), 8.30 (s, 1H), 8.14 (s, 1H), 7.97 (d, J = 8.8 Hz, 1H), 7.79-7.71 (m, 2H), 7.58 (t, J = 6.8 Hz, 1H), 7.40 (dd, J = 2.0, 8.4 Hz, 1H), 7.32 (t, J = 7.2 Hz, 1H), 7.11 (t, J = 8.0 Hz, 1H), 7.02 (dd, J = 2.0, 8.0 Hz, 1H), 6.66 (d, J = 2.0 Hz, 1H), 4.55 (d, J = 9.2 Hz, 1H), 4.36 (d, J = 9.2 Hz, 1H), 3.95 (ddd, J = 4.8, 10.0, 12.0 Hz, 1H), 3.71 (td, J = 6.0, 12.0 Hz, 1H), 3.51-3.41 (m, 2H), 2.97 (ddd, J = 6.0, 10.0, 16.4 Hz, 1H), 2.85-2.70 (m, 4H), 2.34-2.23 (m, 3H), 2.00-1.90 (m, 3H), 1.84-1.67 (m, 7H), 1.63-1.44 (m, 6H), 1.39-1.29 (m, 1H), 1.28-1.17 (m, 2H), 1.01-0.86 (m, 3H), 0.79 (dt, J = 4.0, 12.4 Hz, 1H) |
| I-143 | GE | CI | 947.4 | 10.99 (s, 1H), 10.52 (s, 1H), 8.13 (s, 1H), 7.71 (d, J = 7.6 Hz, 1H), 7.65 (d, J = 7.6 Hz, 1H), 7.62-7.49 (m, 3H), 7.43-7.36 (m, 1H), 7.32 (t, J = 6.8 Hz, 1H), 7.10 (t, J = 7.6 Hz, 1H), 7.03 (d, J = 7.6 Hz, 1H), 6.66 (s, 1H), 5.16-5.10 (m, 1H), 4.52-4.46 (m, 1H), 4.46-4.24 (m, 3H), 3.92 (d, J = 9.2 Hz, 2H), 3.72-3.50 (m, 1H), 3.26 (s, 1H), 3.03-2.94 (m, 1H), 2.92-2.86 (m, 1H), 2.64-2.55 (m, 1H), 2.45 (d, J = 4.8 Hz, 1H), 2.07-1.92 (m, 2H), 1.84 (s, 14H), 1.73-1.42 (m, 10H), 1.05-0.89 (m, 1H), 0.87-0.72 (m, 1H) |
| I-144 | GH | CI | 877.1 | 10.63 (s, 1H), 10.57 (s, 1H), 10.21 (s, 1H), 8.23 (d, J = 7.2 Hz, 1H), 7.70-7.61 (m, 3H), 7.49 (s, 1H), 7.47-7.40 (m, 4H), 7.38-7.32 (m, 1H), 7.15 (t, J = 8.2 Hz, 1H), 7.04 (dd, J = 2.0, 8.4 Hz, 1H), 6.97 (d, J = 8.0 Hz, 1H), 6.68 (d, J = 2.0 Hz, 1H), 4.79-4.73 (m, 1H), 4.71-4.66 (m, 1H), 3.78 (t, J = 6.6 Hz, 2H), 3.00-2.86 (m, 2H), 2.82 (t, J = 6.8 Hz, 2H), 2.15-1.97 (m, 2H), 1.93-1.79 (m, 2H), 1.72-1.48 (m, 8H), 1.47-1.28 (m, 2H), 1.06-0.76 (m, 3H) |
| I-145 | CQ | GI | 939.6 | 11.08 (s, 3H), 8.65-8.10 (m, 2H), 7.83 (d, J = 8.4 Hz, 2H), 7.79-7.56 (m, 4H), 7.18-7.08 (m, 1H), 7.04-6.95 (m, 2H), 6.86 (d, J = 8.0 Hz, 1H), 6.80 (s, 1H), 5.33 (dd, J = 5.2, 12.4 Hz, 1H), 4.86 (d, J = 4.8 Hz, 1H), 3.31 (s, 3H), 3.24 (q, J = 6.4 Hz, 2H), 2.96-2.84 (m, 1H), 2.78-2.58 (m, 4H), 2.06-1.97 (m, 1H), 1.96-1.69 (m, 3H), 1.68-1.42 (m, 6H), 1.40-1.30 (m, 3H), 1.28-1.10 (m, 2H), 0.93 (s, 3H), 0.64 (s, 3H) |
| I-146 | JH | CI | 904.4 | 10.54 (d, J = 20.0 Hz, 2H), 9.56 (s, 1H), 8.64 (s, 1H), 8.14 (s, 1H), 8.00 (dd, J = 2.0, 7.2 Hz, 1H), 7.83-7.74 (m, 3H), 7.61-7.55 (m, 1H), 7.40 (dd, J = 2.0, 8.4 Hz, 1H), 7.35-7.28 (m, 1H), 7.14-7.07 (m, 1H), 7.02 (dd, J = 2.0, 8.0 Hz, 1H), 6.66 (d, J = 2.0 Hz, 1H), 4.55 (d, J = 9.2 Hz, 1H), 4.36 (d, J = 9.0 Hz, 1H), 4.00-3.90 (m, 1H), 3.76-3.67 (m, 1H), 3.05-2.89 (m, 3H), 2.88-2.71 (m, 3H), 2.43 (dd, J = 6.0, 8.8 Hz, 2H), |

TABLE 11-continued

Compounds synthesized via Method 4 using the corresponding amines and acids for the coupling.

| I-#[a] | Amine | Acid | LCMS (ESI, m/z): $[(M + 1)]^+$ | $^1H$ NMR (400 MHz, DMSO) δ |
|---|---|---|---|---|
| | | | | 2.35-2.24 (m, 2H), 2.08-1.98 (m, 2H), 1.94 (d, J = 12.0 Hz, 1H), 1.88-1.72 (m, 7H), 1.64-1.48 (m, 5H), 1.48-1.41 (m, 1H), 1.40-1.29 (m, 1H), 1.28-1.13 (m, 2H), 1.01-0.87 (m, 3H), 0.84-0.74 (m, 1H) |
| I-147 | FC | GI | 970.4 | (Methanol-d4) δ 8.22 (d, J = 5.2 Hz, 1H), 7.68 (t, J = 4.8 Hz, 1H), 7.60-7.51 (m, 1H), 7.18-7.09 (m, 2H), 7.08-6.98 (m, 2H), 6.87 (d, J = 1.2 Hz, 1H), 5.31 (dd, J = 5.6, 12.8 Hz, 1H), 5.14 (d, J = 10.8 Hz, 1H), 4.81 (d, J = 10.8 Hz, 1H), 3.74-3.47 (m, 7H), 3.44 (s, 3H), 3.32-3.28 (m, 2H), 3.26-3.18 (m, 2H), 3.08-2.89 (m, 3H), 2.86-2.76 (m, 4H), 2.69 (d, J = 12.4 Hz, 1H), 2.24-1.95 (m, 7H), 1.94-1.81 (m, 2H), 1.80-1.48 (m, 4H), 1.48-1.36 (m, 3H), 1.35-1.27 (m, 1H), 1.23-1.06 (m, 2H), 1.03 (s, 3H), 0.77 (s, 3H) |
| I-148 | EV | GI | 951.4 | 11.10 (s, 1H), 10.61 (s, 1H), 8.17 (d, J = 5.2 Hz, 1H), 7.73 (d, J = 8.8 Hz, 1H), 7.63 (t, J = 5.2 Hz, 1H), 7.52-7.46 (m, 1H), 7.11 (d, J = 7.2 Hz, 1H), 7.07-7.02 (m, 2H), 7.01-6.95 (m, 1H), 6.71 (d, J = 2.0 Hz, 1H), 5.41-5.34 (m, 1H), 4.57-4.52 (m, 1H), 4.48-4.38 (m, 1H), 3.64 (s, 3H), 3.58-3.40 (m, 3H), 2.95-2.82 (m, 1H), 2.66-2.58 (m, 3H), 2.15-1.96 (m, 5H), 1.95-1.54 (m, 12H), 1.54-1.39 (m, 3H), 1.27-1.17 (m, 3H), 1.16-1.08 (m, 1H), 0.98-0.91 (m, 2H), 0.89 (s, 3H), 0.88 - 0.82 (m, 1H), 0.59 (s, 3H) |
| I-149 | CO | GI | 952.2 | 11.11 (s, 1H), 10.61 (s, 1H), 8.18 (d, J = 5.2 Hz, 1H), 7.73 (d, J = 8.4 Hz, 1H), 7.63 (t, J = 5.2 Hz, 1H), 7.50 (dd, J = 1.2, 8.0 Hz, 1H), 7.22 (s, 1H), 7.05 (dd, J = 2.0, 8.0 Hz, 1H), 6.71 (d, J = 2.0 Hz, 1H), 5.37 (dd, J = 5.2, 12.8 Hz, 1H), 4.57-4.51 (m, 1H), 4.47-4.39 (m, 1H), 3.60-3.40 (m, 3H), 2.93-2.83 (m, 1H), 2.64 (s, 3H), 2.13-1.98 (m, 7H), 1.88-1.69 (m, 10H), 1.67-1.53 (m, 5H), 1.52-1.39 (m, 4H), 1.26-1.17 (m, 4H), 1.12 (d, J = 10.4 Hz, 2H), 0.89 (s, 3H), 0.59 (s, 3H) |
| I-150 | GN | CI | 895.5 | 10.67 (s, 1H), 10.52 (s, 1H), 8.31 (dd, J = 1.2, 6.8 Hz, 1H), 7.76 (d, J = 8.4 Hz, 1H), 7.62-7.55 (m, 2H), 7.45-7.37 (m, 2H), 7.36-7.28 (m, 1H), 7.11 (t, J = 8.0 Hz, 1H), 7.03 (dd, J = 2.0, 8.0 Hz, 1H), 6.94 (t, J = 6.8 Hz, 1H), 6.67 (d, J = 2.0 Hz, 1H), 4.56 (d, J = 9.2 Hz, 1H), 4.42-4.32 (m, 1H), 3.80 (br t, J = 6.4 Hz, 2H), 3.59-3.38 (m, 2H), 2.83 (s, 2H), 2.12 2.06 (m, 3H), 2.00-1.86 (m, 4H), 1.84-1.72 (m, 6H), 1.67-1.53 (m, 6H), 1.53-1.42 (m, 4H), 1.28-1.15 (m, 3H), 0.94-0.87 (m, 2H), 0.86-0.75 (m, 2H) |
| I-151 | CM | GI | 945.3 | 11.15-11.00 (m, 1H), 10.75-10.24 (m, 1H), 8.45-8.08 (m, 1H), 7.80-7.50 (m, 4H), 7.13-7.05 (m, 1H), 7.03-6.98 (m, 2H), 6.85 (d, J = 8.0 Hz, 1H), 6.79-6.67 (m, 1H), 5.33 (dd, J = 5.4, 12.8 Hz, 1H), 4.76-4.25 (m, 2H), 3.53-3.47 (m, 1H), 3.33 (s, 3H), 3.06-2.98 (m, 2H), 2.94 (d, J = 3.2 Hz, 1H), 2.76-2.68 (m, 1H), 2.63-2.57 (m, 3H), 2.09-1.95 (m, 3H), 1.85-1.69 (m, 6H), 1.62-1.54 (m, 3H), 1.46-1.34 (m, 6H), 1.29-1.17 (m, 6H), 0.91 (s, 3H), 0.61 (s, 3H) |
| I-152 | CO | GJ | 944.5 | 11.15 (s, 1H), 10.59 (s, 1H), 7.85-7.71 (m, 3H), 7.59 (t, J = 6.8 Hz, 1H), 7.43 (dd, J = 1.8, 8.2 Hz, 1H), 7.34 (t, J = 7.2 Hz, 2H), 7.26 (d, J = 8.8 Hz, 2H), 6.70 (d, J = 2.0 Hz, 1H), 5.46 (dd, J = 5.6, 12.8 Hz, 1H), 4.57 (d, J = 9.2 Hz, 1H), 4.49-4.35 (m, 1H), 3.84-3.73 (m, 2H), 3.66-3.57 (m, 2H), 3.42 (s, 7H), 3.17-3.05 (m, 2H), 3.00 (d, J = 6.4 Hz, 2H), 2.92-2.83 (m, 1H), 2.77-2.60 (m, 3H), 2.10-1.97 (m, 2H), 1.76 (d, J = 13.2 Hz, 7H), 1.68-1.56 (m, 2H), 1.46-1.32 (m, 3H), 1.28-1.18 (m, 2SH), 1.11-1.01 (m, 1H), 1.00-0.87 (m, 2H) |
| I-153 | CO | GJ | 926.3 | 11.11 (s, 1H), 10.58 (s, 1H), 7.76 (d, J = 8.2 Hz, 1H), 7.60 (t, J = 6.4 Hz, 1H), 7.48-7.40 (m, 1H), 7.38-7.29 (m, 1H), 7.23 (s, 1H), 7.17-7.02 (m, 4H), 6.70 (d, J = 2.0 Hz, 1H), 5.45-5.33 (m, 1H), 4.57 (d, J = 9.2 Hz, 1H), 4.46-4.36 (m, 1H), 3.86-3.71 (m, 2H), 3.68-3.57 (m, 2H), 3.43 (s, 1Hs), 3.34 (s, 3H), 3.31 (s, 2H), 2.97-2.85 (m, 1H), 2.78-2.62 (m, 4H), 2.12-2.01 (m, 4H), 1.90-1.82 (m, 2H), 1.80-1.74 (m, 3H), 1.68-1.61 (m, 2H), 1.47-1.40 (m, 2H), 1.17 (s, 2H), 1.12-1.03 (m, 2H), 0.89-0.81 (m, 4H) |
| I-154 | GT | CI | 967.5 | 11.09 (s, 1H), 10.53 (s, 1H), 7.75 (d, J = 8.4 Hz, 1H), 7.59 (t, J = 6.8 Hz, 1H), 7.44-7.27 (m, 2H), 7.17-6.99 (m, 4H), 6.90 (d, J = 8.0 Hz, 1H), 6.67 (d, J = 2.0 Hz, 1H), 5.35 (dd, J = 5.2, 12.8 Hz, 1H), 4.55 (d, J = 9.2 Hz, 1H), 4.36 (d, J = 9.2 Hz, 1H), 3.62-3.55 (m, 1H), 3.48-3.40 (m, 5H), 3.27 (s, 3H), 2.96-2.85 (m, 3H), 2.78-2.63 (m, 4H), 2.32-2.20 (m, 3H), |

TABLE 11-continued

Compounds synthesized via Method 4 using the corresponding amines and acids for the coupling.

| I-#[a] | Amine | Acid | LCMS (ESI, m/z): $[(M + 1)]^+$ | $^1H$ NMR (400 MHz, DMSO) δ |
|---|---|---|---|---|
| | | | | 2.07 (d, J = 6.8 Hz, 2H), 2.02-1.91 (m, 2H), 1.87-1.65 (m, 9H), 1.65-1.43 (m, 6H), 1.39-1.31 (m, 1H), 1.26-1.10 (m, 2H), 1.02-0.71 (m, 4H) |
| I-155 | GN | GI | 922.4 | 10.66 (s, 1H), 10.61 (s, 1H), 8.30 (d, J = 6.4 Hz, 1H), 8.17 (d, J = 5.2 Hz, 1H), 7.73 (d, J = 8.4 Hz, 1H), 7.63 (t, J = 4.8 Hz, 1H), 7.57 (s, 1H), 7.50 (d, J = 7.2 Hz, 1H), 7.38 (d, J = 7.2 Hz, 1H), 7.05 (d, J = 7.6 Hz, 1H), 6.93 (t, J = 6.8 Hz, 1H), 6.71 (s, 1H), 4.57-4.50 (m, 1H), 4.47-4.39 (m, 1H), 3.79 (t, J = 6.4 Hz, 2H), 3.59-3.51 (m, 1H), 3.49-3.43 (m, 1H), 2.82 (s, 2H), 2.17-2.05 (m, 5H), 1.95-1.84 (m, 3H), 1.84-1.63 (m, 10H), 1.53-1.40 (m, 4H), 1.28-1.18 (m, 4H), 1.17-1.08 (m, 2H), 0.89 (s, 3H), 0.59 (s, 3H) |
| I-156 | GO | GQ | 940.4 | 11.08 (s, 1H), 10.44 (s, 1H), 7.64-7.51 (m, 1H), 7.35 (d, J = 8.4 Hz, 2H), 7.13 (t, J = 8.0 Hz, 1H), 7.06-6.99 (m, 3H), 6.90-6.84 (m, 1H), 6.62 (d, J = 1.2 Hz, 1H), 5.40-5.28 (m, 1H), 4.45-4.32 (m, 2H), 3.97-3.88 (m, 2H), 3.69-3.58 (m, 3H), 2.97 (dd, J = 2.2, 12.2 Hz, 2H), 2.91 (d, J = 4.4 Hz, 2H), 2.80 (s, 3H), 2.73-2.70 (m, 2H), 2.68 (s, 2H), 2.64 (s, 3H), 2.08 (s, 1H), 2.03-1.92 (m, 3H), 1.83-1.72 (m, 4H), 1.67-1.58 (m, 4H), 1.56-1.50 (m, 4H), 1.48-1.41 (m, 3H), 1.38-1.30 (m, 2H), 1.23-1.13 (m, 2H), 1.09-1.04 (m, 1H), 0.96-0.86 (m, 2H) |
| I-157 | EH | GI | 945.4 | 11.06 (s, 1H), 10.60 (s, 1H), 8.17 (d, J = 5.2 Hz, 1H), 7.82 (d, J = 8.8 Hz, 1H), 7.68-7.58 (m, 2H), 7.50 (d, J = 8.0 Hz, 1H), 7.10-7.02 (m, 1H), 7.01-6.94 (m, 2H), 6.87-6.81 (m, 1H), 6.70 (d, J = 2.0 Hz, 1H), 5.38-5.27 (m, 1H), 4.57 (d, J = 8.8 Hz, 1H), 4.45 (t, J = 9.6 Hz, 1H), 3.82-3.75 (m, 1H), 3.68 (d, J = 9.2 Hz, 2H), 3.50 (s, 1H), 3.29 (s, 3H), 3.18 (t, J = 10.4 Hz, 2H), 3.08-2.98 (m, 2H), 2.90-2.82 (m, 1H), 2.64-2.54 (m, 4H), 2.03-1.93 (m, 2H), 1.77-1.67 (m, 2H), 1.63-1.52 (m, 4H), 1.47-1.36 (m, 4H), 1.30-1.14 (m, 4H), 1.13-0.94 (m, 2H), 0.89 (s, 3H), 0.58 (s, 3H) |
| I-158 | GT | DM | 981.3 | 11.08 (s, 1H), 10.53-10.47 (m, 1H), 7.70 (d, J = 8.4 Hz, 1H), 7.60 (t, J = 6.8 Hz, 1H), 7.40 (dd, J = 2.4, 8.2 Hz, 1H), 7.36-7.29 (m, 1H), 7.16-6.94 (m, 4H), 6.88 (d, J = 8.0 Hz, 1H), 6.62 (d, J = 2.0 Hz, 1H), 5.33 (dd, J = 5.2, 12.8 Hz, 1H), 4.34 (d, J = 10.4 Hz, 1H), 4.14 (d, J = 10.4 Hz, 1H), 3.58-3.34 (m, 4H), 3.34-3.20 (m, 1H), 3.29-3.20 (m, 1H), 3.14 (s, 3H), 2.95-2.79 (m, 3H), 2.78 (s, 3H), 2.72-2.57 (m, 4H), 2.23 (s, 3H), 2.09-1.88 (m, 5H), 1.87-1.56 (m, 9H), 1.56-1.32 (m, 6H), 1.26-1.07 (m, 2H), 1.06-0.94 (m, 2H), 0.92-0.77 (m, 2H) |
| I-159 | GU | CI | 967.7 | 11.08 (s, 1H), 10.52 (s, 1H), 7.74 (d, J = 8.4 Hz, 1H), 7.58 (t, J = 7.2 Hz, 1H), 7.40 (dd, J = 2.0, 8.0 Hz, 1H), 7.35-7.28 (m, 1H), 7.10 (t, J = 8.0 Hz, 1H), 7.02 (dd, J = 2.0, 8.0 Hz, 1H), 6.98-6.92 (m, 2H), 6.87 (dd, J = 2.8, 6.0 Hz, 1H), 6.66 (d, J = 2.0 Hz, 1H), 5.40-5.31 (m, 1H), 4.54 (d, J = 8.8 Hz, 1H), 4.41-4.25 (m, 1H), 3.56 (s, 3H), 2.91 (s, 4H), 2.90-2.84 (m, 3H), 2.66-2.59 (m, 1H), 2.24-2.11 (m, 4H), 2.04-1.89 (m, 5H), 1.85-1.69 (m, 6H), 1.66-1.53 (m, 8H), 1.49-1.31 (m, 4H), 1.28-1.12 (m, 3H), 1.01-0.73 (m, 5H) |
| I-160 | GX | CI | 934.4 | 11.08 (s, 1H), 10.59 (s, 1H), 10.36 (s, 1H), 8.27 (d, J = 8.0 Hz, 1H), 7.99 (s, 1H), 7.64 (t, J = 6.8 Hz, 1H), 7.42 (d, J = 8.0 Hz, 1H), 7.36 (t, J = 7.4 Hz, 1H), 7.27 (s, 1H), 7.22 (s, 1H), 7.16 (t, J = 8.2 Hz, 1H), 7.10 (s, 1H), 7.02-6.99 (m, 2H), 6.86 (d, J = 7.6 Hz, 1H), 6.71-6.64 (m, 1H), 5.34 (dd, J = 5.2, 12.0 Hz, 1H), 4.76-4.69 (m, 1H), 4.54 (d, J = 10.0 Hz, 1H), 4.24-4.06 (m, 2H), 3.91 (s, 3H), 3.70 (s, 3H), 3.00-2.92 (m, 2H), 2.66-2.58 (m, 6H), 2.06-1.93 (m, 3H), 1.75-1.51 (m, 10H), 1.42-1.23 (m, 4H), 1.05-0.94 (m, 1H), 0.89-0.81 (m, 1H) |
| I-161 | GY | CI | 926.6 | 11.08 (s, 1H), 10.58 (s, 1H), 10.12 (s, 1H), 8.34 (s, 1H), 8.08 (t, J = 8.4 Hz, 1H), 7.64 (t, J = 6.9 Hz, 1H), 7.46 (dd, J = 2.2, 8.2 Hz, 1H), 7.36 (t, J = 7.0 Hz, 1H), 7.24-7.12 (m, 2H), 7.08-6.98 (m, 4H), 6.86 (d, J = 7.8 Hz, 1H), 6.68 (d, J = 1.8 Hz, 1H), 5.38-5.28 (m, 1H), 4.78-4.70 (m, 1H), 4.67-4.60 (m, 1H), 4.02-3.88 (m, 1H), 3.40 (s, 3H), 2.96-2.84 (m, 1H), 2.66-2.58 (m, 4H), 2.30 (t, J = 7.2 Hz, 2H), 2.08 (s, 3H), 2.08-1.96 (m, 3H), 1.76-1.66 (m, 1H), 1.64-1.56 (m, 4H), 1.56-1.44 (m, 4H), 1.36-1.24 (m, 4H), 1.08-0.78 (m, 3H) |
| I-162 | GZ | CI | 909.6 | 11.04 (s, 1H), 10.58 (s, 1H), 10.32 (s, 1H), 8.24 (s, 1H), 8.20 (d, J = 2.4 Hz, 1H), 7.98 (dd, J = 2.4, 8.8 Hz, 1H), 7.70-7.60 (m, 2H), 7.45 (dd, J = 2.0, 8.0 Hz, 1H), 7.40-7.32 (m, 1H), 7.19-7.11 (m, 1H), 7.05-6.95 (m, 3H), 6.85 (d, J = 8.4 Hz, 1H), 6.68 (d, J = 2.0 Hz, 1H), 5.38-5.28 (m, 1H), 4.76-4.65 |

TABLE 11-continued

Compounds synthesized via Method 4 using the corresponding amines and acids for the coupling.

| I-#[a] | Amine | Acid | LCMS (ESI, m/z): $[(M + 1)]^+$ | $^1H$ NMR (400 MHz, DMSO) δ |
|---|---|---|---|---|
| | | | | (m, 2H), 4.01-3.86 (m, 1H), 3.44-3.38 (m, 3H), 2.59 (t, J = 7.6 Hz, 2H), 2.28 (d, J = 6.8 Hz, 2H), 2.08 (s, 3H), 2.04 (s, 1H), 2.00-1.96 (m, 2H), 1.64-1.54 (m, 6H), 1.52-1.44 (m, 4H), 1.32-1.24 (m, 4H), 1.08-0.94 (m, 3H), 0.92-0.76 (m, 2H) |
| I-163 | HB | CI | 968.2 | 11.13-11.00 (m, 1H), 10.64-10.50 (m, 1H), 10.29 (s, 1H), 7.94 (t, J = 5.6 Hz, 1H), 7.83 (d, J = 8.4 Hz, 1H), 7.68-7.59 (m, 1H), 7.45 (dd, J = 1.6, 8.0 Hz, 1H), 7.39-7.32 (m, 1H), 7.30-7.23 (m, 1H), 7.19-7.07 (m, 1H), 7.03-6.97 (m, 3H), 6.86 (d, J = 7.2 Hz, 1H), 6.66 (d, J = 2.0 Hz, 1H), 5.32 (dd, J = 4.8, 12.0 Hz, 1H), 4.80-4.69 (m, 1H), 4.59-4.51 (m, 1H), 4.46-4.27 (m, 4H), 3.99-3.92 (m, 1H), 3.29 (s, 3H), 2.65-2.56 (m, 2H), 2.07 (s, 1H), 2.06-1.95 (m, 4H), 1.67-1.58 (m, 5H), 1.54 (dd, J = 6.8, 7.6 Hz, 4H), 1.42-1.30 (m, 4H), 1.23 (s, 1H), 1.02-0.80 (m, 3H) |
| I-164 | FN | GI | 922.6 | 10.76 (d, J = 1.4 Hz, 1H), 8.96-8.74 (m, 1H), 8.50-8.44 (m, 1H), 8.28-8.20 (m, 1H), 7.90 (s, 1H), 7.84 (dd, J = 1.5, 7.8 Hz, 1H), 7.78 (s, 1H), 7.64 (t, J = 5.1 Hz, 1H), 7.58-7.46 (m, 1H), 7.14-7.08 (m, 2H), 6.76 (s, 1H), 4.64-4.56 (m, 1H), 3.46 (d, J = 1.3 Hz, 7H), 3.28 (dd, J = 2.4, 6.8 Hz, 1H), 3.22-3.14 (m, 1H), 3.08-2.90 (m, 4H), 2.84 (t, J = 6.2 Hz, 2H), 2.70-2.64 (m, 1H), 2.54 (s, 1H), 2.36-2.30 (m, 2H), 2.16 (dd, J = 3.4, 16.1 Hz, 2H), 2.02-1.92 (m, 2H), 1.88-1.74 (m, 6H), 1.56-1.42 (m, 2H), 1.32-1.16 (m, 4H), 1.12-0.96 (m, 4H), 0.92 (s, 3H), 0.62 (s, 3H) |
| I-165 | GO | HF | 884.2 | 11.09 (s, 1H), 11.06-10.69 (m, 1H), 8.70-8.41 (m, 1H), 7.59 (s, 2H), 7.46-7.38 (m, 1H), 7.24-7.07 (m, 2H), 7.06-6.96 (m, 2H), 6.88 (d, J = 8.4 Hz, 1H), 6.76 (s, 1H), 5.34 (dd, J = 5.2, 12.4 Hz, 2H), 5.19-5.06 (m, 1H), 4.40-4.33 (m, 2H), 3.33 (s, 3H), 3.00-2.83 (m, 2H), 2.74-2.58 (m, 5H), 2.09-1.92 (m, 2H), 1.86-1.68 (m, 3H), 1.65-1.42 (m, 9H), 1.23-0.85 (m, 5H) |
| I-166 | FN | AJ | 998.8 | 10.67 (s, 1H), 8.27 (d, J = 7.0 Hz, 1H), 8.05 ( d, J = 7.6 Hz, 1H), 7.62 (s, 2H), 7.48-7.29 (m, 2H), 7.27-7.21 (m, 1H), 7.19-7.14 (m, 1H), 7.03-6.95 (m, 2H), 6.89 (dd, J = 1.2, 7.1 Hz, 1H), 5.02 ( d, J = 11.0 Hz, 1H), 3.90-3.75 (m, 3H), 3.70-3.44 (m, 3H), 3.20-3.13 (m, 1H), 3.06 ( t, J = 8.9 Hz, 1H), 2.85-2.66 (m, 6H), 2.31-2.05 (m, 6H), 2.04-1.96 (m, 2H), 1.96-1.78 (m, 4H), 1.78-1.61 (m, 5H), 1.54-1.39 (m, 1H), 1.30 (s, 3H), 1.28 (s, 3H), 1.22 (s, 4H), 1.18-1.04 (m, 2H), 1.01-0.80 (m, 2H), 0.54 ( d, J = 6.5 Hz, 3H), 0.41 ( d, J = 6.8 Hz, 3H) |
| I-167 | GN | GF | 897.2 | 10.67 (s, 1H), 8.32 (d, J = 7.2 Hz, 1H), 7.71-7.65 (m, 2H), 7.63 (dd, J = 2.0, 12.8 Hz, 1H), 7.58 (s, 1H), 7.50 (t, J = 7.2 Hz, 1H), 7.40 (d, J = 7.2 Hz, 1H), 7.37-7.33 (m, 1H), 7.33-7.27 (m, 2H), 6.94 (t, J = 7.2 Hz, 1H), 4.61 (d, J = 7.2 Hz, 1H), 4.25 (t, J = 7.6 Hz, 1H), 3.98-3.89 (m, 1H), 3.84-3.75 (m, 3H), 3.54-3.43 (m, 1H), 2.88-2.77 (m, 3H), 2.52 (s, 4H), 2.03-1.93 (m, 2H), 1.92-1.66 (m, 7H), 1.61-1.50 (m, 2H), 1.25-1.11 (m, 4H), 1.07-0.92 (m, 2H), 0.86 (s, 9H) |
| I-168 | DZ | HJ | 917.8 | 11.43-10.59 (m, 1H), 7.36 (s, 4H), 7.06-6.95 (m, 3H), 6.92-6.82 (m, 4H), 6.57 (d, J = 9.2 Hz, 2H), 5.95 (s, 1H), 5.30 (dd, J = 4.8, 12.4 Hz, 1H), 4.46 (q, J = 6.0 Hz, 1H), 4.23 (dd, J = 5.3, 10.4 Hz, 1H), 3.90 (d, J = 19.6 Hz, 1H), 3.73 (s, 3H), 3.57 (d, J = 20.0 Hz, 1H), 3.30 (s, 3H), 3.13 (d, J = 6.4 Hz, 2H), 2.92-2.83 (m, 4H), 2.75 (s, 4H), 2.65-2.57 (m, 5H), 2.30-2.22 (m, 1H), 2.03-1.95 (m, 1H), 1.72 (s, 2H), 1.62-1.57 (m, 2H), 1.55-1.45 (m, 4H), 1.45-1.38 (m, 2H), 1.24 (d, J = 6.0 Hz, 3H), 1.19 (d, J = 6.0 Hz, 3H), 1.13-0.98 (m, 2H). |
| I-169 | HK | CI | 854.1 | 11.14 (s, 1H), 7.72-7.62 (m, 1H), 7.53 (s, 1H), 7.46 (s, 1H), 7.34 (d, J = 8.0 Hz, 2H), 7.27-7.19 (m, 2H), 7.09 (dd, J = 2.8, 4.4 Hz, 2H), 6.80-6.65 (m, 1H), 5.43 (dd, J = 5.2, 12.4 Hz, 1H), 4.71-4.58 (m, 1H), 4.01 (t, J = 6.8 Hz, 2H), 3.78-3.58 (m, 4H), 3.26 (s, 3H), 2.98-2.80 (m, 2H), 2.73-2.65 (m, 6H), 2.12-1.83 (m, 8H), 1.66-1.45 (m, 6H), 1.15 (s, 1H) |
| I-170 | GN | AJ | 998.8 | 10.67 (s, 1H), 8.33 (d, J = 7.2 Hz, 1H), 8.13 (s, 1H), 8.07 (d, J = 7.2 Hz, 1H), 7.59 (s, 1H), 7.42 (d, J = 6.8 Hz, 2H), 7.28-7.20 (m, 1H), 7.19-7.13 (m, 1H), 7.02-6.92 (m, 3H), 5.02 (d, J = 11.2 Hz, 1H), 3.89-3.72 (m, 3H), 3.65-3.45 (m, 3H), 3.42-3.34 (m, 4H), 3.16 (d, J = 13.2 Hz, 2H), 3.11-3.01 (m, 2H), 2.87-2.75 (m, 4H), 2.35-2.32 (m, 1H), 2.18-1.94 (m, 6H), 1.92-1.55 (m, 8H), 1.29 (d, J = 6.9 Hz, 6H), 1.22 (s, 4H), 1.19-1.08 (m, 2H), 1.08-0.91 (m, 2H), 0.54 (d, J = 6.4 Hz, 3H), 0.41 (d, J = 6.8 Hz, 3H) |

TABLE 11-continued

Compounds synthesized via Method 4 using the corresponding amines and acids for the coupling.

| I-#[a] | Amine | Acid | LCMS (ESI, m/z): $[(M + 1)]^+$ | $^1H$ NMR (400 MHz, DMSO) δ |
|---|---|---|---|---|
| I-171 | JD | CI | 912.1 | 11.08 (s, 1H), 10.53 (s, 1H), 8.22 (s, 1H), 7.82 (d, J = 8.4 Hz, 1H), 7.59 (t, J = 7.2 Hz, 1H), 7.46-7.37 (m, 1H), 7.36-7.28 (m, 1H), 7.11 (t, J = 8.1 Hz, 1H), 7.07-6.96 (m, 3H), 6.91-6.82 (m, 1H), 6.67 (d, J = 2.0 Hz, 1H), 5.37-5.30 (m, 1H), 4.56 (d, J = 9.2 Hz, 1H), 4.38 (d, J = 9.2 Hz, 1H), 3.32 (s, 3H), 2.97-2.77 (m, 3H), 2.77-2.69 (m, 1H), 2.58 (s, 3H), 2.31-2.17 (m, 2H), 2.17-2.06 (m, 2H), 2.04-1.91 (m, 2H), 1.89-1.67 (m, 4H), 1.65-1.32 (m, 18H), 1.28-1.12 (m, 1H), 1.04-0.90 (m, 1H), 0.87-0.73 (m, 1H) |
| I-172 | HL | HF | 940.4 | 11.35-10.71 (m, 2H), 8.67-8.48 (m, 1H), 7.68-7.52 (m, 2H), 7.42 (t, J = 7.2 Hz, 1H), 7.22-7.09 (m, 2H), 7.04-6.99 (m, 2H), 6.89-6.83 (m, 1H), 6.77 (s, 1H), 5.98-5.39 (m, 1H), 5.34 (dd, J = 5.2, 12.8 Hz, 1H), 5.15 (d, J = 10.8 Hz, 1H), 3.98-3.70 (m, 3H), 3.42 (t, J = 6.4 Hz, 4H), 3.31 (s, 3H), 2.94-2.85 (m, 1H), 2.76-2.68 (m, 1H), 2.65-2.59 (m, 3H), 2.02-1.97 (m, 1H), 1.92-1.69 (m, 4H), 1.69-1.48 (m, 9H), 1.45-1.30 (m, 5H), 1.13-0.94 (m, 2H) |
| I-173 | CO | AJ | 1027.3 | 11.10 (s, 1H), 8.15 (s, 1H), 8.07-8.01 (m, 1H), 7.29-7.20 (m, 3H), 7.16 (d, J = 8.0 Hz, 2H), 7.08 (s, 1H), 7.03-6.95 (m, 3H), 5.41-5.33 (m, 1H), 5.05-4.97 (m, 1H), 3.89-3.80 (m, 1H), 3.66-3.54 (m, 1H), 3.44-3.37 (m, 3H), 3.10-3.02 (m, 2H), 2.80 (d, J = 13.6 Hz, 2H), 2.19-1.98 (m, 10H), 1.93-1.71 (m, 8H), 1.61 (s, 6H), 1.29 (d, J = 6.8 Hz, 6H), 1.22 (s, 3H), 1.15 (s, 2H), 0.93-0.81 (m, 4H), 0.54 (d, J = 6.4 Hz, 3H), 0.41 (d, J = 6.4 Hz, 3H) |
| I-174 | IN | IL | 912.7 | 11.09 (s, 1H), 10.56 (s, 1H), 7.92-7.74 (m, 1H), 7.59 (t, J = 7.2 Hz, 1H), 7.42 (d, J = 7.2 Hz, 1H), 7.34 (t, J = 7.2 Hz, 1H), 7.19-7.09 (m, 2H), 7.09-6.97 (m, 2H), 6.93 (d, J = 8.0 Hz, 1H), 6.68 (d, J = 1.6 Hz, 1H), 5.34 (dd, J = 5.2, 12.4 Hz, 1H), 4.57 (d, J = 9.2 Hz, 2H), 4.42 (d, J = 1.6 Hz, 1H), 4.09 (d, J = 12.4 Hz, 1H), 3.53-3.44 (m, 1H), 3.39-3.34 (m, 3H), 3.17-3.04 (m, 1H), 2.97-2.85 (m, 1H), 2.69-2.57 (m, 3H), 2.17-1.97 (m, 2H), 1.96-1.52 (m, 13H), 1.51-1.39 (m, 4H), 1.38-1.06 (m, 4H), 1.03-0.89 (m, 1H), 0.86-0.73 (m, 1H) |
| I-175 | (2S,4R)-1-[(2S)-2-amino-3,3-dimethyl butanoyl]-4-hydroxy-N-[[4-(4-methyl-1,3-thiazol-5-yl)phenyl] methyl] pyrrolidine-2-carboxamide (CAS# 1448189-80-7) | HU | 1134.6 | 9.50-9.30 (m, 1H), 9.01-8.96 (m, 1H), 8.64-8.55 (m, 1H), 7.50-7.42 (m, 1H), 7.41-7.36 (m, 4H), 7.34 (s, 4H), 7.02 (s, 1H), 6.93-6.86 (m, 2H), 6.83 (s, 1H), 6.65-6.50 (m, 2H), 5, 2H), 3.89 (d, J = 19.6 Hz, 1H), 3.76 (s, 2H), 3.72 (s, 3H), 3.65-3.58 (m, 8H), 3.16 (d, J = 4.8 Hz, 3H), 3.11 (d, J = 6.8 Hz, 3H), 2.87 (s, 3H), 2.69 (d, J = 5.2 Hz, 2H), 2.43 (s, 3H), 2.01-1.89 (m, 3H), 1.79-1.71 (m, 2H), 1.66-1.56 (m, 1H), 1.41-1.36 (m, 1H), 1.22 (d, J = 6.0 Hz, 3H), 1.17 (d, J = 6.0 Hz, 3H), 1.08-0.98 (m, 2H), 0.97-0.89 (m, 11H) |
| I-176 | HE | HW | 906.6 | 11.08 (s, 1H), 10.58 (s, 1H), 10.20 (s, 1H), 8.14 (s, 1H), 7.70 (d, J = 8.5 Hz, 2H), 7.64 (t, J = 7.2 Hz, 1H), 7.48-7.40 (m, 3H), 7.36 (t, J = 6.9 Hz, 1H), 7.18-7.12 (m, 2H), 7.08-7.00 (m, 2H), 6.98-6.92 (m, 1H), 6.68 (d, J = 1.8 Hz, 1H), 5.38-5.30 (m, 1H), 4.80-4.72 (m, 1H), 4.70 (d, J = 9.2 Hz, 1H), 3.84-3.64 (m, 1H), 3.34 (s, 3H), 2.98-2.78 (m, 3H), 2.76-2.58 (m, 3H), 2.12-1.98 (m, 2H), 1.94-1.76 (m, 3H), 1.74-1.52 (m, 7H), 1.50 (d, J = 8.0 Hz, 1H), 1.40-1.32 (m, 1H), 1.04-0.92 (m, 1H), 0.90-0.77 (m, 1H) |
| I-177 | HE | IU | 941.4 | 11.08 (s, 2H), 9.28-8.45 (m, 1H), 8.41-8.10 (m, 1H), 7.64 (t, J = 5.2 Hz, 2H), 7.15-7.06 (m, 2H), 7.01 (d, J = 8.0 Hz, 1H), 6.91 (d, J = 8.0 Hz, 1H), 6.69 (s, 1H), 5.34 (dd, J = 5.2, 12.8 Hz, 1H), 4.70-4.50 (m, 2H), 4.25-3.94 (m, 1H), 3.60-3.48 (m, 3H), 3.33 (s, 3H), 3.14-3.03 (m, 1H), 2.95-2.84 (m, 1H), 2.84-2.77 (m, 1H), 2.74 (d, J = 5.2 Hz, 4H), 2.06-1.94 (m, 2H), 1.88-1.61 (m, 9H), 1.54-1.38 (m, 5H), 1.37-1.16 (m, 5H), 0.92 (s, 3H), 0.63 (s, 3H) |
| I-178 | IR | IL | 913.7 | 11.06 (s, 1H), 10.54 (d, J = 5.2 Hz, 1H), 8.13 (s, 1H), 7.80 (dd, J = 3.2, 6.4 Hz, 1H), 7.59 (t, J = 6.8 Hz, 1H), 7.42 (d, J = 6.4 Hz, 1H), 7.34 (d, J = 2.4 Hz, 1H), 7.13 (d, J = 7.2 Hz, 1H), 7.03 (d, J = 7.6 Hz, 1H), 6.97 (d, J = 8.4 Hz, 1H), 6.88 (s, 1H), 6.72-6.61 (m, 2H), 5.30 (dd, J = 5.2, 12.8 Hz, 1H), 4.57 (d, J = 9.2 Hz, 1H), 4.39 (d, J = 11.2 Hz, 1H), 3.63 (d, J = 17.6 Hz, 4H), 3.53-3.41 (m, 2H), 3.31 (s, 3H), 3.12-2.98 (m, 4H), |

TABLE 11-continued

Compounds synthesized via Method 4 using the corresponding amines and acids for the coupling.

| I-#[a] | Amine | Acid | LCMS (ESI, m/z): $[(M+1)]^+$ | $^1H$ NMR (400 MHz, DMSO) δ |
|---|---|---|---|---|
| | | | | 2.92-2.81 (m, 1H), 2.65-2.57 (m, 2H), 2.03-1.89 (m, 2H), 1.88-1.28 (m, 16H), 1.04-0.71 (m, 2H) |
| I-179 | IH | IO | 903.4 | 11.08 (s, 1H), 7.36 (s, 4H), 7.11-6.97 (m, 3H), 6.93-6.81 (m, 4H), 6.59 (d, J = 8.8 Hz, 2H), 5.95 (s, 1H), 5.34 (dd, J = 5.6, 12.8 Hz, 1H), 4.52-4.32 (m, 2H), 3.93-3.81 (m, 2H), 3.78-3.70 (m, 3H), 3.57 (d, J = 20.0 Hz, 1H), 3.32 (s, 3H), 3.16 (d, J = 6.4 Hz, 2H), 2.95-2.86 (m, 5H), 2.77-2.60 (m, 5H), 2.43-2.30 (m, 2H), 2.04-1.96 (m, 1H), 1.95-1.86 (m, 1H), 1.66-1.49 (m, 6H), 1.36-1.29 (m, 2H), 1.21 (dd, J = 6.0, 19.6 Hz, 6H), 1.11-0.93 (m, 2H) |
| I-180 | IM | IL | 941.4 | 11.09 (s, 1H), 10.53 (s, 1H), 7.77 (d, J = 8.4 Hz, 1H), 7.59 (t, J = 6.8 Hz, 1H), 7.41 (dd, J = 2.0, 8.0 Hz, 1H), 7.35-7.30 (m, 1H), 7.14-7.10 (m, 1H), 7.10-7.07 (m, 1H), 7.05-6.99 (m, 2H), 6.91 (d, J = 8.0 Hz, 1H), 6.67 (d, J = 2.0 Hz, 1H), 5.34 (dd, J = 5.2, 12.8 Hz, 1H), 4.56 (d, J = 9.2 Hz, 1H), 4.37 (d, J = 9.2 Hz, 1H), 3.54-3.40 (m, 7H), 3.36-3.35 (m, 3H), 2.97-2.84 (m, 1H), 2.84-2.76 (m, 2H), 2.74-2.55 (m, 5H), 2.44 (s, 2H), 2.06-1.93 (m, 2H), 1.88-1.70 (m, 4H), 1.58 (d, J = 10.4 Hz, 4H), 1.49-1.26 (m, 7H), 1.03-0.90 (m, 1H), 0.80 (dt, J = 3.6, 12.4 Hz, 1H) |
| I-181 | IH | IJ | 847.5 | 11.09 (s, 1H), 7.35 (s, 4H), 7.06-7.01 (m, 3H), 6.89 (d, J = 8.8 Hz, 3H), 6.83 (s, 1H), 6.57 (d, J = 8.8 Hz, 2H), 5.94 (s, 1H), 5.34 (dd, J = 5.6, 12.8 Hz, 1H), 4.49-4.34 (m, 2H), 4.00 (d, J = 12.8 Hz, 1H), 3.89 (d, J = 20.0 Hz, 1H), 3.72 (s, 3H), 3.70-3.64 (m, 1H), 3.60-3.51 (m, 1H), 3.31 (s, 3H), 3.14 (d, J = 6.4 Hz, 2H), 2.96-2.88 (m, 2H), 2.87 (s, 3H), 2.76-2.68 (m, 1H), 2.62 (d, J = 17.6 Hz, 1H), 2.48-2.46 (m, 2H), 2.03-1.94 (m, 1H), 1.94-1.80 (m, 1H), 1.59 (d, J = 11.6 Hz, 2H), 1.23 (d, J = 6.0 Hz, 3H), 1.18 (d, J = 6.0 Hz, 3H), 1.01 (d, J = 11.6 Hz, 2H) |
| I-182 | IH | II | 875.4 | 11.11-11.03 (m, 1H), 7.35 (s, 4H), 7.05-6.98 (m, 3H), 6.92-6.82 (m, 4H), 6.59 (d, J = 9.2 Hz, 2H), 5.94 (s, 1H), 5.36-5.30 (m, 1H), 4.49-4.35 (m, 2H), 3.89 (d, J = 19.6 Hz, 1H), 3.84-3.77 (m, 1H), 3.73 (s, 3H), 3.68-3.48 (m, 2H), 3.32-3.32 (m, 3H), 3.16 (d, J = 6.8 Hz, 2H), 2.93 (s, 1H), 2.88 (s, 3H), 2.85 (s, 1H), 2.76-2.62 (m, 3H), 2.45-2.39 (m, 2H), 2.04-1.96 (m, 1H), 1.93-1.86 (m, 1H), 1.85-1.74 (m, 2H), 1.67-1.54 (m, 2H), 1.25-1.17 (m, 6H), 1.16-0.92 (m, 3H) |
| I-183 | IE | IL | 927.2 | 11.10 (s, 1H), 10.52 (s, 1H), 7.77 (d, J = 8.4 Hz, 1H), 7.58 (t, J = 7.2 Hz, 1H), 7.47-7.28 (m, 2H), 7.16-6.95 (m, 5H), 6.67 (d, J = 1.6 Hz, 1H), 5.37 (dd, J = 5.3, 12.8 Hz, 1H), 4.56 (d, J = 9.2 Hz, 1H), 4.37 (t, J = 8.0 Hz, 1H), 3.51 (s, 3H), 3.45 (d, J = 1.6 Hz, 2H), 3.31-3.21 (m, 3H), 2.96-2.84 (m, 1H), 2.78-2.56 (m, 3H), 2.38 (s, 2H), 2.33-2.29 (m, 2H), 2.07-1.79 (m, 4H), 1.78-1.54 (m, 8H), 1.53-1.29 (m, 7H), 1.02-0.88 (m, 1H), 0.84-0.73 (m, 1H) |
| I-217 | FI | IL | 1027.5 | 11.14 (s, 1H), 10.61-10.16 (m, 1H), 9.37-8.98 (m, 1H), 8.82-8.42 (m, 1H), 7.69-7.05 (m, 7H), 6.87-6.55 (m, 1H), 5.42 (dd, J = 5.0, 12.5 Hz, 1H), 5.14-4.79 (m, 1H), 4.74-4.50 (m, 1H), 4.44-4.28 (m, 2H), 3.78-3.75 (m, 1H), 3.97-3.74 (m, 1H), 3.72-3.59 (m, 2H), 3.54-3.45 (m, 1H), 3.38 ( s, 5H), 3.22 (d, J = 11.2 Hz, 2H), 3.16-3.02 (m, 2H), 3.00-2.87 (m, 2H), 2.82-2.72 (m, 1H), 2.67-2.60 (m, 1H), 2.49-2.40 (m, 4H), 2.16-1.88 (m, 4H), 1.85-1.47 (m, 11H), 1.46-1.19 (m, 6H), 1.17-0.69 (m, 3H) |
| I-218 | FI | HW | 1021.5 | 11.08 (s, 1H), 10.58 (s, 1H), 10.20 (s, 1H), 8.16 (s, 1H), 7.68 (d, J = 8.4 Hz, 3H), 7.44 (dd, J = 1.6, 8.0 Hz, 1H), 7.36 (d, J = 8.4 Hz, 3H), 7.20-7.10 (m, 2H), 7.04 (dt, J = 2.8, 5.2 Hz, 2H), 7.00-6.96 (m, 1H), 6.68 (d, J = 1.6 Hz, 1H), 5.40-5.32 (m, 1H), 4.76-4.72 (m, 1H), 4.72-4.68 (m, 1H), 3.68-3.62 (m, 2H), 3.56-3.44 (m, 6H), 3.00-2.82 (m, 2H), 2.74-2.68 (m, 2H), 2.64 (d, J = 18.4 Hz, 2H), 2.20-2.10 (m, 2H), 2.08-1.98 (m, 3H), 1.92-1.72 (m, 6H), 1.70-1.54 (m, 5H), 1.52-1.36 (m, 6H), 1.08-0.78 (m, 2H) |
| I-219 | IM | JU | 956.5 | 11.13 (s, 1H), 10.58 (s, 1H), 7.95 (d, J = 7.2 Hz, 1H), 7.63 (t, J = 6.8 Hz, 1H), 7.44 (d, J = 7.6 Hz, 1H), 7.37 (t, J = 7.2 Hz, 1H), 7.19-7.11 (m, 2H), 7.10-7.04 (m, 2H), 6.95 (d, J = 8.0 Hz, 1H), 6.72 (d, J = 1.6 Hz, 1H), 5.39 (dd, J = 5.2, 12.8 Hz, 1H), 4.63 (d, J = 9.2 Hz, 1H), 4.44 (d, J = 9.2 Hz, 1H), 3.74-3.60 (m, 3H), 3.54 (s, 5H), 3.01-2.91 (m, 2H), 2.89-2.81 (m, 3H), 2.80-2.61 (m, 10H), 2.11-1.94 (m, 3H), 1.93-1.74 (m, 4H), 1.73-1.54 (m, 6H), 1.51 (dd, J = 6.4, 8.0 Hz, 1H), 1.45-1.36 (m, 1H), 1.08-0.93 (m, 1H), 0.91-0.78 (m, 1H) |

TABLE 11-continued

Compounds synthesized via Method 4 using the corresponding amines and acids for the coupling.

| I-#[a] | Amine | Acid | LCMS (ESI, m/z): $[(M + 1)]^+$ | $^1H$ NMR (400 MHz, DMSO) δ |
|---|---|---|---|---|
| I-225 | IM | JX | 985.4 | 11.08 (s, 1H), 10.62 (s, 1H), 8.18 (d, J = 5.2 Hz, 1H), 7.85 (d, J = 8.4 Hz, 1H), 7.63 (t, J = 5.2 Hz, 1H), 7.49 (d, J = 8.0 Hz, 1H), 7.08-7.04 (m, 2H), 7.00 (d, J = 8.0 Hz, 1H), 6.89 (d, J = 8.0 Hz, 1H), 6.71 (d, J = 2.0 Hz, 1H), 5.33 (dd, J = 5.2, 12.4 Hz, 1H), 4.55 (d, J = 8.8 Hz, 1H), 4.44 (d, J = 8.8 Hz, 1H), 3.54 (d, J = 2.8 Hz, 3H), 3.48-3.42 (m, 2H), 2.99-2.72 (m, 6H), 2.65-2.58 (m, 2H), 2.42 (td, J = 1.6, 3.6 Hz, 4H), 2.28-1.94 (m, 6H), 1.83-1.36 (m, 12H), 1.27-0.95 (m, 4H), 0.87 (s, 3H), 0.60-0.52 (m, 3H) |

[a]The reaction was run anywhere from 3-16 hrs at rt. The final products were isolated under standard purification techniques including reverse HPLC and prep-TLC with appropriate solvent conditions.
[b]4Å molecular sieves was used for the coupling, NMI was obmitted.
[c]This amine was synthesized via Steps 1-2 of Intermediate DO.

Example 10 (Method 5): Synthesis of 3-[4-[6-[4-[[4-[1-(4-Chlorophenyl)-7-isopropoxy-6-methoxy-3-oxo-1,4-dihydroisoquinolin-2-yl]-N-methylanilino]methyl]-1-piperidyl]hexyl]-3-methyl-2-oxo-benzimidazol-1-yl]piperidine-2,6-dione (1-84)

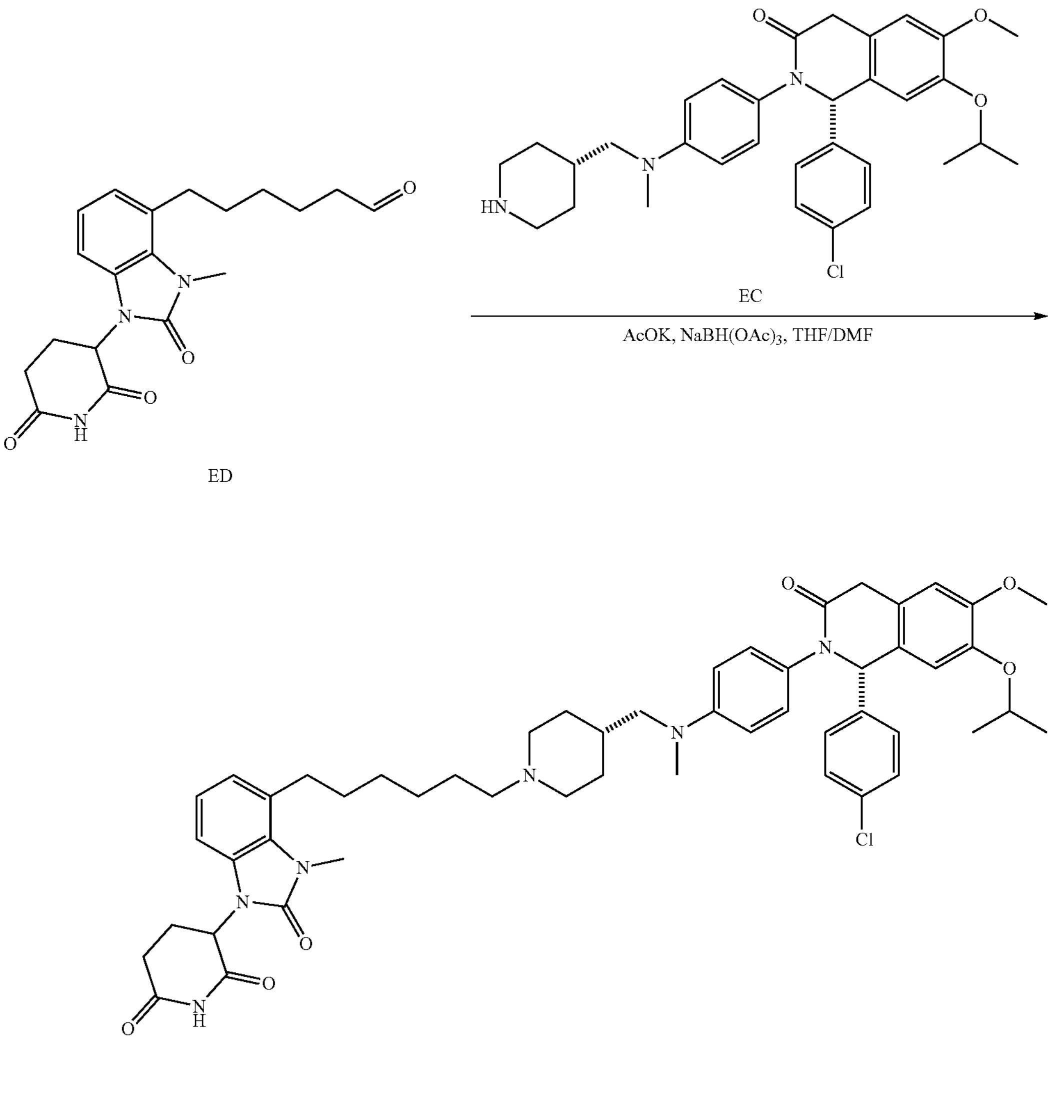

ED

EC

To a solution of 1-(4-chlorophenyl)-7-isopropoxy-6-methoxy-2-[4-[methyl(4-piperidylmethyl)amino] phenyl]-1,4-dihydroisoquinolin-3-one (51.0 mg, 93.0 umol, TFA, Intermediate EC) in THF (1.0 mL) and DMF (0.5 mL) was added AcOK (91.3 mg, 930 umol), then the mixture was stirred at 25° C. for 10 minutes. Next, 6-[1-(2,6-dioxo-3-piperidyl)-3-methyl-2-oxobenzimidazol-4-yl]hexanal (49.9 mg, 139.6 umol, Intermediate ED) was added to the mixture and stirred at 25° C. for 5 minutes, then $NaBH(OAc)_3$ (29.6 mg, 1396 umol) was added to the mixture at 0° C. The reaction mixture was stirred at 25° C. for 0.5 hour. On completion, the mixture was concentrated and purified by prep-HPLC (column: Phenomenex Luna C18 150*25 mm*10 um; mobile phase: [water (0.1% TFA)–ACN]; B %: 33%-63%, 10 min) to give title compound (23.8 mg, 28% yield, TFA) as an off-white solid. LC-MS ($ESI^+$) m/z 889.5 $(M+H)^+$; $^1H$ NMR (400 MHz, DMSO-$d_6$) δ 11.09 (s, 1H), 7.35 (s, 4H), 7.03 (s, 1H), 6.98-6.95 (m, 2H), 6.91 (d, J=8.8 Hz, 2H), 6.87-6.83 (m, 2H), 6.60 (d, J=8.8 Hz, 2H), 5.94 (s, 1H), 5.41-5.31 (m, 1H), 4.48-4.41 (m, 1H), 3.93 (s, 1H), 3.88 (s, 1H), 3.73 (s, 3H), 3.60 (s, 1H), 3.56-3.54 (m, 3H), 3.49-3.41 (m, 2H), 3.20 (d, J=6.5 Hz, 2H), 3.00-2.94 (m, 2H), 2.93-2.87 (m, 6H), 2.73-2.64 (m, 2H), 2.08-1.94 (m, 2H), 1.87-1.76 (m, 3H), 1.68-1.56 (m, 5H), 1.44-1.30 (m, 5H), 1.23 (d, J=6.0 Hz, 3H), 1.18 (d, J=6.0 Hz, 3H).

TABLE 12

Compounds synthesized via Method 5 using the corresponding amines and aldehydes for the coupling.

| I-#[a] | Amine | Aldehyde | LCMS (ESI, m/z): $[(M+1)]^+$ | $^1H$ NMR (400 MHz, DMSO) δ |
|---|---|---|---|---|
| I-85[b] | DZ | DY | 903.3 | 11.07 (s, 1H), 7.35 (s, 4H), 7.05-6.97 (m, 3H), 6.91-6.82 (m, 4H), 6.55 (d, J = 9.2 Hz, 2H), 5.94 (s, 1H), 5.33 (dd, J = 5.2, 12.8 Hz, 1H), 4.45 (td, J= 6.0, 12.0 Hz, 1H), 3.86 (s, 1H), 3.73 (s, 3H), 3.59 (s, 0.5H), 3.54 (s, 0.5H), 3.31 (s, 3H), 3.09 (d, J = 6.4 Hz, 2H), 2.94-2.88 (m, 1H), 2.87 (s, 3H), 2.74-2.58 (m, 4H), 2.45-2.40 (m, 3H), 2.19 (s, 3H), 2.03-1.96 (m, 1H), 1.74-1.66 (m, 4H), 1.62-1.53 (m, 3H), 1.47-1.46 (m, 2H), 1.26 (s, 2H), 1.23 (d, J = 6.0 Hz, 3H), 1.18 (d, J = 6.0 Hz, 5H), 1.01-0.91 (m, 2H) |
| I-86 | JV | EA | 889.5 | 11.07 (s, 1H), 8.19 (s, 1H), 7.35 (s, 4H), 7.05-6.95 (m, 3H), 6.91-6.81 (m, 4H), 6.56 (d, J = 8.8 Hz, 2H), 5.94 (s, 1H), 5.33 (dd, J = 4.4, 13.2 Hz, 1H), 4.45 (quin, J = 6.0 Hz, 1H), 3.89 (d, J = 20.0 Hz, 1H), 3.72 (s, 3H), 3.59 (s, 1H), 3.54 (s, 1H), 3.31 (s, 8H), 2.87 (s, 3H), 2.85 (s, 3H), 2.75-2.61 (m, 2H), 2.25 (d, J = 7.2 Hz, 2H), 2.09-1.93 (m, 2H), 1.90-1.78 (m, 2H), 1.57 (d, J = 9.6 Hz, 4H), 1.41 (d, J = 6.4 Hz, 2H), 1.29 (br d, J = 1.6 Hz, 4H), 1.23 (d, J = 6.0 Hz, 3H), 1.18 (d, J = 6.0 Hz, 3H) |
| I-87[c] | DZ | EE | 903.7 | 11.08 (s, 1H), 7.35 (s, 4H), 7.03 (s, 1H), 6.98-6.91 (m, 2H), 6.86-6.82 (m, 4H), 6.55 (d, J = 9.2 Hz, 2H), 5.94 (s, 1H), 5.36 (dd, J = 5.2, 12.4 Hz, 1H), 4.45 (td, J = 6.0, 12.0 Hz, 1H), 3.89 (d, J = 20.0 Hz, 1H), 3.73 (s, 3H), 3.59 (s, 1H), 3.32-3.31 (m, 3H), 3.09 (d, J = 6.8 Hz, 2H), 2.92-2.81 (m, 6H), 2.76-2.60 (m, 2H), 2.39-2.27 (m, 3H), 2.12 (s, 3H), 2.04-1.94 (m, 1H), 1.69 (d, J = 9.6 Hz, 4H), 1.63-1.52 (m, 3H), 1.38 (t, J = 10.4 Hz, 4H), 1.23 (d, J = 6.0 Hz, 3H), 1.20-1.09 (m, 5H), 1.03-0.87 (m, 2H) |
| I-88[c] | EF | ED | 847.3 | 11.08 (s, 1H), 7.34 (s, 4H), 7.03 (s, 1H), 6.98-6.93 (m, 4H), 6.89-6.81 (m, 4H), 5.98 (s, 1H), 5.36 (dd, J = 5.2, 12.8 Hz, 1H), 4.44 (t, J = 6.0 Hz, 1H), 3.89 (d, J = 20.0 Hz, 1H), 3.73 (s, 3H), 3.62-3.55 (m, 1H), 3.55 (s, 3H), 3.08 (d, J = 4.8 Hz, 4H), 2.94-2.83 (m, 3H), 2.74-2.59 (m, 2H), 2.46 (d, J = 4.4 Hz, 4H), 2.28 (t, J = 7.2 Hz, 2H), 2.04-1.96 (m, 1H), 1.66-1.55 (m, 2H), 1.50-1.33 (m, 6H), 1.23 (d, J = 6.0 Hz, 3H), 1.18 (d, J = 6.0 Hz, 3H) |
| I-125[d] | EK | DY | 900.3 | 11.16-11.02 (m, 1H), 10.94-10.67 (m, 1H), 8.37-8.16 (m, 2H), 7.63-7.52 (m, 1H), 7.51-7.34 (m, 2H), 7.17 (s, 1H), 7.10-6.95 (m, 3H), 6.86 (d, J = 7.2 Hz, 1H), 6.73 (s, 1H), 5.39-5.28 (m, 1H), 4.60 (d, J = 5.6 Hz, 1H), 3.32 (s, 3H), 2.86 (s, 4H), 2.72 (s, 2H), 2.04-1.92 (m, 2H), 1.91-1.72 (m, 5H), 1.67-1.42 (m, 13H), 1.39-1.12 (m, 6H), 1.10-0.83 (m, 6H) |
| I-126 [d] | R | EO | 894.4 | 11.14-10.98 (m, 1H), 10.72-10.48 (m, 1H), 10.00 (s, 1H), 7.68-7.58 (m, 1H), 7.52 (d, J = 8.4 Hz, 2H), 7.44 (dd, J = 2.4, 8.0 Hz, 1H), 7.38-7.32 (m, 1H), 7.26 (d, J = 8.4 Hz, 2H), 7.14 (t, J = 8.0 Hz, 1H), 7.04 (dd, J = 2.0, 8.0 Hz, 1H), 7.00-6.96 (m, 2H), 6.88-6.82 (m, 1H), 6.68 (d, J = 2.0 Hz, 1H), 5.36-5.28 (m, 1H), 4.76-4.68 (m, 1H), 4.68-4.60 (m, 1H), 3.66 (s, 3H), 2.96-2.82 (m, 1H), 2.64-2.56 (m, 2H), 2.35-2.28 (m, 2H), 2.12-1.96 (m, 3H), 1.92-1.76 (m, 2H), 1.72-1.10 (m, 16H), 1.04-0.92 (m, 1H), 0.88-0.76 (m, 1H) |
| I-127[e] | FE | FD | 763.3 | 8.52 (q, J = 4.4 Hz, 1H), 7.78 (t, J = 6.8 Hz, 1H), 7.72 (d, J = 13.6 Hz, 1H), 7.59 (d, J = 1.2 Hz, 1H), 7.55 (t, J = 7.6 Hz, 1H), 7.49 (dd, J = 1.6, 8.0 Hz, 1H), 7.38-7.33 (m, 3H), 7.31 (d, J = 8.0 Hz, 1H), 4.84 (d, J = 7.6 Hz, 1H), 4.72 (d, J = 6.4 Hz, 1H), 4.61 (d, J = 7.2 Hz, 1H), 4.08 (br d, J = 5.2 Hz, 1H), 3.89 (s, 3H), 2.81 (d, J = 4.4 Hz, 3H), 2.70 (t, J = 2.4 Hz, 1H), 2.18-2.09 (m, 3H), 1.87 (dd, J = 5.6, 16.0 Hz, 1H), 1.75-1.66 (m, 2H), 1.50-1.39 (m, 4H), 1.34-1.27 (m, 6H), 0.63 (s, 9H) |

TABLE 12-continued

Compounds synthesized via Method 5 using the corresponding amines and aldehydes for the coupling.

| I-#[a] | Amine | Aldehyde | LCMS (ESI, m/z): $[(M + 1)]^+$ | $^1H$ NMR (400 MHz, DMSO) δ |
|---|---|---|---|---|
| I-184 | GV | GW | 886.2 | 10.58-10.51 (m, 1H), 8.35 (s, 1H), 7.87 (d, J = 7.6 Hz, 1H), 7.76 (d, J = 9.2 Hz, 1H), 7.58 (t, J = 7.6 Hz, 1H), 7.40 (dd, J = 2.0, 8.4 Hz, 1H), 7.35-7.29 (m, 1H), 7.15-7.08 (m, 2H), 7.03 (dd, J = 2.0, 8.0 Hz, 1H), 6.67 (d, J = 2.0 Hz, 1H), 6.47-6.42 (m, 1H), 6.20-6.14 (m, 2H), 4.61-4.51 (m, 1H), 4.42-4.32 (m, 1H), 3.71 (t, J = 6.8 Hz, 2H), 3.07-3.00 (m, 4H), 2.79 (t, J = 6.8 Hz, 2H), 1.98-1.89 (m, 2H), 1.85-1.69 (m, 6H), 1.64-1.54 (m, 6H), 1.53-1.45 (m, 4H), 1.44-1.36 (m, 4H), 1.35 (d, J = 5.2 Hz, 1H), 1.24 (s, 1H), 1.22-1.13 (m, 2H), 1.02-0.90 (m, 3H), 0.83-0.75 (m, 1H) |
| I-185 | HD | GW | 912.3 | 11.08 (s, 1H), 10.52 (s, 1H), 7.78 ( d, J = 8.3 Hz, 1H), 7.58 (t, J = 6.8 Hz, 1H), 7.40 (dd, J = 1.6, 8.1 Hz, 1H), 7.36-7.28 (m, 1H), 7.12 (t, J = 8.1 Hz, 1H), 7.02 (dd, J = 1.6, 8.1 Hz, 1H), 6.92-6.85 (m, 1H), 6.84-6.80 (m, 1H), 6.68 (d, J = 1.9 Hz, 1H), 5.32 (dd, J = 5.6, 12.5 Hz, 1H), 4.56 (d, J = 9.1 Hz, 1H), 4.36 (d, J = 9.3 Hz, 1H), 3.60 (s, 3H), 3.54-3.41 (m, 3H), 3.12-2.99 (m, 2H), 2.93-2.81 (m, 1H), 2.72-2.56 (m, 2H), 2.45 (s, 3H), 2.31-2.14 (m, 5H), 2.00-1.91 (m, 2H), 1.88-1.68 (m, 8H), 1.64-1.52 (m, 5H), 1.47 (d, J = 2.8 Hz, 1H), 1.40-1.30 (m, 1H), 1.29-1.16 (m, 2H), 1.06-0.88 (m, 3H), 0.80 (dt, J = 3.4, 12.2 Hz, 1H) |
| I-186 | HE | GW | 898.2 | 11.09 (s, 1H), 10.53 (s, 1H), 7.79 (d, J = 8.4 Hz, 1H), 7.58 (t, J = 6.8 Hz, 1H), 7.39 (dd, J = 1.6, 8.0 Hz, 1H), 7.35-7.28 (m, 1H), 7.11 (t, J = 8.0 Hz, 1H), 7.08-7.01 (m, 3H), 6.92 (d, J = 8.4 Hz, 1H), 6.67 (d, J = 2.0 Hz, 1H), 5.35 (dd, J = 5.6, 12.8 Hz, 1H), 4.56 (d, J = 9.2 Hz, 1H), 4.37 (d, J = 9.2 Hz, 1H), 3.56-3.38 (m, 2H), 3.34 (s, 3H), 3.27-3.14 (m, 2H), 3.00-2.82 (m, 2H), 2.76-2.67 (m, 2H), 2.65-2.54 (m, 2H), 2.04-1.68 (m, 12H), 1.66-1.41 (m, 6H), 1.40-1.13 (m, 4H), 1.08-0.88 (m, 3H), 0.86-0.74 (m, 1H) |
| I-187 | HG | GW | 928.4 | 11.07 (s, 1H), 10.52 (s, 1H), 7.76 (d, J = 8.4 Hz, 1H), 7.59 (t, J = 6.8 Hz, 1H), 7.41 (d, J = 6.4 Hz, 1H), 7.32 (t, J = 7.2 Hz, 1H), 7.11 (t, J = 8.0 Hz, 1H), 7.03 (dd, J = 1.6, 8.0 Hz, 1H), 6.90 (d, J = 8.4 Hz, 1H), 6.71 (d, J = 8.4 Hz, 1H), 6.66 (d, J = 2.0 Hz, 1H), 5.37-5.26 (m, 1H), 4.56 (d, J = 9.2 Hz, 1H), 4.36 (d, J = 9.2 Hz, 1H), 3.76 (s, 3H), 3.55 (s, 3H), 2.96-2.83 (m, 3H), 2.76-2.67 (m, 1H), 2.65-2.57 (m, 1H), 2.38 (d, J = 12.0 Hz, 2H), 2.13 (d, J = 6.0 Hz, 2H), 2.05-1.88 (m, 5H), 1.88-1.68 (m, 6H), 1.66-1.40 (m, 9H), 1.40-1.30 (m, 1H), 1.28-1.17 (m, 2H), 1.01-0.88 (m, 3H), 0.84-0.71 (m, 1H) |
| I-188 | HI | GW | 1187.8 | 10.52 (s, 1H), 8.99 (s, 1H), 8.63-8.57 (m, 1H), 7.74 (d, J = 8.4 Hz, 1H), 7.58 (d, J = 7.2 Hz, 1H), 7.45-7.38 (m, 5H), 7.37-7.26 (m, 3H), 7.11 (t, J = 8.0 Hz, 1H), 7.05-7.00 (m, 1H), 6.67 (d, J = 1.6 Hz, 1H), 5.22-5.10 (m, 1H), 4.56 (t, J = 9.6 Hz, 2H), 4.47-4.42 (m, 1H), 4.40 (d, J = 7.2 Hz, 1H), 4.36 (d, J = 8.4 Hz, 2H), 4.30-4.21 (m, 2H), 3.97 (s, 2H), 3.71-3.65 (m, 1H), 3.61 (d, J = 6.8 Hz, 3H), 3.54 (d, J = 4.4 Hz, 3H), 2.78-2.71 (m, 2H), 2.11-2.02 (m, 2H), 2.00 (d, J = 6.6 Hz, 2H), 1.95-1.90 (m, 2H), 1.75 (d, J = 16.8 Hz, 8H), 1.64-1.54 (m, 6H), 1.53-1.43 (m, 4H), 1.22-1.05 (m, 6H), 0.95 (s, 9H), 0.86-0.76 (m, 4H) |
| I-189 | JE | DY | 920.1 | 11.08 (s, 1H), 10.57 (s, 1H), 9.91 (s, 1H), 7.63 (t, J = 6.8 Hz, 1H), 7.47-7.41 (m, 2H), 7.35 (t, J = 7.2 Hz, 1H), 7.29-7.24 (m, 1H), 7.17-7.11 (m, 1H), 7.05-7.02 (m, 2H), 6.99 (dd, J = 4.8, 8.4 Hz, 2H), 6.87 (d, J = 8.4 Hz, 1H), 6.68 (d, J = 2.0 Hz, 1H), 5.33 (dd, J = 5.2, 12.4 Hz, 1H), 4.75-4.69 (m, 1H), 4.63 (t, J = 9.2 Hz, 1H), 3.73-3.65 (m, 1H), 3.46 (s, 2H), 3.30 (s, 3H), 2.73 (d, J = 6.0 Hz, 2H), 2.64-2.57 (m, 4H), 2.11-1.91 (m, 4H), 1.88-1.74 (m, 2H), 1.68-1.49 (m, 10H), 1.43-1.28 (m, 4H), 1.15 (s, 1H) |
| I-190 | IY | JC | 882.8 | 10.62-10.47 (m, 1H), 9.55 (s, 1H), 8.62 (s, 1H), 8.01-7.97 (m, 1H), 8.00-7.96 (m, 1H), 7.82-7.74 (m, 2H), 7.70-7.61 (m, 3H), 7.51-7.47 (m, 1H), 7.37-7.27 (m, 3H), 4.63-4.56 (m, 1H), 4.28-4.23 (m, 1H), 4.00-3.88 (m, 2H), 3.84-3.77 (m, 1H), 3.71 (td, J = 6.0, 12.0 Hz, 1H), 3.04-2.92 (m, 2H), 2.80-2.68 (m, 6H), 1.86-1.73 (m, 6H), 1.59-1.52 (m, 1H), 1.47-1.37 (m, 1H), 1.11 (s, 4H), 1.02-0.92 (m, 2H), 0.85 (s, 9H). |
| I-191 | IY | IZ | 873.3 | 10.28 (s, 1H), 8.36-8.23 (m, 2H), 7.69-7.60 (m, 4H), 7.54-7.46 (m, 1H), 7.39-7.25 (m, 3H), 6.91 (dd, J = 1.2, 7.2 Hz, 1H), 4.61 (s, 1H), 4.26 (d, J = 6.0 Hz, 1H), 4.01-3.85 (m, 2H), 3.80 (t, J = 6.8 Hz, 4H), 3.69-3.40 (m, 4H), 2.83 (t, J = 6.4 Hz, 2H), 2.76-2.72 (m, 1H), 1.92-1.66 (m, 6H), 1.55 (dd, J = |

TABLE 12-continued

Compounds synthesized via Method 5 using the corresponding amines and aldehydes for the coupling.

| I-#[a] | Amine | Aldehyde | LCMS (ESI, m/z): $[(M + 1)]^+$ | $^1H$ NMR (400 MHz, DMSO) δ |
|---|---|---|---|---|
| | | | | 9.2, 14.4 Hz, 1H), 1.43 (d, J = 5.6 Hz, 1H), 1.25-1.09 (m, 3H), 1.06-0.92 (m, 2H), 0.89-0.74 (m, 9H) |
| I-192[f] | HM | HP | 972.9 | 11.22-10.92 (m, 1H), 7.42-7.29 (m, 4H), 7.08-6.81 (m, 7H), 6.61-6.49 (m, 2H), 5.98-5.91 (m, 1H), 5.47-5.25 (m, 1H), 4.50-4.39 (m, 1H), 3.94-3.82 (m, 1H), 3.77-3.69 (m, 3H), 3.60 (s, 1H), 3.31-3.23 (m, 4H), 3.21-3.16 (m, 2H), 3.13-3.09 (m, 1H), 3.07-3.01 (m, 2H), 2.93-2.83 (m, 6H), 2.75-2.59 (m, 4H), 2.28-2.17 (m, 1H), 2.26-2.16 (m, 1H), 2.03-1.96 (m, 1H), 1.81-1.69 (m, 3H), 1.68-1.47 (m, 5H), 1.40-1.29 (m, 4H), 1.25-1.23 (m, 1H), 1.27-1.22 (m, 1H), 1.19 (d, J = 6.0 Hz, 3H), 1.16-1.09 (m, 1H), 1.02-0.93 (m, 1H) |
| I-193[f] | HM | HR | 972.8 | 11.07 (s, 1H), 8.24 (s, 1H), 7.35 (d, J = 1.2 Hz, 4H), 7.05-6.96 (m, 3H), 6.89 (d, J = 8.8 Hz, 2H), 6.87-6.82 (m, 2H), 6.55 (d, J = 8.8 Hz, 2H), 5.94 (s, 1H), 5.33 (dd, J = 5.4, 12.8 Hz, 1H), 4.45 (td, J = 6.0, 12.0 Hz, 1H), 3.88 (d, J = 19.6 Hz, 1H), 3.72 (s, 3H), 3.56 (d, J = 20.0 Hz, 1H), 3.28-3.06 (m, 8H), 3.02 (d, J = 11.2 Hz, 2H), 2.88 (d, J = 5.6 Hz, 4H), 2.71 (d, J = 4.4 Hz, 1H), 2.65-2.56 (m, 5H), 2.27-2.14 (m, 1H), 2.00 (dd, J = 5.2, 10.8 Hz, 1H), 1.77 (d, J = 10.4 Hz, 2H), 1.71 (d, J = 9.6 Hz, 2H), 1.65-1.53 (m, 3H), 1.52-1.26 (m, 6H), 1.23 (d, J = 6.0 Hz, 3H), 1.18 (d, J = 6.0 Hz, 3H), 1.15-1.07 (m, 1H), 1.02-0.88 (m, 1H) |
| I-194[g] | HM | HS | 915.8 | 11.08 (s, 1H), 8.20 (s, 1H), 7.36 (s, 4H), 7.06-6.96 (m, 3H), 6.92-6.82 (m, 4H), 6.56 (d, J = 9.0 Hz, 2H), 5.94 (s, 1H), 5.36-5.28 (m, 1H), 4.48 (quin, J = 6.1 Hz, 1H), 3.88 (d, J = 19.8 Hz, 1H), 3.72 (s, 3H), 3.62-3.52 (m, 1H), 3.10 (d, J = 6.9 Hz, 2H), 2.88 (s, 3H), 2.86-2.78 (m, 2H), 2.76-2.68 (m, 1H), 2.66-2.58 (m, 2H), 2.28-2.12 (m, 4H), 2.06-1.92 (m, 2H), 1.82-1.64 (m, 7H), 1.60-1.44 (m, 4H), 1.28-1.12 (m, 12H), 1.02-0.80 (m, 2H) |
| I-195 | DZ | GR | 861.5 | 11.15 (s, 1H), 7.42 (s, 4H), 7.11 (d, J = 6.8 Hz, 2H), 7.05 (d, J = 8.0 Hz, 1H), 6.98-6.91 (m, 3H), 6.90 (s, 1H), 6.62 (d, J = 9.2 Hz, 2H), 6.00 (s, 1H), 5.40 (dd, J = 5.6, 12.8 Hz, 1H), 4.52 (td, J = 6.0, 12.0 Hz, 1H), 3.95 (d, J = 19.6 Hz, 1H), 3.79 (s, 3H), 3.66-3.61 (m, 1H), 3.38 (s, 3H), 3.16 (d, J = 6.4 Hz, 2H), 3.01-2.88 (m, 4H), 2.80-2.68 (m, 5H), 2.40 (d, J = 2.0 Hz, 2H), 2.31 (s, 3H), 2.09-2.04 (m, 1H), 1.78 (t, J = 9.6 Hz, 4H), 1.70-1.61 (m, 1H), 1.52-1.40 (m, 1H), 1.30 (d, J = 6.0 Hz, 3H), 1.25 (d, J = 6.0 Hz, 3H), 1.24-1.18 (m, 1H), 1.11-0.98 (m, 2H) |
| I-196 | IM | IV | 956.4 | 11.08 (s, 1H), 10.62 (s, 1H), 8.19 (s, 1H), 7.76-7.69 (m, 1H), 7.64 (t, J = 4.8 Hz, 1H), 7.50 (d, J = 7.6 Hz, 1H), 7.09-7.04 (m, 2H), 7.00 (d, J = 8.0 Hz, 1H), 6.89 (d, J = 7.2 Hz, 1H), 6.71 (d, J = 2.0 Hz, 1H), 5.34 (dd, J = 5.2, 12.8 Hz, 1H), 4.55 (d, J = 8.8 Hz, 1H), 4.44 (d, J = 9.2 Hz, 1H), 3.51-3.42 (m, 3H), 3.32 (s, 3H), 2.95-2.85 (m, 1H), 2.80-2.62 (m, 4H), 2.51 (s, 2H), 2.45 (d, J = 7.6 Hz, 2H), 2.38-2.29 (m, 4H), 2.11-2.05 (m, 2H), 2.00 (dd, J = 5.2, 10.4 Hz, 1H), 1.85-1.68 (m, 6H), 1.57 (s, 1H), 1.48-1.41 (m, 2H), 1.27-1.18 (m, 3H), 1.17-1.10 (m, 2H), 1.00-0.94 (m, 1H), 0.94-0.91 (m, 1H), 0.90 (s, 3H), 0.87 (s, 1H), 0.60 (s, 3H) |
| I-197 | JA | EA | 889.8 | 11.09 (s, 1H), 7.35 (s, 4H), 7.06-6.96 (m, 3H), 6.93-6.82 (m, 4H), 6.57 (d, J = 9.2 Hz, 2H), 5.95 (s, 1H), 5.34 (dd, J = 5.2, 12.8 Hz, 1H), 4.45 (td, J = 6.0, 12.0 Hz, 1H), 3.89 (d, J = 19.6 Hz, 1H), 3.73 (s, 3H), 3.57 (d, J = 20.0 Hz, 1H), 3.32 (s, 3H), 3.32-3.27 (m, 2H), 3.15 (d, J = 6.4 Hz, 2H), 2.93-2.82 (m, 6H), 2.76-2.60 (m, 4H), 2.26 (t, J = 7.2 Hz, 2H), 2.04-1.96 (m, 1H), 1.84 (t, J = 11.2 Hz, 2H), 1.57 (d, J = 9.2 Hz, 4H), 1.41 (s, 2H), 1.29 (d, J = 3.2 Hz, 3H), 1.24 (d, J = 6.0 Hz, 3H), 1.19 (d, J = 6.0 Hz, 5H). |
| I-198 | IQ | IV | 980.7 | 11.12 (s, 1H), 10.62 (s, 1H), 8.18 (d, J = 5.1 Hz, 1H), 8.14 (s, 1H), 7.74 (d, J = 8.9 Hz, 1H), 7.64 (t, J = 5.1 Hz, 1H), 7.50 (d, J = 8.1 Hz, 1H), 7.24 (s, 1H), 7.08 (s, 2H), 7.06 (d, J = 1.8 Hz, 1H), 7.04 (d, J = 2.0 Hz, 1H), 6.72 (d, J = 1.8 Hz, 1H), 5.38 (dd, J = 5.0, 12.6 Hz, 1H), 4.56-4.52 (m, 1H), 4.48-4.40 (m, 1H), 3.32 (s, 3H), 2.96-2.84 (m, 1H), 2.76-2.68 (m, 2H), 2.56 (s, 4H), 2.12 (s, 5H), 1.86-1.68 (m, 7H), 1.66-1.55 (m, 2H), 1.54-1.39 (m, 4H), 1.30-1.18 (m, 4H), 1.18-1.06 (m, 3H), 1.04-0.84 (m, 7H), 0.60 (s, 3H) |
| I-199 | IY | JC | 882.3 | 10.87-10.31 (m, 1H), 9.28 (s, 1H), 8.55 (s, 1H), 8.28 (s, 1H), 7.96 (d, J = 8.8 Hz, 1H), 7.70-7.68 (m, 1H), 7.78-7.62 (m, 2H), 7.53-7.47 (m, 1H), 7.36-7.28 (m, 3H), 4.61 (d, J = 7.6 Hz, 1H), 4.28-4.20 (m, 1H), 4.01-3.90 (m, 2H), 3.85-3.66 |

TABLE 12-continued

Compounds synthesized via Method 5 using the corresponding amines and aldehydes for the coupling.

| I-#[a] | Amine | Aldehyde | LCMS (ESI, m/z): $[(M + 1)]^+$ | $^1H$ NMR (400 MHz, DMSO) δ |
|---|---|---|---|---|
| | | | | (m, 2H), 3.56-3.43 (m, 1H), 3.04-2.95 (m, 1H), 2.84-2.68 (m, 2H), 2.68 (d, J = 1.6 Hz, 2H), 2.59-2.54 (m, 2H), 2.06-1.93 (m, 2H), 1.91-1.69 (m, 7H), 1.60-1.54 (m, 1H), 1.24 (s, 1H), 1.24-1.22 (m, 1H), 1.17 (d, J = 14.0 Hz, 2H), 1.04-0.95 (m, 2H), 0.86 (s, 9H) |
| I-200 | IY | JC | 1188.6 | 10.55 (s, 2H), 9.25-9.16 (m, 2H), 8.55-8.48 (m, 2H), 8.21 (d, J = 9.6 Hz, 2H), 7.90 (t, J = 8.4 Hz, 2H), 7.71-7.57 (m, 5H), 7.50 (t, J = 7.6 Hz, 1H), 7.38-7.23 (m, 3H), 4.60 (d, J = 7.2 Hz, 1H), 4.24 (t, J = 7.6 Hz, 1H), 3.97-3.83 (m, 3H), 3.81-3.72 (m, 1H), 3.70-3.60 (m, 2H), 3.55-3.43 (m, 1H), 3.30 (s, 3H), 2.99-2.90 (m, 2H), 2.77-2.69 (m, 2H), 2.60-2.56 (m, 5H), 2.21 (d, J = 6.4 Hz, 2H), 1.90-1.83 (m, 3H), 1.76 (d, J = 6.4 Hz, 3H), 1.53-1.45 (m, 2H), 1.24 (s, 1H), 1.18-1.07 (m, 3H), 1.01-0.91 (m, 2H), 0.86-0.81 (m, 1H), 0.77 (s, 9H) |
| I-201 | IH | EA | 889.8 | 11.08 (s, 1H), 7.35 (s, 4H), 7.09-6.96 (m, 3H), 6.92-6.78 (m, 4H), 6.57 (d, J = 9.2 Hz, 2H), 5.95 (s, 1H), 5.34 (dd, J = 5.6, 12.8 Hz, 1H), 4.53-4.36 (m, 1H), 3.89 (d, J = 19.6 Hz, 1H), 3.73 (s, 3H), 3.57 (d, J = 19.6 Hz, 1H), 3.32 (s, 3H), 3.31-3.25 (m, 2H), 3.15 (d, J = 6.4 Hz, 2H), 2.94-2.78 (m, 6H), 2.77-2.58 (m, 4H), 2.26-2.21 (m, 2H), 1.99 (dd, J = 6.4, 13.6 Hz, 2H), 1.81 (t, J = 10.8 Hz, 2H), 1.68-1.52 (m, 5H), 1.45-1.36 (m, 2H), 1.29 (s, 3H), 1.24 (d, J = 5.9 Hz, 3H), 1.19 (d, J = 6.0 Hz, 3H) |
| I-202 | IY | IX | 871.3 | 10.72 (s, 1H), 8.42 (d, J = 7.2 Hz, 1H), 8.38-8.33 (m, 1H), 7.74-7.68 (m, 2H), 7.67-7.62 (m, 1H), 7.56-7.47 (m, 2H), 7.39-7.28 (m, 3H), 7.08-7.02 (m, 1H), 4.63 (d, J = 6.4 Hz, 1H), 4.29 (s, 1H), 3.88 (s, 1H), 3.52-3.44 (m, 3H), 3.21-3.10 (m, 3H), 2.92-2.82 (m, 4H), 2.68 (d, J = 4.8 Hz, 2H), 1.97-1.91 (m, 2H), 1.87-1.75 (m, 4H), 1.64-1.52 (m, 2H), 1.25-1.15 (m, 3H), 1.13-1.05 (m, 2H), 0.87 (s, 9H) |
| I-203 | IW | IV | 951.8 | 10.66 (s, 1H), 10.61 (s, 1H), 8.30 (d, J = 7.2 Hz, 1H), 8.17 (d, J = 5.6 Hz, 1H), 7.72 (d, J = 8.0 Hz, 1H), 7.66-7.60 (m, 1H), 7.57 (s, 1H), 7.52-7.47 (m, 1H), 7.38 (d, J = 7.2 Hz, 1H), 7.05 (d, J = 8.0 Hz, 1H), 6.97-6.89 (m, 1H), 6.70 (d, J = 1.6 Hz, 1H), 4.54 (d, J = 9.2 Hz, 1H), 4.48-4.39 (m, 1H), 3.83-3.74 (m, 2H), 2.67 (d, J = 1.2 Hz, 4H), 1.87-1.62 (m, 19H), 1.51-1.43 (m, 4H), 1.28-1.10 (m, 8H), 0.89 (s, 3H), 0.59 (s, 3H) |
| I-204 | IR | IV | 930.6 | 11.05 (s, 1H), 10.62 (s, 1H), 8.23 (s, 1H), 8.17 (d, J = 5.2 Hz, 1H), 7.74 (d, J = 8.0 Hz, 1H), 7.63 (t, J = 5.2 Hz, 1H), 7.52-7.47 (m, 1H), 7.05 (dd, J = 1.6, 8.0 Hz, 1H), 6.93 (d, J = 8.4 Hz, 1H), 6.83 (d, J = 2.0 Hz, 1H), 6.70 (d, J = 2.0 Hz, 1H), 6.64-6.59 (m, 1H), 5.28 (dd, J = 4.8, 12.8 Hz, 1H), 4.54 (d, J = 8.8 Hz, 1H), 4.43 (d, J = 8.8 Hz, 1H), 3.30 (s, 3H), 3.07 (s, 4H), 2.93-2.83 (m, 1H), 2.14 (d, J = 7.6 Hz, 2H), 2.01-1.92 (m, 2H), 1.88-1.64 (m, 8H), 1.63-1.38 (m, 6H), 1.29-1.05 (m, 8H), 0.95 (s, 2H), 0.89 (s, 3H), 0.59 (s, 3H) |
| I-205 | IE | IV | 942.8 | 11.09 (s, 1H), 10.61 (s, 1H), 8.17 (d, J = 5.2 Hz, 1H), 8.13 (s, 1H), 7.76-7.69 (m, 1H), 7.63 (t, J = 4.8 Hz, 1H), 7.48 (d, J = 8.0 Hz, 1H), 7.13-6.93 (m, 4H), 6.71 (d, J = 1.6 Hz, 1H), 5.40-5.32 (m, 1H), 4.58-4.50 (m, 1H), 4.41 (d, J = 2.0 Hz, 1H), 3.58-3.45 (m, 2H), 3.33 (s, 4H), 3.30 (s, 3H), 2.98-2.83 (m, 1H), 2.52 (s, 2H), 2.12-1.96 (m, 4H), 1.84-1.39 (m, 14H), 1.26-1.06 (m, 6H), 1.01-0.92 (m, 2H), 0.88 (s, 3H), 0.59 (s, 3H) |
| I-206 | DZ | IT | 929.5 | 11.09 (s, 1H), 7.35 (s, 4H), 7.05-6.98 (m, 2H), 6.88 (d, J = 8.9 Hz, 2H), 6.83 (s, 1H), 6.67 (d, J = 8.6 Hz, 1H), 6.55 (d, J = 9.0 Hz, 2H), 5.94 (s, 1H), 5.35-5.29 (m, 1H), 4.45 (td, J = 6.1, 12.3 Hz, 1H), 3.88 (d, J = 19.4 Hz, 1H), 3.73 (d, J = 4.9 Hz, 6H), 3.63-3.59 (m, 3H), 3.54 (s, 1H), 3.09 ( d, J = 7.0 Hz, 2H), 2.86 (s, 3H), 2.15 (s, 3H), 2.02-1.97 (m, 2H), 1.72-1.68 (m, 3H), 1.66-1.61 (m, 2H), 1.58-1.51 (m, 2H), 1.23 (d, J = 5.9 Hz, 6H), 1.18 (d, J = 6.1 Hz, 4H), 1.01-0.93 (m, 3H), 0.86 (t, J = 7.3 Hz, 4H) |
| I-207[f] | IR | GW | 899.4 | 11.05 (s, 1H), 10.51 (s, 1H), 8.14 (s, 1H), 7.76 (d, J = 8.4 Hz, 1H), 7.58 (t, J = 6.8 Hz, 1H), 7.40 (d, J = 8.8 Hz, 1H), 7.35-7.28 (m, 1H), 7.11 (t, J = 8.0 Hz, 1H), 7.04-6.99 (m, 1H), 6.93 (d, J = 8.4 Hz, 1H), 6.83 (s, 1H), 6.66 (d, J = 1.8 Hz, 1H), 6.64-6.59 (m, 1H), 5.34-5.23 (m, 1H), 4.55 (d, J = 9.2 Hz, 1H), 4.36 (d, J = 9.2 Hz, 1H), 3.51-3.39 (m, 1H), 3.30 (s, 3H), 3.08 (s, 4H), 2.95-2.83 (m, 1H), 2.64-2.57 (m, 1H), 2.64-2.57 (m, 1H), 2.14 (d, J = 7.2 Hz, 2H), 2.02-1.88 (m, 2H), 1.87-1.71 (m, 5H), 1.64-1.41 (m, 7H), 1.40-1.10 (m, 4H), 1.04-0.86 (m, 3H), 0.85-0.74 (m, 1H) |

TABLE 12-continued

Compounds synthesized via Method 5 using the corresponding amines and aldehydes for the coupling.

| I-#[a] | Amine | Aldehyde | LCMS (ESI, m/z): $[(M + 1)]^+$ | $^1H$ NMR (400 MHz, DMSO) δ |
|---|---|---|---|---|
| I-208 | IB | IK | 806.4 | 11.07 (s, 1H), 7.34 (s, 4H), 7.05-6.96 (m, 3H), 6.90 (d, J = 8.4 Hz, 2H), 6.87-6.80 (m, 2H), 6.66-6.56 (m, 2H), 5.94 (s, 1H), 5.32 (dd, J = 5.2, 12.0 Hz, 1H), 4.50-4.39 (m, 1H), 3.89 (d, J = 19.6 Hz, 1H), 3.73 (s, 3H), 3.57 (d, J = 19.6 Hz, 1H), 3.31 (s, 3H), 3.28-3.22 (m, 3H), 2.97-2.87 (m, 1H), 2.83 (s, 3H), 2.70 (s, 1H), 2.65-2.55 (m, 3H), 2.04-1.93 (m, 1H), 1.64-1.51 (m, 2H), 1.50-1.38 (m, 2H), 1.29 (s, 5H), 1.23 (d, J = 6.0 Hz, 3H), 1.18 (d, J = 6.0 Hz, 3H) |
| I-209 | ID | EA | 903.3 | 11.08 (s, 1H), 7.37-7.21 (m, 8H), 7.09-6.95 (m, 3H), 6.89-6.80 (m, 2H), 6.17 (s, 1H), 5.33 (dd, J = 5.2, 12.4 Hz, 1H), 4.50-4.37 (m, 1H), 3.96 (d, J = 20.0 Hz, 1H), 3.75 (s, 3H), 3.70-3.62 (m, 1H), 3.44-3.37 (m, 2H), 3.32 (s, 3H), 3.17-3.05 (m, 3H), 2.94-2.85 (m, 1H), 2.75 (s, 2H), 2.67-2.54 (m, 4H), 2.17 (d, J = 6.4 Hz, 2H), 2.04-1.91 (m, 2H), 1.67-1.52 (m, 4H), 1.46 (d, J = 1.4 Hz, 3H), 1.39 (s, 2H), 1.28 (d, J = 3.2 Hz, 3H), 1.23 (d, J = 6.0 Hz, 3H), 1.19 (d, J = 6.0 Hz, 3H) |
| I-210 | DI | HZ | 966.3 | 11.13-11.00 (m, 1H), 10.57 (s, 1H), 10.15 (s, 1H), 7.74-7.68 (m, 1H), 7.62 (s, 1H), 7.47-7.40 (m, 1H), 7.39-7.31 (m, 1H), 7.18-7.12 (m, 1H), 7.04-6.95 (m, 3H), 6.85 (d, J = 7.2 Hz, 1H), 6.78-6.73 (m, 1H), 6.66 (d, J = 2.0 Hz, 1H), 5.36-5.29 (m, 1H), 4.75-4.65 (m, 1H), 4.54 (d, J = 10.0 Hz, 1H), 4.41-4.32 (m, 1H), 4.31-4.20 (m, 3H), 3.98-3.87 (m, 1H), 3.42-3.35 (m, 3H), 2.94-2.82 (m, 1H), 2.75-2.67 (m, 1H), 2.64-2.56 (m, 2H), 2.30 (d, J = 8.0 Hz, 2H), 2.15-2.06 (m, 4H), 2.04-1.96 (m, 3H), 1.76-1.67 (m, 1H), 1.66-1.42 (m, 9H), 1.41-1.35 (m, 1H), 1.34-1.19 (m, 3H), 1.06-0.92 (m, 1H), 0.89-0.75 (m, 1H) |
| I-211 | IC | GR | 916.8 | 11.08 (s, 1H), 8.41 (s, 1H), 7.36 (s, 4H), 7.09-7.03 (m, 2H), 7.02-6.98 (m, 1H), 6.93-6.86 (m, 3H), 6.84 (s, 1H), 6.56 (d, J = 9.0 Hz, 2H), 5.95 (s, 1H), 5.37-5.30 (m, 1H), 4.46 (quin, J = 6.0 Hz, 1H), 3.89 (d, J = 19.5 Hz, 1H), 3.73 (s, 3H), 3.63-3.52 (m, 1H), 3.30 (s, 3H), 3.22-3.16 (m, 2H), 3.11 (d, J = 6.4 Hz, 1H), 2.89 (d, J = 8.4 Hz, 3H), 2.74 (t, J = 7.8 Hz, 1H), 2.24-2.07 (m, 5H), 2.06-1.96 (m, 3H), 1.86-1.65 (m, 6H), 1.63-1.50 (m, 2H), 1.49-1.30 (m, 4H), 1.24 (d, J = 6.0 Hz, 3H), 1.19 (d, J = 6.0 Hz, 3H), 1.15 (s, 2H), 1.06-0.91 (m, 2H) |
| I-212 | DZ | JK | 860.5 | 10.63 (s, 1H), 8.18 (s, 1H), 7.46 (s, 1H), 7.35 (s, 5H), 7.03 (s, 1H), 6.91-6.82 (m, 4H), 6.55 (br d, J = 8.8 Hz, 2H), 5.93 (s, 1H), 4.44 (td, J = 6.0, 12.2 Hz, 1H), 3.92-3.86 (m, 1H), 3.77 (br t, J = 6.9 Hz, 2H), 3.72 (s, 3H), 3.59-3.55 (m, 1H), 3.09 (br d, J = 6.6 Hz, 2H), 2.87 (s, 3H), 2.81 (br t, J = 6.6 Hz, 2H), 2.67 (br s, 4H), 2.33 (br s, 2H), 2.20 (br s, 2H), 1.72 (br s, 5H), 1.64-1.54 (m, 3H), 1.48-1.39 (m, 2H), 1.23 (d, J = 5.9 Hz, 3H), 1.18 (d, J = 5.9 Hz, 3H), 1.06-0.87 (m, 3H) |
| I-220 | JR | GW | 955.4 | 11.07 (d, J = 1.2 Hz, 1H), 10.52 (s, 1H), 7.75 (d, J = 8.4 Hz, 1H), 7.61-7.52 (m, 1H), 7.42-7.37 (m, 1H), 7.34-7.28 (m, 1H), 7.14-7.05 (m, 2H), 7.04-6.97 (m, 2H), 6.88 (d, J = 8.0 Hz, 1H), 6.66 (d, J = 2.0 Hz, 1H), 5.41-5.22 (m, 1H), 4.54 (d, J = 9.6 Hz, 1H), 4.40-4.28 (m, 1H), 3.38 (s, 3H), 2.95-2.87 (m, 3H), 2.87-2.84 (m, 1H), 2.77-2.69 (m, 1H), 2.65-2.54 (m, 6H), 2.12 (d, J = 7.2 Hz, 2H), 2.05-1.87 (m, 3H), 1.85-1.69 (m, 7H), 1.63-1.54 (m, 3H), 1.53-1.39 (m, 3H), 1.39-1.26 (m, 2H), 1.25-1.13 (m, 3H), 1.08-0.70 (m, 5H) |
| I-221 | JS | IV | 937.3 | 10.72-10.49 (m, 2H), 8.34 (d, J = 7.2 Hz, 1H), 8.17 (d, J = 5.2 Hz, 1H), 7.76-7.68 (m, 1H), 7.65-7.61 (m, 1H), 7.60-7.58 (m, 1H), 7.52-7.43 (m, 2H), 7.07-7.01 (m, 1H), 6.98-6.92 (m, 1H), 6.70 (d, J = 2.0 Hz, 1H), 4.57-4.51 (m, 1H), 4.46-4.38 (m, 1H), 3.85-3.75 (m, 2H), 3.60 (s, 2H), 3.57-3.49 (m, 1H), 2.87-2.79 (m, 2H), 2.63-2.54 (m, 4H), 2.07 (d, J = 7.2 Hz, 2H), 1.84-1.70 (m, 6H), 1.70-1.64 (m, 1H), 1.61-1.50 (m, 2H), 1.50-1.38 (m, 4H), 1.28-1.16 (m, 4H), 1.16-1.08 (m, 2H), 1.00-0.90 (m, 2H), 0.88 (s, 3H), 0.88-0.83 (m, 1H), 0.59 (s, 3H) |
| I-222 | FI | IV | 1042.3 | 11.09 (s, 1H), 10.63 (s, 1H), 8.18 (d, J = 2.0 Hz, 1H), 7.73 (d, J = 8.4 Hz, 1H), 7.64 (t, J = 5.2 Hz, 1H), 7.50 (dd, J = 1.6, 8.0 Hz, 1H), 7.12-7.03 (m, 3H), 6.96 (d, J = 8.0 Hz, 1H), 6.71 (d, J = 2.0 Hz, 1H), 5.36 (dd, J = 5.5, 12.4 Hz, 1H), 4.54 (d, J = 8.8 Hz, 1H), 4.43 (d, J = 9.2 Hz, 1H), 3.47 (s, 3H), 3.44-3.43 (m, 2H), 3.39-3.38 (m, 2H), 2.96-2.89 (m, 1H), 2.75-2.60 (m, 7H), 2.13-1.97 (m, 8H), 1.82-1.69 (m, 11H), 1.48-1.41 (m, 4H), 1.40-1.34 (m, 3H), 1.23 ( d, J = 11.2 Hz, 2H), 1.18-1.08 (m, 2H), 0.89 (s, 5H), 0.60 (s, 3H) |

TABLE 12-continued

Compounds synthesized via Method 5 using the corresponding amines and aldehydes for the coupling.

| I-#[a] | Amine | Aldehyde | LCMS (ESI, m/z): $[(M + 1)]^+$ | $^1$H NMR (400 MHz, DMSO) δ |
|---|---|---|---|---|
| I-223 | IC | JK | 915.5 | 10.66-10.58 (m, 1H), 8.26-8.14 (m, 1H), 7.46 (d, J = 1.2 Hz, 1H), 7.34 (s, 4H), 7.03 (s, 1H), 6.91-6.86 (m, 2H), 6.86-6.82 (m, 2H), 6.55 (d, J = 9.2 Hz, 2H), 5.97-5.89 (m, 1H), 4.48-4.41 (m, 1H), 3.94-3.84 (m, 1H), 3.81-3.75 (m, 2H), 3.72 (s, 3H), 3.60-3.52 (m, 1H), 3.18-3.16 (m, 3H), 3.09 (d, J = 6.8 Hz, 3H), 2.90-2.85 (m, 4H), 2.84-2.79 (m, 3H), 1.73-1.57 (m, 7H), 1.48-1.31 (m, 8H), 1.25-1.21 (m, 6H), 1.18 (d, J = 6.0 Hz, 4H), 1.15 (s, 2H) |

[a]The reaction was run for 2 hrs anywhere from −10° C. to rt. The final products were isolated under standard purification techniques including reverse HPLC and prep-TLC with appropriate solvent conditions.
[b]AcOH in DCM was employed for the coupling.
[c]KOAc in DCM was employed for the coupling.
[d]AcOH with TEA in DCM was employed for the coupling.
[e]AcOH in DMP was employed for the coupling.
[f]$NaBH(OAc)_3$, $Et_3SiH$, TFA in ACN at rt for 2 hr was used for the reductive amination.
[g]$Me_4NBH(OAc)_3$, KOAc (2 eq), and HOAc (20 eq) in DCE at rt for 12 h was used for the reductive amination.

Example 11: Synthesis of (3'R,4'S,5'R)-6"-chloro-4'-(3-chloro-2-fluorophenyl)-N-((1r,3R)-3-(3-((1-(2,6-dioxopiperidin-3-yl)-3-methyl-2-oxo-2,3-dihydro-1H-benzo[d]imidazol-5-yl)ethynyl)azetidine-1-carbonyl)cyclobutyl)-2"-oxodispiro[cyclohexane-1,2'-pyrrolidine-3',3"-indoline]-5'-carboxamide (1-89)

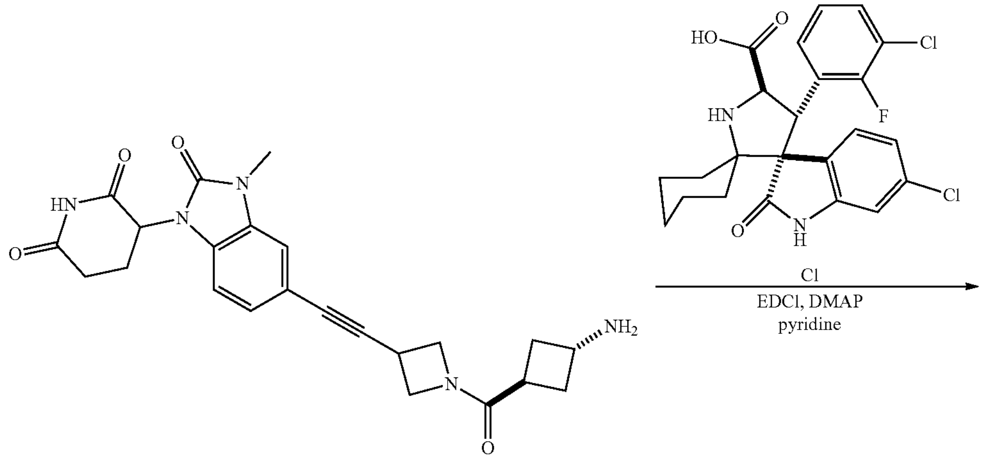

CH

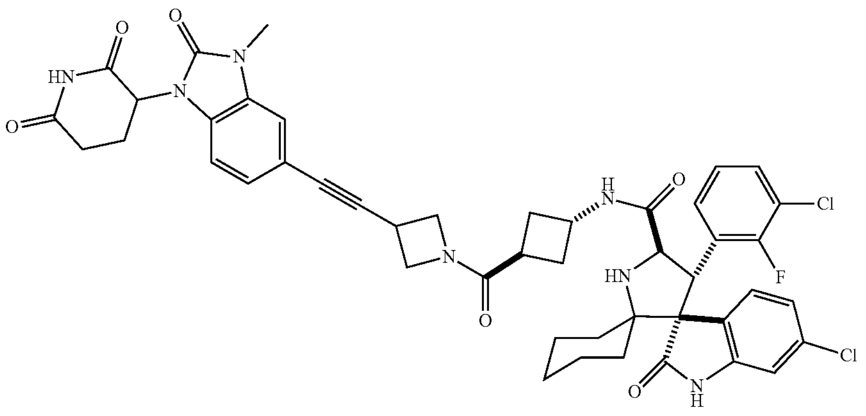

A mixture of chloro-(3-chloro-2-fluoro-phenyl)-oxo-dispiro[BLAH]carboxylic acid (40 mg, 86.3 umol, Intermediate CI), 3-[5-[2-[1-(3-aminocyclobutanecarbonyl)azetidin-3-yl]ethynyl]-3-methyl-2-oxo-benzimidazol-1-yl] piperidine-2,6-dione (37.6 mg, 86.3 umol, Intermediate CH), EDCI (19.8 mg, 103 umol), and DMAP (1.05 mg, 8.63 umol,) was dissolved in pyridine (1 mL) and the resulting solution was heated to 50° C. After 30 minutes, additional 3-[5-[2-[1-(3-aminocyclobutanecarbonyl)azetidin-3-yl] ethynyl]-3-methyl-2-oxo-benzimidazol-1-yl]piperidine-2,6-dione (37.6 mg, 86.3 umol,) was added to the reaction and the mixture was stirred at 50° C. for 1 h. On completion, the reaction mixture was concentrated in vacuo to give a residue. The crude product was purified by prep-HPLC (column: Phenomenex Luna C18 150*25 mm*10 um; mobile phase: [water (0.225% FA)–ACN]; B %: 30%-60%, 11 min) to give the title compound (7.12 mg, 8% yield) as yellow solid. $^1$H NMR (400 MHz, DMSO-d6) δ=11.22-10.95 (m, 1H), 10.53 (s, 1H), 8.24 (d, J=8.8 Hz, 1H), 7.58 (t, J=7.6 Hz, 1H), 7.46-7.39 (m, 1H), 7.36-7.27 (m, 2H), 7.18-7.09 (m, 3H), 7.03 (d, J=7.6 Hz, 1H), 6.67 (s, 1H), 5.45-5.32 (m, 1H), 4.60 (d, J=9.2 Hz, 1H), 4.44-4.34 (m, 2H), 4.31-4.17 (m, 2H), 4.11-4.03 (m, 1H), 3.90-3.83 (m, 1H), 3.77-3.68 (m, 1H), 3.27-3.22 (m, 3H), 3.01-2.86 (m, 2H), 2.72-2.62 (m, 2H), 2.37-2.31 (m, 2H), 2.22-2.13 (m, 2H), 2.10-1.77 (m, 4H), 1.64-1.52 (m, 4H), 1.50-1.43 (m, 1H), 1.35 (s, 1H), 1.01-0.90 (m, 1H), 0.86-0.74 (m, 1H); LC-MS (ESI$^+$) m/z 880.2 $(M+1)^+$.

Example 12. Synthesis of 4-[[(2R,3S,4R,5S)-3-(3-chloro-2-fluoro-phenyl)-4-(4-chloro-2-fluoro-phenyl)-4-cyano-5-(2,2-dimethylpropyl)-1-hexyl-pyrrolidine-2-carbonyl]amino]-3-methoxy-benzoic acid (I-90)

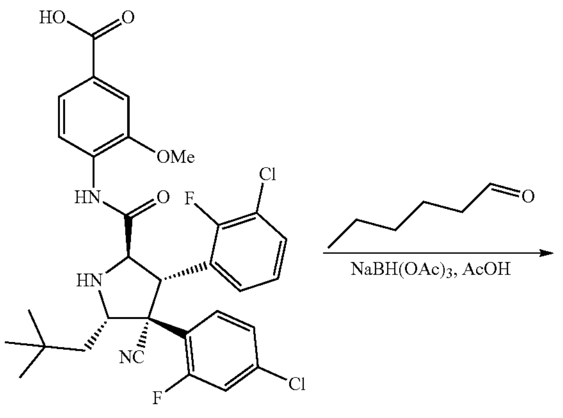

AN

-continued

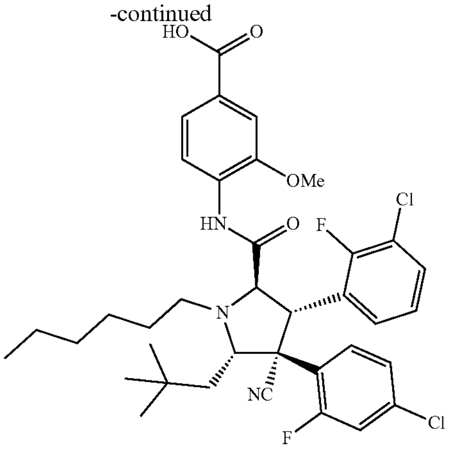

To a solution of 4-[[(2R,3S,4R,5S)-3-(3-chloro-2-fluoro-phenyl)-4-(4-chloro-2-fluoro-phenyl)-4-cyano-5-(2,2-dimethylpropyl)pyrrolidine-2-carbonyl]amino]-3-methoxy-benzoic acid (50.0 mg, 81.1 umol, Intermediate AN) and hexanal (208 mg, 2.08 mmol, CAS #66-25-1) in AcOH (4 mL) was added $NaBH(OAc)_3$ (250 mg, 1.18 mmol) in five portions, at 10 min intervals, at 20° C. The reaction mixture was then stirred at rt for 12 hours. On completion, the reaction mixture was concentrated to give a residue. The residue was purified by Prep-HPLC (column: Phenomenex Luna C18 150*25 mm*10 um; mobile phase: [water (0.225% FA)–ACN]; B %: 85%-100%, 11.5 min) to give the title compound (9.00 mg, 16% yield) was obtained as a white solid. $^1$H NMR (400 MHz, DMSO-$d_6$) δ=13.05 (s, 1H), 10.20 (s, 1H), 8.35 (d, J=8.4 Hz, 1H), 7.71 (t, J=7.2 Hz, 1H), 7.64-7.52 (m, 4H), 7.40-7.32 (m, 3H), 4.75 (d, J=6.4 Hz, 1H), 4.54 (d, J=6.8 Hz, 1H), 4.15 (d, J=9.6 Hz, 1H), 3.90 (s, 3H), 3.05-2.99 (m, 1H), 2.13 (dd, J=9.6, 15.2 Hz, 1H), 1.74-1.65 (m, 1H), 1.58-1.49 (m, 1H), 1.43-1.36 (m, 2H), 1.31-1.23 (m, 5H), 1.07 (d, J=14.8 Hz, 1H), 0.89 (s, 9H), 0.85 (s, 3H); LC-MS (ESI$^+$) m/z 700.4 $(M+1)^+$.

Example 13. Synthesis of 4-[(5S,6R,7S,7aR)-7-(3-chloro-2-fluoro-phenyl)-6-(4-chloro-2-fluoro-phenyl)-6-cyano-5-(2,2-dimethylpropyl)-1-oxo-3-pentyl-3,5,7,7a-tetrahydropyrrolo[1,2-c]imidazol-2-yl]-3-methoxy-benzoic acid (I-91)

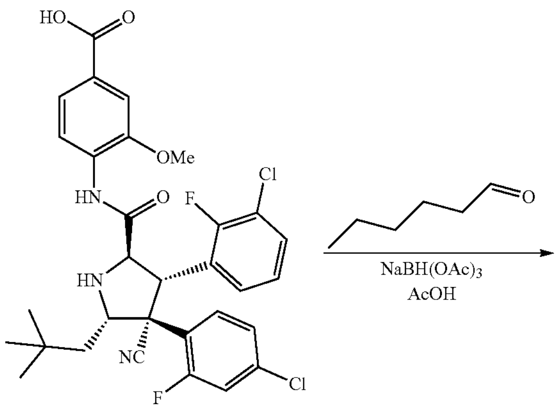

AN

-continued

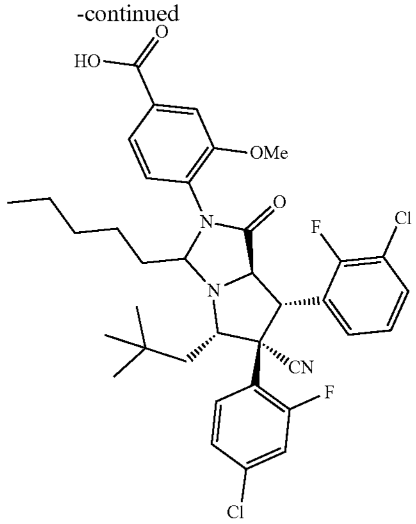

To a solution of 4-[[(2R,3S,4R,5S)-3-(3-chloro-2-fluoro-phenyl)-4-(4-chloro-2-fluoro-phenyl)-4-cyano-5-(2,2-dimethylpropyl)pyrrolidine-2-carbonyl]amino]-3-methoxy-benzoic acid (50.0 mg, 81.1 umol, Intermediate AN) and hexanal (208 mg, 2.08 mmol, CAS #66-25-1) in AcOH (4.0 mL) was added $NaBH(OAc)_3$ (250 mg, 1.18 mmol) in five portions, at 10 mins intervals, at 20° C. The reaction mixture was then stirred at 20° C. for 12 hours. On completion, the reaction mixture was concentrated to give a residue. The residue was purified by Prep-HPLC (column: Phenomenex Luna C18 150*25 mm*10 um; mobile phase: [water (0.225% FA)-ACN]; B %: 85%-100%, 11.5 min) to give the title compound (18 mg, 31% yield) as a white solid. $^1H$ NMR (400 MHz, DMSO-$d_6$) δ=13.43-12.82 (m, 1H), 7.82-7.70 (m, 2H), 7.68-7.61 (m, 2H), 7.59-7.52 (m, 1H), 7.40-7.32 (m, 4H), 4.89 (d, J=7.6 Hz, 1H), 4.72 (d, J=7.6 Hz, 1H), 4.64 (d, J=7.2 Hz, 1H), 4.09 (d, J=5.4 Hz, 1H), 3.91 (s, 3H), 1.89 (dd, J=6.0, 16.0 Hz, 1H), 1.77-1.65 (m, 2H), 1.59-1.45 (m, 2H), 1.36-1.24 (m, 5H), 0.89-0.82 (m, 3H), 0.64 (s, 9H). MS ($ESI^+$) m/z 698.4 $(M+1)^+$.

Example 14. Synthesis of 2-[[4-[[4-[1-(4-Chlorophenyl)-7-isopropoxy-6-methoxy-3-oxo-1,4-dihydroisoquinolin-2-yl]-N-methyl-anilino]methyl]cyclohexyl]amino]-N-[5-[1-(2,6-dioxo-3-piperidyl)-3-methyl-2-oxo-benzimidazol-5-yl]pentyl]acetamide (I-92)

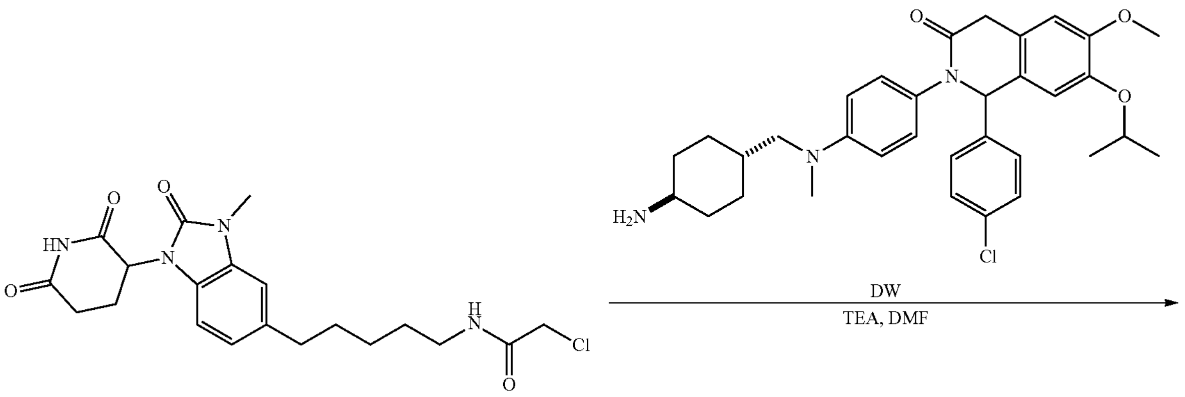

DX

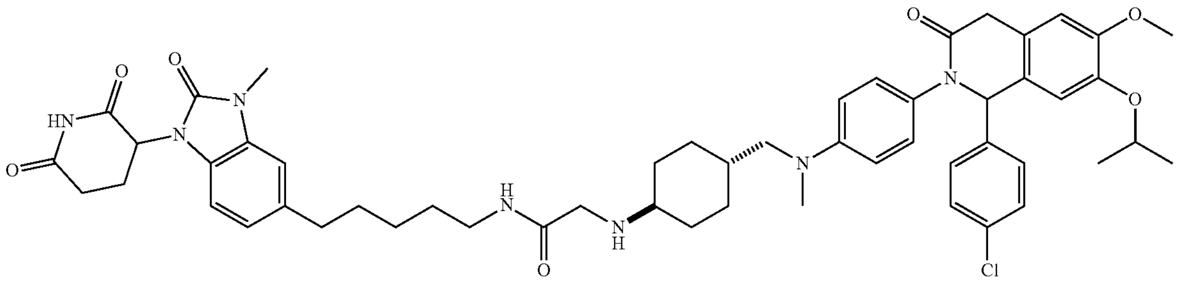

To a solution of 2-[4-[(4-aminocyclohexyl)methyl-methyl-amino]phenyl]-1-(4-chlorophenyl)-7-isopropoxy-6-methoxy-1,4-dihydroisoquinolin-3-one (142 mg, 237 umol, HCl, Intermediate DW) in DMF (1.0 mL) was added TEA (72.1 mg, 712 umol), KI (3.94 mg, 23.7 umol) and 2-chloro-N-[5-[1-(2,6-dioxo-3-piperidyl)-3-methyl-2-oxo-benzimidazol-5-yl]pentyl]acetamide (100 mg, 237 umol, Intermediate DX). The mixture was stirred at 40° C. for 12 hours. On completion, the mixture was concentrated in vacuo to give a residue. The residue was purified by reversed-phase HPLC (column: Phenomenex luna C18 150*25 mm*10 um; mobile phase: [water (0.225% FA)-ACN]; B %: 25%-55%, 10 min) to give the title compound (6.05 mg, 3% yield) as a white solid. $^1$H NMR (400 MHz, DMSO-$d_6$) δ 11.07 (s, 1H), 7.79-7.70 (m, 1H), 7.34 (s, 4H), 7.02 (d, J=7.2 Hz, 2H), 6.98 (d, J=8.0 Hz, 1H), 6.89-6.82 (m, 4H), 6.54 (d, J=9.2 Hz, 2H), 5.93 (s, 1H), 5.33 (dd, J=5.6, 12.8 Hz, 1H), 4.50-4.39 (m, 1H), 3.94-3.84 (m, 1H), 3.72 (s, 3H), 3.61-3.50 (m, 1H), 3.36-3.33 (m, 3H), 3.12-3.03 (m, 6H), 2.86 (s, 3H), 2.73-2.54 (m, 4H), 2.33 (d, J=1.6 Hz, 3H), 2.03-1.93 (m, 2H), 1.83-1.76 (m, 2H), 1.67-1.54 (m, 5H), 1.47-1.39 (m, 2H), 1.30-1.27 (m, 1H), 1.23 (d, J=6.0 Hz, 3H), 1.18 (d, J=6.0 Hz, 3H), 1.00-0.89 (m, 4H); LC-MS (ESI$^+$) m/z 946.7 (M+H)$^+$.

Example 15: Synthesis of (3'R,4'S,5'R)-6"-chloro-4'-(3-chloro-2-fluorophenyl)-N-((1s,3S)-3-hydroxy-3-methylcyclobutyl)-1'-methyl-1"-(non-8-yn-1-yl)-2"-oxodispiro[cyclohexane-1,2'-pyrrolidine-3',3"-indoline]-5'-carboxamide (I-128)

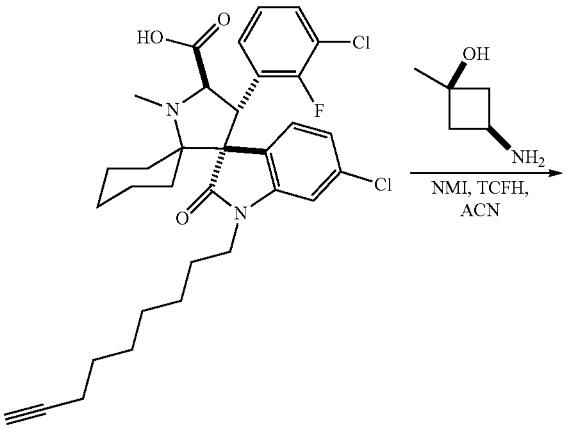

-continued

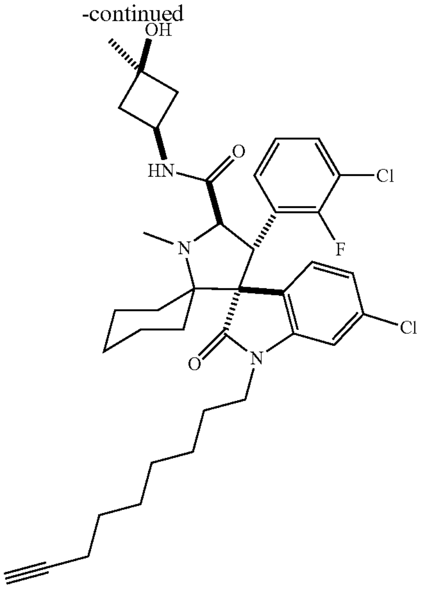

To a solution of chloro-(3-chloro-2-fluoro-phenyl)-methyl-non-8-ynyl-oxo-dispiro[BLAH]carboxylic acid (50.0 mg, 83.3 umol, I-129) in ACN (3 mL) was added N-methylimidazole (34.2 mg, 416 umol), [chloro(dimethylamino)methylene]-dimethyl-ammonium; hexafluorophosphate (70.2 mg, 250 umol) and 3-amino-1-methyl-cyclobutanol (17.2 mg, 125 umol, CAS #1363381-26-3). The mixture was stirred at 25° C. for 1 hour. On completion, the mixture was concentrated in vacuo to give a residue. The residue was purified by reversed-phase HPLC (column: Phenomenex luna C18 150*25 mm*10 um; mobile phase: [water (0.225% FA)-ACN]; B %: 65%-95%, 10 min) to give the title compound (5.87 mg, 8.60 umol, 10% yield) as a brown solid. $^1$H NMR (400 MHz, DMSO-d6) δ=7.56-7.44 (m, 2H), 7.36-7.26 (m, 1H), 7.14-6.99 (m, 3H), 6.89-6.89 (m, 1H), 4.38 (d, J=10.0 Hz, 1H), 3.72 (q, J=7.6 Hz, 1H), 3.53-3.42 (m, 2H), 3.29-3.18 (m, 3H), 2.81 (s, 2H), 2.16-2.08 (m, 4H), 1.94-1.80 (m, 4H), 1.69-1.51 (m, 4H), 1.43-1.34 (m, 3H), 1.27-1.12 (m, 12H), 1.00-0.95 (m, 2H). LC-MS (ESI$^+$) m/z 682.5 (M+H)$^+$.

Example 16: Synthesis of (3'R,4'S,5'R)-6"-chloro-4'-(3-chloro-2-fluorophenyl)-1'-methyl-1"-(non-8-yn-1-yl)-2"-oxodispiro[cyclohexane-1,2'-pyrrolidine-3',3"-indoline]-5'-carboxylic acid (I-129)

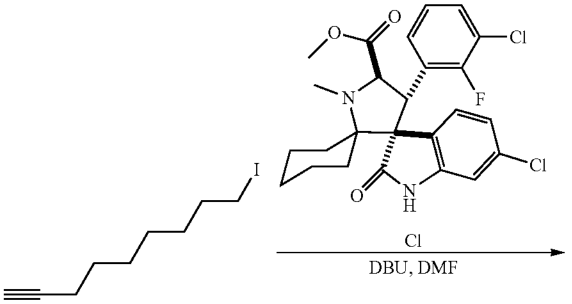

FK

-continued

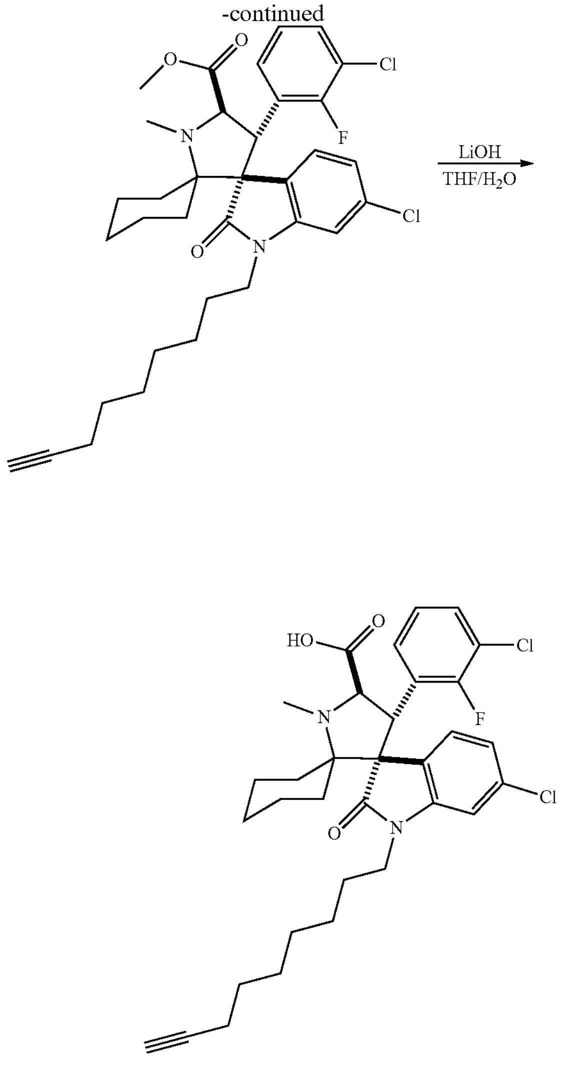

Step 1—Methyl chloro-(3-chloro-2-fluoro-phenyl)-methyl-non-8-ynyl-oxo-dispiro [BLAH] carboxylate To a solution of methyl chloro-(3-chloro-2-fluoro-phenyl)-methyl-oxo-dispiro[BLAH]carboxylate (300 mg, 610 umol, Intermediate CI) in DMF (15 mL) was added DBU (278 mg, 1.83 mmol, 276 uL) and 9-iodonon-1-yne (458 mg, 1.83 mmol, Intermediate FK). The resulting mixture was stirred at 120° C. for 16 hours. On completion, the reaction mixture was poured into water (20 mL) and extracted with ethyl acetate (15 mL×3). The combined organic phase was dried with anhydrous $Na_2SO_4$, filtered and concentrated in vacuo. The residue was purified by column chromatography ($SiO_2$, petroleum ether/ethyl acetate=1:0 to 95:5) to give the title compound (60.0 mg, 16% yield) as brown oil. $^1$H NMR (400 MHz, CHLOROFORM-d) δ=7.57-7.37 (m, 2H), 7.14 (t, J=6.8 Hz, 1H), 7.03 (d, J=7.6 Hz, 1H), 6.95-6.88 (m, 1H), 6.61 (d, J=1.6 Hz, 1H), 4.80 (d, J=10.4 Hz, 1H), 4.52-4.38 (m, 1H), 3.68 (s, 3H), 3.53-3.41 (m, 2H), 2.99 (s, 2H), 2.23-2.14 (m, 3H), 1.98-1.89 (m, 2H), 1.60-1.55 (m, 3H), 1.45-1.42 (m, 2H), 1.41-1.13 (m, 10H), 1.02-0.95 (m, 1H), 0.91-0.80 (m, 1H). LC-MS (ESI$^+$) m/z 613.4 (M+H)$^+$.

Step 2—Chloro-(3-chloro-2-fluoro-phenyl)-methyl-non-8-ynyl-oxo-dispiro[BLAH]carboxylic acid To a solution of methyl chloro-(3-chloro-2-fluoro-phenyl)-methyl-non-8-ynyl-oxo-dispiro[BLAH] carboxylate (60.0 mg, 97.7 umol) in $H_2O$ (2 mL) and THF (2 mL) was added LiOH (7.03 mg, 293 umol). The mixture was stirred at 40° C. for 6 hours. On completion, the reaction mixture was poured into water (5 mL) and extracted with ethyl acetate (3×5 mL). The combined organic phase was dried with anhydrous $Na_2SO_4$, filtered and concentrated in vacuo. The crude product was purified by reversed-phase HPLC (column: Waters xbridge 150*25 mm 10 um; mobile phase: [water (10 mM NH4HCO3)–ACN]; B %: 35%-65%, 11 min) to give the title compound (10.3 mg, 17% yield) as a white solid. $^1$H NMR (400 MHz, DMSO-$d_6$) δ=7.54-7.44 (m, 2H), 7.38-7.31 (m, 1H), 7.13-7.08 (m, 2H), 7.03 (d, J=2.0 Hz, 1H), 4.60 (d, J=10.4 Hz, 1H), 4.27 (d, J=10.8 Hz, 1H), 3.25-3.21 (m, 2H), 2.89-2.82 (m, 3H), 2.75-2.71 (m, 1H), 2.15-2.11 (m, 2H), 2.07-1.97 (m, 1H), 1.88-1.79 (m, 1H), 1.63-1.47 (m, 4H), 1.43-1.35 (m, 4H), 1.30-1.13 (m, 8H), 1.01 (d, J=8.0 Hz, 2H). LC-MS (ESI$^+$) m/z 599.4 (M+H)$^+$.

Example 17: Synthesis of (3'R,4'S,5'R)-6"-chloro-4'-(3-chloro-2-fluorophenyl)-N-(4-(4-((1-(2,6-dioxopiperidin-3-yl)-3-methyl-2-oxo-2,3-dihydro-1H-benzo[d]imidazol-5-yl)ethynyl)piperidine-1-carbonyl)bicyclo[2.2.2]octan-1-yl)-1'-methyl-2"-oxodispiro[cyclohexane-1,2'-pyrrolidine-3',3"-indoline]-5'-carboxamide (I-130)

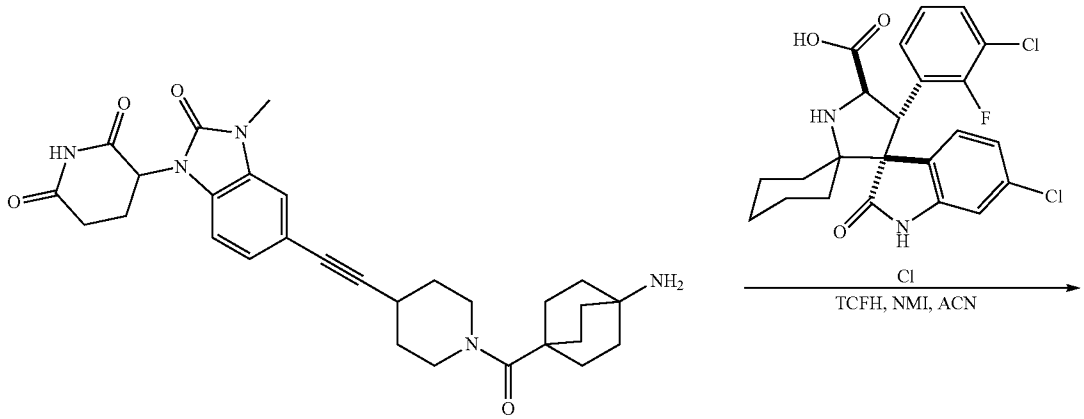

FR

-continued

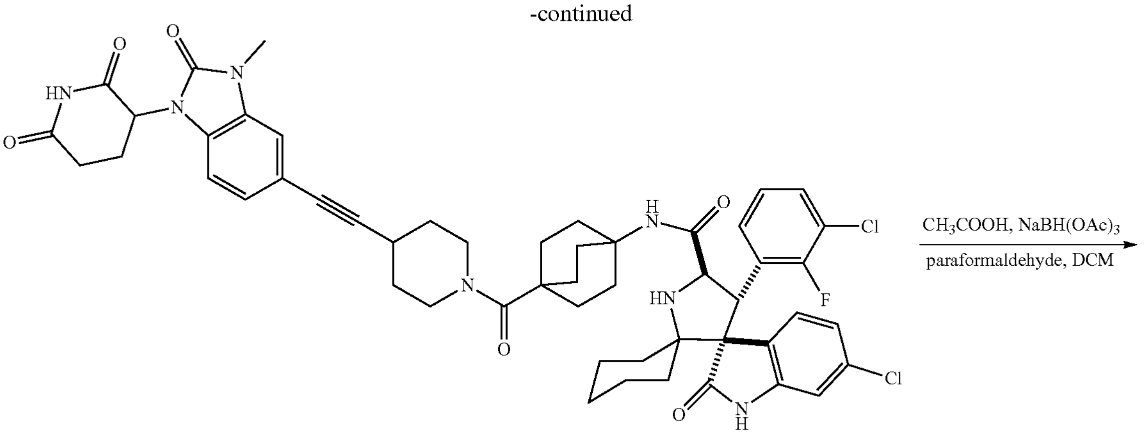

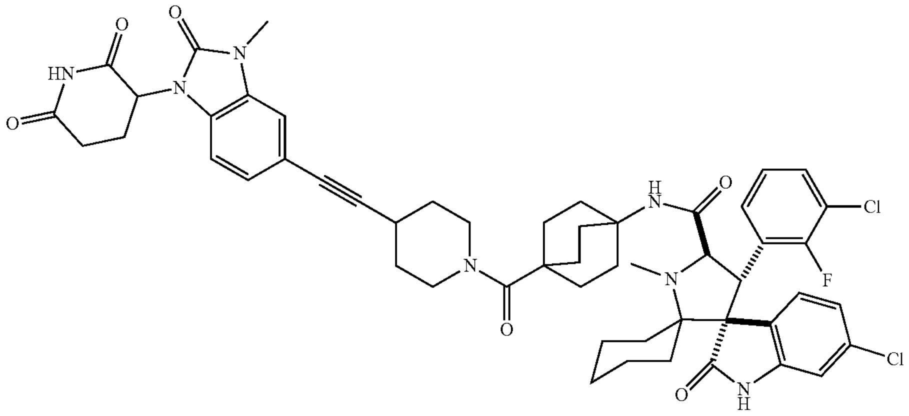

Step 1—Chloro-(3-chloro-2-fluoro-phenyl)-N-[4-[4-[2-[1-(2,6-dioxo-3-piperidyl)-3-methyl-2-oxo-benzimidazol-5-yl]ethynyl]piperidine-1-carbonyl]-1-bicyclo[2.2.2]octanyl]-oxo-dispiro[BLAH]carboxamide To a solution of 3-[5-[2-[1-(4-aminobicyclo[2.2.2]octane-1-carbonyl)-4-piperidyl]ethynyl]-3-methyl-2-oxo-benzimidazol-1-yl]piperidine-2,6-dione (306 mg, 484 umol, TFA, Intermediate FR) and chloro-(3-chloro-2-fluoro-phenyl)-oxo-dispiro[BLAH]carboxylic acid (190 mg, 410 μmol, Intermediate CI) in ACN (10 mL) was added 1-methylimidazole (1.01 g, 12.3 mmol) to adjust the pH=8. Then [chloro(dimethylamino)methylene]-dimethyl-ammonium; hexafluorophosphate (345 mg, 1.23 mmol) was added and the mixture was stirred at 25° C. for 0.5 hour. On completion, the mixture was concentrated to give a residue. The residue was purified by reversed-phase HPLC (0.1% TFA condition) to give the title compound (125 mg, 32% yield) as a white solid. LC-MS ($ESI^+$) m/z 962.3 $(M+H)^+$.

Step 2—Chloro-(3-chloro-2-fluoro-phenyl)-N-[4-[4-[2-[1-(2,6-dioxo-3-piperidyl)-3-methyl-2-oxo-benzimidazol-5-yl]ethynyl]piperidine-1-carbonyl]-1-bicyclo[2.2.2]octanyl]-methyl-oxo-dispiro[BLAH]carboxamide To a solution of chloro-(3-chloro-2-fluoro-phenyl)-N-[4-[4-[2-[1-(2,6-dioxo-3-piperidyl)-3-methyl-2-oxo-benzimidazol-5-yl]ethynyl]piperidine-1-carbonyl]-1-bicyclo[2.2.2]octanyl]-oxo-dispiro[BLAH]carboxamide (125 mg, 129 umol), $CH_3COOH$ (1.31 g, 21.9 mmol) and paraformaldehyde (125 mg) in DCM (2.5 mL) was added $NaBH(OAc)_3$ (138 mg, 649 umol). The mixture was stirred at 25° C. for 12 hours. On completion, the mixture was quenched with saturated $NaHCO_3$ (10 mL) and then extracted with DCM (25 mL×3). The combined organic phase was dried over anhydrous sodium sulfate, filtered and concentrated to give a residue. The mixture was purified by reversed-phase HPLC (column: Phenomenex luna C18 150*25 mm*10 um; mobile phase: [water (0.225% FA)-ACN]; B %: 47%-78%, 10 min) to give the title compound (33.4 mg, 24% yield, FA) as a yellow solid. $^1H$ NMR (400 MHz, DMSO-$d_6$) δ 11.11 (s, 1H), 10.54 (s, 1H), 8.40 (s, 1H), 7.64-7.50 (m, 2H), 7.46-7.36 (m, 1H), 7.36-7.28 (m, 1H), 7.28-7.25 (m, 1H), 7.14-7.08 (m, 3H), 7.07-7.00 (m, 1H), 6.64 (d, J=2.0 Hz, 1H), 6.33-6.25 (m, 1H), 5.47-5.30 (m, 1H), 5.12-4.96 (m, 1H), 4.90-4.80 (m, 1H), 4.36-4.20 (m, 1H), 4.11-4.01 (m, 1H), 3.98-3.86 (m, 2H), 3.29-3.21 (m, 3H), 2.96-2.84 (m, 2H), 2.80 (d, J=7.6 Hz, 3H), 2.74-2.58 (m, 2H), 2.10-1.97 (m, 2H), 1.84 (d, J=8.4 Hz, 15H), 1.65-1.41 (m, 8H), 1.05-0.80 (m, 2H); LC-MS ($ESI^+$) m/z 976.2 $(M+H)^+$.

Example 18: Synthesis of (3'R,4'S,5'R)-6"-chloro-4'-(3-chloro-2-fluorophenyl)-N-(4-(((5-(1-(2,6-dioxopiperidin-3-yl)-3-methyl-2-oxo-2,3-dihydro-1H-benzo[d]imidazol-5-yl)pentyl)(methyl)amino)methyl)bicyclo[2.2.2]octan-1-yl)-1'-ethyl-2"-oxodispiro[cyclohexane-1,2'-pyrrolidine-3',3"-indoline]-5'-carboxamide (I-131)
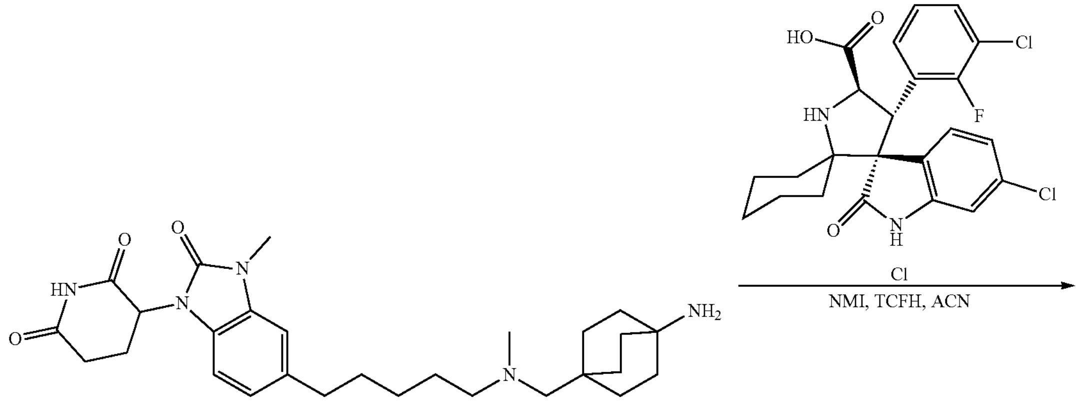
FU
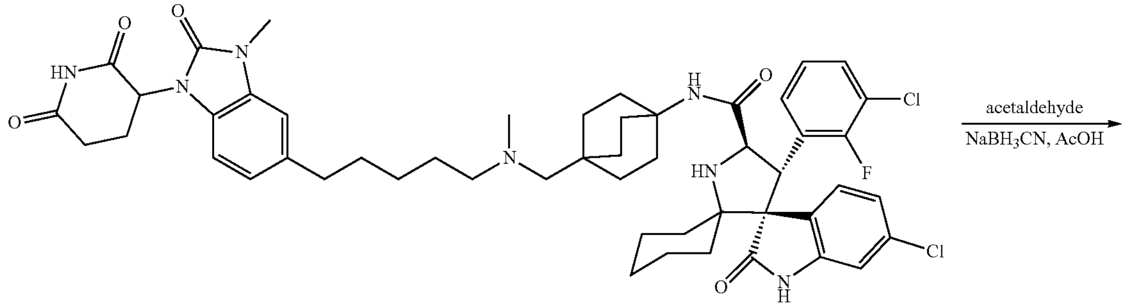
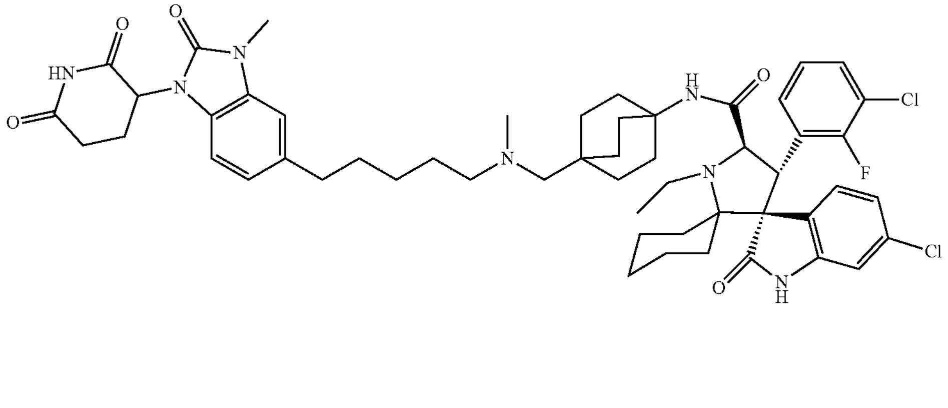

Step 1—Chloro-(3-chloro-2-fluoro-phenyl])-N-[4-[[5-[1-(2,6-dioxo-3-piperidyl)-3-methyl-2-oxo-benzimidazol-5-yl]pentyl-methyl-amino]methyl]-1-bicyclo[2.2.2]octanyl]-oxo-dispiro[BLAH]carboxamide To a mixture of 3-[5-[5-[(4-amino-1-bicyclo[2.2.2]octanyl)methyl-methyl-amino]pentyl]-3-methyl-2-oxo-benzimidazol-1-yl]piperidine-2,6-dione (80.0 mg, 150 umol, HCl, Intermediate FU), chloro-(3-chloro-2-fluoro-phenyl)-oxo-dispiro[BLAH]carboxylic acid (69.6 mg, 150 umol, Intermediate CI) and 1-methylimidazole (370 mg, 4.51 mmol) in ACN (1 mL) was added [chloro(dimethylamino)methylene]-dimethyl-ammonium; hexafluorophosphate (84.3 mg, 300 umol) at 25° C. and the mixture was stirred for 0.5 hour. On completion, the mixture was quenched with $H_2O$ (1 mL), and concentrated to give the title compound (85.0 mg, 60% yield) as a white solid. $^1$H NMR (400 MHz, DMSO-$d_6$) δ 11.08 (s, 1H), 10.53 (s, 1H), 7.72-7.66 (m, 1H), 7.63-7.55 (m, 1H), 7.43-7.33 (m, 2H), 7.09-6.93 (m, 4H), 6.87 (d, J=7.2 Hz, 1H), 6.70-6.64 (m, 1H), 5.37-5.31 (m, 1H), 4.48 (d, J=10.4 Hz, 1H), 4.33-4.25 (m, 1H), 2.99-2.82 (m, 2H), 2.78-2.68 (m, 2H), 2.66-2.58 (m, 4H), 1.80 (s, 5H), 1.68-1.41 (m, 20H), 1.34-1.21 (m, 6H), 1.06-0.60 (m, 5H).

Step 2—Chloro-(3-chloro-2-fluoro-phenyl)-N-[4-[[5-[1-(2,6-dioxo-3-piperidyl)-3-methyl-2-oxo-benzimidazol-5-yl]pentyl-methyl-amino]methyl]-1-bicyclo[2.2.2]octanyl]-ethyl-oxo-dispiro[BLAH] carboxamide To a mixture of chloro-(3-chloro-2-fluoro-phenyl)-N-[4-[[5-[1-(2,6-dioxo-3-piperidyl)-3-methyl-2-oxo-benzimidazol-5-yl]pentyl-methyl-amino]methyl]-1-bicyclo[2.2.2]octanyl]-oxo-dispiro[BLAH] carboxamide (70.0 mg, 74.3 umol) and acetaldehyde (204 mg, 1.86 mmol, 40% solution) in AcOH (5 mL) was added $NaBH(OAc)_3$ (157 mg, 743 umol) and stirred at 25° C. for 12 hours. On completion, the mixture was poured into the water (10 mL) and extracted with DCM (3×10 mL). The combined organic phase was washed with brine (2×10 mL), dried with anhydrous $Na_2SO_4$, filtered and concentrated in vacuo to give the residue. The residue was purified by prep-HPLC (column: Waters xbridge 150*25 mm 10 um; mobile phase: [water (10 mM NH4HCO3)–ACN]; B %: 65%-95%, 11 min and column: Welch Xtimate C18 150*25 mm*5 um; mobile phase: [water (0.05% HCl)–ACN]; B %: 26%-46%, 10 min) to give the title compound (3.44 mg, 4.9% yield) as a white solid. $^1$H NMR (400 MHz, DMSO-$d_6$) δ 11.08 (s, 1H), 10.50 (s, 1H), 7.63 (t, J=7.2 Hz, 1H), 7.39 (d, J=8.8 Hz, 1H), 7.36-7.29 (m, 2H), 7.11 (t, J=8.0 Hz, 1H), 7.05-6.97 (m, 3H), 6.89-6.82 (m, 1H), 6.63 (d, J=2.0 Hz, 1H), 5.36-5.30 (m, 1H), 4.29 (d, J=9.6 Hz, 1H), 3.90 (d, J=9.6 Hz, 1H), 3.30 (s, 3H), 2.94-2.83 (m, 1H), 2.66-2.56 (m, 3H), 2.30-2.24 (m, 2H), 2.15 (s, 3H), 2.06-1.95 (m, 4H), 1.80-1.69 (m, 6H), 1.69-1.49 (m, 8H), 1.48-1.35 (m, 9H), 1.32-1.21 (m, 5H), 1.07 (t, J=7.2 Hz, 3H), 0.89-0.76 (m, 2H); LC-MS (ESI$^+$) m/z 968.5 (M+H)$^+$.

Example 19: Synthesis of (3'R,4'S,5'R)-6"-chloro-4'-(3-chloro-2-fluorophenyl)-1"-(9-(1-(2,6-dioxopiperidin-3-yl)-3-methyl-2-oxo-2,3-dihydro-1H-benzo[d]imidazol-5-yl)non-8-yn-1-yl)-1'-methyl-2"-oxodispiro[cyclohexane-1,2'-pyrrolidine-3',3"-indoline]-5'-carboxylic acid (I-132)

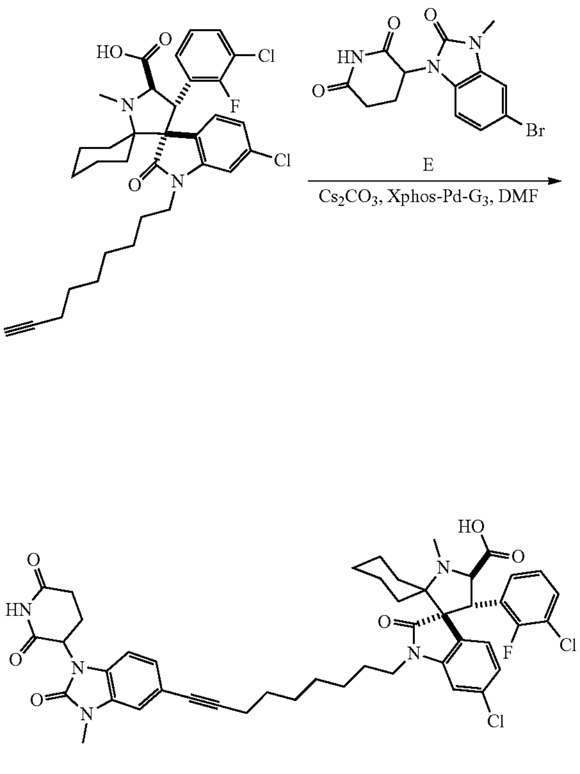

To a solution of chloro-(3-chloro-2-fluoro-phenyl)-methyl-non-8-ynyl-oxo-dispiro[BLAH]carboxylic acid (150 mg, 250 umol, I-129) in DMF (6 mL) was added $Cs_2CO_3$ (407 mg, 1.25 mmol), Xphos-Pd-G3 (21.1 mg, 25.0 umol) and 3-(5-bromo-3-methyl-2-oxo-benzimidazol-1-yl) piperidine-2,6-dione (84.6 mg, 250 umol, Intermediate E). The mixture was stirred at 80° C. for 16 hours under $N_2$ atmosphere. On completion, the reaction mixture was poured into water (10 mL) and extracted with ethyl acetate (3×5 mL). The combined organic phase was dried with anhydrous $Na_2SO_4$, filtered and concentrated in vacuo. The crude product was purified by reversed-phase HPLC (column: Phenomenex Luna C18 150*25 mm*10 um; mobile phase: [water (0.1% TFA)–ACN]; B %: 42%-72%, 10 min) to give the title compound (80.0 mg, 56.0 umol, 22% yield) as a white solid. LC-MS (ESI$^+$) m/z 856.3 (M+H)$^+$.

Example 20: Synthesis of C(3'R,4'S,5'R)-6"-chloro-4'-(3-chloro-2-fluorophenyl)-1"-(9-(1-(2,6-dioxopiperidin-3-yl)-3-methyl-2-oxo-2,3-dihydro-1H-benzo[d]imidazol-4-yl)non-8-yn-1-yl)-N-((1s,3S)-3-hydroxy-3-methylcyclobutyl)-1'-methyl-2"-oxodispiro[cyclohexane-1,2'-pyrrolidine-3',3"-indoline]-5'-carboxamide (I-133)
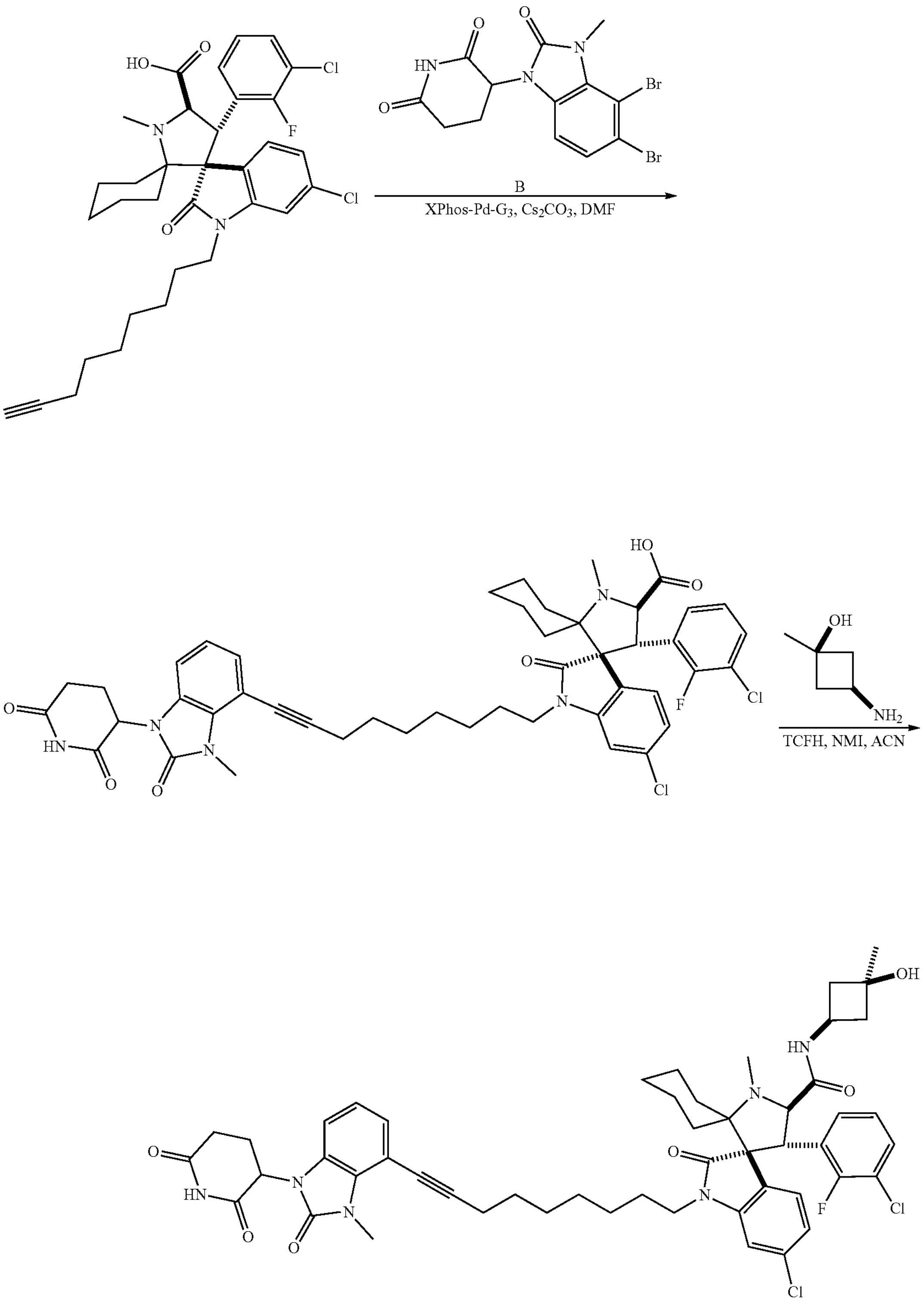

Step 1—Chloro-(3-chloro-2-fluoro-phenyl)-[9-[1-(2,6-dioxo-3-piperidyl)-3-methyl-2-oxo-benzimidazol-4-yl]non-8-ynyl]-methyl-oxo-dispiro[BLAH]carboxylic acid To a solution of chloro-(3-chloro-2-fluoro-phenyl)-methyl-non-8-ynyl-oxo-dispiro[BLAH]carboxylic acid (120 mg, 200 umol, I-129) in DMF (6 mL) was added $Cs_2CO_3$ (326 mg, 1.00 mmol), XPhos-Pd-G3 (16.9 mg, 20.0 umol) and 3-(4-bromo-3-methyl-2-oxo-benzimidazol-1-yl)piperidine-2,6-dione (67.6 mg, 200 umol, Intermediate B). The mixture was stirred at 80° C. for 14 hours at $N_2$ atmosphere. The reaction mixture was poured into water (10 mL) and extracted with ethyl acetate (3×10 mL). The combined organic phases were dried with anhydrous $Na_2SO_4$, filtered and concentrated in vacuo. The residue was purified by reverse phase CC (water (0.1% TFA)–ACN) to give the title compound (10.0 mg, 11.6 umol, 5.8% yield) as a yellow oil. LC-MS ($ESI^+$) m/z 857.2 $(M+2)^+$.

Step 2—Chloro-(3-chloro-2-fluoro-phenyl)-[9-[1-(2,6-dioxo-3-piperidyl)-3-methyl-2-oxo-benzimidazol-4-yl]non-8-ynyl]-N-(3-hydroxy-3-methyl-cyclobutyl)-methyl-oxo-dispiro[BLAH]carboxamide To a solution of chloro-(3-chloro-2-fluoro-phenyl)-[9-[1-(2,6-dioxo-3-piperidyl)-3-methyl-2-oxo-benzimidazol-4-yl]non-8-ynyl]-methyl-oxo-dispiro[BLAH]carboxylic acid (10.0 mg, 11.6 umol) in ACN (1.0 mL) was added 1-methylimidazole (958 ug, 11.6 umol), [chloro(dimethylamino)methylene]-dimethyl-ammonium; hexafluorophosphate (3.27 mg, 11.6 umol) and 3-amino-1-methyl-cyclobutanol (1.18 mg, 11.6 umol, CAS #1363381-26-3). The mixture was stirred at 25° C. for 1 hour. The crude product was purified by reversed-phase HPLC (column: Phenomenex Luna C18 150*25 mm*10 um; mobile phase: [water (0.1% TFA)–ACN]; B %: 46%-76%, 10 min) to give the title compound (1.81 mg, 1.93 umol, 16% yield) as a white solid. $^1H$ NMR (400 MHz, CHLOROFORM-d) δ=7.53 (s, 1H), 7.22-7.17 (m, 2H), 7.14-7.11 (m, 2H), 7.05-6.94 (m, 3H), 6.74 (dd, J=2.8, 4.8 Hz, 1H), 6.68 (s, 1H), 5.30-5.17 (m, 1H), 4.74-4.62 (m, 1H), 3.99-3.89 (m, 1H), 3.80 (s, 3H), 3.54-3.45 (m, 2H), 3.21-3.09 (m, 3H), 3.01-2.64 (m, 6H), 2.47 (t, J=6.4 Hz, 6H), 2.33-2.18 (m, 6H), 1.63-1.57 (m, 5H), 1.42 (dd, J=1.6, 3.2 Hz, 4H), 1.27 (s, 3H), 1.19 (d, J=6.4 Hz, 4H), 1.06-0.80 (m, 2H). LC-MS ($ESI^+$) m/z 941.6 $(M+3)^+$.

Example 21: Synthesis of 4-[(5S,6R,7S,7aR)-7-(3-chloro-2-fluoro-phenyl)-6-(4-chloro-2-fluoro-phenyl)-6-cyano-5-(2,2-dimethylpropyl)-3-[9-[1-(2,6-dioxo-3-piperidyl)-3-methyl-2-oxo-benzimidazol-5-yl]non-8-ynyl]-1-oxo-3,5,7,7a-tetrahydropyrrolo[1,2-c]imidazol-2-yl]-3-methoxy-N-methyl-benzamide (I-213)

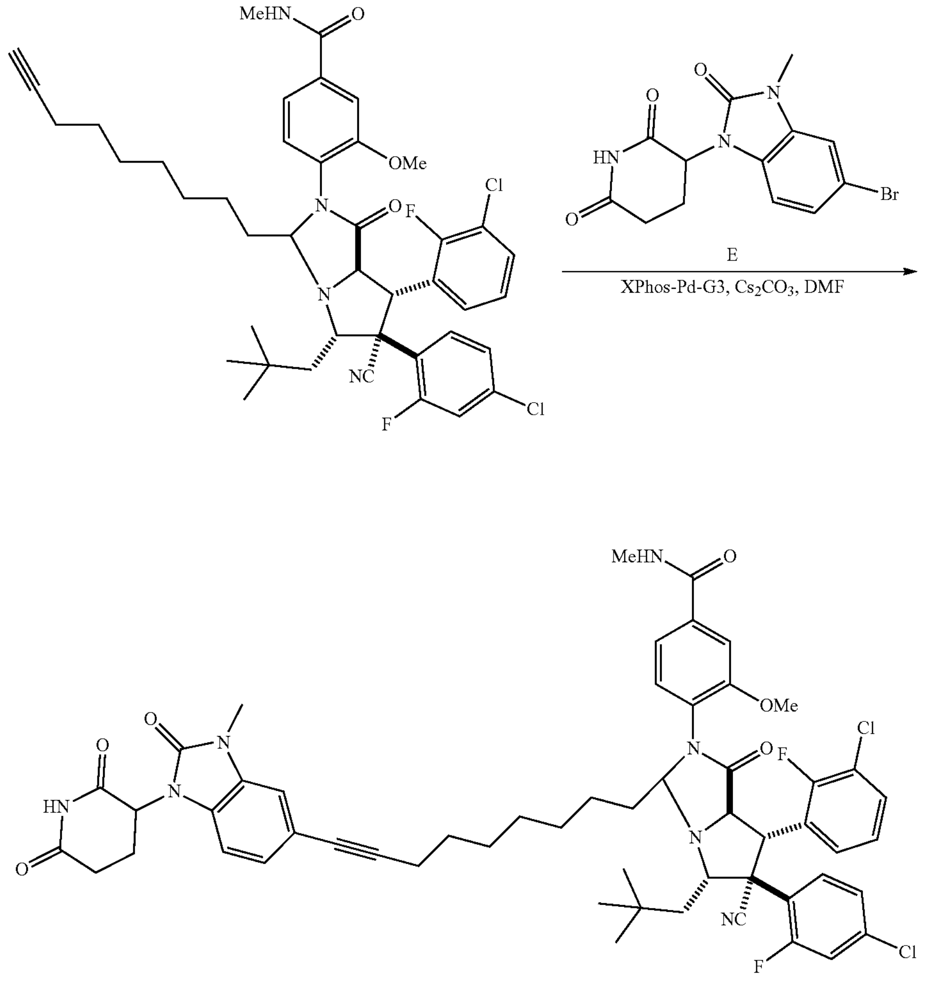

A solution of 3-(5-bromo-3-methyl-2-oxo-benzimidazol-1-yl)piperidine-2,6-dione (6.91 mg, 20.4 umol, Intermediate E), 4-[(5S,6R,7S,7aR)-7-(3-chloro-2-fluoro-phenyl)-6-(4-chloro-2-fluoro-phenyl)-6-cyano-5-(2,2-dimethylpropyl)-3-non-8-ynyl-1-oxo-3,5,7,7a-tetrahydropyrrolo[1,2-c]imidazol-2-yl]-3-methoxy-N-methyl-benzamide (13.0 mg, 17.0 umol, Example I-127), $Cs_2CO_3$ (16.6 mg, 51.0 umol), XPhos Pd G3 (1.44 mg, 1.70 umol) in DMF (0.5 mL) was degassed and purged with $N_2$ three times, and then the mixture was stirred at 80° C. for 3 hrs under $N_2$ atmosphere. On completion, the reaction mixture was concentrated under reduced pressure to afford a residue. The residue was purified by prep-HPLC (column: Phenomenex luna C18 150*25 mm*10 um; mobile phase: [water (0.225% FA)–ACN]; B %: 65%-95%, 10 min) to give the title compound (4.58 mg, 26% yield) as a yellow solid. $^1H$ NMR (400 MHz, DMSO-$d_6$) δ 11.10 (s, 1H), 8.54-8.49 (m, 1H), 7.80-7.75 (m, 1H), 7.75-7.69 (m, 1H), 7.59 (d, J=1.6 Hz, 1H), 7.57-7.52 (m, 1H), 7.49 (dd, J=1.6, 8.0 Hz, 1H), 7.37-7.33 (m, 2H), 7.31 (d, J=8.0 Hz, 1H), 7.21 (s, 1H), 7.07 (s, 2H), 5.40-5.33 (m, 1H), 4.85 (d, J=8.0 Hz, 1H), 4.74-4.69 (m, 1H), 4.64-4.59 (m, 1H), 4.08 (d, J=5.6 Hz, 1H), 3.89 (s, 3H), 3.31-3.31 (m, 3H), 2.91-2.84 (m, 1H), 2.80 (d, J=4.4 Hz, 3H), 2.76-2.67 (m, 1H), 2.66-2.58 (m, 1H), 2.52 (d, J=2.0 Hz, 1H), 2.42-2.37 (m, 2H), 2.06-1.95 (m, 1H), 1.91-1.83 (m, 1H), 1.76-1.65 (m, 2H), 1.59-1.46 (m, 4H), 1.44-1.28 (m, 7H), 0.62 (s, 9H). LC-MS ($ESI^+$) m/z 1020.6 $(M+H)^+$.

Example 22: Synthesis of 4-((3'R,4'S,5'R)-6"-chloro-4'-(3-chloro-2-fluorophenyl)-1'-(10-(1-(2,6-dioxopiperidin-3-yl)-3-methyl-2-oxo-2,3-dihydro-1H-benzo[d]imidazol-5-yl)dec-9-yn-1-yl)-2"-oxodispiro[cyclohexane-1,2'-pyrrolidine-3',3"-indoline]-5'-carboxamido)benzoic acid (I-214)

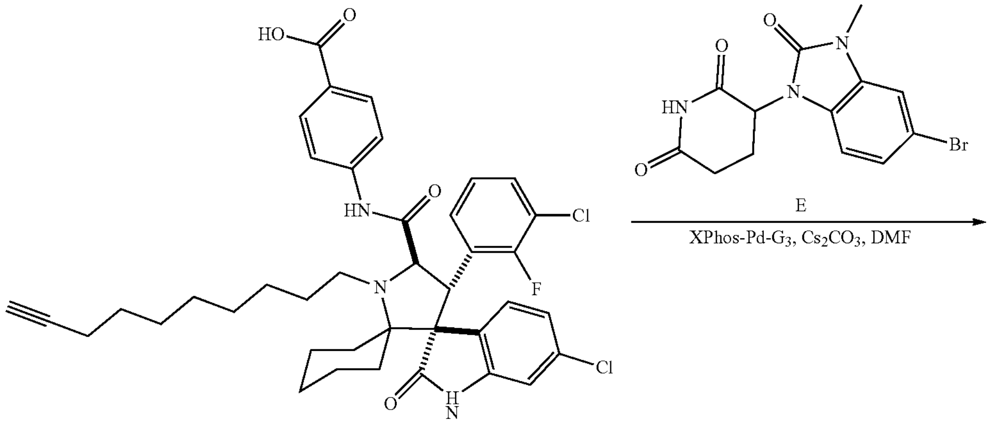

HX

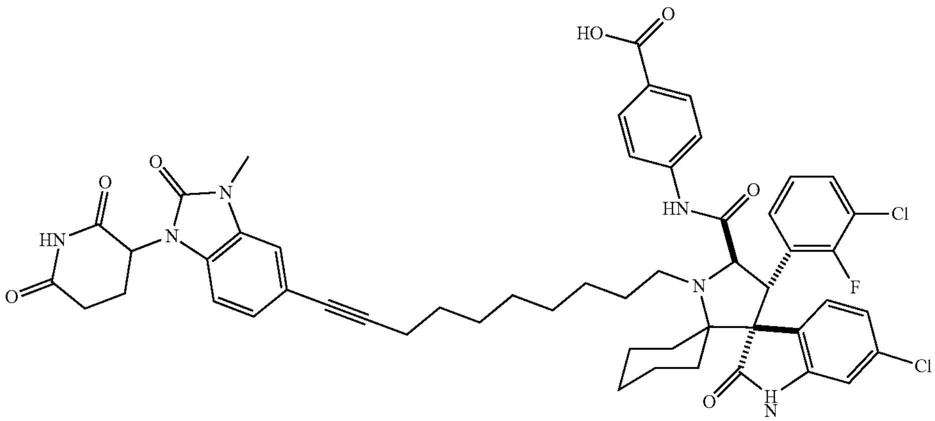

To a mixture of 3-(5-bromo-3-methyl-2-oxo-benzimidazol-1-yl)piperidine-2,6-dione (42.3 mg, 125 umol, Intermediate E) and 4-[[chloro-(3-chloro-2-fluoro-phenyl)-dec-9-ynyl-oxo-dispiro[BLAH]carbonyl]amino] benzoic acid (90.0 mg, 125 umol, Intermediate HX) in DMF (2 mL) was added $Cs_2CO_3$ (122 mg, 375 umol) and [2-(2-aminophenyl) phenyl]palladium(1+); dicyclohexyl-[2-(2,4,6-triisopropylphenyl)phenyl] phosphane; methanesulfonate (10.6 mg, 12.5 umol). The mixture was stirred at 80° C. for 12 hours under $N_2$. On completion, the mixture was quenched with $H_2O$ (10 mL) and extracted with EtOAc (3×10 mL). The organic phase was dried over $Na_2SO_4$, filtered, and concentrated in vacuo to give the crude compound. The crude compound was purified by prep-HPLC (column: Phenomenex Luna C18 150*25 mm*10 um; mobile phase: [water (0.225% FA)–ACN]; B %: 67%-97%) to give the title compound (3.79 mg, 2.9% yield) as a yellow solid. LC-MS ($ESI^+$) m/z 975.3 $(M+H)^*$; $^1H$ NMR (400 MHz, DMSO-$d_6$) δ 13.00-12.54 (m, 1H), 11.11 (s, 1H), 10.53 (s, 1H), 10.07 (s, 1H), 7.89 (d, J=8.4 Hz, 2H), 7.73 (t, J=6.8 Hz, 1H), 7.65 (d, J=8.4 Hz, 2H), 7.49-7.43 (m, 1H), 7.36 (t, J=7.2 Hz, 1H), 7.23 (s, 1H), 7.17 (t, J=8.0 Hz, 1H), 7.08 (s, 2H), 7.05-7.00 (m, 1H), 6.65 (d, J=1.6 Hz, 1H), 5.41-5.34 (m, 1H), 4.61 (d, J=10.0 Hz, 1H), 4.40 (d, J=10.0 Hz, 1H), 3.30 (s, 3H), 2.97-2.84 (m, 1H), 2.75-2.68 (m, 1H), 2.66-2.59 (m, 1H), 2.06-2.00 (m, 1H), 1.93 (d, J=14.0 Hz, 1H), 1.75-1.57 (m, 4H), 1.57-1.48 (m, 5H), 1.46-1.38 (m, 3H), 1.31 (br d, J=1.0 Hz, 4H), 1.27-1.17 (m, 6H), 1.15 (s, 1H), 1.03-0.89 (m, 2H).

Example 23. Cell Viability CTG Assay

Day 0: Compounds or DMSO 60 nL were stamped to the cell plate as the platemap. RS411 cells were centrifuged at 800 rpm for 5 min, suspended with culture medium, and counted with Countess (Invitrogen). The cell density was adjusted to the recommend information. 30 μL of cell solution (1000 cells/well) was added to the assay plate as the platemap and 30 μL of media was added to column 2 and column 23 as the platemap. The plate was spun down briefly. The final concentration of the compounds started at 10 μM (3 fold dilution and 11 doses) and final DMSO concentration was 0.2%. The plate was spun down briefly and incubated at 37° C., 5% $CO_2$ for 1-4 days.

Day 1-4: The assay plate was equilibrated to RT for −10 min and compound precipitation was observed at 96 h. 30 μL CellTiter Glo reagent was added to each well and the plate was centrifuged at 1000 rpm for 30 sec. The plate was shaken for 1 min and centrifuged at 1000 rpm for 30 sec. The plate was incubated at RT for 10 min to stabilize the luminescent signal and the luminescene was read by EnVision.

The RS411 $IC_{50}$ results are shown in Table 13. The letter codes for $IC_{50}$ indicate the concentration of compound required to affect 50% of cells: A (<0.05 μM), B (0.05-0.1 μM), C (0.1-0.5 μM), D (0.5-1.0 μM), and E (>1.0 μM).

TABLE 13

| CTG Results | | |
|---|---|---|
| I-# | CTG Cell Viability Assay - RS411: $IC_{50}$ (μM) | CTG Cell Viability Assay - RS411: Duration (days) |
| I-4 | B | 4 |
| I-5 | E | 4 |
| I-6 | C | 4 |
| I-7 | E | 4 |
| I-8 | E | 4 |
| I-9 | A | 4 |
| I-10 | C | 4 |
| I-11 | E | 4 |
| I-12 | B | 4 |
| I-13 | D | 4 |
| I-14 | A | 4 |
| I-15 | B | 3 |
| I-16 | A | 4 |
| I-17 | A | 4 |
| I-18 | A | 2 |
| I-19 | A | 4 |
| I-20 | C | 4 |
| I-21 | B | 4 |
| I-22 | D | 4 |
| I-23 | E | 4 |
| I-24 | A | 4 |
| I-25 | C | 4 |
| I-26 | B | 4 |
| I-27 | C | 3 |
| I-28 | A | 3 |
| I-29 | A | 4 |
| I-30 | A | 4 |
| I-31 | A | 4 |
| I-32 | C | 4 |
| I-33 | E | 4 |
| I-42 | A | 1 |
| I-43 | A | 1 |
| I-44 | A | 1 |
| I-45 | C | 1 |
| I-46 | A | 1 |
| I-47 | B | 1 |
| I-48 | A | 1 |
| I-49 | A | 1 |
| I-50 | A | 1 |
| I-51 | A | 1 |
| I-52 | A | 1 |
| I-53 | B | 1 |
| I-54 | B | 1 |
| I-55 | B | 1 |
| I-56 | A | 1 |
| I-57 | A | 1 |
| I-58 | A | 1 |
| I-59 | A | 1 |
| I-60 | A | 1 |
| I-61 | A | 1 |
| I-62 | B | 1 |
| I-63 | A | 1 |
| I-64 | A | 1 |
| I-65 | A | 1 |
| I-66 | A | 1 |
| I-67 | A | 1 |
| I-68 | A | 1 |
| I-69 | A | 1 |
| I-70 | A | 1 |
| I-71 | A | 1 |
| I-72 | A | 1 |
| I-76 | C | 1 |
| I-77 | A | 1 |
| I-78 | A | 1 |
| I-79 | A | 1 |
| I-80 | A | 1 |
| I-81 | A | 1 |
| I-82 | A | 1 |
| I-83 | A | 1 |
| I-84 | A | 1 |
| I-85 | A | 1 |

TABLE 13-continued

| CTG Results | | |
|---|---|---|
| I-# | CTG Cell Viability Assay - RS411: $IC_{50}$ (μM) | CTG Cell Viability Assay - RS411: Duration (days) |
| I-86 | A | 1 |
| I-87 | A | 1 |
| I-88 | E | 1 |
| I-89 | A | 1 |
| I-91 | E | 1 |
| I-92 | A | 1 |
| I-93 | A | 1 |
| I-94 | A | 1 |
| I-96 | E | 1 |
| I-97 | A | 1 |
| I-98 | A | 1 |
| I-99 | A | 1 |
| I-100 | A | 1 |
| I-101 | A | 1 |
| I-102 | A | 1 |
| I-103 | A | 1 |
| I-104 | A | 1 |
| I-105 | E | 1 |
| I-106 | A | 1 |
| I-109 | A | 1 |
| I-110 | A | 1 |
| I-111 | A | 1 |
| I-112 | A | 1 |
| I-113 | A | 1 |
| I-114 | A | 1 |
| I-115 | A | 1 |
| I-116 | E | 1 |
| I-117 | A | 1 |
| I-118 | B | 1 |
| I-119 | A | 1 |
| I-120 | E | 1 |
| I-121 | A | 1 |
| I-122 | A | 1 |
| I-123 | A | 1 |
| I-124 | E | 1 |
| I-125 | A | 1 |
| I-126 | A | 1 |
| I-127 | E | 1 |
| I-128 | E | 1 |
| I-129 | E | 1 |
| I-130 | A | 1 |
| I-131 | B | 1 |
| I-134 | A | 1 |
| I-135 | E | 1 |
| I-136 | A | 1 |
| I-137 | A | 1 |
| I-138 | E | 1 |
| I-139 | A | 1 |
| I-140 | D | 1 |
| I-141 | E | 1 |
| I-142 | B | 1 |
| I-143 | A | 1 |
| I-144 | B | 1 |
| I-146 | C | 1 |
| I-147 | A | 1 |
| I-148 | A | 1 |
| I-149 | A | 1 |
| I-150 | A | 1 |
| I-151 | C | 1 |
| I-152 | D | 1 |
| I-153 | A | 1 |
| I-154 | A | 1 |
| I-155 | A | 1 |
| I-156 | E | 1 |
| I-157 | A | 1 |
| I-158 | A | 1 |
| I-159 | A | 1 |
| I-160 | A | 1 |
| I-161 | A | 1 |
| I-163 | A | 1 |
| I-164 | A | 1 |

TABLE 13-continued

| CTG Results | | |
|---|---|---|
| I-# | CTG Cell Viability Assay - RS411: $IC_{50}$ (μM) | CTG Cell Viability Assay - RS411: Duration (days) |
| I-165 | E | 1 |
| I-166 | D | 1 |
| I-167 | E | 1 |
| I-168 | A | 1 |
| I-169 | E | 1 |
| I-170 | C | 1 |
| I-171 | A | 1 |
| I-172 | E | 1 |
| I-173 | C | 1 |
| I-174 | A | 1 |
| I-175 | E | 1 |
| I-176 | A | 1 |
| I-177 | A | 1 |
| I-178 | A | 1 |
| I-179 | A | 1 |
| I-180 | A | 1 |
| I-181 | E | 1 |
| I-182 | A | 1 |
| I-183 | A | 1 |
| I-184 | B | 1 |
| I-185 | A | 1 |
| I-186 | A | 1 |
| I-187 | A | 1 |
| I-188 | E | 1 |
| I-189 | A | 1 |
| I-190 | E | 1 |
| I-191 | E | 1 |
| I-192 | A | 1 |
| I-193 | A | 1 |
| I-194 | A | 1 |
| I-195 | E | 1 |
| I-196 | A | 1 |
| I-197 | E | 1 |
| I-198 | A | 1 |
| I-199 | E | 1 |
| I-200 | E | 1 |
| I-201 | A | 1 |
| I-202 | E | 1 |
| I-203 | A | 1 |
| I-204 | A | 1 |
| I-205 | A | 1 |
| I-206 | A | 1 |
| I-207 | A | 1 |
| I-208 | E | 1 |
| I-209 | E | 1 |
| I-210 | A | 1 |
| I-211 | A | 1 |
| I-212 | E | 1 |
| I-213 | E | 1 |
| I-214 | B | 1 |
| I-224 | A | 1 |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A method of degrading MDM2 protein in a patient or biological sample comprising administering to said patient, or contacting said biological sample with a compound of formula I-bbb-4:

I-bbb-4

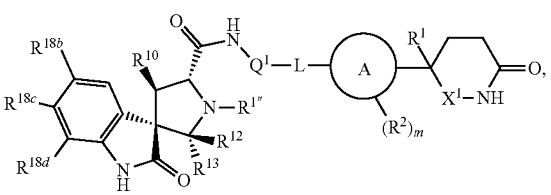

or a pharmaceutical composition thereof, wherein:

$X^1$ is —C(O)—;

$R^1$ is hydrogen;

each $R^2$ is independently $C_{1-6}$ aliphatic, halogen, —CN, or —$OC_{1-6}$ aliphatic;

m is 0, 1, or 2;

Ring A is

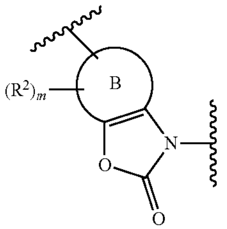

or

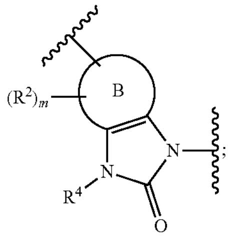

;

$R^4$ is $C_{1-6}$ aliphatic;

Ring B is a fused ring selected from 6-membered aryl or heteroaryl containing 1-2 heteroatoms independently selected from nitrogen, oxygen, and sulfur;

$R^{1''}$ is selected from hydrogen and $C_{1-6}$ aliphatic;

$R^{10}$ is

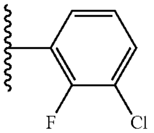

or

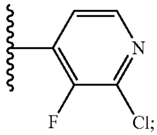

;

$R^{12}$ and $R^{13}$ are taken together to form

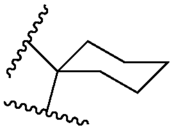

or

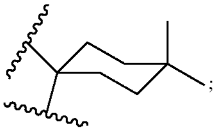

;

$R^{18b}$, $R^{18c}$, and $R^{18d}$ are each independently selected from hydrogen, halogen, $C_{1-6}$ aliphatic, and —$OC_{1-6}$ aliphatic;

$Q^1$ is a bivalent group selected from alkylenyl, phenylenyl, cycloalkylenyl, and heterocyclenyl; and L is

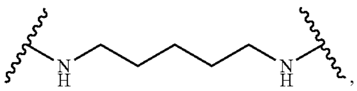

,

-continued

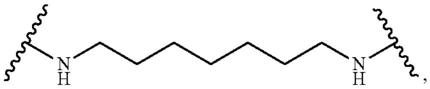

,

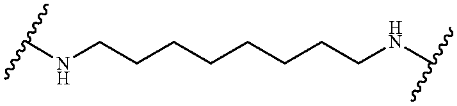

,

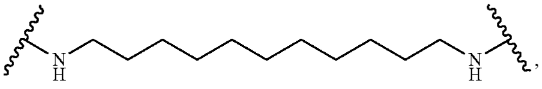

,

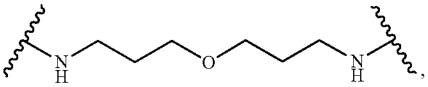

,

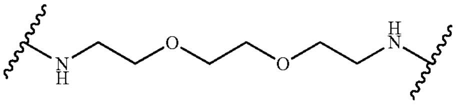

,

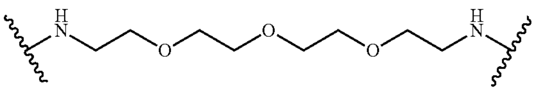

,

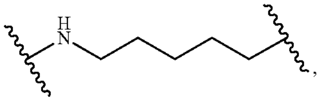

,

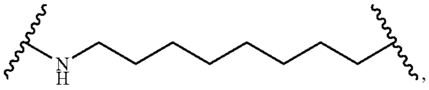

,

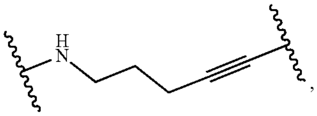

,

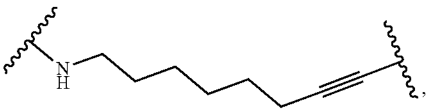

,

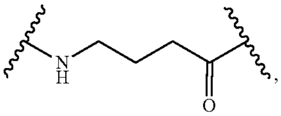

,

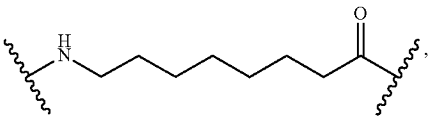

,

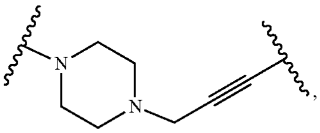

,

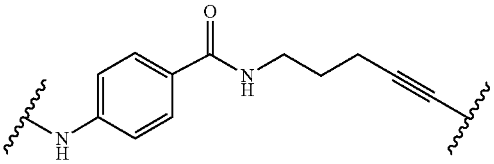

,

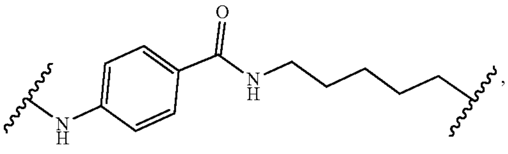

,

-continued
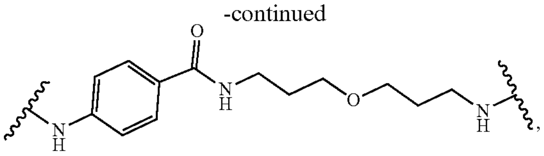
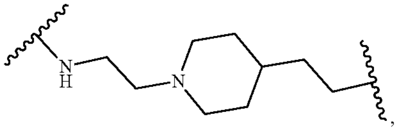
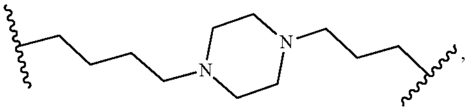
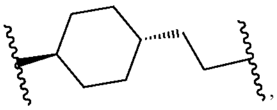
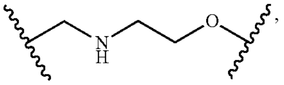
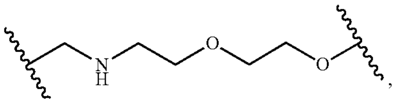
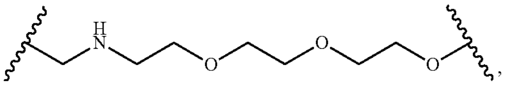
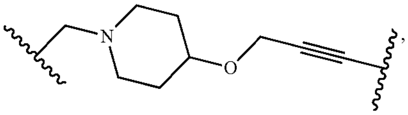
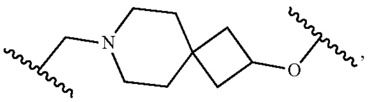
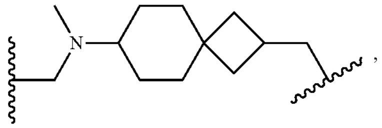
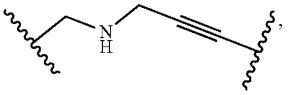
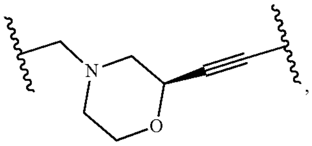
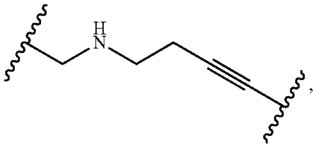
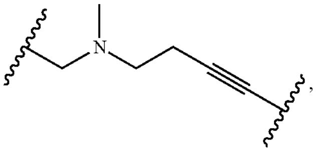
-continued
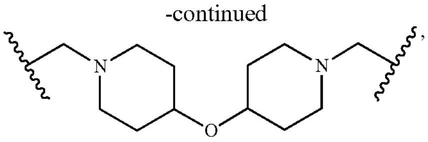
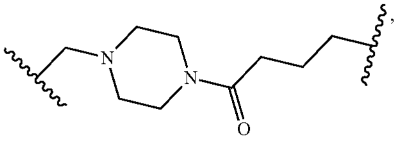
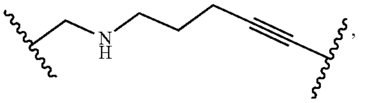
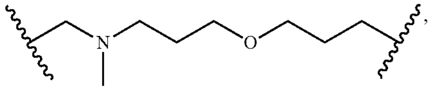
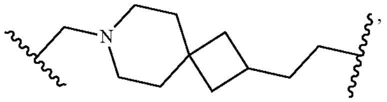
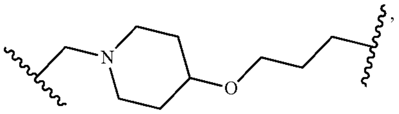
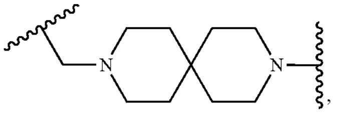
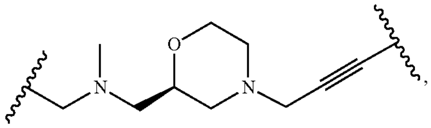
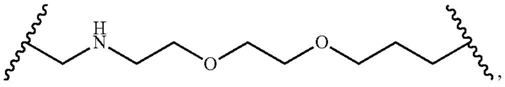
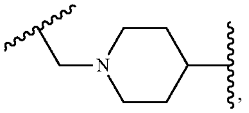
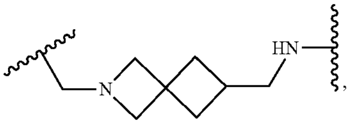
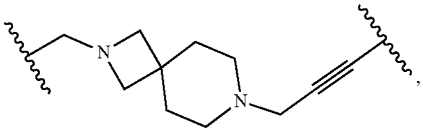
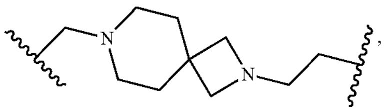
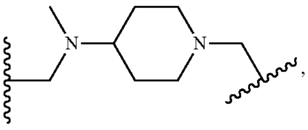
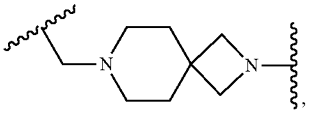

-continued
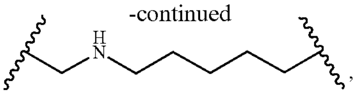,
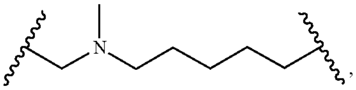,
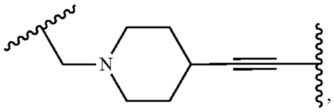,
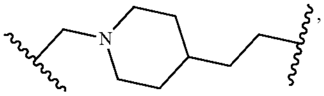,
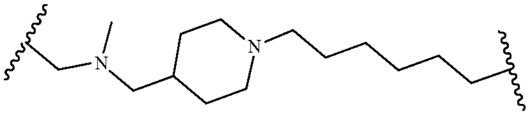,
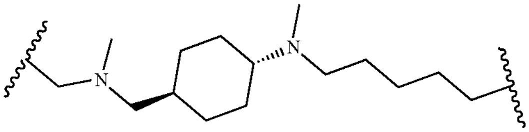,
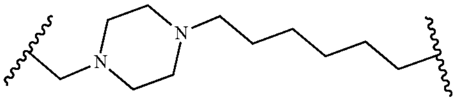,
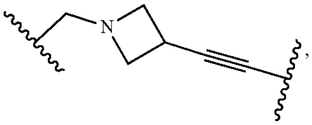,
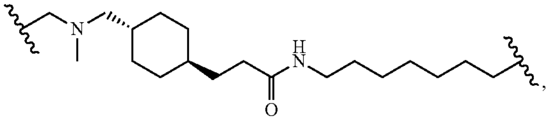,
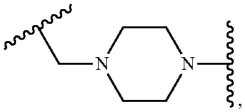,
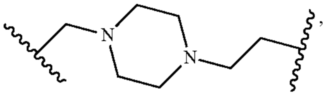,
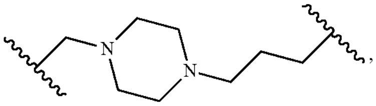,
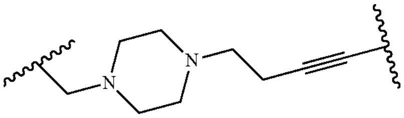,
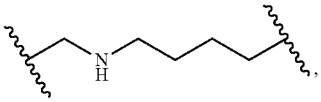,
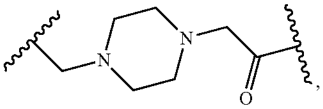,
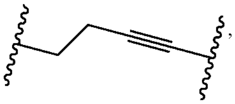,
-continued
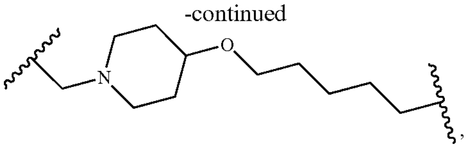,
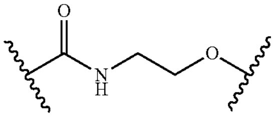,
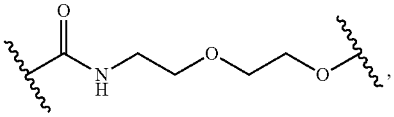,
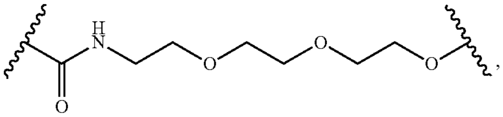,
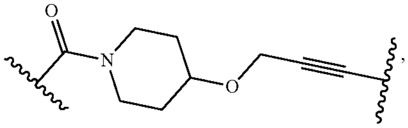,
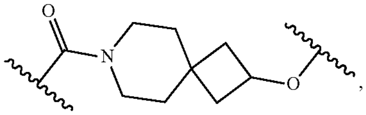,
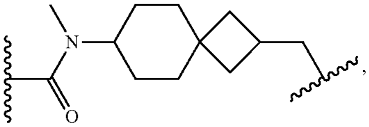,
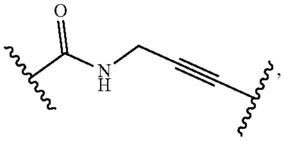,
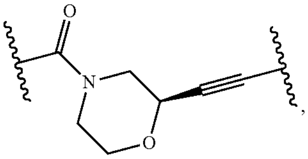,
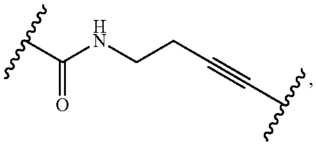,
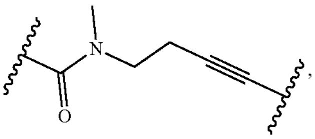,
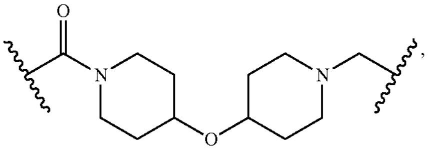,
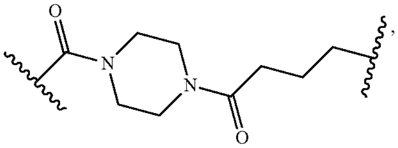, -continued
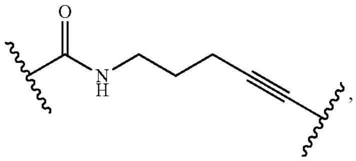
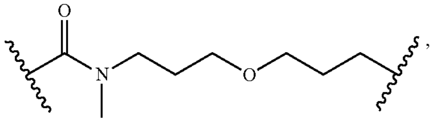
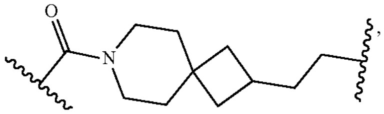
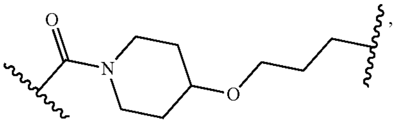
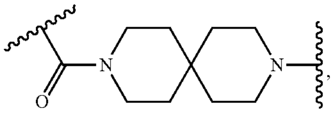
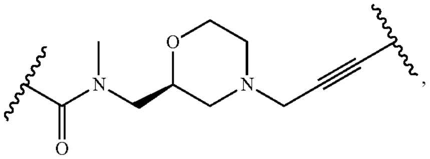
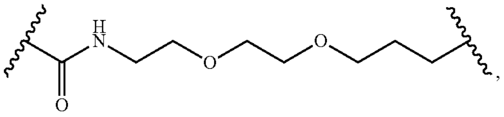
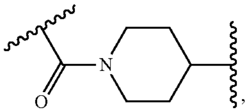
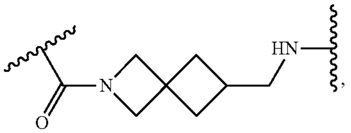
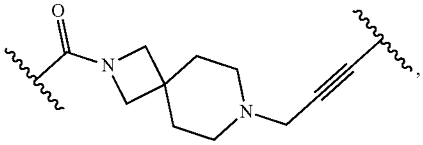
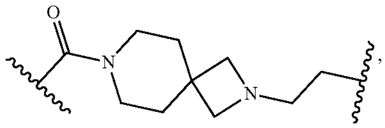
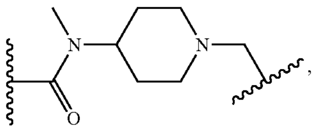
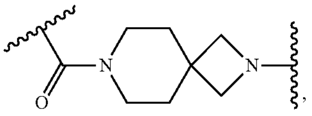
-continued
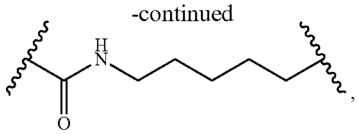
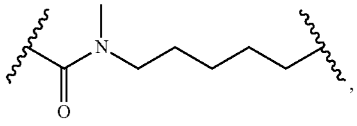
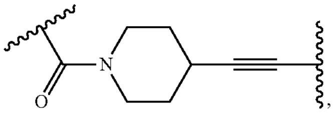
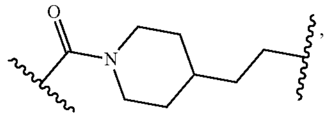
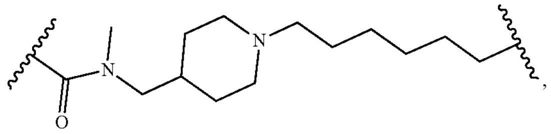
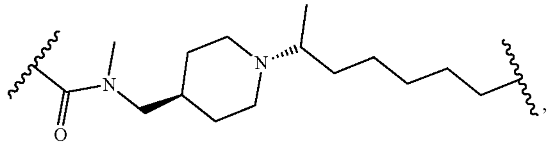
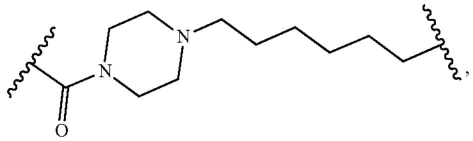
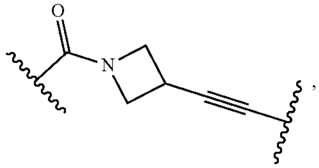
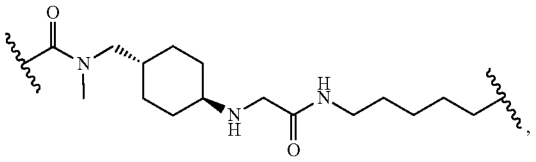
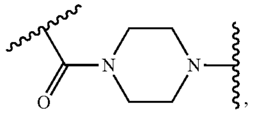
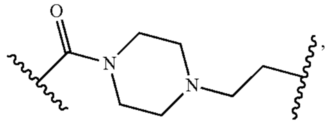
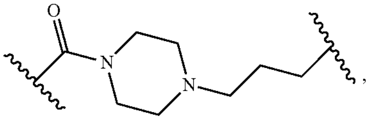
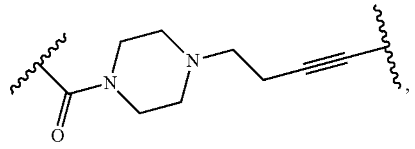

-continued

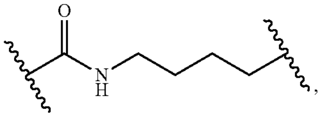,

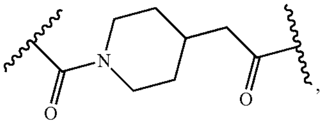,

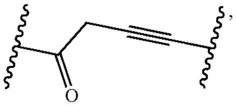, or

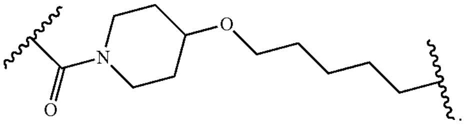.

2. A method of treating an MDM2-mediated disorder, disease, or condition in a patient, comprising administering to said patient a compound of formula I-bbb-4:

I-bbb-4

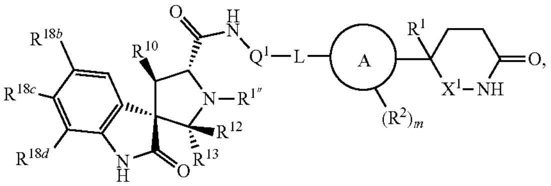

or a pharmaceutical composition thereof, wherein:

$X^1$ is —C(O)—;

$R^1$ is hydrogen;

each $R^2$ is independently $C_{1-6}$ aliphatic, halogen, —CN, or —$OC_{1-6}$ aliphatic;

m is 0, 1, or 2;

Ring A is

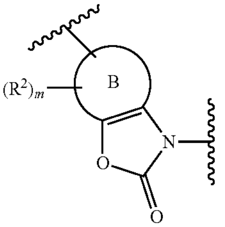 or 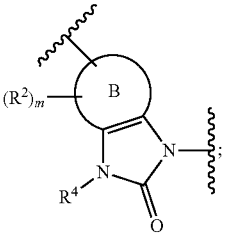;

$R^4$ is $C_{1-6}$ aliphatic;

Ring B is a fused ring selected from 6-membered aryl or heteroaryl containing 1-2 heteroatoms independently selected from nitrogen, oxygen, and sulfur;

$R^{1''}$ is selected from hydrogen and $C_{1-6}$ aliphatic;

$R^{10}$ is

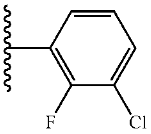 or 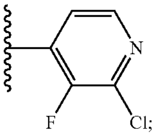;

$R^{12}$ and $R^{13}$ are taken together to form

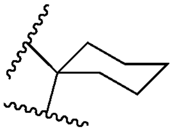 or 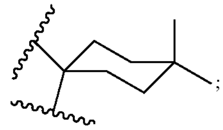;

$R^{18b}$, $R^{18c}$, and $R^{18d}$ are each independently selected from hydrogen, halogen, $C_{1-6}$ aliphatic, and —$OC_{1-6}$ aliphatic;

$Q^1$ is a bivalent group selected from alkylenyl, phenylenyl, cycloalkylenyl, and heterocyclenyl; and L is

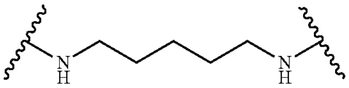,

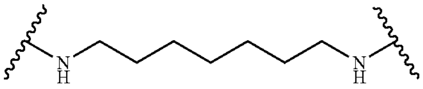,

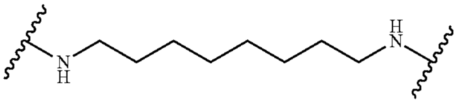,

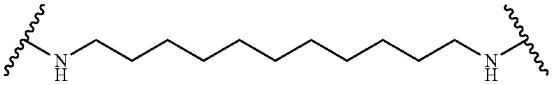,

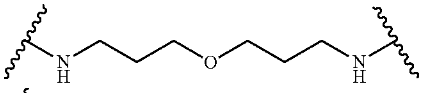,

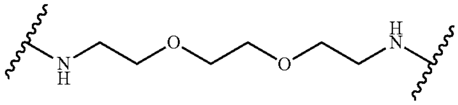,

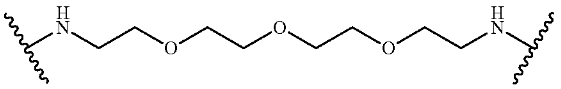,

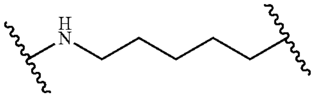,

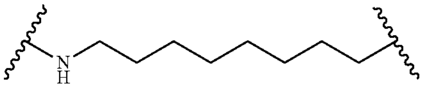,

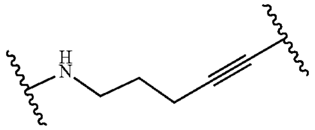,

-continued
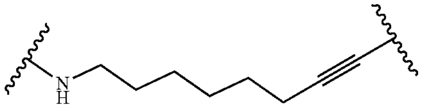,
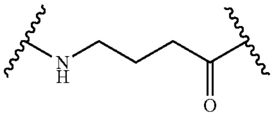,
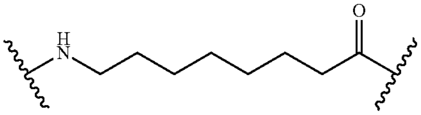,
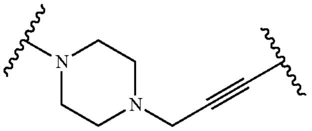,
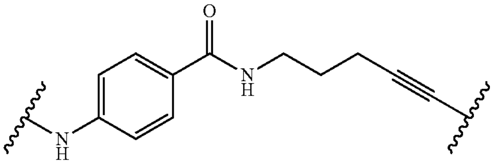,
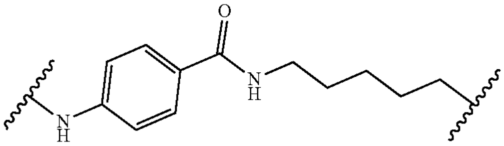,
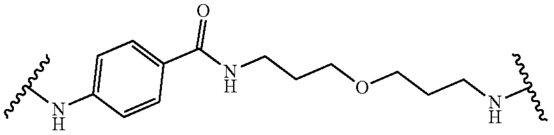,
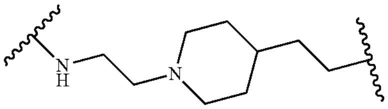,
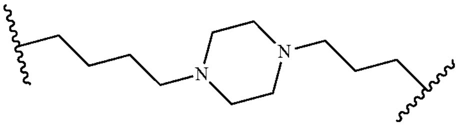,
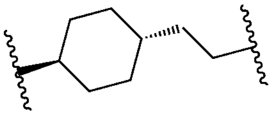,
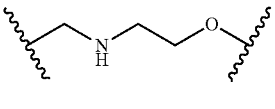,
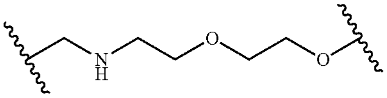,
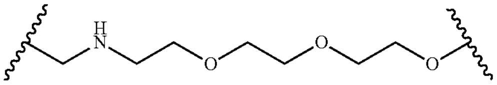,
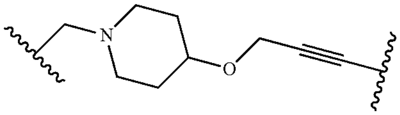,
-continued
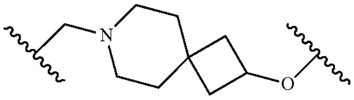,
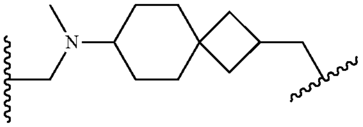,
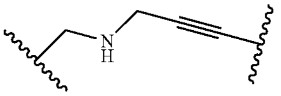,
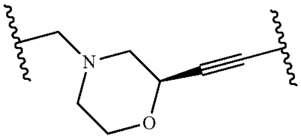,
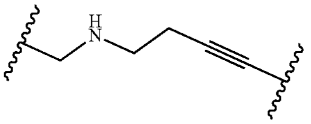,
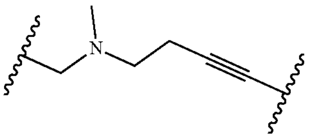,
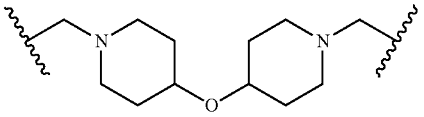,
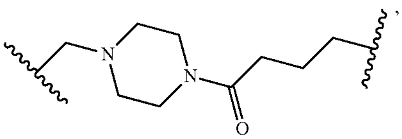,
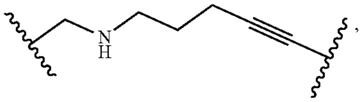,
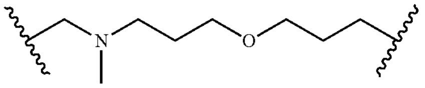,
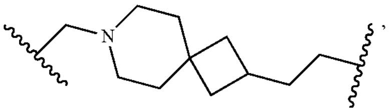,
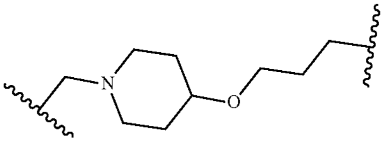,
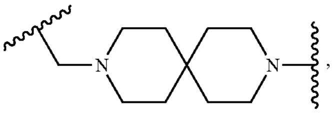,
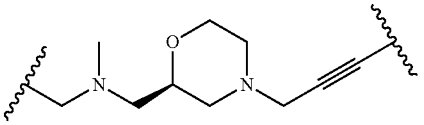, -continued
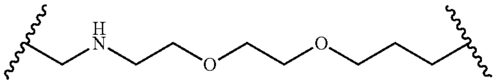
,
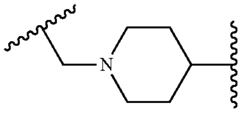
,
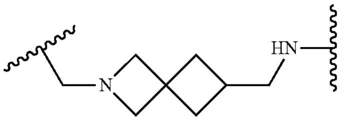
,
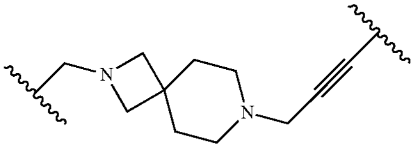
,
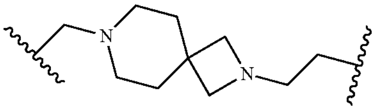
,
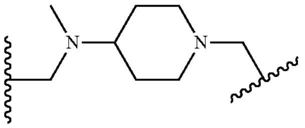
,
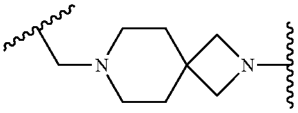
,
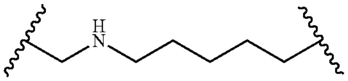
,
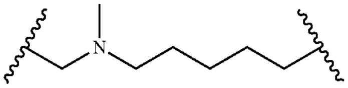
,
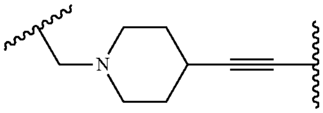
,
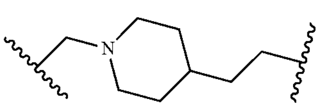
,
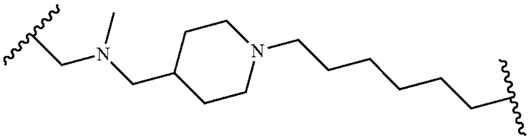
,
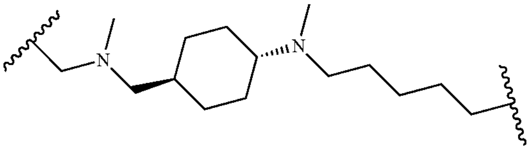
,
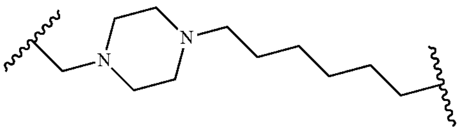
,
-continued
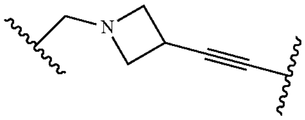
,
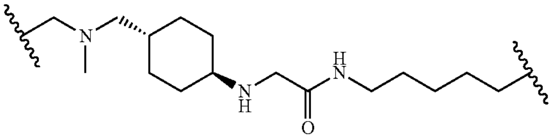
,
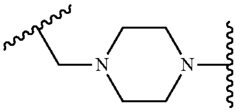
,
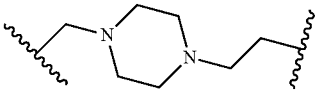
,
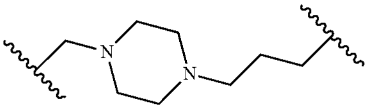
,
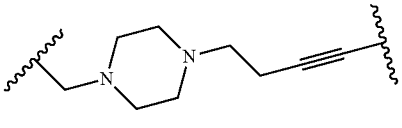
,
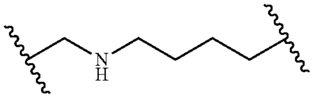
,
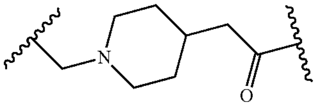
,
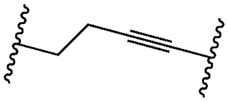
,
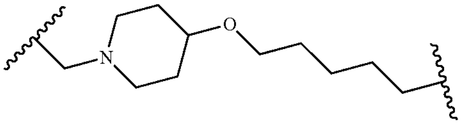
,
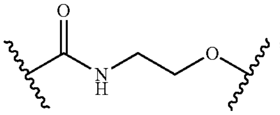
,
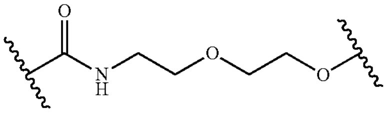
,
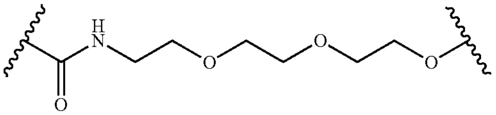
,
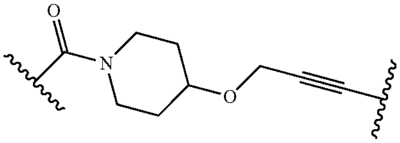
, -continued
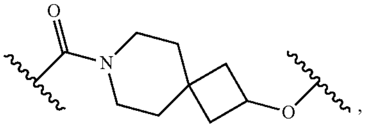
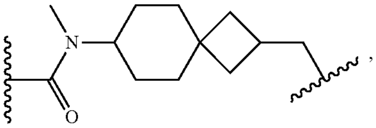
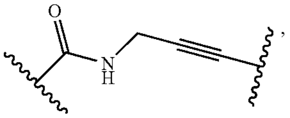
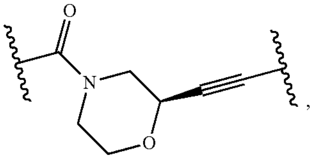
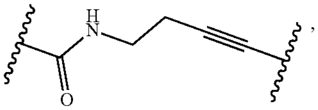
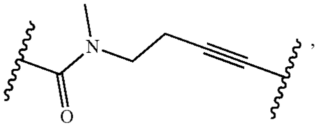
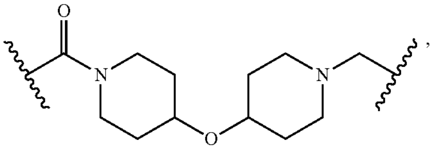
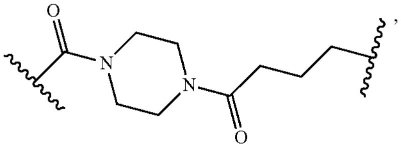
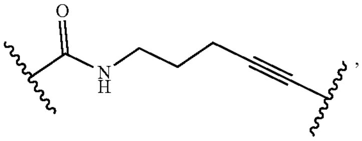
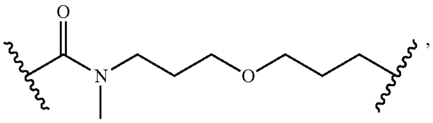
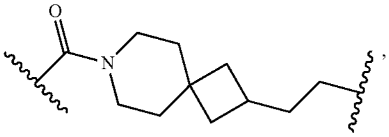
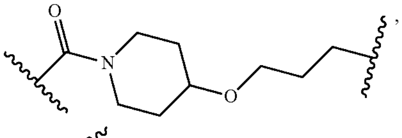
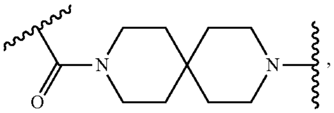
-continued
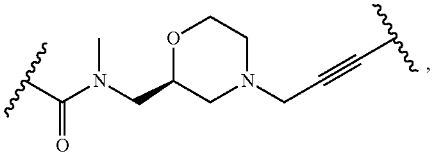
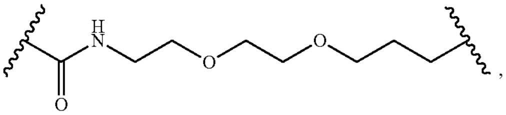
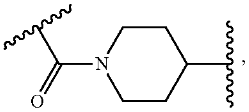
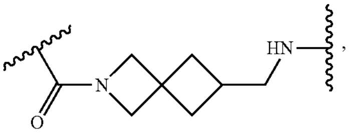
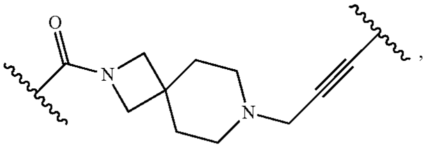
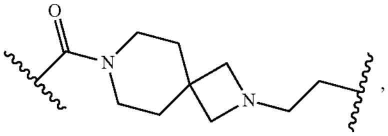
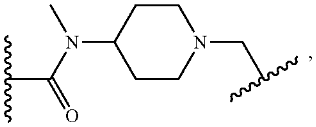
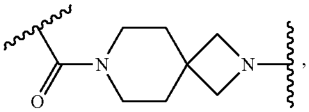
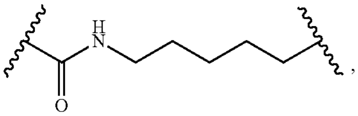
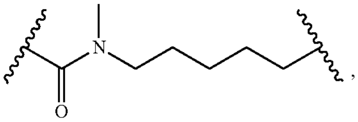
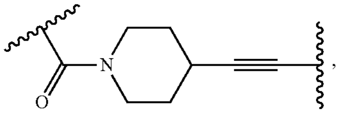
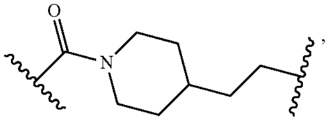
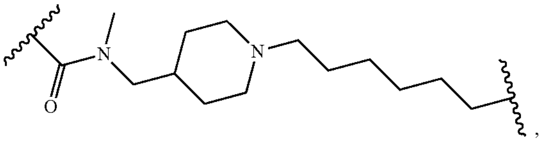

-continued
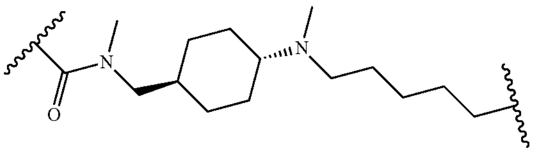
,
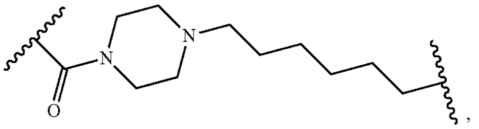
,
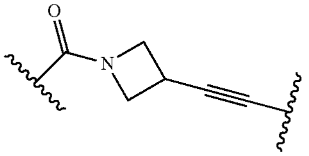
,
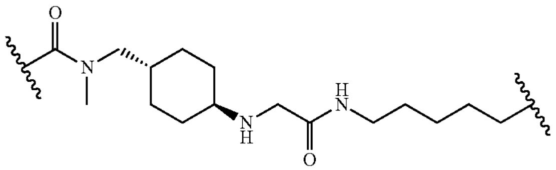
,
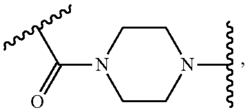
,
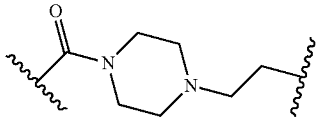
,
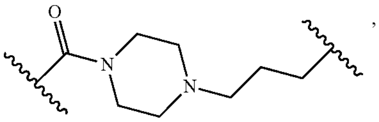
,
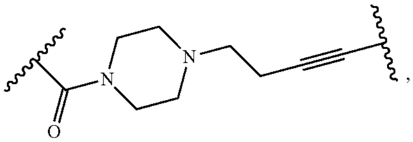
,
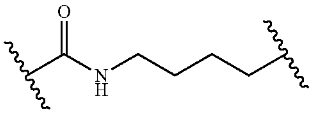
,
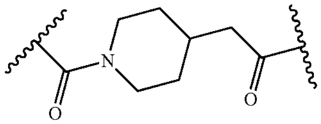
,
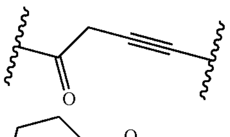
, or
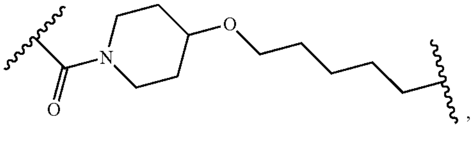
,
wherein the compound of formula I-bbb-4 effectuates degradation of MDM2 protein in the patient, and wherein the MDM2-mediated disorder, disease, or condition is cancer.
3. The method of claim 2, wherein $R^{12}$ and $R^{13}$ are taken together to form
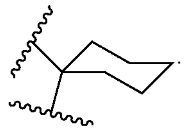 [SMILES: *C1(*)CCCCC1]
.
4. The method of claim 2, wherein $Q^1$ is
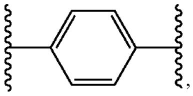
,
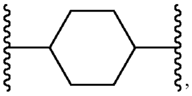
,
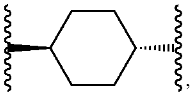
,
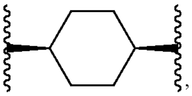
,
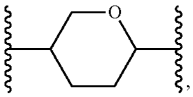
,
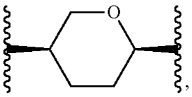
,
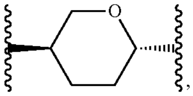
,
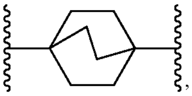
,
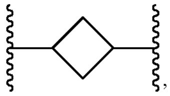
,
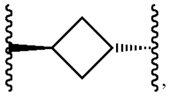
, or
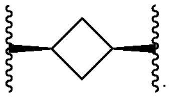
.
5. The method of claim 2, wherein L is
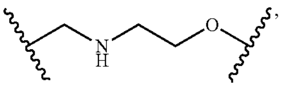
,
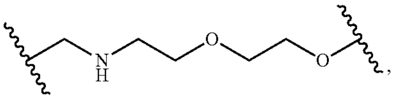
,
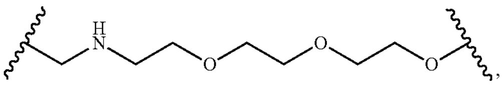
,
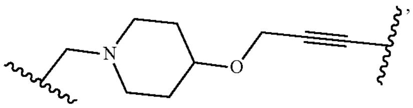
,
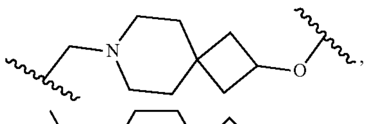
,
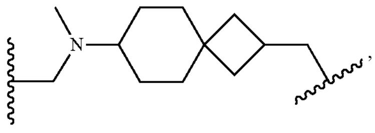
, -continued
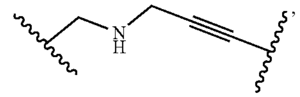,
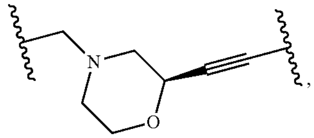,
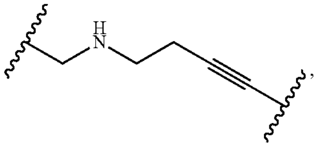,
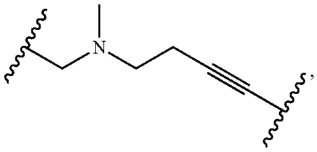,
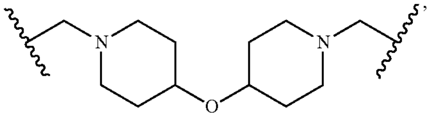,
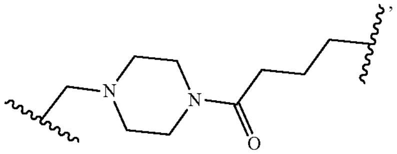,
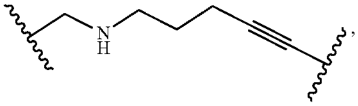,
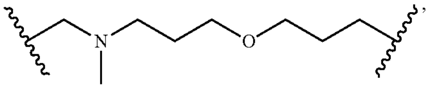,
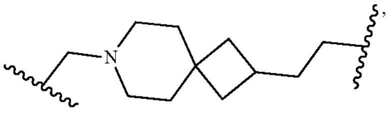,
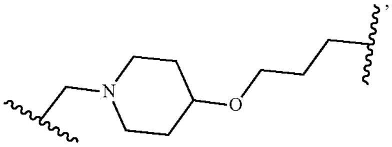,
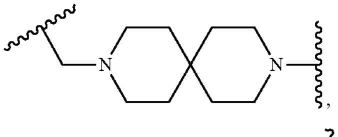,
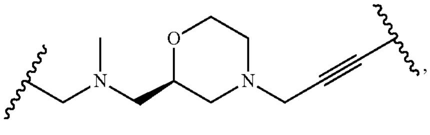,
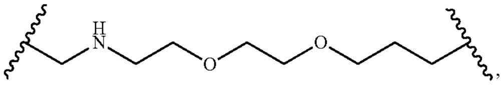,
-continued
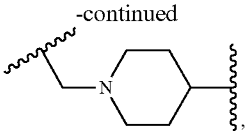,
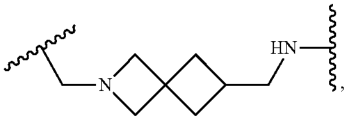,
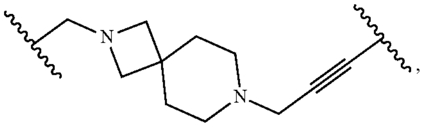,
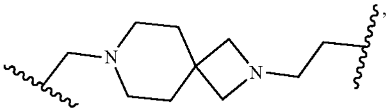,
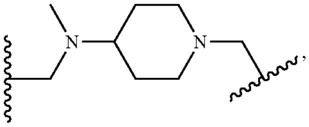,
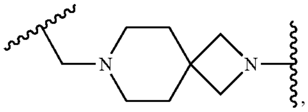,
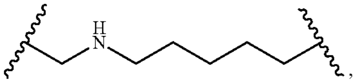,
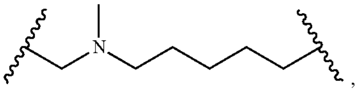,
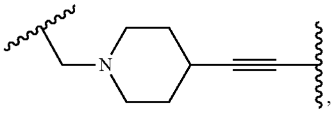,
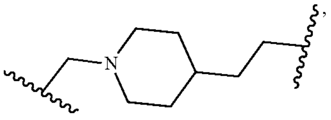,
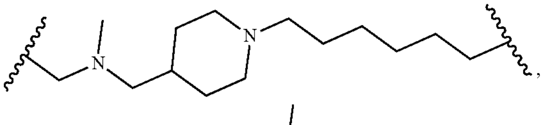,
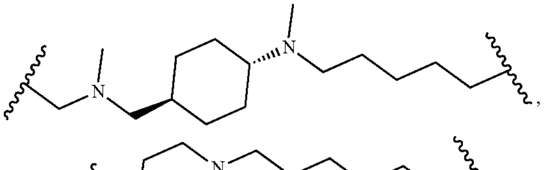,
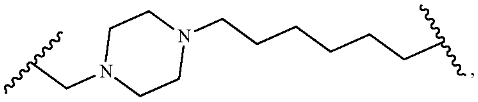,
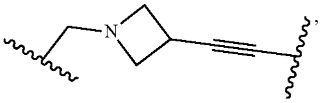,
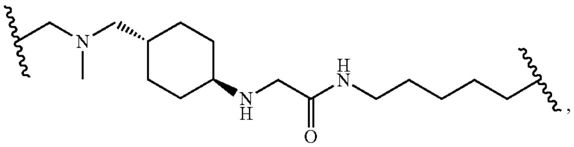, -continued
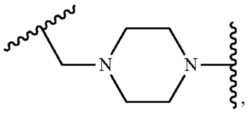,
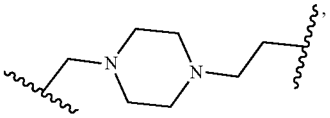,
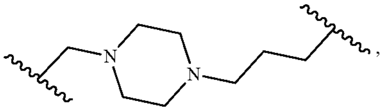,
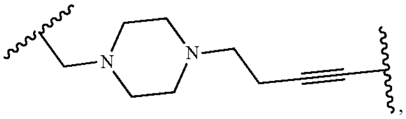,
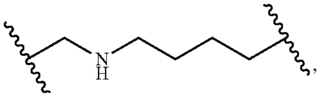,
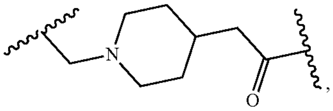, 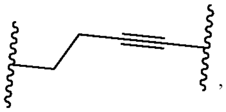,
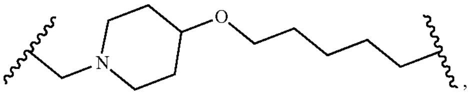,
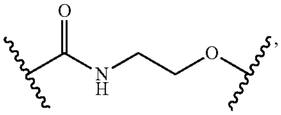,
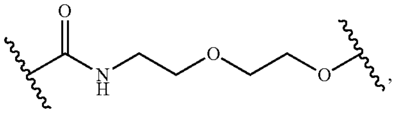,
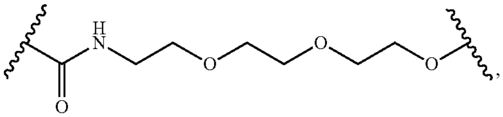,
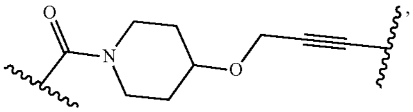,
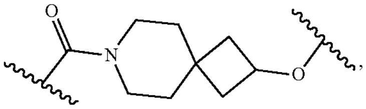,
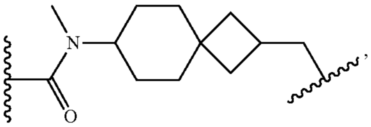,
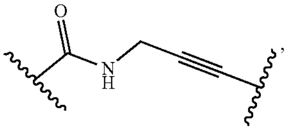,
-continued
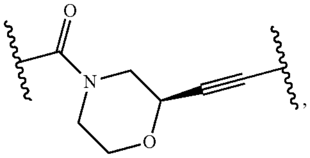,
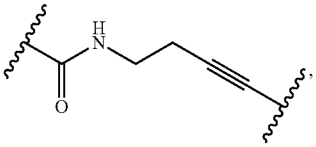,
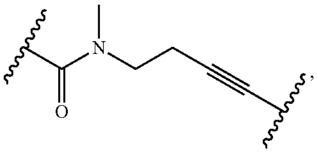,
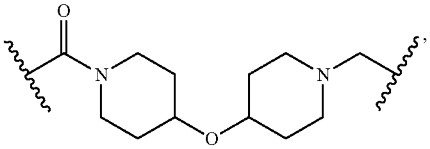,
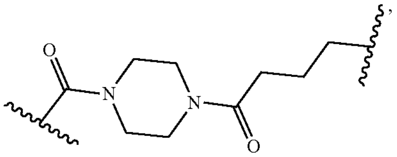,
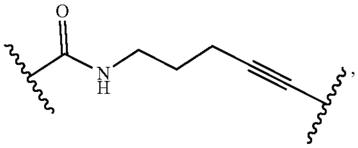,
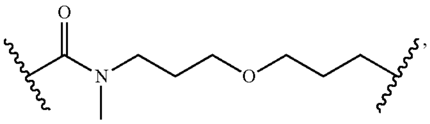,
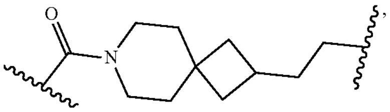,
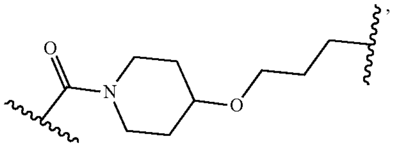,
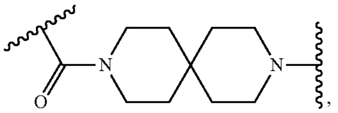,
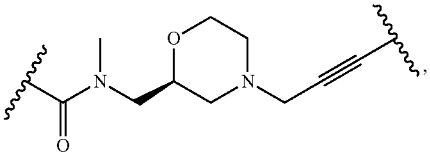,
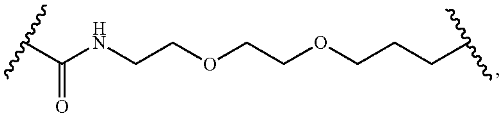, -continued
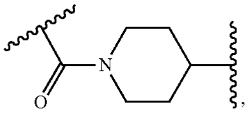,
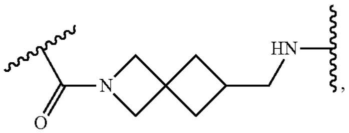,
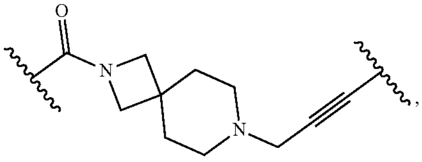,
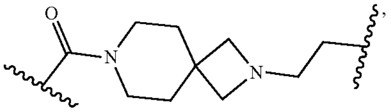,
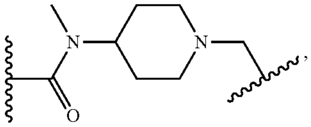,
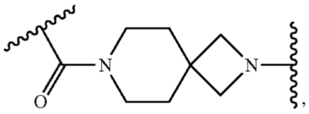,
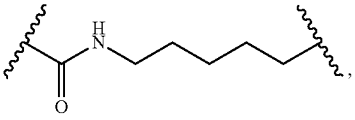,
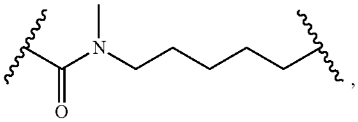,
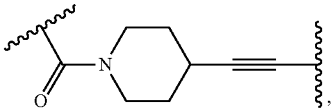,
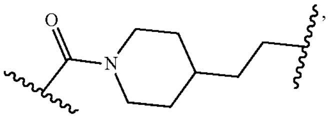,
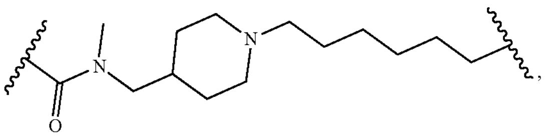,
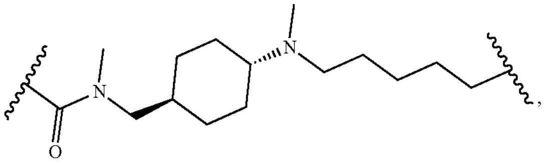,
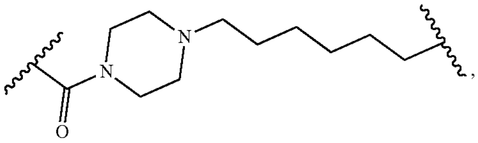,
-continued
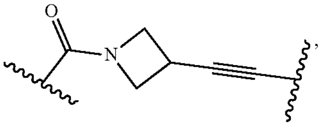,
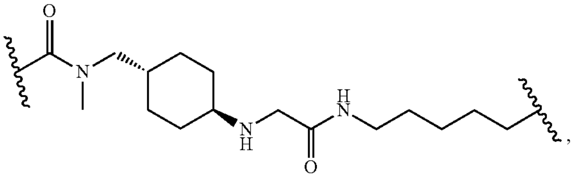,
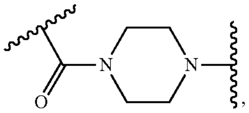,
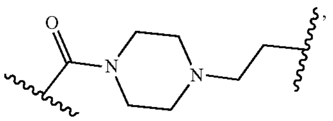,
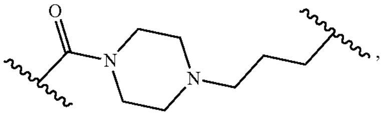,
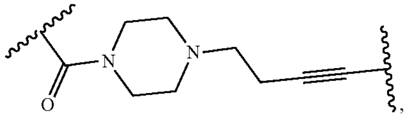,
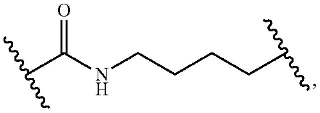,
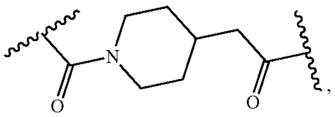,
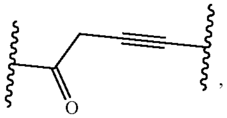, or
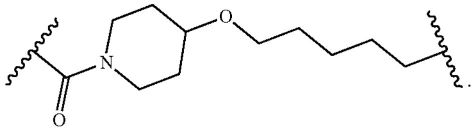.
6. The method of claim 2, wherein
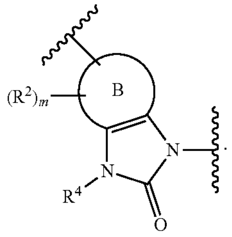.

7. The method of claim 2, wherein
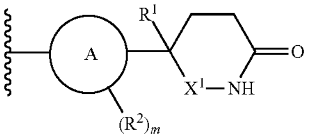
is
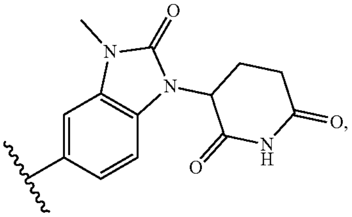
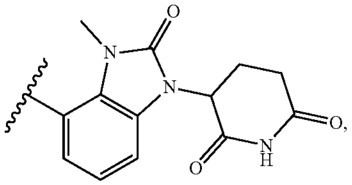
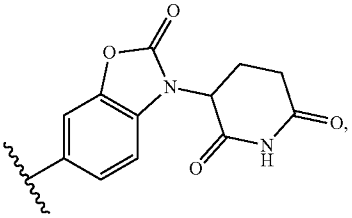
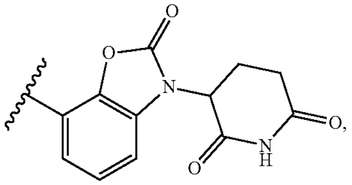
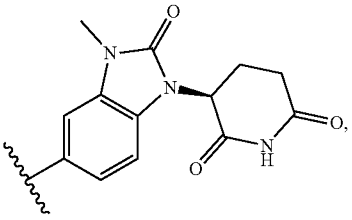
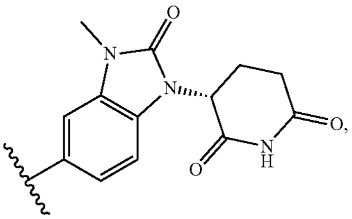
-continued
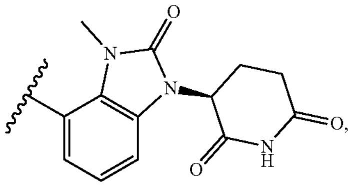
or
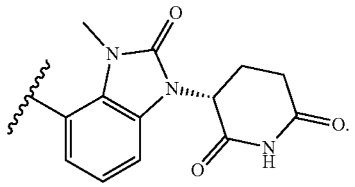
8. The method of claim 2, wherein the compound is a compound of formula I-bbb-5:
I-bbb-5
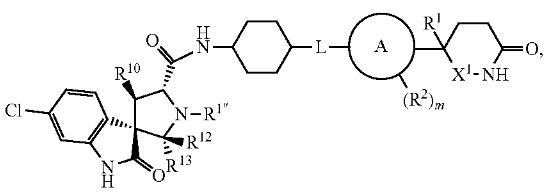
or a pharmaceutical composition thereof.
9. The method of claim 2, wherein the compound is any one of the following formulae:
I-bbb-7
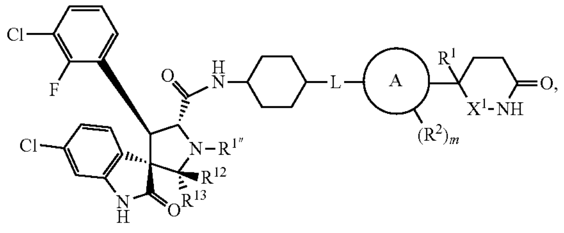
I-bbb-8
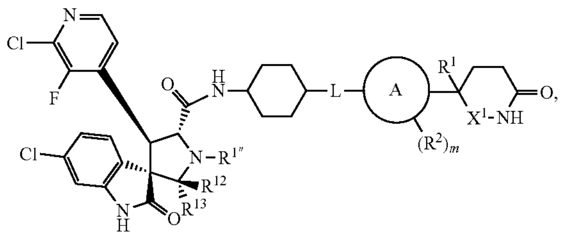
I-bbb-9
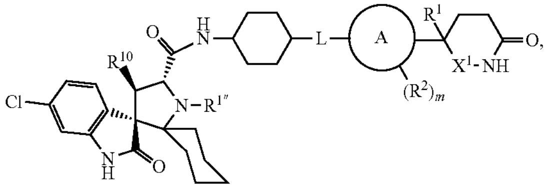

-continued
I-bbb-10
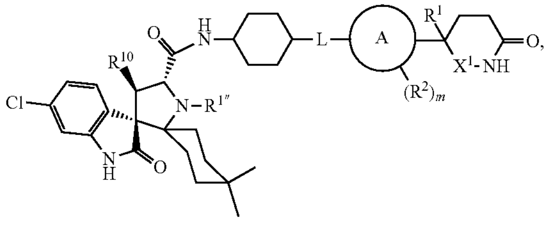
or a pharmaceutical composition thereof.
10. The method of claim 2, wherein the compound is a compound of formula I-bbb-6:
I-bbb-6
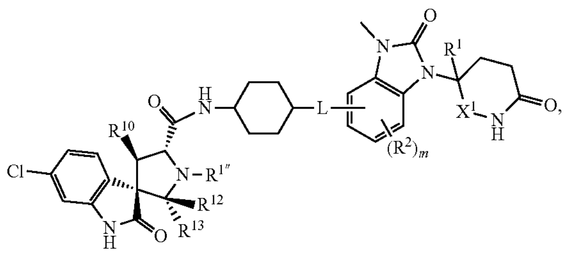
or a pharmaceutical composition thereof.
11. The method of claim 2, wherein the compound is any one of the following formulae:
I-bbb-11
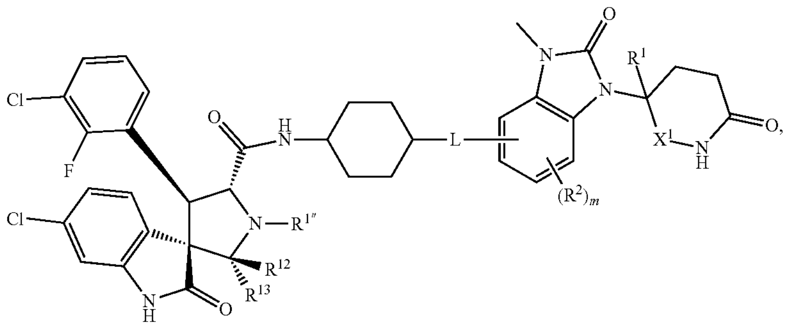
I-bbb-12
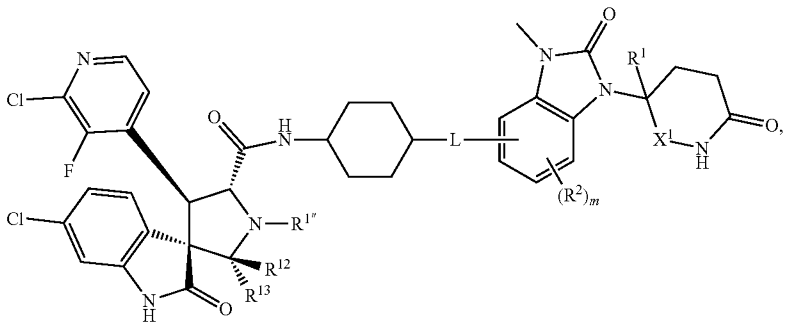
I-bbb-13
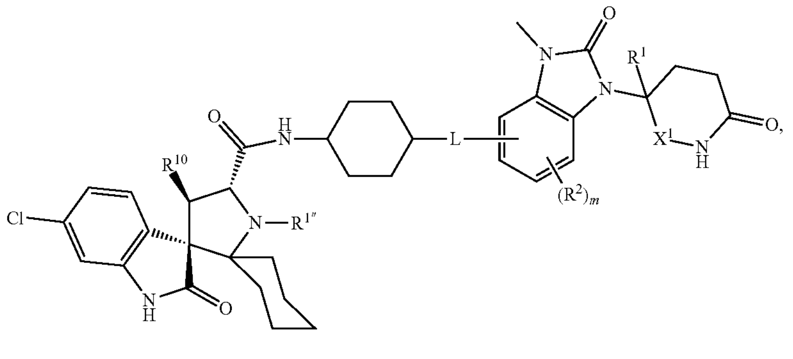

-continued
I-bbb-14
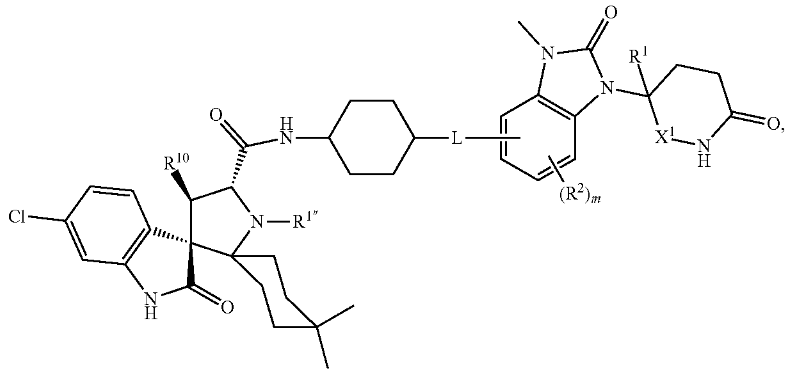
or a pharmaceutical composition thereof.
12. The method of claim 2, wherein the compound is:
I-9
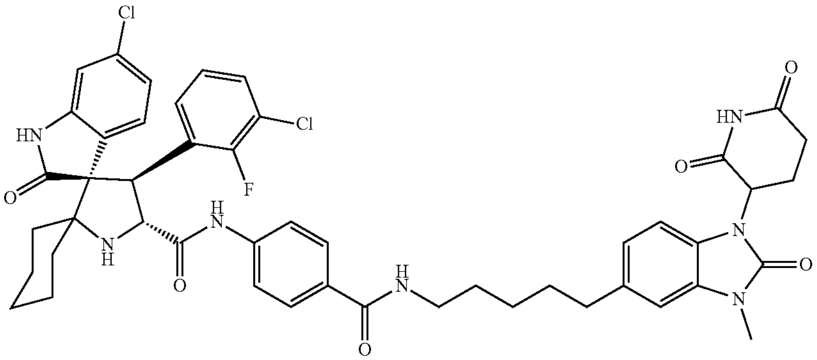
I-18
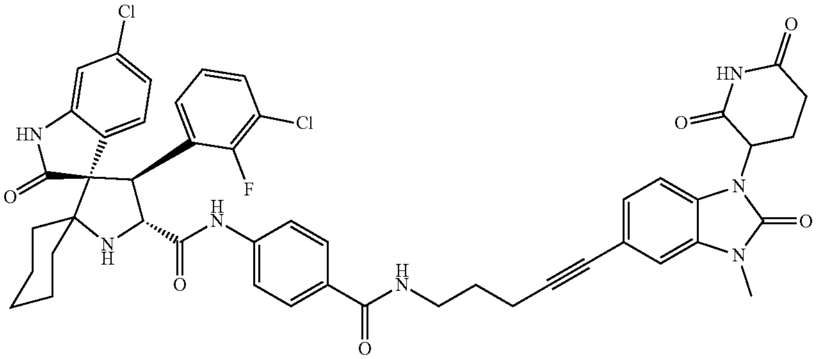
I-40
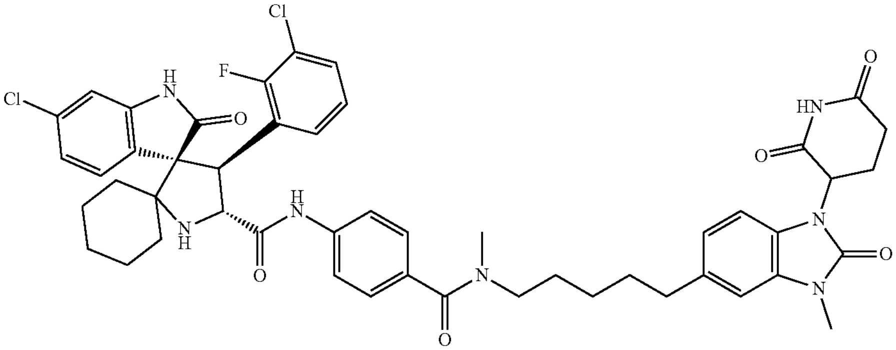

-continued
I-42
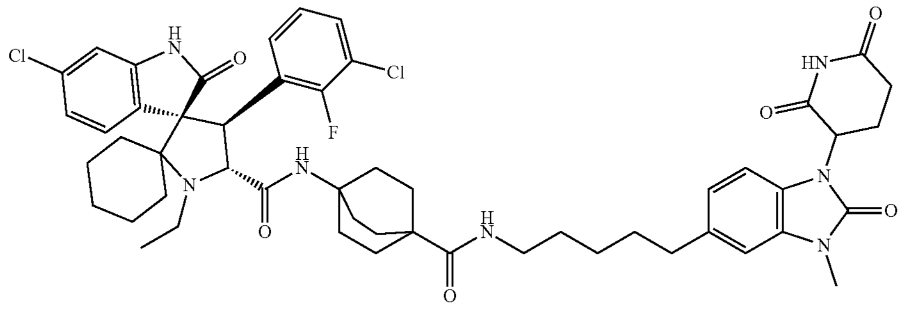
I-43
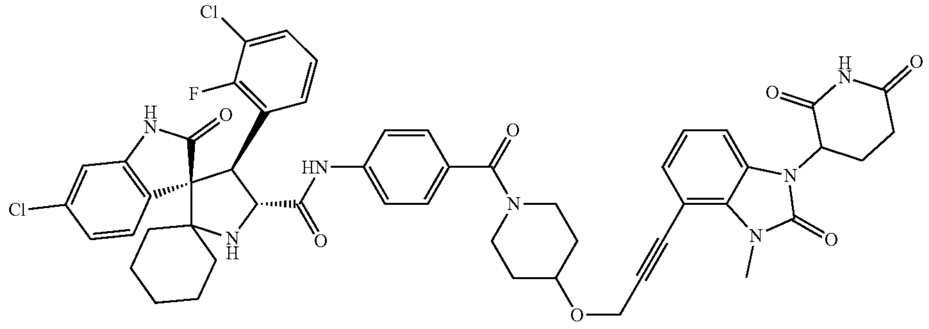
I-44
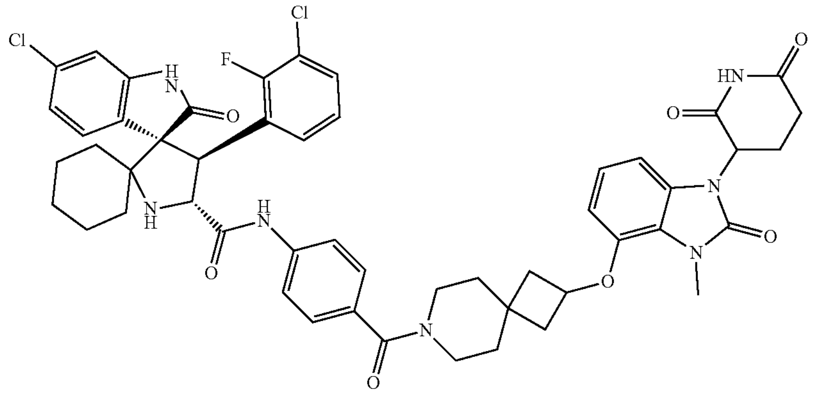
I-45
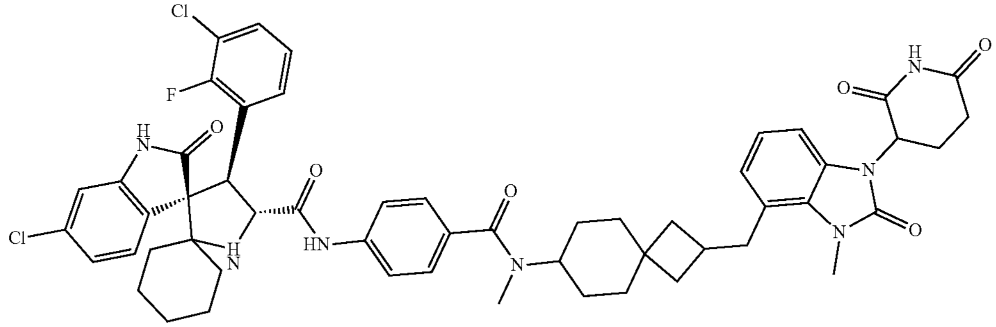

-continued
I-46
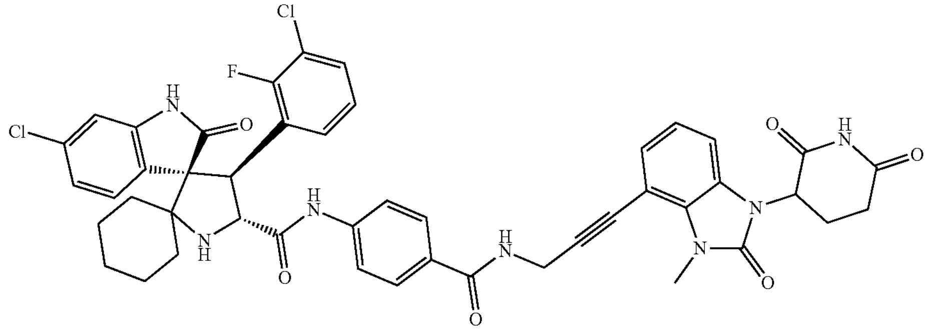
I-47
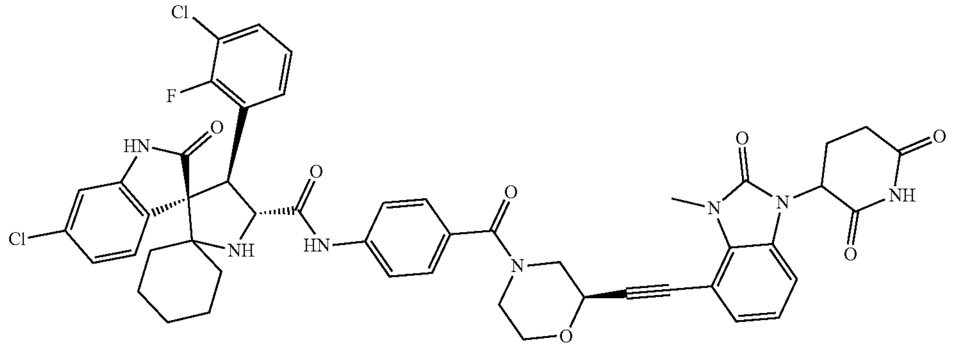
I-48
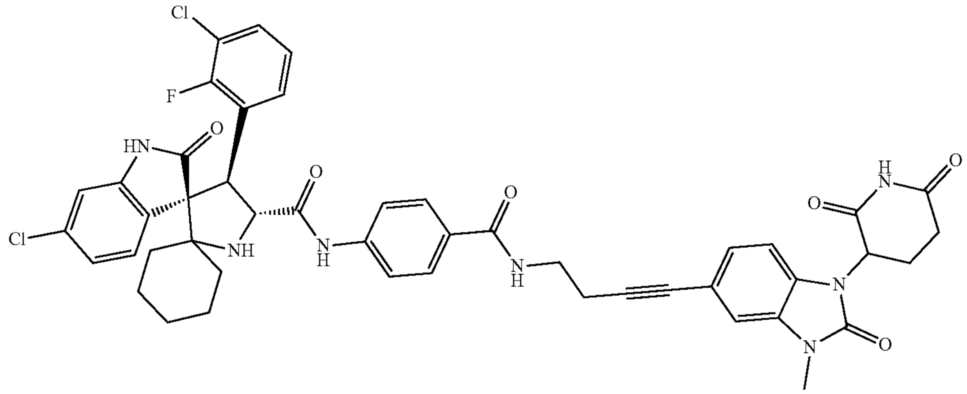
I-49
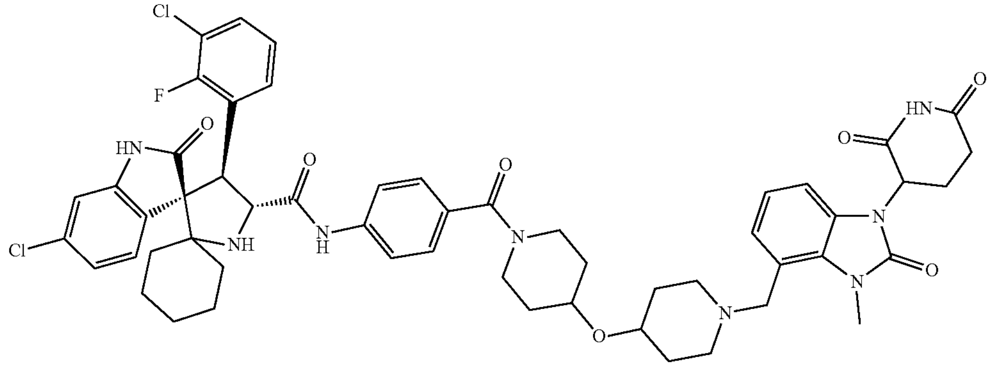

-continued
I-50
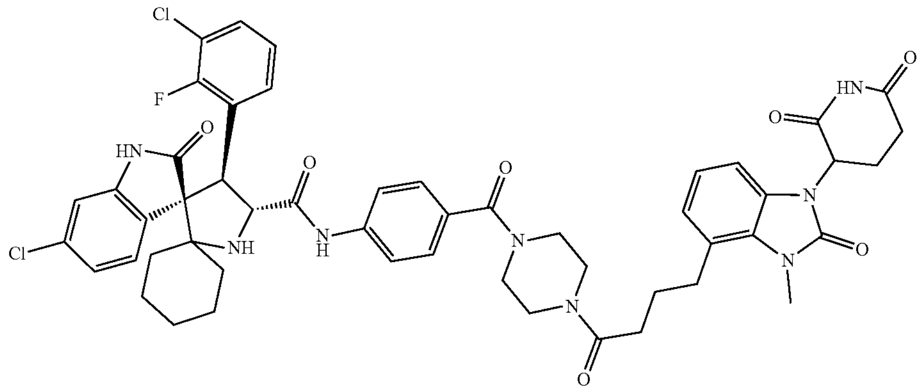
I-51
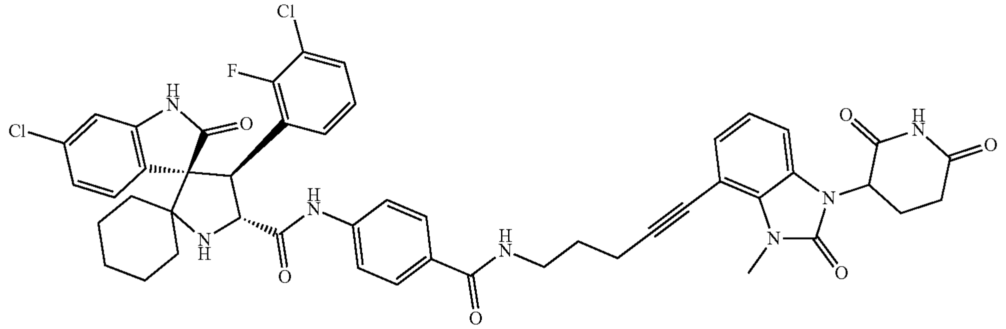
I-52
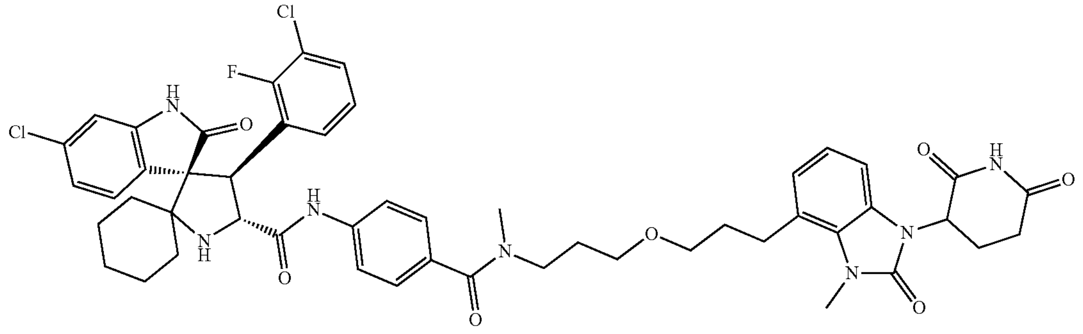
I-53
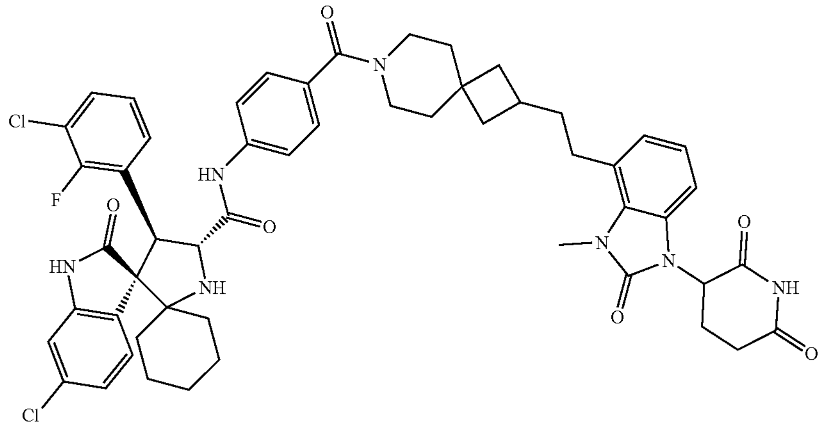

-continued
I-54
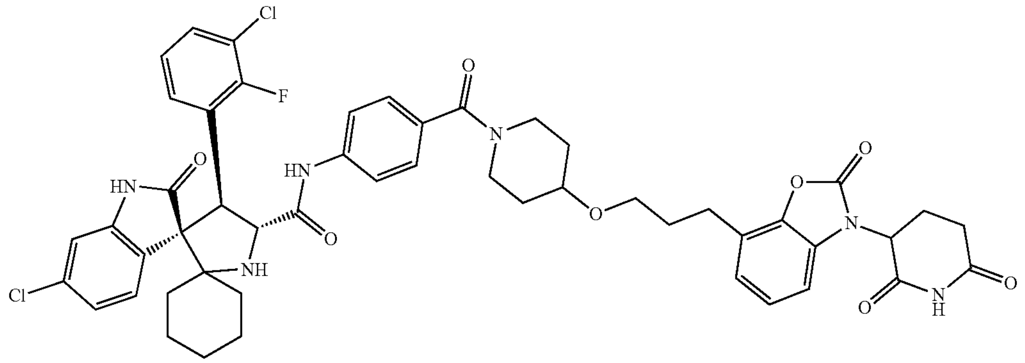
I-55
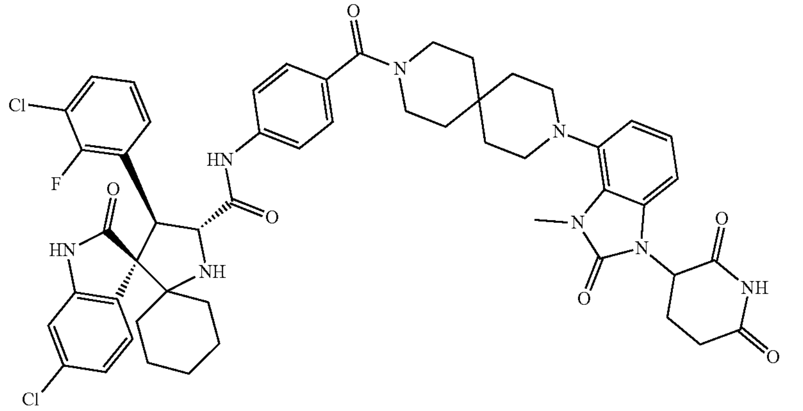
I-56
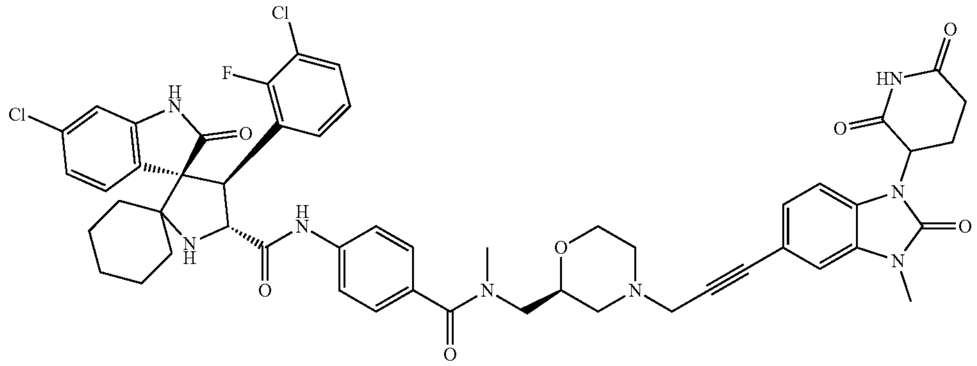
I-57
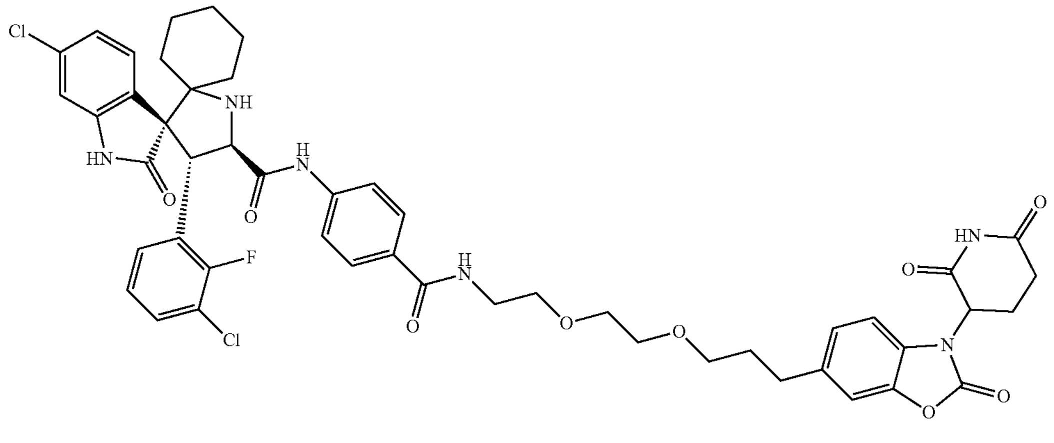

-continued
I-58
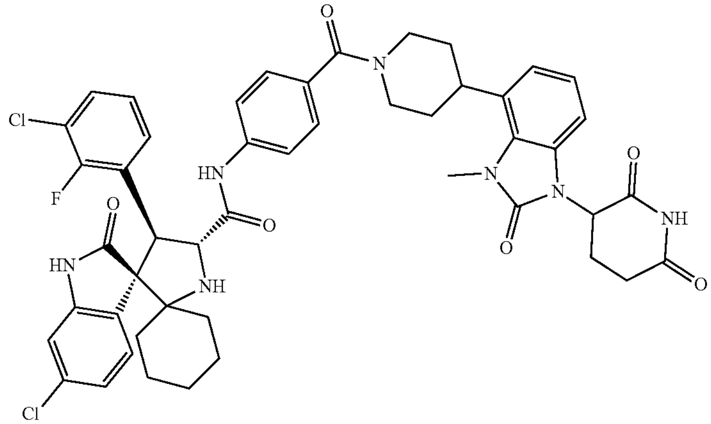
I-59
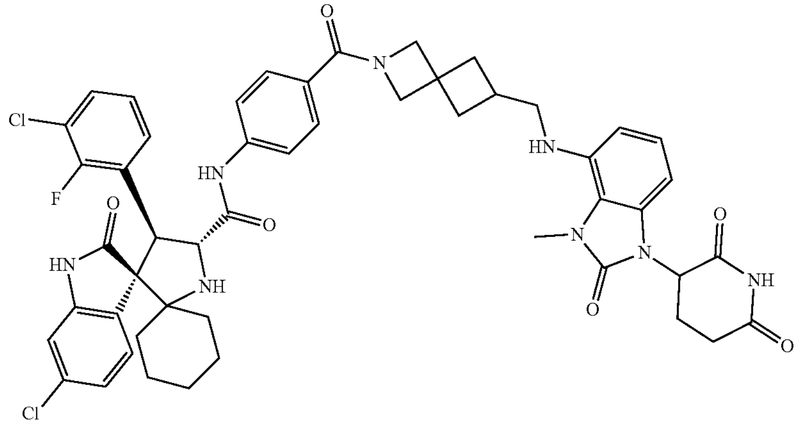
I-60
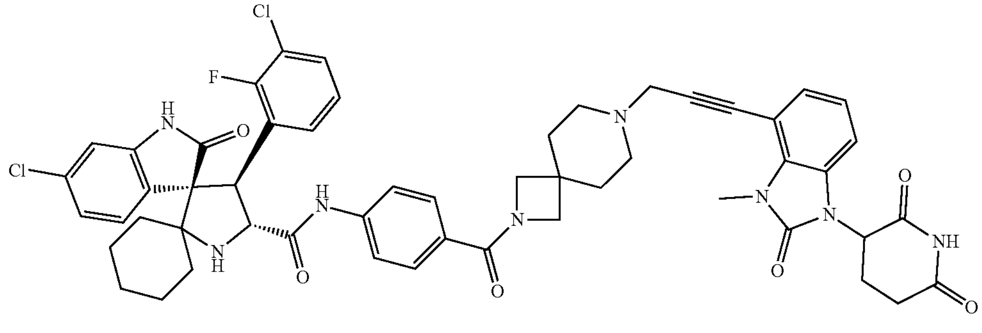
I-61
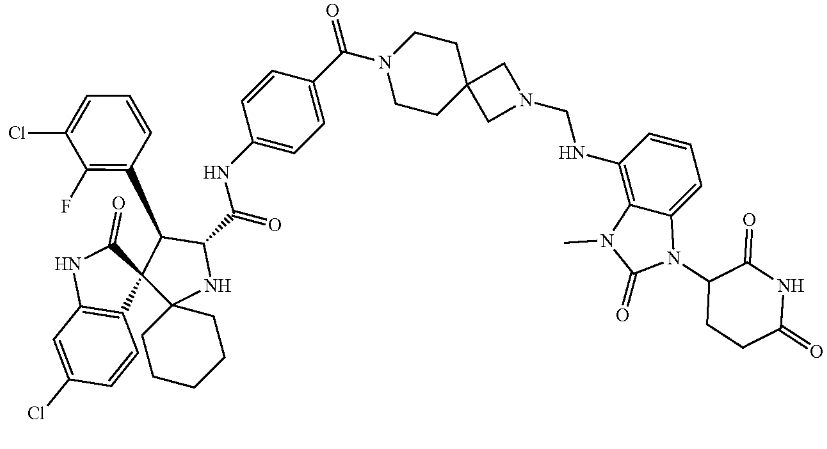

-continued
I-62
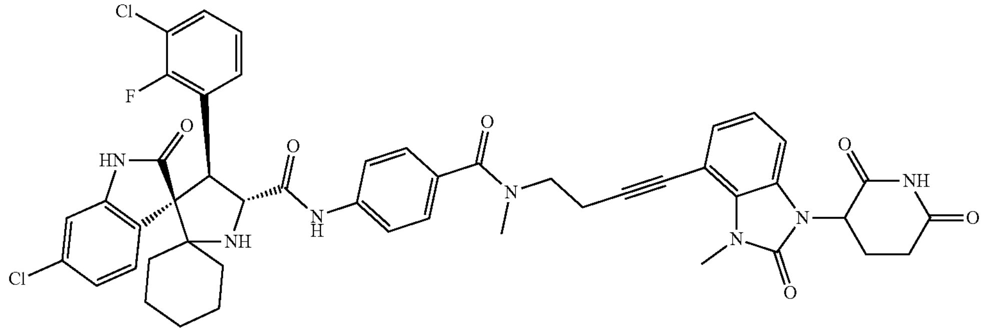
I-63
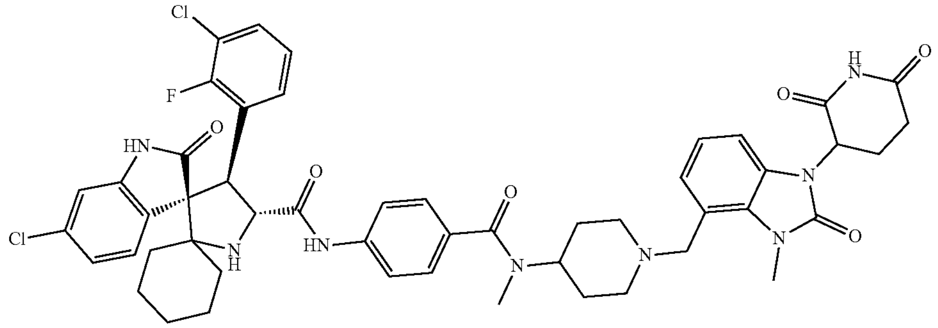
I-64
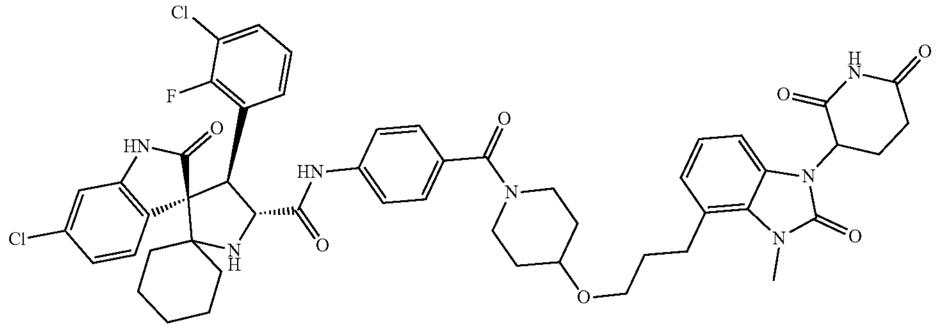
I-65
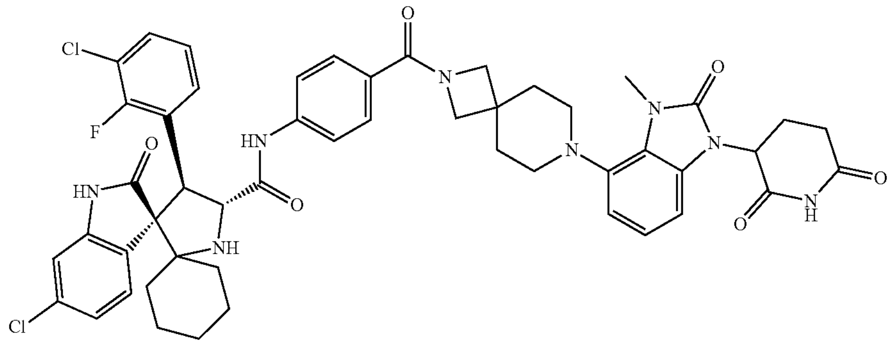

-continued
I-66
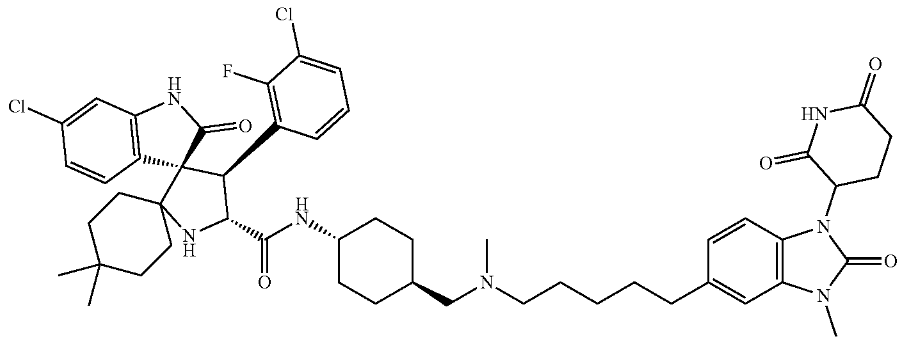
I-67
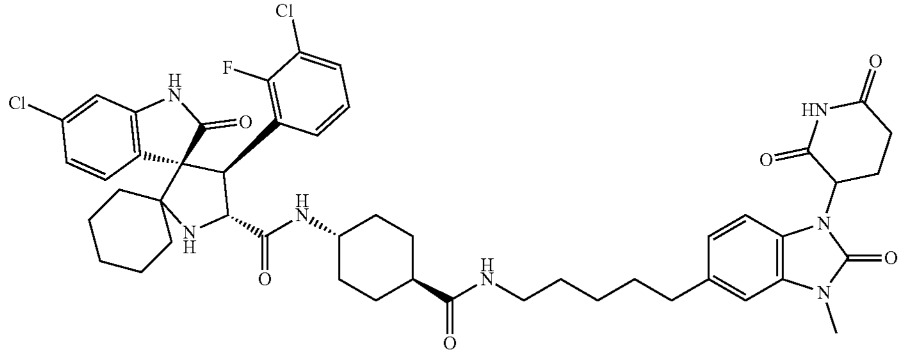
I-68
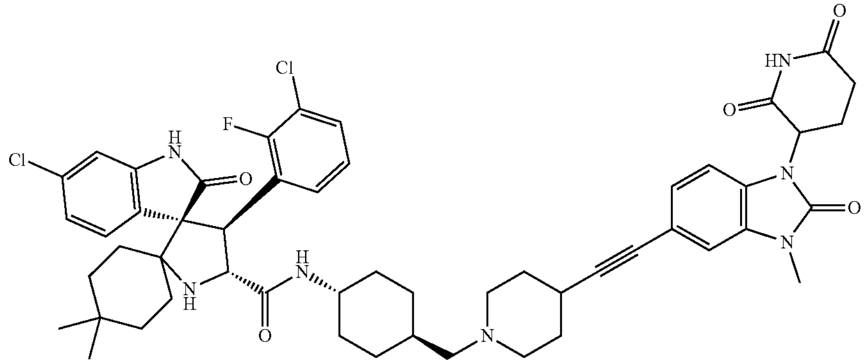
I-69
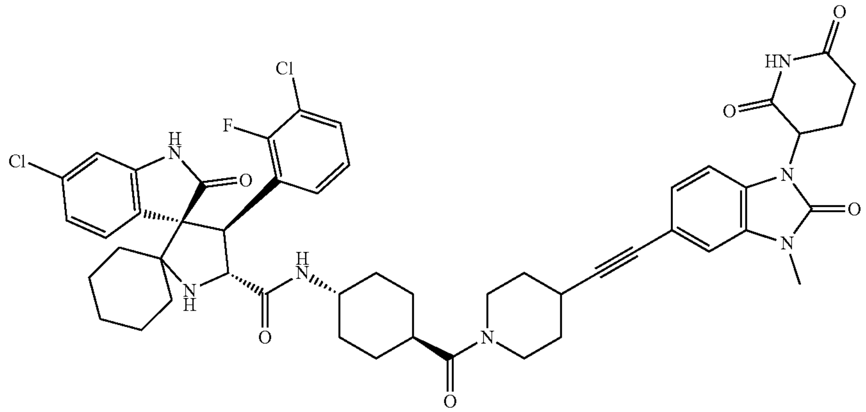

-continued
I-70
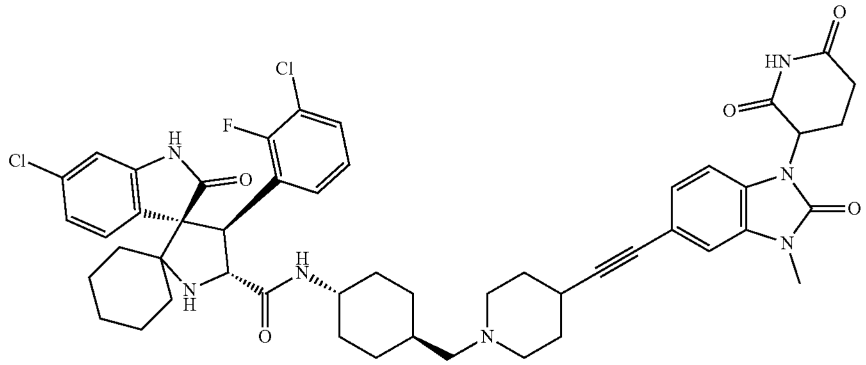
I-71
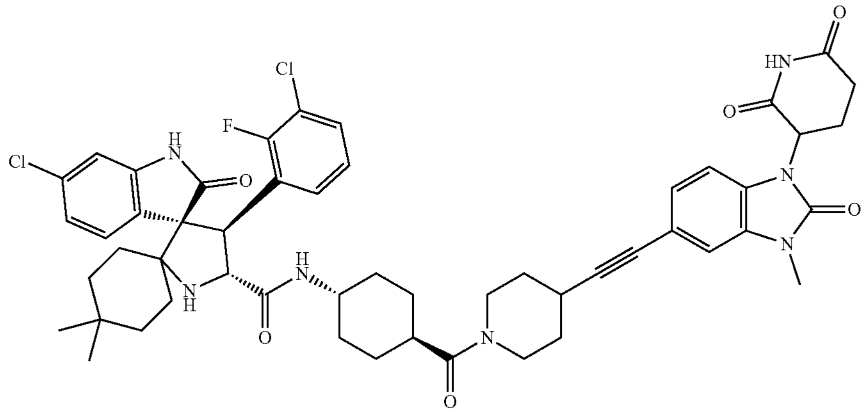
I-72
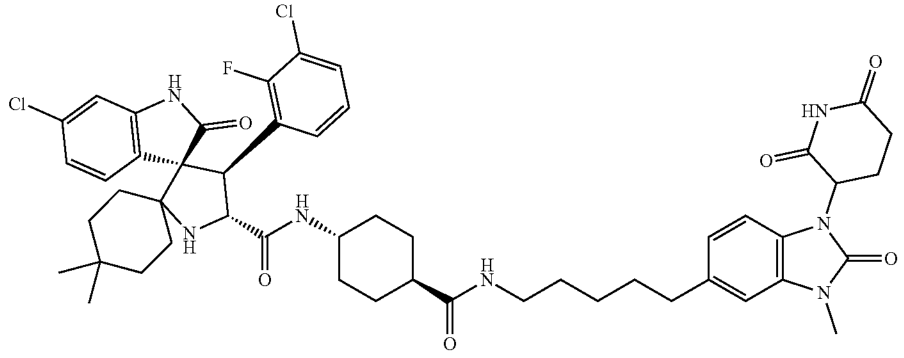
I-73
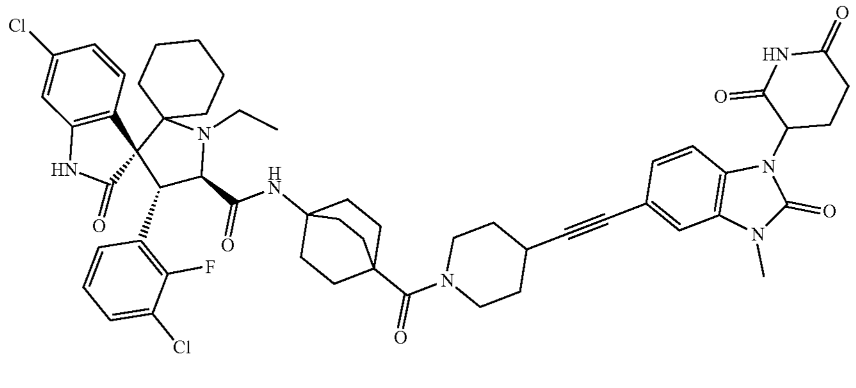

-continued
I-74
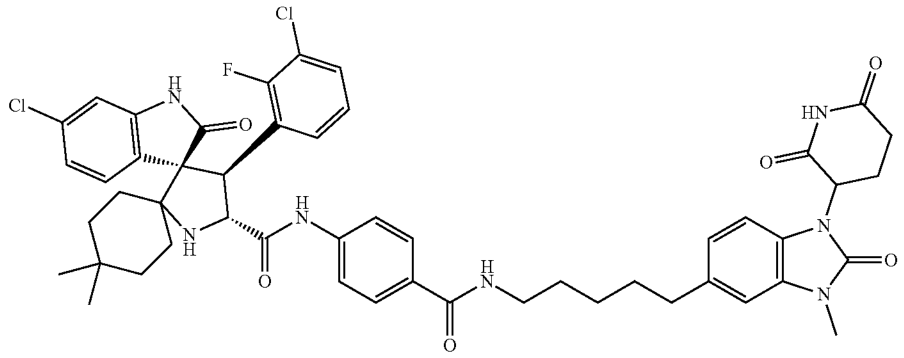
I-75
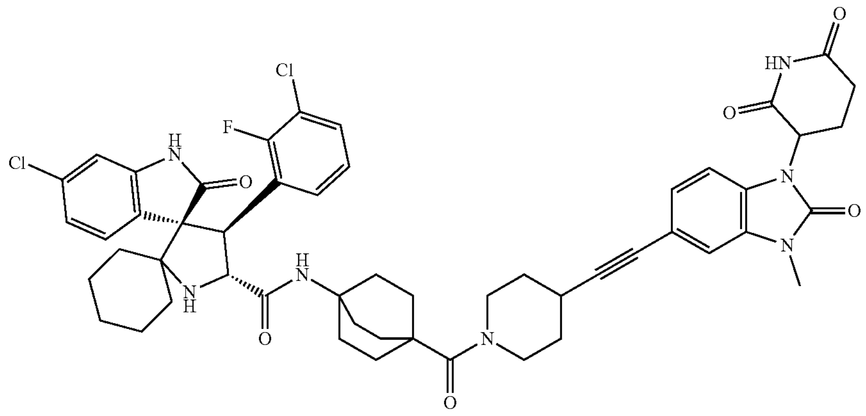
I-76
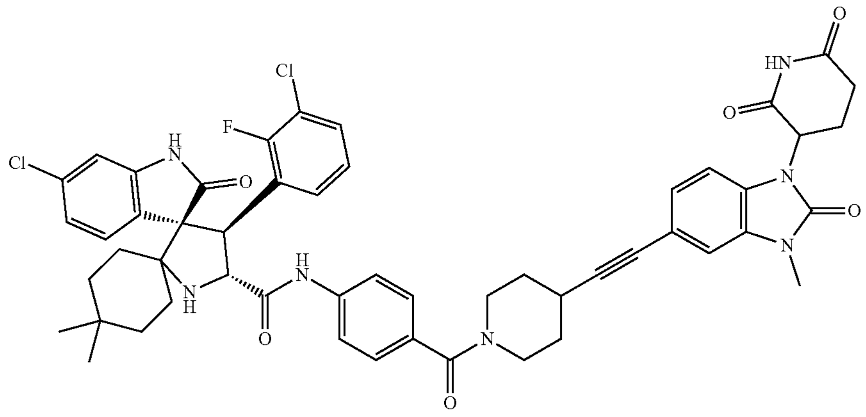
I-77
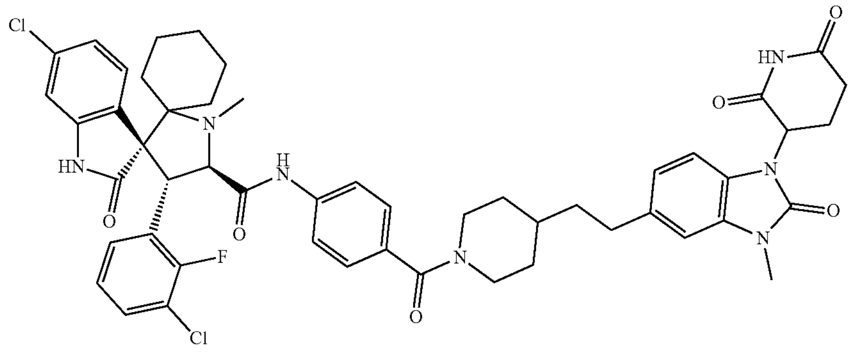

-continued
I-78
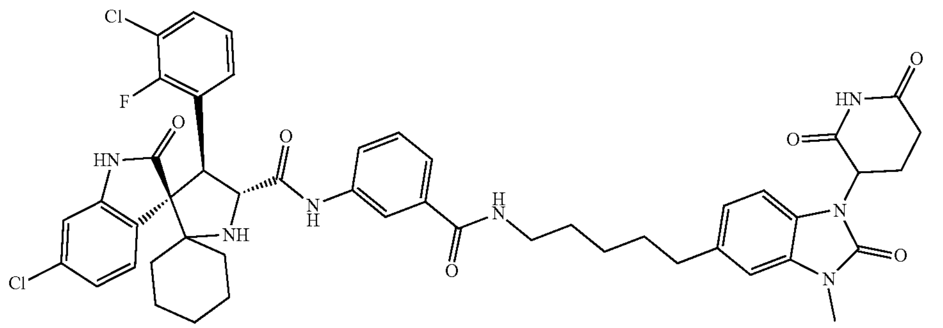
I-79
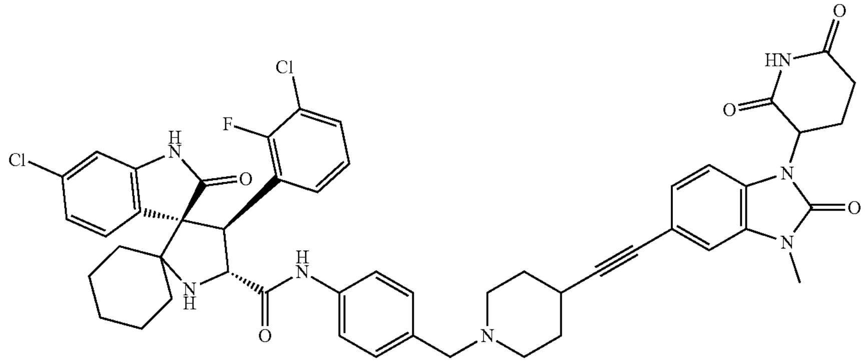
I-80
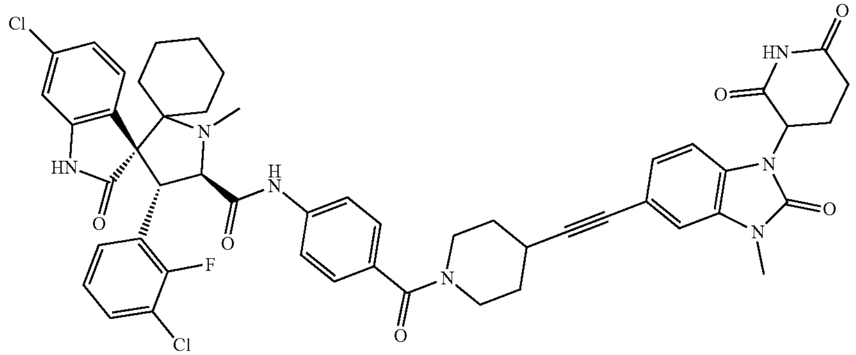
I-81
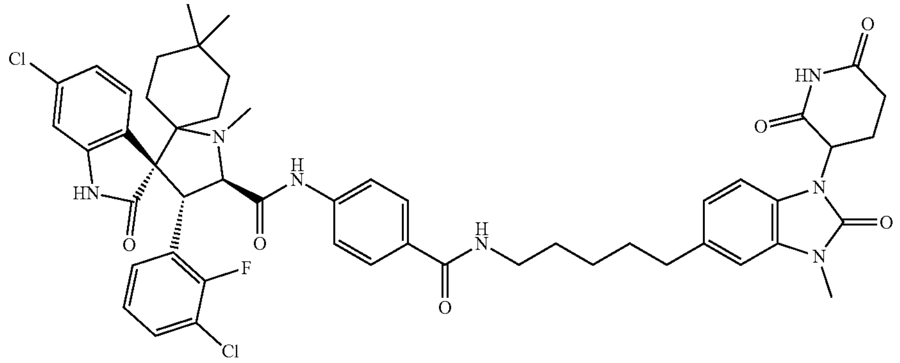

-continued
I-82
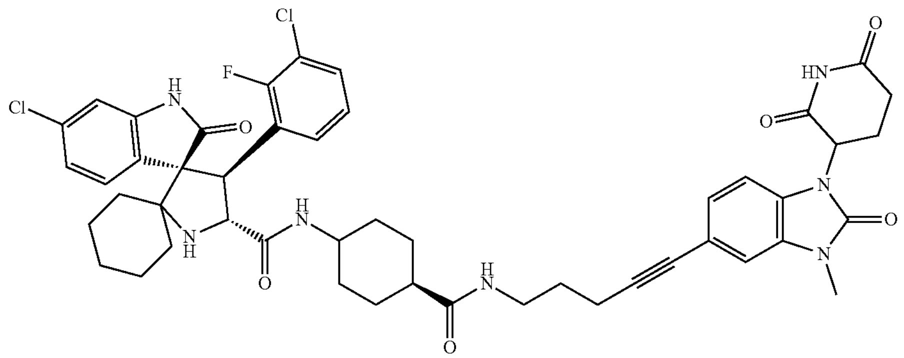
I-83
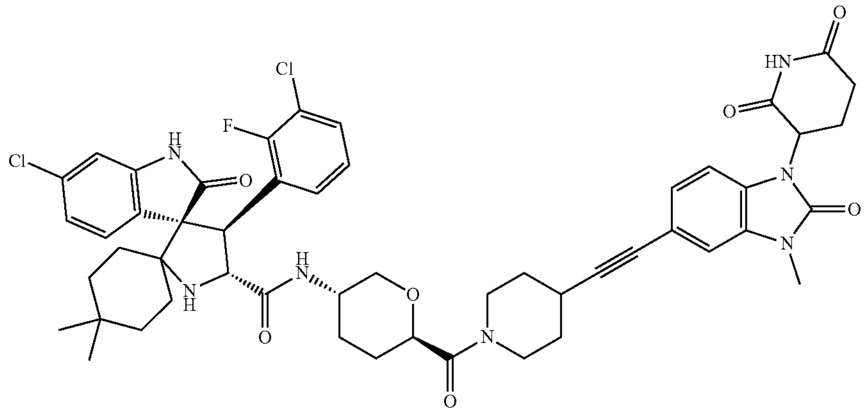
I-89
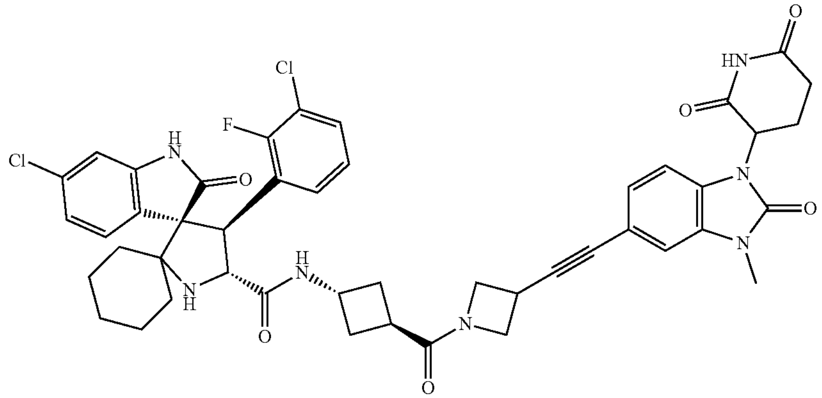
I-93
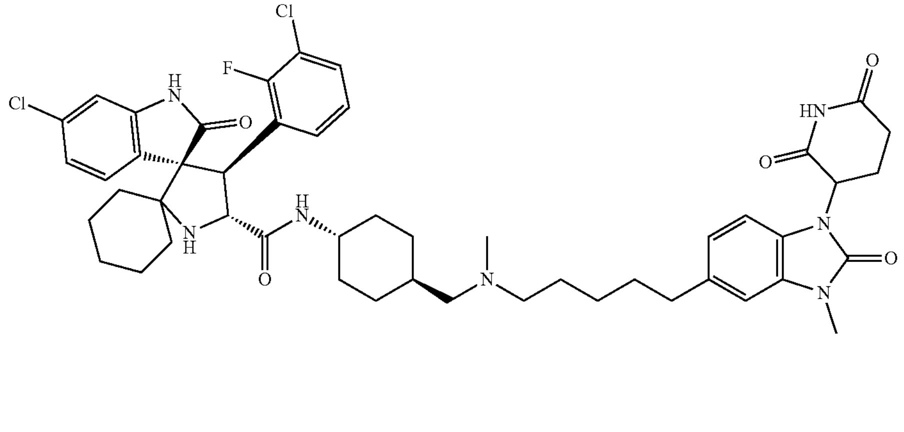

-continued
I-94
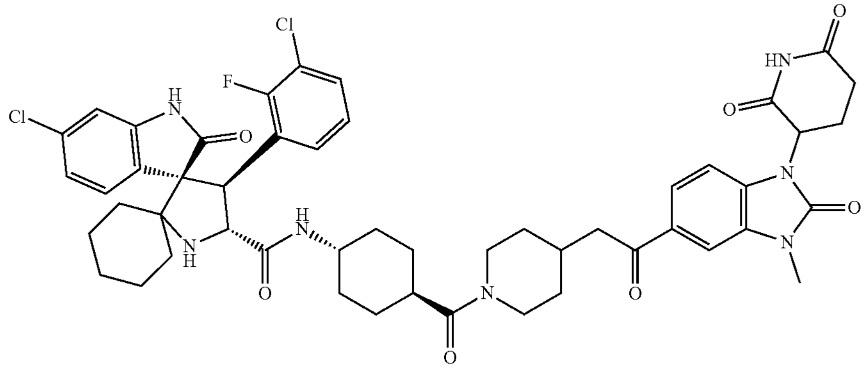
I-97
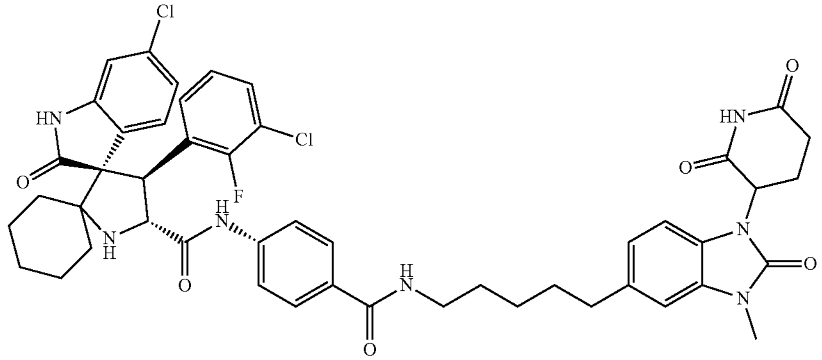
I-98
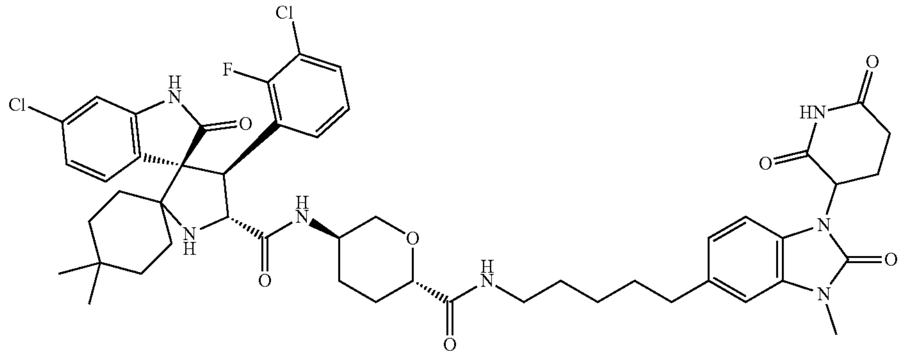
I-99
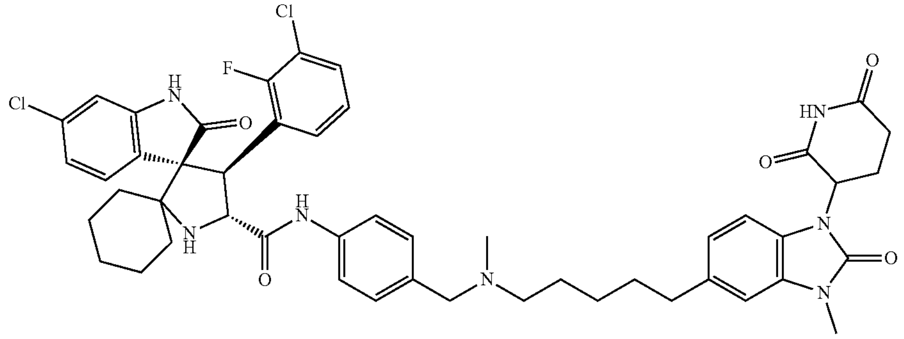

-continued
I-100
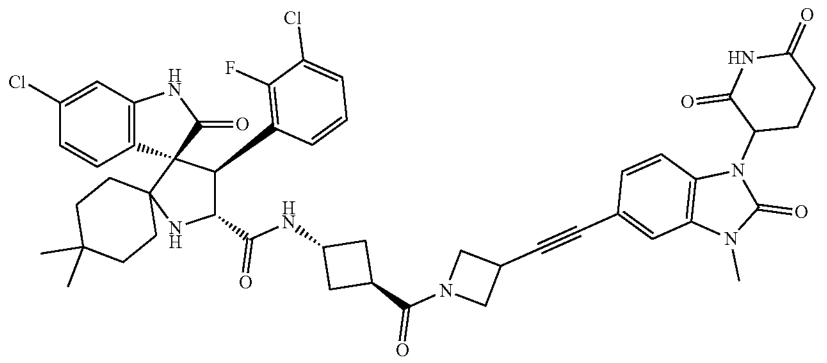
I-101
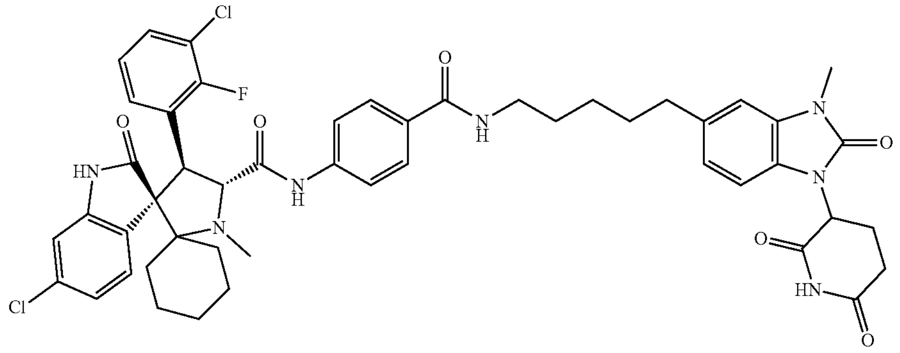
I-102
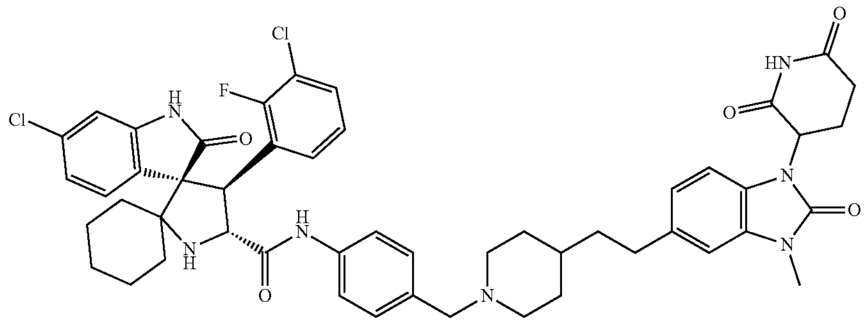
I-103
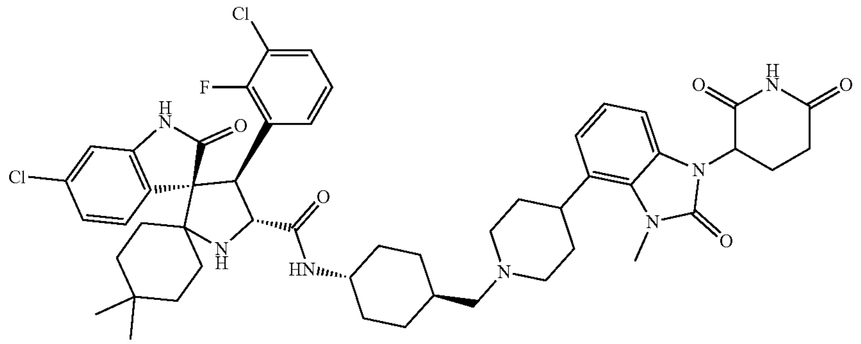

-continued
I-104
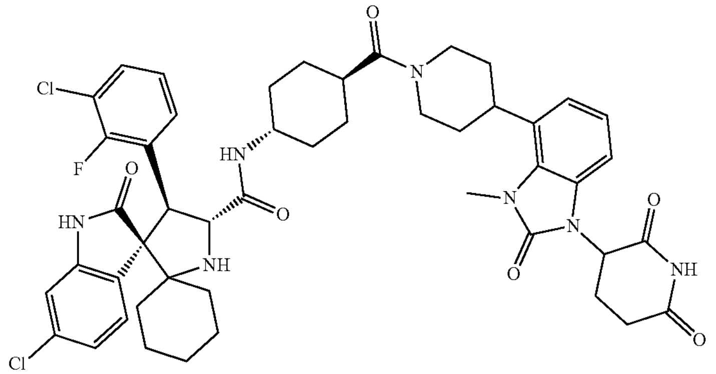
I-107
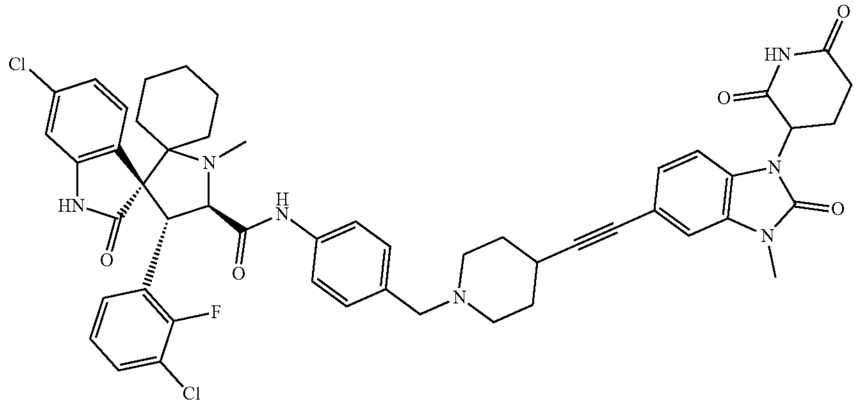
I-108
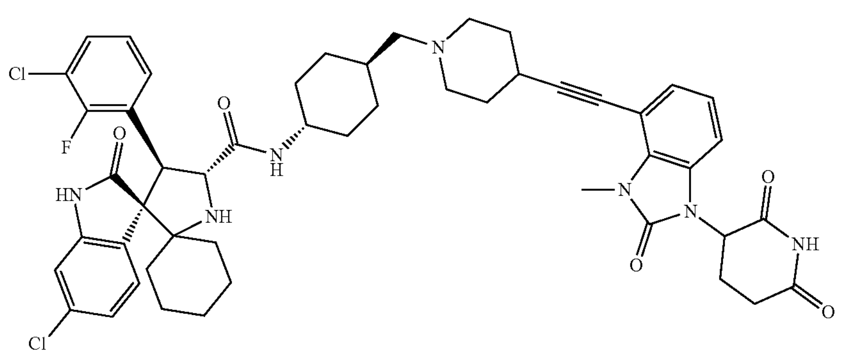
I-109
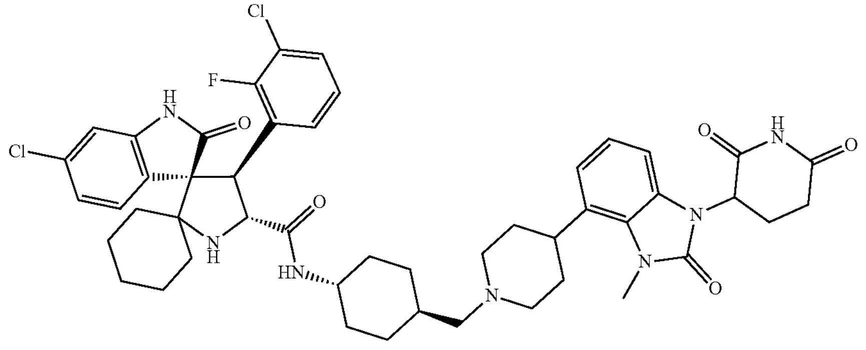

-continued
I-110
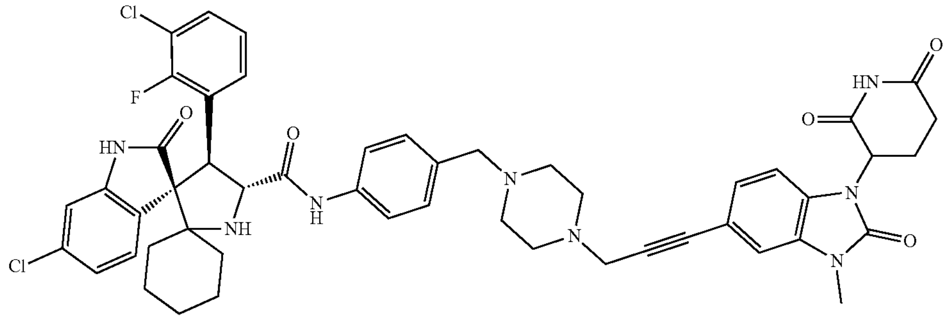
I-111
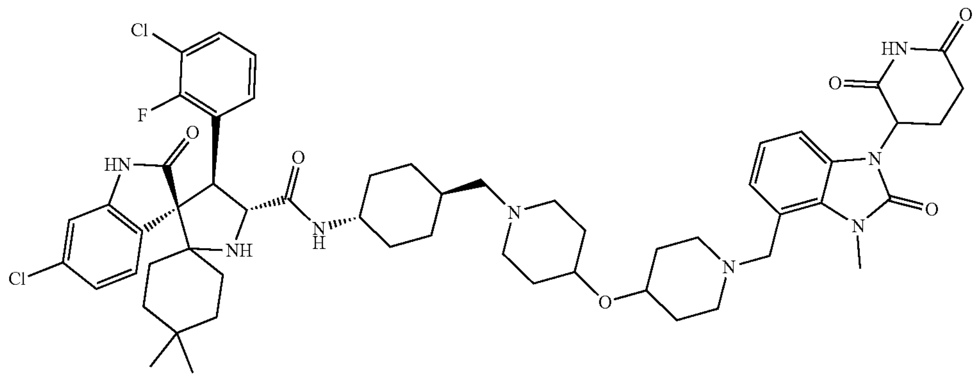
I-112
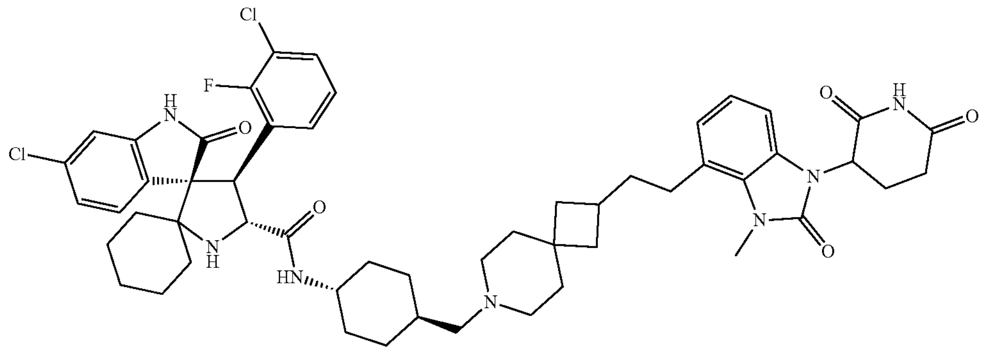
I-113
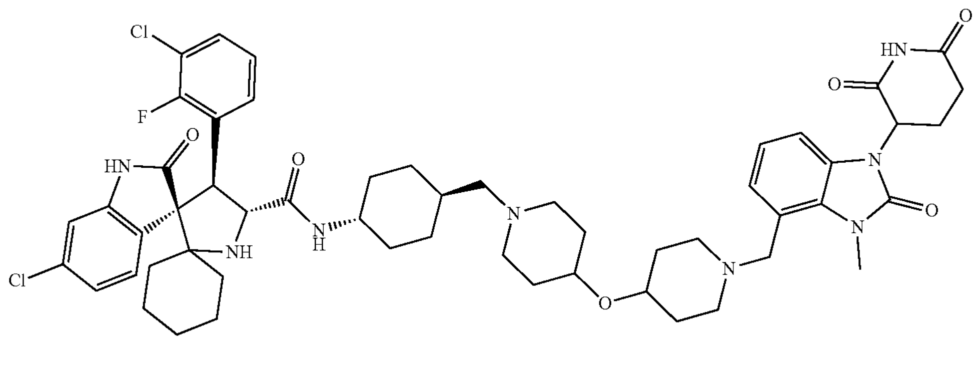

-continued
I-114
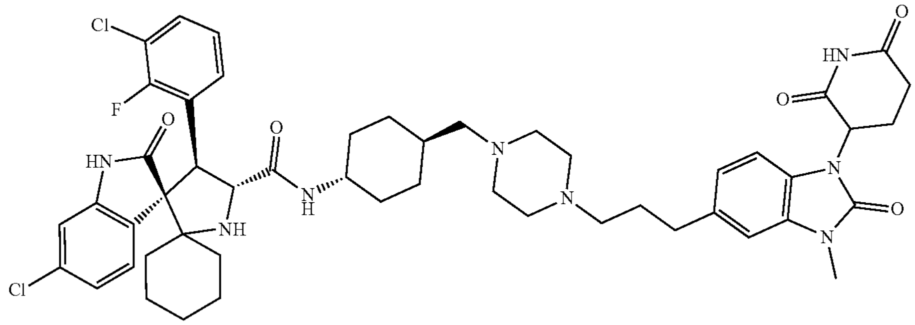
I-115
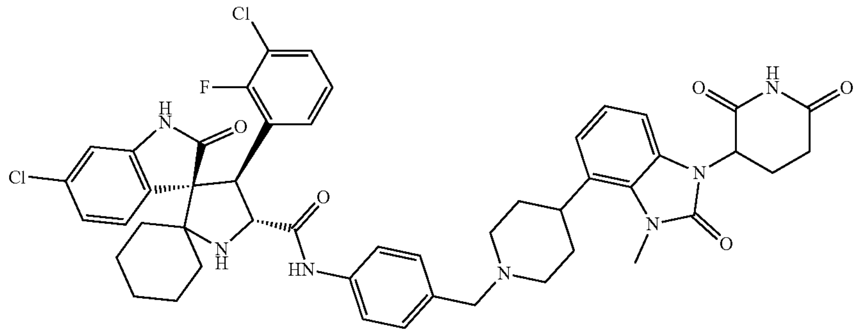
I-117
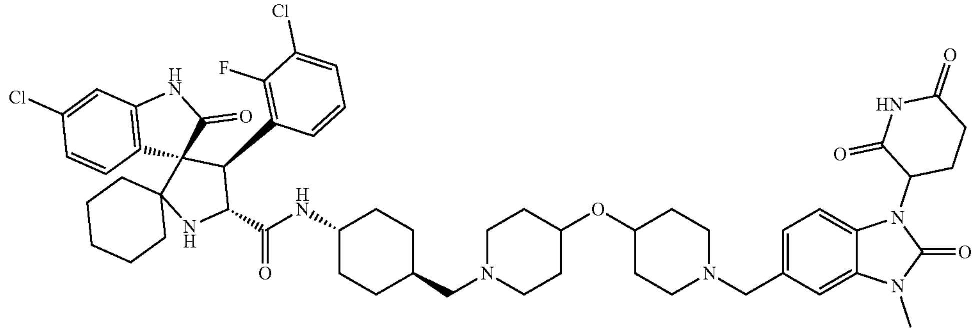
I-121
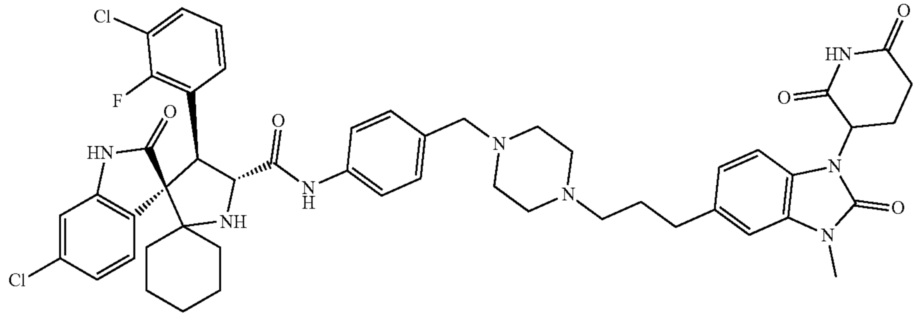

-continued
I-122
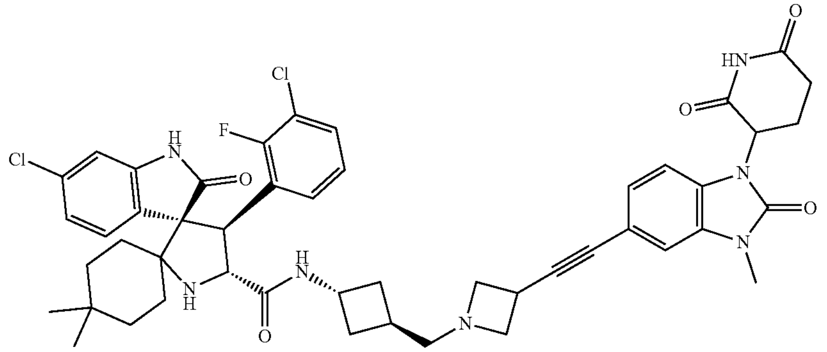
I-123
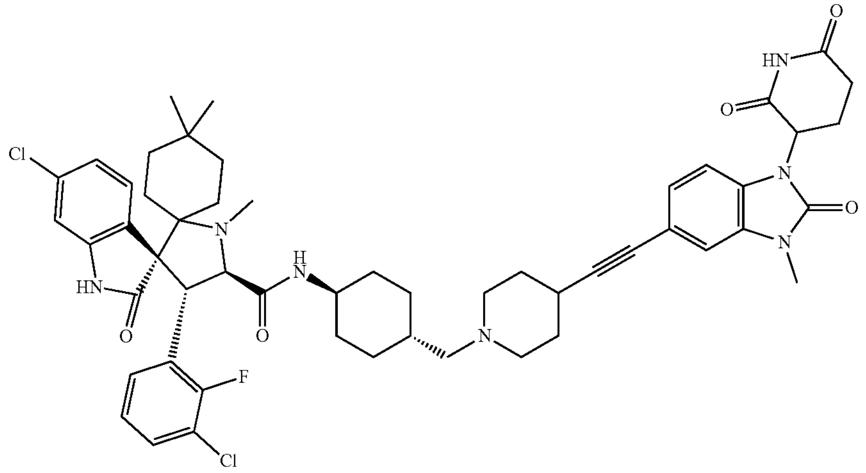
I-125
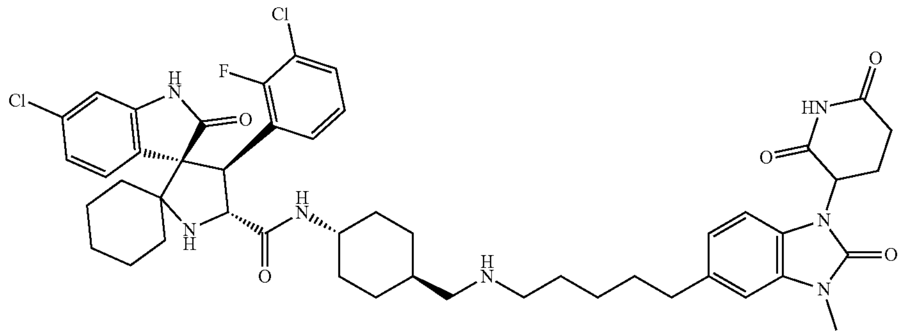
I-126
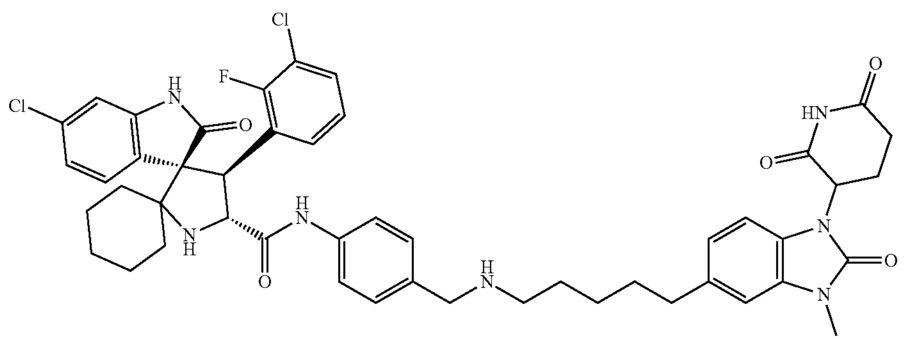

-continued
I-130
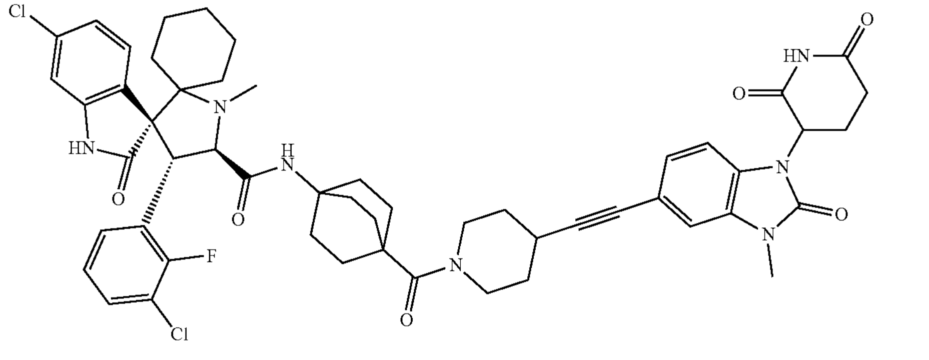
I-131
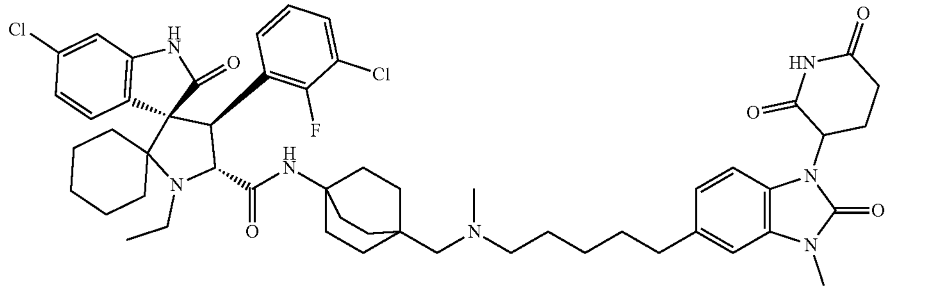
I-136
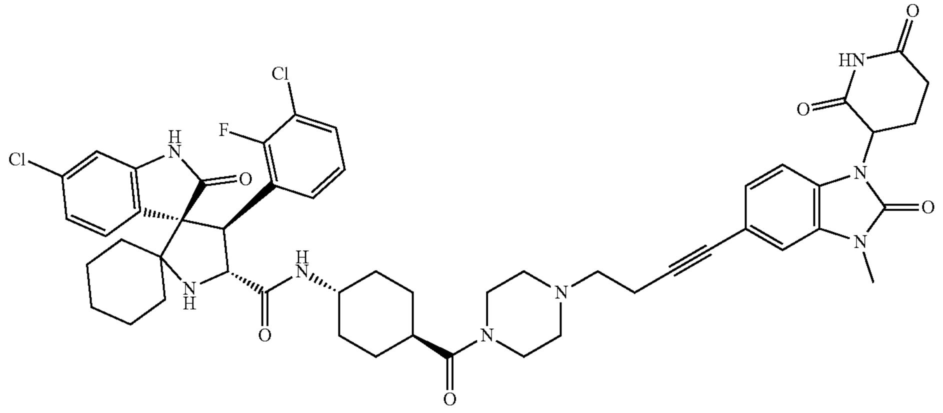
I-137
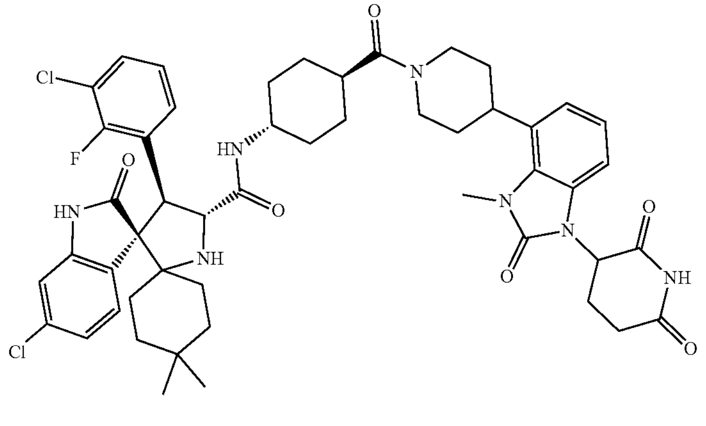

-continued
I-138
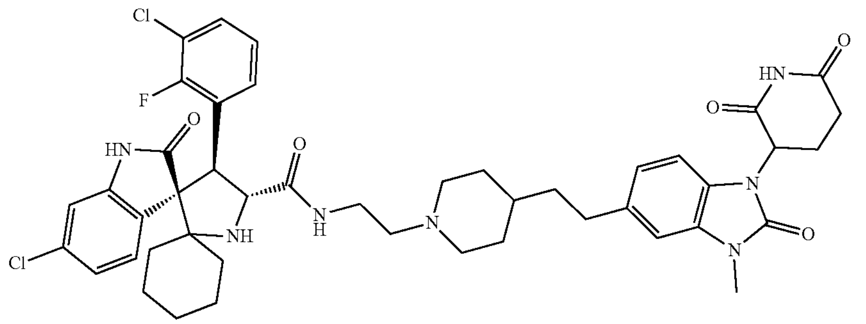
I-139
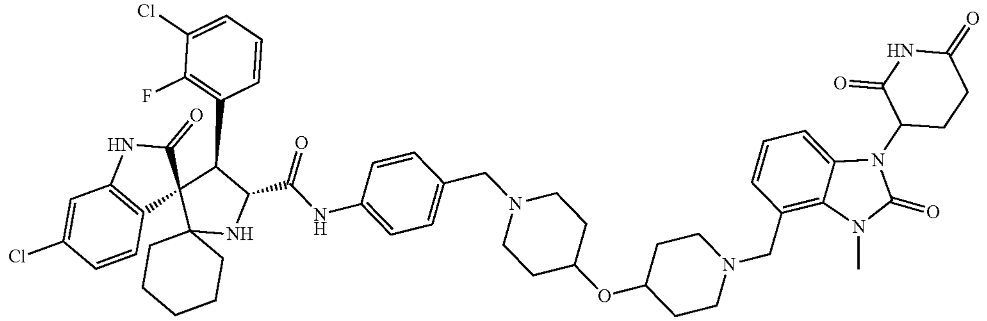
I-141
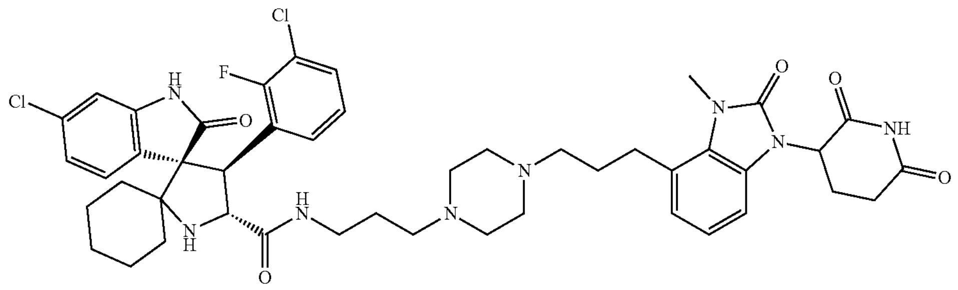
I-145
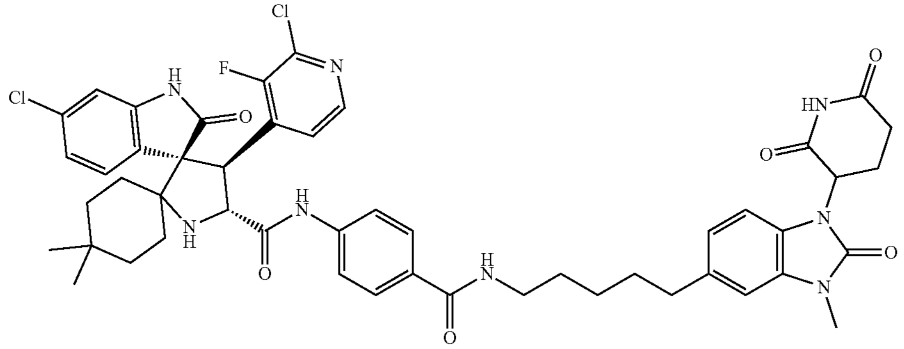

-continued
I-147
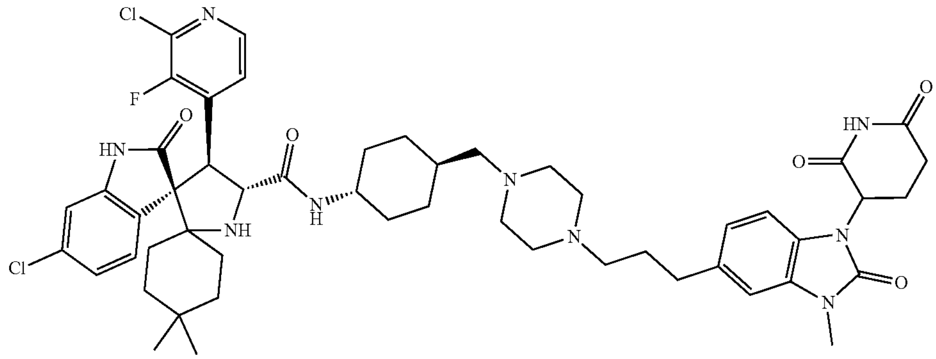
I-148
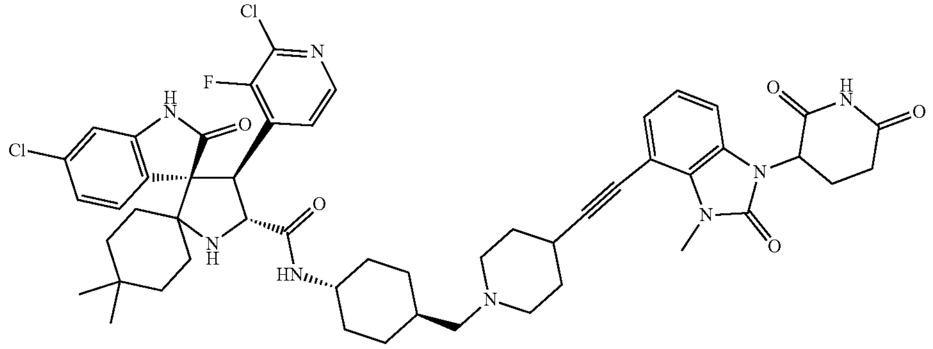
I-149
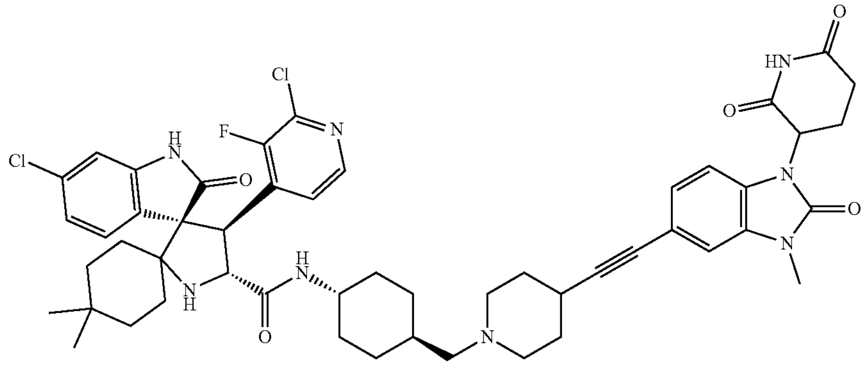
I-151
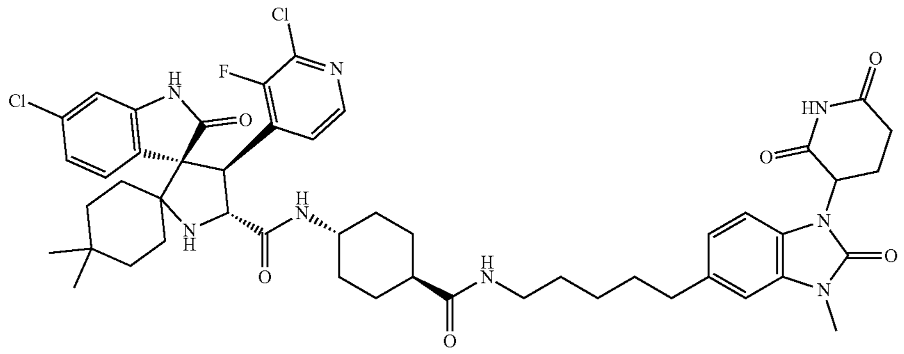

I-152
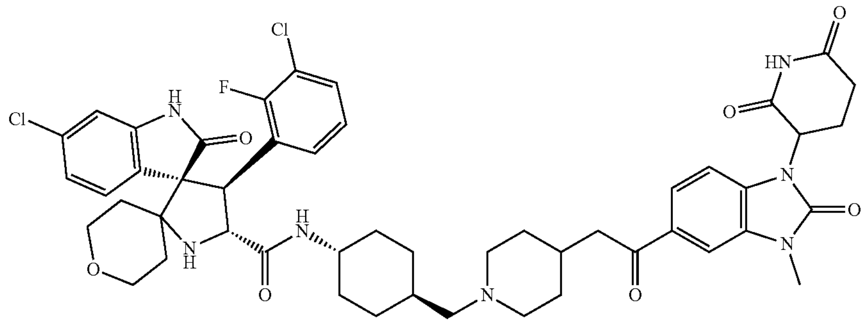
I-153
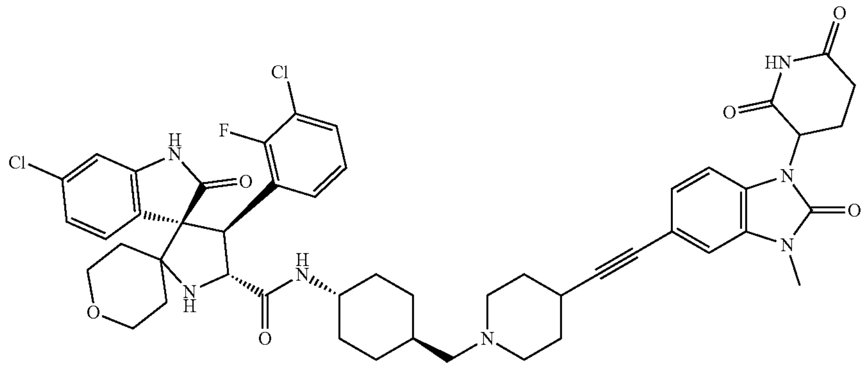
I-154
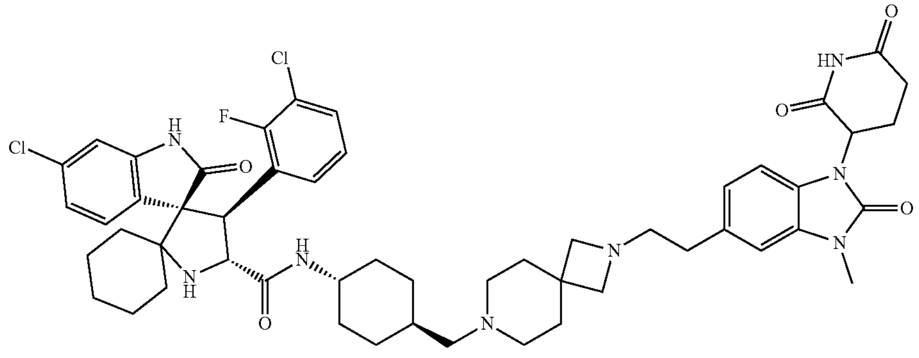
I-157
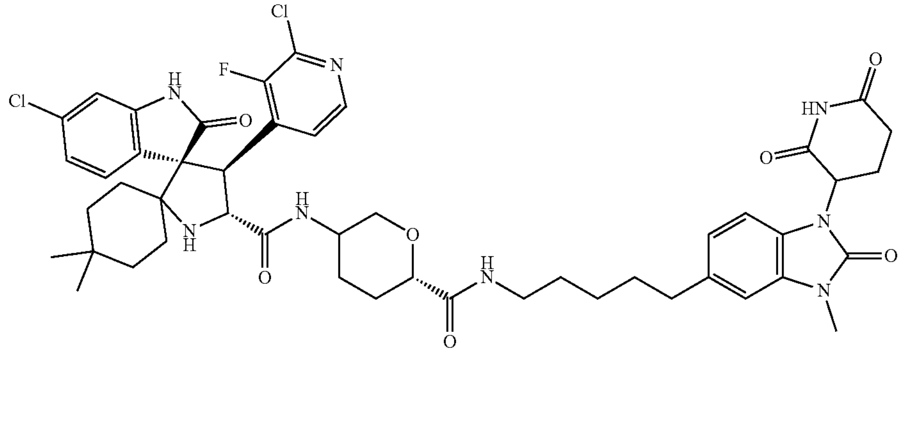

-continued
I-158
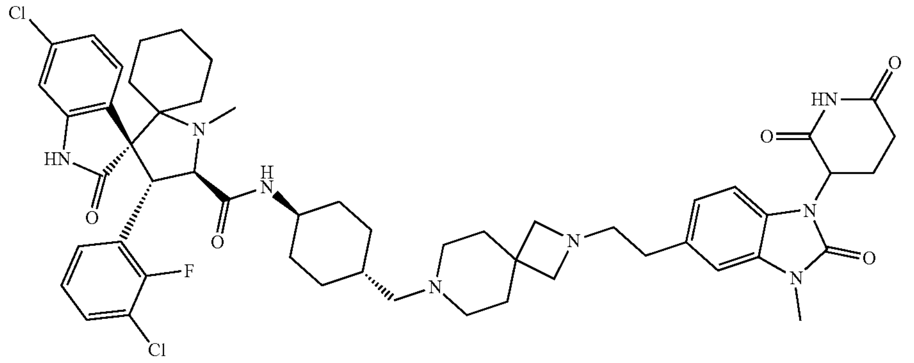
I-159
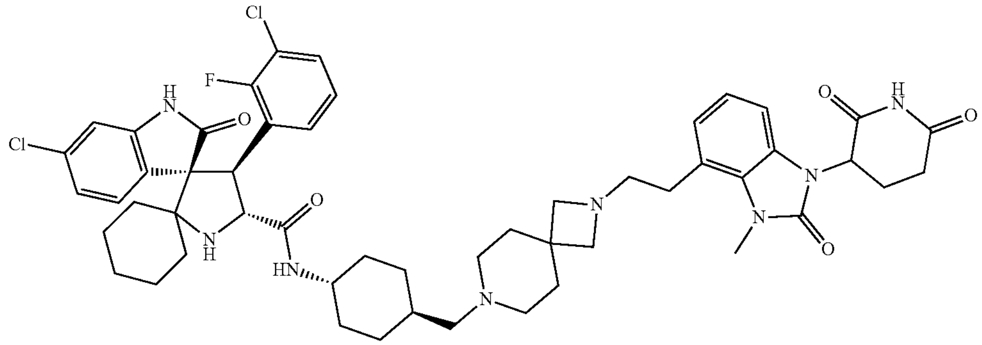
I-160
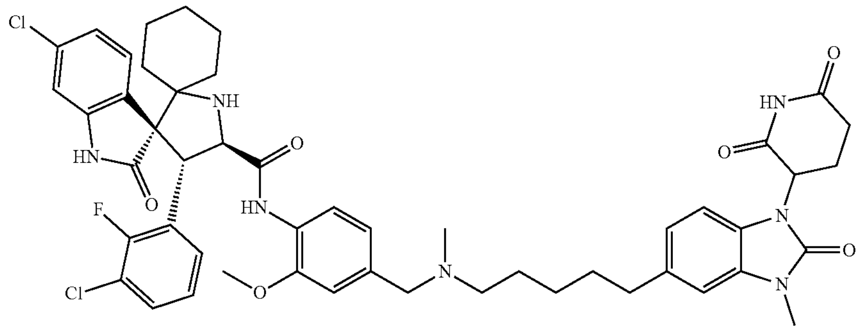
I-161
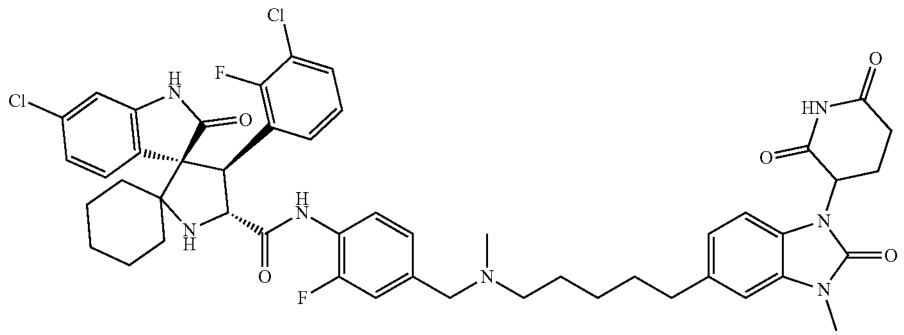

-continued
I-169
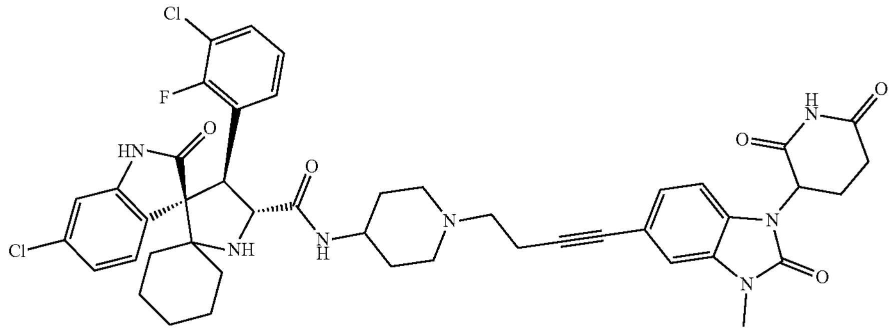
I-171
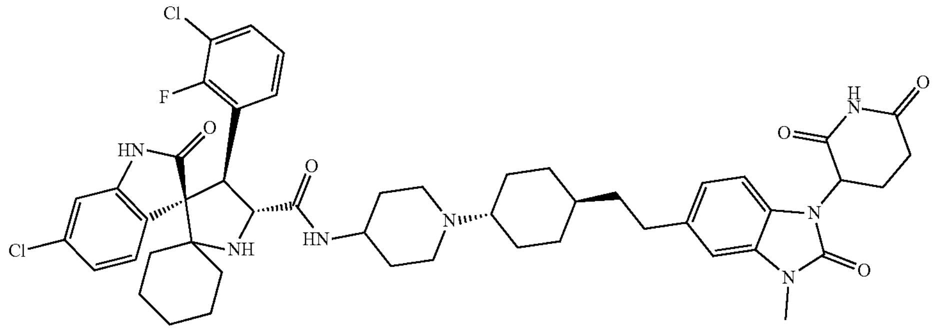
I-174
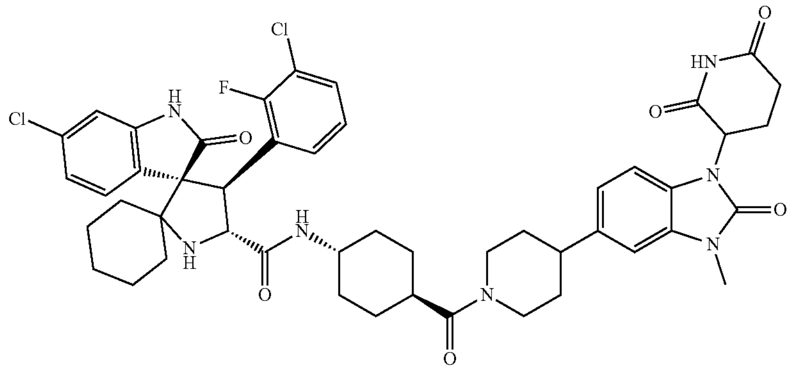
I-176
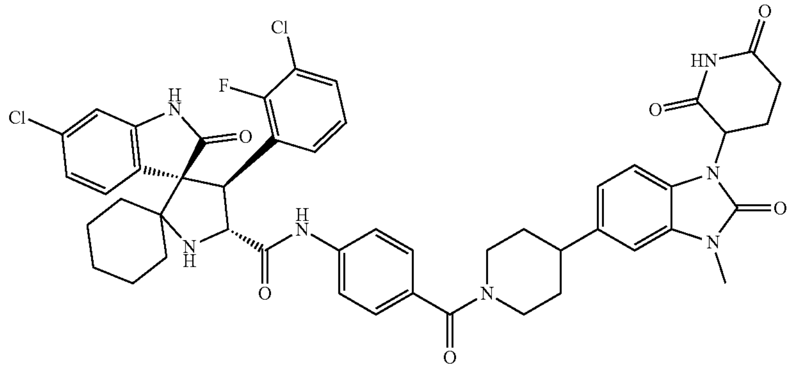

-continued
I-177
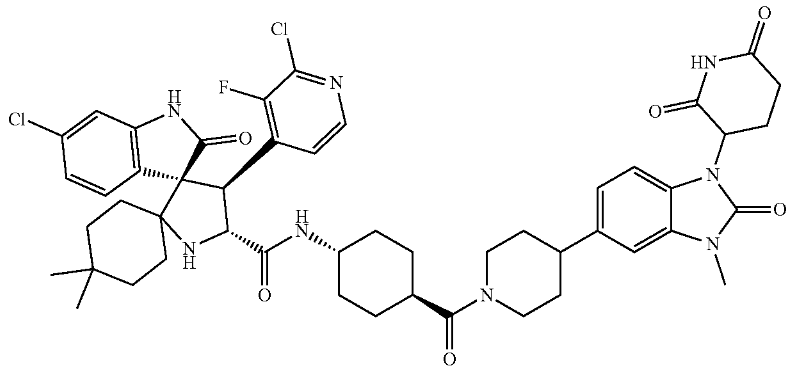
I-178
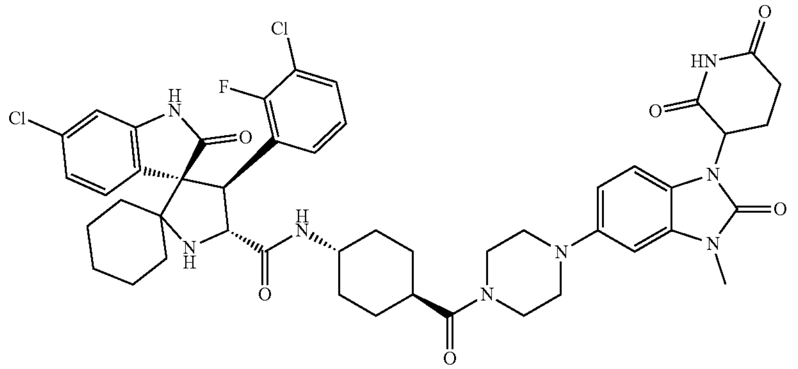
I-180
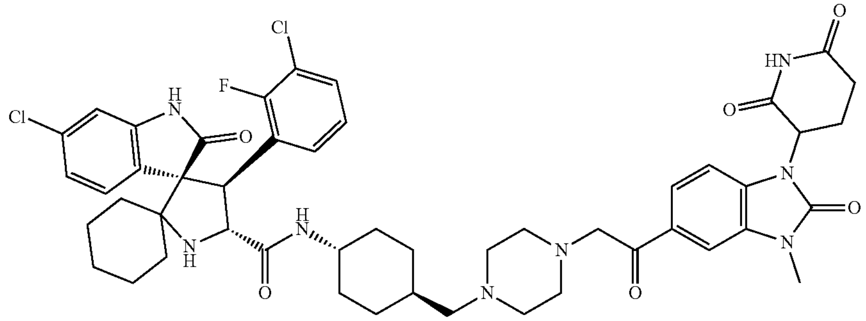
I-183
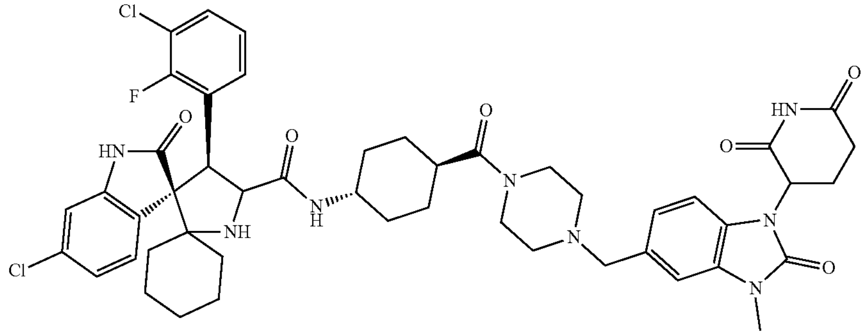

-continued
I-185
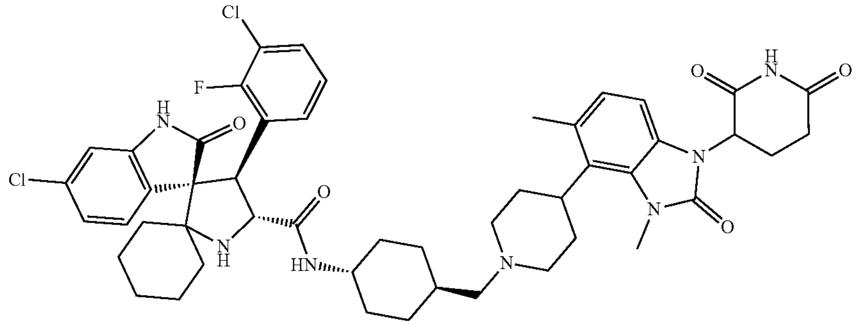
I-186
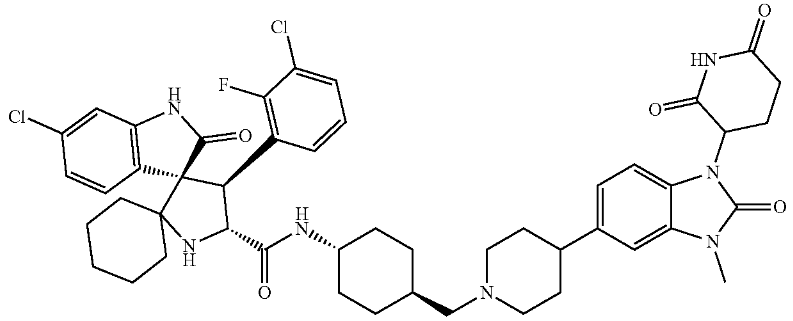
I-187
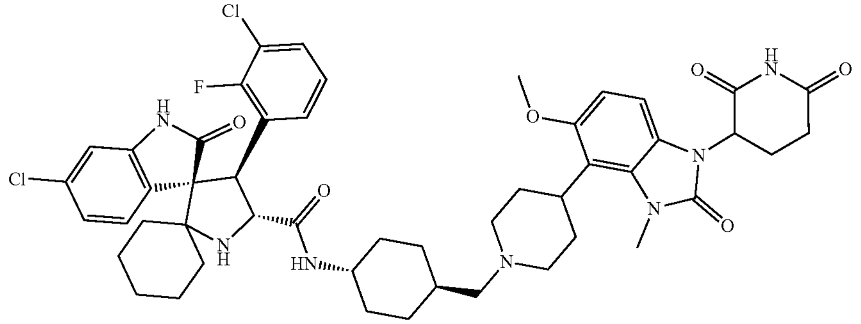
I-189
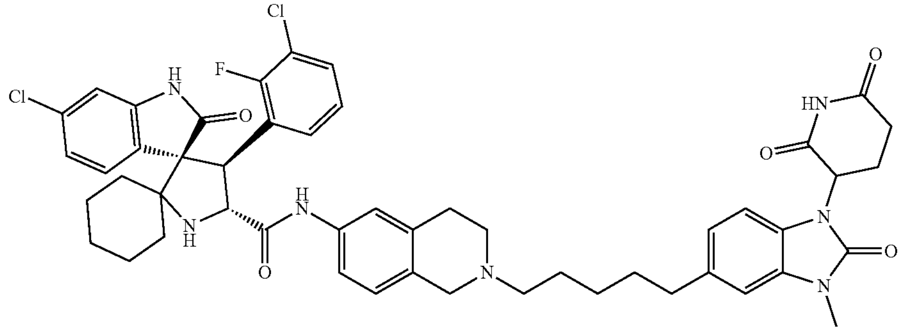
I-196
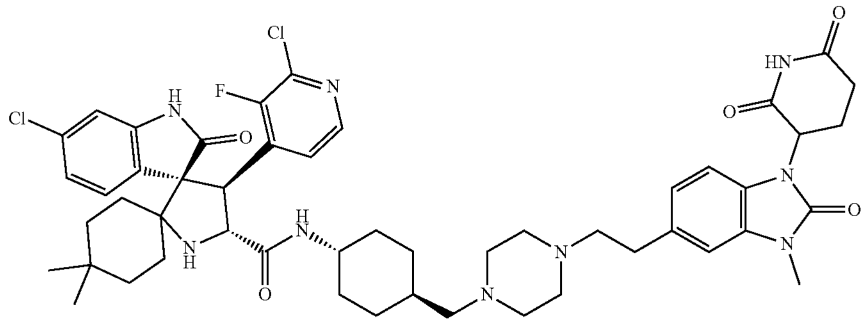

-continued
I-198
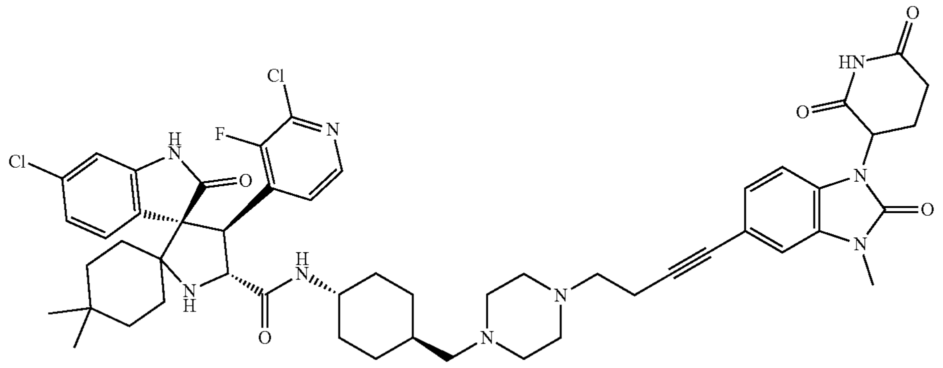
I-204
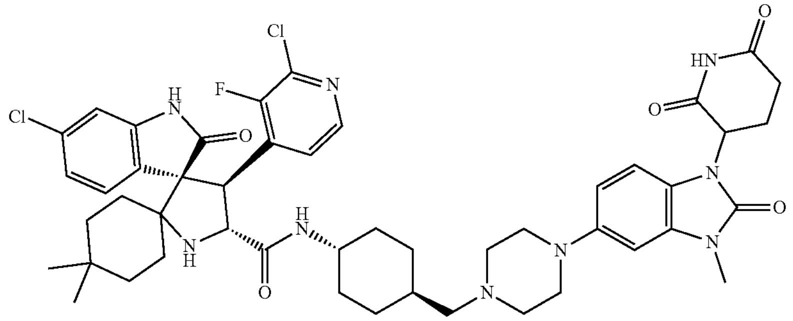
I-205
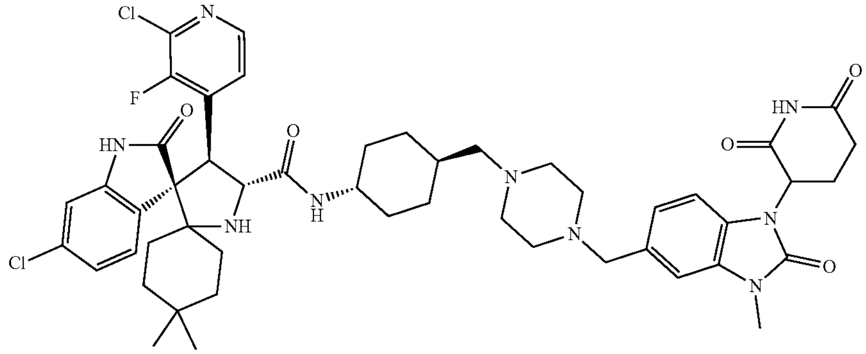
I-207
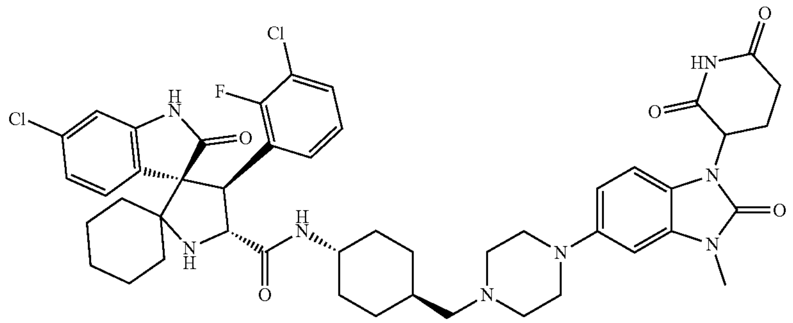

-continued
I-217
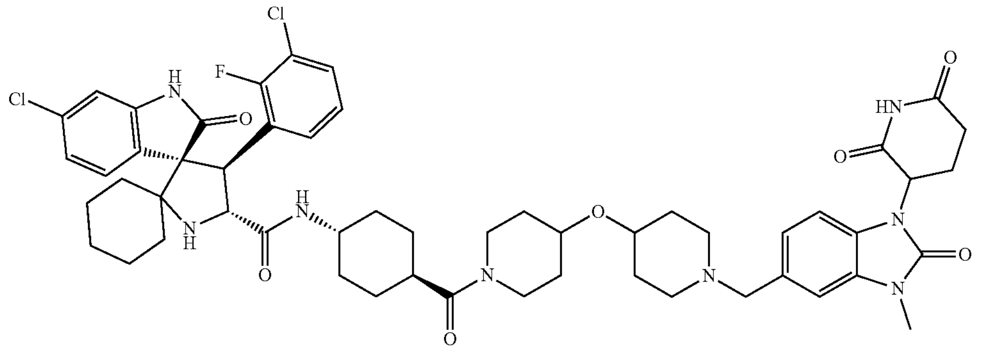
I-218
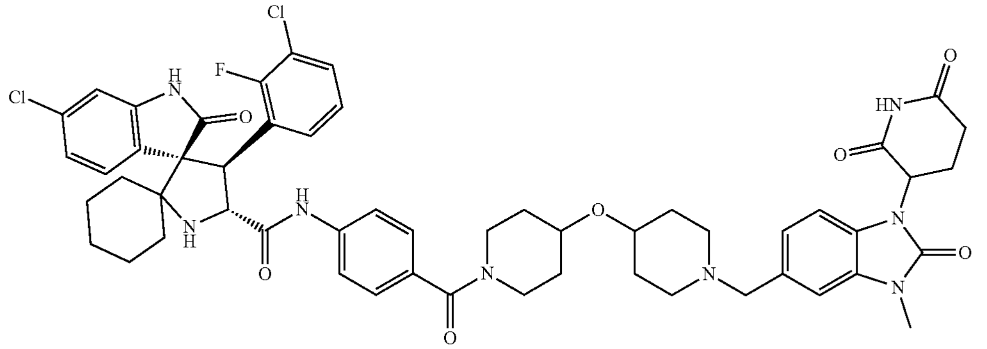
I-219
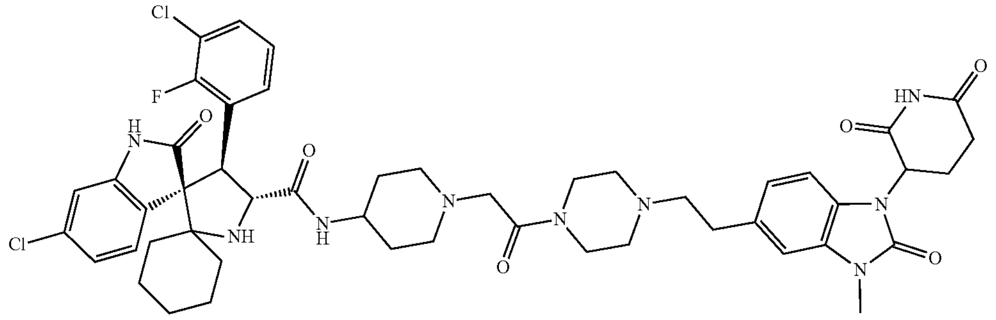
I-220
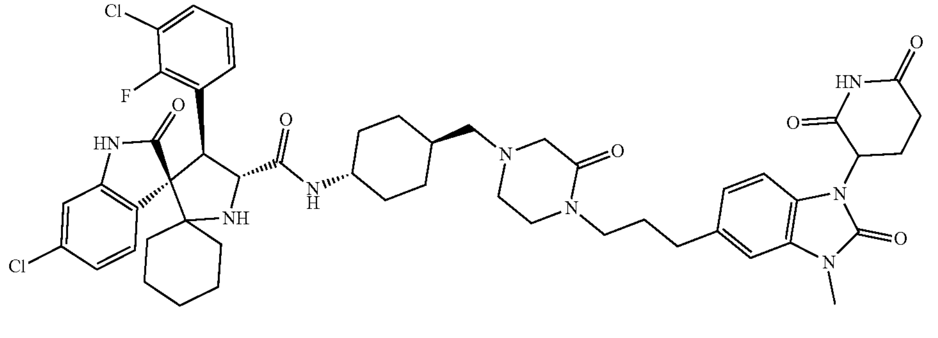

I-222

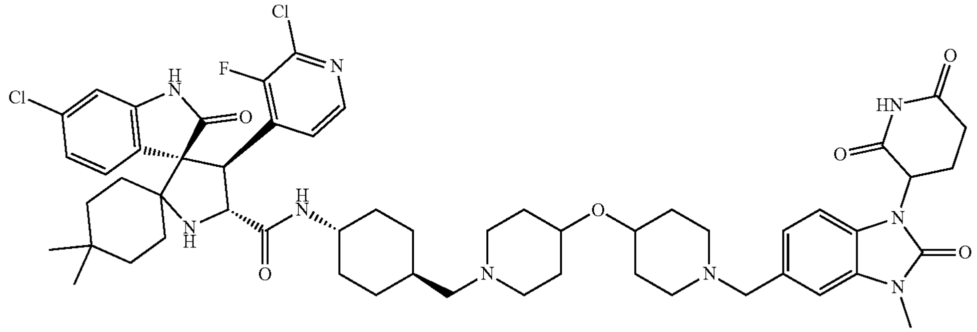

I-224

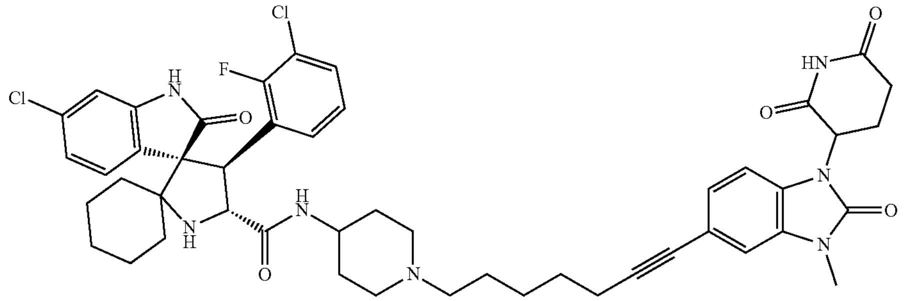

or a pharmaceutically acceptable salt thereof.

13. The method of claim 2, wherein the compound or a pharmaceutically acceptable salt thereof is administered as a pharmaceutical composition comprising a pharmaceutically acceptable carrier, adjuvant, or vehicle.

14. The method of claim 2, wherein the compound is:

I-174

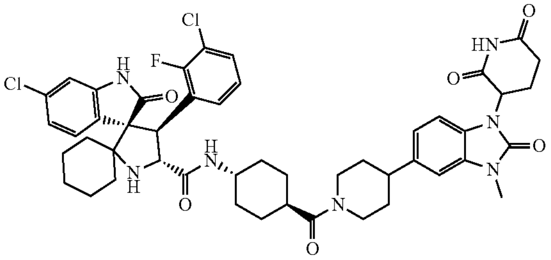

or a pharmaceutically acceptable salt thereof.

15. The method of claim 14, wherein the compound or a pharmaceutically acceptable salt thereof is administered as a pharmaceutical composition comprising a pharmaceutically acceptable carrier, adjuvant, or vehicle.

16. The method of claim 2, wherein the compound is:

I-174

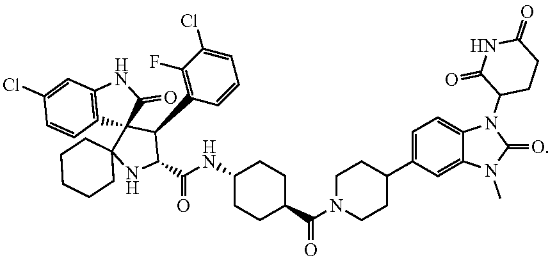

17. The method of claim 16, wherein the compound is administered as a pharmaceutical composition comprising a pharmaceutically acceptable carrier, adjuvant, or vehicle.

18. The method of claim 2, wherein the cancer is selected from adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogenous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma thyroid cancer, transitional cell carcinoma, throat cancer, urachal cancer, urogenital cancer, urothelial carcinoma, uveal melanoma, uterine cancer, verrucous carcinoma, visual pathway ghoma, vulvar cancer, vaginal cancer, Waldenstrom's macroglobulinemia, Warthin's tumor, and Wilms' tumor.

19. The method of claim 2, wherein the cancer is selected from the group consisting of acute monocytic leukemia, acute myelogenous leukemia, chronic myelogenous leukemia, chronic lymphocytic leukemia mixed lineage leukemia, NUT-midline carcinoma, multiple myeloma, small cell lung cancer (SCLC), neuroblastoma, Burkitt's lymphoma, cervical cancer, esophageal cancer, ovarian cancer, colorectal cancer, prostate cancer, and breast cancer.

20. The method of claim 2, further comprising administration of an additional therapeutic agent.

* * * * *